US006689595B1

(12) United States Patent
Benson

(10) Patent No.: US 6,689,595 B1
(45) Date of Patent: Feb. 10, 2004

(54) **CRYSTALLIZATION AND STRUCTURE DETERMINATION OF *STAPHYLOCOCCUS AUREUS* THYMIDYLATE KINASE**

(75) Inventor: Timothy E. Benson, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 115 days.

(21) Appl. No.: 09/632,553

(22) Filed: Aug. 4, 2000

Related U.S. Application Data

(60) Provisional application No. 60/147,117, filed on Aug. 4, 1999.

(51) Int. Cl.[7] .............................. C12N 9/00; C12Q 1/48; C30B 11/10; G01N 33/48; G01N 31/00

(52) U.S. Cl. .......................... 435/183; 435/15; 117/11; 702/19; 702/27; 530/350; 530/355; 530/820; 530/825

(58) Field of Search ................... 702/27, 19; 435/15, 435/183; 117/11; 530/350, 820, 825, 355

(56) References Cited

FOREIGN PATENT DOCUMENTS

| EP | 0 786 519 A2 | 7/1997 |
|----|----|----|
| WO | WO 99/47639 | 9/1999 |
| WO | WO 99/47662 | 9/1999 |
| WO | WO 00/12678 A2 | 3/2000 |
| WO | WO 01/16292 A2 | 3/2001 |

OTHER PUBLICATIONS

Khurana et al., Proc. Natl. Acad. Sci, vol. 95, pp. 6768–6773, Jun. 1998.*
Hampton Research, Crystal Screen, Hampton Research Corp, 27632 El Lazo Road, Laguna Niguel, California.*
Jan Drenth, (In Chapter I pp. 1–9 of "Principle of Protein X–ray Crystallography", 1994, Springer–Verlag New York, Inc).*
Jan Drenth, (In Chapter 3 pp. 63–69 of "Principle of Protein X–ray Crystallography", 1994, Springer–Verlag New York, Inc).*
P.A. Bartlett et al., "CAVEAT: A program to facilitate the structure–derived design of biologically active molecules", *Molecular Recognition: Chemical and Biological Problems*, Special Publ., Royal Chem. Soc., 78 182–196 (1989).
T.E. Benson et al., "An enzyme–substrate complex involved in bacterial cell wall biosynthesis", Nat. Struct. Biol., 2 644–53 (1995).
T.L. Blundell et al., *Protein Crystallography*, Academic Press (1976) (Cover Page, Publication Page and Table of Contents).
H.–J. Böhm, "The computer program LUDI: A new method for the de novo design of enzyme inhibitors", *J. Comp. Aid. Molec. Design.*, 6 61–78 (1992).

D.G. Brown et al., "Crystal structures of the thymidine kinase from herpes simplex virus type–1 in complex with deoxythymidine and Ganciclovir", Nat. Struct. Biol., 2 876–81 (1995).
A.T. Brünger, "X–PLOR version 3.1: A system for X–ray Crystallography and NMR", New Haven: Yale Univ. Press, (1992), (Cover Page, Publication Page and Table of Contents).
Collaborative Computational Project N4, "The CCP4 Suite: Programs for Protein Crystallography", Acta Cryst., D50 760–3 (1994).
M.B. Eisen et al., "HOOK: A program for finding novel molecular architectures that satisfy the chemical and steric requirements of a macromolecule binding site", *Proteins: Struc., Funct., Genet.*, 19 199–221 (1994).
S.V. Evans, "SETOR: Hardware–lighted three–dimensional solid model representations of macromolecules", J. Mol. Graphics, 11 134–8 (1993).
B.C. Finzel, "LORE: Exploiting Database of Known Structures", Meth. Enzymol., 277 230–42 (1997).
L.W. Frick et al., "Effects of 3'–azido–3'–deoxythymidine on the deoxynucleotide triphosphate pools of cultured human cells", Biochem. Biophys. Res. Comm., 154 124–9 (1988).
A. Fridland et al., "Relationship of deoxynucleotide changes to inhibition of DNA synthesis induced by the antiretroviral agent 3'–azido–3'–deoxythymidline and release of its monophosphate by human lymphoid cells (CCRF–CEM)", Mol. Pharmacol., 37 665–70 (1990).
V. Gillet et al., "SPROUT: A program for structure generation", J. Comput. Aided Mol. Design, 7 127–153 (1993).
P.J. Goodford, "A computational procedure for determining energetically favorable binding sites on biologically important macromolecules", J. Med. Chem., 28 849–857 (1985).
D.S. Goodsell et al., "Automated docking of substrates to proteins by simulated annealing", *Proteins: Struct. Funct. Genet.*, 8 195–202 (1990).
W.A. Hendrickson, "Determination of macromolecular structures from anomalous diffraction of synchrotron radiation", Science, 254 51–8 (1991).
W.A. Hendrickson et al., "Selenomethionyl proteins produced for analysis by multiwavelength anomalous diffraction (MAD): a vehicle for direct determination of three–dimensional structure", EMBO J., 9(5) 1665–1672 (1990).

(List continued on next page.)

Primary Examiner—John S. Brusca
Assistant Examiner—Shubo Zhou
(74) Attorney, Agent, or Firm—Mueting, Raasch & Gebhardt, P.A.

(57) ABSTRACT

An unliganded form of *Staphylococcus aureus* thymidylate kinase (*S. aureus* TMK) has been crystallized, and the three dimensional x-ray crystal structure has been solved to 2.3 Å resolution. The x-ray crystal structure is useful for solving the structure of other molecules or molecular complexes, and designing inhibitors of *S. aureus* TMK activity.

6 Claims, 219 Drawing Sheets

OTHER PUBLICATIONS

J.-S. Jiang et al., "Protein hydration observed by X-ray diffraction. Solvation properties of penicillopepsin and neuraminidase crystal structures", *J. Mol. Biol.* 243 100–15 (1994).

P. Kraulis, "Molscript: a program to produce both detailed and schematic plots of protein structures", *J. Appl. Cryst.*, 24 946–50 (1991).

I.D. Kuntz et al., "A geometric approach to macromolecule–ligand interactions", *J. Mol. Biol.*, 161 269–288 (1982).

R.A. Laskowski et al., "PROCHECK: a program to check the stereochemical quality of protein structures", *J. Appl. Cryst.*, 26 283–91 (1993).

E. Lattman, "Use of the Rotation and Translation Functions," in *Meth. Enzymol.*, 115 55–77 (1985).

G. Lauri et al., "CAVEAT: A program to facilitate the design of organic molecules", *J. Comput. Aided Mol. Des.*, 8 51–66 (1994).

A. Lavie et al., "Structure of thymidylate kinase reveals the cause behind the limiting step in AZT activation", *Nature Structural Biology*, 4 601–4 (1997).

A. Lavie et al., "Crystal structure of yeast thymidylate kinase complexed with the bisubstrate inhibitor $P^1$–(5'-Adenosyl) $P^5$–(5'-thymidyl) pentaphosphate ($TP_5A$) at 2.0 Å resolution: Implications for catalysis and AZT activation", *Biochemistry*, 37 3677–86 (1998).

A. Lavie et al., "Structural basis for efficient phosphorylation of 3'–azidothymidine monophosphate by *Escherichia coli* thymidylate kinase", *Proc. Natl. Acad. Sci. USA*, 95 14045–50 (1998).

Y.C. Martin, "3D Database Searching in Drug Design", *J. Med. Chem.*, 35 2145–2154 (1992).

E.C. Meng et al., "Automated Docking with Grid–Based Energy Evaluation", *J. Comp. Chem.*, 13 505–524 (1992).

E.A. Merritt et al., "*Raster 3D* Version 2.0. A Program for Photorealistic Molecular Graphics", *Acta Cryst.*, D50 869–73 (1994).

*Meth. Enzymol.*, 114 & 115, H.W. Wyckoff et al., eds., Academic Press (1985) (cover page, publication page and table of contents).

A. Miranker et al., "Functionally Maps of Binding Sites: A Multiple Copy Simultaneous Search Method", *Proteins: Struct. Funct. Gen.*, 11 29–34 (1991).

Neuhard et al., *Biosynthesis and Conversions of Pyrimidines*, $2^{nd}$ Edition. Washington, D.C.: ASM Press 580–599 (1996).

Y. Nishibata et al., "Automatic creation of drug candidate structures based on receptor structure. Starting point for artifical lead generation." *Tetrahedron*, 47 8985–90 (1991).

C.J. Noren et al., "A general method for site–specific incorporation of unnatural amino acids into proteins", *Science*, 244 182–188 (1989).

D.B. Prince et al., "Streaking to Better Crystals: Crystallization of *S. aureus* Thymidylate Kinase", Poster presented at Recent Advances in Macromolecular Crystallization on Aug. 22–25, 1999, San Diego, California.

J.P. Reynes et al., "*Escherichia coli* Thymidylate Kinase: Molecular Cloning, Nucleotide Sequence, and Genetic Organization of the Corresponding *tmk* Locus", *Journal of Bacteriology*, 178 2804–12 (1996).

M.G. Rossman, ed., "The Molecular Replacement Method. A Collection of Papers on the Use of Non–Crystallographic Symmetry,"*Int. Sci. Rev. Ser.*, No. 13, Gordon & Breach, New York (1972) (cover page, publication page and table of contents).

J.S. Sack, "CHAIN—A crystallographic modeling program", *J. Mol. Graphics*, 6 244–5 (1988).

G.M. Sheldrick et al., "Structure solution by iterative peak–list optimization and tangent expansion in space group *P1*", *Acta Cryst.*, B51 423–31 (1995).

T. Tatusova et al., "BLAST 2 Sequences, a new tool for comparing protein and nucleotide sequences", *FEMS Microbiol Lett*, 174 247–50 (1999) (program available at http://www.ncbi.nlm.nih.gov/gorf/bl2.html).

J. Travis, "Proteins and Organic Solvents Make an Eye–Opening Mix", *Science*, 262 1374 (1993).

G.D. Van Duyne et al., "Atomic structures of the human immunophilin FKBP–12 complexes with FK506 and rapamycin", *J. Mol. Biol.* 229 105–24 (1993).

De la Sierra et al., "Crystallization and preliminary X–ray analysis of the thymidylate kinase from *Mycobacterium tuberculosis,*" *ACTA Crystallographica Section D Biological Crystallography*, 56(2):226–228 (Feb. 2000).

Osterman et al., "Insights into the phosphoryltransfer mechanism of human thymidylate kinase gained from crystal structures of enzyme complexes along the reaction coordinate," *Structure*, 8(6):629–642 (2000).

Haebel et al., "Crystallization and Initial Crystallographic Analysis of the Disulfide Bond Isomerase DsbC in Complex with the α Domain of the Electron Transporter DsbD," *J. of Structural Biology*, 136:162–166 (2001). (Abstract only).

Low et al., "Some Studies of Protein Crystals in a Variety of Different Media," *J. Amer. Chem. Soc.*, 78:1107–1113 (1956).

Nave, "A Description of Imperfections in Protein Crystals," *Acta Cryst.*, D54:848–853 (1998).

Skrzypczak–Jankun et al., "Flash–Freezing Causes a Stress–Induced Modulation in a Crystal Structure of Soybean Lipoxygenase L3," *Acta Cryst.*, D52:959–965 (1996).

Tesmer et al., "Low Temperature Data Collection of Soybean Lipoxygenase," American Crystallographic Association Annual Meeting, Jul. 21–26, 1991, University of Toledo, Toledo, OH.

Wilson et al., "Who Checks the Checkers? Four Validation Tools Applied to Eight Atomic Resolution Structures. EU 3–D Validation Network," *J. Mol. Biol.*, 276:417–436 (1998).

de La Fortelle et al., "SHARP: A Maximum–Likelihood Heavy–Atom Parameter Refinement Program for the MIR and MAD Methods," P. Bourne et al., eds., *Crystallographic Computing 7* (1997).

\* cited by examiner

```
REMARK S. aureus Thymidylate kinase coordinates
REMARK  r= 0.236579 free r= 0.308425
REMARK DATE:16-Jun-99  10:01:57
CRYST1   49.8    90.1    46.5   90.00  101.80  90.00 P 2 1          2
                                X       Y       Z    Occ   B
ATOM     1   N   GLY    2    15.565  30.611   7.591  1.00 45.66      A
ATOM     2   CA  GLY    2    16.755  31.162   6.969  1.00 45.93      A
ATOM     3   C   GLY    2    17.911  31.377   7.940  1.00 46.18      A
ATOM     4   O   GLY    2    18.705  32.317   7.758  1.00 48.32      A
ATOM     5   N   SER    3    17.998  30.531   8.975  1.00 42.96      A
ATOM     6   CA  SER    3    19.072  30.610   9.970  1.00 39.00      A
ATOM     7   CB  SER    3    18.627  29.966  11.292  1.00 40.17      A
ATOM     8   OG  SER    3    19.120  30.700  12.402  1.00 40.63      A
ATOM     9   C   SER    3    20.281  29.874   9.397  1.00 36.56      A
ATOM    10   O   SER    3    20.446  29.839   8.181  1.00 39.31      A
ATOM    11   N   ALA    4    21.128  29.286  10.238  1.00 31.10      A
ATOM    12   CA  ALA    4    22.288  28.569   9.699  1.00 25.76      A
ATOM    13   CB  ALA    4    23.547  29.356  10.017  1.00 29.23      A
ATOM    14   C   ALA    4    22.454  27.088  10.136  1.00 21.31      A
ATOM    15   O   ALA    4    23.384  26.753  10.865  1.00 18.84      A
ATOM    16   N   PHE    5    21.574  26.211   9.653  1.00 17.80      A
ATOM    17   CA  PHE    5    21.613  24.783   9.982  1.00 15.57      A
ATOM    18   CB  PHE    5    20.202  24.333  10.411  1.00 15.42      A
ATOM    19   CG  PHE    5    20.106  22.891  10.864  1.00  9.82      A
ATOM    20   CD1 PHE    5    21.231  22.181  11.241  1.00  7.80      A
ATOM    21   CD2 PHE    5    18.874  22.243  10.880  1.00 12.23      A
ATOM    22   CE1 PHE    5    21.134  20.852  11.625  1.00 10.94      A
ATOM    23   CE2 PHE    5    18.773  20.911  11.266  1.00 12.85      A
ATOM    24   CZ  PHE    5    19.907  20.217  11.633  1.00  9.60      A
ATOM    25   C   PHE    5    22.100  23.956   8.782  1.00 15.42      A
ATOM    26   O   PHE    5    21.319  23.652   7.880  1.00 15.73      A
ATOM    27   N   ILE    6    23.382  23.587   8.776  1.00 14.77      A
ATOM    28   CA  ILE    6    23.960  22.816   7.669  1.00 14.44      A
ATOM    29   CB  ILE    6    25.224  23.507   7.094  1.00 14.35      A
ATOM    30   CG2 ILE    6    25.740  22.739   5.899  1.00 13.40      A
ATOM    31   CG1 ILE    6    24.911  24.947   6.685  1.00 12.20      A
ATOM    32   CD1 ILE    6    26.136  25.851   6.740  1.00 11.34      A
ATOM    33   C   ILE    6    24.373  21.413   8.108  1.00 13.52      A
ATOM    34   O   ILE    6    24.948  21.245   9.177  1.00 11.51      A
ATOM    35   N   THR    7    24.100  20.421   7.258  1.00 14.29      A
ATOM    36   CA  THR    7    24.440  19.020   7.532  1.00 16.52      A
ATOM    37   CB  THR    7    23.198  18.154   7.544  1.00 18.14      A
ATOM    38   OG1 THR    7    22.475  18.365   6.322  1.00 20.48      A
ATOM    39   CG2 THR    7    22.314  18.494   8.753  1.00 20.31      A
ATOM    40   C   THR    7    25.355  18.480   6.437  1.00 16.16      A
ATOM    41   O   THR    7    25.217  18.846   5.274  1.00 16.42      A
ATOM    42   N   PHE    8    26.278  17.598   6.795  1.00 16.88      A
ATOM    43   CA  PHE    8    27.193  17.053   5.799  1.00 17.17      A
ATOM    44   CB  PHE    8    28.647  17.250   6.259  1.00 16.14      A
ATOM    45   CG  PHE    8    29.094  18.704   6.285  1.00 17.67      A
ATOM    46   CD1 PHE    8    28.549  19.600   7.206  1.00 17.53      A
ATOM    47   CD2 PHE    8    30.059  19.177   5.387  1.00 16.84      A
ATOM    48   CE1 PHE    8    28.960  20.935   7.238  1.00 13.97      A
ATOM    49   CE2 PHE    8    30.479  20.519   5.412  1.00 12.30      A
ATOM    50   CZ  PHE    8    29.924  21.393   6.336  1.00 14.49      A
ATOM    51   C   PHE    8    26.914  15.579   5.550  1.00 17.25      A
ATOM    52   O   PHE    8    27.194  14.755   6.394  1.00 18.79      A
```

Fig. 2

| ATOM | 53 | N | GLU | 9 | 26.356 | 15.249 | 4.388 | 1.00 | 17.51 | A |
|------|----|----|-----|---|--------|--------|-------|------|-------|---|
| ATOM | 54 | CA | GLU | 9 | 26.059 | 13.855 | 4.048 | 1.00 | 17.55 | A |
| ATOM | 55 | CB | GLU | 9 | 24.664 | 13.749 | 3.435 | 1.00 | 17.76 | A |
| ATOM | 56 | CG | GLU | 9 | 23.554 | 14.273 | 4.329 | 1.00 | 20.61 | A |
| ATOM | 57 | CD | GLU | 9 | 23.291 | 13.365 | 5.503 | 1.00 | 23.30 | A |
| ATOM | 58 | OE1 | GLU | 9 | 24.062 | 12.399 | 5.690 | 1.00 | 22.58 | A |
| ATOM | 59 | OE2 | GLU | 9 | 22.309 | 13.611 | 6.239 | 1.00 | 26.41 | A |
| ATOM | 60 | C | GLU | 9 | 27.091 | 13.262 | 3.078 | 1.00 | 18.24 | A |
| ATOM | 61 | O | GLU | 9 | 27.844 | 13.988 | 2.432 | 1.00 | 16.08 | A |
| ATOM | 62 | N | GLY | 10 | 27.140 | 11.939 | 2.983 | 1.00 | 18.42 | A |
| ATOM | 63 | CA | GLY | 10 | 28.096 | 11.326 | 2.080 | 1.00 | 18.56 | A |
| ATOM | 64 | C | GLY | 10 | 28.583 | 9.945 | 2.482 | 1.00 | 19.97 | A |
| ATOM | 65 | O | GLY | 10 | 28.526 | 9.564 | 3.649 | 1.00 | 20.35 | A |
| ATOM | 66 | N | PRO | 11 | 29.096 | 9.170 | 1.521 | 1.00 | 20.31 | A |
| ATOM | 67 | CD | PRO | 11 | 29.265 | 9.483 | 0.094 | 1.00 | 20.97 | A |
| ATOM | 68 | CA | PRO | 11 | 29.578 | 7.831 | 1.853 | 1.00 | 20.79 | A |
| ATOM | 69 | CB | PRO | 11 | 29.729 | 7.153 | 0.488 | 1.00 | 23.34 | A |
| ATOM | 70 | CG | PRO | 11 | 29.208 | 8.147 | -0.544 | 1.00 | 21.83 | A |
| ATOM | 71 | C | PRO | 11 | 30.895 | 7.831 | 2.637 | 1.00 | 21.56 | A |
| ATOM | 72 | O | PRO | 11 | 31.562 | 8.860 | 2.777 | 1.00 | 18.77 | A |
| ATOM | 73 | N | GLU | 12 | 31.250 | 6.658 | 3.152 | 1.00 | 21.58 | A |
| ATOM | 74 | CA | GLU | 12 | 32.483 | 6.470 | 3.900 | 1.00 | 21.79 | A |
| ATOM | 75 | CB | GLU | 12 | 32.486 | 5.056 | 4.489 | 1.00 | 26.41 | A |
| ATOM | 76 | CG | GLU | 12 | 33.714 | 4.691 | 5.302 | 1.00 | 33.39 | A |
| ATOM | 77 | CD | GLU | 12 | 33.645 | 5.192 | 6.734 | 1.00 | 35.99 | A |
| ATOM | 78 | OE1 | GLU | 12 | 34.492 | 4.762 | 7.551 | 1.00 | 39.53 | A |
| ATOM | 79 | OE2 | GLU | 12 | 32.755 | 6.014 | 7.039 | 1.00 | 34.50 | A |
| ATOM | 80 | C | GLU | 12 | 33.659 | 6.660 | 2.928 | 1.00 | 19.74 | A |
| ATOM | 81 | O | GLU | 12 | 33.593 | 6.240 | 1.772 | 1.00 | 16.87 | A |
| ATOM | 82 | N | GLY | 13 | 34.727 | 7.295 | 3.393 | 1.00 | 17.80 | A |
| ATOM | 83 | CA | GLY | 13 | 35.863 | 7.520 | 2.525 | 1.00 | 17.26 | A |
| ATOM | 84 | C | GLY | 13 | 35.591 | 8.646 | 1.541 | 1.00 | 18.42 | A |
| ATOM | 85 | O | GLY | 13 | 36.241 | 8.743 | 0.495 | 1.00 | 17.78 | A |
| ATOM | 86 | N | SER | 14 | 34.622 | 9.496 | 1.868 | 1.00 | 16.87 | A |
| ATOM | 87 | CA | SER | 14 | 34.275 | 10.618 | 1.009 | 1.00 | 15.78 | A |
| ATOM | 88 | CB | SER | 14 | 32.762 | 10.892 | 1.057 | 1.00 | 16.79 | A |
| ATOM | 89 | OG | SER | 14 | 32.328 | 11.227 | 2.371 | 1.00 | 12.97 | A |
| ATOM | 90 | C | SER | 14 | 35.045 | 11.844 | 1.478 | 1.00 | 15.93 | A |
| ATOM | 91 | O | SER | 14 | 34.944 | 12.918 | 0.885 | 1.00 | 14.60 | A |
| ATOM | 92 | N | GLY | 15 | 35.829 | 11.664 | 2.537 | 1.00 | 17.21 | A |
| ATOM | 93 | CA | GLY | 15 | 36.612 | 12.757 | 3.082 | 1.00 | 19.59 | A |
| ATOM | 94 | C | GLY | 15 | 35.870 | 13.426 | 4.223 | 1.00 | 22.08 | A |
| ATOM | 95 | O | GLY | 15 | 36.493 | 13.973 | 5.147 | 1.00 | 23.73 | A |
| ATOM | 96 | N | LYS | 16 | 34.541 | 13.362 | 4.144 | 1.00 | 20.23 | A |
| ATOM | 97 | CA | LYS | 16 | 33.634 | 13.934 | 5.126 | 1.00 | 20.26 | A |
| ATOM | 98 | CB | LYS | 16 | 32.590 | 12.894 | 5.520 | 1.00 | 17.48 | A |
| ATOM | 99 | CG | LYS | 16 | 31.498 | 13.450 | 6.400 | 1.00 | 17.72 | A |
| ATOM | 100 | CD | LYS | 16 | 30.173 | 13.476 | 5.664 | 1.00 | 15.45 | A |
| ATOM | 101 | CE | LYS | 16 | 29.204 | 12.495 | 6.280 | 1.00 | 13.15 | A |
| ATOM | 102 | NZ | LYS | 16 | 29.955 | 11.579 | 7.159 | 1.00 | 15.36 | A |
| ATOM | 103 | C | LYS | 16 | 34.238 | 14.538 | 6.399 | 1.00 | 20.99 | A |
| ATOM | 104 | O | LYS | 16 | 34.189 | 15.753 | 6.586 | 1.00 | 20.66 | A |
| ATOM | 105 | N | THR | 17 | 34.803 | 13.702 | 7.268 | 1.00 | 20.95 | A |
| ATOM | 106 | CA | THR | 17 | 35.382 | 14.170 | 8.533 | 1.00 | 22.79 | A |
| ATOM | 107 | CB | THR | 17 | 35.897 | 12.971 | 9.372 | 1.00 | 24.86 | A |
| ATOM | 108 | OG1 | THR | 17 | 36.911 | 13.419 | 10.280 | 1.00 | 27.36 | A |
| ATOM | 109 | CG2 | THR | 17 | 36.460 | 11.874 | 8.473 | 1.00 | 26.75 | A |

Fig. 2A-1

| | | | | | | | | | |
|---|---|---|---|---|---|---|---|---|---|
| ATOM | 110 | C | THR | 17 | 36.501 | 15.222 | 8.421 | 1.00 21.60 | A |
| ATOM | 111 | O | THR | 17 | 36.711 | 16.018 | 9.345 | 1.00 19.85 | A |
| ATOM | 112 | N | THR | 18 | 37.215 | 15.221 | 7.300 | 1.00 19.88 | A |
| ATOM | 113 | CA | THR | 18 | 38.290 | 16.176 | 7.086 | 1.00 18.21 | A |
| ATOM | 114 | CB | THR | 18 | 39.331 | 15.614 | 6.112 | 1.00 19.26 | A |
| ATOM | 115 | OG1 | THR | 18 | 40.319 | 14.904 | 6.859 | 1.00 21.08 | A |
| ATOM | 116 | CG2 | THR | 18 | 40.022 | 16.731 | 5.334 | 1.00 20.76 | A |
| ATOM | 117 | C | THR | 18 | 37.712 | 17.464 | 6.530 | 1.00 17.35 | A |
| ATOM | 118 | O | THR | 18 | 38.115 | 18.555 | 6.912 | 1.00 15.07 | A |
| ATOM | 119 | N | VAL | 19 | 36.752 | 17.339 | 5.627 | 1.00 17.00 | A |
| ATOM | 120 | CA | VAL | 19 | 36.129 | 18.514 | 5.043 | 1.00 18.51 | A |
| ATOM | 121 | CB | VAL | 19 | 35.094 | 18.099 | 3.984 | 1.00 15.71 | A |
| ATOM | 122 | CG1 | VAL | 19 | 34.484 | 19.320 | 3.322 | 1.00 12.75 | A |
| ATOM | 123 | CG2 | VAL | 19 | 35.781 | 17.217 | 2.938 | 1.00 15.82 | A |
| ATOM | 124 | C | VAL | 19 | 35.482 | 19.388 | 6.123 | 1.00 21.42 | A |
| ATOM | 125 | O | VAL | 19 | 35.785 | 20.582 | 6.217 | 1.00 20.10 | A |
| ATOM | 126 | N | ILE | 20 | 34.612 | 18.794 | 6.941 | 1.00 22.67 | A |
| ATOM | 127 | CA | ILE | 20 | 33.932 | 19.514 | 8.028 | 1.00 25.13 | A |
| ATOM | 128 | CB | ILE | 20 | 33.043 | 18.567 | 8.895 | 1.00 24.85 | A |
| ATOM | 129 | CG2 | ILE | 20 | 32.197 | 19.380 | 9.871 | 1.00 25.65 | A |
| ATOM | 130 | CG1 | ILE | 20 | 32.099 | 17.760 | 8.005 | 1.00 29.35 | A |
| ATOM | 131 | CD1 | ILE | 20 | 31.503 | 16.546 | 8.691 | 1.00 31.38 | A |
| ATOM | 132 | C | ILE | 20 | 34.894 | 20.224 | 8.990 | 1.00 25.81 | A |
| ATOM | 133 | O | ILE | 20 | 34.646 | 21.364 | 9.400 | 1.00 25.88 | A |
| ATOM | 134 | N | ASN | 21 | 35.980 | 19.548 | 9.353 | 1.00 26.96 | A |
| ATOM | 135 | CA | ASN | 21 | 36.959 | 20.105 | 10.274 | 1.00 28.55 | A |
| ATOM | 136 | CB | ASN | 21 | 37.940 | 19.028 | 10.721 | 1.00 33.92 | A |
| ATOM | 137 | CG | ASN | 21 | 38.240 | 19.091 | 12.207 | 1.00 38.77 | A |
| ATOM | 138 | OD1 | ASN | 21 | 39.099 | 18.360 | 12.700 | 1.00 42.41 | A |
| ATOM | 139 | ND2 | ASN | 21 | 37.531 | 19.960 | 12.932 | 1.00 39.00 | A |
| ATOM | 140 | C | ASN | 21 | 37.733 | 21.247 | 9.657 | 1.00 27.37 | A |
| ATOM | 141 | O | ASN | 21 | 38.029 | 22.225 | 10.341 | 1.00 27.70 | A |
| ATOM | 142 | N | GLU | 22 | 38.067 | 21.110 | 8.372 | 1.00 26.84 | A |
| ATOM | 143 | CA | GLU | 22 | 38.811 | 22.137 | 7.645 | 1.00 27.50 | A |
| ATOM | 144 | CB | GLU | 22 | 39.507 | 21.538 | 6.412 | 1.00 29.00 | A |
| ATOM | 145 | CG | GLU | 22 | 40.337 | 20.274 | 6.694 | 1.00 37.51 | A |
| ATOM | 146 | CD | GLU | 22 | 41.849 | 20.528 | 6.802 | 1.00 42.36 | A |
| ATOM | 147 | OE1 | GLU | 22 | 42.255 | 21.710 | 6.873 | 1.00 46.23 | A |
| ATOM | 148 | OE2 | GLU | 22 | 42.635 | 19.546 | 6.820 | 1.00 42.33 | A |
| ATOM | 149 | C | GLU | 22 | 37.900 | 23.296 | 7.218 | 1.00 24.64 | A |
| ATOM | 150 | O | GLU | 22 | 38.312 | 24.449 | 7.230 | 1.00 26.17 | A |
| ATOM | 151 | N | VAL | 23 | 36.672 | 22.992 | 6.823 | 1.00 21.05 | A |
| ATOM | 152 | CA | VAL | 23 | 35.745 | 24.042 | 6.436 | 1.00 19.39 | A |
| ATOM | 153 | CB | VAL | 23 | 34.451 | 23.455 | 5.803 | 1.00 19.91 | A |
| ATOM | 154 | CG1 | VAL | 23 | 33.282 | 24.425 | 5.968 | 1.00 16.41 | A |
| ATOM | 155 | CG2 | VAL | 23 | 34.679 | 23.165 | 4.323 | 1.00 16.29 | A |
| ATOM | 156 | C | VAL | 23 | 35.393 | 24.832 | 7.710 | 1.00 19.97 | A |
| ATOM | 157 | O | VAL | 23 | 35.249 | 26.055 | 7.678 | 1.00 20.23 | A |
| ATOM | 158 | N | TYR | 24 | 35.272 | 24.118 | 8.831 | 1.00 19.00 | A |
| ATOM | 159 | CA | TYR | 24 | 34.940 | 24.717 | 10.120 | 1.00 15.00 | A |
| ATOM | 160 | CB | TYR | 24 | 34.794 | 23.630 | 11.191 | 1.00 12.78 | A |
| ATOM | 161 | CG | TYR | 24 | 34.834 | 24.160 | 12.614 | 1.00 9.34 | A |
| ATOM | 162 | CD1 | TYR | 24 | 33.706 | 24.746 | 13.200 | 1.00 11.54 | A |
| ATOM | 163 | CE1 | TYR | 24 | 33.741 | 25.241 | 14.503 | 1.00 6.15 | A |
| ATOM | 164 | CD2 | TYR | 24 | 35.992 | 24.078 | 13.372 | 1.00 7.77 | A |
| ATOM | 165 | CE2 | TYR | 24 | 36.035 | 24.570 | 14.673 | 1.00 9.74 | A |
| ATOM | 166 | CZ | TYR | 24 | 34.907 | 25.142 | 15.226 | 1.00 6.90 | A |

Fig. 2A-2

```
ATOM  167  OH   TYR  24   34.973  25.614  16.501  1.00  13.33      A
ATOM  168  C    TYR  24   36.015  25.699  10.556  1.00  14.44      A
ATOM  169  O    TYR  24   35.757  26.886  10.719  1.00  13.95      A
ATOM  170  N    HIS  25   37.229  25.200  10.734  1.00  15.76      A
ATOM  171  CA   HIS  25   38.335  26.039  11.166  1.00  20.04      A
ATOM  172  CB   HIS  25   39.624  25.241  11.141  1.00  21.45      A
ATOM  173  CG   HIS  25   39.833  24.428  12.374  1.00  25.49      A
ATOM  174  CD2  HIS  25   40.070  24.810  13.656  1.00  27.02      A
ATOM  175  ND1  HIS  25   39.738  23.057  12.396  1.00  27.27      A
ATOM  176  CE1  HIS  25   39.903  22.621  13.625  1.00  28.81      A
ATOM  177  NE2  HIS  25   40.106  23.664  14.417  1.00  29.55      A
ATOM  178  C    HIS  25   38.505  27.303  10.349  1.00  21.20      A
ATOM  179  O    HIS  25   39.249  28.200  10.731  1.00  22.19      A
ATOM  180  N    ARG  26   37.806  27.371   9.225  1.00  23.69      A
ATOM  181  CA   ARG  26   37.882  28.519   8.334  1.00  25.23      A
ATOM  182  CB   ARG  26   37.869  28.041   6.868  1.00  26.42      A
ATOM  183  CG   ARG  26   38.386  29.063   5.852  1.00  30.95      A
ATOM  184  CD   ARG  26   39.377  28.429   4.864  1.00  32.09      A
ATOM  185  NE   ARG  26   39.060  28.770   3.475  1.00  33.53      A
ATOM  186  CZ   ARG  26   39.297  27.974   2.431  1.00  32.41      A
ATOM  187  NH1  ARG  26   38.967  28.382   1.215  1.00  30.59      A
ATOM  188  NH2  ARG  26   39.871  26.783   2.600  1.00  27.39      A
ATOM  189  C    ARG  26   36.719  29.474   8.594  1.00  24.86      A
ATOM  190  O    ARG  26   36.912  30.694   8.608  1.00  26.52      A
ATOM  191  N    LEU  27   35.525  28.911   8.811  1.00  23.07      A
ATOM  192  CA   LEU  27   34.307  29.682   9.064  1.00  20.96      A
ATOM  193  CB   LEU  27   33.057  28.792   8.988  1.00  19.14      A
ATOM  194  CG   LEU  27   32.699  28.002   7.722  1.00  19.04      A
ATOM  195  CD1  LEU  27   31.595  27.001   8.060  1.00  17.26      A
ATOM  196  CD2  LEU  27   32.235  28.934   6.609  1.00  15.23      A
ATOM  197  C    LEU  27   34.305  30.368  10.415  1.00  20.53      A
ATOM  198  O    LEU  27   33.696  31.415  10.572  1.00  19.75      A
ATOM  199  N    VAL  28   34.981  29.785  11.399  1.00  21.80      A
ATOM  200  CA   VAL  28   35.000  30.379  12.735  1.00  23.18      A
ATOM  201  CB   VAL  28   35.746  29.484  13.755  1.00  20.76      A
ATOM  202  CG1  VAL  28   35.193  28.091  13.714  1.00  23.55      A
ATOM  203  CG2  VAL  28   37.237  29.462  13.451  1.00  20.31      A
ATOM  204  C    VAL  28   35.650  31.756  12.742  1.00  22.92      A
ATOM  205  O    VAL  28   35.393  32.572  13.620  1.00  23.32      A
ATOM  206  N    LYS  29   36.493  32.005  11.754  1.00  22.70      A
ATOM  207  CA   LYS  29   37.193  33.270  11.663  1.00  24.04      A
ATOM  208  CB   LYS  29   37.981  33.322  10.357  1.00  22.62      A
ATOM  209  CG   LYS  29   38.945  32.159  10.230  1.00  21.41      A
ATOM  210  CD   LYS  29   40.161  32.534   9.454  1.00  20.91      A
ATOM  211  CE   LYS  29   40.277  31.697   8.203  1.00  17.62      A
ATOM  212  NZ   LYS  29   41.704  31.520   7.813  1.00  19.23      A
ATOM  213  C    LYS  29   36.244  34.450  11.770  1.00  25.21      A
ATOM  214  O    LYS  29   36.507  35.407  12.510  1.00  24.91      A
ATOM  215  N    ASP  30   35.129  34.375  11.053  1.00  26.90      A
ATOM  216  CA   ASP  30   34.164  35.461  11.091  1.00  28.76      A
ATOM  217  CB   ASP  30   34.374  36.396   9.889  1.00  31.50      A
ATOM  218  CG   ASP  30   34.546  35.638   8.586  1.00  34.03      A
ATOM  219  OD1  ASP  30   35.576  35.841   7.890  1.00  32.19      A
ATOM  220  OD2  ASP  30   33.637  34.836   8.264  1.00  34.43      A
ATOM  221  C    ASP  30   32.723  34.976  11.149  1.00  27.12      A
ATOM  222  O    ASP  30   31.828  35.625  10.623  1.00  28.57      A
ATOM  223  N    TYR  31   32.512  33.827  11.788  1.00  24.87      A
```

Fig. 2A-3

| ATOM | 224 | CA  | TYR | 31 | 31.172 | 33.259 | 11.966 | 1.00 | 22.02 | A |
| ATOM | 225 | CB  | TYR | 31 | 30.843 | 32.192 | 10.917 | 1.00 | 20.30 | A |
| ATOM | 226 | CG  | TYR | 31 | 30.526 | 32.735 |  9.555 | 1.00 | 16.72 | A |
| ATOM | 227 | CD1 | TYR | 31 | 31.502 | 32.773 |  8.571 | 1.00 | 18.10 | A |
| ATOM | 228 | CE1 | TYR | 31 | 31.236 | 33.262 |  7.305 | 1.00 | 17.46 | A |
| ATOM | 229 | CD2 | TYR | 31 | 29.259 | 33.202 |  9.245 | 1.00 | 15.65 | A |
| ATOM | 230 | CE2 | TYR | 31 | 28.974 | 33.700 |  7.973 | 1.00 | 17.00 | A |
| ATOM | 231 | CZ  | TYR | 31 | 29.974 | 33.724 |  7.006 | 1.00 | 17.27 | A |
| ATOM | 232 | OH  | TYR | 31 | 29.735 | 34.202 |  5.736 | 1.00 | 17.42 | A |
| ATOM | 233 | C   | TYR | 31 | 31.086 | 32.598 | 13.331 | 1.00 | 20.05 | A |
| ATOM | 234 | O   | TYR | 31 | 32.075 | 32.092 | 13.850 | 1.00 | 20.06 | A |
| ATOM | 235 | N   | ASP | 32 | 29.892 | 32.622 | 13.908 | 1.00 | 19.70 | A |
| ATOM | 236 | CA  | ASP | 32 | 29.636 | 31.990 | 15.190 | 1.00 | 20.95 | A |
| ATOM | 237 | CB  | ASP | 32 | 28.510 | 32.735 | 15.906 | 1.00 | 22.89 | A |
| ATOM | 238 | CG  | ASP | 32 | 28.440 | 32.413 | 17.373 | 1.00 | 24.21 | A |
| ATOM | 239 | OD1 | ASP | 32 | 27.454 | 32.838 | 18.020 | 1.00 | 25.96 | A |
| ATOM | 240 | OD2 | ASP | 32 | 29.363 | 31.739 | 17.872 | 1.00 | 24.55 | A |
| ATOM | 241 | C   | ASP | 32 | 29.181 | 30.597 | 14.751 | 1.00 | 20.33 | A |
| ATOM | 242 | O   | ASP | 32 | 27.988 | 30.300 | 14.671 | 1.00 | 19.92 | A |
| ATOM | 243 | N   | VAL | 33 | 30.148 | 29.753 | 14.424 | 1.00 | 18.61 | A |
| ATOM | 244 | CA  | VAL | 33 | 29.838 | 28.425 | 13.935 | 1.00 | 16.48 | A |
| ATOM | 245 | CB  | VAL | 33 | 30.649 | 28.127 | 12.640 | 1.00 | 15.36 | A |
| ATOM | 246 | CG1 | VAL | 33 | 32.097 | 27.831 | 12.972 | 1.00 | 13.65 | A |
| ATOM | 247 | CG2 | VAL | 33 | 30.022 | 26.967 | 11.892 | 1.00 | 16.60 | A |
| ATOM | 248 | C   | VAL | 33 | 30.077 | 27.337 | 14.968 | 1.00 | 16.76 | A |
| ATOM | 249 | O   | VAL | 33 | 30.983 | 27.426 | 15.800 | 1.00 | 17.16 | A |
| ATOM | 250 | N   | ILE | 34 | 29.241 | 26.306 | 14.910 | 1.00 | 15.58 | A |
| ATOM | 251 | CA  | ILE | 34 | 29.349 | 25.184 | 15.827 | 1.00 | 13.80 | A |
| ATOM | 252 | CB  | ILE | 34 | 28.030 | 25.020 | 16.669 | 1.00 | 12.79 | A |
| ATOM | 253 | CG2 | ILE | 34 | 28.049 | 23.729 | 17.474 | 1.00 | 11.57 | A |
| ATOM | 254 | CG1 | ILE | 34 | 27.919 | 26.145 | 17.680 | 1.00 | 11.47 | A |
| ATOM | 255 | CD1 | ILE | 34 | 29.120 | 26.219 | 18.560 | 1.00 | 10.18 | A |
| ATOM | 256 | C   | ILE | 34 | 29.608 | 23.929 | 14.992 | 1.00 | 13.84 | A |
| ATOM | 257 | O   | ILE | 34 | 29.024 | 23.758 | 13.921 | 1.00 | 12.61 | A |
| ATOM | 258 | N   | MET | 35 | 30.506 | 23.080 | 15.496 | 1.00 | 15.72 | A |
| ATOM | 259 | CA  | MET | 35 | 30.888 | 21.815 | 14.873 | 1.00 | 16.23 | A |
| ATOM | 260 | CB  | MET | 35 | 32.418 | 21.717 | 14.811 | 1.00 | 13.95 | A |
| ATOM | 261 | CG  | MET | 35 | 32.988 | 21.367 | 13.441 | 1.00 | 15.83 | A |
| ATOM | 262 | SD  | MET | 35 | 34.670 | 20.692 | 13.593 | 1.00 | 12.02 | A |
| ATOM | 263 | CE  | MET | 35 | 34.279 | 18.976 | 13.591 | 1.00 | 15.12 | A |
| ATOM | 264 | C   | MET | 35 | 30.342 | 20.672 | 15.746 | 1.00 | 16.39 | A |
| ATOM | 265 | O   | MET | 35 | 30.740 | 20.533 | 16.903 | 1.00 | 14.42 | A |
| ATOM | 266 | N   | THR | 36 | 29.451 | 19.849 | 15.189 | 1.00 | 17.35 | A |
| ATOM | 267 | CA  | THR | 36 | 28.859 | 18.747 | 15.952 | 1.00 | 18.63 | A |
| ATOM | 268 | CB  | THR | 36 | 27.598 | 19.244 | 16.748 | 1.00 | 20.00 | A |
| ATOM | 269 | OG1 | THR | 36 | 27.292 | 18.337 | 17.817 | 1.00 | 18.36 | A |
| ATOM | 270 | CG2 | THR | 36 | 26.395 | 19.337 | 15.833 | 1.00 | 18.79 | A |
| ATOM | 271 | C   | THR | 36 | 28.453 | 17.518 | 15.117 | 1.00 | 18.55 | A |
| ATOM | 272 | O   | THR | 36 | 28.268 | 17.592 | 13.908 | 1.00 | 16.66 | A |
| ATOM | 273 | N   | ARG | 37 | 28.336 | 16.382 | 15.801 | 1.00 | 20.67 | A |
| ATOM | 274 | CA  | ARG | 37 | 27.913 | 15.108 | 15.224 | 1.00 | 20.65 | A |
| ATOM | 275 | CB  | ARG | 37 | 29.115 | 14.269 | 14.796 | 1.00 | 21.76 | A |
| ATOM | 276 | CG  | ARG | 37 | 30.170 | 14.129 | 15.855 | 1.00 | 27.37 | A |
| ATOM | 277 | CD  | ARG | 37 | 31.559 | 14.070 | 15.239 | 1.00 | 35.37 | A |
| ATOM | 278 | NE  | ARG | 37 | 32.614 | 14.108 | 16.256 | 1.00 | 41.53 | A |
| ATOM | 279 | CZ  | ARG | 37 | 33.904 | 14.297 | 15.998 | 1.00 | 42.90 | A |
| ATOM | 280 | NH1 | ARG | 37 | 34.780 | 14.315 | 16.995 | 1.00 | 44.86 | A |

Fig. 2A-4

```
ATOM    281  NH2  ARG    37      34.321  14.468  14.745  1.00  45.05      A
ATOM    282  C    ARG    37      27.186  14.428  16.378  1.00  19.50      A
ATOM    283  O    ARG    37      27.746  14.279  17.466  1.00  16.50      A
ATOM    284  N    GLU    38      25.937  14.038  16.147  1.00  20.18      A
ATOM    285  CA   GLU    38      25.124  13.409  17.182  1.00  22.89      A
ATOM    286  CB   GLU    38      23.692  13.243  16.673  1.00  21.85      A
ATOM    287  CG   GLU    38      23.504  12.081  15.751  1.00  21.08      A
ATOM    288  CD   GLU    38      22.407  12.317  14.761  1.00  22.13      A
ATOM    289  OE1  GLU    38      22.092  11.387  13.993  1.00  24.03      A
ATOM    290  OE2  GLU    38      21.855  13.433  14.745  1.00  22.48      A
ATOM    291  C    GLU    38      25.655  12.066  17.662  1.00  24.77      A
ATOM    292  O    GLU    38      26.215  11.298  16.878  1.00  24.13      A
ATOM    293  N    PRO    39      25.485  11.760  18.965  1.00  26.42      A
ATOM    294  CD   PRO    39      25.937  10.461  19.492  1.00  26.55      A
ATOM    295  CA   PRO    39      24.824  12.562  20.005  1.00  27.84      A
ATOM    296  CB   PRO    39      24.425  11.533  21.055  1.00  26.59      A
ATOM    297  CG   PRO    39      25.457  10.469  20.929  1.00  27.33      A
ATOM    298  C    PRO    39      25.710  13.666  20.595  1.00  28.60      A
ATOM    299  O    PRO    39      25.380  14.268  21.614  1.00  28.12      A
ATOM    300  N    GLY    40      26.835  13.907  19.936  1.00  29.22      A
ATOM    301  CA   GLY    40      27.779  14.929  20.350  1.00  29.42      A
ATOM    302  C    GLY    40      27.642  15.638  21.687  1.00  29.13      A
ATOM    303  O    GLY    40      27.414  16.845  21.729  1.00  27.84      A
ATOM    304  N    GLY    41      27.766  14.904  22.788  1.00  29.09      A
ATOM    305  CA   GLY    41      27.697  15.552  24.089  1.00  29.55      A
ATOM    306  C    GLY    41      26.486  15.357  24.981  1.00  29.02      A
ATOM    307  O    GLY    41      26.641  15.102  26.175  1.00  29.02      A
ATOM    308  N    VAL   42      25.290  15.482  24.419  1.00  27.71      A
ATOM    309  CA   VAL   42      24.065  15.329  25.187  1.00  28.20      A
ATOM    310  CB   VAL   42      22.837  15.443  24.254  1.00  29.48      A
ATOM    311  CG1  VAL   42      21.556  15.453  25.059  1.00  30.80      A
ATOM    312  CG2  VAL   42      22.943  16.720  23.439  1.00  28.44      A
ATOM    313  C    VAL   42      24.058  13.983  25.918  1.00  28.18      A
ATOM    314  O    VAL   42      23.782  12.944  25.331  1.00  28.00      A
ATOM    315  N    PRO    43      24.350  14.000  27.231  1.00  28.18      A
ATOM    316  CD   PRO    43      24.629  15.200  28.040  1.00  26.98      A
ATOM    317  CA   PRO    43      24.389  12.783  28.055  1.00  27.66      A
ATOM    318  CB   PRO    43      24.400  13.311  29.493  1.00  27.31      A
ATOM    319  CG   PRO    43      24.160  14.789  29.385  1.00  28.44      A
ATOM    320  C    PRO    43      23.252  11.791  27.826  1.00  27.06      A
ATOM    321  O    PRO    43      23.488  10.592  27.704  1.00  26.54      A
ATOM    322  N    THR    44      22.022  12.291  27.794  1.00  27.46      A
ATOM    323  CA   THR    44      20.855  11.453  27.588  1.00  27.28      A
ATOM    324  CB   THR    44      19.565  12.259  27.832  1.00  27.35      A
ATOM    325  OG1  THR    44      18.434  11.499  27.408  1.00  30.85      A
ATOM    326  CG2  THR    44      19.615  13.561  27.087  1.00  27.97      A
ATOM    327  C    THR    44      20.870  10.892  26.167  1.00  26.45      A
ATOM    328  O    THR    44      20.434   9.765  25.927  1.00  24.51      A
ATOM    329  N    GLY    45      21.369  11.666  25.212  1.00  27.55      A
ATOM    330  CA   GLY    45      21.433  11.167  23.855  1.00  26.03      A
ATOM    331  C    GLY    45      22.441  10.030  23.815  1.00  25.92      A
ATOM    332  O    GLY    45      22.273   9.037  23.107  1.00  25.66      A
ATOM    333  N    GLU    46      23.502  10.171  24.600  1.00  26.08      A
ATOM    334  CA   GLU    46      24.539   9.156  24.662  1.00  27.70      A
ATOM    335  CB   GLU    46      25.752   9.680  25.420  1.00  30.35      A
ATOM    336  CG   GLU    46      26.066  11.156  25.190  1.00  35.84      A
ATOM    337  CD   GLU    46      27.294  11.372  24.316  1.00  38.67      A
```

Fig. 2A-5

| | | | | | | | | | |
|---|---|---|---|---|---|---|---|---|---|
| ATOM | 338 | OE1 | GLU | 46 | 27.188 | 11.165 | 23.090 | 1.00 40.57 | A |
| ATOM | 339 | OE2 | GLU | 46 | 28.358 | 11.749 | 24.855 | 1.00 39.83 | A |
| ATOM | 340 | C | GLU | 46 | 24.038 | 7.882 | 25.336 | 1.00 28.82 | A |
| ATOM | 341 | O | GLU | 46 | 24.499 | 6.783 | 25.016 | 1.00 29.81 | A |
| ATOM | 342 | N | GLU | 47 | 23.079 | 8.026 | 26.251 | 1.00 29.16 | A |
| ATOM | 343 | CA | GLU | 47 | 22.507 | 6.899 | 26.981 | 1.00 28.33 | A |
| ATOM | 344 | CB | GLU | 47 | 21.505 | 7.370 | 28.032 | 1.00 31.03 | A |
| ATOM | 345 | CG | GLU | 47 | 21.919 | 8.575 | 28.821 | 1.00 35.69 | A |
| ATOM | 346 | CD | GLU | 47 | 22.509 | 8.193 | 30.155 | 1.00 39.30 | A |
| ATOM | 347 | OE1 | GLU | 47 | 21.965 | 7.267 | 30.806 | 1.00 38.20 | A |
| ATOM | 348 | OE2 | GLU | 47 | 23.519 | 8.821 | 30.544 | 1.00 41.18 | A |
| ATOM | 349 | C | GLU | 47 | 21.772 | 5.982 | 26.041 | 1.00 28.66 | A |
| ATOM | 350 | O | GLU | 47 | 21.953 | 4.772 | 26.070 | 1.00 28.63 | A |
| ATOM | 351 | N | ILE | 48 | 20.902 | 6.570 | 25.230 | 1.00 28.67 | A |
| ATOM | 352 | CA | ILE | 48 | 20.132 | 5.801 | 24.273 | 1.00 29.14 | A |
| ATOM | 353 | CB | ILE | 48 | 19.149 | 6.705 | 23.496 | 1.00 27.61 | A |
| ATOM | 354 | CG2 | ILE | 48 | 18.185 | 5.857 | 22.700 | 1.00 26.69 | A |
| ATOM | 355 | CG1 | ILE | 48 | 18.388 | 7.613 | 24.470 | 1.00 26.60 | A |
| ATOM | 356 | CD1 | ILE | 48 | 17.490 | 8.628 | 23.793 | 1.00 25.71 | A |
| ATOM | 357 | C | ILE | 48 | 21.115 | 5.162 | 23.304 | 1.00 29.77 | A |
| ATOM | 358 | O | ILE | 48 | 20.959 | 4.006 | 22.912 | 1.00 29.06 | A |
| ATOM | 359 | N | ARG | 49 | 22.135 | 5.927 | 22.934 | 1.00 32.23 | A |
| ATOM | 360 | CA | ARG | 49 | 23.160 | 5.461 | 22.014 | 1.00 36.58 | A |
| ATOM | 361 | CB | ARG | 49 | 24.187 | 6.577 | 21.777 | 1.00 38.28 | A |
| ATOM | 362 | CG | ARG | 49 | 24.753 | 6.621 | 20.375 | 1.00 40.84 | A |
| ATOM | 363 | CD | ARG | 49 | 23.682 | 7.033 | 19.373 | 1.00 44.51 | A |
| ATOM | 364 | NE | ARG | 49 | 24.221 | 7.784 | 18.240 | 1.00 47.33 | A |
| ATOM | 365 | CZ | ARG | 49 | 25.323 | 7.452 | 17.570 | 1.00 47.80 | A |
| ATOM | 366 | NH1 | ARG | 49 | 26.018 | 6.372 | 17.914 | 1.00 47.10 | A |
| ATOM | 367 | NH2 | ARG | 49 | 25.725 | 8.194 | 16.548 | 1.00 46.92 | A |
| ATOM | 368 | C | ARG | 49 | 23.862 | 4.227 | 22.585 | 1.00 38.44 | A |
| ATOM | 369 | O | ARG | 49 | 24.019 | 3.208 | 21.909 | 1.00 40.42 | A |
| ATOM | 370 | N | LYS | 50 | 24.278 | 4.328 | 23.841 | 1.00 38.03 | A |
| ATOM | 371 | CA | LYS | 50 | 24.975 | 3.248 | 24.525 | 1.00 36.83 | A |
| ATOM | 372 | CB | LYS | 50 | 25.279 | 3.684 | 25.952 | 1.00 37.35 | A |
| ATOM | 373 | CG | LYS | 50 | 25.964 | 2.626 | 26.796 | 1.00 40.72 | A |
| ATOM | 374 | CD | LYS | 50 | 27.429 | 2.960 | 27.030 | 1.00 41.37 | A |
| ATOM | 375 | CE | LYS | 50 | 27.599 | 4.392 | 27.511 | 1.00 44.39 | A |
| ATOM | 376 | NZ | LYS | 50 | 29.032 | 4.798 | 27.561 | 1.00 47.85 | A |
| ATOM | 377 | C | LYS | 50 | 24.213 | 1.919 | 24.551 | 1.00 36.69 | A |
| ATOM | 378 | O | LYS | 50 | 24.817 | 0.854 | 24.671 | 1.00 35.81 | A |
| ATOM | 379 | N | ILE | 51 | 22.890 | 1.982 | 24.439 | 1.00 35.96 | A |
| ATOM | 380 | CA | ILE | 51 | 22.062 | 0.782 | 24.474 | 1.00 35.56 | A |
| ATOM | 381 | CB | ILE | 51 | 20.577 | 1.141 | 24.612 | 1.00 34.05 | A |
| ATOM | 382 | CG2 | ILE | 51 | 19.714 | -0.058 | 24.261 | 1.00 31.47 | A |
| ATOM | 383 | CG1 | ILE | 51 | 20.306 | 1.607 | 26.043 | 1.00 33.91 | A |
| ATOM | 384 | CD1 | ILE | 51 | 18.863 | 1.928 | 26.333 | 1.00 36.27 | A |
| ATOM | 385 | C | ILE | 51 | 22.235 | -0.110 | 23.258 | 1.00 37.00 | A |
| ATOM | 386 | O | ILE | 51 | 22.362 | -1.324 | 23.388 | 1.00 36.83 | A |
| ATOM | 387 | N | VAL | 52 | 22.237 | 0.489 | 22.076 | 1.00 38.92 | A |
| ATOM | 388 | CA | VAL | 52 | 22.391 | -0.282 | 20.858 | 1.00 41.12 | A |
| ATOM | 389 | CB | VAL | 52 | 22.120 | 0.601 | 19.604 | 1.00 40.76 | A |
| ATOM | 390 | CG1 | VAL | 52 | 23.142 | 1.688 | 19.508 | 1.00 42.48 | A |
| ATOM | 391 | CG2 | VAL | 52 | 22.133 | -0.244 | 18.341 | 1.00 41.09 | A |
| ATOM | 392 | C | VAL | 52 | 23.798 | -0.873 | 20.805 | 1.00 42.70 | A |
| ATOM | 393 | O | VAL | 52 | 23.992 | -2.003 | 20.348 | 1.00 43.15 | A |
| ATOM | 394 | N | LEU | 53 | 24.766 | -0.120 | 21.319 | 1.00 44.83 | A |

Fig. 2A-6

| | | | | | | | | | |
|---|---|---|---|---|---|---|---|---|---|
| ATOM | 395 | CA | LEU | 53 | 26.171 | -0.528 | 21.313 | 1.00 47.39 | A |
| ATOM | 396 | CB | LEU | 53 | 27.054 | 0.640 | 21.762 | 1.00 45.93 | A |
| ATOM | 397 | CG | LEU | 53 | 27.020 | 1.876 | 20.855 | 1.00 44.42 | A |
| ATOM | 398 | CD1 | LEU | 53 | 27.969 | 2.933 | 21.381 | 1.00 43.88 | A |
| ATOM | 399 | CD2 | LEU | 53 | 27.393 | 1.480 | 19.436 | 1.00 44.16 | A |
| ATOM | 400 | C | LEU | 53 | 26.536 | -1.773 | 22.115 | 1.00 49.72 | A |
| ATOM | 401 | O | LEU | 53 | 27.392 | -2.553 | 21.689 | 1.00 50.88 | A |
| ATOM | 402 | N | GLU | 54 | 25.908 | -1.966 | 23.272 | 1.00 52.50 | A |
| ATOM | 403 | CA | GLU | 54 | 26.215 | -3.135 | 24.099 | 1.00 55.23 | A |
| ATOM | 404 | CB | GLU | 54 | 26.523 | -2.696 | 25.546 | 1.00 57.10 | A |
| ATOM | 405 | CG | GLU | 54 | 27.503 | -1.501 | 25.668 | 1.00 60.18 | A |
| ATOM | 406 | CD | GLU | 54 | 28.865 | -1.856 | 26.291 | 1.00 61.65 | A |
| ATOM | 407 | OE1 | GLU | 54 | 28.918 | -2.722 | 27.194 | 1.00 62.65 | A |
| ATOM | 408 | OE2 | GLU | 54 | 29.888 | -1.256 | 25.878 | 1.00 60.64 | A |
| ATOM | 409 | C | GLU | 54 | 25.129 | -4.219 | 24.075 | 1.00 54.90 | A |
| ATOM | 410 | O | GLU | 54 | 24.898 | -4.905 | 25.068 | 1.00 55.38 | A |
| ATOM | 411 | N | GLY | 55 | 24.465 | -4.359 | 22.928 | 1.00 55.29 | A |
| ATOM | 412 | CA | GLY | 55 | 23.440 | -5.380 | 22.727 | 1.00 56.52 | A |
| ATOM | 413 | C | GLY | 55 | 23.817 | -5.965 | 21.372 | 1.00 57.57 | A |
| ATOM | 414 | O | GLY | 55 | 23.789 | -5.235 | 20.378 | 1.00 58.88 | A |
| ATOM | 415 | N | ASN | 56 | 24.157 | -7.257 | 21.308 | 1.00 57.68 | A |
| ATOM | 416 | CA | ASN | 56 | 24.625 | -7.847 | 20.038 | 1.00 57.61 | A |
| ATOM | 417 | CB | ASN | 56 | 25.190 | -9.264 | 20.248 | 1.00 58.29 | A |
| ATOM | 418 | CG | ASN | 56 | 24.455 | -10.052 | 21.301 | 1.00 59.27 | A |
| ATOM | 419 | OD1 | ASN | 56 | 24.993 | -11.018 | 21.848 | 1.00 61.14 | A |
| ATOM | 420 | ND2 | ASN | 56 | 23.221 | -9.661 | 21.588 | 1.00 60.14 | A |
| ATOM | 421 | C | ASN | 56 | 23.739 | -7.856 | 18.781 | 1.00 56.28 | A |
| ATOM | 422 | O | ASN | 56 | 23.919 | -7.016 | 17.898 | 1.00 57.68 | A |
| ATOM | 423 | N | ASP | 57 | 22.826 | -8.813 | 18.657 | 1.00 53.31 | A |
| ATOM | 424 | CA | ASP | 57 | 21.994 | -8.847 | 17.457 | 1.00 49.64 | A |
| ATOM | 425 | CB | ASP | 57 | 21.827 | -10.282 | 16.941 | 1.00 55.11 | A |
| ATOM | 426 | CG | ASP | 57 | 21.994 | -11.325 | 18.036 | 1.00 60.39 | A |
| ATOM | 427 | OD1 | ASP | 57 | 21.377 | -11.162 | 19.115 | 1.00 62.29 | A |
| ATOM | 428 | OD2 | ASP | 57 | 22.745 | -12.310 | 17.813 | 1.00 62.30 | A |
| ATOM | 429 | C | ASP | 57 | 20.628 | -8.237 | 17.715 | 1.00 44.53 | A |
| ATOM | 430 | O | ASP | 57 | 19.614 | -8.921 | 17.648 | 1.00 43.89 | A |
| ATOM | 431 | N | MET | 58 | 20.614 | -6.939 | 17.999 | 1.00 37.61 | A |
| ATOM | 432 | CA | MET | 58 | 19.386 | -6.213 | 18.266 | 1.00 30.04 | A |
| ATOM | 433 | CB | MET | 58 | 19.721 | -4.856 | 18.873 | 1.00 27.21 | A |
| ATOM | 434 | CG | MET | 58 | 18.538 | -4.129 | 19.490 | 1.00 21.68 | A |
| ATOM | 435 | SD | MET | 58 | 19.065 | -2.559 | 20.141 | 1.00 13.77 | A |
| ATOM | 436 | CE | MET | 58 | 20.309 | -3.111 | 21.333 | 1.00 15.00 | A |
| ATOM | 437 | C | MET | 58 | 18.589 | -6.008 | 16.987 | 1.00 28.14 | A |
| ATOM | 438 | O | MET | 58 | 19.157 | -5.727 | 15.934 | 1.00 28.52 | A |
| ATOM | 439 | N | ASP | 59 | 17.273 | -6.157 | 17.085 | 1.00 23.91 | A |
| ATOM | 440 | CA | ASP | 59 | 16.418 | -5.960 | 15.928 | 1.00 22.60 | A |
| ATOM | 441 | CB | ASP | 59 | 14.951 | -5.899 | 16.370 | 1.00 23.15 | A |
| ATOM | 442 | CG | ASP | 59 | 14.004 | -5.615 | 15.220 | 1.00 24.20 | A |
| ATOM | 443 | OD1 | ASP | 59 | 13.480 | -6.583 | 14.629 | 1.00 24.88 | A |
| ATOM | 444 | OD2 | ASP | 59 | 13.780 | -4.428 | 14.905 | 1.00 25.85 | A |
| ATOM | 445 | C | ASP | 59 | 16.843 | -4.637 | 15.293 | 1.00 21.41 | A |
| ATOM | 446 | O | ASP | 59 | 17.139 | -3.679 | 16.004 | 1.00 19.52 | A |
| ATOM | 447 | N | ILE | 60 | 16.886 | -4.583 | 13.963 | 1.00 22.14 | A |
| ATOM | 448 | CA | ILE | 60 | 17.296 | -3.365 | 13.279 | 1.00 21.20 | A |
| ATOM | 449 | CB | ILE | 60 | 17.653 | -3.638 | 11.808 | 1.00 18.94 | A |
| ATOM | 450 | CG2 | ILE | 60 | 18.920 | -4.455 | 11.733 | 1.00 18.95 | A |
| ATOM | 451 | CG1 | ILE | 60 | 16.505 | -4.347 | 11.112 | 1.00 17.72 | A |

Fig. 2A-7

| | | | | | | | | | |
|---|---|---|---|---|---|---|---|---|---|
| ATOM | 452 | CD1 | ILE | 60 | 16.510 | -4.136 | 9.614 | 1.00 17.04 | A |
| ATOM | 453 | C | ILE | 60 | 16.277 | -2.226 | 13.354 | 1.00 21.86 | A |
| ATOM | 454 | O | ILE | 60 | 16.653 | -1.054 | 13.317 | 1.00 22.47 | A |
| ATOM | 455 | N | ARG | 61 | 14.993 | -2.554 | 13.453 | 1.00 19.83 | A |
| ATOM | 456 | CA | ARG | 61 | 13.975 | -1.519 | 13.566 | 1.00 19.98 | A |
| ATOM | 457 | CB | ARG | 61 | 12.596 | -2.126 | 13.394 | 1.00 20.07 | A |
| ATOM | 458 | CG | ARG | 61 | 12.292 | -2.512 | 11.979 | 1.00 21.25 | A |
| ATOM | 459 | CD | ARG | 61 | 10.814 | -2.675 | 11.799 | 1.00 23.50 | A |
| ATOM | 460 | NE | ARG | 61 | 10.446 | -2.820 | 10.394 | 1.00 25.00 | A |
| ATOM | 461 | CZ | ARG | 61 | 9.313 | -2.356 | 9.878 | 1.00 27.62 | A |
| ATOM | 462 | NH1 | ARG | 61 | 9.049 | -2.527 | 8.593 | 1.00 28.14 | A |
| ATOM | 463 | NH2 | ARG | 61 | 8.444 | -1.709 | 10.650 | 1.00 31.61 | A |
| ATOM | 464 | C | ARG | 61 | 14.061 | -0.875 | 14.944 | 1.00 19.84 | A |
| ATOM | 465 | O | ARG | 61 | 13.664 | 0.273 | 15.145 | 1.00 20.49 | A |
| ATOM | 466 | N | THR | 62 | 14.587 | -1.640 | 15.889 | 1.00 21.09 | A |
| ATOM | 467 | CA | THR | 62 | 14.731 | -1.208 | 17.269 | 1.00 19.87 | A |
| ATOM | 468 | CB | THR | 62 | 14.911 | -2.442 | 18.194 | 1.00 20.87 | A |
| ATOM | 469 | OG1 | THR | 62 | 13.694 | -3.198 | 18.208 | 1.00 21.98 | A |
| ATOM | 470 | CG2 | THR | 62 | 15.252 | -2.027 | 19.618 | 1.00 19.80 | A |
| ATOM | 471 | C | THR | 62 | 15.913 | -0.263 | 17.425 | 1.00 19.52 | A |
| ATOM | 472 | O | THR | 62 | 15.811 | 0.771 | 18.094 | 1.00 18.28 | A |
| ATOM | 473 | N | GLU | 63 | 17.037 | -0.604 | 16.804 | 1.00 19.15 | A |
| ATOM | 474 | CA | GLU | 63 | 18.220 | 0.250 | 16.903 | 1.00 18.99 | A |
| ATOM | 475 | CB | GLU | 63 | 19.471 | -0.529 | 16.509 | 1.00 19.03 | A |
| ATOM | 476 | CG | GLU | 63 | 19.288 | -1.491 | 15.381 | 1.00 21.37 | A |
| ATOM | 477 | CD | GLU | 63 | 20.619 | -2.034 | 14.930 | 1.00 25.03 | A |
| ATOM | 478 | OE1 | GLU | 63 | 21.082 | -1.623 | 13.840 | 1.00 26.31 | A |
| ATOM | 479 | OE2 | GLU | 63 | 21.212 | -2.856 | 15.664 | 1.00 25.70 | A |
| ATOM | 480 | C | GLU | 63 | 18.088 | 1.509 | 16.050 | 1.00 17.94 | A |
| ATOM | 481 | O | GLU | 63 | 18.832 | 2.467 | 16.211 | 1.00 21.25 | A |
| ATOM | 482 | N | ALA | 64 | 17.138 | 1.491 | 15.132 | 1.00 15.64 | A |
| ATOM | 483 | CA | ALA | 64 | 16.899 | 2.641 | 14.297 | 1.00 15.57 | A |
| ATOM | 484 | CB | ALA | 64 | 16.143 | 2.223 | 13.003 | 1.00 13.61 | A |
| ATOM | 485 | C | ALA | 64 | 16.037 | 3.575 | 15.172 | 1.00 15.81 | A |
| ATOM | 486 | O | ALA | 64 | 16.356 | 4.752 | 15.363 | 1.00 16.61 | A |
| ATOM | 487 | N | MET | 65 | 14.974 | 3.018 | 15.743 | 1.00 13.79 | A |
| ATOM | 488 | CA | MET | 65 | 14.087 | 3.794 | 16.604 | 1.00 13.69 | A |
| ATOM | 489 | CB | MET | 65 | 13.039 | 2.874 | 17.251 | 1.00 12.94 | A |
| ATOM | 490 | CG | MET | 65 | 11.582 | 3.210 | 16.978 | 1.00 11.73 | A |
| ATOM | 491 | SD | MET | 65 | 10.527 | 1.815 | 17.282 | 1.00 6.30 | A |
| ATOM | 492 | CE | MET | 65 | 9.097 | 2.396 | 16.652 | 1.00 5.95 | A |
| ATOM | 493 | C | MET | 65 | 14.926 | 4.462 | 17.699 | 1.00 12.98 | A |
| ATOM | 494 | O | MET | 65 | 14.797 | 5.653 | 17.945 | 1.00 13.88 | A |
| ATOM | 495 | N | LEU | 66 | 15.781 | 3.678 | 18.357 | 1.00 13.83 | A |
| ATOM | 496 | CA | LEU | 66 | 16.629 | 4.188 | 19.433 | 1.00 13.28 | A |
| ATOM | 497 | CB | LEU | 66 | 17.479 | 3.066 | 20.058 | 1.00 13.35 | A |
| ATOM | 498 | CG | LEU | 66 | 16.816 | 2.125 | 21.081 | 1.00 15.56 | A |
| ATOM | 499 | CD1 | LEU | 66 | 17.852 | 1.159 | 21.623 | 1.00 13.13 | A |
| ATOM | 500 | CD2 | LEU | 66 | 16.210 | 2.910 | 22.238 | 1.00 14.87 | A |
| ATOM | 501 | C | LEU | 66 | 17.558 | 5.290 | 18.948 | 1.00 13.84 | A |
| ATOM | 502 | O | LEU | 66 | 17.884 | 6.191 | 19.711 | 1.00 14.62 | A |
| ATOM | 503 | N | PHE | 67 | 17.994 | 5.197 | 17.694 | 1.00 14.84 | A |
| ATOM | 504 | CA | PHE | 67 | 18.898 | 6.196 | 17.109 | 1.00 15.86 | A |
| ATOM | 505 | CB | PHE | 67 | 19.591 | 5.612 | 15.865 | 1.00 17.75 | A |
| ATOM | 506 | CG | PHE | 67 | 21.020 | 5.206 | 16.103 | 1.00 20.57 | A |
| ATOM | 507 | CD1 | PHE | 67 | 22.060 | 6.051 | 15.749 | 1.00 25.92 | A |
| ATOM | 508 | CD2 | PHE | 67 | 21.327 | 3.989 | 16.691 | 1.00 22.84 | A |

Fig. 2A-8

```
ATOM   509  CE1 PHE  67     23.382    5.691   15.974  1.00 26.79      A
ATOM   510  CE2 PHE  67     22.645    3.624   16.921  1.00 23.85      A
ATOM   511  CZ  PHE  67     23.674    4.475   16.563  1.00 23.88      A
ATOM   512  C   PHE  67     18.092    7.441   16.742  1.00 14.03      A
ATOM   513  O   PHE  67     18.580    8.570   16.807  1.00 12.55      A
ATOM   514  N   ALA  68     16.843    7.212   16.364  1.00 13.48      A
ATOM   515  CA  ALA  68     15.953    8.298   16.022  1.00 14.76      A
ATOM   516  CB  ALA  68     14.606    7.734   15.543  1.00 16.19      A
ATOM   517  C   ALA  68     15.742    9.196   17.249  1.00 16.89      A
ATOM   518  O   ALA  68     15.695   10.427   17.121  1.00 16.90      A
ATOM   519  N   ALA  69     15.633    8.556   18.422  1.00 17.12      A
ATOM   520  CA  ALA  69     15.410    9.209   19.715  1.00 14.85      A
ATOM   521  CB  ALA  69     14.931    8.187   20.734  1.00 13.25      A
ATOM   522  C   ALA  69     16.668    9.888   20.216  1.00 16.30      A
ATOM   523  O   ALA  69     16.610   10.831   21.000  1.00 14.16      A
ATOM   524  N   SER  70     17.811    9.374   19.779  1.00 17.73      A
ATOM   525  CA  SER  70     19.103    9.943   20.123  1.00 19.15      A
ATOM   526  CB  SER  70     20.195    8.894   19.867  1.00 17.01      A
ATOM   527  OG  SER  70     21.462    9.336   20.308  1.00 15.22      A
ATOM   528  C   SER  70     19.284   11.179   19.199  1.00 22.47      A
ATOM   529  O   SER  70     19.919   12.180   19.569  1.00 22.68      A
ATOM   530  N   ARG  71     18.700   11.102   18.001  1.00 23.16      A
ATOM   531  CA  ARG  71     18.763   12.187   17.022  1.00 24.02      A
ATOM   532  CB  ARG  71     18.330   11.688   15.642  1.00 23.12      A
ATOM   533  CG  ARG  71     18.342   12.757   14.554  1.00 24.85      A
ATOM   534  CD  ARG  71     17.961   12.183   13.187  1.00 27.81      A
ATOM   535  NE  ARG  71     18.976   11.257   12.684  1.00 33.70      A
ATOM   536  CZ  ARG  71     18.776    9.957   12.474  1.00 36.24      A
ATOM   537  NH1 ARG  71     19.761    9.198   12.019  1.00 39.64      A
ATOM   538  NH2 ARG  71     17.591    9.413   12.713  1.00 36.44      A
ATOM   539  C   ARG  71     17.848   13.320   17.447  1.00 24.53      A
ATOM   540  O   ARG  71     17.976   14.444   16.972  1.00 26.57      A
ATOM   541  N   ARG  72     16.916   13.014   18.336  1.00 26.02      A
ATOM   542  CA  ARG  72     15.978   14.001   18.849  1.00 26.19      A
ATOM   543  CB  ARG  72     14.686   13.301   19.269  1.00 27.68      A
ATOM   544  CG  ARG  72     13.643   14.229   19.823  1.00 30.87      A
ATOM   545  CD  ARG  72     12.452   14.321   18.897  1.00 32.04      A
ATOM   546  NE  ARG  72     11.528   15.370   19.321  1.00 32.80      A
ATOM   547  CZ  ARG  72     11.423   16.554   18.728  1.00 34.02      A
ATOM   548  NH1 ARG  72     10.554   17.441   19.185  1.00 30.93      A
ATOM   549  NH2 ARG  72     12.188   16.849   17.678  1.00 32.67      A
ATOM   550  C   ARG  72     16.569   14.778   20.041  1.00 25.47      A
ATOM   551  O   ARG  72     16.353   15.987   20.173  1.00 25.92      A
ATOM   552  N   GLU  73     17.318   14.089   20.901  1.00 23.88      A
ATOM   553  CA  GLU  73     17.917   14.737   22.069  1.00 23.70      A
ATOM   554  CB  GLU  73     18.510   13.706   23.042  1.00 24.81      A
ATOM   555  CG  GLU  73     17.470   12.934   23.861  1.00 27.04      A
ATOM   556  CD  GLU  73     16.527   13.841   24.631  1.00 27.69      A
ATOM   557  OE1 GLU  73     15.377   14.044   24.180  1.00 26.28      A
ATOM   558  OE2 GLU  73     16.943   14.349   25.694  1.00 32.51      A
ATOM   559  C   GLU  73     19.004   15.682   21.620  1.00 21.89      A
ATOM   560  O   GLU  73     19.059   16.826   22.062  1.00 22.04      A
ATOM   561  N   HIS  74     19.872   15.189   20.744  1.00 20.57      A
ATOM   562  CA  HIS  74     20.972   15.979   20.197  1.00 19.43      A
ATOM   563  CB  HIS  74     21.698   15.169   19.104  1.00 19.74      A
ATOM   564  CG  HIS  74     22.772   15.927   18.381  1.00 18.47      A
ATOM   565  CD2 HIS  74     24.069   16.156   18.689  1.00 17.84      A
```

Fig. 2A-9

| | | | | | | | | |
|---|---|---|---|---|---|---|---|---|
| ATOM | 566 | ND1 | HIS | 74 | 22.561 | 16.519 | 17.151 | 1.00 15.64 | A |
| ATOM | 567 | CE1 | HIS | 74 | 23.689 | 17.079 | 16.739 | 1.00 14.64 | A |
| ATOM | 568 | NE2 | HIS | 74 | 24.615 | 16.870 | 17.654 | 1.00 18.09 | A |
| ATOM | 569 | C | HIS | 74 | 20.413 | 17.267 | 19.599 | 1.00 17.65 | A |
| ATOM | 570 | O | HIS | 74 | 21.003 | 18.342 | 19.723 | 1.00 17.62 | A |
| ATOM | 571 | N | LEU | 75 | 19.255 | 17.129 | 18.969 | 1.00 16.80 | A |
| ATOM | 572 | CA | LEU | 75 | 18.556 | 18.209 | 18.293 | 1.00 17.58 | A |
| ATOM | 573 | CB | LEU | 75 | 17.520 | 17.592 | 17.357 | 1.00 16.00 | A |
| ATOM | 574 | CG | LEU | 75 | 16.787 | 18.482 | 16.373 | 1.00 16.84 | A |
| ATOM | 575 | CD1 | LEU | 75 | 17.606 | 18.574 | 15.095 | 1.00 17.06 | A |
| ATOM | 576 | CD2 | LEU | 75 | 15.401 | 17.910 | 16.101 | 1.00 14.46 | A |
| ATOM | 577 | C | LEU | 75 | 17.876 | 19.181 | 19.238 | 1.00 18.49 | A |
| ATOM | 578 | O | LEU | 75 | 18.017 | 20.390 | 19.103 | 1.00 19.92 | A |
| ATOM | 579 | N | VAL | 76 | 17.128 | 18.642 | 20.189 | 1.00 19.25 | A |
| ATOM | 580 | CA | VAL | 76 | 16.404 | 19.445 | 21.160 | 1.00 21.23 | A |
| ATOM | 581 | CB | VAL | 76 | 15.332 | 18.567 | 21.856 | 1.00 23.42 | A |
| ATOM | 582 | CG1 | VAL | 76 | 14.798 | 19.243 | 23.116 | 1.00 22.32 | A |
| ATOM | 583 | CG2 | VAL | 76 | 14.208 | 18.273 | 20.878 | 1.00 23.82 | A |
| ATOM | 584 | C | VAL | 76 | 17.301 | 20.088 | 22.220 | 1.00 22.23 | A |
| ATOM | 585 | O | VAL | 76 | 17.098 | 21.237 | 22.602 | 1.00 22.44 | A |
| ATOM | 586 | N | LEU | 77 | 18.302 | 19.350 | 22.686 | 1.00 24.07 | A |
| ATOM | 587 | CA | LEU | 77 | 19.197 | 19.844 | 23.731 | 1.00 24.71 | A |
| ATOM | 588 | CB | LEU | 77 | 19.509 | 18.717 | 24.718 | 1.00 24.97 | A |
| ATOM | 589 | CG | LEU | 77 | 18.283 | 18.178 | 25.454 | 1.00 25.12 | A |
| ATOM | 590 | CD1 | LEU | 77 | 18.647 | 16.937 | 26.267 | 1.00 24.22 | A |
| ATOM | 591 | CD2 | LEU | 77 | 17.728 | 19.285 | 26.344 | 1.00 25.02 | A |
| ATOM | 592 | C | LEU | 77 | 20.510 | 20.447 | 23.264 | 1.00 24.28 | A |
| ATOM | 593 | O | LEU | 77 | 21.315 | 20.888 | 24.089 | 1.00 24.26 | A |
| ATOM | 594 | N | LYS | 78 | 20.736 | 20.476 | 21.959 | 1.00 23.77 | A |
| ATOM | 595 | CA | LYS | 78 | 21.988 | 21.024 | 21.457 | 1.00 21.74 | A |
| ATOM | 596 | CB | LYS | 78 | 22.987 | 19.887 | 21.227 | 1.00 22.10 | A |
| ATOM | 597 | CG | LYS | 78 | 24.418 | 20.363 | 21.034 | 1.00 26.45 | A |
| ATOM | 598 | CD | LYS | 78 | 25.341 | 19.227 | 20.609 | 1.00 27.57 | A |
| ATOM | 599 | CE | LYS | 78 | 26.778 | 19.568 | 20.957 | 1.00 28.49 | A |
| ATOM | 600 | NZ | LYS | 78 | 27.735 | 18.750 | 20.168 | 1.00 30.24 | A |
| ATOM | 601 | C | LYS | 78 | 21.849 | 21.847 | 20.177 | 1.00 19.07 | A |
| ATOM | 602 | O | LYS | 78 | 22.330 | 22.974 | 20.103 | 1.00 19.94 | A |
| ATOM | 603 | N | VAL | 79 | 21.178 | 21.294 | 19.178 | 1.00 16.59 | A |
| ATOM | 604 | CA | VAL | 79 | 21.023 | 21.982 | 17.912 | 1.00 15.79 | A |
| ATOM | 605 | CB | VAL | 79 | 20.682 | 20.972 | 16.790 | 1.00 15.19 | A |
| ATOM | 606 | CG1 | VAL | 79 | 20.319 | 21.699 | 15.501 | 1.00 9.66 | A |
| ATOM | 607 | CG2 | VAL | 79 | 21.883 | 20.058 | 16.559 | 1.00 12.64 | A |
| ATOM | 608 | C | VAL | 79 | 20.010 | 23.124 | 17.918 | 1.00 16.55 | A |
| ATOM | 609 | O | VAL | 79 | 20.361 | 24.260 | 17.603 | 1.00 16.63 | A |
| ATOM | 610 | N | ILE | 80 | 18.763 | 22.843 | 18.271 | 1.00 14.58 | A |
| ATOM | 611 | CA | ILE | 80 | 17.753 | 23.891 | 18.284 | 1.00 15.10 | A |
| ATOM | 612 | CB | ILE | 80 | 16.428 | 23.372 | 18.856 | 1.00 13.78 | A |
| ATOM | 613 | CG2 | ILE | 80 | 15.578 | 24.540 | 19.343 | 1.00 12.16 | A |
| ATOM | 614 | CG1 | ILE | 80 | 15.685 | 22.588 | 17.770 | 1.00 9.95 | A |
| ATOM | 615 | CD1 | ILE | 80 | 14.622 | 21.665 | 18.293 | 1.00 8.33 | A |
| ATOM | 616 | C | ILE | 80 | 18.210 | 25.123 | 19.063 | 1.00 18.01 | A |
| ATOM | 617 | O | ILE | 80 | 18.219 | 26.244 | 18.531 | 1.00 19.52 | A |
| ATOM | 618 | N | PRO | 81 | 18.573 | 24.948 | 20.341 | 1.00 19.27 | A |
| ATOM | 619 | CD | PRO | 81 | 18.568 | 23.731 | 21.167 | 1.00 18.02 | A |
| ATOM | 620 | CA | PRO | 81 | 19.024 | 26.125 | 21.086 | 1.00 19.76 | A |
| ATOM | 621 | CB | PRO | 81 | 19.618 | 25.551 | 22.368 | 1.00 18.30 | A |
| ATOM | 622 | CG | PRO | 81 | 19.524 | 24.055 | 22.250 | 1.00 17.68 | A |

Fig. 2A-10

```
ATOM    623  C   PRO    81      20.064  26.911  20.296  1.00 21.52      A
ATOM    624  O   PRO    81      19.884  28.096  20.032  1.00 24.42      A
ATOM    625  N   ALA    82      21.147  26.246  19.910  1.00 20.79      A
ATOM    626  CA  ALA    82      22.212  26.908  19.156  1.00 21.00      A
ATOM    627  CB  ALA    82      23.231  25.883  18.682  1.00 19.36      A
ATOM    628  C   ALA    82      21.681  27.709  17.966  1.00 20.35      A
ATOM    629  O   ALA    82      22.167  28.808  17.685  1.00 21.95      A
ATOM    630  N   LEU    83      20.684  27.163  17.277  1.00 19.97      A
ATOM    631  CA  LEU    83      20.095  27.834  16.130  1.00 20.55      A
ATOM    632  CB  LEU    83      19.140  26.887  15.386  1.00 18.99      A
ATOM    633  CG  LEU    83      19.716  25.588  14.779  1.00 18.41      A
ATOM    634  CD1 LEU    83      18.705  24.977  13.822  1.00 15.72      A
ATOM    635  CD2 LEU    83      21.011  25.871  14.039  1.00 16.05      A
ATOM    636  C   LEU    83      19.349  29.086  16.588  1.00 23.59      A
ATOM    637  O   LEU    83      19.175  30.028  15.814  1.00 23.10      A
ATOM    638  N   LYS    84      18.921  29.094  17.850  1.00 25.75      A
ATOM    639  CA  LYS    84      18.192  30.232  18.416  1.00 27.61      A
ATOM    640  CB  LYS    84      17.167  29.736  19.435  1.00 28.01      A
ATOM    641  CG  LYS    84      15.981  29.070  18.795  1.00 29.06      A
ATOM    642  CD  LYS    84      15.231  28.263  19.815  1.00 31.01      A
ATOM    643  CE  LYS    84      13.946  27.717  19.237  1.00 33.77      A
ATOM    644  NZ  LYS    84      13.330  26.759  20.197  1.00 36.32      A
ATOM    645  C   LYS    84      19.101  31.280  19.061  1.00 27.07      A
ATOM    646  O   LYS    84      18.646  32.367  19.419  1.00 26.91      A
ATOM    647  N   GLU    85      20.373  30.928  19.235  1.00 28.01      A
ATOM    648  CA  GLU    85      21.367  31.843  19.785  1.00 27.28      A
ATOM    649  CB  GLU    85      22.469  31.075  20.523  1.00 29.14      A
ATOM    650  CG  GLU    85      21.952  29.927  21.370  1.00 36.53      A
ATOM    651  CD  GLU    85      23.062  29.140  22.070  1.00 42.07      A
ATOM    652  OE1 GLU    85      22.981  28.955  23.305  1.00 44.49      A
ATOM    653  OE2 GLU    85      24.018  28.702  21.391  1.00 44.75      A
ATOM    654  C   GLU    85      21.948  32.540  18.554  1.00 26.23      A
ATOM    655  O   GLU    85      22.845  33.378  18.661  1.00 26.25      A
ATOM    656  N   GLY    86      21.410  32.167  17.389  1.00 26.07      A
ATOM    657  CA  GLY    86      21.828  32.717  16.111  1.00 26.47      A
ATOM    658  C   GLY    86      23.140  32.155  15.589  1.00 26.86      A
ATOM    659  O   GLY    86      23.925  32.897  14.991  1.00 29.40      A
ATOM    660  N   LYS    87      23.383  30.861  15.798  1.00 24.80      A
ATOM    661  CA  LYS    87      24.630  30.231  15.355  1.00 23.74      A
ATOM    662  CB  LYS    87      25.139  29.249  16.414  1.00 20.75      A
ATOM    663  CG  LYS    87      25.231  29.817  17.791  1.00 19.79      A
ATOM    664  CD  LYS    87      26.236  29.057  18.627  1.00 23.47      A
ATOM    665  CE  LYS    87      27.341  29.981  19.117  1.00 25.56      A
ATOM    666  NZ  LYS    87      28.131  29.426  20.248  1.00 28.30      A
ATOM    667  C   LYS    87      24.542  29.479  14.028  1.00 23.80      A
ATOM    668  O   LYS    87      23.444  29.157  13.557  1.00 23.85      A
ATOM    669  N   VAL    88      25.708  29.229  13.418  1.00 22.55      A
ATOM    670  CA  VAL    88      25.792  28.439  12.182  1.00 20.90      A
ATOM    671  CB  VAL    88      26.983  28.837  11.263  1.00 18.57      A
ATOM    672  CG1 VAL    88      27.025  27.919  10.055  1.00 17.56      A
ATOM    673  CG2 VAL    88      26.862  30.293  10.823  1.00 17.32      A
ATOM    674  C   VAL    88      26.094  27.054  12.743  1.00 20.89      A
ATOM    675  O   VAL    88      26.995  26.904  13.584  1.00 19.91      A
ATOM    676  N   VAL    89      25.355  26.047  12.290  1.00 20.24      A
ATOM    677  CA  VAL    89      25.545  24.698  12.807  1.00 20.70      A
ATOM    678  CB  VAL    89      24.282  24.231  13.596  1.00 20.44      A
ATOM    679  CG1 VAL    89      24.446  22.783  14.042  1.00 20.47      A
```

Fig. 2A-11

| | | | | | | | | | |
|---|---|---|---|---|---|---|---|---|---|
| ATOM | 680 | CG2 | VAL | 89 | 24.054 | 25.139 | 14.807 | 1.00 18.39 | A |
| ATOM | 681 | C | VAL | 89 | 25.870 | 23.678 | 11.730 | 1.00 19.98 | A |
| ATOM | 682 | O | VAL | 89 | 25.033 | 23.374 | 10.884 | 1.00 19.26 | A |
| ATOM | 683 | N | LEU | 90 | 27.096 | 23.160 | 11.771 | 1.00 20.84 | A |
| ATOM | 684 | CA | LEU | 90 | 27.553 | 22.146 | 10.819 | 1.00 21.88 | A |
| ATOM | 685 | CB | LEU | 90 | 29.030 | 22.386 | 10.468 | 1.00 20.28 | A |
| ATOM | 686 | CG | LEU | 90 | 29.474 | 23.858 | 10.350 | 1.00 20.78 | A |
| ATOM | 687 | CD1 | LEU | 90 | 30.958 | 23.947 | 10.019 | 1.00 19.33 | A |
| ATOM | 688 | CD2 | LEU | 90 | 28.668 | 24.552 | 9.265 | 1.00 16.38 | A |
| ATOM | 689 | C | LEU | 90 | 27.382 | 20.774 | 11.488 | 1.00 22.30 | A |
| ATOM | 690 | O | LEU | 90 | 28.056 | 20.475 | 12.473 | 1.00 23.77 | A |
| ATOM | 691 | N | CYS | 91 | 26.471 | 19.959 | 10.957 | 1.00 22.03 | A |
| ATOM | 692 | CA | CYS | 91 | 26.176 | 18.630 | 11.496 | 1.00 21.39 | A |
| ATOM | 693 | CB | CYS | 91 | 24.661 | 18.457 | 11.665 | 1.00 22.53 | A |
| ATOM | 694 | SG | CYS | 91 | 24.144 | 17.040 | 12.697 | 1.00 21.80 | A |
| ATOM | 695 | C | CYS | 91 | 26.699 | 17.530 | 10.588 | 1.00 21.52 | A |
| ATOM | 696 | O | CYS | 91 | 26.354 | 17.477 | 9.409 | 1.00 20.26 | A |
| ATOM | 697 | N | ASP | 92 | 27.517 | 16.642 | 11.148 | 1.00 24.32 | A |
| ATOM | 698 | CA | ASP | 92 | 28.075 | 15.531 | 10.385 | 1.00 26.69 | A |
| ATOM | 699 | CB | ASP | 92 | 28.882 | 14.604 | 11.291 | 1.00 27.62 | A |
| ATOM | 700 | CG | ASP | 92 | 29.926 | 13.815 | 10.522 | 1.00 27.97 | A |
| ATOM | 701 | OD1 | ASP | 92 | 29.592 | 13.260 | 9.449 | 1.00 27.64 | A |
| ATOM | 702 | OD2 | ASP | 92 | 31.084 | 13.746 | 10.989 | 1.00 28.87 | A |
| ATOM | 703 | C | ASP | 92 | 26.960 | 14.753 | 9.698 | 1.00 26.77 | A |
| ATOM | 704 | O | ASP | 92 | 26.741 | 14.921 | 8.504 | 1.00 28.83 | A |
| ATOM | 705 | N | ARG | 93 | 26.235 | 13.923 | 10.440 | 1.00 24.99 | A |
| ATOM | 706 | CA | ARG | 93 | 25.139 | 13.168 | 9.830 | 1.00 24.14 | A |
| ATOM | 707 | CB | ARG | 93 | 25.296 | 11.669 | 10.107 | 1.00 25.33 | A |
| ATOM | 708 | CG | ARG | 93 | 26.725 | 11.168 | 10.049 | 1.00 28.85 | A |
| ATOM | 709 | CD | ARG | 93 | 26.861 | 10.074 | 9.024 | 1.00 31.63 | A |
| ATOM | 710 | NE | ARG | 93 | 28.233 | 9.947 | 8.560 | 1.00 36.01 | A |
| ATOM | 711 | CZ | ARG | 93 | 28.748 | 8.846 | 8.020 | 1.00 37.75 | A |
| ATOM | 712 | NH1 | ARG | 93 | 28.000 | 7.766 | 7.860 | 1.00 41.65 | A |
| ATOM | 713 | NH2 | ARG | 93 | 30.016 | 8.822 | 7.636 | 1.00 38.28 | A |
| ATOM | 714 | C | ARG | 93 | 23.769 | 13.629 | 10.336 | 1.00 22.98 | A |
| ATOM | 715 | O | ARG | 93 | 23.652 | 14.224 | 11.405 | 1.00 22.48 | A |
| ATOM | 716 | N | TYR | 94 | 22.731 | 13.346 | 9.561 | 1.00 21.60 | A |
| ATOM | 717 | CA | TYR | 94 | 21.379 | 13.715 | 9.936 | 1.00 20.59 | A |
| ATOM | 718 | CB | TYR | 94 | 21.077 | 15.167 | 9.522 | 1.00 20.27 | A |
| ATOM | 719 | CG | TYR | 94 | 19.914 | 15.812 | 10.268 | 1.00 19.09 | A |
| ATOM | 720 | CD1 | TYR | 94 | 19.855 | 15.797 | 11.661 | 1.00 17.92 | A |
| ATOM | 721 | CE1 | TYR | 94 | 18.800 | 16.411 | 12.347 | 1.00 20.57 | A |
| ATOM | 722 | CD2 | TYR | 94 | 18.886 | 16.458 | 9.574 | 1.00 21.42 | A |
| ATOM | 723 | CE2 | TYR | 94 | 17.826 | 17.077 | 10.246 | 1.00 21.48 | A |
| ATOM | 724 | CZ | TYR | 94 | 17.795 | 17.051 | 11.629 | 1.00 22.59 | A |
| ATOM | 725 | OH | TYR | 94 | 16.760 | 17.691 | 12.281 | 1.00 23.61 | A |
| ATOM | 726 | C | TYR | 94 | 20.392 | 12.738 | 9.294 | 1.00 20.62 | A |
| ATOM | 727 | O | TYR | 94 | 20.738 | 11.590 | 9.044 | 1.00 21.83 | A |
| ATOM | 728 | N | ILE | 95 | 19.170 | 13.186 | 9.024 | 1.00 18.95 | A |
| ATOM | 729 | CA | ILE | 95 | 18.161 | 12.300 | 8.461 | 1.00 20.80 | A |
| ATOM | 730 | CB | ILE | 95 | 16.851 | 13.066 | 8.131 | 1.00 20.01 | A |
| ATOM | 731 | CG2 | ILE | 95 | 16.064 | 13.324 | 9.414 | 1.00 19.70 | A |
| ATOM | 732 | CG1 | ILE | 95 | 17.165 | 14.389 | 7.434 | 1.00 22.09 | A |
| ATOM | 733 | CD1 | ILE | 95 | 15.929 | 15.142 | 6.961 | 1.00 20.99 | A |
| ATOM | 734 | C | ILE | 95 | 18.611 | 11.527 | 7.228 | 1.00 22.45 | A |
| ATOM | 735 | O | ILE | 95 | 18.399 | 10.315 | 7.139 | 1.00 21.99 | A |
| ATOM | 736 | N | ASP | 96 | 19.247 | 12.223 | 6.292 | 1.00 24.25 | A |

Fig. 2A-12

```
ATOM    737  CA   ASP   96      19.706  11.603   5.056  1.00 23.05      A
ATOM    738  CB   ASP   96      20.469  12.625   4.211  1.00 25.96      A
ATOM    739  CG   ASP   96      19.668  13.896   3.968  1.00 27.19      A
ATOM    740  OD1  ASP   96      18.570  13.798   3.366  1.00 27.07      A
ATOM    741  OD2  ASP   96      20.133  14.982   4.387  1.00 25.89      A
ATOM    742  C    ASP   96      20.563  10.366   5.278  1.00 21.62      A
ATOM    743  O    ASP   96      20.383   9.358   4.600  1.00 22.15      A
ATOM    744  N    SER   97      21.497  10.428   6.215  1.00 19.34      A
ATOM    745  CA   SER   97      22.346   9.275   6.474  1.00 20.14      A
ATOM    746  CB   SER   97      23.453   9.646   7.466  1.00 21.21      A
ATOM    747  OG   SER   97      23.986   8.495   8.092  1.00 26.38      A
ATOM    748  C    SER   97      21.497   8.124   7.018  1.00 19.98      A
ATOM    749  O    SER   97      21.724   6.964   6.698  1.00 17.31      A
ATOM    750  N    SER   98      20.507   8.459   7.837  1.00 20.55      A
ATOM    751  CA   SER   98      19.609   7.469   8.422  1.00 20.64      A
ATOM    752  CB   SER   98      18.667   8.151   9.422  1.00 21.56      A
ATOM    753  OG   SER   98      17.869   7.208  10.110  1.00 22.14      A
ATOM    754  C    SER   98      18.779   6.754   7.358  1.00 21.36      A
ATOM    755  O    SER   98      18.387   5.602   7.526  1.00 22.38      A
ATOM    756  N    LEU   99      18.506   7.450   6.264  1.00 21.90      A
ATOM    757  CA   LEU   99      17.722   6.896   5.170  1.00 21.25      A
ATOM    758  CB   LEU   99      17.226   8.020   4.269  1.00 22.12      A
ATOM    759  CG   LEU   99      15.784   8.463   4.408  1.00 24.85      A
ATOM    760  CD1  LEU   99      15.486   9.498   3.337  1.00 24.82      A
ATOM    761  CD2  LEU   99      14.855   7.257   4.288  1.00 26.36      A
ATOM    762  C    LEU   99      18.526   5.924   4.304  1.00 20.77      A
ATOM    763  O    LEU   99      18.075   4.829   3.998  1.00 18.96      A
ATOM    764  N    ALA  100      19.716   6.355   3.902  1.00 20.92      A
ATOM    765  CA   ALA  100      20.603   5.585   3.024  1.00 19.22      A
ATOM    766  CB   ALA  100      21.773   6.476   2.561  1.00 13.31      A
ATOM    767  C    ALA  100      21.142   4.308   3.629  1.00 17.15      A
ATOM    768  O    ALA  100      21.319   3.304   2.939  1.00 18.18      A
ATOM    769  N    TYR  101      21.416   4.353   4.921  1.00 18.02      A
ATOM    770  CA   TYR  101      21.959   3.203   5.626  1.00 20.84      A
ATOM    771  CB   TYR  101      22.783   3.671   6.832  1.00 19.33      A
ATOM    772  CG   TYR  101      24.146   4.242   6.501  1.00 19.81      A
ATOM    773  CD1  TYR  101      24.320   5.611   6.255  1.00 21.70      A
ATOM    774  CE1  TYR  101      25.595   6.153   6.002  1.00 21.57      A
ATOM    775  CD2  TYR  101      25.270   3.425   6.465  1.00 20.81      A
ATOM    776  CE2  TYR  101      26.550   3.955   6.213  1.00 22.58      A
ATOM    777  CZ   TYR  101      26.703   5.313   5.976  1.00 22.24      A
ATOM    778  OH   TYR  101      27.968   5.809   5.745  1.00 22.15      A
ATOM    779  C    TYR  101      20.865   2.246   6.095  1.00 22.06      A
ATOM    780  O    TYR  101      20.880   1.073   5.744  1.00 20.19      A
ATOM    781  N    GLN  102      19.921   2.753   6.887  1.00 25.20      A
ATOM    782  CA   GLN  102      18.835   1.930   7.427  1.00 27.87      A
ATOM    783  CB   GLN  102      18.204   2.623   8.642  1.00 30.86      A
ATOM    784  CG   GLN  102      19.209   3.153   9.661  1.00 35.49      A
ATOM    785  CD   GLN  102      19.516   2.154  10.771  1.00 39.58      A
ATOM    786  OE1  GLN  102      20.382   2.399  11.612  1.00 40.43      A
ATOM    787  NE2  GLN  102      18.803   1.024  10.778  1.00 40.84      A
ATOM    788  C    GLN  102      17.735   1.576   6.426  1.00 26.37      A
ATOM    789  O    GLN  102      17.367   0.409   6.283  1.00 25.92      A
ATOM    790  N    GLY  103      17.199   2.586   5.751  1.00 25.71      A
ATOM    791  CA   GLY  103      16.144   2.358   4.783  1.00 25.94      A
ATOM    792  C    GLY  103      16.586   1.561   3.568  1.00 26.88      A
ATOM    793  O    GLY  103      15.935   0.581   3.204  1.00 27.07      A
```

Fig. 2A-13

| | | | | | | | | | |
|---|---|---|---|---|---|---|---|---|---|
| ATOM | 794 | N | TYR | 104 | 17.686 | 1.985 | 2.943 | 1.00 26.94 | A |
| ATOM | 795 | CA | TYR | 104 | 18.228 | 1.331 | 1.750 | 1.00 27.19 | A |
| ATOM | 796 | CB | TYR | 104 | 18.933 | 2.354 | 0.852 | 1.00 30.54 | A |
| ATOM | 797 | CG | TYR | 104 | 18.005 | 3.263 | 0.067 | 1.00 34.90 | A |
| ATOM | 798 | CD1 | TYR | 104 | 17.693 | 4.540 | 0.535 | 1.00 36.85 | A |
| ATOM | 799 | CE1 | TYR | 104 | 16.846 | 5.388 | -0.180 | 1.00 38.45 | A |
| ATOM | 800 | CD2 | TYR | 104 | 17.444 | 2.854 | -1.147 | 1.00 36.59 | A |
| ATOM | 801 | CE2 | TYR | 104 | 16.589 | 3.699 | -1.877 | 1.00 38.04 | A |
| ATOM | 802 | CZ | TYR | 104 | 16.292 | 4.967 | -1.383 | 1.00 39.23 | A |
| ATOM | 803 | OH | TYR | 104 | 15.424 | 5.808 | -2.064 | 1.00 38.53 | A |
| ATOM | 804 | C | TYR | 104 | 19.203 | 0.191 | 2.038 | 1.00 26.08 | A |
| ATOM | 805 | O | TYR | 104 | 18.856 | -0.984 | 1.901 | 1.00 26.13 | A |
| ATOM | 806 | N | ALA | 105 | 20.428 | 0.533 | 2.421 | 1.00 23.92 | A |
| ATOM | 807 | CA | ALA | 105 | 21.434 | -0.485 | 2.694 | 1.00 23.91 | A |
| ATOM | 808 | CB | ALA | 105 | 22.658 | 0.157 | 3.342 | 1.00 23.02 | A |
| ATOM | 809 | C | ALA | 105 | 20.917 | -1.646 | 3.552 | 1.00 23.55 | A |
| ATOM | 810 | O | ALA | 105 | 20.992 | -2.799 | 3.140 | 1.00 24.77 | A |
| ATOM | 811 | N | ARG | 106 | 20.389 | -1.347 | 4.736 | 1.00 24.01 | A |
| ATOM | 812 | CA | ARG | 106 | 19.870 | -2.379 | 5.633 | 1.00 22.65 | A |
| ATOM | 813 | CB | ARG | 106 | 19.794 | -1.850 | 7.070 | 1.00 24.32 | A |
| ATOM | 814 | CG | ARG | 106 | 21.128 | -1.555 | 7.715 | 1.00 28.27 | A |
| ATOM | 815 | CD | ARG | 106 | 21.582 | -2.686 | 8.628 | 1.00 33.76 | A |
| ATOM | 816 | NE | ARG | 106 | 23.006 | -2.996 | 8.465 | 1.00 37.41 | A |
| ATOM | 817 | CZ | ARG | 106 | 24.000 | -2.135 | 8.681 | 1.00 38.55 | A |
| ATOM | 818 | NH1 | ARG | 106 | 25.260 | -2.519 | 8.503 | 1.00 40.28 | A |
| ATOM | 819 | NH2 | ARG | 106 | 23.742 | -0.890 | 9.068 | 1.00 39.48 | A |
| ATOM | 820 | C | ARG | 106 | 18.480 | -2.853 | 5.209 | 1.00 21.73 | A |
| ATOM | 821 | O | ARG | 106 | 17.971 | -3.852 | 5.712 | 1.00 20.70 | A |
| ATOM | 822 | N | GLY | 107 | 17.855 | -2.126 | 4.297 | 1.00 22.27 | A |
| ATOM | 823 | CA | GLY | 107 | 16.537 | -2.513 | 3.849 | 1.00 22.90 | A |
| ATOM | 824 | C | GLY | 107 | 15.539 | -2.657 | 4.984 | 1.00 24.59 | A |
| ATOM | 825 | O | GLY | 107 | 15.475 | -3.696 | 5.633 | 1.00 26.41 | A |
| ATOM | 826 | N | ILE | 108 | 14.774 | -1.597 | 5.227 | 1.00 25.03 | A |
| ATOM | 827 | CA | ILE | 108 | 13.727 | -1.568 | 6.245 | 1.00 24.70 | A |
| ATOM | 828 | CB | ILE | 108 | 14.060 | -0.580 | 7.416 | 1.00 24.54 | A |
| ATOM | 829 | CG2 | ILE | 108 | 12.777 | -0.049 | 8.046 | 1.00 23.40 | A |
| ATOM | 830 | CG1 | ILE | 108 | 14.866 | -1.289 | 8.507 | 1.00 24.63 | A |
| ATOM | 831 | CD1 | ILE | 108 | 15.183 | -0.408 | 9.704 | 1.00 21.76 | A |
| ATOM | 832 | C | ILE | 108 | 12.571 | -0.984 | 5.445 | 1.00 24.77 | A |
| ATOM | 833 | O | ILE | 108 | 11.405 | -1.390 | 5.567 | 1.00 25.42 | A |
| ATOM | 834 | N | GLY | 109 | 12.946 | -0.039 | 4.588 | 1.00 23.73 | A |
| ATOM | 835 | CA | GLY | 109 | 12.003 | 0.677 | 3.754 | 1.00 23.72 | A |
| ATOM | 836 | C | GLY | 109 | 12.402 | 2.140 | 3.849 | 1.00 25.69 | A |
| ATOM | 837 | O | GLY | 109 | 12.549 | 2.692 | 4.941 | 1.00 23.78 | A |
| ATOM | 838 | N | VAL | 110 | 12.598 | 2.777 | 2.704 | 1.00 26.91 | A |
| ATOM | 839 | CA | VAL | 110 | 12.993 | 4.175 | 2.684 | 1.00 26.24 | A |
| ATOM | 840 | CB | VAL | 110 | 13.265 | 4.633 | 1.258 | 1.00 26.57 | A |
| ATOM | 841 | CG1 | VAL | 110 | 13.996 | 5.957 | 1.273 | 1.00 25.14 | A |
| ATOM | 842 | CG2 | VAL | 110 | 14.059 | 3.565 | 0.524 | 1.00 28.75 | A |
| ATOM | 843 | C | VAL | 110 | 11.899 | 5.052 | 3.260 | 1.00 26.51 | A |
| ATOM | 844 | O | VAL | 110 | 12.162 | 5.953 | 4.058 | 1.00 25.18 | A |
| ATOM | 845 | N | GLU | 111 | 10.671 | 4.774 | 2.833 | 1.00 28.16 | A |
| ATOM | 846 | CA | GLU | 111 | 9.496 | 5.523 | 3.257 | 1.00 30.38 | A |
| ATOM | 847 | CB | GLU | 111 | 8.287 | 5.123 | 2.405 | 1.00 34.66 | A |
| ATOM | 848 | CG | GLU | 111 | 7.236 | 6.213 | 2.239 | 1.00 40.60 | A |
| ATOM | 849 | CD | GLU | 111 | 7.742 | 7.423 | 1.460 | 1.00 44.78 | A |
| ATOM | 850 | OE1 | GLU | 111 | 8.856 | 7.365 | 0.883 | 1.00 45.65 | A |

Fig. 2A-14

```
ATOM    851  OE2 GLU   111       7.016   8.441   1.428  1.00 45.57           A
ATOM    852  C   GLU   111       9.186   5.284   4.722  1.00 29.21           A
ATOM    853  O   GLU   111       8.683   6.170   5.406  1.00 28.77           A
ATOM    854  N   GLU   112       9.493   4.083   5.200  1.00 28.86           A
ATOM    855  CA  GLU   112       9.243   3.727   6.593  1.00 28.99           A
ATOM    856  CB  GLU   112       9.289   2.210   6.768  1.00 30.84           A
ATOM    857  CG  GLU   112       8.747   1.437   5.577  1.00 34.20           A
ATOM    858  CD  GLU   112       7.794   0.343   5.995  1.00 38.64           A
ATOM    859  OE1 GLU   112       8.176  -0.479   6.861  1.00 40.64           A
ATOM    860  OE2 GLU   112       6.661   0.305   5.463  1.00 40.42           A
ATOM    861  C   GLU   112      10.265   4.381   7.514  1.00 27.76           A
ATOM    862  O   GLU   112       9.908   4.948   8.546  1.00 29.61           A
ATOM    863  N   VAL   113      11.537   4.306   7.138  1.00 24.25           A
ATOM    864  CA  VAL   113      12.605   4.900   7.934  1.00 23.10           A
ATOM    865  CB  VAL   113      14.001   4.498   7.406  1.00 22.03           A
ATOM    866  CG1 VAL   113      15.081   5.222   8.186  1.00 22.29           A
ATOM    867  CG2 VAL   113      14.191   3.005   7.520  1.00 24.34           A
ATOM    868  C   VAL   113      12.518   6.427   7.925  1.00 23.40           A
ATOM    869  O   VAL   113      12.947   7.087   8.870  1.00 22.99           A
ATOM    870  N   ARG   114      11.974   6.979   6.847  1.00 22.64           A
ATOM    871  CA  ARG   114      11.837   8.419   6.713  1.00 22.37           A
ATOM    872  CB  ARG   114      11.542   8.775   5.254  1.00 23.57           A
ATOM    873  CG  ARG   114      11.016  10.186   5.039  1.00 27.30           A
ATOM    874  CD  ARG   114      10.102  10.278   3.820  1.00 29.55           A
ATOM    875  NE  ARG   114      10.753   9.820   2.591  1.00 33.90           A
ATOM    876  CZ  ARG   114      11.789  10.422   2.013  1.00 34.91           A
ATOM    877  NH1 ARG   114      12.301   9.921   0.899  1.00 36.16           A
ATOM    878  NH2 ARG   114      12.315  11.521   2.544  1.00 36.20           A
ATOM    879  C   ARG   114      10.691   8.866   7.608  1.00 23.14           A
ATOM    880  O   ARG   114      10.751   9.916   8.256  1.00 23.93           A
ATOM    881  N   ALA   115       9.643   8.049   7.646  1.00 23.63           A
ATOM    882  CA  ALA   115       8.474   8.344   8.455  1.00 21.89           A
ATOM    883  CB  ALA   115       7.435   7.261   8.298  1.00 22.10           A
ATOM    884  C   ALA   115       8.938   8.404   9.886  1.00 21.76           A
ATOM    885  O   ALA   115       8.389   9.155  10.696  1.00 23.28           A
ATOM    886  N   LEU   116       9.959   7.611  10.191  1.00 17.69           A
ATOM    887  CA  LEU   116      10.509   7.578  11.535  1.00 16.56           A
ATOM    888  CB  LEU   116      11.413   6.356  11.709  1.00 14.55           A
ATOM    889  CG  LEU   116      12.226   6.296  13.006  1.00 15.09           A
ATOM    890  CD1 LEU   116      11.296   5.995  14.177  1.00 16.14           A
ATOM    891  CD2 LEU   116      13.310   5.231  12.890  1.00 13.40           A
ATOM    892  C   LEU   116      11.308   8.844  11.799  1.00 16.31           A
ATOM    893  O   LEU   116      11.265   9.404  12.892  1.00 15.63           A
ATOM    894  N   ASN   117      12.028   9.293  10.780  1.00 17.08           A
ATOM    895  CA  ASN   117      12.851  10.478  10.897  1.00 18.71           A
ATOM    896  CB  ASN   117      13.861  10.502   9.753  1.00 19.97           A
ATOM    897  CG  ASN   117      15.068   9.633  10.046  1.00 23.42           A
ATOM    898  OD1 ASN   117      15.659   9.733  11.119  1.00 21.30           A
ATOM    899  ND2 ASN   117      15.442   8.774   9.095  1.00 26.04           A
ATOM    900  C   ASN   117      12.040  11.768  10.966  1.00 18.06           A
ATOM    901  O   ASN   117      12.436  12.705  11.660  1.00 17.18           A
ATOM    902  N   GLU   118      10.900  11.819  10.283  1.00 19.49           A
ATOM    903  CA  GLU   118      10.060  13.019  10.334  1.00 20.98           A
ATOM    904  CB  GLU   118       8.947  12.941   9.281  1.00 24.57           A
ATOM    905  CG  GLU   118       9.444  12.505   7.897  1.00 30.89           A
ATOM    906  CD  GLU   118       8.757  13.231   6.753  1.00 35.03           A
ATOM    907  OE1 GLU   118       9.457  13.672   5.808  1.00 37.93           A
```

Fig. 2A-15

| | | | | | | | | | |
|---|---|---|---|---|---|---|---|---|---|
| ATOM | 908 | OE2 | GLU | 118 | 7.515 | 13.359 | 6.798 | 1.00 38.18 | A |
| ATOM | 909 | C | GLU | 118 | 9.457 | 13.174 | 11.741 | 1.00 19.53 | A |
| ATOM | 910 | O | GLU | 118 | 9.253 | 14.289 | 12.226 | 1.00 19.89 | A |
| ATOM | 911 | N | PHE | 119 | 9.179 | 12.052 | 12.397 | 1.00 16.90 | A |
| ATOM | 912 | CA | PHE | 119 | 8.616 | 12.072 | 13.740 | 1.00 14.30 | A |
| ATOM | 913 | CB | PHE | 119 | 8.141 | 10.680 | 14.123 | 1.00 13.75 | A |
| ATOM | 914 | CG | PHE | 119 | 7.379 | 10.647 | 15.399 | 1.00 12.63 | A |
| ATOM | 915 | CD1 | PHE | 119 | 5.987 | 10.669 | 15.392 | 1.00 13.78 | A |
| ATOM | 916 | CD2 | PHE | 119 | 8.046 | 10.597 | 16.619 | 1.00 11.27 | A |
| ATOM | 917 | CE1 | PHE | 119 | 5.271 | 10.648 | 16.594 | 1.00 11.57 | A |
| ATOM | 918 | CE2 | PHE | 119 | 7.345 | 10.575 | 17.822 | 1.00 9.33 | A |
| ATOM | 919 | CZ | PHE | 119 | 5.957 | 10.599 | 17.809 | 1.00 11.88 | A |
| ATOM | 920 | C | PHE | 119 | 9.655 | 12.556 | 14.754 | 1.00 12.85 | A |
| ATOM | 921 | O | PHE | 119 | 9.328 | 13.276 | 15.692 | 1.00 12.34 | A |
| ATOM | 922 | N | ALA | 120 | 10.906 | 12.147 | 14.567 | 1.00 12.61 | A |
| ATOM | 923 | CA | ALA | 120 | 12.008 | 12.554 | 15.442 | 1.00 12.28 | A |
| ATOM | 924 | CB | ALA | 120 | 13.182 | 11.624 | 15.248 | 1.00 8.68 | A |
| ATOM | 925 | C | ALA | 120 | 12.457 | 13.992 | 15.155 | 1.00 14.06 | A |
| ATOM | 926 | O | ALA | 120 | 13.087 | 14.631 | 15.993 | 1.00 13.64 | A |
| ATOM | 927 | N | ILE | 121 | 12.130 | 14.487 | 13.961 | 1.00 15.83 | A |
| ATOM | 928 | CA | ILE | 121 | 12.510 | 15.829 | 13.514 | 1.00 16.62 | A |
| ATOM | 929 | CB | ILE | 121 | 12.720 | 15.820 | 11.954 | 1.00 14.14 | A |
| ATOM | 930 | CG2 | ILE | 121 | 12.529 | 17.186 | 11.357 | 1.00 14.79 | A |
| ATOM | 931 | CG1 | ILE | 121 | 14.126 | 15.341 | 11.628 | 1.00 13.16 | A |
| ATOM | 932 | CD1 | ILE | 121 | 15.080 | 15.491 | 12.777 | 1.00 13.15 | A |
| ATOM | 933 | C | ILE | 121 | 11.499 | 16.916 | 13.907 | 1.00 17.84 | A |
| ATOM | 934 | O | ILE | 121 | 11.887 | 18.014 | 14.333 | 1.00 18.70 | A |
| ATOM | 935 | N | ASN | 122 | 10.213 | 16.603 | 13.767 | 1.00 18.22 | A |
| ATOM | 936 | CA | ASN | 122 | 9.144 | 17.537 | 14.079 | 1.00 20.53 | A |
| ATOM | 937 | CB | ASN | 122 | 9.164 | 17.927 | 15.562 | 1.00 19.72 | A |
| ATOM | 938 | CG | ASN | 122 | 7.954 | 18.761 | 15.967 | 1.00 18.32 | A |
| ATOM | 939 | OD1 | ASN | 122 | 6.902 | 18.700 | 15.333 | 1.00 15.61 | A |
| ATOM | 940 | ND2 | ASN | 122 | 8.109 | 19.550 | 17.025 | 1.00 17.45 | A |
| ATOM | 941 | C | ASN | 122 | 9.280 | 18.784 | 13.205 | 1.00 23.78 | A |
| ATOM | 942 | O | ASN | 122 | 9.154 | 19.919 | 13.684 | 1.00 26.55 | A |
| ATOM | 943 | N | GLY | 123 | 9.553 | 18.564 | 11.920 | 1.00 25.65 | A |
| ATOM | 944 | CA | GLY | 123 | 9.670 | 19.663 | 10.969 | 1.00 25.27 | A |
| ATOM | 945 | C | GLY | 123 | 10.977 | 20.428 | 10.860 | 1.00 24.57 | A |
| ATOM | 946 | O | GLY | 123 | 11.023 | 21.487 | 10.243 | 1.00 24.04 | A |
| ATOM | 947 | N | LEU | 124 | 12.043 | 19.914 | 11.450 | 1.00 24.25 | A |
| ATOM | 948 | CA | LEU | 124 | 13.309 | 20.607 | 11.368 | 1.00 25.19 | A |
| ATOM | 949 | CB | LEU | 124 | 13.963 | 20.703 | 12.738 | 1.00 23.50 | A |
| ATOM | 950 | CG | LEU | 124 | 15.246 | 21.532 | 12.711 | 1.00 22.78 | A |
| ATOM | 951 | CD1 | LEU | 124 | 15.001 | 22.839 | 11.979 | 1.00 23.39 | A |
| ATOM | 952 | CD2 | LEU | 124 | 15.701 | 21.784 | 14.129 | 1.00 24.20 | A |
| ATOM | 953 | C | LEU | 124 | 14.262 | 19.924 | 10.404 | 1.00 26.33 | A |
| ATOM | 954 | O | LEU | 124 | 14.865 | 18.900 | 10.729 | 1.00 29.25 | A |
| ATOM | 955 | N | TYR | 125 | 14.383 | 20.481 | 9.206 | 1.00 24.82 | A |
| ATOM | 956 | CA | TYR | 125 | 15.283 | 19.923 | 8.212 | 1.00 26.15 | A |
| ATOM | 957 | CB | TYR | 125 | 14.594 | 19.748 | 6.861 | 1.00 28.22 | A |
| ATOM | 958 | CG | TYR | 125 | 13.328 | 18.946 | 6.938 | 1.00 33.57 | A |
| ATOM | 959 | CD1 | TYR | 125 | 13.350 | 17.555 | 6.834 | 1.00 33.93 | A |
| ATOM | 960 | CE1 | TYR | 125 | 12.184 | 16.816 | 6.941 | 1.00 35.41 | A |
| ATOM | 961 | CD2 | TYR | 125 | 12.102 | 19.579 | 7.148 | 1.00 36.24 | A |
| ATOM | 962 | CE2 | TYR | 125 | 10.933 | 18.850 | 7.257 | 1.00 36.63 | A |
| ATOM | 963 | CZ | TYR | 125 | 10.981 | 17.472 | 7.153 | 1.00 37.06 | A |
| ATOM | 964 | OH | TYR | 125 | 9.813 | 16.759 | 7.270 | 1.00 42.14 | A |

Fig. 2A-16

| | | | | | | | | | |
|---|---|---|---|---|---|---|---|---|---|
| ATOM | 965 | C | TYR | 125 | 16.425 | 20.890 | 8.056 | 1.00 | 23.55 | A |
| ATOM | 966 | O | TYR | 125 | 16.323 | 22.049 | 8.442 | 1.00 | 25.49 | A |
| ATOM | 967 | N | PRO | 126 | 17.544 | 20.417 | 7.499 | 1.00 | 20.61 | A |
| ATOM | 968 | CD | PRO | 126 | 17.836 | 19.054 | 7.028 | 1.00 | 18.09 | A |
| ATOM | 969 | CA | PRO | 126 | 18.679 | 21.321 | 7.319 | 1.00 | 17.72 | A |
| ATOM | 970 | CB | PRO | 126 | 19.759 | 20.419 | 6.715 | 1.00 | 18.63 | A |
| ATOM | 971 | CG | PRO | 126 | 19.327 | 19.012 | 7.070 | 1.00 | 18.55 | A |
| ATOM | 972 | C | PRO | 126 | 18.293 | 22.473 | 6.388 | 1.00 | 16.44 | A |
| ATOM | 973 | O | PRO | 126 | 17.321 | 22.385 | 5.643 | 1.00 | 16.25 | A |
| ATOM | 974 | N | ASP | 127 | 19.040 | 23.565 | 6.453 | 1.00 | 15.85 | A |
| ATOM | 975 | CA | ASP | 127 | 18.776 | 24.695 | 5.583 | 1.00 | 16.90 | A |
| ATOM | 976 | CB | ASP | 127 | 19.154 | 26.002 | 6.279 | 1.00 | 18.60 | A |
| ATOM | 977 | CG | ASP | 127 | 17.970 | 26.642 | 6.984 | 1.00 | 21.07 | A |
| ATOM | 978 | OD1 | ASP | 127 | 16.959 | 26.964 | 6.306 | 1.00 | 22.71 | A |
| ATOM | 979 | OD2 | ASP | 127 | 18.047 | 26.820 | 8.219 | 1.00 | 18.29 | A |
| ATOM | 980 | C | ASP | 127 | 19.613 | 24.491 | 4.324 | 1.00 | 18.15 | A |
| ATOM | 981 | O | ASP | 127 | 19.393 | 25.151 | 3.310 | 1.00 | 19.18 | A |
| ATOM | 982 | N | LEU | 128 | 20.567 | 23.557 | 4.413 | 1.00 | 18.37 | A |
| ATOM | 983 | CA | LEU | 128 | 21.469 | 23.185 | 3.318 | 1.00 | 16.53 | A |
| ATOM | 984 | CB | LEU | 128 | 22.523 | 24.286 | 3.079 | 1.00 | 15.81 | A |
| ATOM | 985 | CG | LEU | 128 | 23.762 | 23.924 | 2.236 | 1.00 | 14.34 | A |
| ATOM | 986 | CD1 | LEU | 128 | 23.384 | 23.972 | 0.764 | 1.00 | 16.21 | A |
| ATOM | 987 | CD2 | LEU | 128 | 24.919 | 24.858 | 2.515 | 1.00 | 8.51 | A |
| ATOM | 988 | C | LEU | 128 | 22.174 | 21.884 | 3.707 | 1.00 | 16.96 | A |
| ATOM | 989 | O | LEU | 128 | 22.682 | 21.771 | 4.818 | 1.00 | 17.05 | A |
| ATOM | 990 | N | THR | 129 | 22.200 | 20.905 | 2.800 | 1.00 | 18.70 | A |
| ATOM | 991 | CA | THR | 129 | 22.861 | 19.614 | 3.062 | 1.00 | 19.58 | A |
| ATOM | 992 | CB | THR | 129 | 21.870 | 18.429 | 2.981 | 1.00 | 19.13 | A |
| ATOM | 993 | OG1 | THR | 129 | 21.084 | 18.375 | 4.178 | 1.00 | 21.93 | A |
| ATOM | 994 | CG2 | THR | 129 | 22.623 | 17.116 | 2.826 | 1.00 | 18.43 | A |
| ATOM | 995 | C | THR | 129 | 23.955 | 19.381 | 2.026 | 1.00 | 18.88 | A |
| ATOM | 996 | O | THR | 129 | 23.665 | 19.248 | 0.837 | 1.00 | 19.90 | A |
| ATOM | 997 | N | ILE | 130 | 25.204 | 19.317 | 2.472 | 1.00 | 17.60 | A |
| ATOM | 998 | CA | ILE | 130 | 26.334 | 19.119 | 1.561 | 1.00 | 16.04 | A |
| ATOM | 999 | CB | ILE | 130 | 27.640 | 19.749 | 2.148 | 1.00 | 16.79 | A |
| ATOM | 1000 | CG2 | ILE | 130 | 28.863 | 19.240 | 1.382 | 1.00 | 17.88 | A |
| ATOM | 1001 | CG1 | ILE | 130 | 27.563 | 21.283 | 2.111 | 1.00 | 17.22 | A |
| ATOM | 1002 | CD1 | ILE | 130 | 27.946 | 21.898 | 0.759 | 1.00 | 15.20 | A |
| ATOM | 1003 | C | ILE | 130 | 26.591 | 17.638 | 1.289 | 1.00 | 14.63 | A |
| ATOM | 1004 | O | ILE | 130 | 27.029 | 16.916 | 2.169 | 1.00 | 13.93 | A |
| ATOM | 1005 | N | TYR | 131 | 26.327 | 17.187 | 0.072 | 1.00 | 13.78 | A |
| ATOM | 1006 | CA | TYR | 131 | 26.568 | 15.796 | -0.261 | 1.00 | 14.00 | A |
| ATOM | 1007 | CB | TYR | 131 | 25.462 | 15.258 | -1.156 | 1.00 | 16.22 | A |
| ATOM | 1008 | CG | TYR | 131 | 25.706 | 13.816 | -1.517 | 1.00 | 18.24 | A |
| ATOM | 1009 | CD1 | TYR | 131 | 25.470 | 12.811 | -0.592 | 1.00 | 19.69 | A |
| ATOM | 1010 | CE1 | TYR | 131 | 25.728 | 11.480 | -0.893 | 1.00 | 20.72 | A |
| ATOM | 1011 | CD2 | TYR | 131 | 26.210 | 13.457 | -2.770 | 1.00 | 20.82 | A |
| ATOM | 1012 | CE2 | TYR | 131 | 26.471 | 12.123 | -3.083 | 1.00 | 20.33 | A |
| ATOM | 1013 | CZ | TYR | 131 | 26.226 | 11.141 | -2.133 | 1.00 | 20.01 | A |
| ATOM | 1014 | OH | TYR | 131 | 26.484 | 9.821 | -2.407 | 1.00 | 22.90 | A |
| ATOM | 1015 | C | TYR | 131 | 27.919 | 15.559 | -0.948 | 1.00 | 13.59 | A |
| ATOM | 1016 | O | TYR | 131 | 28.117 | 15.869 | -2.124 | 1.00 | 13.47 | A |
| ATOM | 1017 | N | LEU | 132 | 28.851 | 15.005 | -0.198 | 1.00 | 12.69 | A |
| ATOM | 1018 | CA | LEU | 132 | 30.158 | 14.712 | -0.736 | 1.00 | 14.00 | A |
| ATOM | 1019 | CB | LEU | 132 | 31.146 | 14.463 | 0.405 | 1.00 | 10.84 | A |
| ATOM | 1020 | CG | LEU | 132 | 31.323 | 15.688 | 1.306 | 1.00 | 11.12 | A |
| ATOM | 1021 | CD1 | LEU | 132 | 32.263 | 15.370 | 2.455 | 1.00 | 15.11 | A |

Fig. 2A-17

| ATOM | 1022 | CD2 | LEU | 132 | 31.883 | 16.845 | 0.487 | 1.00 | 10.94 | A |
|------|------|-----|-----|-----|--------|--------|-------|------|-------|---|
| ATOM | 1023 | C   | LEU | 132 | 30.033 | 13.489 | -1.638 | 1.00 | 16.10 | A |
| ATOM | 1024 | O   | LEU | 132 | 30.097 | 12.337 | -1.186 | 1.00 | 15.70 | A |
| ATOM | 1025 | N   | ASN | 133 | 29.823 | 13.766 | -2.920 | 1.00 | 16.64 | A |
| ATOM | 1026 | CA  | ASN | 133 | 29.679 | 12.745 | -3.955 | 1.00 | 16.26 | A |
| ATOM | 1027 | CB  | ASN | 133 | 29.146 | 13.401 | -5.222 | 1.00 | 15.66 | A |
| ATOM | 1028 | CG  | ASN | 133 | 28.209 | 12.515 | -5.977 | 1.00 | 15.86 | A |
| ATOM | 1029 | OD1 | ASN | 133 | 28.399 | 11.303 | -6.033 | 1.00 | 19.55 | A |
| ATOM | 1030 | ND2 | ASN | 133 | 27.178 | 13.105 | -6.562 | 1.00 | 18.53 | A |
| ATOM | 1031 | C   | ASN | 133 | 30.986 | 12.006 | -4.289 | 1.00 | 16.44 | A |
| ATOM | 1032 | O   | ASN | 133 | 31.804 | 12.495 | -5.070 | 1.00 | 16.93 | A |
| ATOM | 1033 | N   | VAL | 134 | 31.174 | 10.822 | -3.711 | 1.00 | 14.84 | A |
| ATOM | 1034 | CA  | VAL | 134 | 32.376 | 10.026 | -3.959 | 1.00 | 15.03 | A |
| ATOM | 1035 | CB  | VAL | 134 | 33.093 | 9.689  | -2.642 | 1.00 | 13.84 | A |
| ATOM | 1036 | CG1 | VAL | 134 | 32.673 | 8.311  | -2.147 | 1.00 | 15.51 | A |
| ATOM | 1037 | CG2 | VAL | 134 | 34.591 | 9.738  | -2.850 | 1.00 | 12.76 | A |
| ATOM | 1038 | C   | VAL | 134 | 32.027 | 8.723  | -4.679 | 1.00 | 16.69 | A |
| ATOM | 1039 | O   | VAL | 134 | 31.000 | 8.111  | -4.386 | 1.00 | 17.63 | A |
| ATOM | 1040 | N   | SER | 135 | 32.868 | 8.290  | -5.618 | 1.00 | 15.07 | A |
| ATOM | 1041 | CA  | SER | 135 | 32.584 | 7.059  | -6.348 | 1.00 | 15.37 | A |
| ATOM | 1042 | CB  | SER | 135 | 33.284 | 7.051  | -7.711 | 1.00 | 15.13 | A |
| ATOM | 1043 | OG  | SER | 135 | 34.680 | 6.860  | -7.562 | 1.00 | 19.69 | A |
| ATOM | 1044 | C   | SER | 135 | 33.069 | 5.894  | -5.530 | 1.00 | 15.42 | A |
| ATOM | 1045 | O   | SER | 135 | 34.021 | 6.034  | -4.761 | 1.00 | 16.48 | A |
| ATOM | 1046 | N   | ALA | 136 | 32.422 | 4.745  | -5.703 | 1.00 | 15.08 | A |
| ATOM | 1047 | CA  | ALA | 136 | 32.785 | 3.539  | -4.973 | 1.00 | 15.69 | A |
| ATOM | 1048 | CB  | ALA | 136 | 32.012 | 2.351  | -5.517 | 1.00 | 13.23 | A |
| ATOM | 1049 | C   | ALA | 136 | 34.282 | 3.232  | -4.982 | 1.00 | 16.27 | A |
| ATOM | 1050 | O   | ALA | 136 | 34.835 | 2.849  | -3.940 | 1.00 | 17.62 | A |
| ATOM | 1051 | N   | GLU | 137 | 34.936 | 3.417  | -6.136 | 1.00 | 16.13 | A |
| ATOM | 1052 | CA  | GLU | 137 | 36.373 | 3.128  | -6.295 | 1.00 | 16.92 | A |
| ATOM | 1053 | CB  | GLU | 137 | 36.769 | 3.211  | -7.761 | 1.00 | 19.08 | A |
| ATOM | 1054 | CG  | GLU | 137 | 36.099 | 2.193  | -8.627 | 1.00 | 21.24 | A |
| ATOM | 1055 | CD  | GLU | 137 | 34.697 | 2.606  | -9.026 | 1.00 | 26.03 | A |
| ATOM | 1056 | OE1 | GLU | 137 | 34.254 | 3.703  | -8.607 | 1.00 | 26.26 | A |
| ATOM | 1057 | OE2 | GLU | 137 | 34.050 | 1.830  | -9.762 | 1.00 | 24.36 | A |
| ATOM | 1058 | C   | GLU | 137 | 37.329 | 4.010  | -5.519 | 1.00 | 17.18 | A |
| ATOM | 1059 | O   | GLU | 137 | 38.293 | 3.529  | -4.914 | 1.00 | 18.42 | A |
| ATOM | 1060 | N   | VAL | 138 | 37.102 | 5.315  | -5.592 | 1.00 | 16.65 | A |
| ATOM | 1061 | CA  | VAL | 138 | 37.930 | 6.286  | -4.880 | 1.00 | 13.99 | A |
| ATOM | 1062 | CB  | VAL | 138 | 37.571 | 7.729  | -5.317 | 1.00 | 12.36 | A |
| ATOM | 1063 | CG1 | VAL | 138 | 38.315 | 8.722  | -4.480 | 1.00 | 7.64  | A |
| ATOM | 1064 | CG2 | VAL | 138 | 37.876 | 7.909  | -6.812 | 1.00 | 11.17 | A |
| ATOM | 1065 | C   | VAL | 138 | 37.650 | 6.107  | -3.388 | 1.00 | 12.75 | A |
| ATOM | 1066 | O   | VAL | 138 | 38.566 | 6.069  | -2.577 | 1.00 | 12.84 | A |
| ATOM | 1067 | N   | GLY | 139 | 36.372 | 5.979  | -3.040 | 1.00 | 12.35 | A |
| ATOM | 1068 | CA  | GLY | 139 | 35.998 | 5.790  | -1.650 | 1.00 | 13.46 | A |
| ATOM | 1069 | C   | GLY | 139 | 36.696 | 4.593  | -1.031 | 1.00 | 12.84 | A |
| ATOM | 1070 | O   | GLY | 139 | 37.247 | 4.681  | 0.071  | 1.00 | 11.91 | A |
| ATOM | 1071 | N   | ARG | 140 | 36.675 | 3.469  | -1.743 | 1.00 | 14.34 | A |
| ATOM | 1072 | CA  | ARG | 140 | 37.314 | 2.239  | -1.268 | 1.00 | 15.31 | A |
| ATOM | 1073 | CB  | ARG | 140 | 37.279 | 1.164  | -2.357 | 1.00 | 14.32 | A |
| ATOM | 1074 | CG  | ARG | 140 | 38.142 | -0.052 | -2.045 | 1.00 | 13.59 | A |
| ATOM | 1075 | CD  | ARG | 140 | 38.881 | -0.509 | -3.270 | 1.00 | 15.36 | A |
| ATOM | 1076 | NE  | ARG | 140 | 38.006 | -0.522 | -4.439 | 1.00 | 16.56 | A |
| ATOM | 1077 | CZ  | ARG | 140 | 38.406 | -0.294 | -5.685 | 1.00 | 14.11 | A |
| ATOM | 1078 | NH1 | ARG | 140 | 39.684 | -0.029 | -5.942 | 1.00 | 10.53 | A |

Fig. 2A-18

| | | | | | | | | | |
|---|---|---|---|---|---|---|---|---|---|
| ATOM | 1079 | NH2 | ARG | 140 | 37.520 | -0.316 | -6.676 | 1.00 10.78 | A |
| ATOM | 1080 | C | ARG | 140 | 38.762 | 2.472 | -0.878 | 1.00 17.87 | A |
| ATOM | 1081 | O | ARG | 140 | 39.179 | 2.155 | 0.239 | 1.00 18.73 | A |
| ATOM | 1082 | N | GLU | 141 | 39.520 | 3.020 | -1.831 | 1.00 18.85 | A |
| ATOM | 1083 | CA | GLU | 141 | 40.926 | 3.318 | -1.651 | 1.00 19.21 | A |
| ATOM | 1084 | CB | GLU | 141 | 41.460 | 4.071 | -2.871 | 1.00 19.92 | A |
| ATOM | 1085 | CG | GLU | 141 | 41.464 | 3.264 | -4.159 | 1.00 20.18 | A |
| ATOM | 1086 | CD | GLU | 141 | 41.996 | 1.850 | -3.965 | 1.00 23.75 | A |
| ATOM | 1087 | OE1 | GLU | 141 | 41.344 | 0.894 | -4.450 | 1.00 25.20 | A |
| ATOM | 1088 | OE2 | GLU | 141 | 43.063 | 1.678 | -3.332 | 1.00 23.49 | A |
| ATOM | 1089 | C | GLU | 141 | 41.169 | 4.131 | -0.389 | 1.00 22.21 | A |
| ATOM | 1090 | O | GLU | 141 | 42.163 | 3.915 | 0.311 | 1.00 24.64 | A |
| ATOM | 1091 | N | ARG | 142 | 40.258 | 5.057 | -0.084 | 1.00 22.42 | A |
| ATOM | 1092 | CA | ARG | 142 | 40.401 | 5.890 | 1.114 | 1.00 21.25 | A |
| ATOM | 1093 | CB | ARG | 142 | 39.525 | 7.137 | 1.013 | 1.00 20.34 | A |
| ATOM | 1094 | CG | ARG | 142 | 39.897 | 8.047 | -0.125 | 1.00 20.08 | A |
| ATOM | 1095 | CD | ARG | 142 | 39.623 | 9.493 | 0.226 | 1.00 20.93 | A |
| ATOM | 1096 | NE | ARG | 142 | 38.366 | 9.932 | -0.355 | 1.00 20.53 | A |
| ATOM | 1097 | CZ | ARG | 142 | 38.253 | 10.835 | -1.319 | 1.00 17.90 | A |
| ATOM | 1098 | NH1 | ARG | 142 | 39.328 | 11.417 | -1.827 | 1.00 14.20 | A |
| ATOM | 1099 | NH2 | ARG | 142 | 37.054 | 11.120 | -1.797 | 1.00 18.04 | A |
| ATOM | 1100 | C | ARG | 142 | 40.039 | 5.141 | 2.389 | 1.00 21.11 | A |
| ATOM | 1101 | O | ARG | 142 | 40.697 | 5.301 | 3.410 | 1.00 19.58 | A |
| ATOM | 1102 | N | ILE | 143 | 38.988 | 4.332 | 2.333 | 1.00 22.51 | A |
| ATOM | 1103 | CA | ILE | 143 | 38.568 | 3.568 | 3.503 | 1.00 23.25 | A |
| ATOM | 1104 | CB | ILE | 143 | 37.411 | 2.621 | 3.155 | 1.00 23.18 | A |
| ATOM | 1105 | CG2 | ILE | 143 | 37.358 | 1.480 | 4.142 | 1.00 22.70 | A |
| ATOM | 1106 | CG1 | ILE | 143 | 36.091 | 3.389 | 3.120 | 1.00 22.29 | A |
| ATOM | 1107 | CD1 | ILE | 143 | 35.062 | 2.778 | 2.182 | 1.00 18.17 | A |
| ATOM | 1108 | C | ILE | 143 | 39.756 | 2.736 | 3.959 | 1.00 24.57 | A |
| ATOM | 1109 | O | ILE | 143 | 39.989 | 2.561 | 5.152 | 1.00 25.38 | A |
| ATOM | 1110 | N | ILE | 144 | 40.510 | 2.235 | 2.984 | 1.00 26.98 | A |
| ATOM | 1111 | CA | ILE | 144 | 41.686 | 1.408 | 3.243 | 1.00 27.37 | A |
| ATOM | 1112 | CB | ILE | 144 | 42.203 | 0.782 | 1.921 | 1.00 27.49 | A |
| ATOM | 1113 | CG2 | ILE | 144 | 43.384 | -0.149 | 2.198 | 1.00 28.27 | A |
| ATOM | 1114 | CG1 | ILE | 144 | 41.062 | 0.016 | 1.238 | 1.00 27.56 | A |
| ATOM | 1115 | CD1 | ILE | 144 | 41.371 | -0.449 | -0.183 | 1.00 25.30 | A |
| ATOM | 1116 | C | ILE | 144 | 42.823 | 2.180 | 3.919 | 1.00 27.68 | A |
| ATOM | 1117 | O | ILE | 144 | 43.629 | 2.836 | 3.254 | 1.00 29.54 | A |
| ATOM | 1118 | N | ASP | 154 | 39.699 | -4.314 | 1.391 | 1.00 51.55 | A |
| ATOM | 1119 | CA | ASP | 154 | 38.523 | -5.036 | 1.863 | 1.00 51.78 | A |
| ATOM | 1120 | CB | ASP | 154 | 37.385 | -4.059 | 2.230 | 1.00 51.96 | A |
| ATOM | 1121 | CG | ASP | 154 | 37.754 | -2.589 | 2.016 | 1.00 51.95 | A |
| ATOM | 1122 | OD1 | ASP | 154 | 38.798 | -2.137 | 2.546 | 1.00 51.92 | A |
| ATOM | 1123 | OD2 | ASP | 154 | 36.988 | -1.874 | 1.330 | 1.00 50.45 | A |
| ATOM | 1124 | C | ASP | 154 | 38.000 | -6.033 | 0.832 | 1.00 51.96 | A |
| ATOM | 1125 | O | ASP | 154 | 38.590 | -6.199 | -0.236 | 1.00 53.09 | A |
| ATOM | 1126 | N | GLN | 155 | 36.892 | -6.699 | 1.159 | 1.00 50.76 | A |
| ATOM | 1127 | CA | GLN | 155 | 36.277 | -7.663 | 0.251 | 1.00 51.32 | A |
| ATOM | 1128 | CB | GLN | 155 | 36.743 | -9.086 | 0.590 | 1.00 52.85 | A |
| ATOM | 1129 | CG | GLN | 155 | 38.116 | -9.461 | 0.005 | 1.00 56.38 | A |
| ATOM | 1130 | CD | GLN | 155 | 38.077 | -9.789 | -1.486 | 1.00 59.01 | A |
| ATOM | 1131 | OE1 | GLN | 155 | 39.120 | -9.959 | -2.131 | 1.00 61.97 | A |
| ATOM | 1132 | NE2 | GLN | 155 | 36.876 | -9.882 | -2.037 | 1.00 59.84 | A |
| ATOM | 1133 | C | GLN | 155 | 34.742 | -7.555 | 0.297 | 1.00 50.34 | A |
| ATOM | 1134 | O | GLN | 155 | 34.211 | -6.458 | 0.416 | 1.00 50.66 | A |
| ATOM | 1135 | N | GLU | 156 | 34.034 | -8.680 | 0.207 | 1.00 48.71 | A |

Fig. 2A-19

```
ATOM   1136  CA   GLU   156      32.563   -8.684    0.211  1.00 47.47      A
ATOM   1137  CB   GLU   156      32.044  -10.108    0.439  1.00 49.49      A
ATOM   1138  CG   GLU   156      32.365  -11.046   -0.713  1.00 52.78      A
ATOM   1139  CD   GLU   156      33.512  -10.522   -1.559  1.00 55.94      A
ATOM   1140  OE1  GLU   156      34.667  -10.931   -1.304  1.00 58.46      A
ATOM   1141  OE2  GLU   156      33.263   -9.692   -2.463  1.00 56.30      A
ATOM   1142  C    GLU   156      31.909   -7.718    1.199  1.00 45.09      A
ATOM   1143  O    GLU   156      30.730   -7.405    1.088  1.00 44.40      A
ATOM   1144  N    ASP   157      32.686   -7.244    2.162  1.00 45.02      A
ATOM   1145  CA   ASP   157      32.207   -6.290    3.165  1.00 42.71      A
ATOM   1146  CB   ASP   157      33.136   -6.309    4.400  1.00 44.86      A
ATOM   1147  CG   ASP   157      33.787   -7.687    4.647  1.00 45.91      A
ATOM   1148  OD1  ASP   157      34.620   -8.129    3.823  1.00 46.98      A
ATOM   1149  OD2  ASP   157      33.471   -8.325    5.678  1.00 46.41      A
ATOM   1150  C    ASP   157      32.242   -4.893    2.522  1.00 39.90      A
ATOM   1151  O    ASP   157      32.183   -3.868    3.201  1.00 39.56      A
ATOM   1152  N    LEU   158      32.326   -4.890    1.197  1.00 35.08      A
ATOM   1153  CA   LEU   158      32.441   -3.682    0.400  1.00 30.57      A
ATOM   1154  CB   LEU   158      33.700   -3.824   -0.445  1.00 32.56      A
ATOM   1155  CG   LEU   158      34.154   -2.869   -1.537  1.00 34.63      A
ATOM   1156  CD1  LEU   158      35.668   -2.744   -1.452  1.00 32.54      A
ATOM   1157  CD2  LEU   158      33.752   -3.402   -2.905  1.00 38.08      A
ATOM   1158  C    LEU   158      31.224   -3.461   -0.486  1.00 29.36      A
ATOM   1159  O    LEU   158      31.121   -2.456   -1.198  1.00 28.33      A
ATOM   1160  N    LYS   159      30.302   -4.413   -0.448  1.00 26.45      A
ATOM   1161  CA   LYS   159      29.086   -4.310   -1.231  1.00 23.70      A
ATOM   1162  CB   LYS   159      28.536   -5.707   -1.516  1.00 26.09      A
ATOM   1163  CG   LYS   159      27.530   -5.745   -2.644  1.00 27.62      A
ATOM   1164  CD   LYS   159      26.163   -6.044   -2.096  1.00 30.02      A
ATOM   1165  CE   LYS   159      25.084   -5.718   -3.101  1.00 33.24      A
ATOM   1166  NZ   LYS   159      23.747   -5.670   -2.434  1.00 35.50      A
ATOM   1167  C    LYS   159      28.066   -3.462   -0.467  1.00 21.27      A
ATOM   1168  O    LYS   159      27.104   -2.966   -1.045  1.00 16.96      A
ATOM   1169  N    PHE   160      28.282   -3.304    0.837  1.00 20.82      A
ATOM   1170  CA   PHE   160      27.406   -2.480    1.664  1.00 21.15      A
ATOM   1171  CB   PHE   160      27.769   -2.642    3.145  1.00 18.20      A
ATOM   1172  CG   PHE   160      26.905   -1.833    4.091  1.00 18.88      A
ATOM   1173  CD1  PHE   160      25.561   -2.147    4.284  1.00 17.68      A
ATOM   1174  CD2  PHE   160      27.453   -0.780    4.827  1.00 19.06      A
ATOM   1175  CE1  PHE   160      24.774   -1.427    5.208  1.00 18.90      A
ATOM   1176  CE2  PHE   160      26.678   -0.053    5.750  1.00 19.17      A
ATOM   1177  CZ   PHE   160      25.332   -0.379    5.937  1.00 17.69      A
ATOM   1178  C    PHE   160      27.611   -1.025    1.225  1.00 22.85      A
ATOM   1179  O    PHE   160      26.653   -0.322    0.888  1.00 23.35      A
ATOM   1180  N    HIS   161      28.874   -0.595    1.204  1.00 24.22      A
ATOM   1181  CA   HIS   161      29.243    0.766    0.802  1.00 25.47      A
ATOM   1182  CB   HIS   161      30.759    0.928    0.787  1.00 27.63      A
ATOM   1183  CG   HIS   161      31.419    0.384    2.000  1.00 32.09      A
ATOM   1184  CD2  HIS   161      30.933   -0.316    3.049  1.00 34.82      A
ATOM   1185  ND1  HIS   161      32.776    0.550    2.256  1.00 34.79      A
ATOM   1186  CE1  HIS   161      33.071   -0.023    3.396  1.00 36.30      A
ATOM   1187  NE2  HIS   161      31.982   -0.559    3.908  1.00 36.79      A
ATOM   1188  C    HIS   161      28.700    1.125   -0.564  1.00 24.44      A
ATOM   1189  O    HIS   161      28.241    2.240   -0.773  1.00 25.74      A
ATOM   1190  N    GLU   162      28.756    0.192   -1.504  1.00 22.83      A
ATOM   1191  CA   GLU   162      28.241    0.474   -2.830  1.00 22.65      A
ATOM   1192  CB   GLU   162      28.703   -0.600   -3.818  1.00 23.31      A
```

Fig. 2A-20

| | | | | | | | | | |
|---|---|---|---|---|---|---|---|---|---|
| ATOM | 1193 | CG | GLU | 162 | 27.748 | -1.770 | -3.975 | 1.00 28.61 | A |
| ATOM | 1194 | CD | GLU | 162 | 28.170 | -2.730 | -5.082 | 1.00 30.31 | A |
| ATOM | 1195 | OE1 | GLU | 162 | 27.343 | -3.049 | -5.969 | 1.00 26.26 | A |
| ATOM | 1196 | OE2 | GLU | 162 | 29.341 | -3.163 | -5.062 | 1.00 33.07 | A |
| ATOM | 1197 | C | GLU | 162 | 26.718 | 0.545 | -2.769 | 1.00 22.17 | A |
| ATOM | 1198 | O | GLU | 162 | 26.085 | 1.159 | -3.624 | 1.00 22.37 | A |
| ATOM | 1199 | N | LYS | 163 | 26.137 | -0.076 | -1.744 | 1.00 21.89 | A |
| ATOM | 1200 | CA | LYS | 163 | 24.684 | -0.089 | -1.549 | 1.00 21.28 | A |
| ATOM | 1201 | CB | LYS | 163 | 24.277 | -1.234 | -0.624 | 1.00 24.16 | A |
| ATOM | 1202 | CG | LYS | 163 | 22.849 | -1.705 | -0.818 | 1.00 27.09 | A |
| ATOM | 1203 | CD | LYS | 163 | 22.742 | -3.203 | -0.585 | 1.00 28.27 | A |
| ATOM | 1204 | CE | LYS | 163 | 21.319 | -3.703 | -0.793 | 1.00 31.58 | A |
| ATOM | 1205 | NZ | LYS | 163 | 20.331 | -2.614 | -1.060 | 1.00 32.32 | A |
| ATOM | 1206 | C | LYS | 163 | 24.231 | 1.218 | -0.923 | 1.00 21.34 | A |
| ATOM | 1207 | O | LYS | 163 | 23.147 | 1.739 | -1.216 | 1.00 16.85 | A |
| ATOM | 1208 | N | VAL | 164 | 25.080 | 1.721 | -0.032 | 1.00 21.65 | A |
| ATOM | 1209 | CA | VAL | 164 | 24.835 | 2.973 | 0.661 | 1.00 20.57 | A |
| ATOM | 1210 | CB | VAL | 164 | 25.982 | 3.301 | 1.637 | 1.00 20.82 | A |
| ATOM | 1211 | CG1 | VAL | 164 | 25.949 | 4.796 | 1.986 | 1.00 20.62 | A |
| ATOM | 1212 | CG2 | VAL | 164 | 25.892 | 2.418 | 2.879 | 1.00 14.98 | A |
| ATOM | 1213 | C | VAL | 164 | 24.797 | 4.075 | -0.386 | 1.00 20.01 | A |
| ATOM | 1214 | O | VAL | 164 | 23.862 | 4.880 | -0.432 | 1.00 18.78 | A |
| ATOM | 1215 | N | ILE | 165 | 25.845 | 4.105 | -1.206 | 1.00 20.78 | A |
| ATOM | 1216 | CA | ILE | 165 | 25.985 | 5.092 | -2.261 | 1.00 20.28 | A |
| ATOM | 1217 | CB | ILE | 165 | 27.198 | 4.782 | -3.149 | 1.00 19.12 | A |
| ATOM | 1218 | CG2 | ILE | 165 | 27.160 | 5.633 | -4.397 | 1.00 21.64 | A |
| ATOM | 1219 | CG1 | ILE | 165 | 28.487 | 5.086 | -2.389 | 1.00 17.77 | A |
| ATOM | 1220 | CD1 | ILE | 165 | 29.739 | 4.834 | -3.191 | 1.00 17.87 | A |
| ATOM | 1221 | C | ILE | 165 | 24.716 | 5.118 | -3.099 | 1.00 22.78 | A |
| ATOM | 1222 | O | ILE | 165 | 24.224 | 6.188 | -3.459 | 1.00 23.05 | A |
| ATOM | 1223 | N | GLU | 166 | 24.176 | 3.937 | -3.387 | 1.00 24.97 | A |
| ATOM | 1224 | CA | GLU | 166 | 22.939 | 3.827 | -4.159 | 1.00 27.18 | A |
| ATOM | 1225 | CB | GLU | 166 | 22.584 | 2.356 | -4.376 | 1.00 31.42 | A |
| ATOM | 1226 | CG | GLU | 166 | 23.712 | 1.483 | -4.893 | 1.00 37.18 | A |
| ATOM | 1227 | CD | GLU | 166 | 23.230 | 0.093 | -5.321 | 1.00 41.68 | A |
| ATOM | 1228 | OE1 | GLU | 166 | 24.027 | -0.659 | -5.932 | 1.00 41.28 | A |
| ATOM | 1229 | OE2 | GLU | 166 | 22.053 | -0.250 | -5.044 | 1.00 42.53 | A |
| ATOM | 1230 | C | GLU | 166 | 21.750 | 4.521 | -3.466 | 1.00 27.12 | A |
| ATOM | 1231 | O | GLU | 166 | 20.922 | 5.151 | -4.125 | 1.00 26.40 | A |
| ATOM | 1232 | N | GLY | 167 | 21.657 | 4.383 | -2.144 | 1.00 26.20 | A |
| ATOM | 1233 | CA | GLY | 167 | 20.567 | 5.013 | -1.409 | 1.00 23.21 | A |
| ATOM | 1234 | C | GLY | 167 | 20.675 | 6.524 | -1.384 | 1.00 20.91 | A |
| ATOM | 1235 | O | GLY | 167 | 19.678 | 7.245 | -1.429 | 1.00 19.44 | A |
| ATOM | 1236 | N | TYR | 168 | 21.910 | 6.995 | -1.315 | 1.00 21.26 | A |
| ATOM | 1237 | CA | TYR | 168 | 22.206 | 8.415 | -1.302 | 1.00 21.88 | A |
| ATOM | 1238 | CB | TYR | 168 | 23.694 | 8.594 | -1.044 | 1.00 19.28 | A |
| ATOM | 1239 | CG | TYR | 168 | 24.031 | 8.806 | 0.404 | 1.00 16.54 | A |
| ATOM | 1240 | CD1 | TYR | 168 | 25.071 | 8.109 | 1.008 | 1.00 17.79 | A |
| ATOM | 1241 | CE1 | TYR | 168 | 25.424 | 8.352 | 2.332 | 1.00 20.01 | A |
| ATOM | 1242 | CD2 | TYR | 168 | 23.345 | 9.748 | 1.160 | 1.00 19.07 | A |
| ATOM | 1243 | CE2 | TYR | 168 | 23.683 | 10.004 | 2.489 | 1.00 18.60 | A |
| ATOM | 1244 | CZ | TYR | 168 | 24.725 | 9.305 | 3.072 | 1.00 20.26 | A |
| ATOM | 1245 | OH | TYR | 168 | 25.067 | 9.563 | 4.382 | 1.00 21.55 | A |
| ATOM | 1246 | C | TYR | 168 | 21.810 | 9.070 | -2.632 | 1.00 23.66 | A |
| ATOM | 1247 | O | TYR | 168 | 21.275 | 10.179 | -2.650 | 1.00 26.01 | A |
| ATOM | 1248 | N | GLN | 169 | 22.078 | 8.380 | -3.741 | 1.00 25.06 | A |
| ATOM | 1249 | CA | GLN | 169 | 21.740 | 8.884 | -5.070 | 1.00 25.35 | A |

Fig. 2A-21

```
ATOM   1250  CB   GLN  169      22.184   7.905  -6.155  1.00 26.00      A
ATOM   1251  CG   GLN  169      23.626   7.463  -6.053  1.00 29.17      A
ATOM   1252  CD   GLN  169      24.615   8.593  -6.299  1.00 29.94      A
ATOM   1253  OE1  GLN  169      25.820   8.429  -6.095  1.00 29.50      A
ATOM   1254  NE2  GLN  169      24.108   9.749  -6.737  1.00 28.14      A
ATOM   1255  C    GLN  169      20.239   9.066  -5.187  1.00 26.60      A
ATOM   1256  O    GLN  169      19.767  10.051  -5.738  1.00 27.89      A
ATOM   1257  N    GLU  170      19.494   8.098  -4.671  1.00 26.92      A
ATOM   1258  CA   GLU  170      18.040   8.143  -4.714  1.00 28.01      A
ATOM   1259  CB   GLU  170      17.468   6.844  -4.171  1.00 29.99      A
ATOM   1260  CG   GLU  170      16.121   6.500  -4.744  1.00 35.53      A
ATOM   1261  CD   GLU  170      16.204   5.361  -5.728  1.00 39.43      A
ATOM   1262  OE1  GLU  170      15.566   4.317  -5.483  1.00 42.68      A
ATOM   1263  OE2  GLU  170      16.912   5.506  -6.748  1.00 42.38      A
ATOM   1264  C    GLU  170      17.501   9.302  -3.892  1.00 27.62      A
ATOM   1265  O    GLU  170      16.591  10.012  -4.319  1.00 26.01      A
ATOM   1266  N    ILE  171      18.075   9.476  -2.703  1.00 28.74      A
ATOM   1267  CA   ILE  171      17.682  10.536  -1.780  1.00 27.14      A
ATOM   1268  CB   ILE  171      18.521  10.483  -0.499  1.00 26.26      A
ATOM   1269  CG2  ILE  171      18.247  11.703   0.342  1.00 26.85      A
ATOM   1270  CG1  ILE  171      18.202   9.215   0.287  1.00 25.90      A
ATOM   1271  CD1  ILE  171      19.322   8.780   1.191  1.00 25.67      A
ATOM   1272  C    ILE  171      17.879  11.906  -2.410  1.00 28.17      A
ATOM   1273  O    ILE  171      16.912  12.641  -2.637  1.00 28.24      A
ATOM   1274  N    ILE  172      19.139  12.244  -2.680  1.00 27.45      A
ATOM   1275  CA   ILE  172      19.495  13.520  -3.291  1.00 25.70      A
ATOM   1276  CB   ILE  172      21.019  13.624  -3.504  1.00 26.14      A
ATOM   1277  CG2  ILE  172      21.749  13.012  -2.326  1.00 24.71      A
ATOM   1278  CG1  ILE  172      21.415  12.889  -4.790  1.00 29.17      A
ATOM   1279  CD1  ILE  172      22.906  12.768  -5.016  1.00 28.48      A
ATOM   1280  C    ILE  172      18.797  13.657  -4.639  1.00 24.52      A
ATOM   1281  O    ILE  172      18.259  14.715  -4.963  1.00 26.19      A
ATOM   1282  N    PHE  179      19.876  19.984  -2.975  1.00 42.30      A
ATOM   1283  CA   PHE  179      21.092  19.709  -2.209  1.00 38.28      A
ATOM   1284  CB   PHE  179      21.397  18.199  -2.157  1.00 36.78      A
ATOM   1285  CG   PHE  179      20.373  17.380  -1.412  1.00 34.19      A
ATOM   1286  CD1  PHE  179      19.165  17.052  -2.012  1.00 33.67      A
ATOM   1287  CD2  PHE  179      20.634  16.909  -0.129  1.00 31.49      A
ATOM   1288  CE1  PHE  179      18.229  16.263  -1.347  1.00 33.59      A
ATOM   1289  CE2  PHE  179      19.707  16.121   0.543  1.00 32.04      A
ATOM   1290  CZ   PHE  179      18.500  15.797  -0.067  1.00 32.17      A
ATOM   1291  C    PHE  179      22.231  20.384  -2.937  1.00 36.53      A
ATOM   1292  O    PHE  179      22.021  21.059  -3.950  1.00 37.28      A
ATOM   1293  N    LYS  180      23.433  20.178  -2.417  1.00 34.55      A
ATOM   1294  CA   LYS  180      24.644  20.711  -3.003  1.00 32.09      A
ATOM   1295  CB   LYS  180      25.148  21.909  -2.194  1.00 33.81      A
ATOM   1296  CG   LYS  180      24.267  23.151  -2.328  1.00 35.25      A
ATOM   1297  CD   LYS  180      23.799  23.308  -3.767  1.00 37.60      A
ATOM   1298  CE   LYS  180      22.706  24.354  -3.928  1.00 40.95      A
ATOM   1299  NZ   LYS  180      22.097  24.264  -5.300  1.00 42.21      A
ATOM   1300  C    LYS  180      25.642  19.565  -2.959  1.00 31.09      A
ATOM   1301  O    LYS  180      26.255  19.286  -1.925  1.00 29.48      A
ATOM   1302  N    SER  181      25.775  18.874  -4.083  1.00 30.63      A
ATOM   1303  CA   SER  181      26.695  17.760  -4.157  1.00 30.95      A
ATOM   1304  CB   SER  181      26.248  16.771  -5.234  1.00 31.00      A
ATOM   1305  OG   SER  181      27.097  16.850  -6.360  1.00 35.32      A
ATOM   1306  C    SER  181      28.077  18.287  -4.485  1.00 30.42      A
```

Fig. 2A-22

```
ATOM  1307  O    SER  181      28.219  19.175  -5.327  1.00  29.79      A
ATOM  1308  N    VAL  182      29.083  17.743  -3.808  1.00  29.93      A
ATOM  1309  CA   VAL  182      30.473  18.132  -4.030  1.00  28.86      A
ATOM  1310  CB   VAL  182      31.156  18.595  -2.713  1.00  29.85      A
ATOM  1311  CG1  VAL  182      32.649  18.700  -2.914  1.00  30.06      A
ATOM  1312  CG2  VAL  182      30.589  19.930  -2.258  1.00  29.11      A
ATOM  1313  C    VAL  182      31.213  16.908  -4.563  1.00  27.74      A
ATOM  1314  O    VAL  182      30.916  15.785  -4.162  1.00  24.75      A
ATOM  1315  N    ASN  183      32.157  17.116  -5.474  1.00  27.76      A
ATOM  1316  CA   ASN  183      32.888  15.992  -6.020  1.00  28.16      A
ATOM  1317  CB   ASN  183      33.480  16.320  -7.387  1.00  28.79      A
ATOM  1318  CG   ASN  183      34.051  15.091  -8.069  1.00  29.95      A
ATOM  1319  OD1  ASN  183      34.307  14.078  -7.422  1.00  30.78      A
ATOM  1320  ND2  ASN  183      34.244  15.171  -9.382  1.00  33.54      A
ATOM  1321  C    ASN  183      33.999  15.587  -5.076  1.00  28.75      A
ATOM  1322  O    ASN  183      35.077  16.177  -5.081  1.00  29.79      A
ATOM  1323  N    ALA  184      33.730  14.584  -4.250  1.00  30.37      A
ATOM  1324  CA   ALA  184      34.724  14.108  -3.301  1.00  30.80      A
ATOM  1325  CB   ALA  184      34.034  13.424  -2.123  1.00  28.89      A
ATOM  1326  C    ALA  184      35.701  13.142  -3.989  1.00  31.72      A
ATOM  1327  O    ALA  184      36.727  12.784  -3.422  1.00  32.16      A
ATOM  1328  N    ASP  185      35.372  12.743  -5.219  1.00  32.12      A
ATOM  1329  CA   ASP  185      36.190  11.828  -6.014  1.00  33.21      A
ATOM  1330  CB   ASP  185      35.454  11.460  -7.300  1.00  35.05      A
ATOM  1331  CG   ASP  185      35.011  10.024  -7.332  1.00  35.98      A
ATOM  1332  OD1  ASP  185      34.308   9.662  -8.302  1.00  37.72      A
ATOM  1333  OD2  ASP  185      35.355   9.263  -6.403  1.00  37.58      A
ATOM  1334  C    ASP  185      37.513  12.480  -6.397  1.00  33.12      A
ATOM  1335  O    ASP  185      38.332  11.892  -7.095  1.00  32.48      A
ATOM  1336  N    GLN  186      37.699  13.711  -5.947  1.00  33.87      A
ATOM  1337  CA   GLN  186      38.900  14.458  -6.266  1.00  33.88      A
ATOM  1338  CB   GLN  186      38.488  15.757  -6.963  1.00  32.23      A
ATOM  1339  CG   GLN  186      38.302  16.951  -6.072  1.00  32.07      A
ATOM  1340  CD   GLN  186      37.618  18.102  -6.796  1.00  32.19      A
ATOM  1341  OE1  GLN  186      36.687  18.712  -6.276  1.00  31.67      A
ATOM  1342  NE2  GLN  186      38.080  18.399  -8.005  1.00  33.15      A
ATOM  1343  C    GLN  186      39.857  14.703  -5.085  1.00  35.39      A
ATOM  1344  O    GLN  186      39.548  14.347  -3.946  1.00  35.72      A
ATOM  1345  N    PRO  187      41.041  15.295  -5.379  1.00  37.46      A
ATOM  1346  CD   PRO  187      41.373  15.651  -6.769  1.00  39.38      A
ATOM  1347  CA   PRO  187      42.150  15.651  -4.483  1.00  38.69      A
ATOM  1348  CB   PRO  187      42.856  16.790  -5.229  1.00  38.86      A
ATOM  1349  CG   PRO  187      42.620  16.495  -6.651  1.00  38.62      A
ATOM  1350  C    PRO  187      41.941  15.999  -3.015  1.00  39.64      A
ATOM  1351  O    PRO  187      42.921  16.046  -2.285  1.00  41.58      A
ATOM  1352  N    LEU  188      40.709  16.247  -2.575  1.00  40.20      A
ATOM  1353  CA   LEU  188      40.453  16.566  -1.169  1.00  41.35      A
ATOM  1354  CB   LEU  188      41.225  15.608  -0.252  1.00  41.96      A
ATOM  1355  CG   LEU  188      40.611  15.211   1.090  1.00  43.04      A
ATOM  1356  CD1  LEU  188      39.170  14.766   0.912  1.00  41.72      A
ATOM  1357  CD2  LEU  188      41.451  14.088   1.681  1.00  44.00      A
ATOM  1358  C    LEU  188      40.804  18.009  -0.799  1.00  41.41      A
ATOM  1359  O    LEU  188      40.077  18.666  -0.046  1.00  41.06      A
ATOM  1360  N    GLU  189      41.929  18.498  -1.302  1.00  42.04      A
ATOM  1361  CA   GLU  189      42.299  19.878  -1.042  1.00  41.05      A
ATOM  1362  CB   GLU  189      43.731  20.142  -1.529  1.00  42.94      A
ATOM  1363  CG   GLU  189      44.059  21.594  -1.792  1.00  47.35      A
```

Fig. 2A-23

| | | | | | | | | |
|---|---|---|---|---|---|---|---|---|
| ATOM | 1364 | CD | GLU | 189 | 45.179 | 21.749 | -2.797 | 1.00 50.15 | A |
| ATOM | 1365 | OE1 | GLU | 189 | 45.726 | 20.710 | -3.231 | 1.00 53.36 | A |
| ATOM | 1366 | OE2 | GLU | 189 | 45.512 | 22.899 | -3.155 | 1.00 50.14 | A |
| ATOM | 1367 | C | GLU | 189 | 41.282 | 20.689 | -1.846 | 1.00 38.70 | A |
| ATOM | 1368 | O | GLU | 189 | 40.833 | 21.750 | -1.421 | 1.00 38.03 | A |
| ATOM | 1369 | N | ASN | 190 | 40.904 | 20.161 | -3.004 | 1.00 35.53 | A |
| ATOM | 1370 | CA | ASN | 190 | 39.940 | 20.834 | -3.859 | 1.00 34.37 | A |
| ATOM | 1371 | CB | ASN | 190 | 40.047 | 20.303 | -5.296 | 1.00 34.31 | A |
| ATOM | 1372 | CG | ASN | 190 | 41.341 | 20.734 | -5.986 | 1.00 36.77 | A |
| ATOM | 1373 | OD1 | ASN | 190 | 41.327 | 21.257 | -7.107 | 1.00 35.60 | A |
| ATOM | 1374 | ND2 | ASN | 190 | 42.469 | 20.512 | -5.315 | 1.00 36.43 | A |
| ATOM | 1375 | C | ASN | 190 | 38.522 | 20.643 | -3.320 | 1.00 33.41 | A |
| ATOM | 1376 | O | ASN | 190 | 37.700 | 21.550 | -3.402 | 1.00 33.28 | A |
| ATOM | 1377 | N | VAL | 191 | 38.240 | 19.470 | -2.759 | 1.00 32.48 | A |
| ATOM | 1378 | CA | VAL | 191 | 36.913 | 19.202 | -2.227 | 1.00 31.09 | A |
| ATOM | 1379 | CB | VAL | 191 | 36.763 | 17.739 | -1.798 | 1.00 30.46 | A |
| ATOM | 1380 | CG1 | VAL | 191 | 37.400 | 17.521 | -0.447 | 1.00 32.36 | A |
| ATOM | 1381 | CG2 | VAL | 191 | 35.295 | 17.381 | -1.725 | 1.00 32.87 | A |
| ATOM | 1382 | C | VAL | 191 | 36.598 | 20.100 | -1.037 | 1.00 31.27 | A |
| ATOM | 1383 | O | VAL | 191 | 35.462 | 20.526 | -0.857 | 1.00 30.07 | A |
| ATOM | 1384 | N | VAL | 192 | 37.610 | 20.374 | -0.219 | 1.00 32.20 | A |
| ATOM | 1385 | CA | VAL | 192 | 37.440 | 21.232 | 0.946 | 1.00 32.67 | A |
| ATOM | 1386 | CB | VAL | 192 | 38.743 | 21.307 | 1.784 | 1.00 32.41 | A |
| ATOM | 1387 | CG1 | VAL | 192 | 38.729 | 22.543 | 2.679 | 1.00 33.34 | A |
| ATOM | 1388 | CG2 | VAL | 192 | 38.887 | 20.058 | 2.628 | 1.00 32.27 | A |
| ATOM | 1389 | C | VAL | 192 | 37.105 | 22.622 | 0.427 | 1.00 33.96 | A |
| ATOM | 1390 | O | VAL | 192 | 36.217 | 23.299 | 0.947 | 1.00 33.97 | A |
| ATOM | 1391 | N | GLU | 193 | 37.828 | 23.028 | -0.610 | 1.00 34.56 | A |
| ATOM | 1392 | CA | GLU | 193 | 37.645 | 24.329 | -1.232 | 1.00 34.09 | A |
| ATOM | 1393 | CB | GLU | 193 | 38.743 | 24.570 | -2.271 | 1.00 34.75 | A |
| ATOM | 1394 | CG | GLU | 193 | 38.575 | 25.857 | -3.058 | 1.00 38.39 | A |
| ATOM | 1395 | CD | GLU | 193 | 39.397 | 27.002 | -2.485 | 1.00 41.55 | A |
| ATOM | 1396 | OE1 | GLU | 193 | 39.742 | 26.951 | -1.285 | 1.00 42.80 | A |
| ATOM | 1397 | OE2 | GLU | 193 | 39.704 | 27.954 | -3.233 | 1.00 43.71 | A |
| ATOM | 1398 | C | GLU | 193 | 36.280 | 24.398 | -1.902 | 1.00 34.15 | A |
| ATOM | 1399 | O | GLU | 193 | 35.653 | 25.459 | -1.970 | 1.00 31.67 | A |
| ATOM | 1400 | N | ASP | 194 | 35.819 | 23.255 | -2.395 | 1.00 34.06 | A |
| ATOM | 1401 | CA | ASP | 194 | 34.527 | 23.193 | -3.061 | 1.00 35.43 | A |
| ATOM | 1402 | CB | ASP | 194 | 34.361 | 21.852 | -3.778 | 1.00 39.87 | A |
| ATOM | 1403 | CG | ASP | 194 | 35.107 | 21.795 | -5.105 | 1.00 44.74 | A |
| ATOM | 1404 | OD1 | ASP | 194 | 35.313 | 20.676 | -5.627 | 1.00 48.73 | A |
| ATOM | 1405 | OD2 | ASP | 194 | 35.489 | 22.868 | -5.627 | 1.00 45.84 | A |
| ATOM | 1406 | C | ASP | 194 | 33.375 | 23.386 | -2.081 | 1.00 33.60 | A |
| ATOM | 1407 | O | ASP | 194 | 32.388 | 24.049 | -2.397 | 1.00 33.96 | A |
| ATOM | 1408 | N | THR | 195 | 33.506 | 22.806 | -0.892 | 1.00 31.10 | A |
| ATOM | 1409 | CA | THR | 195 | 32.471 | 22.895 | 0.133 | 1.00 28.51 | A |
| ATOM | 1410 | CB | THR | 195 | 32.684 | 21.817 | 1.197 | 1.00 25.86 | A |
| ATOM | 1411 | OG1 | THR | 195 | 33.091 | 20.607 | 0.552 | 1.00 26.64 | A |
| ATOM | 1412 | CG2 | THR | 195 | 31.405 | 21.565 | 1.968 | 1.00 23.67 | A |
| ATOM | 1413 | C | THR | 195 | 32.438 | 24.269 | 0.796 | 1.00 29.39 | A |
| ATOM | 1414 | O | THR | 195 | 31.361 | 24.795 | 1.100 | 1.00 29.07 | A |
| ATOM | 1415 | N | TYR | 196 | 33.617 | 24.848 | 1.019 | 1.00 29.09 | A |
| ATOM | 1416 | CA | TYR | 196 | 33.723 | 26.171 | 1.618 | 1.00 28.41 | A |
| ATOM | 1417 | CB | TYR | 196 | 35.185 | 26.609 | 1.676 | 1.00 27.92 | A |
| ATOM | 1418 | CG | TYR | 196 | 35.377 | 27.947 | 2.343 | 1.00 30.47 | A |
| ATOM | 1419 | CD1 | TYR | 196 | 34.955 | 28.152 | 3.653 | 1.00 30.68 | A |
| ATOM | 1420 | CE1 | TYR | 196 | 35.120 | 29.378 | 4.277 | 1.00 32.91 | A |

Fig. 2A-24

| | | | | | | | | |
|---|---|---|---|---|---|---|---|---|
| ATOM | 1421 | CD2 | TYR | 196 | 35.972 | 29.011 | 1.666 | 1.00 29.95 | A |
| ATOM | 1422 | CE2 | TYR | 196 | 36.142 | 30.247 | 2.283 | 1.00 30.27 | A |
| ATOM | 1423 | CZ | TYR | 196 | 35.715 | 30.421 | 3.587 | 1.00 32.29 | A |
| ATOM | 1424 | OH | TYR | 196 | 35.876 | 31.642 | 4.209 | 1.00 33.58 | A |
| ATOM | 1425 | C | TYR | 196 | 32.922 | 27.194 | 0.807 | 1.00 28.75 | A |
| ATOM | 1426 | O | TYR | 196 | 31.953 | 27.770 | 1.300 | 1.00 28.74 | A |
| ATOM | 1427 | N | GLN | 197 | 33.331 | 27.409 | -0.442 | 1.00 29.70 | A |
| ATOM | 1428 | CA | GLN | 197 | 32.664 | 28.366 | -1.326 | 1.00 30.12 | A |
| ATOM | 1429 | CB | GLN | 197 | 33.244 | 28.307 | -2.748 | 1.00 30.71 | A |
| ATOM | 1430 | CG | GLN | 197 | 34.741 | 28.617 | -2.866 | 1.00 32.91 | A |
| ATOM | 1431 | CD | GLN | 197 | 35.117 | 29.975 | -2.295 | 1.00 34.57 | A |
| ATOM | 1432 | OE1 | GLN | 197 | 36.263 | 30.203 | -1.898 | 1.00 34.65 | A |
| ATOM | 1433 | NE2 | GLN | 197 | 34.152 | 30.883 | -2.250 | 1.00 36.28 | A |
| ATOM | 1434 | C | GLN | 197 | 31.172 | 28.105 | -1.399 | 1.00 29.77 | A |
| ATOM | 1435 | O | GLN | 197 | 30.381 | 29.039 | -1.497 | 1.00 30.98 | A |
| ATOM | 1436 | N | THR | 198 | 30.790 | 26.832 | -1.367 | 1.00 29.67 | A |
| ATOM | 1437 | CA | THR | 198 | 29.381 | 26.457 | -1.428 | 1.00 29.04 | A |
| ATOM | 1438 | CB | THR | 198 | 29.193 | 24.928 | -1.522 | 1.00 30.01 | A |
| ATOM | 1439 | OG1 | THR | 198 | 29.747 | 24.454 | -2.748 | 1.00 31.23 | A |
| ATOM | 1440 | CG2 | THR | 198 | 27.711 | 24.557 | -1.471 | 1.00 29.60 | A |
| ATOM | 1441 | C | THR | 198 | 28.641 | 26.931 | -0.189 | 1.00 28.35 | A |
| ATOM | 1442 | O | THR | 198 | 27.489 | 27.367 | -0.274 | 1.00 29.22 | A |
| ATOM | 1443 | N | ILE | 199 | 29.306 | 26.847 | 0.961 | 1.00 26.89 | A |
| ATOM | 1444 | CA | ILE | 199 | 28.693 | 27.257 | 2.221 | 1.00 26.05 | A |
| ATOM | 1445 | CB | ILE | 199 | 29.491 | 26.726 | 3.425 | 1.00 22.54 | A |
| ATOM | 1446 | CG2 | ILE | 199 | 28.986 | 27.367 | 4.700 | 1.00 22.51 | A |
| ATOM | 1447 | CG1 | ILE | 199 | 29.357 | 25.194 | 3.480 | 1.00 24.49 | A |
| ATOM | 1448 | CD1 | ILE | 199 | 30.265 | 24.503 | 4.476 | 1.00 19.88 | A |
| ATOM | 1449 | C | ILE | 199 | 28.596 | 28.774 | 2.301 | 1.00 26.49 | A |
| ATOM | 1450 | O | ILE | 199 | 27.523 | 29.334 | 2.543 | 1.00 24.95 | A |
| ATOM | 1451 | N | ILE | 200 | 29.721 | 29.438 | 2.092 | 1.00 26.20 | A |
| ATOM | 1452 | CA | ILE | 200 | 29.748 | 30.886 | 2.128 | 1.00 26.94 | A |
| ATOM | 1453 | CB | ILE | 200 | 31.133 | 31.411 | 1.783 | 1.00 24.62 | A |
| ATOM | 1454 | CG2 | ILE | 200 | 31.038 | 32.626 | 0.876 | 1.00 22.99 | A |
| ATOM | 1455 | CG1 | ILE | 200 | 31.860 | 31.751 | 3.069 | 1.00 23.31 | A |
| ATOM | 1456 | CD1 | ILE | 200 | 33.302 | 31.831 | 2.882 | 1.00 27.38 | A |
| ATOM | 1457 | C | ILE | 200 | 28.764 | 31.459 | 1.123 | 1.00 29.12 | A |
| ATOM | 1458 | O | ILE | 200 | 28.002 | 32.381 | 1.428 | 1.00 29.81 | A |
| ATOM | 1459 | N | LYS | 201 | 28.790 | 30.913 | -0.082 | 1.00 29.86 | A |
| ATOM | 1460 | CA | LYS | 201 | 27.906 | 31.386 | -1.119 | 1.00 31.05 | A |
| ATOM | 1461 | CB | LYS | 201 | 27.987 | 30.471 | -2.342 | 1.00 31.60 | A |
| ATOM | 1462 | CG | LYS | 201 | 27.639 | 31.179 | -3.635 | 1.00 33.47 | A |
| ATOM | 1463 | CD | LYS | 201 | 27.753 | 30.259 | -4.839 | 1.00 35.94 | A |
| ATOM | 1464 | CE | LYS | 201 | 26.389 | 29.858 | -5.410 | 1.00 35.63 | A |
| ATOM | 1465 | NZ | LYS | 201 | 25.239 | 30.668 | -4.929 | 1.00 36.73 | A |
| ATOM | 1466 | C | LYS | 201 | 26.497 | 31.407 | -0.560 | 1.00 31.73 | A |
| ATOM | 1467 | O | LYS | 201 | 25.734 | 32.343 | -0.813 | 1.00 33.40 | A |
| ATOM | 1468 | N | TYR | 202 | 26.172 | 30.391 | 0.232 | 1.00 30.79 | A |
| ATOM | 1469 | CA | TYR | 202 | 24.842 | 30.276 | 0.810 | 1.00 29.56 | A |
| ATOM | 1470 | CB | TYR | 202 | 24.578 | 28.829 | 1.235 | 1.00 31.82 | A |
| ATOM | 1471 | CG | TYR | 202 | 23.640 | 28.715 | 2.406 | 1.00 35.00 | A |
| ATOM | 1472 | CD1 | TYR | 202 | 22.257 | 28.736 | 2.225 | 1.00 35.34 | A |
| ATOM | 1473 | CE1 | TYR | 202 | 21.389 | 28.708 | 3.314 | 1.00 37.00 | A |
| ATOM | 1474 | CD2 | TYR | 202 | 24.132 | 28.653 | 3.707 | 1.00 38.46 | A |
| ATOM | 1475 | CE2 | TYR | 202 | 23.272 | 28.624 | 4.804 | 1.00 38.62 | A |
| ATOM | 1476 | CZ | TYR | 202 | 21.902 | 28.654 | 4.598 | 1.00 39.22 | A |
| ATOM | 1477 | OH | TYR | 202 | 21.039 | 28.636 | 5.674 | 1.00 42.22 | A |

Fig. 2A-25

| | | | | | | | | | |
|---|---|---|---|---|---|---|---|---|---|
| ATOM | 1478 | C | TYR | 202 | 24.596 | 31.212 | 1.995 | 1.00 27.29 | A |
| ATOM | 1479 | O | TYR | 202 | 23.524 | 31.815 | 2.118 | 1.00 26.09 | A |
| ATOM | 1480 | N | LEU | 203 | 25.578 | 31.333 | 2.877 | 1.00 24.50 | A |
| ATOM | 1481 | CA | LEU | 203 | 25.412 | 32.197 | 4.036 | 1.00 24.11 | A |
| ATOM | 1482 | CB | LEU | 203 | 26.509 | 31.923 | 5.071 | 1.00 20.94 | A |
| ATOM | 1483 | CG | LEU | 203 | 26.394 | 30.574 | 5.806 | 1.00 18.75 | A |
| ATOM | 1484 | CD1 | LEU | 203 | 27.648 | 30.341 | 6.627 | 1.00 16.76 | A |
| ATOM | 1485 | CD2 | LEU | 203 | 25.157 | 30.557 | 6.697 | 1.00 14.06 | A |
| ATOM | 1486 | C | LEU | 203 | 25.411 | 33.670 | 3.659 | 1.00 24.08 | A |
| ATOM | 1487 | O | LEU | 203 | 25.226 | 34.522 | 4.525 | 1.00 26.06 | A |
| ATOM | 1488 | N | GLY | 1002 | 0.809 | -19.930 | 16.573 | 1.00 42.87 | B |
| ATOM | 1489 | CA | GLY | 1002 | 0.083 | -19.251 | 17.636 | 1.00 41.86 | B |
| ATOM | 1490 | C | GLY | 1002 | -1.401 | -19.161 | 17.372 | 1.00 40.58 | B |
| ATOM | 1491 | O | GLY | 1002 | -1.817 | -19.041 | 16.219 | 1.00 42.44 | B |
| ATOM | 1492 | N | SER | 1003 | -2.205 | -19.220 | 18.429 | 1.00 38.27 | B |
| ATOM | 1493 | CA | SER | 1003 | -3.652 | -19.123 | 18.257 | 1.00 36.49 | B |
| ATOM | 1494 | CB | SER | 1003 | -4.403 | -19.813 | 19.400 | 1.00 34.65 | B |
| ATOM | 1495 | OG | SER | 1003 | -3.688 | -20.916 | 19.905 | 1.00 32.06 | B |
| ATOM | 1496 | C | SER | 1003 | -4.089 | -17.663 | 18.192 | 1.00 34.99 | B |
| ATOM | 1497 | O | SER | 1003 | -4.811 | -17.262 | 17.272 | 1.00 35.62 | B |
| ATOM | 1498 | N | ALA | 1004 | -3.657 | -16.860 | 19.161 | 1.00 32.10 | B |
| ATOM | 1499 | CA | ALA | 1004 | -4.066 | -15.463 | 19.153 | 1.00 28.42 | B |
| ATOM | 1500 | CB | ALA | 1004 | -5.569 | -15.381 | 19.387 | 1.00 30.28 | B |
| ATOM | 1501 | C | ALA | 1004 | -3.355 | -14.503 | 20.096 | 1.00 25.00 | B |
| ATOM | 1502 | O | ALA | 1004 | -2.889 | -14.870 | 21.173 | 1.00 21.35 | B |
| ATOM | 1503 | N | PHE | 1005 | -3.291 | -13.255 | 19.652 | 1.00 23.78 | B |
| ATOM | 1504 | CA | PHE | 1005 | -2.686 | -12.177 | 20.409 | 1.00 21.62 | B |
| ATOM | 1505 | CB | PHE | 1005 | -1.707 | -11.397 | 19.545 | 1.00 22.42 | B |
| ATOM | 1506 | CG | PHE | 1005 | -0.963 | -10.354 | 20.301 | 1.00 26.35 | B |
| ATOM | 1507 | CD1 | PHE | 1005 | -0.773 | -10.489 | 21.675 | 1.00 26.35 | B |
| ATOM | 1508 | CD2 | PHE | 1005 | -0.504 | -9.207 | 19.667 | 1.00 28.38 | B |
| ATOM | 1509 | CE1 | PHE | 1005 | -0.117 | -9.507 | 22.406 | 1.00 27.84 | B |
| ATOM | 1510 | CE2 | PHE | 1005 | 0.155 | -8.214 | 20.392 | 1.00 27.65 | B |
| ATOM | 1511 | CZ | PHE | 1005 | 0.339 | -8.359 | 21.764 | 1.00 28.20 | B |
| ATOM | 1512 | C | PHE | 1005 | -3.835 | -11.270 | 20.818 | 1.00 20.16 | B |
| ATOM | 1513 | O | PHE | 1005 | -4.435 | -10.593 | 19.979 | 1.00 17.59 | B |
| ATOM | 1514 | N | ILE | 1006 | -4.138 | -11.258 | 22.111 | 1.00 21.00 | B |
| ATOM | 1515 | CA | ILE | 1006 | -5.246 | -10.459 | 22.618 | 1.00 20.45 | B |
| ATOM | 1516 | CB | ILE | 1006 | -6.278 | -11.363 | 23.292 | 1.00 19.15 | B |
| ATOM | 1517 | CG2 | ILE | 1006 | -7.524 | -10.566 | 23.643 | 1.00 17.97 | B |
| ATOM | 1518 | CG1 | ILE | 1006 | -6.590 | -12.534 | 22.349 | 1.00 18.66 | B |
| ATOM | 1519 | CD1 | ILE | 1006 | -7.661 | -13.457 | 22.830 | 1.00 18.27 | B |
| ATOM | 1520 | C | ILE | 1006 | -4.791 | -9.379 | 23.575 | 1.00 20.43 | B |
| ATOM | 1521 | O | ILE | 1006 | -4.005 | -9.627 | 24.487 | 1.00 19.25 | B |
| ATOM | 1522 | N | THR | 1007 | -5.281 | -8.170 | 23.342 | 1.00 22.01 | B |
| ATOM | 1523 | CA | THR | 1007 | -4.917 | -7.032 | 24.167 | 1.00 23.15 | B |
| ATOM | 1524 | CB | THR | 1007 | -4.253 | -5.947 | 23.293 | 1.00 22.76 | B |
| ATOM | 1525 | OG1 | THR | 1007 | -5.190 | -5.485 | 22.311 | 1.00 23.22 | B |
| ATOM | 1526 | CG2 | THR | 1007 | -3.045 | -6.527 | 22.556 | 1.00 22.03 | B |
| ATOM | 1527 | C | THR | 1007 | -6.114 | -6.443 | 24.922 | 1.00 23.69 | B |
| ATOM | 1528 | O | THR | 1007 | -7.261 | -6.519 | 24.482 | 1.00 21.68 | B |
| ATOM | 1529 | N | PHE | 1008 | -5.834 | -5.868 | 26.080 | 1.00 26.06 | B |
| ATOM | 1530 | CA | PHE | 1008 | -6.880 | -5.267 | 26.898 | 1.00 28.14 | B |
| ATOM | 1531 | CB | PHE | 1008 | -6.838 | -5.820 | 28.325 | 1.00 29.74 | B |
| ATOM | 1532 | CG | PHE | 1008 | -7.088 | -7.295 | 28.411 | 1.00 32.79 | B |
| ATOM | 1533 | CD1 | PHE | 1008 | -8.116 | -7.790 | 29.208 | 1.00 34.56 | B |
| ATOM | 1534 | CD2 | PHE | 1008 | -6.283 | -8.196 | 27.718 | 1.00 33.13 | B |

Fig. 2A-26

| | | | | | | | | |
|---|---|---|---|---|---|---|---|---|
| ATOM | 1535 | CE1 | PHE | 1008 | -8.346 | -9.165 | 29.305 | 1.00 35.69 | B |
| ATOM | 1536 | CE2 | PHE | 1008 | -6.501 | -9.574 | 27.806 | 1.00 33.60 | B |
| ATOM | 1537 | CZ | PHE | 1008 | -7.535 | -10.056 | 28.609 | 1.00 35.88 | B |
| ATOM | 1538 | C | PHE | 1008 | -6.660 | -3.762 | 26.946 | 1.00 27.74 | B |
| ATOM | 1539 | O | PHE | 1008 | -5.676 | -3.284 | 27.502 | 1.00 24.38 | B |
| ATOM | 1540 | N | GLU | 1009 | -7.579 | -3.008 | 26.368 | 1.00 27.62 | B |
| ATOM | 1541 | CA | GLU | 1009 | -7.429 | -1.568 | 26.380 | 1.00 27.29 | B |
| ATOM | 1542 | CB | GLU | 1009 | -7.546 | -1.034 | 24.957 | 1.00 30.06 | B |
| ATOM | 1543 | CG | GLU | 1009 | -6.345 | -1.420 | 24.101 | 1.00 30.61 | B |
| ATOM | 1544 | CD | GLU | 1009 | -5.053 | -0.756 | 24.575 | 1.00 33.51 | B |
| ATOM | 1545 | OE1 | GLU | 1009 | -3.992 | -1.020 | 23.969 | 1.00 32.69 | B |
| ATOM | 1546 | OE2 | GLU | 1009 | -5.095 | 0.030 | 25.555 | 1.00 33.25 | B |
| ATOM | 1547 | C | GLU | 1009 | -8.435 | -0.906 | 27.306 | 1.00 26.16 | B |
| ATOM | 1548 | O | GLU | 1009 | -9.527 | -1.418 | 27.538 | 1.00 22.48 | B |
| ATOM | 1549 | N | GLY | 1010 | -8.045 | 0.234 | 27.857 | 1.00 27.94 | B |
| ATOM | 1550 | CA | GLY | 1010 | -8.930 | 0.940 | 28.758 | 1.00 29.94 | B |
| ATOM | 1551 | C | GLY | 1010 | -8.186 | 1.929 | 29.624 | 1.00 30.85 | B |
| ATOM | 1552 | O | GLY | 1010 | -7.021 | 1.709 | 29.967 | 1.00 30.29 | B |
| ATOM | 1553 | N | PRO | 1011 | -8.851 | 3.028 | 30.013 | 1.00 31.71 | B |
| ATOM | 1554 | CD | PRO | 1011 | -10.262 | 3.298 | 29.681 | 1.00 32.44 | B |
| ATOM | 1555 | CA | PRO | 1011 | -8.265 | 4.082 | 30.849 | 1.00 31.73 | B |
| ATOM | 1556 | CB | PRO | 1011 | -9.138 | 5.304 | 30.562 | 1.00 32.41 | B |
| ATOM | 1557 | CG | PRO | 1011 | -10.439 | 4.756 | 30.019 | 1.00 32.23 | B |
| ATOM | 1558 | C | PRO | 1011 | -8.245 | 3.747 | 32.331 | 1.00 31.31 | B |
| ATOM | 1559 | O | PRO | 1011 | -8.649 | 2.653 | 32.742 | 1.00 32.99 | B |
| ATOM | 1560 | N | GLU | 1012 | -7.768 | 4.688 | 33.138 | 1.00 29.79 | B |
| ATOM | 1561 | CA | GLU | 1012 | -7.737 | 4.460 | 34.564 | 1.00 27.55 | B |
| ATOM | 1562 | CB | GLU | 1012 | -6.998 | 5.592 | 35.277 | 1.00 29.70 | B |
| ATOM | 1563 | CG | GLU | 1012 | -6.104 | 5.078 | 36.409 | 1.00 34.80 | B |
| ATOM | 1564 | CD | GLU | 1012 | -4.944 | 5.996 | 36.725 | 1.00 37.57 | B |
| ATOM | 1565 | OE1 | GLU | 1012 | -4.121 | 6.247 | 35.822 | 1.00 39.61 | B |
| ATOM | 1566 | OE2 | GLU | 1012 | -4.851 | 6.465 | 37.879 | 1.00 39.54 | B |
| ATOM | 1567 | C | GLU | 1012 | -9.195 | 4.392 | 34.989 | 1.00 23.66 | B |
| ATOM | 1568 | O | GLU | 1012 | -10.072 | 4.875 | 34.274 | 1.00 22.16 | B |
| ATOM | 1569 | N | GLY | 1013 | -9.457 | 3.766 | 36.127 | 1.00 21.66 | B |
| ATOM | 1570 | CA | GLY | 1013 | -10.826 | 3.648 | 36.605 | 1.00 21.23 | B |
| ATOM | 1571 | C | GLY | 1013 | -11.693 | 2.685 | 35.816 | 1.00 19.21 | B |
| ATOM | 1572 | O | GLY | 1013 | -12.881 | 2.548 | 36.106 | 1.00 17.99 | B |
| ATOM | 1573 | N | SER | 1014 | -11.097 | 2.019 | 34.827 | 1.00 19.72 | B |
| ATOM | 1574 | CA | SER | 1014 | -11.803 | 1.055 | 33.985 | 1.00 17.23 | B |
| ATOM | 1575 | CB | SER | 1014 | -11.154 | 0.973 | 32.587 | 1.00 15.73 | B |
| ATOM | 1576 | OG | SER | 1014 | -9.964 | 0.201 | 32.565 | 1.00 6.67 | B |
| ATOM | 1577 | C | SER | 1014 | -11.821 | -0.323 | 34.630 | 1.00 20.08 | B |
| ATOM | 1578 | O | SER | 1014 | -12.659 | -1.160 | 34.292 | 1.00 21.83 | B |
| ATOM | 1579 | N | GLY | 1015 | -10.903 | -0.542 | 35.571 | 1.00 21.90 | B |
| ATOM | 1580 | CA | GLY | 1015 | -10.804 | -1.820 | 36.260 | 1.00 21.91 | B |
| ATOM | 1581 | C | GLY | 1015 | -9.969 | -2.797 | 35.458 | 1.00 22.02 | B |
| ATOM | 1582 | O | GLY | 1015 | -9.981 | -3.996 | 35.711 | 1.00 21.89 | B |
| ATOM | 1583 | N | LYS | 1016 | -9.231 | -2.275 | 34.488 | 1.00 21.98 | B |
| ATOM | 1584 | CA | LYS | 1016 | -8.421 | -3.105 | 33.623 | 1.00 22.53 | B |
| ATOM | 1585 | CB | LYS | 1016 | -7.608 | -2.244 | 32.648 | 1.00 23.14 | B |
| ATOM | 1586 | CG | LYS | 1016 | -7.237 | -2.995 | 31.354 | 1.00 23.43 | B |
| ATOM | 1587 | CD | LYS | 1016 | -6.578 | -2.101 | 30.302 | 1.00 22.86 | B |
| ATOM | 1588 | CE | LYS | 1016 | -5.686 | -1.035 | 30.921 | 1.00 18.96 | B |
| ATOM | 1589 | NZ | LYS | 1016 | -4.279 | -1.489 | 31.073 | 1.00 21.09 | B |
| ATOM | 1590 | C | LYS | 1016 | -7.495 | -4.075 | 34.326 | 1.00 22.81 | B |
| ATOM | 1591 | O | LYS | 1016 | -7.530 | -5.270 | 34.045 | 1.00 25.20 | B |

Fig. 2A-27

| | | | | | | | | | |
|---|---|---|---|---|---|---|---|---|---|
| ATOM | 1592 | N | THR | 1017 | -6.668 | -3.583 | 35.233 | 1.00 23.24 | B |
| ATOM | 1593 | CA | THR | 1017 | -5.725 | -4.449 | 35.923 | 1.00 24.26 | B |
| ATOM | 1594 | CB | THR | 1017 | -4.878 | -3.638 | 36.904 | 1.00 25.41 | B |
| ATOM | 1595 | OG1 | THR | 1017 | -3.840 | -4.463 | 37.446 | 1.00 29.68 | B |
| ATOM | 1596 | CG2 | THR | 1017 | -5.742 | -3.107 | 38.027 | 1.00 29.83 | B |
| ATOM | 1597 | C | THR | 1017 | -6.394 | -5.613 | 36.658 | 1.00 25.17 | B |
| ATOM | 1598 | O | THR | 1017 | -5.852 | -6.719 | 36.708 | 1.00 25.22 | B |
| ATOM | 1599 | N | THR | 1018 | -7.580 | -5.364 | 37.205 | 1.00 26.73 | B |
| ATOM | 1600 | CA | THR | 1018 | -8.328 | -6.378 | 37.950 | 1.00 25.28 | B |
| ATOM | 1601 | CB | THR | 1018 | -9.414 | -5.701 | 38.832 | 1.00 26.80 | B |
| ATOM | 1602 | OG1 | THR | 1018 | -8.770 | -4.874 | 39.808 | 1.00 29.40 | B |
| ATOM | 1603 | CG2 | THR | 1018 | -10.281 | -6.737 | 39.550 | 1.00 22.91 | B |
| ATOM | 1604 | C | THR | 1018 | -8.992 | -7.404 | 37.039 | 1.00 24.21 | B |
| ATOM | 1605 | O | THR | 1018 | -9.045 | -8.594 | 37.359 | 1.00 22.96 | B |
| ATOM | 1606 | N | VAL | 1019 | -9.486 | -6.931 | 35.902 | 1.00 22.37 | B |
| ATOM | 1607 | CA | VAL | 1019 | -10.164 | -7.779 | 34.937 | 1.00 22.87 | B |
| ATOM | 1608 | CB | VAL | 1019 | -10.888 | -6.932 | 33.904 | 1.00 22.80 | B |
| ATOM | 1609 | CG1 | VAL | 1019 | -11.582 | -7.827 | 32.891 | 1.00 23.74 | B |
| ATOM | 1610 | CG2 | VAL | 1019 | -11.872 | -6.020 | 34.597 | 1.00 24.35 | B |
| ATOM | 1611 | C | VAL | 1019 | -9.260 | -8.755 | 34.187 | 1.00 24.10 | B |
| ATOM | 1612 | O | VAL | 1019 | -9.572 | -9.944 | 34.085 | 1.00 25.94 | B |
| ATOM | 1613 | N | ILE | 1020 | -8.151 | -8.256 | 33.655 | 1.00 23.26 | B |
| ATOM | 1614 | CA | ILE | 1020 | -7.236 | -9.101 | 32.900 | 1.00 24.48 | B |
| ATOM | 1615 | CB | ILE | 1020 | -6.017 | -8.277 | 32.367 | 1.00 23.76 | B |
| ATOM | 1616 | CG2 | ILE | 1020 | -5.168 | -7.764 | 33.515 | 1.00 22.68 | B |
| ATOM | 1617 | CG1 | ILE | 1020 | -5.177 | -9.129 | 31.411 | 1.00 22.91 | B |
| ATOM | 1618 | CD1 | ILE | 1020 | -3.957 | -8.407 | 30.849 | 1.00 22.28 | B |
| ATOM | 1619 | C | ILE | 1020 | -6.750 | -10.311 | 33.698 | 1.00 25.69 | B |
| ATOM | 1620 | O | ILE | 1020 | -6.756 | -11.436 | 33.190 | 1.00 24.60 | B |
| ATOM | 1621 | N | ASN | 1021 | -6.358 | -10.090 | 34.950 | 1.00 27.37 | B |
| ATOM | 1622 | CA | ASN | 1021 | -5.868 | -11.169 | 35.794 | 1.00 29.11 | B |
| ATOM | 1623 | CB | ASN | 1021 | -5.226 | -10.598 | 37.059 | 1.00 34.21 | B |
| ATOM | 1624 | CG | ASN | 1021 | -4.618 | -11.680 | 37.944 | 1.00 39.81 | B |
| ATOM | 1625 | OD1 | ASN | 1021 | -4.761 | -11.648 | 39.174 | 1.00 43.11 | B |
| ATOM | 1626 | ND2 | ASN | 1021 | -3.937 | -12.642 | 37.327 | 1.00 39.90 | B |
| ATOM | 1627 | C | ASN | 1021 | -6.942 | -12.190 | 36.166 | 1.00 28.95 | B |
| ATOM | 1628 | O | ASN | 1021 | -6.653 | -13.382 | 36.230 | 1.00 30.74 | B |
| ATOM | 1629 | N | GLU | 1022 | -8.173 | -11.737 | 36.410 | 1.00 29.46 | B |
| ATOM | 1630 | CA | GLU | 1022 | -9.276 | -12.646 | 36.767 | 1.00 28.78 | B |
| ATOM | 1631 | CB | GLU | 1022 | -10.574 | -11.888 | 37.060 | 1.00 33.74 | B |
| ATOM | 1632 | CG | GLU | 1022 | -10.505 | -10.822 | 38.121 | 1.00 40.77 | B |
| ATOM | 1633 | CD | GLU | 1022 | -9.935 | -11.338 | 39.407 | 1.00 44.92 | B |
| ATOM | 1634 | OE1 | GLU | 1022 | -9.841 | -12.578 | 39.561 | 1.00 47.00 | B |
| ATOM | 1635 | OE2 | GLU | 1022 | -9.576 | -10.498 | 40.262 | 1.00 49.32 | B |
| ATOM | 1636 | C | GLU | 1022 | -9.549 | -13.543 | 35.583 | 1.00 26.10 | B |
| ATOM | 1637 | O | GLU | 1022 | -9.694 | -14.759 | 35.713 | 1.00 23.64 | B |
| ATOM | 1638 | N | VAL | 1023 | -9.648 | -12.901 | 34.425 | 1.00 23.86 | B |
| ATOM | 1639 | CA | VAL | 1023 | -9.888 | -13.582 | 33.171 | 1.00 22.29 | B |
| ATOM | 1640 | CB | VAL | 1023 | -9.934 | -12.570 | 32.030 | 1.00 22.20 | B |
| ATOM | 1641 | CG1 | VAL | 1023 | -9.955 | -13.280 | 30.690 | 1.00 24.04 | B |
| ATOM | 1642 | CG2 | VAL | 1023 | -11.140 | -11.691 | 32.200 | 1.00 22.35 | B |
| ATOM | 1643 | C | VAL | 1023 | -8.750 | -14.568 | 32.948 | 1.00 21.29 | B |
| ATOM | 1644 | O | VAL | 1023 | -8.984 | -15.756 | 32.726 | 1.00 23.15 | B |
| ATOM | 1645 | N | TYR | 1024 | -7.523 | -14.066 | 33.033 | 1.00 18.03 | B |
| ATOM | 1646 | CA | TYR | 1024 | -6.335 | -14.880 | 32.852 | 1.00 17.65 | B |
| ATOM | 1647 | CB | TYR | 1024 | -5.068 | -14.071 | 33.177 | 1.00 12.17 | B |
| ATOM | 1648 | CG | TYR | 1024 | -3.778 | -14.867 | 33.102 | 1.00 8.39 | B |

Fig. 2A-28

| | | | | | | | | |
|---|---|---|---|---|---|---|---|---|
| ATOM | 1649 | CD1 | TYR | 1024 | -3.496 | -15.677 | 31.996 | 1.00 | 7.78 | B |
| ATOM | 1650 | CE1 | TYR | 1024 | -2.294 | -16.371 | 31.898 | 1.00 | 6.49 | B |
| ATOM | 1651 | CD2 | TYR | 1024 | -2.824 | -14.780 | 34.110 | 1.00 | 6.31 | B |
| ATOM | 1652 | CE2 | TYR | 1024 | -1.616 | -15.472 | 34.023 | 1.00 | 9.05 | B |
| ATOM | 1653 | CZ | TYR | 1024 | -1.354 | -16.263 | 32.909 | 1.00 | 8.19 | B |
| ATOM | 1654 | OH | TYR | 1024 | -0.129 | -16.900 | 32.794 | 1.00 | 8.39 | B |
| ATOM | 1655 | C | TYR | 1024 | -6.379 | -16.117 | 33.731 | 1.00 | 20.51 | B |
| ATOM | 1656 | O | TYR | 1024 | -6.314 | -17.243 | 33.227 | 1.00 | 19.80 | B |
| ATOM | 1657 | N | HIS | 1025 | -6.485 | -15.904 | 35.044 | 1.00 | 24.09 | B |
| ATOM | 1658 | CA | HIS | 1025 | -6.519 | -17.013 | 35.991 | 1.00 | 29.44 | B |
| ATOM | 1659 | CB | HIS | 1025 | -6.713 | -16.494 | 37.427 | 1.00 | 35.85 | B |
| ATOM | 1660 | CG | HIS | 1025 | -6.492 | -17.545 | 38.478 | 1.00 | 45.17 | B |
| ATOM | 1661 | CD2 | HIS | 1025 | -5.374 | -18.168 | 38.912 | 1.00 | 48.17 | B |
| ATOM | 1662 | ND1 | HIS | 1025 | -7.539 | -18.081 | 39.219 | 1.00 | 47.96 | B |
| ATOM | 1663 | CE1 | HIS | 1025 | -7.052 | -18.995 | 40.055 | 1.00 | 48.98 | B |
| ATOM | 1664 | NE2 | HIS | 1025 | -5.748 | -19.061 | 39.885 | 1.00 | 49.88 | B |
| ATOM | 1665 | C | HIS | 1025 | -7.626 | -18.003 | 35.640 | 1.00 | 30.01 | B |
| ATOM | 1666 | O | HIS | 1025 | -7.472 | -19.218 | 35.829 | 1.00 | 30.15 | B |
| ATOM | 1667 | N | ARG | 1026 | -8.729 | -17.480 | 35.113 | 1.00 | 29.75 | B |
| ATOM | 1668 | CA | ARG | 1026 | -9.873 | -18.298 | 34.736 | 1.00 | 30.27 | B |
| ATOM | 1669 | CB | ARG | 1026 | -11.112 | -17.400 | 34.576 | 1.00 | 31.49 | B |
| ATOM | 1670 | CG | ARG | 1026 | -12.448 | -18.124 | 34.652 | 1.00 | 34.20 | B |
| ATOM | 1671 | CD | ARG | 1026 | -13.622 | -17.150 | 34.748 | 1.00 | 36.10 | B |
| ATOM | 1672 | NE | ARG | 1026 | -13.504 | -16.252 | 35.897 | 1.00 | 39.14 | B |
| ATOM | 1673 | CZ | ARG | 1026 | -14.484 | -15.472 | 36.362 | 1.00 | 40.20 | B |
| ATOM | 1674 | NH1 | ARG | 1026 | -14.267 | -14.692 | 37.417 | 1.00 | 40.00 | B |
| ATOM | 1675 | NH2 | ARG | 1026 | -15.680 | -15.465 | 35.780 | 1.00 | 38.96 | B |
| ATOM | 1676 | C | ARG | 1026 | -9.621 | -19.072 | 33.439 | 1.00 | 30.31 | B |
| ATOM | 1677 | O | ARG | 1026 | -10.124 | -20.180 | 33.267 | 1.00 | 30.26 | B |
| ATOM | 1678 | N | LEU | 1027 | -8.829 | -18.493 | 32.540 | 1.00 | 30.44 | B |
| ATOM | 1679 | CA | LEU | 1027 | -8.548 | -19.119 | 31.256 | 1.00 | 28.40 | B |
| ATOM | 1680 | CB | LEU | 1027 | -8.248 | -18.048 | 30.203 | 1.00 | 27.09 | B |
| ATOM | 1681 | CG | LEU | 1027 | -9.447 | -17.236 | 29.690 | 1.00 | 28.27 | B |
| ATOM | 1682 | CD1 | LEU | 1027 | -8.959 | -16.055 | 28.870 | 1.00 | 28.15 | B |
| ATOM | 1683 | CD2 | LEU | 1027 | -10.359 | -18.121 | 28.852 | 1.00 | 29.72 | B |
| ATOM | 1684 | C | LEU | 1027 | -7.426 | -20.141 | 31.272 | 1.00 | 26.93 | B |
| ATOM | 1685 | O | LEU | 1027 | -7.423 | -21.067 | 30.467 | 1.00 | 25.91 | B |
| ATOM | 1686 | N | VAL | 1028 | -6.481 | -19.979 | 32.189 | 1.00 | 27.68 | B |
| ATOM | 1687 | CA | VAL | 1028 | -5.350 | -20.897 | 32.277 | 1.00 | 29.11 | B |
| ATOM | 1688 | CB | VAL | 1028 | -4.405 | -20.530 | 33.438 | 1.00 | 27.20 | B |
| ATOM | 1689 | CG1 | VAL | 1028 | -3.443 | -21.663 | 33.708 | 1.00 | 28.81 | B |
| ATOM | 1690 | CG2 | VAL | 1028 | -3.645 | -19.275 | 33.095 | 1.00 | 28.05 | B |
| ATOM | 1691 | C | VAL | 1028 | -5.779 | -22.345 | 32.458 | 1.00 | 30.78 | B |
| ATOM | 1692 | O | VAL | 1028 | -5.025 | -23.269 | 32.120 | 1.00 | 31.77 | B |
| ATOM | 1693 | N | LYS | 1029 | -6.984 | -22.538 | 32.986 | 1.00 | 32.21 | B |
| ATOM | 1694 | CA | LYS | 1029 | -7.505 | -23.871 | 33.229 | 1.00 | 34.92 | B |
| ATOM | 1695 | CB | LYS | 1029 | -8.594 | -23.806 | 34.310 | 1.00 | 36.13 | B |
| ATOM | 1696 | CG | LYS | 1029 | -8.085 | -24.116 | 35.715 | 1.00 | 38.35 | B |
| ATOM | 1697 | CD | LYS | 1029 | -7.676 | -22.857 | 36.443 | 1.00 | 39.87 | B |
| ATOM | 1698 | CE | LYS | 1029 | -6.909 | -23.177 | 37.723 | 1.00 | 38.75 | B |
| ATOM | 1699 | NZ | LYS | 1029 | -6.863 | -21.971 | 38.620 | 1.00 | 38.89 | B |
| ATOM | 1700 | C | LYS | 1029 | -8.060 | -24.560 | 31.970 | 1.00 | 34.57 | B |
| ATOM | 1701 | O | LYS | 1029 | -8.253 | -25.778 | 31.972 | 1.00 | 36.68 | B |
| ATOM | 1702 | N | ASP | 1030 | -8.312 | -23.794 | 30.906 | 1.00 | 33.48 | B |
| ATOM | 1703 | CA | ASP | 1030 | -8.870 | -24.351 | 29.671 | 1.00 | 29.73 | B |
| ATOM | 1704 | CB | ASP | 1030 | -10.309 | -23.862 | 29.471 | 1.00 | 29.63 | B |
| ATOM | 1705 | CG | ASP | 1030 | -11.202 | -24.180 | 30.648 | 1.00 | 29.05 | B |

Fig. 2A-29

```
ATOM   1706  OD1 ASP  1030     -10.723 -24.801  31.612  1.00 29.79      B
ATOM   1707  OD2 ASP  1030     -12.385 -23.807  30.621  1.00 30.33      B
ATOM   1708  C   ASP  1030      -8.081 -24.016  28.413  1.00 27.98      B
ATOM   1709  O   ASP  1030      -8.436 -24.468  27.325  1.00 25.91      B
ATOM   1710  N   TYR  1031      -7.024 -23.223  28.549  1.00 25.00      B
ATOM   1711  CA  TYR  1031      -6.245 -22.842  27.375  1.00 21.35      B
ATOM   1712  CB  TYR  1031      -6.729 -21.487  26.837  1.00 19.50      B
ATOM   1713  CG  TYR  1031      -8.182 -21.463  26.436  1.00 16.83      B
ATOM   1714  CD1 TYR  1031      -9.184 -21.204  27.370  1.00 17.00      B
ATOM   1715  CE1 TYR  1031     -10.531 -21.208  27.006  1.00 14.72      B
ATOM   1716  CD2 TYR  1031      -8.557 -21.726  25.129  1.00 18.19      B
ATOM   1717  CE2 TYR  1031      -9.898 -21.733  24.752  1.00 16.91      B
ATOM   1718  CZ  TYR  1031     -10.879 -21.479  25.691  1.00 17.09      B
ATOM   1719  OH  TYR  1031     -12.204 -21.499  25.310  1.00 14.46      B
ATOM   1720  C   TYR  1031      -4.749 -22.762  27.650  1.00 20.89      B
ATOM   1721  O   TYR  1031      -4.294 -22.836  28.794  1.00 18.42      B
ATOM   1722  N   ASP  1032      -3.985 -22.645  26.574  1.00 22.94      B
ATOM   1723  CA  ASP  1032      -2.543 -22.508  26.683  1.00 23.92      B
ATOM   1724  CB  ASP  1032      -1.830 -23.322  25.615  1.00 21.98      B
ATOM   1725  CG  ASP  1032      -0.339 -23.133  25.658  1.00 24.66      B
ATOM   1726  OD1 ASP  1032       0.211 -22.995  26.771  1.00 21.36      B
ATOM   1727  OD2 ASP  1032       0.282 -23.124  24.575  1.00 29.32      B
ATOM   1728  C   ASP  1032      -2.328 -21.026  26.440  1.00 24.95      B
ATOM   1729  O   ASP  1032      -1.995 -20.592  25.331  1.00 24.96      B
ATOM   1730  N   VAL  1033      -2.542 -20.252  27.495  1.00 24.98      B
ATOM   1731  CA  VAL  1033      -2.427 -18.814  27.407  1.00 25.81      B
ATOM   1732  CB  VAL  1033      -3.821 -18.174  27.588  1.00 25.87      B
ATOM   1733  CG1 VAL  1033      -4.481 -18.737  28.830  1.00 28.68      B
ATOM   1734  CG2 VAL  1033      -3.708 -16.661  27.691  1.00 29.49      B
ATOM   1735  C   VAL  1033      -1.477 -18.238  28.445  1.00 25.35      B
ATOM   1736  O   VAL  1033      -1.302 -18.816  29.525  1.00 28.02      B
ATOM   1737  N   ILE  1034      -0.837 -17.118  28.100  1.00 21.73      B
ATOM   1738  CA  ILE  1034       0.046 -16.427  29.030  1.00 18.66      B
ATOM   1739  CB  ILE  1034       1.546 -16.490  28.607  1.00 18.56      B
ATOM   1740  CG2 ILE  1034       1.937 -17.927  28.281  1.00 20.50      B
ATOM   1741  CG1 ILE  1034       1.809 -15.615  27.387  1.00 18.26      B
ATOM   1742  CD1 ILE  1034       3.253 -15.664  26.926  1.00 14.65      B
ATOM   1743  C   ILE  1034      -0.437 -14.979  29.083  1.00 17.98      B
ATOM   1744  O   ILE  1034      -1.212 -14.543  28.236  1.00 17.67      B
ATOM   1745  N   MET  1035      -0.006 -14.240  30.092  1.00 17.36      B
ATOM   1746  CA  MET  1035      -0.421 -12.858  30.242  1.00 17.22      B
ATOM   1747  CB  MET  1035      -1.385 -12.722  31.426  1.00 17.46      B
ATOM   1748  CG  MET  1035      -1.954 -11.331  31.611  1.00 19.72      B
ATOM   1749  SD  MET  1035      -1.983 -10.817  33.359  1.00 22.58      B
ATOM   1750  CE  MET  1035      -0.437  -9.973  33.455  1.00 21.62      B
ATOM   1751  C   MET  1035       0.826 -12.029  30.463  1.00 17.87      B
ATOM   1752  O   MET  1035       1.677 -12.354  31.296  1.00 17.85      B
ATOM   1753  N   THR  1036       0.941 -10.955  29.696  1.00 19.18      B
ATOM   1754  CA  THR  1036       2.105 -10.107  29.799  1.00 20.66      B
ATOM   1755  CB  THR  1036       3.065 -10.396  28.617  1.00 20.80      B
ATOM   1756  OG1 THR  1036       4.356  -9.859  28.904  1.00 23.06      B
ATOM   1757  CG2 THR  1036       2.542  -9.783  27.343  1.00 21.22      B
ATOM   1758  C   THR  1036       1.769  -8.618  29.865  1.00 20.74      B
ATOM   1759  O   THR  1036       0.795  -8.145  29.275  1.00 18.97      B
ATOM   1760  N   ARG  1037       2.582  -7.904  30.633  1.00 22.39      B
ATOM   1761  CA  ARG  1037       2.456  -6.469  30.822  1.00 24.72      B
ATOM   1762  CB  ARG  1037       2.299  -6.126  32.321  1.00 26.66      B
```

Fig. 2A-30

| ATOM | 1763 | CG | ARG | 1037 | 1.562 | -7.191 | 33.162 | 1.00 | 30.81 | B |
|------|------|-----|-----|------|-------|--------|--------|------|-------|---|
| ATOM | 1764 | CD | ARG | 1037 | 1.871 | -7.094 | 34.663 | 1.00 | 32.69 | B |
| ATOM | 1765 | NE | ARG | 1037 | 0.814 | -7.692 | 35.484 | 1.00 | 35.51 | B |
| ATOM | 1766 | CZ | ARG | 1037 | 1.022 | -8.320 | 36.640 | 1.00 | 34.79 | B |
| ATOM | 1767 | NH1 | ARG | 1037 | -0.003 | -8.827 | 37.309 | 1.00 | 34.18 | B |
| ATOM | 1768 | NH2 | ARG | 1037 | 2.250 | -8.438 | 37.126 | 1.00 | 35.46 | B |
| ATOM | 1769 | C | ARG | 1037 | 3.784 | -5.930 | 30.298 | 1.00 | 25.92 | B |
| ATOM | 1770 | O | ARG | 1037 | 4.823 | -6.109 | 30.943 | 1.00 | 25.92 | B |
| ATOM | 1771 | N | GLU | 1038 | 3.766 | -5.294 | 29.129 | 1.00 | 26.43 | B |
| ATOM | 1772 | CA | GLU | 1038 | 5.006 | -4.762 | 28.568 | 1.00 | 28.04 | B |
| ATOM | 1773 | CB | GLU | 1038 | 4.739 | -3.980 | 27.282 | 1.00 | 29.29 | B |
| ATOM | 1774 | CG | GLU | 1038 | 3.757 | -2.830 | 27.395 | 1.00 | 33.57 | B |
| ATOM | 1775 | CD | GLU | 1038 | 3.464 | -2.192 | 26.042 | 1.00 | 34.71 | B |
| ATOM | 1776 | OE1 | GLU | 1038 | 3.599 | -2.878 | 25.001 | 1.00 | 31.34 | B |
| ATOM | 1777 | OE2 | GLU | 1038 | 3.096 | -0.999 | 26.025 | 1.00 | 39.22 | B |
| ATOM | 1778 | C | GLU | 1038 | 5.715 | -3.871 | 29.580 | 1.00 | 27.23 | B |
| ATOM | 1779 | O | GLU | 1038 | 5.074 | -3.145 | 30.345 | 1.00 | 28.46 | B |
| ATOM | 1780 | N | PRO | 1039 | 7.053 | -3.911 | 29.596 | 1.00 | 25.14 | B |
| ATOM | 1781 | CD | PRO | 1039 | 7.846 | -3.123 | 30.555 | 1.00 | 24.99 | B |
| ATOM | 1782 | CA | PRO | 1039 | 7.897 | -4.730 | 28.725 | 1.00 | 24.59 | B |
| ATOM | 1783 | CB | PRO | 1039 | 9.217 | -3.958 | 28.679 | 1.00 | 25.96 | B |
| ATOM | 1784 | CG | PRO | 1039 | 9.216 | -3.094 | 29.945 | 1.00 | 26.84 | B |
| ATOM | 1785 | C | PRO | 1039 | 8.078 | -6.187 | 29.174 | 1.00 | 23.69 | B |
| ATOM | 1786 | O | PRO | 1039 | 8.996 | -6.868 | 28.720 | 1.00 | 23.48 | B |
| ATOM | 1787 | N | GLY | 1040 | 7.212 | -6.645 | 30.077 | 1.00 | 22.37 | B |
| ATOM | 1788 | CA | GLY | 1040 | 7.240 | -8.021 | 30.558 | 1.00 | 18.07 | B |
| ATOM | 1789 | C | GLY | 1040 | 8.540 | -8.678 | 30.990 | 1.00 | 16.70 | B |
| ATOM | 1790 | O | GLY | 1040 | 8.698 | -9.890 | 30.841 | 1.00 | 14.25 | B |
| ATOM | 1791 | N | GLY | 1041 | 9.478 | -7.897 | 31.511 | 1.00 | 16.89 | B |
| ATOM | 1792 | CA | GLY | 1041 | 10.727 | -8.474 | 31.971 | 1.00 | 15.99 | B |
| ATOM | 1793 | C | GLY | 1041 | 11.882 | -8.488 | 30.995 | 1.00 | 16.64 | B |
| ATOM | 1794 | O | GLY | 1041 | 13.023 | -8.675 | 31.409 | 1.00 | 16.87 | B |
| ATOM | 1795 | N | VAL | 1042 | 11.618 | -8.300 | 29.709 | 1.00 | 17.18 | B |
| ATOM | 1796 | CA | VAL | 1042 | 12.703 | -8.298 | 28.740 | 1.00 | 16.78 | B |
| ATOM | 1797 | CB | VAL | 1042 | 12.174 | -8.010 | 27.318 | 1.00 | 14.36 | B |
| ATOM | 1798 | CG1 | VAL | 1042 | 13.289 | -8.164 | 26.303 | 1.00 | 13.73 | B |
| ATOM | 1799 | CG2 | VAL | 1042 | 11.021 | -8.946 | 26.998 | 1.00 | 8.53 | B |
| ATOM | 1800 | C | VAL | 1042 | 13.664 | -7.198 | 29.191 | 1.00 | 19.27 | B |
| ATOM | 1801 | O | VAL | 1042 | 13.311 | -6.023 | 29.223 | 1.00 | 22.22 | B |
| ATOM | 1802 | N | PRO | 1043 | 14.893 | -7.569 | 29.563 | 1.00 | 21.26 | B |
| ATOM | 1803 | CD | PRO | 1043 | 15.436 | -8.934 | 29.561 | 1.00 | 22.32 | B |
| ATOM | 1804 | CA | PRO | 1043 | 15.887 | -6.595 | 30.023 | 1.00 | 24.14 | B |
| ATOM | 1805 | CB | PRO | 1043 | 17.159 | -7.426 | 30.202 | 1.00 | 23.17 | B |
| ATOM | 1806 | CG | PRO | 1043 | 16.904 | -8.696 | 29.464 | 1.00 | 22.80 | B |
| ATOM | 1807 | C | PRO | 1043 | 16.106 | -5.399 | 29.093 | 1.00 | 25.41 | B |
| ATOM | 1808 | O | PRO | 1043 | 16.235 | -4.265 | 29.561 | 1.00 | 25.65 | B |
| ATOM | 1809 | N | THR | 1044 | 16.146 | -5.649 | 27.788 | 1.00 | 25.10 | B |
| ATOM | 1810 | CA | THR | 1044 | 16.359 | -4.577 | 26.825 | 1.00 | 26.61 | B |
| ATOM | 1811 | CB | THR | 1044 | 16.609 | -5.128 | 25.389 | 1.00 | 25.43 | B |
| ATOM | 1812 | OG1 | THR | 1044 | 15.595 | -6.080 | 25.049 | 1.00 | 25.55 | B |
| ATOM | 1813 | CG2 | THR | 1044 | 17.980 | -5.798 | 25.296 | 1.00 | 24.53 | B |
| ATOM | 1814 | C | THR | 1044 | 15.155 | -3.644 | 26.796 | 1.00 | 27.12 | B |
| ATOM | 1815 | O | THR | 1044 | 15.274 | -2.462 | 26.465 | 1.00 | 27.96 | B |
| ATOM | 1816 | N | GLY | 1045 | 13.992 | -4.179 | 27.143 | 1.00 | 26.84 | B |
| ATOM | 1817 | CA | GLY | 1045 | 12.801 | -3.357 | 27.151 | 1.00 | 28.65 | B |
| ATOM | 1818 | C | GLY | 1045 | 12.793 | -2.556 | 28.429 | 1.00 | 30.23 | B |
| ATOM | 1819 | O | GLY | 1045 | 12.274 | -1.438 | 28.483 | 1.00 | 30.19 | B |

Fig. 2A-31

```
ATOM   1820  N    GLU  1046     13.384   -3.147   29.463  1.00  30.98      B
ATOM   1821  CA   GLU  1046     13.473   -2.521   30.772  1.00  31.34      B
ATOM   1822  CB   GLU  1046     14.002   -3.532   31.789  1.00  31.82      B
ATOM   1823  CG   GLU  1046     13.105   -4.749   31.943  1.00  35.60      B
ATOM   1824  CD   GLU  1046     11.665   -4.368   32.224  1.00  37.09      B
ATOM   1825  OE1  GLU  1046     11.454   -3.482   33.078  1.00  37.79      B
ATOM   1826  OE2  GLU  1046     10.748   -4.943   31.594  1.00  38.13      B
ATOM   1827  C    GLU  1046     14.376   -1.294   30.730  1.00  31.03      B
ATOM   1828  O    GLU  1046     14.036   -0.259   31.303  1.00  32.17      B
ATOM   1829  N    GLU  1047     15.514   -1.417   30.043  1.00  29.76      B
ATOM   1830  CA   GLU  1047     16.482   -0.327   29.913  1.00  29.97      B
ATOM   1831  CB   GLU  1047     17.700   -0.800   29.126  1.00  31.47      B
ATOM   1832  CG   GLU  1047     18.528   -1.838   29.838  1.00  34.35      B
ATOM   1833  CD   GLU  1047     19.365   -1.250   30.955  1.00  36.62      B
ATOM   1834  OE1  GLU  1047     18.787   -0.610   31.862  1.00  39.04      B
ATOM   1835  OE2  GLU  1047     20.604   -1.430   30.927  1.00  37.61      B
ATOM   1836  C    GLU  1047     15.888    0.886   29.202  1.00  29.21      B
ATOM   1837  O    GLU  1047     15.844    1.986   29.742  1.00  30.59      B
ATOM   1838  N    ILE  1048     15.460    0.675   27.968  1.00  28.49      B
ATOM   1839  CA   ILE  1048     14.857    1.736   27.183  1.00  27.01      B
ATOM   1840  CB   ILE  1048     14.157    1.152   25.937  1.00  24.70      B
ATOM   1841  CG2  ILE  1048     13.684    2.263   25.031  1.00  22.04      B
ATOM   1842  CG1  ILE  1048     15.124    0.206   25.212  1.00  23.01      B
ATOM   1843  CD1  ILE  1048     14.500   -0.605   24.084  1.00  22.57      B
ATOM   1844  C    ILE  1048     13.841    2.435   28.074  1.00  28.22      B
ATOM   1845  O    ILE  1048     13.855    3.660   28.212  1.00  27.45      B
ATOM   1846  N    ARG  1049     12.984    1.638   28.703  1.00  29.44      B
ATOM   1847  CA   ARG  1049     11.951    2.153   29.591  1.00  32.68      B
ATOM   1848  CB   ARG  1049     11.092    0.998   30.128  1.00  35.21      B
ATOM   1849  CG   ARG  1049      9.704    1.429   30.576  1.00  34.97      B
ATOM   1850  CD   ARG  1049      9.134    0.438   31.576  1.00  39.16      B
ATOM   1851  NE   ARG  1049      7.701    0.618   31.813  1.00  39.91      B
ATOM   1852  CZ   ARG  1049      6.795    0.752   30.850  1.00  42.12      B
ATOM   1853  NH1  ARG  1049      5.515    0.908   31.156  1.00  41.51      B
ATOM   1854  NH2  ARG  1049      7.170    0.731   29.578  1.00  44.49      B
ATOM   1855  C    ARG  1049     12.526    2.954   30.761  1.00  31.23      B
ATOM   1856  O    ARG  1049     11.996    3.999   31.132  1.00  31.36      B
ATOM   1857  N    LYS  1050     13.606    2.456   31.341  1.00  30.60      B
ATOM   1858  CA   LYS  1050     14.235    3.137   32.460  1.00  30.77      B
ATOM   1859  CB   LYS  1050     15.457    2.341   32.927  1.00  29.72      B
ATOM   1860  CG   LYS  1050     16.388    3.084   33.873  1.00  30.52      B
ATOM   1861  CD   LYS  1050     17.585    2.223   34.247  1.00  29.58      B
ATOM   1862  CE   LYS  1050     17.159    1.033   35.091  1.00  28.80      B
ATOM   1863  NZ   LYS  1050     18.316    0.399   35.778  1.00  29.70      B
ATOM   1864  C    LYS  1050     14.628    4.568   32.103  1.00  30.93      B
ATOM   1865  O    LYS  1050     14.361    5.488   32.868  1.00  32.08      B
ATOM   1866  N    ILE  1051     15.260    4.771   30.948  1.00  30.46      B
ATOM   1867  CA   ILE  1051     15.670    6.107   30.509  1.00  27.98      B
ATOM   1868  CB   ILE  1051     16.198    6.089   29.053  1.00  28.31      B
ATOM   1869  CG2  ILE  1051     16.043    7.464   28.414  1.00  25.64      B
ATOM   1870  CG1  ILE  1051     17.665    5.652   29.042  1.00  24.45      B
ATOM   1871  CD1  ILE  1051     18.092    5.013   27.753  1.00  25.76      B
ATOM   1872  C    ILE  1051     14.508    7.103   30.603  1.00  26.49      B
ATOM   1873  O    ILE  1051     14.689    8.229   31.040  1.00  25.11      B
ATOM   1874  N    VAL  1052     13.332    6.687   30.142  1.00  28.11      B
ATOM   1875  CA   VAL  1052     12.128    7.519   30.160  1.00  29.87      B
ATOM   1876  CB   VAL  1052     10.925    6.776   29.522  1.00  30.15      B
```

Fig. 2A-32

| | | | | | | | | |
|---|---|---|---|---|---|---|---|---|
| ATOM | 1877 | CG1 | VAL | 1052 | 9.625 | 7.417 | 29.963 | 1.00 29.45 | B |
| ATOM | 1878 | CG2 | VAL | 1052 | 11.039 | 6.796 | 28.018 | 1.00 30.73 | B |
| ATOM | 1879 | C | VAL | 1052 | 11.760 | 7.876 | 31.588 | 1.00 32.04 | B |
| ATOM | 1880 | O | VAL | 1052 | 11.292 | 8.990 | 31.872 | 1.00 33.79 | B |
| ATOM | 1881 | N | LEU | 1053 | 11.958 | 6.935 | 32.502 | 1.00 32.59 | B |
| ATOM | 1882 | CA | LEU | 1053 | 11.647 | 7.176 | 33.895 | 1.00 33.87 | B |
| ATOM | 1883 | CB | LEU | 1053 | 11.353 | 5.848 | 34.581 | 1.00 31.61 | B |
| ATOM | 1884 | CG | LEU | 1053 | 10.220 | 4.971 | 34.033 | 1.00 29.77 | B |
| ATOM | 1885 | CD1 | LEU | 1053 | 9.941 | 3.836 | 34.989 | 1.00 27.85 | B |
| ATOM | 1886 | CD2 | LEU | 1053 | 8.976 | 5.797 | 33.821 | 1.00 28.12 | B |
| ATOM | 1887 | C | LEU | 1053 | 12.833 | 7.870 | 34.574 | 1.00 36.43 | B |
| ATOM | 1888 | O | LEU | 1053 | 12.696 | 8.443 | 35.651 | 1.00 36.92 | B |
| ATOM | 1889 | N | GLU | 1054 | 13.994 | 7.822 | 33.930 | 1.00 39.41 | B |
| ATOM | 1890 | CA | GLU | 1054 | 15.199 | 8.414 | 34.485 | 1.00 42.97 | B |
| ATOM | 1891 | CB | GLU | 1054 | 16.434 | 7.744 | 33.874 | 1.00 44.41 | B |
| ATOM | 1892 | CG | GLU | 1054 | 16.655 | 6.325 | 34.361 | 1.00 50.00 | B |
| ATOM | 1893 | CD | GLU | 1054 | 17.466 | 6.248 | 35.644 | 1.00 51.72 | B |
| ATOM | 1894 | OE1 | GLU | 1054 | 18.410 | 7.049 | 35.794 | 1.00 55.23 | B |
| ATOM | 1895 | OE2 | GLU | 1054 | 17.166 | 5.384 | 36.500 | 1.00 52.83 | B |
| ATOM | 1896 | C | GLU | 1054 | 15.319 | 9.927 | 34.334 | 1.00 44.14 | B |
| ATOM | 1897 | O | GLU | 1054 | 16.408 | 10.475 | 34.496 | 1.00 45.10 | B |
| ATOM | 1898 | N | GLY | 1055 | 14.227 | 10.612 | 34.026 | 1.00 44.89 | B |
| ATOM | 1899 | CA | GLY | 1055 | 14.324 | 12.055 | 33.888 | 1.00 48.37 | B |
| ATOM | 1900 | C | GLY | 1055 | 13.191 | 12.656 | 33.095 | 1.00 49.90 | B |
| ATOM | 1901 | O | GLY | 1055 | 13.418 | 13.399 | 32.140 | 1.00 51.16 | B |
| ATOM | 1902 | N | ASN | 1056 | 11.972 | 12.323 | 33.513 | 1.00 51.18 | B |
| ATOM | 1903 | CA | ASN | 1056 | 10.728 | 12.762 | 32.880 | 1.00 51.63 | B |
| ATOM | 1904 | CB | ASN | 1056 | 9.539 | 12.223 | 33.688 | 1.00 52.96 | B |
| ATOM | 1905 | CG | ASN | 1056 | 9.879 | 12.000 | 35.160 | 1.00 53.86 | B |
| ATOM | 1906 | OD1 | ASN | 1056 | 9.272 | 11.168 | 35.827 | 1.00 54.15 | B |
| ATOM | 1907 | ND2 | ASN | 1056 | 10.852 | 12.749 | 35.669 | 1.00 54.37 | B |
| ATOM | 1908 | C | ASN | 1056 | 10.549 | 14.272 | 32.631 | 1.00 51.37 | B |
| ATOM | 1909 | O | ASN | 1056 | 9.473 | 14.838 | 32.886 | 1.00 52.18 | B |
| ATOM | 1910 | N | ASP | 1057 | 11.609 | 14.908 | 32.132 | 1.00 49.97 | B |
| ATOM | 1911 | CA | ASP | 1057 | 11.615 | 16.326 | 31.780 | 1.00 46.40 | B |
| ATOM | 1912 | CB | ASP | 1057 | 12.759 | 17.086 | 32.461 | 1.00 49.32 | B |
| ATOM | 1913 | CG | ASP | 1057 | 12.792 | 16.903 | 33.967 | 1.00 52.86 | B |
| ATOM | 1914 | OD1 | ASP | 1057 | 13.266 | 15.840 | 34.425 | 1.00 52.39 | B |
| ATOM | 1915 | OD2 | ASP | 1057 | 12.357 | 17.831 | 34.694 | 1.00 54.20 | B |
| ATOM | 1916 | C | ASP | 1057 | 11.903 | 16.331 | 30.288 | 1.00 42.96 | B |
| ATOM | 1917 | O | ASP | 1057 | 11.955 | 17.383 | 29.658 | 1.00 42.35 | B |
| ATOM | 1918 | N | MET | 1058 | 12.110 | 15.142 | 29.728 | 1.00 38.42 | B |
| ATOM | 1919 | CA | MET | 1058 | 12.428 | 15.040 | 28.314 | 1.00 34.68 | B |
| ATOM | 1920 | CB | MET | 1058 | 13.087 | 13.678 | 27.979 | 1.00 29.43 | B |
| ATOM | 1921 | CG | MET | 1058 | 12.581 | 12.432 | 28.712 | 1.00 22.23 | B |
| ATOM | 1922 | SD | MET | 1058 | 13.055 | 10.864 | 27.848 | 1.00 8.61 | B |
| ATOM | 1923 | CE | MET | 1058 | 14.777 | 10.737 | 28.298 | 1.00 6.43 | B |
| ATOM | 1924 | C | MET | 1058 | 11.243 | 15.291 | 27.391 | 1.00 34.07 | B |
| ATOM | 1925 | O | MET | 1058 | 10.094 | 15.336 | 27.835 | 1.00 34.35 | B |
| ATOM | 1926 | N | ASP | 1059 | 11.555 | 15.474 | 26.107 | 1.00 32.30 | B |
| ATOM | 1927 | CA | ASP | 1059 | 10.579 | 15.712 | 25.046 | 1.00 28.97 | B |
| ATOM | 1928 | CB | ASP | 1059 | 11.321 | 15.844 | 23.713 | 1.00 29.72 | B |
| ATOM | 1929 | CG | ASP | 1059 | 10.447 | 16.384 | 22.613 | 1.00 30.37 | B |
| ATOM | 1930 | OD1 | ASP | 1059 | 10.087 | 15.607 | 21.712 | 1.00 32.29 | B |
| ATOM | 1931 | OD2 | ASP | 1059 | 10.121 | 17.583 | 22.639 | 1.00 33.47 | B |
| ATOM | 1932 | C | ASP | 1059 | 9.600 | 14.539 | 24.972 | 1.00 28.22 | B |
| ATOM | 1933 | O | ASP | 1059 | 10.001 | 13.383 | 25.162 | 1.00 26.20 | B |

Fig. 2A-33

| | | | | | | | | | |
|---|---|---|---|---|---|---|---|---|---|
| ATOM | 1934 | N | ILE | 1060 | 8.323 | 14.815 | 24.698 | 1.00 25.40 | B |
| ATOM | 1935 | CA | ILE | 1060 | 7.364 | 13.725 | 24.615 | 1.00 23.86 | B |
| ATOM | 1936 | CB | ILE | 1060 | 5.889 | 14.191 | 24.730 | 1.00 24.13 | B |
| ATOM | 1937 | CG2 | ILE | 1060 | 5.616 | 14.667 | 26.129 | 1.00 26.24 | B |
| ATOM | 1938 | CG1 | ILE | 1060 | 5.582 | 15.307 | 23.743 | 1.00 25.30 | B |
| ATOM | 1939 | CD1 | ILE | 1060 | 4.111 | 15.713 | 23.765 | 1.00 24.57 | B |
| ATOM | 1940 | C | ILE | 1060 | 7.535 | 12.924 | 23.332 | 1.00 22.61 | B |
| ATOM | 1941 | O | ILE | 1060 | 7.001 | 11.824 | 23.223 | 1.00 23.44 | B |
| ATOM | 1942 | N | ARG | 1061 | 8.273 | 13.461 | 22.363 | 1.00 20.99 | B |
| ATOM | 1943 | CA | ARG | 1061 | 8.503 | 12.720 | 21.124 | 1.00 20.45 | B |
| ATOM | 1944 | CB | ARG | 1061 | 8.998 | 13.630 | 19.994 | 1.00 21.03 | B |
| ATOM | 1945 | CG | ARG | 1061 | 8.020 | 14.738 | 19.613 | 1.00 23.60 | B |
| ATOM | 1946 | CD | ARG | 1061 | 7.910 | 14.928 | 18.108 | 1.00 20.80 | B |
| ATOM | 1947 | NE | ARG | 1061 | 6.589 | 15.426 | 17.759 | 1.00 19.01 | B |
| ATOM | 1948 | CZ | ARG | 1061 | 6.058 | 15.363 | 16.548 | 1.00 18.92 | B |
| ATOM | 1949 | NH1 | ARG | 1061 | 6.736 | 14.812 | 15.548 | 1.00 18.29 | B |
| ATOM | 1950 | NH2 | ARG | 1061 | 4.835 | 15.834 | 16.343 | 1.00 17.05 | B |
| ATOM | 1951 | C | ARG | 1061 | 9.563 | 11.683 | 21.430 | 1.00 18.95 | B |
| ATOM | 1952 | O | ARG | 1061 | 9.490 | 10.549 | 20.954 | 1.00 19.68 | B |
| ATOM | 1953 | N | THR | 1062 | 10.542 | 12.084 | 22.238 | 1.00 19.11 | B |
| ATOM | 1954 | CA | THR | 1062 | 11.640 | 11.212 | 22.653 | 1.00 18.81 | B |
| ATOM | 1955 | CB | THR | 1062 | 12.637 | 11.955 | 23.553 | 1.00 16.28 | B |
| ATOM | 1956 | OG1 | THR | 1062 | 13.142 | 13.103 | 22.875 | 1.00 21.04 | B |
| ATOM | 1957 | CG2 | THR | 1062 | 13.781 | 11.049 | 23.937 | 1.00 13.59 | B |
| ATOM | 1958 | C | THR | 1062 | 11.085 | 10.065 | 23.484 | 1.00 21.57 | B |
| ATOM | 1959 | O | THR | 1062 | 11.536 | 8.921 | 23.383 | 1.00 21.27 | B |
| ATOM | 1960 | N | GLU | 1063 | 10.119 | 10.416 | 24.330 | 1.00 22.15 | B |
| ATOM | 1961 | CA | GLU | 1063 | 9.452 | 9.489 | 25.231 | 1.00 20.15 | B |
| ATOM | 1962 | CB | GLU | 1063 | 8.513 | 10.284 | 26.136 | 1.00 24.67 | B |
| ATOM | 1963 | CG | GLU | 1063 | 8.038 | 9.539 | 27.362 | 1.00 33.22 | B |
| ATOM | 1964 | CD | GLU | 1063 | 6.633 | 9.953 | 27.776 | 1.00 37.24 | B |
| ATOM | 1965 | OE1 | GLU | 1063 | 6.474 | 11.037 | 28.392 | 1.00 37.20 | B |
| ATOM | 1966 | OE2 | GLU | 1063 | 5.685 | 9.191 | 27.482 | 1.00 38.73 | B |
| ATOM | 1967 | C | GLU | 1063 | 8.670 | 8.443 | 24.457 | 1.00 17.42 | B |
| ATOM | 1968 | O | GLU | 1063 | 8.753 | 7.252 | 24.740 | 1.00 15.48 | B |
| ATOM | 1969 | N | ALA | 1064 | 7.927 | 8.903 | 23.459 | 1.00 16.19 | B |
| ATOM | 1970 | CA | ALA | 1064 | 7.110 | 8.040 | 22.619 | 1.00 16.46 | B |
| ATOM | 1971 | CB | ALA | 1064 | 6.137 | 8.884 | 21.822 | 1.00 13.15 | B |
| ATOM | 1972 | C | ALA | 1064 | 7.944 | 7.168 | 21.675 | 1.00 18.81 | B |
| ATOM | 1973 | O | ALA | 1064 | 7.495 | 6.107 | 21.230 | 1.00 19.49 | B |
| ATOM | 1974 | N | MET | 1065 | 9.146 | 7.618 | 21.341 | 1.00 18.41 | B |
| ATOM | 1975 | CA | MET | 1065 | 10.006 | 6.830 | 20.470 | 1.00 18.27 | B |
| ATOM | 1976 | CB | MET | 1065 | 11.068 | 7.723 | 19.806 | 1.00 14.93 | B |
| ATOM | 1977 | CG | MET | 1065 | 10.536 | 8.527 | 18.598 | 1.00 14.02 | B |
| ATOM | 1978 | SD | MET | 1065 | 11.809 | 9.279 | 17.543 | 1.00 5.01 | B |
| ATOM | 1979 | CE | MET | 1065 | 12.396 | 10.510 | 18.660 | 1.00 5.76 | B |
| ATOM | 1980 | C | MET | 1065 | 10.654 | 5.777 | 21.348 | 1.00 18.42 | B |
| ATOM | 1981 | O | MET | 1065 | 10.919 | 4.659 | 20.912 | 1.00 18.34 | B |
| ATOM | 1982 | N | LEU | 1066 | 10.883 | 6.133 | 22.607 | 1.00 19.32 | B |
| ATOM | 1983 | CA | LEU | 1066 | 11.486 | 5.219 | 23.568 | 1.00 19.77 | B |
| ATOM | 1984 | CB | LEU | 1066 | 11.992 | 5.993 | 24.792 | 1.00 17.60 | B |
| ATOM | 1985 | CG | LEU | 1066 | 13.226 | 6.883 | 24.643 | 1.00 17.90 | B |
| ATOM | 1986 | CD1 | LEU | 1066 | 13.634 | 7.442 | 26.010 | 1.00 19.06 | B |
| ATOM | 1987 | CD2 | LEU | 1066 | 14.361 | 6.091 | 24.030 | 1.00 18.79 | B |
| ATOM | 1988 | C | LEU | 1066 | 10.475 | 4.143 | 24.017 | 1.00 21.44 | B |
| ATOM | 1989 | O | LEU | 1066 | 10.871 | 3.019 | 24.337 | 1.00 22.51 | B |
| ATOM | 1990 | N | PHE | 1067 | 9.186 | 4.491 | 24.058 | 1.00 20.56 | B |

Fig. 2A-34

| | | | | | | | | | |
|---|---|---|---|---|---|---|---|---|---|
| ATOM | 1991 | CA | PHE | 1067 | 8.131 | 3.557 | 24.453 | 1.00 22.34 | B |
| ATOM | 1992 | CB | PHE | 1067 | 6.873 | 4.312 | 24.896 | 1.00 23.54 | B |
| ATOM | 1993 | CG | PHE | 1067 | 6.853 | 4.669 | 26.364 | 1.00 26.00 | B |
| ATOM | 1994 | CD1 | PHE | 1067 | 7.151 | 5.961 | 26.779 | 1.00 29.26 | B |
| ATOM | 1995 | CD2 | PHE | 1067 | 6.511 | 3.727 | 27.321 | 1.00 28.46 | B |
| ATOM | 1996 | CE1 | PHE | 1067 | 7.106 | 6.315 | 28.129 | 1.00 31.04 | B |
| ATOM | 1997 | CE2 | PHE | 1067 | 6.461 | 4.064 | 28.675 | 1.00 31.80 | B |
| ATOM | 1998 | CZ | PHE | 1067 | 6.762 | 5.367 | 29.078 | 1.00 31.72 | B |
| ATOM | 1999 | C | PHE | 1067 | 7.780 | 2.650 | 23.285 | 1.00 22.70 | B |
| ATOM | 2000 | O | PHE | 1067 | 7.205 | 1.573 | 23.470 | 1.00 24.34 | B |
| ATOM | 2001 | N | ALA | 1068 | 8.104 | 3.090 | 22.073 | 1.00 19.20 | B |
| ATOM | 2002 | CA | ALA | 1068 | 7.845 | 2.297 | 20.883 | 1.00 16.13 | B |
| ATOM | 2003 | CB | ALA | 1068 | 7.742 | 3.202 | 19.664 | 1.00 16.31 | B |
| ATOM | 2004 | C | ALA | 1068 | 8.985 | 1.297 | 20.724 | 1.00 14.28 | B |
| ATOM | 2005 | O | ALA | 1068 | 8.783 | 0.175 | 20.244 | 1.00 13.00 | B |
| ATOM | 2006 | N | ALA | 1069 | 10.177 | 1.700 | 21.156 | 1.00 11.59 | B |
| ATOM | 2007 | CA | ALA | 1069 | 11.364 | 0.853 | 21.084 | 1.00 12.86 | B |
| ATOM | 2008 | CB | ALA | 1069 | 12.607 | 1.686 | 21.323 | 1.00 8.12 | B |
| ATOM | 2009 | C | ALA | 1069 | 11.281 | -0.261 | 22.119 | 1.00 13.59 | B |
| ATOM | 2010 | O | ALA | 1069 | 11.751 | -1.376 | 21.889 | 1.00 14.95 | B |
| ATOM | 2011 | N | SER | 1070 | 10.690 | 0.043 | 23.272 | 1.00 14.90 | B |
| ATOM | 2012 | CA | SER | 1070 | 10.543 | -0.923 | 24.360 | 1.00 14.47 | B |
| ATOM | 2013 | CB | SER | 1070 | 10.105 | -0.217 | 25.631 | 1.00 14.87 | B |
| ATOM | 2014 | OG | SER | 1070 | 10.211 | -1.078 | 26.744 | 1.00 18.20 | B |
| ATOM | 2015 | C | SER | 1070 | 9.501 | -1.963 | 24.001 | 1.00 15.57 | B |
| ATOM | 2016 | O | SER | 1070 | 9.662 | -3.153 | 24.294 | 1.00 15.28 | B |
| ATOM | 2017 | N | ARG | 1071 | 8.417 | -1.494 | 23.387 | 1.00 16.51 | B |
| ATOM | 2018 | CA | ARG | 1071 | 7.311 | -2.348 | 22.973 | 1.00 16.14 | B |
| ATOM | 2019 | CB | ARG | 1071 | 6.114 | -1.514 | 22.497 | 1.00 16.49 | B |
| ATOM | 2020 | CG | ARG | 1071 | 5.236 | -2.249 | 21.482 | 1.00 18.09 | B |
| ATOM | 2021 | CD | ARG | 1071 | 3.887 | -1.586 | 21.278 | 1.00 19.93 | B |
| ATOM | 2022 | NE | ARG | 1071 | 3.291 | -1.171 | 22.539 | 1.00 25.22 | B |
| ATOM | 2023 | CZ | ARG | 1071 | 2.844 | 0.056 | 22.768 | 1.00 26.85 | B |
| ATOM | 2024 | NH1 | ARG | 1071 | 2.311 | 0.369 | 23.941 | 1.00 28.58 | B |
| ATOM | 2025 | NH2 | ARG | 1071 | 2.935 | 0.971 | 21.814 | 1.00 29.90 | B |
| ATOM | 2026 | C | ARG | 1071 | 7.744 | -3.278 | 21.870 | 1.00 17.63 | B |
| ATOM | 2027 | O | ARG | 1071 | 7.231 | -4.391 | 21.785 | 1.00 20.80 | B |
| ATOM | 2028 | N | ARG | 1072 | 8.666 | -2.835 | 21.016 | 1.00 16.55 | B |
| ATOM | 2029 | CA | ARG | 1072 | 9.150 | -3.680 | 19.928 | 1.00 15.86 | B |
| ATOM | 2030 | CB | ARG | 1072 | 10.014 | -2.886 | 18.951 | 1.00 16.65 | B |
| ATOM | 2031 | CG | ARG | 1072 | 10.874 | -3.755 | 18.043 | 1.00 19.59 | B |
| ATOM | 2032 | CD | ARG | 1072 | 10.676 | -3.384 | 16.589 | 1.00 22.74 | B |
| ATOM | 2033 | NE | ARG | 1072 | 11.084 | -4.432 | 15.661 | 1.00 20.12 | B |
| ATOM | 2034 | CZ | ARG | 1072 | 10.235 | -5.112 | 14.903 | 1.00 20.05 | B |
| ATOM | 2035 | NH1 | ARG | 1072 | 10.689 | -6.046 | 14.084 | 1.00 21.46 | B |
| ATOM | 2036 | NH2 | ARG | 1072 | 8.933 | -4.870 | 14.978 | 1.00 15.76 | B |
| ATOM | 2037 | C | ARG | 1072 | 9.975 | -4.833 | 20.488 | 1.00 14.59 | B |
| ATOM | 2038 | O | ARG | 1072 | 9.792 | -5.991 | 20.106 | 1.00 13.68 | B |
| ATOM | 2039 | N | GLU | 1073 | 10.883 | -4.508 | 21.399 | 1.00 13.23 | B |
| ATOM | 2040 | CA | GLU | 1073 | 11.756 | -5.495 | 22.021 | 1.00 13.86 | B |
| ATOM | 2041 | CB | GLU | 1073 | 12.667 | -4.803 | 23.035 | 1.00 12.81 | B |
| ATOM | 2042 | CG | GLU | 1073 | 13.937 | -4.196 | 22.437 | 1.00 15.67 | B |
| ATOM | 2043 | CD | GLU | 1073 | 14.840 | -5.232 | 21.760 | 1.00 17.93 | B |
| ATOM | 2044 | OE1 | GLU | 1073 | 15.824 | -5.654 | 22.396 | 1.00 19.24 | B |
| ATOM | 2045 | OE2 | GLU | 1073 | 14.580 | -5.629 | 20.600 | 1.00 17.00 | B |
| ATOM | 2046 | C | GLU | 1073 | 10.919 | -6.555 | 22.718 | 1.00 15.94 | B |
| ATOM | 2047 | O | GLU | 1073 | 11.237 | -7.751 | 22.686 | 1.00 15.22 | B |

Fig. 2A-35

```
ATOM   2048  N   HIS  1074      9.838  -6.099  23.342  1.00 16.16      B
ATOM   2049  CA  HIS  1074      8.947  -6.972  24.071  1.00 16.13      B
ATOM   2050  CB  HIS  1074      8.006  -6.133  24.946  1.00 13.85      B
ATOM   2051  CG  HIS  1074      6.895  -6.918  25.576  1.00 10.33      B
ATOM   2052  CD2 HIS  1074      5.631  -7.155  25.172  1.00  6.92      B
ATOM   2053  ND1 HIS  1074      7.050  -7.596  26.775  1.00 10.02      B
ATOM   2054  CE1 HIS  1074      5.919  -8.217  27.066  1.00  7.99      B
ATOM   2055  NE2 HIS  1074      5.043  -7.966  26.111  1.00  6.02      B
ATOM   2056  C   HIS  1074      8.161  -7.774  23.059  1.00 18.20      B
ATOM   2057  O   HIS  1074      7.605  -8.824  23.367  1.00 21.72      B
ATOM   2058  N   LEU  1075      8.111  -7.286  21.835  1.00 19.11      B
ATOM   2059  CA  LEU  1075      7.359  -7.975  20.805  1.00 20.30      B
ATOM   2060  CB  LEU  1075      6.979  -6.993  19.699  1.00 18.54      B
ATOM   2061  CG  LEU  1075      5.596  -7.174  19.079  1.00 18.21      B
ATOM   2062  CD1 LEU  1075      4.520  -7.218  20.166  1.00 16.64      B
ATOM   2063  CD2 LEU  1075      5.345  -6.033  18.114  1.00 14.97      B
ATOM   2064  C   LEU  1075      8.172  -9.117  20.219  1.00 22.06      B
ATOM   2065  O   LEU  1075      7.766 -10.285  20.255  1.00 22.68      B
ATOM   2066  N   VAL  1076      9.343  -8.767  19.709  1.00 22.15      B
ATOM   2067  CA  VAL  1076     10.237  -9.714  19.074  1.00 23.94      B
ATOM   2068  CB  VAL  1076     11.339  -8.940  18.302  1.00 23.36      B
ATOM   2069  CG1 VAL  1076     10.710  -8.082  17.203  1.00 23.52      B
ATOM   2070  CG2 VAL  1076     12.102  -8.048  19.257  1.00 23.44      B
ATOM   2071  C   VAL  1076     10.887 -10.737  20.017  1.00 24.30      B
ATOM   2072  O   VAL  1076     11.227 -11.850  19.602  1.00 24.68      B
ATOM   2073  N   LEU  1077     11.042 -10.375  21.284  1.00 23.35      B
ATOM   2074  CA  LEU  1077     11.681 -11.257  22.252  1.00 20.68      B
ATOM   2075  CB  LEU  1077     12.645 -10.457  23.125  1.00 21.82      B
ATOM   2076  CG  LEU  1077     13.819  -9.765  22.445  1.00 22.63      B
ATOM   2077  CD1 LEU  1077     14.448  -8.760  23.387  1.00 21.45      B
ATOM   2078  CD2 LEU  1077     14.835 -10.815  22.043  1.00 23.05      B
ATOM   2079  C   LEU  1077     10.760 -12.025  23.189  1.00 20.11      B
ATOM   2080  O   LEU  1077     11.221 -12.951  23.859  1.00 20.85      B
ATOM   2081  N   LYS  1078      9.481 -11.658  23.259  1.00 18.79      B
ATOM   2082  CA  LYS  1078      8.562 -12.310  24.192  1.00 17.09      B
ATOM   2083  CB  LYS  1078      8.347 -11.382  25.394  1.00 17.11      B
ATOM   2084  CG  LYS  1078      7.248 -11.801  26.347  1.00 16.13      B
ATOM   2085  CD  LYS  1078      7.689 -11.702  27.801  1.00 15.07      B
ATOM   2086  CE  LYS  1078      6.522 -12.048  28.712  1.00 17.01      B
ATOM   2087  NZ  LYS  1078      6.659 -11.528  30.105  1.00 14.66      B
ATOM   2088  C   LYS  1078      7.208 -12.734  23.618  1.00 17.85      B
ATOM   2089  O   LYS  1078      6.791 -13.881  23.746  1.00 16.99      B
ATOM   2090  N   VAL  1079      6.504 -11.800  23.000  1.00 18.10      B
ATOM   2091  CA  VAL  1079      5.208 -12.112  22.423  1.00 16.16      B
ATOM   2092  CB  VAL  1079      4.439 -10.811  22.084  1.00 13.64      B
ATOM   2093  CG1 VAL  1079      3.118 -11.123  21.380  1.00 12.40      B
ATOM   2094  CG2 VAL  1079      4.170 -10.040  23.368  1.00 11.59      B
ATOM   2095  C   VAL  1079      5.322 -12.994  21.178  1.00 17.11      B
ATOM   2096  O   VAL  1079      4.716 -14.075  21.113  1.00 17.94      B
ATOM   2097  N   ILE  1080      6.105 -12.551  20.198  1.00 16.62      B
ATOM   2098  CA  ILE  1080      6.249 -13.307  18.952  1.00 16.40      B
ATOM   2099  CB  ILE  1080      7.196 -12.586  17.958  1.00 15.17      B
ATOM   2100  CG2 ILE  1080      7.556 -13.511  16.794  1.00 14.75      B
ATOM   2101  CG1 ILE  1080      6.492 -11.332  17.422  1.00 12.43      B
ATOM   2102  CD1 ILE  1080      6.983 -10.869  16.068  1.00 13.32      B
ATOM   2103  C   ILE  1080      6.678 -14.763  19.165  1.00 15.24      B
ATOM   2104  O   ILE  1080      6.043 -15.672  18.640  1.00 18.99      B
```

Fig. 2A-36

| | | | | | | | | | |
|---|---|---|---|---|---|---|---|---|---|
| ATOM | 2105 | N | PRO | 1081 | 7.763 | -15.008 | 19.911 | 1.00 | 13.95 | B |
| ATOM | 2106 | CD | PRO | 1081 | 8.681 | -14.049 | 20.550 | 1.00 | 15.20 | B |
| ATOM | 2107 | CA | PRO | 1081 | 8.174 | -16.399 | 20.137 | 1.00 | 13.22 | B |
| ATOM | 2108 | CB | PRO | 1081 | 9.359 | -16.285 | 21.095 | 1.00 | 11.75 | B |
| ATOM | 2109 | CG | PRO | 1081 | 9.851 | -14.904 | 20.940 | 1.00 | 15.07 | B |
| ATOM | 2110 | C | PRO | 1081 | 7.036 | -17.237 | 20.756 | 1.00 | 15.56 | B |
| ATOM | 2111 | O | PRO | 1081 | 6.805 | -18.379 | 20.342 | 1.00 | 12.94 | B |
| ATOM | 2112 | N | ALA | 1082 | 6.338 | -16.667 | 21.749 | 1.00 | 15.50 | B |
| ATOM | 2113 | CA | ALA | 1082 | 5.237 | -17.355 | 22.437 | 1.00 | 15.31 | B |
| ATOM | 2114 | CB | ALA | 1082 | 4.767 | -16.550 | 23.647 | 1.00 | 14.69 | B |
| ATOM | 2115 | C | ALA | 1082 | 4.075 | -17.593 | 21.499 | 1.00 | 15.19 | B |
| ATOM | 2116 | O | ALA | 1082 | 3.269 | -18.500 | 21.711 | 1.00 | 13.42 | B |
| ATOM | 2117 | N | LEU | 1083 | 3.975 | -16.765 | 20.470 | 1.00 | 15.09 | B |
| ATOM | 2118 | CA | LEU | 1083 | 2.918 | -16.941 | 19.504 | 1.00 | 15.96 | B |
| ATOM | 2119 | CB | LEU | 1083 | 2.698 | -15.642 | 18.735 | 1.00 | 17.04 | B |
| ATOM | 2120 | CG | LEU | 1083 | 2.094 | -14.482 | 19.541 | 1.00 | 17.77 | B |
| ATOM | 2121 | CD1 | LEU | 1083 | 1.974 | -13.256 | 18.650 | 1.00 | 14.42 | B |
| ATOM | 2122 | CD2 | LEU | 1083 | 0.716 | -14.880 | 20.082 | 1.00 | 13.47 | B |
| ATOM | 2123 | C | LEU | 1083 | 3.392 | -18.072 | 18.582 | 1.00 | 18.13 | B |
| ATOM | 2124 | O | LEU | 1083 | 2.610 | -18.924 | 18.169 | 1.00 | 17.94 | B |
| ATOM | 2125 | N | LYS | 1084 | 4.687 | -18.101 | 18.282 | 1.00 | 20.06 | B |
| ATOM | 2126 | CA | LYS | 1084 | 5.240 | -19.156 | 17.430 | 1.00 | 22.98 | B |
| ATOM | 2127 | CB | LYS | 1084 | 6.744 | -18.971 | 17.237 | 1.00 | 23.46 | B |
| ATOM | 2128 | CG | LYS | 1084 | 7.190 | -17.669 | 16.600 | 1.00 | 27.95 | B |
| ATOM | 2129 | CD | LYS | 1084 | 8.721 | -17.601 | 16.635 | 1.00 | 31.73 | B |
| ATOM | 2130 | CE | LYS | 1084 | 9.269 | -16.300 | 16.072 | 1.00 | 32.22 | B |
| ATOM | 2131 | NZ | LYS | 1084 | 10.319 | -15.708 | 16.964 | 1.00 | 32.73 | B |
| ATOM | 2132 | C | LYS | 1084 | 5.012 | -20.517 | 18.104 | 1.00 | 23.71 | B |
| ATOM | 2133 | O | LYS | 1084 | 5.175 | -21.569 | 17.482 | 1.00 | 22.88 | B |
| ATOM | 2134 | N | GLU | 1085 | 4.650 | -20.473 | 19.383 | 1.00 | 25.26 | B |
| ATOM | 2135 | CA | GLU | 1085 | 4.416 | -21.667 | 20.191 | 1.00 | 26.48 | B |
| ATOM | 2136 | CB | GLU | 1085 | 4.922 | -21.440 | 21.612 | 1.00 | 31.70 | B |
| ATOM | 2137 | CG | GLU | 1085 | 6.409 | -21.190 | 21.708 | 1.00 | 37.19 | B |
| ATOM | 2138 | CD | GLU | 1085 | 7.191 | -22.452 | 21.471 | 1.00 | 42.06 | B |
| ATOM | 2139 | OE1 | GLU | 1085 | 6.608 | -23.540 | 21.665 | 1.00 | 44.55 | B |
| ATOM | 2140 | OE2 | GLU | 1085 | 8.376 | -22.366 | 21.088 | 1.00 | 46.19 | B |
| ATOM | 2141 | C | GLU | 1085 | 2.943 | -22.008 | 20.250 | 1.00 | 24.53 | B |
| ATOM | 2142 | O | GLU | 1085 | 2.523 | -22.854 | 21.034 | 1.00 | 23.33 | B |
| ATOM | 2143 | N | GLY | 1086 | 2.155 | -21.333 | 19.433 | 1.00 | 23.68 | B |
| ATOM | 2144 | CA | GLY | 1086 | 0.737 | -21.606 | 19.427 | 1.00 | 23.95 | B |
| ATOM | 2145 | C | GLY | 1086 | 0.002 | -21.032 | 20.615 | 1.00 | 25.01 | B |
| ATOM | 2146 | O | GLY | 1086 | -1.221 | -21.136 | 20.694 | 1.00 | 27.87 | B |
| ATOM | 2147 | N | LYS | 1087 | 0.716 | -20.415 | 21.544 | 1.00 | 23.13 | B |
| ATOM | 2148 | CA | LYS | 1087 | 0.043 | -19.869 | 22.712 | 1.00 | 20.37 | B |
| ATOM | 2149 | CB | LYS | 1087 | 1.057 | -19.481 | 23.795 | 1.00 | 17.74 | B |
| ATOM | 2150 | CG | LYS | 1087 | 1.894 | -20.656 | 24.282 | 1.00 | 17.34 | B |
| ATOM | 2151 | CD | LYS | 1087 | 2.411 | -20.449 | 25.676 | 1.00 | 13.37 | B |
| ATOM | 2152 | CE | LYS | 1087 | 3.893 | -20.280 | 25.632 | 1.00 | 12.04 | B |
| ATOM | 2153 | NZ | LYS | 1087 | 4.576 | -21.530 | 25.976 | 1.00 | 10.91 | B |
| ATOM | 2154 | C | LYS | 1087 | -0.794 | -18.664 | 22.361 | 1.00 | 20.06 | B |
| ATOM | 2155 | O | LYS | 1087 | -0.595 | -18.025 | 21.331 | 1.00 | 19.82 | B |
| ATOM | 2156 | N | VAL | 1088 | -1.784 | -18.391 | 23.195 | 1.00 | 20.09 | B |
| ATOM | 2157 | CA | VAL | 1088 | -2.582 | -17.208 | 22.988 | 1.00 | 19.17 | B |
| ATOM | 2158 | CB | VAL | 1088 | -4.111 | -17.461 | 23.200 | 1.00 | 19.15 | B |
| ATOM | 2159 | CG1 | VAL | 1088 | -4.346 | -18.731 | 23.987 | 1.00 | 17.46 | B |
| ATOM | 2160 | CG2 | VAL | 1088 | -4.752 | -16.250 | 23.866 | 1.00 | 20.39 | B |
| ATOM | 2161 | C | VAL | 1088 | -1.975 | -16.354 | 24.089 | 1.00 | 19.23 | B |

Fig. 2A-37

```
ATOM   2162  O   VAL  1088     -1.705  -16.856  25.182  1.00  16.14     B
ATOM   2163  N   VAL  1089     -1.697  -15.088  23.793  1.00  19.93     B
ATOM   2164  CA  VAL  1089     -1.090  -14.210  24.797  1.00  20.79     B
ATOM   2165  CB  VAL  1089      0.319  -13.777  24.355  1.00  20.97     B
ATOM   2166  CG1 VAL  1089      0.276  -13.315  22.931  1.00  23.46     B
ATOM   2167  CG2 VAL  1089      0.846  -12.676  25.254  1.00  21.64     B
ATOM   2168  C   VAL  1089     -1.930  -12.970  25.094  1.00  19.98     B
ATOM   2169  O   VAL  1089     -2.329  -12.233  24.185  1.00  20.42     B
ATOM   2170  N   LEU  1090     -2.206  -12.753  26.376  1.00  18.26     B
ATOM   2171  CA  LEU  1090     -2.979  -11.596  26.797  1.00  18.09     B
ATOM   2172  CB  LEU  1090     -3.869  -11.960  27.993  1.00  18.46     B
ATOM   2173  CG  LEU  1090     -4.744  -13.213  27.915  1.00  16.30     B
ATOM   2174  CD1 LEU  1090     -5.272  -13.519  29.299  1.00  18.52     B
ATOM   2175  CD2 LEU  1090     -5.911  -12.990  26.965  1.00  15.78     B
ATOM   2176  C   LEU  1090     -2.003  -10.478  27.182  1.00  17.29     B
ATOM   2177  O   LEU  1090     -1.115  -10.688  28.004  1.00  16.83     B
ATOM   2178  N   CYS  1091     -2.160   -9.307  26.567  1.00  16.59     B
ATOM   2179  CA  CYS  1091     -1.298   -8.156  26.837  1.00  19.29     B
ATOM   2180  CB  CYS  1091     -0.601   -7.734  25.547  1.00  20.03     B
ATOM   2181  SG  CYS  1091      0.892   -6.757  25.782  1.00  20.36     B
ATOM   2182  C   CYS  1091     -2.163   -7.013  27.356  1.00  20.41     B
ATOM   2183  O   CYS  1091     -3.246   -6.782  26.833  1.00  20.96     B
ATOM   2184  N   ASP  1092     -1.711   -6.293  28.378  1.00  24.12     B
ATOM   2185  CA  ASP  1092     -2.541   -5.205  28.887  1.00  29.39     B
ATOM   2186  CB  ASP  1092     -2.178   -4.840  30.324  1.00  34.06     B
ATOM   2187  CG  ASP  1092     -0.755   -5.155  30.661  1.00  40.00     B
ATOM   2188  OD1 ASP  1092      0.144   -4.853  29.835  1.00  41.99     B
ATOM   2189  OD2 ASP  1092     -0.534   -5.712  31.760  1.00  44.28     B
ATOM   2190  C   ASP  1092     -2.515   -3.946  28.044  1.00  29.23     B
ATOM   2191  O   ASP  1092     -3.547   -3.508  27.551  1.00  31.28     B
ATOM   2192  N   ARG  1093     -1.348   -3.341  27.880  1.00  30.00     B
ATOM   2193  CA  ARG  1093     -1.257   -2.115  27.093  1.00  30.03     B
ATOM   2194  CB  ARG  1093     -0.364   -1.105  27.826  1.00  33.34     B
ATOM   2195  CG  ARG  1093     -1.079   -0.336  28.937  1.00  41.29     B
ATOM   2196  CD  ARG  1093     -0.116    0.489  29.801  1.00  47.35     B
ATOM   2197  NE  ARG  1093     -0.013   -0.025  31.175  1.00  53.87     B
ATOM   2198  CZ  ARG  1093      0.070    0.731  32.271  1.00  56.53     B
ATOM   2199  NH1 ARG  1093      0.064    2.059  32.186  1.00  57.47     B
ATOM   2200  NH2 ARG  1093      0.163    0.156  33.463  1.00  57.04     B
ATOM   2201  C   ARG  1093     -0.710   -2.384  25.688  1.00  27.93     B
ATOM   2202  O   ARG  1093      0.161   -3.233  25.509  1.00  26.93     B
ATOM   2203  N   TYR  1094     -1.232   -1.676  24.690  1.00  25.26     B
ATOM   2204  CA  TYR  1094     -0.749   -1.842  23.327  1.00  23.35     B
ATOM   2205  CB  TYR  1094     -1.493   -2.967  22.595  1.00  24.45     B
ATOM   2206  CG  TYR  1094     -0.635   -3.606  21.522  1.00  23.14     B
ATOM   2207  CD1 TYR  1094      0.662   -4.029  21.815  1.00  22.25     B
ATOM   2208  CE1 TYR  1094      1.504   -4.534  20.822  1.00  22.52     B
ATOM   2209  CD2 TYR  1094     -1.086   -3.723  20.202  1.00  21.33     B
ATOM   2210  CE2 TYR  1094     -0.252   -4.230  19.197  1.00  21.33     B
ATOM   2211  CZ  TYR  1094      1.042   -4.632  19.518  1.00  23.16     B
ATOM   2212  OH  TYR  1094      1.895   -5.106  18.543  1.00  19.75     B
ATOM   2213  C   TYR  1094     -0.843   -0.551  22.526  1.00  22.64     B
ATOM   2214  O   TYR  1094     -0.866    0.524  23.106  1.00  22.16     B
ATOM   2215  N   ILE  1095     -0.899   -0.665  21.198  1.00  22.73     B
ATOM   2216  CA  ILE  1095     -0.952    0.496  20.310  1.00  23.36     B
ATOM   2217  CB  ILE  1095     -0.908    0.069  18.803  1.00  22.04     B
ATOM   2218  CG2 ILE  1095      0.313   -0.784  18.542  1.00  20.47     B
```

Fig. 2A-38

```
ATOM   2219  CG1 ILE  1095      -2.166  -0.708  18.419  1.00 24.32      B
ATOM   2220  CD1 ILE  1095      -2.104  -1.401  17.034  1.00 22.17      B
ATOM   2221  C   ILE  1095      -2.118   1.469  20.523  1.00 25.34      B
ATOM   2222  O   ILE  1095      -1.920   2.682  20.429  1.00 24.72      B
ATOM   2223  N   ASP  1096      -3.316   0.962  20.814  1.00 26.58      B
ATOM   2224  CA  ASP  1096      -4.474   1.841  21.031  1.00 26.18      B
ATOM   2225  CB  ASP  1096      -5.757   1.042  21.229  1.00 29.67      B
ATOM   2226  CG  ASP  1096      -5.849  -0.128  20.301  1.00 32.52      B
ATOM   2227  OD1 ASP  1096      -5.576   0.058  19.096  1.00 37.98      B
ATOM   2228  OD2 ASP  1096      -6.190  -1.234  20.772  1.00 37.33      B
ATOM   2229  C   ASP  1096      -4.263   2.706  22.249  1.00 23.76      B
ATOM   2230  O   ASP  1096      -4.660   3.860  22.279  1.00 24.70      B
ATOM   2231  N   SER  1097      -3.646   2.134  23.266  1.00 23.24      B
ATOM   2232  CA  SER  1097      -3.371   2.881  24.478  1.00 21.75      B
ATOM   2233  CB  SER  1097      -2.771   1.935  25.516  1.00 20.27      B
ATOM   2234  OG  SER  1097      -1.729   2.562  26.240  1.00 24.66      B
ATOM   2235  C   SER  1097      -2.405   4.035  24.142  1.00 20.76      B
ATOM   2236  O   SER  1097      -2.597   5.167  24.576  1.00 19.17      B
ATOM   2237  N   SER  1098      -1.387   3.733  23.339  1.00 19.41      B
ATOM   2238  CA  SER  1098      -0.387   4.712  22.918  1.00 19.17      B
ATOM   2239  CB  SER  1098       0.614   4.055  21.970  1.00 17.07      B
ATOM   2240  OG  SER  1098       1.836   3.817  22.625  1.00 17.81      B
ATOM   2241  C   SER  1098      -0.990   5.914  22.200  1.00 19.23      B
ATOM   2242  O   SER  1098      -0.652   7.063  22.479  1.00 18.38      B
ATOM   2243  N   LEU  1099      -1.875   5.625  21.257  1.00 20.76      B
ATOM   2244  CA  LEU  1099      -2.525   6.647  20.449  1.00 23.68      B
ATOM   2245  CB  LEU  1099      -3.276   5.987  19.294  1.00 23.63      B
ATOM   2246  CG  LEU  1099      -2.491   5.883  17.993  1.00 24.34      B
ATOM   2247  CD1 LEU  1099      -2.697   4.516  17.382  1.00 28.34      B
ATOM   2248  CD2 LEU  1099      -2.957   6.962  17.046  1.00 23.80      B
ATOM   2249  C   LEU  1099      -3.487   7.546  21.207  1.00 24.50      B
ATOM   2250  O   LEU  1099      -3.527   8.748  20.972  1.00 25.84      B
ATOM   2251  N   ALA  1100      -4.272   6.956  22.100  1.00 24.60      B
ATOM   2252  CA  ALA  1100      -5.249   7.707  22.875  1.00 26.63      B
ATOM   2253  CB  ALA  1100      -6.311   6.762  23.437  1.00 24.22      B
ATOM   2254  C   ALA  1100      -4.618   8.504  24.008  1.00 27.16      B
ATOM   2255  O   ALA  1100      -5.104   9.576  24.365  1.00 28.25      B
ATOM   2256  N   TYR  1101      -3.526   7.984  24.551  1.00 28.71      B
ATOM   2257  CA  TYR  1101      -2.830   8.619  25.667  1.00 32.17      B
ATOM   2258  CB  TYR  1101      -2.132   7.552  26.499  1.00 36.69      B
ATOM   2259  CG  TYR  1101      -1.810   7.980  27.898  1.00 42.99      B
ATOM   2260  CD1 TYR  1101      -2.823   8.275  28.816  1.00 46.53      B
ATOM   2261  CE1 TYR  1101      -2.523   8.650  30.139  1.00 47.35      B
ATOM   2262  CD2 TYR  1101      -0.490   8.050  28.328  1.00 48.46      B
ATOM   2263  CE2 TYR  1101      -0.175   8.424  29.648  1.00 50.82      B
ATOM   2264  CZ  TYR  1101      -1.197   8.709  30.546  1.00 49.52      B
ATOM   2265  OH  TYR  1101      -0.883   9.050  31.841  1.00 50.80      B
ATOM   2266  C   TYR  1101      -1.808   9.669  25.266  1.00 32.14      B
ATOM   2267  O   TYR  1101      -1.622  10.664  25.971  1.00 31.26      B
ATOM   2268  N   GLN  1102      -1.148   9.441  24.134  1.00 32.67      B
ATOM   2269  CA  GLN  1102      -0.126  10.354  23.645  1.00 33.54      B
ATOM   2270  CB  GLN  1102       1.225   9.655  23.618  1.00 37.71      B
ATOM   2271  CG  GLN  1102       1.938   9.610  24.947  1.00 43.46      B
ATOM   2272  CD  GLN  1102       3.051   8.587  24.941  1.00 46.55      B
ATOM   2273  OE1 GLN  1102       4.203   8.905  24.626  1.00 47.76      B
ATOM   2274  NE2 GLN  1102       2.714   7.346  25.281  1.00 47.31      B
ATOM   2275  C   GLN  1102      -0.409  10.897  22.261  1.00 32.44      B
```

Fig. 2A-39

| | | | | | | | | |
|---|---|---|---|---|---|---|---|---|
| ATOM | 2276 | O   | GLN | 1102 |  0.028 | 11.996 | 21.917 | 1.00 32.42 | B |
| ATOM | 2277 | N   | GLY | 1103 | -1.118 | 10.111 | 21.460 | 1.00 31.22 | B |
| ATOM | 2278 | CA  | GLY | 1103 | -1.435 | 10.542 | 20.116 | 1.00 29.67 | B |
| ATOM | 2279 | C   | GLY | 1103 | -2.639 | 11.447 | 20.168 | 1.00 29.68 | B |
| ATOM | 2280 | O   | GLY | 1103 | -2.980 | 12.096 | 19.187 | 1.00 30.37 | B |
| ATOM | 2281 | N   | TYR | 1104 | -3.289 | 11.476 | 21.325 | 1.00 28.58 | B |
| ATOM | 2282 | CA  | TYR | 1104 | -4.462 | 12.307 | 21.512 | 1.00 29.23 | B |
| ATOM | 2283 | CB  | TYR | 1104 | -5.728 | 11.457 | 21.554 | 1.00 30.59 | B |
| ATOM | 2284 | CG  | TYR | 1104 | -7.009 | 12.255 | 21.637 | 1.00 31.86 | B |
| ATOM | 2285 | CD1 | TYR | 1104 | -7.899 | 12.279 | 20.567 | 1.00 32.53 | B |
| ATOM | 2286 | CE1 | TYR | 1104 | -9.092 | 12.995 | 20.639 | 1.00 33.13 | B |
| ATOM | 2287 | CD2 | TYR | 1104 | -7.342 | 12.977 | 22.791 | 1.00 32.72 | B |
| ATOM | 2288 | CE2 | TYR | 1104 | -8.532 | 13.696 | 22.872 | 1.00 32.16 | B |
| ATOM | 2289 | CZ  | TYR | 1104 | -9.399 | 13.698 | 21.793 | 1.00 33.34 | B |
| ATOM | 2290 | OH  | TYR | 1104 | -10.580 | 14.385 | 21.863 | 1.00 37.92 | B |
| ATOM | 2291 | C   | TYR | 1104 | -4.368 | 13.120 | 22.783 | 1.00 29.09 | B |
| ATOM | 2292 | O   | TYR | 1104 | -4.084 | 14.312 | 22.735 | 1.00 30.55 | B |
| ATOM | 2293 | N   | ALA | 1105 | -4.603 | 12.475 | 23.922 | 1.00 28.16 | B |
| ATOM | 2294 | CA  | ALA | 1105 | -4.568 | 13.170 | 25.209 | 1.00 27.49 | B |
| ATOM | 2295 | CB  | ALA | 1105 | -4.724 | 12.193 | 26.336 | 1.00 26.93 | B |
| ATOM | 2296 | C   | ALA | 1105 | -3.311 | 14.002 | 25.421 | 1.00 27.61 | B |
| ATOM | 2297 | O   | ALA | 1105 | -3.292 | 14.903 | 26.251 | 1.00 29.03 | B |
| ATOM | 2298 | N   | ARG | 1106 | -2.245 | 13.687 | 24.706 | 1.00 26.93 | B |
| ATOM | 2299 | CA  | ARG | 1106 | -1.052 | 14.485 | 24.856 | 1.00 26.11 | B |
| ATOM | 2300 | CB  | ARG | 1106 |  0.171 | 13.605 | 25.116 | 1.00 27.36 | B |
| ATOM | 2301 | CG  | ARG | 1106 |  0.512 | 13.521 | 26.585 | 1.00 29.46 | B |
| ATOM | 2302 | CD  | ARG | 1106 |  1.608 | 12.536 | 26.875 | 1.00 33.62 | B |
| ATOM | 2303 | NE  | ARG | 1106 |  2.618 | 13.117 | 27.755 | 1.00 37.68 | B |
| ATOM | 2304 | CZ  | ARG | 1106 |  3.666 | 12.453 | 28.235 | 1.00 38.61 | B |
| ATOM | 2305 | NH1 | ARG | 1106 |  4.538 | 13.059 | 29.030 | 1.00 40.00 | B |
| ATOM | 2306 | NH2 | ARG | 1106 |  3.844 | 11.183 | 27.920 | 1.00 40.54 | B |
| ATOM | 2307 | C   | ARG | 1106 | -0.874 | 15.351 | 23.631 | 1.00 25.76 | B |
| ATOM | 2308 | O   | ARG | 1106 |  0.016 | 16.184 | 23.581 | 1.00 26.37 | B |
| ATOM | 2309 | N   | GLY | 1107 | -1.754 | 15.153 | 22.658 | 1.00 25.32 | B |
| ATOM | 2310 | CA  | GLY | 1107 | -1.727 | 15.945 | 21.454 | 1.00 26.25 | B |
| ATOM | 2311 | C   | GLY | 1107 | -0.520 | 15.858 | 20.547 | 1.00 28.41 | B |
| ATOM | 2312 | O   | GLY | 1107 | -0.138 | 16.860 | 19.953 | 1.00 29.44 | B |
| ATOM | 2313 | N   | ILE | 1108 |  0.099 | 14.689 | 20.437 | 1.00 28.85 | B |
| ATOM | 2314 | CA  | ILE | 1108 |  1.243 | 14.526 | 19.538 | 1.00 27.95 | B |
| ATOM | 2315 | CB  | ILE | 1108 |  2.105 | 13.319 | 19.996 | 1.00 25.67 | B |
| ATOM | 2316 | CG2 | ILE | 1108 |  2.966 | 12.790 | 18.852 | 1.00 27.61 | B |
| ATOM | 2317 | CG1 | ILE | 1108 |  2.971 | 13.750 | 21.168 | 1.00 21.58 | B |
| ATOM | 2318 | CD1 | ILE | 1108 |  3.836 | 12.663 | 21.700 | 1.00 19.73 | B |
| ATOM | 2319 | C   | ILE | 1108 |  0.664 | 14.311 | 18.119 | 1.00 28.18 | B |
| ATOM | 2320 | O   | ILE | 1108 |  1.328 | 14.502 | 17.090 | 1.00 29.06 | B |
| ATOM | 2321 | N   | GLY | 1109 | -0.613 | 13.949 | 18.086 | 1.00 26.80 | B |
| ATOM | 2322 | CA  | GLY | 1109 | -1.283 | 13.706 | 16.828 | 1.00 25.26 | B |
| ATOM | 2323 | C   | GLY | 1109 | -1.502 | 12.222 | 16.631 | 1.00 25.54 | B |
| ATOM | 2324 | O   | GLY | 1109 | -0.606 | 11.418 | 16.864 | 1.00 24.17 | B |
| ATOM | 2325 | N   | VAL | 1110 | -2.705 | 11.868 | 16.202 | 1.00 25.43 | B |
| ATOM | 2326 | CA  | VAL | 1110 | -3.073 | 10.485 | 15.952 | 1.00 26.51 | B |
| ATOM | 2327 | CB  | VAL | 1110 | -4.541 | 10.412 | 15.490 | 1.00 28.72 | B |
| ATOM | 2328 | CG1 | VAL | 1110 | -4.995 |  8.975 | 15.398 | 1.00 32.37 | B |
| ATOM | 2329 | CG2 | VAL | 1110 | -5.422 | 11.182 | 16.455 | 1.00 28.83 | B |
| ATOM | 2330 | C   | VAL | 1110 | -2.169 |  9.887 | 14.865 | 1.00 26.51 | B |
| ATOM | 2331 | O   | VAL | 1110 | -1.415 |  8.948 | 15.115 | 1.00 23.99 | B |
| ATOM | 2332 | N   | GLU | 1111 | -2.267 | 10.449 | 13.660 | 1.00 27.69 | B |

Fig. 2A-40

| | | | | | | | | | |
|---|---|---|---|---|---|---|---|---|---|
| ATOM | 2333 | CA | GLU | 1111 | -1.479 | 10.023 | 12.504 | 1.00 28.73 | B |
| ATOM | 2334 | CB | GLU | 1111 | -1.601 | 11.081 | 11.399 | 1.00 32.99 | B |
| ATOM | 2335 | CG | GLU | 1111 | -1.332 | 10.580 | 9.973 | 1.00 40.15 | B |
| ATOM | 2336 | CD | GLU | 1111 | -1.430 | 11.689 | 8.910 | 1.00 44.62 | B |
| ATOM | 2337 | OE1 | GLU | 1111 | -2.226 | 12.641 | 9.102 | 1.00 45.80 | B |
| ATOM | 2338 | OE2 | GLU | 1111 | -0.709 | 11.607 | 7.883 | 1.00 43.93 | B |
| ATOM | 2339 | C | GLU | 1111 | 0.000 | 9.829 | 12.875 | 1.00 27.92 | B |
| ATOM | 2340 | O | GLU | 1111 | 0.630 | 8.836 | 12.507 | 1.00 26.58 | B |
| ATOM | 2341 | N | GLU | 1112 | 0.548 | 10.790 | 13.611 | 1.00 27.44 | B |
| ATOM | 2342 | CA | GLU | 1112 | 1.939 | 10.734 | 14.026 | 1.00 26.88 | B |
| ATOM | 2343 | CB | GLU | 1112 | 2.307 | 11.994 | 14.814 | 1.00 30.38 | B |
| ATOM | 2344 | CG | GLU | 1112 | 2.355 | 13.265 | 13.982 | 1.00 34.98 | B |
| ATOM | 2345 | CD | GLU | 1112 | 0.980 | 13.762 | 13.615 | 1.00 38.08 | B |
| ATOM | 2346 | OE1 | GLU | 1112 | 0.350 | 13.145 | 12.737 | 1.00 41.07 | B |
| ATOM | 2347 | OE2 | GLU | 1112 | 0.524 | 14.763 | 14.205 | 1.00 43.10 | B |
| ATOM | 2348 | C | GLU | 1112 | 2.233 | 9.504 | 14.885 | 1.00 24.78 | B |
| ATOM | 2349 | O | GLU | 1112 | 3.104 | 8.703 | 14.561 | 1.00 23.69 | B |
| ATOM | 2350 | N | VAL | 1113 | 1.498 | 9.364 | 15.982 | 1.00 22.58 | B |
| ATOM | 2351 | CA | VAL | 1113 | 1.696 | 8.244 | 16.898 | 1.00 21.00 | B |
| ATOM | 2352 | CB | VAL | 1113 | 0.834 | 8.431 | 18.173 | 1.00 20.77 | B |
| ATOM | 2353 | CG1 | VAL | 1113 | 0.795 | 7.142 | 18.993 | 1.00 15.86 | B |
| ATOM | 2354 | CG2 | VAL | 1113 | 1.412 | 9.590 | 19.007 | 1.00 17.95 | B |
| ATOM | 2355 | C | VAL | 1113 | 1.381 | 6.904 | 16.230 | 1.00 22.76 | B |
| ATOM | 2356 | O | VAL | 1113 | 2.094 | 5.923 | 16.426 | 1.00 21.29 | B |
| ATOM | 2357 | N | ARG | 1114 | 0.317 | 6.866 | 15.438 | 1.00 22.71 | B |
| ATOM | 2358 | CA | ARG | 1114 | -0.061 | 5.642 | 14.755 | 1.00 24.17 | B |
| ATOM | 2359 | CB | ARG | 1114 | -1.435 | 5.806 | 14.076 | 1.00 27.34 | B |
| ATOM | 2360 | CG | ARG | 1114 | -1.497 | 5.396 | 12.613 | 1.00 29.25 | B |
| ATOM | 2361 | CD | ARG | 1114 | -2.927 | 5.170 | 12.172 | 1.00 33.08 | B |
| ATOM | 2362 | NE | ARG | 1114 | -3.163 | 5.657 | 10.815 | 1.00 39.60 | B |
| ATOM | 2363 | CZ | ARG | 1114 | -4.314 | 5.521 | 10.161 | 1.00 42.60 | B |
| ATOM | 2364 | NH1 | ARG | 1114 | -4.447 | 5.996 | 8.924 | 1.00 41.67 | B |
| ATOM | 2365 | NH2 | ARG | 1114 | -5.335 | 4.904 | 10.749 | 1.00 45.60 | B |
| ATOM | 2366 | C | ARG | 1114 | 0.989 | 5.217 | 13.735 | 1.00 23.63 | B |
| ATOM | 2367 | O | ARG | 1114 | 1.049 | 4.055 | 13.366 | 1.00 25.12 | B |
| ATOM | 2368 | N | ALA | 1115 | 1.814 | 6.149 | 13.275 | 1.00 23.16 | B |
| ATOM | 2369 | CA | ALA | 1115 | 2.850 | 5.823 | 12.302 | 1.00 23.27 | B |
| ATOM | 2370 | CB | ALA | 1115 | 3.229 | 7.073 | 11.508 | 1.00 23.40 | B |
| ATOM | 2371 | C | ALA | 1115 | 4.061 | 5.288 | 13.056 | 1.00 22.63 | B |
| ATOM | 2372 | O | ALA | 1115 | 4.756 | 4.375 | 12.608 | 1.00 21.65 | B |
| ATOM | 2373 | N | LEU | 1116 | 4.326 | 5.875 | 14.209 | 1.00 21.69 | B |
| ATOM | 2374 | CA | LEU | 1116 | 5.450 | 5.428 | 15.009 | 1.00 22.66 | B |
| ATOM | 2375 | CB | LEU | 1116 | 5.637 | 6.380 | 16.195 | 1.00 19.73 | B |
| ATOM | 2376 | CG | LEU | 1116 | 6.623 | 5.994 | 17.291 | 1.00 19.15 | B |
| ATOM | 2377 | CD1 | LEU | 1116 | 8.026 | 5.762 | 16.720 | 1.00 19.30 | B |
| ATOM | 2378 | CD2 | LEU | 1116 | 6.648 | 7.113 | 18.320 | 1.00 19.80 | B |
| ATOM | 2379 | C | LEU | 1116 | 5.168 | 3.989 | 15.479 | 1.00 23.19 | B |
| ATOM | 2380 | O | LEU | 1116 | 6.087 | 3.180 | 15.638 | 1.00 23.89 | B |
| ATOM | 2381 | N | ASN | 1117 | 3.887 | 3.675 | 15.675 | 1.00 21.59 | B |
| ATOM | 2382 | CA | ASN | 1117 | 3.472 | 2.358 | 16.134 | 1.00 20.92 | B |
| ATOM | 2383 | CB | ASN | 1117 | 2.027 | 2.409 | 16.626 | 1.00 20.90 | B |
| ATOM | 2384 | CG | ASN | 1117 | 1.874 | 3.208 | 17.910 | 1.00 19.28 | B |
| ATOM | 2385 | OD1 | ASN | 1117 | 2.670 | 3.074 | 18.844 | 1.00 21.02 | B |
| ATOM | 2386 | ND2 | ASN | 1117 | 0.851 | 4.044 | 17.962 | 1.00 22.77 | B |
| ATOM | 2387 | C | ASN | 1117 | 3.616 | 1.290 | 15.067 | 1.00 20.73 | B |
| ATOM | 2388 | O | ASN | 1117 | 3.993 | 0.166 | 15.364 | 1.00 22.14 | B |
| ATOM | 2389 | N | GLU | 1118 | 3.304 | 1.637 | 13.826 | 1.00 22.14 | B |

Fig. 2A-41

| | | | | | | | | | |
|---|---|---|---|---|---|---|---|---|---|
| ATOM | 2390 | CA | GLU | 1118 | 3.415 | 0.705 | 12.703 | 1.00 21.22 | B |
| ATOM | 2391 | CB | GLU | 1118 | 2.893 | 1.350 | 11.418 | 1.00 22.82 | B |
| ATOM | 2392 | CG | GLU | 1118 | 1.401 | 1.619 | 11.426 | 1.00 29.23 | B |
| ATOM | 2393 | CD | GLU | 1118 | 0.974 | 2.624 | 10.364 | 1.00 34.01 | B |
| ATOM | 2394 | OE1 | GLU | 1118 | 1.864 | 3.207 | 9.705 | 1.00 37.19 | B |
| ATOM | 2395 | OE2 | GLU | 1118 | -0.251 | 2.831 | 10.189 | 1.00 35.89 | B |
| ATOM | 2396 | C | GLU | 1118 | 4.857 | 0.286 | 12.490 | 1.00 17.92 | B |
| ATOM | 2397 | O | GLU | 1118 | 5.126 | -0.828 | 12.051 | 1.00 17.40 | B |
| ATOM | 2398 | N | PHE | 1119 | 5.779 | 1.191 | 12.797 | 1.00 16.29 | B |
| ATOM | 2399 | CA | PHE | 1119 | 7.198 | 0.921 | 12.633 | 1.00 16.74 | B |
| ATOM | 2400 | CB | PHE | 1119 | 7.987 | 2.235 | 12.687 | 1.00 15.46 | B |
| ATOM | 2401 | CG | PHE | 1119 | 9.425 | 2.101 | 12.269 | 1.00 17.12 | B |
| ATOM | 2402 | CD1 | PHE | 1119 | 9.770 | 2.043 | 10.917 | 1.00 17.63 | B |
| ATOM | 2403 | CD2 | PHE | 1119 | 10.437 | 2.013 | 13.223 | 1.00 16.08 | B |
| ATOM | 2404 | CE1 | PHE | 1119 | 11.100 | 1.895 | 10.522 | 1.00 16.56 | B |
| ATOM | 2405 | CE2 | PHE | 1119 | 11.778 | 1.864 | 12.835 | 1.00 17.38 | B |
| ATOM | 2406 | CZ | PHE | 1119 | 12.102 | 1.805 | 11.478 | 1.00 16.85 | B |
| ATOM | 2407 | C | PHE | 1119 | 7.661 | -0.023 | 13.739 | 1.00 16.33 | B |
| ATOM | 2408 | O | PHE | 1119 | 8.508 | -0.892 | 13.519 | 1.00 15.07 | B |
| ATOM | 2409 | N | ALA | 1120 | 7.081 | 0.157 | 14.922 | 1.00 15.89 | B |
| ATOM | 2410 | CA | ALA | 1120 | 7.406 | -0.651 | 16.099 | 1.00 15.09 | B |
| ATOM | 2411 | CB | ALA | 1120 | 6.891 | 0.030 | 17.376 | 1.00 13.29 | B |
| ATOM | 2412 | C | ALA | 1120 | 6.836 | -2.056 | 16.025 | 1.00 14.89 | B |
| ATOM | 2413 | O | ALA | 1120 | 7.513 | -3.010 | 16.375 | 1.00 12.96 | B |
| ATOM | 2414 | N | ILE | 1121 | 5.590 | -2.171 | 15.570 | 1.00 17.65 | B |
| ATOM | 2415 | CA | ILE | 1121 | 4.922 | -3.462 | 15.491 | 1.00 18.26 | B |
| ATOM | 2416 | CB | ILE | 1121 | 3.434 | -3.351 | 15.936 | 1.00 17.95 | B |
| ATOM | 2417 | CG2 | ILE | 1121 | 3.337 | -2.495 | 17.194 | 1.00 17.06 | B |
| ATOM | 2418 | CG1 | ILE | 1121 | 2.579 | -2.746 | 14.828 | 1.00 15.09 | B |
| ATOM | 2419 | CD1 | ILE | 1121 | 1.134 | -2.568 | 15.225 | 1.00 6.57 | B |
| ATOM | 2420 | C | ILE | 1121 | 4.988 | -4.143 | 14.133 | 1.00 20.38 | B |
| ATOM | 2421 | O | ILE | 1121 | 4.519 | -5.266 | 13.986 | 1.00 24.10 | B |
| ATOM | 2422 | N | ASN | 1122 | 5.568 | -3.470 | 13.148 | 1.00 20.82 | B |
| ATOM | 2423 | CA | ASN | 1122 | 5.719 | -4.035 | 11.807 | 1.00 21.45 | B |
| ATOM | 2424 | CB | ASN | 1122 | 7.061 | -4.768 | 11.698 | 1.00 21.13 | B |
| ATOM | 2425 | CG | ASN | 1122 | 7.440 | -5.078 | 10.271 | 1.00 20.27 | B |
| ATOM | 2426 | OD1 | ASN | 1122 | 6.959 | -4.439 | 9.336 | 1.00 21.11 | B |
| ATOM | 2427 | ND2 | ASN | 1122 | 8.306 | -6.062 | 10.092 | 1.00 20.05 | B |
| ATOM | 2428 | C | ASN | 1122 | 4.612 | -4.990 | 11.381 | 1.00 21.69 | B |
| ATOM | 2429 | O | ASN | 1122 | 4.874 | -6.151 | 11.071 | 1.00 20.30 | B |
| ATOM | 2430 | N | GLY | 1123 | 3.375 | -4.509 | 11.383 | 1.00 23.81 | B |
| ATOM | 2431 | CA | GLY | 1123 | 2.263 | -5.343 | 10.965 | 1.00 24.34 | B |
| ATOM | 2432 | C | GLY | 1123 | 1.588 | -6.201 | 12.024 | 1.00 25.43 | B |
| ATOM | 2433 | O | GLY | 1123 | 0.440 | -6.614 | 11.846 | 1.00 27.35 | B |
| ATOM | 2434 | N | LEU | 1124 | 2.268 | -6.475 | 13.130 | 1.00 24.26 | B |
| ATOM | 2435 | CA | LEU | 1124 | 1.661 | -7.315 | 14.154 | 1.00 23.10 | B |
| ATOM | 2436 | CB | LEU | 1124 | 2.707 | -7.731 | 15.196 | 1.00 22.68 | B |
| ATOM | 2437 | CG | LEU | 1124 | 2.360 | -8.859 | 16.183 | 1.00 23.66 | B |
| ATOM | 2438 | CD1 | LEU | 1124 | 1.776 | -10.070 | 15.460 | 1.00 21.86 | B |
| ATOM | 2439 | CD2 | LEU | 1124 | 3.621 | -9.238 | 16.945 | 1.00 21.50 | B |
| ATOM | 2440 | C | LEU | 1124 | 0.504 | -6.599 | 14.830 | 1.00 22.00 | B |
| ATOM | 2441 | O | LEU | 1124 | 0.716 | -5.765 | 15.697 | 1.00 23.01 | B |
| ATOM | 2442 | N | TYR | 1125 | -0.717 | -6.903 | 14.404 | 1.00 21.14 | B |
| ATOM | 2443 | CA | TYR | 1125 | -1.895 | -6.316 | 15.010 | 1.00 20.80 | B |
| ATOM | 2444 | CB | TYR | 1125 | -2.886 | -5.823 | 13.964 | 1.00 20.70 | B |
| ATOM | 2445 | CG | TYR | 1125 | -2.446 | -4.551 | 13.310 | 1.00 23.73 | B |
| ATOM | 2446 | CD1 | TYR | 1125 | -1.857 | -4.570 | 12.047 | 1.00 23.05 | B |

Fig. 2A-42

| | | | | | | | | | |
|---|---|---|---|---|---|---|---|---|---|
| ATOM | 2447 | CE1 | TYR | 1125 | -1.357 | -3.414 | 11.472 | 1.00 24.88 | B |
| ATOM | 2448 | CD2 | TYR | 1125 | -2.535 | -3.331 | 13.985 | 1.00 23.01 | B |
| ATOM | 2449 | CE2 | TYR | 1125 | -2.035 | -2.161 | 13.418 | 1.00 24.99 | B |
| ATOM | 2450 | CZ | TYR | 1125 | -1.443 | -2.215 | 12.163 | 1.00 25.15 | B |
| ATOM | 2451 | OH | TYR | 1125 | -0.907 | -1.080 | 11.616 | 1.00 28.59 | B |
| ATOM | 2452 | C | TYR | 1125 | -2.534 | -7.422 | 15.819 | 1.00 22.66 | B |
| ATOM | 2453 | O | TYR | 1125 | -2.396 | -8.606 | 15.487 | 1.00 21.46 | B |
| ATOM | 2454 | N | PRO | 1126 | -3.243 | -7.050 | 16.904 | 1.00 23.29 | B |
| ATOM | 2455 | CD | PRO | 1126 | -3.432 | -5.661 | 17.355 | 1.00 24.64 | B |
| ATOM | 2456 | CA | PRO | 1126 | -3.923 | -8.001 | 17.792 | 1.00 22.02 | B |
| ATOM | 2457 | CB | PRO | 1126 | -4.407 | -7.128 | 18.958 | 1.00 22.11 | B |
| ATOM | 2458 | CG | PRO | 1126 | -3.674 | -5.817 | 18.826 | 1.00 22.45 | B |
| ATOM | 2459 | C | PRO | 1126 | -5.078 | -8.695 | 17.089 | 1.00 21.26 | B |
| ATOM | 2460 | O | PRO | 1126 | -5.803 | -8.066 | 16.319 | 1.00 21.43 | B |
| ATOM | 2461 | N | ASP | 1127 | -5.259 | -9.986 | 17.354 | 1.00 20.33 | B |
| ATOM | 2462 | CA | ASP | 1127 | -6.351 | -10.726 | 16.733 | 1.00 20.02 | B |
| ATOM | 2463 | CB | ASP | 1127 | -6.101 | -12.229 | 16.843 | 1.00 19.31 | B |
| ATOM | 2464 | CG | ASP | 1127 | -4.741 | -12.621 | 16.336 | 1.00 19.57 | B |
| ATOM | 2465 | OD1 | ASP | 1127 | -4.513 | -12.526 | 15.111 | 1.00 23.88 | B |
| ATOM | 2466 | OD2 | ASP | 1127 | -3.897 | -13.016 | 17.159 | 1.00 20.10 | B |
| ATOM | 2467 | C | ASP | 1127 | -7.662 | -10.347 | 17.408 | 1.00 20.62 | B |
| ATOM | 2468 | O | ASP | 1127 | -8.730 | -10.450 | 16.806 | 1.00 21.79 | B |
| ATOM | 2469 | N | LEU | 1128 | -7.581 | -9.927 | 18.665 | 1.00 18.84 | B |
| ATOM | 2470 | CA | LEU | 1128 | -8.762 | -9.493 | 19.397 | 1.00 18.05 | B |
| ATOM | 2471 | CB | LEU | 1128 | -9.438 | -10.671 | 20.117 | 1.00 17.38 | B |
| ATOM | 2472 | CG | LEU | 1128 | -10.637 | -10.276 | 20.999 | 1.00 17.18 | B |
| ATOM | 2473 | CD1 | LEU | 1128 | -11.880 | -10.107 | 20.142 | 1.00 16.50 | B |
| ATOM | 2474 | CD2 | LEU | 1128 | -10.872 | -11.314 | 22.063 | 1.00 12.68 | B |
| ATOM | 2475 | C | LEU | 1128 | -8.359 | -8.425 | 20.418 | 1.00 17.71 | B |
| ATOM | 2476 | O | LEU | 1128 | -7.355 | -8.576 | 21.133 | 1.00 14.55 | B |
| ATOM | 2477 | N | THR | 1129 | -9.126 | -7.337 | 20.464 | 1.00 16.59 | B |
| ATOM | 2478 | CA | THR | 1129 | -8.846 | -6.265 | 21.412 | 1.00 17.61 | B |
| ATOM | 2479 | CB | THR | 1129 | -8.430 | -4.957 | 20.698 | 1.00 16.39 | B |
| ATOM | 2480 | OG1 | THR | 1129 | -7.048 | -5.041 | 20.327 | 1.00 18.55 | B |
| ATOM | 2481 | CG2 | THR | 1129 | -8.595 | -3.766 | 21.620 | 1.00 14.98 | B |
| ATOM | 2482 | C | THR | 1129 | -10.061 | -6.005 | 22.293 | 1.00 18.31 | B |
| ATOM | 2483 | O | THR | 1129 | -11.140 | -5.620 | 21.827 | 1.00 16.46 | B |
| ATOM | 2484 | N | ILE | 1130 | -9.873 | -6.215 | 23.586 | 1.00 19.55 | B |
| ATOM | 2485 | CA | ILE | 1130 | -10.949 | -6.019 | 24.534 | 1.00 20.15 | B |
| ATOM | 2486 | CB | ILE | 1130 | -10.839 | -7.066 | 25.654 | 1.00 22.17 | B |
| ATOM | 2487 | CG2 | ILE | 1130 | -9.875 | -6.595 | 26.718 | 1.00 25.57 | B |
| ATOM | 2488 | CG1 | ILE | 1130 | -12.222 | -7.359 | 26.218 | 1.00 24.34 | B |
| ATOM | 2489 | CD1 | ILE | 1130 | -12.901 | -8.558 | 25.553 | 1.00 26.77 | B |
| ATOM | 2490 | C | ILE | 1130 | -10.920 | -4.601 | 25.104 | 1.00 18.05 | B |
| ATOM | 2491 | O | ILE | 1130 | -9.907 | -4.157 | 25.641 | 1.00 15.53 | B |
| ATOM | 2492 | N | TYR | 1131 | -12.032 | -3.888 | 24.964 | 1.00 17.12 | B |
| ATOM | 2493 | CA | TYR | 1131 | -12.111 | -2.524 | 25.463 | 1.00 17.86 | B |
| ATOM | 2494 | CB | TYR | 1131 | -12.551 | -1.568 | 24.356 | 1.00 18.79 | B |
| ATOM | 2495 | CG | TYR | 1131 | -12.617 | -0.125 | 24.814 | 1.00 19.68 | B |
| ATOM | 2496 | CD1 | TYR | 1131 | -11.541 | 0.470 | 25.481 | 1.00 20.60 | B |
| ATOM | 2497 | CE1 | TYR | 1131 | -11.602 | 1.802 | 25.911 | 1.00 20.00 | B |
| ATOM | 2498 | CD2 | TYR | 1131 | -13.753 | 0.645 | 24.581 | 1.00 18.87 | B |
| ATOM | 2499 | CE2 | TYR | 1131 | -13.825 | 1.973 | 25.005 | 1.00 20.13 | B |
| ATOM | 2500 | CZ | TYR | 1131 | -12.746 | 2.548 | 25.665 | 1.00 20.38 | B |
| ATOM | 2501 | OH | TYR | 1131 | -12.815 | 3.864 | 26.074 | 1.00 17.75 | B |
| ATOM | 2502 | C | TYR | 1131 | -13.044 | -2.364 | 26.653 | 1.00 17.45 | B |
| ATOM | 2503 | O | TYR | 1131 | -14.246 | -2.601 | 26.549 | 1.00 19.94 | B |

Fig. 2A-43

```
ATOM   2504  N    LEU  1132     -12.482   -1.963   27.790  1.00 16.82      B
ATOM   2505  CA   LEU  1132     -13.261   -1.749   28.996  1.00 13.12      B
ATOM   2506  CB   LEU  1132     -12.377   -1.918   30.224  1.00 13.87      B
ATOM   2507  CG   LEU  1132     -11.542   -3.196   30.156  1.00 15.01      B
ATOM   2508  CD1  LEU  1132     -10.446   -3.134   31.189  1.00 18.60      B
ATOM   2509  CD2  LEU  1132     -12.419   -4.411   30.393  1.00 15.31      B
ATOM   2510  C    LEU  1132     -13.784   -0.331   28.903  1.00 13.77      B
ATOM   2511  O    LEU  1132     -13.061    0.630   29.155  1.00 11.46      B
ATOM   2512  N    ASN  1133     -15.052   -0.218   28.528  1.00 14.83      B
ATOM   2513  CA   ASN  1133     -15.701    1.063   28.355  1.00 17.29      B
ATOM   2514  CB   ASN  1133     -16.737    0.931   27.252  1.00 18.94      B
ATOM   2515  CG   ASN  1133     -17.218    2.266   26.749  1.00 22.31      B
ATOM   2516  OD1  ASN  1133     -18.225    2.344   26.039  1.00 27.40      B
ATOM   2517  ND2  ASN  1133     -16.505    3.332   27.105  1.00 21.91      B
ATOM   2518  C    ASN  1133     -16.360    1.622   29.617  1.00 19.16      B
ATOM   2519  O    ASN  1133     -17.529    1.350   29.893  1.00 18.88      B
ATOM   2520  N    VAL  1134     -15.609    2.416   30.375  1.00 19.93      B
ATOM   2521  CA   VAL  1134     -16.124    3.014   31.600  1.00 20.22      B
ATOM   2522  CB   VAL  1134     -15.091    2.955   32.743  1.00 22.15      B
ATOM   2523  CG1  VAL  1134     -13.934    3.927   32.464  1.00 21.35      B
ATOM   2524  CG2  VAL  1134     -15.768    3.303   34.074  1.00 22.26      B
ATOM   2525  C    VAL  1134     -16.443    4.469   31.334  1.00 21.33      B
ATOM   2526  O    VAL  1134     -15.802    5.095   30.489  1.00 21.49      B
ATOM   2527  N    SER  1135     -17.429    5.013   32.047  1.00 20.39      B
ATOM   2528  CA   SER  1135     -17.790    6.412   31.866  1.00 19.99      B
ATOM   2529  CB   SER  1135     -19.236    6.671   32.309  1.00 19.66      B
ATOM   2530  OG   SER  1135     -19.427    6.372   33.679  1.00 22.61      B
ATOM   2531  C    SER  1135     -16.820    7.259   32.670  1.00 18.71      B
ATOM   2532  O    SER  1135     -16.182    6.772   33.605  1.00 20.70      B
ATOM   2533  N    ALA  1136     -16.687    8.520   32.285  1.00 17.32      B
ATOM   2534  CA   ALA  1136     -15.786    9.436   32.963  1.00 16.42      B
ATOM   2535  CB   ALA  1136     -15.887   10.826   32.325  1.00 18.19      B
ATOM   2536  C    ALA  1136     -16.137    9.506   34.446  1.00 15.94      B
ATOM   2537  O    ALA  1136     -15.260    9.468   35.308  1.00 16.12      B
ATOM   2538  N    GLU  1137     -17.425    9.602   34.750  1.00 15.49      B
ATOM   2539  CA   GLU  1137     -17.864    9.679   36.136  1.00 19.83      B
ATOM   2540  CB   GLU  1137     -19.365    9.990   36.187  1.00 23.17      B
ATOM   2541  CG   GLU  1137     -19.805   11.031   35.156  1.00 28.97      B
ATOM   2542  CD   GLU  1137     -20.434   10.396   33.920  1.00 35.10      B
ATOM   2543  OE1  GLU  1137     -19.791   10.405   32.842  1.00 34.84      B
ATOM   2544  OE2  GLU  1137     -21.576    9.881   34.030  1.00 39.15      B
ATOM   2545  C    GLU  1137     -17.538    8.406   36.941  1.00 18.07      B
ATOM   2546  O    GLU  1137     -17.012    8.497   38.051  1.00 16.02      B
ATOM   2547  N    VAL  1138     -17.847    7.228   36.394  1.00 19.27      B
ATOM   2548  CA   VAL  1138     -17.554    5.971   37.085  1.00 18.52      B
ATOM   2549  CB   VAL  1138     -18.184    4.748   36.389  1.00 19.37      B
ATOM   2550  CG1  VAL  1138     -17.651    3.457   37.028  1.00 13.33      B
ATOM   2551  CG2  VAL  1138     -19.704    4.817   36.486  1.00 20.40      B
ATOM   2552  C    VAL  1138     -16.052    5.780   37.076  1.00 19.77      B
ATOM   2553  O    VAL  1138     -15.479    5.282   38.039  1.00 20.61      B
ATOM   2554  N    GLY  1139     -15.416    6.168   35.974  1.00 21.06      B
ATOM   2555  CA   GLY  1139     -13.971    6.059   35.877  1.00 20.35      B
ATOM   2556  C    GLY  1139     -13.301    6.852   36.990  1.00 20.15      B
ATOM   2557  O    GLY  1139     -12.312    6.414   37.572  1.00 20.37      B
ATOM   2558  N    ARG  1140     -13.861    8.017   37.298  1.00 20.21      B
ATOM   2559  CA   ARG  1140     -13.346    8.896   38.350  1.00 22.43      B
ATOM   2560  CB   ARG  1140     -14.053   10.259   38.235  1.00 20.13      B
```

Fig. 2A-44

```
ATOM   2561  CG   ARG  1140     -13.556  11.340  39.202  1.00  22.94      B
ATOM   2562  CD   ARG  1140     -14.684  12.235  39.739  1.00  20.22      B
ATOM   2563  NE   ARG  1140     -15.681  12.546  38.723  1.00  17.64      B
ATOM   2564  CZ   ARG  1140     -16.985  12.361  38.873  1.00  17.31      B
ATOM   2565  NH1  ARG  1140     -17.464  11.859  40.004  1.00  17.85      B
ATOM   2566  NH2  ARG  1140     -17.813  12.686  37.891  1.00  16.17      B
ATOM   2567  C    ARG  1140     -13.517   8.307  39.777  1.00  23.64      B
ATOM   2568  O    ARG  1140     -12.574   8.289  40.586  1.00  22.06      B
ATOM   2569  N    GLU  1141     -14.717   7.812  40.068  1.00  24.14      B
ATOM   2570  CA   GLU  1141     -15.024   7.242  41.374  1.00  24.75      B
ATOM   2571  CB   GLU  1141     -16.515   6.969  41.470  1.00  22.97      B
ATOM   2572  CG   GLU  1141     -17.347   8.221  41.315  1.00  27.60      B
ATOM   2573  CD   GLU  1141     -17.062   9.248  42.401  1.00  30.88      B
ATOM   2574  OE1  GLU  1141     -16.549   8.855  43.473  1.00  33.55      B
ATOM   2575  OE2  GLU  1141     -17.347  10.448  42.193  1.00  31.14      B
ATOM   2576  C    GLU  1141     -14.253   5.981  41.708  1.00  25.69      B
ATOM   2577  O    GLU  1141     -13.948   5.730  42.873  1.00  28.51      B
ATOM   2578  N    ARG  1142     -13.939   5.182  40.698  1.00  25.82      B
ATOM   2579  CA   ARG  1142     -13.192   3.952  40.927  1.00  26.19      B
ATOM   2580  CB   ARG  1142     -13.144   3.122  39.638  1.00  26.22      B
ATOM   2581  CG   ARG  1142     -13.794   1.755  39.795  1.00  25.35      B
ATOM   2582  CD   ARG  1142     -13.757   0.924  38.527  1.00  21.26      B
ATOM   2583  NE   ARG  1142     -15.010   0.197  38.377  1.00  18.77      B
ATOM   2584  CZ   ARG  1142     -15.589  -0.051  37.210  1.00  18.03      B
ATOM   2585  NH1  ARG  1142     -16.734  -0.717  37.166  1.00  16.76      B
ATOM   2586  NH2  ARG  1142     -15.015   0.361  36.089  1.00  18.02      B
ATOM   2587  C    ARG  1142     -11.776   4.242  41.428  1.00  26.05      B
ATOM   2588  O    ARG  1142     -11.274   3.543  42.311  1.00  26.26      B
ATOM   2589  N    ILE  1143     -11.149   5.278  40.867  1.00  25.61      B
ATOM   2590  CA   ILE  1143      -9.796   5.692  41.248  1.00  26.53      B
ATOM   2591  CB   ILE  1143      -9.282   6.804  40.322  1.00  24.83      B
ATOM   2592  CG2  ILE  1143      -8.182   7.584  41.013  1.00  24.32      B
ATOM   2593  CG1  ILE  1143      -8.783   6.200  39.006  1.00  24.83      B
ATOM   2594  CD1  ILE  1143      -9.255   6.944  37.758  1.00  20.76      B
ATOM   2595  C    ILE  1143      -9.766   6.232  42.684  1.00  28.39      B
ATOM   2596  O    ILE  1143      -8.823   5.989  43.440  1.00  28.02      B
ATOM   2597  N    ILE  1144     -10.800   6.983  43.040  1.00  29.81      B
ATOM   2598  CA   ILE  1144     -10.913   7.556  44.372  1.00  31.98      B
ATOM   2599  CB   ILE  1144     -11.593   8.948  44.299  1.00  33.00      B
ATOM   2600  CG2  ILE  1144     -13.086   8.821  44.546  1.00  34.57      B
ATOM   2601  CG1  ILE  1144     -10.970   9.889  45.326  1.00  34.56      B
ATOM   2602  CD1  ILE  1144      -9.885  10.798  44.760  1.00  36.28      B
ATOM   2603  C    ILE  1144     -11.718   6.628  45.296  1.00  31.48      B
ATOM   2604  O    ILE  1144     -11.327   5.482  45.551  1.00  32.67      B
ATOM   2605  N    GLN  1155      -8.229  18.229  42.196  1.00  60.55      B
ATOM   2606  CA   GLN  1155      -7.582  17.663  41.021  1.00  60.30      B
ATOM   2607  CB   GLN  1155      -8.084  16.233  40.768  1.00  63.31      B
ATOM   2608  CG   GLN  1155      -8.108  15.325  42.008  1.00  69.16      B
ATOM   2609  CD   GLN  1155      -6.713  14.929  42.502  1.00  73.40      B
ATOM   2610  OE1  GLN  1155      -6.573  14.133  43.443  1.00  74.63      B
ATOM   2611  NE2  GLN  1155      -5.677  15.484  41.870  1.00  75.02      B
ATOM   2612  C    GLN  1155      -7.835  18.520  39.784  1.00  58.58      B
ATOM   2613  O    GLN  1155      -6.895  19.052  39.189  1.00  58.70      B
ATOM   2614  N    GLU  1156      -9.107  18.658  39.408  1.00  56.35      B
ATOM   2615  CA   GLU  1156      -9.493  19.431  38.225  1.00  54.17      B
ATOM   2616  CB   GLU  1156      -9.286  20.929  38.460  1.00  54.85      B
ATOM   2617  CG   GLU  1156     -10.533  21.648  38.936  1.00  54.77      B
```

Fig. 2A-45

```
ATOM   2618  CD  GLU 1156     -11.119  21.003  40.172  1.00 55.73      B
ATOM   2619  OE1 GLU 1156     -10.771  21.441  41.291  1.00 56.94      B
ATOM   2620  OE2 GLU 1156     -11.920  20.054  40.024  1.00 56.37      B
ATOM   2621  C   GLU 1156      -8.649  18.966  37.047  1.00 52.69      B
ATOM   2622  O   GLU 1156      -8.608  19.597  35.988  1.00 51.58      B
ATOM   2623  N   ASP 1157      -7.983  17.837  37.262  1.00 51.79      B
ATOM   2624  CA  ASP 1157      -7.114  17.208  36.282  1.00 49.12      B
ATOM   2625  CB  ASP 1157      -6.082  16.351  37.011  1.00 49.00      B
ATOM   2626  CG  ASP 1157      -4.973  15.892  36.109  1.00 49.78      B
ATOM   2627  OD1 ASP 1157      -4.036  15.226  36.603  1.00 51.42      B
ATOM   2628  OD2 ASP 1157      -5.042  16.205  34.904  1.00 50.10      B
ATOM   2629  C   ASP 1157      -7.951  16.331  35.362  1.00 46.67      B
ATOM   2630  O   ASP 1157      -7.500  15.913  34.297  1.00 45.76      B
ATOM   2631  N   LEU 1158      -9.180  16.067  35.797  1.00 43.63      B
ATOM   2632  CA  LEU 1158     -10.122  15.242  35.055  1.00 41.40      B
ATOM   2633  CB  LEU 1158     -11.512  15.353  35.690  1.00 41.39      B
ATOM   2634  CG  LEU 1158     -11.577  15.579  37.207  1.00 40.74      B
ATOM   2635  CD1 LEU 1158     -12.740  16.491  37.536  1.00 41.01      B
ATOM   2636  CD2 LEU 1158     -11.738  14.252  37.922  1.00 38.87      B
ATOM   2637  C   LEU 1158     -10.187  15.607  33.570  1.00 40.29      B
ATOM   2638  O   LEU 1158     -10.740  14.856  32.764  1.00 40.06      B
ATOM   2639  N   LYS 1159      -9.626  16.761  33.215  1.00 39.05      B
ATOM   2640  CA  LYS 1159      -9.606  17.204  31.825  1.00 38.47      B
ATOM   2641  CB  LYS 1159      -8.943  18.579  31.695  1.00 39.88      B
ATOM   2642  CG  LYS 1159      -9.437  19.644  32.658  1.00 39.66      B
ATOM   2643  CD  LYS 1159      -8.272  20.483  33.184  1.00 41.01      B
ATOM   2644  CE  LYS 1159      -8.177  21.836  32.481  1.00 41.48      B
ATOM   2645  NZ  LYS 1159      -6.763  22.300  32.330  1.00 41.35      B
ATOM   2646  C   LYS 1159      -8.828  16.204  30.965  1.00 37.36      B
ATOM   2647  O   LYS 1159      -9.218  15.910  29.839  1.00 35.09      B
ATOM   2648  N   PHE 1160      -7.720  15.692  31.499  1.00 37.28      B
ATOM   2649  CA  PHE 1160      -6.894  14.715  30.777  1.00 38.90      B
ATOM   2650  CB  PHE 1160      -5.510  14.597  31.439  1.00 38.09      B
ATOM   2651  CG  PHE 1160      -4.518  13.784  30.645  1.00 36.01      B
ATOM   2652  CD1 PHE 1160      -4.578  12.393  30.641  1.00 36.33      B
ATOM   2653  CD2 PHE 1160      -3.507  14.405  29.921  1.00 34.39      B
ATOM   2654  CE1 PHE 1160      -3.644  11.629  29.921  1.00 36.12      B
ATOM   2655  CE2 PHE 1160      -2.566  13.649  29.197  1.00 33.39      B
ATOM   2656  CZ  PHE 1160      -2.635  12.259  29.202  1.00 33.20      B
ATOM   2657  C   PHE 1160      -7.566  13.340  30.733  1.00 39.12      B
ATOM   2658  O   PHE 1160      -7.609  12.693  29.689  1.00 38.57      B
ATOM   2659  N   HIS 1161      -8.071  12.893  31.880  1.00 40.93      B
ATOM   2660  CA  HIS 1161      -8.766  11.610  31.983  1.00 41.61      B
ATOM   2661  CB  HIS 1161      -9.323  11.435  33.403  1.00 45.12      B
ATOM   2662  CG  HIS 1161     -10.034  10.134  33.624  1.00 49.19      B
ATOM   2663  CD2 HIS 1161      -9.568   8.913  33.972  1.00 50.72      B
ATOM   2664  ND1 HIS 1161     -11.406  10.005  33.517  1.00 50.59      B
ATOM   2665  CE1 HIS 1161     -11.748   8.756  33.791  1.00 51.49      B
ATOM   2666  NE2 HIS 1161     -10.653   8.075  34.070  1.00 50.42      B
ATOM   2667  C   HIS 1161      -9.909  11.615  30.966  1.00 40.25      B
ATOM   2668  O   HIS 1161     -10.120  10.649  30.224  1.00 39.65      B
ATOM   2669  N   GLU 1162     -10.648  12.712  30.941  1.00 36.77      B
ATOM   2670  CA  GLU 1162     -11.736  12.835  30.005  1.00 35.45      B
ATOM   2671  CB  GLU 1162     -12.542  14.087  30.316  1.00 37.95      B
ATOM   2672  CG  GLU 1162     -13.880  14.129  29.629  1.00 44.08      B
ATOM   2673  CD  GLU 1162     -14.816  15.150  30.249  1.00 48.30      B
ATOM   2674  OE1 GLU 1162     -14.312  16.152  30.801  1.00 49.51      B
```

Fig. 2A-46

| | | | | | | | | | |
|---|---|---|---|---|---|---|---|---|---|
| ATOM | 2675 | OE2 | GLU | 1162 | -16.052 | 14.954 | 30.186 | 1.00 | 50.60 | B |
| ATOM | 2676 | C | GLU | 1162 | -11.161 | 12.908 | 28.590 | 1.00 | 33.86 | B |
| ATOM | 2677 | O | GLU | 1162 | -11.866 | 12.649 | 27.614 | 1.00 | 32.85 | B |
| ATOM | 2678 | N | LYS | 1163 | -9.881 | 13.260 | 28.481 | 1.00 | 31.94 | B |
| ATOM | 2679 | CA | LYS | 1163 | -9.222 | 13.364 | 27.176 | 1.00 | 31.73 | B |
| ATOM | 2680 | CB | LYS | 1163 | -7.893 | 14.115 | 27.282 | 1.00 | 32.90 | B |
| ATOM | 2681 | CG | LYS | 1163 | -7.950 | 15.612 | 27.073 | 1.00 | 34.32 | B |
| ATOM | 2682 | CD | LYS | 1163 | -6.901 | 16.253 | 27.969 | 1.00 | 38.71 | B |
| ATOM | 2683 | CE | LYS | 1163 | -7.052 | 17.760 | 28.089 | 1.00 | 39.61 | B |
| ATOM | 2684 | NZ | LYS | 1163 | -5.774 | 18.375 | 28.577 | 1.00 | 39.38 | B |
| ATOM | 2685 | C | LYS | 1163 | -8.935 | 11.991 | 26.585 | 1.00 | 29.67 | B |
| ATOM | 2686 | O | LYS | 1163 | -9.203 | 11.746 | 25.411 | 1.00 | 30.23 | B |
| ATOM | 2687 | N | VAL | 1164 | -8.365 | 11.106 | 27.397 | 1.00 | 27.87 | B |
| ATOM | 2688 | CA | VAL | 1164 | -8.038 | 9.762 | 26.946 | 1.00 | 27.20 | B |
| ATOM | 2689 | CB | VAL | 1164 | -7.331 | 8.968 | 28.054 | 1.00 | 26.82 | B |
| ATOM | 2690 | CG1 | VAL | 1164 | -6.748 | 7.686 | 27.472 | 1.00 | 28.40 | B |
| ATOM | 2691 | CG2 | VAL | 1164 | -6.230 | 9.826 | 28.684 | 1.00 | 24.86 | B |
| ATOM | 2692 | C | VAL | 1164 | -9.296 | 9.021 | 26.513 | 1.00 | 28.73 | B |
| ATOM | 2693 | O | VAL | 1164 | -9.333 | 8.439 | 25.432 | 1.00 | 26.76 | B |
| ATOM | 2694 | N | ILE | 1165 | -10.332 | 9.064 | 27.354 | 1.00 | 31.31 | B |
| ATOM | 2695 | CA | ILE | 1165 | -11.603 | 8.399 | 27.058 | 1.00 | 31.66 | B |
| ATOM | 2696 | CB | ILE | 1165 | -12.667 | 8.687 | 28.145 | 1.00 | 32.11 | B |
| ATOM | 2697 | CG2 | ILE | 1165 | -14.013 | 8.082 | 27.733 | 1.00 | 30.75 | B |
| ATOM | 2698 | CG1 | ILE | 1165 | -12.220 | 8.098 | 29.486 | 1.00 | 31.53 | B |
| ATOM | 2699 | CD1 | ILE | 1165 | -13.181 | 8.374 | 30.633 | 1.00 | 31.11 | B |
| ATOM | 2700 | C | ILE | 1165 | -12.174 | 8.820 | 25.706 | 1.00 | 32.95 | B |
| ATOM | 2701 | O | ILE | 1165 | -12.857 | 8.036 | 25.051 | 1.00 | 34.16 | B |
| ATOM | 2702 | N | GLU | 1166 | -11.922 | 10.059 | 25.297 | 1.00 | 34.96 | B |
| ATOM | 2703 | CA | GLU | 1166 | -12.418 | 10.512 | 24.005 | 1.00 | 35.90 | B |
| ATOM | 2704 | CB | GLU | 1166 | -12.439 | 12.042 | 23.911 | 1.00 | 40.19 | B |
| ATOM | 2705 | CG | GLU | 1166 | -13.254 | 12.540 | 22.718 | 1.00 | 48.35 | B |
| ATOM | 2706 | CD | GLU | 1166 | -13.408 | 14.054 | 22.670 | 1.00 | 53.25 | B |
| ATOM | 2707 | OE1 | GLU | 1166 | -13.548 | 14.678 | 23.746 | 1.00 | 56.10 | B |
| ATOM | 2708 | OE2 | GLU | 1166 | -13.395 | 14.621 | 21.553 | 1.00 | 54.50 | B |
| ATOM | 2709 | C | GLU | 1166 | -11.528 | 9.936 | 22.908 | 1.00 | 34.58 | B |
| ATOM | 2710 | O | GLU | 1166 | -11.974 | 9.748 | 21.777 | 1.00 | 35.86 | B |
| ATOM | 2711 | N | GLY | 1167 | -10.270 | 9.654 | 23.248 | 1.00 | 33.49 | B |
| ATOM | 2712 | CA | GLY | 1167 | -9.347 | 9.076 | 22.279 | 1.00 | 29.33 | B |
| ATOM | 2713 | C | GLY | 1167 | -9.755 | 7.646 | 21.953 | 1.00 | 28.37 | B |
| ATOM | 2714 | O | GLY | 1167 | -9.763 | 7.225 | 20.787 | 1.00 | 27.68 | B |
| ATOM | 2715 | N | TYR | 1168 | -10.115 | 6.905 | 22.999 | 1.00 | 26.42 | B |
| ATOM | 2716 | CA | TYR | 1168 | -10.549 | 5.522 | 22.878 | 1.00 | 23.05 | B |
| ATOM | 2717 | CB | TYR | 1168 | -10.635 | 4.886 | 24.266 | 1.00 | 19.40 | B |
| ATOM | 2718 | CG | TYR | 1168 | -9.325 | 4.333 | 24.804 | 1.00 | 17.64 | B |
| ATOM | 2719 | CD1 | TYR | 1168 | -8.857 | 4.689 | 26.070 | 1.00 | 15.43 | B |
| ATOM | 2720 | CE1 | TYR | 1168 | -7.686 | 4.132 | 26.590 | 1.00 | 12.34 | B |
| ATOM | 2721 | CD2 | TYR | 1168 | -8.576 | 3.410 | 24.067 | 1.00 | 18.04 | B |
| ATOM | 2722 | CE2 | TYR | 1168 | -7.396 | 2.848 | 24.587 | 1.00 | 15.67 | B |
| ATOM | 2723 | CZ | TYR | 1168 | -6.965 | 3.212 | 25.847 | 1.00 | 11.37 | B |
| ATOM | 2724 | OH | TYR | 1168 | -5.836 | 2.624 | 26.369 | 1.00 | 11.10 | B |
| ATOM | 2725 | C | TYR | 1168 | -11.916 | 5.465 | 22.200 | 1.00 | 24.16 | B |
| ATOM | 2726 | O | TYR | 1168 | -12.147 | 4.637 | 21.317 | 1.00 | 25.88 | B |
| ATOM | 2727 | N | GLN | 1169 | -12.819 | 6.352 | 22.617 | 1.00 | 24.30 | B |
| ATOM | 2728 | CA | GLN | 1169 | -14.169 | 6.409 | 22.056 | 1.00 | 25.80 | B |
| ATOM | 2729 | CB | GLN | 1169 | -15.003 | 7.482 | 22.769 | 1.00 | 28.84 | B |
| ATOM | 2730 | CG | GLN | 1169 | -15.561 | 7.074 | 24.138 | 1.00 | 32.63 | B |
| ATOM | 2731 | CD | GLN | 1169 | -16.011 | 5.622 | 24.190 | 1.00 | 33.87 | B |

Fig. 2A-47

```
ATOM  2732  OE1  GLN  1169   -15.583    4.849   25.051  1.00  35.90      B
ATOM  2733  NE2  GLN  1169   -16.876    5.244   23.262  1.00  38.23      B
ATOM  2734  C    GLN  1169   -14.118    6.723   20.572  1.00  25.68      B
ATOM  2735  O    GLN  1169   -13.233    7.452   20.114  1.00  27.45      B
ATOM  2736  N    PHE  1179   -12.329   -5.199   17.978  1.00  31.48      B
ATOM  2737  CA   PHE  1179   -12.665   -4.453   19.207  1.00  33.93      B
ATOM  2738  CB   PHE  1179   -12.948   -2.982   18.891  1.00  32.21      B
ATOM  2739  CG   PHE  1179   -11.709   -2.184   18.648  1.00  32.23      B
ATOM  2740  CD1  PHE  1179   -11.266   -1.953   17.354  1.00  31.20      B
ATOM  2741  CD2  PHE  1179   -10.941   -1.733   19.720  1.00  31.42      B
ATOM  2742  CE1  PHE  1179   -10.076   -1.291   17.129  1.00  32.53      B
ATOM  2743  CE2  PHE  1179    -9.749   -1.070   19.505  1.00  29.40      B
ATOM  2744  CZ   PHE  1179    -9.312   -0.849   18.213  1.00  32.25      B
ATOM  2745  C    PHE  1179   -13.860   -5.029   19.939  1.00  33.62      B
ATOM  2746  O    PHE  1179   -14.970   -5.073   19.415  1.00  37.56      B
ATOM  2747  N    LYS  1180   -13.636   -5.463   21.163  1.00  31.85      B
ATOM  2748  CA   LYS  1180   -14.724   -6.001   21.936  1.00  32.44      B
ATOM  2749  CB   LYS  1180   -14.402   -7.386   22.472  1.00  32.29      B
ATOM  2750  CG   LYS  1180   -14.173   -8.419   21.395  1.00  32.85      B
ATOM  2751  CD   LYS  1180   -15.306   -8.408   20.400  1.00  34.11      B
ATOM  2752  CE   LYS  1180   -15.377   -9.731   19.653  1.00  38.27      B
ATOM  2753  NZ   LYS  1180   -16.742  -10.036   19.117  1.00  38.28      B
ATOM  2754  C    LYS  1180   -14.897   -5.041   23.063  1.00  32.57      B
ATOM  2755  O    LYS  1180   -14.092   -5.005   23.993  1.00  35.10      B
ATOM  2756  N    SER  1181   -15.934   -4.229   22.965  1.00  32.74      B
ATOM  2757  CA   SER  1181   -16.187   -3.252   24.003  1.00  33.42      B
ATOM  2758  CB   SER  1181   -16.910   -2.045   23.421  1.00  36.08      B
ATOM  2759  OG   SER  1181   -17.803   -2.468   22.401  1.00  41.17      B
ATOM  2760  C    SER  1181   -17.030   -3.888   25.084  1.00  31.49      B
ATOM  2761  O    SER  1181   -18.041   -4.539   24.810  1.00  30.03      B
ATOM  2762  N    VAL  1182   -16.590   -3.720   26.318  1.00  30.24      B
ATOM  2763  CA   VAL  1182   -17.319   -4.255   27.441  1.00  29.79      B
ATOM  2764  CB   VAL  1182   -16.457   -5.254   28.222  1.00  28.87      B
ATOM  2765  CG1  VAL  1182   -15.334   -4.534   28.908  1.00  30.82      B
ATOM  2766  CG2  VAL  1182   -17.303   -5.996   29.221  1.00  30.09      B
ATOM  2767  C    VAL  1182   -17.673   -3.048   28.302  1.00  30.76      B
ATOM  2768  O    VAL  1182   -16.949   -2.035   28.293  1.00  30.66      B
ATOM  2769  N    ASN  1183   -18.800   -3.145   29.008  1.00  29.22      B
ATOM  2770  CA   ASN  1183   -19.266   -2.068   29.873  1.00  26.49      B
ATOM  2771  CB   ASN  1183   -20.751   -2.241   30.171  1.00  25.97      B
ATOM  2772  CG   ASN  1183   -21.287   -1.154   31.058  1.00  25.94      B
ATOM  2773  OD1  ASN  1183   -20.631   -0.139   31.265  1.00  26.14      B
ATOM  2774  ND2  ASN  1183   -22.485   -1.356   31.595  1.00  26.47      B
ATOM  2775  C    ASN  1183   -18.488   -2.059   31.178  1.00  25.98      B
ATOM  2776  O    ASN  1183   -18.706   -2.897   32.051  1.00  25.60      B
ATOM  2777  N    ALA  1184   -17.589   -1.095   31.318  1.00  25.72      B
ATOM  2778  CA   ALA  1184   -16.775   -1.010   32.516  1.00  25.10      B
ATOM  2779  CB   ALA  1184   -15.465   -0.289   32.198  1.00  23.98      B
ATOM  2780  C    ALA  1184   -17.497   -0.322   33.672  1.00  24.83      B
ATOM  2781  O    ALA  1184   -16.919   -0.131   34.743  1.00  23.64      B
ATOM  2782  N    ASP  1185   -18.762    0.045   33.464  1.00  24.08      B
ATOM  2783  CA   ASP  1185   -19.557    0.719   34.502  1.00  25.60      B
ATOM  2784  CB   ASP  1185   -20.621    1.600   33.855  1.00  24.94      B
ATOM  2785  CG   ASP  1185   -20.064    2.925   33.385  1.00  26.22      B
ATOM  2786  OD1  ASP  1185   -20.733    3.594   32.574  1.00  26.83      B
ATOM  2787  OD2  ASP  1185   -18.957    3.305   33.830  1.00  26.39      B
ATOM  2788  C    ASP  1185   -20.231   -0.201   35.522  1.00  26.43      B
```

Fig. 2A-48

```
ATOM   2789  O    ASP  1185     -20.378    0.168   36.687  1.00  27.46      B
ATOM   2790  N    GLN  1186     -20.655   -1.385   35.089  1.00  26.01      B
ATOM   2791  CA   GLN  1186     -21.287   -2.326   35.998  1.00  24.85      B
ATOM   2792  CB   GLN  1186     -21.920   -3.492   35.230  1.00  25.72      B
ATOM   2793  CG   GLN  1186     -21.002   -4.238   34.305  1.00  25.02      B
ATOM   2794  CD   GLN  1186     -21.762   -5.094   33.307  1.00  25.24      B
ATOM   2795  OE1  GLN  1186     -21.660   -4.895   32.097  1.00  24.55      B
ATOM   2796  NE2  GLN  1186     -22.529   -6.049   33.810  1.00  21.95      B
ATOM   2797  C    GLN  1186     -20.200   -2.811   36.951  1.00  24.39      B
ATOM   2798  O    GLN  1186     -19.017   -2.538   36.751  1.00  26.09      B
ATOM   2799  N    PRO  1187     -20.584   -3.532   38.014  1.00  23.92      B
ATOM   2800  CD   PRO  1187     -21.959   -3.913   38.341  1.00  21.29      B
ATOM   2801  CA   PRO  1187     -19.621   -4.040   39.004  1.00  22.56      B
ATOM   2802  CB   PRO  1187     -20.507   -4.780   40.004  1.00  24.86      B
ATOM   2803  CG   PRO  1187     -21.872   -4.199   39.803  1.00  24.58      B
ATOM   2804  C    PRO  1187     -18.529   -4.932   38.415  1.00  22.14      B
ATOM   2805  O    PRO  1187     -18.747   -5.649   37.443  1.00  20.75      B
ATOM   2806  N    LEU  1188     -17.346   -4.891   39.012  1.00  22.47      B
ATOM   2807  CA   LEU  1188     -16.236   -5.682   38.512  1.00  26.58      B
ATOM   2808  CB   LEU  1188     -15.041   -5.586   39.461  1.00  26.72      B
ATOM   2809  CG   LEU  1188     -13.977   -4.539   39.089  1.00  28.86      B
ATOM   2810  CD1  LEU  1188     -14.552   -3.425   38.218  1.00  25.89      B
ATOM   2811  CD2  LEU  1188     -13.416   -3.965   40.367  1.00  28.88      B
ATOM   2812  C    LEU  1188     -16.584   -7.139   38.251  1.00  27.85      B
ATOM   2813  O    LEU  1188     -16.168   -7.702   37.238  1.00  27.37      B
ATOM   2814  N    GLU  1189     -17.348   -7.745   39.155  1.00  30.54      B
ATOM   2815  CA   GLU  1189     -17.745   -9.146   38.982  1.00  32.92      B
ATOM   2816  CB   GLU  1189     -18.879   -9.516   39.942  1.00  37.08      B
ATOM   2817  CG   GLU  1189     -20.198   -9.905   39.233  1.00  41.54      B
ATOM   2818  CD   GLU  1189     -21.133  -10.748   40.083  1.00  44.57      B
ATOM   2819  OE1  GLU  1189     -20.742  -11.169   41.192  1.00  45.60      B
ATOM   2820  OE2  GLU  1189     -22.267  -10.991   39.627  1.00  45.52      B
ATOM   2821  C    GLU  1189     -18.261   -9.321   37.562  1.00  31.70      B
ATOM   2822  O    GLU  1189     -17.941  -10.292   36.881  1.00  31.65      B
ATOM   2823  N    ASN  1190     -19.043   -8.346   37.117  1.00  31.80      B
ATOM   2824  CA   ASN  1190     -19.644   -8.367   35.792  1.00  33.64      B
ATOM   2825  CB   ASN  1190     -20.749   -7.319   35.715  1.00  35.17      B
ATOM   2826  CG   ASN  1190     -21.913   -7.611   36.651  1.00  36.90      B
ATOM   2827  OD1  ASN  1190     -23.064   -7.640   36.229  1.00  40.73      B
ATOM   2828  ND2  ASN  1190     -21.616   -7.820   37.928  1.00  34.96      B
ATOM   2829  C    ASN  1190     -18.602   -8.107   34.701  1.00  33.70      B
ATOM   2830  O    ASN  1190     -18.513   -8.865   33.725  1.00  35.35      B
ATOM   2831  N    VAL  1191     -17.852   -7.015   34.841  1.00  30.81      B
ATOM   2832  CA   VAL  1191     -16.831   -6.687   33.858  1.00  29.71      B
ATOM   2833  CB   VAL  1191     -15.849   -5.626   34.427  1.00  28.83      B
ATOM   2834  CG1  VAL  1191     -14.845   -5.216   33.363  1.00  27.90      B
ATOM   2835  CG2  VAL  1191     -16.621   -4.432   34.938  1.00  25.92      B
ATOM   2836  C    VAL  1191     -16.052   -7.972   33.515  1.00  29.17      B
ATOM   2837  O    VAL  1191     -15.827   -8.269   32.341  1.00  28.36      B
ATOM   2838  N    VAL  1192     -15.708   -8.751   34.545  1.00  29.21      B
ATOM   2839  CA   VAL  1192     -14.972   -9.992   34.359  1.00  30.67      B
ATOM   2840  CB   VAL  1192     -14.608  -10.684   35.687  1.00  30.86      B
ATOM   2841  CG1  VAL  1192     -13.608  -11.776   35.425  1.00  30.14      B
ATOM   2842  CG2  VAL  1192     -14.062   -9.699   36.671  1.00  30.01      B
ATOM   2843  C    VAL  1192     -15.748  -11.009   33.546  1.00  32.39      B
ATOM   2844  O    VAL  1192     -15.434  -11.256   32.379  1.00  30.84      B
ATOM   2845  N    GLU  1193     -16.779  -11.582   34.168  1.00  33.20      B
```

Fig. 2A-49

| | | | | | | | | | |
|---|---|---|---|---|---|---|---|---|---|
| ATOM | 2846 | CA | GLU | 1193 | -17.592 | -12.590 | 33.483 | 1.00 36.11 | B |
| ATOM | 2847 | CB | GLU | 1193 | -18.878 | -12.866 | 34.295 | 1.00 38.61 | B |
| ATOM | 2848 | CG | GLU | 1193 | -20.023 | -11.850 | 34.197 | 1.00 43.09 | B |
| ATOM | 2849 | CD | GLU | 1193 | -21.244 | -12.230 | 35.071 | 1.00 46.41 | B |
| ATOM | 2850 | OE1 | GLU | 1193 | -21.158 | -13.179 | 35.889 | 1.00 47.71 | B |
| ATOM | 2851 | OE2 | GLU | 1193 | -22.294 | -11.569 | 34.929 | 1.00 45.13 | B |
| ATOM | 2852 | C | GLU | 1193 | -17.924 | -12.145 | 32.053 | 1.00 36.07 | B |
| ATOM | 2853 | O | GLU | 1193 | -17.712 | -12.889 | 31.100 | 1.00 34.08 | B |
| ATOM | 2854 | N | ASP | 1194 | -18.386 | -10.894 | 31.927 | 1.00 36.37 | B |
| ATOM | 2855 | CA | ASP | 1194 | -18.737 | -10.338 | 30.625 | 1.00 36.05 | B |
| ATOM | 2856 | CB | ASP | 1194 | -19.166 | -8.890 | 30.768 | 1.00 37.45 | B |
| ATOM | 2857 | CG | ASP | 1194 | -20.659 | -8.745 | 30.859 | 1.00 38.47 | B |
| ATOM | 2858 | OD1 | ASP | 1194 | -21.333 | -9.773 | 31.093 | 1.00 38.77 | B |
| ATOM | 2859 | OD2 | ASP | 1194 | -21.178 | -7.629 | 30.677 | 1.00 39.84 | B |
| ATOM | 2860 | C | ASP | 1194 | -17.562 | -10.410 | 29.640 | 1.00 35.69 | B |
| ATOM | 2861 | O | ASP | 1194 | -17.722 | -10.689 | 28.453 | 1.00 34.25 | B |
| ATOM | 2862 | N | THR | 1195 | -16.380 | -10.120 | 30.153 | 1.00 36.50 | B |
| ATOM | 2863 | CA | THR | 1195 | -15.166 | -10.119 | 29.342 | 1.00 37.76 | B |
| ATOM | 2864 | CB | THR | 1195 | -14.098 | -9.222 | 30.032 | 1.00 35.13 | B |
| ATOM | 2865 | OG1 | THR | 1195 | -13.181 | -8.705 | 29.061 | 1.00 37.19 | B |
| ATOM | 2866 | CG2 | THR | 1195 | -13.326 | -9.992 | 31.071 | 1.00 35.27 | B |
| ATOM | 2867 | C | THR | 1195 | -14.675 | -11.568 | 29.142 | 1.00 39.18 | B |
| ATOM | 2868 | O | THR | 1195 | -13.952 | -11.872 | 28.181 | 1.00 37.71 | B |
| ATOM | 2869 | N | TYR | 1196 | -15.124 | -12.464 | 30.024 | 1.00 40.59 | B |
| ATOM | 2870 | CA | TYR | 1196 | -14.739 | -13.847 | 29.898 | 1.00 41.26 | B |
| ATOM | 2871 | CB | TYR | 1196 | -15.030 | -14.601 | 31.202 | 1.00 46.57 | B |
| ATOM | 2872 | CG | TYR | 1196 | -14.757 | -16.094 | 31.143 | 1.00 52.95 | B |
| ATOM | 2873 | CD1 | TYR | 1196 | -13.447 | -16.582 | 31.188 | 1.00 55.25 | B |
| ATOM | 2874 | CE1 | TYR | 1196 | -13.187 | -17.945 | 31.149 | 1.00 57.82 | B |
| ATOM | 2875 | CD2 | TYR | 1196 | -15.806 | -17.020 | 31.052 | 1.00 55.50 | B |
| ATOM | 2876 | CE2 | TYR | 1196 | -15.552 | -18.395 | 31.013 | 1.00 57.72 | B |
| ATOM | 2877 | CZ | TYR | 1196 | -14.244 | -18.849 | 31.062 | 1.00 59.11 | B |
| ATOM | 2878 | OH | TYR | 1196 | -14.020 | -20.213 | 31.048 | 1.00 61.94 | B |
| ATOM | 2879 | C | TYR | 1196 | -15.507 | -14.472 | 28.742 | 1.00 39.80 | B |
| ATOM | 2880 | O | TYR | 1196 | -14.917 | -15.122 | 27.881 | 1.00 40.25 | B |
| ATOM | 2881 | N | GLN | 1197 | -16.825 | -14.280 | 28.752 | 1.00 37.01 | B |
| ATOM | 2882 | CA | GLN | 1197 | -17.693 | -14.812 | 27.716 | 1.00 35.43 | B |
| ATOM | 2883 | CB | GLN | 1197 | -19.105 | -14.229 | 27.870 | 1.00 35.57 | B |
| ATOM | 2884 | CG | GLN | 1197 | -20.091 | -15.064 | 28.659 | 1.00 38.57 | B |
| ATOM | 2885 | CD | GLN | 1197 | -19.537 | -16.421 | 29.043 | 1.00 39.93 | B |
| ATOM | 2886 | OE1 | GLN | 1197 | -19.363 | -16.717 | 30.225 | 1.00 37.74 | B |
| ATOM | 2887 | NE2 | GLN | 1197 | -19.247 | -17.255 | 28.038 | 1.00 40.37 | B |
| ATOM | 2888 | C | GLN | 1197 | -17.144 | -14.413 | 26.349 | 1.00 34.68 | B |
| ATOM | 2889 | O | GLN | 1197 | -17.065 | -15.221 | 25.414 | 1.00 34.93 | B |
| ATOM | 2890 | N | THR | 1198 | -16.760 | -13.145 | 26.255 | 1.00 32.88 | B |
| ATOM | 2891 | CA | THR | 1198 | -16.224 | -12.563 | 25.042 | 1.00 31.28 | B |
| ATOM | 2892 | CB | THR | 1198 | -15.828 | -11.089 | 25.303 | 1.00 31.80 | B |
| ATOM | 2893 | OG1 | THR | 1198 | -16.977 | -10.367 | 25.770 | 1.00 28.67 | B |
| ATOM | 2894 | CG2 | THR | 1198 | -15.297 | -10.447 | 24.022 | 1.00 29.57 | B |
| ATOM | 2895 | C | THR | 1198 | -15.013 | -13.284 | 24.437 | 1.00 31.47 | B |
| ATOM | 2896 | O | THR | 1198 | -15.052 | -13.732 | 23.292 | 1.00 29.62 | B |
| ATOM | 2897 | N | ILE | 1199 | -13.937 | -13.358 | 25.221 | 1.00 31.74 | B |
| ATOM | 2898 | CA | ILE | 1199 | -12.691 | -13.987 | 24.779 | 1.00 31.50 | B |
| ATOM | 2899 | CB | ILE | 1199 | -11.608 | -13.884 | 25.867 | 1.00 28.68 | B |
| ATOM | 2900 | CG2 | ILE | 1199 | -10.394 | -14.698 | 25.462 | 1.00 24.35 | B |
| ATOM | 2901 | CG1 | ILE | 1199 | -11.239 | -12.407 | 26.075 | 1.00 26.34 | B |
| ATOM | 2902 | CD1 | ILE | 1199 | -10.226 | -12.146 | 27.180 | 1.00 22.42 | B |

Fig. 2A-50

```
ATOM   2903  C    ILE  1199     -12.873 -15.447  24.417  1.00 33.68       B
ATOM   2904  O    ILE  1199     -12.325 -15.922  23.419  1.00 34.49       B
ATOM   2905  N    ILE  1200     -13.654 -16.145  25.236  1.00 35.59       B
ATOM   2906  CA   ILE  1200     -13.972 -17.555  25.068  1.00 35.35       B
ATOM   2907  CB   ILE  1200     -14.802 -18.059  26.284  1.00 36.60       B
ATOM   2908  CG2  ILE  1200     -15.963 -18.944  25.837  1.00 37.79       B
ATOM   2909  CG1  ILE  1200     -13.868 -18.770  27.269  1.00 37.10       B
ATOM   2910  CD1  ILE  1200     -14.489 -19.944  27.979  1.00 39.41       B
ATOM   2911  C    ILE  1200     -14.775 -17.774  23.780  1.00 35.54       B
ATOM   2912  O    ILE  1200     -14.559 -18.744  23.062  1.00 34.48       B
ATOM   2913  N    LYS  1201     -15.704 -16.864  23.506  1.00 35.83       B
ATOM   2914  CA   LYS  1201     -16.552 -16.955  22.320  1.00 36.57       B
ATOM   2915  CB   LYS  1201     -17.631 -15.873  22.366  1.00 40.26       B
ATOM   2916  CG   LYS  1201     -18.825 -16.155  21.466  1.00 45.75       B
ATOM   2917  CD   LYS  1201     -18.917 -15.129  20.351  1.00 48.41       B
ATOM   2918  CE   LYS  1201     -20.107 -14.210  20.558  1.00 51.56       B
ATOM   2919  NZ   LYS  1201     -20.231 -13.181  19.489  1.00 53.59       B
ATOM   2920  C    LYS  1201     -15.748 -16.789  21.049  1.00 34.21       B
ATOM   2921  O    LYS  1201     -16.084 -17.351  20.012  1.00 35.71       B
ATOM   2922  N    TYR  1202     -14.684 -16.005  21.139  1.00 32.69       B
ATOM   2923  CA   TYR  1202     -13.813 -15.737  20.004  1.00 32.06       B
ATOM   2924  CB   TYR  1202     -13.059 -14.429  20.249  1.00 32.04       B
ATOM   2925  CG   TYR  1202     -11.845 -14.249  19.386  1.00 33.32       B
ATOM   2926  CD1  TYR  1202     -11.967 -13.778  18.080  1.00 34.25       B
ATOM   2927  CE1  TYR  1202     -10.858 -13.579  17.284  1.00 35.32       B
ATOM   2928  CD2  TYR  1202     -10.570 -14.520  19.874  1.00 33.61       B
ATOM   2929  CE2  TYR  1202      -9.446 -14.323  19.080  1.00 34.04       B
ATOM   2930  CZ   TYR  1202      -9.604 -13.851  17.790  1.00 34.45       B
ATOM   2931  OH   TYR  1202      -8.517 -13.627  16.994  1.00 38.43       B
ATOM   2932  C    TYR  1202     -12.825 -16.873  19.807  1.00 30.13       B
ATOM   2933  O    TYR  1202     -12.571 -17.308  18.681  1.00 29.33       B
ATOM   2934  N    LEU  1203     -12.269 -17.331  20.922  1.00 30.06       B
ATOM   2935  CA   LEU  1203     -11.295 -18.409  20.944  1.00 31.23       B
ATOM   2936  CB   LEU  1203     -10.823 -18.641  22.370  1.00 29.49       B
ATOM   2937  CG   LEU  1203      -9.648 -17.820  22.877  1.00 29.98       B
ATOM   2938  CD1  LEU  1203      -9.356 -18.234  24.301  1.00 30.87       B
ATOM   2939  CD2  LEU  1203      -8.435 -18.036  21.984  1.00 29.77       B
ATOM   2940  C    LEU  1203     -11.920 -19.686  20.428  1.00 35.15       B
ATOM   2941  O    LEU  1203     -11.222 -20.656  20.137  1.00 37.00       B
ATOM   2942  N    GLU  1205     -13.240 -19.688  20.313  1.00 38.14       B
ATOM   2943  CA   GLU  1205     -13.936 -20.870  19.847  1.00 40.88       B
ATOM   2944  CB   GLU  1205     -15.268 -21.024  20.592  1.00 41.71       B
ATOM   2945  CG   GLU  1205     -15.246 -22.049  21.733  1.00 42.35       B
ATOM   2946  CD   GLU  1205     -13.858 -22.268  22.326  1.00 45.00       B
ATOM   2947  OE1  GLU  1205     -12.876 -22.379  21.559  1.00 47.85       B
ATOM   2948  OE2  GLU  1205     -13.740 -22.340  23.569  1.00 44.55       B
ATOM   2949  C    GLU  1205     -14.160 -20.896  18.349  1.00 42.03       B
ATOM   2950  O    GLU  1205     -13.956 -21.930  17.714  1.00 44.70       B
ATOM   2951  N    LYS  1206     -14.561 -19.767  17.777  1.00 42.26       B
ATOM   2952  CA   LYS  1206     -14.815 -19.707  16.342  1.00 44.68       B
ATOM   2953  CB   LYS  1206     -15.556 -18.415  15.993  1.00 45.87       B
ATOM   2954  CG   LYS  1206     -14.690 -17.175  15.956  1.00 48.60       B
ATOM   2955  CD   LYS  1206     -15.559 -15.945  15.734  1.00 51.09       B
ATOM   2956  CE   LYS  1206     -14.744 -14.717  15.329  1.00 51.76       B
ATOM   2957  NZ   LYS  1206     -15.638 -13.582  14.948  1.00 50.73       B
ATOM   2958  C    LYS  1206     -13.549 -19.827  15.496  1.00 45.15       B
ATOM   2959  O    LYS  1206     -13.613 -19.785  14.268  1.00 45.03       B
```

Fig. 2A-51

```
ATOM   2960  N   ILE  1207     -12.408 -19.983  16.161  1.00 45.64      B
ATOM   2961  CA  ILE  1207     -11.135 -20.119  15.477  1.00 46.49      B
ATOM   2962  CB  ILE  1207     -10.142 -19.011  15.934  1.00 44.67      B
ATOM   2963  CG2 ILE  1207     -10.858 -17.668  15.945  1.00 42.99      B
ATOM   2964  CG1 ILE  1207      -9.578 -19.319  17.326  1.00 43.35      B
ATOM   2965  CD1 ILE  1207      -8.372 -18.477  17.695  1.00 40.56      B
ATOM   2966  C   ILE  1207     -10.546 -21.505  15.731  1.00 49.19      B
ATOM   2967  O   ILE  1207      -9.765 -22.004  14.926  1.00 50.69      B
ATOM   2968  N   ARG  1208     -10.933 -22.126  16.847  1.00 51.37      B
ATOM   2969  CA  ARG  1208     -10.446 -23.455  17.199  1.00 53.73      B
ATOM   2970  CB  ARG  1208      -9.957 -23.495  18.653  1.00 55.52      B
ATOM   2971  CG  ARG  1208      -9.969 -24.896  19.281  1.00 58.37      B
ATOM   2972  CD  ARG  1208      -8.666 -25.619  19.007  1.00 61.49      B
ATOM   2973  NE  ARG  1208      -8.248 -26.502  20.100  1.00 65.11      B
ATOM   2974  CZ  ARG  1208      -7.068 -27.113  20.161  1.00 66.79      B
ATOM   2975  NH1 ARG  1208      -6.188 -26.934  19.185  1.00 67.81      B
ATOM   2976  NH2 ARG  1208      -6.779 -27.892  21.189  1.00 68.01      B
ATOM   2977  C   ARG  1208     -11.576 -24.452  17.011  1.00 53.91      B
ATOM   2978  O   ARG  1208     -11.642 -25.123  15.983  1.00 55.37      B
ATOM   2979  OH2 TIP3  500      37.299   9.800   4.044  1.00 37.63
ATOM   2980  OH2 TIP3  501      38.757  11.999   6.275  1.00 18.09
ATOM   2981  OH2 TIP3  502      43.991  17.954   3.473  1.00 33.76
ATOM   2982  OH2 TIP3  504      39.230  32.411   4.691  1.00 46.51
ATOM   2983  OH2 TIP3  506      34.991  22.293  17.555  1.00 23.59
ATOM   2984  OH2 TIP3  507      22.200   9.651  16.956  1.00 17.69
ATOM   2985  OH2 TIP3  508      30.284  17.100  19.446  1.00 25.84
ATOM   2986  OH2 TIP3  509      15.592  -7.199  18.885  1.00 43.65
ATOM   2987  OH2 TIP3  510      20.407  15.347  15.916  1.00 27.65
ATOM   2988  OH2 TIP3  511      13.022   4.354  -2.732  1.00 57.50
ATOM   2989  OH2 TIP3  512      16.001  -1.210   0.176  1.00 58.45
ATOM   2990  OH2 TIP3  513       4.718  11.821   7.123  1.00 47.25
ATOM   2991  OH2 TIP3  514      16.004  24.440   9.316  1.00 35.29
ATOM   2992  OH2 TIP3  515      29.581   9.912  -8.341  1.00  6.39
ATOM   2993  OH2 TIP3  516      30.422   4.262  -7.153  1.00 28.66
ATOM   2994  OH2 TIP3  517      30.100   3.080 -11.171  1.00 58.91
ATOM   2995  OH2 TIP3  518      20.652   1.190  -1.526  1.00 25.86
ATOM   2996  OH2 TIP3  519      27.470   2.321  -5.485  1.00 26.21
ATOM   2997  OH2 TIP3  523      -4.307  -2.443  21.738  1.00 28.13
ATOM   2998  OH2 TIP3  525      -0.578  17.057  27.555  1.00 32.90
ATOM   2999  OH2 TIP3  526      34.800   9.578   5.796  1.00 23.73
ATOM   3000  OH2 TIP3  528      32.545  23.778  17.866  1.00 33.02
ATOM   3001  OH2 TIP3  529      42.307  23.527   4.997  1.00 44.19
ATOM   3002  OH2 TIP3  530      31.702  29.905  17.688  1.00 36.41
ATOM   3003  OH2 TIP3  534      14.238  16.302  26.327  1.00 27.51
ATOM   3004  OH2 TIP3  535      21.111  36.027  17.890  1.00 35.07
ATOM   3005  OH2 TIP3  536      17.977  16.366   3.734  1.00 29.01
ATOM   3006  OH2 TIP3  537      29.610   5.124   8.888  1.00 45.45
ATOM   3007  OH2 TIP3  538      17.608  -3.137   0.196  1.00 45.25
ATOM   3008  OH2 TIP3  539       5.670   8.591   4.143  1.00 41.64
ATOM   3009  OH2 TIP3  541       4.763   4.486   9.124  1.00 39.02
ATOM   3010  OH2 TIP3  542       8.207  22.430  10.831  1.00 42.81
ATOM   3011  OH2 TIP3  543      15.118  25.044   5.498  1.00 44.03
ATOM   3012  OH2 TIP3  544      29.511  10.901 -10.894  1.00 39.37
ATOM   3013  OH2 TIP3  545      32.473   0.324  -8.592  1.00 36.37
ATOM   3014  OH2 TIP3  546      35.074  -1.173  -5.291  1.00 24.33
ATOM   3015  OH2 TIP3  547      32.326  -0.577  -3.088  1.00 45.29
ATOM   3016  OH2 TIP3  548      19.617   5.436  -6.168  1.00 46.42
```

Fig. 2A-52

```
ATOM  3017  OH2  TIP3  549   20.033   20.993   -6.648  1.00  39.08
ATOM  3018  OH2  TIP3  550   -3.453    1.470   29.166  1.00  46.16
ATOM  3019  OH2  TIP3  551   -4.477    5.600   29.363  1.00  34.99
ATOM  3020  OH2  TIP3  552   -4.228    8.184   33.673  1.00  45.37
ATOM  3021  OH2  TIP3  553   -6.701    7.382   31.744  1.00  15.89
ATOM  3022  OH2  TIP3  555   -8.152   -2.024   38.723  1.00  21.23
ATOM  3023  OH2  TIP3  556  -13.500  -25.737   34.079  1.00  48.67
ATOM  3024  OH2  TIP3  559  -10.134  -25.678   25.889  1.00  48.31
ATOM  3025  OH2  TIP3  560   -8.075  -25.536   25.083  1.00  19.62
ATOM  3026  OH2  TIP3  561    2.026   -2.806   31.857  1.00  34.40
ATOM  3027  OH2  TIP3  562   17.564   -4.763   32.466  1.00  56.19
ATOM  3028  OH2  TIP3  563   16.014   -4.510   34.331  1.00  51.79
ATOM  3029  OH2  TIP3  564   22.698   -1.920   32.205  1.00  34.66
ATOM  3030  OH2  TIP3  565    6.193    0.377   25.948  1.00  30.51
ATOM  3031  OH2  TIP3  566    6.755   -7.498   14.265  1.00  26.46
ATOM  3032  OH2  TIP3  567    1.159    2.146   26.648  1.00  26.02
ATOM  3033  OH2  TIP3  568    3.360    5.021   24.458  1.00  20.23
ATOM  3034  OH2  TIP3  569    2.353    9.146   28.496  1.00  46.71
ATOM  3035  OH2  TIP3  571   -1.621   -8.543   11.899  1.00  45.04
ATOM  3036  OH2  TIP3  572  -15.832   13.292   36.051  1.00  26.43
ATOM  3037  OH2  TIP3  573   36.096  -11.625    0.873  1.00  20.21
ATOM  3038  OH2  TIP3  576   20.930   29.693   13.526  1.00  36.88
ATOM  3039  OH2  TIP3  577   22.942   32.471   10.116  1.00  37.73
ATOM  3040  OH2  TIP3  578   26.535   34.202   11.511  1.00  50.93
ATOM  3041  OH2  TIP3  580   26.238    7.756   10.835  1.00  35.53
ATOM  3042  OH2  TIP3  581   42.136   22.290    9.682  1.00  46.17
ATOM  3043  OH2  TIP3  582   36.988   16.971   14.090  1.00  31.07
ATOM  3044  OH2  TIP3  583   28.113   36.253    3.573  1.00  54.01
ATOM  3045  OH2  TIP3  584   31.114   17.563   14.487  1.00  23.74
ATOM  3046  OH2  TIP3  585   29.930   11.882   22.432  1.00  39.39
ATOM  3047  OH2  TIP3  586   28.627   12.210   21.660  1.00  37.51
ATOM  3048  OH2  TIP3  587   23.901    8.564   11.019  1.00  31.49
ATOM  3049  OH2  TIP3  588   26.166    9.035   14.316  1.00  47.93
ATOM  3050  OH2  TIP3  589   13.746   -6.969   11.794  1.00  55.03
ATOM  3051  OH2  TIP3  590   17.630   -7.544   12.406  1.00  37.89
ATOM  3052  OH2  TIP3  591   20.379   -7.909   11.148  1.00  27.40
ATOM  3053  OH2  TIP3  593    9.372   -8.416   13.073  1.00  30.57
ATOM  3054  OH2  TIP3  594    6.333   -9.001   12.346  1.00  63.81
ATOM  3055  OH2  TIP3  595    5.699  -11.256   12.667  1.00  39.51
ATOM  3056  OH2  TIP3  597   24.424   28.208   26.490  1.00  55.07
ATOM  3057  OH2  TIP3  600    4.580    4.584    4.718  1.00  43.48
ATOM  3058  OH2  TIP3  601    0.937    7.387    3.853  1.00  57.97
ATOM  3059  OH2  TIP3  602    2.347   14.978    3.868  1.00  45.22
ATOM  3060  OH2  TIP3  603   -0.560   17.052    3.729  1.00  54.60
ATOM  3061  OH2  TIP3  604    3.900    0.613    5.622  1.00  33.60
ATOM  3062  OH2  TIP3  605   16.846    6.390   12.858  1.00  25.87
ATOM  3063  OH2  TIP3  606   10.203   21.845   15.440  1.00  57.58
ATOM  3064  OH2  TIP3  608   33.992    4.807  -11.888  1.00  55.76
ATOM  3065  OH2  TIP3  609   32.088    4.063   -9.902  1.00  37.25
ATOM  3066  OH2  TIP3  610   43.957    6.928   -0.002  1.00  28.91
ATOM  3067  OH2  TIP3  611   25.495   -6.170    1.847  1.00  53.33
ATOM  3068  OH2  TIP3  612   32.114   -3.720   -5.524  1.00  48.53
ATOM  3069  OH2  TIP3  613   31.027   -6.231   -3.996  1.00  23.87
ATOM  3070  OH2  TIP3  614   28.507   -3.477   -8.300  1.00  44.33
ATOM  3071  OH2  TIP3  616   31.457   -3.669  -10.371  1.00  29.92
ATOM  3072  OH2  TIP3  618   19.484    0.314   -4.176  1.00  52.01
ATOM  3073  OH2  TIP3  619   21.084   11.361   -7.754  1.00  32.35
```

Fig. 2A-53

| | | | | | | | |
|---|---|---|---|---|---|---|---|
| ATOM | 3074 | OH2 | TIP3 | 624 | 29.179 | 16.414 | -8.147 | 1.00 23.12 |
| ATOM | 3075 | OH2 | TIP3 | 625 | 28.217 | 18.152 | -11.615 | 1.00 24.45 |
| ATOM | 3076 | OH2 | TIP3 | 626 | -2.622 | 11.332 | 34.963 | 1.00 43.49 |
| ATOM | 3077 | OH2 | TIP3 | 628 | 1.007 | 9.633 | 37.642 | 1.00 37.19 |
| ATOM | 3078 | OH2 | TIP3 | 629 | 1.744 | 7.361 | 39.889 | 1.00 61.00 |
| ATOM | 3079 | OH2 | TIP3 | 630 | -9.712 | 0.515 | 37.881 | 1.00 31.55 |
| ATOM | 3080 | OH2 | TIP3 | 631 | -10.217 | -1.307 | 39.597 | 1.00 26.46 |
| ATOM | 3081 | OH2 | TIP3 | 632 | -4.602 | 0.555 | 35.049 | 1.00 46.29 |
| ATOM | 3082 | OH2 | TIP3 | 633 | 0.406 | -24.863 | 30.031 | 1.00 49.55 |
| ATOM | 3083 | OH2 | TIP3 | 634 | 4.937 | -5.021 | 23.436 | 1.00 21.54 |
| ATOM | 3084 | OH2 | TIP3 | 635 | 14.511 | -7.526 | 33.274 | 1.00 42.67 |
| ATOM | 3085 | OH2 | TIP3 | 636 | 17.764 | -3.257 | 23.832 | 1.00 30.58 |
| ATOM | 3086 | OH2 | TIP3 | 637 | 10.575 | -1.130 | 33.912 | 1.00 48.46 |
| ATOM | 3087 | OH2 | TIP3 | 638 | 5.491 | -0.955 | 33.749 | 1.00 49.13 |
| ATOM | 3088 | OH2 | TIP3 | 639 | 15.500 | 15.224 | 27.892 | 1.00 41.51 |
| ATOM | 3089 | OH2 | TIP3 | 641 | 9.121 | 11.477 | 29.216 | 1.00 41.58 |
| ATOM | 3090 | OH2 | TIP3 | 642 | 18.087 | -7.427 | 21.130 | 1.00 44.59 |
| ATOM | 3091 | OH2 | TIP3 | 643 | 13.139 | -9.763 | 14.592 | 1.00 39.50 |
| ATOM | 3092 | OH2 | TIP3 | 644 | 8.471 | -15.955 | 24.889 | 1.00 29.03 |
| ATOM | 3093 | OH2 | TIP3 | 645 | 8.918 | -19.436 | 19.269 | 1.00 58.43 |
| ATOM | 3094 | OH2 | TIP3 | 646 | 8.317 | -22.468 | 17.407 | 1.00 37.35 |
| ATOM | 3095 | OH2 | TIP3 | 647 | 2.242 | -22.822 | 16.942 | 1.00 37.73 |
| ATOM | 3096 | OH2 | TIP3 | 648 | 4.341 | -22.047 | 14.464 | 1.00 48.23 |
| ATOM | 3097 | OH2 | TIP3 | 649 | 2.958 | -19.447 | 13.642 | 1.00 33.18 |
| ATOM | 3098 | OH2 | TIP3 | 650 | 1.353 | -25.194 | 20.926 | 1.00 51.00 |
| ATOM | 3099 | OH2 | TIP3 | 651 | -1.696 | 19.824 | 23.109 | 1.00 58.49 |
| ATOM | 3100 | OH2 | TIP3 | 653 | 1.940 | 14.682 | 9.762 | 1.00 18.10 |
| ATOM | 3101 | OH2 | TIP3 | 655 | 6.226 | 4.362 | 10.276 | 1.00 38.36 |
| ATOM | 3102 | OH2 | TIP3 | 656 | 6.059 | -1.930 | 9.076 | 1.00 26.19 |
| ATOM | 3103 | OH2 | TIP3 | 657 | -1.695 | -11.127 | 14.091 | 1.00 50.53 |
| ATOM | 3104 | OH2 | TIP3 | 659 | -0.293 | -13.734 | 8.678 | 1.00 37.60 |
| ATOM | 3105 | OH2 | TIP3 | 661 | -16.640 | 6.818 | 28.144 | 1.00 25.26 |
| ATOM | 3106 | OH2 | TIP3 | 662 | -17.931 | 9.011 | 30.213 | 1.00 47.61 |
| ATOM | 3107 | OH2 | TIP3 | 664 | -17.949 | 13.378 | 32.218 | 1.00 36.07 |
| ATOM | 3108 | OH2 | TIP3 | 665 | -7.012 | 2.947 | 44.264 | 1.00 47.20 |
| ATOM | 3109 | OH2 | TIP3 | 666 | -8.590 | 20.473 | 43.414 | 1.00 42.81 |
| ATOM | 3110 | OH2 | TIP3 | 667 | -11.271 | 24.339 | 41.537 | 1.00 53.87 |
| ATOM | 3111 | OH2 | TIP3 | 668 | -11.938 | 26.641 | 38.313 | 1.00 40.91 |
| ATOM | 3112 | OH2 | TIP3 | 669 | -6.115 | 22.520 | 38.617 | 1.00 49.06 |
| ATOM | 3113 | OH2 | TIP3 | 670 | -5.432 | 22.073 | 41.400 | 1.00 33.81 |
| ATOM | 3114 | OH2 | TIP3 | 671 | -5.894 | 24.658 | 41.524 | 1.00 48.57 |
| ATOM | 3115 | OH2 | TIP3 | 672 | -5.968 | 27.317 | 39.288 | 1.00 62.04 |
| ATOM | 3116 | OH2 | TIP3 | 675 | -10.916 | 17.235 | 28.973 | 1.00 19.60 |
| ATOM | 3117 | OH2 | TIP3 | 676 | -12.687 | 17.611 | 29.928 | 1.00 44.23 |
| ATOM | 3118 | OH2 | TIP3 | 677 | -12.376 | 14.997 | 26.011 | 1.00 25.27 |
| ATOM | 3119 | OH2 | TIP3 | 678 | -15.982 | 11.048 | 22.910 | 1.00 36.08 |
| ATOM | 3120 | OH2 | TIP3 | 679 | -15.130 | -12.373 | 21.294 | 1.00 31.35 |
| ATOM | 3121 | OH2 | TIP3 | 680 | -24.525 | -2.963 | 29.740 | 1.00 53.82 |
| ATOM | 3122 | OH2 | TIP3 | 681 | -24.281 | -7.362 | 32.226 | 1.00 46.22 |
| ATOM | 3123 | OH2 | TIP3 | 682 | -25.785 | -7.204 | 29.606 | 1.00 40.17 |
| ATOM | 3124 | OH2 | TIP3 | 683 | -16.683 | -3.185 | 41.795 | 1.00 24.03 |
| ATOM | 3125 | OH2 | TIP3 | 701 | 12.857 | 31.019 | 7.364 | 1.00 54.16 |
| ATOM | 3126 | OH2 | TIP3 | 702 | 37.640 | 5.709 | 5.316 | 1.00 52.52 |
| ATOM | 3127 | OH2 | TIP3 | 705 | 19.919 | -7.084 | 13.950 | 1.00 54.40 |
| ATOM | 3128 | OH2 | TIP3 | 706 | 22.605 | 19.970 | 26.417 | 1.00 47.37 |
| ATOM | 3129 | OH2 | TIP3 | 707 | 24.320 | 21.898 | 25.471 | 1.00 55.75 |
| ATOM | 3130 | OH2 | TIP3 | 708 | 21.853 | 18.372 | 29.036 | 1.00 36.22 |

Fig. 2A-54

```
ATOM  3131 OH2 TIP3 709   21.985  -1.594  11.183 1.00 25.61
ATOM  3132 OH2 TIP3 711    8.853  16.083   9.847 1.00 21.94
ATOM  3133 OH2 TIP3 712    6.511  20.114  13.278 1.00 56.32
ATOM  3134 OH2 TIP3 713    4.281  19.995  16.814 1.00 30.19
ATOM  3135 OH2 TIP3 714    5.434  17.688  13.014 1.00 24.50
ATOM  3136 OH2 TIP3 715   16.706  18.750   3.770 1.00 42.30
ATOM  3137 OH2 TIP3 716   36.108   0.064 -10.727 1.00 56.35
ATOM  3138 OH2 TIP3 717   30.590  -9.134   3.586 1.00 26.39
ATOM  3139 OH2 TIP3 718   32.446  19.916  -7.693 1.00 26.41
ATOM  3140 OH2 TIP3 719   21.678  -2.553  26.350 1.00 17.13
ATOM  3141 OH2 TIP3 720   -2.226 -19.231  13.193 1.00 61.49
ATOM  3142 OH2 TIP3 721   -2.874 -14.571  13.421 1.00 51.98
ATOM  3143 OH2 TIP3 722   -5.200   9.600  36.735 1.00 30.95
ATOM  3144 OH2 TIP3 724   -2.287   3.837  39.477 1.00 36.32
ATOM  3145 OH2 TIP3 726   -7.714 -12.404  40.890 1.00 26.19
ATOM  3146 OH2 TIP3 727   -9.403 -12.901  43.798 1.00 58.25
ATOM  3147 OH2 TIP3 728   18.346   2.718  31.321 1.00 29.06
ATOM  3148 OH2 TIP3 729   15.929  11.925  36.890 1.00 20.48
ATOM  3149 OH2 TIP3 731   11.736 -21.743  17.819 1.00 56.65
ATOM  3150 OH2 TIP3 732   12.835 -19.407  17.439 1.00 47.51
ATOM  3151 OH2 TIP3 734   13.864 -21.140  15.303 1.00 36.90
ATOM  3152 OH2 TIP3 737  -16.126  19.138  31.099 1.00 50.05
END
```

Fig. 2A-55

```
SEQ ID NO:1  1 MGSAFITFEGPEGSGKTTVINEVYHRL..VKDYDVIMTREPGGVPTGEEI 48
               | | :|  || ||.||||  | |   |    .    |.: |||||     |.:
SEQ ID NO:2  1 mrskyiviegleqaqkttarnvvvetleqlgirdmvftrepggtqlaekl 50

49 RKIVLE....GND.MDIRTEAMLFAASRREHLVLKVIPALKEGKVVLCDR 93
               | :||:      |.: .  : | ::|  |.|  : .   :  |||   |  |: ||
            51 rslvldiksvgdevitdkaevlmfyaarvqlvetvikpalangtwvigdr 100

94 YIDSSLAYQGYARGIGVEEVRALNEFAINGLYPDLTIYLNVSAEVGRERI 143
                 : |. ||||  |||    . | :  :     ||||:||.|. ||| .|
           101 hdlstqayqgggrgidqhmlatlrdavlgdfrpdltlyldvtpevglkr. 149

144 IKNSRDQNRLDQEDLKFHEKVIEGYQEIIHNESQRFKSVNADQPLENVVE 193
                 :    : .|::|| |  :    ||:  : .   .:.| ||||  |.:
           150 arargeldrieqesfdffnrtrarylela.aqdksihtidatqpleavmd 198

194 DTYQTIIKYLEKIRSHHHHHH 214
                  |:    :....:  .
           199 airttvthwvkelda...... 213
```

Fig. 5b

```
SEQ ID NO:1  1 ..MGSAFITFEGPEGSGKTTVINEVYHRLVKDYDVIMTREPGGVPTGEEI 48
                 | ||  : .||||   | .|  :|  .  .:    |           |
SEQ ID NO:3  1 mmgrgkliliegldrtgkttqcnilykklqpnckllkfperstrigglin 50

49 RKIVLEGNDMDIRTEAMLFAASRREHLVLKVIPALKEGKVVLCDRYIDSS 98
                :    :    :    .   :||.|.|   |  :|  |:    | |||  :. |||: |
            51 eyltddsfqlsdqaihllfsanrwe.ivdkikkdllegknivmdryvysg 99

99 LAYQGYARGIGVEEVRALNEFAINGLYPDLTIYLNVSAEVGRERIIKNSR 148
                .||     |:|       :.       :    :    |  ||||::|. . :|
           100 vaysa.akgtngmdldwclqpdvgllkpdltlfls.tqdvdnnaeksgfg 147

149 DQNRLDQEDLKFHEKVIEGYQEIIHNESQR.FKSVNADQPLENVVEDTYQ 197
                |:        |  .|| |||   :  :   .::      |  .:    .|:            :::
           148 der...yetvkfqekvkqtfmklldkeirkgdesitivdvtnkgiqevea 194

198 TIIKYLEKIRSHHHHHH..... 214
                |  . .|  :  |  |  |
           195 liwqivepvlsthidhdkfsff 216
```

Fig. 6b

```
INDE -18  0 2 FOBS=  80.5 SIGMA=  17.9 PHAS=   0.0 FOM= 0.00
INDE -18  0 3 FOBS=  80.9 SIGMA=  12.2 PHAS= 180.0 FOM= 0.01
INDE -18  0 4 FOBS=  99.5 SIGMA=   9.8 PHAS= 180.0 FOM= 0.00
INDE -18  0 5 FOBS=  36.6 SIGMA=  44.3 PHAS=   0.0 FOM= 0.04
INDE -18  1 2 FOBS=  92.9 SIGMA=  60.5 PHAS= 156.1 FOM= 0.03
INDE -18  1 3 FOBS=  49.9 SIGMA=  24.7 PHAS=  24.7 FOM= 0.08
INDE -18  1 4 FOBS=  78.0 SIGMA=   9.5 PHAS=  25.2 FOM= 0.03
INDE -18  1 5 FOBS=  43.5 SIGMA=  22.4 PHAS= 187.3 FOM= 0.05
INDE -18  2 2 FOBS= 123.4 SIGMA=  28.9 PHAS= 138.8 FOM= 0.04
INDE -18  2 3 FOBS= 123.7 SIGMA=   6.8 PHAS= 198.1 FOM= 0.14
INDE -18  2 4 FOBS= 198.3 SIGMA= 131.7 PHAS= 113.2 FOM= 0.01
INDE -18  2 5 FOBS=  89.5 SIGMA=  49.4 PHAS= 233.0 FOM= 0.03
INDE -18  3 3 FOBS= 108.6 SIGMA=  67.3 PHAS=  21.4 FOM= 0.04
INDE -18  3 4 FOBS=  74.4 SIGMA=  20.2 PHAS= 107.4 FOM= 0.03
INDE -17  0 1 FOBS= 158.0 SIGMA=   6.2 PHAS= 180.0 FOM= 0.00
INDE -17  0 3 FOBS= 101.4 SIGMA=   8.7 PHAS=   0.0 FOM= 0.15
INDE -17  0 4 FOBS= 236.5 SIGMA=   4.6 PHAS= 180.0 FOM= 0.01
INDE -17  0 5 FOBS=  55.0 SIGMA=  25.8 PHAS= 180.0 FOM= 0.08
INDE -17  0 6 FOBS= 130.1 SIGMA=   6.2 PHAS=   0.0 FOM= 0.14
INDE -17  0 8 FOBS= 118.5 SIGMA=   6.5 PHAS=   0.0 FOM= 0.06
INDE -17  0 9 FOBS=  99.0 SIGMA=  10.6 PHAS=   0.0 FOM= 0.08
INDE -17  1 1 FOBS= 112.5 SIGMA=   5.9 PHAS=  89.6 FOM= 0.02
INDE -17  1 2 FOBS= 105.4 SIGMA=   6.1 PHAS= 285.3 FOM= 0.13
INDE -17  1 3 FOBS= 153.1 SIGMA=   4.2 PHAS= 307.5 FOM= 0.12
INDE -17  1 4 FOBS= 100.4 SIGMA=   6.1 PHAS= 226.8 FOM= 0.28
INDE -17  1 5 FOBS= 180.5 SIGMA=   3.5 PHAS= 320.8 FOM= 0.47
INDE -17  1 6 FOBS= 199.1 SIGMA=   2.9 PHAS= 166.1 FOM= 0.28
INDE -17  1 7 FOBS= 157.8 SIGMA=   3.6 PHAS= 109.9 FOM= 0.16
INDE -17  1 8 FOBS= 130.9 SIGMA=   4.1 PHAS= 339.5 FOM= 0.02
INDE -17  1 9 FOBS=  60.4 SIGMA=  12.9 PHAS= 204.3 FOM= 0.02
INDE -17  2 1 FOBS=  65.9 SIGMA=  12.7 PHAS=  58.1 FOM= 0.06
INDE -17  2 2 FOBS=  63.0 SIGMA=  36.8 PHAS= 300.8 FOM= 0.10
INDE -17  2 3 FOBS=  47.1 SIGMA=  15.3 PHAS= 150.6 FOM= 0.07
INDE -17  2 4 FOBS=  82.5 SIGMA=   7.6 PHAS=   4.5 FOM= 0.07
INDE -17  2 5 FOBS=  90.6 SIGMA=   6.4 PHAS= 288.1 FOM= 0.16
INDE -17  2 6 FOBS=  45.2 SIGMA=  12.7 PHAS= 155.5 FOM= 0.32
INDE -17  2 7 FOBS=  97.9 SIGMA=   5.5 PHAS= 265.9 FOM= 0.05
INDE -17  2 8 FOBS= 164.5 SIGMA=   3.2 PHAS= 320.7 FOM= 0.05
INDE -17  3 1 FOBS=  75.7 SIGMA=   9.7 PHAS= 296.8 FOM= 0.06
INDE -17  3 2 FOBS=  63.9 SIGMA=  10.1 PHAS= 158.0 FOM= 0.10
INDE -17  3 3 FOBS=  79.7 SIGMA=   8.0 PHAS= 145.4 FOM= 0.15
INDE -17  3 4 FOBS=  59.9 SIGMA=  11.5 PHAS= 257.6 FOM= 0.66
INDE -17  3 5 FOBS= 119.5 SIGMA=   4.9 PHAS= 169.8 FOM= 0.10
INDE -17  3 6 FOBS=  73.1 SIGMA=   7.6 PHAS= 280.6 FOM= 0.01
INDE -17  3 7 FOBS=  69.9 SIGMA=   7.8 PHAS= 320.2 FOM= 0.24
INDE -17  3 8 FOBS=  76.6 SIGMA=   6.9 PHAS= 169.3 FOM= 0.10
INDE -17  4 1 FOBS=  90.4 SIGMA=  57.5 PHAS= 165.3 FOM= 0.06
INDE -17  4 3 FOBS=  56.8 SIGMA=  11.2 PHAS= 137.8 FOM= 0.03
INDE -17  4 4 FOBS=  49.7 SIGMA=  17.9 PHAS= 159.7 FOM= 0.07
INDE -17  4 5 FOBS=  52.7 SIGMA=  13.5 PHAS=   6.3 FOM= 0.07
INDE -17  4 6 FOBS=  65.5 SIGMA=   8.6 PHAS= 145.7 FOM= 0.20
INDE -17  4 7 FOBS=  58.3 SIGMA=   9.5 PHAS= 350.0 FOM= 0.65
INDE -17  4 8 FOBS= 153.8 SIGMA=   3.5 PHAS= 238.7 FOM= 0.10
INDE -17  5 1 FOBS=  68.3 SIGMA=  32.1 PHAS= 297.3 FOM= 0.02
INDE -17  5 2 FOBS=  69.7 SIGMA=   9.9 PHAS= 102.9 FOM= 0.31
INDE -17  5 3 FOBS= 152.5 SIGMA=   4.2 PHAS=  15.9 FOM= 0.15
INDE -17  5 4 FOBS=  58.0 SIGMA=  10.7 PHAS= 291.4 FOM= 0.12
INDE -17  5 5 FOBS=  39.6 SIGMA=  19.1 PHAS=  81.8 FOM= 0.09
INDE -17  5 6 FOBS=  73.3 SIGMA=   7.8 PHAS= 280.2 FOM= 0.15
INDE -17  5 7 FOBS= 105.9 SIGMA=   5.1 PHAS= 200.8 FOM= 0.52
INDE -17  5 8 FOBS=  98.1 SIGMA=   5.3 PHAS=  66.5 FOM= 0.09
INDE -17  6 1 FOBS=  45.6 SIGMA=  18.7 PHAS= 221.8 FOM= 0.13
INDE -17  6 2 FOBS=  41.2 SIGMA=  17.6 PHAS=  41.8 FOM= 0.15
INDE -17  6 3 FOBS=  63.5 SIGMA=  35.0 PHAS= 208.3 FOM= 0.02
INDE -17  6 4 FOBS=  68.0 SIGMA=   9.0 PHAS=  13.6 FOM= 0.12
INDE -17  6 5 FOBS=  54.5 SIGMA=  12.7 PHAS=  56.7 FOM= 0.42
INDE -17  6 6 FOBS=  74.5 SIGMA=   7.5 PHAS= 256.7 FOM= 0.81
INDE -17  6 7 FOBS= 192.5 SIGMA=   2.9 PHAS=  28.0 FOM= 0.03
INDE -17  6 8 FOBS=  51.0 SIGMA=  17.3 PHAS= 238.3 FOM= 0.10
INDE -17  7 1 FOBS=  83.5 SIGMA=  35.2 PHAS= 350.3 FOM= 0.01
INDE -17  7 3 FOBS=  79.6 SIGMA=   7.7 PHAS= 167.1 FOM= 0.01
```

Fig. 10

| | | | | | | | | | | |
|---|---|---|---|---|---|---|---|---|---|---|
| INDE | -17 | 7 | 4 | FOBS= | 52.7 | SIGMA= | 23.2 | PHAS= | 328.3 | FOM= | 0.21 |
| INDE | -17 | 7 | 5 | FOBS= | 73.4 | SIGMA= | 7.9 | PHAS= | 123.3 | FOM= | 0.06 |
| INDE | -17 | 7 | 6 | FOBS= | 76.9 | SIGMA= | 7.0 | PHAS= | 1.1 | FOM= | 0.04 |
| INDE | -17 | 7 | 7 | FOBS= | 81.5 | SIGMA= | 6.5 | PHAS= | 256.8 | FOM= | 0.36 |
| INDE | -17 | 8 | 1 | FOBS= | 54.7 | SIGMA= | 14.0 | PHAS= | 328.8 | FOM= | 0.02 |
| INDE | -17 | 8 | 2 | FOBS= | 61.0 | SIGMA= | 33.9 | PHAS= | 98.2 | FOM= | 0.05 |
| INDE | -17 | 8 | 3 | FOBS= | 79.1 | SIGMA= | 8.5 | PHAS= | 278.1 | FOM= | 0.19 |
| INDE | -17 | 8 | 4 | FOBS= | 48.4 | SIGMA= | 12.9 | PHAS= | 100.1 | FOM= | 0.04 |
| INDE | -17 | 8 | 5 | FOBS= | 54.4 | SIGMA= | 11.5 | PHAS= | 68.0 | FOM= | 0.14 |
| INDE | -17 | 8 | 6 | FOBS= | 40.8 | SIGMA= | 17.5 | PHAS= | 277.5 | FOM= | 0.19 |
| INDE | -17 | 8 | 7 | FOBS= | 208.7 | SIGMA= | 2.7 | PHAS= | 59.5 | FOM= | 0.91 |
| INDE | -17 | 9 | 1 | FOBS= | 41.7 | SIGMA= | 15.4 | PHAS= | 36.7 | FOM= | 0.10 |
| INDE | -17 | 9 | 2 | FOBS= | 65.7 | SIGMA= | 13.7 | PHAS= | 205.0 | FOM= | 0.07 |
| INDE | -17 | 9 | 3 | FOBS= | 51.2 | SIGMA= | 13.8 | PHAS= | 144.5 | FOM= | 0.03 |
| INDE | -17 | 9 | 4 | FOBS= | 46.4 | SIGMA= | 21.4 | PHAS= | 42.5 | FOM= | 0.09 |
| INDE | -17 | 9 | 5 | FOBS= | 72.9 | SIGMA= | 7.5 | PHAS= | 24.8 | FOM= | 0.15 |
| INDE | -17 | 9 | 6 | FOBS= | 59.2 | SIGMA= | 11.0 | PHAS= | 148.3 | FOM= | 0.11 |
| INDE | -17 | 10 | 1 | FOBS= | 80.9 | SIGMA= | 8.4 | PHAS= | 16.5 | FOM= | 0.16 |
| INDE | -17 | 10 | 2 | FOBS= | 80.9 | SIGMA= | 8.2 | PHAS= | 201.7 | FOM= | 0.12 |
| INDE | -17 | 10 | 3 | FOBS= | 132.9 | SIGMA= | 5.3 | PHAS= | 33.6 | FOM= | 0.12 |
| INDE | -17 | 10 | 4 | FOBS= | 54.5 | SIGMA= | 18.5 | PHAS= | 278.7 | FOM= | 0.02 |
| INDE | -17 | 10 | 5 | FOBS= | 56.9 | SIGMA= | 12.5 | PHAS= | 235.7 | FOM= | 0.02 |
| INDE | -17 | 10 | 6 | FOBS= | 58.0 | SIGMA= | 32.1 | PHAS= | 34.9 | FOM= | 0.04 |
| INDE | -17 | 11 | 2 | FOBS= | 121.0 | SIGMA= | 9.3 | PHAS= | 37.3 | FOM= | 0.13 |
| INDE | -17 | 11 | 3 | FOBS= | 90.5 | SIGMA= | 6.9 | PHAS= | 349.2 | FOM= | 0.18 |
| INDE | -17 | 11 | 4 | FOBS= | 92.5 | SIGMA= | 9.7 | PHAS= | 90.2 | FOM= | 0.03 |
| INDE | -17 | 11 | 5 | FOBS= | 107.1 | SIGMA= | 19.3 | PHAS= | 310.8 | FOM= | 0.02 |
| INDE | -16 | 0 | 1 | FOBS= | 140.1 | SIGMA= | 7.0 | PHAS= | 180.0 | FOM= | 0.00 |
| INDE | -16 | 0 | 3 | FOBS= | 35.3 | SIGMA= | 44.0 | PHAS= | 180.0 | FOM= | 0.04 |
| INDE | -16 | 0 | 4 | FOBS= | 64.7 | SIGMA= | 14.6 | PHAS= | 0.0 | FOM= | 0.03 |
| INDE | -16 | 0 | 5 | FOBS= | 169.1 | SIGMA= | 5.0 | PHAS= | 180.0 | FOM= | 0.03 |
| INDE | -16 | 0 | 6 | FOBS= | 148.6 | SIGMA= | 5.5 | PHAS= | 180.0 | FOM= | 0.15 |
| INDE | -16 | 0 | 7 | FOBS= | 106.3 | SIGMA= | 7.3 | PHAS= | 0.0 | FOM= | 0.42 |
| INDE | -16 | 0 | 8 | FOBS= | 63.2 | SIGMA= | 11.2 | PHAS= | 180.0 | FOM= | 0.23 |
| INDE | -16 | 0 | 9 | FOBS= | 46.2 | SIGMA= | 14.8 | PHAS= | 180.0 | FOM= | 0.20 |
| INDE | -16 | 0 | 10 | FOBS= | 139.4 | SIGMA= | 5.1 | PHAS= | 0.0 | FOM= | 0.94 |
| INDE | -16 | 1 | 2 | FOBS= | 158.0 | SIGMA= | 4.2 | PHAS= | 287.6 | FOM= | 0.09 |
| INDE | -16 | 1 | 3 | FOBS= | 40.6 | SIGMA= | 21.1 | PHAS= | 293.8 | FOM= | 0.10 |
| INDE | -16 | 1 | 4 | FOBS= | 102.1 | SIGMA= | 6.1 | PHAS= | 55.8 | FOM= | 0.20 |
| INDE | -16 | 1 | 5 | FOBS= | 63.8 | SIGMA= | 10.5 | PHAS= | 226.8 | FOM= | 0.04 |
| INDE | -16 | 1 | 7 | FOBS= | 167.1 | SIGMA= | 3.4 | PHAS= | 75.7 | FOM= | 0.16 |
| INDE | -16 | 1 | 8 | FOBS= | 103.3 | SIGMA= | 4.9 | PHAS= | 172.5 | FOM= | 0.89 |
| INDE | -16 | 1 | 9 | FOBS= | 76.9 | SIGMA= | 6.2 | PHAS= | 350.6 | FOM= | 0.17 |
| INDE | -16 | 2 | 1 | FOBS= | 117.1 | SIGMA= | 5.7 | PHAS= | 254.5 | FOM= | 0.23 |
| INDE | -16 | 2 | 2 | FOBS= | 107.4 | SIGMA= | 6.0 | PHAS= | 8.8 | FOM= | 0.14 |
| INDE | -16 | 2 | 3 | FOBS= | 83.3 | SIGMA= | 7.6 | PHAS= | 130.1 | FOM= | 0.11 |
| INDE | -16 | 2 | 4 | FOBS= | 209.0 | SIGMA= | 3.0 | PHAS= | 301.8 | FOM= | 0.75 |
| INDE | -16 | 2 | 5 | FOBS= | 112.4 | SIGMA= | 5.3 | PHAS= | 162.9 | FOM= | 0.06 |
| INDE | -16 | 2 | 6 | FOBS= | 69.6 | SIGMA= | 8.3 | PHAS= | 306.9 | FOM= | 0.18 |
| INDE | -16 | 2 | 7 | FOBS= | 53.0 | SIGMA= | 11.1 | PHAS= | 148.8 | FOM= | 0.14 |
| INDE | -16 | 2 | 9 | FOBS= | 83.3 | SIGMA= | 6.0 | PHAS= | 287.1 | FOM= | 0.49 |
| INDE | -16 | 2 | 10 | FOBS= | 105.0 | SIGMA= | 4.6 | PHAS= | 85.0 | FOM= | 0.76 |
| INDE | -16 | 3 | 1 | FOBS= | 79.2 | SIGMA= | 8.3 | PHAS= | 311.0 | FOM= | 0.25 |
| INDE | -16 | 3 | 2 | FOBS= | 73.8 | SIGMA= | 9.0 | PHAS= | 98.1 | FOM= | 0.14 |
| INDE | -16 | 3 | 3 | FOBS= | 140.2 | SIGMA= | 4.7 | PHAS= | 228.0 | FOM= | 0.54 |
| INDE | -16 | 3 | 4 | FOBS= | 102.0 | SIGMA= | 5.9 | PHAS= | 14.0 | FOM= | 0.22 |
| INDE | -16 | 3 | 5 | FOBS= | 219.6 | SIGMA= | 2.9 | PHAS= | 95.5 | FOM= | 0.11 |
| INDE | -16 | 3 | 6 | FOBS= | 70.7 | SIGMA= | 8.0 | PHAS= | 210.5 | FOM= | 0.21 |
| INDE | -16 | 3 | 7 | FOBS= | 48.9 | SIGMA= | 27.8 | PHAS= | 48.1 | FOM= | 0.24 |
| INDE | -16 | 3 | 8 | FOBS= | 66.5 | SIGMA= | 7.6 | PHAS= | 271.7 | FOM= | 0.05 |
| INDE | -16 | 3 | 9 | FOBS= | 348.9 | SIGMA= | 1.7 | PHAS= | 271.3 | FOM= | 0.42 |
| INDE | -16 | 3 | 10 | FOBS= | 119.5 | SIGMA= | 3.8 | PHAS= | 253.1 | FOM= | 0.48 |
| INDE | -16 | 4 | 2 | FOBS= | 91.6 | SIGMA= | 7.2 | PHAS= | 213.2 | FOM= | 0.27 |
| INDE | -16 | 4 | 3 | FOBS= | 57.3 | SIGMA= | 28.8 | PHAS= | 313.0 | FOM= | 0.04 |
| INDE | -16 | 4 | 4 | FOBS= | 68.6 | SIGMA= | 54.8 | PHAS= | 349.7 | FOM= | 0.21 |
| INDE | -16 | 4 | 5 | FOBS= | 89.9 | SIGMA= | 6.4 | PHAS= | 218.5 | FOM= | 0.29 |
| INDE | -16 | 4 | 6 | FOBS= | 97.6 | SIGMA= | 5.6 | PHAS= | 274.8 | FOM= | 0.22 |
| INDE | -16 | 4 | 7 | FOBS= | 72.9 | SIGMA= | 7.2 | PHAS= | 1.9 | FOM= | 0.25 |
| INDE | -16 | 4 | 8 | FOBS= | 90.5 | SIGMA= | 5.8 | PHAS= | 140.0 | FOM= | 0.71 |
| INDE | -16 | 4 | 9 | FOBS= | 45.8 | SIGMA= | 11.6 | PHAS= | 17.3 | FOM= | 0.17 |
| INDE | -16 | 4 | 10 | FOBS= | 51.2 | SIGMA= | 29.4 | PHAS= | 205.3 | FOM= | 0.08 |

Fig. 10A-1

```
INDE -16   5   1 FOBS=  111.5 SIGMA=  6.0 PHAS= 191.6 FOM= 0.11
INDE -16   5   2 FOBS=   82.2 SIGMA=  7.8 PHAS=  67.3 FOM= 0.30
INDE -16   5   3 FOBS=   59.2 SIGMA= 14.4 PHAS= 277.0 FOM= 0.19
INDE -16   5   4 FOBS=   60.0 SIGMA= 23.6 PHAS= 107.2 FOM= 0.20
INDE -16   5   5 FOBS=  138.0 SIGMA=  4.3 PHAS= 180.3 FOM= 0.32
INDE -16   5   6 FOBS=   99.2 SIGMA=  5.8 PHAS= 274.7 FOM= 0.69
INDE -16   5   7 FOBS=  204.7 SIGMA=  2.8 PHAS= 132.6 FOM= 0.89
INDE -16   5   8 FOBS=  106.3 SIGMA=  4.7 PHAS= 228.0 FOM= 0.19
INDE -16   5   9 FOBS=  165.9 SIGMA=  3.0 PHAS= 265.7 FOM= 0.62
INDE -16   5  10 FOBS=   65.5 SIGMA=  6.7 PHAS=  34.2 FOM= 0.11
INDE -16   6   1 FOBS=   58.4 SIGMA= 27.9 PHAS=  58.3 FOM= 0.38
INDE -16   6   2 FOBS=   76.0 SIGMA=  8.5 PHAS= 220.7 FOM= 0.10
INDE -16   6   3 FOBS=   63.0 SIGMA= 33.3 PHAS= 211.7 FOM= 0.10
INDE -16   6   4 FOBS=   89.1 SIGMA=  6.7 PHAS=  42.3 FOM= 0.53
INDE -16   6   5 FOBS=  133.2 SIGMA=  4.5 PHAS= 214.1 FOM= 0.77
INDE -16   6   6 FOBS=  191.7 SIGMA=  3.0 PHAS=  66.6 FOM= 0.89
INDE -16   6   7 FOBS=   74.3 SIGMA=  6.8 PHAS= 121.3 FOM= 0.77
INDE -16   6   8 FOBS=  155.7 SIGMA=  3.4 PHAS= 220.3 FOM= 0.91
INDE -16   6   9 FOBS=  101.5 SIGMA=  5.0 PHAS=   7.3 FOM= 0.63
INDE -16   6  10 FOBS=  163.0 SIGMA=  2.9 PHAS= 251.7 FOM= 0.93
INDE -16   7   1 FOBS=   57.1 SIGMA= 16.3 PHAS= 334.5 FOM= 0.15
INDE -16   7   2 FOBS=   58.1 SIGMA= 15.4 PHAS= 121.4 FOM= 0.21
INDE -16   7   3 FOBS=  111.3 SIGMA=  5.5 PHAS= 309.6 FOM= 0.19
INDE -16   7   4 FOBS=   73.8 SIGMA=  7.9 PHAS= 180.8 FOM= 0.07
INDE -16   7   5 FOBS=   41.4 SIGMA= 17.3 PHAS= 153.7 FOM= 0.08
INDE -16   7   6 FOBS=  132.8 SIGMA=  4.2 PHAS=  12.6 FOM= 0.47
INDE -16   7   7 FOBS=  129.1 SIGMA=  4.2 PHAS= 160.6 FOM= 0.62
INDE -16   7   8 FOBS=  267.5 SIGMA=  2.1 PHAS=  28.2 FOM= 0.90
INDE -16   7   9 FOBS=  111.0 SIGMA=  4.3 PHAS=  30.4 FOM= 0.19
INDE -16   7  10 FOBS=  246.9 SIGMA=  4.1 PHAS=  45.1 FOM= 0.68
INDE -16   8   1 FOBS=   64.8 SIGMA= 11.2 PHAS=  92.6 FOM= 0.52
INDE -16   8   2 FOBS=   42.1 SIGMA= 20.3 PHAS= 290.7 FOM= 0.07
INDE -16   8   3 FOBS=   36.5 SIGMA= 15.9 PHAS= 259.5 FOM= 0.26
INDE -16   8   4 FOBS=  131.4 SIGMA=  4.5 PHAS= 143.1 FOM= 0.72
INDE -16   8   5 FOBS=   66.7 SIGMA=  8.3 PHAS= 290.4 FOM= 0.31
INDE -16   8   6 FOBS=   98.2 SIGMA=  5.3 PHAS= 141.7 FOM= 0.90
INDE -16   8   7 FOBS=  145.0 SIGMA=  3.6 PHAS= 344.7 FOM= 0.10
INDE -16   8   8 FOBS=   55.3 SIGMA= 10.1 PHAS= 259.3 FOM= 0.19
INDE -16   8   9 FOBS=  116.2 SIGMA=  4.3 PHAS=  67.8 FOM= 0.87
INDE -16   9   1 FOBS=   81.8 SIGMA=  6.6 PHAS=  77.9 FOM= 0.95
INDE -16   9   2 FOBS=  107.4 SIGMA=  6.6 PHAS= 232.9 FOM= 0.71
INDE -16   9   3 FOBS=   62.5 SIGMA= 83.9 PHAS=   5.5 FOM= 0.29
INDE -16   9   4 FOBS=  130.7 SIGMA=  4.5 PHAS= 148.8 FOM= 0.43
INDE -16   9   5 FOBS=  145.3 SIGMA=  3.9 PHAS= 175.8 FOM= 0.82
INDE -16   9   6 FOBS=  123.7 SIGMA=  4.4 PHAS= 265.4 FOM= 0.70
INDE -16   9   7 FOBS=   86.0 SIGMA=  5.6 PHAS=  32.1 FOM= 0.49
INDE -16   9   8 FOBS=  123.5 SIGMA=  4.0 PHAS= 185.1 FOM= 0.18
INDE -16   9   9 FOBS=  120.3 SIGMA=  4.0 PHAS= 304.2 FOM= 0.25
INDE -16  10   1 FOBS=   61.8 SIGMA= 14.5 PHAS= 188.3 FOM= 0.08
INDE -16  10   2 FOBS=   67.9 SIGMA= 10.3 PHAS= 321.0 FOM= 0.11
INDE -16  10   4 FOBS=  128.7 SIGMA= 82.3 PHAS= 138.2 FOM= 0.02
INDE -16  10   5 FOBS=   85.9 SIGMA=  6.1 PHAS= 234.1 FOM= 0.46
INDE -16  10   6 FOBS=  142.5 SIGMA=  3.8 PHAS= 216.9 FOM= 0.24
INDE -16  10   7 FOBS=   74.7 SIGMA=  6.3 PHAS=  23.2 FOM= 0.27
INDE -16  10   8 FOBS=  230.8 SIGMA=  2.3 PHAS= 263.6 FOM= 0.88
INDE -16  10   9 FOBS=  155.2 SIGMA=  6.4 PHAS= 177.6 FOM= 0.16
INDE -16  11   2 FOBS=  165.9 SIGMA=  4.0 PHAS= 319.9 FOM= 0.30
INDE -16  11   3 FOBS=  174.7 SIGMA=  3.8 PHAS=  52.3 FOM= 0.57
INDE -16  11   4 FOBS=   91.2 SIGMA=  7.1 PHAS= 305.3 FOM= 0.31
INDE -16  11   5 FOBS=   63.6 SIGMA= 11.8 PHAS= 212.4 FOM= 0.03
INDE -16  11   6 FOBS=   33.0 SIGMA= 14.0 PHAS=  64.3 FOM= 0.16
INDE -16  11   7 FOBS=  177.8 SIGMA=  2.8 PHAS= 249.8 FOM= 0.75
INDE -16  11   8 FOBS=  169.7 SIGMA=  2.9 PHAS=  63.2 FOM= 0.30
INDE -16  12   1 FOBS=  144.6 SIGMA=  4.7 PHAS=  10.0 FOM= 0.22
INDE -16  12   2 FOBS=  100.7 SIGMA=  6.4 PHAS=  89.0 FOM= 0.13
INDE -16  12   3 FOBS=  134.1 SIGMA=  4.7 PHAS= 346.0 FOM= 0.09
INDE -16  12   5 FOBS=   55.5 SIGMA= 11.0 PHAS= 115.3 FOM= 0.13
INDE -16  12   6 FOBS=   63.1 SIGMA=  8.2 PHAS= 274.9 FOM= 0.07
INDE -16  12   7 FOBS=   99.1 SIGMA=  4.8 PHAS= 116.7 FOM= 0.12
INDE -16  12   8 FOBS=   73.0 SIGMA=  9.7 PHAS= 274.7 FOM= 0.02
INDE -16  13   1 FOBS=  127.0 SIGMA=  5.3 PHAS= 227.2 FOM= 0.18
```

Fig. 10A-2

```
INDE -16 13  2 FOBS=  46.6 SIGMA= 13.9 PHAS=  44.4 FOM= 0.01
INDE -16 13  3 FOBS=  87.3 SIGMA=  6.8 PHAS= 158.9 FOM= 0.05
INDE -16 13  4 FOBS=  58.7 SIGMA= 34.5 PHAS= 360.0 FOM= 0.07
INDE -16 13  5 FOBS=  62.2 SIGMA= 34.7 PHAS= 146.6 FOM= 0.12
INDE -16 13  6 FOBS= 107.1 SIGMA=  5.3 PHAS= 298.6 FOM= 0.24
INDE -16 13  7 FOBS=  67.6 SIGMA=  7.7 PHAS=  68.8 FOM= 0.05
INDE -16 14  1 FOBS= 150.7 SIGMA= 94.2 PHAS=  84.9 FOM= 0.01
INDE -16 14  2 FOBS=  59.0 SIGMA= 12.8 PHAS= 252.4 FOM= 0.04
INDE -16 14  3 FOBS=  50.6 SIGMA= 16.2 PHAS= 330.2 FOM= 0.01
INDE -16 14  4 FOBS=  45.0 SIGMA= 19.2 PHAS=  68.6 FOM= 0.09
INDE -16 14  5 FOBS= 125.3 SIGMA=  4.2 PHAS= 350.0 FOM= 0.54
INDE -16 14  6 FOBS= 123.1 SIGMA=  4.1 PHAS= 111.5 FOM= 0.50
INDE -16 15  1 FOBS=  54.5 SIGMA= 20.9 PHAS= 241.3 FOM= 0.03
INDE -16 15  2 FOBS=  64.3 SIGMA=  9.9 PHAS=  51.3 FOM= 0.05
INDE -16 15  3 FOBS=  91.9 SIGMA=  6.4 PHAS=  31.3 FOM= 0.13
INDE -16 15  4 FOBS=  83.1 SIGMA=  6.6 PHAS= 261.7 FOM= 0.11
INDE -16 15  5 FOBS=  77.4 SIGMA= 10.8 PHAS= 120.6 FOM= 0.02
INDE -15  0  1 FOBS=  82.1 SIGMA= 11.7 PHAS=   0.0 FOM= 0.08
INDE -15  0  2 FOBS=  57.1 SIGMA= 16.3 PHAS= 180.0 FOM= 0.04
INDE -15  0  3 FOBS= 289.2 SIGMA=  3.3 PHAS=   0.0 FOM= 0.53
INDE -15  0  5 FOBS= 136.1 SIGMA=  6.2 PHAS= 180.0 FOM= 0.02
INDE -15  0  6 FOBS=  92.1 SIGMA=  8.4 PHAS= 180.0 FOM= 0.03
INDE -15  0  7 FOBS= 180.9 SIGMA=  4.3 PHAS=   0.0 FOM= 0.03
INDE -15  0  8 FOBS=  92.4 SIGMA=  7.6 PHAS= 180.0 FOM= 0.00
INDE -15  0  9 FOBS=  68.0 SIGMA=  9.9 PHAS=   0.0 FOM= 0.04
INDE -15  0 10 FOBS=  86.4 SIGMA=  8.2 PHAS= 180.0 FOM= 0.98
INDE -15  0 11 FOBS= 120.6 SIGMA=  6.2 PHAS= 180.0 FOM= 0.83
INDE -15  0 12 FOBS= 300.5 SIGMA=  2.9 PHAS= 180.0 FOM= 0.15
INDE -15  1  1 FOBS=  80.4 SIGMA=  8.5 PHAS= 339.1 FOM= 0.08
INDE -15  1  2 FOBS= 243.0 SIGMA=  2.8 PHAS= 166.3 FOM= 0.76
INDE -15  1  3 FOBS= 179.2 SIGMA=  3.7 PHAS=  67.9 FOM= 0.11
INDE -15  1  4 FOBS=  44.9 SIGMA= 18.4 PHAS= 352.4 FOM= 0.13
INDE -15  1  5 FOBS= 106.2 SIGMA=  5.6 PHAS= 209.4 FOM= 0.61
INDE -15  1  6 FOBS=  67.1 SIGMA=  8.9 PHAS=  11.6 FOM= 0.08
INDE -15  1  7 FOBS=  40.9 SIGMA= 14.6 PHAS=  38.3 FOM= 0.15
INDE -15  1  8 FOBS= 121.1 SIGMA=  4.2 PHAS= 131.4 FOM= 0.40
INDE -15  1  9 FOBS= 155.5 SIGMA=  3.1 PHAS= 321.1 FOM= 0.29
INDE -15  1 10 FOBS= 191.2 SIGMA=  2.5 PHAS=  77.0 FOM= 0.92
INDE -15  1 11 FOBS= 102.6 SIGMA=  5.3 PHAS= 304.7 FOM= 0.33
INDE -15  1 12 FOBS= 106.9 SIGMA=  4.9 PHAS= 172.9 FOM= 0.37
INDE -15  2  1 FOBS=  45.5 SIGMA= 18.8 PHAS= 140.3 FOM= 0.08
INDE -15  2  2 FOBS= 112.5 SIGMA=  5.8 PHAS= 222.3 FOM= 0.09
INDE -15  2  4 FOBS=  76.4 SIGMA=  7.9 PHAS=  77.7 FOM= 0.27
INDE -15  2  5 FOBS= 227.6 SIGMA=  2.7 PHAS= 132.1 FOM= 0.74
INDE -15  2  6 FOBS= 157.3 SIGMA=  3.7 PHAS= 321.5 FOM= 0.60
INDE -15  2  7 FOBS= 193.1 SIGMA=  2.9 PHAS= 148.1 FOM= 0.69
INDE -15  2  8 FOBS= 130.0 SIGMA=  4.0 PHAS= 238.9 FOM= 0.19
INDE -15  2  9 FOBS=  87.5 SIGMA=  5.4 PHAS= 307.9 FOM= 0.50
INDE -15  2 10 FOBS=  92.4 SIGMA=  4.8 PHAS= 200.9 FOM= 0.96
INDE -15  2 11 FOBS= 175.0 SIGMA=  2.9 PHAS=  23.4 FOM= 0.24
INDE -15  2 12 FOBS=  67.5 SIGMA=  9.8 PHAS= 130.5 FOM= 0.05
INDE -15  3  1 FOBS= 209.9 SIGMA=  3.3 PHAS=  35.7 FOM= 0.72
INDE -15  3  2 FOBS=  58.3 SIGMA= 12.5 PHAS= 247.6 FOM= 0.22
INDE -15  3  3 FOBS= 123.7 SIGMA=  5.2 PHAS= 157.4 FOM= 0.11
INDE -15  3  4 FOBS=  40.3 SIGMA= 19.2 PHAS=  75.5 FOM= 0.18
INDE -15  3  5 FOBS= 107.2 SIGMA=  5.5 PHAS= 197.2 FOM= 0.48
INDE -15  3  6 FOBS= 268.0 SIGMA=  2.2 PHAS=  14.3 FOM= 0.34
INDE -15  3  7 FOBS= 228.4 SIGMA=  2.6 PHAS=  85.4 FOM= 0.89
INDE -15  3  8 FOBS= 138.6 SIGMA=  3.8 PHAS= 233.1 FOM= 0.68
INDE -15  3  9 FOBS= 123.0 SIGMA=  4.0 PHAS=  99.5 FOM= 0.75
INDE -15  3 10 FOBS= 100.1 SIGMA=  4.5 PHAS= 258.9 FOM= 0.55
INDE -15  3 11 FOBS=  40.8 SIGMA= 18.2 PHAS= 327.0 FOM= 0.04
INDE -15  3 12 FOBS= 249.4 SIGMA=  2.6 PHAS= 309.0 FOM= 0.87
INDE -15  4  1 FOBS= 147.8 SIGMA=  4.7 PHAS= 302.2 FOM= 0.04
INDE -15  4  2 FOBS= 135.9 SIGMA=  5.0 PHAS= 175.2 FOM= 0.38
INDE -15  4  3 FOBS=  65.3 SIGMA= 10.7 PHAS=  19.9 FOM= 0.14
INDE -15  4  4 FOBS=  39.6 SIGMA= 23.2 PHAS= 183.4 FOM= 0.10
INDE -15  4  5 FOBS=  86.9 SIGMA=  6.6 PHAS= 254.2 FOM= 0.26
INDE -15  4  6 FOBS= 198.4 SIGMA=  2.9 PHAS=  22.8 FOM= 0.60
INDE -15  4  7 FOBS= 289.4 SIGMA=  2.0 PHAS= 146.3 FOM= 0.87
INDE -15  4  8 FOBS= 161.5 SIGMA=  3.4 PHAS= 325.9 FOM= 0.87
```

Fig. 10A-3

```
INDE -15   4   9 FOBS=  170.3 SIGMA=   2.9 PHAS= 111.9 FOM= 0.78
INDE -15   4  10 FOBS=   89.5 SIGMA=   5.0 PHAS= 130.2 FOM= 0.32
INDE -15   4  11 FOBS=   84.8 SIGMA=   5.9 PHAS=  17.9 FOM= 0.69
INDE -15   4  12 FOBS=  106.4 SIGMA=   8.3 PHAS= 129.1 FOM= 0.30
INDE -15   5   1 FOBS=  117.0 SIGMA=   5.9 PHAS= 166.5 FOM= 0.58
INDE -15   5   2 FOBS=  214.6 SIGMA=   3.1 PHAS= 242.2 FOM= 0.62
INDE -15   5   3 FOBS=  101.8 SIGMA=   6.1 PHAS= 307.3 FOM= 0.37
INDE -15   5   4 FOBS=   46.3 SIGMA=  30.3 PHAS= 130.0 FOM= 0.20
INDE -15   5   5 FOBS=  175.8 SIGMA=   3.4 PHAS=   2.1 FOM= 0.58
INDE -15   5   6 FOBS=   87.0 SIGMA=   6.5 PHAS= 111.5 FOM= 0.52
INDE -15   5   7 FOBS=  111.4 SIGMA=   4.7 PHAS= 328.1 FOM= 0.30
INDE -15   5   8 FOBS=   88.4 SIGMA=   5.6 PHAS= 206.0 FOM= 0.21
INDE -15   5   9 FOBS=  136.5 SIGMA=   3.8 PHAS=  92.7 FOM= 0.94
INDE -15   5  10 FOBS=  110.3 SIGMA=   4.6 PHAS= 278.1 FOM= 0.85
INDE -15   5  11 FOBS=   58.6 SIGMA=   7.7 PHAS= 188.6 FOM= 0.04
INDE -15   6   1 FOBS=  100.9 SIGMA=   6.7 PHAS= 134.0 FOM= 0.17
INDE -15   6   2 FOBS=   37.5 SIGMA=  18.4 PHAS= 222.1 FOM= 0.13
INDE -15   6   3 FOBS=  149.1 SIGMA=   4.3 PHAS= 295.8 FOM= 0.75
INDE -15   6   4 FOBS=   40.2 SIGMA=  20.1 PHAS= 200.2 FOM= 0.18
INDE -15   6   5 FOBS=  203.9 SIGMA=   2.9 PHAS=  59.7 FOM= 0.33
INDE -15   6   6 FOBS=  142.5 SIGMA=   4.0 PHAS= 232.8 FOM= 0.43
INDE -15   6   7 FOBS=  295.3 SIGMA=   2.0 PHAS= 230.9 FOM= 0.98
INDE -15   6   8 FOBS=  269.8 SIGMA=   2.0 PHAS= 136.4 FOM= 0.89
INDE -15   6   9 FOBS=  223.1 SIGMA=   2.2 PHAS= 233.8 FOM= 0.90
INDE -15   6  10 FOBS=  123.4 SIGMA=   4.2 PHAS= 138.0 FOM= 0.20
INDE -15   6  11 FOBS=  120.7 SIGMA=   4.0 PHAS= 124.3 FOM= 0.85
INDE -15   7   1 FOBS=   80.0 SIGMA=  10.0 PHAS= 140.1 FOM= 0.31
INDE -15   7   2 FOBS=   93.0 SIGMA=   7.1 PHAS= 296.8 FOM= 0.47
INDE -15   7   3 FOBS=  274.6 SIGMA=   2.4 PHAS= 136.3 FOM= 0.29
INDE -15   7   4 FOBS=  253.1 SIGMA=   2.5 PHAS= 169.3 FOM= 0.96
INDE -15   7   5 FOBS=   40.6 SIGMA=  16.9 PHAS= 359.1 FOM= 0.39
INDE -15   7   6 FOBS=  136.3 SIGMA=   4.1 PHAS= 232.3 FOM= 0.84
INDE -15   7   7 FOBS=   94.1 SIGMA=   5.4 PHAS= 170.5 FOM= 0.25
INDE -15   7   8 FOBS=  187.8 SIGMA=   2.7 PHAS= 273.9 FOM= 0.94
INDE -15   7   9 FOBS=   82.8 SIGMA=   6.0 PHAS= 191.8 FOM= 0.85
INDE -15   7  10 FOBS=  181.9 SIGMA=   2.9 PHAS= 318.1 FOM= 0.91
INDE -15   7  11 FOBS=   68.0 SIGMA=   7.3 PHAS= 182.5 FOM= 0.17
INDE -15   8   1 FOBS=   69.6 SIGMA=  10.2 PHAS= 357.2 FOM= 0.09
INDE -15   8   2 FOBS=  136.1 SIGMA=   5.5 PHAS= 245.0 FOM= 0.14
INDE -15   8   3 FOBS=  141.4 SIGMA=   4.6 PHAS= 161.2 FOM= 0.75
INDE -15   8   4 FOBS=  112.9 SIGMA=   5.3 PHAS= 265.5 FOM= 0.52
INDE -15   8   5 FOBS=  169.1 SIGMA=   3.4 PHAS= 140.9 FOM= 0.05
INDE -15   8   6 FOBS=   39.5 SIGMA=  17.3 PHAS=  82.1 FOM= 0.28
INDE -15   8   7 FOBS=   89.8 SIGMA=   6.0 PHAS= 270.4 FOM= 0.72
INDE -15   8   8 FOBS=  228.7 SIGMA=   2.4 PHAS= 126.6 FOM= 0.93
INDE -15   8   9 FOBS=  257.4 SIGMA=   2.0 PHAS=  82.1 FOM= 0.53
INDE -15   8  10 FOBS=   66.9 SIGMA=   7.5 PHAS= 162.7 FOM= 0.35
INDE -15   8  11 FOBS=  123.8 SIGMA=   3.9 PHAS= 323.6 FOM= 0.60
INDE -15   9   1 FOBS=   49.9 SIGMA=  14.3 PHAS= 225.1 FOM= 0.11
INDE -15   9   2 FOBS=   49.4 SIGMA=  17.2 PHAS=  73.8 FOM= 0.12
INDE -15   9   3 FOBS=   64.9 SIGMA=  15.5 PHAS= 285.6 FOM= 0.05
INDE -15   9   4 FOBS=   69.6 SIGMA=   8.1 PHAS= 145.8 FOM= 0.20
INDE -15   9   5 FOBS=  152.1 SIGMA=   3.8 PHAS=  69.9 FOM= 0.82
INDE -15   9   6 FOBS=  135.5 SIGMA=   4.1 PHAS= 216.0 FOM= 0.80
INDE -15   9   7 FOBS=  189.3 SIGMA=   2.7 PHAS=   6.6 FOM= 0.47
INDE -15   9   8 FOBS=  245.0 SIGMA=   2.2 PHAS=   6.6 FOM= 0.88
INDE -15   9   9 FOBS=  186.2 SIGMA=   2.4 PHAS=  13.1 FOM= 0.92
INDE -15   9  10 FOBS=   79.1 SIGMA=   6.1 PHAS= 236.0 FOM= 0.55
INDE -15   9  11 FOBS=  146.8 SIGMA=   5.5 PHAS= 165.2 FOM= 0.13
INDE -15  10   2 FOBS=   86.2 SIGMA=  65.3 PHAS= 282.7 FOM= 0.23
INDE -15  10   3 FOBS=  125.3 SIGMA=   5.6 PHAS= 130.0 FOM= 0.39
INDE -15  10   4 FOBS=   51.7 SIGMA=  20.3 PHAS=  26.8 FOM= 0.19
INDE -15  10   5 FOBS=   83.2 SIGMA=   6.4 PHAS= 246.3 FOM= 0.34
INDE -15  10   6 FOBS=   83.1 SIGMA=   6.1 PHAS=  82.4 FOM= 0.10
INDE -15  10   7 FOBS=  108.2 SIGMA=   4.5 PHAS= 311.8 FOM= 0.37
INDE -15  10   8 FOBS=  225.5 SIGMA=   2.3 PHAS= 146.4 FOM= 0.99
INDE -15  10   9 FOBS=   89.0 SIGMA=   5.1 PHAS=  11.3 FOM= 0.50
INDE -15  10  10 FOBS=  127.4 SIGMA=   3.5 PHAS=  95.3 FOM= 0.71
INDE -15  11   1 FOBS=   88.5 SIGMA=   7.5 PHAS=   6.1 FOM= 0.23
INDE -15  11   2 FOBS=  134.6 SIGMA=   4.9 PHAS= 211.9 FOM= 0.19
INDE -15  11   3 FOBS=   75.6 SIGMA=   8.2 PHAS=  38.3 FOM= 0.05
```

Fig. 10A-4

```
INDE -15  11   4 FOBS=   91.3 SIGMA=  78.9 PHAS= 117.0 FOM= 0.06
INDE -15  11   5 FOBS=   42.0 SIGMA=  20.0 PHAS= 295.5 FOM= 0.10
INDE -15  11   6 FOBS=  128.1 SIGMA=   4.0 PHAS= 255.2 FOM= 0.04
INDE -15  11   7 FOBS=   63.7 SIGMA=   7.5 PHAS= 104.8 FOM= 0.53
INDE -15  11   8 FOBS=  158.1 SIGMA=   3.0 PHAS=   1.7 FOM= 0.75
INDE -15  11   9 FOBS=  120.3 SIGMA=   3.6 PHAS= 327.7 FOM= 0.54
INDE -15  11  10 FOBS=   40.1 SIGMA=  14.6 PHAS= 103.1 FOM= 0.17
INDE -15  12   1 FOBS=  108.8 SIGMA=   6.1 PHAS= 296.8 FOM= 0.11
INDE -15  12   2 FOBS=   93.5 SIGMA=   6.8 PHAS=  19.4 FOM= 0.05
INDE -15  12   3 FOBS=   57.2 SIGMA=  34.7 PHAS= 123.3 FOM= 0.11
INDE -15  12   4 FOBS=   54.4 SIGMA=  11.9 PHAS=   2.7 FOM= 0.07
INDE -15  12   5 FOBS=   84.1 SIGMA=   6.9 PHAS= 267.5 FOM= 0.23
INDE -15  12   6 FOBS=  102.4 SIGMA=   5.1 PHAS= 155.0 FOM= 0.80
INDE -15  12   7 FOBS=   99.3 SIGMA=   4.5 PHAS= 234.1 FOM= 0.54
INDE -15  12   8 FOBS=  191.0 SIGMA=   2.6 PHAS= 224.6 FOM= 0.53
INDE -15  12   9 FOBS=   50.7 SIGMA=   9.2 PHAS= 146.5 FOM= 0.25
INDE -15  12  10 FOBS=   53.3 SIGMA=  15.4 PHAS= 314.8 FOM= 0.05
INDE -15  13   1 FOBS=   69.3 SIGMA=   9.8 PHAS=  13.4 FOM= 0.04
INDE -15  13   2 FOBS=   84.2 SIGMA=   7.5 PHAS= 105.3 FOM= 0.26
INDE -15  13   3 FOBS=   58.8 SIGMA=  34.3 PHAS= 314.8 FOM= 0.16
INDE -15  13   4 FOBS=   87.0 SIGMA=   6.5 PHAS= 212.0 FOM= 0.04
INDE -15  13   5 FOBS=  103.8 SIGMA=   5.0 PHAS= 356.0 FOM= 0.19
INDE -15  13   6 FOBS=   32.6 SIGMA=   8.9 PHAS=  93.0 FOM= 0.94
INDE -15  13   7 FOBS=   97.6 SIGMA=   4.9 PHAS= 196.5 FOM= 0.18
INDE -15  13   8 FOBS=   61.7 SIGMA=   7.0 PHAS= 345.8 FOM= 0.18
INDE -15  13   9 FOBS=  109.0 SIGMA=   4.7 PHAS= 271.4 FOM= 0.15
INDE -15  14   1 FOBS=   50.9 SIGMA=  12.5 PHAS= 106.4 FOM= 0.04
INDE -15  14   3 FOBS=   36.2 SIGMA=  17.0 PHAS= 328.4 FOM= 0.34
INDE -15  14   4 FOBS=   32.7 SIGMA=  17.7 PHAS= 132.0 FOM= 0.20
INDE -15  14   5 FOBS=   64.8 SIGMA=   7.8 PHAS= 140.9 FOM= 0.01
INDE -15  14   6 FOBS=  124.6 SIGMA=   4.0 PHAS=  68.5 FOM= 0.12
INDE -15  14   7 FOBS=  183.6 SIGMA=   2.9 PHAS= 280.3 FOM= 0.59
INDE -15  14   8 FOBS=  149.9 SIGMA=   3.3 PHAS=  44.8 FOM= 0.75
INDE -15  14   9 FOBS=   59.9 SIGMA=  33.3 PHAS= 191.8 FOM= 0.14
INDE -15  15   1 FOBS=  103.8 SIGMA=   6.4 PHAS= 129.3 FOM= 0.26
INDE -15  15   2 FOBS=   47.8 SIGMA=  12.7 PHAS= 299.4 FOM= 0.06
INDE -15  15   3 FOBS=  138.4 SIGMA=   4.2 PHAS= 150.5 FOM= 0.40
INDE -15  15   4 FOBS=   81.8 SIGMA=   6.9 PHAS= 166.2 FOM= 0.34
INDE -15  15   5 FOBS=   71.8 SIGMA=   7.3 PHAS= 156.8 FOM= 0.33
INDE -15  15   6 FOBS=   57.4 SIGMA=   9.1 PHAS= 121.5 FOM= 0.04
INDE -15  15   7 FOBS=  101.7 SIGMA=   4.4 PHAS= 315.7 FOM= 0.03
INDE -15  15   8 FOBS=   74.7 SIGMA=   6.2 PHAS=  35.4 FOM= 0.25
INDE -15  16   1 FOBS=   62.9 SIGMA=  15.3 PHAS= 285.3 FOM= 0.01
INDE -15  16   2 FOBS=   58.1 SIGMA=  11.6 PHAS= 285.1 FOM= 0.02
INDE -15  16   3 FOBS=  100.2 SIGMA=   5.8 PHAS=  73.4 FOM= 0.15
INDE -15  16   4 FOBS=   58.3 SIGMA=   9.2 PHAS= 273.6 FOM= 0.20
INDE -15  16   5 FOBS=   76.5 SIGMA=  48.3 PHAS= 103.9 FOM= 0.02
INDE -15  16   6 FOBS=   78.6 SIGMA=   5.8 PHAS= 156.9 FOM= 0.28
INDE -15  16   7 FOBS=  133.7 SIGMA=   3.3 PHAS= 268.5 FOM= 0.88
INDE -15  17   1 FOBS=   48.6 SIGMA=  13.7 PHAS= 197.9 FOM= 0.08
INDE -15  17   2 FOBS=   55.1 SIGMA=  12.0 PHAS=  30.6 FOM= 0.19
INDE -15  17   3 FOBS=  136.5 SIGMA=   4.2 PHAS= 314.7 FOM= 0.33
INDE -15  17   4 FOBS=   39.2 SIGMA=  16.9 PHAS= 184.2 FOM= 0.22
INDE -15  17   5 FOBS=  160.1 SIGMA=   3.3 PHAS=  72.3 FOM= 0.92
INDE -15  18   1 FOBS=   83.7 SIGMA=  49.6 PHAS=  42.1 FOM= 0.08
INDE -15  18   2 FOBS=   52.0 SIGMA=  13.1 PHAS= 273.5 FOM= 0.13
INDE -15  18   3 FOBS=  113.0 SIGMA=   5.2 PHAS=  94.4 FOM= 0.49
INDE -15  18   4 FOBS=  156.4 SIGMA=   3.4 PHAS=  18.4 FOM= 0.83
INDE -15  18   5 FOBS=   45.4 SIGMA=  11.6 PHAS= 157.3 FOM= 0.05
INDE -14   0   2 FOBS=  125.0 SIGMA=   7.3 PHAS=   0.0 FOM= 0.12
INDE -14   0   3 FOBS=  170.6 SIGMA=   5.5 PHAS= 180.0 FOM= 0.07
INDE -14   0   4 FOBS=  240.5 SIGMA=   3.7 PHAS=   0.0 FOM= 0.32
INDE -14   0   5 FOBS=  274.5 SIGMA=   3.1 PHAS= 180.0 FOM= 0.28
INDE -14   0   6 FOBS=   73.9 SIGMA=  10.2 PHAS=   0.0 FOM= 0.12
INDE -14   0   7 FOBS=   67.9 SIGMA=  95.1 PHAS= 180.0 FOM= 0.28
INDE -14   0   8 FOBS=   53.8 SIGMA=  12.3 PHAS=   0.0 FOM= 0.14
INDE -14   0   9 FOBS=   39.8 SIGMA=  29.2 PHAS=   0.0 FOM= 0.02
INDE -14   0  10 FOBS=  266.0 SIGMA=   3.5 PHAS= 180.0 FOM= 1.00
INDE -14   0  11 FOBS=   49.1 SIGMA=  11.3 PHAS=   0.0 FOM= 0.11
INDE -14   0  12 FOBS=  146.3 SIGMA=   4.2 PHAS= 180.0 FOM= 0.02
INDE -14   1   1 FOBS=  126.0 SIGMA=   5.4 PHAS=  64.7 FOM= 0.10
```

Fig. 10A-5

```
INDE -14   1   2 FOBS=   82.6 SIGMA=   7.8 PHAS= 223.2 FOM= 0.02
INDE -14   1   3 FOBS=  142.0 SIGMA=   4.5 PHAS= 294.7 FOM= 0.39
INDE -14   1   4 FOBS=  115.7 SIGMA=   5.3 PHAS= 121.8 FOM= 0.23
INDE -14   1   5 FOBS=   76.5 SIGMA=   7.3 PHAS=   0.4 FOM= 0.22
INDE -14   1   6 FOBS=  189.9 SIGMA=   3.0 PHAS= 210.6 FOM= 0.91
INDE -14   1   7 FOBS=   48.0 SIGMA=  11.8 PHAS= 279.6 FOM= 0.11
INDE -14   1   8 FOBS=  278.3 SIGMA=   2.0 PHAS= 278.0 FOM= 0.96
INDE -14   1   9 FOBS=  159.7 SIGMA=   3.3 PHAS= 113.0 FOM= 0.94
INDE -14   1  10 FOBS=   46.3 SIGMA=  14.2 PHAS= 278.8 FOM= 0.35
INDE -14   1  11 FOBS=   99.1 SIGMA=   4.2 PHAS= 150.4 FOM= 0.38
INDE -14   1  12 FOBS=  198.3 SIGMA=   2.1 PHAS= 336.4 FOM= 0.33
INDE -14   1  13 FOBS=   48.2 SIGMA=   7.7 PHAS= 224.6 FOM= 0.17
INDE -14   2   1 FOBS=   52.9 SIGMA=  13.0 PHAS= 132.6 FOM= 0.13
INDE -14   2   2 FOBS=  177.3 SIGMA=   3.9 PHAS= 120.8 FOM= 0.38
INDE -14   2   3 FOBS=  127.5 SIGMA=   4.9 PHAS= 343.6 FOM= 0.20
INDE -14   2   4 FOBS=  174.9 SIGMA=   3.7 PHAS= 320.0 FOM= 0.08
INDE -14   2   5 FOBS=  132.1 SIGMA=   4.4 PHAS= 338.1 FOM= 0.34
INDE -14   2   6 FOBS=   85.0 SIGMA=   6.3 PHAS=  72.8 FOM= 0.08
INDE -14   2   7 FOBS=  130.0 SIGMA=   4.1 PHAS= 273.3 FOM= 0.06
INDE -14   2   8 FOBS=  304.1 SIGMA=   1.9 PHAS= 317.1 FOM= 0.90
INDE -14   2   9 FOBS=  158.3 SIGMA=   3.2 PHAS= 115.0 FOM= 0.93
INDE -14   2  10 FOBS=   51.5 SIGMA=  10.4 PHAS= 345.9 FOM= 0.25
INDE -14   2  11 FOBS=   77.8 SIGMA=   5.2 PHAS=  77.5 FOM= 0.34
INDE -14   2  12 FOBS=   79.6 SIGMA=   4.8 PHAS= 334.4 FOM= 0.65
INDE -14   2  13 FOBS=   87.9 SIGMA=   4.0 PHAS= 181.2 FOM= 0.68
INDE -14   3   1 FOBS=   99.8 SIGMA=  81.6 PHAS= 211.7 FOM= 0.14
INDE -14   3   2 FOBS=   66.1 SIGMA=  11.4 PHAS= 313.2 FOM= 0.04
INDE -14   3   3 FOBS=  188.7 SIGMA=   3.5 PHAS=  28.4 FOM= 0.77
INDE -14   3   4 FOBS=  250.6 SIGMA=   2.5 PHAS= 120.4 FOM= 0.93
INDE -14   3   5 FOBS=   43.5 SIGMA=  18.1 PHAS=   7.0 FOM= 0.13
INDE -14   3   6 FOBS=   41.4 SIGMA=  15.6 PHAS=  62.1 FOM= 0.09
INDE -14   3   7 FOBS=   77.7 SIGMA=   6.6 PHAS= 251.1 FOM= 0.21
INDE -14   3   8 FOBS=  142.6 SIGMA=   3.8 PHAS=  69.6 FOM= 0.66
INDE -14   3   9 FOBS=   79.8 SIGMA=   6.1 PHAS= 265.0 FOM= 0.30
INDE -14   3  10 FOBS=  220.1 SIGMA=   2.5 PHAS= 309.6 FOM= 0.93
INDE -14   3  11 FOBS=   50.6 SIGMA=  10.5 PHAS= 114.9 FOM= 0.58
INDE -14   3  12 FOBS=  239.9 SIGMA=   1.8 PHAS= 246.6 FOM= 0.69
INDE -14   3  13 FOBS=  173.5 SIGMA=   2.2 PHAS= 147.9 FOM= 0.92
INDE -14   4   1 FOBS=  165.2 SIGMA=   4.2 PHAS= 127.0 FOM= 0.61
INDE -14   4   2 FOBS=   37.5 SIGMA=  15.6 PHAS= 334.9 FOM= 0.20
INDE -14   4   3 FOBS=  303.9 SIGMA=   2.2 PHAS=  58.5 FOM= 0.54
INDE -14   4   4 FOBS=  254.1 SIGMA=   2.5 PHAS= 128.9 FOM= 0.87
INDE -14   4   5 FOBS=   51.9 SIGMA=  13.5 PHAS= 354.7 FOM= 0.36
INDE -14   4   6 FOBS=   60.3 SIGMA=   9.5 PHAS= 178.8 FOM= 0.27
INDE -14   4   7 FOBS=  282.5 SIGMA=   2.0 PHAS=  96.6 FOM= 0.47
INDE -14   4   8 FOBS=  325.0 SIGMA=   1.8 PHAS= 346.5 FOM= 1.00
INDE -14   4   9 FOBS=  206.1 SIGMA=   2.4 PHAS= 201.3 FOM= 0.96
INDE -14   4  10 FOBS=  179.2 SIGMA=   3.0 PHAS=  55.5 FOM= 0.53
INDE -14   4  11 FOBS=   31.2 SIGMA=  19.1 PHAS= 121.6 FOM= 0.14
INDE -14   4  12 FOBS=  207.1 SIGMA=   2.0 PHAS= 279.2 FOM= 0.70
INDE -14   4  13 FOBS=  142.1 SIGMA=   3.5 PHAS= 324.2 FOM= 0.87
INDE -14   5   1 FOBS=  156.7 SIGMA=   4.5 PHAS= 312.7 FOM= 0.55
INDE -14   5   3 FOBS=  287.0 SIGMA=   2.3 PHAS=  58.6 FOM= 0.96
INDE -14   5   4 FOBS=  114.9 SIGMA=   5.5 PHAS= 277.2 FOM= 0.81
INDE -14   5   6 FOBS=  149.3 SIGMA=   3.8 PHAS=  84.0 FOM= 0.82
INDE -14   5   7 FOBS=  235.5 SIGMA=   2.3 PHAS=  57.0 FOM= 0.93
INDE -14   5   8 FOBS=  154.2 SIGMA=   3.4 PHAS= 215.8 FOM= 0.70
INDE -14   5   9 FOBS=  194.6 SIGMA=   2.4 PHAS= 307.7 FOM= 0.36
INDE -14   5  10 FOBS=  194.7 SIGMA=   2.3 PHAS= 107.2 FOM= 0.30
INDE -14   5  11 FOBS=   26.8 SIGMA=  15.6 PHAS=  57.1 FOM= 0.50
INDE -14   5  12 FOBS=   73.8 SIGMA=   5.4 PHAS= 283.8 FOM= 0.48
INDE -14   5  13 FOBS=  225.6 SIGMA=   3.5 PHAS= 130.4 FOM= 0.85
INDE -14   6   1 FOBS=  121.0 SIGMA= 120.2 PHAS= 225.7 FOM= 0.23
INDE -14   6   2 FOBS=   73.5 SIGMA=   8.9 PHAS= 101.3 FOM= 0.33
INDE -14   6   3 FOBS=  121.7 SIGMA=   5.1 PHAS= 225.4 FOM= 0.15
INDE -14   6   4 FOBS=  276.9 SIGMA=   2.3 PHAS= 258.8 FOM= 0.89
INDE -14   6   5 FOBS=  136.1 SIGMA=   4.5 PHAS=  85.6 FOM= 0.91
INDE -14   6   7 FOBS=  163.3 SIGMA=   3.1 PHAS= 140.3 FOM= 0.52
INDE -14   6   8 FOBS=  202.7 SIGMA=   2.5 PHAS= 332.2 FOM= 0.83
INDE -14   6   9 FOBS=  114.2 SIGMA=   4.0 PHAS= 144.3 FOM= 0.76
INDE -14   6  10 FOBS=  133.0 SIGMA=   3.6 PHAS=   5.0 FOM= 0.93
```

Fig. 10A-6

```
INDE -14   6 11 FOBS=  134.3 SIGMA=  3.3 PHAS=  215.1 FOM= 0.38
INDE -14   6 12 FOBS=  115.4 SIGMA=  3.4 PHAS=   99.0 FOM= 0.74
INDE -14   7  1 FOBS=   99.1 SIGMA=  7.6 PHAS=  152.8 FOM= 0.23
INDE -14   7  2 FOBS=   93.0 SIGMA=  6.8 PHAS=   36.2 FOM= 0.45
INDE -14   7  3 FOBS=   74.0 SIGMA=  8.1 PHAS=   36.3 FOM= 0.16
INDE -14   7  4 FOBS=  260.2 SIGMA=  2.3 PHAS=  236.3 FOM= 0.74
INDE -14   7  5 FOBS=  362.6 SIGMA=  1.7 PHAS=  296.4 FOM= 0.94
INDE -14   7  6 FOBS=   40.1 SIGMA= 13.0 PHAS=   21.9 FOM= 0.12
INDE -14   7  7 FOBS=  140.0 SIGMA=  3.8 PHAS=  303.2 FOM= 0.83
INDE -14   7  8 FOBS=  124.7 SIGMA=  4.3 PHAS=  125.6 FOM= 0.87
INDE -14   7  9 FOBS=  213.3 SIGMA=  2.2 PHAS=   61.1 FOM= 0.96
INDE -14   7 10 FOBS=  136.5 SIGMA=  3.2 PHAS=  270.6 FOM= 0.34
INDE -14   7 11 FOBS=  207.1 SIGMA=  2.2 PHAS=   93.4 FOM= 0.97
INDE -14   7 12 FOBS=  154.1 SIGMA=  2.6 PHAS=  274.8 FOM= 0.91
INDE -14   8  1 FOBS=   82.9 SIGMA=  8.5 PHAS=  290.6 FOM= 0.28
INDE -14   8  2 FOBS=   50.5 SIGMA= 25.7 PHAS=   41.7 FOM= 0.17
INDE -14   8  3 FOBS=  306.9 SIGMA=  2.2 PHAS=   33.3 FOM= 0.41
INDE -14   8  4 FOBS=  124.0 SIGMA=  4.6 PHAS=  236.6 FOM= 0.26
INDE -14   8  5 FOBS=  154.7 SIGMA=  3.7 PHAS=  173.7 FOM= 0.80
INDE -14   8  6 FOBS=   64.2 SIGMA=  8.6 PHAS=  257.4 FOM= 0.53
INDE -14   8  7 FOBS=  250.3 SIGMA=  2.2 PHAS=  151.9 FOM= 0.95
INDE -14   8  8 FOBS=  123.5 SIGMA=  3.9 PHAS=   31.2 FOM= 0.23
INDE -14   8  9 FOBS=  130.9 SIGMA=  3.7 PHAS=  301.1 FOM= 0.85
INDE -14   8 10 FOBS=   36.1 SIGMA= 13.2 PHAS=  105.6 FOM= 0.53
INDE -14   8 11 FOBS=  114.3 SIGMA=  3.8 PHAS=    2.0 FOM= 0.28
INDE -14   8 12 FOBS=  139.8 SIGMA=  2.8 PHAS=  166.0 FOM= 0.60
INDE -14   9  1 FOBS=  123.1 SIGMA=  5.6 PHAS=  123.6 FOM= 0.17
INDE -14   9  2 FOBS=  145.7 SIGMA=  4.7 PHAS=   71.4 FOM= 0.57
INDE -14   9  3 FOBS=   74.6 SIGMA=  8.9 PHAS=  233.5 FOM= 0.16
INDE -14   9  4 FOBS=  156.2 SIGMA=  3.8 PHAS=  104.1 FOM= 0.81
INDE -14   9  5 FOBS=   57.6 SIGMA=  9.3 PHAS=  267.3 FOM= 0.18
INDE -14   9  6 FOBS=  129.7 SIGMA=  4.1 PHAS=   67.9 FOM= 0.79
INDE -14   9  7 FOBS=   35.4 SIGMA= 15.6 PHAS=  345.6 FOM= 0.24
INDE -14   9  8 FOBS=  229.8 SIGMA=  2.3 PHAS=  235.2 FOM= 0.97
INDE -14   9  9 FOBS=  192.5 SIGMA=  2.8 PHAS=  119.9 FOM= 0.98
INDE -14   9 10 FOBS=  176.9 SIGMA=  2.4 PHAS=  250.7 FOM= 0.71
INDE -14   9 11 FOBS=  120.0 SIGMA=  3.5 PHAS=  256.8 FOM= 0.45
INDE -14   9 12 FOBS=   52.1 SIGMA=  7.2 PHAS=   29.1 FOM= 0.16
INDE -14  10  1 FOBS=  115.0 SIGMA=  6.0 PHAS=   14.0 FOM= 0.22
INDE -14  10  2 FOBS=  294.8 SIGMA=  2.3 PHAS=   30.8 FOM= 0.85
INDE -14  10  3 FOBS=   54.4 SIGMA= 14.5 PHAS=  294.3 FOM= 0.11
INDE -14  10  4 FOBS=   90.3 SIGMA=  6.6 PHAS=  338.8 FOM= 0.11
INDE -14  10  5 FOBS=   91.8 SIGMA=  5.8 PHAS=  161.4 FOM= 0.57
INDE -14  10  6 FOBS=   69.1 SIGMA=  7.3 PHAS=  282.2 FOM= 0.38
INDE -14  10  7 FOBS=   64.7 SIGMA=  7.3 PHAS=  198.1 FOM= 0.10
INDE -14  10  8 FOBS=   62.5 SIGMA=  7.0 PHAS=   68.1 FOM= 0.15
INDE -14  10  9 FOBS=  323.6 SIGMA=  1.9 PHAS=  286.4 FOM= 0.82
INDE -14  10 10 FOBS=  157.8 SIGMA=  2.7 PHAS=  230.7 FOM= 0.78
INDE -14  10 11 FOBS=  167.4 SIGMA=  2.3 PHAS=  320.5 FOM= 0.43
INDE -14  10 12 FOBS=  182.1 SIGMA=  3.6 PHAS=  108.7 FOM= 0.76
INDE -14  11  1 FOBS=   88.9 SIGMA=  7.5 PHAS=  114.6 FOM= 0.23
INDE -14  11  2 FOBS=   64.7 SIGMA=  9.7 PHAS=  349.9 FOM= 0.09
INDE -14  11  3 FOBS=  166.0 SIGMA=  3.9 PHAS=  302.7 FOM= 0.74
INDE -14  11  4 FOBS=   99.2 SIGMA=  6.6 PHAS=   88.4 FOM= 0.43
INDE -14  11  5 FOBS=   86.5 SIGMA=  6.3 PHAS=  325.9 FOM= 0.29
INDE -14  11  6 FOBS=  163.5 SIGMA=  3.0 PHAS=   25.0 FOM= 0.84
INDE -14  11  7 FOBS=  162.8 SIGMA=  3.0 PHAS=   55.9 FOM= 0.50
INDE -14  11  8 FOBS=  124.3 SIGMA=  3.6 PHAS=   13.4 FOM= 0.14
INDE -14  11  9 FOBS=  258.1 SIGMA=  2.2 PHAS=  180.3 FOM= 0.93
INDE -14  11 10 FOBS=   42.8 SIGMA=  9.6 PHAS=  355.7 FOM= 0.16
INDE -14  11 11 FOBS=   73.2 SIGMA=  5.2 PHAS=   16.5 FOM= 0.28
INDE -14  12  1 FOBS=   45.3 SIGMA= 24.6 PHAS=  297.5 FOM= 0.05
INDE -14  12  2 FOBS=   80.2 SIGMA=  8.2 PHAS=  233.4 FOM= 0.26
INDE -14  12  3 FOBS=  140.2 SIGMA=  4.4 PHAS=  117.5 FOM= 0.39
INDE -14  12  4 FOBS=  147.4 SIGMA=  4.1 PHAS=  255.7 FOM= 0.11
INDE -14  12  6 FOBS=  155.4 SIGMA=  3.4 PHAS=   42.0 FOM= 0.11
INDE -14  12  7 FOBS=   28.0 SIGMA= 15.4 PHAS=  123.3 FOM= 0.34
INDE -14  12  8 FOBS=   99.2 SIGMA=  4.3 PHAS=  357.4 FOM= 0.08
INDE -14  12  9 FOBS=  173.8 SIGMA=  3.0 PHAS=  277.3 FOM= 0.92
INDE -14  12 10 FOBS=  118.3 SIGMA=  3.3 PHAS=  113.1 FOM= 0.36
INDE -14  12 11 FOBS=  130.3 SIGMA=  3.0 PHAS=  345.9 FOM= 0.84
```

Fig. 10A-7

```
INDE -14  13   1 FOBS=  127.6 SIGMA=   5.4 PHAS=  308.3 FOM= 0.14
INDE -14  13   2 FOBS=   64.6 SIGMA=  11.0 PHAS=   31.0 FOM= 0.03
INDE -14  13   3 FOBS=  183.3 SIGMA=   3.3 PHAS=  145.1 FOM= 0.87
INDE -14  13   4 FOBS=   94.3 SIGMA=   6.2 PHAS=  271.9 FOM= 0.52
INDE -14  13   5 FOBS=   40.2 SIGMA=  19.0 PHAS=   55.2 FOM= 0.08
INDE -14  13   6 FOBS=  117.6 SIGMA=   4.6 PHAS=   67.7 FOM= 0.15
INDE -14  13   7 FOBS=  129.7 SIGMA=   3.7 PHAS=   15.3 FOM= 0.05
INDE -14  13   8 FOBS=   61.6 SIGMA=   6.7 PHAS=  305.1 FOM= 0.11
INDE -14  13   9 FOBS=   49.8 SIGMA=   8.5 PHAS=  175.8 FOM= 0.05
INDE -14  13  10 FOBS=   68.0 SIGMA=   5.4 PHAS=   24.3 FOM= 0.19
INDE -14  13  11 FOBS=   95.7 SIGMA=   6.1 PHAS=  203.8 FOM= 0.62
INDE -14  14   1 FOBS=  103.7 SIGMA=  94.8 PHAS=  230.5 FOM= 0.11
INDE -14  14   2 FOBS=  109.6 SIGMA=   5.7 PHAS=  126.3 FOM= 0.26
INDE -14  14   3 FOBS=   94.3 SIGMA=   6.1 PHAS=  153.1 FOM= 0.09
INDE -14  14   4 FOBS=  108.2 SIGMA=   5.1 PHAS=  191.1 FOM= 0.67
INDE -14  14   5 FOBS=   90.4 SIGMA=   5.7 PHAS=  102.1 FOM= 0.44
INDE -14  14   6 FOBS=  221.8 SIGMA=   2.2 PHAS=  213.9 FOM= 0.69
INDE -14  14   7 FOBS=   94.9 SIGMA=   5.2 PHAS=  351.3 FOM= 0.70
INDE -14  14   8 FOBS=  108.6 SIGMA=   4.1 PHAS=  104.4 FOM= 0.64
INDE -14  14   9 FOBS=   78.6 SIGMA=   4.6 PHAS=   75.5 FOM= 0.10
INDE -14  14  10 FOBS=   91.9 SIGMA=   3.9 PHAS=  325.7 FOM= 0.17
INDE -14  15   1 FOBS=   58.2 SIGMA=  12.2 PHAS=   78.6 FOM= 0.10
INDE -14  15   2 FOBS=  134.7 SIGMA=   5.1 PHAS=    8.9 FOM= 0.16
INDE -14  15   3 FOBS=   49.4 SIGMA=  29.1 PHAS=  165.2 FOM= 0.15
INDE -14  15   4 FOBS=  187.6 SIGMA=   3.1 PHAS=  355.9 FOM= 0.85
INDE -14  15   5 FOBS=   79.8 SIGMA=   6.1 PHAS=   74.3 FOM= 0.26
INDE -14  15   6 FOBS=   72.9 SIGMA=   6.1 PHAS=  248.5 FOM= 0.02
INDE -14  15   7 FOBS=  122.5 SIGMA=   3.6 PHAS=  357.4 FOM= 0.91
INDE -14  15   8 FOBS=  172.4 SIGMA=   2.9 PHAS=  211.8 FOM= 0.95
INDE -14  15   9 FOBS=  150.2 SIGMA=   3.7 PHAS=  274.1 FOM= 0.64
INDE -14  15  10 FOBS=  106.1 SIGMA=   3.0 PHAS=  244.1 FOM= 0.45
INDE -14  16   1 FOBS=  126.9 SIGMA=   4.9 PHAS=  196.3 FOM= 0.59
INDE -14  16   2 FOBS=   81.3 SIGMA=   8.2 PHAS=   44.4 FOM= 0.12
INDE -14  16   3 FOBS=   38.4 SIGMA=  16.2 PHAS=  294.5 FOM= 0.01
INDE -14  16   4 FOBS=   99.9 SIGMA=   5.2 PHAS=  234.0 FOM= 0.11
INDE -14  16   5 FOBS=   81.9 SIGMA=   6.1 PHAS=  119.7 FOM= 0.43
INDE -14  16   6 FOBS=  156.0 SIGMA=   2.9 PHAS=  288.8 FOM= 0.91
INDE -14  16   7 FOBS=   85.5 SIGMA=   4.6 PHAS=   59.7 FOM= 0.43
INDE -14  16   8 FOBS=   51.9 SIGMA=   8.3 PHAS=  238.7 FOM= 0.19
INDE -14  16   9 FOBS=   89.8 SIGMA=   3.9 PHAS=   64.9 FOM= 0.49
INDE -14  17   1 FOBS=   51.2 SIGMA=  11.8 PHAS=  120.3 FOM= 0.49
INDE -14  17   2 FOBS=  103.5 SIGMA=   5.6 PHAS=    1.4 FOM= 0.67
INDE -14  17   3 FOBS=   64.0 SIGMA=  10.5 PHAS=  182.8 FOM= 0.46
INDE -14  17   4 FOBS=   79.3 SIGMA=   6.5 PHAS=   16.8 FOM= 0.24
INDE -14  17   5 FOBS=   48.7 SIGMA=  22.6 PHAS=  240.5 FOM= 0.05
INDE -14  17   6 FOBS=   56.1 SIGMA=   8.0 PHAS=  147.8 FOM= 0.03
INDE -14  17   7 FOBS=  160.1 SIGMA=   2.5 PHAS=  144.1 FOM= 0.77
INDE -14  17   8 FOBS=  136.5 SIGMA=   4.5 PHAS=  261.3 FOM= 0.81
INDE -14  17   9 FOBS=   75.2 SIGMA=  34.9 PHAS=   42.8 FOM= 0.01
INDE -14  18   1 FOBS=   86.8 SIGMA=   6.5 PHAS=  251.8 FOM= 0.19
INDE -14  18   2 FOBS=  106.0 SIGMA=   5.2 PHAS=  168.3 FOM= 0.35
INDE -14  18   3 FOBS=   77.1 SIGMA=   6.6 PHAS=  220.2 FOM= 0.19
INDE -14  18   4 FOBS=  117.9 SIGMA=   4.6 PHAS=  343.1 FOM= 0.17
INDE -14  18   5 FOBS=   95.8 SIGMA=   4.8 PHAS=  148.8 FOM= 0.63
INDE -14  18   6 FOBS=   62.4 SIGMA=   5.9 PHAS=    9.5 FOM= 0.47
INDE -14  18   7 FOBS=  139.2 SIGMA=   2.6 PHAS=  204.9 FOM= 0.78
INDE -14  18   8 FOBS=   91.7 SIGMA=   7.3 PHAS=  161.3 FOM= 0.22
INDE -14  19   1 FOBS=  148.5 SIGMA=  98.5 PHAS=   59.4 FOM= 0.05
INDE -14  19   2 FOBS=   53.2 SIGMA=  10.4 PHAS=   56.0 FOM= 0.04
INDE -14  19   3 FOBS=   79.7 SIGMA=   7.0 PHAS=  219.4 FOM= 0.49
INDE -14  19   4 FOBS=   68.1 SIGMA=   7.3 PHAS=  109.1 FOM= 0.25
INDE -14  19   5 FOBS=   35.0 SIGMA=  14.9 PHAS=  347.0 FOM= 0.08
INDE -14  19   6 FOBS=   85.5 SIGMA=   4.2 PHAS=  312.1 FOM= 0.85
INDE -14  19   7 FOBS=  109.3 SIGMA=   3.0 PHAS=   12.6 FOM= 0.82
INDE -14  20   1 FOBS=   67.4 SIGMA=  26.5 PHAS=    0.4 FOM= 0.13
INDE -14  20   2 FOBS=   54.4 SIGMA=  17.2 PHAS=  187.7 FOM= 0.28
INDE -14  20   3 FOBS=   56.4 SIGMA=   9.0 PHAS=   30.9 FOM= 0.04
INDE -14  20   4 FOBS=  118.9 SIGMA=   4.0 PHAS=  240.8 FOM= 0.18
INDE -14  20   5 FOBS=   73.7 SIGMA=   6.0 PHAS=  359.0 FOM= 0.54
INDE -14  20   6 FOBS=   83.2 SIGMA=   5.6 PHAS=  257.1 FOM= 0.58
INDE -14  21   1 FOBS=   83.5 SIGMA=  21.7 PHAS=  231.7 FOM= 0.06
```

Fig. 10A-8

```
INDE -14  21   3 FOBS=    55.0 SIGMA=  11.7 PHAS=  342.9 FOM= 0.14
INDE -14  21   4 FOBS=    46.7 SIGMA=  22.6 PHAS=  160.8 FOM= 0.17
INDE -13   0   1 FOBS=   481.6 SIGMA=   2.6 PHAS=  180.0 FOM= 0.67
INDE -13   0   2 FOBS=   193.5 SIGMA=   4.7 PHAS=    0.0 FOM= 0.87
INDE -13   0   3 FOBS=   164.1 SIGMA=   5.5 PHAS=    0.0 FOM= 0.53
INDE -13   0   4 FOBS=   111.4 SIGMA=   6.9 PHAS=    0.0 FOM= 0.56
INDE -13   0   5 FOBS=   103.6 SIGMA=   7.5 PHAS=  180.0 FOM= 0.19
INDE -13   0   6 FOBS=   307.0 SIGMA=   2.7 PHAS=    0.0 FOM= 0.48
INDE -13   0   7 FOBS=   371.0 SIGMA=   2.3 PHAS=    0.0 FOM= 0.05
INDE -13   0   8 FOBS=    69.6 SIGMA=   9.5 PHAS=  180.0 FOM= 0.09
INDE -13   0   9 FOBS=   130.5 SIGMA=   5.1 PHAS=  180.0 FOM= 0.10
INDE -13   0  10 FOBS=   159.2 SIGMA=   4.4 PHAS=    0.0 FOM= 0.99
INDE -13   0  11 FOBS=   117.0 SIGMA=   5.4 PHAS=  180.0 FOM= 0.96
INDE -13   0  13 FOBS=   163.7 SIGMA=   3.1 PHAS=  180.0 FOM= 0.80
INDE -13   0  14 FOBS=    69.0 SIGMA=   8.1 PHAS=  180.0 FOM= 0.67
INDE -13   1   1 FOBS=   165.5 SIGMA=   4.1 PHAS=  101.0 FOM= 0.09
INDE -13   1   2 FOBS=   115.1 SIGMA=   5.5 PHAS=    8.0 FOM= 0.43
INDE -13   1   3 FOBS=   101.2 SIGMA=   5.9 PHAS=  125.9 FOM= 0.44
INDE -13   1   4 FOBS=   286.1 SIGMA=   2.1 PHAS=  331.8 FOM= 0.73
INDE -13   1   5 FOBS=   207.1 SIGMA=   2.8 PHAS=  114.9 FOM= 0.76
INDE -13   1   6 FOBS=   232.6 SIGMA=   2.4 PHAS=  346.5 FOM= 0.61
INDE -13   1   7 FOBS=   152.9 SIGMA=   3.5 PHAS=  202.5 FOM= 0.45
INDE -13   1   8 FOBS=   384.8 SIGMA=   1.6 PHAS=  155.6 FOM= 0.90
INDE -13   1   9 FOBS=    57.8 SIGMA=   7.9 PHAS=  325.0 FOM= 0.47
INDE -13   1  10 FOBS=   169.6 SIGMA=   2.5 PHAS=  299.6 FOM= 0.88
INDE -13   1  11 FOBS=   401.1 SIGMA=   1.3 PHAS=  226.0 FOM= 0.61
INDE -13   1  12 FOBS=   143.1 SIGMA=   2.9 PHAS=  274.4 FOM= 0.90
INDE -13   1  13 FOBS=   142.4 SIGMA=   2.7 PHAS=  183.6 FOM= 0.89
INDE -13   1  14 FOBS=   171.3 SIGMA=   2.2 PHAS=  352.6 FOM= 0.46
INDE -13   2   1 FOBS=   100.1 SIGMA=   6.5 PHAS=  330.4 FOM= 0.14
INDE -13   2   2 FOBS=    68.8 SIGMA=   9.0 PHAS=  280.8 FOM= 0.09
INDE -13   2   3 FOBS=   223.8 SIGMA=   2.8 PHAS=  199.6 FOM= 0.93
INDE -13   2   4 FOBS=   150.5 SIGMA=   4.4 PHAS=  263.4 FOM= 0.70
INDE -13   2   5 FOBS=   102.5 SIGMA=   5.6 PHAS=   29.6 FOM= 0.47
INDE -13   2   6 FOBS=   121.4 SIGMA=   4.8 PHAS=  178.0 FOM= 0.84
INDE -13   2   7 FOBS=    99.3 SIGMA=   5.1 PHAS=  283.1 FOM= 0.54
INDE -13   2   8 FOBS=   219.9 SIGMA=   2.4 PHAS=   70.6 FOM= 0.95
INDE -13   2   9 FOBS=   207.6 SIGMA=   2.3 PHAS=  221.8 FOM= 0.96
INDE -13   2  10 FOBS=   154.5 SIGMA=   3.3 PHAS=   95.7 FOM= 0.87
INDE -13   2  11 FOBS=   309.9 SIGMA=   1.5 PHAS=  241.6 FOM= 0.62
INDE -13   2  12 FOBS=    67.0 SIGMA=   5.9 PHAS=  333.7 FOM= 0.39
INDE -13   2  13 FOBS=   188.7 SIGMA=   2.0 PHAS=  339.6 FOM= 0.94
INDE -13   2  14 FOBS=   228.3 SIGMA=   1.8 PHAS=   81.1 FOM= 0.96
INDE -13   3   2 FOBS=   142.7 SIGMA=   4.5 PHAS=   62.0 FOM= 0.23
INDE -13   3   3 FOBS=   252.1 SIGMA=   2.5 PHAS=  344.2 FOM= 0.23
INDE -13   3   4 FOBS=   278.6 SIGMA=   2.2 PHAS=  195.1 FOM= 0.90
INDE -13   3   5 FOBS=   354.0 SIGMA=   1.8 PHAS=  314.6 FOM= 0.96
INDE -13   3   6 FOBS=   323.7 SIGMA=   1.9 PHAS=  256.7 FOM= 0.94
INDE -13   3   7 FOBS=   109.5 SIGMA=   4.7 PHAS=  332.2 FOM= 0.54
INDE -13   3   8 FOBS=   164.3 SIGMA=   3.0 PHAS=  198.0 FOM= 0.89
INDE -13   3   9 FOBS=    66.3 SIGMA=   6.9 PHAS=  283.2 FOM= 0.42
INDE -13   3  10 FOBS=    54.5 SIGMA=   8.6 PHAS=   51.8 FOM= 0.31
INDE -13   3  11 FOBS=    67.4 SIGMA=   5.9 PHAS=  119.2 FOM= 0.27
INDE -13   3  12 FOBS=   156.8 SIGMA=   2.5 PHAS=  273.0 FOM= 0.19
INDE -13   3  13 FOBS=   236.6 SIGMA=   1.7 PHAS=  135.3 FOM= 0.85
INDE -13   3  14 FOBS=   192.5 SIGMA=   3.3 PHAS=   14.6 FOM= 0.89
INDE -13   4   1 FOBS=   182.8 SIGMA=   3.7 PHAS=  354.0 FOM= 0.38
INDE -13   4   2 FOBS=   156.7 SIGMA=   4.2 PHAS=  134.2 FOM= 0.14
INDE -13   4   3 FOBS=   240.4 SIGMA=   2.6 PHAS=  238.8 FOM= 0.92
INDE -13   4   4 FOBS=   203.0 SIGMA=   3.0 PHAS=  332.8 FOM= 0.75
INDE -13   4   5 FOBS=    46.3 SIGMA=  12.7 PHAS=  169.7 FOM= 0.19
INDE -13   4   6 FOBS=   181.3 SIGMA=   3.0 PHAS=  300.6 FOM= 0.27
INDE -13   4   7 FOBS=   144.0 SIGMA=   3.7 PHAS=   63.0 FOM= 0.77
INDE -13   4   8 FOBS=   203.2 SIGMA=   2.5 PHAS=  235.1 FOM= 0.97
INDE -13   4   9 FOBS=   168.7 SIGMA=   3.0 PHAS=  227.2 FOM= 0.93
INDE -13   4  10 FOBS=   207.2 SIGMA=   2.4 PHAS=  287.6 FOM= 0.73
INDE -13   4  11 FOBS=   251.3 SIGMA=   1.8 PHAS=  265.8 FOM= 0.95
INDE -13   4  12 FOBS=   243.4 SIGMA=   1.7 PHAS=   44.3 FOM= 0.41
INDE -13   4  13 FOBS=   143.8 SIGMA=   2.7 PHAS=   89.0 FOM= 0.73
INDE -13   4  14 FOBS=   178.1 SIGMA=   5.1 PHAS=  138.7 FOM= 0.30
INDE -13   5   1 FOBS=   137.4 SIGMA=   4.9 PHAS=   21.8 FOM= 0.49
```

Fig. 10A-9

| | | | | | | | | | | |
|---|---|---|---|---|---|---|---|---|---|---|
| INDE | -13 | 5 | 2 | FOBS= | 151.2 | SIGMA= | 4.3 | PHAS= | 149.7 | FOM= | 0.14 |
| INDE | -13 | 5 | 3 | FOBS= | 118.8 | SIGMA= | 5.0 | PHAS= | 59.8 | FOM= | 0.10 |
| INDE | -13 | 5 | 4 | FOBS= | 144.0 | SIGMA= | 4.1 | PHAS= | 239.1 | FOM= | 0.09 |
| INDE | -13 | 5 | 5 | FOBS= | 94.0 | SIGMA= | 5.8 | PHAS= | 46.6 | FOM= | 0.15 |
| INDE | -13 | 5 | 6 | FOBS= | 132.8 | SIGMA= | 4.0 | PHAS= | 232.4 | FOM= | 0.11 |
| INDE | -13 | 5 | 7 | FOBS= | 191.0 | SIGMA= | 2.8 | PHAS= | 164.2 | FOM= | 0.90 |
| INDE | -13 | 5 | 8 | FOBS= | 154.0 | SIGMA= | 3.1 | PHAS= | 26.6 | FOM= | 0.15 |
| INDE | -13 | 5 | 9 | FOBS= | 187.1 | SIGMA= | 2.9 | PHAS= | 211.0 | FOM= | 0.87 |
| INDE | -13 | 5 | 10 | FOBS= | 188.0 | SIGMA= | 2.6 | PHAS= | 37.0 | FOM= | 0.93 |
| INDE | -13 | 5 | 11 | FOBS= | 75.2 | SIGMA= | 5.4 | PHAS= | 237.8 | FOM= | 0.50 |
| INDE | -13 | 5 | 12 | FOBS= | 108.9 | SIGMA= | 3.6 | PHAS= | 286.9 | FOM= | 0.89 |
| INDE | -13 | 5 | 13 | FOBS= | 136.5 | SIGMA= | 2.8 | PHAS= | 50.9 | FOM= | 0.87 |
| INDE | -13 | 6 | 1 | FOBS= | 108.8 | SIGMA= | 6.1 | PHAS= | 262.7 | FOM= | 0.43 |
| INDE | -13 | 6 | 2 | FOBS= | 111.6 | SIGMA= | 5.6 | PHAS= | 1.6 | FOM= | 0.36 |
| INDE | -13 | 6 | 3 | FOBS= | 182.7 | SIGMA= | 3.5 | PHAS= | 217.1 | FOM= | 0.90 |
| INDE | -13 | 6 | 4 | FOBS= | 289.4 | SIGMA= | 2.1 | PHAS= | 339.2 | FOM= | 0.97 |
| INDE | -13 | 6 | 5 | FOBS= | 147.7 | SIGMA= | 3.9 | PHAS= | 313.7 | FOM= | 0.87 |
| INDE | -13 | 6 | 6 | FOBS= | 189.7 | SIGMA= | 2.8 | PHAS= | 26.6 | FOM= | 0.83 |
| INDE | -13 | 6 | 7 | FOBS= | 205.2 | SIGMA= | 2.6 | PHAS= | 71.4 | FOM= | 0.96 |
| INDE | -13 | 6 | 8 | FOBS= | 153.1 | SIGMA= | 3.3 | PHAS= | 280.9 | FOM= | 0.90 |
| INDE | -13 | 6 | 9 | FOBS= | 98.5 | SIGMA= | 5.4 | PHAS= | 88.7 | FOM= | 0.46 |
| INDE | -13 | 6 | 10 | FOBS= | 240.0 | SIGMA= | 2.1 | PHAS= | 108.6 | FOM= | 0.12 |
| INDE | -13 | 6 | 11 | FOBS= | 166.8 | SIGMA= | 2.6 | PHAS= | 267.3 | FOM= | 0.96 |
| INDE | -13 | 6 | 12 | FOBS= | 209.7 | SIGMA= | 1.9 | PHAS= | 38.1 | FOM= | 1.00 |
| INDE | -13 | 6 | 13 | FOBS= | 222.2 | SIGMA= | 1.8 | PHAS= | 185.0 | FOM= | 0.97 |
| INDE | -13 | 7 | 1 | FOBS= | 153.2 | SIGMA= | 5.0 | PHAS= | 280.0 | FOM= | 0.51 |
| INDE | -13 | 7 | 2 | FOBS= | 81.3 | SIGMA= | 7.4 | PHAS= | 103.2 | FOM= | 0.28 |
| INDE | -13 | 7 | 3 | FOBS= | 163.9 | SIGMA= | 3.9 | PHAS= | 257.6 | FOM= | 0.85 |
| INDE | -13 | 7 | 4 | FOBS= | 76.6 | SIGMA= | 7.2 | PHAS= | 310.9 | FOM= | 0.24 |
| INDE | -13 | 7 | 5 | FOBS= | 40.7 | SIGMA= | 16.2 | PHAS= | 134.3 | FOM= | 0.34 |
| INDE | -13 | 7 | 6 | FOBS= | 269.8 | SIGMA= | 2.1 | PHAS= | 40.1 | FOM= | 0.96 |
| INDE | -13 | 7 | 7 | FOBS= | 230.0 | SIGMA= | 2.3 | PHAS= | 214.0 | FOM= | 0.31 |
| INDE | -13 | 7 | 8 | FOBS= | 167.0 | SIGMA= | 2.9 | PHAS= | 93.9 | FOM= | 0.66 |
| INDE | -13 | 7 | 9 | FOBS= | 145.8 | SIGMA= | 3.6 | PHAS= | 352.1 | FOM= | 0.20 |
| INDE | -13 | 7 | 10 | FOBS= | 59.2 | SIGMA= | 7.8 | PHAS= | 106.5 | FOM= | 0.16 |
| INDE | -13 | 7 | 11 | FOBS= | 115.1 | SIGMA= | 3.5 | PHAS= | 316.0 | FOM= | 0.53 |
| INDE | -13 | 7 | 12 | FOBS= | 56.8 | SIGMA= | 6.4 | PHAS= | 78.9 | FOM= | 0.12 |
| INDE | -13 | 7 | 13 | FOBS= | 131.2 | SIGMA= | 3.0 | PHAS= | 188.8 | FOM= | 0.81 |
| INDE | -13 | 8 | 1 | FOBS= | 62.9 | SIGMA= | 14.2 | PHAS= | 125.0 | FOM= | 0.13 |
| INDE | -13 | 8 | 2 | FOBS= | 211.0 | SIGMA= | 3.6 | PHAS= | 332.6 | FOM= | 0.71 |
| INDE | -13 | 8 | 3 | FOBS= | 97.1 | SIGMA= | 6.2 | PHAS= | 230.6 | FOM= | 0.68 |
| INDE | -13 | 8 | 4 | FOBS= | 168.7 | SIGMA= | 2.6 | PHAS= | 79.7 | FOM= | 0.96 |
| INDE | -13 | 8 | 5 | FOBS= | 135.6 | SIGMA= | 3.9 | PHAS= | 66.2 | FOM= | 0.42 |
| INDE | -13 | 8 | 6 | FOBS= | 172.6 | SIGMA= | 3.0 | PHAS= | 313.3 | FOM= | 0.60 |
| INDE | -13 | 8 | 7 | FOBS= | 86.5 | SIGMA= | 5.6 | PHAS= | 133.1 | FOM= | 0.48 |
| INDE | -13 | 8 | 8 | FOBS= | 165.6 | SIGMA= | 2.9 | PHAS= | 336.4 | FOM= | 0.80 |
| INDE | -13 | 8 | 9 | FOBS= | 119.2 | SIGMA= | 4.3 | PHAS= | 55.0 | FOM= | 0.36 |
| INDE | -13 | 8 | 10 | FOBS= | 236.6 | SIGMA= | 2.1 | PHAS= | 274.7 | FOM= | 0.90 |
| INDE | -13 | 8 | 11 | FOBS= | 129.2 | SIGMA= | 3.1 | PHAS= | 272.7 | FOM= | 0.56 |
| INDE | -13 | 8 | 12 | FOBS= | 170.3 | SIGMA= | 2.2 | PHAS= | 142.0 | FOM= | 0.16 |
| INDE | -13 | 8 | 13 | FOBS= | 88.9 | SIGMA= | 4.0 | PHAS= | 64.5 | FOM= | 0.68 |
| INDE | -13 | 9 | 1 | FOBS= | 196.2 | SIGMA= | 3.6 | PHAS= | 325.2 | FOM= | 0.86 |
| INDE | -13 | 9 | 2 | FOBS= | 105.1 | SIGMA= | 6.2 | PHAS= | 244.1 | FOM= | 0.55 |
| INDE | -13 | 9 | 3 | FOBS= | 114.3 | SIGMA= | 6.2 | PHAS= | 55.2 | FOM= | 0.56 |
| INDE | -13 | 9 | 4 | FOBS= | 184.0 | SIGMA= | 3.1 | PHAS= | 172.5 | FOM= | 0.05 |
| INDE | -13 | 9 | 5 | FOBS= | 181.3 | SIGMA= | 3.0 | PHAS= | 180.1 | FOM= | 0.44 |
| INDE | -13 | 9 | 6 | FOBS= | 124.6 | SIGMA= | 4.3 | PHAS= | 8.6 | FOM= | 0.87 |
| INDE | -13 | 9 | 7 | FOBS= | 67.3 | SIGMA= | 7.2 | PHAS= | 168.5 | FOM= | 0.37 |
| INDE | -13 | 9 | 8 | FOBS= | 255.7 | SIGMA= | 1.9 | PHAS= | 115.2 | FOM= | 0.44 |
| INDE | -13 | 9 | 9 | FOBS= | 68.4 | SIGMA= | 6.1 | PHAS= | 104.3 | FOM= | 0.20 |
| INDE | -13 | 9 | 10 | FOBS= | 224.5 | SIGMA= | 2.1 | PHAS= | 205.4 | FOM= | 0.95 |
| INDE | -13 | 9 | 11 | FOBS= | 43.9 | SIGMA= | 9.1 | PHAS= | 60.6 | FOM= | 0.13 |
| INDE | -13 | 9 | 12 | FOBS= | 179.8 | SIGMA= | 2.1 | PHAS= | 221.0 | FOM= | 0.96 |
| INDE | -13 | 9 | 13 | FOBS= | 48.4 | SIGMA= | 7.2 | PHAS= | 174.2 | FOM= | 0.14 |
| INDE | -13 | 10 | 1 | FOBS= | 96.0 | SIGMA= | 6.9 | PHAS= | 201.2 | FOM= | 0.21 |
| INDE | -13 | 10 | 2 | FOBS= | 254.7 | SIGMA= | 2.6 | PHAS= | 6.3 | FOM= | 0.73 |
| INDE | -13 | 10 | 3 | FOBS= | 115.0 | SIGMA= | 5.5 | PHAS= | 293.4 | FOM= | 0.15 |
| INDE | -13 | 10 | 4 | FOBS= | 49.7 | SIGMA= | 12.2 | PHAS= | 185.4 | FOM= | 0.19 |
| INDE | -13 | 10 | 5 | FOBS= | 271.6 | SIGMA= | 2.1 | PHAS= | 123.1 | FOM= | 0.92 |
| INDE | -13 | 10 | 6 | FOBS= | 139.1 | SIGMA= | 3.6 | PHAS= | 165.0 | FOM= | 0.22 |
| INDE | -13 | 10 | 7 | FOBS= | 108.4 | SIGMA= | 4.3 | PHAS= | 173.4 | FOM= | 0.24 |

Fig. 10A-10

| | | | | | | | | | | | |
|---|---|---|---|---|---|---|---|---|---|---|---|
| INDE | -13 | 10 | 8 | FOBS= | 193.4 | SIGMA= | 2.4 | PHAS= | 18.7 | FOM= | 0.92 |
| INDE | -13 | 10 | 9 | FOBS= | 83.6 | SIGMA= | 4.9 | PHAS= | 167.5 | FOM= | 0.44 |
| INDE | -13 | 10 | 10 | FOBS= | 112.0 | SIGMA= | 3.8 | PHAS= | 126.5 | FOM= | 0.82 |
| INDE | -13 | 10 | 11 | FOBS= | 77.7 | SIGMA= | 5.3 | PHAS= | 237.0 | FOM= | 0.90 |
| INDE | -13 | 10 | 12 | FOBS= | 124.7 | SIGMA= | 3.1 | PHAS= | 146.5 | FOM= | 0.55 |
| INDE | -13 | 10 | 13 | FOBS= | 116.0 | SIGMA= | 5.2 | PHAS= | 60.2 | FOM= | 0.60 |
| INDE | -13 | 11 | 1 | FOBS= | 147.1 | SIGMA= | 4.9 | PHAS= | 65.0 | FOM= | 0.64 |
| INDE | -13 | 11 | 2 | FOBS= | 93.4 | SIGMA= | 6.8 | PHAS= | 187.4 | FOM= | 0.22 |
| INDE | -13 | 11 | 3 | FOBS= | 131.0 | SIGMA= | 4.7 | PHAS= | 264.9 | FOM= | 0.17 |
| INDE | -13 | 11 | 4 | FOBS= | 59.7 | SIGMA= | 11.9 | PHAS= | 338.7 | FOM= | 0.08 |
| INDE | -13 | 11 | 5 | FOBS= | 126.8 | SIGMA= | 4.4 | PHAS= | 66.3 | FOM= | 0.33 |
| INDE | -13 | 11 | 6 | FOBS= | 59.6 | SIGMA= | 21.5 | PHAS= | 69.5 | FOM= | 0.13 |
| INDE | -13 | 11 | 7 | FOBS= | 142.2 | SIGMA= | 3.3 | PHAS= | 324.3 | FOM= | 0.86 |
| INDE | -13 | 11 | 8 | FOBS= | 177.8 | SIGMA= | 2.7 | PHAS= | 145.3 | FOM= | 0.95 |
| INDE | -13 | 11 | 9 | FOBS= | 236.5 | SIGMA= | 1.8 | PHAS= | 134.8 | FOM= | 0.89 |
| INDE | -13 | 11 | 10 | FOBS= | 174.6 | SIGMA= | 2.3 | PHAS= | 16.8 | FOM= | 0.94 |
| INDE | -13 | 11 | 11 | FOBS= | 55.0 | SIGMA= | 6.6 | PHAS= | 147.4 | FOM= | 0.40 |
| INDE | -13 | 11 | 12 | FOBS= | 30.9 | SIGMA= | 15.5 | PHAS= | 4.1 | FOM= | 0.16 |
| INDE | -13 | 12 | 1 | FOBS= | 142.7 | SIGMA= | 5.4 | PHAS= | 52.9 | FOM= | 0.25 |
| INDE | -13 | 12 | 2 | FOBS= | 201.7 | SIGMA= | 3.2 | PHAS= | 254.6 | FOM= | 0.40 |
| INDE | -13 | 12 | 3 | FOBS= | 320.3 | SIGMA= | 1.9 | PHAS= | 38.9 | FOM= | 0.92 |
| INDE | -13 | 12 | 4 | FOBS= | 185.2 | SIGMA= | 3.0 | PHAS= | 217.4 | FOM= | 0.33 |
| INDE | -13 | 12 | 5 | FOBS= | 104.3 | SIGMA= | 5.5 | PHAS= | 180.3 | FOM= | 0.25 |
| INDE | -13 | 12 | 6 | FOBS= | 66.9 | SIGMA= | 7.6 | PHAS= | 270.8 | FOM= | 0.26 |
| INDE | -13 | 12 | 7 | FOBS= | 135.9 | SIGMA= | 3.3 | PHAS= | 173.3 | FOM= | 0.55 |
| INDE | -13 | 12 | 8 | FOBS= | 240.4 | SIGMA= | 2.3 | PHAS= | 95.0 | FOM= | 0.92 |
| INDE | -13 | 12 | 9 | FOBS= | 160.6 | SIGMA= | 2.8 | PHAS= | 208.3 | FOM= | 0.94 |
| INDE | -13 | 12 | 10 | FOBS= | 78.4 | SIGMA= | 5.4 | PHAS= | 110.1 | FOM= | 0.46 |
| INDE | -13 | 12 | 11 | FOBS= | 152.7 | SIGMA= | 2.4 | PHAS= | 324.2 | FOM= | 0.08 |
| INDE | -13 | 12 | 12 | FOBS= | 165.4 | SIGMA= | 2.2 | PHAS= | 268.0 | FOM= | 0.38 |
| INDE | -13 | 13 | 1 | FOBS= | 110.1 | SIGMA= | 6.5 | PHAS= | 315.4 | FOM= | 0.19 |
| INDE | -13 | 13 | 3 | FOBS= | 70.8 | SIGMA= | 8.4 | PHAS= | 144.5 | FOM= | 0.16 |
| INDE | -13 | 13 | 4 | FOBS= | 165.1 | SIGMA= | 3.5 | PHAS= | 62.2 | FOM= | 0.66 |
| INDE | -13 | 13 | 5 | FOBS= | 74.5 | SIGMA= | 6.9 | PHAS= | 269.0 | FOM= | 0.30 |
| INDE | -13 | 13 | 6 | FOBS= | 251.7 | SIGMA= | 2.2 | PHAS= | 112.8 | FOM= | 0.65 |
| INDE | -13 | 13 | 7 | FOBS= | 153.5 | SIGMA= | 3.3 | PHAS= | 121.1 | FOM= | 0.89 |
| INDE | -13 | 13 | 8 | FOBS= | 113.8 | SIGMA= | 4.5 | PHAS= | 150.9 | FOM= | 0.53 |
| INDE | -13 | 13 | 9 | FOBS= | 113.0 | SIGMA= | 3.2 | PHAS= | 290.8 | FOM= | 0.48 |
| INDE | -13 | 13 | 10 | FOBS= | 141.2 | SIGMA= | 2.8 | PHAS= | 59.9 | FOM= | 0.60 |
| INDE | -13 | 13 | 11 | FOBS= | 118.1 | SIGMA= | 3.0 | PHAS= | 207.5 | FOM= | 0.24 |
| INDE | -13 | 13 | 12 | FOBS= | 165.8 | SIGMA= | 2.5 | PHAS= | 346.2 | FOM= | 0.94 |
| INDE | -13 | 14 | 1 | FOBS= | 113.5 | SIGMA= | 5.6 | PHAS= | 351.8 | FOM= | 0.35 |
| INDE | -13 | 14 | 2 | FOBS= | 112.5 | SIGMA= | 112.5 | PHAS= | 100.9 | FOM= | 0.15 |
| INDE | -13 | 14 | 3 | FOBS= | 57.6 | SIGMA= | 11.3 | PHAS= | 199.3 | FOM= | 0.06 |
| INDE | -13 | 14 | 4 | FOBS= | 49.3 | SIGMA= | 14.4 | PHAS= | 1.3 | FOM= | 0.21 |
| INDE | -13 | 14 | 5 | FOBS= | 58.8 | SIGMA= | 8.6 | PHAS= | 239.1 | FOM= | 0.20 |
| INDE | -13 | 14 | 6 | FOBS= | 123.6 | SIGMA= | 3.8 | PHAS= | 343.6 | FOM= | 0.42 |
| INDE | -13 | 14 | 7 | FOBS= | 145.9 | SIGMA= | 2.9 | PHAS= | 124.3 | FOM= | 0.66 |
| INDE | -13 | 14 | 8 | FOBS= | 59.6 | SIGMA= | 12.0 | PHAS= | 250.0 | FOM= | 0.35 |
| INDE | -13 | 14 | 9 | FOBS= | 136.8 | SIGMA= | 2.5 | PHAS= | 299.8 | FOM= | 0.30 |
| INDE | -13 | 14 | 10 | FOBS= | 63.2 | SIGMA= | 6.1 | PHAS= | 120.9 | FOM= | 0.32 |
| INDE | -13 | 14 | 11 | FOBS= | 60.0 | SIGMA= | 5.2 | PHAS= | 199.5 | FOM= | 0.50 |
| INDE | -13 | 15 | 1 | FOBS= | 257.7 | SIGMA= | 2.6 | PHAS= | 51.4 | FOM= | 0.79 |
| INDE | -13 | 15 | 2 | FOBS= | 166.2 | SIGMA= | 4.0 | PHAS= | 185.9 | FOM= | 0.91 |
| INDE | -13 | 15 | 3 | FOBS= | 48.2 | SIGMA= | 25.9 | PHAS= | 281.2 | FOM= | 0.15 |
| INDE | -13 | 15 | 4 | FOBS= | 97.3 | SIGMA= | 5.6 | PHAS= | 61.1 | FOM= | 0.05 |
| INDE | -13 | 15 | 5 | FOBS= | 201.8 | SIGMA= | 2.4 | PHAS= | 259.6 | FOM= | 0.48 |
| INDE | -13 | 15 | 6 | FOBS= | 125.9 | SIGMA= | 3.4 | PHAS= | 18.6 | FOM= | 0.19 |
| INDE | -13 | 15 | 7 | FOBS= | 106.5 | SIGMA= | 3.5 | PHAS= | 106.7 | FOM= | 0.17 |
| INDE | -13 | 15 | 8 | FOBS= | 187.8 | SIGMA= | 2.5 | PHAS= | 322.9 | FOM= | 0.67 |
| INDE | -13 | 15 | 9 | FOBS= | 218.0 | SIGMA= | 2.1 | PHAS= | 99.2 | FOM= | 0.96 |
| INDE | -13 | 15 | 10 | FOBS= | 169.9 | SIGMA= | 2.2 | PHAS= | 11.9 | FOM= | 0.73 |
| INDE | -13 | 15 | 11 | FOBS= | 140.4 | SIGMA= | 2.6 | PHAS= | 193.7 | FOM= | 0.85 |
| INDE | -13 | 16 | 1 | FOBS= | 143.0 | SIGMA= | 4.4 | PHAS= | 120.0 | FOM= | 0.66 |
| INDE | -13 | 16 | 2 | FOBS= | 108.2 | SIGMA= | 5.3 | PHAS= | 55.3 | FOM= | 0.15 |
| INDE | -13 | 16 | 3 | FOBS= | 48.1 | SIGMA= | 15.1 | PHAS= | 288.6 | FOM= | 0.32 |
| INDE | -13 | 16 | 4 | FOBS= | 61.0 | SIGMA= | 9.4 | PHAS= | 99.7 | FOM= | 0.31 |
| INDE | -13 | 16 | 5 | FOBS= | 108.9 | SIGMA= | 4.3 | PHAS= | 247.4 | FOM= | 0.24 |
| INDE | -13 | 16 | 6 | FOBS= | 77.1 | SIGMA= | 5.1 | PHAS= | 22.6 | FOM= | 0.40 |
| INDE | -13 | 16 | 7 | FOBS= | 60.3 | SIGMA= | 5.1 | PHAS= | 65.2 | FOM= | 0.43 |
| INDE | -13 | 16 | 8 | FOBS= | 97.4 | SIGMA= | 4.2 | PHAS= | 287.0 | FOM= | 0.37 |

Fig. 10A-11

```
INDE -13  16   9 FOBS=   48.4 SIGMA=  14.4 PHAS= 148.6 FOM= 0.13
INDE -13  16  10 FOBS=  144.1 SIGMA=   6.5 PHAS=  54.4 FOM= 0.02
INDE -13  16  11 FOBS=  139.4 SIGMA=  17.5 PHAS= 336.2 FOM= 0.06
INDE -13  17   1 FOBS=   82.7 SIGMA=   7.0 PHAS=  34.8 FOM= 0.18
INDE -13  17   2 FOBS=   59.6 SIGMA=   9.9 PHAS= 193.0 FOM= 0.12
INDE -13  17   3 FOBS=   52.8 SIGMA=  11.3 PHAS= 331.4 FOM= 0.35
INDE -13  17   4 FOBS=   74.0 SIGMA=   6.9 PHAS=  75.0 FOM= 0.11
INDE -13  17   5 FOBS=  114.0 SIGMA=   4.2 PHAS= 251.1 FOM= 0.81
INDE -13  17   6 FOBS=   85.3 SIGMA=   4.5 PHAS=  35.1 FOM= 0.85
INDE -13  17   7 FOBS=   43.3 SIGMA=  32.1 PHAS= 141.6 FOM= 0.23
INDE -13  17   8 FOBS=  105.1 SIGMA=   6.3 PHAS= 322.7 FOM= 0.47
INDE -13  17   9 FOBS=   90.7 SIGMA=   6.8 PHAS= 112.6 FOM= 0.43
INDE -13  17  10 FOBS=  118.5 SIGMA=   8.0 PHAS= 171.4 FOM= 0.12
INDE -13  18   1 FOBS=  103.4 SIGMA=   6.5 PHAS= 172.4 FOM= 0.30
INDE -13  18   2 FOBS=   65.5 SIGMA=   8.6 PHAS=  36.6 FOM= 0.06
INDE -13  18   3 FOBS=  148.0 SIGMA=   3.6 PHAS= 260.7 FOM= 0.85
INDE -13  18   4 FOBS=   42.0 SIGMA=  14.7 PHAS= 168.8 FOM= 0.36
INDE -13  18   5 FOBS=   32.1 SIGMA=  12.2 PHAS= 350.4 FOM= 0.15
INDE -13  18   6 FOBS=   44.4 SIGMA=  22.2 PHAS= 163.6 FOM= 0.33
INDE -13  18   7 FOBS=  235.7 SIGMA=   3.0 PHAS= 294.0 FOM= 0.90
INDE -13  18   8 FOBS=   56.1 SIGMA=  10.9 PHAS= 102.5 FOM= 0.09
INDE -13  18   9 FOBS=   46.3 SIGMA=  33.7 PHAS=  42.3 FOM= 0.31
INDE -13  19   1 FOBS=   34.0 SIGMA=  16.3 PHAS= 263.8 FOM= 0.20
INDE -13  19   2 FOBS=   62.8 SIGMA=   7.8 PHAS= 122.6 FOM= 0.09
INDE -13  19   3 FOBS=  133.8 SIGMA=   3.6 PHAS=  44.2 FOM= 0.14
INDE -13  19   4 FOBS=   70.7 SIGMA=   6.0 PHAS= 283.3 FOM= 0.32
INDE -13  19   5 FOBS=   89.0 SIGMA=   4.2 PHAS= 335.3 FOM= 0.59
INDE -13  19   6 FOBS=  122.8 SIGMA=   6.3 PHAS= 290.4 FOM= 0.72
INDE -13  19   7 FOBS=   73.4 SIGMA=   8.6 PHAS=  74.0 FOM= 0.08
INDE -13  19   8 FOBS=  161.9 SIGMA=   4.0 PHAS=  19.0 FOM= 0.90
INDE -13  19   9 FOBS=  165.9 SIGMA=   3.8 PHAS= 269.6 FOM= 0.12
INDE -13  20   1 FOBS=   19.9 SIGMA=  60.8 PHAS= 197.8 FOM= 1.00
INDE -13  20   2 FOBS=   48.8 SIGMA=   6.1 PHAS= 305.4 FOM= 0.96
INDE -13  20   3 FOBS=   39.0 SIGMA=  17.9 PHAS= 142.6 FOM= 0.03
INDE -13  20   4 FOBS=  231.0 SIGMA=   2.2 PHAS= 182.1 FOM= 0.92
INDE -13  20   5 FOBS=  140.4 SIGMA=   2.8 PHAS= 341.4 FOM= 0.95
INDE -13  20   6 FOBS=   44.7 SIGMA=  19.2 PHAS= 157.1 FOM= 0.14
INDE -13  20   7 FOBS=  155.4 SIGMA=   4.5 PHAS=  80.8 FOM= 0.89
INDE -13  20   8 FOBS=   96.9 SIGMA=   6.0 PHAS=   5.3 FOM= 0.12
INDE -13  21   1 FOBS=   58.8 SIGMA=  10.1 PHAS= 266.5 FOM= 0.20
INDE -13  21   2 FOBS=  106.9 SIGMA=   4.5 PHAS= 276.5 FOM= 0.44
INDE -13  21   3 FOBS=   53.0 SIGMA=  10.7 PHAS=  70.5 FOM= 0.18
INDE -13  21   4 FOBS=  111.4 SIGMA=   3.6 PHAS= 345.7 FOM= 0.89
INDE -13  21   5 FOBS=  104.5 SIGMA=   3.2 PHAS= 134.6 FOM= 0.91
INDE -13  21   6 FOBS=   49.1 SIGMA=  22.0 PHAS= 354.9 FOM= 0.23
INDE -13  21   7 FOBS=   40.5 SIGMA=  15.1 PHAS= 248.6 FOM= 0.06
INDE -13  22   1 FOBS=   53.5 SIGMA=  24.3 PHAS=  47.4 FOM= 0.17
INDE -13  22   3 FOBS=   94.5 SIGMA=   4.7 PHAS= 307.2 FOM= 0.33
INDE -13  22   4 FOBS=   98.4 SIGMA=   4.1 PHAS=  50.9 FOM= 0.08
INDE -13  22   5 FOBS=   53.2 SIGMA=   7.0 PHAS=  16.0 FOM= 0.21
INDE -13  22   6 FOBS=   88.5 SIGMA=  54.7 PHAS= 203.2 FOM= 0.03
INDE -13  23   1 FOBS=  107.8 SIGMA=   5.5 PHAS=  39.3 FOM= 0.51
INDE -13  23   2 FOBS=   58.0 SIGMA=  27.0 PHAS= 188.8 FOM= 0.18
INDE -13  23   3 FOBS=   85.8 SIGMA=   7.7 PHAS=  21.1 FOM= 0.02
INDE -12   0   1 FOBS=   63.6 SIGMA=  95.2 PHAS=   0.0 FOM= 0.05
INDE -12   0   2 FOBS=  266.2 SIGMA=   3.1 PHAS=   0.0 FOM= 0.70
INDE -12   0   3 FOBS=   55.6 SIGMA=  16.0 PHAS= 180.0 FOM= 0.03
INDE -12   0   4 FOBS=  504.2 SIGMA=   2.2 PHAS=   0.0 FOM= 0.44
INDE -12   0   5 FOBS=  529.7 SIGMA=   1.8 PHAS= 180.0 FOM= 0.99
INDE -12   0   6 FOBS=  187.3 SIGMA=   3.7 PHAS= 180.0 FOM= 0.96
INDE -12   0   7 FOBS=  262.5 SIGMA=   2.8 PHAS= 180.0 FOM= 0.95
INDE -12   0   8 FOBS=   67.8 SIGMA=   9.3 PHAS= 180.0 FOM= 0.17
INDE -12   0   9 FOBS=   80.3 SIGMA=  10.7 PHAS= 180.0 FOM= 0.12
INDE -12   0  10 FOBS=  113.1 SIGMA=   5.3 PHAS=   0.0 FOM= 0.00
INDE -12   0  11 FOBS=  208.7 SIGMA=   2.9 PHAS= 180.0 FOM= 0.95
INDE -12   0  12 FOBS=  249.8 SIGMA=   2.4 PHAS=   0.0 FOM= 0.24
INDE -12   0  13 FOBS=  262.6 SIGMA=   2.3 PHAS=   0.0 FOM= 0.76
INDE -12   0  14 FOBS=   29.3 SIGMA=  26.3 PHAS=   0.0 FOM= 0.24
INDE -12   1   1 FOBS=   62.6 SIGMA=  10.0 PHAS= 237.0 FOM= 0.08
INDE -12   1   2 FOBS=  105.4 SIGMA=   5.6 PHAS=  26.8 FOM= 0.66
INDE -12   1   3 FOBS=  322.6 SIGMA=   1.9 PHAS= 331.5 FOM= 0.73
```

Fig. 10A-12

| | | | | | | | | | |
|---|---|---|---|---|---|---|---|---|---|
| INDE | -12 | 1 | 4 | FOBS= | 114.4 | SIGMA= | 4.6 | PHAS= | 71.5 | FOM= | 0.11 |
| INDE | -12 | 1 | 5 | FOBS= | 265.9 | SIGMA= | 2.1 | PHAS= | 253.3 | FOM= | 0.90 |
| INDE | -12 | 1 | 6 | FOBS= | 237.3 | SIGMA= | 2.1 | PHAS= | 158.1 | FOM= | 0.94 |
| INDE | -12 | 1 | 7 | FOBS= | 433.4 | SIGMA= | 1.4 | PHAS= | 79.4 | FOM= | 0.94 |
| INDE | -12 | 1 | 8 | FOBS= | 238.5 | SIGMA= | 2.1 | PHAS= | 242.5 | FOM= | 0.93 |
| INDE | -12 | 1 | 9 | FOBS= | 176.8 | SIGMA= | 3.5 | PHAS= | 282.4 | FOM= | 0.92 |
| INDE | -12 | 1 | 10 | FOBS= | 109.1 | SIGMA= | 3.8 | PHAS= | 106.8 | FOM= | 0.41 |
| INDE | -12 | 1 | 11 | FOBS= | 195.6 | SIGMA= | 2.2 | PHAS= | 224.8 | FOM= | 0.95 |
| INDE | -12 | 1 | 12 | FOBS= | 193.7 | SIGMA= | 2.0 | PHAS= | 162.0 | FOM= | 0.71 |
| INDE | -12 | 1 | 13 | FOBS= | 121.4 | SIGMA= | 3.2 | PHAS= | 222.1 | FOM= | 0.37 |
| INDE | -12 | 1 | 14 | FOBS= | 143.7 | SIGMA= | 2.6 | PHAS= | 110.6 | FOM= | 0.91 |
| INDE | -12 | 2 | 1 | FOBS= | 255.5 | SIGMA= | 2.4 | PHAS= | 357.9 | FOM= | 0.83 |
| INDE | -12 | 2 | 2 | FOBS= | 354.0 | SIGMA= | 1.8 | PHAS= | 151.7 | FOM= | 0.47 |
| INDE | -12 | 2 | 3 | FOBS= | 231.4 | SIGMA= | 2.5 | PHAS= | 229.8 | FOM= | 0.93 |
| INDE | -12 | 2 | 4 | FOBS= | 204.8 | SIGMA= | 2.7 | PHAS= | 26.9 | FOM= | 0.96 |
| INDE | -12 | 2 | 5 | FOBS= | 248.4 | SIGMA= | 2.2 | PHAS= | 208.4 | FOM= | 0.62 |
| INDE | -12 | 2 | 6 | FOBS= | 171.6 | SIGMA= | 2.9 | PHAS= | 1.4 | FOM= | 0.23 |
| INDE | -12 | 2 | 7 | FOBS= | 412.5 | SIGMA= | 1.5 | PHAS= | 225.3 | FOM= | 0.97 |
| INDE | -12 | 2 | 8 | FOBS= | 195.2 | SIGMA= | 2.5 | PHAS= | 224.8 | FOM= | 0.87 |
| INDE | -12 | 2 | 9 | FOBS= | 60.2 | SIGMA= | 9.3 | PHAS= | 39.8 | FOM= | 0.42 |
| INDE | -12 | 2 | 10 | FOBS= | 216.7 | SIGMA= | 2.0 | PHAS= | 243.1 | FOM= | 0.90 |
| INDE | -12 | 2 | 11 | FOBS= | 96.9 | SIGMA= | 4.1 | PHAS= | 259.6 | FOM= | 0.52 |
| INDE | -12 | 2 | 12 | FOBS= | 224.0 | SIGMA= | 1.9 | PHAS= | 349.9 | FOM= | 0.97 |
| INDE | -12 | 2 | 13 | FOBS= | 127.3 | SIGMA= | 3.3 | PHAS= | 215.6 | FOM= | 0.94 |
| INDE | -12 | 2 | 14 | FOBS= | 170.3 | SIGMA= | 2.2 | PHAS= | 49.4 | FOM= | 0.73 |
| INDE | -12 | 3 | 1 | FOBS= | 76.2 | SIGMA= | 7.6 | PHAS= | 14.7 | FOM= | 0.28 |
| INDE | -12 | 3 | 2 | FOBS= | 112.3 | SIGMA= | 5.0 | PHAS= | 111.5 | FOM= | 0.20 |
| INDE | -12 | 3 | 3 | FOBS= | 46.2 | SIGMA= | 12.7 | PHAS= | 224.1 | FOM= | 0.32 |
| INDE | -12 | 3 | 4 | FOBS= | 369.4 | SIGMA= | 1.7 | PHAS= | 98.3 | FOM= | 0.98 |
| INDE | -12 | 3 | 5 | FOBS= | 81.3 | SIGMA= | 5.9 | PHAS= | 318.5 | FOM= | 0.26 |
| INDE | -12 | 3 | 6 | FOBS= | 183.2 | SIGMA= | 2.8 | PHAS= | 215.9 | FOM= | 0.34 |
| INDE | -12 | 3 | 7 | FOBS= | 52.1 | SIGMA= | 22.0 | PHAS= | 82.4 | FOM= | 0.25 |
| INDE | -12 | 3 | 8 | FOBS= | 64.8 | SIGMA= | 6.9 | PHAS= | 310.3 | FOM= | 0.50 |
| INDE | -12 | 3 | 9 | FOBS= | 386.3 | SIGMA= | 1.7 | PHAS= | 64.5 | FOM= | 1.00 |
| INDE | -12 | 3 | 10 | FOBS= | 30.6 | SIGMA= | 12.8 | PHAS= | 170.7 | FOM= | 0.27 |
| INDE | -12 | 3 | 11 | FOBS= | 124.6 | SIGMA= | 3.5 | PHAS= | 1.6 | FOM= | 0.92 |
| INDE | -12 | 3 | 12 | FOBS= | 137.9 | SIGMA= | 2.8 | PHAS= | 329.1 | FOM= | 0.73 |
| INDE | -12 | 3 | 13 | FOBS= | 94.7 | SIGMA= | 4.1 | PHAS= | 156.5 | FOM= | 0.89 |
| INDE | -12 | 3 | 14 | FOBS= | 127.8 | SIGMA= | 3.1 | PHAS= | 255.3 | FOM= | 0.87 |
| INDE | -12 | 4 | 1 | FOBS= | 154.2 | SIGMA= | 4.0 | PHAS= | 11.0 | FOM= | 0.34 |
| INDE | -12 | 4 | 2 | FOBS= | 50.2 | SIGMA= | 21.6 | PHAS= | 175.8 | FOM= | 0.28 |
| INDE | -12 | 4 | 3 | FOBS= | 187.9 | SIGMA= | 2.9 | PHAS= | 61.8 | FOM= | 0.87 |
| INDE | -12 | 4 | 4 | FOBS= | 297.5 | SIGMA= | 1.9 | PHAS= | 317.2 | FOM= | 0.78 |
| INDE | -12 | 4 | 5 | FOBS= | 399.9 | SIGMA= | 1.6 | PHAS= | 22.3 | FOM= | 0.84 |
| INDE | -12 | 4 | 6 | FOBS= | 377.6 | SIGMA= | 1.6 | PHAS= | 317.7 | FOM= | 0.98 |
| INDE | -12 | 4 | 7 | FOBS= | 155.7 | SIGMA= | 3.2 | PHAS= | 244.7 | FOM= | 0.60 |
| INDE | -12 | 4 | 8 | FOBS= | 91.5 | SIGMA= | 5.0 | PHAS= | 333.3 | FOM= | 0.42 |
| INDE | -12 | 4 | 9 | FOBS= | 174.8 | SIGMA= | 2.6 | PHAS= | 36.3 | FOM= | 0.80 |
| INDE | -12 | 4 | 10 | FOBS= | 247.2 | SIGMA= | 1.8 | PHAS= | 302.3 | FOM= | 0.95 |
| INDE | -12 | 4 | 11 | FOBS= | 139.6 | SIGMA= | 3.1 | PHAS= | 24.5 | FOM= | 0.51 |
| INDE | -12 | 4 | 12 | FOBS= | 187.3 | SIGMA= | 2.1 | PHAS= | 73.7 | FOM= | 0.94 |
| INDE | -12 | 4 | 13 | FOBS= | 132.1 | SIGMA= | 3.1 | PHAS= | 285.3 | FOM= | 0.74 |
| INDE | -12 | 4 | 14 | FOBS= | 146.2 | SIGMA= | 2.6 | PHAS= | 306.5 | FOM= | 0.52 |
| INDE | -12 | 5 | 1 | FOBS= | 232.9 | SIGMA= | 2.7 | PHAS= | 173.1 | FOM= | 0.85 |
| INDE | -12 | 5 | 2 | FOBS= | 212.1 | SIGMA= | 2.7 | PHAS= | 161.1 | FOM= | 0.16 |
| INDE | -12 | 5 | 3 | FOBS= | 54.0 | SIGMA= | 10.4 | PHAS= | 307.3 | FOM= | 0.48 |
| INDE | -12 | 5 | 4 | FOBS= | 285.6 | SIGMA= | 2.0 | PHAS= | 65.2 | FOM= | 0.99 |
| INDE | -12 | 5 | 5 | FOBS= | 214.2 | SIGMA= | 2.5 | PHAS= | 169.4 | FOM= | 0.94 |
| INDE | -12 | 5 | 6 | FOBS= | 53.6 | SIGMA= | 9.1 | PHAS= | 325.2 | FOM= | 0.15 |
| INDE | -12 | 5 | 7 | FOBS= | 173.0 | SIGMA= | 3.0 | PHAS= | 157.7 | FOM= | 0.95 |
| INDE | -12 | 5 | 8 | FOBS= | 259.7 | SIGMA= | 2.0 | PHAS= | 290.9 | FOM= | 1.00 |
| INDE | -12 | 5 | 9 | FOBS= | 248.2 | SIGMA= | 1.9 | PHAS= | 52.4 | FOM= | 0.90 |
| INDE | -12 | 5 | 10 | FOBS= | 221.6 | SIGMA= | 2.0 | PHAS= | 256.0 | FOM= | 0.86 |
| INDE | -12 | 5 | 11 | FOBS= | 223.0 | SIGMA= | 1.9 | PHAS= | 330.1 | FOM= | 0.50 |
| INDE | -12 | 5 | 12 | FOBS= | 63.3 | SIGMA= | 6.3 | PHAS= | 118.4 | FOM= | 0.45 |
| INDE | -12 | 5 | 13 | FOBS= | 157.1 | SIGMA= | 2.5 | PHAS= | 324.1 | FOM= | 1.00 |
| INDE | -12 | 5 | 14 | FOBS= | 33.3 | SIGMA= | 18.6 | PHAS= | 115.8 | FOM= | 0.01 |
| INDE | -12 | 6 | 1 | FOBS= | 169.3 | SIGMA= | 3.7 | PHAS= | 280.9 | FOM= | 0.42 |
| INDE | -12 | 6 | 2 | FOBS= | 184.3 | SIGMA= | 3.2 | PHAS= | 149.1 | FOM= | 0.81 |
| INDE | -12 | 6 | 3 | FOBS= | 424.0 | SIGMA= | 1.5 | PHAS= | 127.0 | FOM= | 0.94 |
| INDE | -12 | 6 | 4 | FOBS= | 98.7 | SIGMA= | 5.2 | PHAS= | 188.4 | FOM= | 0.19 |

Fig. 10A-13

```
INDE -12   6   5 FOBS=  417.5 SIGMA=  1.5 PHAS=  62.3 FOM= 0.96
INDE -12   6   6 FOBS=  155.0 SIGMA=  3.2 PHAS=  88.2 FOM= 0.87
INDE -12   6   7 FOBS=  162.0 SIGMA=  3.2 PHAS= 111.8 FOM= 0.85
INDE -12   6   8 FOBS=  324.6 SIGMA=  1.6 PHAS=  86.2 FOM= 0.77
INDE -12   6   9 FOBS=  276.2 SIGMA=  1.7 PHAS= 236.9 FOM= 0.82
INDE -12   6  10 FOBS=   87.6 SIGMA=  5.0 PHAS= 190.3 FOM= 0.78
INDE -12   6  11 FOBS=   93.1 SIGMA=  4.1 PHAS=  80.5 FOM= 0.63
INDE -12   6  12 FOBS=  189.3 SIGMA=  2.1 PHAS= 261.5 FOM= 0.89
INDE -12   6  13 FOBS=   85.7 SIGMA=  4.4 PHAS= 183.1 FOM= 0.23
INDE -12   6  14 FOBS=  114.3 SIGMA=  3.3 PHAS= 181.9 FOM= 0.75
INDE -12   7   1 FOBS=  166.1 SIGMA=  4.4 PHAS= 269.2 FOM= 0.78
INDE -12   7   2 FOBS=   70.0 SIGMA= 45.4 PHAS= 120.8 FOM= 0.10
INDE -12   7   3 FOBS=  107.7 SIGMA=  5.2 PHAS=  28.4 FOM= 0.41
INDE -12   7   4 FOBS=  145.2 SIGMA=  3.8 PHAS= 102.9 FOM= 0.75
INDE -12   7   5 FOBS=   59.0 SIGMA=  8.3 PHAS= 325.8 FOM= 0.07
INDE -12   7   6 FOBS=   30.1 SIGMA= 14.6 PHAS= 135.0 FOM= 0.18
INDE -12   7   7 FOBS=  128.5 SIGMA=  3.8 PHAS= 218.1 FOM= 0.67
INDE -12   7   8 FOBS=  306.1 SIGMA=  1.7 PHAS= 320.6 FOM= 1.00
INDE -12   7   9 FOBS=  137.6 SIGMA=  2.9 PHAS= 358.8 FOM= 0.73
INDE -12   7  10 FOBS=   61.0 SIGMA=  6.6 PHAS= 115.8 FOM= 0.15
INDE -12   7  11 FOBS=  200.8 SIGMA=  2.1 PHAS= 325.0 FOM= 1.00
INDE -12   7  12 FOBS=  197.9 SIGMA=  2.1 PHAS= 147.8 FOM= 1.00
INDE -12   7  13 FOBS=  180.0 SIGMA=  2.1 PHAS= 312.2 FOM= 0.93
INDE -12   7  14 FOBS=  121.6 SIGMA=  3.2 PHAS= 253.9 FOM= 0.73
INDE -12   8   1 FOBS=   40.5 SIGMA= 15.4 PHAS=  64.2 FOM= 0.14
INDE -12   8   2 FOBS=   45.2 SIGMA= 21.2 PHAS= 234.1 FOM= 0.16
INDE -12   8   3 FOBS=  137.9 SIGMA=  4.1 PHAS= 204.5 FOM= 0.52
INDE -12   8   4 FOBS=  250.9 SIGMA=  2.2 PHAS=  13.6 FOM= 0.90
INDE -12   8   5 FOBS=   88.3 SIGMA=  5.8 PHAS= 123.0 FOM= 0.61
INDE -12   8   6 FOBS=   40.3 SIGMA= 13.6 PHAS=  60.4 FOM= 0.21
INDE -12   8   7 FOBS=   56.8 SIGMA=  8.3 PHAS= 290.3 FOM= 0.12
INDE -12   8   8 FOBS=  385.4 SIGMA=  1.7 PHAS= 169.9 FOM= 1.00
INDE -12   8   9 FOBS=   40.5 SIGMA= 11.1 PHAS=  64.9 FOM= 0.29
INDE -12   8  10 FOBS=   93.3 SIGMA=  4.0 PHAS= 172.6 FOM= 0.75
INDE -12   8  11 FOBS=  115.3 SIGMA=  3.4 PHAS= 148.6 FOM= 0.82
INDE -12   8  12 FOBS=   29.6 SIGMA= 13.7 PHAS=  79.1 FOM= 0.18
INDE -12   8  13 FOBS=  214.0 SIGMA=  1.9 PHAS= 268.4 FOM= 0.93
INDE -12   8  14 FOBS=  116.5 SIGMA=  3.3 PHAS= 110.9 FOM= 0.84
INDE -12   9   1 FOBS=   83.4 SIGMA=  7.9 PHAS= 207.4 FOM= 0.28
INDE -12   9   2 FOBS=  332.4 SIGMA=  2.0 PHAS=  67.3 FOM= 0.73
INDE -12   9   3 FOBS=  220.8 SIGMA=  3.0 PHAS= 246.1 FOM= 0.29
INDE -12   9   4 FOBS=  133.7 SIGMA=  4.0 PHAS= 256.5 FOM= 0.81
INDE -12   9   5 FOBS=  138.9 SIGMA=  3.8 PHAS=  50.0 FOM= 0.77
INDE -12   9   6 FOBS=  392.2 SIGMA=  1.5 PHAS=  78.9 FOM= 0.85
INDE -12   9   7 FOBS=  134.1 SIGMA=  3.5 PHAS= 250.9 FOM= 0.67
INDE -12   9   8 FOBS=  154.2 SIGMA=  3.5 PHAS=   0.1 FOM= 0.51
INDE -12   9   9 FOBS=  119.8 SIGMA=  3.5 PHAS= 358.6 FOM= 0.79
INDE -12   9  10 FOBS=  120.1 SIGMA=  3.3 PHAS=  21.1 FOM= 0.34
INDE -12   9  11 FOBS=  141.6 SIGMA=  2.7 PHAS=  13.8 FOM= 0.66
INDE -12   9  12 FOBS=  121.3 SIGMA=  3.1 PHAS= 296.8 FOM= 0.82
INDE -12   9  13 FOBS=   55.7 SIGMA=  6.2 PHAS= 280.4 FOM= 0.26
INDE -12   9  14 FOBS=  231.9 SIGMA=  3.7 PHAS= 164.4 FOM= 0.33
INDE -12  10   1 FOBS=   43.3 SIGMA= 22.1 PHAS=  86.7 FOM= 0.10
INDE -12  10   2 FOBS=  223.8 SIGMA=  2.9 PHAS= 323.0 FOM= 0.95
INDE -12  10   3 FOBS=  229.6 SIGMA=  2.6 PHAS= 189.1 FOM= 0.89
INDE -12  10   4 FOBS=  177.6 SIGMA=  3.5 PHAS= 110.2 FOM= 0.55
INDE -12  10   5 FOBS=   61.0 SIGMA=  8.4 PHAS= 270.6 FOM= 0.20
INDE -12  10   6 FOBS=  251.3 SIGMA=  2.0 PHAS= 259.8 FOM= 0.82
INDE -12  10   7 FOBS=  102.1 SIGMA=  4.4 PHAS=  81.8 FOM= 0.58
INDE -12  10   8 FOBS=  240.8 SIGMA=  2.4 PHAS= 248.3 FOM= 0.97
INDE -12  10   9 FOBS=  252.7 SIGMA=  1.8 PHAS=  41.9 FOM= 1.00
INDE -12  10  10 FOBS=   77.3 SIGMA=  4.9 PHAS= 284.4 FOM= 0.09
INDE -12  10  11 FOBS=  202.1 SIGMA=  1.9 PHAS= 110.6 FOM= 0.96
INDE -12  10  12 FOBS=   32.5 SIGMA= 11.7 PHAS=  14.1 FOM= 0.59
INDE -12  10  13 FOBS=   32.2 SIGMA= 14.3 PHAS= 237.6 FOM= 0.16
INDE -12  11   1 FOBS=  302.2 SIGMA=  2.5 PHAS= 308.0 FOM= 0.84
INDE -12  11   2 FOBS=  330.2 SIGMA=  2.3 PHAS= 352.8 FOM= 0.51
INDE -12  11   3 FOBS=   75.2 SIGMA=  8.0 PHAS= 131.5 FOM= 0.16
INDE -12  11   4 FOBS=  196.8 SIGMA=  2.9 PHAS=  12.1 FOM= 0.59
INDE -12  11   5 FOBS=   71.5 SIGMA=  7.6 PHAS= 125.5 FOM= 0.26
INDE -12  11   6 FOBS=  113.0 SIGMA=  4.1 PHAS=  15.0 FOM= 0.26
```

Fig. 10A-14

```
INDE -12  11   7 FOBS=   55.8 SIGMA=  8.3 PHAS= 168.6 FOM= 0.19
INDE -12  11   8 FOBS=  171.6 SIGMA=  3.0 PHAS= 354.7 FOM= 0.08
INDE -12  11   9 FOBS=  401.0 SIGMA=  1.2 PHAS= 316.3 FOM= 0.94
INDE -12  11  10 FOBS=   51.2 SIGMA=  8.8 PHAS= 166.6 FOM= 0.53
INDE -12  11  11 FOBS=  295.0 SIGMA=  1.4 PHAS= 257.2 FOM= 0.98
INDE -12  11  12 FOBS=  219.3 SIGMA=  1.9 PHAS= 155.7 FOM= 0.74
INDE -12  11  13 FOBS=  163.7 SIGMA=  2.2 PHAS= 209.5 FOM= 0.84
INDE -12  12   1 FOBS=  237.7 SIGMA=  2.9 PHAS= 343.2 FOM= 0.70
INDE -12  12   2 FOBS=  183.2 SIGMA=  3.8 PHAS=  53.4 FOM= 0.37
INDE -12  12   3 FOBS=  183.3 SIGMA=  3.3 PHAS= 219.9 FOM= 0.73
INDE -12  12   4 FOBS=  276.8 SIGMA=  2.1 PHAS= 227.6 FOM= 0.80
INDE -12  12   5 FOBS=  153.0 SIGMA=  3.4 PHAS=  37.1 FOM= 0.88
INDE -12  12   6 FOBS=  120.0 SIGMA=  4.6 PHAS= 240.2 FOM= 0.83
INDE -12  12   7 FOBS=  217.2 SIGMA=  2.0 PHAS=  61.4 FOM= 0.63
INDE -12  12   8 FOBS=  262.7 SIGMA=  1.6 PHAS=  43.3 FOM= 0.80
INDE -12  12   9 FOBS=  108.9 SIGMA=  3.5 PHAS=  28.5 FOM= 0.80
INDE -12  12  10 FOBS=  109.7 SIGMA=  3.4 PHAS= 202.0 FOM= 0.72
INDE -12  12  11 FOBS=  212.4 SIGMA=  1.9 PHAS= 163.7 FOM= 0.91
INDE -12  12  12 FOBS=   67.6 SIGMA=  5.6 PHAS=  49.3 FOM= 0.83
INDE -12  12  13 FOBS=  167.4 SIGMA=  2.3 PHAS= 218.0 FOM= 0.96
INDE -12  13   1 FOBS=  179.7 SIGMA=  3.7 PHAS= 103.5 FOM= 0.40
INDE -12  13   2 FOBS=  175.0 SIGMA=  3.9 PHAS= 252.0 FOM= 0.64
INDE -12  13   3 FOBS=   97.7 SIGMA=  6.6 PHAS= 312.3 FOM= 0.06
INDE -12  13   4 FOBS=   95.5 SIGMA=  5.7 PHAS=  96.7 FOM= 0.35
INDE -12  13   5 FOBS=  205.2 SIGMA=  2.4 PHAS= 295.2 FOM= 0.77
INDE -12  13   6 FOBS=   99.6 SIGMA=  4.6 PHAS= 264.6 FOM= 0.64
INDE -12  13   7 FOBS=  127.8 SIGMA=  3.6 PHAS= 184.9 FOM= 0.80
INDE -12  13   8 FOBS=   83.6 SIGMA=  4.3 PHAS=  24.1 FOM= 0.27
INDE -12  13   9 FOBS=  116.6 SIGMA=  3.0 PHAS= 219.6 FOM= 0.56
INDE -12  13  10 FOBS=   94.9 SIGMA=  3.7 PHAS=  96.9 FOM= 0.26
INDE -12  13  11 FOBS=  149.8 SIGMA=  2.5 PHAS=   1.3 FOM= 0.97
INDE -12  13  12 FOBS=  141.8 SIGMA=  2.7 PHAS= 105.5 FOM= 0.75
INDE -12  13  13 FOBS=   50.1 SIGMA= 31.3 PHAS= 257.5 FOM= 0.19
INDE -12  14   1 FOBS=   90.7 SIGMA=  6.7 PHAS= 321.4 FOM= 0.06
INDE -12  14   3 FOBS=  227.9 SIGMA=  2.8 PHAS=  31.5 FOM= 0.76
INDE -12  14   4 FOBS=  154.9 SIGMA=  3.8 PHAS= 252.1 FOM= 0.68
INDE -12  14   5 FOBS=  175.5 SIGMA=  2.7 PHAS=   9.0 FOM= 0.91
INDE -12  14   6 FOBS=   80.9 SIGMA=  5.1 PHAS= 268.3 FOM= 0.19
INDE -12  14   7 FOBS=  106.5 SIGMA=  3.7 PHAS= 149.4 FOM= 0.84
INDE -12  14   8 FOBS=  124.2 SIGMA=  3.9 PHAS= 254.4 FOM= 0.49
INDE -12  14   9 FOBS=  134.8 SIGMA=  2.6 PHAS= 305.0 FOM= 0.49
INDE -12  14  10 FOBS=  104.2 SIGMA=  3.2 PHAS=  40.6 FOM= 0.27
INDE -12  14  11 FOBS=   94.6 SIGMA=  3.6 PHAS= 278.8 FOM= 0.68
INDE -12  14  12 FOBS=   82.6 SIGMA=  4.1 PHAS= 132.3 FOM= 0.37
INDE -12  15   1 FOBS=  190.5 SIGMA=  3.3 PHAS= 224.3 FOM= 0.67
INDE -12  15   2 FOBS=  242.1 SIGMA=  2.6 PHAS= 350.1 FOM= 0.37
INDE -12  15   3 FOBS=   51.8 SIGMA= 12.4 PHAS=  46.7 FOM= 0.43
INDE -12  15   4 FOBS=  190.4 SIGMA=  3.0 PHAS=  28.6 FOM= 0.82
INDE -12  15   5 FOBS=  159.1 SIGMA=  3.0 PHAS=  20.9 FOM= 0.89
INDE -12  15   6 FOBS=  153.6 SIGMA=  2.5 PHAS= 180.9 FOM= 0.97
INDE -12  15   7 FOBS=  306.4 SIGMA=  2.1 PHAS= 272.8 FOM= 0.94
INDE -12  15   8 FOBS=   91.9 SIGMA=  5.6 PHAS=  21.7 FOM= 0.14
INDE -12  15   9 FOBS=  180.9 SIGMA=  3.6 PHAS= 196.6 FOM= 0.78
INDE -12  15  10 FOBS=  192.4 SIGMA=  3.0 PHAS= 111.3 FOM= 0.42
INDE -12  15  11 FOBS=   39.4 SIGMA=  6.9 PHAS= 281.6 FOM= 0.33
INDE -12  15  12 FOBS=   48.2 SIGMA=  7.0 PHAS= 168.0 FOM= 0.24
INDE -12  16   1 FOBS=   81.4 SIGMA=  8.1 PHAS=  27.2 FOM= 0.05
INDE -12  16   2 FOBS=   52.5 SIGMA= 33.6 PHAS= 222.9 FOM= 0.06
INDE -12  16   3 FOBS=  157.4 SIGMA=  3.5 PHAS=  53.3 FOM= 0.60
INDE -12  16   4 FOBS=  133.5 SIGMA=  3.9 PHAS= 324.4 FOM= 0.68
INDE -12  16   5 FOBS=  117.4 SIGMA=  4.0 PHAS= 122.8 FOM= 0.09
INDE -12  16   6 FOBS=  108.7 SIGMA=  3.1 PHAS= 289.9 FOM= 0.51
INDE -12  16   7 FOBS=   65.6 SIGMA= 11.7 PHAS= 241.5 FOM= 0.37
INDE -12  16   8 FOBS=  110.6 SIGMA=  6.1 PHAS=  16.4 FOM= 0.26
INDE -12  16   9 FOBS=   78.5 SIGMA=  8.3 PHAS=  74.0 FOM= 0.49
INDE -12  16  10 FOBS=   44.4 SIGMA= 21.6 PHAS= 244.9 FOM= 0.10
INDE -12  16  11 FOBS=  148.2 SIGMA=  4.0 PHAS=  64.2 FOM= 0.20
INDE -12  16  12 FOBS=   96.2 SIGMA= 10.0 PHAS=  94.0 FOM= 0.08
INDE -12  17   1 FOBS=   90.1 SIGMA=  7.5 PHAS= 116.0 FOM= 0.37
INDE -12  17   2 FOBS=  137.8 SIGMA=  4.1 PHAS= 337.6 FOM= 0.28
INDE -12  17   3 FOBS=   99.7 SIGMA=  5.2 PHAS=  43.9 FOM= 0.37
```

Fig. 10A-15

```
INDE -12  17   4 FOBS=    41.3 SIGMA=  16.6 PHAS=  218.7 FOM=  0.24
INDE -12  17   5 FOBS=   216.2 SIGMA=   2.7 PHAS=  359.2 FOM=  0.87
INDE -12  17   6 FOBS=    80.2 SIGMA=   4.4 PHAS=  182.3 FOM=  0.18
INDE -12  17   7 FOBS=    64.9 SIGMA=  12.9 PHAS=  259.8 FOM=  0.18
INDE -12  17   8 FOBS=   156.0 SIGMA=   4.6 PHAS=   21.6 FOM=  0.90
INDE -12  17   9 FOBS=    77.5 SIGMA=   8.7 PHAS=  234.9 FOM=  0.70
INDE -12  17  10 FOBS=   112.1 SIGMA=   6.5 PHAS=  317.0 FOM=  0.03
INDE -12  17  11 FOBS=    93.1 SIGMA=   6.7 PHAS=   55.3 FOM=  0.51
INDE -12  18   1 FOBS=   154.2 SIGMA=   4.0 PHAS=   68.2 FOM=  0.80
INDE -12  18   2 FOBS=   134.2 SIGMA=   4.7 PHAS=   30.2 FOM=  0.60
INDE -12  18   3 FOBS=    81.7 SIGMA=   6.0 PHAS=   25.6 FOM=  0.15
INDE -12  18   4 FOBS=    33.9 SIGMA=  14.0 PHAS=  112.3 FOM=  0.12
INDE -12  18   5 FOBS=   179.5 SIGMA=   2.9 PHAS=  355.3 FOM=  0.96
INDE -12  18   6 FOBS=   103.0 SIGMA=   3.2 PHAS=  217.2 FOM=  0.92
INDE -12  18   7 FOBS=    52.6 SIGMA=  16.7 PHAS=  338.9 FOM=  0.39
INDE -12  18   8 FOBS=    70.4 SIGMA=   9.1 PHAS=  200.4 FOM=  0.47
INDE -12  18   9 FOBS=    79.3 SIGMA=   7.6 PHAS=   74.2 FOM=  0.06
INDE -12  18  10 FOBS=    68.4 SIGMA=   9.3 PHAS=   29.3 FOM=  0.42
INDE -12  18  11 FOBS=    75.3 SIGMA=  16.3 PHAS=  144.5 FOM=  0.12
INDE -12  19   1 FOBS=    64.9 SIGMA=   9.0 PHAS=  208.2 FOM=  0.15
INDE -12  19   2 FOBS=   103.5 SIGMA=   6.0 PHAS=  310.0 FOM=  0.11
INDE -12  19   3 FOBS=   116.1 SIGMA=   4.3 PHAS=  241.6 FOM=  0.47
INDE -12  19   4 FOBS=   102.6 SIGMA=   4.0 PHAS=   60.4 FOM=  0.87
INDE -12  19   5 FOBS=   148.6 SIGMA=   3.1 PHAS=  245.9 FOM=  0.75
INDE -12  19   6 FOBS=    27.4 SIGMA=  12.4 PHAS=    2.8 FOM=  0.13
INDE -12  19   7 FOBS=    58.4 SIGMA=  15.0 PHAS=  231.6 FOM=  0.32
INDE -12  19   8 FOBS=   145.8 SIGMA=   5.3 PHAS=  115.5 FOM=  0.14
INDE -12  19   9 FOBS=   250.9 SIGMA=   3.1 PHAS=  308.2 FOM=  0.90
INDE -12  19  10 FOBS=   198.8 SIGMA=   3.2 PHAS=  129.6 FOM=  0.70
INDE -12  20   1 FOBS=    98.0 SIGMA=   5.9 PHAS=   94.8 FOM=  0.38
INDE -12  20   2 FOBS=   265.5 SIGMA=   2.6 PHAS=  351.6 FOM=  0.96
INDE -12  20   3 FOBS=   118.2 SIGMA=   4.6 PHAS=   87.4 FOM=  0.58
INDE -12  20   4 FOBS=    59.4 SIGMA=   7.9 PHAS=  118.5 FOM=  0.07
INDE -12  20   5 FOBS=   315.9 SIGMA=   1.9 PHAS=   15.5 FOM=  1.00
INDE -12  20   6 FOBS=   219.4 SIGMA=   2.7 PHAS=  238.4 FOM=  1.00
INDE -12  20   7 FOBS=   311.9 SIGMA=   3.0 PHAS=  322.7 FOM=  0.07
INDE -12  20   8 FOBS=   167.7 SIGMA=   3.8 PHAS=  216.1 FOM=  0.82
INDE -12  20   9 FOBS=    50.9 SIGMA=  39.4 PHAS=  355.2 FOM=  0.27
INDE -12  21   1 FOBS=    37.1 SIGMA=  16.5 PHAS=  200.8 FOM=  0.19
INDE -12  21   2 FOBS=    99.6 SIGMA=   5.6 PHAS=  142.0 FOM=  0.23
INDE -12  21   3 FOBS=   109.9 SIGMA=   4.2 PHAS=  336.7 FOM=  0.56
INDE -12  21   4 FOBS=    94.8 SIGMA=   4.2 PHAS=  142.8 FOM=  0.62
INDE -12  21   5 FOBS=   149.5 SIGMA=   3.4 PHAS=  323.8 FOM=  0.88
INDE -12  21   6 FOBS=    76.5 SIGMA=   8.4 PHAS=  313.4 FOM=  0.11
INDE -12  21   7 FOBS=   103.1 SIGMA=   6.6 PHAS=   85.3 FOM=  0.18
INDE -12  21   8 FOBS=   172.3 SIGMA=   5.7 PHAS=  270.1 FOM=  0.40
INDE -12  21   9 FOBS=    73.6 SIGMA=   7.3 PHAS=  186.1 FOM=  0.14
INDE -12  22   1 FOBS=    32.7 SIGMA=  25.9 PHAS=  111.3 FOM=  0.49
INDE -12  22   2 FOBS=    31.2 SIGMA=  41.5 PHAS=  290.7 FOM=  0.80
INDE -12  22   3 FOBS=    65.7 SIGMA=   7.4 PHAS=   33.6 FOM=  0.12
INDE -12  22   4 FOBS=   113.7 SIGMA=   3.4 PHAS=  261.8 FOM=  0.70
INDE -12  22   5 FOBS=    69.4 SIGMA=   7.5 PHAS=  188.8 FOM=  0.22
INDE -12  22   6 FOBS=   113.9 SIGMA=   6.0 PHAS=   44.2 FOM=  0.56
INDE -12  22   7 FOBS=    71.8 SIGMA=   8.5 PHAS=  295.4 FOM=  0.10
INDE -12  22   8 FOBS=   101.2 SIGMA=   5.4 PHAS=  189.1 FOM=  0.05
INDE -12  23   1 FOBS=   182.8 SIGMA=   3.2 PHAS=  183.0 FOM=  0.91
INDE -12  23   2 FOBS=    63.4 SIGMA=   7.4 PHAS=   83.0 FOM=  0.21
INDE -12  23   3 FOBS=    51.3 SIGMA=  10.0 PHAS=  251.9 FOM=  0.07
INDE -12  23   4 FOBS=    64.2 SIGMA=   6.4 PHAS=  179.3 FOM=  0.24
INDE -12  23   5 FOBS=    35.5 SIGMA=   8.4 PHAS=   42.1 FOM=  0.19
INDE -12  23   6 FOBS=    57.7 SIGMA=  11.5 PHAS=  226.9 FOM=  0.07
INDE -12  23   7 FOBS=    32.2 SIGMA=  16.0 PHAS=  270.1 FOM=  0.11
INDE -12  24   1 FOBS=    90.3 SIGMA=   5.5 PHAS=   14.5 FOM=  0.10
INDE -12  24   2 FOBS=    71.4 SIGMA=   6.8 PHAS=  355.7 FOM=  0.06
INDE -12  24   3 FOBS=    99.3 SIGMA=   4.5 PHAS=  117.1 FOM=  0.72
INDE -12  24   4 FOBS=    44.8 SIGMA=  21.8 PHAS=  353.8 FOM=  0.14
INDE -12  24   5 FOBS=    92.2 SIGMA=  13.0 PHAS=  214.4 FOM=  0.02
INDE -12  25   2 FOBS=    86.9 SIGMA=  43.7 PHAS=   92.9 FOM=  0.09
INDE -12  25   3 FOBS=   279.1 SIGMA=   3.0 PHAS=  180.0 FOM=  0.04
INDE -11   0   1 FOBS=   106.4 SIGMA=   7.0 PHAS=  180.0 FOM=  0.25
INDE -11   0   2 FOBS=    77.5 SIGMA=   8.7 PHAS=  180.0 FOM=  0.10
```

Fig. 10A-16

```
INDE -11   0   4 FOBS=  161.0 SIGMA=  4.2 PHAS=  180.0 FOM= 0.08
INDE -11   0   5 FOBS=  389.7 SIGMA=  2.0 PHAS=    0.0 FOM= 0.32
INDE -11   0   6 FOBS=   64.8 SIGMA=  9.6 PHAS=  180.0 FOM= 0.20
INDE -11   0   7 FOBS=   64.4 SIGMA=  9.5 PHAS=    0.0 FOM= 0.08
INDE -11   0   8 FOBS=  518.4 SIGMA=  1.7 PHAS=    0.0 FOM= 1.00
INDE -11   0   9 FOBS=   55.2 SIGMA= 10.8 PHAS=  180.0 FOM= 0.10
INDE -11   0  10 FOBS=   49.8 SIGMA= 10.8 PHAS=  180.0 FOM= 0.11
INDE -11   0  11 FOBS=   33.1 SIGMA= 20.0 PHAS=    0.0 FOM= 0.30
INDE -11   0  12 FOBS=  156.8 SIGMA=  3.5 PHAS=  180.0 FOM= 0.44
INDE -11   0  13 FOBS=  140.3 SIGMA=  3.9 PHAS=    0.0 FOM= 0.86
INDE -11   0  14 FOBS=  187.7 SIGMA=  4.3 PHAS=    0.0 FOM= 0.62
INDE -11   0  15 FOBS=   46.4 SIGMA= 13.8 PHAS=  180.0 FOM= 0.04
INDE -11   1   1 FOBS=   92.5 SIGMA=  6.1 PHAS=  156.7 FOM= 0.51
INDE -11   1   2 FOBS=   46.6 SIGMA= 12.9 PHAS=  193.7 FOM= 0.12
INDE -11   1   3 FOBS=  186.6 SIGMA=  2.7 PHAS=  132.4 FOM= 0.97
INDE -11   1   4 FOBS=   51.0 SIGMA= 10.2 PHAS=   99.6 FOM= 0.23
INDE -11   1   5 FOBS=  107.5 SIGMA=  4.4 PHAS=  303.4 FOM= 0.80
INDE -11   1   6 FOBS=  203.9 SIGMA=  2.3 PHAS=  102.2 FOM= 0.93
INDE -11   1   7 FOBS=   77.3 SIGMA=  5.4 PHAS=  167.8 FOM= 0.01
INDE -11   1   8 FOBS=   82.4 SIGMA=  5.0 PHAS=  228.8 FOM= 0.17
INDE -11   1   9 FOBS=  200.0 SIGMA=  2.2 PHAS=  164.2 FOM= 0.80
INDE -11   1  10 FOBS=  102.4 SIGMA=  4.3 PHAS=  337.1 FOM= 0.88
INDE -11   1  11 FOBS=  231.0 SIGMA=  1.8 PHAS=  181.8 FOM= 0.72
INDE -11   1  12 FOBS=  254.9 SIGMA=  1.7 PHAS=   68.3 FOM= 1.00
INDE -11   1  13 FOBS=  218.0 SIGMA=  2.0 PHAS=  283.4 FOM= 0.98
INDE -11   1  14 FOBS=  126.7 SIGMA=  4.3 PHAS=  308.3 FOM= 0.81
INDE -11   1  15 FOBS=   81.1 SIGMA=  5.3 PHAS=  108.8 FOM= 0.29
INDE -11   2   1 FOBS=  116.5 SIGMA=  4.8 PHAS=   65.4 FOM= 0.81
INDE -11   2   2 FOBS=  141.0 SIGMA=  3.8 PHAS=   78.3 FOM= 0.16
INDE -11   2   3 FOBS=  171.8 SIGMA=  3.1 PHAS=  326.0 FOM= 0.96
INDE -11   2   4 FOBS=  278.2 SIGMA=  1.9 PHAS=   95.3 FOM= 0.97
INDE -11   2   5 FOBS=  370.0 SIGMA=  1.5 PHAS=  224.0 FOM= 0.79
INDE -11   2   6 FOBS=  267.0 SIGMA=  1.9 PHAS=  105.6 FOM= 0.87
INDE -11   2   7 FOBS=  170.4 SIGMA=  2.7 PHAS=  176.7 FOM= 0.81
INDE -11   2   8 FOBS=  404.9 SIGMA=  1.3 PHAS=   61.7 FOM= 0.79
INDE -11   2   9 FOBS=  147.9 SIGMA=  2.9 PHAS=  173.7 FOM= 0.15
INDE -11   2  10 FOBS=  285.1 SIGMA=  1.7 PHAS=  217.1 FOM= 0.96
INDE -11   2  11 FOBS=   54.1 SIGMA=  7.7 PHAS=   88.0 FOM= 0.07
INDE -11   2  12 FOBS=   67.7 SIGMA=  5.4 PHAS=  211.6 FOM= 0.18
INDE -11   2  13 FOBS=  115.0 SIGMA=  3.5 PHAS=  231.3 FOM= 0.74
INDE -11   2  14 FOBS=   89.7 SIGMA=  6.1 PHAS=   33.8 FOM= 0.12
INDE -11   2  15 FOBS=   59.9 SIGMA=  8.8 PHAS=  227.4 FOM= 0.41
INDE -11   3   1 FOBS=   79.2 SIGMA=  7.2 PHAS=  105.6 FOM= 0.27
INDE -11   3   2 FOBS=  103.4 SIGMA=  5.3 PHAS=  308.1 FOM= 0.77
INDE -11   3   3 FOBS=  135.8 SIGMA=  3.8 PHAS=  133.8 FOM= 0.89
INDE -11   3   4 FOBS=  324.0 SIGMA=  1.7 PHAS=  218.8 FOM= 0.96
INDE -11   3   5 FOBS=  248.6 SIGMA=  2.0 PHAS=  322.6 FOM= 1.00
INDE -11   3   6 FOBS=  213.5 SIGMA=  2.2 PHAS=  186.0 FOM= 0.90
INDE -11   3   7 FOBS=  152.6 SIGMA=  2.9 PHAS=  285.5 FOM= 0.95
INDE -11   3   8 FOBS=  264.1 SIGMA=  2.0 PHAS=  276.6 FOM= 0.99
INDE -11   3   9 FOBS=  283.6 SIGMA=  1.6 PHAS=  204.9 FOM= 0.94
INDE -11   3  10 FOBS=   94.6 SIGMA=  4.2 PHAS=  213.6 FOM= 0.02
INDE -11   3  11 FOBS=  243.4 SIGMA=  1.7 PHAS=    1.1 FOM= 0.61
INDE -11   3  12 FOBS=   97.2 SIGMA=  4.0 PHAS=  224.1 FOM= 0.19
INDE -11   3  13 FOBS=  207.2 SIGMA=  2.0 PHAS=  295.9 FOM= 0.90
INDE -11   3  14 FOBS=   63.3 SIGMA=  7.7 PHAS=  163.4 FOM= 0.19
INDE -11   3  15 FOBS=  135.2 SIGMA=  3.6 PHAS=  202.5 FOM= 0.49
INDE -11   4   1 FOBS=  155.9 SIGMA=  3.6 PHAS=  265.8 FOM= 0.13
INDE -11   4   2 FOBS=  158.3 SIGMA=  3.4 PHAS=  264.9 FOM= 0.23
INDE -11   4   3 FOBS=  152.8 SIGMA=  3.3 PHAS=  121.9 FOM= 0.27
INDE -11   4   4 FOBS=  386.1 SIGMA=  1.5 PHAS=  317.2 FOM= 0.94
INDE -11   4   5 FOBS=   56.1 SIGMA=  8.7 PHAS=  341.4 FOM= 0.19
INDE -11   4   6 FOBS=  524.8 SIGMA=  1.1 PHAS=  272.7 FOM= 1.00
INDE -11   4   7 FOBS=   61.1 SIGMA=  6.4 PHAS=  147.8 FOM= 0.32
INDE -11   4   8 FOBS=   52.2 SIGMA=  9.3 PHAS=   11.3 FOM= 0.23
INDE -11   4   9 FOBS=  311.3 SIGMA=  1.6 PHAS=   30.6 FOM= 0.98
INDE -11   4  10 FOBS=  172.0 SIGMA=  2.3 PHAS=  159.7 FOM= 0.55
INDE -11   4  11 FOBS=  102.1 SIGMA=  4.1 PHAS=   44.5 FOM= 0.79
INDE -11   4  12 FOBS=  106.2 SIGMA=  3.8 PHAS=  242.4 FOM= 0.80
INDE -11   4  13 FOBS=  150.4 SIGMA=  2.6 PHAS=  222.4 FOM= 0.50
INDE -11   4  14 FOBS=  115.3 SIGMA=  4.3 PHAS=  297.2 FOM= 0.60
```

Fig. 10A-17

| | | | | | | | | | |
|---|---|---|---|---|---|---|---|---|---|
| INDE | -11 | 4 | 15 | FOBS= | 139.8 | SIGMA= | 3.6 | PHAS= | 218.5 | FOM= | 0.52 |
| INDE | -11 | 5 | 1 | FOBS= | 135.9 | SIGMA= | 4.1 | PHAS= | 149.5 | FOM= | 0.26 |
| INDE | -11 | 5 | 2 | FOBS= | 77.3 | SIGMA= | 6.0 | PHAS= | 134.7 | FOM= | 0.66 |
| INDE | -11 | 5 | 3 | FOBS= | 369.4 | SIGMA= | 1.5 | PHAS= | 14.6 | FOM= | 0.93 |
| INDE | -11 | 5 | 4 | FOBS= | 153.5 | SIGMA= | 3.3 | PHAS= | 8.0 | FOM= | 0.83 |
| INDE | -11 | 5 | 5 | FOBS= | 170.2 | SIGMA= | 2.7 | PHAS= | 238.2 | FOM= | 0.18 |
| INDE | -11 | 5 | 6 | FOBS= | 471.7 | SIGMA= | 1.2 | PHAS= | 319.1 | FOM= | 0.89 |
| INDE | -11 | 5 | 7 | FOBS= | 129.6 | SIGMA= | 3.6 | PHAS= | 351.0 | FOM= | 0.94 |
| INDE | -11 | 5 | 8 | FOBS= | 378.0 | SIGMA= | 1.6 | PHAS= | 36.4 | FOM= | 0.95 |
| INDE | -11 | 5 | 9 | FOBS= | 75.1 | SIGMA= | 6.2 | PHAS= | 229.3 | FOM= | 0.45 |
| INDE | -11 | 5 | 10 | FOBS= | 365.2 | SIGMA= | 1.3 | PHAS= | 316.7 | FOM= | 1.00 |
| INDE | -11 | 5 | 11 | FOBS= | 78.1 | SIGMA= | 5.0 | PHAS= | 62.2 | FOM= | 0.57 |
| INDE | -11 | 5 | 12 | FOBS= | 216.6 | SIGMA= | 1.9 | PHAS= | 264.4 | FOM= | 0.34 |
| INDE | -11 | 5 | 13 | FOBS= | 239.4 | SIGMA= | 1.8 | PHAS= | 25.1 | FOM= | 0.34 |
| INDE | -11 | 5 | 14 | FOBS= | 95.8 | SIGMA= | 4.9 | PHAS= | 296.6 | FOM= | 0.15 |
| INDE | -11 | 5 | 15 | FOBS= | 189.6 | SIGMA= | 2.4 | PHAS= | 90.6 | FOM= | 0.72 |
| INDE | -11 | 6 | 1 | FOBS= | 126.3 | SIGMA= | 4.4 | PHAS= | 96.9 | FOM= | 0.75 |
| INDE | -11 | 6 | 2 | FOBS= | 209.6 | SIGMA= | 2.6 | PHAS= | 321.5 | FOM= | 0.82 |
| INDE | -11 | 6 | 3 | FOBS= | 252.6 | SIGMA= | 2.1 | PHAS= | 128.2 | FOM= | 0.89 |
| INDE | -11 | 6 | 4 | FOBS= | 248.5 | SIGMA= | 2.0 | PHAS= | 305.2 | FOM= | 0.94 |
| INDE | -11 | 6 | 5 | FOBS= | 395.6 | SIGMA= | 1.4 | PHAS= | 295.2 | FOM= | 0.88 |
| INDE | -11 | 6 | 6 | FOBS= | 187.0 | SIGMA= | 2.4 | PHAS= | 144.7 | FOM= | 0.21 |
| INDE | -11 | 6 | 7 | FOBS= | 174.7 | SIGMA= | 2.6 | PHAS= | 236.4 | FOM= | 0.90 |
| INDE | -11 | 6 | 8 | FOBS= | 156.0 | SIGMA= | 3.3 | PHAS= | 353.0 | FOM= | 0.90 |
| INDE | -11 | 6 | 9 | FOBS= | 178.6 | SIGMA= | 2.7 | PHAS= | 286.8 | FOM= | 0.95 |
| INDE | -11 | 6 | 10 | FOBS= | 155.6 | SIGMA= | 2.5 | PHAS= | 349.0 | FOM= | 0.47 |
| INDE | -11 | 6 | 11 | FOBS= | 193.8 | SIGMA= | 2.1 | PHAS= | 112.7 | FOM= | 0.96 |
| INDE | -11 | 6 | 12 | FOBS= | 82.5 | SIGMA= | 4.5 | PHAS= | 181.6 | FOM= | 0.64 |
| INDE | -11 | 6 | 13 | FOBS= | 123.5 | SIGMA= | 3.5 | PHAS= | 3.8 | FOM= | 0.71 |
| INDE | -11 | 6 | 14 | FOBS= | 230.8 | SIGMA= | 2.1 | PHAS= | 289.0 | FOM= | 0.61 |
| INDE | -11 | 6 | 15 | FOBS= | 82.7 | SIGMA= | 6.6 | PHAS= | 109.5 | FOM= | 0.10 |
| INDE | -11 | 7 | 1 | FOBS= | 126.5 | SIGMA= | 5.1 | PHAS= | 6.2 | FOM= | 0.05 |
| INDE | -11 | 7 | 2 | FOBS= | 219.1 | SIGMA= | 2.4 | PHAS= | 156.3 | FOM= | 0.95 |
| INDE | -11 | 7 | 3 | FOBS= | 319.4 | SIGMA= | 1.7 | PHAS= | 243.5 | FOM= | 0.88 |
| INDE | -11 | 7 | 4 | FOBS= | 136.0 | SIGMA= | 3.5 | PHAS= | 69.3 | FOM= | 0.57 |
| INDE | -11 | 7 | 5 | FOBS= | 327.6 | SIGMA= | 1.6 | PHAS= | 178.3 | FOM= | 0.95 |
| INDE | -11 | 7 | 6 | FOBS= | 89.3 | SIGMA= | 4.5 | PHAS= | 13.1 | FOM= | 0.75 |
| INDE | -11 | 7 | 7 | FOBS= | 199.6 | SIGMA= | 2.3 | PHAS= | 48.2 | FOM= | 0.91 |
| INDE | -11 | 7 | 8 | FOBS= | 218.8 | SIGMA= | 2.0 | PHAS= | 16.6 | FOM= | 0.85 |
| INDE | -11 | 7 | 9 | FOBS= | 423.1 | SIGMA= | 1.3 | PHAS= | 61.9 | FOM= | 0.91 |
| INDE | -11 | 7 | 10 | FOBS= | 74.7 | SIGMA= | 4.9 | PHAS= | 285.9 | FOM= | 0.56 |
| INDE | -11 | 7 | 11 | FOBS= | 84.1 | SIGMA= | 4.6 | PHAS= | 118.3 | FOM= | 0.80 |
| INDE | -11 | 7 | 12 | FOBS= | 73.5 | SIGMA= | 5.5 | PHAS= | 312.0 | FOM= | 0.77 |
| INDE | -11 | 7 | 13 | FOBS= | 129.1 | SIGMA= | 3.4 | PHAS= | 266.0 | FOM= | 0.70 |
| INDE | -11 | 7 | 14 | FOBS= | 121.9 | SIGMA= | 3.7 | PHAS= | 89.6 | FOM= | 0.65 |
| INDE | -11 | 7 | 15 | FOBS= | 158.0 | SIGMA= | 7.2 | PHAS= | 216.0 | FOM= | 0.25 |
| INDE | -11 | 8 | 1 | FOBS= | 100.2 | SIGMA= | 5.8 | PHAS= | 33.2 | FOM= | 0.56 |
| INDE | -11 | 8 | 2 | FOBS= | 129.0 | SIGMA= | 4.9 | PHAS= | 126.6 | FOM= | 0.59 |
| INDE | -11 | 8 | 3 | FOBS= | 263.3 | SIGMA= | 2.1 | PHAS= | 151.8 | FOM= | 0.84 |
| INDE | -11 | 8 | 4 | FOBS= | 403.2 | SIGMA= | 1.5 | PHAS= | 40.3 | FOM= | 1.00 |
| INDE | -11 | 8 | 5 | FOBS= | 249.9 | SIGMA= | 1.9 | PHAS= | 58.4 | FOM= | 0.52 |
| INDE | -11 | 8 | 6 | FOBS= | 184.1 | SIGMA= | 2.4 | PHAS= | 39.4 | FOM= | 0.87 |
| INDE | -11 | 8 | 7 | FOBS= | 241.1 | SIGMA= | 2.0 | PHAS= | 284.1 | FOM= | 0.97 |
| INDE | -11 | 8 | 8 | FOBS= | 251.9 | SIGMA= | 1.8 | PHAS= | 28.7 | FOM= | 0.94 |
| INDE | -11 | 8 | 9 | FOBS= | 151.8 | SIGMA= | 3.0 | PHAS= | 294.6 | FOM= | 0.80 |
| INDE | -11 | 8 | 10 | FOBS= | 220.0 | SIGMA= | 1.8 | PHAS= | 98.7 | FOM= | 0.87 |
| INDE | -11 | 8 | 11 | FOBS= | 233.0 | SIGMA= | 1.8 | PHAS= | 340.3 | FOM= | 0.89 |
| INDE | -11 | 8 | 12 | FOBS= | 138.9 | SIGMA= | 2.8 | PHAS= | 208.1 | FOM= | 0.87 |
| INDE | -11 | 8 | 13 | FOBS= | 53.7 | SIGMA= | 9.3 | PHAS= | 132.4 | FOM= | 0.58 |
| INDE | -11 | 8 | 14 | FOBS= | 82.7 | SIGMA= | 5.2 | PHAS= | 250.9 | FOM= | 0.77 |
| INDE | -11 | 9 | 1 | FOBS= | 199.0 | SIGMA= | 3.4 | PHAS= | 136.0 | FOM= | 0.36 |
| INDE | -11 | 9 | 2 | FOBS= | 294.1 | SIGMA= | 2.0 | PHAS= | 171.8 | FOM= | 0.95 |
| INDE | -11 | 9 | 3 | FOBS= | 376.7 | SIGMA= | 2.1 | PHAS= | 250.8 | FOM= | 0.86 |
| INDE | -11 | 9 | 4 | FOBS= | 87.3 | SIGMA= | 5.2 | PHAS= | 272.4 | FOM= | 0.17 |
| INDE | -11 | 9 | 5 | FOBS= | 40.1 | SIGMA= | 12.7 | PHAS= | 2.2 | FOM= | 0.10 |
| INDE | -11 | 9 | 6 | FOBS= | 80.7 | SIGMA= | 5.1 | PHAS= | 297.9 | FOM= | 0.63 |
| INDE | -11 | 9 | 7 | FOBS= | 194.2 | SIGMA= | 2.3 | PHAS= | 334.8 | FOM= | 0.92 |
| INDE | -11 | 9 | 8 | FOBS= | 172.0 | SIGMA= | 2.4 | PHAS= | 282.4 | FOM= | 0.83 |
| INDE | -11 | 9 | 9 | FOBS= | 136.8 | SIGMA= | 3.2 | PHAS= | 165.6 | FOM= | 0.88 |
| INDE | -11 | 9 | 10 | FOBS= | 68.4 | SIGMA= | 5.3 | PHAS= | 42.0 | FOM= | 0.81 |
| INDE | -11 | 9 | 11 | FOBS= | 168.0 | SIGMA= | 2.4 | PHAS= | 184.5 | FOM= | 0.94 |

Fig. 10A-18

```
INDE -11   9  12 FOBS=  289.8 SIGMA=   1.5 PHAS=   78.7 FOM= 0.99
INDE -11   9  13 FOBS=  165.1 SIGMA=   2.7 PHAS=  299.8 FOM= 0.96
INDE -11   9  14 FOBS=  150.3 SIGMA=   3.0 PHAS=  158.4 FOM= 0.70
INDE -11  10   1 FOBS=   62.5 SIGMA=  41.1 PHAS=   71.2 FOM= 0.03
INDE -11  10   2 FOBS=  105.8 SIGMA=   6.4 PHAS=  160.5 FOM= 0.08
INDE -11  10   3 FOBS=   68.5 SIGMA=   7.5 PHAS=  331.1 FOM= 0.03
INDE -11  10   4 FOBS=  217.3 SIGMA=   2.6 PHAS=   34.0 FOM= 0.08
INDE -11  10   5 FOBS=  330.5 SIGMA=   1.6 PHAS=  166.3 FOM= 0.98
INDE -11  10   6 FOBS=  285.0 SIGMA=   1.7 PHAS=  313.0 FOM= 0.99
INDE -11  10   7 FOBS=   91.7 SIGMA=   4.6 PHAS=  255.9 FOM= 0.66
INDE -11  10   8 FOBS=  113.1 SIGMA=   3.9 PHAS=   75.5 FOM= 0.94
INDE -11  10   9 FOBS=  293.0 SIGMA=   1.6 PHAS=  182.9 FOM= 0.94
INDE -11  10  10 FOBS=   80.6 SIGMA=   4.6 PHAS=  236.0 FOM= 0.38
INDE -11  10  11 FOBS=  101.9 SIGMA=   3.7 PHAS=  151.1 FOM= 0.80
INDE -11  10  12 FOBS=  236.4 SIGMA=   1.7 PHAS=  246.2 FOM= 1.00
INDE -11  10  13 FOBS=   62.1 SIGMA=   7.3 PHAS=  126.7 FOM= 0.05
INDE -11  10  14 FOBS=   77.2 SIGMA=   5.3 PHAS=   15.9 FOM= 0.27
INDE -11  11   1 FOBS=  139.5 SIGMA= 110.4 PHAS=  193.4 FOM= 0.10
INDE -11  11   2 FOBS=   92.2 SIGMA=   6.7 PHAS=  324.6 FOM= 0.19
INDE -11  11   3 FOBS=   63.5 SIGMA=   9.0 PHAS=  344.2 FOM= 0.17
INDE -11  11   4 FOBS=  191.9 SIGMA=   2.7 PHAS=  181.7 FOM= 0.93
INDE -11  11   5 FOBS=  259.1 SIGMA=   2.2 PHAS=  278.8 FOM= 0.56
INDE -11  11   6 FOBS=  130.7 SIGMA=   3.2 PHAS=  292.2 FOM= 0.51
INDE -11  11   7 FOBS=   47.5 SIGMA=   9.9 PHAS=  114.1 FOM= 0.12
INDE -11  11   8 FOBS=  101.5 SIGMA=   3.6 PHAS=  243.6 FOM= 0.92
INDE -11  11   9 FOBS=  136.7 SIGMA=   3.0 PHAS=  131.7 FOM= 0.89
INDE -11  11  10 FOBS=  279.6 SIGMA=   1.5 PHAS=   37.5 FOM= 1.00
INDE -11  11  11 FOBS=  161.6 SIGMA=   2.4 PHAS=  199.6 FOM= 0.86
INDE -11  11  12 FOBS=  168.4 SIGMA=   2.2 PHAS=  127.7 FOM= 0.91
INDE -11  11  13 FOBS=  198.0 SIGMA=   2.5 PHAS=   33.2 FOM= 0.96
INDE -11  11  14 FOBS=   72.5 SIGMA=   5.3 PHAS=  120.5 FOM= 0.54
INDE -11  12   1 FOBS=  100.2 SIGMA=   6.0 PHAS=   54.6 FOM= 0.46
INDE -11  12   2 FOBS=  162.6 SIGMA=   3.6 PHAS=  287.4 FOM= 0.42
INDE -11  12   3 FOBS=  241.5 SIGMA=   2.5 PHAS=   40.4 FOM= 0.81
INDE -11  12   4 FOBS=  319.6 SIGMA=   2.0 PHAS=  130.7 FOM= 0.91
INDE -11  12   5 FOBS=  290.4 SIGMA=   1.7 PHAS=  172.6 FOM= 0.75
INDE -11  12   6 FOBS=  257.4 SIGMA=   2.0 PHAS=  344.1 FOM= 0.98
INDE -11  12   7 FOBS=  268.6 SIGMA=   2.0 PHAS=  172.5 FOM= 1.00
INDE -11  12   8 FOBS=   98.9 SIGMA=   3.6 PHAS=   48.5 FOM= 0.27
INDE -11  12   9 FOBS=  240.5 SIGMA=   1.7 PHAS=   73.7 FOM= 0.85
INDE -11  12  10 FOBS=  187.7 SIGMA=   2.0 PHAS=  188.6 FOM= 0.81
INDE -11  12  11 FOBS=  188.6 SIGMA=   2.0 PHAS=   14.7 FOM= 0.77
INDE -11  12  12 FOBS=  358.2 SIGMA=   1.6 PHAS=  221.5 FOM= 0.93
INDE -11  12  13 FOBS=  153.6 SIGMA=   3.1 PHAS=  119.4 FOM= 0.56
INDE -11  12  14 FOBS=   67.3 SIGMA=  36.7 PHAS=  351.6 FOM= 0.03
INDE -11  13   1 FOBS=  162.8 SIGMA=   3.7 PHAS=  347.9 FOM= 0.21
INDE -11  13   2 FOBS=  115.2 SIGMA=   4.9 PHAS=  208.1 FOM= 0.04
INDE -11  13   3 FOBS=  186.9 SIGMA=   3.0 PHAS=   38.0 FOM= 0.27
INDE -11  13   4 FOBS=   71.8 SIGMA=   7.6 PHAS=  281.3 FOM= 0.28
INDE -11  13   5 FOBS=  173.8 SIGMA=   2.7 PHAS=   65.4 FOM= 0.94
INDE -11  13   6 FOBS=  101.6 SIGMA=   3.9 PHAS=   11.4 FOM= 0.48
INDE -11  13   7 FOBS=  189.7 SIGMA=   3.8 PHAS=  295.5 FOM= 0.87
INDE -11  13   8 FOBS=  194.6 SIGMA=   1.9 PHAS=   99.4 FOM= 0.97
INDE -11  13   9 FOBS=   52.9 SIGMA=   8.0 PHAS=  200.2 FOM= 0.45
INDE -11  13  10 FOBS=  154.2 SIGMA=   2.2 PHAS=   24.6 FOM= 0.58
INDE -11  13  11 FOBS=  150.5 SIGMA=   2.3 PHAS=  105.3 FOM= 0.84
INDE -11  13  12 FOBS=  171.8 SIGMA=   2.4 PHAS=  161.3 FOM= 0.90
INDE -11  13  13 FOBS=  169.8 SIGMA=   2.8 PHAS=  284.8 FOM= 0.82
INDE -11  14   1 FOBS=  143.3 SIGMA=   4.6 PHAS=  336.9 FOM= 0.41
INDE -11  14   2 FOBS=  282.9 SIGMA=   2.3 PHAS=  152.7 FOM= 0.96
INDE -11  14   3 FOBS=  156.1 SIGMA=   3.5 PHAS=  227.0 FOM= 0.87
INDE -11  14   4 FOBS=  232.4 SIGMA=   2.2 PHAS=  146.1 FOM= 0.90
INDE -11  14   5 FOBS=  303.1 SIGMA=   1.8 PHAS=  324.1 FOM= 0.90
INDE -11  14   6 FOBS=  188.7 SIGMA=   2.4 PHAS=  215.7 FOM= 0.74
INDE -11  14   7 FOBS=  116.4 SIGMA=   4.7 PHAS=  325.6 FOM= 0.79
INDE -11  14   8 FOBS=  168.3 SIGMA=   4.2 PHAS=  118.5 FOM= 0.88
INDE -11  14   9 FOBS=  230.2 SIGMA=   2.0 PHAS=  277.5 FOM= 0.95
INDE -11  14  10 FOBS=  124.5 SIGMA=   2.7 PHAS=   64.9 FOM= 0.43
INDE -11  14  11 FOBS=   87.6 SIGMA=   4.4 PHAS=   85.8 FOM= 0.95
INDE -11  14  12 FOBS=  193.0 SIGMA=   1.9 PHAS=  288.0 FOM= 0.96
INDE -11  14  13 FOBS=  170.1 SIGMA=   2.9 PHAS=  234.7 FOM= 0.44
```

Fig. 10A-19

```
INDE -11  15   1 FOBS=   41.5 SIGMA=  19.2 PHAS= 245.1 FOM= 0.15
INDE -11  15   2 FOBS=   71.9 SIGMA=   7.4 PHAS= 342.5 FOM= 0.15
INDE -11  15   3 FOBS=   87.9 SIGMA=   5.9 PHAS= 169.4 FOM= 0.60
INDE -11  15   4 FOBS=  206.8 SIGMA=   2.7 PHAS=  17.7 FOM= 0.82
INDE -11  15   5 FOBS=  158.8 SIGMA=   2.9 PHAS= 331.0 FOM= 0.82
INDE -11  15   6 FOBS=  277.3 SIGMA=   1.5 PHAS= 123.6 FOM= 0.93
INDE -11  15   7 FOBS=   71.5 SIGMA=  10.1 PHAS=  68.6 FOM= 0.32
INDE -11  15   8 FOBS=  176.5 SIGMA=   3.8 PHAS= 211.1 FOM= 0.20
INDE -11  15   9 FOBS=  159.3 SIGMA=   5.7 PHAS= 157.8 FOM= 0.22
INDE -11  15  10 FOBS=   92.5 SIGMA=   4.9 PHAS=  86.1 FOM= 0.74
INDE -11  15  11 FOBS=  128.1 SIGMA=   2.8 PHAS=  72.6 FOM= 0.86
INDE -11  15  12 FOBS=   91.2 SIGMA=   3.9 PHAS= 242.4 FOM= 0.92
INDE -11  15  13 FOBS=  198.3 SIGMA=   2.7 PHAS=  83.2 FOM= 0.92
INDE -11  16   1 FOBS=   77.8 SIGMA=   8.2 PHAS= 222.8 FOM= 0.50
INDE -11  16   2 FOBS=  260.3 SIGMA=   2.7 PHAS=  89.6 FOM= 0.78
INDE -11  16   3 FOBS=  246.4 SIGMA=   2.2 PHAS= 313.2 FOM= 0.95
INDE -11  16   4 FOBS=  102.4 SIGMA=   4.5 PHAS= 298.8 FOM= 0.13
INDE -11  16   5 FOBS=  215.4 SIGMA=   2.3 PHAS=  81.9 FOM= 0.44
INDE -11  16   6 FOBS=   98.7 SIGMA=   3.8 PHAS= 159.7 FOM= 0.87
INDE -11  16   7 FOBS=  257.7 SIGMA=   3.3 PHAS= 310.2 FOM= 0.61
INDE -11  16   8 FOBS=  112.7 SIGMA=   5.9 PHAS= 191.7 FOM= 0.16
INDE -11  16   9 FOBS=  131.3 SIGMA=   7.0 PHAS= 213.2 FOM= 0.05
INDE -11  16  10 FOBS=   78.5 SIGMA=   7.5 PHAS= 352.6 FOM= 0.10
INDE -11  16  11 FOBS=   80.1 SIGMA=   4.1 PHAS= 251.2 FOM= 0.96
INDE -11  16  12 FOBS=   60.3 SIGMA=   5.4 PHAS=  16.2 FOM= 0.38
INDE -11  17   1 FOBS=  238.3 SIGMA=   2.5 PHAS= 250.8 FOM= 0.87
INDE -11  17   2 FOBS=   49.4 SIGMA=  12.3 PHAS=  59.9 FOM= 0.38
INDE -11  17   3 FOBS=  114.4 SIGMA=   4.3 PHAS= 142.6 FOM= 0.82
INDE -11  17   4 FOBS=  226.0 SIGMA=   2.9 PHAS=  28.2 FOM= 0.48
INDE -11  17   5 FOBS=  167.7 SIGMA=   2.9 PHAS= 100.2 FOM= 0.81
INDE -11  17   6 FOBS=  190.4 SIGMA=   4.0 PHAS= 205.3 FOM= 0.75
INDE -11  17   7 FOBS=   65.3 SIGMA=  48.2 PHAS=   1.9 FOM= 0.14
INDE -11  17   8 FOBS=   90.5 SIGMA=   8.2 PHAS= 276.4 FOM= 0.12
INDE -11  17   9 FOBS=  130.8 SIGMA=   7.3 PHAS= 137.2 FOM= 0.65
INDE -11  17  10 FOBS=   98.2 SIGMA=   6.1 PHAS= 313.2 FOM= 0.35
INDE -11  17  11 FOBS=   40.0 SIGMA=  18.1 PHAS= 209.1 FOM= 0.12
INDE -11  17  12 FOBS=  147.5 SIGMA=   2.8 PHAS=  76.9 FOM= 0.79
INDE -11  18   1 FOBS=  152.3 SIGMA=   4.0 PHAS= 292.2 FOM= 0.24
INDE -11  18   2 FOBS=  284.9 SIGMA=   2.1 PHAS=  65.3 FOM= 0.79
INDE -11  18   3 FOBS=  124.6 SIGMA=   4.8 PHAS= 152.8 FOM= 0.61
INDE -11  18   4 FOBS=   76.0 SIGMA=   5.9 PHAS=  18.4 FOM= 0.58
INDE -11  18   5 FOBS=   80.9 SIGMA=   4.1 PHAS= 294.6 FOM= 0.29
INDE -11  18   6 FOBS=   65.8 SIGMA=  10.5 PHAS= 254.3 FOM= 0.22
INDE -11  18   7 FOBS=  119.3 SIGMA=   6.3 PHAS= 289.0 FOM= 0.24
INDE -11  18   8 FOBS=  101.0 SIGMA=   8.8 PHAS= 116.8 FOM= 0.04
INDE -11  18   9 FOBS=  126.0 SIGMA=   8.5 PHAS= 269.2 FOM= 0.11
INDE -11  18  10 FOBS=  280.8 SIGMA=   2.4 PHAS= 147.4 FOM= 0.23
INDE -11  18  11 FOBS=   83.7 SIGMA=   6.8 PHAS=  29.1 FOM= 0.04
INDE -11  19   1 FOBS=  156.4 SIGMA=   3.9 PHAS= 303.9 FOM= 0.76
INDE -11  19   2 FOBS=   93.6 SIGMA=   5.8 PHAS=  96.8 FOM= 0.48
INDE -11  19   3 FOBS=  261.4 SIGMA=   3.1 PHAS= 334.9 FOM= 0.94
INDE -11  19   4 FOBS=  232.7 SIGMA=   2.4 PHAS= 314.5 FOM= 0.71
INDE -11  19   5 FOBS=  173.4 SIGMA=   2.2 PHAS= 144.1 FOM= 0.81
INDE -11  19   6 FOBS=  129.6 SIGMA=   5.8 PHAS= 279.1 FOM= 0.65
INDE -11  19   7 FOBS=   70.1 SIGMA=   9.9 PHAS=  76.9 FOM= 0.27
INDE -11  19   8 FOBS=  145.1 SIGMA=   5.3 PHAS= 214.8 FOM= 0.55
INDE -11  19   9 FOBS=   77.3 SIGMA=  15.3 PHAS= 195.4 FOM= 0.60
INDE -11  19  10 FOBS=  119.6 SIGMA=   5.1 PHAS= 100.1 FOM= 0.83
INDE -11  19  11 FOBS=  112.5 SIGMA=   5.2 PHAS= 203.0 FOM= 0.52
INDE -11  20   1 FOBS=   48.9 SIGMA=  13.1 PHAS= 359.5 FOM= 0.07
INDE -11  20   2 FOBS=   95.5 SIGMA=   5.4 PHAS= 323.4 FOM= 0.10
INDE -11  20   3 FOBS=   67.2 SIGMA=   7.4 PHAS= 154.8 FOM= 0.06
INDE -11  20   4 FOBS=  155.3 SIGMA=   3.4 PHAS= 323.8 FOM= 0.62
INDE -11  20   5 FOBS=   45.8 SIGMA=   8.1 PHAS= 176.4 FOM= 0.34
INDE -11  20   6 FOBS=  149.9 SIGMA=   4.9 PHAS= 293.9 FOM= 0.86
INDE -11  20   7 FOBS=  318.7 SIGMA=   2.4 PHAS= 245.0 FOM= 0.87
INDE -11  20   8 FOBS=   66.9 SIGMA=   9.7 PHAS= 205.2 FOM= 0.26
INDE -11  20   9 FOBS=  245.3 SIGMA=   4.9 PHAS= 193.4 FOM= 0.06
INDE -11  20  10 FOBS=  102.8 SIGMA=   7.2 PHAS= 214.5 FOM= 0.03
INDE -11  21   1 FOBS=   44.7 SIGMA=  22.3 PHAS= 273.0 FOM= 0.14
INDE -11  21   2 FOBS=   63.5 SIGMA=   8.9 PHAS= 101.5 FOM= 0.25
```

Fig. 10A-20

```
INDE -11  21   3 FOBS=   45.2 SIGMA=  11.5 PHAS= 275.4 FOM= 0.17
INDE -11  21   4 FOBS=  184.5 SIGMA=   2.9 PHAS= 112.4 FOM= 0.54
INDE -11  21   5 FOBS=  132.7 SIGMA=   3.4 PHAS=  96.3 FOM= 0.94
INDE -11  21   6 FOBS=  192.3 SIGMA=   3.7 PHAS= 357.5 FOM= 0.88
INDE -11  21   7 FOBS=   87.5 SIGMA=   8.4 PHAS= 171.1 FOM= 0.76
INDE -11  21   8 FOBS=  144.0 SIGMA=   4.6 PHAS= 327.1 FOM= 0.54
INDE -11  21   9 FOBS=  334.5 SIGMA=   3.0 PHAS=  18.3 FOM= 0.66
INDE -11  21  10 FOBS=   58.0 SIGMA=  21.3 PHAS= 156.1 FOM= 0.19
INDE -11  22   1 FOBS=  136.3 SIGMA=   4.3 PHAS=  52.4 FOM= 0.73
INDE -11  22   2 FOBS=  105.6 SIGMA=   5.0 PHAS= 294.0 FOM= 0.63
INDE -11  22   3 FOBS=  155.8 SIGMA=   3.2 PHAS= 105.0 FOM= 0.92
INDE -11  22   4 FOBS=  203.4 SIGMA=   2.5 PHAS=  72.5 FOM= 0.96
INDE -11  22   5 FOBS=  123.0 SIGMA=   5.9 PHAS= 313.6 FOM= 0.64
INDE -11  22   6 FOBS=   58.9 SIGMA=  11.3 PHAS= 125.1 FOM= 0.37
INDE -11  22   7 FOBS=  154.9 SIGMA=   4.4 PHAS=  49.0 FOM= 0.26
INDE -11  22   8 FOBS=  311.7 SIGMA=   2.6 PHAS= 155.5 FOM= 0.30
INDE -11  22   9 FOBS=   69.4 SIGMA=  25.3 PHAS=  98.3 FOM= 0.12
INDE -11  23   1 FOBS=  115.8 SIGMA=   4.7 PHAS= 337.6 FOM= 0.23
INDE -11  23   2 FOBS=   72.0 SIGMA=   7.0 PHAS= 212.3 FOM= 0.36
INDE -11  23   3 FOBS=   97.4 SIGMA=   4.7 PHAS= 334.8 FOM= 0.25
INDE -11  23   4 FOBS=   92.3 SIGMA=   4.7 PHAS= 280.0 FOM= 0.37
INDE -11  23   5 FOBS=   77.5 SIGMA=   9.0 PHAS= 158.7 FOM= 0.84
INDE -11  23   6 FOBS=  127.6 SIGMA=   3.4 PHAS= 264.4 FOM= 0.84
INDE -11  23   7 FOBS=   50.9 SIGMA=  22.9 PHAS=  53.0 FOM= 0.10
INDE -11  23   8 FOBS=  150.5 SIGMA=   4.2 PHAS= 179.0 FOM= 0.51
INDE -11  24   1 FOBS=   83.2 SIGMA=   6.4 PHAS= 211.6 FOM= 0.22
INDE -11  24   2 FOBS=   44.0 SIGMA=  19.7 PHAS= 324.6 FOM= 0.22
INDE -11  24   3 FOBS=  131.7 SIGMA=   3.7 PHAS=  90.2 FOM= 0.59
INDE -11  24   4 FOBS=   44.0 SIGMA=  12.9 PHAS=  32.6 FOM= 0.04
INDE -11  24   5 FOBS=  194.8 SIGMA=   2.3 PHAS= 109.5 FOM= 0.90
INDE -11  24   6 FOBS=   49.0 SIGMA=   7.3 PHAS= 194.0 FOM= 0.62
INDE -11  24   7 FOBS=  123.5 SIGMA=   5.1 PHAS=  94.7 FOM= 0.49
INDE -11  25   1 FOBS=  209.6 SIGMA=   2.7 PHAS= 219.8 FOM= 0.89
INDE -11  25   2 FOBS=  163.3 SIGMA=   3.0 PHAS=  39.7 FOM= 0.75
INDE -11  25   3 FOBS=   45.0 SIGMA=  10.5 PHAS= 144.8 FOM= 0.11
INDE -11  25   4 FOBS=  170.8 SIGMA=   3.1 PHAS= 316.6 FOM= 0.79
INDE -11  25   5 FOBS=   88.4 SIGMA=   4.0 PHAS=  79.7 FOM= 0.19
INDE -11  25   6 FOBS=  125.3 SIGMA=   4.3 PHAS= 190.1 FOM= 0.17
INDE -11  26   1 FOBS=   52.2 SIGMA=  11.6 PHAS= 276.7 FOM= 0.15
INDE -11  26   2 FOBS=  145.0 SIGMA=   3.5 PHAS=  31.0 FOM= 0.90
INDE -11  26   3 FOBS=   92.7 SIGMA=   5.5 PHAS= 111.5 FOM= 0.52
INDE -11  26   4 FOBS=  121.8 SIGMA=   4.9 PHAS= 349.2 FOM= 0.63
INDE -10   0   1 FOBS=  112.0 SIGMA=   6.3 PHAS= 180.0 FOM= 0.13
INDE -10   0   2 FOBS=  101.5 SIGMA=   6.6 PHAS=   0.0 FOM= 0.06
INDE -10   0   3 FOBS=  201.8 SIGMA=   3.3 PHAS= 180.0 FOM= 0.29
INDE -10   0   4 FOBS=  349.2 SIGMA=   2.1 PHAS= 180.0 FOM= 0.13
INDE -10   0   5 FOBS=  121.3 SIGMA=   5.0 PHAS= 180.0 FOM= 0.14
INDE -10   0   6 FOBS=   99.4 SIGMA=   6.0 PHAS=   0.0 FOM= 0.02
INDE -10   0   7 FOBS=  133.2 SIGMA=   4.2 PHAS=   0.0 FOM= 0.63
INDE -10   0   8 FOBS=  245.9 SIGMA=   3.2 PHAS=   0.0 FOM= 1.00
INDE -10   0   9 FOBS=  519.5 SIGMA=   1.8 PHAS= 180.0 FOM= 1.00
INDE -10   0  10 FOBS=   99.3 SIGMA=   5.8 PHAS= 180.0 FOM= 0.05
INDE -10   0  11 FOBS=  180.5 SIGMA=   3.1 PHAS=   0.0 FOM= 0.58
INDE -10   0  12 FOBS=   92.7 SIGMA=   7.3 PHAS= 180.0 FOM= 0.47
INDE -10   0  13 FOBS=   65.5 SIGMA=  10.4 PHAS=   0.0 FOM= 0.36
INDE -10   0  14 FOBS=   39.8 SIGMA=  28.4 PHAS= 180.0 FOM= 0.47
INDE -10   0  15 FOBS=  269.7 SIGMA=   2.3 PHAS= 180.0 FOM= 0.97
INDE -10   1   1 FOBS=   46.0 SIGMA=  10.7 PHAS= 290.7 FOM= 0.19
INDE -10   1   2 FOBS=  169.0 SIGMA=   2.9 PHAS=  55.2 FOM= 0.25
INDE -10   1   3 FOBS=  232.2 SIGMA=   2.1 PHAS= 201.6 FOM= 0.95
INDE -10   1   4 FOBS=  168.7 SIGMA=   2.8 PHAS= 265.1 FOM= 0.93
INDE -10   1   5 FOBS=  137.2 SIGMA=   3.2 PHAS=  29.3 FOM= 0.23
INDE -10   1   6 FOBS=  322.6 SIGMA=   1.7 PHAS= 133.4 FOM= 0.97
INDE -10   1   7 FOBS=   92.5 SIGMA=   4.4 PHAS= 357.5 FOM= 0.82
INDE -10   1   8 FOBS=  168.0 SIGMA=   2.6 PHAS= 133.1 FOM= 0.69
INDE -10   1   9 FOBS=   97.6 SIGMA=   3.9 PHAS= 182.5 FOM= 0.56
INDE -10   1  10 FOBS=  184.2 SIGMA=   2.2 PHAS= 327.4 FOM= 0.68
INDE -10   1  11 FOBS=   82.4 SIGMA=   4.9 PHAS=  42.9 FOM= 0.59
INDE -10   1  12 FOBS=   49.0 SIGMA=   9.4 PHAS= 280.1 FOM= 0.43
INDE -10   1  13 FOBS=  159.7 SIGMA=   3.3 PHAS=  62.2 FOM= 0.84
INDE -10   1  14 FOBS=  222.3 SIGMA=   1.9 PHAS= 208.5 FOM= 0.82
```

Fig. 10A-21

```
INDE  -10   1  15  FOBS=   182.1  SIGMA=  2.2  PHAS=   73.3  FOM=  0.94
INDE  -10   2   1  FOBS=   159.0  SIGMA=  3.2  PHAS=  119.7  FOM=  0.76
INDE  -10   2   2  FOBS=   371.9  SIGMA=  1.5  PHAS=  185.5  FOM=  0.80
INDE  -10   2   3  FOBS=   221.1  SIGMA=  2.2  PHAS=    8.4  FOM=  0.90
INDE  -10   2   4  FOBS=   150.0  SIGMA=  3.1  PHAS=  324.6  FOM=  0.96
INDE  -10   2   5  FOBS=   274.6  SIGMA=  1.7  PHAS=  175.6  FOM=  0.96
INDE  -10   2   6  FOBS=   425.5  SIGMA=  1.3  PHAS=    8.3  FOM=  0.66
INDE  -10   2   7  FOBS=   336.1  SIGMA=  1.5  PHAS=   41.4  FOM=  0.54
INDE  -10   2   8  FOBS=   110.3  SIGMA=  3.7  PHAS=  254.4  FOM=  0.86
INDE  -10   2   9  FOBS=   316.6  SIGMA=  1.4  PHAS=   36.1  FOM=  1.00
INDE  -10   2  10  FOBS=   319.4  SIGMA=  1.4  PHAS=  237.9  FOM=  0.98
INDE  -10   2  11  FOBS=    99.8  SIGMA=  3.9  PHAS=  255.7  FOM=  0.29
INDE  -10   2  12  FOBS=   188.2  SIGMA=  2.5  PHAS=  107.7  FOM=  0.96
INDE  -10   2  13  FOBS=   156.1  SIGMA=  3.1  PHAS=  327.2  FOM=  0.79
INDE  -10   2  14  FOBS=   293.0  SIGMA=  1.6  PHAS=  189.8  FOM=  0.98
INDE  -10   2  15  FOBS=   141.9  SIGMA=  2.9  PHAS=   53.5  FOM=  0.21
INDE  -10   3   1  FOBS=   291.8  SIGMA=  1.9  PHAS=  222.9  FOM=  0.97
INDE  -10   3   2  FOBS=   320.7  SIGMA=  1.7  PHAS=   85.9  FOM=  0.89
INDE  -10   3   3  FOBS=   201.5  SIGMA=  2.4  PHAS=  177.8  FOM=  0.40
INDE  -10   3   4  FOBS=   273.3  SIGMA=  1.8  PHAS=   98.7  FOM=  0.78
INDE  -10   3   5  FOBS=   141.6  SIGMA=  3.1  PHAS=  179.5  FOM=  0.68
INDE  -10   3   6  FOBS=   154.4  SIGMA=  2.8  PHAS=   95.2  FOM=  0.74
INDE  -10   3   7  FOBS=   147.5  SIGMA=  2.7  PHAS=  122.5  FOM=  0.75
INDE  -10   3   8  FOBS=   350.9  SIGMA=  1.4  PHAS=  167.7  FOM=  0.98
INDE  -10   3   9  FOBS=   168.6  SIGMA=  2.3  PHAS=  272.6  FOM=  0.91
INDE  -10   3  10  FOBS=   339.6  SIGMA=  1.4  PHAS=  275.5  FOM=  0.96
INDE  -10   3  11  FOBS=   340.5  SIGMA=  1.4  PHAS=  116.8  FOM=  0.98
INDE  -10   3  12  FOBS=   192.2  SIGMA=  2.5  PHAS=  342.0  FOM=  0.83
INDE  -10   3  13  FOBS=   370.1  SIGMA=  1.5  PHAS=  133.8  FOM=  0.73
INDE  -10   3  14  FOBS=    68.2  SIGMA=  5.9  PHAS=   97.9  FOM=  0.54
INDE  -10   3  15  FOBS=   104.1  SIGMA=  4.1  PHAS=   69.0  FOM=  0.78
INDE  -10   4   1  FOBS=    63.3  SIGMA=  8.3  PHAS=  221.6  FOM=  0.18
INDE  -10   4   2  FOBS=   230.7  SIGMA=  2.2  PHAS=   74.2  FOM=  0.98
INDE  -10   4   3  FOBS=   375.0  SIGMA=  1.5  PHAS=  183.9  FOM=  0.98
INDE  -10   4   4  FOBS=   332.5  SIGMA=  1.5  PHAS=  227.2  FOM=  0.95
INDE  -10   4   5  FOBS=   440.1  SIGMA=  1.3  PHAS=  117.9  FOM=  0.83
INDE  -10   4   6  FOBS=   102.5  SIGMA=  4.1  PHAS=  138.5  FOM=  0.79
INDE  -10   4   7  FOBS=   215.0  SIGMA=  1.9  PHAS=  308.5  FOM=  0.81
INDE  -10   4   8  FOBS=    56.8  SIGMA=  7.2  PHAS=  194.3  FOM=  0.15
INDE  -10   4   9  FOBS=   492.4  SIGMA=  1.3  PHAS=  329.9  FOM=  0.97
INDE  -10   4  10  FOBS=   343.4  SIGMA=  1.4  PHAS=  140.4  FOM=  0.93
INDE  -10   4  11  FOBS=   408.3  SIGMA=  1.2  PHAS=  224.4  FOM=  0.99
INDE  -10   4  12  FOBS=   392.7  SIGMA=  1.5  PHAS=  269.0  FOM=  0.98
INDE  -10   4  13  FOBS=   255.3  SIGMA=  2.0  PHAS=  187.0  FOM=  0.72
INDE  -10   4  14  FOBS=    79.8  SIGMA=  5.3  PHAS=  163.0  FOM=  0.58
INDE  -10   4  15  FOBS=   191.6  SIGMA=  2.2  PHAS=   49.1  FOM=  0.93
INDE  -10   5   1  FOBS=   159.1  SIGMA=  3.3  PHAS=  229.7  FOM=  0.70
INDE  -10   5   2  FOBS=    88.8  SIGMA=  5.3  PHAS=   35.5  FOM=  0.18
INDE  -10   5   3  FOBS=   482.2  SIGMA=  1.3  PHAS=  322.5  FOM=  0.98
INDE  -10   5   4  FOBS=   189.8  SIGMA=  2.5  PHAS=  304.2  FOM=  0.93
INDE  -10   5   5  FOBS=   366.6  SIGMA=  1.5  PHAS=  244.2  FOM=  0.95
INDE  -10   5   6  FOBS=   464.2  SIGMA=  1.3  PHAS=  210.3  FOM=  0.98
INDE  -10   5   7  FOBS=   163.6  SIGMA=  2.5  PHAS=  347.5  FOM=  0.89
INDE  -10   5   8  FOBS=    61.7  SIGMA=  6.2  PHAS=  101.5  FOM=  0.04
INDE  -10   5   9  FOBS=    78.2  SIGMA=  4.8  PHAS=   46.0  FOM=  0.03
INDE  -10   5  10  FOBS=   100.0  SIGMA=  3.9  PHAS=  323.2  FOM=  0.13
INDE  -10   5  11  FOBS=   185.2  SIGMA=  2.2  PHAS=   86.3  FOM=  0.42
INDE  -10   5  12  FOBS=   200.2  SIGMA=  2.4  PHAS=  171.8  FOM=  0.32
INDE  -10   5  13  FOBS=   192.5  SIGMA=  2.3  PHAS=  213.6  FOM=  0.79
INDE  -10   5  14  FOBS=    69.7  SIGMA=  6.0  PHAS=  327.1  FOM=  0.17
INDE  -10   5  15  FOBS=   190.2  SIGMA=  2.2  PHAS=  239.1  FOM=  0.85
INDE  -10   6   1  FOBS=   100.2  SIGMA=  5.8  PHAS=   92.1  FOM=  0.25
INDE  -10   6   2  FOBS=    96.4  SIGMA=  4.7  PHAS=  278.1  FOM=  0.64
INDE  -10   6   3  FOBS=   153.1  SIGMA=  3.4  PHAS=  347.4  FOM=  0.95
INDE  -10   6   4  FOBS=   316.1  SIGMA=  1.6  PHAS=  325.3  FOM=  0.96
INDE  -10   6   5  FOBS=   225.8  SIGMA=  2.0  PHAS=   50.8  FOM=  0.95
INDE  -10   6   6  FOBS=   168.5  SIGMA=  2.4  PHAS=  140.1  FOM=  0.97
INDE  -10   6   7  FOBS=   154.3  SIGMA=  2.8  PHAS=   69.9  FOM=  0.99
INDE  -10   6   8  FOBS=   163.9  SIGMA=  2.5  PHAS=  353.6  FOM=  0.94
INDE  -10   6   9  FOBS=   226.8  SIGMA=  1.8  PHAS=  110.3  FOM=  0.81
INDE  -10   6  10  FOBS=   256.3  SIGMA=  1.7  PHAS=  333.7  FOM=  0.94
```

Fig. 10A-22

```
INDE -10   6 11 FOBS=  145.3 SIGMA=  2.7 PHAS= 116.6 FOM= 0.17
INDE -10   6 12 FOBS=  130.5 SIGMA=  4.0 PHAS=  69.5 FOM= 0.88
INDE -10   6 13 FOBS=  212.4 SIGMA=  2.0 PHAS= 306.4 FOM= 0.94
INDE -10   6 14 FOBS=  175.7 SIGMA=  2.5 PHAS= 145.3 FOM= 0.82
INDE -10   6 15 FOBS=  240.1 SIGMA=  1.9 PHAS=  81.7 FOM= 0.96
INDE -10   7  1 FOBS=  187.4 SIGMA=  3.4 PHAS= 275.3 FOM= 0.28
INDE -10   7  2 FOBS=  354.0 SIGMA=  1.6 PHAS=  55.5 FOM= 0.73
INDE -10   7  3 FOBS=  216.4 SIGMA=  2.2 PHAS=  96.7 FOM= 0.25
INDE -10   7  4 FOBS=  270.1 SIGMA=  1.8 PHAS=  19.4 FOM= 0.89
INDE -10   7  5 FOBS=   72.5 SIGMA=  5.4 PHAS= 254.3 FOM= 0.36
INDE -10   7  6 FOBS=  104.7 SIGMA=  4.0 PHAS= 283.7 FOM= 0.77
INDE -10   7  7 FOBS=  202.4 SIGMA=  2.4 PHAS= 326.0 FOM= 0.60
INDE -10   7  8 FOBS=  128.5 SIGMA=  3.1 PHAS= 253.5 FOM= 0.91
INDE -10   7  9 FOBS=   53.8 SIGMA=  7.7 PHAS= 317.2 FOM= 0.53
INDE -10   7 10 FOBS=  304.4 SIGMA=  1.5 PHAS= 203.6 FOM= 0.94
INDE -10   7 11 FOBS=  237.0 SIGMA=  1.8 PHAS=  37.4 FOM= 0.92
INDE -10   7 12 FOBS=  219.9 SIGMA=  2.3 PHAS= 235.6 FOM= 0.94
INDE -10   7 13 FOBS=  138.6 SIGMA=  3.0 PHAS= 273.6 FOM= 0.01
INDE -10   7 14 FOBS=  139.3 SIGMA=  3.3 PHAS= 129.3 FOM= 0.85
INDE -10   7 15 FOBS=   82.1 SIGMA=  5.3 PHAS= 120.1 FOM= 0.08
INDE -10   8  1 FOBS=  100.7 SIGMA=  5.8 PHAS=  80.9 FOM= 0.24
INDE -10   8  2 FOBS=  203.6 SIGMA=  3.4 PHAS=  30.2 FOM= 0.79
INDE -10   8  3 FOBS=  175.5 SIGMA=  2.8 PHAS=  48.7 FOM= 0.78
INDE -10   8  4 FOBS=  265.1 SIGMA=  1.8 PHAS= 308.1 FOM= 0.29
INDE -10   8  5 FOBS=  293.1 SIGMA=  1.6 PHAS= 224.7 FOM= 0.88
INDE -10   8  6 FOBS=  230.8 SIGMA=  1.8 PHAS= 110.9 FOM= 0.98
INDE -10   8  7 FOBS=  218.1 SIGMA=  2.2 PHAS=  23.7 FOM= 0.99
INDE -10   8  8 FOBS=   64.7 SIGMA=  5.0 PHAS=  43.1 FOM= 0.84
INDE -10   8  9 FOBS=   89.3 SIGMA=  4.3 PHAS= 267.1 FOM= 0.70
INDE -10   8 10 FOBS=  501.5 SIGMA=  1.2 PHAS=  79.8 FOM= 0.99
INDE -10   8 11 FOBS=  296.1 SIGMA=  1.5 PHAS= 250.7 FOM= 0.96
INDE -10   8 12 FOBS=  147.9 SIGMA=  3.4 PHAS= 184.1 FOM= 0.34
INDE -10   8 13 FOBS=  151.4 SIGMA=  2.5 PHAS= 175.3 FOM= 0.71
INDE -10   8 14 FOBS=   69.9 SIGMA=  6.5 PHAS= 204.6 FOM= 0.06
INDE -10   8 15 FOBS=  152.6 SIGMA=  2.9 PHAS= 220.4 FOM= 0.07
INDE -10   9  1 FOBS=   40.7 SIGMA= 19.1 PHAS= 316.9 FOM= 0.25
INDE -10   9  2 FOBS=   98.3 SIGMA=  5.7 PHAS= 104.4 FOM= 0.01
INDE -10   9  3 FOBS=   94.9 SIGMA=  6.7 PHAS= 171.9 FOM= 0.59
INDE -10   9  4 FOBS=   76.8 SIGMA=  4.9 PHAS= 157.9 FOM= 0.34
INDE -10   9  5 FOBS=  148.6 SIGMA=  2.7 PHAS=  90.3 FOM= 0.62
INDE -10   9  6 FOBS=  368.7 SIGMA=  1.3 PHAS=  88.7 FOM= 0.98
INDE -10   9  7 FOBS=  311.2 SIGMA=  1.7 PHAS=   8.9 FOM= 0.97
INDE -10   9  8 FOBS=  473.0 SIGMA=  1.1 PHAS= 191.0 FOM= 0.97
INDE -10   9  9 FOBS=  261.9 SIGMA=  1.6 PHAS=  25.5 FOM= 0.98
INDE -10   9 10 FOBS=  294.2 SIGMA=  1.4 PHAS= 258.0 FOM= 0.83
INDE -10   9 11 FOBS=  142.0 SIGMA=  2.8 PHAS=  25.2 FOM= 0.63
INDE -10   9 12 FOBS=   49.8 SIGMA= 12.0 PHAS= 333.7 FOM= 0.13
INDE -10   9 13 FOBS=  207.3 SIGMA=  1.9 PHAS= 133.9 FOM= 0.98
INDE -10   9 14 FOBS=  194.7 SIGMA=  2.3 PHAS=  48.3 FOM= 0.62
INDE -10   9 15 FOBS=   49.7 SIGMA=  9.3 PHAS= 283.1 FOM= 0.15
INDE -10  10  1 FOBS=   98.6 SIGMA=  5.4 PHAS= 237.6 FOM= 0.21
INDE -10  10  2 FOBS=  173.4 SIGMA=  3.1 PHAS= 206.4 FOM= 0.94
INDE -10  10  3 FOBS=  126.1 SIGMA=  4.2 PHAS= 288.5 FOM= 0.76
INDE -10  10  4 FOBS=  445.4 SIGMA=  1.7 PHAS=  72.0 FOM= 0.99
INDE -10  10  5 FOBS=   42.2 SIGMA=  9.5 PHAS=  72.6 FOM= 0.61
INDE -10  10  6 FOBS=  167.1 SIGMA=  2.4 PHAS= 316.5 FOM= 0.94
INDE -10  10  7 FOBS=  193.2 SIGMA=  2.0 PHAS= 271.7 FOM= 0.63
INDE -10  10  8 FOBS=   95.6 SIGMA=  3.8 PHAS=  98.8 FOM= 0.71
INDE -10  10  9 FOBS=   99.2 SIGMA=  3.8 PHAS= 265.6 FOM= 0.73
INDE -10  10 10 FOBS=  334.7 SIGMA=  1.3 PHAS=  27.9 FOM= 0.92
INDE -10  10 11 FOBS=  162.3 SIGMA=  2.4 PHAS= 307.9 FOM= 0.84
INDE -10  10 12 FOBS=  148.2 SIGMA=  3.5 PHAS= 147.4 FOM= 0.94
INDE -10  10 13 FOBS=  310.9 SIGMA=  1.4 PHAS=  44.4 FOM= 0.98
INDE -10  10 14 FOBS=  187.9 SIGMA=  2.4 PHAS= 214.6 FOM= 0.86
INDE -10  10 15 FOBS=  137.6 SIGMA=  8.1 PHAS= 212.4 FOM= 0.60
INDE -10  11  1 FOBS=   75.8 SIGMA=  7.1 PHAS= 167.4 FOM= 0.61
INDE -10  11  2 FOBS=   98.6 SIGMA=  5.3 PHAS= 293.9 FOM= 0.58
INDE -10  11  3 FOBS=   65.7 SIGMA=  7.8 PHAS= 216.4 FOM= 0.32
INDE -10  11  4 FOBS=  217.0 SIGMA=  2.3 PHAS=  96.0 FOM= 0.92
INDE -10  11  5 FOBS=  652.5 SIGMA=  1.1 PHAS= 208.6 FOM= 0.95
INDE -10  11  6 FOBS=  451.7 SIGMA=  1.3 PHAS= 350.6 FOM= 0.77
```

Fig. 10A-23

```
INDE -10  11   7 FOBS=  443.7 SIGMA=  1.3 PHAS= 187.1 FOM= 1.00
INDE -10  11   8 FOBS=   99.5 SIGMA=  3.9 PHAS= 132.8 FOM= 0.95
INDE -10  11   9 FOBS=  137.1 SIGMA=  2.6 PHAS= 196.7 FOM= 0.83
INDE -10  11  10 FOBS=  109.6 SIGMA=  3.3 PHAS= 355.0 FOM= 0.89
INDE -10  11  11 FOBS=  207.3 SIGMA=  1.9 PHAS= 123.5 FOM= 0.99
INDE -10  11  12 FOBS=  143.5 SIGMA=  3.4 PHAS= 339.5 FOM= 0.70
INDE -10  11  13 FOBS=  200.9 SIGMA=  1.9 PHAS= 247.0 FOM= 0.96
INDE -10  11  14 FOBS=   94.3 SIGMA=  4.4 PHAS= 169.1 FOM= 0.63
INDE -10  12   1 FOBS=  304.5 SIGMA=  1.9 PHAS= 163.6 FOM= 0.79
INDE -10  12   2 FOBS=  164.9 SIGMA=  3.2 PHAS=  19.8 FOM= 0.63
INDE -10  12   3 FOBS=   77.6 SIGMA=  6.2 PHAS= 112.2 FOM= 0.44
INDE -10  12   4 FOBS=  331.1 SIGMA=  1.9 PHAS=  33.0 FOM= 1.00
INDE -10  12   5 FOBS=  424.0 SIGMA=  1.4 PHAS= 283.7 FOM= 0.97
INDE -10  12   6 FOBS=  166.4 SIGMA=  2.6 PHAS= 219.3 FOM= 0.64
INDE -10  12   7 FOBS=  349.3 SIGMA=  1.6 PHAS=  61.5 FOM= 0.76
INDE -10  12   8 FOBS=  278.6 SIGMA=  1.4 PHAS= 186.1 FOM= 0.81
INDE -10  12   9 FOBS=  209.3 SIGMA=  1.7 PHAS=  23.9 FOM= 0.93
INDE -10  12  10 FOBS=  444.5 SIGMA=  1.1 PHAS=  83.6 FOM= 0.98
INDE -10  12  11 FOBS=  129.9 SIGMA=  2.9 PHAS= 302.2 FOM= 0.69
INDE -10  12  12 FOBS=   43.6 SIGMA= 10.4 PHAS= 276.4 FOM= 0.31
INDE -10  12  13 FOBS=  180.8 SIGMA=  2.2 PHAS=  78.6 FOM= 0.99
INDE -10  12  14 FOBS=  142.9 SIGMA=  2.8 PHAS= 119.6 FOM= 0.30
INDE -10  13   1 FOBS=  311.9 SIGMA=  2.4 PHAS=  76.2 FOM= 0.59
INDE -10  13   2 FOBS=  138.3 SIGMA=  3.9 PHAS=  27.5 FOM= 0.67
INDE -10  13   3 FOBS=  328.0 SIGMA=  1.8 PHAS=   5.6 FOM= 0.94
INDE -10  13   4 FOBS=  368.9 SIGMA=  1.6 PHAS=  59.0 FOM= 0.62
INDE -10  13   5 FOBS=   98.3 SIGMA=  4.0 PHAS=  22.4 FOM= 0.52
INDE -10  13   6 FOBS=  417.9 SIGMA=  2.4 PHAS= 311.7 FOM= 0.97
INDE -10  13   7 FOBS=  210.6 SIGMA=  3.3 PHAS= 286.1 FOM= 0.86
INDE -10  13   8 FOBS=  204.0 SIGMA=  2.1 PHAS=   9.8 FOM= 0.97
INDE -10  13   9 FOBS=  222.4 SIGMA=  1.8 PHAS= 117.5 FOM= 0.93
INDE -10  13  10 FOBS=  220.4 SIGMA=  1.7 PHAS= 238.0 FOM= 0.48
INDE -10  13  11 FOBS=  153.7 SIGMA=  2.5 PHAS=  83.6 FOM= 0.94
INDE -10  13  12 FOBS=  110.4 SIGMA=  4.4 PHAS=  92.1 FOM= 0.92
INDE -10  13  13 FOBS=  144.1 SIGMA=  2.7 PHAS= 353.2 FOM= 0.07
INDE -10  13  14 FOBS=  154.4 SIGMA=  2.5 PHAS=  58.4 FOM= 0.38
INDE -10  14   1 FOBS=  176.2 SIGMA=  3.5 PHAS=  28.8 FOM= 0.82
INDE -10  14   2 FOBS=  199.4 SIGMA=  2.7 PHAS=  60.0 FOM= 0.92
INDE -10  14   3 FOBS=  102.6 SIGMA=  4.7 PHAS= 192.8 FOM= 0.60
INDE -10  14   4 FOBS=  323.6 SIGMA=  1.4 PHAS= 334.9 FOM= 0.78
INDE -10  14   5 FOBS=  211.2 SIGMA=  2.1 PHAS=  93.0 FOM= 0.99
INDE -10  14   6 FOBS=  162.3 SIGMA=  6.5 PHAS= 250.1 FOM= 0.58
INDE -10  14   7 FOBS=   99.0 SIGMA=  8.1 PHAS=  59.0 FOM= 0.02
INDE -10  14   8 FOBS=   67.9 SIGMA=  9.0 PHAS= 138.2 FOM= 0.17
INDE -10  14   9 FOBS=   61.4 SIGMA=  8.9 PHAS=  15.7 FOM= 0.23
INDE -10  14  10 FOBS=  195.0 SIGMA=  2.0 PHAS= 120.2 FOM= 0.92
INDE -10  14  11 FOBS=   77.4 SIGMA=  4.4 PHAS= 280.8 FOM= 0.14
INDE -10  14  12 FOBS=   50.4 SIGMA= 10.4 PHAS=  50.1 FOM= 0.32
INDE -10  14  13 FOBS=  165.6 SIGMA=  2.3 PHAS= 201.4 FOM= 0.20
INDE -10  14  14 FOBS=  126.8 SIGMA=  8.5 PHAS=   7.8 FOM= 0.10
INDE -10  15   1 FOBS=  133.1 SIGMA=  4.4 PHAS= 335.6 FOM= 0.40
INDE -10  15   2 FOBS=  173.2 SIGMA=  3.5 PHAS= 314.9 FOM= 0.05
INDE -10  15   3 FOBS=  161.7 SIGMA=  3.1 PHAS= 215.9 FOM= 0.81
INDE -10  15   4 FOBS=  226.9 SIGMA=  1.9 PHAS= 175.9 FOM= 0.97
INDE -10  15   5 FOBS=  295.9 SIGMA=  1.5 PHAS= 349.6 FOM= 0.92
INDE -10  15   6 FOBS=  203.9 SIGMA=  4.3 PHAS= 252.0 FOM= 0.95
INDE -10  15   7 FOBS=  246.2 SIGMA=  3.8 PHAS= 231.9 FOM= 0.80
INDE -10  15   8 FOBS=  215.6 SIGMA=  3.1 PHAS= 128.0 FOM= 0.59
INDE -10  15   9 FOBS=  130.5 SIGMA=  5.2 PHAS= 235.7 FOM= 0.88
INDE -10  15  10 FOBS=   81.1 SIGMA=  5.7 PHAS= 149.7 FOM= 0.40
INDE -10  15  11 FOBS=  157.4 SIGMA=  2.5 PHAS= 359.3 FOM= 0.50
INDE -10  15  12 FOBS=   68.5 SIGMA=  6.4 PHAS=  45.1 FOM= 0.60
INDE -10  15  13 FOBS=  130.0 SIGMA=  2.9 PHAS= 324.5 FOM= 0.82
INDE -10  16   1 FOBS=  223.6 SIGMA=  2.6 PHAS= 164.8 FOM= 0.83
INDE -10  16   2 FOBS=  252.5 SIGMA=  2.2 PHAS= 194.0 FOM= 0.95
INDE -10  16   3 FOBS=  144.2 SIGMA=  3.7 PHAS= 355.5 FOM= 0.69
INDE -10  16   4 FOBS=  204.9 SIGMA=  2.5 PHAS=  98.2 FOM= 0.90
INDE -10  16   5 FOBS=  119.0 SIGMA=  3.1 PHAS= 130.8 FOM= 0.76
INDE -10  16   6 FOBS=  214.4 SIGMA=  3.4 PHAS= 247.1 FOM= 0.21
INDE -10  16   7 FOBS=  299.8 SIGMA=  3.3 PHAS=  88.2 FOM= 0.96
INDE -10  16   8 FOBS=   43.8 SIGMA= 18.7 PHAS= 251.6 FOM= 0.29
```

Fig. 10A-24

```
INDE -10  16   9 FOBS=  50.6 SIGMA= 12.5 PHAS= 308.7 FOM= 0.16
INDE -10  16  10 FOBS=  50.5 SIGMA=  7.9 PHAS= 124.2 FOM= 0.64
INDE -10  16  11 FOBS=  51.6 SIGMA=  5.0 PHAS=  28.2 FOM= 0.54
INDE -10  16  12 FOBS= 208.5 SIGMA=  2.8 PHAS= 343.4 FOM= 0.72
INDE -10  16  13 FOBS=  44.8 SIGMA=  9.2 PHAS= 171.5 FOM= 0.12
INDE -10  17   1 FOBS= 222.6 SIGMA=  2.6 PHAS= 248.8 FOM= 0.87
INDE -10  17   2 FOBS= 111.9 SIGMA=  5.0 PHAS= 151.2 FOM= 0.34
INDE -10  17   3 FOBS= 318.7 SIGMA=  2.3 PHAS=   0.9 FOM= 0.85
INDE -10  17   4 FOBS= 278.7 SIGMA=  2.4 PHAS= 230.2 FOM= 0.77
INDE -10  17   5 FOBS=  65.9 SIGMA=  5.7 PHAS= 147.4 FOM= 0.68
INDE -10  17   6 FOBS= 135.3 SIGMA=  5.5 PHAS=  46.6 FOM= 0.59
INDE -10  17   7 FOBS= 114.2 SIGMA=  5.9 PHAS= 143.4 FOM= 0.02
INDE -10  17   8 FOBS=  80.8 SIGMA= 11.7 PHAS= 207.7 FOM= 0.11
INDE -10  17   9 FOBS=  43.1 SIGMA= 17.9 PHAS=   5.2 FOM= 0.23
INDE -10  17  10 FOBS=  35.5 SIGMA= 14.3 PHAS= 106.0 FOM= 0.36
INDE -10  17  11 FOBS=  84.8 SIGMA=  3.9 PHAS= 269.6 FOM= 0.97
INDE -10  17  12 FOBS= 146.3 SIGMA=  3.2 PHAS= 192.8 FOM= 0.57
INDE -10  17  13 FOBS= 173.2 SIGMA= 13.0 PHAS= 134.5 FOM= 0.05
INDE -10  18   1 FOBS= 104.9 SIGMA= 82.8 PHAS= 324.3 FOM= 0.07
INDE -10  18   2 FOBS= 154.7 SIGMA=  3.3 PHAS=  38.8 FOM= 0.90
INDE -10  18   3 FOBS= 107.3 SIGMA=  4.8 PHAS= 309.9 FOM= 0.72
INDE -10  18   4 FOBS= 167.7 SIGMA=  3.0 PHAS= 231.8 FOM= 0.86
INDE -10  18   5 FOBS= 165.0 SIGMA=  2.8 PHAS= 134.7 FOM= 0.88
INDE -10  18   6 FOBS= 230.5 SIGMA=  3.1 PHAS=  19.3 FOM= 0.42
INDE -10  18   7 FOBS= 210.6 SIGMA=  3.3 PHAS= 236.2 FOM= 0.24
INDE -10  18   8 FOBS= 277.4 SIGMA=  3.2 PHAS=  57.0 FOM= 0.90
INDE -10  18   9 FOBS= 108.6 SIGMA=  7.5 PHAS=  59.0 FOM= 0.03
INDE -10  18  10 FOBS= 187.2 SIGMA=  3.6 PHAS= 178.2 FOM= 0.62
INDE -10  18  11 FOBS=  90.4 SIGMA=  4.3 PHAS= 285.5 FOM= 0.76
INDE -10  18  12 FOBS=  69.7 SIGMA=  6.2 PHAS= 134.3 FOM= 0.16
INDE -10  19   1 FOBS= 373.6 SIGMA=  2.3 PHAS=  94.8 FOM= 0.96
INDE -10  19   2 FOBS=  96.0 SIGMA=  5.6 PHAS= 205.1 FOM= 0.55
INDE -10  19   3 FOBS= 172.0 SIGMA=  3.3 PHAS= 310.8 FOM= 0.31
INDE -10  19   4 FOBS= 275.3 SIGMA=  1.9 PHAS= 109.9 FOM= 0.93
INDE -10  19   5 FOBS= 207.6 SIGMA=  2.2 PHAS= 302.7 FOM= 0.96
INDE -10  19   6 FOBS= 345.9 SIGMA=  2.3 PHAS=  94.8 FOM= 0.89
INDE -10  19   7 FOBS= 284.8 SIGMA=  2.6 PHAS= 359.2 FOM= 0.88
INDE -10  19   8 FOBS= 139.8 SIGMA=  5.6 PHAS= 246.9 FOM= 0.44
INDE -10  19   9 FOBS= 177.2 SIGMA=  3.6 PHAS= 180.6 FOM= 0.45
INDE -10  19  10 FOBS=  58.4 SIGMA= 13.8 PHAS= 264.6 FOM= 0.36
INDE -10  19  11 FOBS= 185.0 SIGMA=  3.5 PHAS=  68.9 FOM= 0.32
INDE -10  19  12 FOBS= 229.4 SIGMA=  1.9 PHAS=  42.9 FOM= 0.74
INDE -10  20   1 FOBS=  60.4 SIGMA= 10.0 PHAS= 148.8 FOM= 0.05
INDE -10  20   2 FOBS=  49.9 SIGMA= 28.7 PHAS= 187.4 FOM= 0.12
INDE -10  20   3 FOBS= 200.7 SIGMA=  2.5 PHAS=  30.9 FOM= 0.95
INDE -10  20   4 FOBS= 254.9 SIGMA=  2.0 PHAS= 239.5 FOM= 0.71
INDE -10  20   5 FOBS=  56.9 SIGMA= 15.1 PHAS= 149.0 FOM= 0.18
INDE -10  20   6 FOBS= 178.3 SIGMA=  4.0 PHAS=  37.4 FOM= 0.50
INDE -10  20   7 FOBS=  58.6 SIGMA= 29.3 PHAS= 269.7 FOM= 0.03
INDE -10  20   8 FOBS= 236.7 SIGMA=  3.5 PHAS= 148.5 FOM= 0.82
INDE -10  20   9 FOBS= 112.6 SIGMA=  5.6 PHAS= 292.6 FOM= 0.68
INDE -10  20  10 FOBS=  82.5 SIGMA=  7.6 PHAS=  60.7 FOM= 0.12
INDE -10  20  11 FOBS= 224.8 SIGMA=  3.4 PHAS=  52.2 FOM= 0.07
INDE -10  21   1 FOBS= 196.3 SIGMA=  2.9 PHAS= 225.7 FOM= 0.89
INDE -10  21   2 FOBS= 156.9 SIGMA=  3.4 PHAS= 347.4 FOM= 0.90
INDE -10  21   3 FOBS=  72.9 SIGMA=  6.3 PHAS= 226.4 FOM= 0.10
INDE -10  21   4 FOBS= 179.9 SIGMA=  2.6 PHAS= 216.4 FOM= 0.94
INDE -10  21   5 FOBS= 130.7 SIGMA=  2.9 PHAS=  34.4 FOM= 0.86
INDE -10  21   6 FOBS=  98.0 SIGMA=  6.9 PHAS= 127.8 FOM= 0.09
INDE -10  21   7 FOBS= 228.4 SIGMA=  2.9 PHAS=  24.4 FOM= 0.10
INDE -10  21   8 FOBS=  93.3 SIGMA= 10.1 PHAS= 254.6 FOM= 0.46
INDE -10  21   9 FOBS=  78.4 SIGMA=  8.0 PHAS=  64.5 FOM= 0.45
INDE -10  21  10 FOBS=  97.3 SIGMA=  6.2 PHAS= 359.2 FOM= 0.53
INDE -10  21  11 FOBS= 167.5 SIGMA=  5.9 PHAS=  16.9 FOM= 0.45
INDE -10  22   1 FOBS=  48.2 SIGMA= 12.5 PHAS= 315.5 FOM= 0.18
INDE -10  22   2 FOBS=  39.7 SIGMA= 24.1 PHAS=  38.5 FOM= 0.06
INDE -10  22   3 FOBS= 265.6 SIGMA=  2.1 PHAS=  98.8 FOM= 0.81
INDE -10  22   4 FOBS=  35.0 SIGMA= 19.7 PHAS= 216.2 FOM= 0.10
INDE -10  22   5 FOBS=  56.3 SIGMA=  7.6 PHAS=  34.0 FOM= 0.09
INDE -10  22   6 FOBS= 192.2 SIGMA=  3.5 PHAS= 324.4 FOM= 0.24
INDE -10  22   7 FOBS= 268.4 SIGMA=  2.5 PHAS=  84.6 FOM= 0.77
```

Fig. 10A-25

```
INDE -10 22  8 FOBS= 115.8 SIGMA=  8.3 PHAS=  73.9 FOM= 0.89
INDE -10 22  9 FOBS= 175.6 SIGMA=  3.5 PHAS=  63.3 FOM= 0.92
INDE -10 22 10 FOBS= 260.3 SIGMA=  2.3 PHAS= 293.5 FOM= 0.95
INDE -10 23  1 FOBS= 156.9 SIGMA=  3.4 PHAS=  10.5 FOM= 0.48
INDE -10 23  2 FOBS=  40.0 SIGMA= 13.3 PHAS=  60.7 FOM= 0.07
INDE -10 23  3 FOBS=  96.8 SIGMA=  4.8 PHAS= 160.1 FOM= 0.72
INDE -10 23  4 FOBS=  80.2 SIGMA=  7.4 PHAS=  62.5 FOM= 0.37
INDE -10 23  5 FOBS= 136.5 SIGMA=  2.7 PHAS=   9.4 FOM= 0.88
INDE -10 23  6 FOBS= 126.1 SIGMA=  5.3 PHAS= 264.1 FOM= 0.37
INDE -10 23  7 FOBS= 175.8 SIGMA=  3.7 PHAS=  76.7 FOM= 0.96
INDE -10 23  8 FOBS=  57.4 SIGMA= 15.6 PHAS= 350.6 FOM= 0.09
INDE -10 23  9 FOBS=  71.7 SIGMA=  7.8 PHAS= 229.2 FOM= 0.19
INDE -10 24  1 FOBS=  50.0 SIGMA= 10.6 PHAS= 348.9 FOM= 0.30
INDE -10 24  2 FOBS= 133.9 SIGMA=  3.7 PHAS=  99.1 FOM= 0.86
INDE -10 24  3 FOBS= 117.8 SIGMA=  4.0 PHAS= 319.5 FOM= 0.44
INDE -10 24  4 FOBS= 107.1 SIGMA=  5.5 PHAS=   1.7 FOM= 0.53
INDE -10 24  5 FOBS= 149.6 SIGMA=  2.6 PHAS= 231.1 FOM= 0.95
INDE -10 24  6 FOBS= 100.0 SIGMA=  4.7 PHAS=  71.0 FOM= 0.42
INDE -10 24  7 FOBS= 132.8 SIGMA=  4.8 PHAS= 112.7 FOM= 0.21
INDE -10 24  8 FOBS=  53.1 SIGMA= 25.1 PHAS= 165.3 FOM= 0.13
INDE -10 24  9 FOBS= 106.7 SIGMA= 11.9 PHAS= 308.6 FOM= 0.10
INDE -10 25  1 FOBS= 139.9 SIGMA=  3.8 PHAS= 252.7 FOM= 0.79
INDE -10 25  2 FOBS=  44.2 SIGMA= 11.9 PHAS= 133.3 FOM= 0.49
INDE -10 25  3 FOBS= 112.4 SIGMA=  4.1 PHAS= 322.3 FOM= 0.88
INDE -10 25  4 FOBS= 107.7 SIGMA=  4.1 PHAS= 301.8 FOM= 0.20
INDE -10 25  5 FOBS= 131.3 SIGMA=  2.8 PHAS= 220.3 FOM= 0.64
INDE -10 25  6 FOBS= 140.3 SIGMA=  2.6 PHAS= 281.7 FOM= 0.86
INDE -10 25  7 FOBS=  45.6 SIGMA= 18.4 PHAS= 115.2 FOM= 0.31
INDE -10 25  8 FOBS=  73.9 SIGMA= 16.3 PHAS= 283.1 FOM= 0.12
INDE -10 26  1 FOBS= 122.7 SIGMA=  4.2 PHAS= 284.1 FOM= 0.25
INDE -10 26  2 FOBS=  82.5 SIGMA=  5.6 PHAS= 135.6 FOM= 0.14
INDE -10 26  3 FOBS=  97.1 SIGMA=  5.0 PHAS=  79.0 FOM= 0.18
INDE -10 26  4 FOBS=  44.4 SIGMA=  9.1 PHAS=  15.7 FOM= 0.04
INDE -10 26  5 FOBS= 140.1 SIGMA=  2.7 PHAS= 252.2 FOM= 0.84
INDE -10 26  6 FOBS= 109.0 SIGMA=  3.1 PHAS= 111.9 FOM= 0.90
INDE -10 26  7 FOBS= 179.6 SIGMA= 14.8 PHAS= 208.6 FOM= 0.05
INDE -10 27  1 FOBS=  55.2 SIGMA= 10.5 PHAS=   9.6 FOM= 0.21
INDE -10 27  2 FOBS= 222.9 SIGMA=  2.4 PHAS=  89.9 FOM= 0.94
INDE -10 27  3 FOBS= 141.3 SIGMA=  3.9 PHAS= 336.2 FOM= 0.25
INDE -10 27  4 FOBS= 137.1 SIGMA=  2.9 PHAS= 359.4 FOM= 0.71
INDE -10 27  5 FOBS= 199.1 SIGMA=  1.9 PHAS= 272.6 FOM= 0.92
INDE  -9  0  1 FOBS=  93.7 SIGMA=  6.8 PHAS= 180.0 FOM= 0.12
INDE  -9  0  2 FOBS=  42.3 SIGMA= 16.7 PHAS=   0.0 FOM= 0.12
INDE  -9  0  3 FOBS= 184.9 SIGMA=  3.4 PHAS= 180.0 FOM= 0.92
INDE  -9  0  4 FOBS= 160.4 SIGMA=  3.7 PHAS=   0.0 FOM= 0.98
INDE  -9  0  5 FOBS= 115.1 SIGMA=  4.9 PHAS=   0.0 FOM= 0.14
INDE  -9  0  6 FOBS=  28.2 SIGMA= 21.5 PHAS= 180.0 FOM= 0.22
INDE  -9  0  7 FOBS= 170.8 SIGMA=  3.6 PHAS= 180.0 FOM= 1.00
INDE  -9  0  8 FOBS=  43.7 SIGMA=  7.4 PHAS=   0.0 FOM= 0.61
INDE  -9  0  9 FOBS= 129.1 SIGMA=  3.7 PHAS= 180.0 FOM= 0.98
INDE  -9  0 10 FOBS= 430.4 SIGMA=  1.6 PHAS=   0.0 FOM= 1.00
INDE  -9  0 11 FOBS= 345.6 SIGMA=  2.8 PHAS= 180.0 FOM= 1.00
INDE  -9  0 12 FOBS= 371.5 SIGMA=  1.9 PHAS=   0.0 FOM= 1.00
INDE  -9  0 13 FOBS= 539.6 SIGMA=  1.5 PHAS= 180.0 FOM= 1.00
INDE  -9  0 14 FOBS=  54.1 SIGMA= 11.9 PHAS= 180.0 FOM= 0.07
INDE  -9  0 15 FOBS= 131.8 SIGMA=  5.5 PHAS=   0.0 FOM= 0.58
INDE  -9  0 16 FOBS= 196.8 SIGMA=  3.3 PHAS=   0.0 FOM= 0.08
INDE  -9  1  1 FOBS=  79.7 SIGMA=  5.6 PHAS= 263.8 FOM= 0.16
INDE  -9  1  2 FOBS= 205.2 SIGMA=  2.2 PHAS= 100.7 FOM= 0.83
INDE  -9  1  3 FOBS= 150.6 SIGMA=  2.9 PHAS=  39.5 FOM= 0.79
INDE  -9  1  4 FOBS= 229.2 SIGMA=  1.9 PHAS= 242.0 FOM= 0.94
INDE  -9  1  5 FOBS=  90.4 SIGMA=  4.3 PHAS=  89.3 FOM= 0.42
INDE  -9  1  6 FOBS= 138.8 SIGMA=  2.8 PHAS= 187.7 FOM= 0.09
INDE  -9  1  7 FOBS= 179.3 SIGMA=  2.3 PHAS= 173.0 FOM= 0.29
INDE  -9  1  8 FOBS= 259.9 SIGMA=  1.5 PHAS= 160.3 FOM= 0.15
INDE  -9  1  9 FOBS= 321.1 SIGMA=  1.4 PHAS= 289.2 FOM= 0.98
INDE  -9  1 10 FOBS= 139.6 SIGMA=  2.6 PHAS= 226.3 FOM= 0.96
INDE  -9  1 11 FOBS= 168.5 SIGMA=  3.3 PHAS=  68.6 FOM= 0.27
INDE  -9  1 12 FOBS= 284.5 SIGMA=  1.6 PHAS= 226.1 FOM= 0.97
INDE  -9  1 13 FOBS= 129.3 SIGMA=  3.2 PHAS= 256.1 FOM= 0.85
INDE  -9  1 14 FOBS= 166.0 SIGMA=  2.7 PHAS=  15.6 FOM= 0.85
```

Fig. 10A-26

```
INDE  -9  1  15  FOBS=   78.1  SIGMA= 5.9  PHAS=  89.9  FOM= 0.40
INDE  -9  1  16  FOBS=   76.3  SIGMA= 6.0  PHAS= 190.2  FOM= 0.19
INDE  -9  2   1  FOBS=  275.5  SIGMA= 1.9  PHAS= 352.2  FOM= 0.97
INDE  -9  2   2  FOBS=  103.1  SIGMA= 4.7  PHAS= 111.2  FOM= 0.92
INDE  -9  2   3  FOBS=  235.1  SIGMA= 1.9  PHAS= 309.0  FOM= 0.94
INDE  -9  2   4  FOBS=  245.5  SIGMA= 1.7  PHAS= 193.3  FOM= 1.00
INDE  -9  2   5  FOBS=  243.2  SIGMA= 1.7  PHAS= 274.9  FOM= 0.27
INDE  -9  2   6  FOBS=  231.1  SIGMA= 1.8  PHAS= 181.0  FOM= 0.98
INDE  -9  2   7  FOBS=  353.7  SIGMA= 1.4  PHAS= 289.1  FOM= 0.95
INDE  -9  2   8  FOBS=  242.3  SIGMA= 1.6  PHAS=  84.5  FOM= 1.00
INDE  -9  2   9  FOBS=  207.1  SIGMA= 1.8  PHAS= 161.2  FOM= 0.87
INDE  -9  2  10  FOBS=  330.6  SIGMA= 1.4  PHAS= 107.4  FOM= 0.92
INDE  -9  2  11  FOBS=  177.4  SIGMA= 3.0  PHAS= 318.4  FOM= 0.60
INDE  -9  2  12  FOBS=  220.7  SIGMA= 2.0  PHAS=  13.8  FOM= 0.96
INDE  -9  2  13  FOBS=  131.3  SIGMA= 3.5  PHAS= 214.6  FOM= 0.92
INDE  -9  2  14  FOBS=  193.1  SIGMA= 2.2  PHAS= 253.8  FOM= 0.87
INDE  -9  2  15  FOBS=  181.7  SIGMA= 2.5  PHAS= 153.1  FOM= 0.82
INDE  -9  2  16  FOBS=  104.0  SIGMA= 4.5  PHAS= 291.2  FOM= 0.76
INDE  -9  3   1  FOBS=  234.7  SIGMA= 2.0  PHAS= 209.9  FOM= 0.24
INDE  -9  3   2  FOBS=  317.8  SIGMA= 1.6  PHAS=  36.7  FOM= 0.96
INDE  -9  3   3  FOBS=  313.1  SIGMA= 1.5  PHAS= 217.5  FOM= 0.91
INDE  -9  3   4  FOBS=  237.8  SIGMA= 1.8  PHAS= 317.2  FOM= 0.96
INDE  -9  3   5  FOBS=  100.9  SIGMA= 3.4  PHAS= 337.1  FOM= 0.90
INDE  -9  3   6  FOBS=  424.4  SIGMA= 1.1  PHAS= 295.4  FOM= 1.00
INDE  -9  3   7  FOBS=  609.1  SIGMA= 1.2  PHAS= 168.3  FOM= 1.00
INDE  -9  3   8  FOBS=  408.8  SIGMA= 1.2  PHAS= 171.8  FOM= 1.00
INDE  -9  3   9  FOBS=  236.7  SIGMA= 1.6  PHAS= 323.4  FOM= 0.94
INDE  -9  3  10  FOBS=  286.8  SIGMA= 1.5  PHAS= 311.6  FOM= 0.97
INDE  -9  3  11  FOBS=   74.3  SIGMA= 6.2  PHAS= 202.3  FOM= 0.23
INDE  -9  3  12  FOBS=   91.3  SIGMA= 4.7  PHAS= 143.2  FOM= 0.65
INDE  -9  3  13  FOBS=  351.4  SIGMA= 1.4  PHAS=  11.2  FOM= 0.77
INDE  -9  3  14  FOBS=  118.9  SIGMA= 3.9  PHAS= 262.2  FOM= 0.86
INDE  -9  3  15  FOBS=  181.9  SIGMA= 2.5  PHAS=  71.7  FOM= 0.91
INDE  -9  3  16  FOBS=  218.3  SIGMA= 2.2  PHAS= 260.3  FOM= 0.80
INDE  -9  4   1  FOBS=  380.5  SIGMA= 1.4  PHAS= 228.8  FOM= 0.77
INDE  -9  4   2  FOBS=  188.4  SIGMA= 2.4  PHAS= 170.1  FOM= 0.84
INDE  -9  4   3  FOBS=  260.3  SIGMA= 1.8  PHAS=  19.8  FOM= 0.96
INDE  -9  4   4  FOBS=  157.1  SIGMA= 2.7  PHAS= 102.4  FOM= 0.96
INDE  -9  4   5  FOBS=  163.0  SIGMA= 2.5  PHAS= 162.3  FOM= 0.50
INDE  -9  4   6  FOBS=  222.3  SIGMA= 1.8  PHAS=  85.8  FOM= 0.99
INDE  -9  4   7  FOBS=  148.5  SIGMA= 2.7  PHAS= 210.7  FOM= 0.78
INDE  -9  4   8  FOBS=  296.5  SIGMA= 1.4  PHAS= 160.1  FOM= 0.97
INDE  -9  4   9  FOBS=  260.1  SIGMA= 1.5  PHAS= 259.6  FOM= 0.97
INDE  -9  4  10  FOBS=  415.2  SIGMA= 1.2  PHAS=  29.6  FOM= 0.62
INDE  -9  4  11  FOBS=   81.1  SIGMA= 5.0  PHAS= 126.4  FOM= 0.39
INDE  -9  4  12  FOBS=  386.1  SIGMA= 1.4  PHAS= 111.9  FOM= 0.90
INDE  -9  4  13  FOBS=  244.9  SIGMA= 1.9  PHAS= 321.0  FOM= 0.71
INDE  -9  4  14  FOBS=  193.6  SIGMA= 2.2  PHAS=  59.1  FOM= 0.55
INDE  -9  4  15  FOBS=   89.1  SIGMA= 4.8  PHAS=  20.0  FOM= 0.63
INDE  -9  4  16  FOBS=  154.9  SIGMA= 3.0  PHAS= 239.4  FOM= 0.91
INDE  -9  5   1  FOBS=   72.0  SIGMA= 6.9  PHAS=   6.9  FOM= 0.13
INDE  -9  5   2  FOBS=  203.8  SIGMA= 2.2  PHAS=  24.7  FOM= 0.83
INDE  -9  5   3  FOBS=  108.2  SIGMA= 3.7  PHAS= 122.2  FOM= 0.84
INDE  -9  5   4  FOBS=  176.2  SIGMA= 2.3  PHAS=  60.7  FOM= 0.89
INDE  -9  5   5  FOBS=  369.3  SIGMA= 1.2  PHAS=  58.6  FOM= 0.31
INDE  -9  5   6  FOBS=  307.2  SIGMA= 1.5  PHAS=  23.4  FOM= 0.96
INDE  -9  5   7  FOBS=  283.1  SIGMA= 1.4  PHAS= 156.2  FOM= 0.99
INDE  -9  5   8  FOBS=   81.0  SIGMA= 4.6  PHAS= 347.3  FOM= 0.87
INDE  -9  5   9  FOBS=   64.2  SIGMA= 5.3  PHAS= 289.7  FOM= 0.42
INDE  -9  5  10  FOBS=  350.6  SIGMA= 1.3  PHAS= 189.3  FOM= 0.99
INDE  -9  5  11  FOBS=  183.5  SIGMA= 2.2  PHAS= 355.6  FOM= 0.91
INDE  -9  5  12  FOBS=  199.8  SIGMA= 2.2  PHAS= 225.4  FOM= 0.68
INDE  -9  5  13  FOBS=  216.9  SIGMA= 2.1  PHAS= 218.3  FOM= 0.77
INDE  -9  5  14  FOBS=  169.8  SIGMA= 2.5  PHAS= 198.0  FOM= 0.48
INDE  -9  5  15  FOBS=  313.7  SIGMA= 1.6  PHAS= 339.9  FOM= 0.91
INDE  -9  5  16  FOBS=  114.0  SIGMA= 4.5  PHAS= 339.4  FOM= 0.24
INDE  -9  6   1  FOBS=  288.4  SIGMA= 2.4  PHAS= 282.4  FOM= 0.98
INDE  -9  6   2  FOBS=  253.8  SIGMA= 2.0  PHAS= 119.5  FOM= 0.94
INDE  -9  6   3  FOBS=  428.8  SIGMA= 1.3  PHAS= 322.7  FOM= 0.91
INDE  -9  6   4  FOBS=  288.9  SIGMA= 1.5  PHAS= 108.6  FOM= 0.92
INDE  -9  6   5  FOBS=  115.0  SIGMA= 3.4  PHAS= 334.2  FOM= 0.82
```

Fig. 10A-27

```
INDE  -9   6   6 FOBS=  426.7 SIGMA=  1.2 PHAS=  266.7 FOM= 0.98
INDE  -9   6   7 FOBS=  288.1 SIGMA=  1.4 PHAS=  315.7 FOM= 0.95
INDE  -9   6   8 FOBS=  261.5 SIGMA=  1.5 PHAS=  258.0 FOM= 0.36
INDE  -9   6   9 FOBS=  157.3 SIGMA=  2.2 PHAS=  230.3 FOM= 0.86
INDE  -9   6  10 FOBS=   92.9 SIGMA=  4.8 PHAS=  215.2 FOM= 0.50
INDE  -9   6  11 FOBS=  162.9 SIGMA=  2.4 PHAS=  122.7 FOM= 0.34
INDE  -9   6  12 FOBS=  196.2 SIGMA=  2.4 PHAS=   16.3 FOM= 0.69
INDE  -9   6  13 FOBS=  359.7 SIGMA=  1.5 PHAS=  153.8 FOM= 0.97
INDE  -9   6  14 FOBS=   98.6 SIGMA=  4.5 PHAS=  275.4 FOM= 0.82
INDE  -9   6  15 FOBS=  280.5 SIGMA=  1.7 PHAS=   24.3 FOM= 0.38
INDE  -9   6  16 FOBS=   81.4 SIGMA= 12.1 PHAS=  162.0 FOM= 0.08
INDE  -9   7   1 FOBS=  109.2 SIGMA=  4.4 PHAS=  160.1 FOM= 0.72
INDE  -9   7   2 FOBS=  212.7 SIGMA=  2.9 PHAS=  231.5 FOM= 0.97
INDE  -9   7   3 FOBS=  220.0 SIGMA=  2.0 PHAS=  261.5 FOM= 0.95
INDE  -9   7   4 FOBS=  147.0 SIGMA=  2.8 PHAS=  331.2 FOM= 0.11
INDE  -9   7   5 FOBS=  230.6 SIGMA=  1.7 PHAS=  292.0 FOM= 0.88
INDE  -9   7   6 FOBS=  246.7 SIGMA=  1.6 PHAS=  186.7 FOM= 0.30
INDE  -9   7   7 FOBS=  273.3 SIGMA=  1.4 PHAS=  129.5 FOM= 0.98
INDE  -9   7   8 FOBS=   69.4 SIGMA=  4.7 PHAS=   30.2 FOM= 0.27
INDE  -9   7   9 FOBS=  304.6 SIGMA=  1.5 PHAS=  214.5 FOM= 0.20
INDE  -9   7  10 FOBS=   76.1 SIGMA=  6.3 PHAS=  261.2 FOM= 0.12
INDE  -9   7  11 FOBS=  131.3 SIGMA=  3.3 PHAS=  358.2 FOM= 0.90
INDE  -9   7  12 FOBS=  145.8 SIGMA=  3.1 PHAS=  135.6 FOM= 0.76
INDE  -9   7  13 FOBS=   35.9 SIGMA= 11.5 PHAS=  342.7 FOM= 0.07
INDE  -9   7  14 FOBS=  275.8 SIGMA=  1.7 PHAS=  309.1 FOM= 0.97
INDE  -9   7  15 FOBS=  145.5 SIGMA=  3.0 PHAS=   56.3 FOM= 0.91
INDE  -9   8   1 FOBS=  199.1 SIGMA=  2.4 PHAS=  304.4 FOM= 0.91
INDE  -9   8   2 FOBS=  233.9 SIGMA=  2.2 PHAS=  193.4 FOM= 0.95
INDE  -9   8   3 FOBS=  270.9 SIGMA=  1.9 PHAS=  254.7 FOM= 0.88
INDE  -9   8   4 FOBS=  225.6 SIGMA=  1.9 PHAS=   36.1 FOM= 0.96
INDE  -9   8   5 FOBS=  170.2 SIGMA=  2.3 PHAS=  254.9 FOM= 0.98
INDE  -9   8   6 FOBS=  230.3 SIGMA=  1.7 PHAS=   67.2 FOM= 0.72
INDE  -9   8   7 FOBS=  217.1 SIGMA=  1.6 PHAS=   87.0 FOM= 0.94
INDE  -9   8   8 FOBS=  173.9 SIGMA=  2.0 PHAS=  153.9 FOM= 0.91
INDE  -9   8   9 FOBS=  207.1 SIGMA=  1.8 PHAS=  339.4 FOM= 0.85
INDE  -9   8  10 FOBS=  118.8 SIGMA=  4.5 PHAS=  290.1 FOM= 0.56
INDE  -9   8  11 FOBS=  317.2 SIGMA=  1.5 PHAS=  148.6 FOM= 1.00
INDE  -9   8  12 FOBS=  283.9 SIGMA=  1.8 PHAS=  316.6 FOM= 0.97
INDE  -9   8  13 FOBS=  160.4 SIGMA=  2.6 PHAS=  332.0 FOM= 0.74
INDE  -9   8  14 FOBS=  149.2 SIGMA=  2.8 PHAS=  260.6 FOM= 0.47
INDE  -9   8  15 FOBS=   68.5 SIGMA=  6.1 PHAS=   25.6 FOM= 0.13
INDE  -9   9   1 FOBS=  240.6 SIGMA=  2.1 PHAS=  224.0 FOM= 0.72
INDE  -9   9   2 FOBS=  348.7 SIGMA=  1.7 PHAS=   45.4 FOM= 1.00
INDE  -9   9   3 FOBS=  119.4 SIGMA=  4.0 PHAS=  351.6 FOM= 0.70
INDE  -9   9   4 FOBS=  230.0 SIGMA=  2.0 PHAS=  166.1 FOM= 0.95
INDE  -9   9   5 FOBS=   98.9 SIGMA=  3.6 PHAS=  310.0 FOM= 0.61
INDE  -9   9   6 FOBS=   89.7 SIGMA=  4.1 PHAS=  159.2 FOM= 0.55
INDE  -9   9   7 FOBS=  124.1 SIGMA=  2.6 PHAS=  213.9 FOM= 0.94
INDE  -9   9   8 FOBS=  353.0 SIGMA=  1.1 PHAS=  315.5 FOM= 0.97
INDE  -9   9   9 FOBS=   60.1 SIGMA=  5.3 PHAS=   15.6 FOM= 0.68
INDE  -9   9  10 FOBS=  126.8 SIGMA=  3.9 PHAS=  260.6 FOM= 0.53
INDE  -9   9  11 FOBS=   51.4 SIGMA=  7.5 PHAS=   48.6 FOM= 0.09
INDE  -9   9  12 FOBS=  113.0 SIGMA=  3.8 PHAS=   15.0 FOM= 0.87
INDE  -9   9  13 FOBS=  189.7 SIGMA=  2.3 PHAS=  206.1 FOM= 0.80
INDE  -9   9  14 FOBS=  168.3 SIGMA=  2.5 PHAS=   57.0 FOM= 0.18
INDE  -9   9  15 FOBS=   70.3 SIGMA=  6.0 PHAS=  263.9 FOM= 0.18
INDE  -9  10   1 FOBS=  116.0 SIGMA=  4.3 PHAS=  265.3 FOM= 0.10
INDE  -9  10   2 FOBS=   75.2 SIGMA=  5.8 PHAS=  359.7 FOM= 0.46
INDE  -9  10   3 FOBS=  111.4 SIGMA=  3.9 PHAS=  294.6 FOM= 0.91
INDE  -9  10   4 FOBS=  252.5 SIGMA=  1.9 PHAS=  278.8 FOM= 0.93
INDE  -9  10   5 FOBS=  167.8 SIGMA=  2.2 PHAS=   24.6 FOM= 0.27
INDE  -9  10   6 FOBS=  490.5 SIGMA=  1.4 PHAS=   26.8 FOM= 0.95
INDE  -9  10   7 FOBS=  104.4 SIGMA=  2.9 PHAS=  111.2 FOM= 0.93
INDE  -9  10   8 FOBS=   81.9 SIGMA=  4.1 PHAS=  329.9 FOM= 0.92
INDE  -9  10   9 FOBS=   77.3 SIGMA=  4.4 PHAS=  192.4 FOM= 0.89
INDE  -9  10  10 FOBS=  137.9 SIGMA=  3.5 PHAS=  200.6 FOM= 0.28
INDE  -9  10  11 FOBS=  182.1 SIGMA=  2.2 PHAS=  242.9 FOM= 1.00
INDE  -9  10  12 FOBS=  298.1 SIGMA=  1.6 PHAS=  105.9 FOM= 0.99
INDE  -9  10  13 FOBS=  245.9 SIGMA=  2.0 PHAS=  150.2 FOM= 0.68
INDE  -9  10  14 FOBS=   72.3 SIGMA=  4.8 PHAS=  240.9 FOM= 0.97
INDE  -9  10  15 FOBS=  202.0 SIGMA=  2.1 PHAS=  274.6 FOM= 0.86
```

Fig. 10A-28

```
INDE  -9  11   1 FOBS=  106.9 SIGMA=  5.0 PHAS=  327.1 FOM= 0.33
INDE  -9  11   2 FOBS=   61.5 SIGMA=  7.3 PHAS=  151.8 FOM= 0.29
INDE  -9  11   3 FOBS=   58.9 SIGMA=  7.4 PHAS=  262.0 FOM= 0.39
INDE  -9  11   4 FOBS=  242.5 SIGMA=  1.8 PHAS=  298.2 FOM= 0.97
INDE  -9  11   5 FOBS=  336.6 SIGMA=  2.1 PHAS=  165.2 FOM= 0.99
INDE  -9  11   6 FOBS=  488.6 SIGMA=  1.7 PHAS=  335.1 FOM= 0.96
INDE  -9  11   7 FOBS=  161.7 SIGMA=  2.1 PHAS=  315.0 FOM= 0.94
INDE  -9  11   8 FOBS=  290.6 SIGMA=  1.3 PHAS=   96.2 FOM= 0.37
INDE  -9  11   9 FOBS=  372.9 SIGMA=  1.2 PHAS=  105.8 FOM= 0.83
INDE  -9  11  10 FOBS=  220.2 SIGMA=  2.3 PHAS=  121.5 FOM= 0.76
INDE  -9  11  11 FOBS=  167.7 SIGMA=  2.2 PHAS=  186.4 FOM= 0.21
INDE  -9  11  12 FOBS=   88.0 SIGMA=  4.5 PHAS=  305.1 FOM= 0.40
INDE  -9  11  13 FOBS=  131.5 SIGMA=  3.5 PHAS=   39.6 FOM= 0.13
INDE  -9  11  14 FOBS=  128.5 SIGMA=  3.1 PHAS=   73.6 FOM= 0.86
INDE  -9  11  15 FOBS=  147.0 SIGMA=  2.9 PHAS=  255.5 FOM= 0.60
INDE  -9  12   1 FOBS=  369.2 SIGMA=  1.8 PHAS=  282.8 FOM= 0.95
INDE  -9  12   2 FOBS=  218.4 SIGMA=  2.2 PHAS=   57.5 FOM= 0.94
INDE  -9  12   3 FOBS=  112.9 SIGMA=  3.9 PHAS=  342.4 FOM= 0.94
INDE  -9  12   4 FOBS=  241.7 SIGMA=  2.0 PHAS=  194.8 FOM= 0.95
INDE  -9  12   5 FOBS=  360.4 SIGMA=  1.6 PHAS=  229.9 FOM= 0.89
INDE  -9  12   6 FOBS=  196.0 SIGMA=  4.5 PHAS=  285.0 FOM= 0.00
INDE  -9  12   7 FOBS=  204.0 SIGMA=  2.7 PHAS=  289.4 FOM= 0.95
INDE  -9  12   8 FOBS=  458.7 SIGMA=  1.2 PHAS=  279.2 FOM= 0.96
INDE  -9  12   9 FOBS=  215.8 SIGMA=  1.9 PHAS=  280.0 FOM= 0.66
INDE  -9  12  10 FOBS=  146.3 SIGMA=  3.4 PHAS=  160.0 FOM= 0.79
INDE  -9  12  11 FOBS=  197.9 SIGMA=  2.0 PHAS=  224.6 FOM= 0.79
INDE  -9  12  12 FOBS=   58.0 SIGMA=  7.9 PHAS=  158.5 FOM= 0.44
INDE  -9  12  13 FOBS=  141.5 SIGMA=  3.0 PHAS=   47.4 FOM= 0.83
INDE  -9  12  14 FOBS=  217.8 SIGMA=  2.1 PHAS=   98.0 FOM= 0.80
INDE  -9  12  15 FOBS=  160.4 SIGMA=  5.6 PHAS=  168.3 FOM= 0.87
INDE  -9  13   1 FOBS=  255.6 SIGMA=  2.1 PHAS=  357.8 FOM= 0.93
INDE  -9  13   2 FOBS=  100.0 SIGMA=  5.5 PHAS=  171.6 FOM= 0.47
INDE  -9  13   3 FOBS=  258.2 SIGMA=  1.7 PHAS=  230.9 FOM= 0.91
INDE  -9  13   4 FOBS=  268.9 SIGMA=  1.4 PHAS=  293.5 FOM= 0.86
INDE  -9  13   5 FOBS=  251.8 SIGMA=  1.5 PHAS=  178.8 FOM= 0.98
INDE  -9  13   6 FOBS=  413.7 SIGMA=  2.4 PHAS=   23.0 FOM= 0.97
INDE  -9  13   7 FOBS=  211.6 SIGMA=  4.2 PHAS=  129.4 FOM= 0.71
INDE  -9  13   8 FOBS=  116.0 SIGMA=  6.6 PHAS=  323.1 FOM= 0.28
INDE  -9  13   9 FOBS=   73.3 SIGMA=  3.9 PHAS=   86.5 FOM= 0.90
INDE  -9  13  10 FOBS=  229.2 SIGMA=  2.3 PHAS=  204.1 FOM= 0.85
INDE  -9  13  11 FOBS=   91.3 SIGMA=  4.3 PHAS=  123.5 FOM= 0.06
INDE  -9  13  12 FOBS=  175.8 SIGMA=  2.2 PHAS=   36.4 FOM= 0.81
INDE  -9  13  13 FOBS=  108.6 SIGMA=  3.8 PHAS=  155.7 FOM= 0.47
INDE  -9  13  14 FOBS=  182.9 SIGMA=  2.4 PHAS=  268.9 FOM= 0.77
INDE  -9  14   1 FOBS=  577.6 SIGMA=  1.4 PHAS=  127.0 FOM= 0.94
INDE  -9  14   2 FOBS=  196.1 SIGMA=  2.7 PHAS=  301.6 FOM= 0.66
INDE  -9  14   3 FOBS=   84.0 SIGMA=  4.8 PHAS=  320.7 FOM= 0.10
INDE  -9  14   4 FOBS=  242.8 SIGMA=  2.1 PHAS=   83.6 FOM= 0.95
INDE  -9  14   5 FOBS=  242.5 SIGMA=  1.4 PHAS=  265.5 FOM= 0.69
INDE  -9  14   6 FOBS=   67.3 SIGMA=  9.5 PHAS=  312.4 FOM= 0.25
INDE  -9  14   7 FOBS=  101.7 SIGMA=  8.5 PHAS=  196.0 FOM= 0.49
INDE  -9  14   8 FOBS=   92.3 SIGMA=  9.4 PHAS=  328.1 FOM= 0.16
INDE  -9  14   9 FOBS=  379.9 SIGMA=  2.0 PHAS=    4.6 FOM= 0.85
INDE  -9  14  10 FOBS=  239.9 SIGMA=  2.2 PHAS=  120.5 FOM= 0.92
INDE  -9  14  11 FOBS=   44.0 SIGMA= 10.0 PHAS=  310.3 FOM= 0.25
INDE  -9  14  12 FOBS=   78.6 SIGMA=  4.8 PHAS=  191.4 FOM= 0.47
INDE  -9  14  13 FOBS=  152.8 SIGMA=  2.4 PHAS=  210.1 FOM= 0.90
INDE  -9  14  14 FOBS=  165.9 SIGMA=  2.7 PHAS=   26.9 FOM= 0.88
INDE  -9  15   1 FOBS=  335.4 SIGMA=  1.7 PHAS=  197.1 FOM= 1.00
INDE  -9  15   2 FOBS=  392.8 SIGMA=  1.5 PHAS=   17.3 FOM= 0.97
INDE  -9  15   3 FOBS=   94.5 SIGMA=  5.4 PHAS=  222.8 FOM= 0.45
INDE  -9  15   4 FOBS=  555.4 SIGMA=  2.0 PHAS=   36.5 FOM= 0.91
INDE  -9  15   5 FOBS=  467.0 SIGMA=  1.9 PHAS=  303.5 FOM= 0.40
INDE  -9  15   6 FOBS=  327.0 SIGMA=  2.4 PHAS=  119.8 FOM= 0.97
INDE  -9  15   7 FOBS=  118.5 SIGMA=  5.5 PHAS=  286.5 FOM= 0.84
INDE  -9  15   8 FOBS=  340.6 SIGMA=  2.8 PHAS=  168.7 FOM= 0.41
INDE  -9  15   9 FOBS=  123.9 SIGMA=  5.9 PHAS=  240.0 FOM= 0.48
INDE  -9  15  10 FOBS=  155.7 SIGMA=  4.4 PHAS=  291.3 FOM= 0.95
INDE  -9  15  11 FOBS=   78.5 SIGMA=  5.1 PHAS=   19.3 FOM= 0.66
INDE  -9  15  12 FOBS=   82.4 SIGMA=  4.4 PHAS=  116.4 FOM= 0.45
INDE  -9  15  13 FOBS=   94.6 SIGMA=  4.4 PHAS=  236.3 FOM= 0.75
```

Fig. 10A-29

| | | | | | | | | | |
|---|---|---|---|---|---|---|---|---|---|
| INDE | -9 | 15 | 14 | FOBS= | 92.9 | SIGMA= | 5.1 | PHAS= | 119.7 | FOM= | 0.40 |
| INDE | -9 | 16 | 1 | FOBS= | 73.2 | SIGMA= | 7.9 | PHAS= | 81.2 | FOM= | 0.44 |
| INDE | -9 | 16 | 2 | FOBS= | 168.6 | SIGMA= | 2.9 | PHAS= | 327.9 | FOM= | 0.67 |
| INDE | -9 | 16 | 3 | FOBS= | 314.8 | SIGMA= | 1.8 | PHAS= | 104.9 | FOM= | 0.78 |
| INDE | -9 | 16 | 4 | FOBS= | 271.6 | SIGMA= | 2.1 | PHAS= | 341.6 | FOM= | 0.97 |
| INDE | -9 | 16 | 5 | FOBS= | 213.7 | SIGMA= | 3.1 | PHAS= | 107.8 | FOM= | 0.84 |
| INDE | -9 | 16 | 6 | FOBS= | 289.1 | SIGMA= | 2.7 | PHAS= | 44.3 | FOM= | 0.71 |
| INDE | -9 | 16 | 7 | FOBS= | 140.2 | SIGMA= | 4.8 | PHAS= | 213.6 | FOM= | 0.27 |
| INDE | -9 | 16 | 8 | FOBS= | 131.6 | SIGMA= | 6.0 | PHAS= | 62.6 | FOM= | 0.37 |
| INDE | -9 | 16 | 9 | FOBS= | 226.9 | SIGMA= | 3.5 | PHAS= | 234.0 | FOM= | 0.29 |
| INDE | -9 | 16 | 10 | FOBS= | 113.2 | SIGMA= | 3.8 | PHAS= | 184.6 | FOM= | 0.61 |
| INDE | -9 | 16 | 11 | FOBS= | 113.3 | SIGMA= | 2.9 | PHAS= | 201.6 | FOM= | 0.58 |
| INDE | -9 | 16 | 12 | FOBS= | 100.3 | SIGMA= | 3.7 | PHAS= | 227.8 | FOM= | 0.73 |
| INDE | -9 | 16 | 13 | FOBS= | 135.4 | SIGMA= | 2.9 | PHAS= | 122.6 | FOM= | 0.79 |
| INDE | -9 | 17 | 1 | FOBS= | 321.3 | SIGMA= | 1.9 | PHAS= | 55.5 | FOM= | 0.15 |
| INDE | -9 | 17 | 2 | FOBS= | 252.0 | SIGMA= | 2.0 | PHAS= | 110.9 | FOM= | 0.97 |
| INDE | -9 | 17 | 3 | FOBS= | 97.6 | SIGMA= | 4.7 | PHAS= | 349.1 | FOM= | 0.84 |
| INDE | -9 | 17 | 4 | FOBS= | 360.9 | SIGMA= | 1.5 | PHAS= | 84.0 | FOM= | 0.78 |
| INDE | -9 | 17 | 5 | FOBS= | 268.2 | SIGMA= | 2.6 | PHAS= | 256.0 | FOM= | 1.00 |
| INDE | -9 | 17 | 6 | FOBS= | 107.5 | SIGMA= | 6.8 | PHAS= | 96.1 | FOM= | 0.55 |
| INDE | -9 | 17 | 7 | FOBS= | 220.0 | SIGMA= | 3.1 | PHAS= | 202.2 | FOM= | 0.63 |
| INDE | -9 | 17 | 8 | FOBS= | 354.7 | SIGMA= | 2.2 | PHAS= | 42.4 | FOM= | 0.67 |
| INDE | -9 | 17 | 9 | FOBS= | 260.2 | SIGMA= | 3.0 | PHAS= | 348.6 | FOM= | 0.49 |
| INDE | -9 | 17 | 10 | FOBS= | 114.3 | SIGMA= | 4.6 | PHAS= | 228.7 | FOM= | 0.42 |
| INDE | -9 | 17 | 11 | FOBS= | 237.2 | SIGMA= | 1.5 | PHAS= | 109.0 | FOM= | 0.96 |
| INDE | -9 | 17 | 12 | FOBS= | 135.3 | SIGMA= | 2.4 | PHAS= | 102.2 | FOM= | 0.97 |
| INDE | -9 | 17 | 13 | FOBS= | 128.7 | SIGMA= | 3.1 | PHAS= | 103.8 | FOM= | 0.39 |
| INDE | -9 | 18 | 1 | FOBS= | 179.2 | SIGMA= | 3.1 | PHAS= | 115.2 | FOM= | 0.65 |
| INDE | -9 | 18 | 2 | FOBS= | 286.6 | SIGMA= | 2.3 | PHAS= | 333.9 | FOM= | 0.84 |
| INDE | -9 | 18 | 3 | FOBS= | 191.2 | SIGMA= | 2.8 | PHAS= | 79.5 | FOM= | 0.28 |
| INDE | -9 | 18 | 4 | FOBS= | 183.3 | SIGMA= | 2.3 | PHAS= | 144.7 | FOM= | 0.34 |
| INDE | -9 | 18 | 5 | FOBS= | 269.0 | SIGMA= | 2.4 | PHAS= | 315.8 | FOM= | 0.53 |
| INDE | -9 | 18 | 6 | FOBS= | 96.3 | SIGMA= | 7.1 | PHAS= | 147.0 | FOM= | 0.21 |
| INDE | -9 | 18 | 7 | FOBS= | 103.0 | SIGMA= | 6.2 | PHAS= | 89.7 | FOM= | 0.06 |
| INDE | -9 | 18 | 8 | FOBS= | 41.8 | SIGMA= | 22.9 | PHAS= | 268.4 | FOM= | 0.19 |
| INDE | -9 | 18 | 9 | FOBS= | 172.9 | SIGMA= | 3.4 | PHAS= | 283.7 | FOM= | 0.72 |
| INDE | -9 | 18 | 10 | FOBS= | 163.6 | SIGMA= | 4.9 | PHAS= | 16.4 | FOM= | 0.12 |
| INDE | -9 | 18 | 11 | FOBS= | 112.1 | SIGMA= | 2.4 | PHAS= | 146.6 | FOM= | 0.59 |
| INDE | -9 | 18 | 12 | FOBS= | 154.5 | SIGMA= | 2.1 | PHAS= | 285.3 | FOM= | 0.65 |
| INDE | -9 | 18 | 13 | FOBS= | 187.3 | SIGMA= | 1.9 | PHAS= | 198.8 | FOM= | 0.93 |
| INDE | -9 | 19 | 1 | FOBS= | 120.6 | SIGMA= | 4.7 | PHAS= | 276.9 | FOM= | 0.69 |
| INDE | -9 | 19 | 2 | FOBS= | 121.4 | SIGMA= | 4.3 | PHAS= | 79.7 | FOM= | 0.44 |
| INDE | -9 | 19 | 3 | FOBS= | 256.7 | SIGMA= | 1.9 | PHAS= | 23.9 | FOM= | 0.92 |
| INDE | -9 | 19 | 4 | FOBS= | 105.7 | SIGMA= | 4.1 | PHAS= | 198.1 | FOM= | 0.89 |
| INDE | -9 | 19 | 5 | FOBS= | 133.3 | SIGMA= | 4.5 | PHAS= | 21.6 | FOM= | 0.66 |
| INDE | -9 | 19 | 6 | FOBS= | 126.3 | SIGMA= | 5.6 | PHAS= | 167.1 | FOM= | 0.47 |
| INDE | -9 | 19 | 7 | FOBS= | 139.4 | SIGMA= | 4.8 | PHAS= | 212.2 | FOM= | 0.60 |
| INDE | -9 | 19 | 8 | FOBS= | 208.2 | SIGMA= | 3.4 | PHAS= | 32.5 | FOM= | 0.15 |
| INDE | -9 | 19 | 9 | FOBS= | 148.8 | SIGMA= | 4.4 | PHAS= | 142.2 | FOM= | 0.45 |
| INDE | -9 | 19 | 10 | FOBS= | 127.7 | SIGMA= | 5.2 | PHAS= | 193.8 | FOM= | 0.71 |
| INDE | -9 | 19 | 11 | FOBS= | 44.1 | SIGMA= | 5.4 | PHAS= | 106.5 | FOM= | 0.20 |
| INDE | -9 | 19 | 12 | FOBS= | 229.3 | SIGMA= | 2.0 | PHAS= | 231.5 | FOM= | 0.69 |
| INDE | -9 | 20 | 1 | FOBS= | 65.8 | SIGMA= | 8.3 | PHAS= | 133.7 | FOM= | 0.35 |
| INDE | -9 | 20 | 2 | FOBS= | 439.7 | SIGMA= | 1.9 | PHAS= | 22.1 | FOM= | 0.98 |
| INDE | -9 | 20 | 3 | FOBS= | 53.6 | SIGMA= | 8.9 | PHAS= | 272.0 | FOM= | 0.27 |
| INDE | -9 | 20 | 4 | FOBS= | 72.0 | SIGMA= | 7.4 | PHAS= | 112.6 | FOM= | 0.09 |
| INDE | -9 | 20 | 5 | FOBS= | 154.3 | SIGMA= | 2.3 | PHAS= | 195.1 | FOM= | 0.67 |
| INDE | -9 | 20 | 6 | FOBS= | 79.4 | SIGMA= | 8.9 | PHAS= | 239.7 | FOM= | 0.38 |
| INDE | -9 | 20 | 7 | FOBS= | 426.2 | SIGMA= | 2.3 | PHAS= | 112.0 | FOM= | 0.92 |
| INDE | -9 | 20 | 8 | FOBS= | 183.3 | SIGMA= | 3.8 | PHAS= | 48.6 | FOM= | 0.79 |
| INDE | -9 | 20 | 9 | FOBS= | 211.8 | SIGMA= | 3.0 | PHAS= | 119.4 | FOM= | 0.93 |
| INDE | -9 | 20 | 10 | FOBS= | 77.7 | SIGMA= | 7.6 | PHAS= | 341.0 | FOM= | 0.51 |
| INDE | -9 | 20 | 11 | FOBS= | 114.8 | SIGMA= | 2.8 | PHAS= | 220.4 | FOM= | 0.73 |
| INDE | -9 | 20 | 12 | FOBS= | 160.2 | SIGMA= | 2.0 | PHAS= | 43.5 | FOM= | 0.98 |
| INDE | -9 | 21 | 1 | FOBS= | 128.0 | SIGMA= | 4.3 | PHAS= | 206.2 | FOM= | 0.04 |
| INDE | -9 | 21 | 2 | FOBS= | 173.1 | SIGMA= | 2.8 | PHAS= | 115.9 | FOM= | 0.83 |
| INDE | -9 | 21 | 3 | FOBS= | 82.2 | SIGMA= | 5.7 | PHAS= | 347.4 | FOM= | 0.20 |
| INDE | -9 | 21 | 4 | FOBS= | 70.1 | SIGMA= | 8.1 | PHAS= | 331.3 | FOM= | 0.23 |
| INDE | -9 | 21 | 5 | FOBS= | 103.7 | SIGMA= | 3.4 | PHAS= | 135.2 | FOM= | 0.76 |
| INDE | -9 | 21 | 6 | FOBS= | 65.8 | SIGMA= | 43.8 | PHAS= | 351.3 | FOM= | 0.14 |
| INDE | -9 | 21 | 7 | FOBS= | 106.1 | SIGMA= | 6.1 | PHAS= | 34.8 | FOM= | 0.45 |

Fig. 10A-30

```
INDE  -9  21   8 FOBS=  127.4 SIGMA=   5.1 PHAS=  216.7 FOM= 0.52
INDE  -9  21   9 FOBS=   58.9 SIGMA=  10.2 PHAS=  359.4 FOM= 0.26
INDE  -9  21  10 FOBS=   44.7 SIGMA=  18.6 PHAS=  276.1 FOM= 0.04
INDE  -9  21  11 FOBS=  168.8 SIGMA=   1.8 PHAS=  339.0 FOM= 0.76
INDE  -9  22   1 FOBS=  159.7 SIGMA=   3.3 PHAS=  167.2 FOM= 0.72
INDE  -9  22   2 FOBS=   73.3 SIGMA=   6.5 PHAS=  336.5 FOM= 0.36
INDE  -9  22   3 FOBS=   61.3 SIGMA=   7.6 PHAS=  323.8 FOM= 0.27
INDE  -9  22   4 FOBS=  163.8 SIGMA=   2.4 PHAS=    2.1 FOM= 0.96
INDE  -9  22   5 FOBS=  268.8 SIGMA=   1.9 PHAS=  105.6 FOM= 0.95
INDE  -9  22   6 FOBS=   50.6 SIGMA=   8.9 PHAS=  314.4 FOM= 0.59
INDE  -9  22   7 FOBS=   69.9 SIGMA=   9.5 PHAS=  133.0 FOM= 0.54
INDE  -9  22   8 FOBS=  272.5 SIGMA=   2.5 PHAS=    9.9 FOM= 0.77
INDE  -9  22   9 FOBS=   90.3 SIGMA=   6.5 PHAS=  271.1 FOM= 0.54
INDE  -9  22  10 FOBS=  245.9 SIGMA=   2.5 PHAS=  202.4 FOM= 0.68
INDE  -9  22  11 FOBS=  237.7 SIGMA=   2.4 PHAS=  231.1 FOM= 0.94
INDE  -9  23   1 FOBS=  278.7 SIGMA=   2.0 PHAS=  127.1 FOM= 0.92
INDE  -9  23   2 FOBS=   45.8 SIGMA=  11.0 PHAS=  311.5 FOM= 0.29
INDE  -9  23   3 FOBS=  124.4 SIGMA=   3.5 PHAS=  191.4 FOM= 0.24
INDE  -9  23   4 FOBS=  139.5 SIGMA=   2.9 PHAS=  104.6 FOM= 0.64
INDE  -9  23   5 FOBS=   35.5 SIGMA=  16.5 PHAS=  288.9 FOM= 0.18
INDE  -9  23   6 FOBS=   80.7 SIGMA=   4.4 PHAS=  112.2 FOM= 0.77
INDE  -9  23   7 FOBS=  136.7 SIGMA=   4.7 PHAS=  183.8 FOM= 0.24
INDE  -9  23   8 FOBS=   53.7 SIGMA=  11.0 PHAS=  239.7 FOM= 0.14
INDE  -9  23   9 FOBS=  173.4 SIGMA=   3.4 PHAS=  331.5 FOM= 0.90
INDE  -9  23  10 FOBS=  201.8 SIGMA=   3.0 PHAS=  245.0 FOM= 0.98
INDE  -9  24   1 FOBS=   35.8 SIGMA=  13.0 PHAS=  353.1 FOM= 0.29
INDE  -9  24   2 FOBS=  166.4 SIGMA=   2.9 PHAS=  205.5 FOM= 0.81
INDE  -9  24   3 FOBS=  138.0 SIGMA=   4.1 PHAS=  179.2 FOM= 0.33
INDE  -9  24   4 FOBS=   90.0 SIGMA=   4.2 PHAS=  196.6 FOM= 0.28
INDE  -9  24   5 FOBS=  218.2 SIGMA=   1.7 PHAS=  338.1 FOM= 0.85
INDE  -9  24   6 FOBS=  344.2 SIGMA=   1.2 PHAS=  230.9 FOM= 0.96
INDE  -9  24   7 FOBS=   56.2 SIGMA=  12.6 PHAS=  162.8 FOM= 0.41
INDE  -9  24   8 FOBS=   37.6 SIGMA=  15.6 PHAS=   23.6 FOM= 0.34
INDE  -9  24   9 FOBS=  191.6 SIGMA=   2.9 PHAS=   12.2 FOM= 0.82
INDE  -9  25   1 FOBS=   83.5 SIGMA=   6.3 PHAS=  106.6 FOM= 0.22
INDE  -9  25   2 FOBS=   94.1 SIGMA=   4.7 PHAS=  165.5 FOM= 0.79
INDE  -9  25   3 FOBS=  203.2 SIGMA=   2.7 PHAS=   67.9 FOM= 0.19
INDE  -9  25   4 FOBS=   51.8 SIGMA=   7.7 PHAS=   67.0 FOM= 0.32
INDE  -9  25   5 FOBS=  206.2 SIGMA=   1.8 PHAS=  103.3 FOM= 0.97
INDE  -9  25   6 FOBS=  169.8 SIGMA=   2.0 PHAS=  146.2 FOM= 0.98
INDE  -9  25   7 FOBS=  301.6 SIGMA=   2.5 PHAS=   38.9 FOM= 1.00
INDE  -9  25   8 FOBS=  132.6 SIGMA=   4.7 PHAS=  270.8 FOM= 0.31
INDE  -9  25   9 FOBS=   41.0 SIGMA=  17.1 PHAS=  115.2 FOM= 0.21
INDE  -9  26   1 FOBS=  252.3 SIGMA=   2.3 PHAS=   99.3 FOM= 0.69
INDE  -9  26   2 FOBS=  167.8 SIGMA=   2.8 PHAS=  306.7 FOM= 0.47
INDE  -9  26   3 FOBS=  218.5 SIGMA=   2.1 PHAS=  334.3 FOM= 0.90
INDE  -9  26   4 FOBS=   78.9 SIGMA=   4.8 PHAS=  200.5 FOM= 0.59
INDE  -9  26   5 FOBS=  134.3 SIGMA=   2.8 PHAS=  292.6 FOM= 0.73
INDE  -9  26   6 FOBS=  155.5 SIGMA=   2.2 PHAS=  124.3 FOM= 0.90
INDE  -9  26   7 FOBS=  109.9 SIGMA=   3.1 PHAS=  209.6 FOM= 0.16
INDE  -9  26   8 FOBS=   40.7 SIGMA=  14.3 PHAS=  223.0 FOM= 0.04
INDE  -9  27   1 FOBS=   54.8 SIGMA=   8.5 PHAS=  232.0 FOM= 0.41
INDE  -9  27   2 FOBS=  100.4 SIGMA=   5.8 PHAS=  316.0 FOM= 0.70
INDE  -9  27   3 FOBS=   50.6 SIGMA=   9.3 PHAS=  124.0 FOM= 0.16
INDE  -9  27   4 FOBS=  142.5 SIGMA=   2.8 PHAS=  214.6 FOM= 0.80
INDE  -9  27   5 FOBS=   67.6 SIGMA=   5.4 PHAS=   33.3 FOM= 0.78
INDE  -9  27   6 FOBS=  215.0 SIGMA=   1.9 PHAS=  120.2 FOM= 0.98
INDE  -9  27   7 FOBS=  133.0 SIGMA=   4.8 PHAS=   51.0 FOM= 0.46
INDE  -9  28   1 FOBS=  103.2 SIGMA=   4.4 PHAS=  123.1 FOM= 0.23
INDE  -9  28   2 FOBS=   95.6 SIGMA=   5.9 PHAS=  244.6 FOM= 0.03
INDE  -9  28   3 FOBS=  142.2 SIGMA=   3.1 PHAS=  354.8 FOM= 0.20
INDE  -9  28   4 FOBS=   59.0 SIGMA=   6.6 PHAS=  232.8 FOM= 0.19
INDE  -9  28   5 FOBS=  131.1 SIGMA=   2.9 PHAS=   83.4 FOM= 0.44
INDE  -9  29   2 FOBS=  100.0 SIGMA=   8.2 PHAS=   15.7 FOM= 0.12
INDE  -8   0   1 FOBS=  315.2 SIGMA=   2.1 PHAS=    0.0 FOM= 0.94
INDE  -8   0   2 FOBS=   57.1 SIGMA=   9.8 PHAS=  180.0 FOM= 0.38
INDE  -8   0   3 FOBS=  125.4 SIGMA=   4.6 PHAS=    0.0 FOM= 0.25
INDE  -8   0   4 FOBS=  222.0 SIGMA=   2.6 PHAS=    0.0 FOM= 0.98
INDE  -8   0   5 FOBS=  155.3 SIGMA=   3.6 PHAS=  180.0 FOM= 1.00
INDE  -8   0   6 FOBS=   88.3 SIGMA=   5.9 PHAS=    0.0 FOM= 0.85
INDE  -8   0   7 FOBS=  222.5 SIGMA=   2.2 PHAS=  180.0 FOM= 0.13
```

Fig. 10A-31

```
INDE  -8  0   8 FOBS=  142.4 SIGMA=  3.4 PHAS=  180.0 FOM= 0.19
INDE  -8  0   9 FOBS=  149.5 SIGMA=  3.3 PHAS=    0.0 FOM= 0.19
INDE  -8  0  10 FOBS=  150.9 SIGMA=  3.3 PHAS=    0.0 FOM= 0.70
INDE  -8  0  11 FOBS=  327.1 SIGMA=  1.9 PHAS=  180.0 FOM= 0.82
INDE  -8  0  12 FOBS=   55.7 SIGMA= 11.4 PHAS=  180.0 FOM= 0.01
INDE  -8  0  13 FOBS=   42.5 SIGMA= 22.0 PHAS=  180.0 FOM= 0.02
INDE  -8  0  14 FOBS=  355.7 SIGMA=  2.2 PHAS=    0.0 FOM= 1.00
INDE  -8  0  15 FOBS=   93.4 SIGMA=  7.5 PHAS=  180.0 FOM= 0.74
INDE  -8  0  16 FOBS=  201.9 SIGMA=  3.3 PHAS=    0.0 FOM= 0.01
INDE  -8  1   1 FOBS=   87.3 SIGMA=  4.7 PHAS=  157.4 FOM= 0.54
INDE  -8  1   2 FOBS=  255.3 SIGMA=  1.7 PHAS=  212.5 FOM= 0.94
INDE  -8  1   3 FOBS=  261.2 SIGMA=  1.7 PHAS=  322.0 FOM= 0.98
INDE  -8  1   4 FOBS=  126.0 SIGMA=  3.3 PHAS=   92.3 FOM= 0.98
INDE  -8  1   5 FOBS=   89.9 SIGMA=  4.0 PHAS=  199.4 FOM= 0.43
INDE  -8  1   6 FOBS=  384.9 SIGMA=  1.3 PHAS=  358.3 FOM= 0.93
INDE  -8  1   7 FOBS=   87.1 SIGMA=  4.0 PHAS=  161.8 FOM= 0.93
INDE  -8  1   8 FOBS=  258.9 SIGMA=  1.4 PHAS=   89.2 FOM= 0.97
INDE  -8  1   9 FOBS=  214.1 SIGMA=  1.8 PHAS=  338.5 FOM= 0.91
INDE  -8  1  10 FOBS=  125.0 SIGMA=  2.9 PHAS=   93.6 FOM= 0.20
INDE  -8  1  11 FOBS=  168.9 SIGMA=  2.4 PHAS=  228.7 FOM= 0.61
INDE  -8  1  12 FOBS=  210.7 SIGMA=  2.2 PHAS=   90.2 FOM= 0.98
INDE  -8  1  13 FOBS=  229.3 SIGMA=  2.1 PHAS=   73.7 FOM= 0.95
INDE  -8  1  14 FOBS=  289.2 SIGMA=  1.8 PHAS=  100.0 FOM= 0.89
INDE  -8  1  15 FOBS=   72.2 SIGMA=  6.3 PHAS=   61.4 FOM= 0.58
INDE  -8  1  16 FOBS=  107.0 SIGMA=  4.4 PHAS=  225.4 FOM= 0.91
INDE  -8  2   1 FOBS=   74.4 SIGMA=  5.3 PHAS=   37.2 FOM= 0.37
INDE  -8  2   2 FOBS=  157.0 SIGMA=  2.6 PHAS=  342.3 FOM= 0.20
INDE  -8  2   3 FOBS=  114.9 SIGMA=  3.4 PHAS=  349.2 FOM= 0.61
INDE  -8  2   4 FOBS=  114.8 SIGMA=  3.3 PHAS=   45.3 FOM= 0.56
INDE  -8  2   5 FOBS=  187.9 SIGMA=  2.0 PHAS=  305.4 FOM= 0.87
INDE  -8  2   6 FOBS=  175.2 SIGMA=  2.0 PHAS=   79.7 FOM= 0.97
INDE  -8  2   7 FOBS=  244.3 SIGMA=  1.6 PHAS=  186.2 FOM= 0.98
INDE  -8  2   8 FOBS=  151.2 SIGMA=  2.2 PHAS=   65.9 FOM= 0.89
INDE  -8  2   9 FOBS=  133.3 SIGMA=  3.0 PHAS=  107.3 FOM= 0.91
INDE  -8  2  10 FOBS=  185.4 SIGMA=  2.4 PHAS=  196.6 FOM= 0.98
INDE  -8  2  11 FOBS=  258.1 SIGMA=  1.7 PHAS=  285.6 FOM= 0.83
INDE  -8  2  12 FOBS=  305.4 SIGMA=  1.6 PHAS=  326.5 FOM= 0.84
INDE  -8  2  13 FOBS=  223.7 SIGMA=  2.1 PHAS=  101.3 FOM= 0.93
INDE  -8  2  14 FOBS=  170.2 SIGMA=  2.8 PHAS=   55.2 FOM= 0.41
INDE  -8  2  15 FOBS=  174.9 SIGMA=  2.6 PHAS=  150.9 FOM= 0.64
INDE  -8  2  16 FOBS=  139.7 SIGMA=  3.5 PHAS=  278.0 FOM= 0.14
INDE  -8  3   1 FOBS=  176.8 SIGMA=  2.7 PHAS=  131.2 FOM= 0.72
INDE  -8  3   2 FOBS=   43.3 SIGMA=  8.7 PHAS=  186.7 FOM= 0.15
INDE  -8  3   3 FOBS=  171.8 SIGMA=  2.3 PHAS=  264.9 FOM= 0.94
INDE  -8  3   4 FOBS=  133.0 SIGMA=  2.8 PHAS=  227.9 FOM= 0.24
INDE  -8  3   5 FOBS=  239.9 SIGMA=  1.7 PHAS=  148.9 FOM= 0.56
INDE  -8  3   6 FOBS=  270.9 SIGMA=  1.4 PHAS=  131.3 FOM= 0.95
INDE  -8  3   7 FOBS=  130.8 SIGMA=  2.6 PHAS=  205.3 FOM= 0.77
INDE  -8  3   8 FOBS=  153.4 SIGMA=  2.1 PHAS=  186.5 FOM= 0.99
INDE  -8  3   9 FOBS=  144.1 SIGMA=  3.0 PHAS=  141.9 FOM= 0.95
INDE  -8  3  10 FOBS=  241.2 SIGMA=  1.8 PHAS=  202.5 FOM= 0.98
INDE  -8  3  11 FOBS=  625.7 SIGMA=  1.0 PHAS=   24.8 FOM= 1.00
INDE  -8  3  12 FOBS=  154.2 SIGMA=  2.9 PHAS=  233.1 FOM= 0.95
INDE  -8  3  13 FOBS=  149.9 SIGMA=  3.2 PHAS=   72.0 FOM= 0.31
INDE  -8  3  14 FOBS=  156.6 SIGMA=  3.0 PHAS=  138.4 FOM= 0.90
INDE  -8  3  15 FOBS=   47.0 SIGMA=  9.9 PHAS=  173.9 FOM= 0.33
INDE  -8  3  16 FOBS=  161.3 SIGMA=  3.0 PHAS=  253.1 FOM= 0.55
INDE  -8  4   1 FOBS=   91.6 SIGMA=  5.2 PHAS=   74.6 FOM= 0.70
INDE  -8  4   2 FOBS=  214.4 SIGMA=  2.0 PHAS=  136.4 FOM= 0.87
INDE  -8  4   3 FOBS=  304.2 SIGMA=  1.4 PHAS=  332.5 FOM= 0.95
INDE  -8  4   4 FOBS=  112.3 SIGMA=  3.3 PHAS=  192.0 FOM= 0.29
INDE  -8  4   5 FOBS=   84.1 SIGMA=  4.5 PHAS=  209.2 FOM= 0.89
INDE  -8  4   6 FOBS=  342.8 SIGMA=  1.5 PHAS=  313.8 FOM= 0.97
INDE  -8  4   7 FOBS=  249.5 SIGMA=  1.6 PHAS=  260.7 FOM= 0.93
INDE  -8  4   8 FOBS=  258.4 SIGMA=  1.4 PHAS=  180.7 FOM= 0.84
INDE  -8  4   9 FOBS=  146.4 SIGMA=  2.8 PHAS=  177.9 FOM= 0.89
INDE  -8  4  10 FOBS=  217.4 SIGMA=  2.0 PHAS=  323.3 FOM= 0.92
INDE  -8  4  11 FOBS=  242.1 SIGMA=  1.8 PHAS=  236.8 FOM= 0.95
INDE  -8  4  12 FOBS=  120.9 SIGMA=  4.0 PHAS=  159.1 FOM= 0.90
INDE  -8  4  13 FOBS=  101.4 SIGMA=  4.6 PHAS=  287.9 FOM= 0.53
INDE  -8  4  14 FOBS=   79.6 SIGMA=  5.8 PHAS=   82.1 FOM= 0.33
```

Fig. 10A-32

```
INDE  -8  4 15 FOBS=  143.4 SIGMA= 3.6 PHAS= 175.8 FOM= 0.44
INDE  -8  4 16 FOBS=  142.7 SIGMA= 3.4 PHAS=  59.3 FOM= 0.17
INDE  -8  5  1 FOBS=  277.2 SIGMA= 1.9 PHAS= 182.6 FOM= 1.00
INDE  -8  5  2 FOBS=  313.4 SIGMA= 1.6 PHAS= 282.2 FOM= 0.98
INDE  -8  5  3 FOBS=  182.6 SIGMA= 2.1 PHAS= 211.8 FOM= 0.06
INDE  -8  5  4 FOBS=  185.4 SIGMA= 2.0 PHAS= 165.4 FOM= 0.96
INDE  -8  5  5 FOBS=  410.9 SIGMA= 1.2 PHAS= 269.6 FOM= 0.89
INDE  -8  5  6 FOBS=  131.6 SIGMA= 3.1 PHAS=  37.9 FOM= 0.42
INDE  -8  5  7 FOBS=  196.5 SIGMA= 1.9 PHAS= 183.2 FOM= 0.82
INDE  -8  5  8 FOBS=  228.0 SIGMA= 1.5 PHAS= 230.1 FOM= 0.93
INDE  -8  5  9 FOBS=  198.4 SIGMA= 2.2 PHAS=  69.1 FOM= 0.83
INDE  -8  5 10 FOBS=  288.5 SIGMA= 1.6 PHAS= 261.7 FOM= 0.98
INDE  -8  5 11 FOBS=  498.1 SIGMA= 1.3 PHAS= 138.3 FOM= 1.00
INDE  -8  5 12 FOBS=  259.1 SIGMA= 1.8 PHAS=  93.7 FOM= 0.38
INDE  -8  5 13 FOBS=   88.7 SIGMA= 4.9 PHAS= 231.0 FOM= 0.71
INDE  -8  5 14 FOBS=   92.8 SIGMA= 4.8 PHAS=  60.8 FOM= 0.64
INDE  -8  5 15 FOBS=  117.5 SIGMA= 4.2 PHAS= 203.0 FOM= 0.70
INDE  -8  5 16 FOBS=  237.6 SIGMA= 2.1 PHAS= 218.7 FOM= 0.85
INDE  -8  6  1 FOBS=  109.6 SIGMA= 4.6 PHAS=  66.5 FOM= 0.77
INDE  -8  6  2 FOBS=   86.2 SIGMA= 5.1 PHAS= 245.3 FOM= 0.90
INDE  -8  6  3 FOBS=  138.4 SIGMA= 3.1 PHAS=  70.4 FOM= 0.93
INDE  -8  6  4 FOBS=  272.1 SIGMA= 1.4 PHAS= 305.3 FOM= 0.94
INDE  -8  6  5 FOBS=  232.9 SIGMA= 1.7 PHAS=  46.4 FOM= 0.95
INDE  -8  6  6 FOBS=  256.0 SIGMA= 1.7 PHAS= 256.3 FOM= 0.35
INDE  -8  6  7 FOBS=  280.5 SIGMA= 1.4 PHAS= 117.6 FOM= 0.99
INDE  -8  6  8 FOBS=  324.3 SIGMA= 1.3 PHAS=   7.0 FOM= 0.94
INDE  -8  6  9 FOBS=  159.4 SIGMA= 2.7 PHAS=  77.5 FOM= 0.20
INDE  -8  6 10 FOBS=  365.4 SIGMA= 1.3 PHAS= 194.1 FOM= 1.00
INDE  -8  6 11 FOBS=   95.7 SIGMA= 4.5 PHAS= 353.9 FOM= 0.24
INDE  -8  6 12 FOBS=  355.1 SIGMA= 1.4 PHAS=  26.5 FOM= 0.74
INDE  -8  6 13 FOBS=  114.7 SIGMA= 3.9 PHAS= 221.0 FOM= 0.14
INDE  -8  6 14 FOBS=  142.4 SIGMA= 3.3 PHAS= 114.4 FOM= 0.90
INDE  -8  6 15 FOBS=  205.8 SIGMA= 2.2 PHAS= 147.6 FOM= 0.84
INDE  -8  6 16 FOBS=  128.5 SIGMA= 4.0 PHAS= 318.4 FOM= 0.27
INDE  -8  7  1 FOBS=  185.1 SIGMA= 2.4 PHAS= 319.5 FOM= 0.91
INDE  -8  7  2 FOBS=   99.3 SIGMA= 5.6 PHAS=  38.7 FOM= 0.89
INDE  -8  7  3 FOBS=   76.7 SIGMA= 5.0 PHAS= 258.4 FOM= 0.81
INDE  -8  7  4 FOBS=  126.1 SIGMA= 3.0 PHAS= 158.0 FOM= 0.23
INDE  -8  7  5 FOBS=  198.0 SIGMA= 1.8 PHAS=  32.0 FOM= 1.00
INDE  -8  7  6 FOBS=  162.9 SIGMA= 1.9 PHAS= 248.4 FOM= 0.96
INDE  -8  7  7 FOBS=   92.6 SIGMA= 3.8 PHAS=  15.0 FOM= 0.91
INDE  -8  7  8 FOBS=  292.0 SIGMA= 1.3 PHAS= 249.4 FOM= 1.00
INDE  -8  7  9 FOBS=  252.7 SIGMA= 1.8 PHAS= 316.9 FOM= 0.93
INDE  -8  7 10 FOBS=  317.2 SIGMA= 1.4 PHAS=  58.6 FOM= 0.58
INDE  -8  7 11 FOBS=  230.5 SIGMA= 2.0 PHAS=  73.8 FOM= 0.94
INDE  -8  7 12 FOBS=  187.2 SIGMA= 2.3 PHAS= 289.3 FOM= 0.94
INDE  -8  7 13 FOBS=  229.1 SIGMA= 2.0 PHAS=  81.5 FOM= 0.32
INDE  -8  7 14 FOBS=  143.9 SIGMA= 3.1 PHAS= 172.8 FOM= 0.20
INDE  -8  7 15 FOBS=  185.4 SIGMA= 2.5 PHAS= 290.7 FOM= 0.70
INDE  -8  7 16 FOBS=   91.5 SIGMA= 5.5 PHAS= 260.6 FOM= 0.17
INDE  -8  8  1 FOBS=  159.5 SIGMA= 2.8 PHAS= 100.8 FOM= 0.75
INDE  -8  8  2 FOBS=  117.8 SIGMA= 3.7 PHAS= 292.5 FOM= 0.76
INDE  -8  8  3 FOBS=  188.1 SIGMA= 2.7 PHAS=  50.2 FOM= 0.94
INDE  -8  8  4 FOBS=   51.9 SIGMA= 6.3 PHAS= 309.4 FOM= 0.23
INDE  -8  8  5 FOBS=  183.6 SIGMA= 2.0 PHAS=  82.4 FOM= 0.97
INDE  -8  8  6 FOBS=  248.3 SIGMA= 1.3 PHAS= 341.5 FOM= 0.54
INDE  -8  8  7 FOBS=  216.6 SIGMA= 1.6 PHAS= 231.0 FOM= 0.64
INDE  -8  8  8 FOBS=  148.6 SIGMA= 2.1 PHAS= 173.2 FOM= 0.94
INDE  -8  8  9 FOBS=  246.1 SIGMA= 1.9 PHAS= 226.0 FOM= 0.55
INDE  -8  8 10 FOBS=  414.4 SIGMA= 1.2 PHAS=  74.5 FOM= 0.98
INDE  -8  8 11 FOBS=  197.9 SIGMA= 2.3 PHAS= 191.1 FOM= 0.89
INDE  -8  8 12 FOBS=   94.9 SIGMA= 4.4 PHAS= 191.4 FOM= 0.23
INDE  -8  8 13 FOBS=   98.1 SIGMA= 4.5 PHAS=   9.9 FOM= 0.48
INDE  -8  8 14 FOBS=  185.7 SIGMA= 2.4 PHAS= 269.4 FOM= 0.41
INDE  -8  8 15 FOBS=   98.9 SIGMA= 4.7 PHAS= 154.2 FOM= 0.05
INDE  -8  8 16 FOBS=  118.2 SIGMA= 4.8 PHAS= 197.0 FOM= 0.13
INDE  -8  9  1 FOBS=  361.3 SIGMA= 1.6 PHAS= 162.0 FOM= 1.00
INDE  -8  9  2 FOBS=  143.8 SIGMA= 3.0 PHAS=  53.8 FOM= 0.79
INDE  -8  9  3 FOBS=  171.8 SIGMA= 2.2 PHAS= 182.2 FOM= 0.95
INDE  -8  9  4 FOBS=  194.5 SIGMA= 2.4 PHAS= 143.3 FOM= 0.99
INDE  -8  9  5 FOBS=  404.5 SIGMA= 1.4 PHAS= 302.0 FOM= 0.48
```

Fig. 10A-33

```
INDE  -8   9   6 FOBS=   75.9 SIGMA=  3.3 PHAS=  18.6 FOM= 0.93
INDE  -8   9   7 FOBS=  425.1 SIGMA=  1.1 PHAS= 222.1 FOM= 0.98
INDE  -8   9   8 FOBS=  132.0 SIGMA=  2.3 PHAS=  52.1 FOM= 0.90
INDE  -8   9   9 FOBS=  152.5 SIGMA=  2.7 PHAS= 332.7 FOM= 0.82
INDE  -8   9  10 FOBS=  234.7 SIGMA=  1.8 PHAS=   5.2 FOM= 0.93
INDE  -8   9  11 FOBS=  134.7 SIGMA=  3.3 PHAS= 172.9 FOM= 0.66
INDE  -8   9  12 FOBS=  166.9 SIGMA=  2.4 PHAS=  17.1 FOM= 0.94
INDE  -8   9  13 FOBS=  215.3 SIGMA=  2.1 PHAS= 304.2 FOM= 0.97
INDE  -8   9  14 FOBS=  108.7 SIGMA=  4.2 PHAS= 284.6 FOM= 0.15
INDE  -8   9  15 FOBS=  174.1 SIGMA=  2.7 PHAS= 279.0 FOM= 0.86
INDE  -8  10   1 FOBS=   61.1 SIGMA=  8.2 PHAS= 317.4 FOM= 0.22
INDE  -8  10   2 FOBS=  210.3 SIGMA=  2.0 PHAS= 145.8 FOM= 0.94
INDE  -8  10   3 FOBS=   56.9 SIGMA=  6.8 PHAS=  45.9 FOM= 0.54
INDE  -8  10   4 FOBS=  294.6 SIGMA=  1.5 PHAS= 227.7 FOM= 0.96
INDE  -8  10   5 FOBS=  442.8 SIGMA=  1.4 PHAS= 160.8 FOM= 0.93
INDE  -8  10   6 FOBS=  322.9 SIGMA=  1.1 PHAS= 332.2 FOM= 0.44
INDE  -8  10   7 FOBS=  698.9 SIGMA=  0.8 PHAS= 274.3 FOM= 0.65
INDE  -8  10   8 FOBS=  276.3 SIGMA=  1.2 PHAS= 305.8 FOM= 0.74
INDE  -8  10   9 FOBS=   53.7 SIGMA=  7.2 PHAS=  43.7 FOM= 0.45
INDE  -8  10  10 FOBS=  296.1 SIGMA=  1.6 PHAS= 194.5 FOM= 0.89
INDE  -8  10  11 FOBS=  209.1 SIGMA=  2.1 PHAS= 308.4 FOM= 0.31
INDE  -8  10  12 FOBS=  180.2 SIGMA=  2.2 PHAS= 136.3 FOM= 0.81
INDE  -8  10  13 FOBS=  247.5 SIGMA=  1.9 PHAS= 295.2 FOM= 0.93
INDE  -8  10  14 FOBS=  117.4 SIGMA=  4.1 PHAS= 106.3 FOM= 0.89
INDE  -8  10  15 FOBS=  142.2 SIGMA=  3.5 PHAS= 262.3 FOM= 0.91
INDE  -8  11   1 FOBS=  257.0 SIGMA=  1.9 PHAS= 206.7 FOM= 0.96
INDE  -8  11   2 FOBS=  136.0 SIGMA=  3.2 PHAS= 190.2 FOM= 0.92
INDE  -8  11   3 FOBS=  122.6 SIGMA=  3.3 PHAS=  42.7 FOM= 0.96
INDE  -8  11   4 FOBS=  218.4 SIGMA=  1.6 PHAS=  64.4 FOM= 0.95
INDE  -8  11   5 FOBS=  368.7 SIGMA=  2.3 PHAS=   6.0 FOM= 0.64
INDE  -8  11   6 FOBS=  356.9 SIGMA=  2.6 PHAS=  21.2 FOM= 0.80
INDE  -8  11   7 FOBS=  174.1 SIGMA=  2.4 PHAS= 221.2 FOM= 0.72
INDE  -8  11   8 FOBS=  416.3 SIGMA=  0.9 PHAS= 322.1 FOM= 0.98
INDE  -8  11   9 FOBS=  250.2 SIGMA=  1.9 PHAS=  93.6 FOM= 0.96
INDE  -8  11  10 FOBS=  127.8 SIGMA=  3.0 PHAS= 282.1 FOM= 0.91
INDE  -8  11  11 FOBS=  194.2 SIGMA=  2.2 PHAS= 301.0 FOM= 1.00
INDE  -8  11  12 FOBS=   78.2 SIGMA=  6.2 PHAS= 195.8 FOM= 0.66
INDE  -8  11  13 FOBS=  139.5 SIGMA=  3.4 PHAS= 104.7 FOM= 0.91
INDE  -8  11  14 FOBS=   40.5 SIGMA= 27.0 PHAS= 288.2 FOM= 0.42
INDE  -8  11  15 FOBS=   97.6 SIGMA=  4.7 PHAS= 125.2 FOM= 0.41
INDE  -8  12   1 FOBS=  240.8 SIGMA=  2.0 PHAS= 110.1 FOM= 0.95
INDE  -8  12   2 FOBS=   35.7 SIGMA= 15.1 PHAS= 232.2 FOM= 0.09
INDE  -8  12   3 FOBS=  217.3 SIGMA=  1.8 PHAS= 341.4 FOM= 0.70
INDE  -8  12   4 FOBS=   58.6 SIGMA=  4.6 PHAS=  57.4 FOM= 0.42
INDE  -8  12   5 FOBS=  115.3 SIGMA=  5.5 PHAS= 211.4 FOM= 0.56
INDE  -8  12   6 FOBS=  177.5 SIGMA=  3.8 PHAS= 141.6 FOM= 0.93
INDE  -8  12   7 FOBS=  344.8 SIGMA=  3.1 PHAS= 140.9 FOM= 0.95
INDE  -8  12   8 FOBS=  481.7 SIGMA=  0.9 PHAS= 333.8 FOM= 0.89
INDE  -8  12   9 FOBS=  171.4 SIGMA=  2.5 PHAS= 110.3 FOM= 0.98
INDE  -8  12  10 FOBS=  275.4 SIGMA=  1.6 PHAS= 267.2 FOM= 1.00
INDE  -8  12  11 FOBS=  249.3 SIGMA=  1.7 PHAS= 154.5 FOM= 0.30
INDE  -8  12  12 FOBS=  161.7 SIGMA=  3.0 PHAS= 123.4 FOM= 0.76
INDE  -8  12  13 FOBS=  185.1 SIGMA=  2.3 PHAS= 173.0 FOM= 0.93
INDE  -8  12  14 FOBS=   64.0 SIGMA=  6.9 PHAS=  87.2 FOM= 0.28
INDE  -8  12  15 FOBS=   53.4 SIGMA=  8.7 PHAS= 223.1 FOM= 0.01
INDE  -8  13   1 FOBS=  126.2 SIGMA=  3.9 PHAS= 161.8 FOM= 0.91
INDE  -8  13   2 FOBS=   89.0 SIGMA=  4.9 PHAS= 268.6 FOM= 0.52
INDE  -8  13   3 FOBS=  108.5 SIGMA=  4.8 PHAS=  56.5 FOM= 0.71
INDE  -8  13   4 FOBS=  437.8 SIGMA=  1.5 PHAS= 189.5 FOM= 1.00
INDE  -8  13   5 FOBS=  195.0 SIGMA=  3.3 PHAS= 127.4 FOM= 0.66
INDE  -8  13   6 FOBS=  142.9 SIGMA=  4.3 PHAS=  81.2 FOM= 0.33
INDE  -8  13   7 FOBS=  358.9 SIGMA=  2.8 PHAS= 273.4 FOM= 0.97
INDE  -8  13   8 FOBS=  273.9 SIGMA=  2.9 PHAS= 253.7 FOM= 0.25
INDE  -8  13   9 FOBS=  207.9 SIGMA=  2.2 PHAS= 220.0 FOM= 0.97
INDE  -8  13  10 FOBS=  380.3 SIGMA=  1.2 PHAS=  47.5 FOM= 0.65
INDE  -8  13  11 FOBS=  119.4 SIGMA=  3.3 PHAS= 136.4 FOM= 0.92
INDE  -8  13  12 FOBS=   70.5 SIGMA=  7.0 PHAS= 247.7 FOM= 0.54
INDE  -8  13  13 FOBS=  275.5 SIGMA=  1.7 PHAS= 271.2 FOM= 0.74
INDE  -8  13  14 FOBS=  205.7 SIGMA=  2.2 PHAS=   7.0 FOM= 0.76
INDE  -8  13  15 FOBS=  122.1 SIGMA=  4.1 PHAS= 184.5 FOM= 0.66
INDE  -8  14   1 FOBS=  177.4 SIGMA=  2.7 PHAS=  38.9 FOM= 0.93
```

Fig. 10A-34

```
INDE  -8  14   2  FOBS=  302.6  SIGMA=   1.6  PHAS=  329.6  FOM=  0.97
INDE  -8  14   3  FOBS=  122.6  SIGMA=   3.4  PHAS=  167.5  FOM=  0.40
INDE  -8  14   4  FOBS=  212.1  SIGMA=   1.8  PHAS=  143.2  FOM=  1.00
INDE  -8  14   5  FOBS=  297.6  SIGMA=   2.5  PHAS=  269.5  FOM=  0.98
INDE  -8  14   6  FOBS=  295.1  SIGMA=   2.4  PHAS=  136.0  FOM=  0.90
INDE  -8  14   7  FOBS=  264.3  SIGMA=   3.5  PHAS=   51.7  FOM=  0.27
INDE  -8  14   8  FOBS=  495.9  SIGMA=   1.8  PHAS=  196.0  FOM=  0.94
INDE  -8  14   9  FOBS=  142.4  SIGMA=   3.2  PHAS=  183.6  FOM=  0.88
INDE  -8  14  10  FOBS=  141.0  SIGMA=   2.5  PHAS=  168.7  FOM=  0.66
INDE  -8  14  11  FOBS=   84.0  SIGMA=   4.7  PHAS=  180.9  FOM=  0.11
INDE  -8  14  12  FOBS=  101.2  SIGMA=   4.6  PHAS=  313.8  FOM=  0.06
INDE  -8  14  13  FOBS=  196.5  SIGMA=   2.2  PHAS=   34.8  FOM=  0.91
INDE  -8  14  14  FOBS=   96.1  SIGMA=   4.6  PHAS=   16.7  FOM=  0.77
INDE  -8  15   1  FOBS=  201.1  SIGMA=   2.4  PHAS=  151.5  FOM=  0.92
INDE  -8  15   2  FOBS=  127.0  SIGMA=   3.4  PHAS=  255.9  FOM=  0.84
INDE  -8  15   3  FOBS=  204.8  SIGMA=   1.9  PHAS=  257.5  FOM=  0.95
INDE  -8  15   4  FOBS=   49.9  SIGMA=   6.2  PHAS=  121.3  FOM=  0.46
INDE  -8  15   5  FOBS=   63.3  SIGMA=  10.4  PHAS=  275.3  FOM=  0.22
INDE  -8  15   6  FOBS=   81.6  SIGMA=   7.3  PHAS=   17.3  FOM=  0.27
INDE  -8  15   7  FOBS=  284.8  SIGMA=   3.4  PHAS=  168.3  FOM=  0.88
INDE  -8  15   8  FOBS=  175.0  SIGMA=   3.7  PHAS=  277.8  FOM=  0.10
INDE  -8  15   9  FOBS=   34.0  SIGMA=   9.2  PHAS=  341.5  FOM=  0.07
INDE  -8  15  10  FOBS=  144.2  SIGMA=   2.5  PHAS=  196.4  FOM=  0.02
INDE  -8  15  11  FOBS=  103.1  SIGMA=   4.1  PHAS=  213.6  FOM=  0.28
INDE  -8  15  12  FOBS=   81.5  SIGMA=   5.5  PHAS=    0.3  FOM=  0.11
INDE  -8  15  13  FOBS=  125.1  SIGMA=   3.9  PHAS=   43.9  FOM=  0.76
INDE  -8  15  14  FOBS=  136.8  SIGMA=   3.2  PHAS=  136.1  FOM=  0.59
INDE  -8  16   1  FOBS=  254.0  SIGMA=   2.2  PHAS=  102.8  FOM=  0.69
INDE  -8  16   2  FOBS=  149.9  SIGMA=   2.9  PHAS=  108.5  FOM=  0.76
INDE  -8  16   3  FOBS=  234.0  SIGMA=   1.8  PHAS=   77.9  FOM=  0.82
INDE  -8  16   4  FOBS=  348.0  SIGMA=   2.2  PHAS=  130.9  FOM=  0.94
INDE  -8  16   5  FOBS=  518.0  SIGMA=   1.8  PHAS=  292.4  FOM=  0.98
INDE  -8  16   6  FOBS=  429.5  SIGMA=   1.9  PHAS=  237.2  FOM=  0.99
INDE  -8  16   7  FOBS=  206.4  SIGMA=   4.4  PHAS=   29.8  FOM=  0.79
INDE  -8  16   8  FOBS=  239.9  SIGMA=   2.8  PHAS=    5.8  FOM=  0.93
INDE  -8  16   9  FOBS=   91.6  SIGMA=   3.9  PHAS=   98.5  FOM=  0.71
INDE  -8  16  10  FOBS=  124.9  SIGMA=   2.7  PHAS=  189.0  FOM=  0.88
INDE  -8  16  11  FOBS=  136.7  SIGMA=   2.8  PHAS=  337.5  FOM=  0.81
INDE  -8  16  12  FOBS=   82.6  SIGMA=   5.2  PHAS=   98.2  FOM=  0.35
INDE  -8  16  13  FOBS=   97.4  SIGMA=   5.5  PHAS=   15.1  FOM=  0.29
INDE  -8  16  14  FOBS=  125.2  SIGMA=   3.9  PHAS=  209.5  FOM=  0.26
INDE  -8  17   1  FOBS=  209.5  SIGMA=   2.3  PHAS=  242.6  FOM=  0.06
INDE  -8  17   2  FOBS=  261.7  SIGMA=   2.1  PHAS=  254.7  FOM=  0.88
INDE  -8  17   3  FOBS=  235.9  SIGMA=   1.8  PHAS=  131.7  FOM=  0.87
INDE  -8  17   4  FOBS=  146.7  SIGMA=   3.3  PHAS=  171.5  FOM=  0.50
INDE  -8  17   5  FOBS=  635.1  SIGMA=   1.9  PHAS=  337.9  FOM=  0.97
INDE  -8  17   6  FOBS=  288.9  SIGMA=   2.5  PHAS=   39.7  FOM=  1.00
INDE  -8  17   7  FOBS=  428.8  SIGMA=   2.6  PHAS=  105.3  FOM=  0.89
INDE  -8  17   8  FOBS=  185.2  SIGMA=   3.6  PHAS=   97.7  FOM=  0.84
INDE  -8  17   9  FOBS=   54.9  SIGMA=  12.1  PHAS=  218.8  FOM=  0.50
INDE  -8  17  10  FOBS=  132.3  SIGMA=   2.4  PHAS=  137.4  FOM=  0.59
INDE  -8  17  11  FOBS=  273.9  SIGMA=   1.9  PHAS=  287.5  FOM=  0.88
INDE  -8  17  12  FOBS=  115.4  SIGMA=   3.4  PHAS=  321.6  FOM=  0.39
INDE  -8  17  13  FOBS=  142.1  SIGMA=   3.3  PHAS=    3.3  FOM=  0.59
INDE  -8  17  14  FOBS=   92.2  SIGMA=  22.7  PHAS=   70.5  FOM=  0.07
INDE  -8  18   1  FOBS=  203.2  SIGMA=   2.4  PHAS=   99.3  FOM=  0.88
INDE  -8  18   2  FOBS=  251.7  SIGMA=   1.9  PHAS=  176.5  FOM=  0.93
INDE  -8  18   3  FOBS=  119.0  SIGMA=   3.5  PHAS=  199.4  FOM=  0.89
INDE  -8  18   4  FOBS=  232.0  SIGMA=   2.4  PHAS=  284.4  FOM=  0.63
INDE  -8  18   5  FOBS=   58.9  SIGMA=   6.5  PHAS=  231.7  FOM=  0.24
INDE  -8  18   6  FOBS=  165.3  SIGMA=   4.0  PHAS=  353.0  FOM=  0.71
INDE  -8  18   7  FOBS=   43.4  SIGMA=  24.0  PHAS=   12.4  FOM=  0.23
INDE  -8  18   8  FOBS=  135.8  SIGMA=   4.9  PHAS=  205.3  FOM=  0.46
INDE  -8  18   9  FOBS=  147.9  SIGMA=   3.9  PHAS=   34.6  FOM=  0.90
INDE  -8  18  10  FOBS=  150.3  SIGMA=   2.0  PHAS=  275.0  FOM=  1.00
INDE  -8  18  11  FOBS=  203.3  SIGMA=   1.9  PHAS=   68.8  FOM=  0.92
INDE  -8  18  12  FOBS=  137.4  SIGMA=   3.1  PHAS=  274.1  FOM=  1.00
INDE  -8  18  13  FOBS=  353.4  SIGMA=   1.6  PHAS=   35.4  FOM=  0.95
INDE  -8  19   1  FOBS=  133.9  SIGMA=   4.0  PHAS=  284.3  FOM=  0.60
INDE  -8  19   2  FOBS=  141.0  SIGMA=   3.2  PHAS=  230.4  FOM=  0.09
INDE  -8  19   3  FOBS=  281.5  SIGMA=   1.7  PHAS=    3.7  FOM=  0.97
```

Fig. 10A-35

```
INDE  -8  19   4 FOBS=  184.5 SIGMA=  2.1 PHAS=  125.0 FOM= 0.95
INDE  -8  19   5 FOBS=  116.4 SIGMA=  3.0 PHAS=  328.1 FOM= 0.76
INDE  -8  19   6 FOBS=  228.0 SIGMA=  3.1 PHAS=   58.0 FOM= 0.86
INDE  -8  19   7 FOBS=  231.5 SIGMA=  4.0 PHAS=  307.4 FOM= 0.45
INDE  -8  19   8 FOBS=  186.5 SIGMA=  3.4 PHAS=   97.0 FOM= 0.45
INDE  -8  19   9 FOBS=  179.9 SIGMA=  3.3 PHAS=    6.1 FOM= 0.38
INDE  -8  19  10 FOBS=   57.3 SIGMA=  4.7 PHAS=  319.8 FOM= 0.53
INDE  -8  19  11 FOBS=   78.4 SIGMA=  4.5 PHAS=   11.1 FOM= 0.63
INDE  -8  19  12 FOBS=  203.4 SIGMA=  2.0 PHAS=   43.4 FOM= 0.84
INDE  -8  19  13 FOBS=   46.5 SIGMA= 10.1 PHAS=   68.4 FOM= 0.16
INDE  -8  20   1 FOBS=   77.6 SIGMA=  6.4 PHAS=  306.4 FOM= 0.23
INDE  -8  20   2 FOBS=  199.0 SIGMA=  2.5 PHAS=  343.9 FOM= 0.69
INDE  -8  20   3 FOBS=  156.6 SIGMA=  2.6 PHAS=  209.5 FOM= 0.36
INDE  -8  20   4 FOBS=  384.9 SIGMA=  1.4 PHAS=  235.2 FOM= 0.95
INDE  -8  20   5 FOBS=  258.8 SIGMA=  1.4 PHAS=   12.2 FOM= 0.18
INDE  -8  20   6 FOBS=  107.1 SIGMA=  6.2 PHAS=   84.7 FOM= 0.22
INDE  -8  20   7 FOBS=  118.2 SIGMA=  8.0 PHAS=  271.4 FOM= 0.38
INDE  -8  20   8 FOBS=  179.6 SIGMA=  3.5 PHAS=  358.1 FOM= 0.24
INDE  -8  20   9 FOBS=  261.4 SIGMA=  2.5 PHAS=  205.0 FOM= 0.40
INDE  -8  20  10 FOBS=  165.0 SIGMA=  2.2 PHAS=  125.6 FOM= 0.68
INDE  -8  20  11 FOBS=  111.4 SIGMA=  3.3 PHAS=  208.0 FOM= 0.80
INDE  -8  20  12 FOBS=  141.6 SIGMA=  2.6 PHAS=  262.8 FOM= 0.93
INDE  -8  21   1 FOBS=  187.7 SIGMA=  2.7 PHAS=   37.2 FOM= 0.68
INDE  -8  21   2 FOBS=  284.4 SIGMA=  1.8 PHAS=   63.3 FOM= 0.96
INDE  -8  21   3 FOBS=  198.3 SIGMA=  2.7 PHAS=  236.9 FOM= 0.49
INDE  -8  21   4 FOBS=  200.3 SIGMA=  2.3 PHAS=  104.0 FOM= 0.93
INDE  -8  21   5 FOBS=  136.4 SIGMA=  2.5 PHAS=  147.2 FOM= 0.61
INDE  -8  21   6 FOBS=  219.4 SIGMA=  1.8 PHAS=  263.4 FOM= 0.71
INDE  -8  21   7 FOBS=  204.2 SIGMA=  4.3 PHAS=   92.4 FOM= 0.80
INDE  -8  21   8 FOBS=  157.8 SIGMA=  3.7 PHAS=  252.9 FOM= 0.87
INDE  -8  21   9 FOBS=  194.6 SIGMA=  3.0 PHAS=  107.8 FOM= 0.95
INDE  -8  21  10 FOBS=   83.5 SIGMA=  3.3 PHAS=   79.7 FOM= 0.23
INDE  -8  21  11 FOBS=  152.7 SIGMA=  2.5 PHAS=  276.7 FOM= 0.89
INDE  -8  21  12 FOBS=   62.9 SIGMA=  5.9 PHAS=  251.9 FOM= 0.50
INDE  -8  22   1 FOBS=  362.0 SIGMA=  1.7 PHAS=  352.8 FOM= 0.97
INDE  -8  22   2 FOBS=  140.6 SIGMA=  3.6 PHAS=  221.9 FOM= 0.74
INDE  -8  22   3 FOBS=  219.5 SIGMA=  2.6 PHAS=  286.6 FOM= 0.81
INDE  -8  22   4 FOBS=  120.0 SIGMA=  3.5 PHAS=   74.6 FOM= 0.92
INDE  -8  22   5 FOBS=   63.6 SIGMA=  5.5 PHAS=  200.2 FOM= 0.64
INDE  -8  22   6 FOBS=  364.5 SIGMA=  1.1 PHAS=   49.3 FOM= 0.97
INDE  -8  22   7 FOBS=  131.9 SIGMA=  5.0 PHAS=  357.8 FOM= 0.59
INDE  -8  22   8 FOBS=   74.2 SIGMA=  5.9 PHAS=  253.7 FOM= 0.13
INDE  -8  22   9 FOBS=  204.7 SIGMA=  3.0 PHAS=   82.0 FOM= 0.88
INDE  -8  22  10 FOBS=   97.5 SIGMA=  2.7 PHAS=  238.1 FOM= 0.96
INDE  -8  22  11 FOBS=  193.6 SIGMA=  1.8 PHAS=  101.8 FOM= 0.97
INDE  -8  23   1 FOBS=  251.9 SIGMA=  2.3 PHAS=  206.5 FOM= 0.10
INDE  -8  23   2 FOBS=  139.9 SIGMA=  3.3 PHAS=  218.3 FOM= 0.65
INDE  -8  23   3 FOBS=  243.1 SIGMA=  2.2 PHAS=  348.3 FOM= 0.90
INDE  -8  23   4 FOBS=  145.0 SIGMA=  2.8 PHAS=  150.4 FOM= 0.83
INDE  -8  23   5 FOBS=  116.3 SIGMA=  3.2 PHAS=  189.2 FOM= 0.58
INDE  -8  23   6 FOBS=  143.9 SIGMA=  2.3 PHAS=  169.8 FOM= 0.95
INDE  -8  23   7 FOBS=   49.5 SIGMA=  6.1 PHAS=  172.2 FOM= 0.35
INDE  -8  23   8 FOBS=  228.5 SIGMA=  1.6 PHAS=    9.4 FOM= 0.96
INDE  -8  23   9 FOBS=   50.8 SIGMA= 10.0 PHAS=  326.0 FOM= 0.64
INDE  -8  23  10 FOBS=  169.7 SIGMA=  1.7 PHAS=  136.9 FOM= 0.41
INDE  -8  23  11 FOBS=  148.1 SIGMA=  2.3 PHAS=  100.2 FOM= 0.92
INDE  -8  24   1 FOBS=  156.9 SIGMA=  3.6 PHAS=   80.9 FOM= 0.83
INDE  -8  24   2 FOBS=  275.1 SIGMA=  2.1 PHAS=    5.6 FOM= 0.99
INDE  -8  24   3 FOBS=  212.9 SIGMA=  2.1 PHAS=  143.3 FOM= 0.96
INDE  -8  24   4 FOBS=  126.1 SIGMA=  3.2 PHAS=  197.4 FOM= 0.94
INDE  -8  24   5 FOBS=   46.2 SIGMA=  5.5 PHAS=  209.0 FOM= 0.80
INDE  -8  24   6 FOBS=  127.7 SIGMA=  2.6 PHAS=   35.5 FOM= 0.96
INDE  -8  24   7 FOBS=  132.2 SIGMA=  2.9 PHAS=   41.3 FOM= 0.53
INDE  -8  24   8 FOBS=  205.5 SIGMA=  1.8 PHAS=  317.0 FOM= 0.96
INDE  -8  24   9 FOBS=  142.2 SIGMA=  3.1 PHAS=  217.2 FOM= 0.63
INDE  -8  24  10 FOBS=  220.3 SIGMA=  1.5 PHAS=  303.5 FOM= 0.90
INDE  -8  25   1 FOBS=   65.3 SIGMA= 43.8 PHAS=  340.5 FOM= 0.32
INDE  -8  25   2 FOBS=  194.0 SIGMA=  3.3 PHAS=  311.5 FOM= 0.28
INDE  -8  25   3 FOBS=  306.1 SIGMA=  1.6 PHAS=  192.0 FOM= 0.97
INDE  -8  25   4 FOBS=  241.0 SIGMA=  1.8 PHAS=  307.1 FOM= 0.97
INDE  -8  25   5 FOBS=   41.4 SIGMA=  8.8 PHAS=   36.1 FOM= 0.08
```

Fig. 10A-36

```
INDE  -8  25   6  FOBS=   73.0  SIGMA=   4.9  PHAS=  193.8  FOM= 0.37
INDE  -8  25   7  FOBS=  113.4  SIGMA=   2.9  PHAS=   30.6  FOM= 0.61
INDE  -8  25   8  FOBS=  196.0  SIGMA=   1.8  PHAS=  306.6  FOM= 0.95
INDE  -8  25   9  FOBS=  152.9  SIGMA=   3.0  PHAS=  143.9  FOM= 0.87
INDE  -8  26   1  FOBS=  145.5  SIGMA=   3.4  PHAS=  223.7  FOM= 0.85
INDE  -8  26   2  FOBS=   48.4  SIGMA=  16.4  PHAS=  102.3  FOM= 0.20
INDE  -8  26   3  FOBS=  146.6  SIGMA=   3.1  PHAS=  126.0  FOM= 0.17
INDE  -8  26   4  FOBS=   87.2  SIGMA=   4.5  PHAS=   12.4  FOM= 0.18
INDE  -8  26   5  FOBS=  166.7  SIGMA=   2.3  PHAS=  102.8  FOM= 0.63
INDE  -8  26   6  FOBS=   78.1  SIGMA=   4.8  PHAS=  251.6  FOM= 0.82
INDE  -8  26   7  FOBS=  180.0  SIGMA=   1.9  PHAS=  285.6  FOM= 0.83
INDE  -8  26   8  FOBS=  176.8  SIGMA=   2.0  PHAS=  313.4  FOM= 0.81
INDE  -8  26   9  FOBS=  113.5  SIGMA=   7.4  PHAS=  218.6  FOM= 0.53
INDE  -8  27   1  FOBS=   73.5  SIGMA=   5.9  PHAS=  259.6  FOM= 0.32
INDE  -8  27   2  FOBS=  265.3  SIGMA=   1.8  PHAS=  104.5  FOM= 0.49
INDE  -8  27   3  FOBS=  129.6  SIGMA=   3.4  PHAS=  102.6  FOM= 0.43
INDE  -8  27   4  FOBS=   57.7  SIGMA=   7.3  PHAS=  285.3  FOM= 0.29
INDE  -8  27   5  FOBS=   94.4  SIGMA=   4.0  PHAS=  264.2  FOM= 0.52
INDE  -8  27   6  FOBS=  157.4  SIGMA=   2.2  PHAS=   37.1  FOM= 0.59
INDE  -8  27   7  FOBS=  104.2  SIGMA=   3.4  PHAS=  110.7  FOM= 0.09
INDE  -8  27   8  FOBS=  228.8  SIGMA=   2.2  PHAS=    9.1  FOM= 0.72
INDE  -8  28   1  FOBS=  160.1  SIGMA=   3.2  PHAS=  183.7  FOM= 0.76
INDE  -8  28   2  FOBS=   92.2  SIGMA=   4.6  PHAS=  334.4  FOM= 0.69
INDE  -8  28   3  FOBS=  155.1  SIGMA=   2.7  PHAS=  220.1  FOM= 0.78
INDE  -8  28   4  FOBS=   42.9  SIGMA=  10.4  PHAS=  329.8  FOM= 0.14
INDE  -8  28   5  FOBS=   94.4  SIGMA=   4.2  PHAS=  306.3  FOM= 0.07
INDE  -8  28   6  FOBS=  259.8  SIGMA=   1.6  PHAS=  264.2  FOM= 0.53
INDE  -8  28   7  FOBS=   73.2  SIGMA=  31.8  PHAS=  120.5  FOM= 0.06
INDE  -8  29   1  FOBS=   49.6  SIGMA=  16.2  PHAS=  316.7  FOM= 0.18
INDE  -8  29   2  FOBS=  142.9  SIGMA=   3.1  PHAS=  195.2  FOM= 0.74
INDE  -8  29   3  FOBS=   53.9  SIGMA=   7.9  PHAS=  175.0  FOM= 0.03
INDE  -8  29   4  FOBS=   47.4  SIGMA=   8.1  PHAS=  353.8  FOM= 0.20
INDE  -8  29   5  FOBS=   69.9  SIGMA=   5.7  PHAS=  107.3  FOM= 0.29
INDE  -8  30   1  FOBS=  121.3  SIGMA=   9.5  PHAS=  299.4  FOM= 0.06
INDE  -8  30   2  FOBS=   74.0  SIGMA=  15.2  PHAS=   95.4  FOM= 0.09
INDE  -7   0   1  FOBS=  129.6  SIGMA=   4.4  PHAS=    0.0  FOM= 1.00
INDE  -7   0   2  FOBS=  117.6  SIGMA=   4.8  PHAS=  180.0  FOM= 1.00
INDE  -7   0   3  FOBS=  336.5  SIGMA=   1.7  PHAS=  180.0  FOM= 1.00
INDE  -7   0   4  FOBS=   41.3  SIGMA=  12.9  PHAS=  180.0  FOM= 0.22
INDE  -7   0   5  FOBS=  176.5  SIGMA=   2.6  PHAS=  180.0  FOM= 1.00
INDE  -7   0   6  FOBS=  142.4  SIGMA=   3.6  PHAS=  180.0  FOM= 0.02
INDE  -7   0   7  FOBS=   66.6  SIGMA=   7.1  PHAS=  180.0  FOM= 0.77
INDE  -7   0   8  FOBS=  143.7  SIGMA=   4.7  PHAS=    0.0  FOM= 0.99
INDE  -7   0   9  FOBS=  119.5  SIGMA=   4.2  PHAS=  180.0  FOM= 0.77
INDE  -7   0  10  FOBS=  629.5  SIGMA=   1.3  PHAS=    0.0  FOM= 1.00
INDE  -7   0  11  FOBS=  283.5  SIGMA=   2.4  PHAS=    0.0  FOM= 1.00
INDE  -7   0  12  FOBS=  292.1  SIGMA=   2.5  PHAS=  180.0  FOM= 1.00
INDE  -7   0  13  FOBS=   91.0  SIGMA=   7.6  PHAS=    0.0  FOM= 0.04
INDE  -7   0  14  FOBS=  266.4  SIGMA=   2.6  PHAS=  180.0  FOM= 0.94
INDE  -7   0  15  FOBS=   67.8  SIGMA=  10.3  PHAS=  180.0  FOM= 0.36
INDE  -7   0  16  FOBS=   89.7  SIGMA=   7.9  PHAS=    0.0  FOM= 0.02
INDE  -7   1   1  FOBS=  255.8  SIGMA=   1.6  PHAS=  137.7  FOM= 0.98
INDE  -7   1   2  FOBS=  269.3  SIGMA=   1.5  PHAS=  234.0  FOM= 1.00
INDE  -7   1   3  FOBS=  221.8  SIGMA=   1.7  PHAS=   66.4  FOM= 1.00
INDE  -7   1   4  FOBS=  193.9  SIGMA=   1.8  PHAS=  238.2  FOM= 0.93
INDE  -7   1   5  FOBS=  203.2  SIGMA=   1.6  PHAS=  114.0  FOM= 1.00
INDE  -7   1   6  FOBS=  193.6  SIGMA=   1.8  PHAS=  272.5  FOM= 1.00
INDE  -7   1   7  FOBS=  179.7  SIGMA=   1.8  PHAS=  227.6  FOM= 0.99
INDE  -7   1   8  FOBS=  351.9  SIGMA=   1.5  PHAS=   58.9  FOM= 0.98
INDE  -7   1   9  FOBS=  296.6  SIGMA=   1.3  PHAS=  287.6  FOM= 0.95
INDE  -7   1  10  FOBS=  164.0  SIGMA=   2.1  PHAS=  181.2  FOM= 0.97
INDE  -7   1  11  FOBS=  101.7  SIGMA=   4.5  PHAS=  152.8  FOM= 0.85
INDE  -7   1  12  FOBS=  111.0  SIGMA=   4.2  PHAS=  102.2  FOM= 0.47
INDE  -7   1  13  FOBS=  100.0  SIGMA=   4.9  PHAS=  345.1  FOM= 0.57
INDE  -7   1  14  FOBS=  234.3  SIGMA=   2.1  PHAS=  346.3  FOM= 0.94
INDE  -7   1  15  FOBS=  362.0  SIGMA=   1.6  PHAS=  229.2  FOM= 0.92
INDE  -7   1  16  FOBS=  129.4  SIGMA=   4.0  PHAS=  283.0  FOM= 0.04
INDE  -7   2   1  FOBS=  463.8  SIGMA=   1.3  PHAS=    9.5  FOM= 1.00
INDE  -7   2   2  FOBS=  182.8  SIGMA=   2.0  PHAS=   27.8  FOM= 0.92
INDE  -7   2   3  FOBS=  152.9  SIGMA=   2.1  PHAS=  222.7  FOM= 1.00
INDE  -7   2   4  FOBS=  198.7  SIGMA=   1.8  PHAS=  129.2  FOM= 0.99
```

Fig. 10A-37

```
INDE  -7  2   5 FOBS=  207.1 SIGMA= 1.6 PHAS= 232.1 FOM= 0.97
INDE  -7  2   6 FOBS=  188.6 SIGMA= 1.9 PHAS= 351.2 FOM= 0.94
INDE  -7  2   7 FOBS=   78.5 SIGMA= 3.5 PHAS= 100.7 FOM= 0.90
INDE  -7  2   8 FOBS=  220.5 SIGMA= 2.0 PHAS=  33.8 FOM= 0.95
INDE  -7  2   9 FOBS=  531.2 SIGMA= 0.9 PHAS= 292.8 FOM= 0.95
INDE  -7  2  10 FOBS=  303.9 SIGMA= 1.4 PHAS= 211.4 FOM= 0.91
INDE  -7  2  11 FOBS=  196.7 SIGMA= 2.1 PHAS= 190.4 FOM= 0.96
INDE  -7  2  12 FOBS=  169.9 SIGMA= 2.6 PHAS= 125.9 FOM= 0.77
INDE  -7  2  13 FOBS=  117.2 SIGMA= 4.0 PHAS= 208.0 FOM= 0.39
INDE  -7  2  14 FOBS=  170.4 SIGMA= 2.9 PHAS= 228.0 FOM= 0.69
INDE  -7  2  15 FOBS=  183.1 SIGMA= 2.8 PHAS= 252.9 FOM= 0.76
INDE  -7  2  16 FOBS=   71.8 SIGMA= 7.1 PHAS= 325.6 FOM= 0.39
INDE  -7  3   1 FOBS=  312.9 SIGMA= 1.5 PHAS= 246.7 FOM= 0.93
INDE  -7  3   2 FOBS=  295.2 SIGMA= 1.5 PHAS=  62.4 FOM= 0.84
INDE  -7  3   3 FOBS=  203.0 SIGMA= 1.8 PHAS= 206.0 FOM= 0.95
INDE  -7  3   4 FOBS=  252.1 SIGMA= 1.4 PHAS= 199.8 FOM= 0.62
INDE  -7  3   5 FOBS=  174.2 SIGMA= 1.9 PHAS=  25.3 FOM= 0.96
INDE  -7  3   6 FOBS=   72.4 SIGMA= 4.5 PHAS= 189.6 FOM= 0.83
INDE  -7  3   7 FOBS=  114.9 SIGMA= 2.7 PHAS= 249.6 FOM= 0.92
INDE  -7  3   8 FOBS=  402.0 SIGMA= 1.1 PHAS=  30.3 FOM= 0.97
INDE  -7  3   9 FOBS=  125.8 SIGMA= 2.9 PHAS= 322.7 FOM= 0.66
INDE  -7  3  10 FOBS=  264.7 SIGMA= 1.6 PHAS= 139.2 FOM= 0.54
INDE  -7  3  11 FOBS=  272.8 SIGMA= 1.7 PHAS= 315.8 FOM= 0.93
INDE  -7  3  12 FOBS=  250.2 SIGMA= 1.9 PHAS= 149.9 FOM= 0.90
INDE  -7  3  13 FOBS=  103.7 SIGMA= 4.6 PHAS= 225.3 FOM= 0.02
INDE  -7  3  14 FOBS=   94.5 SIGMA= 5.3 PHAS=  79.6 FOM= 0.68
INDE  -7  3  15 FOBS=  112.9 SIGMA= 4.7 PHAS=  21.1 FOM= 0.60
INDE  -7  3  16 FOBS=  114.0 SIGMA= 4.5 PHAS= 238.7 FOM= 0.09
INDE  -7  4   1 FOBS=   95.4 SIGMA= 4.5 PHAS= 255.0 FOM= 0.90
INDE  -7  4   2 FOBS=  103.0 SIGMA= 3.8 PHAS= 289.7 FOM= 0.44
INDE  -7  4   3 FOBS=  104.7 SIGMA= 3.6 PHAS= 183.3 FOM= 0.61
INDE  -7  4   4 FOBS=   81.7 SIGMA= 4.1 PHAS= 277.9 FOM= 0.81
INDE  -7  4   5 FOBS=  178.9 SIGMA= 1.8 PHAS= 172.6 FOM= 1.00
INDE  -7  4   6 FOBS=  102.6 SIGMA= 3.8 PHAS= 174.1 FOM= 0.98
INDE  -7  4   7 FOBS=  196.9 SIGMA= 1.6 PHAS=  44.4 FOM= 0.97
INDE  -7  4   8 FOBS=  281.9 SIGMA= 1.3 PHAS= 230.9 FOM= 0.96
INDE  -7  4   9 FOBS=  577.1 SIGMA= 0.9 PHAS= 206.0 FOM= 1.00
INDE  -7  4  10 FOBS=  112.7 SIGMA= 3.5 PHAS=  54.7 FOM= 0.85
INDE  -7  4  11 FOBS=  132.3 SIGMA= 3.4 PHAS= 103.3 FOM= 0.11
INDE  -7  4  12 FOBS=  209.3 SIGMA= 2.2 PHAS= 359.2 FOM= 0.94
INDE  -7  4  13 FOBS=  146.1 SIGMA= 3.3 PHAS=   2.9 FOM= 0.86
INDE  -7  4  14 FOBS=  248.5 SIGMA= 2.1 PHAS= 149.5 FOM= 0.48
INDE  -7  4  15 FOBS=   68.2 SIGMA= 7.2 PHAS= 287.2 FOM= 0.16
INDE  -7  4  16 FOBS=  170.5 SIGMA= 2.9 PHAS= 307.1 FOM= 0.83
INDE  -7  5   1 FOBS=   66.1 SIGMA= 5.5 PHAS= 185.9 FOM= 0.07
INDE  -7  5   2 FOBS=  211.2 SIGMA= 1.9 PHAS=  47.5 FOM= 0.88
INDE  -7  5   3 FOBS=  205.7 SIGMA= 1.9 PHAS= 100.0 FOM= 0.75
INDE  -7  5   4 FOBS=  233.9 SIGMA= 1.6 PHAS=  12.6 FOM= 0.90
INDE  -7  5   5 FOBS=  277.9 SIGMA= 1.4 PHAS= 170.6 FOM= 0.95
INDE  -7  5   6 FOBS=  173.6 SIGMA= 1.9 PHAS=  57.6 FOM= 0.75
INDE  -7  5   7 FOBS=  206.1 SIGMA= 1.5 PHAS= 209.5 FOM= 0.96
INDE  -7  5   8 FOBS=  479.5 SIGMA= 1.1 PHAS= 124.9 FOM= 0.99
INDE  -7  5   9 FOBS=  352.5 SIGMA= 1.3 PHAS=  87.9 FOM= 0.96
INDE  -7  5  10 FOBS=  169.6 SIGMA= 2.3 PHAS=  28.6 FOM= 0.85
INDE  -7  5  11 FOBS=   72.3 SIGMA= 5.5 PHAS= 200.6 FOM= 0.10
INDE  -7  5  12 FOBS=  227.8 SIGMA= 2.0 PHAS= 307.6 FOM= 0.77
INDE  -7  5  13 FOBS=   60.1 SIGMA= 8.4 PHAS= 309.0 FOM= 0.37
INDE  -7  5  14 FOBS=  144.1 SIGMA= 3.7 PHAS= 258.4 FOM= 0.61
INDE  -7  5  15 FOBS=  211.0 SIGMA= 2.4 PHAS=  14.8 FOM= 0.69
INDE  -7  5  16 FOBS=   84.0 SIGMA= 6.0 PHAS= 227.3 FOM= 0.01
INDE  -7  6   1 FOBS=  169.1 SIGMA= 2.4 PHAS= 274.9 FOM= 0.91
INDE  -7  6   2 FOBS=   85.0 SIGMA= 4.4 PHAS= 100.0 FOM= 0.81
INDE  -7  6   3 FOBS=  200.0 SIGMA= 1.9 PHAS= 301.3 FOM= 0.99
INDE  -7  6   4 FOBS=   60.2 SIGMA= 5.3 PHAS= 202.8 FOM= 0.67
INDE  -7  6   5 FOBS=  152.5 SIGMA= 2.1 PHAS= 115.2 FOM= 0.97
INDE  -7  6   6 FOBS=  183.0 SIGMA= 1.7 PHAS= 232.3 FOM= 0.99
INDE  -7  6   7 FOBS=  221.6 SIGMA= 1.4 PHAS=  39.5 FOM= 0.88
INDE  -7  6   8 FOBS=  341.5 SIGMA= 1.2 PHAS= 184.5 FOM= 0.97
INDE  -7  6   9 FOBS=  215.6 SIGMA= 2.0 PHAS= 317.0 FOM= 0.95
INDE  -7  6  10 FOBS=  290.6 SIGMA= 1.4 PHAS= 127.1 FOM= 0.79
INDE  -7  6  11 FOBS=  256.0 SIGMA= 1.7 PHAS= 268.9 FOM= 0.90
```

Fig. 10A-38

```
INDE  -7   6  12 FOBS=   134.5 SIGMA= 3.6 PHAS=  97.2 FOM= 0.31
INDE  -7   6  13 FOBS=    89.4 SIGMA= 5.6 PHAS=  23.0 FOM= 0.27
INDE  -7   6  14 FOBS=   162.9 SIGMA= 3.2 PHAS=  72.0 FOM= 0.81
INDE  -7   6  15 FOBS=   226.2 SIGMA= 2.2 PHAS= 356.5 FOM= 0.77
INDE  -7   6  16 FOBS=   149.6 SIGMA= 3.5 PHAS= 195.8 FOM= 0.65
INDE  -7   7   1 FOBS=   244.2 SIGMA= 1.7 PHAS=  93.7 FOM= 0.84
INDE  -7   7   2 FOBS=   179.7 SIGMA= 2.0 PHAS=  86.8 FOM= 0.97
INDE  -7   7   3 FOBS=   130.3 SIGMA= 2.6 PHAS= 175.4 FOM= 0.95
INDE  -7   7   4 FOBS=   158.6 SIGMA= 2.0 PHAS= 132.6 FOM= 0.57
INDE  -7   7   5 FOBS=   128.0 SIGMA= 3.2 PHAS= 321.0 FOM= 0.90
INDE  -7   7   6 FOBS=   233.6 SIGMA= 1.2 PHAS= 102.8 FOM= 0.68
INDE  -7   7   7 FOBS=   236.7 SIGMA= 1.3 PHAS= 103.2 FOM= 0.96
INDE  -7   7   8 FOBS=   156.2 SIGMA= 2.0 PHAS= 108.1 FOM= 0.73
INDE  -7   7   9 FOBS=   134.8 SIGMA= 2.8 PHAS=  58.8 FOM= 0.83
INDE  -7   7  10 FOBS=   139.5 SIGMA= 2.6 PHAS= 281.0 FOM= 0.56
INDE  -7   7  11 FOBS=   156.7 SIGMA= 2.6 PHAS= 342.9 FOM= 0.70
INDE  -7   7  12 FOBS=   136.9 SIGMA= 3.5 PHAS=  29.5 FOM= 0.91
INDE  -7   7  13 FOBS=   117.6 SIGMA= 4.2 PHAS= 169.3 FOM= 0.61
INDE  -7   7  14 FOBS=    92.0 SIGMA= 5.4 PHAS= 142.2 FOM= 0.02
INDE  -7   7  15 FOBS=   204.9 SIGMA= 2.4 PHAS= 266.6 FOM= 0.91
INDE  -7   7  16 FOBS=   149.4 SIGMA= 3.5 PHAS= 134.2 FOM= 0.11
INDE  -7   8   1 FOBS=    61.4 SIGMA= 7.3 PHAS= 286.5 FOM= 0.60
INDE  -7   8   2 FOBS=   101.1 SIGMA= 3.4 PHAS= 304.7 FOM= 0.96
INDE  -7   8   3 FOBS=    51.9 SIGMA= 7.3 PHAS= 301.7 FOM= 0.22
INDE  -7   8   4 FOBS=   105.5 SIGMA= 2.6 PHAS= 326.1 FOM= 0.19
INDE  -7   8   5 FOBS=   422.7 SIGMA= 1.0 PHAS= 297.1 FOM= 0.90
INDE  -7   8   6 FOBS=    46.5 SIGMA= 5.8 PHAS= 359.4 FOM= 0.03
INDE  -7   8   7 FOBS=   205.0 SIGMA= 1.5 PHAS= 285.2 FOM= 0.95
INDE  -7   8   8 FOBS=   343.8 SIGMA= 1.1 PHAS= 282.3 FOM= 0.97
INDE  -7   8   9 FOBS=   540.1 SIGMA= 1.0 PHAS= 205.4 FOM= 0.97
INDE  -7   8  10 FOBS=   428.9 SIGMA= 1.3 PHAS= 157.0 FOM= 0.98
INDE  -7   8  11 FOBS=   286.9 SIGMA= 1.7 PHAS= 358.4 FOM= 0.94
INDE  -7   8  12 FOBS=    85.7 SIGMA= 5.3 PHAS= 245.5 FOM= 0.46
INDE  -7   8  13 FOBS=    95.1 SIGMA= 5.1 PHAS=  54.3 FOM= 0.57
INDE  -7   8  14 FOBS=   241.8 SIGMA= 2.1 PHAS= 180.6 FOM= 0.95
INDE  -7   8  15 FOBS=   129.9 SIGMA= 4.0 PHAS= 151.0 FOM= 0.96
INDE  -7   8  16 FOBS=    59.2 SIGMA= 8.6 PHAS=  34.1 FOM= 0.07
INDE  -7   9   1 FOBS=   153.1 SIGMA= 3.1 PHAS= 279.2 FOM= 0.76
INDE  -7   9   2 FOBS=   144.4 SIGMA= 2.6 PHAS=  39.0 FOM= 0.78
INDE  -7   9   3 FOBS=   111.6 SIGMA= 3.0 PHAS= 166.4 FOM= 0.91
INDE  -7   9   4 FOBS=   174.0 SIGMA= 2.0 PHAS=  26.9 FOM= 0.98
INDE  -7   9   5 FOBS=   194.3 SIGMA= 1.6 PHAS= 102.3 FOM= 0.60
INDE  -7   9   6 FOBS=   532.0 SIGMA= 1.3 PHAS= 102.6 FOM= 0.95
INDE  -7   9   7 FOBS=   281.3 SIGMA= 1.3 PHAS= 284.2 FOM= 0.97
INDE  -7   9   8 FOBS=   517.0 SIGMA= 1.0 PHAS=  64.0 FOM= 0.97
INDE  -7   9   9 FOBS=   245.6 SIGMA= 1.5 PHAS= 266.8 FOM= 0.92
INDE  -7   9  10 FOBS=   185.2 SIGMA= 2.0 PHAS= 154.2 FOM= 0.97
INDE  -7   9  11 FOBS=   130.5 SIGMA= 3.7 PHAS= 136.3 FOM= 0.87
INDE  -7   9  12 FOBS=   286.5 SIGMA= 1.7 PHAS=  21.9 FOM= 0.53
INDE  -7   9  13 FOBS=   313.3 SIGMA= 1.7 PHAS= 183.8 FOM= 0.53
INDE  -7   9  14 FOBS=   137.5 SIGMA= 3.7 PHAS= 266.1 FOM= 0.23
INDE  -7   9  15 FOBS=   103.3 SIGMA= 5.0 PHAS=  84.8 FOM= 0.19
INDE  -7   9  16 FOBS=   135.6 SIGMA= 4.0 PHAS= 134.1 FOM= 0.12
INDE  -7  10   1 FOBS=   209.0 SIGMA= 2.0 PHAS= 235.0 FOM= 0.68
INDE  -7  10   2 FOBS=    93.7 SIGMA= 4.7 PHAS= 273.9 FOM= 0.20
INDE  -7  10   3 FOBS=    98.4 SIGMA= 3.4 PHAS=  13.3 FOM= 0.70
INDE  -7  10   4 FOBS=    83.6 SIGMA= 3.5 PHAS= 283.5 FOM= 0.60
INDE  -7  10   5 FOBS=    62.5 SIGMA= 8.2 PHAS= 278.8 FOM= 0.10
INDE  -7  10   6 FOBS=   218.9 SIGMA= 2.3 PHAS= 138.9 FOM= 0.62
INDE  -7  10   7 FOBS=   478.8 SIGMA= 1.0 PHAS=  27.0 FOM= 0.70
INDE  -7  10   8 FOBS=   214.7 SIGMA= 1.7 PHAS=  63.2 FOM= 1.00
INDE  -7  10   9 FOBS=   226.8 SIGMA= 1.7 PHAS= 226.2 FOM= 0.99
INDE  -7  10  10 FOBS=    71.9 SIGMA= 6.2 PHAS= 209.7 FOM= 0.20
INDE  -7  10  11 FOBS=   247.3 SIGMA= 1.9 PHAS=  88.2 FOM= 0.99
INDE  -7  10  12 FOBS=   174.6 SIGMA= 2.8 PHAS= 211.0 FOM= 0.96
INDE  -7  10  13 FOBS=   233.7 SIGMA= 2.0 PHAS= 226.3 FOM= 0.56
INDE  -7  10  14 FOBS=    84.4 SIGMA= 5.7 PHAS= 134.5 FOM= 0.15
INDE  -7  10  15 FOBS=    66.4 SIGMA= 7.6 PHAS= 227.5 FOM= 0.20
INDE  -7  10  16 FOBS=    95.3 SIGMA= 9.5 PHAS=  65.1 FOM= 0.20
INDE  -7  11   1 FOBS=   171.0 SIGMA= 2.3 PHAS=  15.1 FOM= 0.60
INDE  -7  11   2 FOBS=   277.6 SIGMA= 1.4 PHAS=  25.6 FOM= 0.86
```

Fig. 10A-39

| | | | | | | | | | |
|---|---|---|---|---|---|---|---|---|---|
|INDE|-7|11|3|FOBS=|83.4|SIGMA=|4.0|PHAS=|170.6|FOM=|0.83|
|INDE|-7|11|4|FOBS=|197.2|SIGMA=|3.4|PHAS=|127.6|FOM=|0.89|
|INDE|-7|11|5|FOBS=|137.1|SIGMA=|4.5|PHAS=|259.8|FOM=|0.92|
|INDE|-7|11|6|FOBS=|530.5|SIGMA=|1.8|PHAS=|224.0|FOM=|0.99|
|INDE|-7|11|7|FOBS=|193.2|SIGMA=|2.1|PHAS=|354.3|FOM=|0.95|
|INDE|-7|11|8|FOBS=|288.8|SIGMA=|1.2|PHAS=|64.4|FOM=|1.00|
|INDE|-7|11|9|FOBS=|263.8|SIGMA=|1.5|PHAS=|12.0|FOM=|0.93|
|INDE|-7|11|10|FOBS=|114.2|SIGMA=|3.9|PHAS=|92.2|FOM=|0.90|
|INDE|-7|11|11|FOBS=|276.5|SIGMA=|1.7|PHAS=|112.8|FOM=|0.97|
|INDE|-7|11|12|FOBS=|196.7|SIGMA=|2.3|PHAS=|44.4|FOM=|0.84|
|INDE|-7|11|13|FOBS=|205.8|SIGMA=|2.2|PHAS=|125.0|FOM=|0.11|
|INDE|-7|11|14|FOBS=|55.5|SIGMA=|9.3|PHAS=|137.9|FOM=|0.44|
|INDE|-7|11|15|FOBS=|109.9|SIGMA=|4.7|PHAS=|256.2|FOM=|0.75|
|INDE|-7|12|1|FOBS=|102.6|SIGMA=|4.5|PHAS=|261.4|FOM=|0.94|
|INDE|-7|12|2|FOBS=|351.3|SIGMA=|1.2|PHAS=|316.3|FOM=|0.82|
|INDE|-7|12|3|FOBS=|108.6|SIGMA=|3.5|PHAS=|193.1|FOM=|0.92|
|INDE|-7|12|4|FOBS=|115.2|SIGMA=|5.1|PHAS=|204.9|FOM=|0.90|
|INDE|-7|12|5|FOBS=|50.1|SIGMA=|10.9|PHAS=|163.8|FOM=|0.06|
|INDE|-7|12|6|FOBS=|433.3|SIGMA=|2.1|PHAS=|90.9|FOM=|1.00|
|INDE|-7|12|7|FOBS=|128.2|SIGMA=|4.2|PHAS=|154.7|FOM=|0.84|
|INDE|-7|12|8|FOBS=|111.7|SIGMA=|2.5|PHAS=|243.5|FOM=|0.79|
|INDE|-7|12|9|FOBS=|316.3|SIGMA=|1.7|PHAS=|25.8|FOM=|0.47|
|INDE|-7|12|10|FOBS=|179.1|SIGMA=|2.5|PHAS=|50.3|FOM=|0.58|
|INDE|-7|12|11|FOBS=|151.9|SIGMA=|2.8|PHAS=|311.7|FOM=|0.73|
|INDE|-7|12|12|FOBS=|326.2|SIGMA=|1.6|PHAS=|226.6|FOM=|0.98|
|INDE|-7|12|13|FOBS=|227.9|SIGMA=|2.2|PHAS=|7.5|FOM=|0.97|
|INDE|-7|12|14|FOBS=|48.5|SIGMA=|11.7|PHAS=|275.9|FOM=|0.30|
|INDE|-7|12|15|FOBS=|163.9|SIGMA=|3.0|PHAS=|185.9|FOM=|0.76|
|INDE|-7|13|1|FOBS=|212.2|SIGMA=|2.1|PHAS=|217.0|FOM=|0.82|
|INDE|-7|13|2|FOBS=|120.2|SIGMA=|3.7|PHAS=|46.5|FOM=|0.96|
|INDE|-7|13|3|FOBS=|391.6|SIGMA=|1.2|PHAS=|258.9|FOM=|1.00|
|INDE|-7|13|4|FOBS=|127.0|SIGMA=|2.4|PHAS=|47.5|FOM=|0.79|
|INDE|-7|13|5|FOBS=|344.7|SIGMA=|2.1|PHAS=|51.4|FOM=|0.98|
|INDE|-7|13|6|FOBS=|158.6|SIGMA=|3.5|PHAS=|83.4|FOM=|0.65|
|INDE|-7|13|7|FOBS=|165.2|SIGMA=|3.5|PHAS=|146.7|FOM=|0.21|
|INDE|-7|13|8|FOBS=|398.4|SIGMA=|1.1|PHAS=|6.7|FOM=|0.95|
|INDE|-7|13|9|FOBS=|323.1|SIGMA=|2.2|PHAS=|118.3|FOM=|1.00|
|INDE|-7|13|10|FOBS=|200.4|SIGMA=|2.3|PHAS=|281.3|FOM=|0.96|
|INDE|-7|13|11|FOBS=|79.7|SIGMA=|5.8|PHAS=|204.1|FOM=|0.44|
|INDE|-7|13|12|FOBS=|99.4|SIGMA=|4.6|PHAS=|342.0|FOM=|0.67|
|INDE|-7|13|13|FOBS=|49.2|SIGMA=|10.0|PHAS=|304.4|FOM=|0.29|
|INDE|-7|13|14|FOBS=|80.6|SIGMA=|6.6|PHAS=|208.9|FOM=|0.96|
|INDE|-7|13|15|FOBS=|168.9|SIGMA=|2.9|PHAS=|185.7|FOM=|0.92|
|INDE|-7|14|1|FOBS=|195.3|SIGMA=|2.2|PHAS=|278.8|FOM=|0.65|
|INDE|-7|14|2|FOBS=|244.3|SIGMA=|2.0|PHAS=|26.0|FOM=|0.97|
|INDE|-7|14|3|FOBS=|190.3|SIGMA=|1.8|PHAS=|266.9|FOM=|0.97|
|INDE|-7|14|4|FOBS=|609.9|SIGMA=|1.8|PHAS=|17.3|FOM=|0.94|
|INDE|-7|14|5|FOBS=|102.6|SIGMA=|6.3|PHAS=|128.9|FOM=|0.68|
|INDE|-7|14|6|FOBS=|191.3|SIGMA=|3.1|PHAS=|336.3|FOM=|0.93|
|INDE|-7|14|7|FOBS=|319.1|SIGMA=|2.1|PHAS=|20.9|FOM=|0.94|
|INDE|-7|14|8|FOBS=|297.1|SIGMA=|1.0|PHAS=|271.5|FOM=|1.00|
|INDE|-7|14|9|FOBS=|233.5|SIGMA=|1.7|PHAS=|0.8|FOM=|0.98|
|INDE|-7|14|10|FOBS=|136.9|SIGMA=|3.7|PHAS=|277.6|FOM=|0.15|
|INDE|-7|14|11|FOBS=|239.7|SIGMA=|2.4|PHAS=|351.5|FOM=|0.94|
|INDE|-7|14|12|FOBS=|49.7|SIGMA=|10.3|PHAS=|289.7|FOM=|0.27|
|INDE|-7|14|13|FOBS=|126.0|SIGMA=|3.9|PHAS=|199.1|FOM=|0.63|
|INDE|-7|14|14|FOBS=|48.7|SIGMA=|9.9|PHAS=|51.6|FOM=|0.01|
|INDE|-7|14|15|FOBS=|109.6|SIGMA=|4.5|PHAS=|57.5|FOM=|0.10|
|INDE|-7|15|1|FOBS=|285.8|SIGMA=|1.8|PHAS=|208.6|FOM=|0.78|
|INDE|-7|15|2|FOBS=|372.1|SIGMA=|1.4|PHAS=|334.4|FOM=|0.90|
|INDE|-7|15|3|FOBS=|78.4|SIGMA=|4.3|PHAS=|234.0|FOM=|0.01|
|INDE|-7|15|4|FOBS=|62.3|SIGMA=|4.9|PHAS=|86.2|FOM=|0.36|
|INDE|-7|15|5|FOBS=|350.2|SIGMA=|2.1|PHAS=|349.6|FOM=|0.90|
|INDE|-7|15|6|FOBS=|392.9|SIGMA=|1.8|PHAS=|326.4|FOM=|0.98|
|INDE|-7|15|7|FOBS=|167.8|SIGMA=|3.6|PHAS=|150.1|FOM=|0.90|
|INDE|-7|15|8|FOBS=|113.8|SIGMA=|3.2|PHAS=|113.5|FOM=|0.63|
|INDE|-7|15|9|FOBS=|165.4|SIGMA=|2.5|PHAS=|48.0|FOM=|0.87|
|INDE|-7|15|10|FOBS=|525.6|SIGMA=|1.6|PHAS=|14.0|FOM=|1.00|
|INDE|-7|15|11|FOBS=|163.5|SIGMA=|3.4|PHAS=|357.6|FOM=|0.70|
|INDE|-7|15|12|FOBS=|183.9|SIGMA=|2.7|PHAS=|305.1|FOM=|0.80|
|INDE|-7|15|13|FOBS=|230.3|SIGMA=|2.1|PHAS=|91.4|FOM=|0.97|

Fig. 10A-40

```
INDE  -7  15  14  FOBS=  136.3  SIGMA=   3.6  PHAS=  299.7  FOM=  0.79
INDE  -7  16   1  FOBS=  362.9  SIGMA=   2.0  PHAS=  268.2  FOM=  1.00
INDE  -7  16   2  FOBS=  150.4  SIGMA=   2.7  PHAS=  146.0  FOM=  0.88
INDE  -7  16   3  FOBS=  174.9  SIGMA=   2.1  PHAS=  174.4  FOM=  0.29
INDE  -7  16   4  FOBS=  143.6  SIGMA=   1.9  PHAS=  183.4  FOM=  0.97
INDE  -7  16   5  FOBS=  238.5  SIGMA=   2.7  PHAS=   32.6  FOM=  0.93
INDE  -7  16   6  FOBS=  210.8  SIGMA=   2.8  PHAS=  130.5  FOM=  0.80
INDE  -7  16   7  FOBS=  259.5  SIGMA=   2.6  PHAS=  226.3  FOM=  0.82
INDE  -7  16   8  FOBS=   99.3  SIGMA=   3.6  PHAS=  204.3  FOM=  0.73
INDE  -7  16   9  FOBS=  123.9  SIGMA=   3.0  PHAS=  334.6  FOM=  0.91
INDE  -7  16  10  FOBS=  316.3  SIGMA=   1.4  PHAS=  176.0  FOM=  0.97
INDE  -7  16  11  FOBS=   64.6  SIGMA=   7.3  PHAS=  237.9  FOM=  0.11
INDE  -7  16  12  FOBS=   45.2  SIGMA=  10.6  PHAS=   22.1  FOM=  0.17
INDE  -7  16  13  FOBS=  141.2  SIGMA=   3.6  PHAS=  111.3  FOM=  0.76
INDE  -7  16  14  FOBS=  110.2  SIGMA=   4.7  PHAS=  288.2  FOM=  0.45
INDE  -7  17   1  FOBS=  236.0  SIGMA=   1.9  PHAS=   17.1  FOM=  0.95
INDE  -7  17   2  FOBS=  557.0  SIGMA=   1.3  PHAS=   51.5  FOM=  0.97
INDE  -7  17   3  FOBS=   68.5  SIGMA=   5.1  PHAS=  281.0  FOM=  0.72
INDE  -7  17   4  FOBS=  369.0  SIGMA=   1.0  PHAS=  264.6  FOM=  0.66
INDE  -7  17   5  FOBS=  127.7  SIGMA=   2.7  PHAS=  348.7  FOM=  0.89
INDE  -7  17   6  FOBS=  438.7  SIGMA=   1.8  PHAS=  200.3  FOM=  0.98
INDE  -7  17   7  FOBS=  323.0  SIGMA=   2.2  PHAS=  200.4  FOM=  0.85
INDE  -7  17   8  FOBS=   83.2  SIGMA=   3.9  PHAS=  117.4  FOM=  0.79
INDE  -7  17   9  FOBS=  162.1  SIGMA=   2.1  PHAS=  132.3  FOM=  0.76
INDE  -7  17  10  FOBS=  147.4  SIGMA=   2.7  PHAS=   75.8  FOM=  0.93
INDE  -7  17  11  FOBS=  146.6  SIGMA=   2.9  PHAS=  105.3  FOM=  0.07
INDE  -7  17  12  FOBS=  120.9  SIGMA=   3.9  PHAS=  322.1  FOM=  0.77
INDE  -7  17  13  FOBS=   98.5  SIGMA=   4.6  PHAS=   84.0  FOM=  0.46
INDE  -7  17  14  FOBS=  158.9  SIGMA=   3.0  PHAS=  308.1  FOM=  0.73
INDE  -7  18   1  FOBS=  278.7  SIGMA=   1.7  PHAS=   26.6  FOM=  0.98
INDE  -7  18   2  FOBS=  523.6  SIGMA=   1.0  PHAS=  213.2  FOM=  1.00
INDE  -7  18   3  FOBS=  335.4  SIGMA=   1.6  PHAS=  144.2  FOM=  0.94
INDE  -7  18   4  FOBS=  433.1  SIGMA=   1.0  PHAS=    1.5  FOM=  1.00
INDE  -7  18   5  FOBS=  231.8  SIGMA=   1.8  PHAS=  132.2  FOM=  0.97
INDE  -7  18   6  FOBS=  152.3  SIGMA=   3.8  PHAS=    1.2  FOM=  0.89
INDE  -7  18   7  FOBS=  225.1  SIGMA=   3.0  PHAS=  330.6  FOM=  0.54
INDE  -7  18   8  FOBS=   78.1  SIGMA=   3.5  PHAS=   70.8  FOM=  0.81
INDE  -7  18   9  FOBS=   62.9  SIGMA=   5.6  PHAS=  306.4  FOM=  0.54
INDE  -7  18  10  FOBS=  256.8  SIGMA=   1.6  PHAS=  136.6  FOM=  0.97
INDE  -7  18  11  FOBS=  183.6  SIGMA=   2.3  PHAS=    3.5  FOM=  0.95
INDE  -7  18  12  FOBS=  134.1  SIGMA=   3.9  PHAS=  239.9  FOM=  0.74
INDE  -7  18  13  FOBS=  174.2  SIGMA=   2.6  PHAS=   66.8  FOM=  0.86
INDE  -7  19   1  FOBS=  391.7  SIGMA=   1.4  PHAS=   94.3  FOM=  0.39
INDE  -7  19   2  FOBS=  209.0  SIGMA=   2.1  PHAS=  132.0  FOM=  0.82
INDE  -7  19   3  FOBS=  154.0  SIGMA=   3.3  PHAS=  122.0  FOM=  0.18
INDE  -7  19   4  FOBS=  478.9  SIGMA=   1.1  PHAS=   49.5  FOM=  0.99
INDE  -7  19   5  FOBS=  110.8  SIGMA=   3.1  PHAS=  289.2  FOM=  0.84
INDE  -7  19   6  FOBS=  446.5  SIGMA=   1.1  PHAS=  219.5  FOM=  0.91
INDE  -7  19   7  FOBS=  183.1  SIGMA=   2.0  PHAS=    4.0  FOM=  0.97
INDE  -7  19   8  FOBS=   53.9  SIGMA=   5.6  PHAS=  243.6  FOM=  0.55
INDE  -7  19   9  FOBS=   30.3  SIGMA=  10.2  PHAS=   97.2  FOM=  0.12
INDE  -7  19  10  FOBS=  148.7  SIGMA=   2.5  PHAS=  233.7  FOM=  0.90
INDE  -7  19  11  FOBS=  131.4  SIGMA=   3.2  PHAS=  258.2  FOM=  0.22
INDE  -7  19  12  FOBS=  220.9  SIGMA=   2.2  PHAS=  357.9  FOM=  0.76
INDE  -7  19  13  FOBS=  168.9  SIGMA=   2.8  PHAS=  129.0  FOM=  0.09
INDE  -7  20   1  FOBS=  228.7  SIGMA=   2.2  PHAS=  173.8  FOM=  0.94
INDE  -7  20   2  FOBS=  251.5  SIGMA=   1.8  PHAS=  255.7  FOM=  0.57
INDE  -7  20   3  FOBS=  244.1  SIGMA=   1.8  PHAS=   81.9  FOM=  0.97
INDE  -7  20   4  FOBS=  228.4  SIGMA=   1.8  PHAS=  318.3  FOM=  1.00
INDE  -7  20   5  FOBS=  128.2  SIGMA=   2.9  PHAS=  233.4  FOM=  0.77
INDE  -7  20   6  FOBS=  320.2  SIGMA=   1.3  PHAS=   41.0  FOM=  0.98
INDE  -7  20   7  FOBS=   93.5  SIGMA=   3.9  PHAS=  115.2  FOM=  0.34
INDE  -7  20   8  FOBS=  102.4  SIGMA=   2.6  PHAS=  321.2  FOM=  0.67
INDE  -7  20   9  FOBS=  179.8  SIGMA=   2.0  PHAS=  259.8  FOM=  0.75
INDE  -7  20  10  FOBS=   83.4  SIGMA=   4.5  PHAS=  189.9  FOM=  0.06
INDE  -7  20  11  FOBS=  130.6  SIGMA=   3.0  PHAS=  340.5  FOM=  0.33
INDE  -7  20  12  FOBS=  191.2  SIGMA=   2.2  PHAS=  168.4  FOM=  0.85
INDE  -7  20  13  FOBS=   94.9  SIGMA=   5.1  PHAS=  305.0  FOM=  0.55
INDE  -7  21   1  FOBS=  127.2  SIGMA=   4.1  PHAS=  221.9  FOM=  0.77
INDE  -7  21   2  FOBS=   78.6  SIGMA=   4.7  PHAS=  233.9  FOM=  0.85
INDE  -7  21   3  FOBS=   97.9  SIGMA=   4.6  PHAS=  285.3  FOM=  0.91
```

Fig. 10A-41

```
INDE   -7   21    4  FOBS=   298.5  SIGMA=   1.7  PHAS=  134.7  FOM=  0.97
INDE   -7   21    5  FOBS=   111.5  SIGMA=   3.2  PHAS=  147.5  FOM=  0.87
INDE   -7   21    6  FOBS=   355.3  SIGMA=   1.3  PHAS=   93.5  FOM=  0.95
INDE   -7   21    7  FOBS=   344.9  SIGMA=   1.3  PHAS=   96.3  FOM=  0.97
INDE   -7   21    8  FOBS=   129.0  SIGMA=   2.6  PHAS=  146.9  FOM=  0.96
INDE   -7   21    9  FOBS=   309.3  SIGMA=   1.6  PHAS=  281.8  FOM=  0.98
INDE   -7   21   10  FOBS=   121.1  SIGMA=   3.2  PHAS=   23.9  FOM=  0.45
INDE   -7   21   11  FOBS=   188.9  SIGMA=   2.1  PHAS=  265.9  FOM=  1.00
INDE   -7   21   12  FOBS=   167.6  SIGMA=   2.4  PHAS=  133.8  FOM=  0.59
INDE   -7   22    1  FOBS=   279.9  SIGMA=   2.0  PHAS=  296.5  FOM=  0.90
INDE   -7   22    2  FOBS=   246.2  SIGMA=   2.3  PHAS=  347.8  FOM=  0.14
INDE   -7   22    3  FOBS=   146.1  SIGMA=   3.0  PHAS=   96.9  FOM=  0.90
INDE   -7   22    4  FOBS=   107.5  SIGMA=   3.8  PHAS=   24.5  FOM=  0.91
INDE   -7   22    5  FOBS=   150.6  SIGMA=   2.3  PHAS=  344.7  FOM=  0.93
INDE   -7   22    6  FOBS=    55.7  SIGMA=   7.3  PHAS=  265.9  FOM=  0.09
INDE   -7   22    7  FOBS=   176.9  SIGMA=   2.0  PHAS=  295.0  FOM=  0.91
INDE   -7   22    8  FOBS=   350.2  SIGMA=   1.9  PHAS=  313.6  FOM=  0.99
INDE   -7   22    9  FOBS=    60.0  SIGMA=   5.7  PHAS=  308.8  FOM=  0.10
INDE   -7   22   10  FOBS=   158.8  SIGMA=   2.4  PHAS=  220.0  FOM=  0.15
INDE   -7   22   11  FOBS=    66.6  SIGMA=   5.8  PHAS=   57.2  FOM=  0.04
INDE   -7   22   12  FOBS=   180.5  SIGMA=   2.3  PHAS=  184.3  FOM=  0.43
INDE   -7   23    1  FOBS=    98.2  SIGMA=   5.2  PHAS=  268.0  FOM=  0.42
INDE   -7   23    2  FOBS=   344.6  SIGMA=   2.1  PHAS=   67.9  FOM=  0.95
INDE   -7   23    3  FOBS=    67.1  SIGMA=   6.4  PHAS=    2.7  FOM=  0.65
INDE   -7   23    4  FOBS=   100.9  SIGMA=   4.1  PHAS=  144.9  FOM=  0.76
INDE   -7   23    5  FOBS=   165.6  SIGMA=   2.3  PHAS=  104.3  FOM=  0.94
INDE   -7   23    6  FOBS=   320.5  SIGMA=   1.4  PHAS=  350.5  FOM=  0.98
INDE   -7   23    7  FOBS=   158.6  SIGMA=   2.2  PHAS=  326.9  FOM=  0.92
INDE   -7   23    8  FOBS=   151.5  SIGMA=   3.1  PHAS=  155.7  FOM=  0.29
INDE   -7   23    9  FOBS=   194.5  SIGMA=   1.9  PHAS=  149.4  FOM=  0.94
INDE   -7   23   10  FOBS=    99.0  SIGMA=   4.0  PHAS=  104.8  FOM=  0.90
INDE   -7   23   11  FOBS=   208.7  SIGMA=   2.0  PHAS=  291.5  FOM=  0.92
INDE   -7   24    1  FOBS=   165.1  SIGMA=   2.8  PHAS=   53.0  FOM=  0.50
INDE   -7   24    2  FOBS=   169.1  SIGMA=   3.4  PHAS=  153.3  FOM=  0.62
INDE   -7   24    3  FOBS=    86.5  SIGMA=   4.9  PHAS=  121.0  FOM=  0.36
INDE   -7   24    4  FOBS=    95.6  SIGMA=   4.1  PHAS=   39.9  FOM=  0.51
INDE   -7   24    5  FOBS=   288.0  SIGMA=   1.6  PHAS=   83.7  FOM=  0.95
INDE   -7   24    6  FOBS=   382.7  SIGMA=   1.2  PHAS=  325.5  FOM=  1.00
INDE   -7   24    7  FOBS=   212.7  SIGMA=   2.0  PHAS=   78.0  FOM=  0.17
INDE   -7   24    8  FOBS=   177.4  SIGMA=   2.9  PHAS=  127.6  FOM=  0.90
INDE   -7   24    9  FOBS=    63.3  SIGMA=   8.3  PHAS=    2.2  FOM=  0.94
INDE   -7   24   10  FOBS=    83.8  SIGMA=   4.5  PHAS=  171.8  FOM=  0.32
INDE   -7   24   11  FOBS=    96.8  SIGMA=   5.0  PHAS=   14.1  FOM=  0.26
INDE   -7   25    1  FOBS=    77.8  SIGMA=   6.2  PHAS=  317.8  FOM=  0.69
INDE   -7   25    2  FOBS=   131.8  SIGMA=   3.6  PHAS=   53.2  FOM=  0.49
INDE   -7   25    3  FOBS=    50.8  SIGMA=   9.4  PHAS=  175.6  FOM=  0.21
INDE   -7   25    4  FOBS=    62.1  SIGMA=   6.4  PHAS=  195.0  FOM=  0.17
INDE   -7   25    5  FOBS=   262.5  SIGMA=   1.6  PHAS=   91.4  FOM=  1.00
INDE   -7   25    6  FOBS=   150.3  SIGMA=   2.5  PHAS=   16.9  FOM=  0.89
INDE   -7   25    7  FOBS=   246.5  SIGMA=   1.8  PHAS=   47.3  FOM=  0.90
INDE   -7   25    8  FOBS=   126.1  SIGMA=   3.7  PHAS=  353.0  FOM=  0.84
INDE   -7   25    9  FOBS=    86.8  SIGMA=   4.7  PHAS=  345.4  FOM=  0.91
INDE   -7   25   10  FOBS=    41.9  SIGMA=  11.9  PHAS=  139.4  FOM=  0.36
INDE   -7   26    1  FOBS=    96.7  SIGMA=   6.1  PHAS=  325.4  FOM=  0.81
INDE   -7   26    2  FOBS=    79.0  SIGMA=   5.7  PHAS=  210.5  FOM=  0.47
INDE   -7   26    3  FOBS=   109.5  SIGMA=   4.0  PHAS=   99.1  FOM=  0.81
INDE   -7   26    4  FOBS=   156.4  SIGMA=   2.8  PHAS=   29.5  FOM=  0.96
INDE   -7   26    5  FOBS=   163.2  SIGMA=   2.3  PHAS=  105.3  FOM=  0.81
INDE   -7   26    6  FOBS=    91.1  SIGMA=   4.2  PHAS=  245.0  FOM=  0.39
INDE   -7   26    7  FOBS=    61.8  SIGMA=   5.8  PHAS=   10.0  FOM=  0.41
INDE   -7   26    8  FOBS=    57.8  SIGMA=   7.8  PHAS=  282.5  FOM=  0.08
INDE   -7   26    9  FOBS=    52.6  SIGMA=   7.1  PHAS=   85.1  FOM=  0.11
INDE   -7   27    1  FOBS=   196.9  SIGMA=   2.9  PHAS=   36.9  FOM=  0.23
INDE   -7   27    2  FOBS=   248.1  SIGMA=   1.9  PHAS=  153.1  FOM=  0.97
INDE   -7   27    3  FOBS=   164.4  SIGMA=   2.6  PHAS=  309.3  FOM=  0.14
INDE   -7   27    4  FOBS=   111.8  SIGMA=   3.8  PHAS=  305.6  FOM=  0.81
INDE   -7   27    5  FOBS=   201.2  SIGMA=   2.1  PHAS=  145.0  FOM=  0.97
INDE   -7   27    6  FOBS=    83.5  SIGMA=   4.2  PHAS=  301.7  FOM=  0.96
INDE   -7   27    7  FOBS=    99.8  SIGMA=   3.7  PHAS=  329.8  FOM=  0.82
INDE   -7   27    8  FOBS=   123.9  SIGMA=   3.6  PHAS=   86.3  FOM=  0.68
INDE   -7   28    1  FOBS=    48.3  SIGMA=  10.7  PHAS=  102.0  FOM=  0.28
```

Fig. 10A-42

```
INDE  -7  28   2 FOBS=  221.0 SIGMA=  2.0 PHAS= 138.0 FOM= 0.74
INDE  -7  28   3 FOBS=   70.2 SIGMA=  5.8 PHAS=  53.4 FOM= 0.43
INDE  -7  28   4 FOBS=   79.1 SIGMA=  5.0 PHAS= 104.2 FOM= 0.84
INDE  -7  28   5 FOBS=  149.8 SIGMA=  2.5 PHAS=  41.6 FOM= 0.64
INDE  -7  28   6 FOBS=   29.7 SIGMA= 13.3 PHAS=  28.4 FOM= 0.05
INDE  -7  28   7 FOBS=  119.4 SIGMA=  3.2 PHAS= 343.1 FOM= 0.86
INDE  -7  29   1 FOBS=  128.1 SIGMA=  3.5 PHAS=  92.2 FOM= 0.34
INDE  -7  29   2 FOBS=   54.4 SIGMA=  8.2 PHAS=  26.9 FOM= 0.06
INDE  -7  29   3 FOBS=  141.8 SIGMA=  2.9 PHAS=  31.3 FOM= 0.44
INDE  -7  29   4 FOBS=  238.2 SIGMA=  1.8 PHAS=  79.2 FOM= 0.96
INDE  -7  29   5 FOBS=   35.4 SIGMA= 10.2 PHAS= 258.9 FOM= 0.32
INDE  -7  29   6 FOBS=  117.6 SIGMA=  3.4 PHAS= 137.5 FOM= 0.50
INDE  -7  30   1 FOBS=   84.4 SIGMA=  5.1 PHAS=  26.8 FOM= 0.24
INDE  -7  30   2 FOBS=  124.0 SIGMA=  3.5 PHAS=  91.0 FOM= 0.42
INDE  -7  30   3 FOBS=  105.4 SIGMA=  3.9 PHAS=  93.9 FOM= 0.48
INDE  -7  30   4 FOBS=  169.2 SIGMA=  2.3 PHAS=  83.5 FOM= 0.91
INDE  -7  30   5 FOBS=  115.9 SIGMA= 13.2 PHAS=  54.9 FOM= 0.03
INDE  -6   0   1 FOBS=  221.8 SIGMA=  3.0 PHAS=   0.0 FOM= 1.00
INDE  -6   0   2 FOBS=  346.5 SIGMA=  1.6 PHAS=   0.0 FOM= 1.00
INDE  -6   0   3 FOBS=   42.6 SIGMA=  6.2 PHAS=   0.0 FOM= 0.99
INDE  -6   0   4 FOBS=  393.0 SIGMA=  1.6 PHAS=   0.0 FOM= 0.89
INDE  -6   0   5 FOBS=   33.5 SIGMA= 22.6 PHAS=   0.0 FOM= 0.62
INDE  -6   0   6 FOBS=  287.4 SIGMA=  1.6 PHAS=   0.0 FOM= 1.00
INDE  -6   0   7 FOBS=  188.2 SIGMA=  2.2 PHAS= 180.0 FOM= 0.96
INDE  -6   0   8 FOBS=   79.2 SIGMA=  5.5 PHAS= 180.0 FOM= 0.04
INDE  -6   0   9 FOBS=  122.2 SIGMA=  4.4 PHAS=   0.0 FOM= 0.08
INDE  -6   0  10 FOBS=   39.1 SIGMA= 13.9 PHAS=   0.0 FOM= 0.08
INDE  -6   0  11 FOBS=   73.2 SIGMA=  8.8 PHAS= 180.0 FOM= 0.66
INDE  -6   0  12 FOBS=  292.5 SIGMA=  2.5 PHAS=   0.0 FOM= 1.00
INDE  -6   0  13 FOBS=  128.1 SIGMA=  5.8 PHAS=   0.0 FOM= 0.01
INDE  -6   0  14 FOBS=  122.0 SIGMA=  7.0 PHAS= 180.0 FOM= 0.70
INDE  -6   0  15 FOBS=  356.8 SIGMA=  2.5 PHAS=   0.0 FOM= 1.00
INDE  -6   0  16 FOBS=   55.7 SIGMA= 14.0 PHAS= 180.0 FOM= 0.07
INDE  -6   0  17 FOBS=   86.3 SIGMA= 15.1 PHAS= 180.0 FOM= 0.05
INDE  -6   1   1 FOBS=  493.9 SIGMA=  1.3 PHAS= 305.0 FOM= 0.99
INDE  -6   1   2 FOBS=  436.5 SIGMA=  1.2 PHAS=  93.7 FOM= 0.70
INDE  -6   1   3 FOBS=  289.3 SIGMA=  1.3 PHAS=  23.2 FOM= 0.94
INDE  -6   1   4 FOBS=  414.0 SIGMA=  1.1 PHAS= 137.6 FOM= 0.98
INDE  -6   1   5 FOBS=   44.6 SIGMA=  6.6 PHAS= 327.0 FOM= 0.57
INDE  -6   1   6 FOBS=   54.4 SIGMA=  4.8 PHAS= 133.3 FOM= 0.78
INDE  -6   1   7 FOBS=  206.9 SIGMA=  1.7 PHAS= 267.0 FOM= 0.83
INDE  -6   1   8 FOBS=  333.0 SIGMA=  1.1 PHAS=  69.2 FOM= 1.00
INDE  -6   1   9 FOBS=  222.1 SIGMA=  1.7 PHAS= 215.8 FOM= 0.97
INDE  -6   1  10 FOBS=  161.2 SIGMA=  2.3 PHAS=   8.8 FOM= 0.09
INDE  -6   1  11 FOBS=  382.7 SIGMA=  1.3 PHAS=  61.5 FOM= 1.00
INDE  -6   1  12 FOBS=  168.0 SIGMA=  2.7 PHAS= 104.1 FOM= 0.91
INDE  -6   1  13 FOBS=  232.6 SIGMA=  2.2 PHAS=  57.0 FOM= 0.90
INDE  -6   1  14 FOBS=  215.2 SIGMA=  2.4 PHAS= 265.5 FOM= 0.57
INDE  -6   1  15 FOBS=   55.7 SIGMA=  9.9 PHAS= 300.8 FOM= 0.19
INDE  -6   1  16 FOBS=  164.4 SIGMA=  3.6 PHAS=  96.2 FOM= 0.82
INDE  -6   1  17 FOBS=   85.8 SIGMA= 10.6 PHAS= 339.2 FOM= 0.17
INDE  -6   2   1 FOBS=  304.2 SIGMA=  1.3 PHAS=  19.4 FOM= 0.99
INDE  -6   2   2 FOBS=  364.3 SIGMA=  1.3 PHAS= 194.0 FOM= 1.00
INDE  -6   2   3 FOBS=  134.8 SIGMA=  2.6 PHAS= 215.9 FOM= 0.93
INDE  -6   2   4 FOBS=  235.8 SIGMA=  1.4 PHAS=  74.9 FOM= 0.95
INDE  -6   2   5 FOBS=  114.0 SIGMA=  3.0 PHAS= 196.7 FOM= 0.86
INDE  -6   2   6 FOBS=  340.5 SIGMA=  1.1 PHAS=  39.4 FOM= 0.97
INDE  -6   2   7 FOBS=   43.2 SIGMA=  6.6 PHAS= 352.1 FOM= 0.72
INDE  -6   2   8 FOBS=  102.8 SIGMA=  3.3 PHAS= 150.8 FOM= 0.92
INDE  -6   2   9 FOBS=  296.5 SIGMA=  1.3 PHAS= 240.6 FOM= 0.97
INDE  -6   2  10 FOBS=  338.2 SIGMA=  1.3 PHAS=  13.1 FOM= 0.98
INDE  -6   2  11 FOBS=  371.7 SIGMA=  1.3 PHAS= 357.4 FOM= 0.93
INDE  -6   2  12 FOBS=  167.0 SIGMA=  2.8 PHAS=   4.5 FOM= 0.86
INDE  -6   2  13 FOBS=  360.2 SIGMA=  1.6 PHAS= 349.4 FOM= 0.95
INDE  -6   2  14 FOBS=  152.1 SIGMA=  3.6 PHAS= 125.0 FOM= 0.81
INDE  -6   2  15 FOBS=  205.1 SIGMA=  2.6 PHAS= 296.2 FOM= 0.74
INDE  -6   2  16 FOBS=  154.2 SIGMA=  3.7 PHAS= 189.5 FOM= 0.57
INDE  -6   2  17 FOBS=   52.0 SIGMA= 23.9 PHAS= 347.6 FOM= 0.04
INDE  -6   3   1 FOBS=  273.2 SIGMA=  1.3 PHAS=  78.2 FOM= 0.99
INDE  -6   3   2 FOBS=  183.1 SIGMA=  1.9 PHAS=  31.0 FOM= 0.95
INDE  -6   3   3 FOBS=  158.8 SIGMA=  2.2 PHAS= 237.1 FOM= 0.37
```

Fig. 10A-43

```
INDE  -6  3   4 FOBS=  102.3 SIGMA=  2.8 PHAS= 124.5 FOM= 0.96
INDE  -6  3   5 FOBS=  143.6 SIGMA=  2.0 PHAS= 124.5 FOM= 0.98
INDE  -6  3   6 FOBS=   59.8 SIGMA=  4.7 PHAS= 308.1 FOM= 0.81
INDE  -6  3   7 FOBS=  271.7 SIGMA=  1.4 PHAS= 120.2 FOM= 0.87
INDE  -6  3   8 FOBS=  159.5 SIGMA=  1.9 PHAS= 295.6 FOM= 0.94
INDE  -6  3   9 FOBS=  242.6 SIGMA=  1.6 PHAS= 233.5 FOM= 0.97
INDE  -6  3  10 FOBS=  410.1 SIGMA=  1.3 PHAS= 149.6 FOM= 0.88
INDE  -6  3  11 FOBS=  470.0 SIGMA=  1.2 PHAS= 103.1 FOM= 0.97
INDE  -6  3  12 FOBS=  151.9 SIGMA=  3.6 PHAS= 329.1 FOM= 0.89
INDE  -6  3  13 FOBS=  185.7 SIGMA=  2.7 PHAS= 294.5 FOM= 0.75
INDE  -6  3  14 FOBS=  103.8 SIGMA=  5.2 PHAS= 255.6 FOM= 0.29
INDE  -6  3  15 FOBS=  148.3 SIGMA=  3.8 PHAS= 321.6 FOM= 0.19
INDE  -6  3  16 FOBS=   42.0 SIGMA= 19.3 PHAS= 106.9 FOM= 0.09
INDE  -6  4   1 FOBS=  317.8 SIGMA=  1.6 PHAS= 184.4 FOM= 0.94
INDE  -6  4   2 FOBS=   52.6 SIGMA=  5.6 PHAS=  12.4 FOM= 0.16
INDE  -6  4   3 FOBS=   38.7 SIGMA=  7.6 PHAS= 148.8 FOM= 0.15
INDE  -6  4   4 FOBS=  133.5 SIGMA=  2.3 PHAS= 127.9 FOM= 0.51
INDE  -6  4   5 FOBS=  139.1 SIGMA=  1.9 PHAS= 215.6 FOM= 0.84
INDE  -6  4   6 FOBS=  139.7 SIGMA=  1.9 PHAS= 223.0 FOM= 0.83
INDE  -6  4   7 FOBS=  186.2 SIGMA=  1.7 PHAS=  32.8 FOM= 0.95
INDE  -6  4   8 FOBS=  110.5 SIGMA=  3.0 PHAS= 275.6 FOM= 0.77
INDE  -6  4   9 FOBS=  319.6 SIGMA=  1.3 PHAS=  94.6 FOM= 0.95
INDE  -6  4  10 FOBS=  112.6 SIGMA=  3.4 PHAS= 340.8 FOM= 0.96
INDE  -6  4  11 FOBS=  517.4 SIGMA=  1.2 PHAS=  29.2 FOM= 0.98
INDE  -6  4  12 FOBS=  275.7 SIGMA=  1.9 PHAS= 255.1 FOM= 0.41
INDE  -6  4  13 FOBS=  287.4 SIGMA=  1.9 PHAS=   1.7 FOM= 0.20
INDE  -6  4  14 FOBS=  220.0 SIGMA=  2.4 PHAS= 218.6 FOM= 0.74
INDE  -6  4  15 FOBS=   88.8 SIGMA=  6.1 PHAS= 355.6 FOM= 0.16
INDE  -6  4  16 FOBS=   44.5 SIGMA= 12.7 PHAS= 274.1 FOM= 0.02
INDE  -6  5   1 FOBS=  124.2 SIGMA=  3.2 PHAS= 199.6 FOM= 0.96
INDE  -6  5   2 FOBS=   96.6 SIGMA=  3.4 PHAS=  54.6 FOM= 0.95
INDE  -6  5   3 FOBS=  376.5 SIGMA=  1.2 PHAS=  56.4 FOM= 0.62
INDE  -6  5   4 FOBS=   91.4 SIGMA=  3.6 PHAS= 290.1 FOM= 0.96
INDE  -6  5   5 FOBS=  210.8 SIGMA=  1.4 PHAS= 211.2 FOM= 0.92
INDE  -6  5   6 FOBS=  212.8 SIGMA=  1.4 PHAS= 342.9 FOM= 0.78
INDE  -6  5   7 FOBS=  229.8 SIGMA=  1.4 PHAS=  44.1 FOM= 0.97
INDE  -6  5   8 FOBS=   76.3 SIGMA=  4.1 PHAS= 112.8 FOM= 0.73
INDE  -6  5   9 FOBS=   65.1 SIGMA=  5.1 PHAS= 341.7 FOM= 0.32
INDE  -6  5  10 FOBS=  203.9 SIGMA=  2.0 PHAS= 142.9 FOM= 0.77
INDE  -6  5  11 FOBS=  282.1 SIGMA=  1.7 PHAS= 209.9 FOM= 0.96
INDE  -6  5  12 FOBS=  256.6 SIGMA=  2.0 PHAS= 169.9 FOM= 0.42
INDE  -6  5  13 FOBS=   98.6 SIGMA=  5.2 PHAS= 235.5 FOM= 0.74
INDE  -6  5  14 FOBS=  177.7 SIGMA=  2.9 PHAS= 188.0 FOM= 0.89
INDE  -6  5  15 FOBS=  224.4 SIGMA=  2.3 PHAS= 239.3 FOM= 0.11
INDE  -6  5  16 FOBS=  162.4 SIGMA=  3.4 PHAS= 296.7 FOM= 0.74
INDE  -6  6   1 FOBS=  189.1 SIGMA=  2.0 PHAS= 123.5 FOM= 0.97
INDE  -6  6   2 FOBS=   89.2 SIGMA=  4.2 PHAS= 340.3 FOM= 0.13
INDE  -6  6   3 FOBS=  231.4 SIGMA=  1.6 PHAS=  83.0 FOM= 0.59
INDE  -6  6   4 FOBS=  142.8 SIGMA=  2.0 PHAS= 273.7 FOM= 0.84
INDE  -6  6   5 FOBS=  155.1 SIGMA=  1.7 PHAS=  69.4 FOM= 0.99
INDE  -6  6   6 FOBS=   95.8 SIGMA=  3.8 PHAS=  68.8 FOM= 0.43
INDE  -6  6   7 FOBS=  122.8 SIGMA=  2.3 PHAS= 165.2 FOM= 0.95
INDE  -6  6   8 FOBS=  214.8 SIGMA=  1.6 PHAS= 201.2 FOM= 0.95
INDE  -6  6   9 FOBS=  164.6 SIGMA=  2.1 PHAS= 314.8 FOM= 0.26
INDE  -6  6  10 FOBS=  111.6 SIGMA=  3.8 PHAS= 277.2 FOM= 0.73
INDE  -6  6  11 FOBS=  167.2 SIGMA=  2.6 PHAS=  70.5 FOM= 0.28
INDE  -6  6  12 FOBS=  216.5 SIGMA=  2.3 PHAS= 260.1 FOM= 0.91
INDE  -6  6  13 FOBS=  189.1 SIGMA=  2.6 PHAS= 158.8 FOM= 0.64
INDE  -6  6  14 FOBS=  163.0 SIGMA=  3.3 PHAS=  34.3 FOM= 0.09
INDE  -6  6  15 FOBS=  180.3 SIGMA=  2.9 PHAS= 319.8 FOM= 0.47
INDE  -6  6  16 FOBS=  194.7 SIGMA=  2.7 PHAS= 254.2 FOM= 0.24
INDE  -6  7   1 FOBS=  254.6 SIGMA=  1.5 PHAS=  26.9 FOM= 0.61
INDE  -6  7   2 FOBS=   84.2 SIGMA=  3.7 PHAS= 254.0 FOM= 0.19
INDE  -6  7   3 FOBS=  265.9 SIGMA=  1.3 PHAS= 285.6 FOM= 0.87
INDE  -6  7   4 FOBS=   66.1 SIGMA=  3.2 PHAS=  54.1 FOM= 0.62
INDE  -6  7   5 FOBS=   59.4 SIGMA=  3.6 PHAS= 279.5 FOM= 0.61
INDE  -6  7   6 FOBS=  259.0 SIGMA=  1.5 PHAS= 317.4 FOM= 0.89
INDE  -6  7   7 FOBS=  101.4 SIGMA=  2.9 PHAS= 165.5 FOM= 0.52
INDE  -6  7   8 FOBS=  195.1 SIGMA=  1.8 PHAS= 232.8 FOM= 0.94
INDE  -6  7   9 FOBS=  542.2 SIGMA=  1.1 PHAS= 136.0 FOM= 0.98
INDE  -6  7  10 FOBS=  149.6 SIGMA=  2.5 PHAS=  19.5 FOM= 0.91
```

Fig. 10A-44

```
INDE  -6   7  11  FOBS=   167.8  SIGMA=  2.6  PHAS=  312.5  FOM=  0.51
INDE  -6   7  12  FOBS=   175.7  SIGMA=  2.8  PHAS=  118.8  FOM=  0.60
INDE  -6   7  13  FOBS=   160.2  SIGMA=  3.3  PHAS=   53.8  FOM=  0.53
INDE  -6   7  14  FOBS=   264.0  SIGMA=  2.1  PHAS=  338.2  FOM=  0.76
INDE  -6   7  15  FOBS=   102.7  SIGMA=  5.3  PHAS=  174.3  FOM=  0.50
INDE  -6   7  16  FOBS=    76.7  SIGMA=  7.1  PHAS=  345.6  FOM=  0.19
INDE  -6   8   1  FOBS=   125.2  SIGMA=  3.2  PHAS=  129.3  FOM=  0.84
INDE  -6   8   2  FOBS=    63.4  SIGMA=  4.4  PHAS=   59.4  FOM=  0.94
INDE  -6   8   3  FOBS=   151.9  SIGMA=  1.9  PHAS=  144.4  FOM=  0.99
INDE  -6   8   4  FOBS=    60.9  SIGMA=  3.8  PHAS=  120.7  FOM=  0.53
INDE  -6   8   5  FOBS=    94.6  SIGMA=  2.5  PHAS=  188.9  FOM=  0.82
INDE  -6   8   6  FOBS=   163.0  SIGMA=  2.1  PHAS=   89.7  FOM=  0.90
INDE  -6   8   7  FOBS=   107.8  SIGMA=  3.1  PHAS=  355.1  FOM=  0.89
INDE  -6   8   8  FOBS=   440.3  SIGMA=  1.4  PHAS=  209.3  FOM=  0.81
INDE  -6   8   9  FOBS=   120.6  SIGMA=  3.1  PHAS=  144.6  FOM=  0.37
INDE  -6   8  10  FOBS=   200.5  SIGMA=  2.0  PHAS=  130.2  FOM=  0.93
INDE  -6   8  11  FOBS=   548.8  SIGMA=  1.3  PHAS=  350.3  FOM=  0.94
INDE  -6   8  12  FOBS=   249.2  SIGMA=  2.1  PHAS=  107.5  FOM=  0.84
INDE  -6   8  13  FOBS=   102.9  SIGMA=  5.1  PHAS=  244.5  FOM=  0.14
INDE  -6   8  14  FOBS=   132.2  SIGMA=  4.2  PHAS=  225.7  FOM=  0.43
INDE  -6   8  15  FOBS=   144.1  SIGMA=  4.0  PHAS=  285.4  FOM=  0.76
INDE  -6   8  16  FOBS=    81.6  SIGMA=  6.8  PHAS=  155.4  FOM=  0.12
INDE  -6   9   1  FOBS=   113.8  SIGMA=  3.4  PHAS=   25.7  FOM=  0.79
INDE  -6   9   2  FOBS=   125.5  SIGMA=  3.0  PHAS=  102.5  FOM=  0.15
INDE  -6   9   3  FOBS=   149.7  SIGMA=  2.5  PHAS=  259.8  FOM=  0.95
INDE  -6   9   4  FOBS=   124.5  SIGMA=  4.2  PHAS=  313.1  FOM=  0.49
INDE  -6   9   5  FOBS=   205.0  SIGMA=  3.0  PHAS=  237.8  FOM=  0.25
INDE  -6   9   6  FOBS=   125.3  SIGMA=  2.5  PHAS=  241.2  FOM=  0.81
INDE  -6   9   7  FOBS=   475.6  SIGMA=  1.0  PHAS=  317.8  FOM=  1.00
INDE  -6   9   8  FOBS=   116.3  SIGMA=  3.3  PHAS=  286.6  FOM=  0.49
INDE  -6   9   9  FOBS=   358.5  SIGMA=  1.4  PHAS=  233.2  FOM=  0.83
INDE  -6   9  10  FOBS=   167.3  SIGMA=  2.3  PHAS=  342.1  FOM=  0.80
INDE  -6   9  11  FOBS=   171.8  SIGMA=  2.9  PHAS=  216.9  FOM=  0.17
INDE  -6   9  12  FOBS=   147.6  SIGMA=  3.5  PHAS=   14.7  FOM=  0.50
INDE  -6   9  13  FOBS=   116.6  SIGMA=  4.7  PHAS=   85.4  FOM=  0.74
INDE  -6   9  14  FOBS=   149.5  SIGMA=  3.6  PHAS=  301.9  FOM=  0.40
INDE  -6   9  15  FOBS=    72.2  SIGMA=  7.3  PHAS=  266.1  FOM=  0.51
INDE  -6   9  16  FOBS=    87.3  SIGMA=  6.2  PHAS=   42.2  FOM=  0.67
INDE  -6  10   1  FOBS=   251.9  SIGMA=  1.6  PHAS=  119.5  FOM=  0.89
INDE  -6  10   2  FOBS=   115.8  SIGMA=  2.8  PHAS=  358.5  FOM=  0.93
INDE  -6  10   3  FOBS=   222.1  SIGMA=  1.5  PHAS=  210.4  FOM=  0.97
INDE  -6  10   4  FOBS=   103.4  SIGMA=  5.1  PHAS=  205.0  FOM=  0.06
INDE  -6  10   5  FOBS=   286.0  SIGMA=  2.1  PHAS=  353.4  FOM=  0.96
INDE  -6  10   6  FOBS=   347.9  SIGMA=  1.7  PHAS=   70.3  FOM=  0.98
INDE  -6  10   7  FOBS=   309.0  SIGMA=  1.4  PHAS=   80.2  FOM=  0.99
INDE  -6  10   8  FOBS=    53.4  SIGMA=  7.2  PHAS=  256.2  FOM=  0.13
INDE  -6  10   9  FOBS=   298.0  SIGMA=  1.5  PHAS=  219.9  FOM=  0.93
INDE  -6  10  10  FOBS=   138.3  SIGMA=  2.9  PHAS=  189.1  FOM=  0.95
INDE  -6  10  11  FOBS=   290.3  SIGMA=  1.8  PHAS=  316.9  FOM=  0.99
INDE  -6  10  12  FOBS=   322.9  SIGMA=  1.8  PHAS=   82.8  FOM=  0.99
INDE  -6  10  13  FOBS=   139.5  SIGMA=  4.1  PHAS=  330.2  FOM=  0.87
INDE  -6  10  14  FOBS=   100.6  SIGMA=  5.3  PHAS=  153.3  FOM=  0.17
INDE  -6  10  15  FOBS=   154.6  SIGMA=  3.9  PHAS=   75.5  FOM=  0.90
INDE  -6  10  16  FOBS=   111.6  SIGMA=  5.0  PHAS=  239.2  FOM=  0.22
INDE  -6  11   1  FOBS=   161.0  SIGMA=  2.3  PHAS=  329.8  FOM=  0.62
INDE  -6  11   2  FOBS=   115.3  SIGMA=  2.9  PHAS=  152.7  FOM=  0.76
INDE  -6  11   3  FOBS=   163.9  SIGMA=  2.6  PHAS=   15.6  FOM=  0.44
INDE  -6  11   4  FOBS=   272.0  SIGMA=  2.2  PHAS=  354.8  FOM=  0.97
INDE  -6  11   5  FOBS=   312.8  SIGMA=  1.9  PHAS=  182.4  FOM=  0.31
INDE  -6  11   6  FOBS=   329.0  SIGMA=  1.9  PHAS=  185.3  FOM=  0.89
INDE  -6  11   7  FOBS=   357.9  SIGMA=  1.5  PHAS=  356.9  FOM=  1.00
INDE  -6  11   8  FOBS=   333.3  SIGMA=  1.2  PHAS=  122.4  FOM=  0.98
INDE  -6  11   9  FOBS=   463.5  SIGMA=  1.2  PHAS=  241.6  FOM=  0.97
INDE  -6  11  10  FOBS=   337.9  SIGMA=  1.5  PHAS=  118.5  FOM=  0.68
INDE  -6  11  11  FOBS=    79.7  SIGMA=  6.1  PHAS=  194.3  FOM=  0.58
INDE  -6  11  12  FOBS=   297.9  SIGMA=  1.9  PHAS=  294.8  FOM=  0.98
INDE  -6  11  13  FOBS=   189.9  SIGMA=  2.7  PHAS=  201.5  FOM=  0.19
INDE  -6  11  14  FOBS=    96.2  SIGMA=  5.6  PHAS=  116.1  FOM=  0.52
INDE  -6  11  15  FOBS=    70.6  SIGMA=  7.4  PHAS=  314.9  FOM=  0.03
INDE  -6  11  16  FOBS=   155.9  SIGMA=  6.4  PHAS=  154.9  FOM=  0.19
INDE  -6  12   1  FOBS=    85.7  SIGMA=  4.3  PHAS=  154.3  FOM=  0.88
```

Fig. 10A-45

```
INDE  -6  12   2 FOBS=   171.6 SIGMA=   2.1 PHAS=  140.1 FOM= 0.98
INDE  -6  12   3 FOBS=   163.6 SIGMA=   1.6 PHAS=  316.4 FOM= 0.97
INDE  -6  12   4 FOBS=   338.7 SIGMA=   1.9 PHAS=  203.0 FOM= 0.85
INDE  -6  12   5 FOBS=   361.6 SIGMA=   1.8 PHAS=  191.5 FOM= 0.38
INDE  -6  12   6 FOBS=   296.1 SIGMA=   2.1 PHAS=  318.2 FOM= 0.97
INDE  -6  12   7 FOBS=   349.1 SIGMA=   1.1 PHAS=  200.6 FOM= 0.98
INDE  -6  12   8 FOBS=   547.3 SIGMA=   1.5 PHAS=  279.4 FOM= 0.99
INDE  -6  12   9 FOBS=   127.1 SIGMA=   3.3 PHAS=   36.2 FOM= 0.93
INDE  -6  12  10 FOBS=   232.1 SIGMA=   2.2 PHAS=   48.7 FOM= 1.00
INDE  -6  12  11 FOBS=   207.9 SIGMA=   2.3 PHAS=  333.5 FOM= 0.97
INDE  -6  12  12 FOBS=   198.2 SIGMA=   2.4 PHAS=  201.5 FOM= 0.65
INDE  -6  12  13 FOBS=    82.5 SIGMA=   6.2 PHAS=  105.6 FOM= 0.33
INDE  -6  12  14 FOBS=   108.9 SIGMA=   4.9 PHAS=  189.3 FOM= 0.29
INDE  -6  12  15 FOBS=    49.6 SIGMA=  11.4 PHAS=  143.1 FOM= 0.11
INDE  -6  13   1 FOBS=   195.5 SIGMA=   1.9 PHAS=   28.2 FOM= 0.83
INDE  -6  13   2 FOBS=   202.3 SIGMA=   1.7 PHAS=  355.0 FOM= 0.89
INDE  -6  13   3 FOBS=   178.3 SIGMA=   2.0 PHAS=  190.8 FOM= 0.91
INDE  -6  13   4 FOBS=   148.6 SIGMA=   3.8 PHAS=   49.9 FOM= 0.91
INDE  -6  13   5 FOBS=   179.2 SIGMA=   3.2 PHAS=  154.8 FOM= 0.93
INDE  -6  13   6 FOBS=   351.6 SIGMA=   1.9 PHAS=   82.7 FOM= 0.99
INDE  -6  13   7 FOBS=   331.9 SIGMA=   1.0 PHAS=  284.2 FOM= 0.99
INDE  -6  13   8 FOBS=   290.4 SIGMA=   1.3 PHAS=   98.7 FOM= 0.98
INDE  -6  13   9 FOBS=   125.9 SIGMA=   3.7 PHAS=  228.1 FOM= 0.94
INDE  -6  13  10 FOBS=   107.7 SIGMA=   4.9 PHAS=  216.4 FOM= 0.49
INDE  -6  13  11 FOBS=   184.4 SIGMA=   2.7 PHAS=  354.1 FOM= 0.54
INDE  -6  13  12 FOBS=   220.1 SIGMA=   2.2 PHAS=  260.3 FOM= 0.96
INDE  -6  13  13 FOBS=   139.9 SIGMA=   3.9 PHAS=  196.8 FOM= 0.92
INDE  -6  13  14 FOBS=    46.1 SIGMA=  12.4 PHAS=  325.3 FOM= 0.38
INDE  -6  13  15 FOBS=   182.5 SIGMA=   2.9 PHAS=  139.4 FOM= 0.20
INDE  -6  14   1 FOBS=    87.9 SIGMA=   4.3 PHAS=   72.3 FOM= 0.59
INDE  -6  14   2 FOBS=    91.6 SIGMA=   4.0 PHAS=  174.8 FOM= 0.94
INDE  -6  14   3 FOBS=   234.0 SIGMA=   1.7 PHAS=  251.3 FOM= 0.99
INDE  -6  14   4 FOBS=    80.8 SIGMA=   3.8 PHAS=  183.2 FOM= 0.41
INDE  -6  14   5 FOBS=   134.5 SIGMA=   3.9 PHAS=  276.9 FOM= 0.94
INDE  -6  14   6 FOBS=   332.1 SIGMA=   2.0 PHAS=  260.3 FOM= 0.96
INDE  -6  14   7 FOBS=   124.6 SIGMA=   2.4 PHAS=  253.6 FOM= 0.96
INDE  -6  14   8 FOBS=   125.6 SIGMA=   2.8 PHAS=  159.6 FOM= 0.89
INDE  -6  14   9 FOBS=   159.0 SIGMA=   2.7 PHAS=  219.7 FOM= 0.66
INDE  -6  14  10 FOBS=    54.4 SIGMA=   8.9 PHAS=  171.1 FOM= 0.19
INDE  -6  14  11 FOBS=   154.4 SIGMA=   3.6 PHAS=  141.0 FOM= 0.72
INDE  -6  14  12 FOBS=   146.2 SIGMA=   3.8 PHAS=  206.3 FOM= 0.44
INDE  -6  14  13 FOBS=   118.2 SIGMA=   4.2 PHAS=  194.4 FOM= 0.30
INDE  -6  14  14 FOBS=    76.5 SIGMA=   6.8 PHAS=  308.3 FOM= 0.99
INDE  -6  14  15 FOBS=   125.7 SIGMA=   4.3 PHAS=  205.5 FOM= 0.80
INDE  -6  15   1 FOBS=   514.2 SIGMA=   1.1 PHAS=  296.5 FOM= 1.00
INDE  -6  15   2 FOBS=   338.0 SIGMA=   1.2 PHAS=  165.4 FOM= 0.87
INDE  -6  15   3 FOBS=   411.7 SIGMA=   1.2 PHAS=  166.5 FOM= 0.97
INDE  -6  15   4 FOBS=   128.3 SIGMA=   2.2 PHAS=   86.4 FOM= 1.00
INDE  -6  15   5 FOBS=   427.0 SIGMA=   1.8 PHAS=  184.1 FOM= 0.97
INDE  -6  15   6 FOBS=   162.8 SIGMA=   3.4 PHAS=  119.0 FOM= 0.75
INDE  -6  15   7 FOBS=   428.1 SIGMA=   1.0 PHAS=  306.2 FOM= 0.75
INDE  -6  15   8 FOBS=   133.0 SIGMA=   2.5 PHAS=   29.5 FOM= 0.53
INDE  -6  15   9 FOBS=   159.7 SIGMA=   2.6 PHAS=  303.2 FOM= 0.86
INDE  -6  15  10 FOBS=   300.8 SIGMA=   2.0 PHAS=  140.2 FOM= 0.93
INDE  -6  15  11 FOBS=   144.5 SIGMA=   3.4 PHAS=   45.4 FOM= 0.14
INDE  -6  15  12 FOBS=    86.8 SIGMA=   7.4 PHAS=   73.3 FOM= 0.29
INDE  -6  15  13 FOBS=   124.8 SIGMA=   4.5 PHAS=  301.4 FOM= 0.82
INDE  -6  15  14 FOBS=    90.1 SIGMA=   5.8 PHAS=  132.8 FOM= 0.52
INDE  -6  15  15 FOBS=    90.5 SIGMA=   5.5 PHAS=  161.2 FOM= 0.03
INDE  -6  16   1 FOBS=   132.8 SIGMA=   3.0 PHAS=  102.3 FOM= 0.82
INDE  -6  16   2 FOBS=   505.6 SIGMA=   1.3 PHAS=  191.9 FOM= 0.96
INDE  -6  16   3 FOBS=   526.8 SIGMA=   1.1 PHAS=  312.5 FOM= 0.95
INDE  -6  16   4 FOBS=   493.4 SIGMA=   0.8 PHAS=   97.7 FOM= 0.98
INDE  -6  16   5 FOBS=   336.7 SIGMA=   1.6 PHAS=  279.6 FOM= 0.97
INDE  -6  16   6 FOBS=   178.8 SIGMA=   3.2 PHAS=   24.7 FOM= 0.28
INDE  -6  16   7 FOBS=   188.1 SIGMA=   1.7 PHAS=  151.6 FOM= 0.78
INDE  -6  16   8 FOBS=   205.5 SIGMA=   1.9 PHAS=  341.3 FOM= 0.91
INDE  -6  16   9 FOBS=   162.7 SIGMA=   2.6 PHAS=   88.7 FOM= 0.81
INDE  -6  16  10 FOBS=   287.2 SIGMA=   2.1 PHAS=    9.9 FOM= 0.91
INDE  -6  16  11 FOBS=   137.0 SIGMA=   3.4 PHAS=  107.2 FOM= 0.48
INDE  -6  16  12 FOBS=   202.0 SIGMA=   2.6 PHAS=  352.0 FOM= 0.62
```

Fig. 10A-46

```
INDE  -6  16  13  FOBS=  143.3  SIGMA=   4.2  PHAS=  133.7  FOM=  0.51
INDE  -6  16  14  FOBS=  159.9  SIGMA=   3.2  PHAS=  119.1  FOM=  0.64
INDE  -6  17   1  FOBS=  297.2  SIGMA=   1.5  PHAS=   60.3  FOM=  0.92
INDE  -6  17   2  FOBS=  288.9  SIGMA=   1.5  PHAS=  245.8  FOM=  0.95
INDE  -6  17   3  FOBS=  131.3  SIGMA=   2.7  PHAS=  112.4  FOM=  0.34
INDE  -6  17   4  FOBS=  101.1  SIGMA=   3.3  PHAS=   72.4  FOM=  0.88
INDE  -6  17   5  FOBS=   93.5  SIGMA=   3.0  PHAS=  344.9  FOM=  0.90
INDE  -6  17   6  FOBS=  252.6  SIGMA=   2.5  PHAS=    0.0  FOM=  0.80
INDE  -6  17   7  FOBS=   69.9  SIGMA=   4.6  PHAS=  150.1  FOM=  0.76
INDE  -6  17   8  FOBS=  414.5  SIGMA=   1.3  PHAS=  179.2  FOM=  0.77
INDE  -6  17   9  FOBS=  252.2  SIGMA=   1.8  PHAS=  343.7  FOM=  0.95
INDE  -6  17  10  FOBS=  250.6  SIGMA=   2.0  PHAS=  118.5  FOM=  0.79
INDE  -6  17  11  FOBS=  100.9  SIGMA=   4.4  PHAS=  346.1  FOM=  0.27
INDE  -6  17  12  FOBS=   96.0  SIGMA=   4.6  PHAS=   97.3  FOM=  0.39
INDE  -6  17  13  FOBS=  105.9  SIGMA=   5.0  PHAS=  299.8  FOM=  0.80
INDE  -6  17  14  FOBS=   43.1  SIGMA=  20.3  PHAS=  184.9  FOM=  0.12
INDE  -6  18   1  FOBS=  195.9  SIGMA=   2.2  PHAS=  324.1  FOM=  0.79
INDE  -6  18   2  FOBS=  333.9  SIGMA=   1.5  PHAS=   90.6  FOM=  0.98
INDE  -6  18   3  FOBS=  293.0  SIGMA=   1.4  PHAS=    6.9  FOM=  0.97
INDE  -6  18   4  FOBS=  251.7  SIGMA=   1.4  PHAS=  340.3  FOM=  0.99
INDE  -6  18   5  FOBS=  466.0  SIGMA=   1.1  PHAS=  195.0  FOM=  1.00
INDE  -6  18   6  FOBS=  288.8  SIGMA=   1.7  PHAS=  241.9  FOM=  0.97
INDE  -6  18   7  FOBS=  559.9  SIGMA=   1.9  PHAS=  180.1  FOM=  0.89
INDE  -6  18   8  FOBS=  328.8  SIGMA=   1.4  PHAS=  353.8  FOM=  0.99
INDE  -6  18   9  FOBS=  109.7  SIGMA=   4.0  PHAS=  175.6  FOM=  0.16
INDE  -6  18  10  FOBS=  152.5  SIGMA=   3.1  PHAS=   68.6  FOM=  0.87
INDE  -6  18  11  FOBS=   91.7  SIGMA=   4.9  PHAS=  198.6  FOM=  0.08
INDE  -6  18  12  FOBS=  213.5  SIGMA=   2.1  PHAS=  207.1  FOM=  0.97
INDE  -6  18  13  FOBS=  133.3  SIGMA=   3.6  PHAS=  294.8  FOM=  0.81
INDE  -6  18  14  FOBS=   69.4  SIGMA=   7.6  PHAS=  290.2  FOM=  0.06
INDE  -6  19   1  FOBS=  255.7  SIGMA=   1.8  PHAS=    4.6  FOM=  0.94
INDE  -6  19   2  FOBS=  304.4  SIGMA=   1.8  PHAS=  134.7  FOM=  0.82
INDE  -6  19   3  FOBS=  175.7  SIGMA=   2.1  PHAS=   36.8  FOM=  0.36
INDE  -6  19   4  FOBS=  159.0  SIGMA=   2.1  PHAS=  194.4  FOM=  0.95
INDE  -6  19   5  FOBS=  132.1  SIGMA=   2.4  PHAS=  124.3  FOM=  0.70
INDE  -6  19   6  FOBS=  219.7  SIGMA=   2.1  PHAS=  207.1  FOM=  0.96
INDE  -6  19   7  FOBS=  229.0  SIGMA=   1.9  PHAS=  312.0  FOM=  0.72
INDE  -6  19   8  FOBS=  415.7  SIGMA=   1.3  PHAS=  217.4  FOM=  0.99
INDE  -6  19   9  FOBS=  296.0  SIGMA=   1.6  PHAS=  158.0  FOM=  0.97
INDE  -6  19  10  FOBS=  136.2  SIGMA=   3.4  PHAS=   16.9  FOM=  0.04
INDE  -6  19  11  FOBS=  129.3  SIGMA=   4.2  PHAS=   69.9  FOM=  0.75
INDE  -6  19  12  FOBS=  107.2  SIGMA=   4.3  PHAS=  192.7  FOM=  0.39
INDE  -6  19  13  FOBS=  115.9  SIGMA=   4.1  PHAS=  291.6  FOM=  0.26
INDE  -6  20   1  FOBS=  235.8  SIGMA=   2.1  PHAS=  300.2  FOM=  0.93
INDE  -6  20   2  FOBS=  423.2  SIGMA=   1.8  PHAS=  175.6  FOM=  0.99
INDE  -6  20   3  FOBS=  249.6  SIGMA=   1.9  PHAS=  350.1  FOM=  0.98
INDE  -6  20   4  FOBS=  278.7  SIGMA=   1.5  PHAS=   77.5  FOM=  0.96
INDE  -6  20   5  FOBS=  227.6  SIGMA=   1.6  PHAS=  340.3  FOM=  0.71
INDE  -6  20   6  FOBS=  188.2  SIGMA=   2.5  PHAS=  329.9  FOM=  0.83
INDE  -6  20   7  FOBS=  308.9  SIGMA=   1.3  PHAS=  303.5  FOM=  0.96
INDE  -6  20   8  FOBS=  122.0  SIGMA=   3.5  PHAS=  230.5  FOM=  0.83
INDE  -6  20   9  FOBS=   45.8  SIGMA=   8.8  PHAS=  230.8  FOM=  0.30
INDE  -6  20  10  FOBS=   87.0  SIGMA=   5.5  PHAS=   90.7  FOM=  0.83
INDE  -6  20  11  FOBS=  170.8  SIGMA=   2.9  PHAS=  201.8  FOM=  0.73
INDE  -6  20  12  FOBS=  143.6  SIGMA=   3.3  PHAS=  144.5  FOM=  0.56
INDE  -6  20  13  FOBS=  223.8  SIGMA=   2.1  PHAS=  308.3  FOM=  0.84
INDE  -6  21   1  FOBS=  167.3  SIGMA=   2.8  PHAS=  102.6  FOM=  0.11
INDE  -6  21   2  FOBS=  238.4  SIGMA=   2.0  PHAS=   86.8  FOM=  0.26
INDE  -6  21   3  FOBS=  509.5  SIGMA=   1.2  PHAS=  117.8  FOM=  0.98
INDE  -6  21   4  FOBS=  157.6  SIGMA=   2.5  PHAS=  323.4  FOM=  0.87
INDE  -6  21   5  FOBS=  109.3  SIGMA=   3.4  PHAS=  257.7  FOM=  0.87
INDE  -6  21   6  FOBS=  133.8  SIGMA=   3.4  PHAS=  298.1  FOM=  0.92
INDE  -6  21   7  FOBS=  102.6  SIGMA=   3.5  PHAS=  279.0  FOM=  0.51
INDE  -6  21   8  FOBS=  168.3  SIGMA=   2.7  PHAS=  164.5  FOM=  0.93
INDE  -6  21   9  FOBS=  157.2  SIGMA=   2.7  PHAS=  277.7  FOM=  0.80
INDE  -6  21  10  FOBS=   60.8  SIGMA=   6.7  PHAS=   72.7  FOM=  0.06
INDE  -6  21  11  FOBS=  113.4  SIGMA=   4.8  PHAS=  200.8  FOM=  0.78
INDE  -6  21  12  FOBS=  165.2  SIGMA=   3.0  PHAS=  105.8  FOM=  0.73
INDE  -6  21  13  FOBS=   73.0  SIGMA=  20.9  PHAS=  128.6  FOM=  0.06
INDE  -6  22   1  FOBS=   74.9  SIGMA=   5.9  PHAS=   81.2  FOM=  0.40
INDE  -6  22   2  FOBS=  133.7  SIGMA=   3.7  PHAS=  101.6  FOM=  0.93
```

Fig. 10A-47

```
INDE  -6  22   3 FOBS=  253.2 SIGMA=  1.8 PHAS= 297.2 FOM= 0.97
INDE  -6  22   4 FOBS=   66.4 SIGMA=  5.3 PHAS= 102.1 FOM= 0.56
INDE  -6  22   5 FOBS=  167.7 SIGMA=  2.3 PHAS= 355.5 FOM= 0.89
INDE  -6  22   6 FOBS=  145.1 SIGMA=  3.4 PHAS= 266.1 FOM= 0.80
INDE  -6  22   7 FOBS=  121.3 SIGMA=  3.1 PHAS= 264.2 FOM= 0.94
INDE  -6  22   8 FOBS=  301.0 SIGMA=  1.7 PHAS=  28.9 FOM= 0.99
INDE  -6  22   9 FOBS=  209.1 SIGMA=  2.1 PHAS= 200.4 FOM= 0.82
INDE  -6  22  10 FOBS=   69.9 SIGMA=  6.1 PHAS= 186.8 FOM= 0.51
INDE  -6  22  11 FOBS=  177.8 SIGMA=  2.4 PHAS= 195.5 FOM= 0.85
INDE  -6  22  12 FOBS=  151.5 SIGMA=  3.4 PHAS= 170.5 FOM= 0.21
INDE  -6  23   1 FOBS=  208.0 SIGMA=  2.7 PHAS= 213.4 FOM= 0.99
INDE  -6  23   2 FOBS=  226.6 SIGMA=  2.1 PHAS= 240.7 FOM= 0.14
INDE  -6  23   3 FOBS=  227.1 SIGMA=  2.1 PHAS= 217.2 FOM= 1.00
INDE  -6  23   4 FOBS=  295.3 SIGMA=  1.5 PHAS=  48.4 FOM= 1.00
INDE  -6  23   5 FOBS=  183.7 SIGMA=  2.3 PHAS= 295.2 FOM= 0.89
INDE  -6  23   6 FOBS=   48.6 SIGMA=  8.6 PHAS= 105.8 FOM= 0.15
INDE  -6  23   7 FOBS=  256.8 SIGMA=  1.5 PHAS= 274.4 FOM= 0.94
INDE  -6  23   8 FOBS=  149.9 SIGMA=  2.7 PHAS= 266.7 FOM= 0.82
INDE  -6  23   9 FOBS=  162.0 SIGMA=  2.7 PHAS= 253.0 FOM= 0.90
INDE  -6  23  10 FOBS=  163.7 SIGMA=  2.6 PHAS= 314.2 FOM= 0.80
INDE  -6  23  11 FOBS=   49.8 SIGMA=  8.5 PHAS= 247.0 FOM= 0.09
INDE  -6  23  12 FOBS=  198.1 SIGMA=  7.0 PHAS= 259.0 FOM= 0.10
INDE  -6  24   1 FOBS=  148.6 SIGMA=  3.8 PHAS= 326.7 FOM= 0.37
INDE  -6  24   2 FOBS=  258.7 SIGMA=  1.8 PHAS= 128.2 FOM= 0.97
INDE  -6  24   3 FOBS=  181.9 SIGMA=  2.6 PHAS=  39.9 FOM= 0.72
INDE  -6  24   4 FOBS=  137.2 SIGMA=  3.0 PHAS= 197.3 FOM= 0.11
INDE  -6  24   5 FOBS=  166.9 SIGMA=  2.4 PHAS= 300.0 FOM= 0.94
INDE  -6  24   6 FOBS=  156.4 SIGMA=  2.5 PHAS= 262.4 FOM= 0.92
INDE  -6  24   7 FOBS=  194.8 SIGMA=  2.0 PHAS= 190.1 FOM= 0.93
INDE  -6  24   8 FOBS=  390.9 SIGMA=  1.3 PHAS= 156.8 FOM= 0.98
INDE  -6  24   9 FOBS=  167.3 SIGMA=  2.7 PHAS= 126.2 FOM= 0.50
INDE  -6  24  10 FOBS=  127.6 SIGMA=  3.1 PHAS= 319.0 FOM= 0.63
INDE  -6  24  11 FOBS=  183.8 SIGMA=  2.3 PHAS= 290.6 FOM= 0.79
INDE  -6  25   1 FOBS=  266.9 SIGMA=  1.9 PHAS= 124.4 FOM= 0.97
INDE  -6  25   2 FOBS=  206.3 SIGMA=  2.1 PHAS= 351.1 FOM= 0.81
INDE  -6  25   3 FOBS=   86.7 SIGMA=  5.1 PHAS= 318.1 FOM= 0.73
INDE  -6  25   4 FOBS=   58.3 SIGMA=  7.7 PHAS= 154.0 FOM= 0.76
INDE  -6  25   5 FOBS=   70.9 SIGMA=  6.3 PHAS= 222.1 FOM= 0.61
INDE  -6  25   6 FOBS=  244.7 SIGMA=  1.7 PHAS= 335.6 FOM= 0.95
INDE  -6  25   7 FOBS=  200.0 SIGMA=  2.2 PHAS= 260.4 FOM= 0.91
INDE  -6  25   8 FOBS=   78.1 SIGMA=  4.7 PHAS= 341.5 FOM= 0.76
INDE  -6  25   9 FOBS=   50.4 SIGMA=  8.5 PHAS= 100.6 FOM= 0.31
INDE  -6  25  10 FOBS=  139.3 SIGMA=  3.0 PHAS= 211.0 FOM= 0.70
INDE  -6  26   1 FOBS=  299.1 SIGMA=  1.7 PHAS= 280.4 FOM= 0.94
INDE  -6  26   2 FOBS=  135.8 SIGMA=  3.2 PHAS= 221.9 FOM= 0.58
INDE  -6  26   3 FOBS=  176.0 SIGMA=  2.4 PHAS=  12.1 FOM= 0.82
INDE  -6  26   4 FOBS=  161.4 SIGMA=  2.4 PHAS=  11.8 FOM= 0.69
INDE  -6  26   5 FOBS=   51.3 SIGMA=  9.0 PHAS= 305.9 FOM= 0.33
INDE  -6  26   6 FOBS=  123.9 SIGMA=  3.1 PHAS= 345.2 FOM= 0.64
INDE  -6  26   7 FOBS=  150.8 SIGMA=  2.9 PHAS= 100.6 FOM= 0.86
INDE  -6  26   8 FOBS=  184.3 SIGMA=  2.1 PHAS=  73.0 FOM= 0.79
INDE  -6  26   9 FOBS=  193.6 SIGMA=  2.0 PHAS= 273.0 FOM= 0.92
INDE  -6  26  10 FOBS=   79.5 SIGMA=  6.3 PHAS= 224.4 FOM= 0.75
INDE  -6  27   1 FOBS=  164.0 SIGMA=  2.8 PHAS= 103.9 FOM= 0.41
INDE  -6  27   2 FOBS=   45.8 SIGMA= 10.5 PHAS= 205.6 FOM= 0.12
INDE  -6  27   3 FOBS=  336.8 SIGMA=  1.4 PHAS= 272.3 FOM= 0.25
INDE  -6  27   4 FOBS=  212.2 SIGMA=  1.9 PHAS= 345.1 FOM= 0.70
INDE  -6  27   5 FOBS=  286.0 SIGMA=  1.7 PHAS= 241.8 FOM= 0.95
INDE  -6  27   6 FOBS=  159.3 SIGMA=  3.0 PHAS=  91.4 FOM= 0.87
INDE  -6  27   7 FOBS=  308.4 SIGMA=  1.9 PHAS= 206.1 FOM= 0.92
INDE  -6  27   8 FOBS=  178.2 SIGMA=  2.3 PHAS= 337.5 FOM= 1.00
INDE  -6  27   9 FOBS=   27.8 SIGMA= 11.9 PHAS= 161.5 FOM= 0.34
INDE  -6  28   1 FOBS=  151.8 SIGMA=  3.0 PHAS= 136.4 FOM= 0.12
INDE  -6  28   2 FOBS=   88.0 SIGMA=  4.7 PHAS= 274.7 FOM= 0.70
INDE  -6  28   3 FOBS=  105.9 SIGMA=  3.8 PHAS=  91.9 FOM= 0.83
INDE  -6  28   4 FOBS=  185.9 SIGMA=  2.1 PHAS= 173.6 FOM= 0.59
INDE  -6  28   5 FOBS=  159.1 SIGMA=  2.8 PHAS= 262.8 FOM= 0.82
INDE  -6  28   6 FOBS=  230.8 SIGMA=  2.0 PHAS= 166.2 FOM= 0.86
INDE  -6  28   7 FOBS=  140.9 SIGMA=  4.2 PHAS=   1.1 FOM= 0.16
INDE  -6  28   8 FOBS=  168.2 SIGMA=  2.2 PHAS= 125.1 FOM= 0.24
INDE  -6  29   1 FOBS=   88.2 SIGMA=  5.0 PHAS= 193.4 FOM= 0.48
```

Fig. 10A-48

```
INDE  -6  29   2 FOBS=   95.9 SIGMA=  4.4 PHAS= 311.6 FOM= 0.41
INDE  -6  29   3 FOBS=  158.5 SIGMA=  2.6 PHAS=  30.9 FOM= 0.95
INDE  -6  29   4 FOBS=   60.4 SIGMA=  6.7 PHAS= 197.9 FOM= 0.28
INDE  -6  29   5 FOBS=  137.0 SIGMA=  3.2 PHAS= 264.2 FOM= 0.30
INDE  -6  29   6 FOBS=   56.3 SIGMA=  6.2 PHAS= 335.5 FOM= 0.07
INDE  -6  29   7 FOBS=   40.7 SIGMA= 13.6 PHAS= 146.0 FOM= 0.13
INDE  -6  30   1 FOBS=  263.4 SIGMA=  1.8 PHAS= 220.7 FOM= 0.91
INDE  -6  30   2 FOBS=   76.6 SIGMA=  5.3 PHAS=  44.2 FOM= 0.30
INDE  -6  30   3 FOBS=   59.2 SIGMA=  6.3 PHAS= 182.7 FOM= 0.24
INDE  -6  30   4 FOBS=  230.8 SIGMA=  1.8 PHAS= 241.1 FOM= 0.93
INDE  -6  30   5 FOBS=  160.0 SIGMA=  2.8 PHAS=  13.3 FOM= 0.50
INDE  -6  30   6 FOBS=   63.8 SIGMA= 10.4 PHAS=  65.8 FOM= 0.09
INDE  -6  31   1 FOBS=  118.4 SIGMA=  3.8 PHAS= 335.1 FOM= 0.68
INDE  -6  31   2 FOBS=   74.3 SIGMA=  5.7 PHAS=  85.6 FOM= 0.15
INDE  -6  31   3 FOBS=   37.7 SIGMA= 12.2 PHAS= 141.7 FOM= 0.08
INDE  -6  31   4 FOBS=   95.6 SIGMA=  6.7 PHAS= 346.6 FOM= 0.43
INDE  -5   0   1 FOBS=  350.4 SIGMA=  1.6 PHAS=   0.0 FOM= 0.99
INDE  -5   0   2 FOBS=  687.2 SIGMA=  1.2 PHAS=   0.0 FOM= 0.37
INDE  -5   0   3 FOBS=  359.6 SIGMA=  1.7 PHAS=   0.0 FOM= 0.78
INDE  -5   0   4 FOBS=  131.4 SIGMA=  2.8 PHAS=   0.0 FOM= 1.00
INDE  -5   0   5 FOBS=  534.9 SIGMA=  1.3 PHAS= 180.0 FOM= 0.22
INDE  -5   0   6 FOBS=   32.1 SIGMA=  8.3 PHAS=   0.0 FOM= 0.42
INDE  -5   0   7 FOBS=   42.8 SIGMA= 11.2 PHAS= 180.0 FOM= 0.01
INDE  -5   0   8 FOBS=  278.7 SIGMA=  1.9 PHAS=   0.0 FOM= 1.00
INDE  -5   0   9 FOBS=  203.5 SIGMA=  2.6 PHAS=   0.0 FOM= 1.00
INDE  -5   0  10 FOBS=  313.2 SIGMA=  2.1 PHAS= 180.0 FOM= 0.13
INDE  -5   0  11 FOBS=  102.3 SIGMA=  6.1 PHAS=   0.0 FOM= 0.90
INDE  -5   0  12 FOBS=  287.4 SIGMA=  2.6 PHAS= 180.0 FOM= 1.00
INDE  -5   0  13 FOBS=   92.8 SIGMA=  8.6 PHAS= 180.0 FOM= 0.10
INDE  -5   0  14 FOBS=  182.3 SIGMA=  4.5 PHAS=   0.0 FOM= 0.00
INDE  -5   0  15 FOBS=   79.1 SIGMA= 10.6 PHAS= 180.0 FOM= 0.01
INDE  -5   0  16 FOBS=  218.6 SIGMA=  3.8 PHAS= 180.0 FOM= 0.05
INDE  -5   1   1 FOBS=  198.7 SIGMA=  2.2 PHAS= 194.3 FOM= 1.00
INDE  -5   1   2 FOBS=  452.7 SIGMA=  1.2 PHAS= 277.1 FOM= 0.98
INDE  -5   1   3 FOBS=  586.1 SIGMA=  0.8 PHAS=  69.3 FOM= 0.98
INDE  -5   1   4 FOBS=   97.6 SIGMA=  2.9 PHAS=  41.8 FOM= 0.92
INDE  -5   1   5 FOBS=   95.0 SIGMA=  2.7 PHAS= 286.4 FOM= 0.80
INDE  -5   1   6 FOBS=   58.4 SIGMA=  4.5 PHAS= 347.3 FOM= 0.90
INDE  -5   1   7 FOBS=   43.8 SIGMA=  7.5 PHAS= 127.8 FOM= 0.73
INDE  -5   1   8 FOBS=  181.8 SIGMA=  1.8 PHAS=  36.2 FOM= 0.96
INDE  -5   1   9 FOBS=  117.0 SIGMA=  3.2 PHAS= 232.2 FOM= 0.88
INDE  -5   1  10 FOBS=  351.6 SIGMA=  1.4 PHAS=  88.5 FOM= 0.99
INDE  -5   1  11 FOBS=  434.4 SIGMA=  1.3 PHAS= 280.4 FOM= 0.99
INDE  -5   1  12 FOBS=  183.2 SIGMA=  2.9 PHAS= 353.4 FOM= 0.83
INDE  -5   1  13 FOBS=  302.2 SIGMA=  2.0 PHAS= 254.1 FOM= 0.92
INDE  -5   1  14 FOBS=   91.5 SIGMA=  6.8 PHAS= 302.8 FOM= 0.67
INDE  -5   1  15 FOBS=  185.4 SIGMA=  3.3 PHAS= 112.8 FOM= 0.94
INDE  -5   1  16 FOBS=   70.5 SIGMA=  8.4 PHAS= 242.1 FOM= 0.26
INDE  -5   1  17 FOBS=   39.8 SIGMA= 15.8 PHAS= 158.9 FOM= 0.08
INDE  -5   2   1 FOBS=  464.4 SIGMA=  1.5 PHAS=  15.7 FOM= 0.98
INDE  -5   2   2 FOBS=  377.6 SIGMA=  1.0 PHAS= 354.1 FOM= 0.98
INDE  -5   2   3 FOBS=  479.0 SIGMA=  1.0 PHAS=  86.6 FOM= 0.86
INDE  -5   2   4 FOBS=  424.9 SIGMA=  0.9 PHAS= 181.2 FOM= 1.00
INDE  -5   2   5 FOBS=  472.1 SIGMA=  0.9 PHAS=  42.5 FOM= 0.98
INDE  -5   2   6 FOBS=  252.5 SIGMA=  1.1 PHAS= 244.0 FOM= 0.92
INDE  -5   2   7 FOBS=   44.4 SIGMA=  6.9 PHAS= 334.2 FOM= 0.26
INDE  -5   2   8 FOBS=   78.3 SIGMA=  4.2 PHAS= 210.4 FOM= 0.35
INDE  -5   2   9 FOBS=  332.5 SIGMA=  1.4 PHAS= 158.2 FOM= 0.76
INDE  -5   2  10 FOBS=   59.0 SIGMA=  6.9 PHAS= 186.4 FOM= 0.14
INDE  -5   2  11 FOBS=  351.8 SIGMA=  1.4 PHAS= 116.3 FOM= 0.73
INDE  -5   2  12 FOBS=  355.0 SIGMA=  1.6 PHAS= 254.5 FOM= 0.86
INDE  -5   2  13 FOBS=  418.3 SIGMA=  1.6 PHAS=  87.4 FOM= 0.98
INDE  -5   2  14 FOBS=  240.5 SIGMA=  2.4 PHAS= 280.6 FOM= 0.95
INDE  -5   2  15 FOBS=  183.2 SIGMA=  3.2 PHAS= 137.2 FOM= 0.11
INDE  -5   2  16 FOBS=   93.3 SIGMA=  6.6 PHAS= 181.3 FOM= 0.37
INDE  -5   2  17 FOBS=   87.3 SIGMA= 55.1 PHAS=  14.3 FOM= 0.09
INDE  -5   3   1 FOBS=  246.9 SIGMA=  1.4 PHAS= 245.5 FOM= 1.00
INDE  -5   3   2 FOBS=  370.1 SIGMA=  1.1 PHAS= 144.1 FOM= 1.00
INDE  -5   3   3 FOBS=  837.2 SIGMA=  0.8 PHAS= 326.5 FOM= 0.92
INDE  -5   3   4 FOBS=  829.5 SIGMA=  0.9 PHAS=  30.4 FOM= 0.99
INDE  -5   3   5 FOBS=   29.1 SIGMA= 10.6 PHAS= 195.4 FOM= 0.54
```

Fig. 10A-49

```
INDE   -5    3    6 FOBS=    171.5 SIGMA=     1.8 PHAS=     36.8 FOM=  1.00
INDE   -5    3    7 FOBS=    148.8 SIGMA=     1.9 PHAS=    103.3 FOM=  0.96
INDE   -5    3    8 FOBS=    201.2 SIGMA=     1.7 PHAS=    300.8 FOM=  0.69
INDE   -5    3    9 FOBS=    326.4 SIGMA=     1.3 PHAS=    130.7 FOM=  0.12
INDE   -5    3   10 FOBS=     74.1 SIGMA=     5.5 PHAS=    184.9 FOM=  0.03
INDE   -5    3   11 FOBS=    201.0 SIGMA=     2.3 PHAS=     34.2 FOM=  0.90
INDE   -5    3   12 FOBS=    438.8 SIGMA=     1.4 PHAS=    238.3 FOM=  0.98
INDE   -5    3   13 FOBS=    170.7 SIGMA=     3.3 PHAS=    172.4 FOM=  0.11
INDE   -5    3   14 FOBS=    265.3 SIGMA=     2.2 PHAS=    276.6 FOM=  0.92
INDE   -5    3   15 FOBS=    197.5 SIGMA=     3.1 PHAS=    115.8 FOM=  0.89
INDE   -5    3   16 FOBS=     49.1 SIGMA=    26.6 PHAS=    355.7 FOM=  0.07
INDE   -5    3   17 FOBS=     64.2 SIGMA=    11.1 PHAS=      6.2 FOM=  0.06
INDE   -5    4    1 FOBS=    220.9 SIGMA=     1.5 PHAS=    160.5 FOM=  0.86
INDE   -5    4    2 FOBS=    318.0 SIGMA=     1.2 PHAS=     18.7 FOM=  0.99
INDE   -5    4    3 FOBS=    393.6 SIGMA=     1.0 PHAS=    323.7 FOM=  1.00
INDE   -5    4    4 FOBS=    102.7 SIGMA=     3.1 PHAS=    129.0 FOM=  0.95
INDE   -5    4    5 FOBS=    172.4 SIGMA=     1.7 PHAS=     27.9 FOM=  0.99
INDE   -5    4    6 FOBS=    205.7 SIGMA=     1.5 PHAS=    308.8 FOM=  0.89
INDE   -5    4    7 FOBS=    170.0 SIGMA=     1.7 PHAS=     10.5 FOM=  0.69
INDE   -5    4    8 FOBS=    446.2 SIGMA=     1.2 PHAS=    223.8 FOM=  0.99
INDE   -5    4    9 FOBS=    275.9 SIGMA=     1.5 PHAS=    114.3 FOM=  0.90
INDE   -5    4   10 FOBS=     69.5 SIGMA=     5.9 PHAS=    189.9 FOM=  0.18
INDE   -5    4   11 FOBS=    564.5 SIGMA=     1.1 PHAS=    171.7 FOM=  0.98
INDE   -5    4   12 FOBS=    263.6 SIGMA=     2.0 PHAS=    112.3 FOM=  0.92
INDE   -5    4   13 FOBS=    209.3 SIGMA=     2.6 PHAS=    335.0 FOM=  0.89
INDE   -5    4   14 FOBS=     90.7 SIGMA=     6.4 PHAS=     29.5 FOM=  0.13
INDE   -5    4   15 FOBS=     67.1 SIGMA=     8.8 PHAS=    132.4 FOM=  0.06
INDE   -5    4   16 FOBS=    130.7 SIGMA=     4.7 PHAS=    208.1 FOM=  0.49
INDE   -5    4   17 FOBS=     91.5 SIGMA=    12.4 PHAS=     67.8 FOM=  0.04
INDE   -5    5    1 FOBS=    324.1 SIGMA=     1.2 PHAS=     67.5 FOM=  0.93
INDE   -5    5    2 FOBS=    309.5 SIGMA=     1.1 PHAS=    242.9 FOM=  0.96
INDE   -5    5    3 FOBS=    246.0 SIGMA=     1.3 PHAS=    249.6 FOM=  0.95
INDE   -5    5    4 FOBS=     81.3 SIGMA=     2.5 PHAS=    329.5 FOM=  0.60
INDE   -5    5    5 FOBS=    145.1 SIGMA=     1.9 PHAS=    144.8 FOM=  1.00
INDE   -5    5    6 FOBS=    159.3 SIGMA=     1.9 PHAS=    156.9 FOM=  0.98
INDE   -5    5    7 FOBS=    191.1 SIGMA=     1.6 PHAS=     78.3 FOM=  0.95
INDE   -5    5    8 FOBS=    148.9 SIGMA=     2.3 PHAS=    302.1 FOM=  0.78
INDE   -5    5    9 FOBS=    240.6 SIGMA=     1.7 PHAS=    108.5 FOM=  0.79
INDE   -5    5   10 FOBS=    181.6 SIGMA=     2.3 PHAS=    298.7 FOM=  0.68
INDE   -5    5   11 FOBS=    152.6 SIGMA=     3.0 PHAS=    141.6 FOM=  0.25
INDE   -5    5   12 FOBS=    144.6 SIGMA=     3.8 PHAS=    341.3 FOM=  0.58
INDE   -5    5   13 FOBS=    154.2 SIGMA=     3.8 PHAS=     51.2 FOM=  0.42
INDE   -5    5   14 FOBS=    134.3 SIGMA=     4.4 PHAS=     98.4 FOM=  0.16
INDE   -5    5   15 FOBS=    226.6 SIGMA=     2.5 PHAS=    217.5 FOM=  0.72
INDE   -5    5   16 FOBS=    128.5 SIGMA=     4.8 PHAS=    144.0 FOM=  0.16
INDE   -5    6    1 FOBS=    211.8 SIGMA=     1.8 PHAS=    317.6 FOM=  0.95
INDE   -5    6    2 FOBS=    227.6 SIGMA=     1.3 PHAS=    345.0 FOM=  1.00
INDE   -5    6    3 FOBS=    144.1 SIGMA=     2.0 PHAS=     73.3 FOM=  0.90
INDE   -5    6    4 FOBS=     36.2 SIGMA=     5.1 PHAS=     60.6 FOM=  0.39
INDE   -5    6    5 FOBS=     47.1 SIGMA=     6.0 PHAS=    272.3 FOM=  0.26
INDE   -5    6    6 FOBS=    113.2 SIGMA=     2.2 PHAS=    350.6 FOM=  0.93
INDE   -5    6    7 FOBS=    115.8 SIGMA=     2.7 PHAS=    119.8 FOM=  0.71
INDE   -5    6    8 FOBS=    183.1 SIGMA=     1.9 PHAS=    331.3 FOM=  0.97
INDE   -5    6    9 FOBS=    219.0 SIGMA=     1.8 PHAS=    348.4 FOM=  0.99
INDE   -5    6   10 FOBS=    227.4 SIGMA=     1.9 PHAS=    298.9 FOM=  0.93
INDE   -5    6   11 FOBS=    239.5 SIGMA=     2.0 PHAS=    256.8 FOM=  0.87
INDE   -5    6   12 FOBS=    116.9 SIGMA=     4.6 PHAS=    216.1 FOM=  0.27
INDE   -5    6   13 FOBS=    257.5 SIGMA=     2.2 PHAS=    119.2 FOM=  0.86
INDE   -5    6   14 FOBS=     71.8 SIGMA=     7.8 PHAS=     34.8 FOM=  0.10
INDE   -5    6   15 FOBS=     64.0 SIGMA=     9.1 PHAS=    351.6 FOM=  0.01
INDE   -5    6   16 FOBS=     82.6 SIGMA=     7.1 PHAS=    138.1 FOM=  0.03
INDE   -5    7    1 FOBS=    267.0 SIGMA=     1.3 PHAS=     93.3 FOM=  0.97
INDE   -5    7    2 FOBS=    174.4 SIGMA=     1.7 PHAS=    140.7 FOM=  0.93
INDE   -5    7    3 FOBS=    127.2 SIGMA=     3.8 PHAS=    251.9 FOM=  0.89
INDE   -5    7    4 FOBS=     60.0 SIGMA=     7.1 PHAS=    241.0 FOM=  0.38
INDE   -5    7    5 FOBS=     92.3 SIGMA=     3.3 PHAS=    146.0 FOM=  0.80
INDE   -5    7    6 FOBS=    122.8 SIGMA=     2.0 PHAS=    204.8 FOM=  0.83
INDE   -5    7    7 FOBS=    167.5 SIGMA=     2.0 PHAS=     56.1 FOM=  0.26
INDE   -5    7    8 FOBS=    179.2 SIGMA=     2.0 PHAS=     28.2 FOM=  0.51
INDE   -5    7    9 FOBS=    330.7 SIGMA=     1.3 PHAS=    259.0 FOM=  0.96
INDE   -5    7   10 FOBS=    133.1 SIGMA=     3.3 PHAS=    263.6 FOM=  0.81
```

Fig. 10A-50

```
INDE  -5   7  11 FOBS=   393.6 SIGMA=   1.4 PHAS=  290.8 FOM= 0.85
INDE  -5   7  12 FOBS=    69.7 SIGMA=   7.7 PHAS=   34.7 FOM= 0.33
INDE  -5   7  13 FOBS=   249.1 SIGMA=   2.2 PHAS=  231.4 FOM= 0.69
INDE  -5   7  14 FOBS=   173.1 SIGMA=   3.3 PHAS=  345.1 FOM= 0.73
INDE  -5   7  15 FOBS=   247.0 SIGMA=   2.4 PHAS=   92.6 FOM= 0.69
INDE  -5   7  16 FOBS=   156.2 SIGMA=   3.9 PHAS=  261.2 FOM= 0.10
INDE  -5   8   1 FOBS=    47.7 SIGMA=   6.4 PHAS=   96.3 FOM= 0.38
INDE  -5   8   2 FOBS=    36.9 SIGMA=   9.3 PHAS=  310.3 FOM= 0.04
INDE  -5   8   3 FOBS=    98.6 SIGMA=   4.8 PHAS=  216.4 FOM= 0.69
INDE  -5   8   4 FOBS=    81.5 SIGMA=   6.1 PHAS=  146.3 FOM= 0.81
INDE  -5   8   5 FOBS=    93.6 SIGMA=   3.3 PHAS=   29.6 FOM= 0.77
INDE  -5   8   6 FOBS=   161.3 SIGMA=   1.6 PHAS=   77.1 FOM= 0.94
INDE  -5   8   7 FOBS=   246.3 SIGMA=   1.4 PHAS=  134.9 FOM= 0.76
INDE  -5   8   8 FOBS=   253.9 SIGMA=   1.7 PHAS=  231.6 FOM= 0.75
INDE  -5   8   9 FOBS=   313.2 SIGMA=   1.4 PHAS=   67.0 FOM= 0.92
INDE  -5   8  10 FOBS=   134.8 SIGMA=   3.5 PHAS=  319.8 FOM= 0.74
INDE  -5   8  11 FOBS=   527.8 SIGMA=   1.2 PHAS=   23.0 FOM= 0.94
INDE  -5   8  12 FOBS=   232.3 SIGMA=   2.3 PHAS=  231.6 FOM= 0.64
INDE  -5   8  13 FOBS=    37.8 SIGMA=  16.6 PHAS=  289.9 FOM= 0.09
INDE  -5   8  14 FOBS=    83.8 SIGMA=   6.8 PHAS=  115.7 FOM= 0.24
INDE  -5   8  15 FOBS=   160.7 SIGMA=   3.6 PHAS=  130.5 FOM= 0.18
INDE  -5   8  16 FOBS=   171.0 SIGMA=   3.4 PHAS=  345.7 FOM= 0.59
INDE  -5   9   1 FOBS=    69.0 SIGMA=   4.3 PHAS=  100.9 FOM= 0.47
INDE  -5   9   2 FOBS=   147.6 SIGMA=   1.9 PHAS=  160.5 FOM= 0.90
INDE  -5   9   3 FOBS=   160.0 SIGMA=   3.1 PHAS=  267.8 FOM= 0.76
INDE  -5   9   4 FOBS=    62.3 SIGMA=   7.7 PHAS=   72.3 FOM= 0.17
INDE  -5   9   5 FOBS=   214.7 SIGMA=   3.1 PHAS=    4.5 FOM= 0.38
INDE  -5   9   6 FOBS=   141.7 SIGMA=   1.7 PHAS=  166.5 FOM= 0.99
INDE  -5   9   7 FOBS=    56.4 SIGMA=   5.8 PHAS=   74.0 FOM= 0.80
INDE  -5   9   8 FOBS=   273.8 SIGMA=   1.4 PHAS=  165.4 FOM= 1.00
INDE  -5   9   9 FOBS=   158.8 SIGMA=   2.7 PHAS=   20.6 FOM= 0.92
INDE  -5   9  10 FOBS=   388.0 SIGMA=   1.4 PHAS=   63.3 FOM= 0.98
INDE  -5   9  11 FOBS=   134.9 SIGMA=   3.9 PHAS=   15.7 FOM= 0.92
INDE  -5   9  12 FOBS=   164.1 SIGMA=   3.3 PHAS=  291.3 FOM= 0.29
INDE  -5   9  13 FOBS=   187.5 SIGMA=   2.9 PHAS=  146.8 FOM= 0.48
INDE  -5   9  14 FOBS=   146.1 SIGMA=   4.1 PHAS=  269.7 FOM= 0.41
INDE  -5   9  15 FOBS=   213.3 SIGMA=   2.6 PHAS=  151.6 FOM= 0.75
INDE  -5   9  16 FOBS=   104.8 SIGMA=   5.5 PHAS=  342.9 FOM= 0.09
INDE  -5  10   1 FOBS=    90.7 SIGMA=   3.9 PHAS=  302.3 FOM= 0.77
INDE  -5  10   2 FOBS=   129.3 SIGMA=   2.1 PHAS=  219.5 FOM= 0.87
INDE  -5  10   3 FOBS=    34.1 SIGMA=  15.6 PHAS=  153.0 FOM= 0.39
INDE  -5  10   4 FOBS=    99.0 SIGMA=   5.1 PHAS=   65.2 FOM= 0.83
INDE  -5  10   5 FOBS=   304.2 SIGMA=   2.5 PHAS=  226.4 FOM= 0.82
INDE  -5  10   6 FOBS=   159.8 SIGMA=   1.9 PHAS=  142.7 FOM= 0.97
INDE  -5  10   7 FOBS=   296.7 SIGMA=   1.4 PHAS=  294.4 FOM= 0.41
INDE  -5  10   8 FOBS=   126.0 SIGMA=   2.9 PHAS=  134.7 FOM= 0.77
INDE  -5  10   9 FOBS=   221.9 SIGMA=   2.0 PHAS=  331.9 FOM= 0.92
INDE  -5  10  10 FOBS=   514.3 SIGMA=   1.2 PHAS=  249.0 FOM= 0.98
INDE  -5  10  11 FOBS=   202.8 SIGMA=   2.5 PHAS=  291.9 FOM= 0.03
INDE  -5  10  12 FOBS=   148.5 SIGMA=   3.8 PHAS=   66.9 FOM= 0.69
INDE  -5  10  13 FOBS=    58.0 SIGMA=  11.0 PHAS=  187.1 FOM= 0.15
INDE  -5  10  14 FOBS=   101.2 SIGMA=   5.5 PHAS=  249.4 FOM= 0.14
INDE  -5  10  15 FOBS=    43.5 SIGMA=  12.8 PHAS=   13.6 FOM= 0.44
INDE  -5  10  16 FOBS=   122.8 SIGMA=   4.7 PHAS=  235.6 FOM= 0.54
INDE  -5  11   1 FOBS=   107.9 SIGMA=   3.1 PHAS=  276.3 FOM= 0.96
INDE  -5  11   2 FOBS=   123.2 SIGMA=   2.1 PHAS=   47.1 FOM= 1.00
INDE  -5  11   3 FOBS=   164.8 SIGMA=   1.9 PHAS=   18.2 FOM= 0.97
INDE  -5  11   4 FOBS=   136.3 SIGMA=   3.8 PHAS=   88.4 FOM= 0.18
INDE  -5  11   5 FOBS=   198.9 SIGMA=   3.5 PHAS=  194.0 FOM= 0.96
INDE  -5  11   6 FOBS=   565.1 SIGMA=   1.1 PHAS=    0.8 FOM= 1.00
INDE  -5  11   7 FOBS=    55.7 SIGMA=   8.2 PHAS=  168.0 FOM= 0.41
INDE  -5  11   8 FOBS=   340.3 SIGMA=   1.3 PHAS=   56.0 FOM= 1.00
INDE  -5  11   9 FOBS=    85.2 SIGMA=   4.9 PHAS=   75.6 FOM= 0.09
INDE  -5  11  10 FOBS=   103.3 SIGMA=   4.9 PHAS=  101.3 FOM= 0.85
INDE  -5  11  11 FOBS=   430.8 SIGMA=   1.6 PHAS=    8.3 FOM= 1.00
INDE  -5  11  12 FOBS=   224.9 SIGMA=   2.4 PHAS=   85.9 FOM= 0.89
INDE  -5  11  13 FOBS=    65.6 SIGMA=   8.5 PHAS=  254.1 FOM= 0.13
INDE  -5  11  14 FOBS=   163.8 SIGMA=   3.4 PHAS=   30.1 FOM= 0.81
INDE  -5  11  15 FOBS=   135.4 SIGMA=   4.3 PHAS=  158.5 FOM= 0.71
INDE  -5  11  16 FOBS=    64.3 SIGMA=   8.9 PHAS=  294.4 FOM= 0.11
INDE  -5  12   1 FOBS=    44.1 SIGMA=   8.1 PHAS=  133.9 FOM= 0.52
```

Fig. 10A-51

```
INDE  -5  12   2 FOBS=  104.9 SIGMA=  3.0 PHAS= 268.4 FOM= 0.77
INDE  -5  12   3 FOBS=   79.9 SIGMA=  3.0 PHAS= 185.2 FOM= 0.92
INDE  -5  12   4 FOBS=  121.4 SIGMA=  4.3 PHAS= 346.0 FOM= 0.95
INDE  -5  12   5 FOBS=   94.6 SIGMA=  6.7 PHAS= 170.2 FOM= 0.61
INDE  -5  12   6 FOBS=  485.4 SIGMA=  0.9 PHAS= 328.0 FOM= 0.77
INDE  -5  12   7 FOBS=  385.7 SIGMA=  1.2 PHAS= 121.3 FOM= 0.99
INDE  -5  12   8 FOBS=  116.3 SIGMA=  3.4 PHAS= 124.1 FOM= 0.79
INDE  -5  12   9 FOBS=  322.7 SIGMA=  1.6 PHAS= 305.3 FOM= 0.30
INDE  -5  12  10 FOBS=  236.6 SIGMA=  2.0 PHAS= 135.8 FOM= 0.91
INDE  -5  12  11 FOBS=  246.8 SIGMA=  2.4 PHAS=  71.4 FOM= 0.92
INDE  -5  12  12 FOBS=  254.5 SIGMA=  2.3 PHAS= 234.4 FOM= 0.28
INDE  -5  12  13 FOBS=  106.2 SIGMA=  5.2 PHAS= 169.5 FOM= 0.45
INDE  -5  12  14 FOBS=   33.4 SIGMA= 13.9 PHAS=  93.3 FOM= 0.32
INDE  -5  12  15 FOBS=   69.5 SIGMA=  8.2 PHAS=   9.3 FOM= 0.13
INDE  -5  13   1 FOBS=  113.9 SIGMA=  3.0 PHAS= 122.6 FOM= 0.68
INDE  -5  13   2 FOBS=  118.5 SIGMA=  2.9 PHAS= 254.6 FOM= 0.98
INDE  -5  13   3 FOBS=  168.3 SIGMA=  1.6 PHAS=  18.7 FOM= 0.97
INDE  -5  13   4 FOBS=  207.6 SIGMA=  2.0 PHAS= 291.1 FOM= 0.76
INDE  -5  13   5 FOBS=  149.9 SIGMA=  1.6 PHAS= 108.0 FOM= 0.99
INDE  -5  13   6 FOBS=  195.8 SIGMA=  1.5 PHAS= 215.4 FOM= 0.55
INDE  -5  13   7 FOBS=  272.7 SIGMA=  1.4 PHAS= 169.8 FOM= 1.00
INDE  -5  13   8 FOBS=  224.7 SIGMA=  2.0 PHAS= 246.0 FOM= 0.99
INDE  -5  13   9 FOBS=  142.4 SIGMA=  2.9 PHAS= 335.5 FOM= 0.69
INDE  -5  13  10 FOBS=  168.7 SIGMA=  2.9 PHAS=  64.3 FOM= 0.83
INDE  -5  13  11 FOBS=  101.1 SIGMA=  5.6 PHAS=  75.5 FOM= 0.72
INDE  -5  13  12 FOBS=  169.7 SIGMA=  3.4 PHAS=  33.7 FOM= 0.90
INDE  -5  13  13 FOBS=  112.3 SIGMA=  5.1 PHAS=  12.0 FOM= 0.05
INDE  -5  13  14 FOBS=  112.0 SIGMA=  5.2 PHAS=  49.1 FOM= 0.63
INDE  -5  14   1 FOBS=   57.2 SIGMA=  6.1 PHAS= 139.0 FOM= 0.64
INDE  -5  14   2 FOBS=  420.0 SIGMA=  1.2 PHAS=  29.1 FOM= 0.97
INDE  -5  14   3 FOBS=  318.4 SIGMA=  1.2 PHAS= 293.9 FOM= 1.00
INDE  -5  14   4 FOBS=  339.0 SIGMA=  0.9 PHAS= 140.9 FOM= 0.99
INDE  -5  14   5 FOBS=  316.9 SIGMA=  1.3 PHAS= 331.3 FOM= 0.95
INDE  -5  14   6 FOBS=  112.6 SIGMA=  2.8 PHAS=  72.0 FOM= 0.84
INDE  -5  14   7 FOBS=  104.3 SIGMA=  3.6 PHAS= 175.2 FOM= 0.10
INDE  -5  14   8 FOBS=  124.5 SIGMA=  4.2 PHAS= 258.3 FOM= 0.96
INDE  -5  14   9 FOBS=  374.5 SIGMA=  1.4 PHAS= 108.8 FOM= 0.98
INDE  -5  14  10 FOBS=  170.6 SIGMA=  2.7 PHAS= 156.6 FOM= 0.92
INDE  -5  14  11 FOBS=  335.6 SIGMA=  1.8 PHAS= 301.2 FOM= 0.96
INDE  -5  14  12 FOBS=  197.9 SIGMA=  3.2 PHAS= 207.6 FOM= 0.86
INDE  -5  14  13 FOBS=  169.9 SIGMA=  3.5 PHAS= 204.1 FOM= 0.68
INDE  -5  14  14 FOBS=   77.8 SIGMA=  7.0 PHAS= 214.5 FOM= 0.41
INDE  -5  14  15 FOBS=   61.9 SIGMA=  8.8 PHAS=  16.9 FOM= 0.03
INDE  -5  15   1 FOBS=  333.3 SIGMA=  1.3 PHAS= 100.0 FOM= 0.96
INDE  -5  15   2 FOBS=  411.7 SIGMA=  1.2 PHAS= 272.5 FOM= 0.94
INDE  -5  15   3 FOBS=  263.7 SIGMA=  1.2 PHAS= 349.8 FOM= 0.94
INDE  -5  15   4 FOBS=  549.2 SIGMA=  0.7 PHAS=  64.9 FOM= 0.97
INDE  -5  15   5 FOBS=  431.8 SIGMA=  1.0 PHAS= 283.9 FOM= 0.90
INDE  -5  15   6 FOBS=   99.0 SIGMA=  3.8 PHAS= 356.7 FOM= 0.61
INDE  -5  15   7 FOBS=  245.0 SIGMA=  1.6 PHAS= 194.4 FOM= 0.97
INDE  -5  15   8 FOBS=  248.4 SIGMA=  2.0 PHAS=  18.8 FOM= 0.42
INDE  -5  15   9 FOBS=  182.8 SIGMA=  2.4 PHAS=  20.3 FOM= 0.94
INDE  -5  15  10 FOBS=  349.9 SIGMA=  1.6 PHAS= 221.3 FOM= 0.99
INDE  -5  15  11 FOBS=  241.8 SIGMA=  2.1 PHAS= 266.2 FOM= 0.86
INDE  -5  15  12 FOBS=  214.0 SIGMA=  2.4 PHAS= 219.8 FOM= 0.33
INDE  -5  15  13 FOBS=  179.7 SIGMA=  3.8 PHAS=  46.9 FOM= 0.30
INDE  -5  15  14 FOBS=  157.6 SIGMA=  3.9 PHAS= 173.1 FOM= 0.35
INDE  -5  15  15 FOBS=  107.2 SIGMA=  5.5 PHAS= 340.6 FOM= 0.17
INDE  -5  16   1 FOBS=  377.3 SIGMA=  1.3 PHAS= 274.6 FOM= 0.76
INDE  -5  16   2 FOBS=  100.4 SIGMA=  4.3 PHAS= 315.2 FOM= 0.37
INDE  -5  16   3 FOBS=  239.3 SIGMA=  1.5 PHAS= 348.9 FOM= 0.89
INDE  -5  16   4 FOBS=  190.9 SIGMA=  1.6 PHAS=   3.1 FOM= 0.98
INDE  -5  16   5 FOBS=  276.1 SIGMA=  2.3 PHAS= 270.9 FOM= 0.94
INDE  -5  16   6 FOBS=   89.4 SIGMA=  3.5 PHAS= 335.2 FOM= 0.72
INDE  -5  16   7 FOBS=  128.9 SIGMA=  3.0 PHAS= 236.5 FOM= 0.45
INDE  -5  16   8 FOBS=  432.0 SIGMA=  1.2 PHAS=  64.7 FOM= 0.92
INDE  -5  16   9 FOBS=  209.4 SIGMA=  2.3 PHAS= 300.4 FOM= 0.94
INDE  -5  16  10 FOBS=  164.2 SIGMA=  2.9 PHAS= 159.8 FOM= 0.85
INDE  -5  16  11 FOBS=  226.3 SIGMA=  2.2 PHAS= 309.4 FOM= 0.90
INDE  -5  16  12 FOBS=  152.3 SIGMA=  3.6 PHAS= 171.7 FOM= 0.94
INDE  -5  16  13 FOBS=  269.7 SIGMA=  2.1 PHAS= 304.9 FOM= 0.96
```

Fig. 10A-52

```
INDE  -5  16  14  FOBS=   188.2  SIGMA=   3.2  PHAS=  293.5  FOM=  0.65
INDE  -5  16  15  FOBS=    73.1  SIGMA=  19.9  PHAS=   96.2  FOM=  0.04
INDE  -5  17   1  FOBS=   251.5  SIGMA=   1.7  PHAS=  246.1  FOM=  0.94
INDE  -5  17   2  FOBS=   646.3  SIGMA=   1.3  PHAS=  244.4  FOM=  0.95
INDE  -5  17   3  FOBS=   323.6  SIGMA=   1.2  PHAS=  336.5  FOM=  0.93
INDE  -5  17   4  FOBS=   264.9  SIGMA=   1.3  PHAS=  120.4  FOM=  0.80
INDE  -5  17   5  FOBS=   227.8  SIGMA=   2.1  PHAS=    5.8  FOM=  0.78
INDE  -5  17   6  FOBS=   153.3  SIGMA=   2.1  PHAS=   57.7  FOM=  0.93
INDE  -5  17   7  FOBS=   164.0  SIGMA=   2.7  PHAS=  161.0  FOM=  0.88
INDE  -5  17   8  FOBS=   316.9  SIGMA=   1.5  PHAS=  174.9  FOM=  0.82
INDE  -5  17   9  FOBS=   174.3  SIGMA=   3.0  PHAS=  169.3  FOM=  0.24
INDE  -5  17  10  FOBS=   110.2  SIGMA=   4.4  PHAS=   30.4  FOM=  0.21
INDE  -5  17  11  FOBS=   157.3  SIGMA=   3.3  PHAS=   10.5  FOM=  0.20
INDE  -5  17  12  FOBS=    79.5  SIGMA=   6.2  PHAS=  213.5  FOM=  0.36
INDE  -5  17  13  FOBS=   115.4  SIGMA=   4.6  PHAS=   15.5  FOM=  0.54
INDE  -5  17  14  FOBS=    80.6  SIGMA=   6.7  PHAS=  103.8  FOM=  0.10
INDE  -5  18   1  FOBS=   494.1  SIGMA=   1.3  PHAS=  156.9  FOM=  0.99
INDE  -5  18   2  FOBS=   242.6  SIGMA=   1.6  PHAS=  242.9  FOM=  0.96
INDE  -5  18   3  FOBS=   715.3  SIGMA=   0.9  PHAS=  100.5  FOM=  0.99
INDE  -5  18   4  FOBS=   116.1  SIGMA=   3.1  PHAS=  266.3  FOM=  0.88
INDE  -5  18   5  FOBS=   595.3  SIGMA=   1.2  PHAS=   67.4  FOM=  0.97
INDE  -5  18   6  FOBS=    93.6  SIGMA=   3.7  PHAS=  146.8  FOM=  0.77
INDE  -5  18   7  FOBS=   419.9  SIGMA=   1.6  PHAS=  210.2  FOM=  1.00
INDE  -5  18   8  FOBS=   295.3  SIGMA=   1.7  PHAS=  179.0  FOM=  0.61
INDE  -5  18   9  FOBS=   165.8  SIGMA=   3.1  PHAS=  220.1  FOM=  0.72
INDE  -5  18  10  FOBS=    74.0  SIGMA=   6.6  PHAS=  205.8  FOM=  0.10
INDE  -5  18  11  FOBS=   152.4  SIGMA=   3.4  PHAS=  154.0  FOM=  0.17
INDE  -5  18  12  FOBS=   198.8  SIGMA=   2.5  PHAS=   23.7  FOM=  0.14
INDE  -5  18  13  FOBS=   163.1  SIGMA=   3.0  PHAS=   64.6  FOM=  0.66
INDE  -5  18  14  FOBS=   139.3  SIGMA=   3.9  PHAS=  190.5  FOM=  0.70
INDE  -5  19   1  FOBS=   208.1  SIGMA=   2.4  PHAS=  298.2  FOM=  0.97
INDE  -5  19   2  FOBS=   398.4  SIGMA=   1.2  PHAS=   95.6  FOM=  0.70
INDE  -5  19   3  FOBS=   212.2  SIGMA=   1.8  PHAS=  166.2  FOM=  0.49
INDE  -5  19   4  FOBS=   478.5  SIGMA=   1.0  PHAS=  109.1  FOM=  0.98
INDE  -5  19   5  FOBS=    88.6  SIGMA=   5.5  PHAS=  319.3  FOM=  0.33
INDE  -5  19   6  FOBS=   102.2  SIGMA=   3.6  PHAS=  303.0  FOM=  0.80
INDE  -5  19   7  FOBS=   194.6  SIGMA=   2.2  PHAS=  154.5  FOM=  0.96
INDE  -5  19   8  FOBS=   317.1  SIGMA=   1.8  PHAS=   56.3  FOM=  0.98
INDE  -5  19   9  FOBS=   172.5  SIGMA=   3.0  PHAS=  121.6  FOM=  0.45
INDE  -5  19  10  FOBS=   162.6  SIGMA=   2.7  PHAS=   59.9  FOM=  0.92
INDE  -5  19  11  FOBS=   361.1  SIGMA=   1.6  PHAS=  298.2  FOM=  0.97
INDE  -5  19  12  FOBS=   149.0  SIGMA=   3.5  PHAS=   40.1  FOM=  0.22
INDE  -5  19  13  FOBS=    64.4  SIGMA=   7.5  PHAS=  217.4  FOM=  0.19
INDE  -5  19  14  FOBS=    59.1  SIGMA=  22.0  PHAS=   84.9  FOM=  0.02
INDE  -5  20   1  FOBS=   127.5  SIGMA=   4.6  PHAS=  190.6  FOM=  0.70
INDE  -5  20   2  FOBS=   103.8  SIGMA=   4.0  PHAS=  350.9  FOM=  0.53
INDE  -5  20   3  FOBS=   145.8  SIGMA=   2.7  PHAS=  186.2  FOM=  0.98
INDE  -5  20   4  FOBS=   486.5  SIGMA=   1.2  PHAS=   25.3  FOM=  1.00
INDE  -5  20   5  FOBS=   357.1  SIGMA=   1.6  PHAS=  148.6  FOM=  0.91
INDE  -5  20   6  FOBS=   137.5  SIGMA=   2.6  PHAS=   53.1  FOM=  0.96
INDE  -5  20   7  FOBS=   358.4  SIGMA=   1.4  PHAS=  178.8  FOM=  0.89
INDE  -5  20   8  FOBS=   285.0  SIGMA=   1.9  PHAS=  302.5  FOM=  0.15
INDE  -5  20   9  FOBS=   467.0  SIGMA=   1.3  PHAS=   41.0  FOM=  0.57
INDE  -5  20  10  FOBS=    48.5  SIGMA=  13.6  PHAS=  191.1  FOM=  0.11
INDE  -5  20  11  FOBS=   174.6  SIGMA=   2.7  PHAS=  222.3  FOM=  0.86
INDE  -5  20  12  FOBS=    88.8  SIGMA=   5.4  PHAS=  207.5  FOM=  0.22
INDE  -5  21   1  FOBS=   293.9  SIGMA=   2.0  PHAS=  240.9  FOM=  0.81
INDE  -5  21   2  FOBS=   112.7  SIGMA=   3.8  PHAS=  279.7  FOM=  0.93
INDE  -5  21   3  FOBS=   143.0  SIGMA=   2.5  PHAS=  251.0  FOM=  1.00
INDE  -5  21   4  FOBS=   232.3  SIGMA=   1.7  PHAS=   79.7  FOM=  0.81
INDE  -5  21   5  FOBS=   134.4  SIGMA=   3.7  PHAS=  331.0  FOM=  0.91
INDE  -5  21   6  FOBS=   117.8  SIGMA=   3.4  PHAS=   58.3  FOM=  0.58
INDE  -5  21   7  FOBS=   151.8  SIGMA=   2.7  PHAS=  222.4  FOM=  0.42
INDE  -5  21   8  FOBS=   368.1  SIGMA=   1.6  PHAS=   96.5  FOM=  0.71
INDE  -5  21   9  FOBS=   157.5  SIGMA=   2.9  PHAS=  311.4  FOM=  0.01
INDE  -5  21  10  FOBS=   169.0  SIGMA=   3.1  PHAS=   61.3  FOM=  0.37
INDE  -5  21  11  FOBS=    34.8  SIGMA=  14.0  PHAS=   40.8  FOM=  0.31
INDE  -5  21  12  FOBS=   144.8  SIGMA=   3.4  PHAS=  104.6  FOM=  0.83
INDE  -5  21  13  FOBS=   120.8  SIGMA=   4.2  PHAS=  152.2  FOM=  0.20
INDE  -5  22   1  FOBS=   289.7  SIGMA=   1.6  PHAS=   10.8  FOM=  1.00
INDE  -5  22   2  FOBS=   103.7  SIGMA=   4.0  PHAS=  290.3  FOM=  0.80
```

Fig. 10A-53

```
INDE  -5  22   3 FOBS=  202.9 SIGMA=  2.2 PHAS=  200.4 FOM=  0.63
INDE  -5  22   4 FOBS=  149.9 SIGMA=  2.6 PHAS=  332.7 FOM=  0.91
INDE  -5  22   5 FOBS=  195.6 SIGMA=  2.6 PHAS=  285.4 FOM=  0.59
INDE  -5  22   6 FOBS=  538.3 SIGMA=  1.1 PHAS=  349.8 FOM=  0.61
INDE  -5  22   7 FOBS=  135.3 SIGMA=  3.2 PHAS=  354.5 FOM=  0.79
INDE  -5  22   8 FOBS=  257.0 SIGMA=  1.8 PHAS=  245.6 FOM=  0.98
INDE  -5  22   9 FOBS=  129.2 SIGMA=  3.9 PHAS=  154.9 FOM=  0.89
INDE  -5  22  10 FOBS=  113.2 SIGMA=  4.6 PHAS=  330.7 FOM=  0.59
INDE  -5  22  11 FOBS=  198.5 SIGMA=  2.4 PHAS=  230.6 FOM=  0.97
INDE  -5  22  12 FOBS=   98.7 SIGMA=  5.0 PHAS=   48.1 FOM=  0.70
INDE  -5  23   1 FOBS=  195.7 SIGMA=  2.3 PHAS=  138.8 FOM=  0.41
INDE  -5  23   2 FOBS=  259.9 SIGMA=  1.8 PHAS=  218.7 FOM=  0.93
INDE  -5  23   3 FOBS=  168.8 SIGMA=  2.4 PHAS=  300.4 FOM=  0.93
INDE  -5  23   4 FOBS=  129.4 SIGMA=  3.2 PHAS=   83.7 FOM=  0.94
INDE  -5  23   5 FOBS=  208.4 SIGMA=  2.5 PHAS=  289.2 FOM=  0.84
INDE  -5  23   6 FOBS=   80.0 SIGMA=  4.4 PHAS=  323.5 FOM=  0.65
INDE  -5  23   7 FOBS=   67.2 SIGMA=  6.0 PHAS=  249.4 FOM=  0.42
INDE  -5  23   8 FOBS=  127.1 SIGMA=  3.4 PHAS=   84.2 FOM=  0.54
INDE  -5  23   9 FOBS=  176.5 SIGMA=  2.6 PHAS=  112.2 FOM=  0.84
INDE  -5  23  10 FOBS=  146.7 SIGMA=  3.3 PHAS=  239.7 FOM=  0.79
INDE  -5  23  11 FOBS=  136.8 SIGMA=  4.0 PHAS=  173.1 FOM=  0.57
INDE  -5  23  12 FOBS=   85.2 SIGMA=  5.6 PHAS=   36.9 FOM=  0.36
INDE  -5  24   1 FOBS=  339.4 SIGMA=  1.6 PHAS=   96.9 FOM=  0.92
INDE  -5  24   2 FOBS=   87.4 SIGMA=  4.7 PHAS=   14.5 FOM=  0.24
INDE  -5  24   3 FOBS=  294.3 SIGMA=  1.6 PHAS=  303.6 FOM=  0.97
INDE  -5  24   4 FOBS=  217.5 SIGMA=  2.1 PHAS=  258.5 FOM=  0.92
INDE  -5  24   5 FOBS=  383.2 SIGMA=  1.9 PHAS=  344.7 FOM=  0.97
INDE  -5  24   6 FOBS=   71.8 SIGMA=  5.3 PHAS=  268.4 FOM=  0.67
INDE  -5  24   7 FOBS=  164.8 SIGMA=  2.6 PHAS=   15.2 FOM=  0.55
INDE  -5  24   8 FOBS=  324.4 SIGMA=  1.5 PHAS=  296.4 FOM=  0.98
INDE  -5  24   9 FOBS=  154.6 SIGMA=  3.0 PHAS=  168.9 FOM=  0.96
INDE  -5  24  10 FOBS=  118.5 SIGMA=  3.9 PHAS=   15.8 FOM=  0.74
INDE  -5  24  11 FOBS=   67.2 SIGMA=  7.9 PHAS=  341.8 FOM=  0.51
INDE  -5  25   1 FOBS=  151.3 SIGMA=  3.0 PHAS=  223.2 FOM=  0.53
INDE  -5  25   2 FOBS=  213.3 SIGMA=  2.1 PHAS=  273.0 FOM=  0.39
INDE  -5  25   3 FOBS=  266.0 SIGMA=  1.7 PHAS=  121.1 FOM=  0.88
INDE  -5  25   4 FOBS=  150.2 SIGMA=  2.7 PHAS=   83.7 FOM=  0.41
INDE  -5  25   5 FOBS=  162.5 SIGMA=  3.4 PHAS=   33.1 FOM=  0.77
INDE  -5  25   6 FOBS=  187.3 SIGMA=  2.8 PHAS=   66.1 FOM=  0.10
INDE  -5  25   7 FOBS=   50.6 SIGMA=  8.1 PHAS=  341.0 FOM=  0.42
INDE  -5  25   8 FOBS=  144.8 SIGMA=  2.9 PHAS=  205.7 FOM=  0.93
INDE  -5  25   9 FOBS=  288.1 SIGMA=  1.6 PHAS=   66.4 FOM=  0.88
INDE  -5  25  10 FOBS=   84.6 SIGMA=  5.3 PHAS=   24.1 FOM=  0.57
INDE  -5  25  11 FOBS=  138.4 SIGMA=  4.4 PHAS=   89.8 FOM=  0.25
INDE  -5  26   1 FOBS=   99.4 SIGMA=  4.7 PHAS=  157.6 FOM=  0.86
INDE  -5  26   2 FOBS=  353.3 SIGMA=  1.4 PHAS=  115.5 FOM=  0.98
INDE  -5  26   3 FOBS=  362.7 SIGMA=  1.4 PHAS=    2.0 FOM=  0.97
INDE  -5  26   4 FOBS=  162.3 SIGMA=  2.6 PHAS=  315.0 FOM=  0.97
INDE  -5  26   5 FOBS=  131.3 SIGMA=  3.6 PHAS=   55.5 FOM=  0.95
INDE  -5  26   6 FOBS=  206.9 SIGMA=  2.3 PHAS=  179.3 FOM=  0.89
INDE  -5  26   7 FOBS=  209.7 SIGMA=  2.2 PHAS=  245.8 FOM=  0.97
INDE  -5  26   8 FOBS=  184.8 SIGMA=  2.3 PHAS=   79.4 FOM=  0.97
INDE  -5  26   9 FOBS=  152.3 SIGMA=  2.6 PHAS=    8.4 FOM=  0.89
INDE  -5  26  10 FOBS=   49.3 SIGMA=  8.5 PHAS=   75.2 FOM=  0.11
INDE  -5  27   1 FOBS=   70.4 SIGMA=  6.0 PHAS=   56.1 FOM=  0.04
INDE  -5  27   2 FOBS=  211.8 SIGMA=  2.1 PHAS=  351.4 FOM=  0.97
INDE  -5  27   3 FOBS=   86.5 SIGMA=  4.5 PHAS=   32.3 FOM=  0.57
INDE  -5  27   4 FOBS=  127.6 SIGMA=  3.4 PHAS=  209.4 FOM=  0.03
INDE  -5  27   5 FOBS=   99.9 SIGMA=  4.1 PHAS=  270.2 FOM=  0.81
INDE  -5  27   6 FOBS=  156.3 SIGMA=  2.9 PHAS=  292.5 FOM=  0.78
INDE  -5  27   7 FOBS=  162.4 SIGMA=  2.7 PHAS=  127.1 FOM=  0.25
INDE  -5  27   8 FOBS=  203.5 SIGMA=  2.3 PHAS=  353.4 FOM=  0.24
INDE  -5  27   9 FOBS=  233.3 SIGMA=  1.9 PHAS=  242.7 FOM=  0.85
INDE  -5  28   1 FOBS=   85.0 SIGMA=  4.9 PHAS=  237.1 FOM=  0.60
INDE  -5  28   2 FOBS=   50.9 SIGMA=  7.8 PHAS=  263.6 FOM=  0.10
INDE  -5  28   3 FOBS=   89.6 SIGMA=  4.1 PHAS=  322.8 FOM=  0.94
INDE  -5  28   4 FOBS=   86.8 SIGMA=  5.5 PHAS=  269.3 FOM=  0.87
INDE  -5  28   5 FOBS=  380.5 SIGMA=  1.3 PHAS=    5.3 FOM=  0.95
INDE  -5  28   6 FOBS=  280.5 SIGMA=  1.9 PHAS=  223.9 FOM=  0.95
INDE  -5  28   7 FOBS=  171.9 SIGMA=  2.4 PHAS=   75.2 FOM=  0.74
INDE  -5  28   8 FOBS=   86.7 SIGMA=  5.0 PHAS=  358.1 FOM=  0.40
```

Fig. 10A-54

```
INDE  -5  29   1 FOBS=  159.9 SIGMA=  2.7 PHAS= 143.5 FOM= 0.21
INDE  -5  29   2 FOBS=  196.4 SIGMA=  2.2 PHAS=  28.9 FOM= 0.49
INDE  -5  29   3 FOBS=  196.7 SIGMA=  2.1 PHAS= 118.3 FOM= 0.37
INDE  -5  29   4 FOBS=  211.1 SIGMA=  2.2 PHAS= 330.8 FOM= 0.94
INDE  -5  29   5 FOBS=  104.0 SIGMA=  3.8 PHAS= 187.8 FOM= 0.24
INDE  -5  29   6 FOBS=  131.5 SIGMA=  3.6 PHAS= 213.4 FOM= 0.61
INDE  -5  29   7 FOBS=  215.0 SIGMA=  2.1 PHAS=  30.5 FOM= 0.95
INDE  -5  30   1 FOBS=  119.2 SIGMA=  3.6 PHAS=  74.8 FOM= 0.30
INDE  -5  30   2 FOBS=   54.7 SIGMA=  7.1 PHAS=  37.8 FOM= 0.08
INDE  -5  30   3 FOBS=   56.5 SIGMA=  6.8 PHAS= 263.5 FOM= 0.09
INDE  -5  30   4 FOBS=  131.0 SIGMA=  3.5 PHAS= 352.7 FOM= 0.27
INDE  -5  30   5 FOBS=  147.0 SIGMA=  2.7 PHAS= 125.0 FOM= 0.31
INDE  -5  30   6 FOBS=   89.5 SIGMA=  5.1 PHAS= 346.3 FOM= 0.15
INDE  -5  31   1 FOBS=  186.5 SIGMA=  2.3 PHAS= 313.3 FOM= 0.79
INDE  -5  31   2 FOBS=   75.0 SIGMA=  5.2 PHAS=  21.9 FOM= 0.20
INDE  -5  31   3 FOBS=   81.8 SIGMA=  4.8 PHAS= 164.5 FOM= 0.50
INDE  -5  31   4 FOBS=  115.7 SIGMA=  4.0 PHAS= 220.6 FOM= 0.21
INDE  -5  31   5 FOBS=  106.5 SIGMA=  5.2 PHAS=  19.8 FOM= 0.33
INDE  -5  32   1 FOBS=  187.1 SIGMA=  2.4 PHAS= 202.6 FOM= 0.67
INDE  -5  32   2 FOBS=  120.6 SIGMA=  4.1 PHAS= 151.8 FOM= 0.88
INDE  -4   0   1 FOBS=   87.7 SIGMA=  4.5 PHAS= 180.0 FOM= 0.00
INDE  -4   0   2 FOBS=  142.8 SIGMA=  3.0 PHAS=   0.0 FOM= 0.44
INDE  -4   0   3 FOBS= 1003.7 SIGMA=  1.0 PHAS= 180.0 FOM= 1.00
INDE  -4   0   4 FOBS=  936.1 SIGMA=  1.1 PHAS=   0.0 FOM= 1.00
INDE  -4   0   5 FOBS=  136.4 SIGMA=  2.2 PHAS=   0.0 FOM= 1.00
INDE  -4   0   6 FOBS=   93.1 SIGMA=  3.5 PHAS= 180.0 FOM= 1.00
INDE  -4   0   7 FOBS=  245.5 SIGMA=  1.8 PHAS= 180.0 FOM= 1.00
INDE  -4   0   8 FOBS=  262.9 SIGMA=  2.0 PHAS=   0.0 FOM= 0.85
INDE  -4   0   9 FOBS=  151.0 SIGMA=  3.6 PHAS= 180.0 FOM= 0.80
INDE  -4   0  10 FOBS=  246.8 SIGMA=  2.6 PHAS=   0.0 FOM= 0.98
INDE  -4   0  11 FOBS=  305.0 SIGMA=  2.4 PHAS= 180.0 FOM= 1.00
INDE  -4   0  12 FOBS=  376.4 SIGMA=  2.4 PHAS= 180.0 FOM= 1.00
INDE  -4   0  13 FOBS=  112.5 SIGMA=  7.9 PHAS=   0.0 FOM= 0.19
INDE  -4   0  14 FOBS=  156.2 SIGMA=  6.2 PHAS=   0.0 FOM= 0.75
INDE  -4   0  15 FOBS=  171.2 SIGMA=  5.9 PHAS= 180.0 FOM= 0.99
INDE  -4   0  16 FOBS=   85.7 SIGMA= 10.4 PHAS=   0.0 FOM= 0.09
INDE  -4   0  17 FOBS=   88.1 SIGMA= 10.4 PHAS=   0.0 FOM= 0.10
INDE  -4   1   1 FOBS=  383.2 SIGMA=  0.9 PHAS= 127.9 FOM= 1.00
INDE  -4   1   2 FOBS=  603.7 SIGMA=  0.8 PHAS= 160.6 FOM= 1.00
INDE  -4   1   3 FOBS=  448.1 SIGMA=  0.8 PHAS=   5.5 FOM= 0.44
INDE  -4   1   4 FOBS=  712.3 SIGMA=  1.1 PHAS= 313.1 FOM= 0.98
INDE  -4   1   5 FOBS=  140.6 SIGMA=  1.6 PHAS= 208.6 FOM= 0.98
INDE  -4   1   6 FOBS=  415.3 SIGMA=  1.0 PHAS= 338.7 FOM= 0.58
INDE  -4   1   7 FOBS=   64.8 SIGMA=  4.6 PHAS= 248.5 FOM= 0.03
INDE  -4   1   8 FOBS=  102.1 SIGMA=  3.6 PHAS= 325.6 FOM= 0.85
INDE  -4   1   9 FOBS=  154.7 SIGMA=  2.7 PHAS=  68.4 FOM= 0.84
INDE  -4   1  10 FOBS=  241.9 SIGMA=  2.0 PHAS= 311.0 FOM= 0.99
INDE  -4   1  11 FOBS=  176.8 SIGMA=  2.8 PHAS= 224.7 FOM= 0.80
INDE  -4   1  12 FOBS=  356.5 SIGMA=  1.7 PHAS=  99.6 FOM= 0.87
INDE  -4   1  13 FOBS=  420.7 SIGMA=  1.7 PHAS= 294.5 FOM= 1.00
INDE  -4   1  14 FOBS=  504.8 SIGMA=  1.5 PHAS=  87.1 FOM= 0.96
INDE  -4   1  15 FOBS=  173.6 SIGMA=  3.7 PHAS= 316.3 FOM= 0.33
INDE  -4   1  16 FOBS=   91.6 SIGMA=  7.0 PHAS= 347.8 FOM= 0.22
INDE  -4   1  17 FOBS=  123.7 SIGMA=  5.3 PHAS=  54.5 FOM= 0.18
INDE  -4   2   1 FOBS=  397.7 SIGMA=  0.9 PHAS=  99.9 FOM= 0.99
INDE  -4   2   2 FOBS=  263.2 SIGMA=  1.4 PHAS= 208.3 FOM= 0.98
INDE  -4   2   4 FOBS=  341.4 SIGMA=  0.9 PHAS=  74.2 FOM= 0.94
INDE  -4   2   5 FOBS=  257.9 SIGMA=  1.2 PHAS= 300.0 FOM= 1.00
INDE  -4   2   6 FOBS=  314.6 SIGMA=  1.1 PHAS=  80.7 FOM= 0.99
INDE  -4   2   7 FOBS=  116.4 SIGMA=  2.8 PHAS= 163.6 FOM= 0.96
INDE  -4   2   8 FOBS=  183.6 SIGMA=  1.9 PHAS=  69.9 FOM= 0.96
INDE  -4   2   9 FOBS=  141.2 SIGMA=  2.7 PHAS= 136.4 FOM= 0.85
INDE  -4   2  10 FOBS=  342.4 SIGMA=  1.5 PHAS= 284.1 FOM= 0.98
INDE  -4   2  11 FOBS=  307.3 SIGMA=  1.8 PHAS= 352.4 FOM= 1.00
INDE  -4   2  12 FOBS=  270.4 SIGMA=  2.2 PHAS= 255.3 FOM= 0.91
INDE  -4   2  13 FOBS=  299.6 SIGMA=  2.1 PHAS= 287.9 FOM= 0.71
INDE  -4   2  14 FOBS=  259.9 SIGMA=  2.5 PHAS=  70.7 FOM= 0.91
INDE  -4   2  15 FOBS=   81.4 SIGMA=  7.8 PHAS= 228.2 FOM= 0.44
INDE  -4   2  16 FOBS=  261.2 SIGMA=  2.4 PHAS= 326.7 FOM= 0.91
INDE  -4   2  17 FOBS=  147.3 SIGMA=  4.5 PHAS= 102.7 FOM= 0.32
INDE  -4   3   1 FOBS=  536.3 SIGMA=  0.9 PHAS= 343.2 FOM= 0.38
```

Fig. 10A-55

```
INDE  -4  3   2 FOBS=  199.4 SIGMA=  1.5 PHAS= 243.5 FOM= 0.83
INDE  -4  3   3 FOBS=  223.0 SIGMA=  1.2 PHAS= 347.6 FOM= 0.99
INDE  -4  3   4 FOBS=  593.3 SIGMA=  0.9 PHAS= 350.4 FOM= 0.53
INDE  -4  3   5 FOBS=  237.2 SIGMA=  1.2 PHAS= 162.7 FOM= 0.76
INDE  -4  3   6 FOBS=  187.1 SIGMA=  1.5 PHAS= 328.9 FOM= 0.99
INDE  -4  3   7 FOBS=  225.8 SIGMA=  1.4 PHAS= 199.6 FOM= 0.99
INDE  -4  3   8 FOBS=  293.2 SIGMA=  1.3 PHAS= 302.9 FOM= 1.00
INDE  -4  3   9 FOBS=  448.2 SIGMA=  1.1 PHAS= 129.2 FOM= 1.00
INDE  -4  3  10 FOBS=  302.4 SIGMA=  1.6 PHAS= 298.6 FOM= 0.90
INDE  -4  3  11 FOBS=  337.4 SIGMA=  1.6 PHAS= 333.9 FOM= 0.91
INDE  -4  3  12 FOBS=  174.3 SIGMA=  3.2 PHAS= 226.6 FOM= 0.86
INDE  -4  3  13 FOBS=  148.3 SIGMA=  4.3 PHAS= 281.7 FOM= 0.24
INDE  -4  3  14 FOBS=  270.2 SIGMA=  2.3 PHAS=  23.9 FOM= 0.45
INDE  -4  3  15 FOBS=  147.5 SIGMA=  4.5 PHAS=  23.8 FOM= 0.20
INDE  -4  3  16 FOBS=  141.3 SIGMA=  4.7 PHAS= 203.9 FOM= 0.19
INDE  -4  3  17 FOBS=   44.1 SIGMA= 19.6 PHAS= 130.6 FOM= 0.09
INDE  -4  4   1 FOBS=  242.2 SIGMA=  1.5 PHAS= 356.3 FOM= 0.99
INDE  -4  4   2 FOBS=  360.4 SIGMA=  1.1 PHAS=  41.5 FOM= 1.00
INDE  -4  4   3 FOBS=  198.9 SIGMA=  1.4 PHAS= 204.4 FOM= 0.96
INDE  -4  4   4 FOBS=  693.0 SIGMA=  0.9 PHAS= 281.3 FOM= 0.82
INDE  -4  4   5 FOBS=  255.9 SIGMA=  1.1 PHAS=  59.3 FOM= 0.45
INDE  -4  4   6 FOBS=  100.5 SIGMA=  3.1 PHAS= 245.4 FOM= 0.90
INDE  -4  4   7 FOBS=  133.6 SIGMA=  2.3 PHAS= 138.1 FOM= 0.63
INDE  -4  4   8 FOBS=   39.7 SIGMA=  9.1 PHAS=  68.2 FOM= 0.36
INDE  -4  4   9 FOBS=   97.9 SIGMA=  4.2 PHAS= 238.8 FOM= 0.76
INDE  -4  4  10 FOBS=  326.1 SIGMA=  1.5 PHAS= 229.6 FOM= 0.93
INDE  -4  4  11 FOBS=  234.6 SIGMA=  2.2 PHAS= 155.9 FOM= 0.21
INDE  -4  4  12 FOBS=  157.8 SIGMA=  3.9 PHAS= 286.3 FOM= 0.85
INDE  -4  4  13 FOBS=   70.3 SIGMA=  9.0 PHAS=   4.2 FOM= 0.19
INDE  -4  4  14 FOBS=  312.4 SIGMA=  2.1 PHAS=  44.6 FOM= 0.86
INDE  -4  4  15 FOBS=   57.1 SIGMA= 12.7 PHAS= 217.4 FOM= 0.13
INDE  -4  4  16 FOBS=   71.3 SIGMA=  9.2 PHAS=  80.3 FOM= 0.09
INDE  -4  4  17 FOBS=   96.0 SIGMA=  8.5 PHAS= 295.1 FOM= 0.02
INDE  -4  5   1 FOBS=  552.6 SIGMA=  1.2 PHAS= 203.9 FOM= 0.99
INDE  -4  5   2 FOBS=  458.9 SIGMA=  1.0 PHAS= 198.6 FOM= 0.64
INDE  -4  5   3 FOBS=   76.1 SIGMA=  4.5 PHAS= 211.7 FOM= 0.83
INDE  -4  5   4 FOBS=  428.7 SIGMA=  0.7 PHAS= 351.2 FOM= 0.98
INDE  -4  5   5 FOBS=  280.4 SIGMA=  1.0 PHAS=  38.7 FOM= 0.86
INDE  -4  5   6 FOBS=   86.6 SIGMA=  3.5 PHAS= 238.9 FOM= 0.80
INDE  -4  5   7 FOBS=  154.5 SIGMA=  2.3 PHAS= 196.0 FOM= 0.92
INDE  -4  5   8 FOBS=  198.6 SIGMA=  1.9 PHAS= 221.0 FOM= 0.57
INDE  -4  5   9 FOBS=  225.2 SIGMA=  1.8 PHAS= 250.7 FOM= 0.40
INDE  -4  5  10 FOBS=  285.5 SIGMA=  1.7 PHAS= 111.7 FOM= 0.66
INDE  -4  5  11 FOBS=  235.8 SIGMA=  2.2 PHAS= 216.4 FOM= 0.19
INDE  -4  5  12 FOBS=  199.1 SIGMA=  2.9 PHAS= 220.6 FOM= 0.28
INDE  -4  5  13 FOBS=  203.4 SIGMA=  3.0 PHAS=   7.8 FOM= 0.62
INDE  -4  5  14 FOBS=  359.7 SIGMA=  1.9 PHAS= 168.9 FOM= 0.90
INDE  -4  5  15 FOBS=  131.1 SIGMA=  5.0 PHAS= 199.3 FOM= 0.20
INDE  -4  5  16 FOBS=   66.5 SIGMA=  9.9 PHAS= 320.5 FOM= 0.20
INDE  -4  6   1 FOBS=  144.7 SIGMA=  1.8 PHAS= 119.6 FOM= 0.93
INDE  -4  6   2 FOBS=  685.8 SIGMA=  0.7 PHAS=  63.8 FOM= 0.96
INDE  -4  6   3 FOBS=  244.9 SIGMA=  2.3 PHAS= 124.4 FOM= 0.98
INDE  -4  6   4 FOBS=   42.5 SIGMA=  5.3 PHAS= 152.6 FOM= 0.85
INDE  -4  6   5 FOBS=  278.7 SIGMA=  1.0 PHAS= 199.0 FOM= 0.90
INDE  -4  6   6 FOBS=  130.2 SIGMA=  2.2 PHAS= 263.8 FOM= 0.66
INDE  -4  6   7 FOBS=  293.8 SIGMA=  1.3 PHAS= 233.1 FOM= 0.70
INDE  -4  6   8 FOBS=  303.4 SIGMA=  1.5 PHAS=  67.1 FOM= 0.88
INDE  -4  6   9 FOBS=  100.0 SIGMA=  4.2 PHAS= 352.6 FOM= 0.79
INDE  -4  6  10 FOBS=   53.3 SIGMA=  9.0 PHAS= 128.5 FOM= 0.47
INDE  -4  6  11 FOBS=  384.9 SIGMA=  1.5 PHAS=  84.8 FOM= 0.90
INDE  -4  6  12 FOBS=  192.2 SIGMA=  2.9 PHAS=  64.8 FOM= 0.77
INDE  -4  6  13 FOBS=  176.3 SIGMA=  3.5 PHAS= 205.7 FOM= 0.78
INDE  -4  6  14 FOBS=  218.7 SIGMA=  2.8 PHAS=  26.3 FOM= 0.18
INDE  -4  6  15 FOBS=   68.6 SIGMA=  9.9 PHAS= 243.1 FOM= 0.18
INDE  -4  6  16 FOBS=  179.1 SIGMA=  3.6 PHAS= 155.1 FOM= 0.23
INDE  -4  7   1 FOBS=  271.3 SIGMA=  1.3 PHAS= 348.5 FOM= 0.45
INDE  -4  7   2 FOBS=  231.1 SIGMA=  1.3 PHAS=  17.0 FOM= 0.77
INDE  -4  7   3 FOBS=  267.1 SIGMA=  2.2 PHAS= 356.5 FOM= 0.90
INDE  -4  7   4 FOBS=  147.0 SIGMA=  3.7 PHAS= 342.3 FOM= 0.54
INDE  -4  7   5 FOBS=  179.4 SIGMA=  1.4 PHAS= 353.4 FOM= 0.69
INDE  -4  7   6 FOBS=  280.0 SIGMA=  1.2 PHAS=  86.2 FOM= 0.96
```

Fig. 10A-56

```
INDE  -4   7   7 FOBS=  305.1 SIGMA=  1.3 PHAS=   12.2 FOM= 0.97
INDE  -4   7   8 FOBS=  138.6 SIGMA=  2.9 PHAS=   29.4 FOM= 0.85
INDE  -4   7   9 FOBS=  145.2 SIGMA=  3.1 PHAS=  297.5 FOM= 0.94
INDE  -4   7  10 FOBS=  120.3 SIGMA=  4.0 PHAS=  291.8 FOM= 0.19
INDE  -4   7  11 FOBS=  245.9 SIGMA=  2.1 PHAS=  225.6 FOM= 0.87
INDE  -4   7  12 FOBS=   93.7 SIGMA=  6.1 PHAS=  127.6 FOM= 0.23
INDE  -4   7  13 FOBS=  244.5 SIGMA=  2.4 PHAS=  330.6 FOM= 0.14
INDE  -4   7  14 FOBS=   68.2 SIGMA=  9.7 PHAS=  340.5 FOM= 0.22
INDE  -4   7  15 FOBS=  106.1 SIGMA=  5.9 PHAS=  199.0 FOM= 0.30
INDE  -4   7  16 FOBS=  126.6 SIGMA=  5.1 PHAS=   52.0 FOM= 0.22
INDE  -4   8   1 FOBS=  298.1 SIGMA=  1.2 PHAS=  257.1 FOM= 0.80
INDE  -4   8   2 FOBS=  166.3 SIGMA=  1.9 PHAS=  264.8 FOM= 0.56
INDE  -4   8   3 FOBS=  264.0 SIGMA=  2.2 PHAS=  185.1 FOM= 0.80
INDE  -4   8   4 FOBS=  113.2 SIGMA=  4.9 PHAS=  314.2 FOM= 0.90
INDE  -4   8   5 FOBS=  187.6 SIGMA=  1.3 PHAS=  196.3 FOM= 0.97
INDE  -4   8   6 FOBS=  139.0 SIGMA=  2.1 PHAS=   58.6 FOM= 0.74
INDE  -4   8   7 FOBS=  114.7 SIGMA=  2.8 PHAS=  335.6 FOM= 0.92
INDE  -4   8   8 FOBS=  339.8 SIGMA=  1.3 PHAS=  234.2 FOM= 0.97
INDE  -4   8   9 FOBS=   63.3 SIGMA=  7.4 PHAS=  323.3 FOM= 0.34
INDE  -4   8  10 FOBS=  430.2 SIGMA=  1.4 PHAS=  319.2 FOM= 0.75
INDE  -4   8  11 FOBS=  366.3 SIGMA=  1.6 PHAS=  225.9 FOM= 0.89
INDE  -4   8  12 FOBS=  345.1 SIGMA=  1.8 PHAS=   32.4 FOM= 0.95
INDE  -4   8  13 FOBS=   84.2 SIGMA=  6.9 PHAS=   31.4 FOM= 0.10
INDE  -4   8  14 FOBS=  104.0 SIGMA=  5.9 PHAS=  284.1 FOM= 0.26
INDE  -4   8  15 FOBS=   67.4 SIGMA=  9.3 PHAS=  156.8 FOM= 0.41
INDE  -4   8  16 FOBS=   81.6 SIGMA=  7.9 PHAS=  295.5 FOM= 0.13
INDE  -4   9   1 FOBS=  154.9 SIGMA=  1.9 PHAS=  130.6 FOM= 0.99
INDE  -4   9   2 FOBS=  234.5 SIGMA=  1.0 PHAS=  336.3 FOM= 0.99
INDE  -4   9   3 FOBS=  180.2 SIGMA=  3.0 PHAS=   78.4 FOM= 0.84
INDE  -4   9   4 FOBS=  178.2 SIGMA=  3.4 PHAS=  156.8 FOM= 0.95
INDE  -4   9   5 FOBS=  166.5 SIGMA=  1.5 PHAS=   69.7 FOM= 0.98
INDE  -4   9   6 FOBS=  329.0 SIGMA=  1.5 PHAS=   68.5 FOM= 0.76
INDE  -4   9   7 FOBS=  251.7 SIGMA=  1.4 PHAS=  311.8 FOM= 0.96
INDE  -4   9   8 FOBS=  132.8 SIGMA=  2.8 PHAS=   14.9 FOM= 0.73
INDE  -4   9   9 FOBS=  461.5 SIGMA=  1.3 PHAS=   50.0 FOM= 0.07
INDE  -4   9  10 FOBS=  189.6 SIGMA=  2.7 PHAS=  157.3 FOM= 0.83
INDE  -4   9  11 FOBS=  142.9 SIGMA=  4.1 PHAS=  179.1 FOM= 0.73
INDE  -4   9  12 FOBS=  133.2 SIGMA=  4.4 PHAS=   21.9 FOM= 0.13
INDE  -4   9  13 FOBS=  311.5 SIGMA=  2.0 PHAS=    5.8 FOM= 0.90
INDE  -4   9  14 FOBS=  189.8 SIGMA=  3.2 PHAS=  186.7 FOM= 0.80
INDE  -4   9  15 FOBS=  125.5 SIGMA=  4.9 PHAS=  231.9 FOM= 0.10
INDE  -4   9  16 FOBS=  139.0 SIGMA=  4.6 PHAS=   87.7 FOM= 0.53
INDE  -4  10   1 FOBS=  125.1 SIGMA=  2.1 PHAS=  152.5 FOM= 0.95
INDE  -4  10   2 FOBS=  111.3 SIGMA=  2.4 PHAS=  231.2 FOM= 0.98
INDE  -4  10   3 FOBS=  159.5 SIGMA=  2.3 PHAS=  175.3 FOM= 0.90
INDE  -4  10   4 FOBS=   57.9 SIGMA=  6.9 PHAS=  170.6 FOM= 0.23
INDE  -4  10   5 FOBS=  161.3 SIGMA=  1.7 PHAS=  306.2 FOM= 0.98
INDE  -4  10   6 FOBS=  233.1 SIGMA=  1.6 PHAS=   98.4 FOM= 0.97
INDE  -4  10   7 FOBS=  186.2 SIGMA=  2.2 PHAS=  237.0 FOM= 0.97
INDE  -4  10   8 FOBS=  152.6 SIGMA=  2.5 PHAS=  269.2 FOM= 0.64
INDE  -4  10   9 FOBS=  345.5 SIGMA=  1.5 PHAS=   19.8 FOM= 0.87
INDE  -4  10  10 FOBS=  299.9 SIGMA=  1.8 PHAS=  287.1 FOM= 0.96
INDE  -4  10  11 FOBS=  170.3 SIGMA=  3.5 PHAS=  157.2 FOM= 0.70
INDE  -4  10  12 FOBS=   70.6 SIGMA=  8.6 PHAS=  265.0 FOM= 0.29
INDE  -4  10  13 FOBS=  240.8 SIGMA=  2.4 PHAS=  225.2 FOM= 0.38
INDE  -4  10  14 FOBS=   80.8 SIGMA=  7.3 PHAS=  102.4 FOM= 0.31
INDE  -4  10  15 FOBS=   82.5 SIGMA=  7.9 PHAS=  234.5 FOM= 0.75
INDE  -4  10  16 FOBS=  156.2 SIGMA=  4.1 PHAS=  329.2 FOM= 0.47
INDE  -4  11   1 FOBS=  203.9 SIGMA=  1.4 PHAS=  100.1 FOM= 0.96
INDE  -4  11   2 FOBS=  117.5 SIGMA=  2.8 PHAS=  311.1 FOM= 0.93
INDE  -4  11   3 FOBS=  188.7 SIGMA=  1.2 PHAS=   55.9 FOM= 0.97
INDE  -4  11   4 FOBS=  153.8 SIGMA=  2.6 PHAS=  276.0 FOM= 0.84
INDE  -4  11   5 FOBS=  236.4 SIGMA=  1.2 PHAS=  153.4 FOM= 1.00
INDE  -4  11   6 FOBS=  135.4 SIGMA=  3.0 PHAS=  184.2 FOM= 0.91
INDE  -4  11   7 FOBS=  621.8 SIGMA=  0.9 PHAS=  213.6 FOM= 0.92
INDE  -4  11   8 FOBS=  312.0 SIGMA=  1.6 PHAS=   56.6 FOM= 0.97
INDE  -4  11   9 FOBS=  155.1 SIGMA=  2.7 PHAS=  309.1 FOM= 0.91
INDE  -4  11  10 FOBS=  277.4 SIGMA=  1.8 PHAS=  263.0 FOM= 0.84
INDE  -4  11  11 FOBS=  219.7 SIGMA=  2.8 PHAS=  230.7 FOM= 0.46
INDE  -4  11  12 FOBS=  322.8 SIGMA=  2.2 PHAS=   38.2 FOM= 0.87
INDE  -4  11  13 FOBS=  177.5 SIGMA=  3.3 PHAS=   50.0 FOM= 0.66
```

Fig. 10A-57

```
INDE  -4  11  14  FOBS=  138.6  SIGMA=   4.5  PHAS=  194.8  FOM=  0.54
INDE  -4  11  15  FOBS=   71.3  SIGMA=   8.2  PHAS=   39.1  FOM=  0.01
INDE  -4  11  16  FOBS=  149.3  SIGMA=   4.2  PHAS=  226.7  FOM=  0.22
INDE  -4  12   1  FOBS=   32.1  SIGMA=   8.5  PHAS=   63.4  FOM=  0.21
INDE  -4  12   2  FOBS=   72.7  SIGMA=   5.1  PHAS=  264.1  FOM=  0.84
INDE  -4  12   3  FOBS=   50.0  SIGMA=   4.7  PHAS=  142.8  FOM=  0.79
INDE  -4  12   4  FOBS=  144.4  SIGMA=   2.0  PHAS=  288.4  FOM=  0.93
INDE  -4  12   5  FOBS=  177.5  SIGMA=   2.0  PHAS=  115.5  FOM=  0.84
INDE  -4  12   6  FOBS=  135.1  SIGMA=   2.5  PHAS=  286.7  FOM=  0.96
INDE  -4  12   7  FOBS=  201.4  SIGMA=   1.9  PHAS=   34.7  FOM=  0.99
INDE  -4  12   8  FOBS=  261.5  SIGMA=   1.7  PHAS=   87.0  FOM=  1.00
INDE  -4  12   9  FOBS=  206.0  SIGMA=   2.4  PHAS=  251.5  FOM=  0.86
INDE  -4  12  10  FOBS=  314.6  SIGMA=   1.9  PHAS=    1.0  FOM=  0.96
INDE  -4  12  11  FOBS=  144.7  SIGMA=   4.0  PHAS=   15.9  FOM=  0.80
INDE  -4  12  12  FOBS=  103.2  SIGMA=   6.5  PHAS=  343.3  FOM=  0.03
INDE  -4  12  13  FOBS=  201.9  SIGMA=   3.1  PHAS=   37.1  FOM=  0.81
INDE  -4  12  14  FOBS=  172.7  SIGMA=   3.4  PHAS=  191.3  FOM=  0.83
INDE  -4  12  15  FOBS=  250.8  SIGMA=   2.3  PHAS=   85.1  FOM=  0.61
INDE  -4  12  16  FOBS=  111.5  SIGMA=  73.2  PHAS=   99.0  FOM=  0.04
INDE  -4  13   1  FOBS=  316.4  SIGMA=   1.3  PHAS=  171.2  FOM=  0.97
INDE  -4  13   2  FOBS=   70.4  SIGMA=   3.9  PHAS=  342.3  FOM=  0.33
INDE  -4  13   3  FOBS=  194.9  SIGMA=   1.5  PHAS=  308.3  FOM=  0.98
INDE  -4  13   4  FOBS=  186.2  SIGMA=   1.5  PHAS=  207.2  FOM=  0.96
INDE  -4  13   5  FOBS=  194.6  SIGMA=   1.6  PHAS=  303.7  FOM=  0.98
INDE  -4  13   6  FOBS=  243.9  SIGMA=   1.5  PHAS=  120.5  FOM=  0.96
INDE  -4  13   7  FOBS=  126.3  SIGMA=   3.0  PHAS=  264.5  FOM=  0.95
INDE  -4  13   8  FOBS=  247.7  SIGMA=   1.8  PHAS=  201.9  FOM=  0.98
INDE  -4  13   9  FOBS=  234.1  SIGMA=   1.9  PHAS=  328.0  FOM=  0.99
INDE  -4  13  10  FOBS=  261.5  SIGMA=   2.1  PHAS=   59.5  FOM=  0.86
INDE  -4  13  11  FOBS=  179.1  SIGMA=   3.4  PHAS=  145.6  FOM=  0.58
INDE  -4  13  12  FOBS=  196.0  SIGMA=   3.0  PHAS=   64.4  FOM=  0.91
INDE  -4  13  13  FOBS=  267.3  SIGMA=   2.5  PHAS=   85.6  FOM=  0.81
INDE  -4  13  14  FOBS=   83.5  SIGMA=   7.1  PHAS=  113.2  FOM=  0.14
INDE  -4  13  15  FOBS=   72.3  SIGMA=   8.1  PHAS=  136.5  FOM=  0.10
INDE  -4  14   1  FOBS=  279.4  SIGMA=   1.2  PHAS=  209.7  FOM=  0.87
INDE  -4  14   2  FOBS=  161.7  SIGMA=   1.8  PHAS=  104.3  FOM=  0.97
INDE  -4  14   3  FOBS=  121.2  SIGMA=   2.5  PHAS=  153.6  FOM=  0.98
INDE  -4  14   4  FOBS=  174.5  SIGMA=   1.8  PHAS=  243.3  FOM=  0.97
INDE  -4  14   5  FOBS=  248.8  SIGMA=   1.3  PHAS=   55.4  FOM=  0.46
INDE  -4  14   6  FOBS=  353.5  SIGMA=   1.4  PHAS=  179.8  FOM=  0.98
INDE  -4  14   7  FOBS=  336.1  SIGMA=   1.5  PHAS=  299.4  FOM=  0.99
INDE  -4  14   8  FOBS=  252.2  SIGMA=   1.8  PHAS=  195.8  FOM=  0.86
INDE  -4  14   9  FOBS=  323.8  SIGMA=   1.6  PHAS=    4.1  FOM=  0.97
INDE  -4  14  10  FOBS=  370.0  SIGMA=   1.6  PHAS=   18.3  FOM=  1.00
INDE  -4  14  11  FOBS=  172.8  SIGMA=   3.1  PHAS=  343.7  FOM=  0.90
INDE  -4  14  12  FOBS=  158.3  SIGMA=   4.2  PHAS=  218.3  FOM=  0.82
INDE  -4  14  13  FOBS=  182.1  SIGMA=   4.0  PHAS=   86.0  FOM=  0.32
INDE  -4  14  14  FOBS=  152.2  SIGMA=   4.9  PHAS=   39.9  FOM=  0.46
INDE  -4  14  15  FOBS=  121.5  SIGMA=   4.8  PHAS=  205.8  FOM=  0.70
INDE  -4  15   1  FOBS=   44.8  SIGMA=   7.7  PHAS=  258.5  FOM=  0.44
INDE  -4  15   2  FOBS=  132.8  SIGMA=   2.3  PHAS=  134.2  FOM=  0.74
INDE  -4  15   3  FOBS=  619.5  SIGMA=   0.8  PHAS=   14.6  FOM=  0.98
INDE  -4  15   4  FOBS=  154.5  SIGMA=   2.0  PHAS=  150.1  FOM=  1.00
INDE  -4  15   5  FOBS=  216.0  SIGMA=   1.6  PHAS=  178.4  FOM=  0.85
INDE  -4  15   6  FOBS=  296.7  SIGMA=   1.3  PHAS=  221.9  FOM=  0.99
INDE  -4  15   7  FOBS=  225.6  SIGMA=   2.0  PHAS=  345.6  FOM=  0.89
INDE  -4  15   8  FOBS=  143.6  SIGMA=   3.0  PHAS=  237.2  FOM=  0.72
INDE  -4  15   9  FOBS=  529.8  SIGMA=   1.2  PHAS=    4.4  FOM=  0.94
INDE  -4  15  10  FOBS=  279.8  SIGMA=   2.1  PHAS=  171.8  FOM=  0.96
INDE  -4  15  11  FOBS=   87.5  SIGMA=   6.4  PHAS=  308.3  FOM=  0.40
INDE  -4  15  12  FOBS=  113.5  SIGMA=   5.0  PHAS=  316.8  FOM=  0.49
INDE  -4  15  13  FOBS=  173.7  SIGMA=   3.4  PHAS=  106.8  FOM=  0.92
INDE  -4  15  14  FOBS=  118.4  SIGMA=   6.2  PHAS=  302.4  FOM=  0.25
INDE  -4  15  15  FOBS=   47.4  SIGMA=  15.6  PHAS=  160.9  FOM=  0.10
INDE  -4  16   1  FOBS=  339.4  SIGMA=   1.5  PHAS=  248.9  FOM=  0.95
INDE  -4  16   2  FOBS=  333.7  SIGMA=   1.3  PHAS=  312.3  FOM=  0.99
INDE  -4  16   3  FOBS=  262.7  SIGMA=   1.4  PHAS=  167.1  FOM=  0.63
INDE  -4  16   4  FOBS=  605.3  SIGMA=   1.1  PHAS=  281.8  FOM=  1.00
INDE  -4  16   5  FOBS=  259.0  SIGMA=   1.4  PHAS=   54.4  FOM=  0.96
INDE  -4  16   6  FOBS=  370.2  SIGMA=   1.2  PHAS=  232.0  FOM=  0.76
INDE  -4  16   7  FOBS=  264.1  SIGMA=   2.1  PHAS=   35.6  FOM=  0.96
```

Fig. 10A-58

```
INDE  -4  16   8 FOBS=   216.4 SIGMA=   2.1 PHAS=  149.6 FOM=  0.97
INDE  -4  16   9 FOBS=   291.5 SIGMA=   1.8 PHAS=  286.0 FOM=  0.66
INDE  -4  16  10 FOBS=   172.4 SIGMA=   2.9 PHAS=  113.3 FOM=  0.74
INDE  -4  16  11 FOBS=   107.3 SIGMA=   4.9 PHAS=   24.5 FOM=  0.56
INDE  -4  16  12 FOBS=    84.7 SIGMA=   6.3 PHAS=  295.0 FOM=  0.61
INDE  -4  16  13 FOBS=   120.7 SIGMA=   4.7 PHAS=  195.0 FOM=  0.39
INDE  -4  16  14 FOBS=    36.0 SIGMA=  15.3 PHAS=  274.3 FOM=  0.05
INDE  -4  16  15 FOBS=    66.9 SIGMA=  13.2 PHAS=   25.8 FOM=  0.13
INDE  -4  17   1 FOBS=   322.1 SIGMA=   1.6 PHAS=  316.4 FOM=  0.97
INDE  -4  17   2 FOBS=   432.5 SIGMA=   1.1 PHAS=  299.6 FOM=  0.96
INDE  -4  17   3 FOBS=   489.6 SIGMA=   1.1 PHAS=  196.4 FOM=  1.00
INDE  -4  17   4 FOBS=   527.6 SIGMA=   1.0 PHAS=   24.0 FOM=  0.94
INDE  -4  17   5 FOBS=   120.8 SIGMA=   2.9 PHAS=  249.4 FOM=  0.42
INDE  -4  17   6 FOBS=   450.9 SIGMA=   1.5 PHAS=  282.1 FOM=  0.96
INDE  -4  17   7 FOBS=   189.0 SIGMA=   2.2 PHAS=  233.1 FOM=  0.85
INDE  -4  17   8 FOBS=   208.6 SIGMA=   2.2 PHAS=   14.1 FOM=  0.95
INDE  -4  17   9 FOBS=   396.6 SIGMA=   1.5 PHAS=   30.3 FOM=  0.98
INDE  -4  17  10 FOBS=    58.8 SIGMA=   9.1 PHAS=   42.2 FOM=  0.08
INDE  -4  17  11 FOBS=   134.8 SIGMA=   4.3 PHAS=  109.4 FOM=  0.78
INDE  -4  17  12 FOBS=   147.4 SIGMA=   3.9 PHAS=  196.2 FOM=  0.69
INDE  -4  17  13 FOBS=    88.8 SIGMA=   6.2 PHAS=   51.5 FOM=  0.18
INDE  -4  17  14 FOBS=    66.7 SIGMA=   8.1 PHAS=  352.2 FOM=  0.10
INDE  -4  18   1 FOBS=   490.5 SIGMA=   1.3 PHAS=  304.8 FOM=  0.92
INDE  -4  18   2 FOBS=   287.3 SIGMA=   1.4 PHAS=  204.4 FOM=  0.98
INDE  -4  18   3 FOBS=   424.7 SIGMA=   1.1 PHAS=   17.0 FOM=  0.91
INDE  -4  18   4 FOBS=   442.6 SIGMA=   1.2 PHAS=  189.7 FOM=  0.93
INDE  -4  18   5 FOBS=   256.9 SIGMA=   1.6 PHAS=  186.8 FOM=  0.97
INDE  -4  18   6 FOBS=   612.1 SIGMA=   1.4 PHAS=    1.5 FOM=  0.97
INDE  -4  18   7 FOBS=   376.5 SIGMA=   1.4 PHAS=  341.8 FOM=  0.82
INDE  -4  18   8 FOBS=   129.9 SIGMA=   4.6 PHAS=  201.6 FOM=  0.44
INDE  -4  18   9 FOBS=   282.6 SIGMA=   1.8 PHAS=  313.7 FOM=  0.37
INDE  -4  18  10 FOBS=   130.1 SIGMA=   4.1 PHAS=  348.8 FOM=  0.61
INDE  -4  18  11 FOBS=    77.3 SIGMA=   6.7 PHAS=  100.6 FOM=  0.29
INDE  -4  18  12 FOBS=   186.9 SIGMA=   2.9 PHAS=  108.5 FOM=  0.37
INDE  -4  18  13 FOBS=    34.8 SIGMA=  11.9 PHAS=  340.8 FOM=  0.30
INDE  -4  18  14 FOBS=   149.9 SIGMA=   3.7 PHAS=  137.4 FOM=  0.27
INDE  -4  19   1 FOBS=   138.3 SIGMA=   2.7 PHAS=   22.0 FOM=  0.35
INDE  -4  19   2 FOBS=   645.8 SIGMA=   1.2 PHAS=  181.8 FOM=  0.09
INDE  -4  19   3 FOBS=   138.4 SIGMA=   2.5 PHAS=   80.8 FOM=  0.93
INDE  -4  19   4 FOBS=    99.0 SIGMA=   4.2 PHAS=   94.2 FOM=  0.47
INDE  -4  19   5 FOBS=   359.5 SIGMA=   1.4 PHAS=  241.8 FOM=  0.96
INDE  -4  19   6 FOBS=   352.4 SIGMA=   1.5 PHAS=  250.2 FOM=  0.79
INDE  -4  19   7 FOBS=   216.0 SIGMA=   2.1 PHAS=  208.9 FOM=  0.51
INDE  -4  19   8 FOBS=   225.2 SIGMA=   2.7 PHAS=   32.7 FOM=  0.36
INDE  -4  19   9 FOBS=   187.7 SIGMA=   2.6 PHAS=  276.9 FOM=  0.72
INDE  -4  19  10 FOBS=   385.1 SIGMA=   1.5 PHAS=  276.2 FOM=  0.67
INDE  -4  19  11 FOBS=   185.5 SIGMA=   2.8 PHAS=  287.9 FOM=  0.72
INDE  -4  19  12 FOBS=    68.0 SIGMA=   8.1 PHAS=  357.0 FOM=  0.23
INDE  -4  19  13 FOBS=   164.2 SIGMA=   3.4 PHAS=  131.6 FOM=  0.43
INDE  -4  19  14 FOBS=    73.0 SIGMA=   8.3 PHAS=  246.6 FOM=  0.27
INDE  -4  20   1 FOBS=   210.0 SIGMA=   1.9 PHAS=  325.3 FOM=  0.91
INDE  -4  20   2 FOBS=   118.5 SIGMA=   3.5 PHAS=  233.3 FOM=  0.24
INDE  -4  20   3 FOBS=   342.6 SIGMA=   1.4 PHAS=  276.8 FOM=  0.80
INDE  -4  20   4 FOBS=   361.4 SIGMA=   1.7 PHAS=  241.7 FOM=  0.95
INDE  -4  20   5 FOBS=   320.7 SIGMA=   1.4 PHAS=   49.2 FOM=  0.68
INDE  -4  20   6 FOBS=   200.7 SIGMA=   2.2 PHAS=  113.3 FOM=  0.83
INDE  -4  20   7 FOBS=   195.1 SIGMA=   2.3 PHAS=  285.1 FOM=  0.93
INDE  -4  20   8 FOBS=   445.8 SIGMA=   1.5 PHAS=   63.6 FOM=  1.00
INDE  -4  20   9 FOBS=   194.2 SIGMA=   2.5 PHAS=  227.6 FOM=  0.21
INDE  -4  20  10 FOBS=    83.1 SIGMA=   6.2 PHAS=  275.5 FOM=  0.56
INDE  -4  20  11 FOBS=   203.7 SIGMA=   2.5 PHAS=    3.3 FOM=  0.95
INDE  -4  20  12 FOBS=   105.1 SIGMA=   5.0 PHAS=   27.6 FOM=  0.73
INDE  -4  20  13 FOBS=   118.5 SIGMA=   4.5 PHAS=  139.4 FOM=  0.22
INDE  -4  21   1 FOBS=    67.3 SIGMA=   5.9 PHAS=  302.6 FOM=  0.44
INDE  -4  21   2 FOBS=    87.1 SIGMA=   4.4 PHAS=  181.4 FOM=  0.63
INDE  -4  21   3 FOBS=   268.8 SIGMA=   1.7 PHAS=  177.9 FOM=  0.96
INDE  -4  21   4 FOBS=   460.0 SIGMA=   1.7 PHAS=  317.0 FOM=  0.83
INDE  -4  21   5 FOBS=   187.0 SIGMA=   2.1 PHAS=  254.8 FOM=  0.87
INDE  -4  21   6 FOBS=    96.3 SIGMA=   4.8 PHAS=  233.2 FOM=  0.86
INDE  -4  21   7 FOBS=   148.4 SIGMA=   3.2 PHAS=   88.5 FOM=  0.91
INDE  -4  21   8 FOBS=   152.6 SIGMA=   3.0 PHAS=  281.5 FOM=  0.94
```

Fig. 10A-59

```
INDE  -4  21   9 FOBS=  212.5 SIGMA=  2.8 PHAS= 111.3 FOM= 0.97
INDE  -4  21  10 FOBS=  315.3 SIGMA=  1.7 PHAS=  72.7 FOM= 0.96
INDE  -4  21  11 FOBS=  190.6 SIGMA=  2.6 PHAS= 211.2 FOM= 0.14
INDE  -4  21  12 FOBS=  159.3 SIGMA=  3.3 PHAS= 220.5 FOM= 0.33
INDE  -4  21  13 FOBS=  149.7 SIGMA=  3.6 PHAS= 221.0 FOM= 0.08
INDE  -4  22   1 FOBS=  262.3 SIGMA=  1.7 PHAS= 221.3 FOM= 0.84
INDE  -4  22   2 FOBS=  198.0 SIGMA=  2.2 PHAS= 184.0 FOM= 0.94
INDE  -4  22   3 FOBS=   50.6 SIGMA=  7.9 PHAS=  74.3 FOM= 0.32
INDE  -4  22   4 FOBS=  206.0 SIGMA=  3.1 PHAS=  70.2 FOM= 0.69
INDE  -4  22   5 FOBS=   59.9 SIGMA=  7.4 PHAS= 249.1 FOM= 0.39
INDE  -4  22   6 FOBS=  228.8 SIGMA=  2.1 PHAS=  39.9 FOM= 0.97
INDE  -4  22   7 FOBS=  230.4 SIGMA=  2.2 PHAS= 216.2 FOM= 0.98
INDE  -4  22   8 FOBS=   91.4 SIGMA=  4.7 PHAS= 211.0 FOM= 0.60
INDE  -4  22   9 FOBS=  335.8 SIGMA=  1.9 PHAS= 158.2 FOM= 0.94
INDE  -4  22  10 FOBS=  157.0 SIGMA=  3.0 PHAS= 250.5 FOM= 0.90
INDE  -4  22  11 FOBS=  157.8 SIGMA=  3.4 PHAS= 139.3 FOM= 0.85
INDE  -4  22  12 FOBS=  116.5 SIGMA=  4.3 PHAS= 131.3 FOM= 0.57
INDE  -4  23   1 FOBS=  151.9 SIGMA=  2.7 PHAS= 122.4 FOM= 0.97
INDE  -4  23   2 FOBS=  402.4 SIGMA=  1.3 PHAS=  41.0 FOM= 0.32
INDE  -4  23   3 FOBS=  205.7 SIGMA=  2.1 PHAS=  62.1 FOM= 0.98
INDE  -4  23   4 FOBS=  170.6 SIGMA=  3.6 PHAS= 191.9 FOM= 0.55
INDE  -4  23   5 FOBS=  109.8 SIGMA=  4.1 PHAS= 188.5 FOM= 0.72
INDE  -4  23   6 FOBS=  153.2 SIGMA=  2.9 PHAS= 223.4 FOM= 0.94
INDE  -4  23   7 FOBS=  264.6 SIGMA=  1.9 PHAS= 162.9 FOM= 0.97
INDE  -4  23   8 FOBS=  196.7 SIGMA=  2.3 PHAS= 344.6 FOM= 0.80
INDE  -4  23   9 FOBS=  269.6 SIGMA=  2.1 PHAS= 175.2 FOM= 0.86
INDE  -4  23  10 FOBS=  181.0 SIGMA=  2.8 PHAS= 210.4 FOM= 0.76
INDE  -4  23  11 FOBS=   58.1 SIGMA=  8.2 PHAS= 294.5 FOM= 0.05
INDE  -4  23  12 FOBS=   65.4 SIGMA=  7.6 PHAS= 268.3 FOM= 0.21
INDE  -4  24   1 FOBS=   53.2 SIGMA=  8.5 PHAS= 287.6 FOM= 0.18
INDE  -4  24   2 FOBS=  197.0 SIGMA=  2.3 PHAS= 341.2 FOM= 0.96
INDE  -4  24   3 FOBS=  208.9 SIGMA=  2.1 PHAS= 232.0 FOM= 0.97
INDE  -4  24   4 FOBS=  353.0 SIGMA=  1.7 PHAS=  95.8 FOM= 0.82
INDE  -4  24   5 FOBS=  343.3 SIGMA=  1.4 PHAS=  52.2 FOM= 0.73
INDE  -4  24   6 FOBS=  410.4 SIGMA=  1.5 PHAS= 141.6 FOM= 0.96
INDE  -4  24   7 FOBS=  199.7 SIGMA=  2.4 PHAS= 310.8 FOM= 0.86
INDE  -4  24   8 FOBS=   74.8 SIGMA=  5.8 PHAS= 172.6 FOM= 0.47
INDE  -4  24   9 FOBS=   72.8 SIGMA=  5.9 PHAS=  37.9 FOM= 0.10
INDE  -4  24  10 FOBS=  178.7 SIGMA=  3.2 PHAS= 317.3 FOM= 0.61
INDE  -4  24  11 FOBS=  171.8 SIGMA=  2.8 PHAS= 209.7 FOM= 0.45
INDE  -4  25   1 FOBS=  311.6 SIGMA=  1.6 PHAS= 356.3 FOM= 0.99
INDE  -4  25   2 FOBS=  179.6 SIGMA=  2.5 PHAS=  17.8 FOM= 0.80
INDE  -4  25   3 FOBS=  200.5 SIGMA=  2.1 PHAS= 183.1 FOM= 0.76
INDE  -4  25   4 FOBS=  135.1 SIGMA=  4.0 PHAS=   9.3 FOM= 0.92
INDE  -4  25   5 FOBS=  324.6 SIGMA=  1.4 PHAS= 253.1 FOM= 0.99
INDE  -4  25   6 FOBS=   83.8 SIGMA=  5.2 PHAS=   9.6 FOM= 0.24
INDE  -4  25   7 FOBS=  235.4 SIGMA=  2.2 PHAS=  82.2 FOM= 0.84
INDE  -4  25   8 FOBS=  120.6 SIGMA=  3.7 PHAS= 161.1 FOM= 0.83
INDE  -4  25   9 FOBS=  192.8 SIGMA=  2.2 PHAS= 333.2 FOM= 0.82
INDE  -4  25  10 FOBS=  231.1 SIGMA=  2.3 PHAS= 291.6 FOM= 0.62
INDE  -4  25  11 FOBS=   88.1 SIGMA=  5.4 PHAS= 294.3 FOM= 0.26
INDE  -4  26   1 FOBS=  128.9 SIGMA=  3.4 PHAS=  21.0 FOM= 0.03
INDE  -4  26   2 FOBS=   96.5 SIGMA=  4.4 PHAS= 357.3 FOM= 0.82
INDE  -4  26   3 FOBS=  307.6 SIGMA=  1.6 PHAS= 261.6 FOM= 1.00
INDE  -4  26   4 FOBS=  135.4 SIGMA=  4.0 PHAS= 102.0 FOM= 0.90
INDE  -4  26   5 FOBS=  211.1 SIGMA=  2.0 PHAS= 165.5 FOM= 0.92
INDE  -4  26   6 FOBS=  188.6 SIGMA=  2.3 PHAS= 192.7 FOM= 0.39
INDE  -4  26   7 FOBS=  200.4 SIGMA=  2.4 PHAS=  55.1 FOM= 0.83
INDE  -4  26   8 FOBS=  146.9 SIGMA=  3.6 PHAS= 221.0 FOM= 0.93
INDE  -4  26   9 FOBS=  141.9 SIGMA=  3.1 PHAS=  75.2 FOM= 0.85
INDE  -4  26  10 FOBS=  121.9 SIGMA=  4.1 PHAS= 226.9 FOM= 0.74
INDE  -4  27   1 FOBS=   56.0 SIGMA=  7.4 PHAS= 333.0 FOM= 0.05
INDE  -4  27   2 FOBS=  104.4 SIGMA=  4.1 PHAS=  56.2 FOM= 0.49
INDE  -4  27   3 FOBS=  101.5 SIGMA=  4.1 PHAS= 157.7 FOM= 0.37
INDE  -4  27   4 FOBS=  116.6 SIGMA=  4.0 PHAS= 277.1 FOM= 0.59
INDE  -4  27   5 FOBS=  102.5 SIGMA=  4.0 PHAS=  95.2 FOM= 0.78
INDE  -4  27   6 FOBS=  119.0 SIGMA=  3.4 PHAS= 103.0 FOM= 0.84
INDE  -4  27   7 FOBS=  170.9 SIGMA=  2.6 PHAS=  43.5 FOM= 0.33
INDE  -4  27   8 FOBS=  241.8 SIGMA=  2.2 PHAS=  66.9 FOM= 0.95
INDE  -4  27   9 FOBS=  160.7 SIGMA=  3.3 PHAS= 355.2 FOM= 0.92
INDE  -4  27  10 FOBS=  111.0 SIGMA= 19.6 PHAS= 214.8 FOM= 0.02
```

Fig. 10A-60

```
INDE  -4  28   1 FOBS=  162.1 SIGMA=  2.7 PHAS=  32.5 FOM= 0.28
INDE  -4  28   2 FOBS=   36.6 SIGMA= 17.7 PHAS=  22.0 FOM= 0.24
INDE  -4  28   3 FOBS=  117.2 SIGMA=  4.2 PHAS= 211.8 FOM= 0.91
INDE  -4  28   4 FOBS=  242.8 SIGMA=  1.9 PHAS=  92.9 FOM= 1.00
INDE  -4  28   5 FOBS=  153.7 SIGMA=  2.4 PHAS= 151.4 FOM= 0.97
INDE  -4  28   6 FOBS=  132.8 SIGMA=  3.2 PHAS= 192.6 FOM= 0.70
INDE  -4  28   7 FOBS=  187.1 SIGMA=  2.3 PHAS=  19.9 FOM= 0.92
INDE  -4  28   8 FOBS=  148.1 SIGMA=  2.7 PHAS= 160.2 FOM= 0.94
INDE  -4  28   9 FOBS=   97.7 SIGMA=  4.9 PHAS=  13.0 FOM= 0.01
INDE  -4  29   1 FOBS=  196.3 SIGMA=  2.2 PHAS= 235.9 FOM= 0.90
INDE  -4  29   2 FOBS=  117.6 SIGMA=  3.6 PHAS= 209.3 FOM= 0.86
INDE  -4  29   3 FOBS=  191.2 SIGMA=  2.4 PHAS= 133.5 FOM= 0.78
INDE  -4  29   4 FOBS=  124.7 SIGMA=  3.6 PHAS= 343.1 FOM= 0.91
INDE  -4  29   5 FOBS=   32.7 SIGMA= 14.0 PHAS= 206.8 FOM= 0.29
INDE  -4  29   6 FOBS=  184.9 SIGMA=  2.2 PHAS= 268.5 FOM= 0.54
INDE  -4  29   7 FOBS=   73.0 SIGMA=  5.5 PHAS= 143.7 FOM= 0.31
INDE  -4  29   8 FOBS=  244.8 SIGMA=  1.9 PHAS= 277.1 FOM= 0.96
INDE  -4  30   1 FOBS=   30.7 SIGMA= 16.7 PHAS= 241.4 FOM= 0.12
INDE  -4  30   2 FOBS=  148.8 SIGMA=  2.9 PHAS= 239.5 FOM= 0.85
INDE  -4  30   3 FOBS=   41.0 SIGMA= 11.6 PHAS= 301.4 FOM= 0.45
INDE  -4  30   4 FOBS=  197.2 SIGMA=  2.1 PHAS= 282.3 FOM= 0.54
INDE  -4  30   5 FOBS=  205.7 SIGMA=  2.3 PHAS= 230.1 FOM= 0.80
INDE  -4  30   6 FOBS=  180.0 SIGMA=  2.4 PHAS= 153.0 FOM= 0.79
INDE  -4  30   7 FOBS=  147.9 SIGMA=  3.1 PHAS=  19.0 FOM= 0.61
INDE  -4  31   1 FOBS=   68.6 SIGMA=  5.8 PHAS= 138.3 FOM= 0.03
INDE  -4  31   2 FOBS=  163.5 SIGMA=  2.6 PHAS= 213.3 FOM= 0.41
INDE  -4  31   3 FOBS=  133.0 SIGMA=  3.7 PHAS=  19.0 FOM= 0.87
INDE  -4  31   4 FOBS=   88.0 SIGMA=  4.4 PHAS=  51.3 FOM= 0.33
INDE  -4  31   5 FOBS=   83.6 SIGMA=  5.5 PHAS= 171.2 FOM= 0.29
INDE  -4  32   1 FOBS=   63.1 SIGMA=  6.8 PHAS= 271.9 FOM= 0.20
INDE  -4  32   2 FOBS=  133.0 SIGMA=  3.2 PHAS=  39.5 FOM= 0.77
INDE  -4  32   3 FOBS=  242.8 SIGMA=  2.0 PHAS= 312.3 FOM= 0.91
INDE  -4  32   4 FOBS=   84.8 SIGMA= 52.3 PHAS= 346.7 FOM= 0.08
INDE  -3   0   1 FOBS=   35.4 SIGMA=  7.2 PHAS= 180.0 FOM= 0.50
INDE  -3   0   2 FOBS=   78.5 SIGMA=  4.0 PHAS=   0.0 FOM= 0.99
INDE  -3   0   3 FOBS=   44.1 SIGMA=  6.3 PHAS= 180.0 FOM= 0.02
INDE  -3   0   4 FOBS=   86.7 SIGMA=  4.7 PHAS= 180.0 FOM= 1.00
INDE  -3   0   5 FOBS=  485.8 SIGMA=  1.3 PHAS= 180.0 FOM= 1.00
INDE  -3   0   6 FOBS=   22.6 SIGMA= 10.6 PHAS= 180.0 FOM= 0.19
INDE  -3   0   7 FOBS=  184.6 SIGMA=  2.5 PHAS= 180.0 FOM= 0.73
INDE  -3   0   8 FOBS=   56.1 SIGMA= 10.6 PHAS=   0.0 FOM= 0.40
INDE  -3   0   9 FOBS=  550.7 SIGMA=  1.5 PHAS= 180.0 FOM= 1.00
INDE  -3   0  10 FOBS=  549.1 SIGMA=  1.6 PHAS=   0.0 FOM= 1.00
INDE  -3   0  11 FOBS=  261.3 SIGMA=  3.0 PHAS= 180.0 FOM= 0.71
INDE  -3   0  12 FOBS=  186.6 SIGMA=  4.7 PHAS=   0.0 FOM= 0.40
INDE  -3   0  13 FOBS=  171.8 SIGMA=  5.4 PHAS=   0.0 FOM= 0.02
INDE  -3   0  14 FOBS=  277.8 SIGMA=  3.5 PHAS= 180.0 FOM= 0.57
INDE  -3   0  15 FOBS=  273.2 SIGMA=  3.5 PHAS=   0.0 FOM= 0.84
INDE  -3   0  16 FOBS=   40.8 SIGMA= 25.3 PHAS= 180.0 FOM= 0.05
INDE  -3   0  17 FOBS=   66.4 SIGMA= 14.8 PHAS= 180.0 FOM= 0.05
INDE  -3   1   1 FOBS=  320.1 SIGMA=  0.7 PHAS= 324.7 FOM= 0.83
INDE  -3   1   2 FOBS=  274.5 SIGMA=  1.2 PHAS=  17.8 FOM= 0.85
INDE  -3   1   3 FOBS=  366.1 SIGMA=  1.0 PHAS= 283.9 FOM= 0.86
INDE  -3   1   4 FOBS=  550.8 SIGMA=  1.0 PHAS= 229.2 FOM= 0.82
INDE  -3   1   5 FOBS=   95.2 SIGMA=  2.7 PHAS= 296.6 FOM= 0.46
INDE  -3   1   6 FOBS=   87.7 SIGMA=  3.7 PHAS=  43.9 FOM= 0.92
INDE  -3   1   7 FOBS=  179.0 SIGMA=  1.8 PHAS= 177.0 FOM= 0.99
INDE  -3   1   8 FOBS=  245.0 SIGMA=  1.7 PHAS= 137.9 FOM= 1.00
INDE  -3   1   9 FOBS=  197.5 SIGMA=  2.2 PHAS= 154.9 FOM= 0.20
INDE  -3   1  10 FOBS=  221.6 SIGMA=  2.3 PHAS= 296.0 FOM= 0.98
INDE  -3   1  11 FOBS=  304.7 SIGMA=  1.9 PHAS= 190.3 FOM= 0.93
INDE  -3   1  12 FOBS=   75.7 SIGMA=  8.1 PHAS= 287.1 FOM= 0.21
INDE  -3   1  13 FOBS=  154.4 SIGMA=  4.5 PHAS=  84.3 FOM= 0.56
INDE  -3   1  14 FOBS=  397.9 SIGMA=  1.9 PHAS= 152.5 FOM= 0.60
INDE  -3   1  15 FOBS=  119.6 SIGMA=  5.8 PHAS= 193.5 FOM= 0.37
INDE  -3   1  16 FOBS=  140.2 SIGMA=  5.0 PHAS= 113.0 FOM= 0.34
INDE  -3   1  17 FOBS=  103.5 SIGMA=  6.5 PHAS=  53.7 FOM= 0.12
INDE  -3   2   1 FOBS=  387.1 SIGMA=  1.0 PHAS= 219.9 FOM= 0.95
INDE  -3   2   2 FOBS=  212.7 SIGMA=  1.2 PHAS= 231.8 FOM= 0.96
INDE  -3   2   3 FOBS=  669.9 SIGMA=  0.9 PHAS= 129.5 FOM= 1.00
INDE  -3   2   4 FOBS=  471.7 SIGMA=  0.7 PHAS= 337.9 FOM= 0.98
```

Fig. 10A-61

```
INDE   -3   2    5 FOBS=  244.8 SIGMA=  1.1 PHAS= 289.2 FOM= 0.81
INDE   -3   2    6 FOBS=  387.3 SIGMA=  1.2 PHAS= 250.2 FOM= 0.98
INDE   -3   2    7 FOBS=  129.5 SIGMA=  2.5 PHAS= 278.2 FOM= 0.87
INDE   -3   2    8 FOBS=  140.3 SIGMA=  2.7 PHAS= 321.8 FOM= 0.82
INDE   -3   2    9 FOBS=  205.2 SIGMA=  2.1 PHAS= 342.3 FOM= 0.98
INDE   -3   2   10 FOBS=  438.1 SIGMA=  1.3 PHAS= 298.6 FOM= 1.00
INDE   -3   2   11 FOBS=  313.0 SIGMA=  1.9 PHAS= 134.6 FOM= 0.96
INDE   -3   2   12 FOBS=  328.9 SIGMA=  2.0 PHAS=   1.5 FOM= 0.15
INDE   -3   2   13 FOBS=  157.3 SIGMA=  4.3 PHAS= 131.2 FOM= 0.86
INDE   -3   2   14 FOBS=  315.1 SIGMA=  2.2 PHAS= 179.3 FOM= 0.94
INDE   -3   2   15 FOBS=  108.7 SIGMA=  6.2 PHAS=  22.1 FOM= 0.50
INDE   -3   2   16 FOBS=   61.0 SIGMA= 19.9 PHAS= 351.3 FOM= 0.08
INDE   -3   2   17 FOBS=   64.8 SIGMA= 11.5 PHAS= 217.5 FOM= 0.06
INDE   -3   3    1 FOBS=  121.8 SIGMA=  1.9 PHAS= 212.2 FOM= 0.93
INDE   -3   3    2 FOBS=  469.9 SIGMA=  1.1 PHAS= 132.1 FOM= 0.99
INDE   -3   3    3 FOBS=  311.2 SIGMA=  0.6 PHAS= 345.0 FOM= 0.98
INDE   -3   3    4 FOBS=  461.7 SIGMA=  0.7 PHAS=  75.6 FOM= 0.91
INDE   -3   3    5 FOBS=  395.9 SIGMA=  0.9 PHAS= 143.4 FOM= 1.00
INDE   -3   3    6 FOBS=  240.0 SIGMA=  1.3 PHAS= 192.7 FOM= 0.99
INDE   -3   3    7 FOBS=  170.9 SIGMA=  2.3 PHAS= 167.5 FOM= 0.88
INDE   -3   3    8 FOBS=   81.1 SIGMA=  5.2 PHAS=  87.0 FOM= 0.73
INDE   -3   3    9 FOBS=  198.9 SIGMA=  2.2 PHAS= 313.1 FOM= 0.94
INDE   -3   3   10 FOBS=  201.1 SIGMA=  2.7 PHAS=  88.4 FOM= 0.29
INDE   -3   3   11 FOBS=  355.8 SIGMA=  1.7 PHAS=  78.5 FOM= 0.97
INDE   -3   3   12 FOBS=  127.5 SIGMA=  5.1 PHAS=   2.8 FOM= 0.84
INDE   -3   3   13 FOBS=  148.7 SIGMA=  4.6 PHAS= 150.8 FOM= 0.60
INDE   -3   3   14 FOBS=  195.4 SIGMA=  3.5 PHAS= 123.1 FOM= 0.60
INDE   -3   3   15 FOBS=  146.1 SIGMA=  4.8 PHAS=  48.8 FOM= 0.83
INDE   -3   3   16 FOBS=   71.0 SIGMA= 10.1 PHAS= 170.5 FOM= 0.06
INDE   -3   3   17 FOBS=  120.0 SIGMA=  5.8 PHAS= 130.7 FOM= 0.09
INDE   -3   4    1 FOBS=  468.1 SIGMA=  0.7 PHAS=  25.4 FOM= 0.42
INDE   -3   4    2 FOBS=  268.8 SIGMA=  2.0 PHAS= 145.3 FOM= 1.00
INDE   -3   4    3 FOBS=   66.9 SIGMA=  3.0 PHAS= 195.6 FOM= 0.29
INDE   -3   4    4 FOBS=  306.9 SIGMA=  0.8 PHAS= 181.1 FOM= 1.00
INDE   -3   4    5 FOBS=  214.9 SIGMA=  1.2 PHAS= 306.0 FOM= 0.97
INDE   -3   4    6 FOBS=  103.2 SIGMA=  2.9 PHAS=  16.6 FOM= 0.92
INDE   -3   4    7 FOBS=  259.0 SIGMA=  1.8 PHAS= 153.0 FOM= 0.30
INDE   -3   4    8 FOBS=  126.6 SIGMA=  3.9 PHAS=  41.3 FOM= 0.86
INDE   -3   4    9 FOBS=   99.7 SIGMA=  4.6 PHAS= 277.9 FOM= 0.72
INDE   -3   4   10 FOBS=  149.8 SIGMA=  3.2 PHAS= 354.0 FOM= 0.79
INDE   -3   4   11 FOBS=  127.6 SIGMA=  4.3 PHAS= 164.1 FOM= 0.61
INDE   -3   4   12 FOBS=  451.7 SIGMA=  1.5 PHAS= 148.6 FOM= 0.88
INDE   -3   4   13 FOBS=  149.7 SIGMA=  4.5 PHAS= 225.2 FOM= 0.44
INDE   -3   4   14 FOBS=  176.3 SIGMA=  4.1 PHAS= 264.6 FOM= 0.75
INDE   -3   4   15 FOBS=  143.8 SIGMA=  4.8 PHAS= 120.1 FOM= 0.21
INDE   -3   4   16 FOBS=  208.1 SIGMA=  3.3 PHAS= 151.9 FOM= 0.38
INDE   -3   4   17 FOBS=   76.2 SIGMA= 11.6 PHAS= 235.7 FOM= 0.08
INDE   -3   5    1 FOBS=  119.0 SIGMA=  2.0 PHAS= 146.3 FOM= 0.76
INDE   -3   5    2 FOBS=  501.4 SIGMA=  1.2 PHAS=  15.3 FOM= 0.92
INDE   -3   5    3 FOBS=  451.3 SIGMA=  1.5 PHAS=  11.0 FOM= 0.94
INDE   -3   5    4 FOBS=  147.5 SIGMA=  1.5 PHAS=  54.8 FOM= 1.00
INDE   -3   5    5 FOBS=   56.7 SIGMA=  3.9 PHAS=   6.9 FOM= 0.94
INDE   -3   5    6 FOBS=  132.5 SIGMA=  2.2 PHAS= 158.6 FOM= 0.57
INDE   -3   5    7 FOBS=  138.3 SIGMA=  2.3 PHAS= 156.3 FOM= 0.96
INDE   -3   5    8 FOBS=  162.8 SIGMA=  2.5 PHAS= 311.6 FOM= 0.96
INDE   -3   5    9 FOBS=  360.7 SIGMA=  1.4 PHAS= 294.4 FOM= 0.83
INDE   -3   5   10 FOBS=  146.6 SIGMA=  3.3 PHAS= 217.8 FOM= 0.85
INDE   -3   5   11 FOBS=  397.7 SIGMA=  1.7 PHAS=  58.7 FOM= 0.65
INDE   -3   5   12 FOBS=  198.4 SIGMA=  3.0 PHAS= 332.2 FOM= 0.01
INDE   -3   5   13 FOBS=  179.2 SIGMA=  3.7 PHAS= 343.9 FOM= 0.10
INDE   -3   5   14 FOBS=  280.2 SIGMA=  2.4 PHAS=  67.9 FOM= 0.06
INDE   -3   5   15 FOBS=  218.8 SIGMA=  3.1 PHAS=  51.5 FOM= 0.21
INDE   -3   5   16 FOBS=  253.4 SIGMA=  2.6 PHAS= 239.8 FOM= 0.79
INDE   -3   6    1 FOBS=  441.4 SIGMA=  0.8 PHAS= 346.2 FOM= 0.19
INDE   -3   6    2 FOBS=  183.7 SIGMA=  2.9 PHAS= 352.3 FOM= 0.88
INDE   -3   6    3 FOBS=  675.0 SIGMA=  1.3 PHAS= 109.1 FOM= 0.97
INDE   -3   6    4 FOBS=  158.7 SIGMA=  1.8 PHAS= 197.1 FOM= 0.92
INDE   -3   6    5 FOBS=  216.3 SIGMA=  1.3 PHAS=  34.8 FOM= 0.96
INDE   -3   6    6 FOBS=  180.5 SIGMA=  1.8 PHAS=  17.9 FOM= 0.87
INDE   -3   6    7 FOBS=   34.5 SIGMA= 11.4 PHAS= 156.3 FOM= 0.08
INDE   -3   6    8 FOBS=  363.6 SIGMA=  1.3 PHAS= 303.3 FOM= 0.54
```

Fig. 10A-62

```
INDE  -3   6   9 FOBS=  255.8 SIGMA=  2.0 PHAS=  179.9 FOM= 0.24
INDE  -3   6  10 FOBS=  373.1 SIGMA=  1.5 PHAS=  230.6 FOM= 0.71
INDE  -3   6  11 FOBS=  105.3 SIGMA=  5.4 PHAS=  184.7 FOM= 0.72
INDE  -3   6  12 FOBS=  218.5 SIGMA=  2.8 PHAS=  273.6 FOM= 0.46
INDE  -3   6  13 FOBS=  124.5 SIGMA=  5.3 PHAS=   65.4 FOM= 0.14
INDE  -3   6  14 FOBS=  175.3 SIGMA=  4.0 PHAS=  175.4 FOM= 0.52
INDE  -3   6  15 FOBS=   52.6 SIGMA= 15.8 PHAS=  254.0 FOM= 0.11
INDE  -3   6  16 FOBS=  127.9 SIGMA=  5.3 PHAS=  321.9 FOM= 0.07
INDE  -3   7   1 FOBS=  170.1 SIGMA=  1.3 PHAS=   18.4 FOM= 0.83
INDE  -3   7   2 FOBS=  253.6 SIGMA=  2.4 PHAS=  210.6 FOM= 0.86
INDE  -3   7   3 FOBS=  559.9 SIGMA=  1.2 PHAS=  291.9 FOM= 0.94
INDE  -3   7   4 FOBS=  219.6 SIGMA=  1.4 PHAS=  106.1 FOM= 0.95
INDE  -3   7   5 FOBS=   69.7 SIGMA=  4.5 PHAS=  197.2 FOM= 0.85
INDE  -3   7   6 FOBS=  180.0 SIGMA=  1.7 PHAS=  183.3 FOM= 0.93
INDE  -3   7   7 FOBS=  311.9 SIGMA=  1.3 PHAS=  142.7 FOM= 0.33
INDE  -3   7   8 FOBS=  318.0 SIGMA=  1.4 PHAS=  152.9 FOM= 0.85
INDE  -3   7   9 FOBS=  342.9 SIGMA=  1.5 PHAS=  339.1 FOM= 0.22
INDE  -3   7  10 FOBS=  174.0 SIGMA=  3.3 PHAS=  342.9 FOM= 0.36
INDE  -3   7  11 FOBS=  200.6 SIGMA=  2.7 PHAS=  106.3 FOM= 0.03
INDE  -3   7  12 FOBS=  103.7 SIGMA=  6.2 PHAS=  277.7 FOM= 0.15
INDE  -3   7  13 FOBS=  218.0 SIGMA=  2.9 PHAS=  241.0 FOM= 0.67
INDE  -3   7  14 FOBS=  148.1 SIGMA=  4.7 PHAS=  154.3 FOM= 0.35
INDE  -3   7  15 FOBS=   85.1 SIGMA=  8.0 PHAS=  306.2 FOM= 0.40
INDE  -3   7  16 FOBS=  199.3 SIGMA=  3.3 PHAS=  204.1 FOM= 0.70
INDE  -3   8   1 FOBS=  207.3 SIGMA=  1.2 PHAS=  191.5 FOM= 0.95
INDE  -3   8   2 FOBS=  330.5 SIGMA=  0.9 PHAS=   29.8 FOM= 1.00
INDE  -3   8   3 FOBS=  128.7 SIGMA=  3.3 PHAS=  298.3 FOM= 0.28
INDE  -3   8   4 FOBS=  102.7 SIGMA=  2.2 PHAS=   29.2 FOM= 0.85
INDE  -3   8   5 FOBS=   77.8 SIGMA=  4.5 PHAS=  295.0 FOM= 0.84
INDE  -3   8   6 FOBS=  390.4 SIGMA=  1.1 PHAS=  119.0 FOM= 1.00
INDE  -3   8   7 FOBS=  129.6 SIGMA=  2.9 PHAS=   84.5 FOM= 0.89
INDE  -3   8   8 FOBS=  259.4 SIGMA=  1.6 PHAS=   15.9 FOM= 0.94
INDE  -3   8   9 FOBS=  262.7 SIGMA=  1.8 PHAS=   92.0 FOM= 0.98
INDE  -3   8  10 FOBS=  158.9 SIGMA=  3.5 PHAS=   53.1 FOM= 0.94
INDE  -3   8  11 FOBS=  130.4 SIGMA=  5.2 PHAS=   68.8 FOM= 0.16
INDE  -3   8  12 FOBS=  234.6 SIGMA=  2.7 PHAS=  116.9 FOM= 0.54
INDE  -3   8  13 FOBS=   74.4 SIGMA=  8.6 PHAS=   89.9 FOM= 0.06
INDE  -3   8  14 FOBS=   88.3 SIGMA=  7.5 PHAS=  197.9 FOM= 0.30
INDE  -3   8  15 FOBS=  124.9 SIGMA=  5.5 PHAS=  320.6 FOM= 0.24
INDE  -3   8  16 FOBS=   83.7 SIGMA=  7.9 PHAS=   51.4 FOM= 0.19
INDE  -3   9   1 FOBS=  293.3 SIGMA=  1.2 PHAS=   36.5 FOM= 0.98
INDE  -3   9   2 FOBS=  121.1 SIGMA=  1.6 PHAS=   34.8 FOM= 0.83
INDE  -3   9   3 FOBS=   86.1 SIGMA=  2.4 PHAS=  331.8 FOM= 0.91
INDE  -3   9   4 FOBS=  214.8 SIGMA=  1.5 PHAS=  278.8 FOM= 0.96
INDE  -3   9   5 FOBS=  154.0 SIGMA=  2.0 PHAS=   65.7 FOM= 0.93
INDE  -3   9   6 FOBS=  162.9 SIGMA=  2.2 PHAS=  286.8 FOM= 0.70
INDE  -3   9   7 FOBS=  139.9 SIGMA=  2.6 PHAS=   37.1 FOM= 0.97
INDE  -3   9   8 FOBS=  108.0 SIGMA=  4.1 PHAS=   82.3 FOM= 0.76
INDE  -3   9   9 FOBS=  411.5 SIGMA=  1.3 PHAS=  160.2 FOM= 0.98
INDE  -3   9  10 FOBS=  132.2 SIGMA=  3.9 PHAS=   27.6 FOM= 0.92
INDE  -3   9  11 FOBS=  168.2 SIGMA=  3.7 PHAS=  341.3 FOM= 0.72
INDE  -3   9  12 FOBS=  121.3 SIGMA=  5.9 PHAS=  314.7 FOM= 0.05
INDE  -3   9  13 FOBS=  115.5 SIGMA=  5.7 PHAS=  288.4 FOM= 0.12
INDE  -3   9  14 FOBS=   91.1 SIGMA=  7.2 PHAS=  159.8 FOM= 0.18
INDE  -3   9  15 FOBS=  120.5 SIGMA=  5.6 PHAS=   11.4 FOM= 0.22
INDE  -3   9  16 FOBS=   96.5 SIGMA= 52.1 PHAS=  127.4 FOM= 0.06
INDE  -3  10   1 FOBS=  194.8 SIGMA=  1.4 PHAS=  163.4 FOM= 0.96
INDE  -3  10   2 FOBS=  264.3 SIGMA=  1.0 PHAS=  261.5 FOM= 0.98
INDE  -3  10   3 FOBS=  118.1 SIGMA=  2.3 PHAS=  326.7 FOM= 0.98
INDE  -3  10   4 FOBS=  149.9 SIGMA=  1.8 PHAS=  168.5 FOM= 0.96
INDE  -3  10   5 FOBS=   54.9 SIGMA=  4.5 PHAS=  296.1 FOM= 0.89
INDE  -3  10   6 FOBS=  199.3 SIGMA=  1.7 PHAS=   58.9 FOM= 0.97
INDE  -3  10   7 FOBS=  117.7 SIGMA=  3.4 PHAS=  208.6 FOM= 0.87
INDE  -3  10   8 FOBS=  283.7 SIGMA=  1.8 PHAS=  171.1 FOM= 0.95
INDE  -3  10   9 FOBS=  144.3 SIGMA=  3.3 PHAS=  330.4 FOM= 0.91
INDE  -3  10  10 FOBS=  175.3 SIGMA=  2.7 PHAS=  226.0 FOM= 0.89
INDE  -3  10  11 FOBS=  510.6 SIGMA=  1.4 PHAS=    0.5 FOM= 0.66
INDE  -3  10  12 FOBS=  177.4 SIGMA=  4.3 PHAS=    7.8 FOM= 0.59
INDE  -3  10  13 FOBS=  139.3 SIGMA=  5.0 PHAS=   18.5 FOM= 0.65
INDE  -3  10  14 FOBS=   63.5 SIGMA= 11.7 PHAS=  205.9 FOM= 0.25
INDE  -3  10  15 FOBS=   55.3 SIGMA= 13.8 PHAS=   65.0 FOM= 0.40
```

Fig. 10A-63

```
INDE -3 10 16 FOBS=  76.6 SIGMA=  8.7 PHAS=  27.8 FOM= 0.11
INDE -3 11  1 FOBS= 129.1 SIGMA=  1.9 PHAS= 118.5 FOM= 0.83
INDE -3 11  2 FOBS= 202.7 SIGMA=  1.3 PHAS=  66.7 FOM= 1.00
INDE -3 11  3 FOBS= 133.9 SIGMA=  1.8 PHAS= 210.3 FOM= 0.98
INDE -3 11  4 FOBS=  64.9 SIGMA=  4.1 PHAS=  39.9 FOM= 0.71
INDE -3 11  5 FOBS= 164.0 SIGMA=  2.5 PHAS=  45.0 FOM= 0.75
INDE -3 11  6 FOBS= 235.3 SIGMA=  1.6 PHAS=  55.0 FOM= 0.78
INDE -3 11  7 FOBS= 157.1 SIGMA=  2.4 PHAS= 193.2 FOM= 0.27
INDE -3 11  8 FOBS= 501.8 SIGMA=  1.2 PHAS=  64.9 FOM= 0.46
INDE -3 11  9 FOBS= 162.6 SIGMA=  3.2 PHAS=  97.6 FOM= 0.66
INDE -3 11 10 FOBS= 352.1 SIGMA=  1.6 PHAS= 164.5 FOM= 0.83
INDE -3 11 11 FOBS= 193.2 SIGMA=  2.9 PHAS=   1.7 FOM= 0.87
INDE -3 11 12 FOBS=  80.7 SIGMA=  8.2 PHAS= 308.6 FOM= 0.21
INDE -3 11 13 FOBS= 172.2 SIGMA=  4.5 PHAS= 127.2 FOM= 0.19
INDE -3 11 14 FOBS= 133.1 SIGMA=  5.0 PHAS= 229.1 FOM= 0.64
INDE -3 11 15 FOBS=  91.8 SIGMA=  7.0 PHAS=  39.8 FOM= 0.45
INDE -3 11 16 FOBS= 109.1 SIGMA=  6.1 PHAS=  80.0 FOM= 0.15
INDE -3 12  1 FOBS=  35.6 SIGMA=  5.7 PHAS= 342.1 FOM= 0.82
INDE -3 12  2 FOBS= 227.2 SIGMA=  1.3 PHAS= 353.4 FOM= 1.00
INDE -3 12  3 FOBS= 275.8 SIGMA=  1.0 PHAS=  57.6 FOM= 0.35
INDE -3 12  4 FOBS= 134.7 SIGMA=  2.1 PHAS= 216.7 FOM= 0.96
INDE -3 12  5 FOBS= 327.5 SIGMA=  1.3 PHAS= 126.5 FOM= 1.00
INDE -3 12  6 FOBS= 237.2 SIGMA=  1.6 PHAS= 250.7 FOM= 0.97
INDE -3 12  7 FOBS= 202.3 SIGMA=  1.9 PHAS= 228.6 FOM= 0.87
INDE -3 12  8 FOBS= 211.0 SIGMA=  2.2 PHAS= 337.4 FOM= 0.85
INDE -3 12  9 FOBS=  46.4 SIGMA= 11.5 PHAS= 292.2 FOM= 0.16
INDE -3 12 10 FOBS= 278.9 SIGMA=  2.2 PHAS= 203.0 FOM= 0.96
INDE -3 12 11 FOBS=  72.3 SIGMA=  8.5 PHAS= 350.3 FOM= 0.37
INDE -3 12 12 FOBS= 241.4 SIGMA=  2.5 PHAS=  61.5 FOM= 0.34
INDE -3 12 13 FOBS= 175.4 SIGMA=  3.8 PHAS= 257.7 FOM= 0.77
INDE -3 12 14 FOBS=  80.8 SIGMA=  8.9 PHAS= 331.8 FOM= 0.36
INDE -3 12 15 FOBS= 138.2 SIGMA=  4.7 PHAS=  41.0 FOM= 0.27
INDE -3 12 16 FOBS=  91.9 SIGMA= 12.5 PHAS=  76.3 FOM= 0.09
INDE -3 13  1 FOBS=  38.4 SIGMA=  9.0 PHAS= 318.5 FOM= 0.10
INDE -3 13  2 FOBS= 337.5 SIGMA=  1.0 PHAS=  53.9 FOM= 0.97
INDE -3 13  3 FOBS= 133.7 SIGMA=  1.9 PHAS= 290.3 FOM= 1.00
INDE -3 13  4 FOBS= 344.9 SIGMA=  1.4 PHAS= 153.5 FOM= 1.00
INDE -3 13  5 FOBS=  45.0 SIGMA=  7.5 PHAS= 101.4 FOM= 0.37
INDE -3 13  6 FOBS= 146.5 SIGMA=  2.7 PHAS= 282.7 FOM= 0.66
INDE -3 13  7 FOBS= 544.6 SIGMA=  1.0 PHAS= 172.0 FOM= 1.00
INDE -3 13  8 FOBS= 286.7 SIGMA=  1.7 PHAS= 343.2 FOM= 0.91
INDE -3 13  9 FOBS= 109.5 SIGMA=  4.6 PHAS=  74.6 FOM= 0.17
INDE -3 13 10 FOBS= 203.6 SIGMA=  2.6 PHAS= 258.4 FOM= 0.46
INDE -3 13 11 FOBS= 335.0 SIGMA=  1.9 PHAS= 301.4 FOM= 0.94
INDE -3 13 12 FOBS= 184.4 SIGMA=  3.6 PHAS= 329.8 FOM= 0.81
INDE -3 13 13 FOBS=  39.7 SIGMA= 20.0 PHAS= 243.3 FOM= 0.20
INDE -3 13 14 FOBS=  86.2 SIGMA=  8.4 PHAS= 187.0 FOM= 0.23
INDE -3 13 15 FOBS= 127.0 SIGMA=  5.3 PHAS=  13.6 FOM= 0.43
INDE -3 14  1 FOBS= 183.8 SIGMA=  1.8 PHAS= 352.1 FOM= 0.99
INDE -3 14  2 FOBS=  80.1 SIGMA=  3.7 PHAS=  92.3 FOM= 0.83
INDE -3 14  3 FOBS= 196.8 SIGMA=  1.5 PHAS= 327.5 FOM= 0.38
INDE -3 14  4 FOBS= 165.2 SIGMA=  1.8 PHAS= 191.7 FOM= 1.00
INDE -3 14  5 FOBS= 124.8 SIGMA=  2.6 PHAS= 258.6 FOM= 0.89
INDE -3 14  6 FOBS= 336.4 SIGMA=  1.3 PHAS=   5.8 FOM= 0.97
INDE -3 14  7 FOBS= 473.8 SIGMA=  1.2 PHAS= 241.1 FOM= 0.92
INDE -3 14  8 FOBS= 196.3 SIGMA=  2.3 PHAS=   9.5 FOM= 0.90
INDE -3 14  9 FOBS= 294.1 SIGMA=  1.8 PHAS= 121.0 FOM= 1.00
INDE -3 14 10 FOBS= 255.0 SIGMA=  2.3 PHAS= 182.4 FOM= 0.95
INDE -3 14 11 FOBS= 253.4 SIGMA=  2.4 PHAS=  79.4 FOM= 0.95
INDE -3 14 12 FOBS= 153.5 SIGMA=  4.1 PHAS= 198.6 FOM= 0.76
INDE -3 14 13 FOBS=  77.2 SIGMA=  8.8 PHAS= 156.9 FOM= 0.31
INDE -3 14 14 FOBS= 144.8 SIGMA=  5.0 PHAS=  67.1 FOM= 0.64
INDE -3 14 15 FOBS=  85.1 SIGMA=  9.8 PHAS= 233.2 FOM= 0.00
INDE -3 15  1 FOBS= 291.7 SIGMA=  1.3 PHAS= 170.4 FOM= 0.88
INDE -3 15  2 FOBS= 169.8 SIGMA=  1.9 PHAS= 323.0 FOM= 0.30
INDE -3 15  3 FOBS= 493.6 SIGMA=  0.9 PHAS=  92.1 FOM= 0.92
INDE -3 15  4 FOBS= 107.7 SIGMA=  3.1 PHAS= 333.7 FOM= 0.95
INDE -3 15  5 FOBS= 228.3 SIGMA=  1.7 PHAS= 288.2 FOM= 1.00
INDE -3 15  6 FOBS= 226.2 SIGMA=  1.8 PHAS= 160.3 FOM= 0.94
INDE -3 15  7 FOBS= 287.6 SIGMA=  1.8 PHAS=  35.4 FOM= 1.00
INDE -3 15  8 FOBS= 214.8 SIGMA=  2.1 PHAS= 305.7 FOM= 0.96
```

Fig. 10A-64

```
INDE  -3  15   9 FOBS=  179.7 SIGMA=  2.7 PHAS= 307.3 FOM= 0.72
INDE  -3  15  10 FOBS=  244.0 SIGMA=  2.4 PHAS=  29.6 FOM= 0.97
INDE  -3  15  11 FOBS=  317.6 SIGMA=  2.0 PHAS= 204.0 FOM= 0.96
INDE  -3  15  12 FOBS=  148.4 SIGMA=  4.1 PHAS= 194.7 FOM= 0.13
INDE  -3  15  13 FOBS=  174.3 SIGMA=  3.6 PHAS= 109.3 FOM= 0.07
INDE  -3  15  14 FOBS=   69.0 SIGMA=  8.0 PHAS=  96.4 FOM= 0.75
INDE  -3  15  15 FOBS=  125.8 SIGMA=  5.9 PHAS= 213.3 FOM= 0.07
INDE  -3  16   1 FOBS=  147.1 SIGMA=  2.6 PHAS= 243.2 FOM= 0.89
INDE  -3  16   2 FOBS=  550.5 SIGMA=  0.9 PHAS= 106.1 FOM= 0.97
INDE  -3  16   3 FOBS=  164.9 SIGMA=  1.9 PHAS= 196.9 FOM= 0.58
INDE  -3  16   4 FOBS=  233.6 SIGMA=  1.6 PHAS= 340.2 FOM= 0.93
INDE  -3  16   5 FOBS=  367.9 SIGMA=  1.6 PHAS= 255.7 FOM= 0.97
INDE  -3  16   6 FOBS=  103.4 SIGMA=  4.6 PHAS=  39.6 FOM= 0.91
INDE  -3  16   7 FOBS=  237.6 SIGMA=  1.9 PHAS= 306.0 FOM= 0.82
INDE  -3  16   8 FOBS=  336.5 SIGMA=  1.5 PHAS= 236.7 FOM= 0.96
INDE  -3  16   9 FOBS=  267.6 SIGMA=  2.1 PHAS= 353.1 FOM= 0.99
INDE  -3  16  10 FOBS=  223.8 SIGMA=  2.5 PHAS= 199.9 FOM= 0.31
INDE  -3  16  11 FOBS=  166.7 SIGMA=  3.6 PHAS= 206.7 FOM= 0.44
INDE  -3  16  12 FOBS=  209.5 SIGMA=  2.8 PHAS=  61.8 FOM= 0.06
INDE  -3  16  13 FOBS=   61.8 SIGMA=  9.3 PHAS=  84.8 FOM= 0.16
INDE  -3  16  14 FOBS=   75.5 SIGMA=  7.5 PHAS= 287.5 FOM= 0.03
INDE  -3  16  15 FOBS=   68.5 SIGMA= 41.4 PHAS= 257.8 FOM= 0.04
INDE  -3  17   1 FOBS=  264.7 SIGMA=  1.6 PHAS= 131.6 FOM= 0.94
INDE  -3  17   2 FOBS=  301.3 SIGMA=  1.4 PHAS=  51.1 FOM= 0.99
INDE  -3  17   3 FOBS=  415.9 SIGMA=  1.1 PHAS= 187.0 FOM= 0.85
INDE  -3  17   4 FOBS=  281.9 SIGMA=  1.4 PHAS=  87.3 FOM= 0.82
INDE  -3  17   5 FOBS=  283.8 SIGMA=  1.5 PHAS= 130.2 FOM= 0.97
INDE  -3  17   6 FOBS=  192.7 SIGMA=  2.3 PHAS= 336.2 FOM= 0.95
INDE  -3  17   7 FOBS=  512.3 SIGMA=  1.2 PHAS= 148.0 FOM= 0.65
INDE  -3  17   8 FOBS=  445.3 SIGMA=  1.4 PHAS=  89.2 FOM= 0.92
INDE  -3  17   9 FOBS=  343.2 SIGMA=  1.7 PHAS= 128.8 FOM= 0.96
INDE  -3  17  10 FOBS=  116.0 SIGMA=  4.9 PHAS= 232.3 FOM= 0.53
INDE  -3  17  11 FOBS=  194.8 SIGMA=  2.9 PHAS= 114.9 FOM= 0.85
INDE  -3  17  12 FOBS=  135.5 SIGMA=  4.4 PHAS=  16.5 FOM= 0.78
INDE  -3  17  13 FOBS=   90.2 SIGMA=  6.3 PHAS= 220.3 FOM= 0.33
INDE  -3  17  14 FOBS=   70.4 SIGMA=  8.2 PHAS= 193.6 FOM= 0.08
INDE  -3  18   1 FOBS=  214.8 SIGMA=  1.8 PHAS= 176.4 FOM= 0.89
INDE  -3  18   2 FOBS=  304.6 SIGMA=  1.5 PHAS= 177.6 FOM= 0.91
INDE  -3  18   3 FOBS=  370.6 SIGMA=  1.3 PHAS= 222.0 FOM= 1.00
INDE  -3  18   4 FOBS=  463.0 SIGMA=  1.2 PHAS= 111.4 FOM= 0.97
INDE  -3  18   5 FOBS=  430.2 SIGMA=  1.3 PHAS=  57.5 FOM= 0.97
INDE  -3  18   6 FOBS=  403.6 SIGMA=  1.2 PHAS= 246.0 FOM= 0.98
INDE  -3  18   7 FOBS=  306.3 SIGMA=  1.6 PHAS= 313.9 FOM= 0.82
INDE  -3  18   8 FOBS=   49.2 SIGMA=  9.4 PHAS= 134.5 FOM= 0.17
INDE  -3  18   9 FOBS=  147.6 SIGMA=  3.6 PHAS=  51.7 FOM= 0.77
INDE  -3  18  10 FOBS=  164.1 SIGMA=  3.4 PHAS= 139.4 FOM= 0.12
INDE  -3  18  11 FOBS=   80.5 SIGMA=  7.0 PHAS= 325.1 FOM= 0.11
INDE  -3  18  12 FOBS=   97.0 SIGMA=  6.0 PHAS= 116.3 FOM= 0.06
INDE  -3  18  13 FOBS=  195.7 SIGMA=  2.9 PHAS= 284.2 FOM= 0.64
INDE  -3  18  14 FOBS=  161.6 SIGMA=  3.7 PHAS=  59.1 FOM= 0.09
INDE  -3  19   1 FOBS=  123.8 SIGMA=  3.1 PHAS=   6.5 FOM= 0.46
INDE  -3  19   2 FOBS=  468.2 SIGMA=  1.2 PHAS= 223.6 FOM= 0.97
INDE  -3  19   3 FOBS=  344.4 SIGMA=  1.5 PHAS= 115.4 FOM= 0.97
INDE  -3  19   4 FOBS=  441.8 SIGMA=  1.3 PHAS= 226.4 FOM= 0.70
INDE  -3  19   5 FOBS=  241.8 SIGMA=  1.8 PHAS= 350.1 FOM= 0.41
INDE  -3  19   6 FOBS=  169.5 SIGMA=  2.4 PHAS=  12.5 FOM= 0.25
INDE  -3  19   7 FOBS=  224.9 SIGMA=  2.3 PHAS= 328.7 FOM= 0.80
INDE  -3  19   8 FOBS=  189.8 SIGMA=  2.6 PHAS= 180.3 FOM= 0.35
INDE  -3  19   9 FOBS=  170.9 SIGMA=  3.2 PHAS=  95.7 FOM= 0.12
INDE  -3  19  10 FOBS=  188.1 SIGMA=  2.8 PHAS= 215.5 FOM= 0.52
INDE  -3  19  11 FOBS=   68.7 SIGMA=  7.8 PHAS= 236.4 FOM= 0.10
INDE  -3  19  12 FOBS=  147.8 SIGMA=  4.1 PHAS= 126.7 FOM= 0.34
INDE  -3  19  13 FOBS=  115.5 SIGMA=  5.0 PHAS= 303.4 FOM= 0.06
INDE  -3  19  14 FOBS=   81.1 SIGMA=  6.9 PHAS= 209.3 FOM= 0.04
INDE  -3  20   1 FOBS=  141.1 SIGMA=  2.8 PHAS= 121.3 FOM= 0.84
INDE  -3  20   2 FOBS=  322.7 SIGMA=  1.3 PHAS= 126.7 FOM= 0.74
INDE  -3  20   3 FOBS=  383.6 SIGMA=  1.3 PHAS=  99.7 FOM= 0.92
INDE  -3  20   4 FOBS=  145.0 SIGMA=  2.9 PHAS= 332.6 FOM= 0.78
INDE  -3  20   5 FOBS=  423.2 SIGMA=  1.3 PHAS=  90.7 FOM= 0.99
INDE  -3  20   6 FOBS=  413.8 SIGMA=  1.4 PHAS= 283.7 FOM= 0.95
INDE  -3  20   7 FOBS=  317.5 SIGMA=  1.8 PHAS= 182.6 FOM= 0.97
```

Fig. 10A-65

```
INDE  -3  20   8 FOBS=   457.2 SIGMA=   1.3 PHAS=   23.5 FOM= 0.93
INDE  -3  20   9 FOBS=   166.0 SIGMA=   3.2 PHAS=  184.8 FOM= 0.91
INDE  -3  20  10 FOBS=   197.4 SIGMA=   2.6 PHAS=   47.6 FOM= 0.92
INDE  -3  20  11 FOBS=   190.0 SIGMA=   2.9 PHAS=   83.7 FOM= 0.25
INDE  -3  20  12 FOBS=   117.4 SIGMA=   4.9 PHAS=   68.6 FOM= 0.23
INDE  -3  20  13 FOBS=   137.6 SIGMA=   4.3 PHAS=   97.9 FOM= 0.04
INDE  -3  21   1 FOBS=   202.1 SIGMA=   2.1 PHAS=   42.4 FOM= 0.41
INDE  -3  21   2 FOBS=   133.3 SIGMA=   2.8 PHAS=   69.7 FOM= 0.95
INDE  -3  21   3 FOBS=   307.5 SIGMA=   1.8 PHAS=  183.4 FOM= 0.94
INDE  -3  21   4 FOBS=   224.2 SIGMA=   2.0 PHAS=  310.8 FOM= 0.79
INDE  -3  21   5 FOBS=   276.8 SIGMA=   2.0 PHAS=  292.1 FOM= 0.96
INDE  -3  21   6 FOBS=   391.1 SIGMA=   1.5 PHAS=  143.9 FOM= 0.97
INDE  -3  21   7 FOBS=   181.6 SIGMA=   2.8 PHAS=   73.7 FOM= 0.17
INDE  -3  21   8 FOBS=    87.5 SIGMA=   5.2 PHAS=   88.7 FOM= 0.07
INDE  -3  21   9 FOBS=   118.0 SIGMA=   4.3 PHAS=    2.8 FOM= 0.72
INDE  -3  21  10 FOBS=   220.7 SIGMA=   2.4 PHAS=  246.9 FOM= 0.72
INDE  -3  21  11 FOBS=    78.5 SIGMA=   6.5 PHAS=  217.3 FOM= 0.12
INDE  -3  21  12 FOBS=    55.5 SIGMA=   9.8 PHAS=  345.9 FOM= 0.22
INDE  -3  21  13 FOBS=    67.4 SIGMA=   8.2 PHAS=  237.3 FOM= 0.11
INDE  -3  22   1 FOBS=    78.3 SIGMA=   4.3 PHAS=  164.0 FOM= 0.92
INDE  -3  22   2 FOBS=   317.3 SIGMA=   1.5 PHAS=  216.9 FOM= 0.98
INDE  -3  22   3 FOBS=    84.3 SIGMA=   5.7 PHAS=   42.1 FOM= 0.48
INDE  -3  22   4 FOBS=   253.8 SIGMA=   1.8 PHAS=   68.5 FOM= 0.98
INDE  -3  22   5 FOBS=   153.2 SIGMA=   3.0 PHAS=   12.7 FOM= 0.89
INDE  -3  22   6 FOBS=   147.0 SIGMA=   3.5 PHAS=  337.2 FOM= 0.25
INDE  -3  22   7 FOBS=   240.2 SIGMA=   2.0 PHAS=   62.9 FOM= 0.18
INDE  -3  22   8 FOBS=   135.3 SIGMA=   3.9 PHAS=  125.7 FOM= 0.77
INDE  -3  22   9 FOBS=   169.0 SIGMA=   2.8 PHAS=   48.2 FOM= 0.90
INDE  -3  22  10 FOBS=   129.4 SIGMA=   4.5 PHAS=   89.9 FOM= 0.83
INDE  -3  22  11 FOBS=   154.3 SIGMA=   3.6 PHAS=   39.1 FOM= 0.94
INDE  -3  22  12 FOBS=   190.5 SIGMA=   2.9 PHAS=  340.4 FOM= 0.82
INDE  -3  23   1 FOBS=   164.2 SIGMA=   2.6 PHAS=   12.8 FOM= 0.66
INDE  -3  23   2 FOBS=   204.9 SIGMA=   2.1 PHAS=   81.5 FOM= 0.54
INDE  -3  23   3 FOBS=   429.5 SIGMA=   1.7 PHAS=   76.2 FOM= 0.95
INDE  -3  23   4 FOBS=    93.7 SIGMA=   4.4 PHAS=  311.3 FOM= 0.84
INDE  -3  23   5 FOBS=   226.0 SIGMA=   2.2 PHAS=  141.1 FOM= 0.96
INDE  -3  23   6 FOBS=   142.5 SIGMA=   3.6 PHAS=  133.5 FOM= 0.86
INDE  -3  23   7 FOBS=    97.2 SIGMA=   5.4 PHAS=   88.2 FOM= 0.93
INDE  -3  23   8 FOBS=   305.3 SIGMA=   1.9 PHAS=  263.0 FOM= 0.99
INDE  -3  23   9 FOBS=   234.7 SIGMA=   2.1 PHAS=   71.7 FOM= 0.65
INDE  -3  23  10 FOBS=   140.2 SIGMA=   4.0 PHAS=   41.8 FOM= 0.69
INDE  -3  23  11 FOBS=    60.5 SIGMA=   9.7 PHAS=  217.1 FOM= 0.21
INDE  -3  23  12 FOBS=   134.8 SIGMA=   3.9 PHAS=   66.8 FOM= 0.29
INDE  -3  24   1 FOBS=   223.9 SIGMA=   2.1 PHAS=  162.5 FOM= 0.74
INDE  -3  24   2 FOBS=   278.9 SIGMA=   1.7 PHAS=  278.2 FOM= 0.92
INDE  -3  24   3 FOBS=   167.6 SIGMA=   3.4 PHAS=  225.6 FOM= 0.89
INDE  -3  24   4 FOBS=   252.2 SIGMA=   1.8 PHAS=   66.9 FOM= 0.93
INDE  -3  24   5 FOBS=   243.5 SIGMA=   1.9 PHAS=  178.6 FOM= 0.65
INDE  -3  24   6 FOBS=   241.0 SIGMA=   2.1 PHAS=  285.3 FOM= 0.97
INDE  -3  24   7 FOBS=   153.2 SIGMA=   3.6 PHAS=   30.0 FOM= 0.69
INDE  -3  24   8 FOBS=   256.4 SIGMA=   2.4 PHAS=  227.1 FOM= 0.94
INDE  -3  24   9 FOBS=    95.2 SIGMA=   5.0 PHAS=   52.4 FOM= 0.73
INDE  -3  24  10 FOBS=   139.8 SIGMA=   3.6 PHAS=  157.7 FOM= 0.71
INDE  -3  24  11 FOBS=   154.8 SIGMA=   3.5 PHAS=  221.8 FOM= 0.28
INDE  -3  25   1 FOBS=   216.9 SIGMA=   2.1 PHAS=  232.6 FOM= 0.18
INDE  -3  25   2 FOBS=   121.4 SIGMA=   3.8 PHAS=   73.0 FOM= 0.80
INDE  -3  25   3 FOBS=   344.3 SIGMA=   2.0 PHAS=  173.0 FOM= 0.99
INDE  -3  25   4 FOBS=   135.2 SIGMA=   3.4 PHAS=  126.0 FOM= 0.95
INDE  -3  25   5 FOBS=   369.0 SIGMA=   1.5 PHAS=   64.1 FOM= 0.96
INDE  -3  25   6 FOBS=   305.3 SIGMA=   1.7 PHAS=  310.3 FOM= 0.95
INDE  -3  25   7 FOBS=   150.8 SIGMA=   3.3 PHAS=  138.0 FOM= 0.94
INDE  -3  25   8 FOBS=   284.9 SIGMA=   2.1 PHAS=  240.0 FOM= 0.97
INDE  -3  25   9 FOBS=   145.1 SIGMA=   4.0 PHAS=  132.8 FOM= 0.68
INDE  -3  25  10 FOBS=   186.9 SIGMA=   2.5 PHAS=   16.1 FOM= 0.89
INDE  -3  25  11 FOBS=   119.0 SIGMA=   4.4 PHAS=   59.2 FOM= 0.89
INDE  -3  26   1 FOBS=   166.3 SIGMA=   2.7 PHAS=  356.6 FOM= 0.61
INDE  -3  26   2 FOBS=   212.8 SIGMA=   2.1 PHAS=  283.5 FOM= 0.50
INDE  -3  26   3 FOBS=    43.3 SIGMA=  13.6 PHAS=  167.7 FOM= 0.08
INDE  -3  26   4 FOBS=   298.8 SIGMA=   1.6 PHAS=   97.8 FOM= 0.88
INDE  -3  26   5 FOBS=    65.5 SIGMA=   6.3 PHAS=  170.4 FOM= 0.19
INDE  -3  26   6 FOBS=   149.9 SIGMA=   3.2 PHAS=  154.1 FOM= 0.09
```

Fig. 10A-66

```
INDE  -3  26   7 FOBS=  156.6 SIGMA=   2.9 PHAS= 347.3 FOM= 0.67
INDE  -3  26   8 FOBS=   99.5 SIGMA=   4.5 PHAS= 245.1 FOM= 0.57
INDE  -3  26   9 FOBS=  161.3 SIGMA=   3.6 PHAS= 282.2 FOM= 0.17
INDE  -3  26  10 FOBS=  115.7 SIGMA=   4.1 PHAS= 278.5 FOM= 0.21
INDE  -3  27   1 FOBS=   71.1 SIGMA=   5.9 PHAS=  70.9 FOM= 0.31
INDE  -3  27   2 FOBS=   62.0 SIGMA=   6.3 PHAS= 100.5 FOM= 0.45
INDE  -3  27   3 FOBS=  110.6 SIGMA=   5.2 PHAS= 293.8 FOM= 0.92
INDE  -3  27   4 FOBS=  218.5 SIGMA=   2.1 PHAS= 198.0 FOM= 0.98
INDE  -3  27   5 FOBS=   79.5 SIGMA=   5.3 PHAS= 116.2 FOM= 0.33
INDE  -3  27   6 FOBS=  143.7 SIGMA=   3.2 PHAS=  31.4 FOM= 0.84
INDE  -3  27   7 FOBS=  176.1 SIGMA=   2.4 PHAS= 333.2 FOM= 0.72
INDE  -3  27   8 FOBS=  161.9 SIGMA=   2.8 PHAS=  40.0 FOM= 0.90
INDE  -3  27   9 FOBS=   40.6 SIGMA=  18.5 PHAS= 182.7 FOM= 0.06
INDE  -3  27  10 FOBS=   84.4 SIGMA=   7.6 PHAS= 350.0 FOM= 0.05
INDE  -3  28   1 FOBS=  130.0 SIGMA=   3.5 PHAS=  35.6 FOM= 0.90
INDE  -3  28   2 FOBS=  110.1 SIGMA=   3.8 PHAS= 330.8 FOM= 0.86
INDE  -3  28   3 FOBS=  141.8 SIGMA=   3.7 PHAS=  68.5 FOM= 0.68
INDE  -3  28   4 FOBS=  249.9 SIGMA=   1.8 PHAS= 229.9 FOM= 0.97
INDE  -3  28   5 FOBS=  150.2 SIGMA=   2.8 PHAS=  14.4 FOM= 0.19
INDE  -3  28   6 FOBS=   44.4 SIGMA=  11.0 PHAS= 339.1 FOM= 0.27
INDE  -3  28   7 FOBS=   74.3 SIGMA=   5.8 PHAS= 175.6 FOM= 0.80
INDE  -3  28   8 FOBS=  128.0 SIGMA=   3.4 PHAS=  99.8 FOM= 0.41
INDE  -3  28   9 FOBS=   56.6 SIGMA=   7.6 PHAS= 347.6 FOM= 0.18
INDE  -3  29   1 FOBS=  276.6 SIGMA=   1.7 PHAS= 244.2 FOM= 0.57
INDE  -3  29   2 FOBS=  161.2 SIGMA=   2.5 PHAS=  85.4 FOM= 0.94
INDE  -3  29   3 FOBS=  230.5 SIGMA=   1.9 PHAS= 223.3 FOM= 0.85
INDE  -3  29   4 FOBS=  133.6 SIGMA=   3.1 PHAS= 315.2 FOM= 0.48
INDE  -3  29   5 FOBS=  198.3 SIGMA=   2.1 PHAS= 116.9 FOM= 0.95
INDE  -3  29   6 FOBS=  162.5 SIGMA=   2.7 PHAS= 174.2 FOM= 0.35
INDE  -3  29   7 FOBS=  124.8 SIGMA=   3.5 PHAS= 109.7 FOM= 0.79
INDE  -3  29   8 FOBS=  145.0 SIGMA=   3.2 PHAS=  62.4 FOM= 0.89
INDE  -3  30   1 FOBS=  139.8 SIGMA=   3.4 PHAS=  28.4 FOM= 0.93
INDE  -3  30   2 FOBS=  162.1 SIGMA=   2.7 PHAS= 111.1 FOM= 0.92
INDE  -3  30   3 FOBS=  141.4 SIGMA=   3.1 PHAS=  78.7 FOM= 0.87
INDE  -3  30   4 FOBS=  136.9 SIGMA=   3.4 PHAS=   2.7 FOM= 0.88
INDE  -3  30   5 FOBS=  189.7 SIGMA=   2.3 PHAS= 212.1 FOM= 0.75
INDE  -3  30   6 FOBS=   58.4 SIGMA=   7.4 PHAS= 197.5 FOM= 0.42
INDE  -3  30   7 FOBS=  122.1 SIGMA=   3.6 PHAS= 340.9 FOM= 0.38
INDE  -3  31   1 FOBS=  121.1 SIGMA=   3.6 PHAS= 156.8 FOM= 0.11
INDE  -3  31   2 FOBS=  168.0 SIGMA=   2.8 PHAS= 243.9 FOM= 0.32
INDE  -3  31   3 FOBS=   56.9 SIGMA=   7.2 PHAS= 306.0 FOM= 0.08
INDE  -3  31   4 FOBS=  174.4 SIGMA=   2.6 PHAS= 216.7 FOM= 0.54
INDE  -3  31   5 FOBS=  199.7 SIGMA=   2.2 PHAS= 141.9 FOM= 0.73
INDE  -3  31   6 FOBS=  184.0 SIGMA=   2.5 PHAS= 207.1 FOM= 0.73
INDE  -3  32   1 FOBS=  215.8 SIGMA=   2.1 PHAS= 199.4 FOM= 0.89
INDE  -3  32   2 FOBS=   66.4 SIGMA=   6.8 PHAS= 311.0 FOM= 0.31
INDE  -3  32   3 FOBS=  228.9 SIGMA=   1.9 PHAS= 108.4 FOM= 0.87
INDE  -3  32   4 FOBS=   71.2 SIGMA=   6.5 PHAS= 114.7 FOM= 0.10
INDE  -3  33   1 FOBS=  175.4 SIGMA=   9.8 PHAS= 202.1 FOM= 0.04
INDE  -2   0   2 FOBS=   28.6 SIGMA=   7.7 PHAS=   0.0 FOM= 0.47
INDE  -2   0   3 FOBS=  214.4 SIGMA=   1.5 PHAS= 180.0 FOM= 1.00
INDE  -2   0   4 FOBS=  695.4 SIGMA=   1.4 PHAS=   0.0 FOM= 0.94
INDE  -2   0   5 FOBS=  679.5 SIGMA=   1.3 PHAS= 180.0 FOM= 0.91
INDE  -2   0   6 FOBS=  530.5 SIGMA=   1.6 PHAS=   0.0 FOM= 0.36
INDE  -2   0   7 FOBS=  420.4 SIGMA=   1.5 PHAS=   0.0 FOM= 0.96
INDE  -2   0   8 FOBS=   55.8 SIGMA=  11.6 PHAS= 180.0 FOM= 0.40
INDE  -2   0   9 FOBS=  266.5 SIGMA=   2.7 PHAS=   0.0 FOM= 1.00
INDE  -2   0  10 FOBS=  369.9 SIGMA=   2.3 PHAS= 180.0 FOM= 0.97
INDE  -2   0  11 FOBS=   56.2 SIGMA=  14.4 PHAS= 180.0 FOM= 0.03
INDE  -2   0  12 FOBS=  121.2 SIGMA=   7.7 PHAS= 180.0 FOM= 0.37
INDE  -2   0  13 FOBS=   45.8 SIGMA=  21.8 PHAS= 180.0 FOM= 0.11
INDE  -2   0  14 FOBS=  108.1 SIGMA=   9.6 PHAS=   0.0 FOM= 0.02
INDE  -2   0  15 FOBS=   55.6 SIGMA=  19.6 PHAS=   0.0 FOM= 0.20
INDE  -2   1   2 FOBS=   86.3 SIGMA=   1.8 PHAS= 102.7 FOM= 0.97
INDE  -2   1   3 FOBS=  160.5 SIGMA=   1.0 PHAS=  98.2 FOM= 0.85
INDE  -2   1   4 FOBS=  524.7 SIGMA=   0.8 PHAS= 293.6 FOM= 0.98
INDE  -2   1   5 FOBS=  465.2 SIGMA=   1.3 PHAS= 265.1 FOM= 1.00
INDE  -2   1   6 FOBS=  372.2 SIGMA=   1.2 PHAS= 302.5 FOM= 1.00
INDE  -2   1   7 FOBS=  197.0 SIGMA=   2.2 PHAS= 359.9 FOM= 0.29
INDE  -2   1   8 FOBS=  130.8 SIGMA=   3.2 PHAS= 136.6 FOM= 0.19
INDE  -2   1   9 FOBS=  169.8 SIGMA=   2.8 PHAS= 329.8 FOM= 0.92
```

Fig. 10A-67

```
INDE  -2  1  10  FOBS=  201.6  SIGMA=   2.6  PHAS=  217.5  FOM=  0.93
INDE  -2  1  11  FOBS=  189.4  SIGMA=   3.0  PHAS=  190.2  FOM=  0.93
INDE  -2  1  12  FOBS=  250.7  SIGMA=   2.5  PHAS=  133.8  FOM=  0.35
INDE  -2  1  13  FOBS=  149.5  SIGMA=   4.8  PHAS=   30.7  FOM=  0.79
INDE  -2  1  14  FOBS=   60.9  SIGMA=  13.1  PHAS=  321.1  FOM=  0.14
INDE  -2  1  15  FOBS=  127.6  SIGMA=   5.7  PHAS=  213.4  FOM=  0.13
INDE  -2  1  16  FOBS=  150.3  SIGMA=   4.9  PHAS=  200.7  FOM=  0.29
INDE  -2  1  17  FOBS=   72.7  SIGMA=  10.1  PHAS=  331.1  FOM=  0.08
INDE  -2  2   2  FOBS=  282.5  SIGMA=   1.3  PHAS=  157.1  FOM=  0.92
INDE  -2  2   3  FOBS=  100.0  SIGMA=   1.6  PHAS=  173.4  FOM=  0.91
INDE  -2  2   4  FOBS=  384.1  SIGMA=   1.1  PHAS=  142.6  FOM=  0.82
INDE  -2  2   5  FOBS=  219.9  SIGMA=   1.3  PHAS=  312.7  FOM=  0.96
INDE  -2  2   6  FOBS=  338.6  SIGMA=   1.1  PHAS=  301.2  FOM=  0.36
INDE  -2  2   7  FOBS=  121.2  SIGMA=   3.8  PHAS=   55.1  FOM=  0.95
INDE  -2  2   8  FOBS=  236.2  SIGMA=   1.9  PHAS=  248.6  FOM=  0.97
INDE  -2  2   9  FOBS=  478.1  SIGMA=   1.2  PHAS=   31.6  FOM=  0.85
INDE  -2  2  10  FOBS=  347.3  SIGMA=   1.7  PHAS=  233.9  FOM=  0.92
INDE  -2  2  11  FOBS=  293.1  SIGMA=   2.1  PHAS=  117.8  FOM=  0.90
INDE  -2  2  12  FOBS=  168.2  SIGMA=   4.2  PHAS=   74.7  FOM=  0.67
INDE  -2  2  13  FOBS=  193.8  SIGMA=   3.6  PHAS=  334.9  FOM=  0.38
INDE  -2  2  14  FOBS=  102.0  SIGMA=   7.0  PHAS=  209.9  FOM=  0.03
INDE  -2  2  15  FOBS=  107.7  SIGMA=   6.6  PHAS=   69.4  FOM=  0.08
INDE  -2  2  16  FOBS=   80.4  SIGMA=   8.9  PHAS=  234.7  FOM=  0.04
INDE  -2  2  17  FOBS=   80.4  SIGMA=  10.1  PHAS=   10.6  FOM=  0.07
INDE  -2  3   1  FOBS=  111.1  SIGMA=   2.7  PHAS=  329.8  FOM=  0.94
INDE  -2  3   2  FOBS=  159.5  SIGMA=   2.1  PHAS=  124.6  FOM=  0.63
INDE  -2  3   3  FOBS=  211.0  SIGMA=   1.0  PHAS=  299.3  FOM=  0.75
INDE  -2  3   4  FOBS=  640.0  SIGMA=   0.7  PHAS=  337.9  FOM=  0.98
INDE  -2  3   5  FOBS=  196.8  SIGMA=   1.4  PHAS=   56.7  FOM=  0.91
INDE  -2  3   6  FOBS=  288.6  SIGMA=   1.2  PHAS=  292.2  FOM=  0.98
INDE  -2  3   7  FOBS=  109.5  SIGMA=   3.7  PHAS=  216.8  FOM=  0.88
INDE  -2  3   8  FOBS=   55.5  SIGMA=   9.9  PHAS=  160.9  FOM=  0.42
INDE  -2  3   9  FOBS=  151.0  SIGMA=   3.7  PHAS=    9.8  FOM=  0.96
INDE  -2  3  10  FOBS=  243.5  SIGMA=   2.2  PHAS=  177.6  FOM=  0.97
INDE  -2  3  11  FOBS=  372.6  SIGMA=   1.7  PHAS=  132.5  FOM=  0.82
INDE  -2  3  12  FOBS=  238.9  SIGMA=   2.7  PHAS=  212.8  FOM=  0.46
INDE  -2  3  13  FOBS=  237.6  SIGMA=   2.9  PHAS=  211.8  FOM=  0.39
INDE  -2  3  14  FOBS=  305.0  SIGMA=   2.4  PHAS=  355.1  FOM=  0.82
INDE  -2  3  15  FOBS=  106.8  SIGMA=   6.8  PHAS=  180.7  FOM=  0.39
INDE  -2  3  16  FOBS=  144.5  SIGMA=   5.0  PHAS=  281.5  FOM=  0.43
INDE  -2  3  17  FOBS=  180.5  SIGMA=   6.7  PHAS=    9.3  FOM=  0.08
INDE  -2  4   1  FOBS=  131.6  SIGMA=   2.5  PHAS=  255.9  FOM=  0.93
INDE  -2  4   2  FOBS=  272.9  SIGMA=   1.4  PHAS=  235.9  FOM=  0.99
INDE  -2  4   3  FOBS=  407.7  SIGMA=   1.0  PHAS=  167.5  FOM=  0.98
INDE  -2  4   4  FOBS=  217.6  SIGMA=   1.1  PHAS=  111.4  FOM=  0.99
INDE  -2  4   5  FOBS=  152.0  SIGMA=   1.8  PHAS=  247.7  FOM=  0.95
INDE  -2  4   6  FOBS=  194.7  SIGMA=   1.7  PHAS=  171.5  FOM=  1.00
INDE  -2  4   7  FOBS=  308.9  SIGMA=   1.3  PHAS=  110.1  FOM=  0.98
INDE  -2  4   8  FOBS=   91.6  SIGMA=   5.0  PHAS=  226.7  FOM=  0.45
INDE  -2  4   9  FOBS=  128.5  SIGMA=   4.5  PHAS=  333.0  FOM=  0.63
INDE  -2  4  10  FOBS=   68.6  SIGMA=   7.9  PHAS=  140.3  FOM=  0.21
INDE  -2  4  11  FOBS=  181.3  SIGMA=   3.2  PHAS=  111.8  FOM=  0.32
INDE  -2  4  12  FOBS=  470.0  SIGMA=   1.6  PHAS=   25.8  FOM=  0.97
INDE  -2  4  13  FOBS=  202.3  SIGMA=   3.5  PHAS=  157.6  FOM=  0.33
INDE  -2  4  14  FOBS=  295.9  SIGMA=   2.4  PHAS=  105.8  FOM=  0.57
INDE  -2  4  15  FOBS=   88.8  SIGMA=   8.0  PHAS=   29.1  FOM=  0.40
INDE  -2  4  16  FOBS=   68.8  SIGMA=  10.5  PHAS=  269.7  FOM=  0.05
INDE  -2  5   1  FOBS=  269.8  SIGMA=   1.6  PHAS=  202.9  FOM=  1.00
INDE  -2  5   2  FOBS=  257.3  SIGMA=   1.5  PHAS=  107.5  FOM=  0.97
INDE  -2  5   3  FOBS=  509.8  SIGMA=   1.0  PHAS=  185.7  FOM=  0.96
INDE  -2  5   4  FOBS=  158.3  SIGMA=   1.5  PHAS=  310.8  FOM=  0.65
INDE  -2  5   5  FOBS=  227.3  SIGMA=   1.3  PHAS=  161.2  FOM=  0.89
INDE  -2  5   6  FOBS=  119.6  SIGMA=   2.6  PHAS=   41.2  FOM=  0.92
INDE  -2  5   7  FOBS=   77.0  SIGMA=   5.0  PHAS=   67.7  FOM=  0.53
INDE  -2  5   8  FOBS=  205.5  SIGMA=   2.1  PHAS=  271.9  FOM=  0.79
INDE  -2  5   9  FOBS=  117.9  SIGMA=   4.8  PHAS=   75.8  FOM=  0.43
INDE  -2  5  10  FOBS=  222.0  SIGMA=   2.7  PHAS=  163.8  FOM=  0.49
INDE  -2  5  11  FOBS=  139.1  SIGMA=   4.4  PHAS=  254.6  FOM=  0.56
INDE  -2  5  12  FOBS=  120.4  SIGMA=   5.7  PHAS=  113.3  FOM=  0.06
INDE  -2  5  13  FOBS=  485.9  SIGMA=   1.7  PHAS=  162.8  FOM=  0.96
INDE  -2  5  14  FOBS=  193.4  SIGMA=   3.9  PHAS=    6.3  FOM=  0.60
```

Fig. 10A-68

```
INDE  -2   5  15 FOBS=  201.2 SIGMA=  3.6 PHAS= 331.4 FOM= 0.43
INDE  -2   5  16 FOBS=   69.1 SIGMA= 10.3 PHAS= 152.2 FOM= 0.08
INDE  -2   6   1 FOBS=  314.8 SIGMA=  0.8 PHAS= 104.3 FOM= 0.46
INDE  -2   6   2 FOBS=  340.1 SIGMA=  1.5 PHAS= 251.1 FOM= 0.94
INDE  -2   6   3 FOBS=  243.9 SIGMA=  1.1 PHAS= 319.6 FOM= 0.82
INDE  -2   6   4 FOBS=  227.9 SIGMA=  1.4 PHAS=  51.6 FOM= 0.88
INDE  -2   6   5 FOBS=  215.2 SIGMA=  1.5 PHAS= 153.0 FOM= 0.87
INDE  -2   6   6 FOBS=  183.1 SIGMA=  1.8 PHAS= 315.1 FOM= 0.58
INDE  -2   6   7 FOBS=  119.7 SIGMA=  3.0 PHAS= 189.9 FOM= 0.93
INDE  -2   6   8 FOBS=  108.7 SIGMA=  4.2 PHAS= 136.0 FOM= 0.46
INDE  -2   6   9 FOBS=  291.6 SIGMA=  1.8 PHAS= 213.5 FOM= 0.14
INDE  -2   6  10 FOBS=  183.2 SIGMA=  3.3 PHAS= 208.6 FOM= 0.61
INDE  -2   6  11 FOBS=   88.7 SIGMA=  7.0 PHAS= 280.4 FOM= 0.14
INDE  -2   6  12 FOBS=  480.6 SIGMA=  1.6 PHAS=  69.1 FOM= 0.93
INDE  -2   6  13 FOBS=  218.7 SIGMA=  3.5 PHAS= 289.8 FOM= 0.66
INDE  -2   6  14 FOBS=   57.3 SIGMA= 12.8 PHAS= 241.8 FOM= 0.07
INDE  -2   6  15 FOBS=  139.5 SIGMA=  5.3 PHAS=  45.1 FOM= 0.44
INDE  -2   6  16 FOBS=   69.3 SIGMA= 11.1 PHAS= 284.7 FOM= 0.11
INDE  -2   7   1 FOBS=   31.4 SIGMA=  8.0 PHAS= 210.3 FOM= 0.33
INDE  -2   7   2 FOBS=  243.6 SIGMA=  0.9 PHAS=  41.1 FOM= 0.33
INDE  -2   7   3 FOBS=  206.7 SIGMA=  1.2 PHAS= 129.9 FOM= 0.99
INDE  -2   7   4 FOBS=  496.8 SIGMA=  1.0 PHAS= 336.2 FOM= 0.99
INDE  -2   7   5 FOBS=  181.0 SIGMA=  2.0 PHAS=  81.8 FOM= 0.98
INDE  -2   7   6 FOBS=  215.1 SIGMA=  1.7 PHAS= 250.8 FOM= 0.98
INDE  -2   7   7 FOBS=  308.3 SIGMA=  1.4 PHAS=  42.5 FOM= 0.96
INDE  -2   7   8 FOBS=  370.6 SIGMA=  1.3 PHAS= 308.6 FOM= 0.90
INDE  -2   7   9 FOBS=  299.2 SIGMA=  1.8 PHAS= 234.9 FOM= 0.96
INDE  -2   7  10 FOBS=  208.4 SIGMA=  2.6 PHAS= 204.3 FOM= 0.79
INDE  -2   7  11 FOBS=  231.3 SIGMA=  2.9 PHAS= 237.2 FOM= 0.51
INDE  -2   7  12 FOBS=  233.2 SIGMA=  2.9 PHAS= 343.0 FOM= 0.67
INDE  -2   7  13 FOBS=   82.2 SIGMA=  8.7 PHAS= 137.4 FOM= 0.04
INDE  -2   7  14 FOBS=  192.8 SIGMA=  3.8 PHAS= 134.1 FOM= 0.06
INDE  -2   7  15 FOBS=   53.1 SIGMA= 14.1 PHAS=  15.7 FOM= 0.03
INDE  -2   7  16 FOBS=  146.7 SIGMA=  5.0 PHAS=  94.4 FOM= 0.07
INDE  -2   8   1 FOBS=  172.1 SIGMA=  1.3 PHAS= 152.8 FOM= 0.80
INDE  -2   8   2 FOBS=  308.9 SIGMA=  1.1 PHAS= 298.8 FOM= 0.86
INDE  -2   8   3 FOBS=  270.1 SIGMA=  1.2 PHAS= 236.7 FOM= 1.00
INDE  -2   8   4 FOBS=  306.8 SIGMA=  1.2 PHAS= 281.8 FOM= 0.15
INDE  -2   8   5 FOBS=  100.1 SIGMA=  3.1 PHAS=  87.5 FOM= 0.76
INDE  -2   8   6 FOBS=  115.5 SIGMA=  3.7 PHAS= 247.8 FOM= 0.64
INDE  -2   8   7 FOBS=  384.1 SIGMA=  1.2 PHAS= 252.6 FOM= 0.91
INDE  -2   8   8 FOBS=  378.4 SIGMA=  1.3 PHAS= 102.0 FOM= 0.65
INDE  -2   8   9 FOBS=  140.5 SIGMA=  3.7 PHAS=  55.8 FOM= 0.78
INDE  -2   8  10 FOBS=  373.6 SIGMA=  1.6 PHAS= 152.4 FOM= 0.97
INDE  -2   8  11 FOBS=  134.7 SIGMA=  5.0 PHAS= 299.3 FOM= 0.58
INDE  -2   8  12 FOBS=  184.5 SIGMA=  4.1 PHAS= 276.4 FOM= 0.11
INDE  -2   8  13 FOBS=  141.2 SIGMA=  5.1 PHAS= 168.1 FOM= 0.24
INDE  -2   8  14 FOBS=  162.1 SIGMA=  4.6 PHAS=  59.4 FOM= 0.10
INDE  -2   8  15 FOBS=  146.1 SIGMA=  5.0 PHAS= 331.9 FOM= 0.23
INDE  -2   8  16 FOBS=   56.3 SIGMA= 14.9 PHAS= 222.0 FOM= 0.05
INDE  -2   9   1 FOBS=  233.9 SIGMA=  1.1 PHAS= 141.2 FOM= 0.97
INDE  -2   9   2 FOBS=  294.7 SIGMA=  0.9 PHAS= 308.9 FOM= 0.82
INDE  -2   9   3 FOBS=  139.1 SIGMA=  1.7 PHAS= 121.8 FOM= 0.88
INDE  -2   9   4 FOBS=  114.7 SIGMA=  2.2 PHAS=  40.0 FOM= 0.98
INDE  -2   9   5 FOBS=  353.9 SIGMA=  1.1 PHAS=  50.0 FOM= 0.98
INDE  -2   9   6 FOBS=  251.2 SIGMA=  1.5 PHAS= 333.1 FOM= 0.50
INDE  -2   9   7 FOBS=  253.8 SIGMA=  1.9 PHAS=  34.7 FOM= 0.87
INDE  -2   9   8 FOBS=  213.5 SIGMA=  2.1 PHAS=  58.1 FOM= 0.90
INDE  -2   9   9 FOBS=  197.0 SIGMA=  2.4 PHAS=  51.7 FOM= 0.79
INDE  -2   9  10 FOBS=  102.9 SIGMA=  5.5 PHAS= 181.0 FOM= 0.74
INDE  -2   9  11 FOBS=  354.3 SIGMA=  1.9 PHAS= 235.0 FOM= 0.95
INDE  -2   9  12 FOBS=   81.6 SIGMA=  9.3 PHAS=  34.6 FOM= 0.06
INDE  -2   9  13 FOBS=  205.5 SIGMA=  3.8 PHAS= 111.7 FOM= 0.79
INDE  -2   9  14 FOBS=  239.2 SIGMA=  3.0 PHAS= 354.1 FOM= 0.96
INDE  -2   9  15 FOBS=   67.8 SIGMA= 10.5 PHAS= 136.0 FOM= 0.23
INDE  -2   9  16 FOBS=   59.1 SIGMA= 13.3 PHAS= 116.5 FOM= 0.10
INDE  -2  10   1 FOBS=  212.0 SIGMA=  1.2 PHAS= 291.9 FOM= 0.98
INDE  -2  10   2 FOBS=  302.8 SIGMA=  0.9 PHAS= 341.3 FOM= 0.27
INDE  -2  10   3 FOBS=   71.1 SIGMA=  3.7 PHAS= 198.7 FOM= 0.88
INDE  -2  10   4 FOBS=  123.7 SIGMA=  2.3 PHAS= 124.4 FOM= 0.55
INDE  -2  10   5 FOBS=  115.3 SIGMA=  3.3 PHAS= 207.4 FOM= 0.92
```

Fig. 10A-69

```
INDE  -2  10   6 FOBS=  137.8 SIGMA=  2.6 PHAS=  133.9 FOM= 0.34
INDE  -2  10   7 FOBS=   76.7 SIGMA=  5.4 PHAS=    9.4 FOM= 0.83
INDE  -2  10   8 FOBS=  431.9 SIGMA=  1.4 PHAS=   88.9 FOM= 1.00
INDE  -2  10   9 FOBS=  106.6 SIGMA=  5.1 PHAS=  254.5 FOM= 0.29
INDE  -2  10  10 FOBS=  189.6 SIGMA=  2.8 PHAS=  117.7 FOM= 0.87
INDE  -2  10  11 FOBS=  158.3 SIGMA=  4.2 PHAS=  317.7 FOM= 0.59
INDE  -2  10  12 FOBS=  243.8 SIGMA=  2.7 PHAS=  244.1 FOM= 0.95
INDE  -2  10  13 FOBS=  314.0 SIGMA=  2.5 PHAS=   33.6 FOM= 0.46
INDE  -2  10  14 FOBS=  170.4 SIGMA=  4.5 PHAS=  265.5 FOM= 0.09
INDE  -2  10  15 FOBS=  100.1 SIGMA=  7.2 PHAS=   72.2 FOM= 0.73
INDE  -2  10  16 FOBS=   90.3 SIGMA=  7.9 PHAS=  232.0 FOM= 0.07
INDE  -2  11   1 FOBS=  297.2 SIGMA=  1.0 PHAS=    6.2 FOM= 0.98
INDE  -2  11   2 FOBS=  244.1 SIGMA=  1.1 PHAS=  316.8 FOM= 0.89
INDE  -2  11   3 FOBS=   79.2 SIGMA=  3.4 PHAS=   26.4 FOM= 0.91
INDE  -2  11   4 FOBS=   79.7 SIGMA=  3.9 PHAS=  126.8 FOM= 0.89
INDE  -2  11   5 FOBS=   65.6 SIGMA=  4.8 PHAS=  121.8 FOM= 0.80
INDE  -2  11   6 FOBS=   97.0 SIGMA=  3.5 PHAS=  189.0 FOM= 0.96
INDE  -2  11   7 FOBS=   79.6 SIGMA=  5.2 PHAS=  180.4 FOM= 0.64
INDE  -2  11   8 FOBS=  358.8 SIGMA=  1.5 PHAS=  191.2 FOM= 0.98
INDE  -2  11   9 FOBS=  232.9 SIGMA=  2.2 PHAS=  266.4 FOM= 0.97
INDE  -2  11  10 FOBS=  110.4 SIGMA=  5.4 PHAS=   55.1 FOM= 0.66
INDE  -2  11  11 FOBS=  141.5 SIGMA=  4.6 PHAS=   29.8 FOM= 0.33
INDE  -2  11  12 FOBS=  234.1 SIGMA=  2.8 PHAS=  224.0 FOM= 0.63
INDE  -2  11  13 FOBS=  209.8 SIGMA=  3.4 PHAS=  158.9 FOM= 0.63
INDE  -2  11  14 FOBS=   81.9 SIGMA=  9.8 PHAS=  330.6 FOM= 0.37
INDE  -2  11  15 FOBS=  191.4 SIGMA=  3.8 PHAS=  204.1 FOM= 0.73
INDE  -2  11  16 FOBS=  109.8 SIGMA=  6.5 PHAS=   19.0 FOM= 0.16
INDE  -2  12   1 FOBS=  131.3 SIGMA=  2.1 PHAS=   65.6 FOM= 0.94
INDE  -2  12   2 FOBS=  142.2 SIGMA=  2.0 PHAS=  298.2 FOM= 0.85
INDE  -2  12   3 FOBS=  350.2 SIGMA=  1.1 PHAS=  354.2 FOM= 0.96
INDE  -2  12   4 FOBS=  167.4 SIGMA=  2.0 PHAS=  316.7 FOM= 0.98
INDE  -2  12   5 FOBS=  231.3 SIGMA=  1.6 PHAS=   10.9 FOM= 0.99
INDE  -2  12   6 FOBS=  126.0 SIGMA=  3.3 PHAS=   97.1 FOM= 0.71
INDE  -2  12   7 FOBS=  188.4 SIGMA=  2.3 PHAS=  136.2 FOM= 0.85
INDE  -2  12   8 FOBS=  144.5 SIGMA=  3.0 PHAS=   84.5 FOM= 0.95
INDE  -2  12   9 FOBS=   66.5 SIGMA=  7.4 PHAS=  230.6 FOM= 0.01
INDE  -2  12  10 FOBS=  169.2 SIGMA=  3.3 PHAS=  149.7 FOM= 0.89
INDE  -2  12  11 FOBS=   92.7 SIGMA=  8.0 PHAS=  256.7 FOM= 0.39
INDE  -2  12  12 FOBS=   71.1 SIGMA= 10.3 PHAS=   22.2 FOM= 0.23
INDE  -2  12  13 FOBS=  220.4 SIGMA=  3.0 PHAS=  334.0 FOM= 0.20
INDE  -2  12  14 FOBS=  127.1 SIGMA=  6.2 PHAS=  100.7 FOM= 0.09
INDE  -2  12  15 FOBS=  179.4 SIGMA=  4.5 PHAS=   95.2 FOM= 0.29
INDE  -2  13   1 FOBS=  101.6 SIGMA=  2.9 PHAS=   59.9 FOM= 0.95
INDE  -2  13   2 FOBS=   34.2 SIGMA=  8.5 PHAS=  199.3 FOM= 0.34
INDE  -2  13   3 FOBS=  243.5 SIGMA=  1.3 PHAS=  293.8 FOM= 0.95
INDE  -2  13   4 FOBS=  112.9 SIGMA=  3.2 PHAS=  256.3 FOM= 0.76
INDE  -2  13   5 FOBS=   63.1 SIGMA=  5.0 PHAS=  173.6 FOM= 0.90
INDE  -2  13   6 FOBS=  304.5 SIGMA=  1.5 PHAS=   65.4 FOM= 0.98
INDE  -2  13   7 FOBS=  447.8 SIGMA=  1.2 PHAS=  359.5 FOM= 0.76
INDE  -2  13   8 FOBS=  233.4 SIGMA=  2.1 PHAS=  300.2 FOM= 0.88
INDE  -2  13   9 FOBS=  238.4 SIGMA=  2.1 PHAS=  231.3 FOM= 0.97
INDE  -2  13  10 FOBS=   83.6 SIGMA=  6.6 PHAS=  276.0 FOM= 0.53
INDE  -2  13  11 FOBS=  144.3 SIGMA=  4.5 PHAS=   88.4 FOM= 0.39
INDE  -2  13  12 FOBS=  253.5 SIGMA=  2.6 PHAS=  295.0 FOM= 0.57
INDE  -2  13  13 FOBS=   55.0 SIGMA= 25.6 PHAS=  189.6 FOM= 0.20
INDE  -2  13  14 FOBS=  145.3 SIGMA=  5.3 PHAS=   59.4 FOM= 0.44
INDE  -2  13  15 FOBS=   55.7 SIGMA= 17.7 PHAS=  215.7 FOM= 0.06
INDE  -2  14   1 FOBS=  196.2 SIGMA=  1.8 PHAS=   71.2 FOM= 0.88
INDE  -2  14   2 FOBS=  395.6 SIGMA=  1.0 PHAS=   69.8 FOM= 0.97
INDE  -2  14   3 FOBS=  233.4 SIGMA=  1.5 PHAS=  311.9 FOM= 0.99
INDE  -2  14   4 FOBS=  372.9 SIGMA=  1.2 PHAS=  138.9 FOM= 1.00
INDE  -2  14   5 FOBS=  298.4 SIGMA=  1.4 PHAS=   80.6 FOM= 0.95
INDE  -2  14   6 FOBS=  134.3 SIGMA=  2.8 PHAS=  147.8 FOM= 0.88
INDE  -2  14   7 FOBS=  445.1 SIGMA=  1.4 PHAS=  217.6 FOM= 0.96
INDE  -2  14   8 FOBS=  160.3 SIGMA=  3.1 PHAS=   24.9 FOM= 0.95
INDE  -2  14   9 FOBS=  170.6 SIGMA=  3.1 PHAS=  290.0 FOM= 0.79
INDE  -2  14  10 FOBS=  238.3 SIGMA=  2.4 PHAS=  172.4 FOM= 0.44
INDE  -2  14  11 FOBS=  340.3 SIGMA=  1.9 PHAS=  294.5 FOM= 0.96
INDE  -2  14  12 FOBS=  105.1 SIGMA=  6.2 PHAS=   40.6 FOM= 0.78
INDE  -2  14  13 FOBS=   76.4 SIGMA=  8.4 PHAS=  268.7 FOM= 0.24
INDE  -2  14  14 FOBS=   97.5 SIGMA=  7.1 PHAS=  274.7 FOM= 0.29
```

Fig. 10A-70

```
INDE  -2  14  15  FOBS=   82.2  SIGMA=   8.9  PHAS=   75.9  FOM=  0.02
INDE  -2  15   1  FOBS=  170.5  SIGMA=   2.0  PHAS=  344.0  FOM=  0.96
INDE  -2  15   2  FOBS=  189.0  SIGMA=   1.9  PHAS=  158.2  FOM=  0.98
INDE  -2  15   3  FOBS=  490.7  SIGMA=   1.1  PHAS=  253.3  FOM=  0.90
INDE  -2  15   4  FOBS=  322.2  SIGMA=   1.4  PHAS=  147.8  FOM=  0.92
INDE  -2  15   5  FOBS=  424.2  SIGMA=   1.1  PHAS=   28.8  FOM=  0.96
INDE  -2  15   6  FOBS=  500.7  SIGMA=   1.3  PHAS=  139.1  FOM=  0.99
INDE  -2  15   7  FOBS=  267.1  SIGMA=   1.8  PHAS=  320.6  FOM=  0.93
INDE  -2  15   8  FOBS=  393.9  SIGMA=   1.5  PHAS=  137.2  FOM=  0.92
INDE  -2  15   9  FOBS=  219.9  SIGMA=   2.4  PHAS=  220.9  FOM=  0.80
INDE  -2  15  10  FOBS=  167.2  SIGMA=   3.6  PHAS=  321.2  FOM=  0.54
INDE  -2  15  11  FOBS=  271.1  SIGMA=   2.3  PHAS=   15.5  FOM=  0.90
INDE  -2  15  12  FOBS=  117.7  SIGMA=   5.3  PHAS=  288.2  FOM=  0.26
INDE  -2  15  13  FOBS=  221.6  SIGMA=   2.8  PHAS=  319.8  FOM=  0.85
INDE  -2  15  14  FOBS=   96.7  SIGMA=   6.5  PHAS=  348.9  FOM=  0.58
INDE  -2  15  15  FOBS=  114.5  SIGMA=   5.7  PHAS=  175.2  FOM=  0.20
INDE  -2  16   1  FOBS=  126.5  SIGMA=   2.6  PHAS=  127.5  FOM=  0.81
INDE  -2  16   2  FOBS=  122.8  SIGMA=   3.0  PHAS=  109.7  FOM=  0.94
INDE  -2  16   3  FOBS=  190.2  SIGMA=   1.9  PHAS=  192.9  FOM=  0.97
INDE  -2  16   4  FOBS=  472.2  SIGMA=   1.1  PHAS=  211.6  FOM=  0.98
INDE  -2  16   5  FOBS=  499.8  SIGMA=   1.6  PHAS=  268.5  FOM=  0.99
INDE  -2  16   6  FOBS=  482.0  SIGMA=   1.2  PHAS=  159.5  FOM=  0.97
INDE  -2  16   7  FOBS=  176.8  SIGMA=   2.4  PHAS=  106.9  FOM=  0.74
INDE  -2  16   8  FOBS=  230.1  SIGMA=   2.4  PHAS=  252.3  FOM=  0.92
INDE  -2  16   9  FOBS=   35.2  SIGMA=  14.5  PHAS=  199.9  FOM=  0.31
INDE  -2  16  10  FOBS=  228.5  SIGMA=   2.6  PHAS=   87.1  FOM=  0.96
INDE  -2  16  11  FOBS=  151.3  SIGMA=   4.2  PHAS=   21.4  FOM=  0.78
INDE  -2  16  12  FOBS=  103.4  SIGMA=   5.7  PHAS=   99.6  FOM=  0.65
INDE  -2  16  13  FOBS=  123.9  SIGMA=   5.0  PHAS=  130.7  FOM=  0.22
INDE  -2  16  14  FOBS=   81.3  SIGMA=   7.4  PHAS=   17.7  FOM=  0.12
INDE  -2  16  15  FOBS=   97.5  SIGMA=  11.1  PHAS=  258.3  FOM=  0.30
INDE  -2  17   1  FOBS=  204.3  SIGMA=   1.8  PHAS=  125.8  FOM=  0.96
INDE  -2  17   2  FOBS=  216.5  SIGMA=   1.7  PHAS=  192.9  FOM=  0.89
INDE  -2  17   3  FOBS=  157.4  SIGMA=   2.6  PHAS=  355.5  FOM=  0.83
INDE  -2  17   4  FOBS=  305.4  SIGMA=   1.5  PHAS=   12.1  FOM=  0.97
INDE  -2  17   5  FOBS=  316.1  SIGMA=   1.8  PHAS=   18.3  FOM=  0.72
INDE  -2  17   6  FOBS=  397.0  SIGMA=   1.3  PHAS=  206.3  FOM=  0.79
INDE  -2  17   7  FOBS=  374.0  SIGMA=   1.4  PHAS=  294.3  FOM=  1.00
INDE  -2  17   8  FOBS=  155.9  SIGMA=   3.1  PHAS=  340.5  FOM=  0.87
INDE  -2  17   9  FOBS=  143.5  SIGMA=   4.2  PHAS=  155.1  FOM=  0.63
INDE  -2  17  10  FOBS=  236.4  SIGMA=   2.4  PHAS=   34.7  FOM=  0.34
INDE  -2  17  11  FOBS=  154.9  SIGMA=   4.1  PHAS=  266.6  FOM=  0.83
INDE  -2  17  12  FOBS=  182.6  SIGMA=   3.3  PHAS=   45.0  FOM=  0.38
INDE  -2  17  13  FOBS=   43.1  SIGMA=  18.4  PHAS=   88.5  FOM=  0.14
INDE  -2  17  14  FOBS=  175.5  SIGMA=   3.5  PHAS=  310.3  FOM=  0.46
INDE  -2  18   1  FOBS=  125.7  SIGMA=   2.8  PHAS=  311.5  FOM=  0.87
INDE  -2  18   2  FOBS=  570.4  SIGMA=   1.0  PHAS=  294.3  FOM=  0.86
INDE  -2  18   3  FOBS=  269.2  SIGMA=   1.7  PHAS=  113.3  FOM=  0.94
INDE  -2  18   4  FOBS=  415.2  SIGMA=   1.5  PHAS=   38.6  FOM=  1.00
INDE  -2  18   5  FOBS=  377.3  SIGMA=   1.9  PHAS=  188.7  FOM=  0.63
INDE  -2  18   6  FOBS=  229.6  SIGMA=   1.9  PHAS=  144.7  FOM=  0.76
INDE  -2  18   7  FOBS=  323.3  SIGMA=   1.6  PHAS=  121.4  FOM=  0.98
INDE  -2  18   8  FOBS=  194.1  SIGMA=   2.6  PHAS=  138.1  FOM=  0.89
INDE  -2  18   9  FOBS=  268.7  SIGMA=   2.4  PHAS=  217.6  FOM=  0.58
INDE  -2  18  10  FOBS=  159.1  SIGMA=   3.9  PHAS=  235.9  FOM=  0.50
INDE  -2  18  11  FOBS=  135.9  SIGMA=   4.4  PHAS=  124.9  FOM=  0.17
INDE  -2  18  12  FOBS=  160.4  SIGMA=   3.9  PHAS=  143.8  FOM=  0.04
INDE  -2  18  13  FOBS=   86.1  SIGMA=   6.6  PHAS=  134.4  FOM=  0.39
INDE  -2  18  14  FOBS=   81.4  SIGMA=   7.3  PHAS=  311.8  FOM=  0.02
INDE  -2  19   1  FOBS=   84.1  SIGMA=   3.9  PHAS=  224.9  FOM=  0.92
INDE  -2  19   2  FOBS=  256.8  SIGMA=   1.6  PHAS=  353.0  FOM=  0.17
INDE  -2  19   3  FOBS=  174.7  SIGMA=   2.1  PHAS=  115.2  FOM=  0.95
INDE  -2  19   4  FOBS=  177.3  SIGMA=   2.5  PHAS=  305.5  FOM=  0.38
INDE  -2  19   5  FOBS=  349.6  SIGMA=   1.6  PHAS=  125.5  FOM=  0.94
INDE  -2  19   6  FOBS=  477.5  SIGMA=   1.2  PHAS=   16.2  FOM=  0.91
INDE  -2  19   7  FOBS=  286.4  SIGMA=   1.8  PHAS=  193.7  FOM=  0.78
INDE  -2  19   8  FOBS=   71.1  SIGMA=   7.0  PHAS=   95.7  FOM=  0.13
INDE  -2  19   9  FOBS=  124.5  SIGMA=   4.7  PHAS=   15.2  FOM=  0.15
INDE  -2  19  10  FOBS=  189.0  SIGMA=   3.1  PHAS=   79.4  FOM=  0.54
INDE  -2  19  11  FOBS=  152.0  SIGMA=   4.1  PHAS=   33.5  FOM=  0.60
INDE  -2  19  12  FOBS=  121.3  SIGMA=   4.9  PHAS=  102.8  FOM=  0.03
```

Fig. 10A-71

```
INDE  -2  19  13  FOBS=  138.3  SIGMA=   4.4  PHAS=  114.1  FOM=  0.17
INDE  -2  19  14  FOBS=   96.0  SIGMA=   7.0  PHAS=  313.4  FOM=  0.12
INDE  -2  20   1  FOBS=  337.2  SIGMA=   1.4  PHAS=  145.7  FOM=  0.80
INDE  -2  20   2  FOBS=  277.1  SIGMA=   1.7  PHAS=  283.1  FOM=  0.53
INDE  -2  20   3  FOBS=   71.8  SIGMA=   5.2  PHAS=  285.9  FOM=  0.47
INDE  -2  20   4  FOBS=   73.3  SIGMA=   5.2  PHAS=  156.9  FOM=  0.58
INDE  -2  20   5  FOBS=  225.4  SIGMA=   2.3  PHAS=  277.9  FOM=  0.51
INDE  -2  20   6  FOBS=  559.8  SIGMA=   1.6  PHAS=  314.8  FOM=  0.80
INDE  -2  20   7  FOBS=   57.0  SIGMA=   8.1  PHAS=   55.9  FOM=  0.10
INDE  -2  20   8  FOBS=  211.3  SIGMA=   2.4  PHAS=  255.4  FOM=  0.74
INDE  -2  20   9  FOBS=   67.7  SIGMA=   7.9  PHAS=  133.7  FOM=  0.09
INDE  -2  20  10  FOBS=  204.9  SIGMA=   2.8  PHAS=    3.0  FOM=  0.69
INDE  -2  20  11  FOBS=  164.7  SIGMA=   3.8  PHAS=  194.7  FOM=  0.78
INDE  -2  20  12  FOBS=  138.3  SIGMA=   4.3  PHAS=   41.6  FOM=  0.11
INDE  -2  20  13  FOBS=  106.6  SIGMA=   5.5  PHAS=  288.0  FOM=  0.14
INDE  -2  21   1  FOBS=  128.7  SIGMA=   3.1  PHAS=  150.0  FOM=  0.77
INDE  -2  21   2  FOBS=  122.6  SIGMA=   3.4  PHAS=    0.9  FOM=  0.54
INDE  -2  21   3  FOBS=  325.4  SIGMA=   1.4  PHAS=  356.2  FOM=  0.63
INDE  -2  21   4  FOBS=  350.4  SIGMA=   1.5  PHAS=   52.5  FOM=  0.97
INDE  -2  21   5  FOBS=  167.4  SIGMA=   2.7  PHAS=  193.3  FOM=  0.51
INDE  -2  21   6  FOBS=  194.2  SIGMA=   2.9  PHAS=  313.0  FOM=  0.94
INDE  -2  21   7  FOBS=  190.6  SIGMA=   2.8  PHAS=  243.9  FOM=  0.57
INDE  -2  21   8  FOBS=  130.0  SIGMA=   3.9  PHAS=  291.6  FOM=  0.04
INDE  -2  21   9  FOBS=  406.7  SIGMA=   1.5  PHAS=   41.4  FOM=  1.00
INDE  -2  21  10  FOBS=  207.7  SIGMA=   3.0  PHAS=  233.1  FOM=  0.86
INDE  -2  21  11  FOBS=   58.0  SIGMA=   9.8  PHAS=  144.1  FOM=  0.05
INDE  -2  21  12  FOBS=   53.5  SIGMA=  29.6  PHAS=   17.1  FOM=  0.12
INDE  -2  21  13  FOBS=   72.6  SIGMA=   7.7  PHAS=  338.8  FOM=  0.13
INDE  -2  22   1  FOBS=   92.7  SIGMA=   4.2  PHAS=   55.7  FOM=  0.72
INDE  -2  22   2  FOBS=   87.3  SIGMA=   5.7  PHAS=  107.1  FOM=  0.81
INDE  -2  22   3  FOBS=  391.3  SIGMA=   1.3  PHAS=  341.4  FOM=  0.97
INDE  -2  22   4  FOBS=  124.6  SIGMA=   3.4  PHAS=   46.4  FOM=  0.94
INDE  -2  22   5  FOBS=  488.7  SIGMA=   1.2  PHAS=  289.6  FOM=  0.97
INDE  -2  22   6  FOBS=  254.6  SIGMA=   2.2  PHAS=  175.5  FOM=  0.89
INDE  -2  22   7  FOBS=  343.5  SIGMA=   1.9  PHAS=  129.1  FOM=  0.99
INDE  -2  22   8  FOBS=  231.7  SIGMA=   2.3  PHAS=   65.0  FOM=  0.99
INDE  -2  22   9  FOBS=  205.1  SIGMA=   2.5  PHAS=  251.4  FOM=  0.63
INDE  -2  22  10  FOBS=  164.2  SIGMA=   3.4  PHAS=  181.6  FOM=  0.07
INDE  -2  22  11  FOBS=  132.7  SIGMA=   4.3  PHAS=  359.7  FOM=  0.31
INDE  -2  22  12  FOBS=   66.6  SIGMA=   8.5  PHAS=   19.3  FOM=  0.12
INDE  -2  23   1  FOBS=  110.6  SIGMA=   3.7  PHAS=  139.2  FOM=  0.90
INDE  -2  23   2  FOBS=  432.0  SIGMA=   1.7  PHAS=   16.8  FOM=  1.00
INDE  -2  23   3  FOBS=  261.7  SIGMA=   1.7  PHAS=  352.1  FOM=  0.79
INDE  -2  23   4  FOBS=  311.4  SIGMA=   1.6  PHAS=  315.8  FOM=  0.97
INDE  -2  23   5  FOBS=  123.2  SIGMA=   3.8  PHAS=  335.1  FOM=  0.92
INDE  -2  23   6  FOBS=  205.5  SIGMA=   2.2  PHAS=  243.5  FOM=  0.60
INDE  -2  23   7  FOBS=   78.0  SIGMA=   7.2  PHAS=  328.3  FOM=  0.03
INDE  -2  23   8  FOBS=  241.3  SIGMA=   2.5  PHAS=  323.4  FOM=  0.87
INDE  -2  23   9  FOBS=  155.3  SIGMA=   3.2  PHAS=   43.0  FOM=  0.68
INDE  -2  23  10  FOBS=   95.0  SIGMA=   5.2  PHAS=   30.5  FOM=  0.11
INDE  -2  23  11  FOBS=  124.8  SIGMA=   4.9  PHAS=  357.2  FOM=  0.64
INDE  -2  23  12  FOBS=  110.7  SIGMA=   5.1  PHAS=  143.7  FOM=  0.17
INDE  -2  24   1  FOBS=   93.2  SIGMA=   4.3  PHAS=  121.9  FOM=  0.53
INDE  -2  24   2  FOBS=  360.0  SIGMA=   2.0  PHAS=  146.7  FOM=  1.00
INDE  -2  24   3  FOBS=  110.0  SIGMA=   4.0  PHAS=   56.3  FOM=  0.96
INDE  -2  24   4  FOBS=  165.0  SIGMA=   2.5  PHAS=   13.0  FOM=  0.93
INDE  -2  24   5  FOBS=  127.3  SIGMA=   3.7  PHAS=  238.1  FOM=  0.29
INDE  -2  24   6  FOBS=  163.2  SIGMA=   2.8  PHAS=  226.5  FOM=  0.91
INDE  -2  24   7  FOBS=  273.1  SIGMA=   2.3  PHAS=   47.9  FOM=  0.95
INDE  -2  24   8  FOBS=  200.7  SIGMA=   2.8  PHAS=  307.0  FOM=  0.91
INDE  -2  24   9  FOBS=  117.8  SIGMA=   4.8  PHAS=  223.9  FOM=  0.79
INDE  -2  24  10  FOBS=  161.1  SIGMA=   3.3  PHAS=   42.3  FOM=  0.59
INDE  -2  24  11  FOBS=  114.2  SIGMA=   5.0  PHAS=  265.2  FOM=  0.73
INDE  -2  24  12  FOBS=   77.2  SIGMA=  32.4  PHAS=  189.6  FOM=  0.20
INDE  -2  25   1  FOBS=  175.2  SIGMA=   2.4  PHAS=   35.3  FOM=  0.85
INDE  -2  25   2  FOBS=  124.6  SIGMA=   5.0  PHAS=    6.8  FOM=  0.62
INDE  -2  25   3  FOBS=  151.3  SIGMA=   2.8  PHAS=  233.1  FOM=  0.86
INDE  -2  25   4  FOBS=  274.4  SIGMA=   1.7  PHAS=  338.5  FOM=  0.54
INDE  -2  25   5  FOBS=  183.3  SIGMA=   2.5  PHAS=  343.8  FOM=  0.80
INDE  -2  25   6  FOBS=  170.3  SIGMA=   2.7  PHAS=  334.0  FOM=  0.83
INDE  -2  25   7  FOBS=  145.3  SIGMA=   3.4  PHAS=  140.7  FOM=  0.19
```

Fig. 10A-72

```
INDE  -2  25   8  FOBS=  157.8  SIGMA=   3.1  PHAS=    1.9  FOM=  0.33
INDE  -2  25   9  FOBS=  227.2  SIGMA=   2.3  PHAS=  154.8  FOM=  0.88
INDE  -2  25  10  FOBS=   37.9  SIGMA=  19.9  PHAS=  318.5  FOM=  0.19
INDE  -2  25  11  FOBS=  150.6  SIGMA=   3.7  PHAS=  160.3  FOM=  0.54
INDE  -2  26   1  FOBS=  141.6  SIGMA=   3.0  PHAS=   85.7  FOM=  0.82
INDE  -2  26   2  FOBS=  237.1  SIGMA=   2.7  PHAS=  170.1  FOM=  0.13
INDE  -2  26   3  FOBS=  210.2  SIGMA=   2.0  PHAS=  231.5  FOM=  0.97
INDE  -2  26   4  FOBS=  331.2  SIGMA=   1.5  PHAS=   23.9  FOM=  0.99
INDE  -2  26   5  FOBS=   62.7  SIGMA=   7.4  PHAS=   58.5  FOM=  0.29
INDE  -2  26   6  FOBS=  113.0  SIGMA=   4.2  PHAS=   75.3  FOM=  0.83
INDE  -2  26   7  FOBS=  140.6  SIGMA=   3.4  PHAS=  267.0  FOM=  0.96
INDE  -2  26   8  FOBS=  172.6  SIGMA=   3.2  PHAS=   63.1  FOM=  0.90
INDE  -2  26   9  FOBS=  125.9  SIGMA=   3.8  PHAS=  237.8  FOM=  0.10
INDE  -2  26  10  FOBS=   55.6  SIGMA=   9.0  PHAS=  227.1  FOM=  0.10
INDE  -2  27   1  FOBS=  221.3  SIGMA=   2.0  PHAS=  209.2  FOM=  0.49
INDE  -2  27   2  FOBS=  100.4  SIGMA=   6.0  PHAS=   17.1  FOM=  0.44
INDE  -2  27   3  FOBS=  195.1  SIGMA=   2.2  PHAS=  301.5  FOM=  0.95
INDE  -2  27   4  FOBS=  269.5  SIGMA=   1.9  PHAS=  354.7  FOM=  0.96
INDE  -2  27   5  FOBS=   68.1  SIGMA=   6.5  PHAS=  272.2  FOM=  0.13
INDE  -2  27   6  FOBS=   97.0  SIGMA=   4.5  PHAS=  187.6  FOM=  0.38
INDE  -2  27   7  FOBS=  135.6  SIGMA=   3.4  PHAS=  285.0  FOM=  0.57
INDE  -2  27   8  FOBS=  190.9  SIGMA=   2.8  PHAS=  287.0  FOM=  0.87
INDE  -2  27   9  FOBS=  120.3  SIGMA=   3.9  PHAS=  225.4  FOM=  0.85
INDE  -2  27  10  FOBS=  127.6  SIGMA=   5.0  PHAS=  332.0  FOM=  0.51
INDE  -2  28   1  FOBS=  331.7  SIGMA=   1.5  PHAS=   56.8  FOM=  0.83
INDE  -2  28   2  FOBS=  282.6  SIGMA=   2.0  PHAS=  198.4  FOM=  0.08
INDE  -2  28   3  FOBS=   80.8  SIGMA=   5.1  PHAS=  155.2  FOM=  0.12
INDE  -2  28   4  FOBS=   51.7  SIGMA=   8.2  PHAS=  283.0  FOM=  0.19
INDE  -2  28   5  FOBS=  139.0  SIGMA=   3.3  PHAS=   51.1  FOM=  0.84
INDE  -2  28   6  FOBS=  193.3  SIGMA=   2.3  PHAS=  102.1  FOM=  0.39
INDE  -2  28   7  FOBS=  210.3  SIGMA=   2.2  PHAS=  317.3  FOM=  0.97
INDE  -2  28   8  FOBS=  224.0  SIGMA=   2.2  PHAS=   94.1  FOM=  0.96
INDE  -2  28   9  FOBS=  166.4  SIGMA=   3.0  PHAS=  304.4  FOM=  0.19
INDE  -2  29   1  FOBS=   47.3  SIGMA=   8.8  PHAS=  141.6  FOM=  0.23
INDE  -2  29   2  FOBS=  126.0  SIGMA=   4.1  PHAS=    8.3  FOM=  0.77
INDE  -2  29   3  FOBS=  111.4  SIGMA=   3.7  PHAS=   73.6  FOM=  0.25
INDE  -2  29   4  FOBS=  194.1  SIGMA=   2.3  PHAS=  125.4  FOM=  0.96
INDE  -2  29   5  FOBS=  141.9  SIGMA=   3.2  PHAS=   48.9  FOM=  0.71
INDE  -2  29   6  FOBS=  188.5  SIGMA=   2.4  PHAS=  300.0  FOM=  0.95
INDE  -2  29   7  FOBS=  166.7  SIGMA=   2.6  PHAS=  186.6  FOM=  0.49
INDE  -2  29   8  FOBS=  114.7  SIGMA=   3.9  PHAS=  108.5  FOM=  0.05
INDE  -2  30   1  FOBS=   44.1  SIGMA=  10.1  PHAS=  270.4  FOM=  0.16
INDE  -2  30   2  FOBS=  201.4  SIGMA=   2.2  PHAS=   55.5  FOM=  0.95
INDE  -2  30   3  FOBS=  229.1  SIGMA=   1.9  PHAS=  233.9  FOM=  0.96
INDE  -2  30   4  FOBS=   88.6  SIGMA=   4.6  PHAS=   80.5  FOM=  0.60
INDE  -2  30   5  FOBS=  117.6  SIGMA=   3.8  PHAS=  303.5  FOM=  0.78
INDE  -2  30   6  FOBS=  208.5  SIGMA=   2.1  PHAS=   28.7  FOM=  0.76
INDE  -2  30   7  FOBS=   90.0  SIGMA=   4.7  PHAS=  108.2  FOM=  0.24
INDE  -2  31   1  FOBS=  205.0  SIGMA=   2.3  PHAS=  290.6  FOM=  0.69
INDE  -2  31   2  FOBS=   59.2  SIGMA=   5.4  PHAS=  217.6  FOM=  0.74
INDE  -2  31   3  FOBS=   35.5  SIGMA=  16.9  PHAS=  140.3  FOM=  0.15
INDE  -2  31   4  FOBS=  126.1  SIGMA=   3.3  PHAS=    4.2  FOM=  0.69
INDE  -2  31   5  FOBS=   27.5  SIGMA=  14.2  PHAS=  351.5  FOM=  0.05
INDE  -2  31   6  FOBS=  103.4  SIGMA=   4.2  PHAS=  109.2  FOM=  0.30
INDE  -2  32   1  FOBS=   82.5  SIGMA=   5.5  PHAS=   61.1  FOM=  0.26
INDE  -2  32   2  FOBS=   53.5  SIGMA=   7.9  PHAS=  127.9  FOM=  0.25
INDE  -2  32   3  FOBS=   34.3  SIGMA=  14.5  PHAS=  301.5  FOM=  0.21
INDE  -2  32   4  FOBS=   77.2  SIGMA=   5.1  PHAS=    5.5  FOM=  0.02
INDE  -2  33   1  FOBS=  162.0  SIGMA=   3.3  PHAS=  235.4  FOM=  0.81
INDE  -2  33   2  FOBS=   58.2  SIGMA=  10.2  PHAS=  289.9  FOM=  0.13
INDE  -1   0   3  FOBS=  147.4  SIGMA=   1.8  PHAS=    0.0  FOM=  1.00
INDE  -1   0   4  FOBS=  183.4  SIGMA=   1.9  PHAS=  180.0  FOM=  0.12
INDE  -1   0   5  FOBS=   91.4  SIGMA=   4.3  PHAS=    0.0  FOM=  1.00
INDE  -1   0   6  FOBS=  295.3  SIGMA=   1.9  PHAS=  180.0  FOM=  1.00
INDE  -1   0   7  FOBS=   64.3  SIGMA=  11.9  PHAS=    0.0  FOM=  0.20
INDE  -1   0   8  FOBS=  142.3  SIGMA=   5.0  PHAS=  180.0  FOM=  0.71
INDE  -1   0   9  FOBS=   51.8  SIGMA=  14.0  PHAS=    0.0  FOM=  0.36
INDE  -1   0  10  FOBS=  289.4  SIGMA=   2.8  PHAS=  180.0  FOM=  0.00
INDE  -1   0  11  FOBS=  100.7  SIGMA=   8.8  PHAS=  180.0  FOM=  0.03
INDE  -1   0  12  FOBS=  224.8  SIGMA=   4.5  PHAS=    0.0  FOM=  0.55
INDE  -1   0  13  FOBS=   91.2  SIGMA=  11.7  PHAS=  180.0  FOM=  0.13
```

Fig. 10A-73

```
INDE  -1  0 14 FOBS=   65.4 SIGMA= 17.0 PHAS=   0.0 FOM= 0.08
INDE  -1  0 15 FOBS=   38.4 SIGMA= 46.3 PHAS= 180.0 FOM= 0.15
INDE  -1  0 16 FOBS=  104.6 SIGMA= 10.2 PHAS= 180.0 FOM= 0.04
INDE  -1  1  3 FOBS=  189.9 SIGMA=  1.0 PHAS= 329.7 FOM= 0.95
INDE  -1  1  4 FOBS=  424.4 SIGMA=  1.0 PHAS= 128.5 FOM= 1.00
INDE  -1  1  5 FOBS=  379.5 SIGMA=  1.2 PHAS= 110.3 FOM= 0.98
INDE  -1  1  6 FOBS=  307.5 SIGMA=  1.4 PHAS= 279.7 FOM= 0.98
INDE  -1  1  7 FOBS=  487.2 SIGMA=  1.4 PHAS= 136.2 FOM= 0.98
INDE  -1  1  8 FOBS=  134.5 SIGMA=  4.5 PHAS= 285.5 FOM= 0.94
INDE  -1  1  9 FOBS=  105.9 SIGMA=  5.1 PHAS=  61.2 FOM= 0.76
INDE  -1  1 10 FOBS=  219.5 SIGMA=  2.6 PHAS= 170.9 FOM= 0.12
INDE  -1  1 11 FOBS=   57.3 SIGMA= 12.1 PHAS= 264.7 FOM= 0.17
INDE  -1  1 12 FOBS=  193.5 SIGMA=  3.6 PHAS=  10.4 FOM= 0.60
INDE  -1  1 13 FOBS=  211.5 SIGMA=  3.6 PHAS= 119.2 FOM= 0.12
INDE  -1  1 14 FOBS=  204.5 SIGMA=  3.8 PHAS= 120.7 FOM= 0.40
INDE  -1  1 15 FOBS=  116.7 SIGMA=  6.4 PHAS= 358.0 FOM= 0.14
INDE  -1  1 16 FOBS=   92.4 SIGMA=  7.9 PHAS= 343.4 FOM= 0.18
INDE  -1  2  2 FOBS=  201.5 SIGMA=  1.1 PHAS= 168.1 FOM= 1.00
INDE  -1  2  3 FOBS=  536.4 SIGMA=  0.7 PHAS= 124.9 FOM= 1.00
INDE  -1  2  4 FOBS=  378.3 SIGMA=  0.8 PHAS=  62.9 FOM= 0.99
INDE  -1  2  5 FOBS=  253.0 SIGMA=  1.5 PHAS= 253.7 FOM= 0.97
INDE  -1  2  6 FOBS=  574.6 SIGMA=  1.2 PHAS= 229.6 FOM= 0.58
INDE  -1  2  7 FOBS=  163.5 SIGMA=  2.5 PHAS=  53.0 FOM= 0.45
INDE  -1  2  8 FOBS=  184.5 SIGMA=  2.8 PHAS= 196.9 FOM= 0.52
INDE  -1  2  9 FOBS=  123.5 SIGMA=  5.0 PHAS=  25.7 FOM= 0.88
INDE  -1  2 10 FOBS=  195.2 SIGMA=  2.9 PHAS= 155.6 FOM= 0.92
INDE  -1  2 11 FOBS=  204.1 SIGMA=  3.0 PHAS= 246.4 FOM= 0.85
INDE  -1  2 12 FOBS=  282.8 SIGMA=  2.5 PHAS=  20.2 FOM= 0.61
INDE  -1  2 13 FOBS=  103.0 SIGMA=  7.2 PHAS= 130.5 FOM= 0.43
INDE  -1  2 14 FOBS=   83.8 SIGMA=  9.0 PHAS= 320.5 FOM= 0.38
INDE  -1  2 15 FOBS=   76.2 SIGMA=  9.7 PHAS= 252.8 FOM= 0.08
INDE  -1  2 16 FOBS=  144.1 SIGMA=  5.3 PHAS= 199.5 FOM= 0.07
INDE  -1  3  2 FOBS=  166.0 SIGMA=  1.5 PHAS=  55.2 FOM= 0.71
INDE  -1  3  3 FOBS=  157.2 SIGMA=  1.3 PHAS= 257.4 FOM= 1.00
INDE  -1  3  4 FOBS=  429.4 SIGMA=  0.9 PHAS=  85.9 FOM= 0.97
INDE  -1  3  5 FOBS=  185.4 SIGMA=  1.9 PHAS=  20.7 FOM= 0.08
INDE  -1  3  6 FOBS=  359.5 SIGMA=  1.1 PHAS= 329.9 FOM= 0.99
INDE  -1  3  7 FOBS=  177.6 SIGMA=  2.2 PHAS= 187.9 FOM= 0.10
INDE  -1  3  8 FOBS=  221.7 SIGMA=  2.2 PHAS= 299.2 FOM= 0.64
INDE  -1  3  9 FOBS=  245.8 SIGMA=  2.4 PHAS= 206.3 FOM= 0.93
INDE  -1  3 10 FOBS=   70.9 SIGMA=  8.4 PHAS=   4.0 FOM= 0.05
INDE  -1  3 11 FOBS=  162.9 SIGMA=  4.1 PHAS= 266.6 FOM= 0.28
INDE  -1  3 12 FOBS=  194.4 SIGMA=  3.7 PHAS= 224.7 FOM= 0.35
INDE  -1  3 13 FOBS=   84.5 SIGMA=  9.1 PHAS=  33.4 FOM= 0.24
INDE  -1  3 14 FOBS=  199.2 SIGMA=  4.0 PHAS= 236.8 FOM= 0.68
INDE  -1  3 15 FOBS=   79.3 SIGMA=  9.4 PHAS= 106.5 FOM= 0.26
INDE  -1  3 16 FOBS=  190.2 SIGMA=  4.1 PHAS=  89.1 FOM= 0.26
INDE  -1  4  1 FOBS=  177.5 SIGMA=  1.6 PHAS= 144.3 FOM= 0.99
INDE  -1  4  2 FOBS=  136.2 SIGMA=  1.3 PHAS=  28.7 FOM= 0.97
INDE  -1  4  3 FOBS=  184.0 SIGMA=  1.1 PHAS=  51.0 FOM= 0.96
INDE  -1  4  4 FOBS=   99.0 SIGMA=  2.6 PHAS= 285.0 FOM= 0.98
INDE  -1  4  5 FOBS=  336.9 SIGMA=  1.2 PHAS= 321.1 FOM= 1.00
INDE  -1  4  6 FOBS=  230.7 SIGMA=  1.6 PHAS= 103.7 FOM= 0.85
INDE  -1  4  7 FOBS=  141.6 SIGMA=  2.8 PHAS=   3.5 FOM= 0.97
INDE  -1  4  8 FOBS=  201.3 SIGMA=  2.3 PHAS= 287.0 FOM= 0.52
INDE  -1  4  9 FOBS=  176.9 SIGMA=  3.0 PHAS= 308.0 FOM= 0.79
INDE  -1  4 10 FOBS=  197.7 SIGMA=  3.3 PHAS= 112.1 FOM= 0.77
INDE  -1  4 11 FOBS=  288.2 SIGMA=  2.3 PHAS=  87.1 FOM= 0.95
INDE  -1  4 12 FOBS=  216.8 SIGMA=  3.3 PHAS=  86.9 FOM= 0.39
INDE  -1  4 13 FOBS=  189.8 SIGMA=  4.1 PHAS= 295.7 FOM= 0.50
INDE  -1  4 14 FOBS=   53.6 SIGMA= 14.0 PHAS= 130.8 FOM= 0.22
INDE  -1  4 15 FOBS=   63.4 SIGMA= 45.5 PHAS= 289.7 FOM= 0.07
INDE  -1  4 16 FOBS=   51.0 SIGMA= 15.1 PHAS= 333.9 FOM= 0.04
INDE  -1  5  1 FOBS=  167.6 SIGMA=  1.9 PHAS= 242.0 FOM= 0.74
INDE  -1  5  2 FOBS=  405.5 SIGMA=  0.8 PHAS=   9.1 FOM= 0.71
INDE  -1  5  3 FOBS=  265.0 SIGMA=  1.2 PHAS= 267.7 FOM= 0.84
INDE  -1  5  4 FOBS=  281.2 SIGMA=  1.1 PHAS= 243.7 FOM= 0.97
INDE  -1  5  5 FOBS=  195.5 SIGMA=  1.6 PHAS= 313.9 FOM= 0.33
INDE  -1  5  6 FOBS=  139.4 SIGMA=  2.5 PHAS=  75.4 FOM= 0.90
INDE  -1  5  7 FOBS=  116.0 SIGMA=  3.9 PHAS= 215.2 FOM= 0.93
INDE  -1  5  8 FOBS=  259.2 SIGMA=  1.9 PHAS=  67.5 FOM= 0.95
```

Fig. 10A-74

```
INDE  -1  5   9 FOBS=  64.5 SIGMA=  8.2 PHAS= 275.8 FOM= 0.30
INDE  -1  5  10 FOBS= 360.7 SIGMA=  1.8 PHAS= 149.5 FOM= 0.97
INDE  -1  5  11 FOBS= 125.4 SIGMA=  6.1 PHAS= 335.7 FOM= 0.51
INDE  -1  5  12 FOBS= 217.7 SIGMA=  3.3 PHAS= 209.1 FOM= 0.04
INDE  -1  5  13 FOBS= 140.8 SIGMA=  5.5 PHAS=  67.9 FOM= 0.38
INDE  -1  5  14 FOBS= 102.3 SIGMA=  7.4 PHAS= 204.2 FOM= 0.20
INDE  -1  5  15 FOBS= 176.1 SIGMA=  4.5 PHAS= 131.5 FOM= 0.32
INDE  -1  5  16 FOBS= 153.1 SIGMA=  5.0 PHAS= 268.5 FOM= 0.12
INDE  -1  6   1 FOBS= 273.9 SIGMA=  0.9 PHAS= 129.9 FOM= 0.92
INDE  -1  6   2 FOBS= 414.0 SIGMA=  0.9 PHAS=   3.5 FOM= 0.83
INDE  -1  6   3 FOBS= 224.0 SIGMA=  1.2 PHAS=  95.3 FOM= 0.98
INDE  -1  6   4 FOBS= 213.5 SIGMA=  1.3 PHAS=   8.3 FOM= 0.95
INDE  -1  6   5 FOBS= 171.2 SIGMA=  1.9 PHAS=  16.3 FOM= 0.70
INDE  -1  6   6 FOBS= 100.6 SIGMA=  3.9 PHAS=  68.7 FOM= 0.59
INDE  -1  6   7 FOBS= 123.2 SIGMA=  3.6 PHAS= 281.0 FOM= 0.04
INDE  -1  6   8 FOBS= 142.8 SIGMA=  3.5 PHAS= 249.3 FOM= 0.64
INDE  -1  6   9 FOBS= 153.3 SIGMA=  3.4 PHAS= 189.3 FOM= 0.05
INDE  -1  6  10 FOBS= 112.0 SIGMA=  5.4 PHAS= 236.9 FOM= 0.10
INDE  -1  6  11 FOBS= 167.6 SIGMA=  4.6 PHAS=  27.1 FOM= 0.05
INDE  -1  6  12 FOBS= 123.5 SIGMA=  6.7 PHAS=   5.0 FOM= 0.03
INDE  -1  6  13 FOBS= 164.6 SIGMA=  4.8 PHAS= 237.1 FOM= 0.43
INDE  -1  6  14 FOBS=  82.4 SIGMA=  9.8 PHAS= 343.4 FOM= 0.15
INDE  -1  6  15 FOBS=  88.3 SIGMA=  8.5 PHAS=  27.4 FOM= 0.04
INDE  -1  6  16 FOBS=  61.4 SIGMA= 15.8 PHAS= 163.6 FOM= 0.06
INDE  -1  7   1 FOBS=  86.4 SIGMA=  2.7 PHAS= 210.1 FOM= 0.90
INDE  -1  7   2 FOBS=  90.6 SIGMA=  2.2 PHAS=  46.6 FOM= 0.94
INDE  -1  7   3 FOBS= 272.8 SIGMA=  1.0 PHAS= 154.2 FOM= 0.91
INDE  -1  7   4 FOBS= 402.2 SIGMA=  1.0 PHAS= 343.7 FOM= 0.98
INDE  -1  7   5 FOBS= 225.2 SIGMA=  1.5 PHAS=  90.9 FOM= 0.98
INDE  -1  7   6 FOBS= 129.3 SIGMA=  2.8 PHAS= 159.1 FOM= 0.84
INDE  -1  7   7 FOBS= 132.0 SIGMA=  3.4 PHAS= 323.7 FOM= 0.65
INDE  -1  7   8 FOBS= 329.2 SIGMA=  1.6 PHAS=  59.7 FOM= 0.77
INDE  -1  7   9 FOBS= 309.0 SIGMA=  1.8 PHAS= 160.7 FOM= 0.89
INDE  -1  7  10 FOBS= 173.7 SIGMA=  3.3 PHAS= 340.3 FOM= 0.76
INDE  -1  7  11 FOBS= 219.8 SIGMA=  3.0 PHAS= 257.4 FOM= 0.62
INDE  -1  7  12 FOBS= 155.9 SIGMA=  5.8 PHAS= 136.0 FOM= 0.38
INDE  -1  7  13 FOBS=  71.4 SIGMA= 11.0 PHAS= 285.5 FOM= 0.08
INDE  -1  7  14 FOBS= 109.9 SIGMA=  6.9 PHAS= 326.0 FOM= 0.10
INDE  -1  7  15 FOBS= 188.3 SIGMA=  4.1 PHAS= 175.1 FOM= 0.55
INDE  -1  7  16 FOBS= 146.6 SIGMA=  5.2 PHAS= 324.0 FOM= 0.04
INDE  -1  8   1 FOBS= 178.5 SIGMA=  2.0 PHAS= 303.1 FOM= 0.09
INDE  -1  8   2 FOBS= 183.9 SIGMA=  1.4 PHAS= 153.0 FOM= 0.93
INDE  -1  8   3 FOBS= 308.3 SIGMA=  1.0 PHAS=  55.3 FOM= 0.85
INDE  -1  8   4 FOBS= 230.8 SIGMA=  1.4 PHAS= 110.9 FOM= 0.94
INDE  -1  8   5 FOBS=  33.8 SIGMA= 13.3 PHAS= 190.4 FOM= 0.32
INDE  -1  8   6 FOBS=  89.8 SIGMA=  4.5 PHAS= 357.0 FOM= 0.84
INDE  -1  8   7 FOBS= 147.6 SIGMA=  3.2 PHAS= 160.3 FOM= 0.54
INDE  -1  8   8 FOBS= 170.0 SIGMA=  2.8 PHAS=  59.0 FOM= 0.76
INDE  -1  8   9 FOBS= 161.9 SIGMA=  3.2 PHAS= 172.1 FOM= 0.76
INDE  -1  8  10 FOBS= 273.4 SIGMA=  2.2 PHAS= 269.7 FOM= 0.24
INDE  -1  8  11 FOBS= 198.1 SIGMA=  2.3 PHAS= 358.3 FOM= 0.55
INDE  -1  8  12 FOBS=  73.0 SIGMA= 10.6 PHAS= 289.3 FOM= 0.13
INDE  -1  8  13 FOBS= 340.1 SIGMA=  2.6 PHAS= 151.1 FOM= 0.62
INDE  -1  8  14 FOBS= 164.0 SIGMA=  4.9 PHAS=  33.8 FOM= 0.47
INDE  -1  8  15 FOBS= 129.7 SIGMA=  5.8 PHAS= 215.2 FOM= 0.12
INDE  -1  8  16 FOBS=  52.6 SIGMA= 15.2 PHAS= 256.9 FOM= 0.05
INDE  -1  9   1 FOBS= 199.1 SIGMA=  1.5 PHAS= 209.5 FOM= 0.94
INDE  -1  9   2 FOBS= 238.9 SIGMA=  1.2 PHAS= 333.5 FOM= 0.99
INDE  -1  9   3 FOBS= 200.5 SIGMA=  1.4 PHAS= 159.2 FOM= 0.74
INDE  -1  9   4 FOBS= 162.3 SIGMA=  1.9 PHAS= 187.6 FOM= 0.89
INDE  -1  9   5 FOBS= 125.3 SIGMA=  3.4 PHAS= 261.5 FOM= 0.97
INDE  -1  9   6 FOBS=  62.6 SIGMA=  5.4 PHAS= 249.5 FOM= 0.45
INDE  -1  9   7 FOBS= 125.4 SIGMA=  3.6 PHAS=  60.6 FOM= 0.85
INDE  -1  9   8 FOBS= 696.0 SIGMA=  1.3 PHAS= 259.7 FOM= 0.95
INDE  -1  9   9 FOBS=  99.1 SIGMA=  5.6 PHAS=  56.1 FOM= 0.49
INDE  -1  9  10 FOBS= 188.4 SIGMA=  3.1 PHAS=  70.8 FOM= 0.06
INDE  -1  9  11 FOBS=  84.1 SIGMA=  8.2 PHAS= 327.3 FOM= 0.26
INDE  -1  9  12 FOBS= 213.4 SIGMA=  3.4 PHAS= 188.9 FOM= 0.51
INDE  -1  9  13 FOBS=  68.1 SIGMA= 12.9 PHAS=   9.3 FOM= 0.07
INDE  -1  9  14 FOBS=  84.6 SIGMA= 10.3 PHAS= 120.0 FOM= 0.12
INDE  -1  9  15 FOBS= 151.9 SIGMA=  5.1 PHAS= 294.8 FOM= 0.35
```

Fig. 10A-75

```
INDE  -1   9  16  FOBS=   67.1  SIGMA=  11.8  PHAS=  214.7  FOM= 0.00
INDE  -1  10   1  FOBS=  109.7  SIGMA=   2.2  PHAS=  276.0  FOM= 0.50
INDE  -1  10   2  FOBS=  288.1  SIGMA=   1.2  PHAS=  244.9  FOM= 0.96
INDE  -1  10   3  FOBS=  302.0  SIGMA=   1.1  PHAS=  224.2  FOM= 0.88
INDE  -1  10   4  FOBS=  120.9  SIGMA=   2.5  PHAS=  184.1  FOM= 0.71
INDE  -1  10   5  FOBS=   96.9  SIGMA=   3.4  PHAS=  344.2  FOM= 0.90
INDE  -1  10   6  FOBS=   74.6  SIGMA=   5.6  PHAS=   42.1  FOM= 0.80
INDE  -1  10   7  FOBS=  293.4  SIGMA=   1.6  PHAS=  191.1  FOM= 0.92
INDE  -1  10   8  FOBS=  221.6  SIGMA=   2.2  PHAS=  357.2  FOM= 0.95
INDE  -1  10   9  FOBS=  506.2  SIGMA=   1.5  PHAS=  104.4  FOM= 0.99
INDE  -1  10  10  FOBS=  119.9  SIGMA=   5.6  PHAS=  233.7  FOM= 0.13
INDE  -1  10  11  FOBS=  200.3  SIGMA=   3.4  PHAS=  263.7  FOM= 0.66
INDE  -1  10  12  FOBS=   62.8  SIGMA=  11.7  PHAS=  121.7  FOM= 0.16
INDE  -1  10  13  FOBS=   94.2  SIGMA=   7.8  PHAS=  193.6  FOM= 0.02
INDE  -1  10  14  FOBS=  160.5  SIGMA=   5.5  PHAS=   38.4  FOM= 0.34
INDE  -1  10  15  FOBS=  104.9  SIGMA=   8.1  PHAS=  322.7  FOM= 0.19
INDE  -1  10  16  FOBS=   68.6  SIGMA=  11.4  PHAS=   89.9  FOM= 0.01
INDE  -1  11   1  FOBS=  259.6  SIGMA=   1.2  PHAS=  206.5  FOM= 1.00
INDE  -1  11   2  FOBS=  339.8  SIGMA=   1.0  PHAS=  221.9  FOM= 1.00
INDE  -1  11   3  FOBS=  317.4  SIGMA=   1.1  PHAS=  312.8  FOM= 0.99
INDE  -1  11   4  FOBS=  301.0  SIGMA=   1.3  PHAS=  148.2  FOM= 0.98
INDE  -1  11   5  FOBS=  247.3  SIGMA=   1.5  PHAS=  260.3  FOM= 0.99
INDE  -1  11   6  FOBS=  136.6  SIGMA=   3.3  PHAS=   42.0  FOM= 0.89
INDE  -1  11   7  FOBS=  161.8  SIGMA=   2.5  PHAS=  346.3  FOM= 0.89
INDE  -1  11   8  FOBS=  202.0  SIGMA=   2.4  PHAS=   73.1  FOM= 0.87
INDE  -1  11   9  FOBS=  386.6  SIGMA=   1.6  PHAS=    2.0  FOM= 0.76
INDE  -1  11  10  FOBS=  289.2  SIGMA=   2.2  PHAS=   81.6  FOM= 0.93
INDE  -1  11  11  FOBS=  190.9  SIGMA=   4.2  PHAS=  336.9  FOM= 0.18
INDE  -1  11  12  FOBS=  337.9  SIGMA=   2.4  PHAS=  115.5  FOM= 0.97
INDE  -1  11  13  FOBS=  135.8  SIGMA=   5.6  PHAS=   34.9  FOM= 0.78
INDE  -1  11  14  FOBS=  130.8  SIGMA=   5.8  PHAS=  270.4  FOM= 0.43
INDE  -1  11  15  FOBS=   44.8  SIGMA=  21.1  PHAS=  113.7  FOM= 0.09
INDE  -1  11  16  FOBS=  122.3  SIGMA=   9.3  PHAS=   18.4  FOM= 0.12
INDE  -1  12   1  FOBS=  130.1  SIGMA=   2.1  PHAS=    2.7  FOM= 0.97
INDE  -1  12   2  FOBS=   98.7  SIGMA=   3.0  PHAS=  334.1  FOM= 0.96
INDE  -1  12   3  FOBS=  194.7  SIGMA=   1.6  PHAS=  267.8  FOM= 0.62
INDE  -1  12   4  FOBS=  232.9  SIGMA=   1.5  PHAS=  218.2  FOM= 0.99
INDE  -1  12   5  FOBS=  174.7  SIGMA=   2.1  PHAS=  165.2  FOM= 0.97
INDE  -1  12   6  FOBS=   61.9  SIGMA=   6.1  PHAS=  123.4  FOM= 0.05
INDE  -1  12   7  FOBS=  232.1  SIGMA=   1.9  PHAS=  251.2  FOM= 0.81
INDE  -1  12   8  FOBS=  201.5  SIGMA=   2.4  PHAS=  127.4  FOM= 0.76
INDE  -1  12   9  FOBS=  316.6  SIGMA=   1.8  PHAS=  162.4  FOM= 0.98
INDE  -1  12  10  FOBS=  218.7  SIGMA=   2.8  PHAS=  159.9  FOM= 0.93
INDE  -1  12  11  FOBS=  132.6  SIGMA=   5.2  PHAS=  337.6  FOM= 0.77
INDE  -1  12  12  FOBS=  211.6  SIGMA=   3.7  PHAS=  221.8  FOM= 0.20
INDE  -1  12  13  FOBS=  248.0  SIGMA=   3.2  PHAS=  214.6  FOM= 0.63
INDE  -1  12  14  FOBS=   47.0  SIGMA=  20.0  PHAS=  120.4  FOM= 0.33
INDE  -1  12  15  FOBS=  101.1  SIGMA=   7.4  PHAS=  236.0  FOM= 0.06
INDE  -1  13   1  FOBS=  226.3  SIGMA=   1.6  PHAS=  118.3  FOM= 0.96
INDE  -1  13   2  FOBS=  337.0  SIGMA=   1.5  PHAS=  245.3  FOM= 1.00
INDE  -1  13   3  FOBS=  122.5  SIGMA=   2.8  PHAS=  272.4  FOM= 0.95
INDE  -1  13   4  FOBS=   97.6  SIGMA=   3.5  PHAS=  274.9  FOM= 0.89
INDE  -1  13   5  FOBS=  188.7  SIGMA=   2.0  PHAS=  312.1  FOM= 0.80
INDE  -1  13   6  FOBS=  140.9  SIGMA=   2.6  PHAS=  134.7  FOM= 0.90
INDE  -1  13   7  FOBS=  213.0  SIGMA=   2.4  PHAS=  223.3  FOM= 0.97
INDE  -1  13   8  FOBS=  126.7  SIGMA=   4.2  PHAS=   46.2  FOM= 0.86
INDE  -1  13   9  FOBS=  155.8  SIGMA=   3.6  PHAS=  323.5  FOM= 0.80
INDE  -1  13  10  FOBS=  270.5  SIGMA=   2.3  PHAS=  109.6  FOM= 0.96
INDE  -1  13  11  FOBS=   63.8  SIGMA=  10.5  PHAS=  340.5  FOM= 0.22
INDE  -1  13  12  FOBS=  195.0  SIGMA=   3.7  PHAS=  219.9  FOM= 0.58
INDE  -1  13  13  FOBS=   52.5  SIGMA=  14.1  PHAS=   25.1  FOM= 0.23
INDE  -1  13  14  FOBS=   59.2  SIGMA=  18.4  PHAS=  205.1  FOM= 0.05
INDE  -1  13  15  FOBS=   85.1  SIGMA=   9.8  PHAS=  230.9  FOM= 0.11
INDE  -1  14   1  FOBS=   73.9  SIGMA=   4.3  PHAS=  100.7  FOM= 0.86
INDE  -1  14   2  FOBS=  252.5  SIGMA=   1.7  PHAS=  328.6  FOM= 1.00
INDE  -1  14   3  FOBS=  158.2  SIGMA=   2.6  PHAS=  198.8  FOM= 0.89
INDE  -1  14   4  FOBS=  463.3  SIGMA=   1.2  PHAS=  316.9  FOM= 0.08
INDE  -1  14   5  FOBS=  131.8  SIGMA=   2.9  PHAS=  217.4  FOM= 0.93
INDE  -1  14   6  FOBS=   65.1  SIGMA=   6.3  PHAS=   62.8  FOM= 0.72
INDE  -1  14   7  FOBS=  412.2  SIGMA=   1.3  PHAS=  302.6  FOM= 0.97
INDE  -1  14   8  FOBS=  445.6  SIGMA=   1.3  PHAS=   28.8  FOM= 0.89
```

Fig. 10A-76

```
INDE  -1  14   9 FOBS=  215.4 SIGMA=   2.4 PHAS=  223.1 FOM=  0.87
INDE  -1  14  10 FOBS=  211.7 SIGMA=   2.8 PHAS=  154.3 FOM=  0.78
INDE  -1  14  11 FOBS=  337.3 SIGMA=   2.1 PHAS=  205.3 FOM=  0.87
INDE  -1  14  12 FOBS=  132.1 SIGMA=   5.2 PHAS=  310.1 FOM=  0.07
INDE  -1  14  13 FOBS=  183.7 SIGMA=   3.7 PHAS=   10.3 FOM=  0.24
INDE  -1  14  14 FOBS=  129.1 SIGMA=   5.5 PHAS=  163.2 FOM=  0.78
INDE  -1  15   1 FOBS=  121.9 SIGMA=   2.6 PHAS=  238.7 FOM=  0.44
INDE  -1  15   2 FOBS=  165.5 SIGMA=   2.4 PHAS=  241.7 FOM=  0.84
INDE  -1  15   3 FOBS=   73.6 SIGMA=   4.5 PHAS=  319.6 FOM=  0.65
INDE  -1  15   4 FOBS=  138.5 SIGMA=   2.4 PHAS=   59.4 FOM=  0.77
INDE  -1  15   5 FOBS=  514.5 SIGMA=   1.1 PHAS=  134.5 FOM=  0.98
INDE  -1  15   6 FOBS=  300.1 SIGMA=   1.6 PHAS=  249.5 FOM=  0.93
INDE  -1  15   7 FOBS=  172.7 SIGMA=   2.6 PHAS=   20.4 FOM=  0.92
INDE  -1  15   8 FOBS=  104.3 SIGMA=   5.4 PHAS=  117.2 FOM=  0.86
INDE  -1  15   9 FOBS=   82.2 SIGMA=   6.6 PHAS=  276.9 FOM=  0.15
INDE  -1  15  10 FOBS=  207.1 SIGMA=   3.0 PHAS=  248.5 FOM=  0.89
INDE  -1  15  11 FOBS=  211.0 SIGMA=   3.0 PHAS=  287.1 FOM=  0.93
INDE  -1  15  12 FOBS=   72.3 SIGMA=   9.3 PHAS=  196.6 FOM=  0.18
INDE  -1  15  13 FOBS=  112.5 SIGMA=   5.9 PHAS=  265.4 FOM=  0.12
INDE  -1  15  14 FOBS=   82.8 SIGMA=   8.4 PHAS=   64.3 FOM=  0.06
INDE  -1  15  15 FOBS=  107.2 SIGMA=   6.4 PHAS=  211.4 FOM=  0.01
INDE  -1  16   1 FOBS=  160.0 SIGMA=   2.1 PHAS=  279.4 FOM=  0.88
INDE  -1  16   2 FOBS=  216.4 SIGMA=   1.7 PHAS=   19.8 FOM=  0.93
INDE  -1  16   3 FOBS=  209.3 SIGMA=   2.1 PHAS=  149.1 FOM=  0.99
INDE  -1  16   4 FOBS=  221.7 SIGMA=   1.9 PHAS=    3.6 FOM=  0.98
INDE  -1  16   5 FOBS=  126.8 SIGMA=   3.2 PHAS=  225.6 FOM=  0.25
INDE  -1  16   6 FOBS=  161.3 SIGMA=   2.5 PHAS=   55.4 FOM=  0.35
INDE  -1  16   7 FOBS=  504.7 SIGMA=   1.2 PHAS=   59.0 FOM=  1.00
INDE  -1  16   8 FOBS=  221.1 SIGMA=   2.3 PHAS=  289.4 FOM=  0.76
INDE  -1  16   9 FOBS=  222.6 SIGMA=   2.5 PHAS=   65.7 FOM=  0.65
INDE  -1  16  10 FOBS=  193.6 SIGMA=   3.1 PHAS=  264.2 FOM=  0.29
INDE  -1  16  11 FOBS=  133.7 SIGMA=   4.8 PHAS=   70.8 FOM=  0.37
INDE  -1  16  12 FOBS=  158.1 SIGMA=   4.2 PHAS=  249.4 FOM=  0.02
INDE  -1  16  13 FOBS=  165.7 SIGMA=   4.1 PHAS=  255.3 FOM=  0.22
INDE  -1  16  14 FOBS=  131.7 SIGMA=   5.0 PHAS=   46.2 FOM=  0.21
INDE  -1  17   1 FOBS=  250.7 SIGMA=   1.5 PHAS=  225.0 FOM=  0.60
INDE  -1  17   2 FOBS=  122.5 SIGMA=   2.8 PHAS=  147.6 FOM=  0.87
INDE  -1  17   3 FOBS=  119.3 SIGMA=   3.3 PHAS=  142.1 FOM=  0.97
INDE  -1  17   4 FOBS=  384.9 SIGMA=   1.5 PHAS=  340.3 FOM=  0.97
INDE  -1  17   5 FOBS=  344.9 SIGMA=   1.5 PHAS=  189.9 FOM=  0.79
INDE  -1  17   6 FOBS=   98.9 SIGMA=   4.4 PHAS=   30.6 FOM=  0.74
INDE  -1  17   7 FOBS=  296.2 SIGMA=   1.8 PHAS=  121.4 FOM=  0.82
INDE  -1  17   8 FOBS=  102.9 SIGMA=   5.1 PHAS=  195.6 FOM=  0.28
INDE  -1  17   9 FOBS=  178.0 SIGMA=   3.8 PHAS=  116.2 FOM=  0.07
INDE  -1  17  10 FOBS=  103.7 SIGMA=   5.7 PHAS=  114.4 FOM=  0.11
INDE  -1  17  11 FOBS=   57.4 SIGMA=  10.6 PHAS=   19.0 FOM=  0.06
INDE  -1  17  12 FOBS=   82.2 SIGMA=   8.2 PHAS=  244.3 FOM=  0.40
INDE  -1  17  13 FOBS=  127.2 SIGMA=   5.0 PHAS=  132.5 FOM=  0.24
INDE  -1  17  14 FOBS=  153.5 SIGMA=   4.3 PHAS=  129.6 FOM=  0.55
INDE  -1  18   1 FOBS=  504.9 SIGMA=   1.3 PHAS=  152.1 FOM=  0.99
INDE  -1  18   2 FOBS=  350.4 SIGMA=   1.2 PHAS=  195.6 FOM=  0.98
INDE  -1  18   3 FOBS=  170.2 SIGMA=   2.3 PHAS=  305.6 FOM=  0.57
INDE  -1  18   4 FOBS=  445.3 SIGMA=   1.7 PHAS=    1.2 FOM=  0.85
INDE  -1  18   5 FOBS=  167.8 SIGMA=   2.8 PHAS=   76.7 FOM=  0.30
INDE  -1  18   6 FOBS=  311.9 SIGMA=   1.7 PHAS=  285.7 FOM=  0.73
INDE  -1  18   7 FOBS=  432.7 SIGMA=   1.4 PHAS=  303.3 FOM=  0.91
INDE  -1  18   8 FOBS=  115.8 SIGMA=   4.5 PHAS=  335.9 FOM=  0.78
INDE  -1  18   9 FOBS=   94.2 SIGMA=   6.6 PHAS=  115.1 FOM=  0.69
INDE  -1  18  10 FOBS=  306.9 SIGMA=   2.1 PHAS=  232.9 FOM=  0.49
INDE  -1  18  11 FOBS=   98.5 SIGMA=   6.1 PHAS=  323.5 FOM=  0.26
INDE  -1  18  12 FOBS=   48.3 SIGMA=  24.2 PHAS=  110.6 FOM=  0.24
INDE  -1  18  13 FOBS=   82.9 SIGMA=   7.4 PHAS=  242.9 FOM=  0.19
INDE  -1  18  14 FOBS=   83.9 SIGMA=   7.5 PHAS=  266.4 FOM=  0.06
INDE  -1  19   1 FOBS=  263.1 SIGMA=   1.5 PHAS=  228.0 FOM=  0.96
INDE  -1  19   2 FOBS=  322.8 SIGMA=   1.3 PHAS=  330.0 FOM=  1.00
INDE  -1  19   3 FOBS=  164.2 SIGMA=   2.3 PHAS=    0.1 FOM=  0.13
INDE  -1  19   4 FOBS=  256.5 SIGMA=   1.7 PHAS=  152.4 FOM=  0.98
INDE  -1  19   5 FOBS=  304.3 SIGMA=   1.8 PHAS=   45.2 FOM=  0.99
INDE  -1  19   6 FOBS=  184.6 SIGMA=   2.7 PHAS=  168.7 FOM=  0.46
INDE  -1  19   7 FOBS=  119.2 SIGMA=   4.7 PHAS=  192.2 FOM=  0.35
INDE  -1  19   8 FOBS=  341.3 SIGMA=   1.8 PHAS=  152.1 FOM=  0.44
```

Fig. 10A-77

```
INDE  -1  19   9 FOBS=  139.9 SIGMA=   4.1 PHAS=  92.5 FOM= 0.13
INDE  -1  19  10 FOBS=  239.3 SIGMA=   2.5 PHAS= 340.9 FOM= 0.82
INDE  -1  19  11 FOBS=   56.1 SIGMA=  12.2 PHAS= 188.5 FOM= 0.03
INDE  -1  19  12 FOBS=   34.5 SIGMA=  15.3 PHAS=  69.0 FOM= 0.17
INDE  -1  19  13 FOBS=   73.9 SIGMA=   8.3 PHAS= 259.7 FOM= 0.12
INDE  -1  19  14 FOBS=  104.4 SIGMA=  22.9 PHAS= 146.3 FOM= 0.02
INDE  -1  20   1 FOBS=  169.9 SIGMA=   2.2 PHAS= 194.8 FOM= 0.97
INDE  -1  20   2 FOBS=  441.2 SIGMA=   1.1 PHAS= 236.8 FOM= 0.86
INDE  -1  20   3 FOBS=  132.4 SIGMA=   3.0 PHAS= 138.4 FOM= 0.84
INDE  -1  20   4 FOBS=  105.0 SIGMA=   3.9 PHAS= 101.2 FOM= 0.68
INDE  -1  20   5 FOBS=  138.5 SIGMA=   3.4 PHAS=  85.5 FOM= 0.45
INDE  -1  20   6 FOBS=  341.3 SIGMA=   1.8 PHAS=  83.1 FOM= 0.86
INDE  -1  20   7 FOBS=  153.4 SIGMA=   3.7 PHAS=  28.5 FOM= 0.19
INDE  -1  20   8 FOBS=  296.6 SIGMA=   2.0 PHAS= 285.6 FOM= 0.89
INDE  -1  20   9 FOBS=  144.9 SIGMA=   4.1 PHAS= 154.1 FOM= 0.43
INDE  -1  20  10 FOBS=  146.2 SIGMA=   4.5 PHAS= 227.9 FOM= 0.59
INDE  -1  20  11 FOBS=  174.6 SIGMA=   3.6 PHAS= 314.1 FOM= 0.53
INDE  -1  20  12 FOBS=   98.2 SIGMA=   6.2 PHAS= 183.6 FOM= 0.56
INDE  -1  20  13 FOBS=  101.9 SIGMA=   5.8 PHAS=  18.4 FOM= 0.46
INDE  -1  21   1 FOBS=  276.8 SIGMA=   1.6 PHAS= 201.1 FOM= 0.96
INDE  -1  21   2 FOBS=  313.3 SIGMA=   1.4 PHAS= 159.0 FOM= 0.91
INDE  -1  21   3 FOBS=   74.3 SIGMA=   5.2 PHAS=  88.3 FOM= 0.77
INDE  -1  21   4 FOBS=  442.8 SIGMA=   1.2 PHAS= 195.7 FOM= 1.00
INDE  -1  21   5 FOBS=  149.2 SIGMA=   3.5 PHAS= 155.4 FOM= 0.62
INDE  -1  21   6 FOBS=  259.2 SIGMA=   2.2 PHAS= 269.2 FOM= 0.96
INDE  -1  21   7 FOBS=  157.3 SIGMA=   3.8 PHAS=   4.0 FOM= 0.26
INDE  -1  21   8 FOBS=  151.3 SIGMA=   4.2 PHAS= 133.6 FOM= 0.39
INDE  -1  21   9 FOBS=  183.9 SIGMA=   3.0 PHAS= 131.2 FOM= 0.60
INDE  -1  21  10 FOBS=  214.7 SIGMA=   2.9 PHAS= 291.3 FOM= 0.22
INDE  -1  21  11 FOBS=  120.3 SIGMA=   4.9 PHAS= 315.5 FOM= 0.07
INDE  -1  21  12 FOBS=  191.2 SIGMA=   3.1 PHAS= 168.3 FOM= 0.78
INDE  -1  21  13 FOBS=   37.7 SIGMA=  16.4 PHAS=   5.8 FOM= 0.10
INDE  -1  22   1 FOBS=  115.6 SIGMA=   3.7 PHAS= 245.9 FOM= 0.94
INDE  -1  22   2 FOBS=  314.8 SIGMA=   1.5 PHAS= 349.4 FOM= 0.98
INDE  -1  22   3 FOBS=  128.7 SIGMA=   3.5 PHAS=  99.8 FOM= 0.95
INDE  -1  22   4 FOBS=  257.3 SIGMA=   1.8 PHAS= 100.3 FOM= 0.95
INDE  -1  22   5 FOBS=   85.0 SIGMA=   5.9 PHAS= 107.0 FOM= 0.31
INDE  -1  22   6 FOBS=  215.6 SIGMA=   2.5 PHAS= 133.1 FOM= 0.94
INDE  -1  22   7 FOBS=   58.6 SIGMA=   9.1 PHAS= 257.1 FOM= 0.19
INDE  -1  22   8 FOBS=  162.8 SIGMA=   3.6 PHAS= 164.6 FOM= 0.61
INDE  -1  22   9 FOBS=  315.6 SIGMA=   2.1 PHAS=   2.4 FOM= 0.68
INDE  -1  22  10 FOBS=  276.5 SIGMA=   2.1 PHAS= 132.3 FOM= 0.63
INDE  -1  22  11 FOBS=   51.5 SIGMA=  12.1 PHAS= 160.9 FOM= 0.35
INDE  -1  22  12 FOBS=  148.0 SIGMA=   4.1 PHAS= 269.3 FOM= 0.06
INDE  -1  23   1 FOBS=  368.3 SIGMA=   1.9 PHAS=  44.8 FOM= 0.97
INDE  -1  23   2 FOBS=  307.7 SIGMA=   1.5 PHAS= 148.1 FOM= 0.96
INDE  -1  23   3 FOBS=  139.9 SIGMA=   3.2 PHAS=  53.6 FOM= 0.94
INDE  -1  23   4 FOBS=   47.5 SIGMA=   8.9 PHAS= 288.9 FOM= 0.18
INDE  -1  23   5 FOBS=  169.6 SIGMA=   2.7 PHAS= 270.8 FOM= 0.95
INDE  -1  23   6 FOBS=   69.9 SIGMA=   6.6 PHAS= 217.7 FOM= 0.14
INDE  -1  23   7 FOBS=  405.8 SIGMA=   1.5 PHAS= 148.0 FOM= 0.94
INDE  -1  23   8 FOBS=  177.4 SIGMA=   3.0 PHAS= 100.9 FOM= 0.88
INDE  -1  23   9 FOBS=   51.9 SIGMA=  14.0 PHAS= 286.7 FOM= 0.29
INDE  -1  23  10 FOBS=  233.6 SIGMA=   2.7 PHAS= 226.2 FOM= 0.94
INDE  -1  23  11 FOBS=  172.2 SIGMA=   3.8 PHAS= 319.7 FOM= 0.77
INDE  -1  23  12 FOBS=  141.0 SIGMA=   4.3 PHAS= 337.3 FOM= 0.59
INDE  -1  24   1 FOBS=  273.8 SIGMA=   2.4 PHAS= 210.6 FOM= 0.47
INDE  -1  24   2 FOBS=  335.3 SIGMA=   1.5 PHAS= 341.9 FOM= 1.00
INDE  -1  24   3 FOBS=  134.4 SIGMA=   3.5 PHAS=  93.8 FOM= 0.95
INDE  -1  24   4 FOBS=  212.1 SIGMA=   2.3 PHAS= 340.8 FOM= 0.97
INDE  -1  24   5 FOBS=  184.0 SIGMA=   2.6 PHAS= 286.9 FOM= 0.63
INDE  -1  24   6 FOBS=  267.8 SIGMA=   2.3 PHAS= 208.9 FOM= 1.00
INDE  -1  24   7 FOBS=  162.0 SIGMA=   2.9 PHAS= 111.1 FOM= 0.93
INDE  -1  24   8 FOBS=  118.0 SIGMA=   4.4 PHAS= 140.0 FOM= 0.14
INDE  -1  24   9 FOBS=  121.0 SIGMA=   4.5 PHAS= 171.3 FOM= 0.80
INDE  -1  24  10 FOBS=   93.4 SIGMA=   6.5 PHAS=  55.1 FOM= 0.63
INDE  -1  24  11 FOBS=  157.7 SIGMA=   4.2 PHAS= 309.3 FOM= 0.06
INDE  -1  25   1 FOBS=  296.7 SIGMA=   2.3 PHAS=  24.4 FOM= 0.61
INDE  -1  25   2 FOBS=  355.4 SIGMA=   1.4 PHAS=   7.7 FOM= 0.97
INDE  -1  25   3 FOBS=   99.6 SIGMA=   4.5 PHAS=  22.5 FOM= 0.89
INDE  -1  25   4 FOBS=  202.8 SIGMA=   2.4 PHAS= 342.7 FOM= 0.96
```

Fig. 10A-78

```
INDE  -1  25   5  FOBS=  386.6  SIGMA=   1.5  PHAS=  288.1  FOM=  0.94
INDE  -1  25   6  FOBS=  222.0  SIGMA=   2.5  PHAS=  160.9  FOM=  0.90
INDE  -1  25   7  FOBS=   68.7  SIGMA=   6.0  PHAS=  151.1  FOM=  0.77
INDE  -1  25   8  FOBS=   85.3  SIGMA=   5.8  PHAS=  199.7  FOM=  0.71
INDE  -1  25   9  FOBS=  160.3  SIGMA=   3.3  PHAS=  290.6  FOM=  0.26
INDE  -1  25  10  FOBS=   78.1  SIGMA=   6.5  PHAS=   58.2  FOM=  0.19
INDE  -1  25  11  FOBS=   49.4  SIGMA=  12.5  PHAS=  117.5  FOM=  0.10
INDE  -1  26   1  FOBS=  258.0  SIGMA=   2.6  PHAS=  232.7  FOM=  0.96
INDE  -1  26   2  FOBS=  254.0  SIGMA=   1.8  PHAS=  292.2  FOM=  0.98
INDE  -1  26   3  FOBS=  161.3  SIGMA=   2.7  PHAS=   20.8  FOM=  0.81
INDE  -1  26   4  FOBS=  159.6  SIGMA=   2.9  PHAS=   66.0  FOM=  0.73
INDE  -1  26   5  FOBS=  238.6  SIGMA=   2.0  PHAS=    3.6  FOM=  0.81
INDE  -1  26   6  FOBS=  141.0  SIGMA=   3.4  PHAS=  299.0  FOM=  0.12
INDE  -1  26   7  FOBS=  176.6  SIGMA=   2.9  PHAS=  306.6  FOM=  0.86
INDE  -1  26   8  FOBS=   49.4  SIGMA=  10.9  PHAS=  223.0  FOM=  0.13
INDE  -1  26   9  FOBS=   73.0  SIGMA=   6.8  PHAS=  295.6  FOM=  0.10
INDE  -1  26  10  FOBS=  164.8  SIGMA=   3.2  PHAS=   91.8  FOM=  0.89
INDE  -1  27   1  FOBS=   51.2  SIGMA=  12.0  PHAS=  270.5  FOM=  0.17
INDE  -1  27   2  FOBS=  139.9  SIGMA=   3.1  PHAS=  114.4  FOM=  0.94
INDE  -1  27   3  FOBS=  128.8  SIGMA=   3.5  PHAS=   79.4  FOM=  0.86
INDE  -1  27   4  FOBS=  348.9  SIGMA=   1.6  PHAS=  175.5  FOM=  0.72
INDE  -1  27   5  FOBS=  204.9  SIGMA=   2.3  PHAS=  280.0  FOM=  0.87
INDE  -1  27   6  FOBS=  231.8  SIGMA=   2.1  PHAS=  163.1  FOM=  0.96
INDE  -1  27   7  FOBS=  114.3  SIGMA=   4.9  PHAS=  358.7  FOM=  0.77
INDE  -1  27   8  FOBS=  195.4  SIGMA=   2.5  PHAS=  169.8  FOM=  0.95
INDE  -1  27   9  FOBS=  141.1  SIGMA=   3.6  PHAS=    8.8  FOM=  0.28
INDE  -1  27  10  FOBS=  132.0  SIGMA=   5.6  PHAS=  115.0  FOM=  0.00
INDE  -1  28   1  FOBS=   93.1  SIGMA=   6.5  PHAS=  340.2  FOM=  0.15
INDE  -1  28   2  FOBS=  163.3  SIGMA=   2.5  PHAS=  259.4  FOM=  0.87
INDE  -1  28   3  FOBS=   42.1  SIGMA=  23.0  PHAS=  288.0  FOM=  0.22
INDE  -1  28   4  FOBS=  111.5  SIGMA=   4.1  PHAS=  320.7  FOM=  0.14
INDE  -1  28   5  FOBS=  168.7  SIGMA=   2.6  PHAS=  261.8  FOM=  0.83
INDE  -1  28   6  FOBS=  277.7  SIGMA=   1.8  PHAS=  284.6  FOM=  0.89
INDE  -1  28   7  FOBS=  177.2  SIGMA=   3.0  PHAS=  156.2  FOM=  0.25
INDE  -1  28   8  FOBS=  244.9  SIGMA=   2.0  PHAS=    4.8  FOM=  0.74
INDE  -1  28   9  FOBS=   70.4  SIGMA=   6.7  PHAS=  196.4  FOM=  0.02
INDE  -1  29   1  FOBS=  192.8  SIGMA=   2.7  PHAS=  342.2  FOM=  0.20
INDE  -1  29   2  FOBS=  233.8  SIGMA=   1.9  PHAS=  338.1  FOM=  0.91
INDE  -1  29   3  FOBS=  371.4  SIGMA=   1.4  PHAS=  288.6  FOM=  0.99
INDE  -1  29   4  FOBS=  202.4  SIGMA=   2.3  PHAS=  137.1  FOM=  0.21
INDE  -1  29   5  FOBS=   45.0  SIGMA=  13.0  PHAS=   97.4  FOM=  0.20
INDE  -1  29   6  FOBS=  154.5  SIGMA=   3.1  PHAS=  314.9  FOM=  0.81
INDE  -1  29   7  FOBS=   93.0  SIGMA=   4.9  PHAS=  280.7  FOM=  0.49
INDE  -1  29   8  FOBS=  125.4  SIGMA=   4.3  PHAS=  252.6  FOM=  0.82
INDE  -1  30   1  FOBS=  112.6  SIGMA=   4.2  PHAS=   78.3  FOM=  0.55
INDE  -1  30   2  FOBS=  202.4  SIGMA=   2.1  PHAS=  324.8  FOM=  0.49
INDE  -1  30   3  FOBS=  129.4  SIGMA=   3.4  PHAS=  324.5  FOM=  0.46
INDE  -1  30   4  FOBS=  114.4  SIGMA=   4.0  PHAS=  145.0  FOM=  0.83
INDE  -1  30   5  FOBS=   47.8  SIGMA=   8.6  PHAS=   40.3  FOM=  0.11
INDE  -1  30   6  FOBS=  148.4  SIGMA=   3.1  PHAS=   27.4  FOM=  0.90
INDE  -1  30   7  FOBS=  205.1  SIGMA=   2.3  PHAS=  177.3  FOM=  0.95
INDE  -1  31   1  FOBS=  217.4  SIGMA=   2.1  PHAS=  326.3  FOM=  0.96
INDE  -1  31   2  FOBS=  108.6  SIGMA=   4.2  PHAS=  271.2  FOM=  0.77
INDE  -1  31   3  FOBS=  116.7  SIGMA=   3.6  PHAS=  217.0  FOM=  0.22
INDE  -1  31   4  FOBS=  152.8  SIGMA=   2.9  PHAS=  275.1  FOM=  0.65
INDE  -1  31   5  FOBS=   70.5  SIGMA=   6.0  PHAS=  264.7  FOM=  0.32
INDE  -1  31   6  FOBS=  117.3  SIGMA=   3.7  PHAS=  218.0  FOM=  0.10
INDE  -1  32   1  FOBS=  141.0  SIGMA=   3.1  PHAS=   15.2  FOM=  0.83
INDE  -1  32   2  FOBS=  106.5  SIGMA=   4.2  PHAS=  299.0  FOM=  0.12
INDE  -1  32   3  FOBS=  165.9  SIGMA=   2.4  PHAS=  358.2  FOM=  0.70
INDE  -1  32   4  FOBS=   68.5  SIGMA=   6.1  PHAS=  268.6  FOM=  0.48
INDE  -1  32   5  FOBS=   78.1  SIGMA=  14.2  PHAS=  325.3  FOM=  0.04
INDE  -1  33   1  FOBS=   93.1  SIGMA=   4.4  PHAS=   56.7  FOM=  0.26
INDE  -1  33   2  FOBS=   41.4  SIGMA=  14.7  PHAS=  183.1  FOM=  0.08
INDE   0   0   3  FOBS=   55.7  SIGMA=   6.6  PHAS=    0.0  FOM=  0.77
INDE   0   0   4  FOBS=  198.5  SIGMA=   2.0  PHAS=    0.0  FOM=  0.33
INDE   0   0   5  FOBS=  254.1  SIGMA=   2.0  PHAS=  180.0  FOM=  0.99
INDE   0   0   6  FOBS=   79.4  SIGMA=   7.0  PHAS=    0.0  FOM=  0.74
INDE   0   0   8  FOBS=  206.2  SIGMA=   4.7  PHAS=    0.0  FOM=  0.58
INDE   0   0   9  FOBS=   95.0  SIGMA=   9.7  PHAS=  180.0  FOM=  0.65
INDE   0   0  10  FOBS=  683.6  SIGMA=   2.0  PHAS=  180.0  FOM=  1.00
```

Fig. 10A-79

```
INDE  0  0  11  FOBS=   75.0  SIGMA= 12.6  PHAS=    0.0  FOM= 0.06
INDE  0  0  12  FOBS=  339.9  SIGMA=  3.3  PHAS=  180.0  FOM= 1.00
INDE  0  0  13  FOBS=  142.9  SIGMA=  8.2  PHAS=    0.0  FOM= 0.47
INDE  0  0  14  FOBS=   53.7  SIGMA= 29.8  PHAS=  180.0  FOM= 0.06
INDE  0  0  15  FOBS=  123.2  SIGMA=  9.2  PHAS=  180.0  FOM= 0.10
INDE  0  0  16  FOBS=   45.2  SIGMA= 29.0  PHAS=    0.0  FOM= 0.04
INDE  0  1   3  FOBS=  481.1  SIGMA=  0.8  PHAS=   51.8  FOM= 1.00
INDE  0  1   4  FOBS=  127.8  SIGMA=  1.9  PHAS=   41.3  FOM= 1.00
INDE  0  1   5  FOBS=  245.0  SIGMA=  1.4  PHAS=    4.0  FOM= 0.79
INDE  0  1   6  FOBS=  254.0  SIGMA=  1.6  PHAS=  231.7  FOM= 0.97
INDE  0  1   7  FOBS=  138.3  SIGMA=  3.8  PHAS=   75.8  FOM= 0.11
INDE  0  1   8  FOBS=  192.2  SIGMA=  3.1  PHAS=  150.5  FOM= 0.68
INDE  0  1   9  FOBS=  114.2  SIGMA=  5.8  PHAS=   63.1  FOM= 0.50
INDE  0  1  10  FOBS=  187.3  SIGMA=  3.4  PHAS=  349.6  FOM= 0.25
INDE  0  1  11  FOBS=  221.7  SIGMA=  3.1  PHAS=  199.5  FOM= 0.67
INDE  0  1  12  FOBS=  228.0  SIGMA=  3.3  PHAS=   67.9  FOM= 0.07
INDE  0  1  13  FOBS=  261.4  SIGMA=  3.0  PHAS=  239.4  FOM= 0.88
INDE  0  1  14  FOBS=   88.4  SIGMA=  8.9  PHAS=  121.7  FOM= 0.26
INDE  0  1  15  FOBS=  235.2  SIGMA=  3.3  PHAS=  177.3  FOM= 0.84
INDE  0  1  16  FOBS=   88.0  SIGMA=  8.9  PHAS=   50.9  FOM= 0.04
INDE  0  2   3  FOBS=  288.0  SIGMA=  0.8  PHAS=  297.3  FOM= 0.99
INDE  0  2   4  FOBS=  335.1  SIGMA=  1.1  PHAS=  241.7  FOM= 0.98
INDE  0  2   5  FOBS=  485.4  SIGMA=  1.1  PHAS=  231.7  FOM= 1.00
INDE  0  2   6  FOBS=  262.8  SIGMA=  1.8  PHAS=  263.1  FOM= 0.68
INDE  0  2   7  FOBS=  359.8  SIGMA=  1.6  PHAS=  146.3  FOM= 0.95
INDE  0  2   8  FOBS=  247.6  SIGMA=  2.1  PHAS=   37.2  FOM= 1.00
INDE  0  2   9  FOBS=  155.0  SIGMA=  3.7  PHAS=   14.5  FOM= 0.82
INDE  0  2  10  FOBS=  105.3  SIGMA=  7.1  PHAS=  106.2  FOM= 0.64
INDE  0  2  11  FOBS=  388.6  SIGMA=  1.9  PHAS=  349.8  FOM= 0.94
INDE  0  2  12  FOBS=  170.8  SIGMA=  4.7  PHAS=  286.6  FOM= 0.32
INDE  0  2  13  FOBS=  348.1  SIGMA=  2.3  PHAS=   89.7  FOM= 0.46
INDE  0  2  14  FOBS=  177.0  SIGMA=  4.7  PHAS=  172.9  FOM= 0.43
INDE  0  2  15  FOBS=  106.8  SIGMA=  7.7  PHAS=  280.4  FOM= 0.01
INDE  0  2  16  FOBS=   58.7  SIGMA= 15.9  PHAS=   50.6  FOM= 0.06
INDE  0  3   2  FOBS=  190.0  SIGMA=  1.1  PHAS=   90.2  FOM= 0.97
INDE  0  3   3  FOBS=  169.9  SIGMA=  1.3  PHAS=  222.5  FOM= 0.95
INDE  0  3   4  FOBS=  425.3  SIGMA=  1.1  PHAS=  167.5  FOM= 0.90
INDE  0  3   5  FOBS=  286.7  SIGMA=  1.3  PHAS=   61.1  FOM= 0.65
INDE  0  3   6  FOBS=  408.0  SIGMA=  1.3  PHAS=  206.8  FOM= 0.98
INDE  0  3   7  FOBS=  140.5  SIGMA=  3.6  PHAS=   19.0  FOM= 0.87
INDE  0  3   8  FOBS=   55.8  SIGMA= 10.1  PHAS=  172.5  FOM= 0.03
INDE  0  3   9  FOBS=   93.5  SIGMA=  6.2  PHAS=   81.8  FOM= 0.65
INDE  0  3  10  FOBS=  363.4  SIGMA=  2.1  PHAS=  271.8  FOM= 0.96
INDE  0  3  11  FOBS=  179.5  SIGMA=  4.5  PHAS=   67.9  FOM= 0.09
INDE  0  3  12  FOBS=  153.5  SIGMA=  5.1  PHAS=  163.6  FOM= 0.18
INDE  0  3  13  FOBS=  232.6  SIGMA=  3.4  PHAS=   13.6  FOM= 0.61
INDE  0  3  14  FOBS=  147.7  SIGMA=  5.5  PHAS=    5.6  FOM= 0.26
INDE  0  3  15  FOBS=  117.5  SIGMA=  6.7  PHAS=  255.2  FOM= 0.12
INDE  0  3  16  FOBS=   88.3  SIGMA=  8.7  PHAS=  218.4  FOM= 0.11
INDE  0  4   2  FOBS=  167.9  SIGMA=  1.0  PHAS=   82.9  FOM= 0.31
INDE  0  4   3  FOBS=  265.4  SIGMA=  1.0  PHAS=   31.3  FOM= 0.92
INDE  0  4   4  FOBS=  223.5  SIGMA=  1.4  PHAS=  103.1  FOM= 0.99
INDE  0  4   5  FOBS=  140.9  SIGMA=  2.5  PHAS=  265.9  FOM= 0.94
INDE  0  4   6  FOBS=  340.6  SIGMA=  1.3  PHAS=  338.6  FOM= 0.98
INDE  0  4   7  FOBS=  187.3  SIGMA=  2.4  PHAS=  343.4  FOM= 0.80
INDE  0  4   8  FOBS=  149.9  SIGMA=  3.7  PHAS=  206.8  FOM= 0.95
INDE  0  4   9  FOBS=  255.7  SIGMA=  2.2  PHAS=  265.9  FOM= 0.95
INDE  0  4  10  FOBS=  207.3  SIGMA=  3.1  PHAS=  119.7  FOM= 0.67
INDE  0  4  11  FOBS=  222.7  SIGMA=  3.5  PHAS=  267.4  FOM= 0.08
INDE  0  4  12  FOBS=  168.6  SIGMA=  5.0  PHAS=  156.1  FOM= 0.20
INDE  0  4  13  FOBS=  172.9  SIGMA=  4.8  PHAS=   49.7  FOM= 0.07
INDE  0  4  14  FOBS=  143.0  SIGMA=  5.7  PHAS=  282.8  FOM= 0.27
INDE  0  4  15  FOBS=   40.2  SIGMA= 18.0  PHAS=  170.8  FOM= 0.26
INDE  0  4  16  FOBS=  111.7  SIGMA=  7.0  PHAS=  149.8  FOM= 0.24
INDE  0  5   1  FOBS=  153.2  SIGMA=  1.1  PHAS=  333.5  FOM= 1.00
INDE  0  5   2  FOBS=   41.3  SIGMA=  4.0  PHAS=  238.2  FOM= 0.88
INDE  0  5   3  FOBS=  103.1  SIGMA=  2.3  PHAS=   58.9  FOM= 0.56
INDE  0  5   4  FOBS=  389.1  SIGMA=  1.1  PHAS=  332.6  FOM= 0.97
INDE  0  5   5  FOBS=  327.4  SIGMA=  1.3  PHAS=  337.5  FOM= 0.98
INDE  0  5   6  FOBS=  214.4  SIGMA=  1.9  PHAS=  261.0  FOM= 0.95
INDE  0  5   7  FOBS=  220.1  SIGMA=  2.1  PHAS=  318.9  FOM= 0.75
```

Fig. 10A-80

```
INDE  0  5   8 FOBS=  324.0 SIGMA=   1.7 PHAS= 179.9 FOM= 0.91
INDE  0  5   9 FOBS=  162.0 SIGMA=   3.4 PHAS= 356.8 FOM= 0.10
INDE  0  5  10 FOBS=  130.0 SIGMA=   5.1 PHAS= 339.1 FOM= 0.63
INDE  0  5  11 FOBS=  211.8 SIGMA=   3.3 PHAS= 313.4 FOM= 0.83
INDE  0  5  12 FOBS=   63.0 SIGMA=  15.2 PHAS=   9.7 FOM= 0.14
INDE  0  5  13 FOBS=  103.9 SIGMA=   7.7 PHAS= 282.5 FOM= 0.18
INDE  0  5  14 FOBS=  327.1 SIGMA=   2.5 PHAS= 229.3 FOM= 0.90
INDE  0  5  15 FOBS=   52.0 SIGMA=  39.2 PHAS=  14.1 FOM= 0.04
INDE  0  5  16 FOBS=   87.1 SIGMA=  46.4 PHAS= 320.8 FOM= 0.07
INDE  0  6   0 FOBS=   77.8 SIGMA=   3.0 PHAS= 246.1 FOM= 0.81
INDE  0  6   1 FOBS=  483.5 SIGMA=   0.8 PHAS= 109.2 FOM= 0.50
INDE  0  6   2 FOBS=  100.1 SIGMA=   2.1 PHAS= 247.1 FOM= 0.97
INDE  0  6   3 FOBS=  183.6 SIGMA=   1.5 PHAS=  45.7 FOM= 0.97
INDE  0  6   4 FOBS=   67.8 SIGMA=   5.5 PHAS=  89.8 FOM= 0.60
INDE  0  6   5 FOBS=  291.9 SIGMA=   1.5 PHAS= 255.4 FOM= 0.99
INDE  0  6   6 FOBS=  138.1 SIGMA=   2.9 PHAS= 210.2 FOM= 0.78
INDE  0  6   7 FOBS=  151.6 SIGMA=   2.9 PHAS=  10.0 FOM= 0.84
INDE  0  6   8 FOBS=   96.5 SIGMA=   5.4 PHAS= 339.1 FOM= 0.17
INDE  0  6   9 FOBS=  260.2 SIGMA=   2.2 PHAS= 338.7 FOM= 0.95
INDE  0  6  10 FOBS=   68.1 SIGMA=   9.9 PHAS= 159.7 FOM= 0.23
INDE  0  6  11 FOBS=  248.1 SIGMA=   2.8 PHAS=  61.2 FOM= 0.69
INDE  0  6  12 FOBS=  399.6 SIGMA=   2.3 PHAS= 199.3 FOM= 0.88
INDE  0  6  13 FOBS=   53.1 SIGMA=  16.0 PHAS= 204.4 FOM= 0.11
INDE  0  6  14 FOBS=  278.6 SIGMA=   2.8 PHAS=  34.8 FOM= 0.73
INDE  0  6  15 FOBS=   75.1 SIGMA=  10.2 PHAS= 264.5 FOM= 0.19
INDE  0  6  16 FOBS=   85.6 SIGMA=   9.1 PHAS=  17.6 FOM= 0.03
INDE  0  7   1 FOBS=  291.9 SIGMA=   1.0 PHAS= 315.8 FOM= 1.00
INDE  0  7   2 FOBS=  342.0 SIGMA=   1.0 PHAS=  50.5 FOM= 0.94
INDE  0  7   3 FOBS=  351.8 SIGMA=   1.1 PHAS= 123.5 FOM= 1.00
INDE  0  7   4 FOBS=  164.0 SIGMA=   1.9 PHAS= 340.1 FOM= 0.94
INDE  0  7   5 FOBS=  111.0 SIGMA=   3.2 PHAS= 251.6 FOM= 0.92
INDE  0  7   6 FOBS=  133.2 SIGMA=   3.6 PHAS= 199.1 FOM= 0.96
INDE  0  7   7 FOBS=  160.9 SIGMA=   2.9 PHAS= 120.3 FOM= 0.78
INDE  0  7   8 FOBS=  273.7 SIGMA=   1.9 PHAS= 221.0 FOM= 0.92
INDE  0  7   9 FOBS=  233.0 SIGMA=   2.4 PHAS= 213.6 FOM= 0.89
INDE  0  7  10 FOBS=  282.9 SIGMA=   2.3 PHAS=  10.9 FOM= 0.30
INDE  0  7  11 FOBS=  196.9 SIGMA=   3.6 PHAS=   5.5 FOM= 0.37
INDE  0  7  12 FOBS=  373.4 SIGMA=   2.2 PHAS=  23.6 FOM= 0.37
INDE  0  7  13 FOBS=  260.6 SIGMA=   3.4 PHAS=  46.1 FOM= 0.42
INDE  0  7  14 FOBS=  189.6 SIGMA=   4.9 PHAS= 353.0 FOM= 0.08
INDE  0  7  15 FOBS=   69.1 SIGMA=  11.4 PHAS= 324.7 FOM= 0.06
INDE  0  7  16 FOBS=   49.8 SIGMA=  34.1 PHAS= 101.3 FOM= 0.01
INDE  0  8   0 FOBS=  150.4 SIGMA=   2.8 PHAS= 211.0 FOM= 0.99
INDE  0  8   1 FOBS=  128.5 SIGMA=   2.0 PHAS= 241.6 FOM= 0.94
INDE  0  8   2 FOBS=  188.4 SIGMA=   1.5 PHAS= 168.5 FOM= 0.95
INDE  0  8   3 FOBS=  185.7 SIGMA=   1.5 PHAS=  64.4 FOM= 0.97
INDE  0  8   4 FOBS=  157.4 SIGMA=   1.9 PHAS= 267.9 FOM= 0.88
INDE  0  8   5 FOBS=  166.4 SIGMA=   2.4 PHAS= 133.2 FOM= 0.26
INDE  0  8   6 FOBS=  145.9 SIGMA=   2.7 PHAS= 269.7 FOM= 0.75
INDE  0  8   7 FOBS=  106.6 SIGMA=   4.6 PHAS= 252.4 FOM= 0.72
INDE  0  8   8 FOBS=   78.2 SIGMA=   7.4 PHAS= 339.3 FOM= 0.18
INDE  0  8   9 FOBS=  180.6 SIGMA=   3.1 PHAS=  73.1 FOM= 0.80
INDE  0  8  10 FOBS=   93.0 SIGMA=   7.0 PHAS=  44.7 FOM= 0.49
INDE  0  8  11 FOBS=  153.2 SIGMA=   4.9 PHAS=  32.9 FOM= 0.24
INDE  0  8  12 FOBS=  143.8 SIGMA=   5.7 PHAS= 136.5 FOM= 0.42
INDE  0  8  13 FOBS=  136.9 SIGMA=   6.1 PHAS= 344.4 FOM= 0.35
INDE  0  8  14 FOBS=  156.4 SIGMA=   6.2 PHAS= 255.1 FOM= 0.04
INDE  0  8  15 FOBS=  100.4 SIGMA=   7.7 PHAS= 166.5 FOM= 0.16
INDE  0  8  16 FOBS=   94.1 SIGMA=   8.3 PHAS= 348.0 FOM= 0.06
INDE  0  9   1 FOBS=  158.0 SIGMA=   1.9 PHAS= 244.5 FOM= 0.72
INDE  0  9   2 FOBS=   47.9 SIGMA=   5.3 PHAS= 241.0 FOM= 0.29
INDE  0  9   3 FOBS=  133.7 SIGMA=   2.0 PHAS= 148.9 FOM= 0.89
INDE  0  9   4 FOBS=   73.7 SIGMA=   3.9 PHAS= 336.9 FOM= 0.76
INDE  0  9   5 FOBS=   50.9 SIGMA=   6.9 PHAS= 279.1 FOM= 0.30
INDE  0  9   6 FOBS=  146.5 SIGMA=   2.7 PHAS= 324.3 FOM= 0.70
INDE  0  9   7 FOBS=  197.4 SIGMA=   2.3 PHAS= 113.9 FOM= 0.64
INDE  0  9   8 FOBS=   33.8 SIGMA=  15.4 PHAS= 202.9 FOM= 0.05
INDE  0  9   9 FOBS=  178.3 SIGMA=   3.8 PHAS= 296.3 FOM= 0.16
INDE  0  9  10 FOBS=  254.6 SIGMA=   2.5 PHAS= 275.4 FOM= 0.76
INDE  0  9  11 FOBS=  128.8 SIGMA=   5.8 PHAS= 151.1 FOM= 0.35
INDE  0  9  12 FOBS=  352.9 SIGMA=   2.2 PHAS=  56.7 FOM= 0.14
```

Fig. 10A-81

| | | | | | | | | | |
|---|---|---|---|---|---|---|---|---|---|
| INDE | 0 | 9 | 13 | FOBS= | 297.9 | SIGMA= | 2.6 | PHAS= | 311.9 | FOM= | 0.22 |
| INDE | 0 | 9 | 14 | FOBS= | 172.0 | SIGMA= | 4.8 | PHAS= | 105.1 | FOM= | 0.34 |
| INDE | 0 | 9 | 15 | FOBS= | 150.0 | SIGMA= | 6.3 | PHAS= | 296.1 | FOM= | 0.03 |
| INDE | 0 | 9 | 16 | FOBS= | 72.1 | SIGMA= | 10.9 | PHAS= | 342.5 | FOM= | 0.07 |
| INDE | 0 | 10 | 0 | FOBS= | 376.8 | SIGMA= | 1.6 | PHAS= | 229.0 | FOM= | 0.07 |
| INDE | 0 | 10 | 1 | FOBS= | 141.7 | SIGMA= | 1.7 | PHAS= | 48.6 | FOM= | 0.97 |
| INDE | 0 | 10 | 2 | FOBS= | 214.6 | SIGMA= | 1.3 | PHAS= | 166.0 | FOM= | 0.65 |
| INDE | 0 | 10 | 3 | FOBS= | 244.5 | SIGMA= | 1.4 | PHAS= | 96.5 | FOM= | 1.00 |
| INDE | 0 | 10 | 4 | FOBS= | 150.9 | SIGMA= | 2.1 | PHAS= | 351.9 | FOM= | 0.96 |
| INDE | 0 | 10 | 5 | FOBS= | 189.3 | SIGMA= | 2.0 | PHAS= | 77.5 | FOM= | 0.97 |
| INDE | 0 | 10 | 6 | FOBS= | 63.3 | SIGMA= | 7.1 | PHAS= | 156.0 | FOM= | 0.25 |
| INDE | 0 | 10 | 7 | FOBS= | 195.6 | SIGMA= | 2.4 | PHAS= | 229.5 | FOM= | 0.47 |
| INDE | 0 | 10 | 8 | FOBS= | 246.8 | SIGMA= | 2.1 | PHAS= | 303.0 | FOM= | 0.95 |
| INDE | 0 | 10 | 9 | FOBS= | 201.9 | SIGMA= | 3.1 | PHAS= | 264.0 | FOM= | 0.95 |
| INDE | 0 | 10 | 10 | FOBS= | 425.2 | SIGMA= | 2.2 | PHAS= | 235.4 | FOM= | 0.97 |
| INDE | 0 | 10 | 11 | FOBS= | 133.9 | SIGMA= | 6.5 | PHAS= | 333.1 | FOM= | 0.10 |
| INDE | 0 | 10 | 12 | FOBS= | 153.3 | SIGMA= | 5.3 | PHAS= | 208.1 | FOM= | 0.75 |
| INDE | 0 | 10 | 13 | FOBS= | 172.9 | SIGMA= | 4.8 | PHAS= | 110.7 | FOM= | 0.78 |
| INDE | 0 | 10 | 14 | FOBS= | 147.7 | SIGMA= | 5.4 | PHAS= | 2.1 | FOM= | 0.05 |
| INDE | 0 | 10 | 15 | FOBS= | 146.2 | SIGMA= | 6.1 | PHAS= | 64.9 | FOM= | 0.05 |
| INDE | 0 | 10 | 16 | FOBS= | 85.6 | SIGMA= | 18.8 | PHAS= | 71.9 | FOM= | 0.07 |
| INDE | 0 | 11 | 1 | FOBS= | 281.5 | SIGMA= | 1.4 | PHAS= | 258.3 | FOM= | 0.96 |
| INDE | 0 | 11 | 2 | FOBS= | 121.1 | SIGMA= | 2.2 | PHAS= | 181.2 | FOM= | 0.77 |
| INDE | 0 | 11 | 3 | FOBS= | 245.5 | SIGMA= | 1.4 | PHAS= | 36.2 | FOM= | 0.98 |
| INDE | 0 | 11 | 4 | FOBS= | 290.2 | SIGMA= | 1.4 | PHAS= | 201.2 | FOM= | 1.00 |
| INDE | 0 | 11 | 5 | FOBS= | 176.5 | SIGMA= | 2.1 | PHAS= | 64.3 | FOM= | 0.93 |
| INDE | 0 | 11 | 6 | FOBS= | 59.5 | SIGMA= | 6.0 | PHAS= | 201.3 | FOM= | 0.83 |
| INDE | 0 | 11 | 7 | FOBS= | 153.7 | SIGMA= | 2.8 | PHAS= | 175.1 | FOM= | 0.97 |
| INDE | 0 | 11 | 8 | FOBS= | 312.6 | SIGMA= | 1.8 | PHAS= | 45.3 | FOM= | 0.78 |
| INDE | 0 | 11 | 9 | FOBS= | 81.4 | SIGMA= | 7.2 | PHAS= | 172.1 | FOM= | 0.59 |
| INDE | 0 | 11 | 10 | FOBS= | 119.0 | SIGMA= | 5.6 | PHAS= | 35.6 | FOM= | 0.76 |
| INDE | 0 | 11 | 11 | FOBS= | 142.3 | SIGMA= | 5.5 | PHAS= | 194.3 | FOM= | 0.39 |
| INDE | 0 | 11 | 12 | FOBS= | 171.9 | SIGMA= | 5.3 | PHAS= | 184.9 | FOM= | 0.01 |
| INDE | 0 | 11 | 13 | FOBS= | 75.6 | SIGMA= | 11.3 | PHAS= | 48.0 | FOM= | 0.14 |
| INDE | 0 | 11 | 14 | FOBS= | 53.4 | SIGMA= | 20.2 | PHAS= | 242.2 | FOM= | 0.08 |
| INDE | 0 | 11 | 15 | FOBS= | 89.1 | SIGMA= | 8.5 | PHAS= | 298.4 | FOM= | 0.04 |
| INDE | 0 | 12 | 0 | FOBS= | 257.9 | SIGMA= | 1.8 | PHAS= | 244.0 | FOM= | 0.97 |
| INDE | 0 | 12 | 1 | FOBS= | 197.4 | SIGMA= | 1.9 | PHAS= | 151.6 | FOM= | 0.96 |
| INDE | 0 | 12 | 2 | FOBS= | 51.0 | SIGMA= | 5.9 | PHAS= | 25.6 | FOM= | 0.41 |
| INDE | 0 | 12 | 3 | FOBS= | 230.1 | SIGMA= | 1.6 | PHAS= | 105.6 | FOM= | 0.77 |
| INDE | 0 | 12 | 4 | FOBS= | 37.1 | SIGMA= | 6.4 | PHAS= | 327.1 | FOM= | 0.60 |
| INDE | 0 | 12 | 5 | FOBS= | 245.4 | SIGMA= | 1.7 | PHAS= | 75.1 | FOM= | 0.99 |
| INDE | 0 | 12 | 6 | FOBS= | 212.5 | SIGMA= | 2.0 | PHAS= | 239.8 | FOM= | 0.94 |
| INDE | 0 | 12 | 7 | FOBS= | 326.7 | SIGMA= | 1.7 | PHAS= | 53.0 | FOM= | 1.00 |
| INDE | 0 | 12 | 8 | FOBS= | 249.1 | SIGMA= | 2.2 | PHAS= | 160.1 | FOM= | 0.99 |
| INDE | 0 | 12 | 9 | FOBS= | 311.7 | SIGMA= | 2.0 | PHAS= | 26.3 | FOM= | 0.97 |
| INDE | 0 | 12 | 10 | FOBS= | 196.8 | SIGMA= | 3.3 | PHAS= | 301.0 | FOM= | 0.16 |
| INDE | 0 | 12 | 11 | FOBS= | 289.7 | SIGMA= | 2.5 | PHAS= | 158.3 | FOM= | 0.78 |
| INDE | 0 | 12 | 12 | FOBS= | 78.0 | SIGMA= | 10.5 | PHAS= | 302.8 | FOM= | 0.05 |
| INDE | 0 | 12 | 13 | FOBS= | 64.8 | SIGMA= | 12.4 | PHAS= | 104.4 | FOM= | 0.13 |
| INDE | 0 | 12 | 14 | FOBS= | 116.4 | SIGMA= | 7.4 | PHAS= | 256.4 | FOM= | 0.27 |
| INDE | 0 | 12 | 15 | FOBS= | 90.5 | SIGMA= | 9.5 | PHAS= | 173.6 | FOM= | 0.04 |
| INDE | 0 | 13 | 1 | FOBS= | 32.7 | SIGMA= | 9.0 | PHAS= | 139.8 | FOM= | 0.45 |
| INDE | 0 | 13 | 2 | FOBS= | 107.3 | SIGMA= | 4.2 | PHAS= | 2.0 | FOM= | 0.93 |
| INDE | 0 | 13 | 3 | FOBS= | 220.5 | SIGMA= | 1.8 | PHAS= | 261.9 | FOM= | 0.99 |
| INDE | 0 | 13 | 4 | FOBS= | 134.9 | SIGMA= | 2.6 | PHAS= | 191.1 | FOM= | 0.91 |
| INDE | 0 | 13 | 5 | FOBS= | 111.0 | SIGMA= | 3.7 | PHAS= | 78.6 | FOM= | 0.92 |
| INDE | 0 | 13 | 6 | FOBS= | 353.3 | SIGMA= | 1.4 | PHAS= | 150.0 | FOM= | 1.00 |
| INDE | 0 | 13 | 7 | FOBS= | 153.4 | SIGMA= | 2.9 | PHAS= | 134.9 | FOM= | 0.45 |
| INDE | 0 | 13 | 8 | FOBS= | 118.5 | SIGMA= | 4.7 | PHAS= | 155.9 | FOM= | 0.70 |
| INDE | 0 | 13 | 9 | FOBS= | 139.3 | SIGMA= | 4.2 | PHAS= | 342.8 | FOM= | 0.85 |
| INDE | 0 | 13 | 10 | FOBS= | 150.7 | SIGMA= | 4.6 | PHAS= | 48.5 | FOM= | 0.87 |
| INDE | 0 | 13 | 11 | FOBS= | 151.8 | SIGMA= | 5.0 | PHAS= | 122.4 | FOM= | 0.82 |
| INDE | 0 | 13 | 12 | FOBS= | 138.4 | SIGMA= | 5.3 | PHAS= | 79.1 | FOM= | 0.35 |
| INDE | 0 | 13 | 13 | FOBS= | 206.7 | SIGMA= | 3.6 | PHAS= | 207.4 | FOM= | 0.42 |
| INDE | 0 | 13 | 14 | FOBS= | 45.9 | SIGMA= | 18.2 | PHAS= | 186.0 | FOM= | 0.30 |
| INDE | 0 | 13 | 15 | FOBS= | 53.5 | SIGMA= | 30.0 | PHAS= | 39.4 | FOM= | 0.06 |
| INDE | 0 | 14 | 0 | FOBS= | 238.2 | SIGMA= | 2.1 | PHAS= | 82.9 | FOM= | 0.97 |
| INDE | 0 | 14 | 1 | FOBS= | 127.7 | SIGMA= | 2.3 | PHAS= | 187.6 | FOM= | 0.99 |
| INDE | 0 | 14 | 2 | FOBS= | 102.0 | SIGMA= | 3.5 | PHAS= | 62.6 | FOM= | 0.94 |
| INDE | 0 | 14 | 3 | FOBS= | 265.7 | SIGMA= | 1.6 | PHAS= | 198.5 | FOM= | 0.95 |

Fig. 10A-82

| | | | | | | | | | | | |
|---|---|---|---|---|---|---|---|---|---|---|---|
| INDE | 0 | 14 | 4 | FOBS= | 311.9 | SIGMA= | 1.5 | PHAS= | 120.7 | FOM= | 0.95 |
| INDE | 0 | 14 | 5 | FOBS= | 309.3 | SIGMA= | 1.5 | PHAS= | 191.7 | FOM= | 1.00 |
| INDE | 0 | 14 | 6 | FOBS= | 270.9 | SIGMA= | 1.7 | PHAS= | 78.9 | FOM= | 0.90 |
| INDE | 0 | 14 | 7 | FOBS= | 400.0 | SIGMA= | 1.4 | PHAS= | 202.5 | FOM= | 0.20 |
| INDE | 0 | 14 | 8 | FOBS= | 327.4 | SIGMA= | 1.9 | PHAS= | 337.7 | FOM= | 0.43 |
| INDE | 0 | 14 | 9 | FOBS= | 220.1 | SIGMA= | 2.6 | PHAS= | 230.2 | FOM= | 0.77 |
| INDE | 0 | 14 | 10 | FOBS= | 341.1 | SIGMA= | 2.1 | PHAS= | 202.5 | FOM= | 0.83 |
| INDE | 0 | 14 | 11 | FOBS= | 256.5 | SIGMA= | 2.7 | PHAS= | 119.2 | FOM= | 0.73 |
| INDE | 0 | 14 | 12 | FOBS= | 90.0 | SIGMA= | 8.1 | PHAS= | 268.6 | FOM= | 0.51 |
| INDE | 0 | 14 | 13 | FOBS= | 106.7 | SIGMA= | 6.7 | PHAS= | 83.5 | FOM= | 0.36 |
| INDE | 0 | 14 | 14 | FOBS= | 50.3 | SIGMA= | 18.9 | PHAS= | 43.8 | FOM= | 0.05 |
| INDE | 0 | 14 | 15 | FOBS= | 70.0 | SIGMA= | 10.7 | PHAS= | 320.3 | FOM= | 0.15 |
| INDE | 0 | 15 | 1 | FOBS= | 73.0 | SIGMA= | 4.0 | PHAS= | 141.6 | FOM= | 0.96 |
| INDE | 0 | 15 | 2 | FOBS= | 140.9 | SIGMA= | 2.2 | PHAS= | 302.5 | FOM= | 1.00 |
| INDE | 0 | 15 | 3 | FOBS= | 128.3 | SIGMA= | 3.3 | PHAS= | 290.2 | FOM= | 0.95 |
| INDE | 0 | 15 | 4 | FOBS= | 232.5 | SIGMA= | 2.0 | PHAS= | 194.4 | FOM= | 0.64 |
| INDE | 0 | 15 | 5 | FOBS= | 253.2 | SIGMA= | 1.9 | PHAS= | 175.4 | FOM= | 0.97 |
| INDE | 0 | 15 | 6 | FOBS= | 334.4 | SIGMA= | 1.5 | PHAS= | 275.6 | FOM= | 0.95 |
| INDE | 0 | 15 | 7 | FOBS= | 447.2 | SIGMA= | 1.3 | PHAS= | 144.1 | FOM= | 0.95 |
| INDE | 0 | 15 | 8 | FOBS= | 389.1 | SIGMA= | 1.5 | PHAS= | 14.6 | FOM= | 0.90 |
| INDE | 0 | 15 | 9 | FOBS= | 112.6 | SIGMA= | 5.2 | PHAS= | 278.5 | FOM= | 0.21 |
| INDE | 0 | 15 | 10 | FOBS= | 125.7 | SIGMA= | 5.4 | PHAS= | 111.1 | FOM= | 0.73 |
| INDE | 0 | 15 | 11 | FOBS= | 202.8 | SIGMA= | 3.3 | PHAS= | 85.8 | FOM= | 0.64 |
| INDE | 0 | 15 | 12 | FOBS= | 166.7 | SIGMA= | 4.3 | PHAS= | 311.0 | FOM= | 0.24 |
| INDE | 0 | 15 | 13 | FOBS= | 136.2 | SIGMA= | 5.3 | PHAS= | 91.5 | FOM= | 0.29 |
| INDE | 0 | 15 | 14 | FOBS= | 160.8 | SIGMA= | 4.5 | PHAS= | 316.0 | FOM= | 0.86 |
| INDE | 0 | 15 | 15 | FOBS= | 56.0 | SIGMA= | 24.0 | PHAS= | 74.2 | FOM= | 0.16 |
| INDE | 0 | 16 | 0 | FOBS= | 292.8 | SIGMA= | 1.9 | PHAS= | 111.0 | FOM= | 0.54 |
| INDE | 0 | 16 | 1 | FOBS= | 183.1 | SIGMA= | 1.9 | PHAS= | 125.6 | FOM= | 0.91 |
| INDE | 0 | 16 | 2 | FOBS= | 113.7 | SIGMA= | 3.1 | PHAS= | 259.8 | FOM= | 0.52 |
| INDE | 0 | 16 | 3 | FOBS= | 181.8 | SIGMA= | 2.0 | PHAS= | 333.0 | FOM= | 0.22 |
| INDE | 0 | 16 | 4 | FOBS= | 333.5 | SIGMA= | 1.5 | PHAS= | 314.0 | FOM= | 0.82 |
| INDE | 0 | 16 | 5 | FOBS= | 202.8 | SIGMA= | 2.4 | PHAS= | 35.4 | FOM= | 0.11 |
| INDE | 0 | 16 | 6 | FOBS= | 175.9 | SIGMA= | 2.8 | PHAS= | 297.5 | FOM= | 0.56 |
| INDE | 0 | 16 | 7 | FOBS= | 162.9 | SIGMA= | 3.1 | PHAS= | 191.0 | FOM= | 0.15 |
| INDE | 0 | 16 | 8 | FOBS= | 306.0 | SIGMA= | 1.9 | PHAS= | 271.9 | FOM= | 0.84 |
| INDE | 0 | 16 | 9 | FOBS= | 417.8 | SIGMA= | 1.8 | PHAS= | 6.3 | FOM= | 0.39 |
| INDE | 0 | 16 | 10 | FOBS= | 286.6 | SIGMA= | 2.3 | PHAS= | 278.3 | FOM= | 0.93 |
| INDE | 0 | 16 | 11 | FOBS= | 102.7 | SIGMA= | 6.6 | PHAS= | 124.9 | FOM= | 0.27 |
| INDE | 0 | 16 | 12 | FOBS= | 177.1 | SIGMA= | 4.0 | PHAS= | 316.8 | FOM= | 0.13 |
| INDE | 0 | 16 | 13 | FOBS= | 162.5 | SIGMA= | 4.4 | PHAS= | 261.6 | FOM= | 0.72 |
| INDE | 0 | 16 | 14 | FOBS= | 165.0 | SIGMA= | 4.4 | PHAS= | 160.9 | FOM= | 0.42 |
| INDE | 0 | 17 | 1 | FOBS= | 118.5 | SIGMA= | 3.1 | PHAS= | 268.1 | FOM= | 0.93 |
| INDE | 0 | 17 | 2 | FOBS= | 440.9 | SIGMA= | 1.1 | PHAS= | 293.5 | FOM= | 0.97 |
| INDE | 0 | 17 | 3 | FOBS= | 166.8 | SIGMA= | 2.5 | PHAS= | 134.5 | FOM= | 0.95 |
| INDE | 0 | 17 | 4 | FOBS= | 239.9 | SIGMA= | 1.8 | PHAS= | 358.6 | FOM= | 0.95 |
| INDE | 0 | 17 | 5 | FOBS= | 493.7 | SIGMA= | 1.4 | PHAS= | 67.7 | FOM= | 0.43 |
| INDE | 0 | 17 | 6 | FOBS= | 343.7 | SIGMA= | 1.8 | PHAS= | 322.0 | FOM= | 0.95 |
| INDE | 0 | 17 | 7 | FOBS= | 236.4 | SIGMA= | 2.2 | PHAS= | 100.0 | FOM= | 0.72 |
| INDE | 0 | 17 | 8 | FOBS= | 163.7 | SIGMA= | 3.3 | PHAS= | 307.9 | FOM= | 0.71 |
| INDE | 0 | 17 | 9 | FOBS= | 169.3 | SIGMA= | 3.8 | PHAS= | 332.5 | FOM= | 0.75 |
| INDE | 0 | 17 | 10 | FOBS= | 283.2 | SIGMA= | 2.3 | PHAS= | 58.8 | FOM= | 0.92 |
| INDE | 0 | 17 | 11 | FOBS= | 83.4 | SIGMA= | 7.7 | PHAS= | 280.1 | FOM= | 0.21 |
| INDE | 0 | 17 | 12 | FOBS= | 67.0 | SIGMA= | 9.9 | PHAS= | 211.0 | FOM= | 0.11 |
| INDE | 0 | 17 | 13 | FOBS= | 58.4 | SIGMA= | 11.8 | PHAS= | 103.4 | FOM= | 0.25 |
| INDE | 0 | 17 | 14 | FOBS= | 163.7 | SIGMA= | 4.3 | PHAS= | 189.4 | FOM= | 0.02 |
| INDE | 0 | 18 | 0 | FOBS= | 375.7 | SIGMA= | 1.7 | PHAS= | 340.1 | FOM= | 0.94 |
| INDE | 0 | 18 | 1 | FOBS= | 175.8 | SIGMA= | 2.1 | PHAS= | 328.4 | FOM= | 0.83 |
| INDE | 0 | 18 | 2 | FOBS= | 198.3 | SIGMA= | 2.0 | PHAS= | 353.2 | FOM= | 0.94 |
| INDE | 0 | 18 | 3 | FOBS= | 338.5 | SIGMA= | 1.5 | PHAS= | 91.0 | FOM= | 0.98 |
| INDE | 0 | 18 | 4 | FOBS= | 310.4 | SIGMA= | 1.6 | PHAS= | 356.4 | FOM= | 0.85 |
| INDE | 0 | 18 | 5 | FOBS= | 210.3 | SIGMA= | 2.1 | PHAS= | 119.4 | FOM= | 0.92 |
| INDE | 0 | 18 | 6 | FOBS= | 113.4 | SIGMA= | 4.9 | PHAS= | 140.2 | FOM= | 0.40 |
| INDE | 0 | 18 | 7 | FOBS= | 90.3 | SIGMA= | 6.0 | PHAS= | 50.1 | FOM= | 0.52 |
| INDE | 0 | 18 | 8 | FOBS= | 64.5 | SIGMA= | 8.7 | PHAS= | 252.4 | FOM= | 0.09 |
| INDE | 0 | 18 | 9 | FOBS= | 275.6 | SIGMA= | 2.2 | PHAS= | 241.7 | FOM= | 0.93 |
| INDE | 0 | 18 | 10 | FOBS= | 248.8 | SIGMA= | 2.4 | PHAS= | 215.7 | FOM= | 0.95 |
| INDE | 0 | 18 | 11 | FOBS= | 55.7 | SIGMA= | 11.4 | PHAS= | 188.3 | FOM= | 0.09 |
| INDE | 0 | 18 | 12 | FOBS= | 65.7 | SIGMA= | 10.1 | PHAS= | 229.0 | FOM= | 0.19 |
| INDE | 0 | 18 | 13 | FOBS= | 135.0 | SIGMA= | 4.9 | PHAS= | 323.3 | FOM= | 0.40 |
| INDE | 0 | 18 | 14 | FOBS= | 73.6 | SIGMA= | 9.2 | PHAS= | 86.1 | FOM= | 0.01 |

Fig. 10A-83

| | | | | | | | | | | |
|---|---|---|---|---|---|---|---|---|---|---|
| INDE | 0 | 19 | 1 | FOBS= | 215.2 | SIGMA= | 1.8 | PHAS= | 118.9 | FOM= | 0.79 |
| INDE | 0 | 19 | 2 | FOBS= | 59.3 | SIGMA= | 6.1 | PHAS= | 25.4 | FOM= | 0.24 |
| INDE | 0 | 19 | 3 | FOBS= | 146.5 | SIGMA= | 2.7 | PHAS= | 167.4 | FOM= | 0.55 |
| INDE | 0 | 19 | 4 | FOBS= | 236.7 | SIGMA= | 1.9 | PHAS= | 216.7 | FOM= | 0.97 |
| INDE | 0 | 19 | 5 | FOBS= | 217.5 | SIGMA= | 2.1 | PHAS= | 243.8 | FOM= | 0.84 |
| INDE | 0 | 19 | 6 | FOBS= | 482.2 | SIGMA= | 1.3 | PHAS= | 18.1 | FOM= | 1.00 |
| INDE | 0 | 19 | 7 | FOBS= | 302.8 | SIGMA= | 2.2 | PHAS= | 323.4 | FOM= | 0.96 |
| INDE | 0 | 19 | 8 | FOBS= | 267.1 | SIGMA= | 2.4 | PHAS= | 146.9 | FOM= | 0.05 |
| INDE | 0 | 19 | 9 | FOBS= | 256.6 | SIGMA= | 2.3 | PHAS= | 188.3 | FOM= | 0.37 |
| INDE | 0 | 19 | 10 | FOBS= | 214.5 | SIGMA= | 3.1 | PHAS= | 112.2 | FOM= | 0.57 |
| INDE | 0 | 19 | 11 | FOBS= | 112.7 | SIGMA= | 5.5 | PHAS= | 256.0 | FOM= | 0.16 |
| INDE | 0 | 19 | 12 | FOBS= | 125.1 | SIGMA= | 5.1 | PHAS= | 133.7 | FOM= | 0.25 |
| INDE | 0 | 19 | 13 | FOBS= | 117.9 | SIGMA= | 5.6 | PHAS= | 74.6 | FOM= | 0.47 |
| INDE | 0 | 20 | 0 | FOBS= | 377.7 | SIGMA= | 1.7 | PHAS= | 109.4 | FOM= | 0.96 |
| INDE | 0 | 20 | 1 | FOBS= | 215.0 | SIGMA= | 1.9 | PHAS= | 353.1 | FOM= | 0.98 |
| INDE | 0 | 20 | 2 | FOBS= | 272.4 | SIGMA= | 1.7 | PHAS= | 3.5 | FOM= | 0.97 |
| INDE | 0 | 20 | 3 | FOBS= | 75.1 | SIGMA= | 5.1 | PHAS= | 266.2 | FOM= | 0.45 |
| INDE | 0 | 20 | 4 | FOBS= | 298.7 | SIGMA= | 1.6 | PHAS= | 151.9 | FOM= | 0.95 |
| INDE | 0 | 20 | 5 | FOBS= | 176.2 | SIGMA= | 2.6 | PHAS= | 37.8 | FOM= | 0.85 |
| INDE | 0 | 20 | 6 | FOBS= | 256.9 | SIGMA= | 2.0 | PHAS= | 218.8 | FOM= | 0.87 |
| INDE | 0 | 20 | 7 | FOBS= | 58.0 | SIGMA= | 10.8 | PHAS= | 237.3 | FOM= | 0.27 |
| INDE | 0 | 20 | 8 | FOBS= | 421.9 | SIGMA= | 1.8 | PHAS= | 297.2 | FOM= | 0.92 |
| INDE | 0 | 20 | 9 | FOBS= | 133.0 | SIGMA= | 4.7 | PHAS= | 132.7 | FOM= | 0.20 |
| INDE | 0 | 20 | 10 | FOBS= | 130.4 | SIGMA= | 4.8 | PHAS= | 296.2 | FOM= | 0.18 |
| INDE | 0 | 20 | 11 | FOBS= | 262.3 | SIGMA= | 2.4 | PHAS= | 356.9 | FOM= | 0.15 |
| INDE | 0 | 20 | 12 | FOBS= | 142.3 | SIGMA= | 4.5 | PHAS= | 359.9 | FOM= | 0.91 |
| INDE | 0 | 20 | 13 | FOBS= | 142.5 | SIGMA= | 4.5 | PHAS= | 312.7 | FOM= | 0.03 |
| INDE | 0 | 21 | 1 | FOBS= | 264.9 | SIGMA= | 1.6 | PHAS= | 69.7 | FOM= | 0.90 |
| INDE | 0 | 21 | 2 | FOBS= | 248.6 | SIGMA= | 1.8 | PHAS= | 266.0 | FOM= | 0.93 |
| INDE | 0 | 21 | 3 | FOBS= | 155.9 | SIGMA= | 2.7 | PHAS= | 249.0 | FOM= | 0.92 |
| INDE | 0 | 21 | 4 | FOBS= | 177.1 | SIGMA= | 2.7 | PHAS= | 250.8 | FOM= | 0.89 |
| INDE | 0 | 21 | 5 | FOBS= | 165.1 | SIGMA= | 2.8 | PHAS= | 142.1 | FOM= | 0.10 |
| INDE | 0 | 21 | 6 | FOBS= | 321.8 | SIGMA= | 1.7 | PHAS= | 57.7 | FOM= | 0.92 |
| INDE | 0 | 21 | 7 | FOBS= | 215.7 | SIGMA= | 2.5 | PHAS= | 24.8 | FOM= | 0.86 |
| INDE | 0 | 21 | 8 | FOBS= | 110.8 | SIGMA= | 5.5 | PHAS= | 119.7 | FOM= | 0.40 |
| INDE | 0 | 21 | 9 | FOBS= | 62.1 | SIGMA= | 10.9 | PHAS= | 211.9 | FOM= | 0.16 |
| INDE | 0 | 21 | 10 | FOBS= | 73.8 | SIGMA= | 7.6 | PHAS= | 26.5 | FOM= | 0.22 |
| INDE | 0 | 21 | 11 | FOBS= | 83.1 | SIGMA= | 7.8 | PHAS= | 115.7 | FOM= | 0.15 |
| INDE | 0 | 21 | 12 | FOBS= | 47.8 | SIGMA= | 14.0 | PHAS= | 262.3 | FOM= | 0.09 |
| INDE | 0 | 21 | 13 | FOBS= | 120.7 | SIGMA= | 6.8 | PHAS= | 134.9 | FOM= | 0.08 |
| INDE | 0 | 22 | 0 | FOBS= | 225.3 | SIGMA= | 2.5 | PHAS= | 353.1 | FOM= | 0.89 |
| INDE | 0 | 22 | 1 | FOBS= | 361.9 | SIGMA= | 1.3 | PHAS= | 25.5 | FOM= | 0.97 |
| INDE | 0 | 22 | 2 | FOBS= | 285.1 | SIGMA= | 1.7 | PHAS= | 223.8 | FOM= | 0.91 |
| INDE | 0 | 22 | 3 | FOBS= | 230.2 | SIGMA= | 2.0 | PHAS= | 111.1 | FOM= | 0.62 |
| INDE | 0 | 22 | 4 | FOBS= | 128.7 | SIGMA= | 4.2 | PHAS= | 330.3 | FOM= | 0.84 |
| INDE | 0 | 22 | 5 | FOBS= | 134.1 | SIGMA= | 3.7 | PHAS= | 246.3 | FOM= | 0.89 |
| INDE | 0 | 22 | 6 | FOBS= | 291.8 | SIGMA= | 1.9 | PHAS= | 323.5 | FOM= | 0.94 |
| INDE | 0 | 22 | 7 | FOBS= | 208.3 | SIGMA= | 2.7 | PHAS= | 322.3 | FOM= | 0.23 |
| INDE | 0 | 22 | 8 | FOBS= | 242.5 | SIGMA= | 2.4 | PHAS= | 210.8 | FOM= | 0.92 |
| INDE | 0 | 22 | 9 | FOBS= | 177.4 | SIGMA= | 3.6 | PHAS= | 173.1 | FOM= | 0.64 |
| INDE | 0 | 22 | 10 | FOBS= | 207.8 | SIGMA= | 3.1 | PHAS= | 24.4 | FOM= | 0.39 |
| INDE | 0 | 22 | 11 | FOBS= | 185.6 | SIGMA= | 3.5 | PHAS= | 164.4 | FOM= | 0.87 |
| INDE | 0 | 22 | 12 | FOBS= | 129.9 | SIGMA= | 4.7 | PHAS= | 53.0 | FOM= | 0.18 |
| INDE | 0 | 23 | 1 | FOBS= | 644.7 | SIGMA= | 1.0 | PHAS= | 238.6 | FOM= | 0.98 |
| INDE | 0 | 23 | 2 | FOBS= | 144.2 | SIGMA= | 2.7 | PHAS= | 201.3 | FOM= | 0.96 |
| INDE | 0 | 23 | 3 | FOBS= | 328.4 | SIGMA= | 1.6 | PHAS= | 320.3 | FOM= | 0.99 |
| INDE | 0 | 23 | 4 | FOBS= | 91.5 | SIGMA= | 5.0 | PHAS= | 269.1 | FOM= | 0.08 |
| INDE | 0 | 23 | 5 | FOBS= | 125.7 | SIGMA= | 3.9 | PHAS= | 144.5 | FOM= | 0.63 |
| INDE | 0 | 23 | 6 | FOBS= | 149.2 | SIGMA= | 3.4 | PHAS= | 18.6 | FOM= | 0.83 |
| INDE | 0 | 23 | 7 | FOBS= | 176.4 | SIGMA= | 2.9 | PHAS= | 185.7 | FOM= | 0.83 |
| INDE | 0 | 23 | 8 | FOBS= | 214.6 | SIGMA= | 2.5 | PHAS= | 283.7 | FOM= | 0.60 |
| INDE | 0 | 23 | 9 | FOBS= | 291.3 | SIGMA= | 2.3 | PHAS= | 42.9 | FOM= | 0.90 |
| INDE | 0 | 23 | 10 | FOBS= | 189.9 | SIGMA= | 3.1 | PHAS= | 23.7 | FOM= | 0.36 |
| INDE | 0 | 23 | 11 | FOBS= | 281.1 | SIGMA= | 2.6 | PHAS= | 275.3 | FOM= | 0.92 |
| INDE | 0 | 23 | 12 | FOBS= | 67.5 | SIGMA= | 8.7 | PHAS= | 60.7 | FOM= | 0.08 |
| INDE | 0 | 24 | 0 | FOBS= | 427.4 | SIGMA= | 2.5 | PHAS= | 170.9 | FOM= | 0.99 |
| INDE | 0 | 24 | 1 | FOBS= | 194.9 | SIGMA= | 2.2 | PHAS= | 97.3 | FOM= | 0.92 |
| INDE | 0 | 24 | 2 | FOBS= | 322.5 | SIGMA= | 1.6 | PHAS= | 67.1 | FOM= | 0.73 |
| INDE | 0 | 24 | 3 | FOBS= | 326.6 | SIGMA= | 1.7 | PHAS= | 236.3 | FOM= | 0.95 |
| INDE | 0 | 24 | 4 | FOBS= | 155.6 | SIGMA= | 3.0 | PHAS= | 141.0 | FOM= | 0.89 |
| INDE | 0 | 24 | 5 | FOBS= | 304.6 | SIGMA= | 2.0 | PHAS= | 103.4 | FOM= | 0.91 |

Fig. 10A-84

```
INDE   0   24    6  FOBS=    43.9  SIGMA=   12.4  PHAS=   187.3  FOM=   0.08
INDE   0   24    7  FOBS=   202.5  SIGMA=    2.6  PHAS=    25.7  FOM=   0.66
INDE   0   24    8  FOBS=   197.6  SIGMA=    2.8  PHAS=    63.2  FOM=   0.45
INDE   0   24    9  FOBS=   121.8  SIGMA=    4.6  PHAS=    86.4  FOM=   0.51
INDE   0   24   10  FOBS=   168.4  SIGMA=    3.6  PHAS=   233.8  FOM=   0.94
INDE   0   24   11  FOBS=    61.5  SIGMA=   10.0  PHAS=   102.5  FOM=   0.05
INDE   0   25    1  FOBS=    82.4  SIGMA=    5.6  PHAS=   340.3  FOM=   0.88
INDE   0   25    2  FOBS=    52.0  SIGMA=   10.3  PHAS=   115.6  FOM=   0.60
INDE   0   25    3  FOBS=   230.3  SIGMA=    2.1  PHAS=    73.2  FOM=   0.98
INDE   0   25    4  FOBS=   189.6  SIGMA=    2.4  PHAS=   147.6  FOM=   0.94
INDE   0   25    5  FOBS=   179.4  SIGMA=    3.0  PHAS=   346.2  FOM=   0.86
INDE   0   25    6  FOBS=    45.1  SIGMA=   10.6  PHAS=   246.1  FOM=   0.34
INDE   0   25    7  FOBS=   239.1  SIGMA=    2.3  PHAS=   101.6  FOM=   0.97
INDE   0   25    8  FOBS=   124.6  SIGMA=    4.1  PHAS=   221.1  FOM=   0.73
INDE   0   25    9  FOBS=    49.4  SIGMA=   37.4  PHAS=   212.7  FOM=   0.32
INDE   0   25   10  FOBS=   157.4  SIGMA=    3.7  PHAS=    51.3  FOM=   0.79
INDE   0   25   11  FOBS=   155.8  SIGMA=    4.1  PHAS=    22.3  FOM=   0.91
INDE   0   26    0  FOBS=   220.1  SIGMA=    4.1  PHAS=   225.2  FOM=   0.04
INDE   0   26    1  FOBS=   176.5  SIGMA=    2.5  PHAS=    58.5  FOM=   0.10
INDE   0   26    2  FOBS=   233.3  SIGMA=    2.0  PHAS=    50.8  FOM=   0.87
INDE   0   26    3  FOBS=   250.3  SIGMA=    2.0  PHAS=    40.5  FOM=   0.86
INDE   0   26    4  FOBS=   201.7  SIGMA=    2.4  PHAS=   327.0  FOM=   0.92
INDE   0   26    5  FOBS=   131.6  SIGMA=    3.9  PHAS=   116.6  FOM=   0.81
INDE   0   26    6  FOBS=   104.6  SIGMA=    4.6  PHAS=    90.5  FOM=   0.03
INDE   0   26    7  FOBS=   133.1  SIGMA=    3.8  PHAS=   132.5  FOM=   0.85
INDE   0   26    8  FOBS=   241.1  SIGMA=    2.2  PHAS=   263.8  FOM=   0.98
INDE   0   26    9  FOBS=    67.2  SIGMA=    7.7  PHAS=   141.8  FOM=   0.17
INDE   0   26   10  FOBS=    75.3  SIGMA=    6.9  PHAS=   301.2  FOM=   0.19
INDE   0   27    1  FOBS=    81.9  SIGMA=    5.1  PHAS=   185.5  FOM=   0.13
INDE   0   27    2  FOBS=   299.4  SIGMA=    1.7  PHAS=   232.9  FOM=   0.96
INDE   0   27    3  FOBS=   119.7  SIGMA=    3.9  PHAS=   288.7  FOM=   0.92
INDE   0   27    4  FOBS=    72.6  SIGMA=    6.0  PHAS=   229.7  FOM=   0.15
INDE   0   27    5  FOBS=   178.7  SIGMA=    2.6  PHAS=   298.2  FOM=   0.93
INDE   0   27    6  FOBS=   147.4  SIGMA=    4.0  PHAS=    47.6  FOM=   0.94
INDE   0   27    7  FOBS=   284.4  SIGMA=    1.9  PHAS=   264.7  FOM=   0.95
INDE   0   27    8  FOBS=    62.0  SIGMA=    8.2  PHAS=   358.4  FOM=   0.03
INDE   0   27    9  FOBS=    53.5  SIGMA=    9.3  PHAS=   345.4  FOM=   0.14
INDE   0   27   10  FOBS=   143.2  SIGMA=   18.7  PHAS=   149.2  FOM=   0.05
INDE   0   28    0  FOBS=   153.4  SIGMA=    5.6  PHAS=    10.7  FOM=   0.26
INDE   0   28    1  FOBS=   157.8  SIGMA=    2.8  PHAS=     6.7  FOM=   0.35
INDE   0   28    2  FOBS=   118.8  SIGMA=    3.8  PHAS=     2.0  FOM=   0.67
INDE   0   28    3  FOBS=    68.6  SIGMA=    6.6  PHAS=   231.2  FOM=   0.40
INDE   0   28    4  FOBS=    80.3  SIGMA=    5.5  PHAS=   114.3  FOM=   0.23
INDE   0   28    5  FOBS=   107.1  SIGMA=    4.2  PHAS=   354.6  FOM=   0.19
INDE   0   28    6  FOBS=   105.3  SIGMA=    5.1  PHAS=   167.8  FOM=   0.07
INDE   0   28    7  FOBS=   155.5  SIGMA=    3.2  PHAS=   109.7  FOM=   0.93
INDE   0   28    8  FOBS=    69.8  SIGMA=    7.4  PHAS=   279.3  FOM=   0.33
INDE   0   28    9  FOBS=   151.9  SIGMA=    4.1  PHAS=   162.2  FOM=   0.70
INDE   0   29    1  FOBS=   252.1  SIGMA=    1.8  PHAS=   294.4  FOM=   0.76
INDE   0   29    2  FOBS=   115.5  SIGMA=    3.9  PHAS=   246.1  FOM=   0.80
INDE   0   29    3  FOBS=   186.0  SIGMA=    2.4  PHAS=   219.2  FOM=   0.88
INDE   0   29    4  FOBS=   179.7  SIGMA=    2.4  PHAS=    89.9  FOM=   0.88
INDE   0   29    5  FOBS=   306.1  SIGMA=    1.7  PHAS=   250.4  FOM=   0.89
INDE   0   29    6  FOBS=   178.0  SIGMA=    2.7  PHAS=   109.7  FOM=   0.78
INDE   0   29    7  FOBS=    88.5  SIGMA=    5.7  PHAS=   321.6  FOM=   0.55
INDE   0   29    8  FOBS=   176.8  SIGMA=    2.8  PHAS=    70.7  FOM=   0.11
INDE   0   30    0  FOBS=   385.9  SIGMA=    2.0  PHAS=    14.8  FOM=   0.86
INDE   0   30    1  FOBS=   151.0  SIGMA=    2.8  PHAS=   240.8  FOM=   0.56
INDE   0   30    2  FOBS=    54.8  SIGMA=    7.5  PHAS=   109.6  FOM=   0.19
INDE   0   30    3  FOBS=   236.3  SIGMA=    2.0  PHAS=   314.7  FOM=   0.93
INDE   0   30    4  FOBS=   143.4  SIGMA=    3.2  PHAS=   109.8  FOM=   0.69
INDE   0   30    5  FOBS=    70.5  SIGMA=    6.0  PHAS=   128.9  FOM=   0.04
INDE   0   30    6  FOBS=   115.8  SIGMA=    3.9  PHAS=    47.3  FOM=   0.39
INDE   0   30    7  FOBS=    60.6  SIGMA=    8.6  PHAS=    20.3  FOM=   0.03
INDE   0   31    1  FOBS=   155.4  SIGMA=    3.0  PHAS=   192.6  FOM=   0.94
INDE   0   31    2  FOBS=   173.5  SIGMA=    2.5  PHAS=   316.3  FOM=   0.96
INDE   0   31    3  FOBS=   121.4  SIGMA=    3.7  PHAS=   156.9  FOM=   0.47
INDE   0   31    4  FOBS=    91.5  SIGMA=    4.6  PHAS=    78.6  FOM=   0.09
INDE   0   31    5  FOBS=    44.3  SIGMA=   10.0  PHAS=    97.6  FOM=   0.10
INDE   0   31    6  FOBS=   181.6  SIGMA=    2.5  PHAS=    10.5  FOM=   0.90
INDE   0   32    0  FOBS=    61.6  SIGMA=    9.2  PHAS=   104.5  FOM=   0.03
```

Fig. 10A-85

```
INDE  0  32   1 FOBS=  141.9 SIGMA=   3.1 PHAS= 283.7 FOM= 0.31
INDE  0  32   2 FOBS=   95.4 SIGMA=   4.3 PHAS=  25.0 FOM= 0.75
INDE  0  32   3 FOBS=  141.2 SIGMA=   3.1 PHAS= 265.6 FOM= 0.60
INDE  0  32   4 FOBS=   44.6 SIGMA=  10.1 PHAS=  97.3 FOM= 0.14
INDE  0  33   1 FOBS=   58.2 SIGMA=   8.9 PHAS= 320.5 FOM= 0.29
INDE  0  33   2 FOBS=  213.1 SIGMA=   2.1 PHAS= 318.2 FOM= 0.96
INDE  1   0   2 FOBS=  396.4 SIGMA=   0.9 PHAS= 180.0 FOM= 0.70
INDE  1   0   3 FOBS=  397.6 SIGMA=   1.4 PHAS= 180.0 FOM= 1.00
INDE  1   0   4 FOBS=  491.9 SIGMA=   1.5 PHAS=   0.0 FOM= 1.00
INDE  1   0   5 FOBS=  322.6 SIGMA=   1.8 PHAS= 180.0 FOM= 0.05
INDE  1   0   6 FOBS=  298.8 SIGMA=   2.1 PHAS=   0.0 FOM= 1.00
INDE  1   0   7 FOBS=  270.1 SIGMA=   2.7 PHAS=   0.0 FOM= 0.99
INDE  1   0   8 FOBS=  144.3 SIGMA=   6.0 PHAS=   0.0 FOM= 0.14
INDE  1   0   9 FOBS=   58.0 SIGMA=  19.4 PHAS= 180.0 FOM= 0.22
INDE  1   0  10 FOBS=  303.0 SIGMA=   4.0 PHAS=   0.0 FOM= 0.37
INDE  1   0  11 FOBS=  526.7 SIGMA=   2.7 PHAS= 180.0 FOM= 0.00
INDE  1   0  12 FOBS=  116.1 SIGMA=  10.2 PHAS= 180.0 FOM= 0.04
INDE  1   0  13 FOBS=   57.7 SIGMA=  23.1 PHAS= 180.0 FOM= 0.10
INDE  1   0  14 FOBS=   58.8 SIGMA=  23.7 PHAS=   0.0 FOM= 0.01
INDE  1   0  15 FOBS=   44.4 SIGMA=  51.0 PHAS=   0.0 FOM= 0.14
INDE  1   0  16 FOBS=  124.4 SIGMA=   9.4 PHAS= 180.0 FOM= 0.28
INDE  1   1   2 FOBS=   88.1 SIGMA=   2.4 PHAS= 149.2 FOM= 0.92
INDE  1   1   3 FOBS=  206.6 SIGMA=   1.3 PHAS=   8.9 FOM= 0.97
INDE  1   1   4 FOBS=  383.0 SIGMA=   1.0 PHAS= 107.6 FOM= 0.98
INDE  1   1   5 FOBS=  325.4 SIGMA=   1.3 PHAS= 297.9 FOM= 1.00
INDE  1   1   6 FOBS=  316.5 SIGMA=   1.5 PHAS= 327.6 FOM= 0.77
INDE  1   1   7 FOBS=  174.5 SIGMA=   2.9 PHAS= 311.7 FOM= 0.94
INDE  1   1   8 FOBS=  158.2 SIGMA=   3.7 PHAS=  55.8 FOM= 0.90
INDE  1   1   9 FOBS=  145.2 SIGMA=   5.3 PHAS= 314.6 FOM= 0.84
INDE  1   1  10 FOBS=  303.7 SIGMA=   2.6 PHAS=  18.6 FOM= 0.87
INDE  1   1  11 FOBS=  408.8 SIGMA=   2.1 PHAS= 214.7 FOM= 0.82
INDE  1   1  12 FOBS=  279.5 SIGMA=   2.9 PHAS= 155.4 FOM= 0.95
INDE  1   1  13 FOBS=  178.5 SIGMA=   5.0 PHAS= 102.9 FOM= 0.77
INDE  1   1  14 FOBS=   90.6 SIGMA=   9.2 PHAS= 309.3 FOM= 0.22
INDE  1   1  15 FOBS=   55.2 SIGMA=  14.7 PHAS= 169.7 FOM= 0.13
INDE  1   1  16 FOBS=  124.7 SIGMA=   6.6 PHAS= 118.8 FOM= 0.06
INDE  1   2   2 FOBS=  261.8 SIGMA=   1.3 PHAS=  65.6 FOM= 0.98
INDE  1   2   3 FOBS=  332.8 SIGMA=   0.9 PHAS=  96.7 FOM= 1.00
INDE  1   2   4 FOBS=  173.5 SIGMA=   1.9 PHAS=  34.9 FOM= 0.85
INDE  1   2   5 FOBS=  329.1 SIGMA=   1.3 PHAS= 220.2 FOM= 0.30
INDE  1   2   6 FOBS=  198.2 SIGMA=   2.2 PHAS= 154.0 FOM= 0.08
INDE  1   2   7 FOBS=   44.5 SIGMA=  11.8 PHAS=  81.9 FOM= 0.13
INDE  1   2   8 FOBS=  197.7 SIGMA=   3.2 PHAS= 302.6 FOM= 0.78
INDE  1   2   9 FOBS=  226.8 SIGMA=   2.7 PHAS= 165.2 FOM= 0.72
INDE  1   2  10 FOBS=  326.8 SIGMA=   2.2 PHAS= 125.8 FOM= 0.88
INDE  1   2  11 FOBS=  200.0 SIGMA=   4.3 PHAS= 236.5 FOM= 0.82
INDE  1   2  12 FOBS=  113.2 SIGMA=   7.4 PHAS= 307.4 FOM= 0.27
INDE  1   2  13 FOBS=  197.5 SIGMA=   4.4 PHAS= 256.2 FOM= 0.42
INDE  1   2  14 FOBS=   66.0 SIGMA=  13.6 PHAS= 176.6 FOM= 0.22
INDE  1   2  15 FOBS=  111.3 SIGMA=   7.3 PHAS= 356.9 FOM= 0.14
INDE  1   2  16 FOBS=   67.5 SIGMA=  13.2 PHAS= 303.7 FOM= 0.02
INDE  1   3   2 FOBS=  301.0 SIGMA=   1.0 PHAS= 131.7 FOM= 0.78
INDE  1   3   3 FOBS=  303.7 SIGMA=   1.2 PHAS= 314.8 FOM= 0.97
INDE  1   3   4 FOBS=  393.6 SIGMA=   1.1 PHAS= 238.5 FOM= 0.99
INDE  1   3   5 FOBS=  386.7 SIGMA=   1.3 PHAS= 212.5 FOM= 1.00
INDE  1   3   6 FOBS=  169.4 SIGMA=   2.6 PHAS= 165.7 FOM= 0.78
INDE  1   3   7 FOBS=  139.5 SIGMA=   4.2 PHAS= 225.5 FOM= 0.47
INDE  1   3   8 FOBS=  236.3 SIGMA=   2.4 PHAS= 140.3 FOM= 0.92
INDE  1   3   9 FOBS=  331.2 SIGMA=   1.9 PHAS=  72.5 FOM= 0.96
INDE  1   3  10 FOBS=  298.4 SIGMA=   2.3 PHAS= 174.0 FOM= 0.83
INDE  1   3  11 FOBS=  260.7 SIGMA=   3.2 PHAS= 103.0 FOM= 0.46
INDE  1   3  12 FOBS=  378.0 SIGMA=   2.5 PHAS= 134.6 FOM= 0.44
INDE  1   3  13 FOBS=  381.2 SIGMA=   2.3 PHAS= 191.7 FOM= 0.91
INDE  1   3  14 FOBS=  144.4 SIGMA=   5.9 PHAS= 359.6 FOM= 0.25
INDE  1   3  15 FOBS=   43.8 SIGMA=  18.6 PHAS= 321.4 FOM= 0.15
INDE  1   3  16 FOBS=   66.3 SIGMA=  13.7 PHAS= 147.5 FOM= 0.10
INDE  1   4   1 FOBS=  254.9 SIGMA=   1.3 PHAS= 325.5 FOM= 0.98
INDE  1   4   2 FOBS=  215.1 SIGMA=   1.0 PHAS= 131.2 FOM= 0.96
INDE  1   4   3 FOBS=  332.6 SIGMA=   1.0 PHAS= 257.7 FOM= 0.94
INDE  1   4   4 FOBS=  408.5 SIGMA=   1.1 PHAS= 174.3 FOM= 0.90
INDE  1   4   5 FOBS=  132.8 SIGMA=   3.1 PHAS=  57.8 FOM= 0.60
```

Fig. 10A-86

```
INDE  1  4   6 FOBS=  361.8 SIGMA=  1.6 PHAS= 192.2 FOM= 0.91
INDE  1  4   7 FOBS=   72.0 SIGMA=  7.3 PHAS=  51.2 FOM= 0.14
INDE  1  4   8 FOBS=  132.0 SIGMA=  4.3 PHAS=  32.8 FOM= 0.34
INDE  1  4   9 FOBS=  164.2 SIGMA=  4.1 PHAS= 143.8 FOM= 0.80
INDE  1  4  10 FOBS=  303.9 SIGMA=  2.3 PHAS= 354.4 FOM= 0.96
INDE  1  4  11 FOBS=  223.2 SIGMA=  3.4 PHAS= 193.4 FOM= 0.80
INDE  1  4  12 FOBS=  140.6 SIGMA=  6.8 PHAS= 358.8 FOM= 0.21
INDE  1  4  13 FOBS=   96.4 SIGMA=  9.5 PHAS=  28.6 FOM= 0.17
INDE  1  4  14 FOBS=  134.7 SIGMA=  6.2 PHAS= 215.7 FOM= 0.13
INDE  1  4  15 FOBS=   76.7 SIGMA= 10.8 PHAS=  77.2 FOM= 0.14
INDE  1  4  16 FOBS=   76.0 SIGMA= 32.2 PHAS= 147.6 FOM= 0.01
INDE  1  5   0 FOBS=  251.4 SIGMA=  1.6 PHAS=  89.4 FOM= 1.00
INDE  1  5   1 FOBS=  108.7 SIGMA=  1.7 PHAS= 184.9 FOM= 0.73
INDE  1  5   2 FOBS=  145.1 SIGMA=  1.7 PHAS=  27.3 FOM= 0.92
INDE  1  5   3 FOBS=  256.4 SIGMA=  1.1 PHAS=  75.2 FOM= 1.00
INDE  1  5   4 FOBS=   39.8 SIGMA=  8.4 PHAS=  54.7 FOM= 0.33
INDE  1  5   5 FOBS=  134.1 SIGMA=  3.9 PHAS= 227.6 FOM= 0.72
INDE  1  5   6 FOBS=   66.4 SIGMA=  7.6 PHAS=  45.6 FOM= 0.27
INDE  1  5   7 FOBS=   43.5 SIGMA= 22.3 PHAS= 273.7 FOM= 0.25
INDE  1  5   8 FOBS=  139.7 SIGMA=  4.2 PHAS= 110.4 FOM= 0.57
INDE  1  5   9 FOBS=  600.0 SIGMA=  1.3 PHAS=  27.2 FOM= 0.90
INDE  1  5  10 FOBS=  176.5 SIGMA=  4.3 PHAS= 251.4 FOM= 0.82
INDE  1  5  11 FOBS=  194.0 SIGMA=  4.0 PHAS=  52.7 FOM= 0.64
INDE  1  5  12 FOBS=   73.8 SIGMA= 11.8 PHAS= 121.7 FOM= 0.06
INDE  1  5  13 FOBS=  123.7 SIGMA=  7.8 PHAS= 330.4 FOM= 0.07
INDE  1  5  14 FOBS=  116.9 SIGMA=  7.1 PHAS= 216.4 FOM= 0.03
INDE  1  5  15 FOBS=   50.6 SIGMA= 14.9 PHAS= 124.3 FOM= 0.03
INDE  1  5  16 FOBS=   70.8 SIGMA= 11.9 PHAS= 148.6 FOM= 0.02
INDE  1  6   0 FOBS=  220.3 SIGMA=  1.2 PHAS= 129.1 FOM= 0.99
INDE  1  6   1 FOBS=  112.1 SIGMA=  1.8 PHAS= 107.9 FOM= 0.92
INDE  1  6   2 FOBS=  174.4 SIGMA=  1.5 PHAS= 267.4 FOM= 0.92
INDE  1  6   3 FOBS=  405.5 SIGMA=  0.9 PHAS= 125.0 FOM= 0.98
INDE  1  6   4 FOBS=  235.2 SIGMA=  1.5 PHAS= 220.1 FOM= 0.97
INDE  1  6   5 FOBS=  150.9 SIGMA=  2.7 PHAS= 200.5 FOM= 0.84
INDE  1  6   6 FOBS=  209.6 SIGMA=  2.5 PHAS= 252.0 FOM= 0.98
INDE  1  6   7 FOBS=   67.8 SIGMA=  7.8 PHAS= 134.3 FOM= 0.44
INDE  1  6   8 FOBS=  220.6 SIGMA=  2.5 PHAS=  26.9 FOM= 0.37
INDE  1  6   9 FOBS=  236.4 SIGMA=  2.6 PHAS= 202.1 FOM= 0.86
INDE  1  6  10 FOBS=  452.2 SIGMA=  1.7 PHAS= 136.7 FOM= 0.62
INDE  1  6  11 FOBS=  171.1 SIGMA=  4.7 PHAS=  94.3 FOM= 0.61
INDE  1  6  12 FOBS=  376.2 SIGMA=  2.3 PHAS= 125.9 FOM= 0.28
INDE  1  6  13 FOBS=  214.5 SIGMA=  4.2 PHAS= 320.0 FOM= 0.32
INDE  1  6  14 FOBS=   90.0 SIGMA= 10.7 PHAS= 195.3 FOM= 0.19
INDE  1  6  15 FOBS=  130.4 SIGMA=  6.3 PHAS=  90.0 FOM= 0.42
INDE  1  6  16 FOBS=   58.3 SIGMA= 32.8 PHAS= 333.4 FOM= 0.06
INDE  1  7   0 FOBS=  136.9 SIGMA=  1.7 PHAS=  36.3 FOM= 0.97
INDE  1  7   1 FOBS=  245.8 SIGMA=  1.2 PHAS= 331.1 FOM= 0.95
INDE  1  7   2 FOBS=  399.0 SIGMA=  1.2 PHAS= 143.2 FOM= 0.97
INDE  1  7   3 FOBS=  121.0 SIGMA=  2.5 PHAS= 270.7 FOM= 0.96
INDE  1  7   4 FOBS=   83.9 SIGMA=  4.5 PHAS= 255.3 FOM= 0.21
INDE  1  7   5 FOBS=  116.3 SIGMA=  3.9 PHAS= 258.3 FOM= 0.84
INDE  1  7   6 FOBS=  148.2 SIGMA=  2.9 PHAS= 351.7 FOM= 0.42
INDE  1  7   7 FOBS=  229.5 SIGMA=  2.4 PHAS= 258.1 FOM= 0.35
INDE  1  7   8 FOBS=  221.3 SIGMA=  2.7 PHAS= 105.6 FOM= 0.83
INDE  1  7   9 FOBS=  159.4 SIGMA=  4.2 PHAS= 225.9 FOM= 0.51
INDE  1  7  10 FOBS=  245.9 SIGMA=  2.8 PHAS=  95.5 FOM= 0.65
INDE  1  7  11 FOBS=  132.2 SIGMA=  5.9 PHAS= 108.3 FOM= 0.15
INDE  1  7  12 FOBS=  162.0 SIGMA=  5.4 PHAS= 236.3 FOM= 0.64
INDE  1  7  13 FOBS=   49.2 SIGMA= 15.7 PHAS=  76.9 FOM= 0.13
INDE  1  7  14 FOBS=  232.4 SIGMA=  4.1 PHAS= 151.2 FOM= 0.72
INDE  1  7  15 FOBS=  172.9 SIGMA=  5.0 PHAS= 333.0 FOM= 0.98
INDE  1  7  16 FOBS=   71.4 SIGMA= 12.2 PHAS= 124.0 FOM= 0.02
INDE  1  8   0 FOBS=  314.9 SIGMA=  1.2 PHAS= 115.6 FOM= 1.00
INDE  1  8   1 FOBS=  298.0 SIGMA=  1.2 PHAS= 142.7 FOM= 1.00
INDE  1  8   2 FOBS=   99.1 SIGMA=  2.4 PHAS= 332.5 FOM= 0.93
INDE  1  8   3 FOBS=  129.8 SIGMA=  2.5 PHAS=  95.1 FOM= 0.95
INDE  1  8   4 FOBS=  216.2 SIGMA=  1.7 PHAS= 231.0 FOM= 0.97
INDE  1  8   5 FOBS=  103.1 SIGMA=  3.9 PHAS= 194.4 FOM= 0.46
INDE  1  8   6 FOBS=   99.8 SIGMA=  4.5 PHAS= 140.4 FOM= 0.52
INDE  1  8   7 FOBS=  138.5 SIGMA=  3.7 PHAS= 303.5 FOM= 0.52
INDE  1  8   8 FOBS=  159.8 SIGMA=  3.4 PHAS= 345.1 FOM= 0.45
```

Fig. 10A-87

```
INDE     1    8    9 FOBS=   144.0 SIGMA=   5.4 PHAS=  140.6 FOM=  0.16
INDE     1    8   10 FOBS=   276.9 SIGMA=   2.5 PHAS=  139.0 FOM=  0.04
INDE     1    8   11 FOBS=    66.3 SIGMA=  13.8 PHAS=  332.2 FOM=  0.10
INDE     1    8   12 FOBS=   222.6 SIGMA=   3.6 PHAS=  253.6 FOM=  0.08
INDE     1    8   13 FOBS=    71.0 SIGMA=  11.7 PHAS=  105.2 FOM=  0.16
INDE     1    8   14 FOBS=   232.5 SIGMA=   3.6 PHAS=  304.4 FOM=  0.53
INDE     1    8   15 FOBS=    92.4 SIGMA=  10.2 PHAS=   28.3 FOM=  0.02
INDE     1    8   16 FOBS=   108.3 SIGMA=   8.2 PHAS=  153.6 FOM=  0.17
INDE     1    9    0 FOBS=   183.9 SIGMA=   1.8 PHAS=   47.7 FOM=  0.92
INDE     1    9    1 FOBS=    34.7 SIGMA=   6.7 PHAS=  312.3 FOM=  0.52
INDE     1    9    2 FOBS=   110.4 SIGMA=   2.7 PHAS=  129.5 FOM=  0.70
INDE     1    9    3 FOBS=   283.2 SIGMA=   1.2 PHAS=  252.9 FOM=  0.94
INDE     1    9    4 FOBS=   125.8 SIGMA=   3.0 PHAS=    9.1 FOM=  0.92
INDE     1    9    5 FOBS=   162.1 SIGMA=   2.5 PHAS=  192.0 FOM=  0.86
INDE     1    9    6 FOBS=    71.4 SIGMA=   6.9 PHAS=  292.3 FOM=  0.18
INDE     1    9    7 FOBS=    65.6 SIGMA=   7.6 PHAS=  314.1 FOM=  0.39
INDE     1    9    8 FOBS=   117.7 SIGMA=   4.8 PHAS=  189.7 FOM=  0.85
INDE     1    9    9 FOBS=   408.4 SIGMA=   1.8 PHAS=  333.6 FOM=  0.96
INDE     1    9   10 FOBS=   146.0 SIGMA=   5.7 PHAS=   40.7 FOM=  0.05
INDE     1    9   11 FOBS=   211.0 SIGMA=   4.3 PHAS=  120.4 FOM=  0.44
INDE     1    9   12 FOBS=   240.3 SIGMA=   3.4 PHAS=  267.7 FOM=  0.42
INDE     1    9   13 FOBS=    49.7 SIGMA=  18.1 PHAS=   88.5 FOM=  0.08
INDE     1    9   14 FOBS=    83.1 SIGMA=   9.6 PHAS=  278.1 FOM=  0.08
INDE     1    9   15 FOBS=    62.4 SIGMA=  18.3 PHAS=   32.0 FOM=  0.03
INDE     1   10    0 FOBS=    72.8 SIGMA=   3.6 PHAS=  215.0 FOM=  0.40
INDE     1   10    1 FOBS=   262.4 SIGMA=   1.5 PHAS=  258.6 FOM=  0.86
INDE     1   10    2 FOBS=   126.7 SIGMA=   2.8 PHAS=  204.2 FOM=  0.89
INDE     1   10    3 FOBS=   176.3 SIGMA=   1.7 PHAS=  105.5 FOM=  0.97
INDE     1   10    4 FOBS=   128.1 SIGMA=   2.8 PHAS=  159.2 FOM=  0.92
INDE     1   10    5 FOBS=   143.8 SIGMA=   2.8 PHAS=  264.9 FOM=  0.41
INDE     1   10    6 FOBS=   162.8 SIGMA=   2.7 PHAS=   39.5 FOM=  0.93
INDE     1   10    7 FOBS=   173.1 SIGMA=   2.8 PHAS=  150.3 FOM=  0.90
INDE     1   10    8 FOBS=   288.4 SIGMA=   2.0 PHAS=  338.4 FOM=  0.78
INDE     1   10    9 FOBS=   285.9 SIGMA=   2.2 PHAS=   25.2 FOM=  0.06
INDE     1   10   10 FOBS=   240.9 SIGMA=   2.9 PHAS=   14.1 FOM=  0.25
INDE     1   10   11 FOBS=   251.4 SIGMA=   3.3 PHAS=   66.2 FOM=  0.24
INDE     1   10   12 FOBS=   219.8 SIGMA=   4.2 PHAS=  328.8 FOM=  0.28
INDE     1   10   13 FOBS=   180.2 SIGMA=   5.2 PHAS=  135.4 FOM=  0.09
INDE     1   10   14 FOBS=   123.6 SIGMA=   6.5 PHAS=  131.4 FOM=  0.10
INDE     1   10   15 FOBS=   129.6 SIGMA=   6.2 PHAS=  324.0 FOM=  0.06
INDE     1   11    0 FOBS=   131.9 SIGMA=   2.2 PHAS=  184.6 FOM=  0.98
INDE     1   11    1 FOBS=   185.8 SIGMA=   1.9 PHAS=  129.3 FOM=  0.79
INDE     1   11    2 FOBS=   106.2 SIGMA=   3.6 PHAS=   21.1 FOM=  0.60
INDE     1   11    3 FOBS=    59.4 SIGMA=   5.7 PHAS=   95.1 FOM=  0.67
INDE     1   11    4 FOBS=   144.9 SIGMA=   2.3 PHAS=  227.2 FOM=  1.00
INDE     1   11    5 FOBS=   207.5 SIGMA=   1.9 PHAS=  322.0 FOM=  0.98
INDE     1   11    6 FOBS=   252.0 SIGMA=   1.9 PHAS=  241.1 FOM=  0.93
INDE     1   11    7 FOBS=   353.7 SIGMA=   1.8 PHAS=   78.6 FOM=  0.94
INDE     1   11    8 FOBS=   379.0 SIGMA=   1.6 PHAS=  307.9 FOM=  0.96
INDE     1   11    9 FOBS=    67.4 SIGMA=   9.7 PHAS=  358.8 FOM=  0.39
INDE     1   11   10 FOBS=   409.2 SIGMA=   1.9 PHAS=  133.2 FOM=  0.90
INDE     1   11   11 FOBS=   381.8 SIGMA=   2.2 PHAS=  347.1 FOM=  0.87
INDE     1   11   12 FOBS=   148.1 SIGMA=   5.5 PHAS=  310.4 FOM=  0.28
INDE     1   11   13 FOBS=   192.4 SIGMA=   4.9 PHAS=  207.6 FOM=  0.73
INDE     1   11   14 FOBS=    99.8 SIGMA=   9.0 PHAS=   32.5 FOM=  0.18
INDE     1   11   15 FOBS=   174.2 SIGMA=   5.4 PHAS=  340.7 FOM=  0.27
INDE     1   12    0 FOBS=    85.2 SIGMA=   3.7 PHAS=  329.6 FOM=  0.17
INDE     1   12    1 FOBS=    88.1 SIGMA=   3.0 PHAS=    0.1 FOM=  1.00
INDE     1   12    2 FOBS=    76.7 SIGMA=   5.4 PHAS=  116.4 FOM=  0.84
INDE     1   12    3 FOBS=   129.5 SIGMA=   3.0 PHAS=   82.0 FOM=  0.28
INDE     1   12    4 FOBS=    83.1 SIGMA=   4.7 PHAS=  140.1 FOM=  0.74
INDE     1   12    5 FOBS=   309.5 SIGMA=   1.5 PHAS=  293.5 FOM=  0.99
INDE     1   12    6 FOBS=   261.0 SIGMA=   1.8 PHAS=  121.3 FOM=  0.66
INDE     1   12    7 FOBS=   491.7 SIGMA=   1.4 PHAS=   22.7 FOM=  0.90
INDE     1   12    8 FOBS=   264.2 SIGMA=   2.3 PHAS=  268.5 FOM=  0.98
INDE     1   12    9 FOBS=   172.7 SIGMA=   3.7 PHAS=  118.7 FOM=  0.83
INDE     1   12   10 FOBS=   299.1 SIGMA=   2.4 PHAS=   26.8 FOM=  0.79
INDE     1   12   11 FOBS=   156.2 SIGMA=   5.0 PHAS=  330.6 FOM=  0.80
INDE     1   12   12 FOBS=   115.1 SIGMA=   6.7 PHAS=   56.8 FOM=  0.49
INDE     1   12   13 FOBS=    74.8 SIGMA=  10.3 PHAS=   70.1 FOM=  0.23
INDE     1   12   14 FOBS=    86.1 SIGMA=   9.3 PHAS=  245.9 FOM=  0.57
```

Fig. 10A-88

```
INDE   1  12  15  FOBS=    59.1  SIGMA=   15.0  PHAS=   98.4  FOM=  0.04
INDE   1  13   0  FOBS=    96.8  SIGMA=    3.0  PHAS=  143.3  FOM=  1.00
INDE   1  13   1  FOBS=    94.9  SIGMA=    4.4  PHAS=   34.8  FOM=  0.92
INDE   1  13   2  FOBS=   142.1  SIGMA=    2.2  PHAS=  319.8  FOM=  0.85
INDE   1  13   3  FOBS=   179.7  SIGMA=    2.3  PHAS=  125.2  FOM=  1.00
INDE   1  13   4  FOBS=   110.1  SIGMA=    4.0  PHAS=   47.1  FOM=  0.90
INDE   1  13   5  FOBS=   108.6  SIGMA=    3.9  PHAS=  228.9  FOM=  0.91
INDE   1  13   6  FOBS=   166.8  SIGMA=    2.7  PHAS=   18.8  FOM=  0.85
INDE   1  13   7  FOBS=   173.8  SIGMA=    2.9  PHAS=  345.5  FOM=  0.56
INDE   1  13   8  FOBS=   201.4  SIGMA=    3.1  PHAS=  244.1  FOM=  0.73
INDE   1  13   9  FOBS=   206.5  SIGMA=    3.0  PHAS=  112.3  FOM=  0.91
INDE   1  13  10  FOBS=   118.4  SIGMA=    5.9  PHAS=  320.0  FOM=  0.53
INDE   1  13  11  FOBS=    81.0  SIGMA=    9.1  PHAS=  196.6  FOM=  0.07
INDE   1  13  12  FOBS=   121.6  SIGMA=    6.5  PHAS=   35.2  FOM=  0.65
INDE   1  13  13  FOBS=   153.4  SIGMA=    5.2  PHAS=  259.6  FOM=  0.49
INDE   1  13  14  FOBS=    74.3  SIGMA=   11.1  PHAS=   95.5  FOM=  0.03
INDE   1  13  15  FOBS=   830.4  SIGMA=  678.6  PHAS=   72.5  FOM=  0.00
INDE   1  14   0  FOBS=   185.9  SIGMA=    1.7  PHAS=  162.0  FOM=  0.96
INDE   1  14   1  FOBS=   177.8  SIGMA=    2.1  PHAS=   14.7  FOM=  0.87
INDE   1  14   2  FOBS=   159.8  SIGMA=    2.1  PHAS=  105.3  FOM=  0.56
INDE   1  14   3  FOBS=   180.9  SIGMA=    2.1  PHAS=  310.8  FOM=  0.88
INDE   1  14   4  FOBS=    55.8  SIGMA=    7.4  PHAS=  195.3  FOM=  0.44
INDE   1  14   5  FOBS=   157.4  SIGMA=    2.8  PHAS=  288.2  FOM=  0.90
INDE   1  14   6  FOBS=   134.3  SIGMA=    3.5  PHAS=  358.7  FOM=  1.00
INDE   1  14   7  FOBS=   241.4  SIGMA=    2.2  PHAS=    9.2  FOM=  0.96
INDE   1  14   8  FOBS=   132.1  SIGMA=    4.5  PHAS=  121.5  FOM=  0.24
INDE   1  14   9  FOBS=   286.1  SIGMA=    2.3  PHAS=  324.7  FOM=  0.95
INDE   1  14  10  FOBS=   331.9  SIGMA=    2.2  PHAS=   32.3  FOM=  0.89
INDE   1  14  11  FOBS=   128.1  SIGMA=    5.6  PHAS=    3.6  FOM=  0.01
INDE   1  14  12  FOBS=   197.5  SIGMA=    3.9  PHAS=  125.0  FOM=  0.55
INDE   1  14  13  FOBS=    51.4  SIGMA=   16.1  PHAS=  347.3  FOM=  0.08
INDE   1  14  14  FOBS=    70.6  SIGMA=   10.5  PHAS=  268.6  FOM=  0.05
INDE   1  14  15  FOBS=    58.7  SIGMA=   22.9  PHAS=  124.8  FOM=  0.09
INDE   1  15   0  FOBS=    23.4  SIGMA=   12.1  PHAS=  244.0  FOM=  0.14
INDE   1  15   1  FOBS=   161.4  SIGMA=    2.1  PHAS=   58.4  FOM=  0.77
INDE   1  15   2  FOBS=   203.3  SIGMA=    1.8  PHAS=  344.0  FOM=  0.96
INDE   1  15   3  FOBS=   164.6  SIGMA=    2.3  PHAS=   75.8  FOM=  0.81
INDE   1  15   4  FOBS=    40.3  SIGMA=    9.6  PHAS=   42.2  FOM=  0.13
INDE   1  15   5  FOBS=   402.2  SIGMA=    1.5  PHAS=  170.2  FOM=  0.97
INDE   1  15   6  FOBS=   163.4  SIGMA=    3.1  PHAS=  219.4  FOM=  0.11
INDE   1  15   7  FOBS=    53.9  SIGMA=   12.1  PHAS=   99.9  FOM=  0.21
INDE   1  15   8  FOBS=    55.3  SIGMA=   13.0  PHAS=  273.5  FOM=  0.28
INDE   1  15   9  FOBS=   133.2  SIGMA=    5.4  PHAS=  115.5  FOM=  0.27
INDE   1  15  10  FOBS=   123.8  SIGMA=    5.7  PHAS=  252.7  FOM=  0.03
INDE   1  15  11  FOBS=    84.2  SIGMA=    8.2  PHAS=  217.6  FOM=  0.03
INDE   1  15  12  FOBS=   179.4  SIGMA=    4.2  PHAS=   78.1  FOM=  0.10
INDE   1  15  13  FOBS=    38.9  SIGMA=   15.7  PHAS=  286.4  FOM=  0.16
INDE   1  15  14  FOBS=   112.6  SIGMA=    6.5  PHAS=  176.9  FOM=  0.33
INDE   1  16   0  FOBS=   336.0  SIGMA=    1.2  PHAS=  320.8  FOM=  0.94
INDE   1  16   1  FOBS=   210.3  SIGMA=    1.7  PHAS=   52.5  FOM=  0.97
INDE   1  16   2  FOBS=   123.8  SIGMA=    3.1  PHAS=   84.5  FOM=  0.95
INDE   1  16   3  FOBS=   144.4  SIGMA=    2.5  PHAS=  248.3  FOM=  0.92
INDE   1  16   4  FOBS=   155.3  SIGMA=    2.7  PHAS=   92.5  FOM=  0.80
INDE   1  16   5  FOBS=   153.3  SIGMA=    3.1  PHAS=  234.6  FOM=  0.91
INDE   1  16   6  FOBS=   248.2  SIGMA=    2.3  PHAS=   49.1  FOM=  0.94
INDE   1  16   7  FOBS=    45.2  SIGMA=   12.4  PHAS=  167.2  FOM=  0.21
INDE   1  16   8  FOBS=   197.1  SIGMA=    2.9  PHAS=  230.4  FOM=  0.04
INDE   1  16   9  FOBS=   237.1  SIGMA=    3.0  PHAS=  322.4  FOM=  0.52
INDE   1  16  10  FOBS=   134.6  SIGMA=    5.1  PHAS=  234.1  FOM=  0.86
INDE   1  16  11  FOBS=   271.5  SIGMA=    2.5  PHAS=  104.8  FOM=  0.90
INDE   1  16  12  FOBS=   225.4  SIGMA=    3.2  PHAS=   65.0  FOM=  0.19
INDE   1  16  13  FOBS=    38.4  SIGMA=   16.8  PHAS=  106.3  FOM=  0.24
INDE   1  16  14  FOBS=    43.2  SIGMA=   18.9  PHAS=  302.7  FOM=  0.09
INDE   1  17   0  FOBS=    84.3  SIGMA=    4.0  PHAS=  181.6  FOM=  0.54
INDE   1  17   1  FOBS=   335.5  SIGMA=    1.3  PHAS=  129.3  FOM=  0.91
INDE   1  17   2  FOBS=   440.8  SIGMA=    1.3  PHAS=  333.8  FOM=  0.99
INDE   1  17   3  FOBS=   536.3  SIGMA=    1.0  PHAS=  140.6  FOM=  0.98
INDE   1  17   4  FOBS=   251.0  SIGMA=    1.8  PHAS=  329.4  FOM=  0.44
INDE   1  17   5  FOBS=   246.3  SIGMA=    2.0  PHAS=   87.9  FOM=  0.85
INDE   1  17   6  FOBS=   111.9  SIGMA=    4.7  PHAS=  177.3  FOM=  0.39
INDE   1  17   7  FOBS=   136.6  SIGMA=    4.4  PHAS=   75.7  FOM=  0.33
```

Fig. 10A-89

```
INDE   1   17    8  FOBS=    74.3  SIGMA=   8.0  PHAS=   29.2  FOM=  0.02
INDE   1   17    9  FOBS=   272.7  SIGMA=   2.4  PHAS=  132.6  FOM=  0.05
INDE   1   17   10  FOBS=   216.5  SIGMA=   3.1  PHAS=  203.8  FOM=  0.23
INDE   1   17   11  FOBS=    76.6  SIGMA=   8.8  PHAS=  177.5  FOM=  0.03
INDE   1   17   12  FOBS=   146.3  SIGMA=   4.8  PHAS=  106.6  FOM=  0.42
INDE   1   17   13  FOBS=    89.5  SIGMA=   7.9  PHAS=  266.3  FOM=  0.03
INDE   1   17   14  FOBS=    77.4  SIGMA=   9.3  PHAS=  144.7  FOM=  0.08
INDE   1   18    0  FOBS=   123.0  SIGMA=   2.8  PHAS=  163.7  FOM=  0.93
INDE   1   18    1  FOBS=   330.9  SIGMA=   1.3  PHAS=   71.4  FOM=  0.99
INDE   1   18    2  FOBS=   548.6  SIGMA=   1.1  PHAS=  221.4  FOM=  1.00
INDE   1   18    3  FOBS=   118.4  SIGMA=   3.4  PHAS=   59.7  FOM=  0.59
INDE   1   18    4  FOBS=   232.2  SIGMA=   1.9  PHAS=  242.0  FOM=  0.94
INDE   1   18    5  FOBS=   395.6  SIGMA=   1.4  PHAS=  271.1  FOM=  0.91
INDE   1   18    6  FOBS=   383.4  SIGMA=   1.5  PHAS=  169.9  FOM=  0.91
INDE   1   18    7  FOBS=   395.7  SIGMA=   1.8  PHAS=  223.0  FOM=  0.71
INDE   1   18    8  FOBS=   116.7  SIGMA=   5.6  PHAS=  348.5  FOM=  0.14
INDE   1   18    9  FOBS=   263.7  SIGMA=   2.4  PHAS=  323.6  FOM=  0.42
INDE   1   18   10  FOBS=    80.0  SIGMA=   8.9  PHAS=  160.1  FOM=  0.13
INDE   1   18   11  FOBS=    81.5  SIGMA=   8.5  PHAS=   39.5  FOM=  0.27
INDE   1   18   12  FOBS=   108.8  SIGMA=   6.2  PHAS=  302.0  FOM=  0.22
INDE   1   18   13  FOBS=    72.4  SIGMA=   9.3  PHAS=  207.6  FOM=  0.06
INDE   1   19    0  FOBS=   359.9  SIGMA=   1.2  PHAS=   99.0  FOM=  0.76
INDE   1   19    1  FOBS=   140.4  SIGMA=   2.9  PHAS=  138.4  FOM=  0.26
INDE   1   19    2  FOBS=   294.7  SIGMA=   1.5  PHAS=  227.2  FOM=  0.67
INDE   1   19    3  FOBS=   322.1  SIGMA=   1.5  PHAS=  138.3  FOM=  0.90
INDE   1   19    4  FOBS=   137.7  SIGMA=   3.3  PHAS=  327.8  FOM=  0.80
INDE   1   19    5  FOBS=   219.9  SIGMA=   2.2  PHAS=   92.0  FOM=  0.95
INDE   1   19    6  FOBS=   237.7  SIGMA=   2.2  PHAS=  304.1  FOM=  0.38
INDE   1   19    7  FOBS=   185.7  SIGMA=   2.9  PHAS=  183.8  FOM=  0.97
INDE   1   19    8  FOBS=   117.4  SIGMA=   5.9  PHAS=  171.2  FOM=  0.75
INDE   1   19    9  FOBS=   282.0  SIGMA=   2.5  PHAS=   38.6  FOM=  0.05
INDE   1   19   10  FOBS=   105.9  SIGMA=   6.4  PHAS=    5.3  FOM=  0.63
INDE   1   19   11  FOBS=   141.8  SIGMA=   4.7  PHAS=  160.2  FOM=  0.74
INDE   1   19   12  FOBS=    93.3  SIGMA=   7.0  PHAS=  127.0  FOM=  0.22
INDE   1   19   13  FOBS=   105.4  SIGMA=   6.3  PHAS=   33.1  FOM=  0.02
INDE   1   20    0  FOBS=   115.1  SIGMA=   3.5  PHAS=  316.9  FOM=  0.91
INDE   1   20    1  FOBS=   439.2  SIGMA=   1.3  PHAS=  167.5  FOM=  0.98
INDE   1   20    2  FOBS=   268.3  SIGMA=   1.7  PHAS=  324.0  FOM=  0.98
INDE   1   20    3  FOBS=    95.8  SIGMA=   4.2  PHAS=  355.1  FOM=  0.06
INDE   1   20    4  FOBS=   152.4  SIGMA=   2.8  PHAS=  334.9  FOM=  0.79
INDE   1   20    5  FOBS=   336.0  SIGMA=   1.6  PHAS=  254.7  FOM=  0.34
INDE   1   20    6  FOBS=    94.5  SIGMA=   5.5  PHAS=   97.1  FOM=  0.13
INDE   1   20    7  FOBS=   125.4  SIGMA=   4.6  PHAS=  254.8  FOM=  0.17
INDE   1   20    8  FOBS=   128.6  SIGMA=   4.7  PHAS=  293.9  FOM=  0.78
INDE   1   20    9  FOBS=   174.8  SIGMA=   3.9  PHAS=  151.4  FOM=  0.74
INDE   1   20   10  FOBS=    57.2  SIGMA=  11.3  PHAS=   54.7  FOM=  0.09
INDE   1   20   11  FOBS=   189.9  SIGMA=   3.8  PHAS=  318.5  FOM=  0.46
INDE   1   20   12  FOBS=    89.0  SIGMA=   7.2  PHAS=   97.1  FOM=  0.10
INDE   1   20   13  FOBS=    63.1  SIGMA=  10.8  PHAS=   82.9  FOM=  0.05
INDE   1   21    0  FOBS=   420.3  SIGMA=   1.2  PHAS=  204.8  FOM=  0.99
INDE   1   21    1  FOBS=   204.3  SIGMA=   2.0  PHAS=  309.9  FOM=  0.92
INDE   1   21    2  FOBS=   398.4  SIGMA=   1.3  PHAS=   67.2  FOM=  0.93
INDE   1   21    3  FOBS=   198.7  SIGMA=   2.5  PHAS=  187.8  FOM=  0.89
INDE   1   21    4  FOBS=   134.3  SIGMA=   3.4  PHAS=   74.5  FOM=  0.47
INDE   1   21    5  FOBS=   274.1  SIGMA=   1.9  PHAS=  234.2  FOM=  0.82
INDE   1   21    6  FOBS=   180.0  SIGMA=   3.1  PHAS=  114.9  FOM=  0.18
INDE   1   21    7  FOBS=   325.7  SIGMA=   1.9  PHAS=  216.4  FOM=  0.64
INDE   1   21    8  FOBS=   246.8  SIGMA=   2.4  PHAS=  297.0  FOM=  0.82
INDE   1   21    9  FOBS=   178.7  SIGMA=   3.4  PHAS=    5.4  FOM=  0.60
INDE   1   21   10  FOBS=   143.6  SIGMA=   4.8  PHAS=  163.6  FOM=  0.47
INDE   1   21   11  FOBS=    53.3  SIGMA=  13.5  PHAS=  257.3  FOM=  0.24
INDE   1   21   12  FOBS=   123.1  SIGMA=   5.4  PHAS=   42.0  FOM=  0.53
INDE   1   22    0  FOBS=   135.1  SIGMA=   3.0  PHAS=  156.1  FOM=  0.37
INDE   1   22    1  FOBS=   223.7  SIGMA=   1.9  PHAS=  342.8  FOM=  0.21
INDE   1   22    2  FOBS=   368.4  SIGMA=   1.4  PHAS=  179.4  FOM=  0.96
INDE   1   22    3  FOBS=   286.1  SIGMA=   1.9  PHAS=  214.5  FOM=  0.67
INDE   1   22    4  FOBS=    71.8  SIGMA=   6.3  PHAS=  138.2  FOM=  0.11
INDE   1   22    5  FOBS=   122.0  SIGMA=   4.2  PHAS=  162.9  FOM=  0.72
INDE   1   22    6  FOBS=   123.0  SIGMA=   4.6  PHAS=  221.7  FOM=  0.68
INDE   1   22    7  FOBS=   304.9  SIGMA=   2.0  PHAS=   50.5  FOM=  0.86
INDE   1   22    8  FOBS=   186.0  SIGMA=   3.1  PHAS=  259.7  FOM=  0.10
```

Fig. 10A-90

| | | | | | | | | | |
|---|---|---|---|---|---|---|---|---|---|
| INDE | 1 | 22 | 9 | FOBS= | 127.7 | SIGMA= | 4.7 | PHAS= | 350.1 | FOM= | 0.35 |
| INDE | 1 | 22 | 10 | FOBS= | 112.9 | SIGMA= | 5.4 | PHAS= | 138.8 | FOM= | 0.44 |
| INDE | 1 | 22 | 11 | FOBS= | 173.0 | SIGMA= | 4.3 | PHAS= | 17.5 | FOM= | 0.73 |
| INDE | 1 | 22 | 12 | FOBS= | 87.4 | SIGMA= | 7.2 | PHAS= | 80.2 | FOM= | 0.19 |
| INDE | 1 | 23 | 0 | FOBS= | 176.0 | SIGMA= | 2.3 | PHAS= | 150.2 | FOM= | 0.47 |
| INDE | 1 | 23 | 1 | FOBS= | 252.0 | SIGMA= | 1.8 | PHAS= | 315.5 | FOM= | 0.97 |
| INDE | 1 | 23 | 2 | FOBS= | 369.2 | SIGMA= | 1.5 | PHAS= | 128.9 | FOM= | 0.88 |
| INDE | 1 | 23 | 3 | FOBS= | 236.7 | SIGMA= | 2.1 | PHAS= | 38.9 | FOM= | 0.93 |
| INDE | 1 | 23 | 4 | FOBS= | 222.4 | SIGMA= | 2.2 | PHAS= | 174.7 | FOM= | 0.95 |
| INDE | 1 | 23 | 5 | FOBS= | 210.7 | SIGMA= | 2.4 | PHAS= | 132.8 | FOM= | 0.09 |
| INDE | 1 | 23 | 6 | FOBS= | 343.0 | SIGMA= | 1.7 | PHAS= | 243.2 | FOM= | 0.27 |
| INDE | 1 | 23 | 7 | FOBS= | 228.1 | SIGMA= | 2.5 | PHAS= | 151.3 | FOM= | 0.30 |
| INDE | 1 | 23 | 8 | FOBS= | 62.1 | SIGMA= | 9.5 | PHAS= | 255.5 | FOM= | 0.23 |
| INDE | 1 | 23 | 9 | FOBS= | 77.7 | SIGMA= | 7.2 | PHAS= | 130.6 | FOM= | 0.28 |
| INDE | 1 | 23 | 10 | FOBS= | 42.7 | SIGMA= | 13.5 | PHAS= | 306.0 | FOM= | 0.16 |
| INDE | 1 | 23 | 11 | FOBS= | 109.4 | SIGMA= | 5.4 | PHAS= | 245.4 | FOM= | 0.07 |
| INDE | 1 | 23 | 12 | FOBS= | 150.7 | SIGMA= | 15.2 | PHAS= | 95.7 | FOM= | 0.03 |
| INDE | 1 | 24 | 0 | FOBS= | 193.5 | SIGMA= | 2.3 | PHAS= | 185.3 | FOM= | 0.26 |
| INDE | 1 | 24 | 1 | FOBS= | 459.8 | SIGMA= | 1.3 | PHAS= | 327.7 | FOM= | 0.84 |
| INDE | 1 | 24 | 2 | FOBS= | 172.6 | SIGMA= | 2.6 | PHAS= | 324.0 | FOM= | 0.94 |
| INDE | 1 | 24 | 3 | FOBS= | 300.8 | SIGMA= | 1.8 | PHAS= | 297.7 | FOM= | 0.99 |
| INDE | 1 | 24 | 4 | FOBS= | 166.5 | SIGMA= | 3.1 | PHAS= | 357.6 | FOM= | 0.69 |
| INDE | 1 | 24 | 5 | FOBS= | 63.7 | SIGMA= | 10.0 | PHAS= | 167.7 | FOM= | 0.16 |
| INDE | 1 | 24 | 6 | FOBS= | 190.3 | SIGMA= | 2.6 | PHAS= | 124.7 | FOM= | 0.38 |
| INDE | 1 | 24 | 7 | FOBS= | 180.5 | SIGMA= | 3.2 | PHAS= | 222.7 | FOM= | 0.96 |
| INDE | 1 | 24 | 8 | FOBS= | 54.0 | SIGMA= | 11.6 | PHAS= | 76.4 | FOM= | 0.20 |
| INDE | 1 | 24 | 9 | FOBS= | 98.2 | SIGMA= | 5.8 | PHAS= | 20.3 | FOM= | 0.44 |
| INDE | 1 | 24 | 10 | FOBS= | 67.2 | SIGMA= | 8.9 | PHAS= | 135.5 | FOM= | 0.13 |
| INDE | 1 | 24 | 11 | FOBS= | 111.1 | SIGMA= | 5.2 | PHAS= | 262.1 | FOM= | 0.06 |
| INDE | 1 | 25 | 0 | FOBS= | 264.8 | SIGMA= | 1.8 | PHAS= | 222.1 | FOM= | 0.96 |
| INDE | 1 | 25 | 1 | FOBS= | 203.3 | SIGMA= | 2.2 | PHAS= | 164.5 | FOM= | 0.92 |
| INDE | 1 | 25 | 2 | FOBS= | 125.0 | SIGMA= | 4.1 | PHAS= | 248.2 | FOM= | 0.90 |
| INDE | 1 | 25 | 3 | FOBS= | 88.8 | SIGMA= | 5.1 | PHAS= | 106.4 | FOM= | 0.46 |
| INDE | 1 | 25 | 4 | FOBS= | 415.6 | SIGMA= | 1.6 | PHAS= | 244.1 | FOM= | 0.91 |
| INDE | 1 | 25 | 5 | FOBS= | 244.9 | SIGMA= | 2.2 | PHAS= | 356.0 | FOM= | 0.94 |
| INDE | 1 | 25 | 6 | FOBS= | 198.3 | SIGMA= | 2.6 | PHAS= | 216.1 | FOM= | 0.92 |
| INDE | 1 | 25 | 7 | FOBS= | 131.1 | SIGMA= | 4.1 | PHAS= | 175.3 | FOM= | 0.08 |
| INDE | 1 | 25 | 8 | FOBS= | 51.1 | SIGMA= | 11.3 | PHAS= | 326.2 | FOM= | 0.17 |
| INDE | 1 | 25 | 9 | FOBS= | 175.3 | SIGMA= | 3.3 | PHAS= | 156.6 | FOM= | 0.31 |
| INDE | 1 | 25 | 10 | FOBS= | 140.3 | SIGMA= | 4.1 | PHAS= | 274.6 | FOM= | 0.41 |
| INDE | 1 | 25 | 11 | FOBS= | 104.9 | SIGMA= | 26.9 | PHAS= | 126.3 | FOM= | 0.01 |
| INDE | 1 | 26 | 0 | FOBS= | 106.8 | SIGMA= | 4.1 | PHAS= | 43.2 | FOM= | 0.19 |
| INDE | 1 | 26 | 1 | FOBS= | 410.9 | SIGMA= | 1.4 | PHAS= | 81.6 | FOM= | 0.99 |
| INDE | 1 | 26 | 2 | FOBS= | 168.3 | SIGMA= | 3.0 | PHAS= | 231.3 | FOM= | 0.99 |
| INDE | 1 | 26 | 3 | FOBS= | 75.8 | SIGMA= | 5.7 | PHAS= | 1.1 | FOM= | 0.38 |
| INDE | 1 | 26 | 4 | FOBS= | 101.6 | SIGMA= | 5.3 | PHAS= | 274.7 | FOM= | 0.36 |
| INDE | 1 | 26 | 5 | FOBS= | 129.6 | SIGMA= | 4.0 | PHAS= | 251.3 | FOM= | 0.81 |
| INDE | 1 | 26 | 6 | FOBS= | 108.3 | SIGMA= | 4.8 | PHAS= | 154.7 | FOM= | 0.84 |
| INDE | 1 | 26 | 7 | FOBS= | 128.5 | SIGMA= | 4.0 | PHAS= | 63.4 | FOM= | 0.53 |
| INDE | 1 | 26 | 8 | FOBS= | 54.4 | SIGMA= | 9.5 | PHAS= | 51.2 | FOM= | 0.26 |
| INDE | 1 | 26 | 9 | FOBS= | 126.7 | SIGMA= | 4.4 | PHAS= | 310.2 | FOM= | 0.24 |
| INDE | 1 | 26 | 10 | FOBS= | 69.4 | SIGMA= | 8.3 | PHAS= | 291.0 | FOM= | 0.13 |
| INDE | 1 | 27 | 0 | FOBS= | 163.4 | SIGMA= | 2.5 | PHAS= | 197.6 | FOM= | 0.92 |
| INDE | 1 | 27 | 1 | FOBS= | 253.9 | SIGMA= | 1.9 | PHAS= | 268.2 | FOM= | 0.94 |
| INDE | 1 | 27 | 2 | FOBS= | 140.9 | SIGMA= | 3.4 | PHAS= | 97.4 | FOM= | 0.33 |
| INDE | 1 | 27 | 3 | FOBS= | 177.2 | SIGMA= | 2.7 | PHAS= | 338.3 | FOM= | 0.74 |
| INDE | 1 | 27 | 4 | FOBS= | 158.2 | SIGMA= | 2.9 | PHAS= | 48.3 | FOM= | 0.67 |
| INDE | 1 | 27 | 5 | FOBS= | 122.7 | SIGMA= | 4.4 | PHAS= | 250.9 | FOM= | 0.18 |
| INDE | 1 | 27 | 6 | FOBS= | 128.0 | SIGMA= | 4.0 | PHAS= | 249.2 | FOM= | 0.64 |
| INDE | 1 | 27 | 7 | FOBS= | 91.4 | SIGMA= | 5.5 | PHAS= | 85.5 | FOM= | 0.57 |
| INDE | 1 | 27 | 8 | FOBS= | 59.0 | SIGMA= | 8.9 | PHAS= | 248.4 | FOM= | 0.04 |
| INDE | 1 | 27 | 9 | FOBS= | 98.0 | SIGMA= | 5.5 | PHAS= | 210.2 | FOM= | 0.53 |
| INDE | 1 | 28 | 0 | FOBS= | 155.7 | SIGMA= | 2.7 | PHAS= | 99.8 | FOM= | 0.84 |
| INDE | 1 | 28 | 1 | FOBS= | 287.8 | SIGMA= | 1.8 | PHAS= | 147.3 | FOM= | 0.96 |
| INDE | 1 | 28 | 2 | FOBS= | 292.9 | SIGMA= | 1.8 | PHAS= | 198.6 | FOM= | 0.93 |
| INDE | 1 | 28 | 3 | FOBS= | 108.0 | SIGMA= | 4.3 | PHAS= | 115.8 | FOM= | 0.79 |
| INDE | 1 | 28 | 4 | FOBS= | 164.4 | SIGMA= | 2.8 | PHAS= | 122.2 | FOM= | 0.57 |
| INDE | 1 | 28 | 5 | FOBS= | 255.9 | SIGMA= | 2.3 | PHAS= | 349.4 | FOM= | 0.71 |
| INDE | 1 | 28 | 6 | FOBS= | 62.1 | SIGMA= | 8.3 | PHAS= | 64.0 | FOM= | 0.43 |
| INDE | 1 | 28 | 7 | FOBS= | 53.0 | SIGMA= | 10.4 | PHAS= | 329.1 | FOM= | 0.24 |
| INDE | 1 | 28 | 8 | FOBS= | 82.0 | SIGMA= | 5.9 | PHAS= | 229.4 | FOM= | 0.37 |

Fig. 10A-91

| | | | | | | | | | | |
|---|---|---|---|---|---|---|---|---|---|---|
| INDE | 1 | 28 | 9 | FOBS= | 55.2 | SIGMA= | 24.6 | PHAS= | 13.8 | FOM= | 0.07 |
| INDE | 1 | 29 | 0 | FOBS= | 73.5 | SIGMA= | 5.5 | PHAS= | 177.0 | FOM= | 0.06 |
| INDE | 1 | 29 | 1 | FOBS= | 273.6 | SIGMA= | 1.8 | PHAS= | 263.8 | FOM= | 0.65 |
| INDE | 1 | 29 | 2 | FOBS= | 83.7 | SIGMA= | 5.2 | PHAS= | 145.3 | FOM= | 0.17 |
| INDE | 1 | 29 | 3 | FOBS= | 93.2 | SIGMA= | 4.8 | PHAS= | 326.1 | FOM= | 0.36 |
| INDE | 1 | 29 | 4 | FOBS= | 143.8 | SIGMA= | 3.2 | PHAS= | 42.5 | FOM= | 0.80 |
| INDE | 1 | 29 | 5 | FOBS= | 57.0 | SIGMA= | 9.3 | PHAS= | 4.6 | FOM= | 0.23 |
| INDE | 1 | 29 | 6 | FOBS= | 36.6 | SIGMA= | 12.9 | PHAS= | 209.0 | FOM= | 0.06 |
| INDE | 1 | 29 | 7 | FOBS= | 76.8 | SIGMA= | 6.3 | PHAS= | 194.9 | FOM= | 0.40 |
| INDE | 1 | 29 | 8 | FOBS= | 93.3 | SIGMA= | 6.6 | PHAS= | 54.5 | FOM= | 0.35 |
| INDE | 1 | 30 | 0 | FOBS= | 76.6 | SIGMA= | 5.2 | PHAS= | 238.2 | FOM= | 0.12 |
| INDE | 1 | 30 | 1 | FOBS= | 125.2 | SIGMA= | 3.5 | PHAS= | 319.8 | FOM= | 0.42 |
| INDE | 1 | 30 | 2 | FOBS= | 153.1 | SIGMA= | 2.9 | PHAS= | 228.6 | FOM= | 0.38 |
| INDE | 1 | 30 | 3 | FOBS= | 185.8 | SIGMA= | 2.4 | PHAS= | 210.0 | FOM= | 0.18 |
| INDE | 1 | 30 | 4 | FOBS= | 132.0 | SIGMA= | 3.5 | PHAS= | 312.7 | FOM= | 0.68 |
| INDE | 1 | 30 | 5 | FOBS= | 59.2 | SIGMA= | 7.4 | PHAS= | 15.3 | FOM= | 0.04 |
| INDE | 1 | 30 | 6 | FOBS= | 125.8 | SIGMA= | 4.5 | PHAS= | 114.4 | FOM= | 0.17 |
| INDE | 1 | 30 | 7 | FOBS= | 148.5 | SIGMA= | 4.3 | PHAS= | 31.3 | FOM= | 0.62 |
| INDE | 1 | 31 | 0 | FOBS= | 226.1 | SIGMA= | 2.2 | PHAS= | 326.7 | FOM= | 0.97 |
| INDE | 1 | 31 | 1 | FOBS= | 186.5 | SIGMA= | 2.3 | PHAS= | 26.6 | FOM= | 0.55 |
| INDE | 1 | 31 | 2 | FOBS= | 46.1 | SIGMA= | 10.7 | PHAS= | 143.2 | FOM= | 0.93 |
| INDE | 1 | 31 | 3 | FOBS= | 119.4 | SIGMA= | 3.7 | PHAS= | 252.0 | FOM= | 0.88 |
| INDE | 1 | 31 | 4 | FOBS= | 57.9 | SIGMA= | 7.9 | PHAS= | 143.1 | FOM= | 0.23 |
| INDE | 1 | 31 | 5 | FOBS= | 106.2 | SIGMA= | 4.2 | PHAS= | 188.0 | FOM= | 0.11 |
| INDE | 1 | 31 | 6 | FOBS= | 145.4 | SIGMA= | 6.0 | PHAS= | 126.0 | FOM= | 0.16 |
| INDE | 1 | 32 | 0 | FOBS= | 67.5 | SIGMA= | 6.6 | PHAS= | 167.2 | FOM= | 0.16 |
| INDE | 1 | 32 | 2 | FOBS= | 170.1 | SIGMA= | 2.5 | PHAS= | 340.3 | FOM= | 0.48 |
| INDE | 1 | 32 | 3 | FOBS= | 129.5 | SIGMA= | 3.4 | PHAS= | 68.2 | FOM= | 0.69 |
| INDE | 1 | 32 | 4 | FOBS= | 115.1 | SIGMA= | 3.9 | PHAS= | 192.5 | FOM= | 0.84 |
| INDE | 1 | 33 | 0 | FOBS= | 135.5 | SIGMA= | 3.5 | PHAS= | 101.2 | FOM= | 0.28 |
| INDE | 1 | 33 | 1 | FOBS= | 93.1 | SIGMA= | 4.5 | PHAS= | 40.0 | FOM= | 0.06 |
| INDE | 1 | 33 | 2 | FOBS= | 91.0 | SIGMA= | 4.9 | PHAS= | 21.8 | FOM= | 0.49 |
| INDE | 2 | 0 | 1 | FOBS= | 27.9 | SIGMA= | 9.2 | PHAS= | 0.0 | FOM= | 0.28 |
| INDE | 2 | 0 | 2 | FOBS= | 199.2 | SIGMA= | 1.7 | PHAS= | 0.0 | FOM= | 0.33 |
| INDE | 2 | 0 | 3 | FOBS= | 435.4 | SIGMA= | 1.2 | PHAS= | 0.0 | FOM= | 1.00 |
| INDE | 2 | 0 | 4 | FOBS= | 466.8 | SIGMA= | 1.3 | PHAS= | 180.0 | FOM= | 1.00 |
| INDE | 2 | 0 | 5 | FOBS= | 89.1 | SIGMA= | 6.9 | PHAS= | 0.0 | FOM= | 0.02 |
| INDE | 2 | 0 | 6 | FOBS= | 550.5 | SIGMA= | 1.5 | PHAS= | 180.0 | FOM= | 0.99 |
| INDE | 2 | 0 | 7 | FOBS= | 238.7 | SIGMA= | 3.2 | PHAS= | 0.0 | FOM= | 0.73 |
| INDE | 2 | 0 | 8 | FOBS= | 127.4 | SIGMA= | 6.7 | PHAS= | 180.0 | FOM= | 0.17 |
| INDE | 2 | 0 | 9 | FOBS= | 184.8 | SIGMA= | 4.9 | PHAS= | 0.0 | FOM= | 0.03 |
| INDE | 2 | 0 | 10 | FOBS= | 142.7 | SIGMA= | 10.2 | PHAS= | 180.0 | FOM= | 0.58 |
| INDE | 2 | 0 | 11 | FOBS= | 85.7 | SIGMA= | 18.8 | PHAS= | 0.0 | FOM= | 0.01 |
| INDE | 2 | 0 | 12 | FOBS= | 107.0 | SIGMA= | 11.5 | PHAS= | 0.0 | FOM= | 0.02 |
| INDE | 2 | 0 | 13 | FOBS= | 307.2 | SIGMA= | 4.1 | PHAS= | 180.0 | FOM= | 1.00 |
| INDE | 2 | 0 | 14 | FOBS= | 148.6 | SIGMA= | 8.6 | PHAS= | 0.0 | FOM= | 0.09 |
| INDE | 2 | 0 | 15 | FOBS= | 35.7 | SIGMA= | 44.9 | PHAS= | 0.0 | FOM= | 0.27 |
| INDE | 2 | 1 | 1 | FOBS= | 60.2 | SIGMA= | 3.0 | PHAS= | 101.7 | FOM= | 0.55 |
| INDE | 2 | 1 | 2 | FOBS= | 96.7 | SIGMA= | 2.6 | PHAS= | 325.3 | FOM= | 0.98 |
| INDE | 2 | 1 | 3 | FOBS= | 593.3 | SIGMA= | 0.8 | PHAS= | 157.2 | FOM= | 0.92 |
| INDE | 2 | 1 | 4 | FOBS= | 349.6 | SIGMA= | 1.2 | PHAS= | 83.1 | FOM= | 0.97 |
| INDE | 2 | 1 | 5 | FOBS= | 403.0 | SIGMA= | 1.2 | PHAS= | 251.3 | FOM= | 0.75 |
| INDE | 2 | 1 | 6 | FOBS= | 150.6 | SIGMA= | 3.4 | PHAS= | 184.3 | FOM= | 0.90 |
| INDE | 2 | 1 | 7 | FOBS= | 145.4 | SIGMA= | 4.0 | PHAS= | 11.3 | FOM= | 0.93 |
| INDE | 2 | 1 | 8 | FOBS= | 240.9 | SIGMA= | 2.4 | PHAS= | 233.9 | FOM= | 0.97 |
| INDE | 2 | 1 | 9 | FOBS= | 315.4 | SIGMA= | 2.2 | PHAS= | 181.9 | FOM= | 0.97 |
| INDE | 2 | 1 | 10 | FOBS= | 235.6 | SIGMA= | 3.7 | PHAS= | 27.8 | FOM= | 0.49 |
| INDE | 2 | 1 | 11 | FOBS= | 167.5 | SIGMA= | 5.7 | PHAS= | 261.9 | FOM= | 0.74 |
| INDE | 2 | 1 | 12 | FOBS= | 156.5 | SIGMA= | 6.3 | PHAS= | 55.5 | FOM= | 0.62 |
| INDE | 2 | 1 | 13 | FOBS= | 321.4 | SIGMA= | 2.7 | PHAS= | 319.5 | FOM= | 0.70 |
| INDE | 2 | 1 | 14 | FOBS= | 203.5 | SIGMA= | 4.4 | PHAS= | 1.7 | FOM= | 0.35 |
| INDE | 2 | 1 | 15 | FOBS= | 49.5 | SIGMA= | 49.9 | PHAS= | 103.6 | FOM= | 0.17 |
| INDE | 2 | 1 | 16 | FOBS= | 121.4 | SIGMA= | 7.0 | PHAS= | 161.9 | FOM= | 0.18 |
| INDE | 2 | 2 | 1 | FOBS= | 274.5 | SIGMA= | 1.0 | PHAS= | 303.8 | FOM= | 0.86 |
| INDE | 2 | 2 | 2 | FOBS= | 200.8 | SIGMA= | 1.3 | PHAS= | 101.6 | FOM= | 0.95 |
| INDE | 2 | 2 | 3 | FOBS= | 134.1 | SIGMA= | 2.6 | PHAS= | 35.1 | FOM= | 0.11 |
| INDE | 2 | 2 | 4 | FOBS= | 259.9 | SIGMA= | 1.5 | PHAS= | 295.2 | FOM= | 0.98 |
| INDE | 2 | 2 | 5 | FOBS= | 126.2 | SIGMA= | 3.6 | PHAS= | 298.7 | FOM= | 0.93 |
| INDE | 2 | 2 | 6 | FOBS= | 209.6 | SIGMA= | 2.2 | PHAS= | 302.9 | FOM= | 0.85 |
| INDE | 2 | 2 | 7 | FOBS= | 172.6 | SIGMA= | 3.0 | PHAS= | 251.9 | FOM= | 0.86 |
| INDE | 2 | 2 | 8 | FOBS= | 195.6 | SIGMA= | 3.2 | PHAS= | 277.2 | FOM= | 0.91 |

Fig. 10A-92

```
INDE   2  15  11  FOBS=   129.0  SIGMA=   5.8  PHAS=   120.6  FOM=  0.44
INDE   2  15  12  FOBS=    77.9  SIGMA=   9.6  PHAS=   295.4  FOM=  0.26
INDE   2  15  13  FOBS=    67.4  SIGMA=  11.1  PHAS=   188.5  FOM=  0.28
INDE   2  15  14  FOBS=    60.3  SIGMA=  12.2  PHAS=    17.5  FOM=  0.07
INDE   2  16   0  FOBS=    78.3  SIGMA=   4.5  PHAS=   333.2  FOM=  0.76
INDE   2  16   1  FOBS=   186.0  SIGMA=   1.9  PHAS=   149.3  FOM=  0.95
INDE   2  16   2  FOBS=   147.9  SIGMA=   2.5  PHAS=   182.9  FOM=  0.91
INDE   2  16   3  FOBS=    71.4  SIGMA=   5.5  PHAS=   153.9  FOM=  0.12
INDE   2  16   4  FOBS=   275.3  SIGMA=   1.7  PHAS=    59.9  FOM=  0.95
INDE   2  16   5  FOBS=   211.8  SIGMA=   2.2  PHAS=    48.4  FOM=  0.89
INDE   2  16   6  FOBS=   135.4  SIGMA=   3.9  PHAS=   150.0  FOM=  0.44
INDE   2  16   7  FOBS=   141.0  SIGMA=   4.6  PHAS=   129.1  FOM=  0.45
INDE   2  16   8  FOBS=   128.6  SIGMA=   5.2  PHAS=   237.3  FOM=  0.23
INDE   2  16   9  FOBS=   107.5  SIGMA=   6.4  PHAS=   200.2  FOM=  0.49
INDE   2  16  10  FOBS=    75.1  SIGMA=  10.1  PHAS=     6.7  FOM=  0.21
INDE   2  16  11  FOBS=    57.0  SIGMA=  14.1  PHAS=   203.5  FOM=  0.14
INDE   2  16  12  FOBS=    83.6  SIGMA=   8.8  PHAS=   160.4  FOM=  0.00
INDE   2  16  13  FOBS=   110.1  SIGMA=   6.7  PHAS=    66.4  FOM=  0.21
INDE   2  16  14  FOBS=    51.8  SIGMA=  22.5  PHAS=   197.0  FOM=  0.07
INDE   2  17   0  FOBS=   103.3  SIGMA=   3.5  PHAS=    42.3  FOM=  0.51
INDE   2  17   1  FOBS=    71.0  SIGMA=   5.7  PHAS=   163.7  FOM=  0.37
INDE   2  17   2  FOBS=   250.7  SIGMA=   1.6  PHAS=   235.7  FOM=  0.73
INDE   2  17   3  FOBS=   294.0  SIGMA=   1.6  PHAS=   189.9  FOM=  0.75
INDE   2  17   4  FOBS=    86.3  SIGMA=   5.1  PHAS=   323.6  FOM=  0.12
INDE   2  17   5  FOBS=   220.9  SIGMA=   2.3  PHAS=   268.9  FOM=  0.99
INDE   2  17   6  FOBS=   293.8  SIGMA=   1.8  PHAS=   206.1  FOM=  0.97
INDE   2  17   7  FOBS=   356.8  SIGMA=   1.7  PHAS=    84.4  FOM=  0.78
INDE   2  17   8  FOBS=   176.8  SIGMA=   4.1  PHAS=   169.9  FOM=  0.27
INDE   2  17   9  FOBS=   131.1  SIGMA=   5.6  PHAS=    48.1  FOM=  0.48
INDE   2  17  10  FOBS=   267.4  SIGMA=   2.8  PHAS=   131.5  FOM=  0.75
INDE   2  17  11  FOBS=    43.9  SIGMA=  20.5  PHAS=   119.8  FOM=  0.17
INDE   2  17  12  FOBS=    67.8  SIGMA=  11.3  PHAS=   359.7  FOM=  0.16
INDE   2  17  13  FOBS=    99.0  SIGMA=   7.2  PHAS=   203.3  FOM=  0.02
INDE   2  17  14  FOBS=    87.0  SIGMA=  43.0  PHAS=   110.7  FOM=  0.04
INDE   2  18   0  FOBS=    56.5  SIGMA=   6.4  PHAS=   267.1  FOM=  0.48
INDE   2  18   1  FOBS=   177.2  SIGMA=   2.5  PHAS=   316.5  FOM=  0.83
INDE   2  18   2  FOBS=   189.8  SIGMA=   2.1  PHAS=    61.7  FOM=  0.99
INDE   2  18   3  FOBS=   368.2  SIGMA=   1.4  PHAS=   258.1  FOM=  0.96
INDE   2  18   4  FOBS=   364.0  SIGMA=   1.5  PHAS=   192.0  FOM=  0.14
INDE   2  18   5  FOBS=   224.2  SIGMA=   2.2  PHAS=   170.2  FOM=  0.88
INDE   2  18   6  FOBS=   161.1  SIGMA=   3.3  PHAS=   341.5  FOM=  0.79
INDE   2  18   7  FOBS=   229.9  SIGMA=   2.5  PHAS=   358.6  FOM=  0.93
INDE   2  18   8  FOBS=    43.3  SIGMA=  16.6  PHAS=     2.1  FOM=  0.21
INDE   2  18   9  FOBS=   209.5  SIGMA=   3.6  PHAS=   127.9  FOM=  0.51
INDE   2  18  10  FOBS=   123.9  SIGMA=   6.4  PHAS=   198.6  FOM=  0.20
INDE   2  18  11  FOBS=   160.8  SIGMA=   4.4  PHAS=   314.5  FOM=  0.25
INDE   2  18  12  FOBS=    38.8  SIGMA=  29.8  PHAS=    61.3  FOM=  0.11
INDE   2  18  13  FOBS=    68.9  SIGMA=  10.6  PHAS=   219.2  FOM=  0.02
INDE   2  19   0  FOBS=   254.2  SIGMA=   1.6  PHAS=    91.2  FOM=  0.97
INDE   2  19   1  FOBS=   346.1  SIGMA=   1.3  PHAS=    10.2  FOM=  0.92
INDE   2  19   2  FOBS=   231.6  SIGMA=   1.8  PHAS=   287.4  FOM=  0.91
INDE   2  19   3  FOBS=    94.5  SIGMA=   4.5  PHAS=   249.2  FOM=  0.44
INDE   2  19   4  FOBS=    44.7  SIGMA=  11.6  PHAS=    81.5  FOM=  0.15
INDE   2  19   5  FOBS=   164.6  SIGMA=   3.0  PHAS=   126.3  FOM=  0.79
INDE   2  19   6  FOBS=   146.4  SIGMA=   3.8  PHAS=    73.1  FOM=  0.53
INDE   2  19   7  FOBS=   212.4  SIGMA=   2.7  PHAS=   274.2  FOM=  0.69
INDE   2  19   8  FOBS=   289.8  SIGMA=   2.2  PHAS=    87.0  FOM=  0.84
INDE   2  19   9  FOBS=    75.3  SIGMA=   8.9  PHAS=   193.5  FOM=  0.27
INDE   2  19  10  FOBS=    50.1  SIGMA=  16.3  PHAS=   311.6  FOM=  0.07
INDE   2  19  11  FOBS=   223.3  SIGMA=   3.1  PHAS=   103.2  FOM=  0.81
INDE   2  19  12  FOBS=   159.1  SIGMA=   4.5  PHAS=   284.6  FOM=  0.39
INDE   2  19  13  FOBS=    56.3  SIGMA=  12.4  PHAS=   202.6  FOM=  0.05
INDE   2  20   0  FOBS=   206.4  SIGMA=   2.0  PHAS=   291.0  FOM=  0.81
INDE   2  20   1  FOBS=   233.0  SIGMA=   1.9  PHAS=   198.3  FOM=  0.56
INDE   2  20   2  FOBS=   180.8  SIGMA=   2.2  PHAS=   115.7  FOM=  0.84
INDE   2  20   3  FOBS=   363.0  SIGMA=   1.4  PHAS=    22.5  FOM=  0.99
INDE   2  20   4  FOBS=   140.4  SIGMA=   3.6  PHAS=    44.2  FOM=  0.34
INDE   2  20   5  FOBS=   226.5  SIGMA=   3.1  PHAS=   107.8  FOM=  0.95
INDE   2  20   6  FOBS=   220.0  SIGMA=   2.5  PHAS=   295.7  FOM=  0.89
INDE   2  20   7  FOBS=    49.1  SIGMA=  12.2  PHAS=   139.0  FOM=  0.21
INDE   2  20   8  FOBS=   110.4  SIGMA=   5.7  PHAS=   261.1  FOM=  0.62
```

Fig. 10A-96

```
INDE   2  20   9 FOBS=    98.3 SIGMA=   6.2 PHAS=   28.0 FOM= 0.21
INDE   2  20  10 FOBS=   101.5 SIGMA=   6.5 PHAS=   11.6 FOM= 0.07
INDE   2  20  11 FOBS=   121.6 SIGMA=   7.1 PHAS=  288.7 FOM= 0.25
INDE   2  20  12 FOBS=   129.8 SIGMA=   5.4 PHAS=  212.0 FOM= 0.47
INDE   2  21   0 FOBS=   292.4 SIGMA=   1.5 PHAS=  226.0 FOM= 0.92
INDE   2  21   1 FOBS=   263.9 SIGMA=   1.7 PHAS=  178.2 FOM= 0.95
INDE   2  21   2 FOBS=   257.1 SIGMA=   2.0 PHAS=   71.3 FOM= 0.90
INDE   2  21   3 FOBS=   300.5 SIGMA=   1.7 PHAS=  334.7 FOM= 0.97
INDE   2  21   4 FOBS=   150.5 SIGMA=   3.5 PHAS=  298.4 FOM= 0.82
INDE   2  21   5 FOBS=   201.2 SIGMA=   2.7 PHAS=   31.0 FOM= 0.55
INDE   2  21   6 FOBS=    84.9 SIGMA=   6.8 PHAS=  345.3 FOM= 0.62
INDE   2  21   7 FOBS=    93.2 SIGMA=   6.1 PHAS=  161.0 FOM= 0.61
INDE   2  21   8 FOBS=   256.6 SIGMA=   2.4 PHAS=  265.4 FOM= 0.21
INDE   2  21   9 FOBS=   177.3 SIGMA=   3.6 PHAS=  177.3 FOM= 0.48
INDE   2  21  10 FOBS=   132.0 SIGMA=   4.8 PHAS=  265.0 FOM= 0.19
INDE   2  21  11 FOBS=    36.4 SIGMA=  18.0 PHAS=   66.3 FOM= 0.08
INDE   2  21  12 FOBS=    63.8 SIGMA=  12.5 PHAS=  189.7 FOM= 0.02
INDE   2  22   0 FOBS=   289.4 SIGMA=   1.6 PHAS=  177.3 FOM= 0.89
INDE   2  22   1 FOBS=   287.4 SIGMA=   1.7 PHAS=  159.0 FOM= 0.94
INDE   2  22   2 FOBS=   268.4 SIGMA=   2.0 PHAS=  288.0 FOM= 0.95
INDE   2  22   3 FOBS=    35.7 SIGMA=  14.6 PHAS=    4.4 FOM= 0.07
INDE   2  22   4 FOBS=   102.1 SIGMA=   4.7 PHAS=  249.9 FOM= 0.82
INDE   2  22   5 FOBS=   163.7 SIGMA=   3.5 PHAS=   81.0 FOM= 0.79
INDE   2  22   6 FOBS=   171.0 SIGMA=   3.4 PHAS=  349.4 FOM= 0.56
INDE   2  22   7 FOBS=   159.0 SIGMA=   3.9 PHAS=  176.4 FOM= 0.91
INDE   2  22   8 FOBS=   124.3 SIGMA=   4.7 PHAS=  270.8 FOM= 0.38
INDE   2  22   9 FOBS=    92.1 SIGMA=   6.5 PHAS=  170.5 FOM= 0.14
INDE   2  22  10 FOBS=   103.3 SIGMA=   5.7 PHAS=   20.9 FOM= 0.40
INDE   2  22  11 FOBS=    65.4 SIGMA=   9.9 PHAS=   56.2 FOM= 0.03
INDE   2  22  12 FOBS=    72.3 SIGMA=  11.1 PHAS=  156.4 FOM= 0.03
INDE   2  23   0 FOBS=   112.1 SIGMA=   3.8 PHAS=   99.4 FOM= 0.51
INDE   2  23   1 FOBS=   184.6 SIGMA=   2.5 PHAS=  337.0 FOM= 0.80
INDE   2  23   2 FOBS=   315.9 SIGMA=   1.6 PHAS=   59.6 FOM= 0.82
INDE   2  23   3 FOBS=   363.5 SIGMA=   1.5 PHAS=  192.7 FOM= 0.97
INDE   2  23   4 FOBS=   161.8 SIGMA=   3.1 PHAS=  166.6 FOM= 0.89
INDE   2  23   5 FOBS=   172.5 SIGMA=   3.1 PHAS=   98.6 FOM= 0.25
INDE   2  23   6 FOBS=   225.2 SIGMA=   2.6 PHAS=  150.1 FOM= 0.80
INDE   2  23   7 FOBS=   117.4 SIGMA=   5.1 PHAS=  264.8 FOM= 0.76
INDE   2  23   8 FOBS=   174.1 SIGMA=   3.5 PHAS=   43.2 FOM= 0.50
INDE   2  23   9 FOBS=    62.9 SIGMA=   9.2 PHAS=   45.7 FOM= 0.06
INDE   2  23  10 FOBS=    71.4 SIGMA=   8.6 PHAS=  243.9 FOM= 0.73
INDE   2  23  11 FOBS=    88.0 SIGMA=   6.7 PHAS=   82.5 FOM= 0.26
INDE   2  24   0 FOBS=   247.7 SIGMA=   1.9 PHAS=   85.6 FOM= 1.00
INDE   2  24   1 FOBS=    70.7 SIGMA=   6.7 PHAS=  216.8 FOM= 0.70
INDE   2  24   2 FOBS=   108.0 SIGMA=   4.2 PHAS=  237.2 FOM= 0.09
INDE   2  24   3 FOBS=   229.6 SIGMA=   2.4 PHAS=  141.2 FOM= 0.19
INDE   2  24   4 FOBS=   109.9 SIGMA=   4.7 PHAS=  116.1 FOM= 0.43
INDE   2  24   5 FOBS=   154.3 SIGMA=   3.6 PHAS=   23.6 FOM= 0.28
INDE   2  24   6 FOBS=    98.7 SIGMA=   5.6 PHAS=  304.5 FOM= 0.14
INDE   2  24   7 FOBS=    41.5 SIGMA=  14.4 PHAS=  359.8 FOM= 0.14
INDE   2  24   8 FOBS=   129.8 SIGMA=   4.4 PHAS=  109.8 FOM= 0.26
INDE   2  24   9 FOBS=    68.7 SIGMA=   9.5 PHAS=  165.7 FOM= 0.19
INDE   2  24  10 FOBS=   222.9 SIGMA=   2.7 PHAS=   37.8 FOM= 0.88
INDE   2  24  11 FOBS=    97.5 SIGMA=   6.7 PHAS=   89.4 FOM= 0.19
INDE   2  25   0 FOBS=   145.3 SIGMA=   3.1 PHAS=   55.1 FOM= 0.77
INDE   2  25   1 FOBS=   106.8 SIGMA=   4.3 PHAS=   94.3 FOM= 0.83
INDE   2  25   2 FOBS=   164.2 SIGMA=   2.9 PHAS=    3.9 FOM= 0.97
INDE   2  25   3 FOBS=   122.1 SIGMA=   4.7 PHAS=   89.7 FOM= 0.74
INDE   2  25   4 FOBS=   169.5 SIGMA=   3.0 PHAS=  282.3 FOM= 0.19
INDE   2  25   5 FOBS=   312.0 SIGMA=   1.8 PHAS=   56.9 FOM= 0.97
INDE   2  25   6 FOBS=    81.1 SIGMA=   6.6 PHAS=   14.1 FOM= 0.31
INDE   2  25   7 FOBS=    96.7 SIGMA=   5.9 PHAS=  268.0 FOM= 0.33
INDE   2  25   8 FOBS=   137.2 SIGMA=   4.2 PHAS=  304.4 FOM= 0.11
INDE   2  25   9 FOBS=    77.2 SIGMA=   7.4 PHAS=   24.1 FOM= 0.32
INDE   2  25  10 FOBS=    57.3 SIGMA=  11.2 PHAS=  266.4 FOM= 0.12
INDE   2  26   0 FOBS=   221.5 SIGMA=   2.1 PHAS=  114.2 FOM= 0.98
INDE   2  26   1 FOBS=   157.9 SIGMA=   2.8 PHAS=   94.7 FOM= 0.96
INDE   2  26   2 FOBS=   111.7 SIGMA=   4.2 PHAS=  325.5 FOM= 0.86
INDE   2  26   3 FOBS=   260.4 SIGMA=   2.2 PHAS=  167.6 FOM= 0.62
INDE   2  26   4 FOBS=   233.5 SIGMA=   2.2 PHAS=  307.1 FOM= 0.66
INDE   2  26   5 FOBS=   209.0 SIGMA=   2.5 PHAS=  112.2 FOM= 0.95
```

Fig. 10A-97

```
INDE   2  26   6  FOBS=   436.6  SIGMA=    1.6  PHAS=   325.9  FOM=  0.94
INDE   2  26   7  FOBS=   238.0  SIGMA=    2.4  PHAS=   165.4  FOM=  0.95
INDE   2  26   8  FOBS=   206.3  SIGMA=    2.8  PHAS=     9.1  FOM=  0.95
INDE   2  26   9  FOBS=   274.1  SIGMA=    2.2  PHAS=   202.4  FOM=  0.79
INDE   2  26  10  FOBS=   129.5  SIGMA=    8.7  PHAS=    60.5  FOM=  0.22
INDE   2  27   0  FOBS=   290.2  SIGMA=    1.7  PHAS=   131.2  FOM=  0.91
INDE   2  27   1  FOBS=    44.5  SIGMA=   11.9  PHAS=   177.5  FOM=  0.10
INDE   2  27   2  FOBS=   201.2  SIGMA=    2.3  PHAS=    48.9  FOM=  0.89
INDE   2  27   3  FOBS=   169.5  SIGMA=    2.6  PHAS=   351.1  FOM=  0.95
INDE   2  27   4  FOBS=   190.3  SIGMA=    2.8  PHAS=   135.9  FOM=  0.90
INDE   2  27   5  FOBS=   123.8  SIGMA=    4.2  PHAS=   317.7  FOM=  0.62
INDE   2  27   6  FOBS=    51.8  SIGMA=    9.7  PHAS=   179.2  FOM=  0.43
INDE   2  27   7  FOBS=   198.8  SIGMA=    2.8  PHAS=    51.8  FOM=  0.94
INDE   2  27   8  FOBS=    90.3  SIGMA=    6.1  PHAS=   323.6  FOM=  0.22
INDE   2  27   9  FOBS=   177.4  SIGMA=    3.2  PHAS=   266.6  FOM=  0.49
INDE   2  28   0  FOBS=    76.0  SIGMA=    5.6  PHAS=   102.3  FOM=  0.67
INDE   2  28   1  FOBS=   243.4  SIGMA=    2.0  PHAS=   324.3  FOM=  0.96
INDE   2  28   2  FOBS=   288.1  SIGMA=    1.8  PHAS=    61.8  FOM=  0.98
INDE   2  28   3  FOBS=   230.2  SIGMA=    2.1  PHAS=   290.0  FOM=  0.95
INDE   2  28   4  FOBS=   122.5  SIGMA=    4.6  PHAS=   338.1  FOM=  0.64
INDE   2  28   5  FOBS=   145.0  SIGMA=    3.5  PHAS=   222.4  FOM=  0.88
INDE   2  28   6  FOBS=   112.8  SIGMA=    4.6  PHAS=   355.2  FOM=  0.68
INDE   2  28   7  FOBS=    70.6  SIGMA=    7.3  PHAS=    89.2  FOM=  0.03
INDE   2  28   8  FOBS=    44.8  SIGMA=   12.0  PHAS=   255.5  FOM=  0.02
INDE   2  29   0  FOBS=   234.8  SIGMA=    2.0  PHAS=     5.4  FOM=  0.23
INDE   2  29   1  FOBS=   167.6  SIGMA=    2.7  PHAS=   132.5  FOM=  0.54
INDE   2  29   2  FOBS=   155.8  SIGMA=    2.9  PHAS=    61.3  FOM=  0.93
INDE   2  29   3  FOBS=   155.1  SIGMA=    3.0  PHAS=    15.8  FOM=  0.20
INDE   2  29   4  FOBS=    56.4  SIGMA=    9.3  PHAS=   272.9  FOM=  0.05
INDE   2  29   5  FOBS=    44.7  SIGMA=   12.2  PHAS=   104.8  FOM=  0.28
INDE   2  29   6  FOBS=   110.5  SIGMA=    4.5  PHAS=   325.4  FOM=  0.21
INDE   2  29   7  FOBS=   113.5  SIGMA=    4.5  PHAS=   343.1  FOM=  0.15
INDE   2  30   0  FOBS=    44.4  SIGMA=   16.5  PHAS=   111.3  FOM=  0.21
INDE   2  30   1  FOBS=   291.6  SIGMA=    1.7  PHAS=   247.7  FOM=  0.77
INDE   2  30   2  FOBS=   127.6  SIGMA=    3.5  PHAS=    24.7  FOM=  0.69
INDE   2  30   3  FOBS=   133.0  SIGMA=    3.5  PHAS=   143.4  FOM=  0.85
INDE   2  30   4  FOBS=   114.6  SIGMA=    4.0  PHAS=   291.0  FOM=  0.55
INDE   2  30   5  FOBS=    90.5  SIGMA=    6.0  PHAS=     8.3  FOM=  0.05
INDE   2  30   6  FOBS=   105.9  SIGMA=    4.6  PHAS=   131.5  FOM=  0.15
INDE   2  31   0  FOBS=   175.8  SIGMA=    2.4  PHAS=   213.9  FOM=  0.71
INDE   2  31   1  FOBS=    74.2  SIGMA=    5.6  PHAS=   332.1  FOM=  0.85
INDE   2  31   2  FOBS=    61.7  SIGMA=    6.8  PHAS=   100.3  FOM=  0.08
INDE   2  31   3  FOBS=   176.7  SIGMA=    2.6  PHAS=   195.1  FOM=  0.59
INDE   2  31   4  FOBS=   144.0  SIGMA=    3.2  PHAS=    27.7  FOM=  0.87
INDE   2  31   5  FOBS=    40.0  SIGMA=   18.0  PHAS=   127.4  FOM=  0.08
INDE   2  32   0  FOBS=   147.3  SIGMA=    3.0  PHAS=   286.2  FOM=  0.81
INDE   2  32   1  FOBS=   105.9  SIGMA=    4.0  PHAS=   227.0  FOM=  0.75
INDE   2  32   2  FOBS=    74.3  SIGMA=    5.6  PHAS=   345.2  FOM=  0.18
INDE   2  32   3  FOBS=    85.5  SIGMA=    5.1  PHAS=   334.8  FOM=  0.02
INDE   2  32   4  FOBS=   108.7  SIGMA=    5.1  PHAS=   357.8  FOM=  0.10
INDE   2  33   0  FOBS=    98.5  SIGMA=    4.3  PHAS=   260.6  FOM=  0.16
INDE   2  33   1  FOBS=   134.1  SIGMA=    3.5  PHAS=   173.2  FOM=  0.86
INDE   3   0   0  FOBS=    45.3  SIGMA=    5.6  PHAS=   180.0  FOM=  0.36
INDE   3   0   1  FOBS=   100.4  SIGMA=    3.6  PHAS=     0.0  FOM=  0.07
INDE   3   0   2  FOBS=    25.8  SIGMA=   20.0  PHAS=   180.0  FOM=  0.40
INDE   3   0   3  FOBS=   204.2  SIGMA=    2.3  PHAS=   180.0  FOM=  1.00
INDE   3   0   4  FOBS=   328.3  SIGMA=    1.9  PHAS=     0.0  FOM=  1.00
INDE   3   0   5  FOBS=   253.6  SIGMA=    2.7  PHAS=     0.0  FOM=  0.64
INDE   3   0   6  FOBS=   348.5  SIGMA=    2.3  PHAS=     0.0  FOM=  1.00
INDE   3   0   7  FOBS=   112.9  SIGMA=    8.6  PHAS=   180.0  FOM=  0.94
INDE   3   0   8  FOBS=   337.5  SIGMA=    2.9  PHAS=     0.0  FOM=  1.00
INDE   3   0   9  FOBS=   245.2  SIGMA=    4.2  PHAS=   180.0  FOM=  0.15
INDE   3   0  10  FOBS=   218.3  SIGMA=    5.1  PHAS=   180.0  FOM=  0.26
INDE   3   0  11  FOBS=   139.3  SIGMA=   10.3  PHAS=     0.0  FOM=  0.01
INDE   3   0  12  FOBS=   107.2  SIGMA=   16.6  PHAS=   180.0  FOM=  0.01
INDE   3   0  13  FOBS=    80.4  SIGMA=   16.0  PHAS=     0.0  FOM=  0.05
INDE   3   0  14  FOBS=   110.6  SIGMA=   11.5  PHAS=   180.0  FOM=  0.03
INDE   3   0  15  FOBS=    54.4  SIGMA=   22.8  PHAS=   180.0  FOM=  0.02
INDE   3   0  16  FOBS=   268.3  SIGMA=  407.0  PHAS=     0.0  FOM=  0.02
INDE   3   1   0  FOBS=   123.4  SIGMA=    1.6  PHAS=    64.7  FOM=  0.75
INDE   3   1   1  FOBS=   167.8  SIGMA=    1.5  PHAS=   182.1  FOM=  0.81
```

Fig. 10A-98

| | | | | | | | | | | | |
|---|---|---|---|---|---|---|---|---|---|---|---|
| INDE | 2 | 2 | 9 | FOBS= | 255.3 | SIGMA= | 2.9 | PHAS= | 57.4 | FOM= | 0.76 |
| INDE | 2 | 2 | 10 | FOBS= | 243.1 | SIGMA= | 3.0 | PHAS= | 53.4 | FOM= | 0.08 |
| INDE | 2 | 2 | 11 | FOBS= | 155.0 | SIGMA= | 5.5 | PHAS= | 191.4 | FOM= | 0.26 |
| INDE | 2 | 2 | 12 | FOBS= | 108.9 | SIGMA= | 9.2 | PHAS= | 16.9 | FOM= | 0.14 |
| INDE | 2 | 2 | 13 | FOBS= | 109.7 | SIGMA= | 8.0 | PHAS= | 149.2 | FOM= | 0.15 |
| INDE | 2 | 2 | 14 | FOBS= | 139.9 | SIGMA= | 6.3 | PHAS= | 50.5 | FOM= | 0.28 |
| INDE | 2 | 2 | 15 | FOBS= | 50.9 | SIGMA= | 85.9 | PHAS= | 199.7 | FOM= | 0.18 |
| INDE | 2 | 2 | 16 | FOBS= | 128.8 | SIGMA= | 6.6 | PHAS= | 164.2 | FOM= | 0.05 |
| INDE | 2 | 3 | 0 | FOBS= | 247.2 | SIGMA= | 1.0 | PHAS= | 349.9 | FOM= | 0.79 |
| INDE | 2 | 3 | 1 | FOBS= | 215.2 | SIGMA= | 1.0 | PHAS= | 293.6 | FOM= | 1.00 |
| INDE | 2 | 3 | 2 | FOBS= | 312.3 | SIGMA= | 0.9 | PHAS= | 159.3 | FOM= | 1.00 |
| INDE | 2 | 3 | 3 | FOBS= | 367.2 | SIGMA= | 1.3 | PHAS= | 343.3 | FOM= | 0.98 |
| INDE | 2 | 3 | 4 | FOBS= | 363.7 | SIGMA= | 1.3 | PHAS= | 90.5 | FOM= | 0.98 |
| INDE | 2 | 3 | 5 | FOBS= | 177.4 | SIGMA= | 2.4 | PHAS= | 15.2 | FOM= | 0.87 |
| INDE | 2 | 3 | 6 | FOBS= | 193.0 | SIGMA= | 2.5 | PHAS= | 40.8 | FOM= | 0.92 |
| INDE | 2 | 3 | 7 | FOBS= | 50.5 | SIGMA= | 12.7 | PHAS= | 156.3 | FOM= | 0.10 |
| INDE | 2 | 3 | 8 | FOBS= | 150.5 | SIGMA= | 4.6 | PHAS= | 145.1 | FOM= | 0.52 |
| INDE | 2 | 3 | 9 | FOBS= | 309.6 | SIGMA= | 2.2 | PHAS= | 302.5 | FOM= | 0.89 |
| INDE | 2 | 3 | 10 | FOBS= | 131.1 | SIGMA= | 5.7 | PHAS= | 18.8 | FOM= | 0.17 |
| INDE | 2 | 3 | 11 | FOBS= | 215.8 | SIGMA= | 3.8 | PHAS= | 200.1 | FOM= | 0.64 |
| INDE | 2 | 3 | 12 | FOBS= | 88.7 | SIGMA= | 10.4 | PHAS= | 115.9 | FOM= | 0.05 |
| INDE | 2 | 3 | 13 | FOBS= | 288.9 | SIGMA= | 3.3 | PHAS= | 329.8 | FOM= | 0.51 |
| INDE | 2 | 3 | 14 | FOBS= | 140.6 | SIGMA= | 6.2 | PHAS= | 178.9 | FOM= | 0.11 |
| INDE | 2 | 3 | 15 | FOBS= | 53.9 | SIGMA= | 14.1 | PHAS= | 147.1 | FOM= | 0.45 |
| INDE | 2 | 3 | 16 | FOBS= | 95.5 | SIGMA= | 8.8 | PHAS= | 25.7 | FOM= | 0.05 |
| INDE | 2 | 4 | 0 | FOBS= | 130.8 | SIGMA= | 2.0 | PHAS= | 164.3 | FOM= | 0.95 |
| INDE | 2 | 4 | 1 | FOBS= | 216.8 | SIGMA= | 1.1 | PHAS= | 8.8 | FOM= | 0.95 |
| INDE | 2 | 4 | 2 | FOBS= | 243.0 | SIGMA= | 1.2 | PHAS= | 312.4 | FOM= | 0.99 |
| INDE | 2 | 4 | 3 | FOBS= | 234.3 | SIGMA= | 1.4 | PHAS= | 74.5 | FOM= | 0.76 |
| INDE | 2 | 4 | 4 | FOBS= | 195.9 | SIGMA= | 1.8 | PHAS= | 300.7 | FOM= | 0.94 |
| INDE | 2 | 4 | 5 | FOBS= | 333.8 | SIGMA= | 1.6 | PHAS= | 275.3 | FOM= | 1.00 |
| INDE | 2 | 4 | 6 | FOBS= | 331.2 | SIGMA= | 1.6 | PHAS= | 73.6 | FOM= | 0.97 |
| INDE | 2 | 4 | 7 | FOBS= | 130.4 | SIGMA= | 4.9 | PHAS= | 198.5 | FOM= | 0.03 |
| INDE | 2 | 4 | 8 | FOBS= | 214.5 | SIGMA= | 3.0 | PHAS= | 111.4 | FOM= | 0.48 |
| INDE | 2 | 4 | 9 | FOBS= | 268.5 | SIGMA= | 2.5 | PHAS= | 84.3 | FOM= | 0.90 |
| INDE | 2 | 4 | 10 | FOBS= | 86.4 | SIGMA= | 8.4 | PHAS= | 119.6 | FOM= | 0.09 |
| INDE | 2 | 4 | 11 | FOBS= | 398.9 | SIGMA= | 2.1 | PHAS= | 183.9 | FOM= | 0.54 |
| INDE | 2 | 4 | 12 | FOBS= | 108.8 | SIGMA= | 8.0 | PHAS= | 316.3 | FOM= | 0.11 |
| INDE | 2 | 4 | 13 | FOBS= | 150.6 | SIGMA= | 6.7 | PHAS= | 140.7 | FOM= | 0.06 |
| INDE | 2 | 4 | 14 | FOBS= | 266.3 | SIGMA= | 3.5 | PHAS= | 139.9 | FOM= | 0.32 |
| INDE | 2 | 4 | 15 | FOBS= | 84.9 | SIGMA= | 9.8 | PHAS= | 284.4 | FOM= | 0.05 |
| INDE | 2 | 4 | 16 | FOBS= | 126.3 | SIGMA= | 6.7 | PHAS= | 229.8 | FOM= | 0.02 |
| INDE | 2 | 5 | 0 | FOBS= | 199.4 | SIGMA= | 1.5 | PHAS= | 36.1 | FOM= | 0.95 |
| INDE | 2 | 5 | 1 | FOBS= | 557.5 | SIGMA= | 0.8 | PHAS= | 327.7 | FOM= | 0.98 |
| INDE | 2 | 5 | 2 | FOBS= | 303.0 | SIGMA= | 1.0 | PHAS= | 45.1 | FOM= | 0.97 |
| INDE | 2 | 5 | 3 | FOBS= | 295.3 | SIGMA= | 1.2 | PHAS= | 333.1 | FOM= | 0.92 |
| INDE | 2 | 5 | 4 | FOBS= | 177.9 | SIGMA= | 2.2 | PHAS= | 258.2 | FOM= | 0.99 |
| INDE | 2 | 5 | 5 | FOBS= | 111.1 | SIGMA= | 4.0 | PHAS= | 30.0 | FOM= | 0.90 |
| INDE | 2 | 5 | 6 | FOBS= | 138.6 | SIGMA= | 4.0 | PHAS= | 326.8 | FOM= | 0.14 |
| INDE | 2 | 5 | 7 | FOBS= | 195.9 | SIGMA= | 3.1 | PHAS= | 220.6 | FOM= | 0.34 |
| INDE | 2 | 5 | 8 | FOBS= | 509.2 | SIGMA= | 1.4 | PHAS= | 136.9 | FOM= | 0.91 |
| INDE | 2 | 5 | 9 | FOBS= | 66.0 | SIGMA= | 10.3 | PHAS= | 291.1 | FOM= | 0.08 |
| INDE | 2 | 5 | 10 | FOBS= | 364.6 | SIGMA= | 2.1 | PHAS= | 134.4 | FOM= | 0.90 |
| INDE | 2 | 5 | 11 | FOBS= | 105.2 | SIGMA= | 8.3 | PHAS= | 248.1 | FOM= | 0.16 |
| INDE | 2 | 5 | 12 | FOBS= | 73.6 | SIGMA= | 13.2 | PHAS= | 63.5 | FOM= | 0.02 |
| INDE | 2 | 5 | 13 | FOBS= | 183.9 | SIGMA= | 4.9 | PHAS= | 86.3 | FOM= | 0.72 |
| INDE | 2 | 5 | 14 | FOBS= | 66.7 | SIGMA= | 15.7 | PHAS= | 309.1 | FOM= | 0.27 |
| INDE | 2 | 5 | 15 | FOBS= | 87.4 | SIGMA= | 10.0 | PHAS= | 207.5 | FOM= | 0.07 |
| INDE | 2 | 5 | 16 | FOBS= | 66.9 | SIGMA= | 23.2 | PHAS= | 102.1 | FOM= | 0.08 |
| INDE | 2 | 6 | 0 | FOBS= | 61.0 | SIGMA= | 3.3 | PHAS= | 27.2 | FOM= | 0.94 |
| INDE | 2 | 6 | 1 | FOBS= | 206.1 | SIGMA= | 1.3 | PHAS= | 322.3 | FOM= | 0.90 |
| INDE | 2 | 6 | 2 | FOBS= | 344.3 | SIGMA= | 1.0 | PHAS= | 54.7 | FOM= | 0.99 |
| INDE | 2 | 6 | 3 | FOBS= | 106.3 | SIGMA= | 3.2 | PHAS= | 324.3 | FOM= | 0.56 |
| INDE | 2 | 6 | 4 | FOBS= | 520.9 | SIGMA= | 0.9 | PHAS= | 354.6 | FOM= | 0.75 |
| INDE | 2 | 6 | 5 | FOBS= | 272.3 | SIGMA= | 1.9 | PHAS= | 28.6 | FOM= | 0.74 |
| INDE | 2 | 6 | 6 | FOBS= | 257.5 | SIGMA= | 2.2 | PHAS= | 0.5 | FOM= | 0.08 |
| INDE | 2 | 6 | 7 | FOBS= | 286.6 | SIGMA= | 2.2 | PHAS= | 275.7 | FOM= | 0.87 |
| INDE | 2 | 6 | 8 | FOBS= | 309.7 | SIGMA= | 2.1 | PHAS= | 101.8 | FOM= | 0.98 |
| INDE | 2 | 6 | 9 | FOBS= | 272.3 | SIGMA= | 2.5 | PHAS= | 316.8 | FOM= | 0.37 |
| INDE | 2 | 6 | 10 | FOBS= | 228.8 | SIGMA= | 3.2 | PHAS= | 287.4 | FOM= | 0.82 |
| INDE | 2 | 6 | 11 | FOBS= | 185.3 | SIGMA= | 4.7 | PHAS= | 169.5 | FOM= | 0.37 |

Fig. 10A-93

| | | | | | | | | | | | | |
|---|---|---|---|---|---|---|---|---|---|---|---|---|
| INDE | 2 | 6 | 12 | FOBS= | 208.4 | SIGMA= | 4.4 | PHAS= | 90.2 | FOM= | 0.39 |
| INDE | 2 | 6 | 13 | FOBS= | 68.2 | SIGMA= | 15.9 | PHAS= | 276.6 | FOM= | 0.11 |
| INDE | 2 | 6 | 14 | FOBS= | 114.7 | SIGMA= | 7.6 | PHAS= | 232.5 | FOM= | 0.10 |
| INDE | 2 | 6 | 15 | FOBS= | 54.8 | SIGMA= | 31.0 | PHAS= | 15.3 | FOM= | 0.07 |
| INDE | 2 | 6 | 16 | FOBS= | 58.5 | SIGMA= | 25.4 | PHAS= | 260.2 | FOM= | 0.03 |
| INDE | 2 | 7 | 0 | FOBS= | 213.8 | SIGMA= | 1.3 | PHAS= | 127.0 | FOM= | 0.97 |
| INDE | 2 | 7 | 1 | FOBS= | 268.4 | SIGMA= | 1.3 | PHAS= | 15.0 | FOM= | 0.63 |
| INDE | 2 | 7 | 2 | FOBS= | 263.3 | SIGMA= | 1.3 | PHAS= | 123.1 | FOM= | 0.88 |
| INDE | 2 | 7 | 3 | FOBS= | 271.9 | SIGMA= | 1.3 | PHAS= | 30.2 | FOM= | 0.66 |
| INDE | 2 | 7 | 4 | FOBS= | 187.3 | SIGMA= | 2.1 | PHAS= | 35.0 | FOM= | 0.94 |
| INDE | 2 | 7 | 5 | FOBS= | 68.2 | SIGMA= | 6.8 | PHAS= | 277.9 | FOM= | 0.03 |
| INDE | 2 | 7 | 6 | FOBS= | 37.4 | SIGMA= | 18.8 | PHAS= | 308.6 | FOM= | 0.26 |
| INDE | 2 | 7 | 7 | FOBS= | 134.0 | SIGMA= | 4.3 | PHAS= | 152.0 | FOM= | 0.81 |
| INDE | 2 | 7 | 8 | FOBS= | 224.9 | SIGMA= | 2.7 | PHAS= | 261.1 | FOM= | 0.83 |
| INDE | 2 | 7 | 9 | FOBS= | 184.2 | SIGMA= | 4.7 | PHAS= | 285.0 | FOM= | 0.90 |
| INDE | 2 | 7 | 10 | FOBS= | 332.2 | SIGMA= | 2.3 | PHAS= | 156.0 | FOM= | 0.90 |
| INDE | 2 | 7 | 11 | FOBS= | 119.3 | SIGMA= | 7.4 | PHAS= | 131.1 | FOM= | 0.41 |
| INDE | 2 | 7 | 12 | FOBS= | 147.7 | SIGMA= | 6.0 | PHAS= | 327.3 | FOM= | 0.53 |
| INDE | 2 | 7 | 13 | FOBS= | 188.4 | SIGMA= | 4.7 | PHAS= | 208.0 | FOM= | 0.57 |
| INDE | 2 | 7 | 14 | FOBS= | 65.7 | SIGMA= | 14.1 | PHAS= | 57.7 | FOM= | 0.06 |
| INDE | 2 | 7 | 15 | FOBS= | 63.7 | SIGMA= | 39.0 | PHAS= | 149.9 | FOM= | 0.03 |
| INDE | 2 | 8 | 0 | FOBS= | 67.8 | SIGMA= | 3.9 | PHAS= | 155.1 | FOM= | 0.47 |
| INDE | 2 | 8 | 1 | FOBS= | 242.7 | SIGMA= | 1.4 | PHAS= | 263.7 | FOM= | 0.98 |
| INDE | 2 | 8 | 2 | FOBS= | 272.0 | SIGMA= | 1.4 | PHAS= | 44.4 | FOM= | 0.86 |
| INDE | 2 | 8 | 3 | FOBS= | 315.0 | SIGMA= | 1.4 | PHAS= | 148.8 | FOM= | 1.00 |
| INDE | 2 | 8 | 4 | FOBS= | 135.3 | SIGMA= | 3.1 | PHAS= | 108.4 | FOM= | 0.89 |
| INDE | 2 | 8 | 5 | FOBS= | 122.9 | SIGMA= | 3.9 | PHAS= | 98.0 | FOM= | 0.67 |
| INDE | 2 | 8 | 6 | FOBS= | 121.5 | SIGMA= | 4.5 | PHAS= | 112.8 | FOM= | 0.80 |
| INDE | 2 | 8 | 7 | FOBS= | 195.4 | SIGMA= | 2.6 | PHAS= | 253.2 | FOM= | 0.18 |
| INDE | 2 | 8 | 8 | FOBS= | 319.6 | SIGMA= | 2.0 | PHAS= | 213.7 | FOM= | 0.25 |
| INDE | 2 | 8 | 9 | FOBS= | 206.5 | SIGMA= | 3.4 | PHAS= | 280.4 | FOM= | 0.86 |
| INDE | 2 | 8 | 10 | FOBS= | 389.5 | SIGMA= | 2.4 | PHAS= | 118.3 | FOM= | 0.95 |
| INDE | 2 | 8 | 11 | FOBS= | 71.8 | SIGMA= | 16.9 | PHAS= | 246.3 | FOM= | 0.10 |
| INDE | 2 | 8 | 12 | FOBS= | 190.5 | SIGMA= | 4.7 | PHAS= | 256.1 | FOM= | 0.41 |
| INDE | 2 | 8 | 13 | FOBS= | 141.3 | SIGMA= | 6.2 | PHAS= | 129.0 | FOM= | 0.49 |
| INDE | 2 | 8 | 14 | FOBS= | 87.6 | SIGMA= | 9.6 | PHAS= | 260.8 | FOM= | 0.02 |
| INDE | 2 | 8 | 15 | FOBS= | 49.9 | SIGMA= | 22.3 | PHAS= | 25.4 | FOM= | 0.05 |
| INDE | 2 | 9 | 0 | FOBS= | 128.1 | SIGMA= | 1.8 | PHAS= | 202.8 | FOM= | 0.82 |
| INDE | 2 | 9 | 1 | FOBS= | 63.2 | SIGMA= | 5.1 | PHAS= | 309.0 | FOM= | 0.56 |
| INDE | 2 | 9 | 2 | FOBS= | 145.0 | SIGMA= | 2.4 | PHAS= | 88.2 | FOM= | 0.86 |
| INDE | 2 | 9 | 3 | FOBS= | 49.5 | SIGMA= | 7.1 | PHAS= | 323.9 | FOM= | 0.19 |
| INDE | 2 | 9 | 4 | FOBS= | 152.6 | SIGMA= | 2.8 | PHAS= | 18.2 | FOM= | 0.90 |
| INDE | 2 | 9 | 5 | FOBS= | 77.3 | SIGMA= | 5.5 | PHAS= | 303.6 | FOM= | 0.57 |
| INDE | 2 | 9 | 6 | FOBS= | 231.0 | SIGMA= | 2.1 | PHAS= | 2.0 | FOM= | 0.78 |
| INDE | 2 | 9 | 7 | FOBS= | 179.7 | SIGMA= | 2.9 | PHAS= | 115.2 | FOM= | 0.58 |
| INDE | 2 | 9 | 8 | FOBS= | 208.0 | SIGMA= | 2.9 | PHAS= | 250.1 | FOM= | 0.73 |
| INDE | 2 | 9 | 9 | FOBS= | 68.7 | SIGMA= | 10.5 | PHAS= | 134.7 | FOM= | 0.15 |
| INDE | 2 | 9 | 10 | FOBS= | 283.8 | SIGMA= | 2.7 | PHAS= | 142.1 | FOM= | 0.60 |
| INDE | 2 | 9 | 11 | FOBS= | 166.2 | SIGMA= | 6.0 | PHAS= | 245.8 | FOM= | 0.56 |
| INDE | 2 | 9 | 12 | FOBS= | 275.3 | SIGMA= | 3.5 | PHAS= | 45.7 | FOM= | 0.44 |
| INDE | 2 | 9 | 13 | FOBS= | 127.6 | SIGMA= | 7.4 | PHAS= | 147.0 | FOM= | 0.29 |
| INDE | 2 | 9 | 14 | FOBS= | 50.2 | SIGMA= | 17.8 | PHAS= | 347.2 | FOM= | 0.17 |
| INDE | 2 | 9 | 15 | FOBS= | 104.0 | SIGMA= | 8.0 | PHAS= | 104.5 | FOM= | 0.04 |
| INDE | 2 | 10 | 0 | FOBS= | 94.9 | SIGMA= | 2.9 | PHAS= | 303.5 | FOM= | 0.97 |
| INDE | 2 | 10 | 1 | FOBS= | 173.9 | SIGMA= | 1.7 | PHAS= | 290.4 | FOM= | 0.96 |
| INDE | 2 | 10 | 2 | FOBS= | 141.0 | SIGMA= | 2.4 | PHAS= | 326.0 | FOM= | 0.94 |
| INDE | 2 | 10 | 3 | FOBS= | 101.8 | SIGMA= | 4.4 | PHAS= | 232.8 | FOM= | 0.64 |
| INDE | 2 | 10 | 4 | FOBS= | 258.8 | SIGMA= | 1.6 | PHAS= | 239.1 | FOM= | 0.93 |
| INDE | 2 | 10 | 5 | FOBS= | 139.4 | SIGMA= | 3.3 | PHAS= | 269.2 | FOM= | 0.86 |
| INDE | 2 | 10 | 6 | FOBS= | 189.5 | SIGMA= | 2.5 | PHAS= | 124.7 | FOM= | 0.58 |
| INDE | 2 | 10 | 7 | FOBS= | 118.9 | SIGMA= | 5.0 | PHAS= | 266.3 | FOM= | 0.03 |
| INDE | 2 | 10 | 8 | FOBS= | 63.4 | SIGMA= | 9.8 | PHAS= | 247.3 | FOM= | 0.09 |
| INDE | 2 | 10 | 9 | FOBS= | 101.4 | SIGMA= | 6.4 | PHAS= | 69.9 | FOM= | 0.18 |
| INDE | 2 | 10 | 10 | FOBS= | 317.0 | SIGMA= | 2.4 | PHAS= | 207.8 | FOM= | 0.53 |
| INDE | 2 | 10 | 11 | FOBS= | 121.3 | SIGMA= | 6.9 | PHAS= | 235.3 | FOM= | 0.36 |
| INDE | 2 | 10 | 12 | FOBS= | 251.4 | SIGMA= | 3.3 | PHAS= | 153.1 | FOM= | 0.83 |
| INDE | 2 | 10 | 13 | FOBS= | 151.0 | SIGMA= | 6.8 | PHAS= | 207.4 | FOM= | 0.42 |
| INDE | 2 | 10 | 14 | FOBS= | 69.3 | SIGMA= | 15.5 | PHAS= | 6.0 | FOM= | 0.14 |
| INDE | 2 | 11 | 0 | FOBS= | 139.2 | SIGMA= | 2.0 | PHAS= | 3.9 | FOM= | 0.99 |
| INDE | 2 | 11 | 1 | FOBS= | 157.6 | SIGMA= | 1.9 | PHAS= | 50.9 | FOM= | 0.86 |
| INDE | 2 | 11 | 2 | FOBS= | 205.8 | SIGMA= | 1.7 | PHAS= | 333.4 | FOM= | 0.76 |

Fig. 10A-94

```
INDE  2 11  3 FOBS= 129.0 SIGMA=  3.8 PHAS= 340.4 FOM= 0.77
INDE  2 11  4 FOBS= 117.4 SIGMA=  4.0 PHAS= 196.2 FOM= 0.95
INDE  2 11  5 FOBS= 111.7 SIGMA=  4.0 PHAS= 353.2 FOM= 0.19
INDE  2 11  6 FOBS= 300.3 SIGMA=  1.7 PHAS=  61.7 FOM= 0.94
INDE  2 11  7 FOBS= 414.0 SIGMA=  1.5 PHAS= 234.5 FOM= 0.95
INDE  2 11  8 FOBS= 124.4 SIGMA=  5.0 PHAS=   9.8 FOM= 0.55
INDE  2 11  9 FOBS= 560.9 SIGMA=  2.0 PHAS= 244.2 FOM= 1.00
INDE  2 11 10 FOBS= 310.2 SIGMA=  2.4 PHAS= 125.9 FOM= 0.64
INDE  2 11 11 FOBS= 117.1 SIGMA=  6.8 PHAS= 343.6 FOM= 0.37
INDE  2 11 12 FOBS= 194.5 SIGMA=  4.3 PHAS= 141.2 FOM= 0.56
INDE  2 11 13 FOBS=  63.0 SIGMA= 14.3 PHAS= 174.8 FOM= 0.02
INDE  2 11 14 FOBS= 150.0 SIGMA=  5.7 PHAS=  11.3 FOM= 0.56
INDE  2 11 15 FOBS=  92.8 SIGMA= 10.3 PHAS= 178.1 FOM= 0.07
INDE  2 12  0 FOBS= 159.7 SIGMA=  1.8 PHAS= 344.5 FOM= 0.98
INDE  2 12  1 FOBS= 238.5 SIGMA=  1.6 PHAS= 163.2 FOM= 0.93
INDE  2 12  2 FOBS=  98.5 SIGMA=  3.8 PHAS= 283.1 FOM= 0.93
INDE  2 12  3 FOBS= 254.5 SIGMA=  1.5 PHAS= 231.8 FOM= 0.94
INDE  2 12  4 FOBS= 121.1 SIGMA=  4.2 PHAS= 116.7 FOM= 0.89
INDE  2 12  5 FOBS= 104.9 SIGMA=  4.5 PHAS= 345.2 FOM= 0.95
INDE  2 12  6 FOBS= 153.1 SIGMA=  3.6 PHAS=  61.4 FOM= 0.96
INDE  2 12  7 FOBS= 321.9 SIGMA=  1.8 PHAS=  70.0 FOM= 0.70
INDE  2 12  8 FOBS= 635.0 SIGMA=  1.7 PHAS= 293.6 FOM= 1.00
INDE  2 12  9 FOBS= 376.2 SIGMA=  1.9 PHAS= 132.9 FOM= 0.96
INDE  2 12 10 FOBS= 392.0 SIGMA=  2.1 PHAS= 117.0 FOM= 0.76
INDE  2 12 11 FOBS= 132.4 SIGMA=  5.9 PHAS= 309.1 FOM= 0.20
INDE  2 12 12 FOBS= 157.3 SIGMA=  5.2 PHAS= 170.5 FOM= 0.20
INDE  2 12 13 FOBS=  68.8 SIGMA= 11.4 PHAS= 317.7 FOM= 0.03
INDE  2 12 14 FOBS= 108.9 SIGMA=  7.2 PHAS=  88.3 FOM= 0.13
INDE  2 12 15 FOBS=  74.5 SIGMA= 11.1 PHAS= 290.1 FOM= 0.07
INDE  2 13  0 FOBS= 246.7 SIGMA=  1.8 PHAS= 271.0 FOM= 0.92
INDE  2 13  1 FOBS= 185.7 SIGMA=  2.0 PHAS= 262.0 FOM= 0.98
INDE  2 13  2 FOBS=  65.8 SIGMA=  4.5 PHAS=  14.7 FOM= 0.91
INDE  2 13  3 FOBS=  79.5 SIGMA=  5.0 PHAS= 340.1 FOM= 0.87
INDE  2 13  4 FOBS= 154.1 SIGMA=  2.9 PHAS= 115.9 FOM= 0.96
INDE  2 13  5 FOBS= 128.2 SIGMA=  4.0 PHAS= 195.5 FOM= 0.79
INDE  2 13  6 FOBS= 225.9 SIGMA=  2.5 PHAS= 318.0 FOM= 0.96
INDE  2 13  7 FOBS= 170.6 SIGMA=  3.3 PHAS= 313.8 FOM= 0.94
INDE  2 13  8 FOBS= 240.7 SIGMA=  2.7 PHAS= 352.4 FOM= 0.81
INDE  2 13  9 FOBS=  77.7 SIGMA=  8.7 PHAS=  43.7 FOM= 0.13
INDE  2 13 10 FOBS=  94.9 SIGMA=  7.7 PHAS= 170.4 FOM= 0.12
INDE  2 13 11 FOBS= 169.6 SIGMA=  4.7 PHAS= 340.9 FOM= 0.46
INDE  2 13 12 FOBS=  65.4 SIGMA= 11.9 PHAS= 199.8 FOM= 0.09
INDE  2 13 13 FOBS= 148.9 SIGMA=  5.4 PHAS= 114.8 FOM= 0.66
INDE  2 13 14 FOBS=  41.9 SIGMA= 18.1 PHAS= 307.3 FOM= 0.16
INDE  2 13 15 FOBS= 110.9 SIGMA= 22.9 PHAS= 185.4 FOM= 0.07
INDE  2 14  0 FOBS= 253.4 SIGMA=  1.6 PHAS= 310.1 FOM= 0.95
INDE  2 14  1 FOBS= 232.6 SIGMA=  1.5 PHAS= 170.9 FOM= 0.98
INDE  2 14  2 FOBS= 238.4 SIGMA=  1.7 PHAS=   8.8 FOM= 0.94
INDE  2 14  3 FOBS= 156.8 SIGMA=  2.4 PHAS= 184.2 FOM= 0.89
INDE  2 14  4 FOBS= 152.4 SIGMA=  2.8 PHAS=  71.9 FOM= 0.77
INDE  2 14  5 FOBS= 159.8 SIGMA=  3.2 PHAS=  87.2 FOM= 0.82
INDE  2 14  6 FOBS= 342.8 SIGMA=  1.9 PHAS=  58.0 FOM= 0.85
INDE  2 14  7 FOBS= 227.3 SIGMA=  2.5 PHAS= 179.4 FOM= 0.73
INDE  2 14  8 FOBS= 286.4 SIGMA=  2.1 PHAS= 265.8 FOM= 0.87
INDE  2 14  9 FOBS= 173.8 SIGMA=  4.2 PHAS=  92.6 FOM= 0.53
INDE  2 14 10 FOBS= 184.9 SIGMA=  4.2 PHAS= 343.8 FOM= 0.93
INDE  2 14 11 FOBS= 250.6 SIGMA=  3.0 PHAS= 185.6 FOM= 0.68
INDE  2 14 12 FOBS= 189.3 SIGMA=  4.1 PHAS= 172.3 FOM= 0.81
INDE  2 14 13 FOBS= 130.0 SIGMA=  6.0 PHAS= 347.3 FOM= 0.22
INDE  2 14 14 FOBS=  74.1 SIGMA= 25.4 PHAS= 164.2 FOM= 0.02
INDE  2 15  0 FOBS=  54.4 SIGMA=  6.1 PHAS= 121.0 FOM= 0.45
INDE  2 15  1 FOBS= 215.8 SIGMA=  1.7 PHAS=  35.4 FOM= 1.00
INDE  2 15  2 FOBS= 279.5 SIGMA=  1.5 PHAS= 275.3 FOM= 0.96
INDE  2 15  3 FOBS= 277.2 SIGMA=  1.6 PHAS= 294.6 FOM= 0.12
INDE  2 15  4 FOBS= 149.2 SIGMA=  2.8 PHAS= 279.0 FOM= 0.19
INDE  2 15  5 FOBS= 171.4 SIGMA=  2.7 PHAS= 116.2 FOM= 0.53
INDE  2 15  6 FOBS= 312.3 SIGMA=  2.0 PHAS= 297.7 FOM= 0.89
INDE  2 15  7 FOBS= 232.4 SIGMA=  2.8 PHAS= 225.0 FOM= 0.86
INDE  2 15  8 FOBS= 296.5 SIGMA=  2.2 PHAS= 103.2 FOM= 0.92
INDE  2 15  9 FOBS= 148.1 SIGMA=  5.3 PHAS=  16.4 FOM= 0.72
INDE  2 15 10 FOBS=  95.2 SIGMA=  7.4 PHAS= 150.7 FOM= 0.47
```

Fig. 10A-95

```
INDE  3  1   2 FOBS=   376.1 SIGMA=   0.9 PHAS=  306.5 FOM= 0.93
INDE  3  1   3 FOBS=   752.9 SIGMA=   1.0 PHAS=   39.0 FOM= 0.40
INDE  3  1   4 FOBS=   322.1 SIGMA=   1.3 PHAS=  249.5 FOM= 1.00
INDE  3  1   5 FOBS=   126.5 SIGMA=   3.9 PHAS=  208.5 FOM= 0.88
INDE  3  1   6 FOBS=   200.3 SIGMA=   2.7 PHAS=  102.8 FOM= 0.79
INDE  3  1   7 FOBS=   226.2 SIGMA=   2.5 PHAS=  127.1 FOM= 0.26
INDE  3  1   8 FOBS=   134.0 SIGMA=   5.0 PHAS=  312.9 FOM= 0.59
INDE  3  1   9 FOBS=   177.8 SIGMA=   4.4 PHAS=  186.3 FOM= 0.12
INDE  3  1  10 FOBS=    72.9 SIGMA=  12.2 PHAS=  190.5 FOM= 0.13
INDE  3  1  11 FOBS=   232.1 SIGMA=   4.4 PHAS=  313.9 FOM= 0.22
INDE  3  1  12 FOBS=   187.2 SIGMA=   5.8 PHAS=  328.6 FOM= 0.08
INDE  3  1  13 FOBS=   193.8 SIGMA=   5.4 PHAS=  225.3 FOM= 0.30
INDE  3  1  14 FOBS=   230.8 SIGMA=   3.8 PHAS=  108.3 FOM= 0.37
INDE  3  1  15 FOBS=    83.8 SIGMA=  10.9 PHAS=   41.7 FOM= 0.07
INDE  3  1  16 FOBS=    85.0 SIGMA=  42.0 PHAS=  237.4 FOM= 0.05
INDE  3  2   0 FOBS=   166.1 SIGMA=   1.6 PHAS=   49.3 FOM= 1.00
INDE  3  2   1 FOBS=   260.8 SIGMA=   1.0 PHAS=  270.6 FOM= 0.99
INDE  3  2   2 FOBS=   497.2 SIGMA=   0.8 PHAS=   28.1 FOM= 0.99
INDE  3  2   3 FOBS=   513.7 SIGMA=   1.3 PHAS=  236.3 FOM= 0.98
INDE  3  2   4 FOBS=   183.9 SIGMA=   2.5 PHAS=  178.0 FOM= 0.82
INDE  3  2   5 FOBS=   140.9 SIGMA=   3.6 PHAS=  228.2 FOM= 0.25
INDE  3  2   6 FOBS=    92.9 SIGMA=   5.9 PHAS=   94.3 FOM= 0.47
INDE  3  2   7 FOBS=   101.2 SIGMA=  79.9 PHAS=  213.8 FOM= 0.25
INDE  3  2   8 FOBS=    65.5 SIGMA=  10.1 PHAS=  350.4 FOM= 0.12
INDE  3  2   9 FOBS=   426.2 SIGMA=   1.9 PHAS=  101.1 FOM= 0.96
INDE  3  2  10 FOBS=    85.1 SIGMA=  10.9 PHAS=   49.1 FOM= 0.13
INDE  3  2  11 FOBS=   157.4 SIGMA=   6.2 PHAS=  274.0 FOM= 0.48
INDE  3  2  12 FOBS=   209.7 SIGMA=   4.6 PHAS=  196.9 FOM= 0.75
INDE  3  2  13 FOBS=   186.0 SIGMA=   5.8 PHAS=   68.9 FOM= 0.37
INDE  3  2  14 FOBS=   147.6 SIGMA=   6.5 PHAS=  327.3 FOM= 0.24
INDE  3  2  15 FOBS=    59.6 SIGMA=  16.1 PHAS=  247.0 FOM= 0.05
INDE  3  3   0 FOBS=    52.4 SIGMA=   4.0 PHAS=    9.4 FOM= 0.84
INDE  3  3   1 FOBS=    46.8 SIGMA=   4.8 PHAS=   27.9 FOM= 0.32
INDE  3  3   2 FOBS=   239.1 SIGMA=   1.4 PHAS=  215.2 FOM= 0.83
INDE  3  3   3 FOBS=   355.1 SIGMA=   1.1 PHAS=  112.5 FOM= 0.99
INDE  3  3   4 FOBS=   321.0 SIGMA=   1.4 PHAS=  326.0 FOM= 0.98
INDE  3  3   5 FOBS=   112.5 SIGMA=   5.1 PHAS=  195.6 FOM= 0.50
INDE  3  3   6 FOBS=   277.2 SIGMA=   1.9 PHAS=  213.8 FOM= 0.90
INDE  3  3   7 FOBS=   196.3 SIGMA=   3.0 PHAS=  262.7 FOM= 0.84
INDE  3  3   8 FOBS=   259.4 SIGMA=   2.4 PHAS=  172.6 FOM= 0.87
INDE  3  3   9 FOBS=   154.9 SIGMA=   5.5 PHAS=  354.9 FOM= 0.59
INDE  3  3  10 FOBS=   312.5 SIGMA=   2.8 PHAS=  290.5 FOM= 0.72
INDE  3  3  11 FOBS=   209.9 SIGMA=   4.6 PHAS=  250.0 FOM= 0.22
INDE  3  3  12 FOBS=   362.7 SIGMA=   2.5 PHAS=  327.5 FOM= 0.91
INDE  3  3  13 FOBS=    46.0 SIGMA=  26.7 PHAS=  334.1 FOM= 0.10
INDE  3  3  14 FOBS=    86.7 SIGMA=  11.9 PHAS=  196.9 FOM= 0.03
INDE  3  3  15 FOBS=   112.6 SIGMA=   7.9 PHAS=  147.5 FOM= 0.06
INDE  3  4   0 FOBS=   369.6 SIGMA=   0.9 PHAS=  264.3 FOM= 1.00
INDE  3  4   1 FOBS=   107.9 SIGMA=   2.5 PHAS=   59.9 FOM= 0.86
INDE  3  4   2 FOBS=    61.1 SIGMA=   5.0 PHAS=  302.4 FOM= 0.43
INDE  3  4   3 FOBS=   193.7 SIGMA=   1.9 PHAS=   23.9 FOM= 0.97
INDE  3  4   4 FOBS=   129.7 SIGMA=   3.7 PHAS=  284.8 FOM= 0.36
INDE  3  4   5 FOBS=   108.4 SIGMA=   4.2 PHAS=   70.4 FOM= 0.77
INDE  3  4   6 FOBS=   133.9 SIGMA=   4.8 PHAS=  298.1 FOM= 0.79
INDE  3  4   7 FOBS=   155.8 SIGMA=   3.9 PHAS=  231.2 FOM= 0.21
INDE  3  4   8 FOBS=   141.5 SIGMA=   5.1 PHAS=  105.2 FOM= 0.67
INDE  3  4   9 FOBS=    96.4 SIGMA=   8.9 PHAS=    7.3 FOM= 0.25
INDE  3  4  10 FOBS=   328.1 SIGMA=   2.4 PHAS=  335.4 FOM= 0.41
INDE  3  4  11 FOBS=   306.7 SIGMA=   2.9 PHAS=   44.5 FOM= 0.84
INDE  3  4  12 FOBS=   178.3 SIGMA=   5.3 PHAS=  256.4 FOM= 0.29
INDE  3  4  13 FOBS=   155.1 SIGMA=   6.0 PHAS=   85.0 FOM= 0.02
INDE  3  4  14 FOBS=    78.6 SIGMA=  14.9 PHAS=   50.6 FOM= 0.06
INDE  3  4  15 FOBS=    90.7 SIGMA=  44.3 PHAS=  238.2 FOM= 0.04
INDE  3  5   0 FOBS=   364.9 SIGMA=   1.1 PHAS=   86.1 FOM= 0.97
INDE  3  5   1 FOBS=   406.5 SIGMA=   1.0 PHAS=  335.2 FOM= 0.96
INDE  3  5   2 FOBS=   292.2 SIGMA=   1.2 PHAS=   93.8 FOM= 0.98
INDE  3  5   3 FOBS=   384.3 SIGMA=   1.1 PHAS=  163.5 FOM= 0.99
INDE  3  5   4 FOBS=    83.8 SIGMA=   4.9 PHAS=  185.3 FOM= 0.70
INDE  3  5   5 FOBS=   115.2 SIGMA=   4.2 PHAS=   10.8 FOM= 0.91
INDE  3  5   6 FOBS=   230.5 SIGMA=   2.3 PHAS=  178.7 FOM= 0.91
INDE  3  5   7 FOBS=   101.9 SIGMA=   6.7 PHAS=  209.8 FOM= 0.46
```

Fig. 10A-99

```
INDE   3   5    8 FOBS=  153.9 SIGMA=   5.2 PHAS=  333.9 FOM=  0.83
INDE   3   5    9 FOBS=  234.2 SIGMA=   3.3 PHAS=  356.2 FOM=  0.24
INDE   3   5   10 FOBS=  139.2 SIGMA=   5.8 PHAS=   87.8 FOM=  0.08
INDE   3   5   11 FOBS=  146.5 SIGMA=   6.3 PHAS=  304.2 FOM=  0.03
INDE   3   5   12 FOBS=  103.1 SIGMA=   9.3 PHAS=  126.8 FOM=  0.06
INDE   3   5   13 FOBS=   51.5 SIGMA=  17.8 PHAS=   28.8 FOM=  0.10
INDE   3   5   14 FOBS=  118.4 SIGMA=   7.5 PHAS=  157.2 FOM=  0.22
INDE   3   5   15 FOBS=   92.0 SIGMA=  11.1 PHAS=  327.2 FOM=  0.03
INDE   3   6    0 FOBS=  183.7 SIGMA=   1.8 PHAS=   63.7 FOM=  0.18
INDE   3   6    1 FOBS=  183.6 SIGMA=   1.7 PHAS=  258.9 FOM=  0.96
INDE   3   6    2 FOBS=  382.2 SIGMA=   1.1 PHAS=  290.6 FOM=  0.98
INDE   3   6    3 FOBS=  116.1 SIGMA=   3.4 PHAS=  231.2 FOM=  0.84
INDE   3   6    4 FOBS=  114.2 SIGMA=   3.8 PHAS=   23.5 FOM=  0.75
INDE   3   6    5 FOBS=  223.2 SIGMA=   2.3 PHAS=  192.5 FOM=  0.94
INDE   3   6    6 FOBS=  151.0 SIGMA=   3.7 PHAS=  165.9 FOM=  0.16
INDE   3   6    7 FOBS=  202.5 SIGMA=   3.3 PHAS=  254.7 FOM=  0.16
INDE   3   6    8 FOBS=  223.1 SIGMA=   3.2 PHAS=  177.8 FOM=  0.43
INDE   3   6    9 FOBS=  242.1 SIGMA=   3.7 PHAS=   57.2 FOM=  0.94
INDE   3   6   10 FOBS=  175.5 SIGMA=   4.8 PHAS=  200.8 FOM=  0.68
INDE   3   6   11 FOBS=  109.1 SIGMA=   9.0 PHAS=  278.8 FOM=  0.10
INDE   3   6   12 FOBS=  169.3 SIGMA=   5.5 PHAS=   61.1 FOM=  0.47
INDE   3   6   13 FOBS=  158.3 SIGMA=   5.8 PHAS=  142.6 FOM=  0.06
INDE   3   6   14 FOBS=   52.9 SIGMA=  22.8 PHAS=    3.4 FOM=  0.10
INDE   3   6   15 FOBS=  142.3 SIGMA=   6.2 PHAS=  297.4 FOM=  0.08
INDE   3   7    0 FOBS=  363.7 SIGMA=   1.0 PHAS=  300.4 FOM=  0.96
INDE   3   7    1 FOBS=  102.3 SIGMA=   3.1 PHAS=   43.0 FOM=  0.92
INDE   3   7    2 FOBS=  139.7 SIGMA=   2.5 PHAS=  311.8 FOM=  0.92
INDE   3   7    3 FOBS=   97.6 SIGMA=   3.8 PHAS=  349.3 FOM=  0.50
INDE   3   7    4 FOBS=  164.7 SIGMA=   2.5 PHAS=  246.2 FOM=  0.57
INDE   3   7    5 FOBS=  124.6 SIGMA=   3.9 PHAS=  153.5 FOM=  0.24
INDE   3   7    6 FOBS=   42.1 SIGMA=  13.4 PHAS=  326.2 FOM=  0.25
INDE   3   7    7 FOBS=   58.1 SIGMA=  10.5 PHAS=  157.6 FOM=  0.09
INDE   3   7    8 FOBS=  180.3 SIGMA=   3.6 PHAS=   30.4 FOM=  0.24
INDE   3   7    9 FOBS=  451.4 SIGMA=   2.0 PHAS=   23.4 FOM=  0.56
INDE   3   7   10 FOBS=  153.2 SIGMA=   6.4 PHAS=  264.0 FOM=  0.10
INDE   3   7   11 FOBS=  160.1 SIGMA=   6.8 PHAS=  322.5 FOM=  0.03
INDE   3   7   12 FOBS=  133.5 SIGMA=   6.8 PHAS=  145.3 FOM=  0.46
INDE   3   7   13 FOBS=  117.7 SIGMA=   7.7 PHAS=   25.9 FOM=  0.42
INDE   3   7   14 FOBS=  142.4 SIGMA=   6.2 PHAS=  243.0 FOM=  0.09
INDE   3   7   15 FOBS=  102.3 SIGMA=   8.6 PHAS=  159.1 FOM=  0.17
INDE   3   8    0 FOBS=  199.0 SIGMA=   1.4 PHAS=   31.4 FOM=  0.92
INDE   3   8    1 FOBS=  305.6 SIGMA=   1.4 PHAS=  241.6 FOM=  1.00
INDE   3   8    2 FOBS=  295.7 SIGMA=   1.4 PHAS=  103.1 FOM=  0.88
INDE   3   8    3 FOBS=   77.6 SIGMA=   5.1 PHAS=  268.0 FOM=  0.40
INDE   3   8    4 FOBS=  168.9 SIGMA=   2.4 PHAS=   39.5 FOM=  0.90
INDE   3   8    5 FOBS=  198.3 SIGMA=   2.6 PHAS=   11.3 FOM=  0.27
INDE   3   8    6 FOBS=   62.4 SIGMA=   9.4 PHAS=  274.5 FOM=  0.19
INDE   3   8    7 FOBS=  183.7 SIGMA=   3.0 PHAS=  271.0 FOM=  0.93
INDE   3   8    8 FOBS=  241.5 SIGMA=   2.6 PHAS=  142.4 FOM=  0.72
INDE   3   8    9 FOBS=  182.2 SIGMA=   4.1 PHAS=   74.2 FOM=  0.42
INDE   3   8   10 FOBS=  111.6 SIGMA=   7.7 PHAS=  252.4 FOM=  0.40
INDE   3   8   11 FOBS=  201.9 SIGMA=   6.0 PHAS=   98.6 FOM=  0.22
INDE   3   8   12 FOBS=  363.4 SIGMA=   3.1 PHAS=  121.1 FOM=  0.21
INDE   3   8   13 FOBS=  147.4 SIGMA=   6.6 PHAS=  318.1 FOM=  0.44
INDE   3   8   14 FOBS=  129.1 SIGMA=   6.8 PHAS=  121.0 FOM=  0.38
INDE   3   8   15 FOBS=   46.1 SIGMA=  22.0 PHAS=    4.1 FOM=  0.14
INDE   3   9    0 FOBS=  122.0 SIGMA=   2.0 PHAS=  239.1 FOM=  1.00
INDE   3   9    1 FOBS=  435.5 SIGMA=   1.3 PHAS=  104.6 FOM=  0.85
INDE   3   9    2 FOBS=   60.2 SIGMA=   5.6 PHAS=  197.4 FOM=  0.76
INDE   3   9    3 FOBS=  103.0 SIGMA=   4.1 PHAS=   35.3 FOM=  0.84
INDE   3   9    4 FOBS=  171.7 SIGMA=   2.7 PHAS=  323.4 FOM=  0.88
INDE   3   9    5 FOBS=   78.9 SIGMA=   6.7 PHAS=  214.9 FOM=  0.38
INDE   3   9    6 FOBS=  172.2 SIGMA=   3.2 PHAS=  101.8 FOM=  0.08
INDE   3   9    7 FOBS=  197.1 SIGMA=   2.8 PHAS=  269.3 FOM=  0.93
INDE   3   9    8 FOBS=  389.9 SIGMA=   1.8 PHAS=  204.5 FOM=  0.92
INDE   3   9    9 FOBS=  224.7 SIGMA=   3.2 PHAS=  142.6 FOM=  0.43
INDE   3   9   10 FOBS=  292.0 SIGMA=   2.8 PHAS=  151.9 FOM=  0.92
INDE   3   9   11 FOBS=  117.3 SIGMA=   7.6 PHAS=    9.4 FOM=  0.23
INDE   3   9   12 FOBS=  142.5 SIGMA=   6.4 PHAS=  174.7 FOM=  0.25
INDE   3   9   13 FOBS=  176.4 SIGMA=   6.0 PHAS=  308.3 FOM=  0.07
INDE   3   9   14 FOBS=   43.6 SIGMA=  23.3 PHAS=  101.0 FOM=  0.10
```

Fig. 10A-100

```
INDE  3   9  15  FOBS=   66.2  SIGMA=  14.9  PHAS=  298.9  FOM=  0.02
INDE  3  10   0  FOBS=   99.0  SIGMA=   2.5  PHAS=  263.5  FOM=  0.97
INDE  3  10   1  FOBS=  269.4  SIGMA=   1.3  PHAS=  278.7  FOM=  0.99
INDE  3  10   2  FOBS=   71.4  SIGMA=   4.9  PHAS=  278.1  FOM=  0.41
INDE  3  10   3  FOBS=  152.0  SIGMA=   3.2  PHAS=   92.9  FOM=  0.97
INDE  3  10   4  FOBS=  204.2  SIGMA=   2.8  PHAS=  215.9  FOM=  0.96
INDE  3  10   5  FOBS=  231.6  SIGMA=   2.3  PHAS=   23.9  FOM=  0.52
INDE  3  10   6  FOBS=  387.0  SIGMA=   1.5  PHAS=  121.3  FOM=  0.96
INDE  3  10   7  FOBS=  265.3  SIGMA=   2.5  PHAS=  266.1  FOM=  0.93
INDE  3  10   8  FOBS=  108.5  SIGMA=   6.0  PHAS=   62.6  FOM=  0.62
INDE  3  10   9  FOBS=  203.3  SIGMA=   3.5  PHAS=  163.9  FOM=  0.68
INDE  3  10  10  FOBS=  189.4  SIGMA=   4.4  PHAS=  309.5  FOM=  0.28
INDE  3  10  11  FOBS=  102.3  SIGMA=   8.1  PHAS=  335.2  FOM=  0.28
INDE  3  10  12  FOBS=   54.4  SIGMA=  21.6  PHAS=  230.1  FOM=  0.12
INDE  3  10  13  FOBS=  101.9  SIGMA=   8.2  PHAS=   19.0  FOM=  0.11
INDE  3  10  14  FOBS=   46.6  SIGMA=  20.6  PHAS=  100.5  FOM=  0.02
INDE  3  10  15  FOBS=  107.8  SIGMA=   9.0  PHAS=  288.0  FOM=  0.04
INDE  3  11   0  FOBS=  137.5  SIGMA=   2.3  PHAS=  293.7  FOM=  0.97
INDE  3  11   1  FOBS=   82.3  SIGMA=   4.2  PHAS=   88.2  FOM=  0.87
INDE  3  11   2  FOBS=  124.9  SIGMA=   2.9  PHAS=  240.5  FOM=  0.66
INDE  3  11   3  FOBS=   79.3  SIGMA=   5.4  PHAS=  175.2  FOM=  0.18
INDE  3  11   4  FOBS=   97.0  SIGMA=   5.6  PHAS=   95.1  FOM=  0.06
INDE  3  11   5  FOBS=  126.1  SIGMA=   4.1  PHAS=  154.7  FOM=  0.05
INDE  3  11   6  FOBS=  279.0  SIGMA=   2.0  PHAS=   83.8  FOM=  0.82
INDE  3  11   7  FOBS=  293.0  SIGMA=   2.0  PHAS=  185.4  FOM=  0.41
INDE  3  11   8  FOBS=  196.9  SIGMA=   3.2  PHAS=    0.1  FOM=  0.46
INDE  3  11   9  FOBS=  386.9  SIGMA=   2.0  PHAS=  152.7  FOM=  0.95
INDE  3  11  10  FOBS=  313.0  SIGMA=   2.6  PHAS=   29.1  FOM=  0.81
INDE  3  11  11  FOBS=   73.7  SIGMA=  11.2  PHAS=   20.3  FOM=  0.13
INDE  3  11  12  FOBS=   59.3  SIGMA=  16.1  PHAS=  143.7  FOM=  0.15
INDE  3  11  13  FOBS=  112.8  SIGMA=   7.4  PHAS=  284.8  FOM=  0.25
INDE  3  11  14  FOBS=   46.9  SIGMA=  20.2  PHAS=  127.9  FOM=  0.04
INDE  3  11  15  FOBS=  134.3  SIGMA=  10.5  PHAS=  354.8  FOM=  0.01
INDE  3  12   0  FOBS=  148.4  SIGMA=   2.0  PHAS=  348.6  FOM=  0.97
INDE  3  12   1  FOBS=  191.7  SIGMA=   1.8  PHAS=  271.4  FOM=  0.82
INDE  3  12   2  FOBS=   73.2  SIGMA=   5.6  PHAS=  341.9  FOM=  0.82
INDE  3  12   3  FOBS=  131.6  SIGMA=   3.5  PHAS=    0.6  FOM=  0.94
INDE  3  12   4  FOBS=  125.5  SIGMA=   3.7  PHAS=  136.3  FOM=  0.81
INDE  3  12   5  FOBS=  178.5  SIGMA=   3.0  PHAS=  219.4  FOM=  0.57
INDE  3  12   6  FOBS=  462.6  SIGMA=   1.5  PHAS=  267.1  FOM=  0.37
INDE  3  12   7  FOBS=  466.0  SIGMA=   1.5  PHAS=  235.6  FOM=  0.91
INDE  3  12   8  FOBS=  349.5  SIGMA=   2.2  PHAS=  152.5  FOM=  0.97
INDE  3  12   9  FOBS=  102.5  SIGMA=   6.9  PHAS=  294.1  FOM=  0.26
INDE  3  12  10  FOBS=  139.5  SIGMA=   5.6  PHAS=  353.1  FOM=  0.06
INDE  3  12  11  FOBS=   78.7  SIGMA=  11.1  PHAS=   45.2  FOM=  0.23
INDE  3  12  12  FOBS=  261.0  SIGMA=   3.2  PHAS=  275.6  FOM=  0.92
INDE  3  12  13  FOBS=   91.3  SIGMA=   8.9  PHAS=  166.7  FOM=  0.06
INDE  3  12  14  FOBS=   96.2  SIGMA=   8.4  PHAS=  126.1  FOM=  0.19
INDE  3  13   0  FOBS=  111.7  SIGMA=   2.8  PHAS=  115.1  FOM=  0.96
INDE  3  13   1  FOBS=  232.3  SIGMA=   1.6  PHAS=   95.2  FOM=  0.97
INDE  3  13   2  FOBS=   62.4  SIGMA=   6.5  PHAS=   27.8  FOM=  0.71
INDE  3  13   3  FOBS=  244.8  SIGMA=   1.8  PHAS=   71.7  FOM=  0.94
INDE  3  13   4  FOBS=  217.4  SIGMA=   2.2  PHAS=  303.8  FOM=  0.90
INDE  3  13   5  FOBS=  213.5  SIGMA=   2.3  PHAS=  209.6  FOM=  0.91
INDE  3  13   6  FOBS=  380.5  SIGMA=   1.8  PHAS=  312.8  FOM=  0.98
INDE  3  13   7  FOBS=   69.9  SIGMA=   8.5  PHAS=  359.8  FOM=  0.12
INDE  3  13   8  FOBS=   92.1  SIGMA=   6.7  PHAS=  334.8  FOM=  0.28
INDE  3  13   9  FOBS=  140.0  SIGMA=   5.3  PHAS=  120.1  FOM=  0.70
INDE  3  13  10  FOBS=  218.8  SIGMA=   3.6  PHAS=   25.3  FOM=  0.83
INDE  3  13  11  FOBS=  278.1  SIGMA=   2.8  PHAS=  329.5  FOM=  0.84
INDE  3  13  12  FOBS=  124.3  SIGMA=   6.4  PHAS=  115.5  FOM=  0.16
INDE  3  13  13  FOBS=  123.9  SIGMA=   6.6  PHAS=   25.7  FOM=  0.56
INDE  3  13  14  FOBS=   55.5  SIGMA=  16.2  PHAS=  189.3  FOM=  0.05
INDE  3  14   0  FOBS=   53.8  SIGMA=   5.9  PHAS=  148.4  FOM=  0.29
INDE  3  14   1  FOBS=   36.6  SIGMA=  12.7  PHAS=  216.1  FOM=  0.20
INDE  3  14   2  FOBS=  173.2  SIGMA=   2.2  PHAS=   27.5  FOM=  0.80
INDE  3  14   3  FOBS=  131.6  SIGMA=   3.4  PHAS=  124.0  FOM=  0.55
INDE  3  14   4  FOBS=  318.4  SIGMA=   1.6  PHAS=  191.3  FOM=  0.93
INDE  3  14   5  FOBS=  177.3  SIGMA=   2.8  PHAS=   19.6  FOM=  0.84
INDE  3  14   6  FOBS=   86.6  SIGMA=   6.3  PHAS=   73.1  FOM=  0.23
INDE  3  14   7  FOBS=  183.0  SIGMA=   3.6  PHAS=  239.3  FOM=  0.82
```

Fig. 10A-101

```
INDE  3 14  8 FOBS=  471.6 SIGMA=   1.7 PHAS= 225.0 FOM= 0.96
INDE  3 14  9 FOBS=  162.1 SIGMA=   5.1 PHAS= 348.4 FOM= 0.83
INDE  3 14 10 FOBS=  156.9 SIGMA=   5.0 PHAS= 244.8 FOM= 0.71
INDE  3 14 11 FOBS=   85.6 SIGMA=   9.2 PHAS= 227.3 FOM= 0.13
INDE  3 14 12 FOBS=  154.4 SIGMA=   5.1 PHAS=  44.6 FOM= 0.21
INDE  3 14 13 FOBS=   74.4 SIGMA=   9.7 PHAS= 207.6 FOM= 0.10
INDE  3 14 14 FOBS=   41.0 SIGMA=  18.1 PHAS= 352.7 FOM= 0.02
INDE  3 15  0 FOBS=  188.5 SIGMA=   1.9 PHAS=   3.1 FOM= 0.48
INDE  3 15  1 FOBS=  125.8 SIGMA=   3.0 PHAS=  98.5 FOM= 0.90
INDE  3 15  2 FOBS=  109.8 SIGMA=   4.1 PHAS=  15.6 FOM= 0.96
INDE  3 15  3 FOBS=  178.0 SIGMA=   2.3 PHAS= 194.5 FOM= 0.52
INDE  3 15  4 FOBS=   54.5 SIGMA=   8.1 PHAS= 288.5 FOM= 0.65
INDE  3 15  5 FOBS=  328.1 SIGMA=   1.7 PHAS=  55.2 FOM= 0.99
INDE  3 15  6 FOBS=  137.5 SIGMA=   4.1 PHAS= 338.3 FOM= 0.89
INDE  3 15  7 FOBS=   60.3 SIGMA=  11.1 PHAS= 204.6 FOM= 0.13
INDE  3 15  8 FOBS=  291.2 SIGMA=   2.6 PHAS= 354.0 FOM= 0.91
INDE  3 15  9 FOBS=  249.3 SIGMA=   3.2 PHAS= 317.0 FOM= 0.76
INDE  3 15 10 FOBS=   58.0 SIGMA=  13.5 PHAS=  60.5 FOM= 0.07
INDE  3 15 11 FOBS=   65.4 SIGMA=  11.5 PHAS= 224.4 FOM= 0.09
INDE  3 15 12 FOBS=   65.5 SIGMA=  14.2 PHAS= 117.1 FOM= 0.22
INDE  3 15 13 FOBS=   97.4 SIGMA=   7.7 PHAS= 311.6 FOM= 0.18
INDE  3 15 14 FOBS=   79.5 SIGMA=   9.8 PHAS=  48.7 FOM= 0.08
INDE  3 16  0 FOBS=  136.1 SIGMA=   2.5 PHAS= 146.4 FOM= 0.69
INDE  3 16  1 FOBS=  276.0 SIGMA=   1.5 PHAS=  88.9 FOM= 1.00
INDE  3 16  2 FOBS=  232.6 SIGMA=   1.9 PHAS= 288.4 FOM= 0.73
INDE  3 16  3 FOBS=  302.7 SIGMA=   1.6 PHAS= 202.7 FOM= 0.99
INDE  3 16  4 FOBS=  113.0 SIGMA=   4.1 PHAS= 341.6 FOM= 0.74
INDE  3 16  5 FOBS=   53.2 SIGMA=   9.5 PHAS= 338.1 FOM= 0.07
INDE  3 16  6 FOBS=  192.0 SIGMA=   2.9 PHAS= 248.4 FOM= 0.73
INDE  3 16  7 FOBS=  263.5 SIGMA=   2.3 PHAS= 300.8 FOM= 0.38
INDE  3 16  8 FOBS=  234.6 SIGMA=   3.2 PHAS= 218.0 FOM= 0.10
INDE  3 16  9 FOBS=  227.5 SIGMA=   3.5 PHAS= 129.0 FOM= 0.33
INDE  3 16 10 FOBS=  189.5 SIGMA=   4.4 PHAS= 278.3 FOM= 0.46
INDE  3 16 11 FOBS=  178.4 SIGMA=   4.3 PHAS=  22.9 FOM= 0.34
INDE  3 16 12 FOBS=   91.1 SIGMA=   8.1 PHAS=  20.1 FOM= 0.15
INDE  3 16 13 FOBS=   53.4 SIGMA=  24.2 PHAS= 264.8 FOM= 0.15
INDE  3 17  0 FOBS=  210.4 SIGMA=   2.0 PHAS= 197.9 FOM= 0.98
INDE  3 17  1 FOBS=  192.3 SIGMA=   2.0 PHAS=   0.2 FOM= 0.85
INDE  3 17  2 FOBS=  373.7 SIGMA=   1.3 PHAS= 238.8 FOM= 1.00
INDE  3 17  3 FOBS=  217.4 SIGMA=   2.1 PHAS= 117.1 FOM= 0.95
INDE  3 17  4 FOBS=  425.1 SIGMA=   1.3 PHAS= 350.4 FOM= 0.87
INDE  3 17  5 FOBS=  160.1 SIGMA=   3.2 PHAS= 209.4 FOM= 0.67
INDE  3 17  6 FOBS=  145.9 SIGMA=   4.0 PHAS=   4.9 FOM= 0.88
INDE  3 17  7 FOBS=  250.1 SIGMA=   2.5 PHAS=  88.0 FOM= 0.67
INDE  3 17  8 FOBS=  304.3 SIGMA=   2.3 PHAS= 199.9 FOM= 0.40
INDE  3 17  9 FOBS=  124.0 SIGMA=   6.5 PHAS= 249.8 FOM= 0.70
INDE  3 17 10 FOBS=  329.2 SIGMA=   2.8 PHAS= 285.1 FOM= 0.89
INDE  3 17 11 FOBS=   70.8 SIGMA=  10.7 PHAS= 339.5 FOM= 0.12
INDE  3 17 12 FOBS=   76.8 SIGMA=   9.3 PHAS= 232.6 FOM= 0.27
INDE  3 17 13 FOBS=   70.7 SIGMA=  10.6 PHAS=  47.7 FOM= 0.02
INDE  3 18  0 FOBS=  449.8 SIGMA=   1.3 PHAS= 178.6 FOM= 0.94
INDE  3 18  1 FOBS=  122.1 SIGMA=   3.3 PHAS= 162.4 FOM= 0.86
INDE  3 18  2 FOBS=  330.3 SIGMA=   1.5 PHAS= 283.9 FOM= 0.94
INDE  3 18  3 FOBS=  664.6 SIGMA=   1.1 PHAS= 101.1 FOM= 0.99
INDE  3 18  4 FOBS=   76.8 SIGMA=   5.9 PHAS= 299.6 FOM= 0.24
INDE  3 18  5 FOBS=   87.2 SIGMA=   5.7 PHAS=  57.2 FOM= 0.62
INDE  3 18  6 FOBS=  270.8 SIGMA=   2.2 PHAS= 202.5 FOM= 0.93
INDE  3 18  7 FOBS=  173.5 SIGMA=   3.7 PHAS=  17.6 FOM= 0.54
INDE  3 18  8 FOBS=  190.4 SIGMA=   3.5 PHAS= 205.9 FOM= 0.12
INDE  3 18  9 FOBS=  291.8 SIGMA=   2.4 PHAS= 329.9 FOM= 0.65
INDE  3 18 10 FOBS=   74.6 SIGMA=  10.9 PHAS= 297.4 FOM= 0.05
INDE  3 18 11 FOBS=  117.2 SIGMA= 130.9 PHAS= 185.7 FOM= 0.08
INDE  3 18 12 FOBS=   88.2 SIGMA=   8.1 PHAS= 349.1 FOM= 0.03
INDE  3 18 13 FOBS=   82.5 SIGMA=   8.7 PHAS=  21.0 FOM= 0.07
INDE  3 19  0 FOBS=  122.4 SIGMA=   3.2 PHAS= 148.5 FOM= 0.79
INDE  3 19  1 FOBS=  150.2 SIGMA=   2.5 PHAS= 250.8 FOM= 0.93
INDE  3 19  2 FOBS=  348.1 SIGMA=   1.5 PHAS= 148.7 FOM= 0.94
INDE  3 19  3 FOBS=  219.5 SIGMA=   2.1 PHAS= 261.4 FOM= 0.50
INDE  3 19  4 FOBS=  331.0 SIGMA=   1.7 PHAS= 283.0 FOM= 0.94
INDE  3 19  5 FOBS=  372.0 SIGMA=   1.6 PHAS= 267.2 FOM= 0.95
INDE  3 19  6 FOBS=  116.3 SIGMA=   4.9 PHAS= 253.3 FOM= 0.05
```

Fig. 10A-102

```
INDE  3  19   7 FOBS=  201.8 SIGMA=   3.1 PHAS=  167.0 FOM=  0.53
INDE  3  19   8 FOBS=   84.9 SIGMA=   7.5 PHAS=  350.7 FOM=  0.31
INDE  3  19   9 FOBS=   95.6 SIGMA=   6.8 PHAS=  285.1 FOM=  0.16
INDE  3  19  10 FOBS=  110.9 SIGMA=   6.3 PHAS=  144.3 FOM=  0.25
INDE  3  19  11 FOBS=  179.0 SIGMA=   5.2 PHAS=  323.8 FOM=  0.66
INDE  3  19  12 FOBS=   86.5 SIGMA=   8.7 PHAS=  307.8 FOM=  0.03
INDE  3  19  13 FOBS=  156.4 SIGMA=  24.0 PHAS=  202.3 FOM=  0.05
INDE  3  20   0 FOBS=  324.6 SIGMA=   1.4 PHAS=  103.4 FOM=  0.96
INDE  3  20   1 FOBS=  217.5 SIGMA=   1.9 PHAS=   50.8 FOM=  0.59
INDE  3  20   2 FOBS=  249.6 SIGMA=   1.8 PHAS=  336.2 FOM=  0.96
INDE  3  20   3 FOBS=   77.6 SIGMA=   5.9 PHAS=  174.9 FOM=  0.34
INDE  3  20   4 FOBS=  167.2 SIGMA=   3.0 PHAS=  252.4 FOM=  0.71
INDE  3  20   5 FOBS=  184.3 SIGMA=   2.9 PHAS=  201.6 FOM=  0.44
INDE  3  20   6 FOBS=  436.0 SIGMA=   1.7 PHAS=  302.4 FOM=  0.98
INDE  3  20   7 FOBS=  286.9 SIGMA=   2.2 PHAS=  345.4 FOM=  0.04
INDE  3  20   8 FOBS=  131.3 SIGMA=   4.9 PHAS=  166.2 FOM=  0.05
INDE  3  20   9 FOBS=   73.6 SIGMA=   8.8 PHAS=  255.7 FOM=  0.23
INDE  3  20  10 FOBS=  210.4 SIGMA=   3.2 PHAS=  349.6 FOM=  0.49
INDE  3  20  11 FOBS=  106.1 SIGMA=   7.0 PHAS=   36.4 FOM=  0.40
INDE  3  20  12 FOBS=   44.6 SIGMA=  18.3 PHAS=  246.7 FOM=  0.10
INDE  3  21   0 FOBS=  267.8 SIGMA=   1.7 PHAS=  316.6 FOM=  0.96
INDE  3  21   1 FOBS=  132.1 SIGMA=   3.8 PHAS=   77.5 FOM=  0.79
INDE  3  21   2 FOBS=  199.2 SIGMA=   2.2 PHAS=  321.0 FOM=  0.60
INDE  3  21   3 FOBS=  271.4 SIGMA=   1.9 PHAS=   43.1 FOM=  0.98
INDE  3  21   4 FOBS=  107.9 SIGMA=   5.0 PHAS=  241.4 FOM=  0.53
INDE  3  21   5 FOBS=  218.8 SIGMA=   2.6 PHAS=  184.8 FOM=  0.13
INDE  3  21   6 FOBS=  188.7 SIGMA=   3.1 PHAS=   62.4 FOM=  0.67
INDE  3  21   7 FOBS=   42.8 SIGMA=  19.7 PHAS=  342.2 FOM=  0.16
INDE  3  21   8 FOBS=   63.2 SIGMA=  15.0 PHAS=  184.3 FOM=  0.09
INDE  3  21   9 FOBS=  221.9 SIGMA=   3.0 PHAS=  107.7 FOM=  0.49
INDE  3  21  10 FOBS=   54.1 SIGMA=  14.8 PHAS=   11.4 FOM=  0.29
INDE  3  21  11 FOBS=  101.5 SIGMA=   6.4 PHAS=  264.0 FOM=  0.14
INDE  3  21  12 FOBS=   51.1 SIGMA=  15.1 PHAS=  214.1 FOM=  0.09
INDE  3  22   0 FOBS=  139.7 SIGMA=   3.1 PHAS=  300.7 FOM=  0.34
INDE  3  22   1 FOBS=  110.9 SIGMA=   4.6 PHAS=  106.7 FOM=  0.85
INDE  3  22   2 FOBS=  326.2 SIGMA=   1.6 PHAS=   19.4 FOM=  0.98
INDE  3  22   3 FOBS=  256.7 SIGMA=   2.0 PHAS=   25.0 FOM=  0.25
INDE  3  22   4 FOBS=  228.7 SIGMA=   2.5 PHAS=  241.6 FOM=  0.75
INDE  3  22   5 FOBS=  288.5 SIGMA=   2.1 PHAS=  182.5 FOM=  0.24
INDE  3  22   6 FOBS=  172.6 SIGMA=   3.3 PHAS=  115.9 FOM=  0.38
INDE  3  22   7 FOBS=   77.0 SIGMA=   7.5 PHAS=  214.6 FOM=  0.48
INDE  3  22   8 FOBS=  121.0 SIGMA=   5.1 PHAS=  103.4 FOM=  0.72
INDE  3  22   9 FOBS=  227.3 SIGMA=   2.8 PHAS=  348.8 FOM=  0.75
INDE  3  22  10 FOBS=  144.6 SIGMA=   4.5 PHAS=  338.2 FOM=  0.53
INDE  3  22  11 FOBS=   36.1 SIGMA=  17.6 PHAS=  163.9 FOM=  0.14
INDE  3  23   0 FOBS=  137.7 SIGMA=   3.1 PHAS=  246.0 FOM=  0.21
INDE  3  23   1 FOBS=  158.5 SIGMA=   2.8 PHAS=  151.8 FOM=  0.89
INDE  3  23   2 FOBS=   76.9 SIGMA=   6.1 PHAS=  359.7 FOM=  0.45
INDE  3  23   3 FOBS=  289.8 SIGMA=   1.9 PHAS=  141.5 FOM=  0.52
INDE  3  23   4 FOBS=  214.5 SIGMA=   2.4 PHAS=   44.0 FOM=  0.96
INDE  3  23   5 FOBS=   64.5 SIGMA=   8.4 PHAS=  100.8 FOM=  0.50
INDE  3  23   6 FOBS=   41.0 SIGMA=  16.4 PHAS=  221.0 FOM=  0.24
INDE  3  23   7 FOBS=  136.5 SIGMA=   4.3 PHAS=  319.1 FOM=  0.25
INDE  3  23   8 FOBS=  143.4 SIGMA=   4.3 PHAS=  139.9 FOM=  0.74
INDE  3  23   9 FOBS=  123.5 SIGMA=   5.0 PHAS=  329.9 FOM=  0.49
INDE  3  23  10 FOBS=  126.1 SIGMA=   4.9 PHAS=  260.1 FOM=  0.19
INDE  3  23  11 FOBS=  160.5 SIGMA=   4.0 PHAS=  265.5 FOM=  0.14
INDE  3  24   0 FOBS=  357.2 SIGMA=   1.5 PHAS=  311.7 FOM=  0.86
INDE  3  24   1 FOBS=  110.5 SIGMA=   4.2 PHAS=  352.7 FOM=  0.69
INDE  3  24   2 FOBS=  180.4 SIGMA=   3.1 PHAS=  303.4 FOM=  0.03
INDE  3  24   3 FOBS=  150.8 SIGMA=   3.6 PHAS=  191.0 FOM=  0.90
INDE  3  24   4 FOBS=  122.4 SIGMA=   4.5 PHAS=  101.2 FOM=  0.82
INDE  3  24   5 FOBS=  160.7 SIGMA=   3.6 PHAS=  269.7 FOM=  0.19
INDE  3  24   6 FOBS=  113.4 SIGMA=   5.1 PHAS=  143.3 FOM=  0.52
INDE  3  24   7 FOBS=  254.8 SIGMA=   2.4 PHAS=  270.6 FOM=  0.90
INDE  3  24   8 FOBS=   71.0 SIGMA=   8.3 PHAS=  111.5 FOM=  0.10
INDE  3  24   9 FOBS=   36.5 SIGMA=  18.2 PHAS=  193.8 FOM=  0.05
INDE  3  24  10 FOBS=   95.3 SIGMA=   6.4 PHAS=  328.9 FOM=  0.05
INDE  3  25   0 FOBS=  260.9 SIGMA=   1.9 PHAS=   14.1 FOM=  0.98
INDE  3  25   1 FOBS=  249.9 SIGMA=   2.0 PHAS=  328.5 FOM=  0.97
INDE  3  25   2 FOBS=  130.8 SIGMA=   4.3 PHAS=  218.3 FOM=  0.85
```

Fig. 10A-103

```
INDE   3  25   3  FOBS=    190.6  SIGMA=    2.6  PHAS=    213.1  FOM=  0.90
INDE   3  25   4  FOBS=     47.4  SIGMA=   30.1  PHAS=    254.9  FOM=  0.16
INDE   3  25   5  FOBS=    185.5  SIGMA=    3.1  PHAS=    145.4  FOM=  0.92
INDE   3  25   6  FOBS=     87.4  SIGMA=    6.4  PHAS=    277.6  FOM=  0.05
INDE   3  25   7  FOBS=     65.8  SIGMA=    8.8  PHAS=    111.9  FOM=  0.11
INDE   3  25   8  FOBS=     99.9  SIGMA=    5.8  PHAS=    114.2  FOM=  0.48
INDE   3  25   9  FOBS=    139.9  SIGMA=    4.3  PHAS=    334.8  FOM=  0.50
INDE   3  25  10  FOBS=     44.1  SIGMA=   19.6  PHAS=     71.5  FOM=  0.11
INDE   3  26   0  FOBS=     56.9  SIGMA=    7.9  PHAS=    267.8  FOM=  0.34
INDE   3  26   1  FOBS=    245.1  SIGMA=    2.0  PHAS=    267.2  FOM=  0.84
INDE   3  26   2  FOBS=     65.3  SIGMA=    8.4  PHAS=    322.1  FOM=  0.16
INDE   3  26   3  FOBS=     96.0  SIGMA=    5.0  PHAS=    190.0  FOM=  0.08
INDE   3  26   4  FOBS=    316.9  SIGMA=    1.9  PHAS=    277.5  FOM=  0.91
INDE   3  26   5  FOBS=    241.7  SIGMA=    2.3  PHAS=     45.9  FOM=  0.87
INDE   3  26   6  FOBS=     89.1  SIGMA=    6.2  PHAS=    156.4  FOM=  0.09
INDE   3  26   7  FOBS=     59.9  SIGMA=   39.0  PHAS=    158.2  FOM=  0.02
INDE   3  26   8  FOBS=    108.8  SIGMA=    5.1  PHAS=    213.8  FOM=  0.05
INDE   3  26   9  FOBS=    109.1  SIGMA=    5.2  PHAS=    306.9  FOM=  0.09
INDE   3  27   0  FOBS=    188.9  SIGMA=    2.3  PHAS=     23.6  FOM=  0.99
INDE   3  27   1  FOBS=     38.4  SIGMA=   11.0  PHAS=    359.8  FOM=  0.29
INDE   3  27   2  FOBS=    228.6  SIGMA=    2.1  PHAS=     93.8  FOM=  0.94
INDE   3  27   3  FOBS=    222.5  SIGMA=    2.5  PHAS=    324.4  FOM=  0.17
INDE   3  27   4  FOBS=     63.9  SIGMA=    8.1  PHAS=     67.5  FOM=  0.14
INDE   3  27   5  FOBS=     88.7  SIGMA=    5.6  PHAS=    223.6  FOM=  0.19
INDE   3  27   6  FOBS=    160.1  SIGMA=    3.5  PHAS=    344.3  FOM=  0.51
INDE   3  27   7  FOBS=    108.7  SIGMA=    5.1  PHAS=    282.2  FOM=  0.23
INDE   3  27   8  FOBS=     81.2  SIGMA=    6.7  PHAS=     99.9  FOM=  0.19
INDE   3  27   9  FOBS=    190.4  SIGMA=   15.1  PHAS=    304.9  FOM=  0.05
INDE   3  28   0  FOBS=    114.5  SIGMA=    3.9  PHAS=    190.7  FOM=  0.53
INDE   3  28   1  FOBS=    156.8  SIGMA=    2.9  PHAS=     27.9  FOM=  0.49
INDE   3  28   2  FOBS=     84.1  SIGMA=    5.3  PHAS=     26.2  FOM=  0.23
INDE   3  28   3  FOBS=     81.9  SIGMA=    6.9  PHAS=    213.9  FOM=  0.45
INDE   3  28   4  FOBS=    134.5  SIGMA=    3.7  PHAS=     68.2  FOM=  0.66
INDE   3  28   5  FOBS=     98.5  SIGMA=    5.1  PHAS=    313.0  FOM=  0.39
INDE   3  28   6  FOBS=    244.0  SIGMA=    2.4  PHAS=     88.8  FOM=  0.93
INDE   3  28   7  FOBS=     46.9  SIGMA=   12.7  PHAS=     10.0  FOM=  0.14
INDE   3  28   8  FOBS=     85.2  SIGMA=    7.0  PHAS=    321.9  FOM=  0.05
INDE   3  29   0  FOBS=    203.5  SIGMA=    2.2  PHAS=    199.2  FOM=  0.65
INDE   3  29   1  FOBS=     85.1  SIGMA=    5.1  PHAS=     33.2  FOM=  0.38
INDE   3  29   2  FOBS=     49.7  SIGMA=    8.8  PHAS=    217.2  FOM=  0.42
INDE   3  29   3  FOBS=    210.7  SIGMA=    2.6  PHAS=    272.5  FOM=  0.72
INDE   3  29   4  FOBS=    174.2  SIGMA=    2.8  PHAS=     63.4  FOM=  0.62
INDE   3  29   5  FOBS=     58.5  SIGMA=    8.5  PHAS=    227.4  FOM=  0.23
INDE   3  29   6  FOBS=    131.4  SIGMA=    4.1  PHAS=     72.3  FOM=  0.78
INDE   3  29   7  FOBS=     68.8  SIGMA=    8.7  PHAS=    308.2  FOM=  0.27
INDE   3  30   0  FOBS=     59.8  SIGMA=    7.1  PHAS=    237.3  FOM=  0.20
INDE   3  30   1  FOBS=    126.9  SIGMA=    3.6  PHAS=    149.4  FOM=  0.57
INDE   3  30   2  FOBS=    300.8  SIGMA=    1.7  PHAS=     16.1  FOM=  0.84
INDE   3  30   3  FOBS=     65.8  SIGMA=    7.1  PHAS=    292.0  FOM=  0.91
INDE   3  30   4  FOBS=     89.0  SIGMA=    6.0  PHAS=     65.0  FOM=  0.37
INDE   3  30   5  FOBS=    174.3  SIGMA=    2.8  PHAS=    152.5  FOM=  0.08
INDE   3  30   6  FOBS=     82.3  SIGMA=    7.0  PHAS=    229.6  FOM=  0.23
INDE   3  31   0  FOBS=    145.3  SIGMA=    3.0  PHAS=    176.7  FOM=  0.73
INDE   3  31   1  FOBS=     39.9  SIGMA=   11.5  PHAS=    257.4  FOM=  0.06
INDE   3  31   2  FOBS=    116.9  SIGMA=    3.9  PHAS=     58.9  FOM=  0.76
INDE   3  31   3  FOBS=     43.4  SIGMA=   10.2  PHAS=    138.0  FOM=  0.12
INDE   3  31   4  FOBS=    186.7  SIGMA=    3.0  PHAS=    227.7  FOM=  0.42
INDE   3  31   5  FOBS=     62.7  SIGMA=   15.5  PHAS=    347.2  FOM=  0.17
INDE   3  32   0  FOBS=    122.7  SIGMA=    3.5  PHAS=    305.6  FOM=  0.30
INDE   3  32   1  FOBS=    254.4  SIGMA=    1.8  PHAS=     54.3  FOM=  0.92
INDE   3  32   2  FOBS=    134.4  SIGMA=    3.5  PHAS=    161.6  FOM=  0.64
INDE   3  32   3  FOBS=     59.8  SIGMA=    7.6  PHAS=    316.7  FOM=  0.07
INDE   3  33   0  FOBS=     74.9  SIGMA=   24.8  PHAS=    126.6  FOM=  0.06
INDE   4   0   0  FOBS=    638.0  SIGMA=    1.0  PHAS=      0.0  FOM=  0.87
INDE   4   0   1  FOBS=     74.9  SIGMA=    6.0  PHAS=    180.0  FOM=  0.93
INDE   4   0   2  FOBS=     59.3  SIGMA=    9.7  PHAS=      0.0  FOM=  0.11
INDE   4   0   3  FOBS=     35.7  SIGMA=   23.1  PHAS=    180.0  FOM=  0.14
INDE   4   0   4  FOBS=    241.5  SIGMA=    2.7  PHAS=      0.0  FOM=  0.04
INDE   4   0   5  FOBS=     71.8  SIGMA=   10.6  PHAS=      0.0  FOM=  0.29
INDE   4   0   6  FOBS=     35.4  SIGMA=   23.7  PHAS=    180.0  FOM=  0.25
INDE   4   0   7  FOBS=     58.4  SIGMA=   17.0  PHAS=      0.0  FOM=  0.25
```

Fig. 10A-104

```
INDE   4   0    8  FOBS=    212.4  SIGMA=      4.6  PHAS=    180.0  FOM=   0.51
INDE   4   0    9  FOBS=    210.5  SIGMA=      6.1  PHAS=    180.0  FOM=   0.01
INDE   4   0   10  FOBS=    306.9  SIGMA=      4.0  PHAS=      0.0  FOM=   0.78
INDE   4   0   11  FOBS=    173.8  SIGMA=     10.0  PHAS=    180.0  FOM=   0.05
INDE   4   0   12  FOBS=     58.6  SIGMA=     23.8  PHAS=      0.0  FOM=   0.00
INDE   4   0   13  FOBS=     63.0  SIGMA=     25.0  PHAS=      0.0  FOM=   0.11
INDE   4   0   14  FOBS=     89.8  SIGMA=     14.9  PHAS=    180.0  FOM=   0.04
INDE   4   1    0  FOBS=    369.5  SIGMA=      1.0  PHAS=     93.8  FOM=   1.00
INDE   4   1    1  FOBS=    807.4  SIGMA=      0.7  PHAS=     87.9  FOM=   1.00
INDE   4   1    2  FOBS=    399.4  SIGMA=      1.1  PHAS=    117.8  FOM=   0.97
INDE   4   1    3  FOBS=    165.5  SIGMA=      2.3  PHAS=      4.4  FOM=   0.94
INDE   4   1    4  FOBS=    266.4  SIGMA=      2.0  PHAS=    118.1  FOM=   0.95
INDE   4   1    5  FOBS=    185.5  SIGMA=      2.7  PHAS=    245.4  FOM=   0.43
INDE   4   1    6  FOBS=     45.2  SIGMA=     12.9  PHAS=    154.5  FOM=   0.03
INDE   4   1    7  FOBS=     50.1  SIGMA=     14.0  PHAS=    283.2  FOM=   0.27
INDE   4   1    8  FOBS=    272.3  SIGMA=      2.6  PHAS=    179.9  FOM=   0.96
INDE   4   1    9  FOBS=    211.0  SIGMA=      4.4  PHAS=    308.2  FOM=   0.66
INDE   4   1   10  FOBS=    299.7  SIGMA=      2.8  PHAS=    199.6  FOM=   0.48
INDE   4   1   11  FOBS=    218.3  SIGMA=      5.2  PHAS=    207.8  FOM=   0.20
INDE   4   1   12  FOBS=    255.2  SIGMA=      4.1  PHAS=     35.5  FOM=   0.83
INDE   4   1   13  FOBS=     64.7  SIGMA=     15.9  PHAS=    215.5  FOM=   0.05
INDE   4   1   14  FOBS=     94.4  SIGMA=    109.9  PHAS=    130.0  FOM=   0.10
INDE   4   1   15  FOBS=     98.7  SIGMA=      9.1  PHAS=    330.3  FOM=   0.07
INDE   4   2    0  FOBS=    424.6  SIGMA=      1.1  PHAS=     65.7  FOM=   0.69
INDE   4   2    1  FOBS=     50.4  SIGMA=      5.5  PHAS=    150.7  FOM=   0.64
INDE   4   2    2  FOBS=    363.9  SIGMA=      1.1  PHAS=     29.0  FOM=   1.00
INDE   4   2    3  FOBS=    447.7  SIGMA=      1.1  PHAS=    152.6  FOM=   0.90
INDE   4   2    4  FOBS=    212.7  SIGMA=      2.1  PHAS=     19.1  FOM=   0.96
INDE   4   2    5  FOBS=    161.8  SIGMA=      3.9  PHAS=    276.9  FOM=   0.93
INDE   4   2    6  FOBS=    165.7  SIGMA=      3.6  PHAS=    127.9  FOM=   0.86
INDE   4   2    7  FOBS=    264.6  SIGMA=      2.4  PHAS=     69.0  FOM=   0.95
INDE   4   2    8  FOBS=    228.5  SIGMA=      3.2  PHAS=    294.3  FOM=   0.85
INDE   4   2    9  FOBS=    221.3  SIGMA=      3.9  PHAS=    259.9  FOM=   0.25
INDE   4   2   10  FOBS=    324.4  SIGMA=      2.6  PHAS=    255.3  FOM=   0.82
INDE   4   2   11  FOBS=    354.3  SIGMA=      3.7  PHAS=    245.6  FOM=   0.04
INDE   4   2   12  FOBS=    130.5  SIGMA=      7.9  PHAS=     22.0  FOM=   0.04
INDE   4   2   13  FOBS=    145.8  SIGMA=      6.5  PHAS=    327.4  FOM=   0.02
INDE   4   2   14  FOBS=     45.9  SIGMA=     21.1  PHAS=    138.5  FOM=   0.09
INDE   4   2   15  FOBS=     90.5  SIGMA=     56.0  PHAS=     29.7  FOM=   0.01
INDE   4   3    0  FOBS=    350.4  SIGMA=      1.1  PHAS=      8.5  FOM=   0.88
INDE   4   3    1  FOBS=    309.6  SIGMA=      1.1  PHAS=    311.0  FOM=   1.00
INDE   4   3    2  FOBS=    599.1  SIGMA=      0.9  PHAS=     69.6  FOM=   0.62
INDE   4   3    3  FOBS=    207.6  SIGMA=      1.9  PHAS=    297.6  FOM=   1.00
INDE   4   3    4  FOBS=     92.0  SIGMA=      5.0  PHAS=    221.7  FOM=   0.88
INDE   4   3    5  FOBS=    119.3  SIGMA=      4.4  PHAS=    159.3  FOM=   0.10
INDE   4   3    6  FOBS=    177.2  SIGMA=      3.8  PHAS=     93.2  FOM=   0.92
INDE   4   3    7  FOBS=    291.0  SIGMA=      2.2  PHAS=    344.9  FOM=   0.99
INDE   4   3    8  FOBS=    265.3  SIGMA=      2.7  PHAS=    297.1  FOM=   0.31
INDE   4   3    9  FOBS=    288.8  SIGMA=      2.8  PHAS=     26.9  FOM=   0.54
INDE   4   3   10  FOBS=    100.1  SIGMA=      9.4  PHAS=     40.0  FOM=   0.01
INDE   4   3   11  FOBS=    123.1  SIGMA=     11.2  PHAS=    353.0  FOM=   0.06
INDE   4   3   12  FOBS=     86.1  SIGMA=     10.8  PHAS=     18.1  FOM=   0.11
INDE   4   3   13  FOBS=     88.1  SIGMA=     11.2  PHAS=    176.7  FOM=   0.21
INDE   4   3   14  FOBS=     82.1  SIGMA=     10.9  PHAS=     56.8  FOM=   0.15
INDE   4   3   15  FOBS=     78.9  SIGMA=     13.5  PHAS=    318.6  FOM=   0.02
INDE   4   4    0  FOBS=    174.8  SIGMA=      1.8  PHAS=    227.8  FOM=   1.00
INDE   4   4    1  FOBS=    160.9  SIGMA=      2.3  PHAS=    199.9  FOM=   0.99
INDE   4   4    2  FOBS=    166.6  SIGMA=      2.1  PHAS=    283.3  FOM=   0.96
INDE   4   4    3  FOBS=     60.6  SIGMA=      6.1  PHAS=     57.3  FOM=   0.84
INDE   4   4    4  FOBS=     94.4  SIGMA=      4.6  PHAS=     80.6  FOM=   0.60
INDE   4   4    5  FOBS=    148.6  SIGMA=      3.5  PHAS=     88.3  FOM=   0.41
INDE   4   4    6  FOBS=    131.7  SIGMA=      4.5  PHAS=    238.9  FOM=   0.20
INDE   4   4    7  FOBS=    167.4  SIGMA=      4.6  PHAS=     69.2  FOM=   0.25
INDE   4   4    8  FOBS=    241.7  SIGMA=      2.9  PHAS=     85.4  FOM=   0.65
INDE   4   4    9  FOBS=    186.7  SIGMA=      4.8  PHAS=     95.2  FOM=   0.51
INDE   4   4   10  FOBS=    166.8  SIGMA=      6.1  PHAS=    330.6  FOM=   0.34
INDE   4   4   11  FOBS=    203.6  SIGMA=      5.3  PHAS=    231.0  FOM=   0.40
INDE   4   4   12  FOBS=    106.3  SIGMA=      9.1  PHAS=    189.3  FOM=   0.20
INDE   4   4   13  FOBS=    117.9  SIGMA=      8.0  PHAS=     38.6  FOM=   0.15
INDE   4   4   14  FOBS=     69.3  SIGMA=     53.1  PHAS=    309.5  FOM=   0.12
INDE   4   4   15  FOBS=     46.8  SIGMA=     20.5  PHAS=    150.8  FOM=   0.10
```

Fig. 10A-105

```
INDE  4  5   0  FOBS=  147.8  SIGMA=   2.1  PHAS=   94.9  FOM=  0.94
INDE  4  5   1  FOBS=  349.5  SIGMA=   1.3  PHAS=   18.7  FOM=  0.94
INDE  4  5   2  FOBS=  333.6  SIGMA=   1.3  PHAS=   62.9  FOM=  0.82
INDE  4  5   3  FOBS=  196.5  SIGMA=   2.1  PHAS=  309.3  FOM=  0.83
INDE  4  5   4  FOBS=  172.4  SIGMA=   2.6  PHAS=  263.4  FOM=  0.84
INDE  4  5   5  FOBS=   54.2  SIGMA=  10.1  PHAS=  302.2  FOM=  0.13
INDE  4  5   6  FOBS=  145.4  SIGMA=   4.0  PHAS=  342.1  FOM=  0.58
INDE  4  5   7  FOBS=  277.8  SIGMA=   2.3  PHAS=  201.9  FOM=  0.39
INDE  4  5   8  FOBS=  207.3  SIGMA=   4.0  PHAS=  107.4  FOM=  0.49
INDE  4  5   9  FOBS=  193.2  SIGMA=   5.5  PHAS=   39.7  FOM=  0.05
INDE  4  5  10  FOBS=  200.3  SIGMA=   4.9  PHAS=  296.6  FOM=  0.27
INDE  4  5  11  FOBS=  163.7  SIGMA=   6.0  PHAS=  111.8  FOM=  0.61
INDE  4  5  12  FOBS=  139.1  SIGMA=   6.7  PHAS=  317.5  FOM=  0.12
INDE  4  5  13  FOBS=   83.4  SIGMA=  10.8  PHAS=  305.4  FOM=  0.12
INDE  4  5  14  FOBS=   66.1  SIGMA=  15.1  PHAS=  117.7  FOM=  0.33
INDE  4  5  15  FOBS=   77.5  SIGMA=  12.7  PHAS=  273.4  FOM=  0.05
INDE  4  6   0  FOBS=  321.3  SIGMA=   1.1  PHAS=  137.0  FOM=  0.15
INDE  4  6   1  FOBS=  257.1  SIGMA=   1.5  PHAS=   26.2  FOM=  0.73
INDE  4  6   2  FOBS=  178.9  SIGMA=   2.3  PHAS=  277.8  FOM=  0.34
INDE  4  6   3  FOBS=   88.0  SIGMA=   4.8  PHAS=  328.9  FOM=  0.50
INDE  4  6   4  FOBS=  144.6  SIGMA=   3.2  PHAS=  115.3  FOM=  0.93
INDE  4  6   5  FOBS=  172.2  SIGMA=   2.9  PHAS=  131.3  FOM=  0.79
INDE  4  6   6  FOBS=  291.0  SIGMA=   2.0  PHAS=  228.7  FOM=  0.81
INDE  4  6   7  FOBS=  208.4  SIGMA=   3.0  PHAS=  332.3  FOM=  0.91
INDE  4  6   8  FOBS=  144.4  SIGMA=   5.6  PHAS=  127.7  FOM=  0.34
INDE  4  6   9  FOBS=  565.4  SIGMA=   2.5  PHAS=  275.2  FOM=  0.63
INDE  4  6  10  FOBS=  273.9  SIGMA=   3.8  PHAS=  123.0  FOM=  0.33
INDE  4  6  11  FOBS=  147.7  SIGMA=   7.1  PHAS=  293.9  FOM=  0.29
INDE  4  6  12  FOBS=  122.4  SIGMA=   7.6  PHAS=  217.4  FOM=  0.26
INDE  4  6  13  FOBS=   82.9  SIGMA=  11.3  PHAS=  113.4  FOM=  0.18
INDE  4  6  14  FOBS=   74.8  SIGMA=  12.0  PHAS=  282.4  FOM=  0.33
INDE  4  6  15  FOBS=   48.7  SIGMA=  23.0  PHAS=  236.5  FOM=  0.03
INDE  4  7   0  FOBS=   95.1  SIGMA=   3.3  PHAS=  199.2  FOM=  0.37
INDE  4  7   1  FOBS=  118.6  SIGMA=   2.8  PHAS=   74.7  FOM=  0.21
INDE  4  7   2  FOBS=  151.4  SIGMA=   2.8  PHAS=  121.3  FOM=  0.79
INDE  4  7   3  FOBS=   73.2  SIGMA=   6.0  PHAS=  116.3  FOM=  0.71
INDE  4  7   4  FOBS=   89.2  SIGMA=   5.6  PHAS=  209.5  FOM=  0.56
INDE  4  7   5  FOBS=   89.3  SIGMA=   5.5  PHAS=   21.0  FOM=  0.25
INDE  4  7   6  FOBS=  150.4  SIGMA=   4.3  PHAS=  159.4  FOM=  0.47
INDE  4  7   7  FOBS=   76.4  SIGMA=   8.0  PHAS=  269.4  FOM=  0.14
INDE  4  7   8  FOBS=  338.4  SIGMA=   2.4  PHAS=  124.1  FOM=  0.35
INDE  4  7   9  FOBS=  176.4  SIGMA=   4.6  PHAS=  206.4  FOM=  0.39
INDE  4  7  10  FOBS=  332.6  SIGMA=   2.7  PHAS=  272.8  FOM=  0.86
INDE  4  7  11  FOBS=   99.9  SIGMA=  11.6  PHAS=  154.8  FOM=  0.06
INDE  4  7  12  FOBS=   79.9  SIGMA=  14.3  PHAS=  135.7  FOM=  0.06
INDE  4  7  13  FOBS=   95.9  SIGMA=  10.0  PHAS=  352.5  FOM=  0.11
INDE  4  7  14  FOBS=   98.8  SIGMA=   9.0  PHAS=  209.6  FOM=  0.02
INDE  4  7  15  FOBS=  150.1  SIGMA=   6.0  PHAS=  280.3  FOM=  0.03
INDE  4  8   0  FOBS=  144.9  SIGMA=   2.1  PHAS=   16.4  FOM=  0.91
INDE  4  8   1  FOBS=  102.1  SIGMA=   3.4  PHAS=   84.8  FOM=  0.17
INDE  4  8   2  FOBS=  218.9  SIGMA=   1.7  PHAS=  157.6  FOM=  0.92
INDE  4  8   3  FOBS=  175.0  SIGMA=   2.6  PHAS=   14.7  FOM=  0.80
INDE  4  8   4  FOBS=  239.8  SIGMA=   2.1  PHAS=  350.4  FOM=  0.91
INDE  4  8   5  FOBS=  120.4  SIGMA=   4.1  PHAS=  206.5  FOM=  0.43
INDE  4  8   6  FOBS=  176.4  SIGMA=   3.2  PHAS=   86.5  FOM=  0.14
INDE  4  8   7  FOBS=   73.9  SIGMA=  10.0  PHAS=  245.1  FOM=  0.21
INDE  4  8   8  FOBS=  230.8  SIGMA=   3.1  PHAS=   48.7  FOM=  0.95
INDE  4  8   9  FOBS=  319.5  SIGMA=   2.4  PHAS=   21.1  FOM=  0.78
INDE  4  8  10  FOBS=  207.2  SIGMA=   4.6  PHAS=  216.1  FOM=  0.05
INDE  4  8  11  FOBS=  129.8  SIGMA=   7.0  PHAS=  171.1  FOM=  0.15
INDE  4  8  12  FOBS=  146.1  SIGMA=   6.4  PHAS=  358.5  FOM=  0.03
INDE  4  8  13  FOBS=  128.8  SIGMA=   8.2  PHAS=   58.2  FOM=  0.09
INDE  4  8  14  FOBS=   85.9  SIGMA=  11.9  PHAS=  251.5  FOM=  0.06
INDE  4  8  15  FOBS=   62.6  SIGMA=  19.4  PHAS=  133.5  FOM=  0.02
INDE  4  9   0  FOBS=  216.8  SIGMA=   1.5  PHAS=   29.5  FOM=  0.96
INDE  4  9   1  FOBS=  256.7  SIGMA=   1.5  PHAS=  114.4  FOM=  1.00
INDE  4  9   2  FOBS=  145.4  SIGMA=   2.7  PHAS=  340.5  FOM=  0.93
INDE  4  9   3  FOBS=   57.6  SIGMA=   7.4  PHAS=  122.8  FOM=  0.12
INDE  4  9   4  FOBS=  235.5  SIGMA=   2.3  PHAS=  228.8  FOM=  0.79
INDE  4  9   5  FOBS=   53.9  SIGMA=  11.4  PHAS=   29.0  FOM=  0.34
INDE  4  9   6  FOBS=  247.0  SIGMA=   2.6  PHAS=  204.0  FOM=  0.94
```

Fig. 10A-106

```
INDE   4    9    7  FOBS=   438.4  SIGMA=    1.8  PHAS=     5.9  FOM=  0.88
INDE   4    9    8  FOBS=   336.4  SIGMA=    2.2  PHAS=    22.1  FOM=  0.94
INDE   4    9    9  FOBS=   168.6  SIGMA=    4.7  PHAS=   263.8  FOM=  0.76
INDE   4    9   10  FOBS=   305.6  SIGMA=    3.0  PHAS=   322.1  FOM=  0.87
INDE   4    9   11  FOBS=   119.5  SIGMA=    7.7  PHAS=    91.8  FOM=  0.40
INDE   4    9   12  FOBS=    76.4  SIGMA=   11.3  PHAS=   300.4  FOM=  0.15
INDE   4    9   13  FOBS=   137.0  SIGMA=    6.4  PHAS=   220.4  FOM=  0.04
INDE   4    9   14  FOBS=    42.7  SIGMA=   20.1  PHAS=   156.7  FOM=  0.09
INDE   4    9   15  FOBS=   119.7  SIGMA=   76.0  PHAS=    13.2  FOM=  0.03
INDE   4   10    0  FOBS=   221.4  SIGMA=    1.5  PHAS=   147.5  FOM=  0.98
INDE   4   10    1  FOBS=    78.8  SIGMA=    4.5  PHAS=   251.9  FOM=  0.41
INDE   4   10    2  FOBS=   227.0  SIGMA=    1.8  PHAS=    67.9  FOM=  0.86
INDE   4   10    3  FOBS=   218.9  SIGMA=    2.1  PHAS=   144.4  FOM=  0.96
INDE   4   10    4  FOBS=   155.6  SIGMA=    3.3  PHAS=    12.5  FOM=  0.66
INDE   4   10    5  FOBS=    43.5  SIGMA=   18.8  PHAS=   309.5  FOM=  0.42
INDE   4   10    6  FOBS=   348.2  SIGMA=    2.1  PHAS=   257.3  FOM=  0.90
INDE   4   10    7  FOBS=   335.9  SIGMA=    2.0  PHAS=   341.5  FOM=  0.87
INDE   4   10    8  FOBS=    87.8  SIGMA=    7.7  PHAS=   307.0  FOM=  0.04
INDE   4   10    9  FOBS=    55.1  SIGMA=   17.6  PHAS=   232.7  FOM=  0.19
INDE   4   10   10  FOBS=   394.5  SIGMA=    2.7  PHAS=    94.9  FOM=  0.95
INDE   4   10   11  FOBS=   115.3  SIGMA=    7.3  PHAS=   120.2  FOM=  0.12
INDE   4   10   12  FOBS=    90.9  SIGMA=    9.5  PHAS=   285.8  FOM=  0.25
INDE   4   10   13  FOBS=    49.4  SIGMA=   25.1  PHAS=   110.2  FOM=  0.09
INDE   4   10   14  FOBS=   109.4  SIGMA=   70.9  PHAS=   158.0  FOM=  0.03
INDE   4   11    0  FOBS=    97.6  SIGMA=    3.5  PHAS=   109.1  FOM=  0.86
INDE   4   11    1  FOBS=   129.7  SIGMA=    2.6  PHAS=   177.1  FOM=  0.97
INDE   4   11    2  FOBS=    57.8  SIGMA=    6.6  PHAS=    95.5  FOM=  0.30
INDE   4   11    3  FOBS=   174.9  SIGMA=    2.5  PHAS=   127.0  FOM=  0.85
INDE   4   11    4  FOBS=   155.8  SIGMA=    3.4  PHAS=   279.0  FOM=  0.92
INDE   4   11    5  FOBS=   256.9  SIGMA=    2.8  PHAS=    60.1  FOM=  0.06
INDE   4   11    6  FOBS=   355.1  SIGMA=    2.0  PHAS=   321.3  FOM=  0.99
INDE   4   11    7  FOBS=   238.9  SIGMA=    3.0  PHAS=   335.7  FOM=  0.97
INDE   4   11    8  FOBS=    68.1  SIGMA=   13.1  PHAS=   193.4  FOM=  0.07
INDE   4   11    9  FOBS=    82.9  SIGMA=    9.6  PHAS=   134.2  FOM=  0.12
INDE   4   11   10  FOBS=   130.1  SIGMA=    6.4  PHAS=    38.4  FOM=  0.18
INDE   4   11   11  FOBS=    80.7  SIGMA=   10.4  PHAS=   174.0  FOM=  0.21
INDE   4   11   12  FOBS=   163.0  SIGMA=    5.3  PHAS=    36.9  FOM=  0.24
INDE   4   11   13  FOBS=    67.5  SIGMA=   13.0  PHAS=   148.0  FOM=  0.24
INDE   4   11   14  FOBS=    42.7  SIGMA=   17.8  PHAS=   270.9  FOM=  0.05
INDE   4   12    0  FOBS=   255.4  SIGMA=    1.4  PHAS=   267.9  FOM=  0.90
INDE   4   12    1  FOBS=   169.9  SIGMA=    2.2  PHAS=   190.2  FOM=  0.78
INDE   4   12    2  FOBS=    99.2  SIGMA=    4.1  PHAS=   171.7  FOM=  0.89
INDE   4   12    3  FOBS=   192.2  SIGMA=    2.2  PHAS=   169.9  FOM=  0.95
INDE   4   12    4  FOBS=   165.7  SIGMA=    3.2  PHAS=   239.6  FOM=  0.44
INDE   4   12    5  FOBS=   214.7  SIGMA=    2.4  PHAS=   144.0  FOM=  0.72
INDE   4   12    6  FOBS=    88.6  SIGMA=    7.2  PHAS=   286.0  FOM=  0.30
INDE   4   12    7  FOBS=   334.1  SIGMA=    2.2  PHAS=   348.1  FOM=  0.07
INDE   4   12    8  FOBS=   102.8  SIGMA=    6.5  PHAS=    15.1  FOM=  0.37
INDE   4   12    9  FOBS=   134.5  SIGMA=    6.3  PHAS=   203.3  FOM=  0.60
INDE   4   12   10  FOBS=   171.0  SIGMA=    4.9  PHAS=     4.3  FOM=  0.66
INDE   4   12   11  FOBS=    80.5  SIGMA=   10.2  PHAS=   268.4  FOM=  0.03
INDE   4   12   12  FOBS=    53.8  SIGMA=   16.0  PHAS=   184.0  FOM=  0.06
INDE   4   12   13  FOBS=    63.8  SIGMA=   12.7  PHAS=    62.0  FOM=  0.09
INDE   4   12   14  FOBS=    58.1  SIGMA=   15.9  PHAS=   285.2  FOM=  0.04
INDE   4   13    0  FOBS=   153.9  SIGMA=    2.3  PHAS=   158.9  FOM=  0.95
INDE   4   13    1  FOBS=   247.7  SIGMA=    1.6  PHAS=   306.2  FOM=  0.94
INDE   4   13    2  FOBS=   240.5  SIGMA=    1.8  PHAS=   215.3  FOM=  0.91
INDE   4   13    3  FOBS=   167.1  SIGMA=    3.1  PHAS=   208.0  FOM=  0.87
INDE   4   13    4  FOBS=   253.9  SIGMA=    2.0  PHAS=   326.1  FOM=  0.95
INDE   4   13    5  FOBS=    88.5  SIGMA=    5.7  PHAS=   121.4  FOM=  0.18
INDE   4   13    6  FOBS=   163.6  SIGMA=    3.6  PHAS=   176.2  FOM=  0.38
INDE   4   13    7  FOBS=    95.9  SIGMA=    7.3  PHAS=    34.1  FOM=  0.45
INDE   4   13    8  FOBS=   165.2  SIGMA=    4.7  PHAS=   252.0  FOM=  0.83
INDE   4   13    9  FOBS=   120.0  SIGMA=    7.0  PHAS=    60.8  FOM=  0.05
INDE   4   13   10  FOBS=    65.8  SIGMA=   12.5  PHAS=    26.3  FOM=  0.13
INDE   4   13   11  FOBS=   172.1  SIGMA=    4.8  PHAS=   145.2  FOM=  0.49
INDE   4   13   12  FOBS=   173.6  SIGMA=    4.7  PHAS=   319.5  FOM=  0.01
INDE   4   13   13  FOBS=    78.8  SIGMA=   10.7  PHAS=   162.0  FOM=  0.09
INDE   4   13   14  FOBS=    64.5  SIGMA=   15.1  PHAS=    76.0  FOM=  0.03
INDE   4   14    0  FOBS=   332.1  SIGMA=    1.2  PHAS=   290.7  FOM=  1.00
INDE   4   14    1  FOBS=   269.0  SIGMA=    1.6  PHAS=   238.9  FOM=  0.94
```

Fig. 10A-107

```
INDE  4  14   2  FOBS=   135.5  SIGMA=   3.5  PHAS=   79.2  FOM=  0.95
INDE  4  14   3  FOBS=   315.0  SIGMA=   1.6  PHAS=  296.2  FOM=  0.95
INDE  4  14   4  FOBS=    42.7  SIGMA=  11.4  PHAS=  274.4  FOM=  0.18
INDE  4  14   5  FOBS=   241.4  SIGMA=   2.2  PHAS=  216.2  FOM=  0.96
INDE  4  14   6  FOBS=   307.1  SIGMA=   2.0  PHAS=  293.3  FOM=  0.73
INDE  4  14   7  FOBS=   235.0  SIGMA=   2.7  PHAS=  152.8  FOM=  0.57
INDE  4  14   8  FOBS=   217.6  SIGMA=   3.6  PHAS=   34.6  FOM=  0.51
INDE  4  14   9  FOBS=   116.4  SIGMA=   7.5  PHAS=  194.9  FOM=  0.42
INDE  4  14  10  FOBS=   156.9  SIGMA=   5.0  PHAS=   69.0  FOM=  0.47
INDE  4  14  11  FOBS=    95.6  SIGMA=   8.1  PHAS=  257.2  FOM=  0.14
INDE  4  14  12  FOBS=   142.2  SIGMA=   5.6  PHAS=  197.9  FOM=  0.36
INDE  4  14  13  FOBS=   106.0  SIGMA=   7.4  PHAS=  146.6  FOM=  0.50
INDE  4  14  14  FOBS=    77.6  SIGMA=  36.6  PHAS=  305.9  FOM=  0.05
INDE  4  15   0  FOBS=   111.0  SIGMA=   3.6  PHAS=  219.4  FOM=  0.77
INDE  4  15   1  FOBS=    90.9  SIGMA=   4.6  PHAS=  204.0  FOM=  0.57
INDE  4  15   2  FOBS=   119.7  SIGMA=   4.1  PHAS=  352.8  FOM=  0.77
INDE  4  15   3  FOBS=   335.0  SIGMA=   1.5  PHAS=  302.1  FOM=  0.96
INDE  4  15   4  FOBS=   128.8  SIGMA=   4.0  PHAS=   88.8  FOM=  0.78
INDE  4  15   5  FOBS=   372.2  SIGMA=   1.7  PHAS=  328.1  FOM=  0.87
INDE  4  15   6  FOBS=   316.2  SIGMA=   2.0  PHAS=   38.8  FOM=  0.96
INDE  4  15   7  FOBS=   105.3  SIGMA=   6.0  PHAS=  236.2  FOM=  0.11
INDE  4  15   8  FOBS=   179.8  SIGMA=   4.1  PHAS=  224.5  FOM=  0.46
INDE  4  15   9  FOBS=   188.4  SIGMA=   4.4  PHAS=  136.4  FOM=  0.80
INDE  4  15  10  FOBS=   126.1  SIGMA=   6.6  PHAS=   20.5  FOM=  0.47
INDE  4  15  11  FOBS=   230.2  SIGMA=   3.4  PHAS=  230.6  FOM=  0.79
INDE  4  15  12  FOBS=   108.6  SIGMA=   7.1  PHAS=  103.8  FOM=  0.33
INDE  4  15  13  FOBS=    48.1  SIGMA=  26.4  PHAS=    7.9  FOM=  0.08
INDE  4  16   0  FOBS=   119.1  SIGMA=   3.2  PHAS=   32.2  FOM=  0.98
INDE  4  16   1  FOBS=   263.8  SIGMA=   1.9  PHAS=   36.0  FOM=  0.99
INDE  4  16   2  FOBS=   373.3  SIGMA=   1.3  PHAS=   26.1  FOM=  0.95
INDE  4  16   3  FOBS=   406.5  SIGMA=   1.4  PHAS=  301.2  FOM=  0.95
INDE  4  16   4  FOBS=   264.5  SIGMA=   2.0  PHAS=  132.8  FOM=  0.95
INDE  4  16   5  FOBS=   178.9  SIGMA=   2.9  PHAS=  301.2  FOM=  0.95
INDE  4  16   6  FOBS=   168.9  SIGMA=   3.7  PHAS=   11.6  FOM=  0.90
INDE  4  16   7  FOBS=   165.6  SIGMA=   4.1  PHAS=  184.6  FOM=  0.92
INDE  4  16   8  FOBS=   187.0  SIGMA=   3.9  PHAS=  146.2  FOM=  0.88
INDE  4  16   9  FOBS=   320.0  SIGMA=   2.3  PHAS=  227.9  FOM=  0.67
INDE  4  16  10  FOBS=   101.2  SIGMA=   9.5  PHAS=  195.7  FOM=  0.33
INDE  4  16  11  FOBS=    86.0  SIGMA=   9.0  PHAS=   97.5  FOM=  0.08
INDE  4  16  12  FOBS=    72.1  SIGMA=  10.5  PHAS=  354.9  FOM=  0.28
INDE  4  16  13  FOBS=    75.3  SIGMA=  10.7  PHAS=  195.0  FOM=  0.04
INDE  4  17   0  FOBS=   413.7  SIGMA=   1.3  PHAS=   55.3  FOM=  0.92
INDE  4  17   1  FOBS=   245.6  SIGMA=   1.8  PHAS=   29.0  FOM=  0.95
INDE  4  17   2  FOBS=   211.1  SIGMA=   2.1  PHAS=  277.0  FOM=  0.72
INDE  4  17   3  FOBS=   344.1  SIGMA=   1.6  PHAS=  286.1  FOM=  0.98
INDE  4  17   4  FOBS=   371.5  SIGMA=   1.6  PHAS=   62.3  FOM=  0.96
INDE  4  17   5  FOBS=   202.7  SIGMA=   2.7  PHAS=  221.1  FOM=  0.88
INDE  4  17   6  FOBS=   124.5  SIGMA=   4.8  PHAS=  300.7  FOM=  0.75
INDE  4  17   7  FOBS=    96.7  SIGMA=   6.8  PHAS=   74.5  FOM=  0.18
INDE  4  17   8  FOBS=   185.1  SIGMA=   3.9  PHAS=  349.0  FOM=  0.62
INDE  4  17   9  FOBS=   202.5  SIGMA=   3.6  PHAS=  213.9  FOM=  0.79
INDE  4  17  10  FOBS=    87.3  SIGMA=   8.7  PHAS=  312.0  FOM=  0.16
INDE  4  17  11  FOBS=    94.8  SIGMA=   8.4  PHAS=  128.2  FOM=  0.20
INDE  4  17  12  FOBS=   101.9  SIGMA=   7.3  PHAS=  267.8  FOM=  0.01
INDE  4  17  13  FOBS=   102.5  SIGMA=   7.3  PHAS=   78.7  FOM=  0.06
INDE  4  18   0  FOBS=   106.0  SIGMA=   3.9  PHAS=  187.7  FOM=  0.80
INDE  4  18   1  FOBS=   517.4  SIGMA=   1.1  PHAS=  302.9  FOM=  0.97
INDE  4  18   2  FOBS=   135.7  SIGMA=   3.4  PHAS=  211.3  FOM=  0.78
INDE  4  18   3  FOBS=   204.2  SIGMA=   2.4  PHAS=   97.0  FOM=  0.84
INDE  4  18   4  FOBS=   137.7  SIGMA=   3.9  PHAS=   83.5  FOM=  0.84
INDE  4  18   5  FOBS=   174.6  SIGMA=   3.1  PHAS=   15.5  FOM=  0.94
INDE  4  18   6  FOBS=   359.4  SIGMA=   1.9  PHAS=  233.0  FOM=  0.93
INDE  4  18   7  FOBS=   203.0  SIGMA=   3.3  PHAS=  146.1  FOM=  0.20
INDE  4  18   8  FOBS=   223.9  SIGMA=   3.1  PHAS=  173.3  FOM=  0.50
INDE  4  18   9  FOBS=    83.3  SIGMA=   8.1  PHAS=    3.6  FOM=  0.12
INDE  4  18  10  FOBS=   156.8  SIGMA=   4.7  PHAS=  235.1  FOM=  0.03
INDE  4  18  11  FOBS=    92.5  SIGMA=   9.0  PHAS=  123.3  FOM=  0.22
INDE  4  18  12  FOBS=   107.4  SIGMA=   7.5  PHAS=  283.7  FOM=  0.12
INDE  4  19   0  FOBS=   106.4  SIGMA=   3.7  PHAS=  140.4  FOM=  0.46
INDE  4  19   1  FOBS=   400.7  SIGMA=   1.3  PHAS=  266.9  FOM=  1.00
INDE  4  19   2  FOBS=   273.5  SIGMA=   1.8  PHAS=   61.7  FOM=  1.00
```

Fig. 10A-108

```
INDE  4 19  3 FOBS=  218.1 SIGMA=  2.2 PHAS= 335.0 FOM= 0.89
INDE  4 19  4 FOBS=  446.7 SIGMA=  1.5 PHAS=  68.8 FOM= 0.62
INDE  4 19  5 FOBS=   95.0 SIGMA=  6.1 PHAS=  71.3 FOM= 0.28
INDE  4 19  6 FOBS=  160.1 SIGMA=  4.0 PHAS= 168.2 FOM= 0.34
INDE  4 19  7 FOBS=  209.2 SIGMA=  3.1 PHAS= 107.5 FOM= 0.40
INDE  4 19  8 FOBS=  284.1 SIGMA=  2.4 PHAS=  25.8 FOM= 0.08
INDE  4 19  9 FOBS=   98.4 SIGMA=  6.8 PHAS= 257.1 FOM= 0.04
INDE  4 19 10 FOBS=  154.3 SIGMA=  4.6 PHAS= 321.0 FOM= 0.16
INDE  4 19 11 FOBS=  135.9 SIGMA=  5.9 PHAS= 213.8 FOM= 0.71
INDE  4 19 12 FOBS=   72.1 SIGMA= 11.9 PHAS=  17.5 FOM= 0.03
INDE  4 20  0 FOBS=  131.4 SIGMA=  3.7 PHAS= 174.4 FOM= 0.85
INDE  4 20  1 FOBS=  311.1 SIGMA=  1.5 PHAS= 329.0 FOM= 0.75
INDE  4 20  2 FOBS=  165.3 SIGMA=  2.9 PHAS= 325.8 FOM= 0.75
INDE  4 20  3 FOBS=  238.6 SIGMA=  2.2 PHAS= 120.0 FOM= 0.91
INDE  4 20  4 FOBS=  173.0 SIGMA=  3.0 PHAS= 299.4 FOM= 0.14
INDE  4 20  5 FOBS=  110.8 SIGMA=  5.2 PHAS= 261.1 FOM= 0.03
INDE  4 20  6 FOBS=  247.4 SIGMA=  2.5 PHAS= 210.0 FOM= 0.17
INDE  4 20  7 FOBS=  317.4 SIGMA=  2.1 PHAS= 291.4 FOM= 0.82
INDE  4 20  8 FOBS=   76.5 SIGMA=  8.5 PHAS=  17.6 FOM= 0.06
INDE  4 20  9 FOBS=   60.4 SIGMA= 12.2 PHAS= 200.9 FOM= 0.06
INDE  4 20 10 FOBS=   90.4 SIGMA=  7.4 PHAS= 230.5 FOM= 0.05
INDE  4 20 11 FOBS=  106.2 SIGMA=  6.7 PHAS= 105.2 FOM= 0.09
INDE  4 20 12 FOBS=   62.1 SIGMA= 13.8 PHAS=   7.2 FOM= 0.05
INDE  4 21  0 FOBS=  139.3 SIGMA=  3.6 PHAS= 273.1 FOM= 0.20
INDE  4 21  1 FOBS=  145.3 SIGMA=  2.8 PHAS= 121.5 FOM= 0.95
INDE  4 21  2 FOBS=  204.3 SIGMA=  2.4 PHAS=  32.6 FOM= 0.93
INDE  4 21  3 FOBS=  176.4 SIGMA=  3.2 PHAS= 208.5 FOM= 0.96
INDE  4 21  4 FOBS=   91.3 SIGMA=  5.9 PHAS=  82.5 FOM= 0.80
INDE  4 21  5 FOBS=   52.4 SIGMA= 24.8 PHAS= 171.3 FOM= 0.13
INDE  4 21  6 FOBS=  119.3 SIGMA=  5.1 PHAS= 239.6 FOM= 0.20
INDE  4 21  7 FOBS=   53.8 SIGMA= 12.6 PHAS=  73.5 FOM= 0.33
INDE  4 21  8 FOBS=   73.8 SIGMA=  8.7 PHAS= 290.8 FOM= 0.15
INDE  4 21  9 FOBS=  141.0 SIGMA=  4.8 PHAS= 216.8 FOM= 0.15
INDE  4 21 10 FOBS=  120.7 SIGMA=  5.5 PHAS=  91.5 FOM= 0.32
INDE  4 21 11 FOBS=   70.0 SIGMA= 10.4 PHAS= 325.2 FOM= 0.02
INDE  4 22  0 FOBS=  194.6 SIGMA=  2.7 PHAS= 101.0 FOM= 0.92
INDE  4 22  1 FOBS=  231.4 SIGMA=  2.1 PHAS= 231.2 FOM= 0.94
INDE  4 22  2 FOBS=  359.6 SIGMA=  1.6 PHAS=  32.2 FOM= 0.98
INDE  4 22  3 FOBS=  261.7 SIGMA=  2.1 PHAS= 164.2 FOM= 0.91
INDE  4 22  4 FOBS=  235.7 SIGMA=  2.4 PHAS= 343.2 FOM= 0.89
INDE  4 22  5 FOBS=  192.5 SIGMA=  3.0 PHAS=  51.5 FOM= 0.93
INDE  4 22  6 FOBS=   98.0 SIGMA=  5.9 PHAS= 206.7 FOM= 0.12
INDE  4 22  7 FOBS=  118.9 SIGMA=  5.2 PHAS= 312.6 FOM= 0.14
INDE  4 22  8 FOBS=   72.0 SIGMA=  8.8 PHAS= 245.0 FOM= 0.25
INDE  4 22  9 FOBS=  116.6 SIGMA=  5.6 PHAS= 151.8 FOM= 0.10
INDE  4 22 10 FOBS=   59.0 SIGMA= 12.4 PHAS=  67.6 FOM= 0.15
INDE  4 22 11 FOBS=   77.5 SIGMA=  8.5 PHAS= 225.8 FOM= 0.14
INDE  4 23  0 FOBS=   70.8 SIGMA=  6.2 PHAS= 248.5 FOM= 0.45
INDE  4 23  1 FOBS=   83.2 SIGMA=  5.6 PHAS= 100.7 FOM= 0.18
INDE  4 23  2 FOBS=  161.1 SIGMA=  3.2 PHAS=  15.5 FOM= 0.60
INDE  4 23  3 FOBS=  111.2 SIGMA=  4.8 PHAS= 214.8 FOM= 0.10
INDE  4 23  4 FOBS=  197.0 SIGMA=  2.9 PHAS=  54.0 FOM= 0.46
INDE  4 23  5 FOBS=   90.1 SIGMA=  6.2 PHAS= 289.0 FOM= 0.26
INDE  4 23  6 FOBS=   42.1 SIGMA= 18.1 PHAS=   1.6 FOM= 0.33
INDE  4 23  7 FOBS=  111.8 SIGMA=  5.4 PHAS= 110.2 FOM= 0.31
INDE  4 23  8 FOBS=  157.6 SIGMA=  4.0 PHAS= 132.9 FOM= 0.37
INDE  4 23  9 FOBS=  118.4 SIGMA=  5.6 PHAS=  25.3 FOM= 0.81
INDE  4 23 10 FOBS=   76.0 SIGMA=  8.7 PHAS= 246.0 FOM= 0.05
INDE  4 24  0 FOBS=  212.4 SIGMA=  2.3 PHAS= 171.0 FOM= 0.99
INDE  4 24  1 FOBS=  203.6 SIGMA=  2.9 PHAS=  40.3 FOM= 0.82
INDE  4 24  2 FOBS=  215.2 SIGMA=  2.3 PHAS= 193.1 FOM= 0.43
INDE  4 24  3 FOBS=  146.1 SIGMA=  3.8 PHAS= 144.0 FOM= 0.39
INDE  4 24  4 FOBS=  147.8 SIGMA=  4.0 PHAS= 310.9 FOM= 0.41
INDE  4 24  5 FOBS=   76.6 SIGMA=  7.5 PHAS=  91.2 FOM= 0.36
INDE  4 24  6 FOBS=  257.0 SIGMA=  2.4 PHAS=  71.1 FOM= 0.93
INDE  4 24  7 FOBS=  132.0 SIGMA=  4.6 PHAS= 210.4 FOM= 0.68
INDE  4 24  8 FOBS=   41.2 SIGMA= 15.9 PHAS= 108.1 FOM= 0.05
INDE  4 24  9 FOBS=   69.6 SIGMA=  8.4 PHAS= 320.4 FOM= 0.08
INDE  4 24 10 FOBS=   86.5 SIGMA=  7.3 PHAS= 223.2 FOM= 0.30
INDE  4 25  0 FOBS=  118.1 SIGMA=  3.9 PHAS= 258.5 FOM= 0.73
INDE  4 25  1 FOBS=  189.7 SIGMA=  2.9 PHAS= 239.1 FOM= 0.54
```

Fig. 10A-109

| | | | | | | | | | | |
|---|---|---|---|---|---|---|---|---|---|---|
| INDE | 4 | 25 | 2 | FOBS= | 137.6 | SIGMA= | 3.7 | PHAS= | 175.8 | FOM= | 0.24 |
| INDE | 4 | 25 | 3 | FOBS= | 71.2 | SIGMA= | 7.1 | PHAS= | 199.8 | FOM= | 0.29 |
| INDE | 4 | 25 | 4 | FOBS= | 230.4 | SIGMA= | 2.5 | PHAS= | 16.6 | FOM= | 0.87 |
| INDE | 4 | 25 | 5 | FOBS= | 85.2 | SIGMA= | 6.6 | PHAS= | 200.7 | FOM= | 0.19 |
| INDE | 4 | 25 | 6 | FOBS= | 94.7 | SIGMA= | 6.0 | PHAS= | 261.4 | FOM= | 0.13 |
| INDE | 4 | 25 | 7 | FOBS= | 129.0 | SIGMA= | 4.5 | PHAS= | 122.1 | FOM= | 0.37 |
| INDE | 4 | 25 | 8 | FOBS= | 100.5 | SIGMA= | 5.8 | PHAS= | 14.3 | FOM= | 0.27 |
| INDE | 4 | 25 | 9 | FOBS= | 59.3 | SIGMA= | 10.7 | PHAS= | 152.1 | FOM= | 0.03 |
| INDE | 4 | 26 | 0 | FOBS= | 106.8 | SIGMA= | 4.3 | PHAS= | 213.1 | FOM= | 0.54 |
| INDE | 4 | 26 | 1 | FOBS= | 62.8 | SIGMA= | 7.7 | PHAS= | 289.2 | FOM= | 0.20 |
| INDE | 4 | 26 | 2 | FOBS= | 97.6 | SIGMA= | 4.9 | PHAS= | 250.3 | FOM= | 0.61 |
| INDE | 4 | 26 | 3 | FOBS= | 199.1 | SIGMA= | 2.5 | PHAS= | 116.9 | FOM= | 0.23 |
| INDE | 4 | 26 | 4 | FOBS= | 123.8 | SIGMA= | 4.5 | PHAS= | 351.2 | FOM= | 0.62 |
| INDE | 4 | 26 | 5 | FOBS= | 37.1 | SIGMA= | 13.1 | PHAS= | 204.6 | FOM= | 0.37 |
| INDE | 4 | 26 | 6 | FOBS= | 39.4 | SIGMA= | 19.4 | PHAS= | 2.8 | FOM= | 0.11 |
| INDE | 4 | 26 | 7 | FOBS= | 115.9 | SIGMA= | 4.9 | PHAS= | 295.6 | FOM= | 0.21 |
| INDE | 4 | 26 | 8 | FOBS= | 159.7 | SIGMA= | 3.8 | PHAS= | 258.1 | FOM= | 0.69 |
| INDE | 4 | 26 | 9 | FOBS= | 73.4 | SIGMA= | 10.2 | PHAS= | 30.0 | FOM= | 0.11 |
| INDE | 4 | 27 | 0 | FOBS= | 88.5 | SIGMA= | 4.8 | PHAS= | 97.5 | FOM= | 0.43 |
| INDE | 4 | 27 | 1 | FOBS= | 184.0 | SIGMA= | 2.4 | PHAS= | 347.8 | FOM= | 0.95 |
| INDE | 4 | 27 | 2 | FOBS= | 52.5 | SIGMA= | 14.2 | PHAS= | 15.5 | FOM= | 0.18 |
| INDE | 4 | 27 | 3 | FOBS= | 37.2 | SIGMA= | 12.9 | PHAS= | 284.8 | FOM= | 0.20 |
| INDE | 4 | 27 | 4 | FOBS= | 90.9 | SIGMA= | 5.6 | PHAS= | 105.6 | FOM= | 0.52 |
| INDE | 4 | 27 | 5 | FOBS= | 138.5 | SIGMA= | 4.1 | PHAS= | 69.6 | FOM= | 0.56 |
| INDE | 4 | 27 | 6 | FOBS= | 49.4 | SIGMA= | 13.0 | PHAS= | 270.9 | FOM= | 0.51 |
| INDE | 4 | 27 | 7 | FOBS= | 56.6 | SIGMA= | 10.9 | PHAS= | 111.9 | FOM= | 0.05 |
| INDE | 4 | 27 | 8 | FOBS= | 72.9 | SIGMA= | 7.9 | PHAS= | 358.0 | FOM= | 0.04 |
| INDE | 4 | 28 | 0 | FOBS= | 225.4 | SIGMA= | 2.1 | PHAS= | 51.8 | FOM= | 0.84 |
| INDE | 4 | 28 | 1 | FOBS= | 45.5 | SIGMA= | 9.8 | PHAS= | 101.9 | FOM= | 0.16 |
| INDE | 4 | 28 | 2 | FOBS= | 53.0 | SIGMA= | 11.4 | PHAS= | 312.5 | FOM= | 0.36 |
| INDE | 4 | 28 | 3 | FOBS= | 135.4 | SIGMA= | 3.7 | PHAS= | 122.7 | FOM= | 0.61 |
| INDE | 4 | 28 | 4 | FOBS= | 251.3 | SIGMA= | 2.2 | PHAS= | 202.0 | FOM= | 0.72 |
| INDE | 4 | 28 | 5 | FOBS= | 167.2 | SIGMA= | 3.4 | PHAS= | 307.5 | FOM= | 0.96 |
| INDE | 4 | 28 | 6 | FOBS= | 99.2 | SIGMA= | 5.5 | PHAS= | 244.2 | FOM= | 0.24 |
| INDE | 4 | 28 | 7 | FOBS= | 122.9 | SIGMA= | 4.6 | PHAS= | 346.8 | FOM= | 0.14 |
| INDE | 4 | 29 | 0 | FOBS= | 147.1 | SIGMA= | 3.1 | PHAS= | 57.5 | FOM= | 0.25 |
| INDE | 4 | 29 | 1 | FOBS= | 45.4 | SIGMA= | 9.9 | PHAS= | 276.5 | FOM= | 0.33 |
| INDE | 4 | 29 | 2 | FOBS= | 113.8 | SIGMA= | 4.4 | PHAS= | 65.6 | FOM= | 0.71 |
| INDE | 4 | 29 | 3 | FOBS= | 191.0 | SIGMA= | 2.6 | PHAS= | 142.9 | FOM= | 0.18 |
| INDE | 4 | 29 | 4 | FOBS= | 173.1 | SIGMA= | 3.0 | PHAS= | 259.4 | FOM= | 0.83 |
| INDE | 4 | 29 | 5 | FOBS= | 189.6 | SIGMA= | 2.7 | PHAS= | 93.9 | FOM= | 0.38 |
| INDE | 4 | 29 | 6 | FOBS= | 146.4 | SIGMA= | 3.8 | PHAS= | 299.4 | FOM= | 0.42 |
| INDE | 4 | 30 | 0 | FOBS= | 81.7 | SIGMA= | 5.3 | PHAS= | 300.9 | FOM= | 0.62 |
| INDE | 4 | 30 | 1 | FOBS= | 130.4 | SIGMA= | 3.6 | PHAS= | 169.7 | FOM= | 0.80 |
| INDE | 4 | 30 | 2 | FOBS= | 39.9 | SIGMA= | 11.8 | PHAS= | 101.6 | FOM= | 0.06 |
| INDE | 4 | 30 | 3 | FOBS= | 54.0 | SIGMA= | 26.8 | PHAS= | 333.1 | FOM= | 0.06 |
| INDE | 4 | 30 | 4 | FOBS= | 46.1 | SIGMA= | 11.3 | PHAS= | 283.8 | FOM= | 0.04 |
| INDE | 4 | 30 | 5 | FOBS= | 106.3 | SIGMA= | 4.8 | PHAS= | 123.7 | FOM= | 0.29 |
| INDE | 4 | 31 | 0 | FOBS= | 52.4 | SIGMA= | 8.1 | PHAS= | 143.3 | FOM= | 0.13 |
| INDE | 4 | 31 | 1 | FOBS= | 77.9 | SIGMA= | 5.5 | PHAS= | 4.8 | FOM= | 0.06 |
| INDE | 4 | 31 | 2 | FOBS= | 135.3 | SIGMA= | 3.4 | PHAS= | 259.6 | FOM= | 0.36 |
| INDE | 4 | 31 | 3 | FOBS= | 102.4 | SIGMA= | 61.9 | PHAS= | 345.7 | FOM= | 0.07 |
| INDE | 4 | 31 | 4 | FOBS= | 122.7 | SIGMA= | 4.5 | PHAS= | 269.2 | FOM= | 0.24 |
| INDE | 4 | 32 | 0 | FOBS= | 109.1 | SIGMA= | 3.9 | PHAS= | 116.8 | FOM= | 0.23 |
| INDE | 4 | 32 | 1 | FOBS= | 98.5 | SIGMA= | 4.4 | PHAS= | 66.2 | FOM= | 0.18 |
| INDE | 4 | 32 | 2 | FOBS= | 99.3 | SIGMA= | 4.7 | PHAS= | 322.7 | FOM= | 0.04 |
| INDE | 5 | 0 | 0 | FOBS= | 693.7 | SIGMA= | 1.1 | PHAS= | 0.0 | FOM= | 1.00 |
| INDE | 5 | 0 | 1 | FOBS= | 348.6 | SIGMA= | 1.6 | PHAS= | 180.0 | FOM= | 1.00 |
| INDE | 5 | 0 | 2 | FOBS= | 78.0 | SIGMA= | 7.0 | PHAS= | 0.0 | FOM= | 0.24 |
| INDE | 5 | 0 | 3 | FOBS= | 39.3 | SIGMA= | 13.9 | PHAS= | 180.0 | FOM= | 0.09 |
| INDE | 5 | 0 | 4 | FOBS= | 89.8 | SIGMA= | 11.5 | PHAS= | 0.0 | FOM= | 0.22 |
| INDE | 5 | 0 | 5 | FOBS= | 164.1 | SIGMA= | 4.8 | PHAS= | 180.0 | FOM= | 0.09 |
| INDE | 5 | 0 | 6 | FOBS= | 163.1 | SIGMA= | 5.9 | PHAS= | 180.0 | FOM= | 0.38 |
| INDE | 5 | 0 | 7 | FOBS= | 75.8 | SIGMA= | 13.3 | PHAS= | 0.0 | FOM= | 0.08 |
| INDE | 5 | 0 | 8 | FOBS= | 177.6 | SIGMA= | 7.1 | PHAS= | 0.0 | FOM= | 0.07 |
| INDE | 5 | 0 | 9 | FOBS= | 251.5 | SIGMA= | 4.9 | PHAS= | 0.0 | FOM= | 0.03 |
| INDE | 5 | 0 | 10 | FOBS= | 158.3 | SIGMA= | 31.5 | PHAS= | 0.0 | FOM= | 0.06 |
| INDE | 5 | 0 | 11 | FOBS= | 193.2 | SIGMA= | 10.0 | PHAS= | 180.0 | FOM= | 0.06 |
| INDE | 5 | 0 | 12 | FOBS= | 47.8 | SIGMA= | 30.2 | PHAS= | 0.0 | FOM= | 0.13 |
| INDE | 5 | 0 | 13 | FOBS= | 64.4 | SIGMA= | 25.3 | PHAS= | 180.0 | FOM= | 0.02 |
| INDE | 5 | 0 | 14 | FOBS= | 59.3 | SIGMA= | 44.6 | PHAS= | 180.0 | FOM= | 0.01 |

Fig. 10A-110

```
INDE    5   1    0  FOBS=   228.3  SIGMA=   1.6  PHAS=  122.5  FOM=  0.96
INDE    5   1    1  FOBS=   429.0  SIGMA=   1.1  PHAS=  283.9  FOM=  1.00
INDE    5   1    2  FOBS=   413.3  SIGMA=   1.1  PHAS=  111.1  FOM=  0.98
INDE    5   1    3  FOBS=   231.4  SIGMA=   2.7  PHAS=  303.0  FOM=  0.99
INDE    5   1    4  FOBS=   149.9  SIGMA=   3.5  PHAS=  331.5  FOM=  0.73
INDE    5   1    5  FOBS=   163.9  SIGMA=   4.4  PHAS=   49.9  FOM=  0.78
INDE    5   1    6  FOBS=    44.2  SIGMA=  15.6  PHAS=  276.9  FOM=  0.32
INDE    5   1    7  FOBS=   318.6  SIGMA=   2.2  PHAS=   55.0  FOM=  0.83
INDE    5   1    8  FOBS=   223.7  SIGMA=   3.9  PHAS=  350.6  FOM=  0.33
INDE    5   1    9  FOBS=   274.0  SIGMA=   3.2  PHAS=  165.9  FOM=  0.19
INDE    5   1   10  FOBS=   383.6  SIGMA=   2.6  PHAS=   86.3  FOM=  0.26
INDE    5   1   11  FOBS=   230.0  SIGMA=   4.7  PHAS=   30.8  FOM=  0.18
INDE    5   1   12  FOBS=    85.0  SIGMA=  11.8  PHAS=  145.2  FOM=  0.09
INDE    5   1   13  FOBS=    89.9  SIGMA=  12.0  PHAS=   31.4  FOM=  0.03
INDE    5   1   14  FOBS=    54.6  SIGMA=  37.5  PHAS=  261.8  FOM=  0.09
INDE    5   1   15  FOBS=    89.8  SIGMA=  11.5  PHAS=  153.5  FOM=  0.05
INDE    5   2    0  FOBS=   171.5  SIGMA=   2.0  PHAS=    3.6  FOM=  0.98
INDE    5   2    1  FOBS=   199.4  SIGMA=   2.3  PHAS=  229.3  FOM=  0.55
INDE    5   2    2  FOBS=   282.4  SIGMA=   1.7  PHAS=  131.1  FOM=  0.93
INDE    5   2    3  FOBS=   212.3  SIGMA=   2.1  PHAS=   10.2  FOM=  0.89
INDE    5   2    4  FOBS=   175.6  SIGMA=   2.8  PHAS=  358.1  FOM=  0.89
INDE    5   2    5  FOBS=   256.8  SIGMA=   2.2  PHAS=  186.6  FOM=  0.86
INDE    5   2    6  FOBS=   250.5  SIGMA=   2.8  PHAS=    5.9  FOM=  0.92
INDE    5   2    7  FOBS=    57.1  SIGMA=  12.7  PHAS=   93.4  FOM=  0.21
INDE    5   2    8  FOBS=   407.3  SIGMA=   2.5  PHAS=  162.6  FOM=  0.56
INDE    5   2    9  FOBS=   184.9  SIGMA=   4.9  PHAS=  228.6  FOM=  0.14
INDE    5   2   10  FOBS=   361.2  SIGMA=   3.1  PHAS=  287.6  FOM=  0.67
INDE    5   2   11  FOBS=   175.7  SIGMA=   6.1  PHAS=  140.5  FOM=  0.16
INDE    5   2   12  FOBS=    92.7  SIGMA=  11.6  PHAS=   32.8  FOM=  0.11
INDE    5   2   13  FOBS=    71.1  SIGMA=  14.5  PHAS=  299.2  FOM=  0.12
INDE    5   2   14  FOBS=    68.4  SIGMA=  36.1  PHAS=  147.8  FOM=  0.05
INDE    5   2   15  FOBS=   100.1  SIGMA=  10.9  PHAS=   49.8  FOM=  0.07
INDE    5   3    0  FOBS=   286.6  SIGMA=   1.4  PHAS=  224.4  FOM=  0.95
INDE    5   3    1  FOBS=   328.9  SIGMA=   1.4  PHAS=  138.4  FOM=  0.98
INDE    5   3    2  FOBS=   314.0  SIGMA=   1.5  PHAS=   58.6  FOM=  0.94
INDE    5   3    3  FOBS=    61.9  SIGMA=   6.9  PHAS=  148.2  FOM=  0.23
INDE    5   3    4  FOBS=   235.8  SIGMA=   2.4  PHAS=   15.9  FOM=  0.86
INDE    5   3    5  FOBS=   340.0  SIGMA=   1.7  PHAS=   82.5  FOM=  0.55
INDE    5   3    6  FOBS=   229.0  SIGMA=   2.6  PHAS=  177.6  FOM=  0.30
INDE    5   3    7  FOBS=   177.6  SIGMA=   4.8  PHAS=  232.3  FOM=  0.85
INDE    5   3    8  FOBS=    86.7  SIGMA=  11.4  PHAS=    0.1  FOM=  0.38
INDE    5   3    9  FOBS=   301.3  SIGMA=   2.8  PHAS=  279.8  FOM=  0.84
INDE    5   3   10  FOBS=   148.8  SIGMA=   8.7  PHAS=  348.3  FOM=  0.24
INDE    5   3   11  FOBS=   166.6  SIGMA=   6.4  PHAS=  108.2  FOM=  0.37
INDE    5   3   12  FOBS=   108.3  SIGMA=   9.9  PHAS=  327.4  FOM=  0.23
INDE    5   3   13  FOBS=   101.1  SIGMA=   9.9  PHAS=  122.2  FOM=  0.28
INDE    5   3   14  FOBS=    72.1  SIGMA=  13.0  PHAS=  248.9  FOM=  0.01
INDE    5   3   15  FOBS=    80.6  SIGMA=  12.4  PHAS=  341.3  FOM=  0.04
INDE    5   4    0  FOBS=   132.0  SIGMA=   2.5  PHAS=  297.5  FOM=  0.50
INDE    5   4    1  FOBS=   242.6  SIGMA=   1.8  PHAS=  278.8  FOM=  0.94
INDE    5   4    2  FOBS=    72.9  SIGMA=   5.8  PHAS=  124.7  FOM=  0.38
INDE    5   4    3  FOBS=   156.4  SIGMA=   2.8  PHAS=  267.2  FOM=  0.79
INDE    5   4    4  FOBS=    74.3  SIGMA=   7.0  PHAS=  353.3  FOM=  0.58
INDE    5   4    5  FOBS=   271.5  SIGMA=   2.1  PHAS=  132.8  FOM=  0.74
INDE    5   4    6  FOBS=   217.1  SIGMA=   2.8  PHAS=  227.7  FOM=  0.89
INDE    5   4    7  FOBS=   295.6  SIGMA=   2.3  PHAS=  328.9  FOM=  0.82
INDE    5   4    8  FOBS=   247.6  SIGMA=   3.8  PHAS=  297.8  FOM=  0.88
INDE    5   4    9  FOBS=   164.9  SIGMA=   6.3  PHAS=  106.8  FOM=  0.42
INDE    5   4   10  FOBS=   115.9  SIGMA=  11.2  PHAS=   26.5  FOM=  0.12
INDE    5   4   11  FOBS=   115.4  SIGMA=  10.1  PHAS=  273.7  FOM=  0.11
INDE    5   4   12  FOBS=   213.7  SIGMA=   4.7  PHAS=  136.6  FOM=  0.12
INDE    5   4   13  FOBS=   104.3  SIGMA=   9.1  PHAS=  279.6  FOM=  0.02
INDE    5   4   14  FOBS=    62.8  SIGMA=  37.9  PHAS=   16.2  FOM=  0.00
INDE    5   4   15  FOBS=    66.1  SIGMA=  32.1  PHAS=   23.6  FOM=  0.17
INDE    5   5    0  FOBS=   306.3  SIGMA=   1.4  PHAS=  231.6  FOM=  0.93
INDE    5   5    1  FOBS=   172.4  SIGMA=   2.1  PHAS=  155.8  FOM=  0.94
INDE    5   5    2  FOBS=   259.8  SIGMA=   1.9  PHAS=  195.8  FOM=  0.70
INDE    5   5    3  FOBS=   150.0  SIGMA=   3.2  PHAS=  192.8  FOM=  0.77
INDE    5   5    4  FOBS=   191.4  SIGMA=   2.6  PHAS=    7.3  FOM=  0.96
INDE    5   5    5  FOBS=   255.0  SIGMA=   2.4  PHAS=  182.7  FOM=  0.99
INDE    5   5    6  FOBS=   418.0  SIGMA=   1.6  PHAS=  358.4  FOM=  0.93
```

Fig. 10A-111

```
INDE   5   5    7 FOBS=  166.2 SIGMA=    4.3 PHAS= 338.7 FOM= 0.79
INDE   5   5    8 FOBS=  251.2 SIGMA=    3.1 PHAS=  53.2 FOM= 0.95
INDE   5   5    9 FOBS=  340.5 SIGMA=    2.5 PHAS=  59.0 FOM= 0.90
INDE   5   5   10 FOBS=  108.7 SIGMA=   13.2 PHAS= 348.8 FOM= 0.03
INDE   5   5   11 FOBS=  126.0 SIGMA=    9.5 PHAS= 105.0 FOM= 0.13
INDE   5   5   12 FOBS=  124.6 SIGMA=    7.7 PHAS= 337.2 FOM= 0.33
INDE   5   5   13 FOBS=  259.2 SIGMA=    3.6 PHAS= 129.6 FOM= 0.77
INDE   5   5   14 FOBS=   66.4 SIGMA=   36.7 PHAS= 346.4 FOM= 0.04
INDE   5   5   15 FOBS=  485.3 SIGMA=  323.2 PHAS= 231.1 FOM= 0.01
INDE   5   6    0 FOBS=  116.0 SIGMA=    3.1 PHAS= 335.0 FOM= 0.87
INDE   5   6    1 FOBS=  118.7 SIGMA=    3.3 PHAS= 231.2 FOM= 0.79
INDE   5   6    2 FOBS=  377.5 SIGMA=    1.3 PHAS= 236.0 FOM= 0.45
INDE   5   6    3 FOBS=   64.8 SIGMA=    7.3 PHAS= 243.4 FOM= 0.41
INDE   5   6    4 FOBS=  177.9 SIGMA=    3.0 PHAS=  99.4 FOM= 0.11
INDE   5   6    5 FOBS=   59.2 SIGMA=    9.0 PHAS=  66.5 FOM= 0.18
INDE   5   6    6 FOBS=  200.5 SIGMA=    3.3 PHAS= 236.3 FOM= 0.65
INDE   5   6    7 FOBS=  139.9 SIGMA=    4.8 PHAS= 348.3 FOM= 0.31
INDE   5   6    8 FOBS=  222.8 SIGMA=    3.3 PHAS= 211.6 FOM= 0.66
INDE   5   6    9 FOBS=  179.1 SIGMA=    5.4 PHAS=  75.7 FOM= 0.10
INDE   5   6   10 FOBS=  159.2 SIGMA=    7.0 PHAS= 306.8 FOM= 0.18
INDE   5   6   11 FOBS=  216.1 SIGMA=    5.2 PHAS= 112.2 FOM= 0.41
INDE   5   6   12 FOBS=   64.4 SIGMA=   18.1 PHAS=  73.7 FOM= 0.02
INDE   5   6   13 FOBS=  107.7 SIGMA=   10.0 PHAS=  30.5 FOM= 0.05
INDE   5   6   14 FOBS=  121.6 SIGMA=    7.5 PHAS= 254.4 FOM= 0.13
INDE   5   7    0 FOBS=  218.1 SIGMA=    1.6 PHAS= 298.7 FOM= 1.00
INDE   5   7    1 FOBS=  154.4 SIGMA=    2.4 PHAS=  66.5 FOM= 0.52
INDE   5   7    2 FOBS=  189.6 SIGMA=    2.2 PHAS= 134.7 FOM= 0.96
INDE   5   7    3 FOBS=  182.9 SIGMA=    2.6 PHAS= 301.7 FOM= 0.60
INDE   5   7    4 FOBS=  178.8 SIGMA=    3.2 PHAS=  50.1 FOM= 0.88
INDE   5   7    5 FOBS=   59.5 SIGMA=   10.1 PHAS= 200.9 FOM= 0.22
INDE   5   7    6 FOBS=   87.1 SIGMA=    6.9 PHAS= 316.7 FOM= 0.23
INDE   5   7    7 FOBS=  188.5 SIGMA=    3.7 PHAS=  45.3 FOM= 0.75
INDE   5   7    8 FOBS=  190.4 SIGMA=    4.5 PHAS= 110.1 FOM= 0.56
INDE   5   7    9 FOBS=   88.3 SIGMA=   10.7 PHAS=   5.1 FOM= 0.20
INDE   5   7   10 FOBS=  352.9 SIGMA=    2.9 PHAS= 124.1 FOM= 0.24
INDE   5   7   11 FOBS=   71.4 SIGMA=   13.9 PHAS= 178.9 FOM= 0.03
INDE   5   7   12 FOBS=  285.7 SIGMA=    3.2 PHAS= 283.2 FOM= 0.71
INDE   5   7   13 FOBS=   58.7 SIGMA=   19.3 PHAS= 149.2 FOM= 0.13
INDE   5   7   14 FOBS=   79.5 SIGMA=   13.4 PHAS= 344.6 FOM= 0.02
INDE   5   8    0 FOBS=  302.4 SIGMA=    1.4 PHAS=  58.2 FOM= 0.52
INDE   5   8    1 FOBS=  224.2 SIGMA=    1.8 PHAS= 217.5 FOM= 0.97
INDE   5   8    2 FOBS=   38.2 SIGMA=   13.6 PHAS=  55.0 FOM= 0.41
INDE   5   8    3 FOBS=  101.5 SIGMA=    4.6 PHAS= 134.2 FOM= 0.56
INDE   5   8    4 FOBS=  262.7 SIGMA=    2.3 PHAS= 251.3 FOM= 0.78
INDE   5   8    5 FOBS=   68.8 SIGMA=    8.0 PHAS= 145.3 FOM= 0.44
INDE   5   8    6 FOBS=   96.3 SIGMA=    6.3 PHAS= 250.5 FOM= 0.16
INDE   5   8    7 FOBS=  204.3 SIGMA=    3.8 PHAS=  34.3 FOM= 0.30
INDE   5   8    8 FOBS=  130.1 SIGMA=    6.5 PHAS= 255.4 FOM= 0.23
INDE   5   8    9 FOBS=  209.8 SIGMA=    4.2 PHAS= 148.1 FOM= 0.35
INDE   5   8   10 FOBS=  207.0 SIGMA=    4.4 PHAS= 345.7 FOM= 0.19
INDE   5   8   11 FOBS=  223.4 SIGMA=    4.0 PHAS= 312.0 FOM= 0.74
INDE   5   8   12 FOBS=  213.9 SIGMA=    4.4 PHAS=  89.7 FOM= 0.35
INDE   5   8   13 FOBS=   74.4 SIGMA=   12.5 PHAS=  60.8 FOM= 0.12
INDE   5   8   14 FOBS=   95.6 SIGMA=    9.4 PHAS= 196.8 FOM= 0.17
INDE   5   9    0 FOBS=  203.4 SIGMA=    1.9 PHAS= 227.8 FOM= 0.90
INDE   5   9    1 FOBS=   72.5 SIGMA=    5.2 PHAS=  69.3 FOM= 0.23
INDE   5   9    2 FOBS=  209.0 SIGMA=    2.0 PHAS= 283.5 FOM= 0.97
INDE   5   9    3 FOBS=   88.3 SIGMA=    6.0 PHAS= 248.0 FOM= 0.83
INDE   5   9    4 FOBS=   43.3 SIGMA=   11.5 PHAS=  51.0 FOM= 0.34
INDE   5   9    5 FOBS=  144.9 SIGMA=    4.4 PHAS=  37.8 FOM= 0.81
INDE   5   9    6 FOBS=  250.4 SIGMA=    2.9 PHAS= 305.4 FOM= 0.97
INDE   5   9    7 FOBS=  266.6 SIGMA=    2.8 PHAS= 351.0 FOM= 0.61
INDE   5   9    8 FOBS=  198.8 SIGMA=    4.0 PHAS= 170.2 FOM= 0.51
INDE   5   9    9 FOBS=   55.9 SIGMA=   17.4 PHAS=   5.9 FOM= 0.10
INDE   5   9   10 FOBS=  247.9 SIGMA=    3.5 PHAS= 233.1 FOM= 0.76
INDE   5   9   11 FOBS=  112.9 SIGMA=    7.6 PHAS= 220.6 FOM= 0.10
INDE   5   9   12 FOBS=   80.1 SIGMA=   11.9 PHAS=  73.1 FOM= 0.16
INDE   5   9   13 FOBS=   44.5 SIGMA=   21.4 PHAS= 273.0 FOM= 0.22
INDE   5   9   14 FOBS=  124.2 SIGMA=    7.0 PHAS= 323.8 FOM= 0.08
INDE   5  10    0 FOBS=   35.7 SIGMA=   11.4 PHAS= 158.8 FOM= 0.27
INDE   5  10    1 FOBS=  257.0 SIGMA=    1.6 PHAS= 264.1 FOM= 0.74
```

Fig. 10A-112

```
INDE   5   10    2  FOBS=    199.3  SIGMA=    2.2  PHAS=     75.4  FOM=   0.85
INDE   5   10    3  FOBS=    174.6  SIGMA=    2.7  PHAS=    309.9  FOM=   0.83
INDE   5   10    4  FOBS=    146.3  SIGMA=    3.6  PHAS=    187.2  FOM=   0.79
INDE   5   10    5  FOBS=    192.3  SIGMA=    3.0  PHAS=    121.0  FOM=   0.40
INDE   5   10    6  FOBS=    332.4  SIGMA=    2.6  PHAS=    305.2  FOM=   0.97
INDE   5   10    7  FOBS=    394.6  SIGMA=    2.3  PHAS=    124.5  FOM=   0.97
INDE   5   10    8  FOBS=    194.0  SIGMA=    4.2  PHAS=    234.8  FOM=   0.52
INDE   5   10    9  FOBS=    215.5  SIGMA=    3.9  PHAS=    315.6  FOM=   0.84
INDE   5   10   10  FOBS=     62.9  SIGMA=   14.1  PHAS=    124.4  FOM=   0.10
INDE   5   10   11  FOBS=     96.7  SIGMA=    8.7  PHAS=    170.6  FOM=   0.10
INDE   5   10   12  FOBS=    178.2  SIGMA=    4.9  PHAS=     33.7  FOM=   0.13
INDE   5   10   13  FOBS=     84.3  SIGMA=    9.7  PHAS=    264.0  FOM=   0.42
INDE   5   10   14  FOBS=     51.1  SIGMA=   23.5  PHAS=    113.9  FOM=   0.02
INDE   5   11    0  FOBS=    147.5  SIGMA=    2.4  PHAS=    210.6  FOM=   0.66
INDE   5   11    1  FOBS=    143.1  SIGMA=    2.9  PHAS=    269.7  FOM=   0.94
INDE   5   11    2  FOBS=    160.8  SIGMA=    2.6  PHAS=      0.8  FOM=   0.91
INDE   5   11    3  FOBS=    245.3  SIGMA=    2.0  PHAS=    306.2  FOM=   0.52
INDE   5   11    4  FOBS=    227.7  SIGMA=    2.3  PHAS=    161.4  FOM=   0.56
INDE   5   11    5  FOBS=    144.9  SIGMA=    4.2  PHAS=    254.9  FOM=   0.10
INDE   5   11    6  FOBS=    395.1  SIGMA=    2.0  PHAS=    343.0  FOM=   0.65
INDE   5   11    7  FOBS=    249.8  SIGMA=    3.0  PHAS=    189.9  FOM=   0.93
INDE   5   11    8  FOBS=    191.9  SIGMA=    4.7  PHAS=    318.3  FOM=   0.68
INDE   5   11    9  FOBS=     81.8  SIGMA=   10.8  PHAS=    261.5  FOM=   0.14
INDE   5   11   10  FOBS=    239.2  SIGMA=    3.5  PHAS=    111.0  FOM=   0.93
INDE   5   11   11  FOBS=     72.0  SIGMA=   12.2  PHAS=    328.6  FOM=   0.11
INDE   5   11   12  FOBS=    107.5  SIGMA=    7.7  PHAS=    297.1  FOM=   0.10
INDE   5   11   13  FOBS=    123.1  SIGMA=    6.8  PHAS=    117.1  FOM=   0.04
INDE   5   11   14  FOBS=     58.3  SIGMA=   15.4  PHAS=     80.8  FOM=   0.01
INDE   5   12    0  FOBS=    104.0  SIGMA=    3.6  PHAS=    314.5  FOM=   0.39
INDE   5   12    1  FOBS=    110.8  SIGMA=    3.7  PHAS=     92.2  FOM=   0.46
INDE   5   12    2  FOBS=    173.7  SIGMA=    2.5  PHAS=    315.7  FOM=   0.93
INDE   5   12    3  FOBS=    153.7  SIGMA=    3.1  PHAS=    254.5  FOM=   0.11
INDE   5   12    4  FOBS=    142.7  SIGMA=    4.0  PHAS=    340.8  FOM=   0.38
INDE   5   12    5  FOBS=    127.6  SIGMA=    5.2  PHAS=    274.9  FOM=   0.53
INDE   5   12    6  FOBS=    152.6  SIGMA=    4.5  PHAS=    281.0  FOM=   0.14
INDE   5   12    7  FOBS=    508.5  SIGMA=    1.8  PHAS=    247.2  FOM=   0.99
INDE   5   12    8  FOBS=    126.4  SIGMA=    6.6  PHAS=    273.8  FOM=   0.52
INDE   5   12    9  FOBS=    131.8  SIGMA=    6.9  PHAS=     77.3  FOM=   0.16
INDE   5   12   10  FOBS=     59.5  SIGMA=   14.0  PHAS=    165.6  FOM=   0.07
INDE   5   12   11  FOBS=     70.2  SIGMA=   11.6  PHAS=    289.7  FOM=   0.12
INDE   5   12   12  FOBS=     45.1  SIGMA=   18.9  PHAS=    104.4  FOM=   0.15
INDE   5   12   13  FOBS=     43.0  SIGMA=   16.5  PHAS=    223.0  FOM=   0.06
INDE   5   12   14  FOBS=     82.8  SIGMA=   45.6  PHAS=      7.3  FOM=   0.06
INDE   5   13    0  FOBS=    252.3  SIGMA=    1.6  PHAS=    112.5  FOM=   0.92
INDE   5   13    1  FOBS=    212.9  SIGMA=    1.9  PHAS=    282.4  FOM=   0.89
INDE   5   13    2  FOBS=    170.9  SIGMA=    2.5  PHAS=    122.0  FOM=   0.86
INDE   5   13    3  FOBS=    444.0  SIGMA=    1.3  PHAS=     93.1  FOM=   0.99
INDE   5   13    4  FOBS=    279.4  SIGMA=    2.2  PHAS=    258.7  FOM=   0.97
INDE   5   13    5  FOBS=     91.4  SIGMA=    6.6  PHAS=    136.2  FOM=   0.31
INDE   5   13    6  FOBS=    450.3  SIGMA=    1.6  PHAS=     88.1  FOM=   0.90
INDE   5   13    7  FOBS=    129.0  SIGMA=    5.3  PHAS=    196.6  FOM=   0.62
INDE   5   13    8  FOBS=    363.2  SIGMA=    2.2  PHAS=    253.5  FOM=   0.66
INDE   5   13    9  FOBS=     50.7  SIGMA=   26.7  PHAS=    347.4  FOM=   0.12
INDE   5   13   10  FOBS=    163.7  SIGMA=    5.1  PHAS=    222.1  FOM=   0.47
INDE   5   13   11  FOBS=    120.4  SIGMA=    6.8  PHAS=      9.9  FOM=   0.18
INDE   5   13   12  FOBS=    162.4  SIGMA=    5.1  PHAS=    300.4  FOM=   0.05
INDE   5   13   13  FOBS=     65.6  SIGMA=   29.7  PHAS=    172.2  FOM=   0.05
INDE   5   14    0  FOBS=    213.4  SIGMA=    1.9  PHAS=     43.4  FOM=   0.97
INDE   5   14    1  FOBS=    379.4  SIGMA=    1.5  PHAS=    119.4  FOM=   1.00
INDE   5   14    2  FOBS=    258.2  SIGMA=    1.9  PHAS=     77.6  FOM=   0.84
INDE   5   14    3  FOBS=    229.5  SIGMA=    2.4  PHAS=    247.0  FOM=   0.94
INDE   5   14    4  FOBS=    421.4  SIGMA=    1.6  PHAS=    167.2  FOM=   0.95
INDE   5   14    5  FOBS=    372.6  SIGMA=    1.7  PHAS=     53.1  FOM=   0.91
INDE   5   14    6  FOBS=    317.7  SIGMA=    2.1  PHAS=     99.7  FOM=   0.21
INDE   5   14    7  FOBS=    169.7  SIGMA=    4.2  PHAS=     49.3  FOM=   0.77
INDE   5   14    8  FOBS=    150.7  SIGMA=    5.1  PHAS=    269.2  FOM=   0.43
INDE   5   14    9  FOBS=    173.3  SIGMA=    4.7  PHAS=     64.7  FOM=   0.22
INDE   5   14   10  FOBS=     97.1  SIGMA=    8.8  PHAS=     61.5  FOM=   0.02
INDE   5   14   11  FOBS=    181.2  SIGMA=    4.6  PHAS=    356.6  FOM=   0.29
INDE   5   14   12  FOBS=     42.5  SIGMA=   19.8  PHAS=    167.9  FOM=   0.26
INDE   5   14   13  FOBS=     57.3  SIGMA=   18.6  PHAS=    276.7  FOM=   0.03
```

Fig. 10A-113

| | | | | | | | | | |
|---|---|---|---|---|---|---|---|---|---|
| INDE | 5 | 15 | 0 | FOBS= | 198.0 | SIGMA= | 2.0 | PHAS= | 222.1 | FOM= | 0.75 |
| INDE | 5 | 15 | 1 | FOBS= | 182.8 | SIGMA= | 2.3 | PHAS= | 24.0 | FOM= | 0.81 |
| INDE | 5 | 15 | 2 | FOBS= | 495.6 | SIGMA= | 1.3 | PHAS= | 273.9 | FOM= | 0.98 |
| INDE | 5 | 15 | 3 | FOBS= | 688.8 | SIGMA= | 1.5 | PHAS= | 80.2 | FOM= | 0.99 |
| INDE | 5 | 15 | 4 | FOBS= | 254.1 | SIGMA= | 2.2 | PHAS= | 186.6 | FOM= | 0.91 |
| INDE | 5 | 15 | 5 | FOBS= | 228.4 | SIGMA= | 2.5 | PHAS= | 116.4 | FOM= | 0.94 |
| INDE | 5 | 15 | 6 | FOBS= | 166.1 | SIGMA= | 3.8 | PHAS= | 350.8 | FOM= | 0.71 |
| INDE | 5 | 15 | 7 | FOBS= | 197.4 | SIGMA= | 3.6 | PHAS= | 351.0 | FOM= | 0.85 |
| INDE | 5 | 15 | 8 | FOBS= | 183.6 | SIGMA= | 4.2 | PHAS= | 175.0 | FOM= | 0.89 |
| INDE | 5 | 15 | 9 | FOBS= | 67.7 | SIGMA= | 11.0 | PHAS= | 9.8 | FOM= | 0.19 |
| INDE | 5 | 15 | 10 | FOBS= | 149.3 | SIGMA= | 6.6 | PHAS= | 27.3 | FOM= | 0.07 |
| INDE | 5 | 15 | 11 | FOBS= | 74.5 | SIGMA= | 11.7 | PHAS= | 207.3 | FOM= | 0.05 |
| INDE | 5 | 15 | 12 | FOBS= | 59.8 | SIGMA= | 14.5 | PHAS= | 292.0 | FOM= | 0.03 |
| INDE | 5 | 15 | 13 | FOBS= | 48.7 | SIGMA= | 22.4 | PHAS= | 159.5 | FOM= | 0.04 |
| INDE | 5 | 16 | 0 | FOBS= | 72.0 | SIGMA= | 5.3 | PHAS= | 34.5 | FOM= | 0.77 |
| INDE | 5 | 16 | 1 | FOBS= | 283.1 | SIGMA= | 1.7 | PHAS= | 271.3 | FOM= | 0.96 |
| INDE | 5 | 16 | 2 | FOBS= | 281.0 | SIGMA= | 2.0 | PHAS= | 138.5 | FOM= | 0.94 |
| INDE | 5 | 16 | 3 | FOBS= | 448.5 | SIGMA= | 1.4 | PHAS= | 254.1 | FOM= | 0.95 |
| INDE | 5 | 16 | 4 | FOBS= | 421.8 | SIGMA= | 1.5 | PHAS= | 197.3 | FOM= | 0.98 |
| INDE | 5 | 16 | 5 | FOBS= | 83.3 | SIGMA= | 7.1 | PHAS= | 29.6 | FOM= | 0.51 |
| INDE | 5 | 16 | 6 | FOBS= | 165.8 | SIGMA= | 3.9 | PHAS= | 132.2 | FOM= | 0.04 |
| INDE | 5 | 16 | 7 | FOBS= | 252.8 | SIGMA= | 2.7 | PHAS= | 156.2 | FOM= | 0.55 |
| INDE | 5 | 16 | 8 | FOBS= | 244.8 | SIGMA= | 3.0 | PHAS= | 304.0 | FOM= | 0.50 |
| INDE | 5 | 16 | 9 | FOBS= | 84.2 | SIGMA= | 61.5 | PHAS= | 82.7 | FOM= | 0.07 |
| INDE | 5 | 16 | 10 | FOBS= | 86.1 | SIGMA= | 9.6 | PHAS= | 35.8 | FOM= | 0.14 |
| INDE | 5 | 16 | 11 | FOBS= | 79.8 | SIGMA= | 10.4 | PHAS= | 272.6 | FOM= | 0.26 |
| INDE | 5 | 16 | 13 | FOBS= | 102.6 | SIGMA= | 66.1 | PHAS= | 34.0 | FOM= | 0.06 |
| INDE | 5 | 17 | 0 | FOBS= | 223.4 | SIGMA= | 2.0 | PHAS= | 234.1 | FOM= | 0.99 |
| INDE | 5 | 17 | 1 | FOBS= | 286.0 | SIGMA= | 1.8 | PHAS= | 110.1 | FOM= | 1.00 |
| INDE | 5 | 17 | 2 | FOBS= | 220.8 | SIGMA= | 2.2 | PHAS= | 308.0 | FOM= | 0.46 |
| INDE | 5 | 17 | 3 | FOBS= | 303.5 | SIGMA= | 1.8 | PHAS= | 24.0 | FOM= | 0.98 |
| INDE | 5 | 17 | 4 | FOBS= | 104.6 | SIGMA= | 5.3 | PHAS= | 109.0 | FOM= | 0.32 |
| INDE | 5 | 17 | 5 | FOBS= | 104.1 | SIGMA= | 5.7 | PHAS= | 104.0 | FOM= | 0.23 |
| INDE | 5 | 17 | 6 | FOBS= | 151.1 | SIGMA= | 4.4 | PHAS= | 267.5 | FOM= | 0.18 |
| INDE | 5 | 17 | 7 | FOBS= | 267.6 | SIGMA= | 2.6 | PHAS= | 70.1 | FOM= | 0.44 |
| INDE | 5 | 17 | 8 | FOBS= | 102.9 | SIGMA= | 6.8 | PHAS= | 121.3 | FOM= | 0.23 |
| INDE | 5 | 17 | 9 | FOBS= | 102.5 | SIGMA= | 7.1 | PHAS= | 278.8 | FOM= | 0.19 |
| INDE | 5 | 17 | 10 | FOBS= | 51.1 | SIGMA= | 16.0 | PHAS= | 252.8 | FOM= | 0.17 |
| INDE | 5 | 17 | 11 | FOBS= | 105.9 | SIGMA= | 7.9 | PHAS= | 174.5 | FOM= | 0.14 |
| INDE | 5 | 17 | 12 | FOBS= | 48.4 | SIGMA= | 21.0 | PHAS= | 52.7 | FOM= | 0.11 |
| INDE | 5 | 18 | 0 | FOBS= | 261.4 | SIGMA= | 1.9 | PHAS= | 82.7 | FOM= | 0.97 |
| INDE | 5 | 18 | 1 | FOBS= | 383.0 | SIGMA= | 1.4 | PHAS= | 321.2 | FOM= | 0.93 |
| INDE | 5 | 18 | 2 | FOBS= | 57.5 | SIGMA= | 8.1 | PHAS= | 136.9 | FOM= | 0.07 |
| INDE | 5 | 18 | 3 | FOBS= | 347.6 | SIGMA= | 1.7 | PHAS= | 236.4 | FOM= | 0.63 |
| INDE | 5 | 18 | 4 | FOBS= | 335.2 | SIGMA= | 1.8 | PHAS= | 254.6 | FOM= | 0.90 |
| INDE | 5 | 18 | 5 | FOBS= | 345.2 | SIGMA= | 2.0 | PHAS= | 155.3 | FOM= | 0.91 |
| INDE | 5 | 18 | 6 | FOBS= | 68.7 | SIGMA= | 12.6 | PHAS= | 260.1 | FOM= | 0.36 |
| INDE | 5 | 18 | 8 | FOBS= | 123.8 | SIGMA= | 5.7 | PHAS= | 89.7 | FOM= | 0.31 |
| INDE | 5 | 18 | 9 | FOBS= | 186.8 | SIGMA= | 4.3 | PHAS= | 347.8 | FOM= | 0.74 |
| INDE | 5 | 18 | 10 | FOBS= | 58.4 | SIGMA= | 13.0 | PHAS= | 128.7 | FOM= | 0.20 |
| INDE | 5 | 18 | 11 | FOBS= | 66.4 | SIGMA= | 12.9 | PHAS= | 324.2 | FOM= | 0.05 |
| INDE | 5 | 18 | 12 | FOBS= | 87.9 | SIGMA= | 8.7 | PHAS= | 145.0 | FOM= | 0.01 |
| INDE | 5 | 19 | 0 | FOBS= | 168.7 | SIGMA= | 2.8 | PHAS= | 357.6 | FOM= | 0.61 |
| INDE | 5 | 19 | 1 | FOBS= | 68.6 | SIGMA= | 6.5 | PHAS= | 350.8 | FOM= | 0.42 |
| INDE | 5 | 19 | 2 | FOBS= | 351.8 | SIGMA= | 1.6 | PHAS= | 194.5 | FOM= | 1.00 |
| INDE | 5 | 19 | 3 | FOBS= | 99.4 | SIGMA= | 5.3 | PHAS= | 42.3 | FOM= | 0.35 |
| INDE | 5 | 19 | 4 | FOBS= | 254.9 | SIGMA= | 2.3 | PHAS= | 152.1 | FOM= | 0.62 |
| INDE | 5 | 19 | 5 | FOBS= | 302.8 | SIGMA= | 2.2 | PHAS= | 352.5 | FOM= | 0.73 |
| INDE | 5 | 19 | 6 | FOBS= | 115.0 | SIGMA= | 5.7 | PHAS= | 145.6 | FOM= | 0.08 |
| INDE | 5 | 19 | 7 | FOBS= | 89.4 | SIGMA= | 7.4 | PHAS= | 81.8 | FOM= | 0.19 |
| INDE | 5 | 19 | 8 | FOBS= | 85.8 | SIGMA= | 8.2 | PHAS= | 265.7 | FOM= | 0.17 |
| INDE | 5 | 19 | 9 | FOBS= | 83.1 | SIGMA= | 8.3 | PHAS= | 103.4 | FOM= | 0.02 |
| INDE | 5 | 19 | 10 | FOBS= | 75.0 | SIGMA= | 9.3 | PHAS= | 94.8 | FOM= | 0.08 |
| INDE | 5 | 19 | 11 | FOBS= | 104.9 | SIGMA= | 7.1 | PHAS= | 202.5 | FOM= | 0.02 |
| INDE | 5 | 19 | 12 | FOBS= | 76.1 | SIGMA= | 15.0 | PHAS= | 106.8 | FOM= | 0.06 |
| INDE | 5 | 20 | 0 | FOBS= | 227.3 | SIGMA= | 1.9 | PHAS= | 218.7 | FOM= | 0.44 |
| INDE | 5 | 20 | 1 | FOBS= | 347.0 | SIGMA= | 1.5 | PHAS= | 309.9 | FOM= | 0.52 |
| INDE | 5 | 20 | 2 | FOBS= | 394.0 | SIGMA= | 1.5 | PHAS= | 180.0 | FOM= | 0.97 |
| INDE | 5 | 20 | 3 | FOBS= | 270.6 | SIGMA= | 2.1 | PHAS= | 114.9 | FOM= | 0.94 |
| INDE | 5 | 20 | 4 | FOBS= | 146.9 | SIGMA= | 4.1 | PHAS= | 134.7 | FOM= | 0.22 |
| INDE | 5 | 20 | 5 | FOBS= | 119.8 | SIGMA= | 5.3 | PHAS= | 260.3 | FOM= | 0.28 |

Fig. 10A-114

```
INDE  5  20   6 FOBS=  260.6 SIGMA=   2.5 PHAS= 290.0 FOM= 0.88
INDE  5  20   7 FOBS=   80.0 SIGMA=   8.1 PHAS= 181.8 FOM= 0.17
INDE  5  20   8 FOBS=  135.2 SIGMA=   5.1 PHAS= 301.6 FOM= 0.06
INDE  5  20   9 FOBS=  190.7 SIGMA=   3.8 PHAS= 353.0 FOM= 0.77
INDE  5  20  10 FOBS=   46.6 SIGMA=  15.0 PHAS= 164.2 FOM= 0.52
INDE  5  20  11 FOBS=  167.0 SIGMA=   4.3 PHAS= 247.7 FOM= 0.11
INDE  5  21   0 FOBS=  367.0 SIGMA=   1.4 PHAS= 296.7 FOM= 0.96
INDE  5  21   1 FOBS=  163.6 SIGMA=   3.0 PHAS= 119.3 FOM= 0.86
INDE  5  21   2 FOBS=   61.8 SIGMA=   8.4 PHAS= 205.5 FOM= 0.22
INDE  5  21   3 FOBS=  259.4 SIGMA=   2.2 PHAS= 247.2 FOM= 0.33
INDE  5  21   4 FOBS=  187.1 SIGMA=   3.2 PHAS= 216.4 FOM= 0.38
INDE  5  21   5 FOBS=   68.2 SIGMA=   8.8 PHAS= 311.0 FOM= 0.11
INDE  5  21   6 FOBS=   94.3 SIGMA=   6.6 PHAS= 106.4 FOM= 0.15
INDE  5  21   7 FOBS=  150.3 SIGMA=   4.5 PHAS= 107.5 FOM= 0.17
INDE  5  21   8 FOBS=  138.9 SIGMA=   5.0 PHAS=  58.0 FOM= 0.55
INDE  5  21   9 FOBS=   39.9 SIGMA=  18.5 PHAS= 288.5 FOM= 0.04
INDE  5  21  10 FOBS=   56.6 SIGMA=  27.5 PHAS= 163.7 FOM= 0.08
INDE  5  21  11 FOBS=   64.2 SIGMA=  11.1 PHAS=   6.4 FOM= 0.03
INDE  5  22   0 FOBS=  190.0 SIGMA=   2.4 PHAS= 216.7 FOM= 0.94
INDE  5  22   1 FOBS=  397.6 SIGMA=   1.5 PHAS=  44.9 FOM= 1.00
INDE  5  22   2 FOBS=  471.6 SIGMA=   1.5 PHAS= 228.9 FOM= 0.98
INDE  5  22   3 FOBS=   50.7 SIGMA=  18.5 PHAS= 331.6 FOM= 0.30
INDE  5  22   4 FOBS=   92.6 SIGMA=   6.0 PHAS=  10.7 FOM= 0.52
INDE  5  22   5 FOBS=  205.4 SIGMA=   2.9 PHAS=  94.2 FOM= 0.61
INDE  5  22   6 FOBS=  180.8 SIGMA=   3.5 PHAS= 141.1 FOM= 0.79
INDE  5  22   7 FOBS=   61.2 SIGMA=  11.4 PHAS= 337.5 FOM= 0.06
INDE  5  22   8 FOBS=  160.5 SIGMA=   4.2 PHAS= 346.2 FOM= 0.18
INDE  5  22   9 FOBS=   67.3 SIGMA=   9.9 PHAS= 150.8 FOM= 0.39
INDE  5  22  10 FOBS=   61.5 SIGMA=  25.7 PHAS= 208.8 FOM= 0.08
INDE  5  23   0 FOBS=   87.6 SIGMA=   5.9 PHAS= 319.7 FOM= 0.22
INDE  5  23   1 FOBS=  181.2 SIGMA=   2.7 PHAS= 332.9 FOM= 0.79
INDE  5  23   2 FOBS=  103.6 SIGMA=   5.4 PHAS= 187.0 FOM= 0.77
INDE  5  23   3 FOBS=   62.2 SIGMA=   8.8 PHAS=  12.4 FOM= 0.38
INDE  5  23   4 FOBS=  113.0 SIGMA=   5.1 PHAS= 267.5 FOM= 0.01
INDE  5  23   5 FOBS=   90.2 SIGMA=   6.7 PHAS= 234.0 FOM= 0.55
INDE  5  23   6 FOBS=  119.3 SIGMA=   5.1 PHAS= 324.9 FOM= 0.16
INDE  5  23   7 FOBS=   36.5 SIGMA=  14.9 PHAS= 334.7 FOM= 0.19
INDE  5  23   8 FOBS=  108.5 SIGMA=   6.0 PHAS= 203.5 FOM= 0.43
INDE  5  23   9 FOBS=   46.8 SIGMA=  22.2 PHAS= 103.9 FOM= 0.08
INDE  5  23  10 FOBS=  111.8 SIGMA=   5.9 PHAS=   4.4 FOM= 0.06
INDE  5  24   0 FOBS=  155.4 SIGMA=   3.9 PHAS= 324.2 FOM= 0.95
INDE  5  24   1 FOBS=  108.3 SIGMA=   4.9 PHAS= 147.5 FOM= 0.89
INDE  5  24   2 FOBS=  222.5 SIGMA=   2.4 PHAS= 290.6 FOM= 0.63
INDE  5  24   3 FOBS=  301.2 SIGMA=   2.0 PHAS= 298.6 FOM= 0.89
INDE  5  24   4 FOBS=  104.1 SIGMA=   5.2 PHAS=  90.2 FOM= 0.33
INDE  5  24   5 FOBS=   47.0 SIGMA=  14.8 PHAS= 354.6 FOM= 0.27
INDE  5  24   6 FOBS=   69.4 SIGMA=   8.6 PHAS= 100.8 FOM= 0.27
INDE  5  24   7 FOBS=  102.6 SIGMA=   5.9 PHAS= 262.8 FOM= 0.48
INDE  5  24   8 FOBS=  112.5 SIGMA=   5.6 PHAS=  17.3 FOM= 0.11
INDE  5  24   9 FOBS=   77.2 SIGMA=   8.3 PHAS= 131.0 FOM= 0.01
INDE  5  25   0 FOBS=  165.2 SIGMA=   3.4 PHAS= 330.7 FOM= 0.82
INDE  5  25   1 FOBS=   48.4 SIGMA=  12.1 PHAS=  83.9 FOM= 0.35
INDE  5  25   2 FOBS=  119.8 SIGMA=   4.2 PHAS=  46.9 FOM= 0.48
INDE  5  25   3 FOBS=   83.2 SIGMA=   6.5 PHAS= 277.2 FOM= 0.10
INDE  5  25   4 FOBS=   63.1 SIGMA=   8.6 PHAS= 151.9 FOM= 0.24
INDE  5  25   5 FOBS=   46.4 SIGMA=  12.0 PHAS= 324.8 FOM= 0.18
INDE  5  25   6 FOBS=  105.8 SIGMA=   5.5 PHAS= 193.6 FOM= 0.31
INDE  5  25   7 FOBS=   45.7 SIGMA=  39.7 PHAS= 238.6 FOM= 0.13
INDE  5  25   8 FOBS=   56.9 SIGMA=  14.0 PHAS= 353.5 FOM= 0.01
INDE  5  25   9 FOBS=  185.9 SIGMA=   3.8 PHAS= 136.5 FOM= 0.52
INDE  5  26   0 FOBS=  189.4 SIGMA=   2.5 PHAS=  94.6 FOM= 0.92
INDE  5  26   1 FOBS=   82.1 SIGMA=   5.8 PHAS= 244.0 FOM= 0.47
INDE  5  26   2 FOBS=  112.2 SIGMA=   4.5 PHAS=  77.6 FOM= 0.28
INDE  5  26   3 FOBS=  127.3 SIGMA=   4.3 PHAS=  88.8 FOM= 0.48
INDE  5  26   4 FOBS=  216.1 SIGMA=   2.6 PHAS= 275.2 FOM= 0.79
INDE  5  26   5 FOBS=  105.2 SIGMA=   5.4 PHAS=  86.9 FOM= 0.61
INDE  5  26   6 FOBS=  131.5 SIGMA=   4.4 PHAS= 223.6 FOM= 0.29
INDE  5  26   7 FOBS=   55.2 SIGMA=  19.6 PHAS=  14.3 FOM= 0.05
INDE  5  26   8 FOBS=   46.6 SIGMA=  20.4 PHAS=  29.7 FOM= 0.13
INDE  5  27   0 FOBS=   71.9 SIGMA=   6.4 PHAS= 283.1 FOM= 0.61
INDE  5  27   1 FOBS=  175.9 SIGMA=   3.2 PHAS=   2.6 FOM= 0.66
```

Fig. 10A-115

```
INDE   5  27   2  FOBS=  209.1  SIGMA=   2.4  PHAS=  174.7  FOM=  0.58
INDE   5  27   3  FOBS=  120.0  SIGMA=   4.5  PHAS=  340.8  FOM=  0.47
INDE   5  27   4  FOBS=   59.9  SIGMA=  38.8  PHAS=  124.8  FOM=  0.14
INDE   5  27   5  FOBS=   45.8  SIGMA=  13.0  PHAS=  313.6  FOM=  0.17
INDE   5  27   6  FOBS=   59.3  SIGMA=   9.8  PHAS=  170.9  FOM=  0.07
INDE   5  27   7  FOBS=   83.0  SIGMA=   6.9  PHAS=  145.9  FOM=  0.05
INDE   5  28   0  FOBS=  103.3  SIGMA=   4.5  PHAS=  164.9  FOM=  0.78
INDE   5  28   1  FOBS=   66.3  SIGMA=   8.4  PHAS=  283.8  FOM=  0.04
INDE   5  28   2  FOBS=   53.4  SIGMA=   8.7  PHAS=  227.8  FOM=  0.10
INDE   5  28   3  FOBS=  244.9  SIGMA=   2.2  PHAS=   54.6  FOM=  0.87
INDE   5  28   4  FOBS=   56.4  SIGMA=   9.1  PHAS=  201.6  FOM=  0.23
INDE   5  28   5  FOBS=   86.9  SIGMA=   6.2  PHAS=  135.3  FOM=  0.23
INDE   5  28   6  FOBS=   72.3  SIGMA=   8.0  PHAS=  347.0  FOM=  0.28
INDE   5  28   7  FOBS=  163.4  SIGMA=  13.5  PHAS=  191.0  FOM=  0.01
INDE   5  29   0  FOBS=   77.1  SIGMA=   5.7  PHAS=  178.4  FOM=  0.22
INDE   5  29   1  FOBS=   49.3  SIGMA=  10.0  PHAS=  326.6  FOM=  0.10
INDE   5  29   2  FOBS=  155.7  SIGMA=   3.1  PHAS=   23.5  FOM=  0.71
INDE   5  29   3  FOBS=  122.2  SIGMA=   4.2  PHAS=  242.3  FOM=  0.41
INDE   5  29   4  FOBS=  171.4  SIGMA=   3.2  PHAS=  195.5  FOM=  0.36
INDE   5  29   5  FOBS=  133.9  SIGMA=   4.2  PHAS=  293.4  FOM=  0.66
INDE   5  29   6  FOBS=   53.2  SIGMA=  22.7  PHAS=  169.4  FOM=  0.11
INDE   5  30   0  FOBS=  125.9  SIGMA=   3.6  PHAS=  358.2  FOM=  0.16
INDE   5  30   1  FOBS=   83.9  SIGMA=   5.2  PHAS=  311.7  FOM=  0.46
INDE   5  30   2  FOBS=  117.7  SIGMA=   5.0  PHAS=  236.1  FOM=  0.74
INDE   5  30   3  FOBS=   58.2  SIGMA=   9.3  PHAS=   85.5  FOM=  0.11
INDE   5  30   4  FOBS=  114.3  SIGMA=   4.5  PHAS=  235.2  FOM=  0.68
INDE   5  31   0  FOBS=  109.0  SIGMA=   4.1  PHAS=   24.6  FOM=  0.53
INDE   5  31   1  FOBS=  263.2  SIGMA=   1.9  PHAS=  329.4  FOM=  0.85
INDE   5  31   2  FOBS=  148.8  SIGMA=   3.9  PHAS=  162.7  FOM=  0.42
INDE   5  31   3  FOBS=   89.0  SIGMA=   6.8  PHAS=   48.4  FOM=  0.28
INDE   5  32   0  FOBS=  151.1  SIGMA=   3.4  PHAS=   27.2  FOM=  0.80
INDE   6   0   0  FOBS=  485.0  SIGMA=   1.8  PHAS=    0.0  FOM=  0.96
INDE   6   0   1  FOBS=  130.1  SIGMA=   5.4  PHAS=    0.0  FOM=  0.59
INDE   6   0   2  FOBS=  234.7  SIGMA=   2.8  PHAS=  180.0  FOM=  0.24
INDE   6   0   3  FOBS=  209.0  SIGMA=   3.3  PHAS=    0.0  FOM=  1.00
INDE   6   0   4  FOBS=  243.0  SIGMA=   3.3  PHAS=  180.0  FOM=  0.97
INDE   6   0   5  FOBS=  168.5  SIGMA=   7.9  PHAS=    0.0  FOM=  0.07
INDE   6   0   6  FOBS=  428.4  SIGMA=   2.5  PHAS=    0.0  FOM=  0.73
INDE   6   0   7  FOBS=   49.5  SIGMA=  47.2  PHAS=  180.0  FOM=  0.31
INDE   6   0   8  FOBS=   62.5  SIGMA=  96.6  PHAS=    0.0  FOM=  0.01
INDE   6   0   9  FOBS=  106.6  SIGMA=  13.4  PHAS=    0.0  FOM=  0.03
INDE   6   0  10  FOBS=  378.5  SIGMA=   4.1  PHAS=    0.0  FOM=  0.77
INDE   6   0  11  FOBS=  117.0  SIGMA=  12.6  PHAS=    0.0  FOM=  0.02
INDE   6   0  12  FOBS=  106.7  SIGMA=  13.4  PHAS=  180.0  FOM=  0.00
INDE   6   0  13  FOBS=   61.6  SIGMA=  22.0  PHAS=  180.0  FOM=  0.02
INDE   6   0  14  FOBS=  124.9  SIGMA=  11.2  PHAS=    0.0  FOM=  0.07
INDE   6   1   0  FOBS=  216.6  SIGMA=   2.4  PHAS=  287.5  FOM=  1.00
INDE   6   1   1  FOBS=   97.0  SIGMA=   4.7  PHAS=   38.2  FOM=  0.91
INDE   6   1   2  FOBS=  166.6  SIGMA=   2.9  PHAS=  271.7  FOM=  0.37
INDE   6   1   3  FOBS=   62.4  SIGMA=   8.7  PHAS=  231.7  FOM=  0.16
INDE   6   1   4  FOBS=   78.0  SIGMA=   7.6  PHAS=  353.7  FOM=  0.15
INDE   6   1   5  FOBS=  134.1  SIGMA=   4.7  PHAS=  335.9  FOM=  0.53
INDE   6   1   6  FOBS=  291.5  SIGMA=   2.7  PHAS=  156.9  FOM=  0.79
INDE   6   1   7  FOBS=  219.0  SIGMA=   4.0  PHAS=  284.4  FOM=  0.13
INDE   6   1   8  FOBS=   70.1  SIGMA=  14.8  PHAS=  323.2  FOM=  0.09
INDE   6   1   9  FOBS=  100.1  SIGMA=   9.8  PHAS=  102.8  FOM=  0.10
INDE   6   1  10  FOBS=  210.4  SIGMA=   6.2  PHAS=  154.6  FOM=  0.01
INDE   6   1  11  FOBS=  172.9  SIGMA=   6.1  PHAS=  219.6  FOM=  0.03
INDE   6   1  12  FOBS=   63.6  SIGMA=  17.2  PHAS=   94.5  FOM=  0.14
INDE   6   1  13  FOBS=   48.4  SIGMA=  21.7  PHAS=  247.0  FOM=  0.06
INDE   6   1  14  FOBS=   51.4  SIGMA=  22.2  PHAS=  270.7  FOM=  0.01
INDE   6   2   0  FOBS=  520.6  SIGMA=   1.0  PHAS=  180.9  FOM=  0.98
INDE   6   2   1  FOBS=  257.2  SIGMA=   1.9  PHAS=   56.9  FOM=  0.96
INDE   6   2   2  FOBS=   73.4  SIGMA=   7.2  PHAS=  220.2  FOM=  0.78
INDE   6   2   3  FOBS=   55.2  SIGMA=   9.4  PHAS=  347.3  FOM=  0.39
INDE   6   2   4  FOBS=  157.4  SIGMA=   4.1  PHAS=   35.8  FOM=  0.12
INDE   6   2   5  FOBS=  192.4  SIGMA=   3.2  PHAS=  202.0  FOM=  0.89
INDE   6   2   6  FOBS=   89.1  SIGMA=   7.4  PHAS=   79.4  FOM=  0.13
INDE   6   2   7  FOBS=  108.2  SIGMA=   8.5  PHAS=   19.5  FOM=  0.43
INDE   6   2   8  FOBS=   62.7  SIGMA=  16.9  PHAS=  119.1  FOM=  0.19
INDE   6   2   9  FOBS=  369.0  SIGMA=   2.8  PHAS=  146.7  FOM=  0.86
```

Fig. 10A-116

```
INDE  6  2  10  FOBS=  259.0  SIGMA=   4.3  PHAS=  237.2  FOM=  0.69
INDE  6  2  11  FOBS=  123.4  SIGMA=   8.2  PHAS=  173.6  FOM=  0.13
INDE  6  2  12  FOBS=   89.3  SIGMA=  12.2  PHAS=  244.1  FOM=  0.05
INDE  6  2  13  FOBS=   64.4  SIGMA=  15.8  PHAS=  239.2  FOM=  0.05
INDE  6  2  14  FOBS=  129.0  SIGMA=  85.1  PHAS=   15.5  FOM=  0.03
INDE  6  3   0  FOBS=  229.1  SIGMA=   1.7  PHAS=  200.3  FOM=  0.95
INDE  6  3   1  FOBS=  144.6  SIGMA=   3.0  PHAS=   87.7  FOM=  0.83
INDE  6  3   2  FOBS=  141.5  SIGMA=   3.7  PHAS=  293.3  FOM=  0.86
INDE  6  3   3  FOBS=  214.7  SIGMA=   2.4  PHAS=   44.9  FOM=  0.16
INDE  6  3   4  FOBS=   58.7  SIGMA=   9.0  PHAS=  113.3  FOM=  0.46
INDE  6  3   5  FOBS=  284.4  SIGMA=   2.1  PHAS=  239.1  FOM=  0.91
INDE  6  3   6  FOBS=  217.7  SIGMA=   3.0  PHAS=  313.0  FOM=  0.71
INDE  6  3   7  FOBS=  379.4  SIGMA=   2.1  PHAS=   18.1  FOM=  0.93
INDE  6  3   8  FOBS=  169.2  SIGMA=   5.5  PHAS=  281.3  FOM=  0.23
INDE  6  3   9  FOBS=  108.1  SIGMA=  10.8  PHAS=  297.4  FOM=  0.03
INDE  6  3  10  FOBS=   97.5  SIGMA=  15.0  PHAS=   52.9  FOM=  0.17
INDE  6  3  11  FOBS=  133.1  SIGMA=   7.6  PHAS=  187.3  FOM=  0.21
INDE  6  3  12  FOBS=   83.5  SIGMA=  12.2  PHAS=   51.5  FOM=  0.12
INDE  6  3  13  FOBS=   96.6  SIGMA=  11.2  PHAS=  304.0  FOM=  0.07
INDE  6  3  14  FOBS=   65.3  SIGMA=  40.5  PHAS=  174.3  FOM=  0.02
INDE  6  4   0  FOBS=   69.5  SIGMA=   5.7  PHAS=   80.8  FOM=  0.26
INDE  6  4   1  FOBS=  208.2  SIGMA=   2.0  PHAS=  298.7  FOM=  0.91
INDE  6  4   2  FOBS=  223.7  SIGMA=   2.3  PHAS=   83.3  FOM=  0.94
INDE  6  4   3  FOBS=   51.5  SIGMA=  10.9  PHAS=  153.8  FOM=  0.48
INDE  6  4   4  FOBS=   75.6  SIGMA=   7.3  PHAS=   29.8  FOM=  0.29
INDE  6  4   5  FOBS=  278.9  SIGMA=   2.4  PHAS=   51.8  FOM=  0.82
INDE  6  4   6  FOBS=   62.2  SIGMA=  10.5  PHAS=  146.1  FOM=  0.21
INDE  6  4   7  FOBS=  273.0  SIGMA=   2.8  PHAS=  260.6  FOM=  0.76
INDE  6  4   8  FOBS=  258.7  SIGMA=   3.1  PHAS=  166.9  FOM=  0.53
INDE  6  4   9  FOBS=  116.7  SIGMA=   8.6  PHAS=   43.3  FOM=  0.11
INDE  6  4  10  FOBS=  260.9  SIGMA=   4.6  PHAS=  167.0  FOM=  0.67
INDE  6  4  11  FOBS=  116.0  SIGMA=   9.9  PHAS=   60.9  FOM=  0.07
INDE  6  4  12  FOBS=   80.0  SIGMA=  14.1  PHAS=  347.8  FOM=  0.13
INDE  6  4  13  FOBS=  102.9  SIGMA=   9.6  PHAS=  168.5  FOM=  0.39
INDE  6  4  14  FOBS=   66.7  SIGMA=  18.2  PHAS=   43.5  FOM=  0.03
INDE  6  5   0  FOBS=   54.8  SIGMA=   6.7  PHAS=  296.9  FOM=  0.31
INDE  6  5   1  FOBS=  289.9  SIGMA=   1.8  PHAS=   42.5  FOM=  0.94
INDE  6  5   2  FOBS=  222.1  SIGMA=   2.1  PHAS=  213.2  FOM=  0.97
INDE  6  5   3  FOBS=  205.2  SIGMA=   2.8  PHAS=  354.8  FOM=  0.94
INDE  6  5   4  FOBS=   64.7  SIGMA=   8.8  PHAS=  146.3  FOM=  0.12
INDE  6  5   5  FOBS=  199.6  SIGMA=   2.9  PHAS=  162.9  FOM=  0.46
INDE  6  5   6  FOBS=   57.6  SIGMA=  12.1  PHAS=  234.1  FOM=  0.06
INDE  6  5   7  FOBS=  259.6  SIGMA=   2.9  PHAS=  163.9  FOM=  0.88
INDE  6  5   8  FOBS=   69.4  SIGMA=  13.1  PHAS=  333.5  FOM=  0.09
INDE  6  5   9  FOBS=  170.8  SIGMA=   5.6  PHAS=  248.5  FOM=  0.31
INDE  6  5  10  FOBS=  299.7  SIGMA=   3.2  PHAS=  246.7  FOM=  0.83
INDE  6  5  11  FOBS=  114.1  SIGMA=  10.5  PHAS=  273.5  FOM=  0.19
INDE  6  5  12  FOBS=  100.3  SIGMA=  82.4  PHAS=  161.8  FOM=  0.11
INDE  6  5  13  FOBS=  118.0  SIGMA=   9.2  PHAS=  122.1  FOM=  0.10
INDE  6  5  14  FOBS=  128.5  SIGMA=   8.0  PHAS=   32.8  FOM=  0.04
INDE  6  6   0  FOBS=  197.2  SIGMA=   2.2  PHAS=  131.9  FOM=  0.99
INDE  6  6   1  FOBS=  223.4  SIGMA=   1.9  PHAS=  208.2  FOM=  0.61
INDE  6  6   2  FOBS=  228.0  SIGMA=   2.1  PHAS=   44.3  FOM=  0.95
INDE  6  6   3  FOBS=  200.1  SIGMA=   2.5  PHAS=  224.1  FOM=  0.93
INDE  6  6   4  FOBS=   82.3  SIGMA=   7.1  PHAS=   82.4  FOM=  0.47
INDE  6  6   5  FOBS=  101.7  SIGMA=   6.0  PHAS=  167.2  FOM=  0.08
INDE  6  6   6  FOBS=  213.6  SIGMA=   3.4  PHAS=   94.8  FOM=  0.78
INDE  6  6   7  FOBS=  344.3  SIGMA=   2.4  PHAS=  297.2  FOM=  0.93
INDE  6  6   8  FOBS=  281.7  SIGMA=   2.5  PHAS=  119.8  FOM=  0.86
INDE  6  6   9  FOBS=  360.6  SIGMA=   2.9  PHAS=   49.9  FOM=  0.91
INDE  6  6  10  FOBS=   77.0  SIGMA=  13.6  PHAS=  346.1  FOM=  0.01
INDE  6  6  11  FOBS=  145.1  SIGMA=   7.4  PHAS=  310.4  FOM=  0.16
INDE  6  6  12  FOBS=  116.1  SIGMA=   8.1  PHAS=   60.7  FOM=  0.21
INDE  6  6  13  FOBS=   77.0  SIGMA=  13.2  PHAS=  215.2  FOM=  0.27
INDE  6  6  14  FOBS=   64.5  SIGMA=  19.2  PHAS=  353.7  FOM=  0.03
INDE  6  7   0  FOBS=  197.1  SIGMA=   2.0  PHAS=   30.6  FOM=  0.69
INDE  6  7   1  FOBS=  258.5  SIGMA=   1.7  PHAS=   77.0  FOM=  0.76
INDE  6  7   2  FOBS=  158.2  SIGMA=   3.0  PHAS=  138.0  FOM=  0.89
INDE  6  7   3  FOBS=  201.3  SIGMA=   2.5  PHAS=  284.8  FOM=  0.98
INDE  6  7   4  FOBS=  133.9  SIGMA=   4.3  PHAS=  234.3  FOM=  0.78
INDE  6  7   5  FOBS=  257.4  SIGMA=   2.6  PHAS=  124.5  FOM=  0.42
```

Fig. 10A-117

```
INDE    6   7    6 FOBS=   508.2 SIGMA=   1.8 PHAS=  309.0 FOM= 0.97
INDE    6   7    7 FOBS=   265.4 SIGMA=   2.7 PHAS=  120.3 FOM= 0.88
INDE    6   7    8 FOBS=    84.9 SIGMA=   9.0 PHAS=   20.1 FOM= 0.14
INDE    6   7    9 FOBS=   142.5 SIGMA=   6.5 PHAS=  300.1 FOM= 0.11
INDE    6   7   10 FOBS=   111.9 SIGMA=   9.0 PHAS=  106.9 FOM= 0.05
INDE    6   7   11 FOBS=    48.7 SIGMA=  19.2 PHAS=  327.1 FOM= 0.07
INDE    6   7   12 FOBS=    77.5 SIGMA=  12.2 PHAS=  155.1 FOM= 0.07
INDE    6   8    0 FOBS=   131.7 SIGMA=   2.9 PHAS=   57.3 FOM= 0.83
INDE    6   8    1 FOBS=   117.1 SIGMA=   3.8 PHAS=   49.7 FOM= 0.74
INDE    6   8    2 FOBS=   254.3 SIGMA=   1.9 PHAS=  299.0 FOM= 0.65
INDE    6   8    3 FOBS=   205.2 SIGMA=   2.5 PHAS=    2.7 FOM= 0.82
INDE    6   8    4 FOBS=   149.8 SIGMA=   3.8 PHAS=  187.3 FOM= 0.87
INDE    6   8    5 FOBS=   124.6 SIGMA=   4.7 PHAS=  150.4 FOM= 0.70
INDE    6   8    6 FOBS=   229.3 SIGMA=   3.3 PHAS=   42.2 FOM= 0.95
INDE    6   8    7 FOBS=   364.6 SIGMA=   2.8 PHAS=  159.3 FOM= 0.85
INDE    6   8    8 FOBS=   285.6 SIGMA=   2.9 PHAS=  229.5 FOM= 0.84
INDE    6   8    9 FOBS=   119.9 SIGMA=   8.5 PHAS=  105.4 FOM= 0.23
INDE    6   8   10 FOBS=   185.1 SIGMA=   5.4 PHAS=  186.6 FOM= 0.28
INDE    6   8   11 FOBS=    61.6 SIGMA=  17.7 PHAS=  280.9 FOM= 0.09
INDE    6   8   12 FOBS=    75.2 SIGMA=  11.7 PHAS=  103.4 FOM= 0.06
INDE    6   8   13 FOBS=    96.1 SIGMA=   9.3 PHAS=  329.8 FOM= 0.02
INDE    6   8   14 FOBS=    51.4 SIGMA=  23.2 PHAS=   24.2 FOM= 0.01
INDE    6   9    0 FOBS=   245.5 SIGMA=   1.7 PHAS=  143.9 FOM= 0.73
INDE    6   9    1 FOBS=   145.0 SIGMA=   3.0 PHAS=  269.7 FOM= 0.90
INDE    6   9    2 FOBS=   271.8 SIGMA=   1.8 PHAS=  135.7 FOM= 0.98
INDE    6   9    3 FOBS=   192.0 SIGMA=   2.7 PHAS=  288.9 FOM= 0.34
INDE    6   9    4 FOBS=    62.6 SIGMA=   8.3 PHAS=  255.1 FOM= 0.02
INDE    6   9    5 FOBS=   273.1 SIGMA=   2.3 PHAS=  179.3 FOM= 0.35
INDE    6   9    6 FOBS=   245.9 SIGMA=   2.8 PHAS=   99.5 FOM= 0.61
INDE    6   9    7 FOBS=    92.6 SIGMA=   8.3 PHAS=  289.8 FOM= 0.08
INDE    6   9    8 FOBS=   157.4 SIGMA=   6.3 PHAS=  310.9 FOM= 0.04
INDE    6   9    9 FOBS=    84.5 SIGMA=  11.2 PHAS=  115.8 FOM= 0.16
INDE    6   9   10 FOBS=    49.8 SIGMA=  29.1 PHAS=  255.7 FOM= 0.04
INDE    6   9   11 FOBS=   117.6 SIGMA=   7.4 PHAS=  321.6 FOM= 0.16
INDE    6   9   12 FOBS=   123.9 SIGMA=   7.0 PHAS=  145.3 FOM= 0.14
INDE    6   9   13 FOBS=    94.1 SIGMA=   9.1 PHAS=  178.7 FOM= 0.02
INDE    6   9   14 FOBS=    99.2 SIGMA=  31.1 PHAS=  313.6 FOM= 0.05
INDE    6  10    0 FOBS=   110.1 SIGMA=   3.9 PHAS=  341.9 FOM= 0.86
INDE    6  10    1 FOBS=   223.9 SIGMA=   2.0 PHAS=  164.3 FOM= 0.95
INDE    6  10    2 FOBS=   139.6 SIGMA=   3.5 PHAS=  338.4 FOM= 0.68
INDE    6  10    3 FOBS=    35.8 SIGMA=  14.7 PHAS=  352.6 FOM= 0.26
INDE    6  10    4 FOBS=   176.6 SIGMA=   3.0 PHAS=  270.1 FOM= 0.81
INDE    6  10    5 FOBS=   237.2 SIGMA=   2.6 PHAS=  187.1 FOM= 0.85
INDE    6  10    6 FOBS=   101.2 SIGMA=   6.5 PHAS=  338.1 FOM= 0.41
INDE    6  10    7 FOBS=   160.6 SIGMA=   5.4 PHAS=  176.6 FOM= 0.36
INDE    6  10    8 FOBS=   221.5 SIGMA=   5.0 PHAS=  147.5 FOM= 0.74
INDE    6  10    9 FOBS=   144.6 SIGMA=   5.9 PHAS=   42.3 FOM= 0.08
INDE    6  10   10 FOBS=    80.4 SIGMA=  10.7 PHAS=  253.1 FOM= 0.24
INDE    6  10   11 FOBS=    86.0 SIGMA=  10.0 PHAS=   68.9 FOM= 0.09
INDE    6  10   12 FOBS=   125.3 SIGMA=   6.8 PHAS=  112.0 FOM= 0.17
INDE    6  10   13 FOBS=    73.4 SIGMA=  12.8 PHAS=  283.7 FOM= 0.09
INDE    6  11    0 FOBS=   143.1 SIGMA=   2.9 PHAS=   31.7 FOM= 0.58
INDE    6  11    1 FOBS=    93.6 SIGMA=   4.7 PHAS=  145.5 FOM= 0.56
INDE    6  11    2 FOBS=   235.1 SIGMA=   2.1 PHAS=  108.3 FOM= 0.62
INDE    6  11    3 FOBS=    45.8 SIGMA=  15.6 PHAS=  295.4 FOM= 0.18
INDE    6  11    4 FOBS=   202.7 SIGMA=   2.9 PHAS=  123.4 FOM= 0.93
INDE    6  11    5 FOBS=   126.7 SIGMA=   4.7 PHAS=  154.9 FOM= 0.46
INDE    6  11    6 FOBS=   258.0 SIGMA=   2.7 PHAS=  330.1 FOM= 0.33
INDE    6  11    7 FOBS=    65.3 SIGMA=  15.0 PHAS=  154.5 FOM= 0.10
INDE    6  11    8 FOBS=   198.2 SIGMA=   4.6 PHAS=  319.5 FOM= 0.64
INDE    6  11    9 FOBS=    42.5 SIGMA=  19.6 PHAS=  260.7 FOM= 0.01
INDE    6  11   10 FOBS=    59.5 SIGMA=  14.2 PHAS=  238.8 FOM= 0.06
INDE    6  11   11 FOBS=   158.5 SIGMA=   5.4 PHAS=  141.5 FOM= 0.20
INDE    6  11   12 FOBS=   106.4 SIGMA=   7.7 PHAS=  297.1 FOM= 0.11
INDE    6  11   13 FOBS=    96.8 SIGMA=   8.9 PHAS=  168.6 FOM= 0.07
INDE    6  12    0 FOBS=    86.0 SIGMA=   5.1 PHAS=   38.3 FOM= 0.57
INDE    6  12    1 FOBS=   124.6 SIGMA=   3.8 PHAS=  153.3 FOM= 0.62
INDE    6  12    2 FOBS=    62.1 SIGMA=   7.1 PHAS=  336.0 FOM= 0.36
INDE    6  12    3 FOBS=   194.7 SIGMA=   2.6 PHAS=   19.1 FOM= 0.71
INDE    6  12    4 FOBS=   127.8 SIGMA=   4.4 PHAS=  258.3 FOM= 0.55
INDE    6  12    5 FOBS=    81.5 SIGMA=   7.7 PHAS=  326.8 FOM= 0.66
```

Fig. 10A-118

```
INDE   6  12   6  FOBS=   136.5  SIGMA=    5.6  PHAS=  342.0  FOM=  0.36
INDE   6  12   7  FOBS=   150.3  SIGMA=    5.2  PHAS=  307.5  FOM=  0.08
INDE   6  12   8  FOBS=   208.2  SIGMA=    4.0  PHAS=  327.2  FOM=  0.58
INDE   6  12   9  FOBS=   210.9  SIGMA=    4.9  PHAS=  175.3  FOM=  0.57
INDE   6  12  10  FOBS=    54.4  SIGMA=   26.2  PHAS=  276.3  FOM=  0.05
INDE   6  12  11  FOBS=   127.8  SIGMA=    6.5  PHAS=  124.0  FOM=  0.29
INDE   6  12  12  FOBS=    42.7  SIGMA=   19.8  PHAS=  292.1  FOM=  0.38
INDE   6  12  13  FOBS=    45.4  SIGMA=   24.9  PHAS=  155.3  FOM=  0.04
INDE   6  13   0  FOBS=   200.1  SIGMA=    2.1  PHAS=  348.0  FOM=  0.96
INDE   6  13   1  FOBS=   128.8  SIGMA=    3.9  PHAS=  249.4  FOM=  0.94
INDE   6  13   2  FOBS=   280.4  SIGMA=    1.9  PHAS=   11.0  FOM=  0.87
INDE   6  13   3  FOBS=    43.6  SIGMA=   23.3  PHAS=   18.8  FOM=  0.22
INDE   6  13   4  FOBS=    78.2  SIGMA=    7.4  PHAS=  244.6  FOM=  0.39
INDE   6  13   5  FOBS=   186.1  SIGMA=    3.6  PHAS=  132.9  FOM=  0.63
INDE   6  13   6  FOBS=   350.7  SIGMA=    2.2  PHAS=  248.5  FOM=  0.76
INDE   6  13   7  FOBS=   157.2  SIGMA=    4.8  PHAS=  180.9  FOM=  0.46
INDE   6  13   8  FOBS=   155.4  SIGMA=    5.2  PHAS=  272.2  FOM=  0.65
INDE   6  13   9  FOBS=   131.7  SIGMA=    6.8  PHAS=  101.9  FOM=  0.20
INDE   6  13  10  FOBS=   149.7  SIGMA=    6.1  PHAS=   29.8  FOM=  0.20
INDE   6  13  11  FOBS=    83.0  SIGMA=   10.2  PHAS=  308.7  FOM=  0.05
INDE   6  13  12  FOBS=    49.4  SIGMA=   26.4  PHAS=  213.0  FOM=  0.02
INDE   6  13  13  FOBS=    49.1  SIGMA=   22.2  PHAS=   50.4  FOM=  0.05
INDE   6  14   0  FOBS=    63.4  SIGMA=    5.8  PHAS=   77.2  FOM=  0.57
INDE   6  14   1  FOBS=   178.3  SIGMA=    2.5  PHAS=  189.0  FOM=  0.26
INDE   6  14   2  FOBS=    85.2  SIGMA=    5.4  PHAS=  270.2  FOM=  0.47
INDE   6  14   3  FOBS=   439.3  SIGMA=    1.4  PHAS=  225.3  FOM=  0.95
INDE   6  14   4  FOBS=   159.6  SIGMA=    4.3  PHAS=   59.4  FOM=  0.69
INDE   6  14   5  FOBS=   305.8  SIGMA=    2.4  PHAS=  307.3  FOM=  0.10
INDE   6  14   6  FOBS=   200.5  SIGMA=    3.5  PHAS=  134.3  FOM=  0.56
INDE   6  14   7  FOBS=   371.3  SIGMA=    2.2  PHAS=   75.3  FOM=  0.78
INDE   6  14   8  FOBS=   223.8  SIGMA=    3.5  PHAS=  314.1  FOM=  0.12
INDE   6  14   9  FOBS=   173.1  SIGMA=    4.6  PHAS=  311.3  FOM=  0.18
INDE   6  14  10  FOBS=   108.8  SIGMA=    8.4  PHAS=  295.5  FOM=  0.15
INDE   6  14  11  FOBS=    63.6  SIGMA=   13.5  PHAS=  166.7  FOM=  0.06
INDE   6  14  12  FOBS=    68.6  SIGMA=   12.4  PHAS=   10.2  FOM=  0.07
INDE   6  14  13  FOBS=    84.0  SIGMA=   44.9  PHAS=  220.5  FOM=  0.04
INDE   6  15   0  FOBS=   240.0  SIGMA=    1.9  PHAS=   91.5  FOM=  0.99
INDE   6  15   1  FOBS=   221.2  SIGMA=    2.1  PHAS=  192.7  FOM=  0.78
INDE   6  15   2  FOBS=   174.5  SIGMA=    2.8  PHAS=  131.1  FOM=  0.77
INDE   6  15   3  FOBS=    83.3  SIGMA=    6.9  PHAS=  351.2  FOM=  0.53
INDE   6  15   4  FOBS=   288.0  SIGMA=    2.3  PHAS=  101.4  FOM=  0.81
INDE   6  15   5  FOBS=   172.4  SIGMA=    3.8  PHAS=  129.2  FOM=  0.49
INDE   6  15   6  FOBS=   147.6  SIGMA=    4.8  PHAS=  247.2  FOM=  0.68
INDE   6  15   7  FOBS=   107.0  SIGMA=    7.0  PHAS=  152.9  FOM=  0.06
INDE   6  15   8  FOBS=   161.3  SIGMA=    4.9  PHAS=   67.0  FOM=  0.35
INDE   6  15   9  FOBS=    66.4  SIGMA=   16.4  PHAS=  224.3  FOM=  0.17
INDE   6  15  10  FOBS=   183.1  SIGMA=    5.0  PHAS=  205.1  FOM=  0.14
INDE   6  15  11  FOBS=    76.3  SIGMA=   10.6  PHAS=   29.9  FOM=  0.19
INDE   6  15  12  FOBS=   157.5  SIGMA=    5.8  PHAS=  282.7  FOM=  0.42
INDE   6  16   0  FOBS=   576.5  SIGMA=    1.5  PHAS=  157.0  FOM=  0.90
INDE   6  16   1  FOBS=   497.1  SIGMA=    1.2  PHAS=  156.7  FOM=  0.66
INDE   6  16   2  FOBS=   410.0  SIGMA=    1.5  PHAS=  149.4  FOM=  0.11
INDE   6  16   3  FOBS=   341.6  SIGMA=    1.9  PHAS=  301.9  FOM=  0.21
INDE   6  16   4  FOBS=    69.9  SIGMA=    8.7  PHAS=   65.6  FOM=  0.13
INDE   6  16   5  FOBS=   278.2  SIGMA=    2.3  PHAS=  313.2  FOM=  0.94
INDE   6  16   6  FOBS=   161.7  SIGMA=    4.4  PHAS=  320.0  FOM=  0.28
INDE   6  16   8  FOBS=   154.4  SIGMA=    5.0  PHAS=  310.7  FOM=  0.75
INDE   6  16   9  FOBS=   108.0  SIGMA=    7.0  PHAS=  105.2  FOM=  0.27
INDE   6  16  10  FOBS=   109.3  SIGMA=    7.1  PHAS=  339.6  FOM=  0.29
INDE   6  16  11  FOBS=    31.7  SIGMA=   21.5  PHAS=  250.6  FOM=  0.44
INDE   6  16  12  FOBS=    53.6  SIGMA=   17.0  PHAS=  156.4  FOM=  0.05
INDE   6  17   0  FOBS=   230.5  SIGMA=    2.0  PHAS=  191.6  FOM=  0.92
INDE   6  17   1  FOBS=   129.2  SIGMA=    3.9  PHAS=  259.3  FOM=  0.07
INDE   6  17   2  FOBS=   119.6  SIGMA=    4.8  PHAS=   90.0  FOM=  0.61
INDE   6  17   3  FOBS=    94.7  SIGMA=    6.0  PHAS=   35.5  FOM=  0.18
INDE   6  17   4  FOBS=   254.2  SIGMA=    2.3  PHAS=   57.2  FOM=  0.94
INDE   6  17   5  FOBS=    78.8  SIGMA=    8.2  PHAS=  132.4  FOM=  0.30
INDE   6  17   6  FOBS=   314.4  SIGMA=    2.3  PHAS=   97.2  FOM=  0.95
INDE   6  17   7  FOBS=    93.3  SIGMA=    7.7  PHAS=  164.8  FOM=  0.50
INDE   6  17   8  FOBS=   134.6  SIGMA=    5.5  PHAS=  129.3  FOM=  0.18
INDE   6  17   9  FOBS=   111.4  SIGMA=    6.7  PHAS=  359.6  FOM=  0.30
```

Fig. 10A-119

```
INDE  6  17  10  FOBS=   59.8  SIGMA=  12.8  PHAS= 225.3  FOM= 0.17
INDE  6  17  11  FOBS=  144.6  SIGMA=   5.8  PHAS= 161.9  FOM= 0.03
INDE  6  17  12  FOBS=  108.9  SIGMA=   7.0  PHAS= 240.7  FOM= 0.02
INDE  6  18   0  FOBS=   72.5  SIGMA=   6.1  PHAS= 181.9  FOM= 0.41
INDE  6  18   1  FOBS=  118.4  SIGMA=   4.7  PHAS= 118.8  FOM= 0.72
INDE  6  18   2  FOBS=   82.3  SIGMA=   6.9  PHAS= 341.9  FOM= 0.08
INDE  6  18   3  FOBS=  158.6  SIGMA=   3.6  PHAS= 157.5  FOM= 0.21
INDE  6  18   4  FOBS=  274.9  SIGMA=   2.2  PHAS= 313.4  FOM= 0.96
INDE  6  18   5  FOBS=  292.3  SIGMA=   2.3  PHAS=  76.6  FOM= 0.93
INDE  6  18   6  FOBS=  183.6  SIGMA=   3.8  PHAS=  45.2  FOM= 0.04
INDE  6  18   7  FOBS=   97.1  SIGMA=   7.1  PHAS= 152.9  FOM= 0.24
INDE  6  18   8  FOBS=   47.1  SIGMA=  17.8  PHAS=   9.3  FOM= 0.15
INDE  6  18   9  FOBS=   68.5  SIGMA=  10.4  PHAS=  97.1  FOM= 0.14
INDE  6  18  10  FOBS=   98.5  SIGMA=   7.5  PHAS= 253.1  FOM= 0.39
INDE  6  18  11  FOBS=   75.6  SIGMA=  11.2  PHAS= 134.5  FOM= 0.02
INDE  6  19   0  FOBS=  253.1  SIGMA=   2.0  PHAS=  25.6  FOM= 0.74
INDE  6  19   1  FOBS=  144.2  SIGMA=   3.9  PHAS=  70.0  FOM= 0.86
INDE  6  19   2  FOBS=  306.3  SIGMA=   1.9  PHAS= 168.5  FOM= 0.86
INDE  6  19   3  FOBS=  300.5  SIGMA=   2.0  PHAS= 290.5  FOM= 0.91
INDE  6  19   4  FOBS=   96.4  SIGMA=   6.6  PHAS=  53.3  FOM= 0.28
INDE  6  19   5  FOBS=  269.2  SIGMA=   2.5  PHAS= 321.2  FOM= 0.64
INDE  6  19   6  FOBS=   58.8  SIGMA=  12.4  PHAS= 106.0  FOM= 0.08
INDE  6  19   7  FOBS=  206.9  SIGMA=   3.3  PHAS= 241.5  FOM= 0.45
INDE  6  19   8  FOBS=   51.0  SIGMA=  25.7  PHAS=  33.7  FOM= 0.05
INDE  6  19   9  FOBS=   39.8  SIGMA=  18.6  PHAS=  26.0  FOM= 0.09
INDE  6  19  10  FOBS=   63.4  SIGMA=  11.7  PHAS= 214.7  FOM= 0.12
INDE  6  19  11  FOBS=   88.9  SIGMA=   8.0  PHAS= 338.7  FOM= 0.18
INDE  6  20   0  FOBS=  105.2  SIGMA=   5.0  PHAS= 354.7  FOM= 0.40
INDE  6  20   1  FOBS=  243.5  SIGMA=   2.1  PHAS= 108.0  FOM= 0.87
INDE  6  20   2  FOBS=  326.0  SIGMA=   1.8  PHAS= 239.8  FOM= 0.99
INDE  6  20   3  FOBS=  309.8  SIGMA=   2.0  PHAS=  38.9  FOM= 0.94
INDE  6  20   4  FOBS=  331.9  SIGMA=   2.0  PHAS= 148.0  FOM= 0.20
INDE  6  20   5  FOBS=  139.3  SIGMA=   4.7  PHAS= 261.5  FOM= 0.17
INDE  6  20   6  FOBS=  125.5  SIGMA=   5.3  PHAS= 164.5  FOM= 0.06
INDE  6  20   7  FOBS=  103.0  SIGMA=   6.6  PHAS=  83.3  FOM= 0.03
INDE  6  20   8  FOBS=   81.8  SIGMA=   8.2  PHAS= 342.5  FOM= 0.13
INDE  6  20   9  FOBS=  130.9  SIGMA=   5.4  PHAS= 211.0  FOM= 0.48
INDE  6  20  10  FOBS=  147.7  SIGMA=   4.8  PHAS=  44.2  FOM= 0.16
INDE  6  21   0  FOBS=  308.6  SIGMA=   1.8  PHAS= 142.8  FOM= 0.81
INDE  6  21   1  FOBS=  335.4  SIGMA=   1.8  PHAS= 173.0  FOM= 1.00
INDE  6  21   2  FOBS=  255.7  SIGMA=   2.2  PHAS=  48.3  FOM= 0.74
INDE  6  21   3  FOBS=  260.8  SIGMA=   2.3  PHAS= 315.4  FOM= 0.59
INDE  6  21   4  FOBS=  116.2  SIGMA=   5.3  PHAS= 187.8  FOM= 0.35
INDE  6  21   5  FOBS=   37.0  SIGMA=  16.6  PHAS= 298.5  FOM= 0.19
INDE  6  21   6  FOBS=  228.9  SIGMA=   2.9  PHAS=  35.3  FOM= 0.79
INDE  6  21   7  FOBS=   87.7  SIGMA=   7.5  PHAS= 247.4  FOM= 0.16
INDE  6  21   8  FOBS=   63.2  SIGMA=  13.6  PHAS= 295.1  FOM= 0.09
INDE  6  21   9  FOBS=  142.7  SIGMA=   4.7  PHAS=  77.8  FOM= 0.93
INDE  6  21  10  FOBS=   76.6  SIGMA=   8.8  PHAS= 232.3  FOM= 0.10
INDE  6  22   0  FOBS=  340.3  SIGMA=   1.7  PHAS= 102.8  FOM= 0.64
INDE  6  22   1  FOBS=  120.1  SIGMA=   4.4  PHAS= 197.6  FOM= 0.16
INDE  6  22   2  FOBS=  117.1  SIGMA=   4.7  PHAS=  65.0  FOM= 0.18
INDE  6  22   3  FOBS=  237.4  SIGMA=   2.4  PHAS= 302.7  FOM= 0.93
INDE  6  22   4  FOBS=  114.5  SIGMA=   5.3  PHAS= 348.0  FOM= 0.19
INDE  6  22   5  FOBS=  200.5  SIGMA=   3.2  PHAS= 355.1  FOM= 0.84
INDE  6  22   6  FOBS=   98.1  SIGMA=   6.5  PHAS= 195.4  FOM= 0.01
INDE  6  22   7  FOBS=   52.0  SIGMA=  13.4  PHAS= 163.5  FOM= 0.01
INDE  6  22   8  FOBS=   62.2  SIGMA=  11.5  PHAS=  20.9  FOM= 0.25
INDE  6  22   9  FOBS=   40.1  SIGMA=  17.0  PHAS= 199.5  FOM= 0.06
INDE  6  22  10  FOBS=   44.0  SIGMA=  19.4  PHAS= 198.7  FOM= 0.02
INDE  6  23   0  FOBS=  135.8  SIGMA=   3.6  PHAS= 302.4  FOM= 0.95
INDE  6  23   1  FOBS=  113.7  SIGMA=   4.7  PHAS= 157.5  FOM= 0.71
INDE  6  23   2  FOBS=   95.1  SIGMA=   5.6  PHAS= 305.6  FOM= 0.11
INDE  6  23   3  FOBS=  164.7  SIGMA=   3.4  PHAS= 165.9  FOM= 0.28
INDE  6  23   4  FOBS=   66.7  SIGMA=   8.6  PHAS= 295.9  FOM= 0.15
INDE  6  23   5  FOBS=  156.3  SIGMA=   4.1  PHAS=  70.4  FOM= 0.18
INDE  6  23   6  FOBS=  163.7  SIGMA=   4.0  PHAS= 274.5  FOM= 0.42
INDE  6  23   7  FOBS=  166.9  SIGMA=   4.0  PHAS=  92.5  FOM= 0.54
INDE  6  23   8  FOBS=   98.2  SIGMA=   6.5  PHAS=  67.2  FOM= 0.14
INDE  6  23   9  FOBS=  107.7  SIGMA=   6.2  PHAS= 160.5  FOM= 0.28
INDE  6  24   0  FOBS=  203.9  SIGMA=   2.3  PHAS= 192.6  FOM= 0.30
```

Fig. 10A-120

```
INDE   6  24   1 FOBS=  125.2 SIGMA=   4.3 PHAS=  256.1 FOM=  0.63
INDE   6  24   2 FOBS=  323.4 SIGMA=   1.9 PHAS=   84.4 FOM=  0.88
INDE   6  24   3 FOBS=   96.2 SIGMA=   5.7 PHAS=  109.4 FOM=  0.11
INDE   6  24   4 FOBS=  103.7 SIGMA=   5.5 PHAS=  321.7 FOM=  0.27
INDE   6  24   5 FOBS=  128.3 SIGMA=   4.7 PHAS=  198.4 FOM=  0.24
INDE   6  24   6 FOBS=  193.5 SIGMA=   3.2 PHAS=  173.7 FOM=  0.06
INDE   6  24   7 FOBS=   36.8 SIGMA=  16.5 PHAS=   13.3 FOM=  0.38
INDE   6  24   8 FOBS=   62.5 SIGMA=  10.6 PHAS=  227.3 FOM=  0.10
INDE   6  24   9 FOBS=   54.7 SIGMA=  14.3 PHAS=  128.5 FOM=  0.08
INDE   6  25   0 FOBS=  123.1 SIGMA=   4.1 PHAS=  108.7 FOM=  0.83
INDE   6  25   1 FOBS=  169.7 SIGMA=   3.2 PHAS=  137.9 FOM=  0.83
INDE   6  25   2 FOBS=  191.0 SIGMA=   2.9 PHAS=  343.5 FOM=  0.77
INDE   6  25   3 FOBS=   93.5 SIGMA=   5.8 PHAS=   48.6 FOM=  0.05
INDE   6  25   4 FOBS=   70.3 SIGMA=   8.8 PHAS=  275.1 FOM=  0.36
INDE   6  25   5 FOBS=   68.7 SIGMA=   8.9 PHAS=  129.2 FOM=  0.26
INDE   6  25   6 FOBS=  142.7 SIGMA=   4.3 PHAS=   36.2 FOM=  0.69
INDE   6  25   7 FOBS=  100.2 SIGMA=   6.1 PHAS=  261.6 FOM=  0.02
INDE   6  25   8 FOBS=   93.9 SIGMA=   6.6 PHAS=  139.8 FOM=  0.15
INDE   6  26   0 FOBS=  234.0 SIGMA=   2.4 PHAS=  157.0 FOM=  0.69
INDE   6  26   1 FOBS=  126.8 SIGMA=   4.0 PHAS=  104.1 FOM=  0.07
INDE   6  26   2 FOBS=  192.4 SIGMA=   2.8 PHAS=  276.6 FOM=  0.92
INDE   6  26   3 FOBS=  157.5 SIGMA=   3.6 PHAS=  126.5 FOM=  0.58
INDE   6  26   4 FOBS=   51.5 SIGMA=  25.5 PHAS=  159.0 FOM=  0.15
INDE   6  26   5 FOBS=   40.2 SIGMA=  20.9 PHAS=  358.6 FOM=  0.26
INDE   6  26   6 FOBS=   86.3 SIGMA=   6.7 PHAS=  243.2 FOM=  0.16
INDE   6  26   7 FOBS=   89.5 SIGMA=   6.6 PHAS=  173.6 FOM=  0.12
INDE   6  27   0 FOBS=  147.0 SIGMA=   3.9 PHAS=   51.3 FOM=  0.60
INDE   6  27   1 FOBS=   75.4 SIGMA=   6.5 PHAS=   27.9 FOM=  0.56
INDE   6  27   2 FOBS=  102.3 SIGMA=   5.0 PHAS=  153.4 FOM=  0.05
INDE   6  27   3 FOBS=  224.9 SIGMA=   2.5 PHAS=  138.1 FOM=  0.96
INDE   6  27   4 FOBS=  104.5 SIGMA=   5.6 PHAS=  300.8 FOM=  0.81
INDE   6  27   5 FOBS=   47.5 SIGMA=  22.5 PHAS=  165.4 FOM=  0.20
INDE   6  27   6 FOBS=   60.0 SIGMA=   9.7 PHAS=   98.6 FOM=  0.04
INDE   6  27   7 FOBS=   73.1 SIGMA=  40.4 PHAS=  311.8 FOM=  0.06
INDE   6  28   0 FOBS=  193.6 SIGMA=   2.9 PHAS=  285.9 FOM=  0.88
INDE   6  28   1 FOBS=   72.0 SIGMA=   6.7 PHAS=  163.2 FOM=  0.48
INDE   6  28   2 FOBS=  105.0 SIGMA=   4.7 PHAS=   54.9 FOM=  0.19
INDE   6  28   3 FOBS=  189.2 SIGMA=   2.9 PHAS=  333.7 FOM=  0.88
INDE   6  28   4 FOBS=  113.0 SIGMA=   4.8 PHAS=  168.9 FOM=  0.17
INDE   6  28   5 FOBS=   54.8 SIGMA=  10.2 PHAS=  105.5 FOM=  0.14
INDE   6  28   6 FOBS=   79.5 SIGMA=   8.9 PHAS=  287.7 FOM=  0.08
INDE   6  29   0 FOBS=   83.6 SIGMA=   5.4 PHAS=  252.1 FOM=  0.78
INDE   6  29   1 FOBS=   85.7 SIGMA=   5.9 PHAS=  114.2 FOM=  0.96
INDE   6  29   2 FOBS=  116.3 SIGMA=   4.4 PHAS=  356.9 FOM=  0.83
INDE   6  29   3 FOBS=  123.0 SIGMA=   4.3 PHAS=  248.2 FOM=  0.28
INDE   6  29   4 FOBS=  204.8 SIGMA=   2.8 PHAS=  137.8 FOM=  0.59
INDE   6  29   5 FOBS=  180.1 SIGMA=   4.8 PHAS=  347.5 FOM=  0.61
INDE   6  30   0 FOBS=  305.2 SIGMA=   1.7 PHAS=  115.9 FOM=  0.97
INDE   6  30   1 FOBS=   66.0 SIGMA=   8.4 PHAS=  316.9 FOM=  0.14
INDE   6  30   2 FOBS=  145.4 SIGMA=   3.4 PHAS=   82.6 FOM=  0.25
INDE   6  30   3 FOBS=   40.2 SIGMA=  23.8 PHAS=  135.7 FOM=  0.10
INDE   6  31   0 FOBS=  203.8 SIGMA=   2.3 PHAS=   17.1 FOM=  0.89
INDE   6  31   1 FOBS=   54.1 SIGMA=  11.5 PHAS=  181.5 FOM=  0.07
INDE   6  31   2 FOBS=  105.4 SIGMA=  23.7 PHAS=  312.8 FOM=  0.05
INDE   7   0   0 FOBS=  310.2 SIGMA=   2.5 PHAS=  180.0 FOM=  0.74
INDE   7   0   1 FOBS=  366.7 SIGMA=   2.7 PHAS=  180.0 FOM=  1.00
INDE   7   0   2 FOBS=  204.3 SIGMA=   4.0 PHAS=    0.0 FOM=  1.00
INDE   7   0   3 FOBS=   86.2 SIGMA=  10.3 PHAS=    0.0 FOM=  0.13
INDE   7   0   4 FOBS=   46.9 SIGMA=  16.3 PHAS=  180.0 FOM=  0.27
INDE   7   0   5 FOBS=  273.9 SIGMA=   3.4 PHAS=    0.0 FOM=  0.00
INDE   7   0   6 FOBS=  304.3 SIGMA=   4.4 PHAS=  180.0 FOM=  0.75
INDE   7   0   7 FOBS=  131.1 SIGMA=  15.3 PHAS=  180.0 FOM=  0.06
INDE   7   0   8 FOBS=  116.3 SIGMA=  12.4 PHAS=  180.0 FOM=  0.03
INDE   7   0  10 FOBS=  171.2 SIGMA=   9.0 PHAS=    0.0 FOM=  0.21
INDE   7   0  11 FOBS=   43.3 SIGMA=  27.6 PHAS=  180.0 FOM=  0.12
INDE   7   0  12 FOBS=  182.1 SIGMA=   8.1 PHAS=  180.0 FOM=  0.15
INDE   7   0  13 FOBS=   52.7 SIGMA=  36.2 PHAS=    0.0 FOM=  0.07
INDE   7   0  14 FOBS=   47.7 SIGMA=  30.9 PHAS=  180.0 FOM=  0.05
INDE   7   1   0 FOBS=  391.7 SIGMA=   1.4 PHAS=  309.5 FOM=  0.97
INDE   7   1   1 FOBS=  165.5 SIGMA=   3.5 PHAS=   36.2 FOM=  0.43
INDE   7   1   2 FOBS=   41.7 SIGMA=  14.3 PHAS=  343.3 FOM=  0.36
```

Fig. 10A-121

```
INDE   7  1   3 FOBS=    213.7 SIGMA=   2.6 PHAS=    282.1 FOM=  0.95
INDE   7  1   4 FOBS=     90.7 SIGMA=   6.1 PHAS=    255.5 FOM=  0.10
INDE   7  1   5 FOBS=    141.4 SIGMA=   5.4 PHAS=    256.9 FOM=  0.25
INDE   7  1   6 FOBS=    273.3 SIGMA=   3.1 PHAS=     76.3 FOM=  0.94
INDE   7  1   7 FOBS=    311.4 SIGMA=   2.8 PHAS=    326.8 FOM=  0.90
INDE   7  1   8 FOBS=    228.8 SIGMA=   4.8 PHAS=    331.6 FOM=  0.04
INDE   7  1   9 FOBS=    139.4 SIGMA=   8.3 PHAS=     67.4 FOM=  0.08
INDE   7  1  10 FOBS=    214.4 SIGMA=   5.3 PHAS=    281.4 FOM=  0.31
INDE   7  1  11 FOBS=    172.4 SIGMA=   6.1 PHAS=    142.4 FOM=  0.18
INDE   7  1  12 FOBS=     49.4 SIGMA=  21.0 PHAS=    347.1 FOM=  0.11
INDE   7  1  13 FOBS=     89.3 SIGMA=  11.2 PHAS=    101.4 FOM=  0.02
INDE   7  1  14 FOBS=     79.4 SIGMA=  13.4 PHAS=    151.6 FOM=  0.02
INDE   7  2   0 FOBS=    354.0 SIGMA=   1.5 PHAS=     78.3 FOM=  0.91
INDE   7  2   1 FOBS=    109.9 SIGMA=   4.1 PHAS=    235.0 FOM=  0.31
INDE   7  2   2 FOBS=    216.3 SIGMA=   2.6 PHAS=    356.1 FOM=  0.59
INDE   7  2   3 FOBS=    208.5 SIGMA=   2.7 PHAS=    208.0 FOM=  0.84
INDE   7  2   4 FOBS=     47.0 SIGMA=  23.2 PHAS=     47.4 FOM=  0.05
INDE   7  2   5 FOBS=     37.7 SIGMA=  16.1 PHAS=     95.5 FOM=  0.18
INDE   7  2   6 FOBS=    284.1 SIGMA=   2.6 PHAS=    338.6 FOM=  0.95
INDE   7  2   7 FOBS=    108.6 SIGMA=   8.0 PHAS=    149.9 FOM=  0.02
INDE   7  2   8 FOBS=    169.1 SIGMA=   5.6 PHAS=     95.0 FOM=  0.57
INDE   7  2   9 FOBS=     81.5 SIGMA=  16.7 PHAS=    220.9 FOM=  0.08
INDE   7  2  10 FOBS=    188.2 SIGMA=   6.7 PHAS=    329.7 FOM=  0.02
INDE   7  2  11 FOBS=    282.6 SIGMA=   3.6 PHAS=     14.0 FOM=  0.67
INDE   7  2  12 FOBS=     57.2 SIGMA=  18.4 PHAS=    144.6 FOM=  0.12
INDE   7  2  13 FOBS=     98.2 SIGMA=  10.0 PHAS=    331.0 FOM=  0.01
INDE   7  2  14 FOBS=     93.0 SIGMA=  58.7 PHAS=    297.2 FOM=  0.03
INDE   7  3   0 FOBS=    177.7 SIGMA=   2.3 PHAS=     20.9 FOM=  0.53
INDE   7  3   1 FOBS=    168.2 SIGMA=   3.0 PHAS=    152.4 FOM=  0.83
INDE   7  3   2 FOBS=     53.9 SIGMA=   8.9 PHAS=      2.8 FOM=  0.23
INDE   7  3   3 FOBS=    106.6 SIGMA=   5.5 PHAS=    273.1 FOM=  0.60
INDE   7  3   4 FOBS=    332.4 SIGMA=   2.0 PHAS=     61.9 FOM=  0.81
INDE   7  3   5 FOBS=    168.1 SIGMA=   4.0 PHAS=    212.1 FOM=  0.52
INDE   7  3   6 FOBS=    300.9 SIGMA=   2.4 PHAS=    188.7 FOM=  0.45
INDE   7  3   7 FOBS=    352.5 SIGMA=   2.6 PHAS=    109.5 FOM=  0.74
INDE   7  3   8 FOBS=    129.4 SIGMA=   6.9 PHAS=     30.8 FOM=  0.19
INDE   7  3   9 FOBS=    190.4 SIGMA=   5.9 PHAS=    150.7 FOM=  0.33
INDE   7  3  10 FOBS=    124.9 SIGMA=  10.1 PHAS=      3.0 FOM=  0.21
INDE   7  3  11 FOBS=     81.9 SIGMA=  16.1 PHAS=    155.4 FOM=  0.14
INDE   7  3  12 FOBS=     54.2 SIGMA=  18.8 PHAS=     27.3 FOM=  0.04
INDE   7  3  13 FOBS=     65.5 SIGMA=  18.6 PHAS=    280.9 FOM=  0.04
INDE   7  3  14 FOBS=     87.3 SIGMA=  43.6 PHAS=    132.3 FOM=  0.03
INDE   7  4   0 FOBS=     54.1 SIGMA=   8.5 PHAS=     53.3 FOM=  0.26
INDE   7  4   1 FOBS=     63.4 SIGMA=   6.7 PHAS=    343.0 FOM=  0.09
INDE   7  4   2 FOBS=    203.0 SIGMA=   2.5 PHAS=    112.8 FOM=  0.94
INDE   7  4   3 FOBS=     37.5 SIGMA=  20.4 PHAS=    359.8 FOM=  0.24
INDE   7  4   4 FOBS=    166.2 SIGMA=   4.0 PHAS=    223.2 FOM=  0.59
INDE   7  4   5 FOBS=     45.2 SIGMA=  15.9 PHAS=     94.6 FOM=  0.19
INDE   7  4   6 FOBS=    221.6 SIGMA=   3.3 PHAS=    279.7 FOM=  0.93
INDE   7  4   7 FOBS=    178.5 SIGMA=   4.5 PHAS=    330.3 FOM=  0.56
INDE   7  4   8 FOBS=     63.5 SIGMA=  15.0 PHAS=     33.4 FOM=  0.16
INDE   7  4   9 FOBS=     71.2 SIGMA=  31.9 PHAS=    299.0 FOM=  0.10
INDE   7  4  10 FOBS=     51.9 SIGMA=  24.7 PHAS=    179.6 FOM=  0.13
INDE   7  4  11 FOBS=     66.0 SIGMA=  24.8 PHAS=     20.0 FOM=  0.16
INDE   7  4  12 FOBS=     51.5 SIGMA=  19.0 PHAS=    227.5 FOM=  0.04
INDE   7  4  13 FOBS=    110.8 SIGMA=  11.1 PHAS=     37.6 FOM=  0.03
INDE   7  4  14 FOBS=    118.0 SIGMA=  74.6 PHAS=    142.9 FOM=  0.01
INDE   7  5   0 FOBS=     86.6 SIGMA=   4.8 PHAS=     95.8 FOM=  0.46
INDE   7  5   1 FOBS=    222.5 SIGMA=   2.1 PHAS=    254.2 FOM=  0.64
INDE   7  5   2 FOBS=    141.3 SIGMA=   4.2 PHAS=    285.5 FOM=  0.72
INDE   7  5   3 FOBS=    132.1 SIGMA=   4.3 PHAS=    247.6 FOM=  0.54
INDE   7  5   4 FOBS=     99.4 SIGMA=   6.0 PHAS=     44.6 FOM=  0.43
INDE   7  5   5 FOBS=     39.3 SIGMA=  20.1 PHAS=    278.3 FOM=  0.30
INDE   7  5   6 FOBS=    389.2 SIGMA=   2.7 PHAS=    346.5 FOM=  0.67
INDE   7  5   7 FOBS=    152.2 SIGMA=   5.2 PHAS=    162.3 FOM=  0.52
INDE   7  5   8 FOBS=     79.6 SIGMA=  12.5 PHAS=    286.6 FOM=  0.26
INDE   7  5   9 FOBS=    114.9 SIGMA=   8.5 PHAS=    190.2 FOM=  0.06
INDE   7  5  10 FOBS=    133.2 SIGMA=   7.1 PHAS=    215.1 FOM=  0.10
INDE   7  5  11 FOBS=     65.5 SIGMA=  24.3 PHAS=      1.7 FOM=  0.07
INDE   7  5  12 FOBS=     75.6 SIGMA=  14.3 PHAS=    156.0 FOM=  0.02
INDE   7  5  13 FOBS=    129.6 SIGMA=   8.3 PHAS=    314.4 FOM=  0.05
```

Fig. 10A-122

```
INDE   7   6    0 FOBS=   125.3 SIGMA=   3.5 PHAS=  323.9 FOM= 0.44
INDE   7   6    1 FOBS=   126.9 SIGMA=   4.5 PHAS=  334.2 FOM= 0.85
INDE   7   6    2 FOBS=    72.7 SIGMA=   6.7 PHAS=  258.4 FOM= 0.15
INDE   7   6    3 FOBS=   149.4 SIGMA=   3.7 PHAS=  215.9 FOM= 0.94
INDE   7   6    4 FOBS=   152.8 SIGMA=   3.7 PHAS=  108.8 FOM= 0.94
INDE   7   6    5 FOBS=   190.5 SIGMA=   4.1 PHAS=  170.8 FOM= 0.39
INDE   7   6    6 FOBS=   100.7 SIGMA=   8.7 PHAS=  347.0 FOM= 0.67
INDE   7   6    7 FOBS=   269.5 SIGMA=   3.0 PHAS=  189.0 FOM= 0.90
INDE   7   6    8 FOBS=   176.3 SIGMA=   5.2 PHAS=  325.7 FOM= 0.62
INDE   7   6    9 FOBS=    63.7 SIGMA=  23.0 PHAS=  129.2 FOM= 0.03
INDE   7   6   10 FOBS=   146.1 SIGMA=   6.3 PHAS=  282.2 FOM= 0.36
INDE   7   6   11 FOBS=    89.8 SIGMA=  10.8 PHAS=  334.9 FOM= 0.24
INDE   7   6   12 FOBS=    73.9 SIGMA=  14.3 PHAS=  225.9 FOM= 0.09
INDE   7   6   13 FOBS=   103.3 SIGMA=   8.9 PHAS=  208.8 FOM= 0.06
INDE   7   7    0 FOBS=   193.4 SIGMA=   2.7 PHAS=   17.0 FOM= 0.97
INDE   7   7    1 FOBS=    56.3 SIGMA=   8.2 PHAS=  157.4 FOM= 0.18
INDE   7   7    2 FOBS=    93.7 SIGMA=   5.5 PHAS=  308.7 FOM= 0.27
INDE   7   7    3 FOBS=   118.8 SIGMA=   4.6 PHAS=  308.0 FOM= 0.07
INDE   7   7    4 FOBS=   395.5 SIGMA=   1.7 PHAS=  327.6 FOM= 0.55
INDE   7   7    5 FOBS=   241.8 SIGMA=   2.6 PHAS=  136.4 FOM= 0.54
INDE   7   7    6 FOBS=    99.0 SIGMA=   8.0 PHAS=   80.8 FOM= 0.12
INDE   7   7    7 FOBS=   160.4 SIGMA=   6.0 PHAS=  302.8 FOM= 0.35
INDE   7   7    8 FOBS=   134.2 SIGMA=   6.5 PHAS=  287.2 FOM= 0.12
INDE   7   7    9 FOBS=   217.2 SIGMA=   4.3 PHAS=  119.7 FOM= 0.82
INDE   7   7   10 FOBS=   169.6 SIGMA=   5.6 PHAS=  289.3 FOM= 0.28
INDE   7   7   11 FOBS=   105.0 SIGMA=   9.6 PHAS=   49.5 FOM= 0.17
INDE   7   7   12 FOBS=   117.8 SIGMA=   7.7 PHAS=  114.3 FOM= 0.28
INDE   7   7   13 FOBS=    69.0 SIGMA=  38.3 PHAS=  327.0 FOM= 0.06
INDE   7   8    0 FOBS=   174.3 SIGMA=   2.5 PHAS=  206.5 FOM= 0.80
INDE   7   8    1 FOBS=   148.3 SIGMA=   3.4 PHAS=  225.5 FOM= 0.91
INDE   7   8    2 FOBS=    71.0 SIGMA=   6.9 PHAS=    7.9 FOM= 0.60
INDE   7   8    3 FOBS=   139.9 SIGMA=   3.9 PHAS=  184.1 FOM= 0.78
INDE   7   8    4 FOBS=   278.8 SIGMA=   2.2 PHAS=   66.7 FOM= 0.92
INDE   7   8    5 FOBS=   151.1 SIGMA=   4.4 PHAS=  225.9 FOM= 0.01
INDE   7   8    6 FOBS=   241.0 SIGMA=   3.0 PHAS=  109.2 FOM= 0.27
INDE   7   8    7 FOBS=   105.5 SIGMA=   8.8 PHAS=  265.0 FOM= 0.11
INDE   7   8    8 FOBS=   140.3 SIGMA=   6.8 PHAS=  126.5 FOM= 0.38
INDE   7   8    9 FOBS=   131.5 SIGMA=   6.8 PHAS=  315.3 FOM= 0.09
INDE   7   8   10 FOBS=   150.4 SIGMA=   6.6 PHAS=   30.9 FOM= 0.36
INDE   7   8   11 FOBS=    47.5 SIGMA=  26.0 PHAS=  121.1 FOM= 0.13
INDE   7   8   12 FOBS=    76.2 SIGMA=  11.6 PHAS=  253.8 FOM= 0.12
INDE   7   8   13 FOBS=    52.9 SIGMA=  19.9 PHAS=  356.9 FOM= 0.03
INDE   7   9    0 FOBS=   176.4 SIGMA=   2.6 PHAS=   43.6 FOM= 0.84
INDE   7   9    1 FOBS=   138.0 SIGMA=   3.5 PHAS=   50.6 FOM= 0.88
INDE   7   9    2 FOBS=   227.3 SIGMA=   2.3 PHAS=    0.5 FOM= 0.97
INDE   7   9    3 FOBS=   233.4 SIGMA=   2.4 PHAS=  154.0 FOM= 0.90
INDE   7   9    4 FOBS=   185.8 SIGMA=   3.2 PHAS=  189.7 FOM= 0.80
INDE   7   9    5 FOBS=   174.8 SIGMA=   4.0 PHAS=   45.1 FOM= 0.87
INDE   7   9    6 FOBS=   207.2 SIGMA=   3.4 PHAS=  204.7 FOM= 0.87
INDE   7   9    7 FOBS=    76.5 SIGMA=  29.7 PHAS=  275.3 FOM= 0.03
INDE   7   9    8 FOBS=    75.5 SIGMA=  14.6 PHAS=  109.1 FOM= 0.07
INDE   7   9    9 FOBS=    96.8 SIGMA=  10.3 PHAS=  342.9 FOM= 0.02
INDE   7   9   10 FOBS=   101.9 SIGMA=   8.4 PHAS=  300.5 FOM= 0.03
INDE   7   9   11 FOBS=   109.2 SIGMA=   7.7 PHAS=  214.2 FOM= 0.29
INDE   7   9   12 FOBS=    65.6 SIGMA=  25.4 PHAS=   47.0 FOM= 0.08
INDE   7  10    0 FOBS=   154.5 SIGMA=   2.9 PHAS=  116.2 FOM= 0.51
INDE   7  10    1 FOBS=   315.7 SIGMA=   1.6 PHAS=  309.0 FOM= 0.95
INDE   7  10    2 FOBS=   157.9 SIGMA=   3.3 PHAS=  325.8 FOM= 0.55
INDE   7  10    3 FOBS=   362.5 SIGMA=   1.7 PHAS=  230.0 FOM= 0.66
INDE   7  10    4 FOBS=    42.9 SIGMA=  18.9 PHAS=  247.5 FOM= 0.14
INDE   7  10    5 FOBS=   203.9 SIGMA=   3.3 PHAS=   78.4 FOM= 0.80
INDE   7  10    6 FOBS=   107.5 SIGMA=   6.6 PHAS=  275.0 FOM= 0.23
INDE   7  10    7 FOBS=   155.9 SIGMA=   5.0 PHAS=  350.0 FOM= 0.07
INDE   7  10    8 FOBS=   169.7 SIGMA=   6.4 PHAS=  145.1 FOM= 0.21
INDE   7  10    9 FOBS=   131.1 SIGMA=   8.8 PHAS=  120.3 FOM= 0.03
INDE   7  10   10 FOBS=   100.6 SIGMA=   9.0 PHAS=  310.1 FOM= 0.20
INDE   7  10   11 FOBS=   146.7 SIGMA=   5.9 PHAS=  152.9 FOM= 0.05
INDE   7  10   12 FOBS=    73.9 SIGMA=  13.5 PHAS=   84.8 FOM= 0.02
INDE   7  10   13 FOBS=    43.0 SIGMA=  18.4 PHAS=  337.2 FOM= 0.03
INDE   7  11    0 FOBS=   214.0 SIGMA=   2.1 PHAS=   54.5 FOM= 0.61
INDE   7  11    1 FOBS=   328.9 SIGMA=   1.6 PHAS=  184.9 FOM= 1.00
```

Fig. 10A-123

```
INDE    7   11    2  FOBS=    128.9  SIGMA=    4.5  PHAS=    26.7  FOM=  0.93
INDE    7   11    3  FOBS=    114.9  SIGMA=    5.0  PHAS=   229.0  FOM=  0.71
INDE    7   11    4  FOBS=    148.5  SIGMA=    4.3  PHAS=   186.9  FOM=  0.60
INDE    7   11    5  FOBS=    237.0  SIGMA=    2.8  PHAS=   321.4  FOM=  0.92
INDE    7   11    6  FOBS=     59.6  SIGMA=   13.7  PHAS=   204.0  FOM=  0.18
INDE    7   11    7  FOBS=    393.9  SIGMA=    2.2  PHAS=    30.9  FOM=  0.50
INDE    7   11    8  FOBS=    298.0  SIGMA=    3.1  PHAS=   323.9  FOM=  0.83
INDE    7   11    9  FOBS=     74.7  SIGMA=   13.7  PHAS=   320.7  FOM=  0.07
INDE    7   11   10  FOBS=    163.8  SIGMA=    5.9  PHAS=   333.3  FOM=  0.15
INDE    7   11   11  FOBS=     51.7  SIGMA=   21.5  PHAS=   161.4  FOM=  0.11
INDE    7   11   12  FOBS=    211.4  SIGMA=    4.3  PHAS=   151.0  FOM=  0.13
INDE    7   11   13  FOBS=    122.6  SIGMA=    7.2  PHAS=    86.1  FOM=  0.13
INDE    7   12    0  FOBS=     98.4  SIGMA=    4.6  PHAS=   351.8  FOM=  0.69
INDE    7   12    1  FOBS=    147.8  SIGMA=    3.5  PHAS=   261.6  FOM=  0.61
INDE    7   12    2  FOBS=    106.9  SIGMA=    4.9  PHAS=   255.4  FOM=  0.42
INDE    7   12    3  FOBS=    254.2  SIGMA=    2.3  PHAS=    10.2  FOM=  0.26
INDE    7   12    4  FOBS=    192.1  SIGMA=    3.3  PHAS=   183.1  FOM=  0.05
INDE    7   12    5  FOBS=    120.2  SIGMA=    5.5  PHAS=   108.5  FOM=  0.54
INDE    7   12    6  FOBS=    172.0  SIGMA=    4.5  PHAS=   272.5  FOM=  0.86
INDE    7   12    7  FOBS=    379.0  SIGMA=    2.5  PHAS=   213.8  FOM=  0.84
INDE    7   12    8  FOBS=    216.9  SIGMA=    4.2  PHAS=   111.0  FOM=  0.63
INDE    7   12    9  FOBS=     81.9  SIGMA=   11.1  PHAS=   264.4  FOM=  0.19
INDE    7   12   10  FOBS=    171.8  SIGMA=    5.2  PHAS=   132.4  FOM=  0.27
INDE    7   12   11  FOBS=     63.8  SIGMA=   15.0  PHAS=    59.1  FOM=  0.13
INDE    7   12   12  FOBS=     68.7  SIGMA=   14.1  PHAS=   309.6  FOM=  0.01
INDE    7   13    0  FOBS=    154.5  SIGMA=    3.1  PHAS=    49.6  FOM=  0.87
INDE    7   13    1  FOBS=    203.7  SIGMA=    2.5  PHAS=   190.9  FOM=  0.83
INDE    7   13    2  FOBS=    137.5  SIGMA=    4.1  PHAS=   309.0  FOM=  0.85
INDE    7   13    3  FOBS=    391.4  SIGMA=    1.7  PHAS=    64.3  FOM=  0.96
INDE    7   13    4  FOBS=    262.9  SIGMA=    2.4  PHAS=   131.9  FOM=  0.86
INDE    7   13    5  FOBS=    116.9  SIGMA=    5.6  PHAS=   356.6  FOM=  0.24
INDE    7   13    6  FOBS=    107.5  SIGMA=    7.5  PHAS=   289.7  FOM=  0.42
INDE    7   13    7  FOBS=     45.0  SIGMA=   24.7  PHAS=    76.1  FOM=  0.25
INDE    7   13    8  FOBS=     87.6  SIGMA=    9.3  PHAS=   268.1  FOM=  0.12
INDE    7   13    9  FOBS=     97.3  SIGMA=    8.3  PHAS=   265.0  FOM=  0.17
INDE    7   13   10  FOBS=    149.5  SIGMA=    5.5  PHAS=   327.1  FOM=  0.05
INDE    7   13   11  FOBS=     93.0  SIGMA=    9.2  PHAS=   221.8  FOM=  0.09
INDE    7   13   12  FOBS=    146.1  SIGMA=   94.1  PHAS=   307.1  FOM=  0.01
INDE    7   14    0  FOBS=    280.3  SIGMA=    1.8  PHAS=    51.6  FOM=  0.93
INDE    7   14    1  FOBS=    209.3  SIGMA=    2.6  PHAS=   317.4  FOM=  0.97
INDE    7   14    2  FOBS=    352.9  SIGMA=    1.7  PHAS=    11.0  FOM=  0.94
INDE    7   14    3  FOBS=    327.0  SIGMA=    1.9  PHAS=   136.9  FOM=  0.96
INDE    7   14    4  FOBS=    117.9  SIGMA=    5.3  PHAS=   352.2  FOM=  0.85
INDE    7   14    5  FOBS=    256.2  SIGMA=    2.7  PHAS=   334.8  FOM=  0.39
INDE    7   14    6  FOBS=    334.7  SIGMA=    2.9  PHAS=   102.3  FOM=  0.68
INDE    7   14    7  FOBS=     44.9  SIGMA=   22.0  PHAS=   262.9  FOM=  0.12
INDE    7   14    8  FOBS=     84.0  SIGMA=    9.0  PHAS=   128.8  FOM=  0.03
INDE    7   14    9  FOBS=     69.6  SIGMA=   13.0  PHAS=   346.9  FOM=  0.08
INDE    7   14   10  FOBS=     74.7  SIGMA=   13.6  PHAS=   149.6  FOM=  0.11
INDE    7   14   11  FOBS=     29.8  SIGMA=   20.0  PHAS=   353.1  FOM=  0.41
INDE    7   14   12  FOBS=    113.4  SIGMA=    7.5  PHAS=   261.3  FOM=  0.05
INDE    7   15    0  FOBS=    137.2  SIGMA=    3.2  PHAS=   126.7  FOM=  0.91
INDE    7   15    1  FOBS=    123.8  SIGMA=    4.2  PHAS=    26.4  FOM=  0.74
INDE    7   15    2  FOBS=    148.4  SIGMA=    3.8  PHAS=    43.4  FOM=  0.25
INDE    7   15    3  FOBS=    118.7  SIGMA=    5.1  PHAS=   316.4  FOM=  0.43
INDE    7   15    4  FOBS=    131.2  SIGMA=    5.0  PHAS=    33.7  FOM=  0.10
INDE    7   15    5  FOBS=    312.1  SIGMA=    2.9  PHAS=   108.2  FOM=  0.61
INDE    7   15    6  FOBS=    267.7  SIGMA=    2.9  PHAS=   104.1  FOM=  0.44
INDE    7   15    7  FOBS=    134.3  SIGMA=    5.8  PHAS=   328.3  FOM=  0.05
INDE    7   15    8  FOBS=     83.9  SIGMA=   67.6  PHAS=   173.6  FOM=  0.07
INDE    7   15    9  FOBS=    114.3  SIGMA=    7.2  PHAS=    53.8  FOM=  0.03
INDE    7   15   10  FOBS=     64.0  SIGMA=   12.4  PHAS=   296.8  FOM=  0.05
INDE    7   15   11  FOBS=     75.0  SIGMA=   11.1  PHAS=   146.6  FOM=  0.02
INDE    7   16    0  FOBS=    509.1  SIGMA=    1.7  PHAS=   119.7  FOM=  0.98
INDE    7   16    1  FOBS=    267.1  SIGMA=    2.0  PHAS=    65.7  FOM=  0.81
INDE    7   16    2  FOBS=    281.2  SIGMA=    2.0  PHAS=   329.4  FOM=  0.77
INDE    7   16    3  FOBS=    184.4  SIGMA=    3.4  PHAS=   167.3  FOM=  0.83
INDE    7   16    4  FOBS=    151.6  SIGMA=    4.9  PHAS=   342.2  FOM=  0.40
INDE    7   16    5  FOBS=    112.2  SIGMA=    6.9  PHAS=   289.2  FOM=  0.20
INDE    7   16    6  FOBS=    171.9  SIGMA=    4.4  PHAS=    76.2  FOM=  0.32
INDE    7   16    7  FOBS=     80.9  SIGMA=    9.2  PHAS=   335.5  FOM=  0.12
```

Fig. 10A-124

```
INDE    7   16    8  FOBS=    119.2  SIGMA=    6.4  PHAS=   214.4  FOM=   0.24
INDE    7   16    9  FOBS=     92.5  SIGMA=    8.5  PHAS=   337.5  FOM=   0.06
INDE    7   16   10  FOBS=     49.9  SIGMA=   25.3  PHAS=   218.5  FOM=   0.02
INDE    7   16   11  FOBS=     51.8  SIGMA=   15.8  PHAS=    88.3  FOM=   0.07
INDE    7   17    0  FOBS=    429.8  SIGMA=    1.5  PHAS=   347.6  FOM=   0.98
INDE    7   17    1  FOBS=    306.4  SIGMA=    1.8  PHAS=   209.7  FOM=   0.63
INDE    7   17    2  FOBS=    210.9  SIGMA=    2.6  PHAS=    65.9  FOM=   0.46
INDE    7   17    3  FOBS=    141.5  SIGMA=    4.6  PHAS=   310.0  FOM=   0.55
INDE    7   17    4  FOBS=    128.0  SIGMA=    5.6  PHAS=   145.5  FOM=   0.14
INDE    7   17    5  FOBS=    204.4  SIGMA=    3.4  PHAS=   199.3  FOM=   0.35
INDE    7   17    6  FOBS=    239.5  SIGMA=    3.0  PHAS=   198.9  FOM=   0.62
INDE    7   17    7  FOBS=    144.5  SIGMA=    5.1  PHAS=   343.3  FOM=   0.10
INDE    7   17    8  FOBS=     63.2  SIGMA=   15.6  PHAS=   342.6  FOM=   0.07
INDE    7   17    9  FOBS=    117.5  SIGMA=    6.4  PHAS=   162.6  FOM=   0.32
INDE    7   17   10  FOBS=    127.2  SIGMA=    6.0  PHAS=    39.8  FOM=   0.86
INDE    7   17   11  FOBS=     58.1  SIGMA=   26.6  PHAS=   279.2  FOM=   0.09
INDE    7   18    0  FOBS=    194.0  SIGMA=    2.5  PHAS=   294.4  FOM=   0.16
INDE    7   18    1  FOBS=    362.0  SIGMA=    1.6  PHAS=   131.6  FOM=   0.95
INDE    7   18    2  FOBS=     74.7  SIGMA=    8.0  PHAS=   285.4  FOM=   0.12
INDE    7   18    3  FOBS=    255.0  SIGMA=    2.6  PHAS=   118.0  FOM=   0.12
INDE    7   18    4  FOBS=    110.8  SIGMA=    5.9  PHAS=   181.6  FOM=   0.19
INDE    7   18    5  FOBS=    114.5  SIGMA=    6.0  PHAS=   222.9  FOM=   0.04
INDE    7   18    6  FOBS=     82.1  SIGMA=    8.6  PHAS=   123.0  FOM=   0.10
INDE    7   18    7  FOBS=    211.5  SIGMA=    3.4  PHAS=   352.4  FOM=   0.90
INDE    7   18    8  FOBS=     42.5  SIGMA=   14.9  PHAS=   174.5  FOM=   0.26
INDE    7   18    9  FOBS=     54.3  SIGMA=   13.4  PHAS=    60.9  FOM=   0.16
INDE    7   18   10  FOBS=     77.4  SIGMA=    9.5  PHAS=   319.1  FOM=   0.11
INDE    7   18   11  FOBS=    145.5  SIGMA=    5.6  PHAS=   240.7  FOM=   0.29
INDE    7   19    0  FOBS=    218.1  SIGMA=    2.3  PHAS=   127.5  FOM=   0.43
INDE    7   19    1  FOBS=    136.1  SIGMA=    4.4  PHAS=   107.4  FOM=   0.09
INDE    7   19    2  FOBS=    213.9  SIGMA=    3.5  PHAS=   355.1  FOM=   0.90
INDE    7   19    3  FOBS=     61.4  SIGMA=   10.3  PHAS=   152.9  FOM=   0.07
INDE    7   19    4  FOBS=     71.7  SIGMA=    9.7  PHAS=   258.9  FOM=   0.46
INDE    7   19    5  FOBS=    212.6  SIGMA=    3.4  PHAS=    61.6  FOM=   0.93
INDE    7   19    6  FOBS=    175.4  SIGMA=    4.1  PHAS=   328.2  FOM=   0.18
INDE    7   19    7  FOBS=     98.2  SIGMA=    7.1  PHAS=   286.8  FOM=   0.40
INDE    7   19    8  FOBS=     81.6  SIGMA=    8.5  PHAS=    44.7  FOM=   0.26
INDE    7   19    9  FOBS=     93.4  SIGMA=    7.6  PHAS=   258.9  FOM=   0.42
INDE    7   19   10  FOBS=     60.7  SIGMA=   12.3  PHAS=   105.2  FOM=   0.02
INDE    7   20    0  FOBS=    236.1  SIGMA=    2.2  PHAS=   269.5  FOM=   0.38
INDE    7   20    1  FOBS=    348.6  SIGMA=    1.9  PHAS=   310.4  FOM=   0.53
INDE    7   20    2  FOBS=    328.9  SIGMA=    1.9  PHAS=   174.2  FOM=   0.63
INDE    7   20    3  FOBS=    163.4  SIGMA=    3.8  PHAS=   287.1  FOM=   0.66
INDE    7   20    4  FOBS=    216.1  SIGMA=    3.0  PHAS=   139.6  FOM=   0.75
INDE    7   20    5  FOBS=     58.0  SIGMA=   11.6  PHAS=     5.5  FOM=   0.17
INDE    7   20    6  FOBS=     66.3  SIGMA=   11.0  PHAS=   198.7  FOM=   0.41
INDE    7   20    7  FOBS=     52.3  SIGMA=   13.6  PHAS=    13.6  FOM=   0.16
INDE    7   20    8  FOBS=     66.1  SIGMA=   10.9  PHAS=    65.3  FOM=   0.09
INDE    7   20    9  FOBS=     82.9  SIGMA=    8.7  PHAS=   282.7  FOM=   0.05
INDE    7   20   10  FOBS=    112.5  SIGMA=    6.3  PHAS=    20.6  FOM=   0.05
INDE    7   21    0  FOBS=     94.5  SIGMA=    5.9  PHAS=   359.6  FOM=   0.66
INDE    7   21    1  FOBS=    205.5  SIGMA=    2.8  PHAS=   352.5  FOM=   0.93
INDE    7   21    2  FOBS=    183.5  SIGMA=    3.1  PHAS=   174.2  FOM=   0.04
INDE    7   21    3  FOBS=    263.8  SIGMA=    2.3  PHAS=   234.7  FOM=   0.78
INDE    7   21    4  FOBS=    223.8  SIGMA=    2.8  PHAS=   205.1  FOM=   0.52
INDE    7   21    5  FOBS=    185.1  SIGMA=    3.6  PHAS=   166.6  FOM=   0.29
INDE    7   21    6  FOBS=     97.5  SIGMA=    6.8  PHAS=   306.7  FOM=   0.08
INDE    7   21    7  FOBS=    130.1  SIGMA=    5.2  PHAS=   123.1  FOM=   0.35
INDE    7   21    8  FOBS=    124.1  SIGMA=    5.6  PHAS=   145.2  FOM=   0.56
INDE    7   21    9  FOBS=     40.0  SIGMA=   17.1  PHAS=   272.6  FOM=   0.19
INDE    7   21   10  FOBS=     84.0  SIGMA=   30.6  PHAS=    73.7  FOM=   0.06
INDE    7   22    0  FOBS=    244.0  SIGMA=    2.5  PHAS=    56.7  FOM=   0.41
INDE    7   22    1  FOBS=    167.6  SIGMA=    3.2  PHAS=   278.4  FOM=   0.58
INDE    7   22    2  FOBS=    226.0  SIGMA=    2.5  PHAS=   112.7  FOM=   0.71
INDE    7   22    3  FOBS=    173.1  SIGMA=    3.5  PHAS=   124.5  FOM=   0.04
INDE    7   22    4  FOBS=    223.8  SIGMA=    2.8  PHAS=   344.0  FOM=   0.58
INDE    7   22    6  FOBS=    198.9  SIGMA=    3.3  PHAS=   211.7  FOM=   0.22
INDE    7   22    7  FOBS=     59.7  SIGMA=   12.6  PHAS=   257.7  FOM=   0.07
INDE    7   22    8  FOBS=     64.8  SIGMA=   12.1  PHAS=   145.0  FOM=   0.04
INDE    7   22    9  FOBS=    122.4  SIGMA=    5.6  PHAS=    25.4  FOM=   0.22
INDE    7   23    0  FOBS=     74.8  SIGMA=    6.7  PHAS=   244.5  FOM=   0.49
```

Fig. 10A-125

| | | | | | | | | | | | |
|---|---|---|---|---|---|---|---|---|---|---|---|
| INDE | 7 | 23 | 1 | FOBS= | 236.9 | SIGMA= | 2.3 | PHAS= | 85.5 | FOM= | 0.86 |
| INDE | 7 | 23 | 2 | FOBS= | 104.5 | SIGMA= | 5.2 | PHAS= | 33.0 | FOM= | 0.15 |
| INDE | 7 | 23 | 3 | FOBS= | 106.0 | SIGMA= | 5.5 | PHAS= | 265.4 | FOM= | 0.19 |
| INDE | 7 | 23 | 4 | FOBS= | 57.6 | SIGMA= | 11.6 | PHAS= | 84.1 | FOM= | 0.18 |
| INDE | 7 | 23 | 5 | FOBS= | 117.1 | SIGMA= | 5.3 | PHAS= | 224.8 | FOM= | 0.05 |
| INDE | 7 | 23 | 6 | FOBS= | 67.2 | SIGMA= | 10.3 | PHAS= | 252.8 | FOM= | 0.15 |
| INDE | 7 | 23 | 7 | FOBS= | 30.0 | SIGMA= | 20.7 | PHAS= | 89.2 | FOM= | 0.40 |
| INDE | 7 | 23 | 8 | FOBS= | 72.5 | SIGMA= | 9.3 | PHAS= | 313.0 | FOM= | 0.02 |
| INDE | 7 | 23 | 9 | FOBS= | 359.8 | SIGMA= | 239.5 | PHAS= | 279.7 | FOM= | 0.01 |
| INDE | 7 | 24 | 0 | FOBS= | 116.8 | SIGMA= | 4.6 | PHAS= | 145.8 | FOM= | 0.84 |
| INDE | 7 | 24 | 1 | FOBS= | 83.9 | SIGMA= | 6.3 | PHAS= | 278.4 | FOM= | 0.61 |
| INDE | 7 | 24 | 2 | FOBS= | 235.6 | SIGMA= | 2.5 | PHAS= | 334.9 | FOM= | 0.28 |
| INDE | 7 | 24 | 3 | FOBS= | 86.7 | SIGMA= | 6.6 | PHAS= | 149.4 | FOM= | 0.37 |
| INDE | 7 | 24 | 4 | FOBS= | 147.7 | SIGMA= | 4.2 | PHAS= | 270.3 | FOM= | 0.57 |
| INDE | 7 | 24 | 5 | FOBS= | 63.1 | SIGMA= | 10.7 | PHAS= | 215.1 | FOM= | 0.17 |
| INDE | 7 | 24 | 6 | FOBS= | 58.2 | SIGMA= | 11.0 | PHAS= | 121.8 | FOM= | 0.25 |
| INDE | 7 | 24 | 7 | FOBS= | 92.4 | SIGMA= | 6.8 | PHAS= | 64.9 | FOM= | 0.31 |
| INDE | 7 | 24 | 8 | FOBS= | 60.8 | SIGMA= | 12.1 | PHAS= | 195.9 | FOM= | 0.06 |
| INDE | 7 | 25 | 0 | FOBS= | 96.6 | SIGMA= | 5.4 | PHAS= | 262.4 | FOM= | 0.65 |
| INDE | 7 | 25 | 1 | FOBS= | 39.9 | SIGMA= | 19.8 | PHAS= | 56.5 | FOM= | 0.04 |
| INDE | 7 | 25 | 2 | FOBS= | 208.3 | SIGMA= | 2.8 | PHAS= | 79.9 | FOM= | 0.96 |
| INDE | 7 | 25 | 3 | FOBS= | 107.5 | SIGMA= | 5.1 | PHAS= | 278.2 | FOM= | 0.30 |
| INDE | 7 | 25 | 4 | FOBS= | 107.9 | SIGMA= | 5.3 | PHAS= | 118.7 | FOM= | 0.08 |
| INDE | 7 | 25 | 5 | FOBS= | 83.7 | SIGMA= | 7.2 | PHAS= | 148.7 | FOM= | 0.25 |
| INDE | 7 | 25 | 6 | FOBS= | 107.2 | SIGMA= | 5.7 | PHAS= | 14.6 | FOM= | 0.07 |
| INDE | 7 | 25 | 7 | FOBS= | 75.2 | SIGMA= | 8.8 | PHAS= | 321.9 | FOM= | 0.03 |
| INDE | 7 | 26 | 0 | FOBS= | 49.8 | SIGMA= | 10.2 | PHAS= | 210.5 | FOM= | 0.34 |
| INDE | 7 | 26 | 1 | FOBS= | 64.3 | SIGMA= | 8.4 | PHAS= | 134.7 | FOM= | 0.11 |
| INDE | 7 | 26 | 2 | FOBS= | 55.0 | SIGMA= | 10.2 | PHAS= | 331.7 | FOM= | 0.18 |
| INDE | 7 | 26 | 3 | FOBS= | 207.5 | SIGMA= | 2.9 | PHAS= | 276.4 | FOM= | 0.75 |
| INDE | 7 | 26 | 4 | FOBS= | 97.8 | SIGMA= | 5.7 | PHAS= | 123.8 | FOM= | 0.60 |
| INDE | 7 | 26 | 5 | FOBS= | 64.4 | SIGMA= | 9.2 | PHAS= | 241.5 | FOM= | 0.06 |
| INDE | 7 | 26 | 6 | FOBS= | 60.7 | SIGMA= | 10.2 | PHAS= | 63.6 | FOM= | 0.17 |
| INDE | 7 | 26 | 7 | FOBS= | 90.2 | SIGMA= | 56.6 | PHAS= | 298.8 | FOM= | 0.03 |
| INDE | 7 | 27 | 0 | FOBS= | 87.6 | SIGMA= | 5.2 | PHAS= | 196.8 | FOM= | 0.23 |
| INDE | 7 | 27 | 1 | FOBS= | 82.5 | SIGMA= | 6.0 | PHAS= | 250.6 | FOM= | 0.37 |
| INDE | 7 | 27 | 2 | FOBS= | 80.8 | SIGMA= | 6.4 | PHAS= | 91.6 | FOM= | 0.10 |
| INDE | 7 | 27 | 3 | FOBS= | 140.8 | SIGMA= | 4.0 | PHAS= | 311.4 | FOM= | 0.26 |
| INDE | 7 | 27 | 4 | FOBS= | 64.0 | SIGMA= | 20.8 | PHAS= | 187.0 | FOM= | 0.13 |
| INDE | 7 | 27 | 5 | FOBS= | 118.5 | SIGMA= | 4.9 | PHAS= | 73.4 | FOM= | 0.25 |
| INDE | 7 | 27 | 6 | FOBS= | 90.3 | SIGMA= | 8.1 | PHAS= | 196.8 | FOM= | 0.06 |
| INDE | 7 | 28 | 0 | FOBS= | 170.4 | SIGMA= | 2.7 | PHAS= | 311.3 | FOM= | 0.71 |
| INDE | 7 | 28 | 1 | FOBS= | 133.2 | SIGMA= | 3.8 | PHAS= | 33.3 | FOM= | 0.76 |
| INDE | 7 | 28 | 2 | FOBS= | 67.7 | SIGMA= | 7.7 | PHAS= | 232.5 | FOM= | 0.07 |
| INDE | 7 | 28 | 3 | FOBS= | 114.0 | SIGMA= | 4.8 | PHAS= | 258.3 | FOM= | 0.43 |
| INDE | 7 | 28 | 4 | FOBS= | 50.9 | SIGMA= | 11.2 | PHAS= | 69.3 | FOM= | 0.11 |
| INDE | 7 | 28 | 5 | FOBS= | 65.3 | SIGMA= | 37.0 | PHAS= | 264.9 | FOM= | 0.04 |
| INDE | 7 | 29 | 0 | FOBS= | 145.8 | SIGMA= | 3.9 | PHAS= | 21.1 | FOM= | 0.49 |
| INDE | 7 | 29 | 1 | FOBS= | 83.9 | SIGMA= | 5.8 | PHAS= | 265.0 | FOM= | 0.46 |
| INDE | 7 | 29 | 2 | FOBS= | 159.0 | SIGMA= | 3.6 | PHAS= | 311.1 | FOM= | 0.46 |
| INDE | 7 | 29 | 3 | FOBS= | 116.6 | SIGMA= | 16.8 | PHAS= | 263.6 | FOM= | 0.06 |
| INDE | 7 | 30 | 0 | FOBS= | 86.5 | SIGMA= | 6.2 | PHAS= | 317.4 | FOM= | 0.09 |
| INDE | 7 | 30 | 1 | FOBS= | 143.0 | SIGMA= | 3.4 | PHAS= | 216.6 | FOM= | 0.22 |
| INDE | 7 | 30 | 2 | FOBS= | 192.3 | SIGMA= | 3.4 | PHAS= | 91.4 | FOM= | 0.35 |
| INDE | 8 | 0 | 0 | FOBS= | 32.8 | SIGMA= | 18.1 | PHAS= | 0.0 | FOM= | 0.24 |
| INDE | 8 | 0 | 1 | FOBS= | 55.1 | SIGMA= | 15.6 | PHAS= | 180.0 | FOM= | 0.35 |
| INDE | 8 | 0 | 2 | FOBS= | 71.2 | SIGMA= | 13.6 | PHAS= | 180.0 | FOM= | 0.01 |
| INDE | 8 | 0 | 3 | FOBS= | 51.4 | SIGMA= | 66.3 | PHAS= | 0.0 | FOM= | 0.12 |
| INDE | 8 | 0 | 4 | FOBS= | 118.3 | SIGMA= | 7.2 | PHAS= | 180.0 | FOM= | 0.18 |
| INDE | 8 | 0 | 5 | FOBS= | 46.1 | SIGMA= | 66.4 | PHAS= | 180.0 | FOM= | 0.04 |
| INDE | 8 | 0 | 6 | FOBS= | 291.1 | SIGMA= | 3.8 | PHAS= | 0.0 | FOM= | 0.18 |
| INDE | 8 | 0 | 7 | FOBS= | 105.9 | SIGMA= | 11.4 | PHAS= | 0.0 | FOM= | 0.08 |
| INDE | 8 | 0 | 8 | FOBS= | 218.7 | SIGMA= | 11.8 | PHAS= | 180.0 | FOM= | 0.29 |
| INDE | 8 | 0 | 9 | FOBS= | 64.6 | SIGMA= | 100.8 | PHAS= | 180.0 | FOM= | 0.05 |
| INDE | 8 | 0 | 10 | FOBS= | 50.9 | SIGMA= | 58.4 | PHAS= | 0.0 | FOM= | 0.23 |
| INDE | 8 | 0 | 11 | FOBS= | 33.1 | SIGMA= | 49.0 | PHAS= | 180.0 | FOM= | 0.08 |
| INDE | 8 | 0 | 12 | FOBS= | 121.8 | SIGMA= | 11.6 | PHAS= | 180.0 | FOM= | 0.16 |
| INDE | 8 | 0 | 13 | FOBS= | 64.4 | SIGMA= | 47.8 | PHAS= | 0.0 | FOM= | 0.03 |
| INDE | 8 | 1 | 0 | FOBS= | 178.1 | SIGMA= | 2.6 | PHAS= | 120.7 | FOM= | 0.82 |
| INDE | 8 | 1 | 1 | FOBS= | 62.6 | SIGMA= | 8.4 | PHAS= | 278.7 | FOM= | 0.26 |
| INDE | 8 | 1 | 2 | FOBS= | 113.5 | SIGMA= | 5.2 | PHAS= | 109.0 | FOM= | 0.08 |

Fig. 10A-126

| | | | | | | | | | |
|---|---|---|---|---|---|---|---|---|---|
| INDE | 8 | 1 | 3 | FOBS= | 165.2 | SIGMA= | 3.9 | PHAS= | 331.4 | FOM= | 0.85 |
| INDE | 8 | 1 | 4 | FOBS= | 273.2 | SIGMA= | 2.5 | PHAS= | 79.8 | FOM= | 0.97 |
| INDE | 8 | 1 | 5 | FOBS= | 138.8 | SIGMA= | 5.0 | PHAS= | 40.7 | FOM= | 0.31 |
| INDE | 8 | 1 | 6 | FOBS= | 111.3 | SIGMA= | 6.8 | PHAS= | 269.5 | FOM= | 0.64 |
| INDE | 8 | 1 | 7 | FOBS= | 191.0 | SIGMA= | 5.6 | PHAS= | 155.1 | FOM= | 0.46 |
| INDE | 8 | 1 | 8 | FOBS= | 157.4 | SIGMA= | 6.6 | PHAS= | 247.0 | FOM= | 0.26 |
| INDE | 8 | 1 | 9 | FOBS= | 52.1 | SIGMA= | 23.0 | PHAS= | 341.9 | FOM= | 0.16 |
| INDE | 8 | 1 | 10 | FOBS= | 123.7 | SIGMA= | 10.3 | PHAS= | 107.9 | FOM= | 0.09 |
| INDE | 8 | 1 | 11 | FOBS= | 74.8 | SIGMA= | 16.4 | PHAS= | 235.0 | FOM= | 0.09 |
| INDE | 8 | 1 | 12 | FOBS= | 168.7 | SIGMA= | 6.0 | PHAS= | 5.0 | FOM= | 0.06 |
| INDE | 8 | 1 | 13 | FOBS= | 94.6 | SIGMA= | 11.0 | PHAS= | 59.1 | FOM= | 0.03 |
| INDE | 8 | 2 | 0 | FOBS= | 113.3 | SIGMA= | 4.6 | PHAS= | 287.8 | FOM= | 0.30 |
| INDE | 8 | 2 | 1 | FOBS= | 312.8 | SIGMA= | 2.0 | PHAS= | 46.6 | FOM= | 0.84 |
| INDE | 8 | 2 | 2 | FOBS= | 33.1 | SIGMA= | 15.9 | PHAS= | 8.7 | FOM= | 0.28 |
| INDE | 8 | 2 | 3 | FOBS= | 91.9 | SIGMA= | 6.8 | PHAS= | 257.7 | FOM= | 0.47 |
| INDE | 8 | 2 | 4 | FOBS= | 84.9 | SIGMA= | 8.4 | PHAS= | 122.0 | FOM= | 0.28 |
| INDE | 8 | 2 | 5 | FOBS= | 302.2 | SIGMA= | 2.5 | PHAS= | 271.8 | FOM= | 0.90 |
| INDE | 8 | 2 | 7 | FOBS= | 138.2 | SIGMA= | 6.3 | PHAS= | 344.1 | FOM= | 0.17 |
| INDE | 8 | 2 | 8 | FOBS= | 159.8 | SIGMA= | 6.4 | PHAS= | 156.8 | FOM= | 0.13 |
| INDE | 8 | 2 | 9 | FOBS= | 81.4 | SIGMA= | 14.6 | PHAS= | 165.5 | FOM= | 0.03 |
| INDE | 8 | 2 | 10 | FOBS= | 95.1 | SIGMA= | 11.6 | PHAS= | 326.8 | FOM= | 0.06 |
| INDE | 8 | 2 | 11 | FOBS= | 102.7 | SIGMA= | 12.4 | PHAS= | 239.0 | FOM= | 0.05 |
| INDE | 8 | 2 | 12 | FOBS= | 113.9 | SIGMA= | 10.4 | PHAS= | 54.8 | FOM= | 0.28 |
| INDE | 8 | 2 | 13 | FOBS= | 65.3 | SIGMA= | 20.6 | PHAS= | 215.0 | FOM= | 0.01 |
| INDE | 8 | 3 | 0 | FOBS= | 248.8 | SIGMA= | 2.2 | PHAS= | 111.6 | FOM= | 0.96 |
| INDE | 8 | 3 | 1 | FOBS= | 241.1 | SIGMA= | 2.7 | PHAS= | 321.7 | FOM= | 0.97 |
| INDE | 8 | 3 | 2 | FOBS= | 202.9 | SIGMA= | 2.7 | PHAS= | 308.8 | FOM= | 0.96 |
| INDE | 8 | 3 | 3 | FOBS= | 116.9 | SIGMA= | 4.9 | PHAS= | 28.9 | FOM= | 0.80 |
| INDE | 8 | 3 | 4 | FOBS= | 108.7 | SIGMA= | 6.2 | PHAS= | 350.0 | FOM= | 0.39 |
| INDE | 8 | 3 | 5 | FOBS= | 141.0 | SIGMA= | 6.9 | PHAS= | 176.6 | FOM= | 0.19 |
| INDE | 8 | 3 | 6 | FOBS= | 299.2 | SIGMA= | 2.6 | PHAS= | 48.1 | FOM= | 0.86 |
| INDE | 8 | 3 | 7 | FOBS= | 66.0 | SIGMA= | 12.9 | PHAS= | 231.1 | FOM= | 0.23 |
| INDE | 8 | 3 | 8 | FOBS= | 107.6 | SIGMA= | 9.4 | PHAS= | 52.4 | FOM= | 0.18 |
| INDE | 8 | 3 | 9 | FOBS= | 104.0 | SIGMA= | 9.5 | PHAS= | 350.5 | FOM= | 0.09 |
| INDE | 8 | 3 | 10 | FOBS= | 51.3 | SIGMA= | 22.8 | PHAS= | 233.4 | FOM= | 0.05 |
| INDE | 8 | 3 | 11 | FOBS= | 129.0 | SIGMA= | 7.6 | PHAS= | 43.6 | FOM= | 0.17 |
| INDE | 8 | 3 | 12 | FOBS= | 43.7 | SIGMA= | 20.3 | PHAS= | 244.1 | FOM= | 0.25 |
| INDE | 8 | 3 | 13 | FOBS= | 79.3 | SIGMA= | 16.9 | PHAS= | 298.6 | FOM= | 0.00 |
| INDE | 8 | 4 | 0 | FOBS= | 96.1 | SIGMA= | 5.2 | PHAS= | 333.4 | FOM= | 0.54 |
| INDE | 8 | 4 | 1 | FOBS= | 91.8 | SIGMA= | 5.2 | PHAS= | 204.1 | FOM= | 0.09 |
| INDE | 8 | 4 | 2 | FOBS= | 83.9 | SIGMA= | 6.1 | PHAS= | 79.3 | FOM= | 0.12 |
| INDE | 8 | 4 | 3 | FOBS= | 92.6 | SIGMA= | 6.0 | PHAS= | 173.0 | FOM= | 0.23 |
| INDE | 8 | 4 | 4 | FOBS= | 129.8 | SIGMA= | 5.5 | PHAS= | 217.1 | FOM= | 0.28 |
| INDE | 8 | 4 | 5 | FOBS= | 236.0 | SIGMA= | 3.4 | PHAS= | 40.4 | FOM= | 0.90 |
| INDE | 8 | 4 | 6 | FOBS= | 89.1 | SIGMA= | 10.2 | PHAS= | 167.2 | FOM= | 0.27 |
| INDE | 8 | 4 | 8 | FOBS= | 49.7 | SIGMA= | 28.9 | PHAS= | 32.3 | FOM= | 0.04 |
| INDE | 8 | 4 | 9 | FOBS= | 209.7 | SIGMA= | 4.8 | PHAS= | 181.1 | FOM= | 0.23 |
| INDE | 8 | 4 | 10 | FOBS= | 112.0 | SIGMA= | 8.5 | PHAS= | 350.0 | FOM= | 0.09 |
| INDE | 8 | 4 | 11 | FOBS= | 62.5 | SIGMA= | 32.9 | PHAS= | 195.1 | FOM= | 0.04 |
| INDE | 8 | 4 | 12 | FOBS= | 133.7 | SIGMA= | 6.9 | PHAS= | 76.8 | FOM= | 0.52 |
| INDE | 8 | 4 | 13 | FOBS= | 75.6 | SIGMA= | 14.5 | PHAS= | 9.3 | FOM= | 0.03 |
| INDE | 8 | 5 | 0 | FOBS= | 218.6 | SIGMA= | 2.2 | PHAS= | 118.9 | FOM= | 0.92 |
| INDE | 8 | 5 | 1 | FOBS= | 85.9 | SIGMA= | 6.1 | PHAS= | 86.5 | FOM= | 0.72 |
| INDE | 8 | 5 | 2 | FOBS= | 143.5 | SIGMA= | 3.9 | PHAS= | 212.3 | FOM= | 0.95 |
| INDE | 8 | 5 | 3 | FOBS= | 169.8 | SIGMA= | 4.2 | PHAS= | 76.9 | FOM= | 0.65 |
| INDE | 8 | 5 | 4 | FOBS= | 50.3 | SIGMA= | 12.7 | PHAS= | 49.5 | FOM= | 0.05 |
| INDE | 8 | 5 | 5 | FOBS= | 58.0 | SIGMA= | 33.8 | PHAS= | 260.4 | FOM= | 0.04 |
| INDE | 8 | 5 | 6 | FOBS= | 157.6 | SIGMA= | 6.3 | PHAS= | 109.1 | FOM= | 0.19 |
| INDE | 8 | 5 | 7 | FOBS= | 56.4 | SIGMA= | 19.6 | PHAS= | 293.4 | FOM= | 0.11 |
| INDE | 8 | 5 | 8 | FOBS= | 190.2 | SIGMA= | 5.3 | PHAS= | 67.6 | FOM= | 0.74 |
| INDE | 8 | 5 | 9 | FOBS= | 296.5 | SIGMA= | 3.2 | PHAS= | 232.0 | FOM= | 0.83 |
| INDE | 8 | 5 | 10 | FOBS= | 146.9 | SIGMA= | 6.4 | PHAS= | 309.5 | FOM= | 0.21 |
| INDE | 8 | 5 | 11 | FOBS= | 80.1 | SIGMA= | 11.8 | PHAS= | 108.3 | FOM= | 0.23 |
| INDE | 8 | 5 | 12 | FOBS= | 66.6 | SIGMA= | 18.2 | PHAS= | 340.6 | FOM= | 0.04 |
| INDE | 8 | 5 | 13 | FOBS= | 52.1 | SIGMA= | 21.7 | PHAS= | 239.2 | FOM= | 0.03 |
| INDE | 8 | 6 | 0 | FOBS= | 104.0 | SIGMA= | 4.5 | PHAS= | 118.3 | FOM= | 0.46 |
| INDE | 8 | 6 | 1 | FOBS= | 75.4 | SIGMA= | 6.4 | PHAS= | 257.5 | FOM= | 0.14 |
| INDE | 8 | 6 | 2 | FOBS= | 142.6 | SIGMA= | 4.5 | PHAS= | 145.1 | FOM= | 0.38 |
| INDE | 8 | 6 | 3 | FOBS= | 299.5 | SIGMA= | 2.1 | PHAS= | 345.9 | FOM= | 0.33 |
| INDE | 8 | 6 | 4 | FOBS= | 118.1 | SIGMA= | 5.5 | PHAS= | 196.9 | FOM= | 0.48 |
| INDE | 8 | 6 | 5 | FOBS= | 262.1 | SIGMA= | 3.0 | PHAS= | 332.0 | FOM= | 0.97 |

Fig. 10A-127

```
INDE  8   6   6  FOBS=   167.9  SIGMA=   4.7  PHAS=   128.7  FOM=  0.17
INDE  8   6   7  FOBS=    66.0  SIGMA=  16.3  PHAS=   115.3  FOM=  0.11
INDE  8   6   8  FOBS=    46.0  SIGMA=  20.8  PHAS=   324.6  FOM=  0.17
INDE  8   6   9  FOBS=    79.9  SIGMA=  11.9  PHAS=   224.3  FOM=  0.23
INDE  8   6  10  FOBS=    58.9  SIGMA=  16.6  PHAS=    86.3  FOM=  0.19
INDE  8   6  11  FOBS=   113.4  SIGMA=   8.0  PHAS=   326.5  FOM=  0.02
INDE  8   6  12  FOBS=    65.7  SIGMA=  26.3  PHAS=   255.0  FOM=  0.04
INDE  8   6  13  FOBS=    77.8  SIGMA=  13.3  PHAS=    98.2  FOM=  0.07
INDE  8   7   0  FOBS=   196.6  SIGMA=   2.5  PHAS=   219.1  FOM=  0.55
INDE  8   7   1  FOBS=    49.3  SIGMA=  12.4  PHAS=   310.8  FOM=  0.16
INDE  8   7   2  FOBS=   103.6  SIGMA=   5.3  PHAS=   147.3  FOM=  0.25
INDE  8   7   3  FOBS=    95.5  SIGMA=   6.2  PHAS=   183.4  FOM=  0.61
INDE  8   7   4  FOBS=   273.7  SIGMA=   2.4  PHAS=   240.3  FOM=  0.90
INDE  8   7   5  FOBS=   161.8  SIGMA=   4.4  PHAS=   126.6  FOM=  0.20
INDE  8   7   6  FOBS=   253.4  SIGMA=   3.2  PHAS=   216.0  FOM=  0.95
INDE  8   7   7  FOBS=   115.1  SIGMA=   9.1  PHAS=   329.3  FOM=  0.45
INDE  8   7   8  FOBS=   164.5  SIGMA=   6.3  PHAS=   142.0  FOM=  0.07
INDE  8   7   9  FOBS=    45.5  SIGMA=  19.3  PHAS=   172.7  FOM=  0.18
INDE  8   7  10  FOBS=    62.2  SIGMA=  16.5  PHAS=     7.4  FOM=  0.17
INDE  8   7  11  FOBS=    60.1  SIGMA=  18.8  PHAS=   216.4  FOM=  0.06
INDE  8   7  12  FOBS=   119.8  SIGMA=   8.4  PHAS=    26.3  FOM=  0.03
INDE  8   7  13  FOBS=    89.8  SIGMA=  10.8  PHAS=   124.7  FOM=  0.02
INDE  8   8   0  FOBS=   205.9  SIGMA=   2.4  PHAS=   289.6  FOM=  0.86
INDE  8   8   1  FOBS=   166.3  SIGMA=   3.0  PHAS=    12.4  FOM=  0.89
INDE  8   8   2  FOBS=   248.8  SIGMA=   2.3  PHAS=   151.5  FOM=  0.92
INDE  8   8   3  FOBS=    89.3  SIGMA=   6.6  PHAS=   294.2  FOM=  0.43
INDE  8   8   4  FOBS=   239.5  SIGMA=   2.9  PHAS=   259.8  FOM=  0.23
INDE  8   8   5  FOBS=   200.7  SIGMA=   3.5  PHAS=   166.7  FOM=  0.11
INDE  8   8   6  FOBS=   256.1  SIGMA=   2.9  PHAS=   322.2  FOM=  0.23
INDE  8   8   7  FOBS=    68.8  SIGMA=  17.8  PHAS=   336.6  FOM=  0.07
INDE  8   8   8  FOBS=    67.3  SIGMA=  26.3  PHAS=   122.1  FOM=  0.10
INDE  8   8   9  FOBS=   156.0  SIGMA=   6.2  PHAS=   186.8  FOM=  0.39
INDE  8   8  10  FOBS=   118.4  SIGMA=   7.4  PHAS=   357.8  FOM=  0.25
INDE  8   8  11  FOBS=   125.0  SIGMA=   7.8  PHAS=   204.4  FOM=  0.04
INDE  8   8  12  FOBS=    88.6  SIGMA=  10.8  PHAS=   223.3  FOM=  0.04
INDE  8   9   0  FOBS=   145.4  SIGMA=   4.1  PHAS=   200.0  FOM=  0.91
INDE  8   9   1  FOBS=   347.6  SIGMA=   1.6  PHAS=   216.7  FOM=  0.92
INDE  8   9   2  FOBS=   200.4  SIGMA=   2.8  PHAS=   141.8  FOM=  0.91
INDE  8   9   3  FOBS=    98.7  SIGMA=   6.1  PHAS=   193.7  FOM=  0.49
INDE  8   9   4  FOBS=   118.1  SIGMA=   5.6  PHAS=   331.5  FOM=  0.04
INDE  8   9   5  FOBS=    49.1  SIGMA=  18.7  PHAS=    54.3  FOM=  0.09
INDE  8   9   6  FOBS=   291.3  SIGMA=   2.6  PHAS=     2.8  FOM=  0.53
INDE  8   9   7  FOBS=    71.1  SIGMA=  12.6  PHAS=   103.2  FOM=  0.06
INDE  8   9   8  FOBS=   234.0  SIGMA=   4.0  PHAS=   170.4  FOM=  0.31
INDE  8   9   9  FOBS=    46.7  SIGMA=  21.3  PHAS=   316.5  FOM=  0.04
INDE  8   9  10  FOBS=   121.8  SIGMA=   8.1  PHAS=    57.4  FOM=  0.16
INDE  8   9  11  FOBS=    70.2  SIGMA=  43.2  PHAS=   214.6  FOM=  0.16
INDE  8   9  12  FOBS=    77.8  SIGMA=  11.8  PHAS=   303.2  FOM=  0.03
INDE  8  10   0  FOBS=   177.5  SIGMA=   2.8  PHAS=   123.6  FOM=  0.92
INDE  8  10   1  FOBS=   192.0  SIGMA=   2.7  PHAS=   357.2  FOM=  0.87
INDE  8  10   2  FOBS=   374.7  SIGMA=   1.7  PHAS=   329.0  FOM=  0.67
INDE  8  10   3  FOBS=   206.2  SIGMA=   3.0  PHAS=   148.9  FOM=  0.79
INDE  8  10   4  FOBS=   262.3  SIGMA=   2.5  PHAS=    69.8  FOM=  0.30
INDE  8  10   5  FOBS=   249.1  SIGMA=   2.8  PHAS=   198.2  FOM=  0.43
INDE  8  10   7  FOBS=   160.8  SIGMA=   5.3  PHAS=    39.2  FOM=  0.19
INDE  8  10   8  FOBS=   194.4  SIGMA=   4.7  PHAS=   334.9  FOM=  0.27
INDE  8  10   9  FOBS=    90.4  SIGMA=  10.0  PHAS=   274.4  FOM=  0.13
INDE  8  10  10  FOBS=   106.5  SIGMA=  10.8  PHAS=    69.5  FOM=  0.08
INDE  8  10  11  FOBS=    50.2  SIGMA=  33.8  PHAS=   244.4  FOM=  0.08
INDE  8  10  12  FOBS=   168.1  SIGMA=   5.2  PHAS=    77.7  FOM=  0.01
INDE  8  11   0  FOBS=   105.9  SIGMA=   4.8  PHAS=   225.2  FOM=  0.91
INDE  8  11   1  FOBS=   107.9  SIGMA=   4.9  PHAS=    32.0  FOM=  0.87
INDE  8  11   2  FOBS=   117.1  SIGMA=   4.8  PHAS=   243.0  FOM=  0.64
INDE  8  11   3  FOBS=    89.4  SIGMA=   6.9  PHAS=   287.5  FOM=  0.07
INDE  8  11   4  FOBS=   329.3  SIGMA=   2.1  PHAS=   155.7  FOM=  0.77
INDE  8  11   5  FOBS=    70.8  SIGMA=  10.0  PHAS=   203.4  FOM=  0.15
INDE  8  11   6  FOBS=    72.7  SIGMA=  10.8  PHAS=    24.3  FOM=  0.29
INDE  8  11   7  FOBS=    69.1  SIGMA=  41.3  PHAS=   190.9  FOM=  0.09
INDE  8  11   8  FOBS=   163.7  SIGMA=   5.1  PHAS=   116.4  FOM=  0.10
INDE  8  11   9  FOBS=   127.5  SIGMA=   8.1  PHAS=    34.4  FOM=  0.08
INDE  8  11  10  FOBS=   148.0  SIGMA=   6.5  PHAS=     2.1  FOM=  0.01
```

Fig. 10A-128

```
INDE  8  11  11  FOBS=   41.1  SIGMA=  19.0  PHAS=  222.9  FOM= 0.41
INDE  8  11  12  FOBS=   81.8  SIGMA=  13.3  PHAS=   66.6  FOM= 0.02
INDE  8  12   0  FOBS=  154.0  SIGMA=   3.4  PHAS=  182.1  FOM= 0.94
INDE  8  12   1  FOBS=  244.6  SIGMA=   2.2  PHAS=    4.8  FOM= 0.84
INDE  8  12   2  FOBS=  357.8  SIGMA=   1.8  PHAS=   55.2  FOM= 0.97
INDE  8  12   3  FOBS=  288.8  SIGMA=   2.2  PHAS=  157.5  FOM= 0.97
INDE  8  12   4  FOBS=  390.8  SIGMA=   1.8  PHAS=  287.5  FOM= 0.89
INDE  8  12   5  FOBS=   93.4  SIGMA=   7.7  PHAS=  121.8  FOM= 0.14
INDE  8  12   6  FOBS=  125.6  SIGMA=   6.3  PHAS=  302.7  FOM= 0.16
INDE  8  12   7  FOBS=  128.4  SIGMA=   6.3  PHAS=  217.7  FOM= 0.14
INDE  8  12   8  FOBS=  122.7  SIGMA=   7.4  PHAS=   98.4  FOM= 0.07
INDE  8  12   9  FOBS=  107.1  SIGMA=   8.8  PHAS=   67.4  FOM= 0.12
INDE  8  12  10  FOBS=   99.8  SIGMA=   8.5  PHAS=  248.3  FOM= 0.05
INDE  8  12  11  FOBS=   75.7  SIGMA=  11.9  PHAS=  227.7  FOM= 0.02
INDE  8  13   0  FOBS=  278.2  SIGMA=   1.9  PHAS=  223.8  FOM= 0.93
INDE  8  13   1  FOBS=  177.7  SIGMA=   3.0  PHAS=  325.4  FOM= 0.92
INDE  8  13   2  FOBS=  120.7  SIGMA=   5.1  PHAS=  262.6  FOM= 0.79
INDE  8  13   3  FOBS=  176.0  SIGMA=   3.5  PHAS=  230.0  FOM= 0.12
INDE  8  13   4  FOBS=  206.4  SIGMA=   3.2  PHAS=  156.6  FOM= 0.85
INDE  8  13   5  FOBS=  441.1  SIGMA=   2.0  PHAS=   36.5  FOM= 0.94
INDE  8  13   6  FOBS=  266.7  SIGMA=   3.0  PHAS=  307.9  FOM= 0.54
INDE  8  13   7  FOBS=  222.8  SIGMA=   4.1  PHAS=  205.4  FOM= 0.57
INDE  8  13   8  FOBS=  124.4  SIGMA=   7.5  PHAS=  169.7  FOM= 0.14
INDE  8  13   9  FOBS=   99.6  SIGMA=   8.0  PHAS=  262.4  FOM= 0.11
INDE  8  13  10  FOBS=   91.3  SIGMA=   8.9  PHAS=  245.8  FOM= 0.12
INDE  8  13  11  FOBS=  110.2  SIGMA=   7.6  PHAS=  105.3  FOM= 0.19
INDE  8  14   0  FOBS=  133.4  SIGMA=   4.0  PHAS=   62.5  FOM= 0.13
INDE  8  14   1  FOBS=  185.4  SIGMA=   2.9  PHAS=   16.1  FOM= 0.76
INDE  8  14   2  FOBS=  261.0  SIGMA=   2.3  PHAS=  211.0  FOM= 0.52
INDE  8  14   3  FOBS=  326.2  SIGMA=   2.0  PHAS=  204.1  FOM= 0.26
INDE  8  14   4  FOBS=   99.7  SIGMA=   6.7  PHAS=   54.5  FOM= 0.13
INDE  8  14   5  FOBS=  370.0  SIGMA=   2.3  PHAS=    4.4  FOM= 0.90
INDE  8  14   6  FOBS=  206.3  SIGMA=   4.0  PHAS=   13.6  FOM= 0.06
INDE  8  14   7  FOBS=  165.3  SIGMA=   5.7  PHAS=  164.0  FOM= 0.64
INDE  8  14   8  FOBS=   74.9  SIGMA=  11.5  PHAS=  305.4  FOM= 0.31
INDE  8  14   9  FOBS=  179.0  SIGMA=   4.5  PHAS=  324.3  FOM= 0.20
INDE  8  14  10  FOBS=   93.3  SIGMA=   9.2  PHAS=  142.3  FOM= 0.32
INDE  8  14  11  FOBS=  113.6  SIGMA=   7.0  PHAS=  199.7  FOM= 0.04
INDE  8  15   0  FOBS=  243.7  SIGMA=   2.2  PHAS=  136.6  FOM= 0.68
INDE  8  15   1  FOBS=  370.0  SIGMA=   1.7  PHAS=  210.0  FOM= 0.50
INDE  8  15   2  FOBS=  102.6  SIGMA=   5.7  PHAS=   91.6  FOM= 0.03
INDE  8  15   3  FOBS=  138.4  SIGMA=   4.7  PHAS=  208.3  FOM= 0.35
INDE  8  15   4  FOBS=  122.2  SIGMA=   5.7  PHAS=   83.3  FOM= 0.42
INDE  8  15   5  FOBS=  313.1  SIGMA=   2.7  PHAS=  288.9  FOM= 0.76
INDE  8  15   6  FOBS=   41.9  SIGMA=  19.1  PHAS=  124.1  FOM= 0.14
INDE  8  15   7  FOBS=   67.9  SIGMA=  12.5  PHAS=    1.2  FOM= 0.19
INDE  8  15   8  FOBS=   79.7  SIGMA=   9.6  PHAS=  234.0  FOM= 0.13
INDE  8  15   9  FOBS=   96.8  SIGMA=   7.8  PHAS=  112.7  FOM= 0.10
INDE  8  15  10  FOBS=   88.0  SIGMA=   9.3  PHAS=  276.1  FOM= 0.06
INDE  8  15  11  FOBS=   59.0  SIGMA=  13.9  PHAS=  152.2  FOM= 0.05
INDE  8  16   0  FOBS=  559.9  SIGMA=   1.9  PHAS=  359.2  FOM= 0.87
INDE  8  16   1  FOBS=  195.9  SIGMA=   2.9  PHAS=  300.3  FOM= 0.78
INDE  8  16   2  FOBS=  284.8  SIGMA=   2.2  PHAS=  181.5  FOM= 0.86
INDE  8  16   3  FOBS=  217.4  SIGMA=   3.0  PHAS=  261.5  FOM= 0.64
INDE  8  16   4  FOBS=  122.2  SIGMA=   5.9  PHAS=  179.8  FOM= 0.28
INDE  8  16   5  FOBS=  193.8  SIGMA=   4.3  PHAS=  200.7  FOM= 0.27
INDE  8  16   6  FOBS=   70.9  SIGMA=  11.6  PHAS=  347.1  FOM= 0.11
INDE  8  16   7  FOBS=   50.3  SIGMA=  32.4  PHAS=  177.1  FOM= 0.11
INDE  8  16   8  FOBS=  123.3  SIGMA=   6.3  PHAS=  116.7  FOM= 0.40
INDE  8  16   9  FOBS=   73.0  SIGMA=  12.0  PHAS=  208.8  FOM= 0.03
INDE  8  16  10  FOBS=   62.4  SIGMA=  13.3  PHAS=   94.8  FOM= 0.02
INDE  8  16  11  FOBS=   65.8  SIGMA=  12.9  PHAS=   21.1  FOM= 0.01
INDE  8  17   0  FOBS=  377.9  SIGMA=   1.8  PHAS=  132.2  FOM= 0.86
INDE  8  17   1  FOBS=   88.0  SIGMA=   6.3  PHAS=  287.1  FOM= 0.35
INDE  8  17   2  FOBS=  131.9  SIGMA=   4.7  PHAS=  357.7  FOM= 0.64
INDE  8  17   4  FOBS=  179.1  SIGMA= 265.2  PHAS=   34.2  FOM= 0.20
INDE  8  17   5  FOBS=  141.1  SIGMA=   5.9  PHAS=  344.2  FOM= 0.03
INDE  8  17   6  FOBS=  191.6  SIGMA=   3.9  PHAS=  212.0  FOM= 0.10
INDE  8  17   7  FOBS=   71.6  SIGMA=  10.5  PHAS=   56.6  FOM= 0.16
INDE  8  17   8  FOBS=   76.0  SIGMA=   9.8  PHAS=  285.2  FOM= 0.08
INDE  8  17   9  FOBS=   65.1  SIGMA=  11.9  PHAS=  138.3  FOM= 0.18
```

Fig. 10A-129

```
INDE   8  17  10  FOBS=   101.0  SIGMA=  55.5  PHAS=   21.7  FOM=  0.04
INDE   8  18   0  FOBS=   272.3  SIGMA=   2.1  PHAS=  155.7  FOM=  0.93
INDE   8  18   1  FOBS=   241.6  SIGMA=   2.4  PHAS=  321.9  FOM=  0.83
INDE   8  18   2  FOBS=   113.9  SIGMA=   5.4  PHAS=  225.7  FOM=  0.27
INDE   8  18   3  FOBS=    87.8  SIGMA=   8.2  PHAS=  325.6  FOM=  0.12
INDE   8  18   4  FOBS=   180.4  SIGMA=   4.3  PHAS=  252.2  FOM=  0.35
INDE   8  18   5  FOBS=   164.1  SIGMA=   4.5  PHAS=  218.7  FOM=  0.80
INDE   8  18   6  FOBS=   249.9  SIGMA=   3.2  PHAS=  334.0  FOM=  0.90
INDE   8  18   7  FOBS=    81.2  SIGMA=   8.8  PHAS=  326.4  FOM=  0.04
INDE   8  18   8  FOBS=   132.7  SIGMA=   5.6  PHAS=  215.6  FOM=  0.29
INDE   8  18   9  FOBS=    61.3  SIGMA=  35.0  PHAS=  286.6  FOM=  0.07
INDE   8  19   0  FOBS=   162.5  SIGMA=   3.4  PHAS=  293.3  FOM=  0.40
INDE   8  19   1  FOBS=   187.4  SIGMA=   3.2  PHAS=   58.0  FOM=  0.45
INDE   8  19   2  FOBS=   121.3  SIGMA=   5.3  PHAS=   91.7  FOM=  0.35
INDE   8  19   3  FOBS=   130.6  SIGMA=   5.5  PHAS=  351.5  FOM=  0.49
INDE   8  19   4  FOBS=    95.4  SIGMA=   7.3  PHAS=  155.7  FOM=  0.03
INDE   8  19   5  FOBS=   338.0  SIGMA=   2.3  PHAS=  113.3  FOM=  0.00
INDE   8  19   6  FOBS=   102.1  SIGMA=   6.9  PHAS=  306.7  FOM=  0.28
INDE   8  19   7  FOBS=   102.9  SIGMA=   6.8  PHAS=  181.3  FOM=  0.29
INDE   8  19   8  FOBS=    74.2  SIGMA=   9.9  PHAS=  236.9  FOM=  0.31
INDE   8  19   9  FOBS=    77.3  SIGMA=   9.3  PHAS=   99.2  FOM=  0.07
INDE   8  19  10  FOBS=    71.3  SIGMA=  10.5  PHAS=   28.5  FOM=  0.03
INDE   8  20   0  FOBS=   151.3  SIGMA=   3.7  PHAS=  108.3  FOM=  0.91
INDE   8  20   1  FOBS=   189.0  SIGMA=   3.0  PHAS=   90.5  FOM=  0.54
INDE   8  20   2  FOBS=   151.1  SIGMA=   4.7  PHAS=   29.3  FOM=  0.18
INDE   8  20   3  FOBS=   193.3  SIGMA=   3.5  PHAS=   19.3  FOM=  0.61
INDE   8  20   4  FOBS=    45.2  SIGMA=  27.2  PHAS=  358.1  FOM=  0.18
INDE   8  20   5  FOBS=   210.1  SIGMA=   3.3  PHAS=  101.4  FOM=  0.86
INDE   8  20   6  FOBS=   144.5  SIGMA=   4.9  PHAS=  114.5  FOM=  0.42
INDE   8  20   7  FOBS=    77.8  SIGMA=   9.1  PHAS=  198.1  FOM=  0.10
INDE   8  20   8  FOBS=    62.1  SIGMA=  12.5  PHAS=  122.9  FOM=  0.04
INDE   8  21   0  FOBS=    94.1  SIGMA=   5.6  PHAS=   71.5  FOM=  0.08
INDE   8  21   1  FOBS=    88.3  SIGMA=   6.9  PHAS=  356.4  FOM=  0.31
INDE   8  21   2  FOBS=   170.5  SIGMA=   3.9  PHAS=   80.0  FOM=  0.18
INDE   8  21   3  FOBS=    70.4  SIGMA=   9.3  PHAS=  259.6  FOM=  0.14
INDE   8  21   4  FOBS=   209.1  SIGMA=   3.2  PHAS=   74.5  FOM=  0.79
INDE   8  21   5  FOBS=    81.6  SIGMA=   8.2  PHAS=  276.2  FOM=  0.09
INDE   8  21   6  FOBS=   227.0  SIGMA=   3.0  PHAS=  347.3  FOM=  0.82
INDE   8  21   7  FOBS=   119.5  SIGMA=   5.8  PHAS=  121.6  FOM=  0.57
INDE   8  21   8  FOBS=    62.4  SIGMA=  11.0  PHAS=  290.8  FOM=  0.02
INDE   8  21   9  FOBS=    76.3  SIGMA=   9.5  PHAS=  294.5  FOM=  0.02
INDE   8  22   0  FOBS=   145.2  SIGMA=   4.0  PHAS=  183.4  FOM=  0.69
INDE   8  22   1  FOBS=   173.0  SIGMA=   3.6  PHAS=  259.3  FOM=  0.45
INDE   8  22   2  FOBS=    76.1  SIGMA=   7.5  PHAS=  113.0  FOM=  0.41
INDE   8  22   3  FOBS=    74.9  SIGMA=   8.3  PHAS=  252.4  FOM=  0.03
INDE   8  22   4  FOBS=    96.8  SIGMA=   6.4  PHAS=  322.5  FOM=  0.45
INDE   8  22   5  FOBS=    95.1  SIGMA=   6.9  PHAS=  255.2  FOM=  0.16
INDE   8  22   6  FOBS=    50.2  SIGMA=  19.7  PHAS=    9.6  FOM=  0.12
INDE   8  22   7  FOBS=    63.4  SIGMA=  10.3  PHAS=  132.0  FOM=  0.08
INDE   8  22   8  FOBS=    84.9  SIGMA=   8.0  PHAS=  339.5  FOM=  0.27
INDE   8  23   0  FOBS=   134.0  SIGMA=   4.3  PHAS=  219.1  FOM=  0.74
INDE   8  23   1  FOBS=   127.6  SIGMA=   4.4  PHAS=   72.7  FOM=  0.77
INDE   8  23   2  FOBS=    52.0  SIGMA=  11.8  PHAS=  344.5  FOM=  0.06
INDE   8  23   3  FOBS=   136.3  SIGMA=   4.5  PHAS=  248.8  FOM=  0.39
INDE   8  23   4  FOBS=    40.9  SIGMA=  21.1  PHAS=   92.2  FOM=  0.10
INDE   8  23   5  FOBS=    53.8  SIGMA=  12.8  PHAS=  205.0  FOM=  0.07
INDE   8  23   6  FOBS=    45.8  SIGMA=  12.6  PHAS=  342.9  FOM=  0.40
INDE   8  23   7  FOBS=    99.3  SIGMA=   6.6  PHAS=  287.5  FOM=  0.03
INDE   8  24   0  FOBS=    85.7  SIGMA=   6.0  PHAS=  255.5  FOM=  0.16
INDE   8  24   1  FOBS=    77.7  SIGMA=   6.8  PHAS=   73.5  FOM=  0.04
INDE   8  24   2  FOBS=    80.5  SIGMA=   6.8  PHAS=  254.1  FOM=  0.11
INDE   8  24   3  FOBS=    98.8  SIGMA=  83.8  PHAS=   30.2  FOM=  0.08
INDE   8  24   4  FOBS=   111.6  SIGMA=   5.4  PHAS=  131.6  FOM=  0.20
INDE   8  24   5  FOBS=   134.2  SIGMA=   4.7  PHAS=   15.5  FOM=  0.57
INDE   8  24   6  FOBS=    89.7  SIGMA=   7.0  PHAS=  302.0  FOM=  0.03
INDE   8  24   7  FOBS=    95.1  SIGMA=   6.7  PHAS=  193.0  FOM=  0.14
INDE   8  25   0  FOBS=   138.1  SIGMA=   3.9  PHAS=  303.1  FOM=  0.42
INDE   8  25   1  FOBS=    53.6  SIGMA=  10.3  PHAS=   24.0  FOM=  0.11
INDE   8  25   2  FOBS=   121.3  SIGMA=   4.5  PHAS=  115.5  FOM=  0.13
INDE   8  25   3  FOBS=    48.8  SIGMA=  12.1  PHAS=  190.0  FOM=  0.19
INDE   8  25   4  FOBS=   105.1  SIGMA=   5.7  PHAS=   13.9  FOM=  0.63
```

Fig. 10A-130

```
INDE  8 25  5 FOBS=  78.3 SIGMA=  8.0 PHAS= 308.3 FOM= 0.10
INDE  8 25  6 FOBS= 125.3 SIGMA=  5.0 PHAS= 127.6 FOM= 0.22
INDE  8 26  0 FOBS= 109.1 SIGMA=  4.9 PHAS=  37.9 FOM= 0.75
INDE  8 26  1 FOBS= 130.3 SIGMA=  4.1 PHAS= 140.0 FOM= 0.36
INDE  8 26  2 FOBS=  37.4 SIGMA= 15.9 PHAS= 201.9 FOM= 0.30
INDE  8 26  3 FOBS=  75.5 SIGMA=  7.8 PHAS=  34.9 FOM= 0.93
INDE  8 26  4 FOBS=  95.3 SIGMA=  6.1 PHAS= 312.2 FOM= 0.44
INDE  8 26  5 FOBS=  67.1 SIGMA=  9.1 PHAS= 180.3 FOM= 0.18
INDE  8 26  6 FOBS=  76.0 SIGMA= 41.7 PHAS= 352.1 FOM= 0.07
INDE  8 27  0 FOBS=  35.3 SIGMA= 14.4 PHAS= 283.8 FOM= 0.45
INDE  8 27  1 FOBS=  40.0 SIGMA= 12.5 PHAS= 154.4 FOM= 0.63
INDE  8 27  2 FOBS=  97.7 SIGMA=  5.5 PHAS=  63.7 FOM= 0.14
INDE  8 27  3 FOBS=  70.4 SIGMA=  7.8 PHAS= 278.2 FOM= 0.02
INDE  8 27  4 FOBS= 143.7 SIGMA=  4.1 PHAS= 194.6 FOM= 0.46
INDE  8 27  5 FOBS= 117.9 SIGMA= 10.2 PHAS=  34.5 FOM= 0.14
INDE  8 28  0 FOBS= 149.1 SIGMA=  3.1 PHAS=  23.7 FOM= 0.66
INDE  8 28  1 FOBS=  83.1 SIGMA=  6.0 PHAS=  10.8 FOM= 0.03
INDE  8 28  2 FOBS=  71.7 SIGMA= 35.6 PHAS= 262.4 FOM= 0.12
INDE  8 28  3 FOBS=  68.3 SIGMA=  8.0 PHAS= 149.4 FOM= 0.17
INDE  8 29  0 FOBS= 148.9 SIGMA=  3.2 PHAS=  26.6 FOM= 0.62
INDE  8 29  1 FOBS=  81.3 SIGMA=  6.0 PHAS= 280.1 FOM= 0.10
INDE  8 29  2 FOBS= 108.5 SIGMA=  6.0 PHAS= 243.8 FOM= 0.03
INDE  9  0  0 FOBS=  42.8 SIGMA= 14.8 PHAS= 180.0 FOM= 0.10
INDE  9  0  1 FOBS=  66.2 SIGMA= 10.2 PHAS=   0.0 FOM= 0.13
INDE  9  0  2 FOBS= 269.5 SIGMA=  3.2 PHAS= 180.0 FOM= 1.00
INDE  9  0  3 FOBS= 146.0 SIGMA= 10.3 PHAS=   0.0 FOM= 0.00
INDE  9  0  4 FOBS= 261.0 SIGMA=  6.7 PHAS=   0.0 FOM= 0.95
INDE  9  0  5 FOBS= 622.8 SIGMA=  3.0 PHAS= 180.0 FOM= 1.00
INDE  9  0  6 FOBS= 154.5 SIGMA=  7.4 PHAS=   0.0 FOM= 0.40
INDE  9  0  7 FOBS= 235.8 SIGMA=  5.4 PHAS=   0.0 FOM= 0.21
INDE  9  0  8 FOBS=  54.6 SIGMA= 30.6 PHAS= 180.0 FOM= 0.01
INDE  9  0  9 FOBS= 182.9 SIGMA=  9.5 PHAS= 180.0 FOM= 0.04
INDE  9  0 10 FOBS= 118.3 SIGMA= 21.7 PHAS= 180.0 FOM= 0.00
INDE  9  0 11 FOBS=  53.0 SIGMA= 36.3 PHAS=   0.0 FOM= 0.13
INDE  9  0 12 FOBS= 104.1 SIGMA= 13.7 PHAS= 180.0 FOM= 0.04
INDE  9  1  0 FOBS= 302.7 SIGMA=  1.8 PHAS= 225.2 FOM= 0.96
INDE  9  1  1 FOBS= 214.6 SIGMA=  2.5 PHAS= 138.8 FOM= 0.96
INDE  9  1  2 FOBS= 110.3 SIGMA=  5.6 PHAS= 289.1 FOM= 0.26
INDE  9  1  3 FOBS= 254.4 SIGMA=  2.8 PHAS= 100.7 FOM= 0.83
INDE  9  1  4 FOBS= 252.1 SIGMA=  4.0 PHAS= 199.7 FOM= 0.48
INDE  9  1  5 FOBS= 155.2 SIGMA=  5.3 PHAS= 131.4 FOM= 0.17
INDE  9  1  6 FOBS=  79.6 SIGMA=  9.5 PHAS=  34.7 FOM= 0.05
INDE  9  1  7 FOBS=  84.1 SIGMA= 11.1 PHAS=  40.9 FOM= 0.04
INDE  9  1  8 FOBS= 158.1 SIGMA=  7.6 PHAS= 274.1 FOM= 0.27
INDE  9  1  9 FOBS= 114.3 SIGMA= 10.5 PHAS= 119.3 FOM= 0.09
INDE  9  1 10 FOBS=  86.7 SIGMA= 13.0 PHAS=   5.5 FOM= 0.12
INDE  9  1 11 FOBS=  85.3 SIGMA= 14.1 PHAS= 212.4 FOM= 0.09
INDE  9  1 12 FOBS=  91.8 SIGMA= 57.4 PHAS= 201.6 FOM= 0.02
INDE  9  2  0 FOBS= 201.6 SIGMA=  2.5 PHAS= 264.2 FOM= 0.94
INDE  9  2  1 FOBS= 105.6 SIGMA=  5.2 PHAS= 115.9 FOM= 0.59
INDE  9  2  2 FOBS= 422.9 SIGMA=  2.1 PHAS= 349.2 FOM= 0.91
INDE  9  2  3 FOBS= 423.1 SIGMA=  1.8 PHAS= 275.8 FOM= 0.75
INDE  9  2  4 FOBS= 178.5 SIGMA=  4.1 PHAS= 239.2 FOM= 0.41
INDE  9  2  5 FOBS=  67.9 SIGMA= 13.1 PHAS= 185.7 FOM= 0.08
INDE  9  2  6 FOBS= 214.6 SIGMA=  4.1 PHAS=  13.0 FOM= 0.75
INDE  9  2  7 FOBS= 376.1 SIGMA=  3.5 PHAS= 278.3 FOM= 0.87
INDE  9  2  8 FOBS=  97.1 SIGMA= 13.0 PHAS= 133.3 FOM= 0.05
INDE  9  2  9 FOBS= 118.0 SIGMA=  8.2 PHAS= 126.8 FOM= 0.30
INDE  9  2 10 FOBS= 113.7 SIGMA=  9.0 PHAS= 275.2 FOM= 0.12
INDE  9  2 11 FOBS=  86.1 SIGMA= 11.1 PHAS= 171.7 FOM= 0.08
INDE  9  2 12 FOBS=  61.3 SIGMA= 23.7 PHAS=  11.5 FOM= 0.01
INDE  9  3  0 FOBS= 166.3 SIGMA=  3.1 PHAS= 162.7 FOM= 0.81
INDE  9  3  1 FOBS= 164.3 SIGMA=  3.9 PHAS= 267.7 FOM= 0.59
INDE  9  3  2 FOBS= 137.8 SIGMA=  4.5 PHAS= 149.4 FOM= 0.74
INDE  9  3  3 FOBS= 195.8 SIGMA=  3.2 PHAS= 221.7 FOM= 0.62
INDE  9  3  4 FOBS= 189.5 SIGMA=  3.7 PHAS=  44.8 FOM= 0.20
INDE  9  3  5 FOBS= 224.8 SIGMA=  3.9 PHAS=  36.1 FOM= 0.54
INDE  9  3  6 FOBS= 220.8 SIGMA=  4.5 PHAS= 267.0 FOM= 0.86
INDE  9  3  7 FOBS=  93.0 SIGMA= 11.5 PHAS= 163.1 FOM= 0.12
INDE  9  3  8 FOBS= 108.1 SIGMA=  8.7 PHAS= 162.3 FOM= 0.01
INDE  9  3  9 FOBS= 155.3 SIGMA=  6.2 PHAS= 337.7 FOM= 0.12
```

Fig. 10A-131

```
INDE  9  3  10  FOBS=   161.8  SIGMA=   6.0  PHAS=  101.9  FOM=  0.07
INDE  9  3  11  FOBS=    65.9  SIGMA=  14.1  PHAS=  226.2  FOM=  0.03
INDE  9  3  12  FOBS=    84.2  SIGMA=  11.7  PHAS=  202.4  FOM=  0.01
INDE  9  4   0  FOBS=   205.0  SIGMA=   2.9  PHAS=  196.5  FOM=  0.88
INDE  9  4   1  FOBS=   128.1  SIGMA=   4.7  PHAS=   62.7  FOM=  0.36
INDE  9  4   2  FOBS=   418.1  SIGMA=   1.7  PHAS=  305.6  FOM=  0.95
INDE  9  4   4  FOBS=   392.1  SIGMA=   2.1  PHAS=  253.7  FOM=  0.96
INDE  9  4   5  FOBS=   176.9  SIGMA=   4.9  PHAS=   17.4  FOM=  0.14
INDE  9  4   6  FOBS=    85.6  SIGMA=  10.4  PHAS=  135.7  FOM=  0.24
INDE  9  4   8  FOBS=    65.5  SIGMA=  41.2  PHAS=  223.7  FOM=  0.06
INDE  9  4   9  FOBS=   212.5  SIGMA=   4.5  PHAS=   55.9  FOM=  0.37
INDE  9  4  10  FOBS=   123.2  SIGMA=   7.6  PHAS=  292.9  FOM=  0.08
INDE  9  4  11  FOBS=    73.0  SIGMA=  16.5  PHAS=  194.5  FOM=  0.22
INDE  9  4  12  FOBS=    90.3  SIGMA=  10.9  PHAS=  348.1  FOM=  0.07
INDE  9  5   0  FOBS=   223.6  SIGMA=   2.9  PHAS=  265.7  FOM=  0.96
INDE  9  5   1  FOBS=   183.3  SIGMA=   3.0  PHAS=  323.1  FOM=  0.85
INDE  9  5   2  FOBS=    80.3  SIGMA=   7.0  PHAS=   72.0  FOM=  0.69
INDE  9  5   3  FOBS=   249.2  SIGMA=   2.6  PHAS=  146.9  FOM=  0.93
INDE  9  5   4  FOBS=   199.6  SIGMA=   4.0  PHAS=   66.2  FOM=  0.32
INDE  9  5   5  FOBS=   297.0  SIGMA=   2.6  PHAS=  138.4  FOM=  0.93
INDE  9  5   6  FOBS=    89.3  SIGMA=  10.6  PHAS=  308.4  FOM=  0.20
INDE  9  5   8  FOBS=    81.2  SIGMA=  14.8  PHAS=   89.3  FOM=  0.15
INDE  9  5   9  FOBS=    94.4  SIGMA=  10.1  PHAS=  302.7  FOM=  0.06
INDE  9  5  10  FOBS=    73.4  SIGMA=  13.2  PHAS=  177.9  FOM=  0.06
INDE  9  5  11  FOBS=    56.3  SIGMA=  15.8  PHAS=   10.5  FOM=  0.13
INDE  9  6   0  FOBS=   170.1  SIGMA=   3.3  PHAS=  213.9  FOM=  0.85
INDE  9  6   1  FOBS=   170.7  SIGMA=   3.2  PHAS=  153.5  FOM=  0.33
INDE  9  6   2  FOBS=   292.9  SIGMA=   2.1  PHAS=  237.0  FOM=  0.96
INDE  9  6   3  FOBS=   184.6  SIGMA=   4.2  PHAS=  123.0  FOM=  0.40
INDE  9  6   4  FOBS=   219.3  SIGMA=   3.3  PHAS=   79.2  FOM=  0.49
INDE  9  6   5  FOBS=    57.4  SIGMA=  14.5  PHAS=  294.5  FOM=  0.01
INDE  9  6   6  FOBS=   337.7  SIGMA=   2.5  PHAS=   36.8  FOM=  0.82
INDE  9  6   7  FOBS=   156.0  SIGMA=   6.6  PHAS=   92.5  FOM=  0.71
INDE  9  6   8  FOBS=    70.2  SIGMA=  47.8  PHAS=  223.9  FOM=  0.08
INDE  9  6   9  FOBS=    48.9  SIGMA=  17.4  PHAS=  322.8  FOM=  0.15
INDE  9  6  10  FOBS=    46.7  SIGMA=  17.3  PHAS=   84.5  FOM=  0.13
INDE  9  6  11  FOBS=    55.5  SIGMA=  30.1  PHAS=  192.1  FOM=  0.40
INDE  9  6  12  FOBS=    63.3  SIGMA=  16.5  PHAS=   18.7  FOM=  0.05
INDE  9  7   0  FOBS=    54.9  SIGMA=   9.0  PHAS=  121.4  FOM=  0.13
INDE  9  7   1  FOBS=   189.2  SIGMA=   3.0  PHAS=   39.9  FOM=  0.77
INDE  9  7   2  FOBS=    77.2  SIGMA=   9.4  PHAS=  149.0  FOM=  0.15
INDE  9  7   3  FOBS=    92.3  SIGMA=   7.1  PHAS=  165.3  FOM=  0.21
INDE  9  7   4  FOBS=   288.9  SIGMA=   2.7  PHAS=   12.1  FOM=  0.92
INDE  9  7   5  FOBS=   289.9  SIGMA=   2.6  PHAS=  323.0  FOM=  0.52
INDE  9  7   6  FOBS=   129.0  SIGMA=   6.5  PHAS=   69.8  FOM=  0.03
INDE  9  7   7  FOBS=    96.1  SIGMA=  12.7  PHAS=  138.3  FOM=  0.14
INDE  9  7   9  FOBS=   171.0  SIGMA=   6.1  PHAS=  281.1  FOM=  0.40
INDE  9  7  10  FOBS=    62.4  SIGMA=  16.7  PHAS=  149.5  FOM=  0.27
INDE  9  7  11  FOBS=    66.6  SIGMA=  15.4  PHAS=  349.6  FOM=  0.10
INDE  9  7  12  FOBS=    73.7  SIGMA=  13.7  PHAS=  286.2  FOM=  0.01
INDE  9  8   0  FOBS=    60.3  SIGMA=   8.6  PHAS=  275.1  FOM=  0.09
INDE  9  8   1  FOBS=   303.6  SIGMA=   2.0  PHAS=  102.2  FOM=  0.92
INDE  9  8   2  FOBS=    65.2  SIGMA=  10.0  PHAS=  125.9  FOM=  0.14
INDE  9  8   3  FOBS=   188.8  SIGMA=   3.4  PHAS=    9.8  FOM=  0.44
INDE  9  8   4  FOBS=   238.4  SIGMA=   2.9  PHAS=   26.2  FOM=  0.83
INDE  9  8   5  FOBS=   299.6  SIGMA=   2.9  PHAS=  233.3  FOM=  0.86
INDE  9  8   7  FOBS=   165.0  SIGMA=   5.3  PHAS=  126.6  FOM=  0.38
INDE  9  8   8  FOBS=    60.6  SIGMA=  31.5  PHAS=  259.8  FOM=  0.12
INDE  9  8   9  FOBS=   122.7  SIGMA=   7.4  PHAS=  141.1  FOM=  0.09
INDE  9  8  10  FOBS=   115.1  SIGMA=   8.4  PHAS=   91.0  FOM=  0.10
INDE  9  8  11  FOBS=    87.8  SIGMA=  10.8  PHAS=  359.6  FOM=  0.06
INDE  9  8  12  FOBS=   123.7  SIGMA=   7.4  PHAS=  217.5  FOM=  0.26
INDE  9  9   1  FOBS=   113.7  SIGMA=   5.6  PHAS=   41.3  FOM=  0.13
INDE  9  9   2  FOBS=   226.2  SIGMA=   2.7  PHAS=  168.7  FOM=  0.69
INDE  9  9   3  FOBS=   167.3  SIGMA=   4.0  PHAS=   92.2  FOM=  0.07
INDE  9  9   4  FOBS=   187.1  SIGMA=   3.8  PHAS=   37.4  FOM=  0.38
INDE  9  9   5  FOBS=   122.5  SIGMA=   6.4  PHAS=  167.3  FOM=  0.38
INDE  9  9   6  FOBS=   127.6  SIGMA=   6.5  PHAS=   99.6  FOM=  0.45
INDE  9  9   7  FOBS=   163.9  SIGMA=   5.2  PHAS=  329.8  FOM=  0.11
INDE  9  9   8  FOBS=    68.3  SIGMA=  49.9  PHAS=  199.2  FOM=  0.12
INDE  9  9   9  FOBS=   129.1  SIGMA=   6.7  PHAS=  356.3  FOM=  0.18
```

Fig. 10A-132

```
INDE   9   9  10 FOBS=  103.5 SIGMA=  8.6 PHAS= 227.8 FOM= 0.04
INDE   9   9  11 FOBS=  110.1 SIGMA= 66.8 PHAS= 314.7 FOM= 0.02
INDE   9   9  12 FOBS=  156.0 SIGMA= 87.0 PHAS= 119.0 FOM= 0.00
INDE   9  10   0 FOBS=  125.9 SIGMA=  4.8 PHAS= 168.8 FOM= 0.63
INDE   9  10   1 FOBS=   70.5 SIGMA=  7.2 PHAS= 235.7 FOM= 0.26
INDE   9  10   2 FOBS=  270.9 SIGMA=  2.3 PHAS= 148.1 FOM= 0.92
INDE   9  10   3 FOBS=  101.1 SIGMA=  6.5 PHAS= 329.2 FOM= 0.41
INDE   9  10   4 FOBS=  120.8 SIGMA=  5.7 PHAS= 178.2 FOM= 0.37
INDE   9  10   6 FOBS=  133.1 SIGMA=  6.4 PHAS=  12.4 FOM= 0.17
INDE   9  10   7 FOBS=  165.0 SIGMA=  5.3 PHAS= 232.5 FOM= 0.09
INDE   9  10   8 FOBS=   83.5 SIGMA= 10.3 PHAS= 312.1 FOM= 0.04
INDE   9  10   9 FOBS=   66.8 SIGMA= 14.5 PHAS=  88.3 FOM= 0.08
INDE   9  10  10 FOBS=   59.8 SIGMA= 29.8 PHAS= 232.8 FOM= 0.10
INDE   9  10  11 FOBS=   71.8 SIGMA= 15.7 PHAS= 335.8 FOM= 0.03
INDE   9  11   0 FOBS=  439.6 SIGMA=  1.6 PHAS= 259.5 FOM= 0.89
INDE   9  11   1 FOBS=  124.5 SIGMA=  4.7 PHAS= 169.7 FOM= 0.34
INDE   9  11   2 FOBS=  145.7 SIGMA=  4.4 PHAS= 323.6 FOM= 0.46
INDE   9  11   3 FOBS=  135.9 SIGMA=  4.9 PHAS=  65.7 FOM= 0.11
INDE   9  11   4 FOBS=  285.7 SIGMA=  2.5 PHAS= 260.4 FOM= 0.84
INDE   9  11   5 FOBS=  210.0 SIGMA=  3.8 PHAS= 312.7 FOM= 0.72
INDE   9  11   6 FOBS=   48.2 SIGMA= 15.8 PHAS=  39.4 FOM= 0.08
INDE   9  11   7 FOBS=  136.8 SIGMA=  6.0 PHAS=  83.4 FOM= 0.15
INDE   9  11   8 FOBS=   58.0 SIGMA= 14.2 PHAS= 219.4 FOM= 0.15
INDE   9  11   9 FOBS=   57.8 SIGMA= 27.6 PHAS=  34.5 FOM= 0.08
INDE   9  11  10 FOBS=   88.4 SIGMA= 10.5 PHAS=  75.4 FOM= 0.07
INDE   9  11  11 FOBS=   68.1 SIGMA= 14.7 PHAS= 261.4 FOM= 0.02
INDE   9  12   0 FOBS=  221.4 SIGMA=  2.4 PHAS=   1.9 FOM= 0.93
INDE   9  12   1 FOBS=  108.4 SIGMA=  5.3 PHAS= 146.2 FOM= 0.23
INDE   9  12   2 FOBS=  120.7 SIGMA=  5.1 PHAS= 263.3 FOM= 0.17
INDE   9  12   3 FOBS=  151.3 SIGMA=  4.5 PHAS= 155.3 FOM= 0.22
INDE   9  12   4 FOBS=  105.1 SIGMA=  6.8 PHAS= 183.6 FOM= 0.07
INDE   9  12   5 FOBS=  189.9 SIGMA=  4.6 PHAS=  77.9 FOM= 0.62
INDE   9  12   6 FOBS=  195.6 SIGMA=  4.2 PHAS= 104.5 FOM= 0.59
INDE   9  12   7 FOBS=  118.1 SIGMA=  6.8 PHAS= 284.4 FOM= 0.11
INDE   9  12   8 FOBS=   45.7 SIGMA= 16.7 PHAS= 278.6 FOM= 0.06
INDE   9  12   9 FOBS=  102.1 SIGMA=  9.4 PHAS= 128.2 FOM= 0.22
INDE   9  12  10 FOBS=   66.9 SIGMA= 13.4 PHAS= 272.5 FOM= 0.73
INDE   9  12  11 FOBS=   78.2 SIGMA= 49.9 PHAS= 228.5 FOM= 0.04
INDE   9  13   0 FOBS=  143.0 SIGMA=  3.8 PHAS=  74.6 FOM= 0.47
INDE   9  13   1 FOBS=  175.3 SIGMA=  3.2 PHAS= 219.9 FOM= 0.47
INDE   9  13   2 FOBS=   53.7 SIGMA= 12.5 PHAS= 173.0 FOM= 0.06
INDE   9  13   3 FOBS=  139.9 SIGMA=  5.0 PHAS= 338.7 FOM= 0.68
INDE   9  13   5 FOBS=  208.4 SIGMA=  3.7 PHAS= 356.8 FOM= 0.68
INDE   9  13   6 FOBS=  127.4 SIGMA=  6.2 PHAS=  30.0 FOM= 0.29
INDE   9  13   8 FOBS=   73.9 SIGMA= 11.3 PHAS=  83.3 FOM= 0.11
INDE   9  13   9 FOBS=   95.1 SIGMA=  9.6 PHAS= 322.8 FOM= 0.07
INDE   9  13  10 FOBS=   77.0 SIGMA= 11.4 PHAS= 271.2 FOM= 0.05
INDE   9  13  11 FOBS=   96.1 SIGMA=  8.4 PHAS=  76.4 FOM= 0.03
INDE   9  14   0 FOBS=   44.4 SIGMA= 13.7 PHAS= 158.8 FOM= 0.04
INDE   9  14   1 FOBS=  165.5 SIGMA=  3.7 PHAS= 172.2 FOM= 0.57
INDE   9  14   2 FOBS=  154.9 SIGMA=  4.2 PHAS= 226.6 FOM= 0.67
INDE   9  14   3 FOBS=  165.2 SIGMA=  4.3 PHAS= 350.5 FOM= 0.11
INDE   9  14   4 FOBS=   40.7 SIGMA= 20.0 PHAS= 119.7 FOM= 0.15
INDE   9  14   5 FOBS=   85.4 SIGMA=  9.0 PHAS=  39.6 FOM= 0.19
INDE   9  14   6 FOBS=  222.8 SIGMA=  3.7 PHAS= 154.6 FOM= 0.50
INDE   9  14   7 FOBS=   95.0 SIGMA=  8.5 PHAS=  41.8 FOM= 0.19
INDE   9  14   8 FOBS=   57.6 SIGMA= 21.7 PHAS= 255.9 FOM= 0.01
INDE   9  14   9 FOBS=   61.6 SIGMA= 15.7 PHAS= 288.8 FOM= 0.10
INDE   9  15   0 FOBS=  116.4 SIGMA=  4.8 PHAS= 129.7 FOM= 0.71
INDE   9  15   1 FOBS=  496.5 SIGMA=  1.7 PHAS= 307.8 FOM= 0.95
INDE   9  15   2 FOBS=  157.6 SIGMA=  4.2 PHAS= 115.3 FOM= 0.81
INDE   9  15   3 FOBS=  158.7 SIGMA=  4.5 PHAS= 350.5 FOM= 0.82
INDE   9  15   4 FOBS=  219.7 SIGMA=  3.3 PHAS= 207.6 FOM= 0.60
INDE   9  15   5 FOBS=   94.0 SIGMA=  8.0 PHAS= 206.5 FOM= 0.05
INDE   9  15   6 FOBS=  152.1 SIGMA=  5.1 PHAS= 356.5 FOM= 0.18
INDE   9  15   7 FOBS=   88.8 SIGMA=  9.7 PHAS= 262.1 FOM= 0.09
INDE   9  15   8 FOBS=   70.2 SIGMA= 12.8 PHAS=  33.6 FOM= 0.09
INDE   9  16   0 FOBS=   86.7 SIGMA=  6.6 PHAS= 350.1 FOM= 0.05
INDE   9  16   1 FOBS=  157.5 SIGMA=  4.4 PHAS= 260.7 FOM= 0.51
INDE   9  16   2 FOBS=  160.7 SIGMA=  4.2 PHAS= 123.8 FOM= 0.56
INDE   9  16   3 FOBS=   54.1 SIGMA= 16.3 PHAS= 324.2 FOM= 0.10
```

Fig. 10A-133

```
INDE  9 16  4 FOBS=  85.5 SIGMA=   8.7 PHAS= 145.6 FOM= 0.13
INDE  9 16  5 FOBS= 135.6 SIGMA=   5.5 PHAS= 313.3 FOM= 0.10
INDE  9 16  6 FOBS=  42.4 SIGMA=  17.5 PHAS= 265.2 FOM= 0.07
INDE  9 16  7 FOBS=  78.3 SIGMA=  62.3 PHAS=  63.9 FOM= 0.12
INDE  9 16  8 FOBS=  59.7 SIGMA=  13.4 PHAS= 254.3 FOM= 0.19
INDE  9 16 10 FOBS=  73.0 SIGMA=  10.8 PHAS=  88.5 FOM= 0.03
INDE  9 17  0 FOBS= 278.9 SIGMA=   2.2 PHAS= 232.8 FOM= 0.95
INDE  9 17  1 FOBS= 268.0 SIGMA=   2.5 PHAS=  17.2 FOM= 0.95
INDE  9 17  2 FOBS= 199.7 SIGMA=   3.7 PHAS= 217.2 FOM= 0.62
INDE  9 17  3 FOBS= 416.7 SIGMA=   2.1 PHAS=  83.3 FOM= 0.92
INDE  9 17  4 FOBS= 138.5 SIGMA=   5.3 PHAS= 264.1 FOM= 0.57
INDE  9 17  5 FOBS=  58.7 SIGMA=  13.5 PHAS= 165.9 FOM= 0.05
INDE  9 17  6 FOBS=  97.1 SIGMA=   8.6 PHAS= 102.6 FOM= 0.23
INDE  9 17  7 FOBS= 115.0 SIGMA=   6.6 PHAS= 260.4 FOM= 0.30
INDE  9 17  8 FOBS=  86.1 SIGMA=   8.6 PHAS= 127.0 FOM= 0.17
INDE  9 17  9 FOBS=  47.6 SIGMA=  22.4 PHAS= 357.7 FOM= 0.06
INDE  9 17 10 FOBS=  79.3 SIGMA=  39.0 PHAS= 194.3 FOM= 0.08
INDE  9 18  0 FOBS= 108.2 SIGMA=   5.6 PHAS= 344.0 FOM= 0.61
INDE  9 18  1 FOBS=  92.0 SIGMA=   6.6 PHAS= 348.0 FOM= 0.22
INDE  9 18  2 FOBS= 271.4 SIGMA=   2.4 PHAS= 107.4 FOM= 0.84
INDE  9 18  3 FOBS=  68.8 SIGMA=  10.4 PHAS= 336.0 FOM= 0.21
INDE  9 18  4 FOBS= 184.3 SIGMA=   4.2 PHAS= 171.5 FOM= 0.84
INDE  9 18  5 FOBS=  81.8 SIGMA=  10.1 PHAS= 287.0 FOM= 0.05
INDE  9 18  6 FOBS= 103.4 SIGMA=   7.2 PHAS= 213.8 FOM= 0.17
INDE  9 18  7 FOBS= 101.5 SIGMA=   7.2 PHAS= 131.4 FOM= 0.23
INDE  9 18  8 FOBS=  69.7 SIGMA=  10.5 PHAS=   0.9 FOM= 0.11
INDE  9 18  9 FOBS= 129.7 SIGMA=   5.7 PHAS= 125.3 FOM= 0.16
INDE  9 19  0 FOBS= 159.9 SIGMA=   3.6 PHAS= 322.4 FOM= 0.37
INDE  9 19  1 FOBS=  50.6 SIGMA=  24.4 PHAS=  90.1 FOM= 0.17
INDE  9 19  2 FOBS=  90.5 SIGMA=   6.8 PHAS= 341.0 FOM= 0.16
INDE  9 19  3 FOBS= 233.7 SIGMA=   2.8 PHAS= 353.0 FOM= 0.71
INDE  9 19  4 FOBS= 188.4 SIGMA=   4.3 PHAS=  76.4 FOM= 0.21
INDE  9 19  5 FOBS= 114.6 SIGMA=   7.0 PHAS= 236.1 FOM= 0.50
INDE  9 19  6 FOBS= 121.9 SIGMA=   6.1 PHAS= 107.1 FOM= 0.47
INDE  9 19  7 FOBS=  78.4 SIGMA=   9.3 PHAS= 332.1 FOM= 0.19
INDE  9 19  8 FOBS=  68.0 SIGMA=  12.4 PHAS= 207.5 FOM= 0.03
INDE  9 19  9 FOBS=  91.0 SIGMA=   8.5 PHAS=  93.2 FOM= 0.02
INDE  9 20  0 FOBS=  91.7 SIGMA=   6.6 PHAS= 303.3 FOM= 0.24
INDE  9 20  1 FOBS= 206.6 SIGMA=   2.9 PHAS= 125.2 FOM= 0.62
INDE  9 20  2 FOBS= 279.3 SIGMA=   2.3 PHAS= 260.9 FOM= 0.47
INDE  9 20  3 FOBS= 121.7 SIGMA=   6.0 PHAS=  18.2 FOM= 0.49
INDE  9 20  4 FOBS= 212.1 SIGMA=   3.5 PHAS= 136.5 FOM= 0.80
INDE  9 20  5 FOBS= 213.4 SIGMA=   3.8 PHAS=   7.3 FOM= 0.67
INDE  9 20  6 FOBS=  61.7 SIGMA=  11.9 PHAS=  49.2 FOM= 0.11
INDE  9 20  7 FOBS=  63.5 SIGMA=  36.2 PHAS= 223.3 FOM= 0.16
INDE  9 20  8 FOBS=  62.1 SIGMA=  13.7 PHAS=  39.3 FOM= 0.07
INDE  9 21  0 FOBS= 252.0 SIGMA=   2.3 PHAS= 137.4 FOM= 0.92
INDE  9 21  1 FOBS= 104.6 SIGMA=   5.7 PHAS= 161.0 FOM= 0.51
INDE  9 21  2 FOBS=  85.8 SIGMA=   7.9 PHAS= 269.9 FOM= 0.24
INDE  9 21  3 FOBS= 167.6 SIGMA=   4.5 PHAS= 320.8 FOM= 0.22
INDE  9 21  4 FOBS= 102.8 SIGMA=   6.4 PHAS=  84.1 FOM= 0.33
INDE  9 21  5 FOBS= 125.6 SIGMA=   5.4 PHAS= 268.6 FOM= 0.28
INDE  9 21  6 FOBS= 121.7 SIGMA=   5.6 PHAS= 177.6 FOM= 0.01
INDE  9 21  7 FOBS= 103.8 SIGMA=   6.8 PHAS= 181.4 FOM= 0.05
INDE  9 21  8 FOBS=  66.5 SIGMA=  42.5 PHAS=  24.5 FOM= 0.06
INDE  9 22  0 FOBS= 259.8 SIGMA=   2.3 PHAS= 322.9 FOM= 0.82
INDE  9 22  1 FOBS= 123.6 SIGMA=   4.8 PHAS= 318.2 FOM= 0.10
INDE  9 22  2 FOBS=  81.2 SIGMA=   8.6 PHAS= 253.7 FOM= 0.19
INDE  9 22  3 FOBS= 121.4 SIGMA= 142.3 PHAS=  99.0 FOM= 0.12
INDE  9 22  4 FOBS=  89.6 SIGMA=   7.1 PHAS= 116.9 FOM= 0.10
INDE  9 22  5 FOBS=  59.2 SIGMA=  11.5 PHAS= 334.4 FOM= 0.29
INDE  9 22  6 FOBS=  65.6 SIGMA=  11.2 PHAS= 122.9 FOM= 0.06
INDE  9 22  7 FOBS=  85.5 SIGMA=   8.0 PHAS= 327.2 FOM= 0.08
INDE  9 23  0 FOBS= 114.3 SIGMA=   5.2 PHAS=   0.7 FOM= 0.79
INDE  9 23  1 FOBS=  53.7 SIGMA=  12.9 PHAS= 117.7 FOM= 0.09
INDE  9 23  2 FOBS= 321.0 SIGMA=   2.0 PHAS= 154.6 FOM= 0.96
INDE  9 23  3 FOBS= 116.0 SIGMA=   5.3 PHAS= 354.1 FOM= 0.36
INDE  9 23  4 FOBS=  44.7 SIGMA=  29.0 PHAS= 213.4 FOM= 0.08
INDE  9 23  5 FOBS= 144.1 SIGMA=   4.6 PHAS=  16.9 FOM= 0.11
INDE  9 23  6 FOBS=  64.5 SIGMA=  26.7 PHAS= 117.9 FOM= 0.05
INDE  9 23  7 FOBS=  39.9 SIGMA=  16.8 PHAS= 264.3 FOM= 0.08
```

Fig. 10A-134

```
INDE    9  24   0  FOBS=   62.2  SIGMA=   9.6  PHAS=  106.9  FOM=  0.13
INDE    9  24   1  FOBS=  116.5  SIGMA=   5.4  PHAS=  238.3  FOM=  0.52
INDE    9  24   2  FOBS=   92.5  SIGMA=   6.2  PHAS=   70.2  FOM=  0.22
INDE    9  24   3  FOBS=   92.4  SIGMA=   6.4  PHAS=    3.2  FOM=  0.16
INDE    9  24   4  FOBS=   46.9  SIGMA=  23.1  PHAS=  163.6  FOM=  0.09
INDE    9  24   5  FOBS=   77.0  SIGMA=   8.3  PHAS=   56.2  FOM=  0.12
INDE    9  24   6  FOBS=   92.9  SIGMA=   7.0  PHAS=  103.4  FOM=  0.05
INDE    9  25   0  FOBS=  183.4  SIGMA=   3.2  PHAS=   58.0  FOM=  0.81
INDE    9  25   1  FOBS=  168.4  SIGMA=   3.2  PHAS=  228.5  FOM=  0.54
INDE    9  25   2  FOBS=  178.3  SIGMA=   3.2  PHAS=  255.4  FOM=  0.70
INDE    9  25   3  FOBS=   69.3  SIGMA=   8.5  PHAS=  141.9  FOM=  0.08
INDE    9  25   4  FOBS=  121.3  SIGMA=   5.0  PHAS=  196.4  FOM=  0.19
INDE    9  25   5  FOBS=   44.1  SIGMA=  25.2  PHAS=  354.6  FOM=  0.08
INDE    9  26   0  FOBS=   64.1  SIGMA=   7.7  PHAS=   20.6  FOM=  0.39
INDE    9  26   1  FOBS=  117.4  SIGMA=  77.1  PHAS=  304.5  FOM=  0.03
INDE    9  26   2  FOBS=  125.6  SIGMA=   4.4  PHAS=  329.7  FOM=  0.09
INDE    9  26   3  FOBS=   84.2  SIGMA=   6.9  PHAS=  125.7  FOM=  0.09
INDE    9  26   4  FOBS=   63.5  SIGMA=   9.7  PHAS=  349.6  FOM=  0.11
INDE    9  27   0  FOBS=  129.8  SIGMA=   3.9  PHAS=   63.5  FOM=  0.51
INDE    9  27   1  FOBS=  133.8  SIGMA=   3.9  PHAS=  226.1  FOM=  0.08
INDE    9  27   2  FOBS=   83.8  SIGMA=  51.9  PHAS=  347.4  FOM=  0.01
INDE    9  27   3  FOBS=   80.4  SIGMA=   6.8  PHAS=  101.9  FOM=  0.02
INDE    9  28   0  FOBS=   70.5  SIGMA=   6.9  PHAS=  332.3  FOM=  0.13
INDE    9  28   1  FOBS=   48.9  SIGMA=  19.6  PHAS=  168.4  FOM=  0.12
INDE    9  28   2  FOBS=   77.7  SIGMA=  12.6  PHAS=   85.3  FOM=  0.06
INDE   10   0   1  FOBS=  160.1  SIGMA=   5.2  PHAS=  180.0  FOM=  0.04
INDE   10   0   2  FOBS=  202.6  SIGMA=   8.0  PHAS=    0.0  FOM=  0.11
INDE   10   0   3  FOBS=  343.8  SIGMA=   2.9  PHAS=  180.0  FOM=  0.52
INDE   10   0   4  FOBS=  103.3  SIGMA=  12.1  PHAS=  180.0  FOM=  0.12
INDE   10   0   5  FOBS=   67.4  SIGMA=  21.9  PHAS=    0.0  FOM=  0.12
INDE   10   0   6  FOBS=  179.1  SIGMA=   8.3  PHAS=  180.0  FOM=  0.58
INDE   10   0   7  FOBS=  222.9  SIGMA=   5.7  PHAS=    0.0  FOM=  0.12
INDE   10   0   8  FOBS=   46.5  SIGMA=  55.7  PHAS=    0.0  FOM=  0.11
INDE   10   0   9  FOBS=   94.7  SIGMA= 264.0  PHAS=  180.0  FOM=  0.11
INDE   10   0  10  FOBS=   56.3  SIGMA=  43.0  PHAS=  180.0  FOM=  0.02
INDE   10   0  11  FOBS=   71.7  SIGMA=  27.9  PHAS=    0.0  FOM=  0.02
INDE   10   0  12  FOBS=   86.9  SIGMA=  42.3  PHAS=    0.0  FOM=  0.01
INDE   10   1   0  FOBS=  123.8  SIGMA=   4.3  PHAS=  226.8  FOM=  0.79
INDE   10   1   1  FOBS=  428.1  SIGMA=   1.7  PHAS=   48.3  FOM=  0.77
INDE   10   1   2  FOBS=  425.5  SIGMA=   1.7  PHAS=  291.5  FOM=  0.84
INDE   10   1   3  FOBS=  157.4  SIGMA=   5.0  PHAS=  104.8  FOM=  0.32
INDE   10   1   4  FOBS=  251.5  SIGMA=   3.5  PHAS=  355.3  FOM=  0.60
INDE   10   1   5  FOBS=  345.3  SIGMA=   3.0  PHAS=  266.4  FOM=  0.84
INDE   10   1   6  FOBS=   81.1  SIGMA=  12.0  PHAS=  133.5  FOM=  0.09
INDE   10   1   7  FOBS=  143.3  SIGMA=   6.2  PHAS=  359.7  FOM=  0.23
INDE   10   1   8  FOBS=   67.7  SIGMA=  14.4  PHAS=  243.1  FOM=  0.06
INDE   10   1   9  FOBS=   49.0  SIGMA=  21.6  PHAS=  175.8  FOM=  0.08
INDE   10   1  10  FOBS=   57.9  SIGMA=  33.2  PHAS=   25.3  FOM=  0.13
INDE   10   1  11  FOBS=   70.5  SIGMA=  17.7  PHAS=  265.4  FOM=  0.00
INDE   10   1  12  FOBS=  101.5  SIGMA=  53.3  PHAS=  205.1  FOM=  0.01
INDE   10   2   0  FOBS=   79.2  SIGMA=   6.5  PHAS=   39.6  FOM=  0.37
INDE   10   2   1  FOBS=  211.8  SIGMA=   2.8  PHAS=  206.0  FOM=  0.91
INDE   10   2   2  FOBS=  239.4  SIGMA=   3.2  PHAS=  136.3  FOM=  0.93
INDE   10   2   3  FOBS=  306.1  SIGMA=   2.6  PHAS=   32.9  FOM=  0.93
INDE   10   2   4  FOBS=  139.0  SIGMA=   5.6  PHAS=  237.8  FOM=  0.28
INDE   10   2   5  FOBS=  137.5  SIGMA=   6.3  PHAS=  113.8  FOM=  0.29
INDE   10   2   6  FOBS=  106.2  SIGMA=   9.2  PHAS=  310.0  FOM=  0.04
INDE   10   2   7  FOBS=   81.1  SIGMA=  13.3  PHAS=  292.9  FOM=  0.02
INDE   10   2   8  FOBS=   52.8  SIGMA=  19.6  PHAS=  169.2  FOM=  0.03
INDE   10   2   9  FOBS=  150.5  SIGMA=   7.4  PHAS=  130.6  FOM=  0.05
INDE   10   2  10  FOBS=  152.1  SIGMA=   7.3  PHAS=   48.7  FOM=  0.06
INDE   10   2  11  FOBS=  111.7  SIGMA=  70.6  PHAS=  275.4  FOM=  0.03
INDE   10   3   0  FOBS=  352.6  SIGMA=   1.9  PHAS=  236.8  FOM=  0.92
INDE   10   3   1  FOBS=  116.4  SIGMA=   5.1  PHAS=  176.5  FOM=  0.70
INDE   10   3   2  FOBS=  249.4  SIGMA=   3.0  PHAS=   57.0  FOM=  0.47
INDE   10   3   3  FOBS=  156.1  SIGMA=   4.9  PHAS=  279.6  FOM=  0.57
INDE   10   3   4  FOBS=  152.8  SIGMA=   4.7  PHAS=  190.8  FOM=  0.74
INDE   10   3   5  FOBS=   97.4  SIGMA=   8.6  PHAS=  276.5  FOM=  0.03
INDE   10   3   6  FOBS=   82.7  SIGMA=  11.2  PHAS=  317.7  FOM=  0.09
INDE   10   3   7  FOBS=  159.6  SIGMA=   6.8  PHAS=    6.5  FOM=  0.11
INDE   10   3   8  FOBS=   75.1  SIGMA=  14.5  PHAS=  186.4  FOM=  0.07
```

Fig. 10A-135

```
INDE  10   3   9 FOBS=   57.4 SIGMA=  17.9 PHAS= 111.4 FOM= 0.01
INDE  10   3  10 FOBS=   48.5 SIGMA=  23.3 PHAS= 355.7 FOM= 0.14
INDE  10   3  11 FOBS=   99.8 SIGMA=  44.8 PHAS= 204.7 FOM= 0.04
INDE  10   4   0 FOBS=  288.8 SIGMA=   2.1 PHAS= 268.5 FOM= 0.96
INDE  10   4   1 FOBS=  386.5 SIGMA=   2.3 PHAS=  98.7 FOM= 0.97
INDE  10   4   2 FOBS=  199.9 SIGMA=   3.7 PHAS= 166.5 FOM= 0.75
INDE  10   4   3 FOBS=  157.7 SIGMA=   4.3 PHAS=  43.6 FOM= 0.15
INDE  10   4   4 FOBS=  215.3 SIGMA=   3.4 PHAS= 186.9 FOM= 0.60
INDE  10   4   5 FOBS=  179.0 SIGMA=   6.5 PHAS=  43.1 FOM= 0.56
INDE  10   4   6 FOBS=  128.9 SIGMA=   8.8 PHAS= 213.1 FOM= 0.50
INDE  10   4   7 FOBS=   56.2 SIGMA=  22.3 PHAS= 129.2 FOM= 0.00
INDE  10   4   8 FOBS=  196.1 SIGMA=   5.1 PHAS=  98.4 FOM= 0.26
INDE  10   4   9 FOBS=   46.3 SIGMA=  20.4 PHAS= 180.2 FOM= 0.20
INDE  10   4  10 FOBS=  342.6 SIGMA=   2.1 PHAS= 129.9 FOM= 0.93
INDE  10   5   0 FOBS=  125.4 SIGMA=   5.4 PHAS=  34.6 FOM= 0.40
INDE  10   5   1 FOBS=   48.2 SIGMA=  23.9 PHAS= 134.5 FOM= 0.07
INDE  10   5   2 FOBS=  331.6 SIGMA=   2.2 PHAS= 283.8 FOM= 0.92
INDE  10   5   3 FOBS=  122.7 SIGMA=   9.5 PHAS= 227.3 FOM= 0.11
INDE  10   5   6 FOBS=  179.6 SIGMA= 849.6 PHAS= 158.1 FOM= 0.04
INDE  10   5   7 FOBS=  118.7 SIGMA=   7.9 PHAS= 344.9 FOM= 0.21
INDE  10   5   8 FOBS=   85.9 SIGMA=  13.2 PHAS= 130.0 FOM= 0.08
INDE  10   5   9 FOBS=  104.2 SIGMA=   9.0 PHAS= 273.0 FOM= 0.03
INDE  10   5  10 FOBS=   70.6 SIGMA=  14.8 PHAS= 282.8 FOM= 0.05
INDE  10   5  11 FOBS=  222.4 SIGMA=   2.9 PHAS= 153.1 FOM= 0.65
INDE  10   6   0 FOBS=  254.8 SIGMA=   2.7 PHAS= 355.7 FOM= 0.91
INDE  10   6   1 FOBS=   51.1 SIGMA=  11.9 PHAS= 217.4 FOM= 0.23
INDE  10   6   2 FOBS=  193.1 SIGMA=   3.6 PHAS=  42.7 FOM= 0.77
INDE  10   6   3 FOBS=  194.7 SIGMA=   4.1 PHAS= 151.2 FOM= 0.80
INDE  10   6   4 FOBS=   67.6 SIGMA=  42.8 PHAS= 233.4 FOM= 0.11
INDE  10   6   5 FOBS=   71.6 SIGMA=  15.0 PHAS=  46.7 FOM= 0.28
INDE  10   6   6 FOBS=  183.7 SIGMA=   5.4 PHAS= 284.7 FOM= 0.24
INDE  10   6   7 FOBS=   60.6 SIGMA=  31.5 PHAS= 251.6 FOM= 0.19
INDE  10   6  10 FOBS=   57.5 SIGMA=  27.2 PHAS=  93.0 FOM= 0.04
INDE  10   6  11 FOBS=  117.3 SIGMA=   5.3 PHAS= 205.9 FOM= 0.64
INDE  10   7   0 FOBS=  309.0 SIGMA=   2.1 PHAS= 313.1 FOM= 0.82
INDE  10   7   1 FOBS=  155.8 SIGMA=   4.2 PHAS= 156.7 FOM= 0.36
INDE  10   7   2 FOBS=   75.1 SIGMA=   9.6 PHAS= 301.5 FOM= 0.17
INDE  10   7   3 FOBS=   66.4 SIGMA=  15.0 PHAS= 135.3 FOM= 0.25
INDE  10   7   4 FOBS=   52.7 SIGMA=  25.8 PHAS= 340.7 FOM= 0.05
INDE  10   7   6 FOBS=  109.0 SIGMA=   8.8 PHAS= 186.8 FOM= 0.40
INDE  10   7   7 FOBS=   79.9 SIGMA=  65.4 PHAS= 343.4 FOM= 0.15
INDE  10   7   8 FOBS=   47.1 SIGMA=  20.0 PHAS= 218.8 FOM= 0.03
INDE  10   7   9 FOBS=   64.0 SIGMA=  14.0 PHAS= 162.0 FOM= 0.23
INDE  10   7  10 FOBS=   51.9 SIGMA=  24.2 PHAS= 357.3 FOM= 0.02
INDE  10   7  11 FOBS=  310.6 SIGMA=   2.0 PHAS= 165.3 FOM= 0.74
INDE  10   8   0 FOBS=  294.9 SIGMA=   2.1 PHAS= 201.8 FOM= 0.86
INDE  10   8   1 FOBS=  200.3 SIGMA=   3.3 PHAS= 214.4 FOM= 0.86
INDE  10   8   2 FOBS=  100.1 SIGMA=   7.9 PHAS= 126.2 FOM= 0.12
INDE  10   8   3 FOBS=  169.7 SIGMA=   4.7 PHAS= 136.1 FOM= 0.61
INDE  10   8   4 FOBS=  209.1 SIGMA=   4.0 PHAS= 340.5 FOM= 0.93
INDE  10   8   5 FOBS=  147.1 SIGMA=   5.7 PHAS= 320.7 FOM= 0.23
INDE  10   8   6 FOBS=  105.8 SIGMA=   7.9 PHAS= 318.8 FOM= 0.03
INDE  10   8   7 FOBS=   60.0 SIGMA=  19.0 PHAS= 336.6 FOM= 0.08
INDE  10   8   8 FOBS=  107.3 SIGMA= 108.4 PHAS= 151.5 FOM= 0.09
INDE  10   8   9 FOBS=   60.8 SIGMA=  14.6 PHAS= 274.1 FOM= 0.03
INDE  10   8  10 FOBS=   53.7 SIGMA=  23.8 PHAS=  70.9 FOM= 0.07
INDE  10   8  11 FOBS=  192.1 SIGMA=   3.0 PHAS=  75.8 FOM= 0.19
INDE  10   9   0 FOBS=  330.4 SIGMA=   2.2 PHAS= 340.8 FOM= 0.82
INDE  10   9   1 FOBS=  137.7 SIGMA=   5.5 PHAS= 285.0 FOM= 0.34
INDE  10   9   2 FOBS=  214.1 SIGMA=   3.3 PHAS= 339.8 FOM= 0.76
INDE  10   9   3 FOBS=  213.5 SIGMA=   3.6 PHAS= 171.3 FOM= 0.65
INDE  10   9   4 FOBS=  310.3 SIGMA=   2.9 PHAS= 324.4 FOM= 0.84
INDE  10   9   5 FOBS=  111.2 SIGMA=   7.8 PHAS= 124.4 FOM= 0.37
INDE  10   9   6 FOBS=   52.1 SIGMA=  19.2 PHAS= 203.5 FOM= 0.09
INDE  10   9   7 FOBS=   49.5 SIGMA=  22.2 PHAS= 327.2 FOM= 0.19
INDE  10   9   8 FOBS=  107.7 SIGMA=   7.9 PHAS= 155.9 FOM= 0.21
INDE  10   9   9 FOBS=   73.5 SIGMA=  30.6 PHAS=  32.8 FOM= 0.03
INDE  10   9  10 FOBS=   66.3 SIGMA=  21.6 PHAS=   0.5 FOM= 0.04
INDE  10  10   0 FOBS=  193.4 SIGMA=   3.0 PHAS=  45.2 FOM= 0.91
INDE  10  10   1 FOBS=   67.7 SIGMA=  10.6 PHAS= 200.3 FOM= 0.10
INDE  10  10   2 FOBS=   54.5 SIGMA=  12.3 PHAS=  81.8 FOM= 0.20
```

Fig. 10A-136

| | | | | | | | | | | |
|---|---|---|---|---|---|---|---|---|---|---|
| INDE | 10 | 10 | 3 | FOBS= | 57.1 | SIGMA= | 12.7 | PHAS= | 284.4 | FOM= | 0.14 |
| INDE | 10 | 10 | 5 | FOBS= | 246.2 | SIGMA= | 3.8 | PHAS= | 79.7 | FOM= | 0.71 |
| INDE | 10 | 10 | 6 | FOBS= | 150.6 | SIGMA= | 5.6 | PHAS= | 222.3 | FOM= | 0.09 |
| INDE | 10 | 10 | 7 | FOBS= | 55.0 | SIGMA= | 17.0 | PHAS= | 290.3 | FOM= | 0.13 |
| INDE | 10 | 10 | 8 | FOBS= | 53.2 | SIGMA= | 27.9 | PHAS= | 32.1 | FOM= | 0.04 |
| INDE | 10 | 10 | 9 | FOBS= | 53.0 | SIGMA= | 23.9 | PHAS= | 137.8 | FOM= | 0.12 |
| INDE | 10 | 10 | 10 | FOBS= | 61.0 | SIGMA= | 16.0 | PHAS= | 333.1 | FOM= | 0.05 |
| INDE | 10 | 10 | 11 | FOBS= | 71.3 | SIGMA= | 14.7 | PHAS= | 297.0 | FOM= | 0.00 |
| INDE | 10 | 11 | 0 | FOBS= | 240.2 | SIGMA= | 2.5 | PHAS= | 143.3 | FOM= | 0.92 |
| INDE | 10 | 11 | 1 | FOBS= | 41.4 | SIGMA= | 19.2 | PHAS= | 157.9 | FOM= | 0.21 |
| INDE | 10 | 11 | 2 | FOBS= | 92.6 | SIGMA= | 7.2 | PHAS= | 264.9 | FOM= | 0.30 |
| INDE | 10 | 11 | 3 | FOBS= | 246.2 | SIGMA= | 2.9 | PHAS= | 110.2 | FOM= | 0.86 |
| INDE | 10 | 11 | 6 | FOBS= | 178.7 | SIGMA= | 4.7 | PHAS= | 333.6 | FOM= | 0.08 |
| INDE | 10 | 11 | 7 | FOBS= | 54.2 | SIGMA= | 32.9 | PHAS= | 263.8 | FOM= | 0.01 |
| INDE | 10 | 11 | 9 | FOBS= | 53.5 | SIGMA= | 36.0 | PHAS= | 209.9 | FOM= | 0.13 |
| INDE | 10 | 11 | 10 | FOBS= | 53.9 | SIGMA= | 16.5 | PHAS= | 320.3 | FOM= | 0.04 |
| INDE | 10 | 12 | 0 | FOBS= | 169.8 | SIGMA= | 4.1 | PHAS= | 150.2 | FOM= | 0.68 |
| INDE | 10 | 12 | 1 | FOBS= | 199.4 | SIGMA= | 3.2 | PHAS= | 289.8 | FOM= | 0.88 |
| INDE | 10 | 12 | 2 | FOBS= | 185.0 | SIGMA= | 3.8 | PHAS= | 116.0 | FOM= | 0.09 |
| INDE | 10 | 12 | 3 | FOBS= | 174.4 | SIGMA= | 4.4 | PHAS= | 297.9 | FOM= | 0.15 |
| INDE | 10 | 12 | 4 | FOBS= | 73.9 | SIGMA= | 10.3 | PHAS= | 258.1 | FOM= | 0.06 |
| INDE | 10 | 12 | 5 | FOBS= | 82.2 | SIGMA= | 9.5 | PHAS= | 300.4 | FOM= | 0.07 |
| INDE | 10 | 12 | 6 | FOBS= | 93.0 | SIGMA= | 8.7 | PHAS= | 125.1 | FOM= | 0.32 |
| INDE | 10 | 12 | 7 | FOBS= | 72.1 | SIGMA= | 13.0 | PHAS= | 237.9 | FOM= | 0.05 |
| INDE | 10 | 12 | 8 | FOBS= | 60.9 | SIGMA= | 40.9 | PHAS= | 300.0 | FOM= | 0.03 |
| INDE | 10 | 12 | 9 | FOBS= | 46.8 | SIGMA= | 22.1 | PHAS= | 19.0 | FOM= | 0.10 |
| INDE | 10 | 12 | 10 | FOBS= | 65.7 | SIGMA= | 16.9 | PHAS= | 72.9 | FOM= | 0.01 |
| INDE | 10 | 13 | 0 | FOBS= | 205.3 | SIGMA= | 2.9 | PHAS= | 44.4 | FOM= | 0.54 |
| INDE | 10 | 13 | 1 | FOBS= | 60.2 | SIGMA= | 10.3 | PHAS= | 259.0 | FOM= | 0.19 |
| INDE | 10 | 13 | 2 | FOBS= | 52.6 | SIGMA= | 13.3 | PHAS= | 82.5 | FOM= | 0.15 |
| INDE | 10 | 13 | 3 | FOBS= | 111.9 | SIGMA= | 6.7 | PHAS= | 303.0 | FOM= | 0.09 |
| INDE | 10 | 13 | 4 | FOBS= | 59.6 | SIGMA= | 20.5 | PHAS= | 271.7 | FOM= | 0.05 |
| INDE | 10 | 13 | 5 | FOBS= | 108.1 | SIGMA= | 7.1 | PHAS= | 190.2 | FOM= | 0.19 |
| INDE | 10 | 13 | 6 | FOBS= | 61.7 | SIGMA= | 13.8 | PHAS= | 226.3 | FOM= | 0.03 |
| INDE | 10 | 13 | 7 | FOBS= | 123.1 | SIGMA= | 6.4 | PHAS= | 273.0 | FOM= | 0.12 |
| INDE | 10 | 13 | 8 | FOBS= | 77.1 | SIGMA= | 49.2 | PHAS= | 73.4 | FOM= | 0.02 |
| INDE | 10 | 13 | 9 | FOBS= | 67.0 | SIGMA= | 14.4 | PHAS= | 147.7 | FOM= | 0.02 |
| INDE | 10 | 14 | 0 | FOBS= | 258.6 | SIGMA= | 2.3 | PHAS= | 96.3 | FOM= | 0.81 |
| INDE | 10 | 14 | 1 | FOBS= | 133.1 | SIGMA= | 4.9 | PHAS= | 196.9 | FOM= | 0.19 |
| INDE | 10 | 14 | 2 | FOBS= | 235.0 | SIGMA= | 3.0 | PHAS= | 338.0 | FOM= | 0.79 |
| INDE | 10 | 14 | 3 | FOBS= | 72.9 | SIGMA= | 10.5 | PHAS= | 143.7 | FOM= | 0.05 |
| INDE | 10 | 14 | 4 | FOBS= | 235.0 | SIGMA= | 3.2 | PHAS= | 55.1 | FOM= | 0.12 |
| INDE | 10 | 14 | 5 | FOBS= | 73.8 | SIGMA= | 11.0 | PHAS= | 179.1 | FOM= | 0.05 |
| INDE | 10 | 14 | 6 | FOBS= | 66.2 | SIGMA= | 12.0 | PHAS= | 9.6 | FOM= | 0.18 |
| INDE | 10 | 14 | 7 | FOBS= | 96.3 | SIGMA= | 8.0 | PHAS= | 248.7 | FOM= | 0.27 |
| INDE | 10 | 14 | 8 | FOBS= | 63.3 | SIGMA= | 13.1 | PHAS= | 83.6 | FOM= | 0.17 |
| INDE | 10 | 14 | 9 | FOBS= | 61.8 | SIGMA= | 31.3 | PHAS= | 359.2 | FOM= | 0.05 |
| INDE | 10 | 14 | 10 | FOBS= | 62.4 | SIGMA= | 15.6 | PHAS= | 224.8 | FOM= | 0.09 |
| INDE | 10 | 15 | 0 | FOBS= | 87.5 | SIGMA= | 6.9 | PHAS= | 140.8 | FOM= | 0.02 |
| INDE | 10 | 15 | 1 | FOBS= | 342.0 | SIGMA= | 2.0 | PHAS= | 336.2 | FOM= | 0.67 |
| INDE | 10 | 15 | 2 | FOBS= | 149.8 | SIGMA= | 4.7 | PHAS= | 66.1 | FOM= | 0.40 |
| INDE | 10 | 15 | 3 | FOBS= | 109.0 | SIGMA= | 6.6 | PHAS= | 216.2 | FOM= | 0.33 |
| INDE | 10 | 15 | 4 | FOBS= | 60.6 | SIGMA= | 28.6 | PHAS= | 83.7 | FOM= | 0.13 |
| INDE | 10 | 15 | 5 | FOBS= | 80.5 | SIGMA= | 9.3 | PHAS= | 27.5 | FOM= | 0.14 |
| INDE | 10 | 15 | 6 | FOBS= | 41.0 | SIGMA= | 18.7 | PHAS= | 248.3 | FOM= | 0.19 |
| INDE | 10 | 15 | 7 | FOBS= | 118.2 | SIGMA= | 6.5 | PHAS= | 176.2 | FOM= | 0.37 |
| INDE | 10 | 15 | 8 | FOBS= | 49.1 | SIGMA= | 48.9 | PHAS= | 345.2 | FOM= | 0.36 |
| INDE | 10 | 15 | 9 | FOBS= | 79.8 | SIGMA= | 10.9 | PHAS= | 251.9 | FOM= | 0.03 |
| INDE | 10 | 16 | 0 | FOBS= | 260.9 | SIGMA= | 2.4 | PHAS= | 335.1 | FOM= | 0.75 |
| INDE | 10 | 16 | 1 | FOBS= | 113.9 | SIGMA= | 5.8 | PHAS= | 96.7 | FOM= | 0.37 |
| INDE | 10 | 16 | 2 | FOBS= | 176.6 | SIGMA= | 3.9 | PHAS= | 127.9 | FOM= | 0.86 |
| INDE | 10 | 16 | 3 | FOBS= | 123.9 | SIGMA= | 5.8 | PHAS= | 188.9 | FOM= | 0.46 |
| INDE | 10 | 16 | 4 | FOBS= | 133.6 | SIGMA= | 5.5 | PHAS= | 9.9 | FOM= | 0.05 |
| INDE | 10 | 16 | 6 | FOBS= | 175.3 | SIGMA= | 4.4 | PHAS= | 190.1 | FOM= | 0.51 |
| INDE | 10 | 16 | 7 | FOBS= | 68.2 | SIGMA= | 11.8 | PHAS= | 21.2 | FOM= | 0.11 |
| INDE | 10 | 16 | 8 | FOBS= | 63.3 | SIGMA= | 13.6 | PHAS= | 272.6 | FOM= | 0.05 |
| INDE | 10 | 16 | 9 | FOBS= | 72.0 | SIGMA= | 10.5 | PHAS= | 175.1 | FOM= | 0.02 |
| INDE | 10 | 17 | 0 | FOBS= | 308.6 | SIGMA= | 2.1 | PHAS= | 296.5 | FOM= | 0.92 |
| INDE | 10 | 17 | 1 | FOBS= | 145.6 | SIGMA= | 4.6 | PHAS= | 200.9 | FOM= | 0.80 |
| INDE | 10 | 17 | 2 | FOBS= | 171.4 | SIGMA= | 4.1 | PHAS= | 30.7 | FOM= | 0.50 |
| INDE | 10 | 17 | 3 | FOBS= | 101.0 | SIGMA= | 6.8 | PHAS= | 65.4 | FOM= | 0.44 |

Fig. 10A-137

```
INDE  10  17   4  FOBS=   49.4  SIGMA=   22.5  PHAS=  213.2  FOM=  0.28
INDE  10  17   5  FOBS=   63.4  SIGMA=   12.2  PHAS=  358.3  FOM=  0.07
INDE  10  17   6  FOBS=   60.9  SIGMA=   20.8  PHAS=   38.1  FOM=  0.12
INDE  10  17   7  FOBS=   70.5  SIGMA=   12.8  PHAS=  180.8  FOM=  0.22
INDE  10  17   8  FOBS=  123.2  SIGMA=    6.2  PHAS=  338.9  FOM=  0.07
INDE  10  17   9  FOBS=   89.5  SIGMA=    9.2  PHAS=  185.6  FOM=  0.04
INDE  10  18   0  FOBS=  132.2  SIGMA=    4.8  PHAS=  230.7  FOM=  0.60
INDE  10  18   1  FOBS=  116.2  SIGMA=    5.7  PHAS=  115.5  FOM=  0.55
INDE  10  18   2  FOBS=   70.2  SIGMA=   48.0  PHAS=    3.3  FOM=  0.19
INDE  10  18   3  FOBS=  135.3  SIGMA=    5.2  PHAS=  145.6  FOM=  0.56
INDE  10  18   4  FOBS=  118.1  SIGMA=    6.0  PHAS=   60.1  FOM=  0.09
INDE  10  18   5  FOBS=   67.9  SIGMA=   10.9  PHAS=   15.6  FOM=  0.03
INDE  10  18   6  FOBS=   88.5  SIGMA=    9.3  PHAS=  197.7  FOM=  0.21
INDE  10  18   7  FOBS=   81.2  SIGMA=    9.0  PHAS=  321.7  FOM=  0.07
INDE  10  18   8  FOBS=   37.7  SIGMA=   17.7  PHAS=  331.8  FOM=  0.04
INDE  10  19   0  FOBS=  111.2  SIGMA=    5.2  PHAS=  150.6  FOM=  0.55
INDE  10  19   1  FOBS=  120.3  SIGMA=    5.3  PHAS=  226.4  FOM=  0.21
INDE  10  19   2  FOBS=  165.8  SIGMA=    4.1  PHAS=  119.8  FOM=  0.33
INDE  10  19   3  FOBS=  203.8  SIGMA=    3.5  PHAS=  100.0  FOM=  0.78
INDE  10  19   5  FOBS=  127.2  SIGMA=    6.3  PHAS=   95.7  FOM=  0.04
INDE  10  19   6  FOBS=   42.9  SIGMA=   30.7  PHAS=  291.9  FOM=  0.01
INDE  10  19   7  FOBS=   54.1  SIGMA=   16.5  PHAS=  262.7  FOM=  0.02
INDE  10  19   8  FOBS=   83.9  SIGMA=    9.5  PHAS=   25.5  FOM=  0.09
INDE  10  20   0  FOBS=  161.2  SIGMA=    3.8  PHAS=  297.7  FOM=  0.60
INDE  10  20   1  FOBS=  104.8  SIGMA=    5.8  PHAS=  224.1  FOM=  0.03
INDE  10  20   2  FOBS=  112.9  SIGMA=    5.7  PHAS=  353.0  FOM=  0.16
INDE  10  20   4  FOBS=  117.7  SIGMA=  132.4  PHAS=  270.4  FOM=  0.12
INDE  10  20   5  FOBS=   78.1  SIGMA=    9.6  PHAS=   64.4  FOM=  0.09
INDE  10  20   6  FOBS=   53.6  SIGMA=   20.1  PHAS=  146.8  FOM=  0.03
INDE  10  20   7  FOBS=   63.6  SIGMA=   12.3  PHAS=   20.5  FOM=  0.02
INDE  10  21   0  FOBS=  183.2  SIGMA=    3.4  PHAS=   65.6  FOM=  0.81
INDE  10  21   1  FOBS=   58.3  SIGMA=   10.8  PHAS=  206.5  FOM=  0.28
INDE  10  21   2  FOBS=  118.8  SIGMA=    5.3  PHAS=   76.0  FOM=  0.47
INDE  10  21   3  FOBS=   97.1  SIGMA=    6.7  PHAS=   91.9  FOM=  0.16
INDE  10  21   4  FOBS=   77.4  SIGMA=    9.5  PHAS=  259.0  FOM=  0.07
INDE  10  21   5  FOBS=   95.4  SIGMA=    7.2  PHAS=   94.8  FOM=  0.90
INDE  10  21   6  FOBS=   90.0  SIGMA=    7.6  PHAS=  261.3  FOM=  0.01
INDE  10  21   7  FOBS=   73.9  SIGMA=   11.3  PHAS=  298.2  FOM=  0.15
INDE  10  22   0  FOBS=   90.7  SIGMA=    6.4  PHAS=  135.8  FOM=  0.52
INDE  10  22   1  FOBS=   53.7  SIGMA=   11.7  PHAS=  218.3  FOM=  0.05
INDE  10  22   2  FOBS=  115.7  SIGMA=    5.4  PHAS=   43.7  FOM=  0.50
INDE  10  22   3  FOBS=  116.7  SIGMA=    6.2  PHAS=  153.5  FOM=  0.32
INDE  10  22   4  FOBS=   68.8  SIGMA=    9.3  PHAS=  236.1  FOM=  0.34
INDE  10  22   5  FOBS=   39.3  SIGMA=   17.2  PHAS=   48.3  FOM=  0.07
INDE  10  22   6  FOBS=  109.1  SIGMA=    6.1  PHAS=  324.5  FOM=  0.10
INDE  10  23   0  FOBS=  125.1  SIGMA=    4.5  PHAS=  106.0  FOM=  0.06
INDE  10  23   1  FOBS=   90.7  SIGMA=    6.4  PHAS=  334.1  FOM=  0.24
INDE  10  23   2  FOBS=   61.5  SIGMA=   11.2  PHAS=  104.4  FOM=  0.13
INDE  10  23   3  FOBS=  126.9  SIGMA=    5.7  PHAS=  197.9  FOM=  0.77
INDE  10  23   4  FOBS=   41.0  SIGMA=   18.0  PHAS=  351.6  FOM=  0.17
INDE  10  23   5  FOBS=  103.1  SIGMA=    6.3  PHAS=  194.4  FOM=  0.09
INDE  10  24   0  FOBS=   37.7  SIGMA=   15.3  PHAS=   59.1  FOM=  0.14
INDE  10  24   1  FOBS=  109.3  SIGMA=    5.8  PHAS=  191.2  FOM=  0.37
INDE  10  24   2  FOBS=  101.3  SIGMA=    5.6  PHAS=  280.9  FOM=  0.96
INDE  10  24   3  FOBS=   74.0  SIGMA=    8.7  PHAS=  126.0  FOM=  0.04
INDE  10  24   4  FOBS=  153.8  SIGMA=    4.3  PHAS=  274.5  FOM=  0.12
INDE  10  24   5  FOBS=   64.8  SIGMA=   11.3  PHAS=  198.1  FOM=  0.05
INDE  10  25   0  FOBS=  126.6  SIGMA=    4.5  PHAS=  215.1  FOM=  0.24
INDE  10  25   1  FOBS=   35.9  SIGMA=   14.3  PHAS=  233.9  FOM=  0.09
INDE  10  25   2  FOBS=   61.3  SIGMA=   11.0  PHAS=   76.2  FOM=  0.06
INDE  10  25   3  FOBS=   45.7  SIGMA=   18.0  PHAS=  230.5  FOM=  0.10
INDE  10  25   4  FOBS=   97.7  SIGMA=    6.8  PHAS=  253.9  FOM=  0.04
INDE  10  26   0  FOBS=   44.6  SIGMA=   21.0  PHAS=  202.7  FOM=  0.06
INDE  10  26   1  FOBS=  103.3  SIGMA=    5.5  PHAS=  182.2  FOM=  0.12
INDE  10  26   2  FOBS=   39.5  SIGMA=   21.1  PHAS=  339.9  FOM=  0.04
INDE  10  26   3  FOBS=   47.8  SIGMA=   18.4  PHAS=  188.9  FOM=  0.11
INDE  10  27   0  FOBS=  110.3  SIGMA=    4.9  PHAS=    2.1  FOM=  0.54
INDE  10  27   1  FOBS=   99.5  SIGMA=    5.7  PHAS=  239.8  FOM=  0.21
INDE  11   0   0  FOBS=  384.6  SIGMA=    2.4  PHAS=  180.0  FOM=  0.40
INDE  11   0   1  FOBS=   73.7  SIGMA=   12.4  PHAS=  180.0  FOM=  0.28
INDE  11   0   2  FOBS=  223.1  SIGMA=    5.9  PHAS=  180.0  FOM=  0.40
```

Fig. 10A-138

```
INDE  11  0   3  FOBS=   111.1  SIGMA=    8.7  PHAS=   180.0  FOM=  0.08
INDE  11  0   4  FOBS=    53.6  SIGMA=   21.7  PHAS=     0.0  FOM=  0.04
INDE  11  0   5  FOBS=    77.3  SIGMA=   16.2  PHAS=     0.0  FOM=  0.02
INDE  11  0   6  FOBS=    30.9  SIGMA=   36.1  PHAS=   180.0  FOM=  0.03
INDE  11  0   7  FOBS=    32.0  SIGMA=   33.8  PHAS=   180.0  FOM=  0.00
INDE  11  0   8  FOBS=    44.2  SIGMA=   55.5  PHAS=     0.0  FOM=  0.05
INDE  11  0   9  FOBS=   116.3  SIGMA=   10.7  PHAS=   180.0  FOM=  0.03
INDE  11  0  10  FOBS=   124.1  SIGMA=   10.8  PHAS=     0.0  FOM=  0.05
INDE  11  0  11  FOBS=    47.2  SIGMA=   30.0  PHAS=     0.0  FOM=  0.01
INDE  11  1   0  FOBS=    81.5  SIGMA=    7.6  PHAS=    98.3  FOM=  0.65
INDE  11  1   1  FOBS=   126.7  SIGMA=    5.0  PHAS=   309.9  FOM=  0.72
INDE  11  1   2  FOBS=   130.8  SIGMA=    5.0  PHAS=   228.7  FOM=  0.12
INDE  11  1   3  FOBS=   355.6  SIGMA=    2.3  PHAS=    74.6  FOM=  0.81
INDE  11  1   4  FOBS=   239.2  SIGMA=    3.6  PHAS=   293.9  FOM=  0.63
INDE  11  1   5  FOBS=   252.2  SIGMA=    3.8  PHAS=   174.9  FOM=  0.55
INDE  11  1   6  FOBS=    89.5  SIGMA=   12.2  PHAS=   294.9  FOM=  0.06
INDE  11  1   7  FOBS=    68.4  SIGMA=   15.6  PHAS=    97.9  FOM=  0.11
INDE  11  1   8  FOBS=    63.9  SIGMA=   18.3  PHAS=   270.2  FOM=  0.02
INDE  11  1   9  FOBS=    56.1  SIGMA=   18.0  PHAS=   272.1  FOM=  0.06
INDE  11  1  10  FOBS=    77.6  SIGMA=   12.6  PHAS=   190.8  FOM=  0.05
INDE  11  1  11  FOBS=    75.4  SIGMA=   14.0  PHAS=    22.6  FOM=  0.01
INDE  11  2   0  FOBS=   123.9  SIGMA=    4.7  PHAS=   281.1  FOM=  0.41
INDE  11  2   1  FOBS=   143.7  SIGMA=    4.3  PHAS=   133.3  FOM=  0.23
INDE  11  2   2  FOBS=    84.4  SIGMA=    7.9  PHAS=   133.1  FOM=  0.11
INDE  11  2   3  FOBS=    51.9  SIGMA=   14.9  PHAS=   160.6  FOM=  0.11
INDE  11  2   4  FOBS=   119.7  SIGMA=    7.6  PHAS=   301.9  FOM=  0.19
INDE  11  2   5  FOBS=    82.6  SIGMA=   13.9  PHAS=   334.6  FOM=  0.02
INDE  11  2   6  FOBS=   199.4  SIGMA=    4.4  PHAS=   122.1  FOM=  0.28
INDE  11  2   7  FOBS=    66.5  SIGMA=   33.5  PHAS=   355.7  FOM=  0.02
INDE  11  2   8  FOBS=   148.9  SIGMA=    6.9  PHAS=   312.4  FOM=  0.29
INDE  11  2   9  FOBS=    79.2  SIGMA=   11.8  PHAS=   123.7  FOM=  0.10
INDE  11  2  10  FOBS=    66.7  SIGMA=   16.0  PHAS=    89.7  FOM=  0.02
INDE  11  2  11  FOBS=   249.2  SIGMA=  165.9  PHAS=   307.3  FOM=  0.02
INDE  11  3   0  FOBS=   187.4  SIGMA=    3.1  PHAS=   333.9  FOM=  0.39
INDE  11  3   1  FOBS=   240.3  SIGMA=    2.7  PHAS=    38.4  FOM=  0.81
INDE  11  3   2  FOBS=   224.7  SIGMA=    3.1  PHAS=   263.2  FOM=  0.83
INDE  11  3   3  FOBS=   237.0  SIGMA=    3.5  PHAS=    25.4  FOM=  0.82
INDE  11  3   4  FOBS=   129.5  SIGMA=    6.7  PHAS=    88.3  FOM=  0.05
INDE  11  3   6  FOBS=    50.4  SIGMA=   24.6  PHAS=    41.6  FOM=  0.08
INDE  11  3   7  FOBS=    69.6  SIGMA=   32.5  PHAS=   311.0  FOM=  0.06
INDE  11  3   8  FOBS=    92.2  SIGMA=   10.2  PHAS=   157.7  FOM=  0.11
INDE  11  3  10  FOBS=    59.7  SIGMA=   29.7  PHAS=   277.8  FOM=  0.07
INDE  11  3  11  FOBS=    81.0  SIGMA=   13.0  PHAS=    43.0  FOM=  0.04
INDE  11  4   0  FOBS=   149.5  SIGMA=    4.0  PHAS=   285.7  FOM=  0.56
INDE  11  4   1  FOBS=   144.2  SIGMA=    4.7  PHAS=   304.7  FOM=  0.66
INDE  11  4   2  FOBS=   178.7  SIGMA=    4.1  PHAS=   335.4  FOM=  0.74
INDE  11  4   3  FOBS=   229.2  SIGMA=    3.7  PHAS=     9.4  FOM=  0.55
INDE  11  4   4  FOBS=   107.0  SIGMA=    7.7  PHAS=   180.5  FOM=  0.43
INDE  11  4   5  FOBS=    72.4  SIGMA=   11.2  PHAS=    11.5  FOM=  0.12
INDE  11  4   6  FOBS=   120.8  SIGMA=  112.0  PHAS=   337.0  FOM=  0.12
INDE  11  4   7  FOBS=    57.0  SIGMA=   24.9  PHAS=   163.2  FOM=  0.11
INDE  11  4   8  FOBS=   104.7  SIGMA=    9.8  PHAS=   296.8  FOM=  0.01
INDE  11  4   9  FOBS=    62.4  SIGMA=   18.5  PHAS=   329.6  FOM=  0.03
INDE  11  4  11  FOBS=   141.1  SIGMA=   82.1  PHAS=   204.2  FOM=  0.00
INDE  11  5   0  FOBS=   101.0  SIGMA=    6.5  PHAS=   168.0  FOM=  0.18
INDE  11  5   1  FOBS=   171.3  SIGMA=    4.3  PHAS=   128.0  FOM=  0.76
INDE  11  5   2  FOBS=   152.1  SIGMA=    5.3  PHAS=   347.5  FOM=  0.35
INDE  11  5   3  FOBS=   145.0  SIGMA=    7.1  PHAS=   160.3  FOM=  0.31
INDE  11  5   4  FOBS=   102.8  SIGMA=    7.6  PHAS=   136.6  FOM=  0.04
INDE  11  5   6  FOBS=   139.8  SIGMA=    6.6  PHAS=    12.9  FOM=  0.28
INDE  11  5   7  FOBS=    80.4  SIGMA=   12.9  PHAS=   278.8  FOM=  0.11
INDE  11  5   8  FOBS=   119.9  SIGMA=    8.6  PHAS=   316.3  FOM=  0.07
INDE  11  5   9  FOBS=    43.4  SIGMA=   23.5  PHAS=    82.9  FOM=  0.13
INDE  11  5  10  FOBS=    54.4  SIGMA=   29.6  PHAS=   263.8  FOM=  0.07
INDE  11  6   0  FOBS=   138.2  SIGMA=    4.6  PHAS=   103.8  FOM=  0.76
INDE  11  6   1  FOBS=   587.8  SIGMA=    1.7  PHAS=    19.1  FOM=  0.69
INDE  11  6   2  FOBS=    77.8  SIGMA=    9.8  PHAS=   244.0  FOM=  0.06
INDE  11  6   3  FOBS=   116.9  SIGMA=    6.3  PHAS=    90.9  FOM=  0.44
INDE  11  6   4  FOBS=   110.8  SIGMA=    7.9  PHAS=   258.6  FOM=  0.44
INDE  11  6   5  FOBS=    94.6  SIGMA=    9.6  PHAS=    96.6  FOM=  0.30
INDE  11  6   6  FOBS=   100.0  SIGMA=    9.6  PHAS=   279.0  FOM=  0.05
```

Fig. 10A-139

```
INDE  11   6   7 FOBS=  121.1 SIGMA=   8.7 PHAS=  151.9 FOM= 0.07
INDE  11   6   8 FOBS=  102.4 SIGMA=   8.6 PHAS=   25.2 FOM= 0.15
INDE  11   6   9 FOBS=   57.5 SIGMA=  31.8 PHAS=  223.6 FOM= 0.08
INDE  11   6  10 FOBS=   68.3 SIGMA=  13.1 PHAS=  343.7 FOM= 0.01
INDE  11   7   0 FOBS=  311.8 SIGMA=   2.4 PHAS=  125.5 FOM= 0.79
INDE  11   7   1 FOBS=   78.0 SIGMA=   9.5 PHAS=  130.5 FOM= 0.32
INDE  11   7   2 FOBS=  143.6 SIGMA=   4.9 PHAS=   40.0 FOM= 0.79
INDE  11   7   3 FOBS=   63.2 SIGMA=  12.3 PHAS=  162.1 FOM= 0.20
INDE  11   7   4 FOBS=  162.5 SIGMA=   5.2 PHAS=  269.1 FOM= 0.39
INDE  11   7   5 FOBS=  116.3 SIGMA=   8.5 PHAS=   39.0 FOM= 0.56
INDE  11   7   6 FOBS=   83.4 SIGMA=  11.7 PHAS=  167.8 FOM= 0.29
INDE  11   7   7 FOBS=   89.0 SIGMA=  10.5 PHAS=   11.7 FOM= 0.10
INDE  11   7   9 FOBS=  112.2 SIGMA=   7.6 PHAS=  119.2 FOM= 0.06
INDE  11   7  10 FOBS=   59.0 SIGMA=  15.2 PHAS=  320.4 FOM= 0.04
INDE  11   8   0 FOBS=  271.2 SIGMA=   2.6 PHAS=  231.3 FOM= 0.93
INDE  11   8   1 FOBS=  234.6 SIGMA=   3.1 PHAS=   57.5 FOM= 0.59
INDE  11   8   2 FOBS=  183.4 SIGMA=   3.9 PHAS=  229.9 FOM= 0.59
INDE  11   8   3 FOBS=  149.6 SIGMA=   5.2 PHAS=  144.6 FOM= 0.29
INDE  11   8   5 FOBS=  164.3 SIGMA=   5.7 PHAS=   53.4 FOM= 0.29
INDE  11   8   6 FOBS=  125.6 SIGMA=   6.7 PHAS=  216.8 FOM= 0.06
INDE  11   8   7 FOBS=  114.3 SIGMA=   7.3 PHAS=  262.6 FOM= 0.05
INDE  11   8   8 FOBS=   61.6 SIGMA=  15.8 PHAS=   70.3 FOM= 0.21
INDE  11   8   9 FOBS=   38.0 SIGMA=  15.5 PHAS=  263.0 FOM= 0.89
INDE  11   8  10 FOBS=   80.0 SIGMA=  11.2 PHAS=  207.8 FOM= 0.04
INDE  11   9   0 FOBS=  251.2 SIGMA=   2.7 PHAS=  336.2 FOM= 0.96
INDE  11   9   1 FOBS=  232.4 SIGMA=   2.9 PHAS=  198.2 FOM= 0.93
INDE  11   9   2 FOBS=  145.3 SIGMA=   5.0 PHAS=  233.8 FOM= 0.43
INDE  11   9   3 FOBS=  246.6 SIGMA=   3.6 PHAS=   43.3 FOM= 0.85
INDE  11   9   4 FOBS=   54.6 SIGMA=  27.1 PHAS=  275.1 FOM= 0.03
INDE  11   9   6 FOBS=  221.2 SIGMA=   3.8 PHAS=  228.1 FOM= 0.77
INDE  11   9   7 FOBS=   59.0 SIGMA=  14.1 PHAS=   80.2 FOM= 0.17
INDE  11   9   8 FOBS=  101.1 SIGMA=  97.3 PHAS=  240.8 FOM= 0.07
INDE  11   9   9 FOBS=   58.5 SIGMA=  25.1 PHAS=  253.2 FOM= 0.07
INDE  11   9  10 FOBS=   35.5 SIGMA=  22.3 PHAS=   99.5 FOM= 0.13
INDE  11  10   0 FOBS=  112.4 SIGMA=   5.5 PHAS=  137.9 FOM= 0.09
INDE  11  10   1 FOBS=   98.1 SIGMA=   6.7 PHAS=  355.9 FOM= 0.44
INDE  11  10   2 FOBS=  125.1 SIGMA=   6.7 PHAS=  132.1 FOM= 0.07
INDE  11  10   3 FOBS=   45.4 SIGMA=  23.2 PHAS=  118.6 FOM= 0.20
INDE  11  10   4 FOBS=   81.2 SIGMA=  10.1 PHAS=  328.8 FOM= 0.42
INDE  11  10   5 FOBS=   90.5 SIGMA=   9.2 PHAS=  117.0 FOM= 0.16
INDE  11  10   6 FOBS=   67.8 SIGMA=  15.4 PHAS=  105.3 FOM= 0.12
INDE  11  10   7 FOBS=  129.7 SIGMA=   6.4 PHAS=  338.7 FOM= 0.20
INDE  11  10   8 FOBS=   93.5 SIGMA=   8.8 PHAS=  218.9 FOM= 0.02
INDE  11  10   9 FOBS=   87.6 SIGMA=  10.5 PHAS=   46.5 FOM= 0.01
INDE  11  10  10 FOBS=   56.5 SIGMA=  27.0 PHAS=   99.2 FOM= 0.03
INDE  11  11   0 FOBS=  222.3 SIGMA=   2.8 PHAS=  333.6 FOM= 0.84
INDE  11  11   1 FOBS=  209.5 SIGMA=   3.4 PHAS=  132.2 FOM= 0.12
INDE  11  11   2 FOBS=  122.9 SIGMA=   6.8 PHAS=  112.0 FOM= 0.09
INDE  11  11   3 FOBS=   49.9 SIGMA=  19.4 PHAS=  291.8 FOM= 0.08
INDE  11  11   5 FOBS=  175.4 SIGMA=   4.7 PHAS=  200.3 FOM= 0.60
INDE  11  11   6 FOBS=   59.8 SIGMA=  17.4 PHAS=  289.6 FOM= 0.09
INDE  11  11   7 FOBS=   76.9 SIGMA=  10.9 PHAS=   21.4 FOM= 0.18
INDE  11  11   8 FOBS=   45.6 SIGMA=  22.7 PHAS=  149.3 FOM= 0.19
INDE  11  11   9 FOBS=   57.7 SIGMA=  31.4 PHAS=  284.3 FOM= 0.01
INDE  11  12   0 FOBS=  189.8 SIGMA=   3.5 PHAS=  237.1 FOM= 0.31
INDE  11  12   1 FOBS=   87.9 SIGMA=   9.0 PHAS=  216.3 FOM= 0.05
INDE  11  12   2 FOBS=   85.7 SIGMA=   9.0 PHAS=   37.8 FOM= 0.11
INDE  11  12   3 FOBS=  125.0 SIGMA=   6.1 PHAS=  117.0 FOM= 0.04
INDE  11  12   4 FOBS=  178.4 SIGMA=   4.5 PHAS=  278.2 FOM= 0.18
INDE  11  12   6 FOBS=   69.8 SIGMA=  13.1 PHAS=  275.6 FOM= 0.10
INDE  11  12   7 FOBS=   55.1 SIGMA=  18.3 PHAS=   65.2 FOM= 0.06
INDE  11  12   8 FOBS=   85.6 SIGMA=   9.2 PHAS=  185.9 FOM= 0.44
INDE  11  12   9 FOBS=   48.9 SIGMA=  25.6 PHAS=  319.6 FOM= 0.03
INDE  11  13   0 FOBS=  162.2 SIGMA=   4.7 PHAS=  339.1 FOM= 0.13
INDE  11  13   1 FOBS=  142.6 SIGMA=   5.0 PHAS=  142.7 FOM= 0.45
INDE  11  13   3 FOBS=   75.8 SIGMA=  10.4 PHAS=  172.1 FOM= 0.04
INDE  11  13   4 FOBS=  143.0 SIGMA=   5.4 PHAS=   45.1 FOM= 0.13
INDE  11  13   5 FOBS=  121.8 SIGMA=   6.4 PHAS=  306.6 FOM= 0.11
INDE  11  13   6 FOBS=   91.8 SIGMA=   8.7 PHAS=  122.7 FOM= 0.23
INDE  11  13   7 FOBS=  103.8 SIGMA=   7.5 PHAS=   16.6 FOM= 0.10
INDE  11  13   8 FOBS=   90.1 SIGMA=   8.6 PHAS=  246.8 FOM= 0.03
```

Fig. 10A-140

```
INDE 11 13 9 FOBS=   101.5 SIGMA= 59.5 PHAS=  75.4 FOM= 0.03
INDE 11 14 0 FOBS=   131.7 SIGMA=  5.6 PHAS= 128.6 FOM= 0.18
INDE 11 14 1 FOBS=   134.7 SIGMA=  5.1 PHAS= 205.2 FOM= 0.34
INDE 11 14 2 FOBS=   160.2 SIGMA=  4.6 PHAS= 151.1 FOM= 0.23
INDE 11 14 3 FOBS=   213.1 SIGMA=  4.1 PHAS= 345.7 FOM= 0.49
INDE 11 14 4 FOBS=    74.5 SIGMA= 10.1 PHAS= 196.2 FOM= 0.21
INDE 11 14 5 FOBS=   159.8 SIGMA=  4.9 PHAS= 101.8 FOM= 0.12
INDE 11 14 6 FOBS=    58.1 SIGMA= 13.8 PHAS= 314.2 FOM= 0.08
INDE 11 14 7 FOBS=    47.8 SIGMA= 32.8 PHAS= 171.3 FOM= 0.05
INDE 11 14 8 FOBS=    92.2 SIGMA=  8.6 PHAS= 255.1 FOM= 0.02
INDE 11 14 9 FOBS=    67.0 SIGMA= 12.7 PHAS= 319.4 FOM= 0.00
INDE 11 15 0 FOBS=   171.1 SIGMA=  3.9 PHAS= 312.3 FOM= 0.89
INDE 11 15 1 FOBS=    97.1 SIGMA=  6.8 PHAS=  98.4 FOM= 0.25
INDE 11 15 2 FOBS=    80.3 SIGMA=  8.8 PHAS=   4.1 FOM= 0.28
INDE 11 15 3 FOBS=    92.0 SIGMA=  7.8 PHAS= 239.7 FOM= 0.31
INDE 11 15 4 FOBS=    66.6 SIGMA= 17.3 PHAS= 172.2 FOM= 0.06
INDE 11 15 5 FOBS=    63.9 SIGMA= 12.4 PHAS=  10.2 FOM= 0.28
INDE 11 15 6 FOBS=    82.7 SIGMA=  9.4 PHAS= 220.7 FOM= 0.14
INDE 11 15 7 FOBS=    35.4 SIGMA= 20.2 PHAS= 280.4 FOM= 0.41
INDE 11 15 8 FOBS=    56.4 SIGMA= 14.8 PHAS=  81.9 FOM= 0.02
INDE 11 16 0 FOBS=   175.2 SIGMA=  3.8 PHAS= 110.5 FOM= 0.72
INDE 11 16 1 FOBS=   175.4 SIGMA=  4.0 PHAS=  47.4 FOM= 0.46
INDE 11 16 2 FOBS=   129.2 SIGMA=  5.5 PHAS= 226.5 FOM= 0.57
INDE 11 16 3 FOBS=    77.3 SIGMA=  9.2 PHAS=   4.3 FOM= 0.13
INDE 11 16 4 FOBS=    72.1 SIGMA= 10.2 PHAS= 316.2 FOM= 0.01
INDE 11 16 5 FOBS=   143.0 SIGMA=  5.3 PHAS=  91.2 FOM= 0.20
INDE 11 16 6 FOBS=    53.1 SIGMA= 36.0 PHAS= 249.2 FOM= 0.16
INDE 11 16 7 FOBS=    84.4 SIGMA=  9.1 PHAS= 161.0 FOM= 0.02
INDE 11 16 8 FOBS=    67.3 SIGMA= 13.2 PHAS= 111.7 FOM= 0.10
INDE 11 17 0 FOBS=   214.6 SIGMA=  2.9 PHAS=  24.8 FOM= 0.64
INDE 11 17 1 FOBS=   279.2 SIGMA=  2.3 PHAS= 121.7 FOM= 0.93
INDE 11 17 2 FOBS=    48.3 SIGMA= 22.4 PHAS=   1.0 FOM= 0.09
INDE 11 17 3 FOBS=   115.3 SIGMA=  6.1 PHAS= 192.3 FOM= 0.07
INDE 11 17 4 FOBS=    86.2 SIGMA=  8.2 PHAS= 177.3 FOM= 0.01
INDE 11 17 5 FOBS=   114.8 SIGMA=  6.4 PHAS= 303.6 FOM= 0.25
INDE 11 17 6 FOBS=    41.2 SIGMA= 42.3 PHAS= 184.4 FOM= 0.34
INDE 11 17 7 FOBS=    85.6 SIGMA=  8.6 PHAS=  58.1 FOM= 0.02
INDE 11 17 8 FOBS=    84.4 SIGMA= 12.4 PHAS= 268.3 FOM= 0.03
INDE 11 18 0 FOBS=   207.3 SIGMA=  3.0 PHAS= 115.2 FOM= 0.73
INDE 11 18 1 FOBS=    54.0 SIGMA= 33.3 PHAS= 315.3 FOM= 0.11
INDE 11 18 2 FOBS=   153.2 SIGMA=  4.5 PHAS= 259.9 FOM= 0.11
INDE 11 18 3 FOBS=    87.9 SIGMA=  7.7 PHAS=  47.2 FOM= 0.25
INDE 11 18 4 FOBS=    57.2 SIGMA= 40.5 PHAS= 284.9 FOM= 0.22
INDE 11 18 5 FOBS=    55.4 SIGMA= 13.7 PHAS= 119.5 FOM= 0.06
INDE 11 18 6 FOBS=    82.5 SIGMA= 45.1 PHAS= 290.4 FOM= 0.11
INDE 11 19 0 FOBS=    78.5 SIGMA=  7.9 PHAS= 129.7 FOM= 0.14
INDE 11 19 1 FOBS=    44.8 SIGMA= 24.1 PHAS= 253.1 FOM= 0.05
INDE 11 19 2 FOBS=    57.8 SIGMA= 12.1 PHAS=  64.0 FOM= 0.20
INDE 11 19 3 FOBS=    45.6 SIGMA= 15.2 PHAS= 252.3 FOM= 0.21
INDE 11 19 4 FOBS=    48.2 SIGMA= 17.3 PHAS=  92.4 FOM= 0.04
INDE 11 19 5 FOBS=    72.5 SIGMA= 10.2 PHAS=  97.3 FOM= 0.09
INDE 11 19 6 FOBS=    56.7 SIGMA= 14.1 PHAS= 273.1 FOM= 0.06
INDE 11 19 7 FOBS=    83.8 SIGMA= 10.3 PHAS=  77.0 FOM= 0.02
INDE 11 20 0 FOBS=    86.7 SIGMA=  7.4 PHAS= 168.7 FOM= 0.58
INDE 11 20 1 FOBS=    68.0 SIGMA=  9.3 PHAS= 347.1 FOM= 0.13
INDE 11 20 2 FOBS=    63.0 SIGMA= 43.5 PHAS=  35.4 FOM= 0.02
INDE 11 20 3 FOBS=   126.9 SIGMA=  5.5 PHAS= 172.0 FOM= 0.54
INDE 11 20 5 FOBS=    55.2 SIGMA= 14.4 PHAS= 238.2 FOM= 0.02
INDE 11 20 6 FOBS=    77.0 SIGMA= 11.4 PHAS= 168.7 FOM= 0.05
INDE 11 21 0 FOBS=    58.9 SIGMA=  9.5 PHAS= 324.8 FOM= 0.11
INDE 11 21 1 FOBS=    59.6 SIGMA= 10.4 PHAS=   7.5 FOM= 0.15
INDE 11 21 2 FOBS=    39.4 SIGMA= 18.2 PHAS= 156.4 FOM= 0.28
INDE 11 21 3 FOBS=    57.0 SIGMA= 13.0 PHAS= 335.0 FOM= 0.30
INDE 11 21 4 FOBS=    90.2 SIGMA=  7.4 PHAS=  55.6 FOM= 0.03
INDE 11 21 5 FOBS=    52.6 SIGMA= 20.1 PHAS= 164.6 FOM= 0.07
INDE 11 21 6 FOBS=    80.6 SIGMA= 15.7 PHAS= 357.7 FOM= 0.02
INDE 11 22 0 FOBS=    52.2 SIGMA= 11.7 PHAS= 218.5 FOM= 0.20
INDE 11 22 1 FOBS=    84.7 SIGMA=  6.9 PHAS= 239.1 FOM= 0.12
INDE 11 22 2 FOBS=    74.2 SIGMA=  8.4 PHAS=  72.8 FOM= 0.55
INDE 11 22 3 FOBS=    83.1 SIGMA=  7.7 PHAS= 203.2 FOM= 0.16
INDE 11 22 4 FOBS=    56.3 SIGMA= 32.5 PHAS= 118.0 FOM= 0.05
```

Fig. 10A-141

```
INDE  11  22   5  FOBS=   60.4  SIGMA=  12.4  PHAS=  209.1  FOM=  0.03
INDE  11  23   0  FOBS=   35.6  SIGMA=  19.6  PHAS=  219.6  FOM=  0.41
INDE  11  23   1  FOBS=   91.2  SIGMA=   6.4  PHAS=  295.4  FOM=  0.27
INDE  11  23   2  FOBS=  126.0  SIGMA=   4.9  PHAS=  131.2  FOM=  0.11
INDE  11  23   3  FOBS=   63.6  SIGMA=  12.6  PHAS=  225.7  FOM=  0.11
INDE  11  24   0  FOBS=   64.9  SIGMA=   8.5  PHAS=  358.8  FOM=  0.02
INDE  11  24   1  FOBS=  114.4  SIGMA=   5.1  PHAS=  310.6  FOM=  0.17
INDE  11  24   2  FOBS=  231.7  SIGMA=   3.0  PHAS=  156.7  FOM=  0.93
INDE  11  24   3  FOBS=   87.0  SIGMA=   7.8  PHAS=   30.0  FOM=  0.20
INDE  11  25   0  FOBS=   56.3  SIGMA=  10.5  PHAS=  307.1  FOM=  0.01
INDE  11  25   1  FOBS=   91.6  SIGMA=   6.4  PHAS=  256.7  FOM=  0.16
INDE  11  25   2  FOBS=   59.1  SIGMA=  12.7  PHAS=  105.8  FOM=  0.03
INDE  11  26   0  FOBS=   73.4  SIGMA=  43.4  PHAS=  217.9  FOM=  0.01
INDE  12   0   0  FOBS=  154.1  SIGMA=   5.9  PHAS=    0.0  FOM=  0.17
INDE  12   0   1  FOBS=   52.3  SIGMA=  19.7  PHAS=    0.0  FOM=  0.11
INDE  12   0   2  FOBS=   89.2  SIGMA=  11.7  PHAS=  180.0  FOM=  0.24
INDE  12   0   3  FOBS=   94.2  SIGMA=  11.7  PHAS=  180.0  FOM=  0.01
INDE  12   0   4  FOBS=  368.1  SIGMA=   3.9  PHAS=  180.0  FOM=  0.33
INDE  12   0   5  FOBS=   56.7  SIGMA=  21.2  PHAS=  180.0  FOM=  0.02
INDE  12   0   6  FOBS=  107.4  SIGMA=  10.9  PHAS=  180.0  FOM=  0.08
INDE  12   0   7  FOBS=   57.1  SIGMA=  88.5  PHAS=    0.0  FOM=  0.03
INDE  12   0   8  FOBS=   89.5  SIGMA=  18.8  PHAS=    0.0  FOM=  0.01
INDE  12   0   9  FOBS=   51.4  SIGMA=  26.8  PHAS=  180.0  FOM=  0.01
INDE  12   0  10  FOBS=   98.2  SIGMA=  12.8  PHAS=  180.0  FOM=  0.03
INDE  12   1   0  FOBS=  258.3  SIGMA=   2.5  PHAS=  333.1  FOM=  0.49
INDE  12   1   1  FOBS=  190.6  SIGMA=   3.6  PHAS=  237.6  FOM=  0.68
INDE  12   1   2  FOBS=  153.9  SIGMA=   4.7  PHAS=  259.6  FOM=  0.20
INDE  12   1   3  FOBS=  102.6  SIGMA=   8.3  PHAS=   31.7  FOM=  0.07
INDE  12   1   4  FOBS=  143.4  SIGMA=   6.2  PHAS=  178.9  FOM=  0.22
INDE  12   1   5  FOBS=  127.4  SIGMA=   6.4  PHAS=  275.1  FOM=  0.08
INDE  12   1   6  FOBS=  196.8  SIGMA=   4.7  PHAS=  287.6  FOM=  0.03
INDE  12   1   7  FOBS=   94.4  SIGMA=  10.5  PHAS=   71.7  FOM=  0.04
INDE  12   1   8  FOBS=  108.2  SIGMA=   9.1  PHAS=   56.4  FOM=  0.09
INDE  12   1   9  FOBS=   94.2  SIGMA=  10.1  PHAS=  212.8  FOM=  0.02
INDE  12   1  10  FOBS=   63.0  SIGMA=  29.9  PHAS=   39.3  FOM=  0.02
INDE  12   2   0  FOBS=   89.1  SIGMA=   7.0  PHAS=  191.6  FOM=  0.24
INDE  12   2   1  FOBS=  103.5  SIGMA=   6.3  PHAS=   93.4  FOM=  0.27
INDE  12   2   2  FOBS=  151.9  SIGMA=   5.1  PHAS=   31.6  FOM=  0.33
INDE  12   2   3  FOBS=  103.4  SIGMA=   7.6  PHAS=  174.8  FOM=  0.28
INDE  12   2   4  FOBS=   71.9  SIGMA=  10.7  PHAS=  114.6  FOM=  0.02
INDE  12   2   5  FOBS=  105.1  SIGMA=   9.4  PHAS=  296.3  FOM=  0.33
INDE  12   2   6  FOBS=  109.5  SIGMA=   8.9  PHAS=  101.2  FOM=  0.18
INDE  12   2   7  FOBS=  144.6  SIGMA=   6.4  PHAS=  358.0  FOM=  0.04
INDE  12   2   9  FOBS=  136.0  SIGMA=   7.4  PHAS=  198.5  FOM=  0.02
INDE  12   3   0  FOBS=   61.6  SIGMA=  39.3  PHAS=   23.3  FOM=  0.07
INDE  12   3   1  FOBS=   39.1  SIGMA=  16.8  PHAS=  283.9  FOM=  0.16
INDE  12   3   2  FOBS=  140.8  SIGMA=   5.7  PHAS=  229.4  FOM=  0.60
INDE  12   3   3  FOBS=   95.6  SIGMA=   8.3  PHAS=   21.5  FOM=  0.12
INDE  12   3   4  FOBS=  108.1  SIGMA=   7.7  PHAS=  256.8  FOM=  0.25
INDE  12   3   5  FOBS=   49.0  SIGMA=  26.4  PHAS=   90.6  FOM=  0.12
INDE  12   3   6  FOBS=   86.2  SIGMA=  10.8  PHAS=  161.9  FOM=  0.06
INDE  12   3   7  FOBS=   46.0  SIGMA=  23.0  PHAS=  307.9  FOM=  0.11
INDE  12   3   8  FOBS=   57.8  SIGMA=  15.7  PHAS=   49.2  FOM=  0.16
INDE  12   3   9  FOBS=   59.9  SIGMA=  16.8  PHAS=  212.1  FOM=  0.06
INDE  12   3  10  FOBS=   81.0  SIGMA=  39.7  PHAS=   41.6  FOM=  0.02
INDE  12   4   0  FOBS=   81.3  SIGMA=   7.7  PHAS=  278.1  FOM=  0.24
INDE  12   4   1  FOBS=  206.4  SIGMA=   3.7  PHAS=  230.3  FOM=  0.81
INDE  12   4   2  FOBS=   98.6  SIGMA=   7.3  PHAS=   82.1  FOM=  0.28
INDE  12   4   3  FOBS=  156.2  SIGMA=   5.2  PHAS=   16.7  FOM=  0.32
INDE  12   4   4  FOBS=   46.7  SIGMA=  27.5  PHAS=  155.3  FOM=  0.09
INDE  12   4   5  FOBS=  142.2  SIGMA=   6.5  PHAS=  304.6  FOM=  0.06
INDE  12   4   6  FOBS=   57.7  SIGMA=  18.2  PHAS=  150.9  FOM=  0.07
INDE  12   4   7  FOBS=   60.2  SIGMA=  17.6  PHAS=  351.5  FOM=  0.13
INDE  12   4   8  FOBS=   73.6  SIGMA=  12.2  PHAS=  168.5  FOM=  0.17
INDE  12   4   9  FOBS=   57.5  SIGMA=  17.1  PHAS=  143.2  FOM=  0.04
INDE  12   4  10  FOBS=   80.6  SIGMA=  44.6  PHAS=  354.2  FOM=  0.10
INDE  12   5   0  FOBS=   95.3  SIGMA=   7.5  PHAS=  180.3  FOM=  0.39
INDE  12   5   1  FOBS=  213.3  SIGMA=   3.3  PHAS=  338.5  FOM=  0.77
INDE  12   5   2  FOBS=   86.0  SIGMA=   8.5  PHAS=  118.2  FOM=  0.07
INDE  12   5   3  FOBS=  232.8  SIGMA=   4.2  PHAS=  149.3  FOM=  0.23
INDE  12   5   4  FOBS=  181.8  SIGMA=   5.7  PHAS=  340.8  FOM=  0.52
```

Fig. 10A-142

```
INDE   12    5    5  FOBS=     83.8  SIGMA=    9.9  PHAS=   125.5  FOM=  0.13
INDE   12    5    6  FOBS=     62.6  SIGMA=   13.8  PHAS=   333.3  FOM=  0.16
INDE   12    5    7  FOBS=     75.1  SIGMA=   12.7  PHAS=   222.6  FOM=  0.17
INDE   12    5    8  FOBS=     87.4  SIGMA=   11.4  PHAS=   108.4  FOM=  0.17
INDE   12    5    9  FOBS=     67.5  SIGMA=   15.4  PHAS=   340.1  FOM=  0.03
INDE   12    5   10  FOBS=    107.3  SIGMA=   63.2  PHAS=   123.6  FOM=  0.02
INDE   12    6    0  FOBS=    252.0  SIGMA=    3.0  PHAS=    21.4  FOM=  0.75
INDE   12    6    1  FOBS=    154.5  SIGMA=    4.6  PHAS=   299.0  FOM=  0.59
INDE   12    6    2  FOBS=    145.8  SIGMA=    5.6  PHAS=    14.9  FOM=  0.54
INDE   12    6    3  FOBS=    182.7  SIGMA=    5.1  PHAS=   275.1  FOM=  0.66
INDE   12    6    4  FOBS=    126.0  SIGMA=    6.3  PHAS=   114.7  FOM=  0.25
INDE   12    6    5  FOBS=     65.8  SIGMA=   11.9  PHAS=    55.5  FOM=  0.13
INDE   12    6    6  FOBS=    112.4  SIGMA=    7.5  PHAS=   224.1  FOM=  0.39
INDE   12    6    7  FOBS=     58.4  SIGMA=   17.6  PHAS=    53.8  FOM=  0.10
INDE   12    6    8  FOBS=     79.7  SIGMA=   12.2  PHAS=   123.0  FOM=  0.08
INDE   12    6    9  FOBS=     52.3  SIGMA=   20.7  PHAS=   230.3  FOM=  0.04
INDE   12    7    0  FOBS=    193.3  SIGMA=    3.6  PHAS=   114.2  FOM=  0.93
INDE   12    7    1  FOBS=    160.3  SIGMA=    5.0  PHAS=   296.0  FOM=  0.70
INDE   12    7    2  FOBS=    293.4  SIGMA=    3.0  PHAS=   335.6  FOM=  0.23
INDE   12    7    3  FOBS=    108.5  SIGMA=    7.5  PHAS=   206.4  FOM=  0.42
INDE   12    7    4  FOBS=    177.2  SIGMA=    4.7  PHAS=    11.1  FOM=  0.68
INDE   12    7    5  FOBS=     53.3  SIGMA=   29.8  PHAS=   176.8  FOM=  0.11
INDE   12    7    6  FOBS=     46.8  SIGMA=   19.6  PHAS=    34.2  FOM=  0.12
INDE   12    7    7  FOBS=    119.2  SIGMA=    8.8  PHAS=   193.8  FOM=  0.08
INDE   12    7    8  FOBS=     51.2  SIGMA=   16.0  PHAS=   156.2  FOM=  0.41
INDE   12    7    9  FOBS=     57.8  SIGMA=   19.8  PHAS=     6.7  FOM=  0.06
INDE   12    8    0  FOBS=     68.9  SIGMA=   11.0  PHAS=   212.1  FOM=  0.03
INDE   12    8    1  FOBS=     68.7  SIGMA=   12.1  PHAS=   296.9  FOM=  0.16
INDE   12    8    2  FOBS=    201.9  SIGMA=    4.2  PHAS=    62.4  FOM=  0.85
INDE   12    8    3  FOBS=    213.8  SIGMA=    3.9  PHAS=   333.3  FOM=  0.94
INDE   12    8    4  FOBS=     82.1  SIGMA=   12.6  PHAS=    36.8  FOM=  0.17
INDE   12    8    5  FOBS=     80.4  SIGMA=   16.9  PHAS=    93.3  FOM=  0.08
INDE   12    8    6  FOBS=    149.9  SIGMA=    6.4  PHAS=   313.4  FOM=  0.51
INDE   12    8    7  FOBS=     68.6  SIGMA=   19.8  PHAS=   104.1  FOM=  0.03
INDE   12    8    8  FOBS=     44.3  SIGMA=   19.9  PHAS=    54.8  FOM=  0.02
INDE   12    8    9  FOBS=     87.4  SIGMA=    9.7  PHAS=   311.3  FOM=  0.03
INDE   12    9    0  FOBS=    226.9  SIGMA=    3.6  PHAS=   182.2  FOM=  0.84
INDE   12    9    1  FOBS=     87.0  SIGMA=   56.9  PHAS=    56.0  FOM=  0.08
INDE   12    9    2  FOBS=    114.6  SIGMA=    6.7  PHAS=   324.2  FOM=  0.31
INDE   12    9    3  FOBS=     61.3  SIGMA=   23.0  PHAS=   230.1  FOM=  0.03
INDE   12    9    4  FOBS=    221.3  SIGMA=    3.8  PHAS=   123.6  FOM=  0.73
INDE   12    9    5  FOBS=    126.7  SIGMA=    7.4  PHAS=   296.1  FOM=  0.41
INDE   12    9    6  FOBS=     67.1  SIGMA=   13.0  PHAS=   297.0  FOM=  0.10
INDE   12    9    7  FOBS=     39.4  SIGMA=   17.1  PHAS=    72.7  FOM=  0.17
INDE   12    9    8  FOBS=     73.4  SIGMA=   17.7  PHAS=   167.8  FOM=  0.01
INDE   12    9    9  FOBS=     89.3  SIGMA=    9.3  PHAS=   348.4  FOM=  0.03
INDE   12   10    0  FOBS=    105.8  SIGMA=    7.2  PHAS=   162.2  FOM=  0.24
INDE   12   10    1  FOBS=     74.3  SIGMA=   10.1  PHAS=   292.6  FOM=  0.29
INDE   12   10    2  FOBS=    119.3  SIGMA=    6.3  PHAS=   146.3  FOM=  0.25
INDE   12   10    3  FOBS=    100.6  SIGMA=    7.8  PHAS=   252.2  FOM=  0.08
INDE   12   10    4  FOBS=    123.2  SIGMA=    7.3  PHAS=    73.7  FOM=  0.27
INDE   12   10    5  FOBS=     92.6  SIGMA=   31.6  PHAS=   259.6  FOM=  0.10
INDE   12   10    6  FOBS=    119.8  SIGMA=    6.8  PHAS=    82.6  FOM=  0.03
INDE   12   10    7  FOBS=    137.3  SIGMA=    6.1  PHAS=   152.9  FOM=  0.44
INDE   12   10    8  FOBS=     57.5  SIGMA=   16.1  PHAS=   306.9  FOM=  0.07
INDE   12   10    9  FOBS=    106.9  SIGMA=    8.5  PHAS=    20.7  FOM=  0.01
INDE   12   11    0  FOBS=    194.4  SIGMA=    3.6  PHAS=   337.2  FOM=  0.57
INDE   12   11    1  FOBS=    130.8  SIGMA=    5.4  PHAS=     8.5  FOM=  0.11
INDE   12   11    2  FOBS=    276.9  SIGMA=    3.2  PHAS=   189.8  FOM=  0.93
INDE   12   11    3  FOBS=    105.3  SIGMA=    8.2  PHAS=   301.3  FOM=  0.06
INDE   12   11    4  FOBS=     76.6  SIGMA=   10.4  PHAS=    18.2  FOM=  0.09
INDE   12   11    5  FOBS=     95.6  SIGMA=    8.4  PHAS=   187.3  FOM=  0.18
INDE   12   11    6  FOBS=    103.9  SIGMA=    7.7  PHAS=   201.0  FOM=  0.02
INDE   12   11    7  FOBS=     76.8  SIGMA=   10.0  PHAS=     5.7  FOM=  0.18
INDE   12   11    8  FOBS=     86.2  SIGMA=   51.0  PHAS=   283.7  FOM=  0.04
INDE   12   12    0  FOBS=    214.7  SIGMA=    3.1  PHAS=   171.9  FOM=  0.40
INDE   12   12    1  FOBS=     87.3  SIGMA=    8.1  PHAS=   176.9  FOM=  0.08
INDE   12   12    2  FOBS=     83.0  SIGMA=    9.8  PHAS=    92.4  FOM=  0.08
INDE   12   12    3  FOBS=     45.2  SIGMA=   22.0  PHAS=   312.3  FOM=  0.11
INDE   12   12    4  FOBS=     91.1  SIGMA=    8.4  PHAS=   174.9  FOM=  0.07
INDE   12   12    5  FOBS=    110.3  SIGMA=    7.1  PHAS=   264.6  FOM=  0.08
```

Fig. 10A-143

```
INDE 12 12  6 FOBS=  57.1 SIGMA= 16.6 PHAS=  38.3 FOM= 0.12
INDE 12 12  7 FOBS= 122.6 SIGMA=  6.6 PHAS= 175.9 FOM= 0.03
INDE 12 13  0 FOBS= 153.4 SIGMA=  4.4 PHAS= 198.8 FOM= 0.29
INDE 12 13  1 FOBS=  89.2 SIGMA=  9.0 PHAS= 351.7 FOM= 0.22
INDE 12 13  2 FOBS= 139.8 SIGMA=  5.9 PHAS= 210.3 FOM= 0.23
INDE 12 13  3 FOBS=  50.1 SIGMA= 26.6 PHAS= 279.3 FOM= 0.10
INDE 12 13  4 FOBS=  68.0 SIGMA= 14.2 PHAS= 305.5 FOM= 0.02
INDE 12 13  5 FOBS=  73.7 SIGMA= 11.0 PHAS= 106.2 FOM= 0.09
INDE 12 13  6 FOBS=  59.6 SIGMA= 25.4 PHAS= 304.3 FOM= 0.12
INDE 12 13  7 FOBS=  63.6 SIGMA= 13.4 PHAS= 178.3 FOM= 0.02
INDE 12 13  8 FOBS= 331.2 SIGMA=220.6 PHAS=   8.1 FOM= 0.01
INDE 12 14  0 FOBS=  82.2 SIGMA=  8.4 PHAS=  64.7 FOM= 0.28
INDE 12 14  1 FOBS=  98.7 SIGMA=  7.8 PHAS= 243.8 FOM= 0.34
INDE 12 14  2 FOBS= 128.9 SIGMA=  5.7 PHAS= 351.4 FOM= 0.12
INDE 12 14  3 FOBS= 141.5 SIGMA=  5.3 PHAS= 346.1 FOM= 0.06
INDE 12 14  4 FOBS=  99.1 SIGMA=  7.6 PHAS=  53.6 FOM= 0.06
INDE 12 14  5 FOBS=  75.1 SIGMA= 10.9 PHAS= 235.7 FOM= 0.08
INDE 12 14  6 FOBS= 118.6 SIGMA=  6.4 PHAS= 263.6 FOM= 0.28
INDE 12 14  7 FOBS=  42.8 SIGMA= 18.8 PHAS=  37.8 FOM= 0.04
INDE 12 14  8 FOBS=  78.9 SIGMA= 13.6 PHAS= 186.5 FOM= 0.03
INDE 12 15  0 FOBS=  57.1 SIGMA= 18.9 PHAS= 162.9 FOM= 0.26
INDE 12 15  1 FOBS= 118.5 SIGMA=  5.8 PHAS= 226.6 FOM= 0.13
INDE 12 15  2 FOBS=  44.1 SIGMA= 19.7 PHAS= 105.0 FOM= 0.06
INDE 12 15  3 FOBS= 143.1 SIGMA=  5.2 PHAS= 104.5 FOM= 0.29
INDE 12 15  4 FOBS= 118.2 SIGMA=  6.2 PHAS= 233.0 FOM= 0.23
INDE 12 15  5 FOBS= 128.8 SIGMA=  5.9 PHAS= 117.6 FOM= 0.22
INDE 12 15  6 FOBS=  69.4 SIGMA= 12.1 PHAS=  34.2 FOM= 0.11
INDE 12 15  7 FOBS=  57.0 SIGMA= 34.4 PHAS= 217.8 FOM= 0.04
INDE 12 16  0 FOBS= 115.8 SIGMA=  6.0 PHAS= 223.5 FOM= 0.09
INDE 12 16  1 FOBS= 204.2 SIGMA=  3.3 PHAS= 264.6 FOM= 0.26
INDE 12 16  2 FOBS= 132.1 SIGMA=  5.4 PHAS= 131.9 FOM= 0.74
INDE 12 16  3 FOBS=  43.2 SIGMA= 17.4 PHAS= 249.7 FOM= 0.27
INDE 12 16  4 FOBS=  37.8 SIGMA= 17.7 PHAS=  36.3 FOM= 0.11
INDE 12 16  5 FOBS=  75.9 SIGMA= 10.0 PHAS=  97.9 FOM= 0.43
INDE 12 16  6 FOBS= 142.1 SIGMA=  5.4 PHAS= 105.2 FOM= 0.10
INDE 12 16  7 FOBS= 138.4 SIGMA= 91.8 PHAS= 117.9 FOM= 0.01
INDE 12 17  0 FOBS=  40.7 SIGMA= 18.8 PHAS= 172.1 FOM= 0.17
INDE 12 17  1 FOBS=  76.4 SIGMA=  8.6 PHAS=  40.7 FOM= 0.19
INDE 12 17  2 FOBS=  69.3 SIGMA= 10.4 PHAS= 270.4 FOM= 0.24
INDE 12 17  3 FOBS= 121.6 SIGMA=  5.9 PHAS= 145.7 FOM= 0.18
INDE 12 17  4 FOBS= 104.6 SIGMA=  7.0 PHAS= 104.1 FOM= 0.61
INDE 12 17  5 FOBS=  48.2 SIGMA= 23.5 PHAS= 229.1 FOM= 0.06
INDE 12 17  6 FOBS=  52.0 SIGMA= 17.6 PHAS= 289.7 FOM= 0.02
INDE 12 18  0 FOBS=  85.4 SIGMA= 68.0 PHAS= 337.1 FOM= 0.06
INDE 12 18  1 FOBS= 142.0 SIGMA=  4.7 PHAS= 344.2 FOM= 0.76
INDE 12 18  2 FOBS=  75.0 SIGMA=  9.1 PHAS= 147.2 FOM= 0.10
INDE 12 18  3 FOBS=  45.4 SIGMA= 22.8 PHAS= 300.2 FOM= 0.08
INDE 12 18  4 FOBS=  81.7 SIGMA=  7.0 PHAS=   0.2 FOM= 0.92
INDE 12 18  5 FOBS= 107.8 SIGMA=  6.6 PHAS= 168.6 FOM= 0.03
INDE 12 18  6 FOBS=  63.9 SIGMA= 14.2 PHAS= 357.3 FOM= 0.04
INDE 12 19  0 FOBS=  78.3 SIGMA=  7.8 PHAS= 284.5 FOM= 0.21
INDE 12 19  1 FOBS=  65.3 SIGMA= 38.4 PHAS= 136.7 FOM= 0.13
INDE 12 19  2 FOBS=  53.1 SIGMA= 25.0 PHAS=  50.9 FOM= 0.03
INDE 12 19  3 FOBS= 118.0 SIGMA=  5.7 PHAS= 260.3 FOM= 0.47
INDE 12 19  4 FOBS=  47.3 SIGMA= 22.8 PHAS=  56.3 FOM= 0.07
INDE 12 19  5 FOBS= 129.6 SIGMA=  5.5 PHAS=  71.5 FOM= 0.12
INDE 12 20  0 FOBS=  70.8 SIGMA=  8.6 PHAS= 246.0 FOM= 0.08
INDE 12 20  1 FOBS= 133.4 SIGMA=  4.8 PHAS=  49.9 FOM= 0.16
INDE 12 20  2 FOBS=  77.5 SIGMA=  7.9 PHAS= 210.8 FOM= 0.21
INDE 12 20  4 FOBS=  49.5 SIGMA= 15.1 PHAS= 185.3 FOM= 0.05
INDE 12 20  5 FOBS= 119.1 SIGMA= 69.3 PHAS= 216.8 FOM= 0.01
INDE 12 21  0 FOBS=  37.5 SIGMA= 16.1 PHAS= 309.8 FOM= 0.35
INDE 12 21  1 FOBS=  78.9 SIGMA=  6.9 PHAS=  50.8 FOM= 0.93
INDE 12 21  2 FOBS=  97.2 SIGMA= 56.4 PHAS= 158.9 FOM= 0.06
INDE 12 21  3 FOBS=  99.7 SIGMA=  6.7 PHAS= 223.5 FOM= 0.12
INDE 12 21  4 FOBS=  62.7 SIGMA= 37.2 PHAS=  63.8 FOM= 0.07
INDE 12 22  0 FOBS=  71.4 SIGMA=  7.9 PHAS= 337.9 FOM= 0.20
INDE 12 22  1 FOBS=  84.5 SIGMA=  7.0 PHAS=  89.9 FOM= 0.06
INDE 12 22  2 FOBS=  59.5 SIGMA= 24.5 PHAS= 241.3 FOM= 0.07
INDE 12 22  3 FOBS= 103.1 SIGMA=  6.4 PHAS= 342.3 FOM= 0.25
INDE 12 23  0 FOBS=  84.8 SIGMA=  6.6 PHAS= 187.8 FOM= 0.07
```

Fig. 10A-144

```
INDE  12 24 1 FOBS=   44.9 SIGMA= 22.7 PHAS= 103.7 FOM= 0.13
INDE  13  0 0 FOBS=   74.5 SIGMA= 16.9 PHAS=   0.0 FOM= 0.01
INDE  13  0 1 FOBS=  563.3 SIGMA=  3.1 PHAS= 180.0 FOM= 0.12
INDE  13  0 2 FOBS=   88.4 SIGMA= 11.6 PHAS=   0.0 FOM= 0.01
INDE  13  0 3 FOBS=  209.1 SIGMA=  5.5 PHAS= 180.0 FOM= 0.16
INDE  13  0 4 FOBS=   76.7 SIGMA= 17.9 PHAS=   0.0 FOM= 0.03
INDE  13  0 5 FOBS=  166.0 SIGMA=  7.1 PHAS=   0.0 FOM= 0.21
INDE  13  0 6 FOBS=  147.0 SIGMA=  8.1 PHAS= 180.0 FOM= 0.07
INDE  13  0 7 FOBS=   28.4 SIGMA= 30.6 PHAS= 180.0 FOM= 0.02
INDE  13  0 8 FOBS=   98.7 SIGMA= 12.5 PHAS= 180.0 FOM= 0.10
INDE  13  0 9 FOBS=  123.0 SIGMA= 14.8 PHAS= 180.0 FOM= 0.01
INDE  13  1 0 FOBS=   96.6 SIGMA=  7.2 PHAS= 333.7 FOM= 0.19
INDE  13  1 1 FOBS=   59.0 SIGMA= 17.9 PHAS= 127.0 FOM= 0.04
INDE  13  1 2 FOBS=   65.6 SIGMA= 15.7 PHAS= 189.0 FOM= 0.05
INDE  13  1 3 FOBS=  168.8 SIGMA=  5.2 PHAS=  12.1 FOM= 0.13
INDE  13  1 4 FOBS=  192.5 SIGMA=  4.6 PHAS=  68.5 FOM= 0.39
INDE  13  1 5 FOBS=   69.8 SIGMA= 12.3 PHAS= 172.9 FOM= 0.05
INDE  13  1 6 FOBS=  181.8 SIGMA=  5.0 PHAS= 134.9 FOM= 0.36
INDE  13  1 7 FOBS=   42.3 SIGMA= 19.6 PHAS=  43.5 FOM= 0.15
INDE  13  1 8 FOBS=  105.5 SIGMA=  9.9 PHAS=  55.0 FOM= 0.01
INDE  13  2 1 FOBS=  178.5 SIGMA=  4.3 PHAS= 271.3 FOM= 0.42
INDE  13  2 2 FOBS=   87.9 SIGMA=  8.6 PHAS=  31.9 FOM= 0.09
INDE  13  2 3 FOBS=  110.8 SIGMA=  7.3 PHAS= 134.3 FOM= 0.18
INDE  13  2 4 FOBS=   90.7 SIGMA=  9.1 PHAS= 307.0 FOM= 0.17
INDE  13  2 5 FOBS=   59.8 SIGMA= 16.0 PHAS= 157.8 FOM= 0.05
INDE  13  2 6 FOBS=  163.3 SIGMA=  5.2 PHAS= 354.7 FOM= 0.20
INDE  13  2 7 FOBS=   49.3 SIGMA= 27.4 PHAS= 137.9 FOM= 0.07
INDE  13  2 8 FOBS=   78.8 SIGMA= 12.3 PHAS= 171.1 FOM= 0.02
INDE  13  2 9 FOBS=   74.4 SIGMA= 20.0 PHAS= 292.1 FOM= 0.08
INDE  13  3 0 FOBS=  173.8 SIGMA=  4.1 PHAS= 356.9 FOM= 0.05
INDE  13  3 1 FOBS=   86.3 SIGMA=  8.4 PHAS= 344.9 FOM= 0.09
INDE  13  3 2 FOBS=   82.7 SIGMA= 10.5 PHAS=  66.7 FOM= 0.11
INDE  13  3 3 FOBS=   78.1 SIGMA=  9.7 PHAS= 237.3 FOM= 0.16
INDE  13  3 4 FOBS=   54.5 SIGMA= 23.3 PHAS= 358.7 FOM= 0.03
INDE  13  3 5 FOBS=   66.7 SIGMA= 17.4 PHAS=   5.9 FOM= 0.05
INDE  13  3 6 FOBS=  105.9 SIGMA=  8.5 PHAS= 176.6 FOM= 0.25
INDE  13  3 7 FOBS=   83.3 SIGMA= 11.3 PHAS=  60.8 FOM= 0.15
INDE  13  3 8 FOBS=   96.8 SIGMA=  8.8 PHAS= 333.0 FOM= 0.02
INDE  13  3 9 FOBS=   53.0 SIGMA= 28.7 PHAS= 164.9 FOM= 0.01
INDE  13  4 0 FOBS=  233.7 SIGMA=  3.1 PHAS= 269.9 FOM= 0.82
INDE  13  4 1 FOBS=   92.9 SIGMA=  8.5 PHAS=  40.9 FOM= 0.35
INDE  13  4 2 FOBS=   56.5 SIGMA= 14.5 PHAS= 200.6 FOM= 0.12
INDE  13  4 3 FOBS=  101.6 SIGMA=  7.6 PHAS= 128.6 FOM= 0.15
INDE  13  4 4 FOBS=   65.9 SIGMA= 20.9 PHAS= 346.6 FOM= 0.18
INDE  13  4 5 FOBS=  108.4 SIGMA=  8.1 PHAS= 207.1 FOM= 0.36
INDE  13  4 6 FOBS=   84.3 SIGMA= 12.8 PHAS= 357.8 FOM= 0.09
INDE  13  4 7 FOBS=  102.8 SIGMA=  8.0 PHAS=   9.0 FOM= 0.32
INDE  13  4 8 FOBS=   75.7 SIGMA= 11.8 PHAS= 210.0 FOM= 0.02
INDE  13  5 0 FOBS=   64.2 SIGMA= 24.8 PHAS= 311.1 FOM= 0.19
INDE  13  5 1 FOBS=   56.9 SIGMA= 26.7 PHAS= 233.3 FOM= 0.13
INDE  13  5 2 FOBS=   60.1 SIGMA= 13.9 PHAS= 105.0 FOM= 0.26
INDE  13  5 3 FOBS=  103.1 SIGMA=  7.4 PHAS= 318.0 FOM= 0.13
INDE  13  5 4 FOBS=   49.9 SIGMA= 27.4 PHAS= 214.7 FOM= 0.06
INDE  13  5 5 FOBS=  167.3 SIGMA=  5.7 PHAS=  31.0 FOM= 0.13
INDE  13  5 6 FOBS=   54.7 SIGMA= 15.2 PHAS= 312.4 FOM= 0.10
INDE  13  5 7 FOBS=   94.3 SIGMA=  8.3 PHAS=  87.3 FOM= 0.34
INDE  13  5 8 FOBS=   55.8 SIGMA= 19.0 PHAS= 245.2 FOM= 0.04
INDE  13  6 0 FOBS=  171.9 SIGMA=  4.9 PHAS= 253.0 FOM= 0.84
INDE  13  6 1 FOBS=  179.8 SIGMA=  4.5 PHAS=  74.3 FOM= 0.89
INDE  13  6 2 FOBS=  239.3 SIGMA=  3.2 PHAS= 239.0 FOM= 0.69
INDE  13  6 3 FOBS=  180.2 SIGMA=  4.7 PHAS= 290.3 FOM= 0.18
INDE  13  6 4 FOBS=   96.8 SIGMA=  9.7 PHAS=  36.0 FOM= 0.31
INDE  13  6 5 FOBS=   41.7 SIGMA= 21.4 PHAS= 202.6 FOM= 0.16
INDE  13  6 6 FOBS=   53.0 SIGMA= 15.7 PHAS=   4.6 FOM= 0.11
INDE  13  6 7 FOBS=   89.8 SIGMA=  9.9 PHAS= 345.8 FOM= 0.01
INDE  13  6 8 FOBS=   59.6 SIGMA= 15.3 PHAS= 187.8 FOM= 0.03
INDE  13  7 0 FOBS=   64.6 SIGMA= 11.6 PHAS= 101.5 FOM= 0.08
INDE  13  7 1 FOBS=   89.6 SIGMA=  8.4 PHAS= 301.0 FOM= 0.16
INDE  13  7 2 FOBS=  128.9 SIGMA=  5.9 PHAS= 178.8 FOM= 0.09
INDE  13  7 3 FOBS=  190.1 SIGMA=  5.2 PHAS= 341.9 FOM= 0.15
INDE  13  7 4 FOBS=  110.3 SIGMA=  8.1 PHAS= 183.3 FOM= 0.19
```

Fig. 10A-145

```
INDE  13   7   5 FOBS=   95.7 SIGMA=   8.2 PHAS= 299.9 FOM= 0.02
INDE  13   7   6 FOBS=   76.5 SIGMA=  10.9 PHAS= 321.9 FOM= 0.11
INDE  13   7   7 FOBS=   64.4 SIGMA=  14.7 PHAS= 148.0 FOM= 0.10
INDE  13   7   8 FOBS=   89.0 SIGMA=  10.2 PHAS=   7.6 FOM= 0.03
INDE  13   8   0 FOBS=  110.8 SIGMA=   6.5 PHAS= 320.6 FOM= 0.46
INDE  13   8   1 FOBS=   90.2 SIGMA=  70.3 PHAS=  77.4 FOM= 0.16
INDE  13   8   2 FOBS=   95.5 SIGMA=   9.7 PHAS= 243.3 FOM= 0.06
INDE  13   8   3 FOBS=  188.4 SIGMA=   4.9 PHAS= 173.9 FOM= 0.14
INDE  13   8   4 FOBS=   40.6 SIGMA=  19.8 PHAS=  87.4 FOM= 0.05
INDE  13   8   5 FOBS=  136.1 SIGMA=   5.9 PHAS=  20.3 FOM= 0.21
INDE  13   8   6 FOBS=   51.2 SIGMA=  30.6 PHAS= 131.0 FOM= 0.11
INDE  13   8   7 FOBS=   42.9 SIGMA=  23.0 PHAS= 230.8 FOM= 0.02
INDE  13   8   8 FOBS=   44.2 SIGMA=  24.2 PHAS= 330.4 FOM= 0.20
INDE  13   9   0 FOBS=  152.3 SIGMA=   4.8 PHAS=  20.9 FOM= 0.69
INDE  13   9   1 FOBS=  107.2 SIGMA=   7.1 PHAS= 125.1 FOM= 0.15
INDE  13   9   2 FOBS=  106.6 SIGMA=   8.2 PHAS= 178.0 FOM= 0.20
INDE  13   9   3 FOBS=   41.7 SIGMA=  18.4 PHAS= 345.7 FOM= 0.17
INDE  13   9   4 FOBS=   83.9 SIGMA=   9.6 PHAS= 173.3 FOM= 0.07
INDE  13   9   5 FOBS=  106.7 SIGMA=   7.6 PHAS= 277.0 FOM= 0.09
INDE  13   9   6 FOBS=   76.0 SIGMA= 127.3 PHAS= 326.3 FOM= 0.14
INDE  13   9   7 FOBS=   93.6 SIGMA=   9.9 PHAS= 249.1 FOM= 0.04
INDE  13   9   8 FOBS=   98.7 SIGMA=  10.2 PHAS= 159.9 FOM= 0.07
INDE  13  10   0 FOBS=  220.4 SIGMA=   3.4 PHAS=  15.4 FOM= 0.46
INDE  13  10   1 FOBS=   78.2 SIGMA=  11.2 PHAS= 149.1 FOM= 0.08
INDE  13  10   2 FOBS=   98.4 SIGMA=   8.2 PHAS= 275.1 FOM= 0.13
INDE  13  10   3 FOBS=   56.4 SIGMA=  32.8 PHAS=  83.9 FOM= 0.05
INDE  13  10   4 FOBS=   52.4 SIGMA=  25.8 PHAS= 168.9 FOM= 0.13
INDE  13  10   5 FOBS=   76.6 SIGMA=  14.0 PHAS= 332.6 FOM= 0.13
INDE  13  10   6 FOBS=   38.5 SIGMA=  17.7 PHAS= 208.6 FOM= 0.26
INDE  13  10   7 FOBS=   76.5 SIGMA=  11.3 PHAS= 167.8 FOM= 0.04
INDE  13  11   0 FOBS=  125.5 SIGMA=   6.4 PHAS=  40.8 FOM= 0.37
INDE  13  11   1 FOBS=  105.6 SIGMA=   7.3 PHAS=  95.7 FOM= 0.11
INDE  13  11   2 FOBS=  113.4 SIGMA=   6.4 PHAS= 263.6 FOM= 0.28
INDE  13  11   3 FOBS=  133.3 SIGMA=   5.7 PHAS= 116.4 FOM= 0.15
INDE  13  11   4 FOBS=   94.4 SIGMA=   9.1 PHAS= 337.0 FOM= 0.04
INDE  13  11   5 FOBS=   44.1 SIGMA=  20.0 PHAS= 290.1 FOM= 0.12
INDE  13  11   6 FOBS=  159.5 SIGMA=   5.1 PHAS= 216.2 FOM= 0.32
INDE  13  11   7 FOBS=   62.0 SIGMA=  13.8 PHAS= 336.7 FOM= 0.04
INDE  13  12   0 FOBS=  118.7 SIGMA=   6.5 PHAS= 147.6 FOM= 0.13
INDE  13  12   1 FOBS=   64.8 SIGMA=  13.0 PHAS= 229.8 FOM= 0.05
INDE  13  12   2 FOBS=   81.9 SIGMA=   8.8 PHAS= 212.8 FOM= 0.07
INDE  13  12   3 FOBS=   56.5 SIGMA=  14.8 PHAS=  64.6 FOM= 0.16
INDE  13  12   4 FOBS=   77.8 SIGMA=  11.5 PHAS= 298.8 FOM= 0.12
INDE  13  12   5 FOBS=   78.7 SIGMA=   9.7 PHAS= 173.6 FOM= 0.13
INDE  13  12   6 FOBS=   59.7 SIGMA=  33.0 PHAS=  44.4 FOM= 0.02
INDE  13  12   7 FOBS=   91.7 SIGMA=   8.6 PHAS=  84.0 FOM= 0.03
INDE  13  13   0 FOBS=  139.0 SIGMA=   4.9 PHAS= 276.6 FOM= 0.44
INDE  13  13   1 FOBS=   45.6 SIGMA=  26.1 PHAS= 167.2 FOM= 0.07
INDE  13  13   2 FOBS=   71.9 SIGMA=  10.8 PHAS=  76.9 FOM= 0.14
INDE  13  13   3 FOBS=  117.8 SIGMA=   7.2 PHAS= 220.3 FOM= 0.04
INDE  13  13   4 FOBS=   70.5 SIGMA=  13.5 PHAS= 250.6 FOM= 0.08
INDE  13  13   5 FOBS=   49.0 SIGMA=  12.5 PHAS=  41.5 FOM= 0.78
INDE  13  13   6 FOBS=   42.0 SIGMA=  18.6 PHAS= 137.7 FOM= 0.03
INDE  13  13   7 FOBS=  102.7 SIGMA=   7.8 PHAS= 230.6 FOM= 0.07
INDE  13  14   0 FOBS=  173.6 SIGMA=   4.0 PHAS= 264.6 FOM= 0.49
INDE  13  14   1 FOBS=  126.8 SIGMA=   5.7 PHAS=  58.6 FOM= 0.74
INDE  13  14   2 FOBS=   53.9 SIGMA=  15.4 PHAS= 238.8 FOM= 0.24
INDE  13  14   3 FOBS=  112.1 SIGMA= 114.3 PHAS= 299.9 FOM= 0.05
INDE  13  14   4 FOBS=  142.4 SIGMA=   5.4 PHAS=  10.2 FOM= 0.33
INDE  13  14   5 FOBS=   87.7 SIGMA=  47.3 PHAS= 202.9 FOM= 0.05
INDE  13  14   6 FOBS=   42.5 SIGMA=  18.3 PHAS= 295.4 FOM= 0.01
INDE  13  15   0 FOBS=  110.6 SIGMA=   5.8 PHAS= 108.3 FOM= 0.16
INDE  13  15   1 FOBS=   65.2 SIGMA=  34.0 PHAS= 256.3 FOM= 0.22
INDE  13  15   2 FOBS=   72.9 SIGMA=  10.4 PHAS= 160.6 FOM= 0.04
INDE  13  15   4 FOBS=   73.3 SIGMA=   9.0 PHAS= 174.5 FOM= 0.72
INDE  13  15   6 FOBS=   74.2 SIGMA=  10.4 PHAS=  11.8 FOM= 0.05
INDE  13  16   0 FOBS=   96.8 SIGMA=   7.0 PHAS= 320.6 FOM= 0.42
INDE  13  16   1 FOBS=   56.6 SIGMA=  40.0 PHAS=  90.1 FOM= 0.15
INDE  13  16   2 FOBS=   73.2 SIGMA=   9.5 PHAS= 273.7 FOM= 0.01
INDE  13  16   3 FOBS=   96.0 SIGMA=   7.2 PHAS= 281.8 FOM= 0.20
INDE  13  16   4 FOBS=   72.2 SIGMA=  31.5 PHAS= 129.6 FOM= 0.04
```

Fig. 10A-146

| | | | | | | | | | | |
|---|---|---|---|---|---|---|---|---|---|---|
| INDE | 13 | 16 | 5 | FOBS= | 40.3 | SIGMA= | 17.1 | PHAS= | 323.8 | FOM= | 0.05 |
| INDE | 13 | 16 | 6 | FOBS= | 89.8 | SIGMA= | 43.2 | PHAS= | 120.3 | FOM= | 0.07 |
| INDE | 13 | 17 | 0 | FOBS= | 60.6 | SIGMA= | 29.8 | PHAS= | 299.2 | FOM= | 0.06 |
| INDE | 13 | 17 | 1 | FOBS= | 66.2 | SIGMA= | 10.1 | PHAS= | 83.0 | FOM= | 0.13 |
| INDE | 13 | 17 | 2 | FOBS= | 68.1 | SIGMA= | 10.0 | PHAS= | 219.2 | FOM= | 0.30 |
| INDE | 13 | 17 | 3 | FOBS= | 81.1 | SIGMA= | 8.6 | PHAS= | 28.4 | FOM= | 0.23 |
| INDE | 13 | 17 | 4 | FOBS= | 56.4 | SIGMA= | 13.8 | PHAS= | 159.4 | FOM= | 0.12 |
| INDE | 13 | 17 | 5 | FOBS= | 64.8 | SIGMA= | 15.5 | PHAS= | 160.4 | FOM= | 0.01 |
| INDE | 13 | 18 | 0 | FOBS= | 157.4 | SIGMA= | 4.4 | PHAS= | 21.5 | FOM= | 0.42 |
| INDE | 13 | 18 | 1 | FOBS= | 36.3 | SIGMA= | 19.9 | PHAS= | 98.2 | FOM= | 0.14 |
| INDE | 13 | 18 | 2 | FOBS= | 88.7 | SIGMA= | 7.7 | PHAS= | 240.8 | FOM= | 0.11 |
| INDE | 13 | 18 | 3 | FOBS= | 40.4 | SIGMA= | 20.3 | PHAS= | 219.2 | FOM= | 0.01 |
| INDE | 13 | 18 | 4 | FOBS= | 43.1 | SIGMA= | 18.1 | PHAS= | 138.6 | FOM= | 0.06 |
| INDE | 13 | 19 | 0 | FOBS= | 46.9 | SIGMA= | 18.2 | PHAS= | 17.9 | FOM= | 0.46 |
| INDE | 13 | 19 | 1 | FOBS= | 51.0 | SIGMA= | 13.6 | PHAS= | 60.2 | FOM= | 0.09 |
| INDE | 13 | 19 | 2 | FOBS= | 66.6 | SIGMA= | 10.1 | PHAS= | 200.3 | FOM= | 0.17 |
| INDE | 13 | 19 | 3 | FOBS= | 59.8 | SIGMA= | 11.3 | PHAS= | 44.9 | FOM= | 0.07 |
| INDE | 13 | 19 | 4 | FOBS= | 175.4 | SIGMA= | 116.7 | PHAS= | 300.8 | FOM= | 0.00 |
| INDE | 13 | 20 | 0 | FOBS= | 41.2 | SIGMA= | 18.6 | PHAS= | 33.7 | FOM= | 0.09 |
| INDE | 13 | 20 | 1 | FOBS= | 81.4 | SIGMA= | 7.8 | PHAS= | 215.5 | FOM= | 0.27 |
| INDE | 13 | 20 | 2 | FOBS= | 62.7 | SIGMA= | 38.3 | PHAS= | 28.5 | FOM= | 0.02 |
| INDE | 13 | 20 | 3 | FOBS= | 269.7 | SIGMA= | 179.6 | PHAS= | 14.2 | FOM= | 0.03 |
| INDE | 13 | 21 | 0 | FOBS= | 60.3 | SIGMA= | 10.9 | PHAS= | 185.0 | FOM= | 0.04 |
| INDE | 13 | 21 | 1 | FOBS= | 65.2 | SIGMA= | 10.3 | PHAS= | 113.5 | FOM= | 0.06 |
| INDE | 13 | 22 | 0 | FOBS= | 80.5 | SIGMA= | 40.2 | PHAS= | 64.2 | FOM= | 0.11 |
| INDE | 13 | 22 | 1 | FOBS= | 84.6 | SIGMA= | 7.9 | PHAS= | 32.4 | FOM= | 0.03 |
| INDE | 14 | 0 | 0 | FOBS= | 31.3 | SIGMA= | 30.5 | PHAS= | 180.0 | FOM= | 0.16 |
| INDE | 14 | 0 | 2 | FOBS= | 71.4 | SIGMA= | 15.2 | PHAS= | 0.0 | FOM= | 0.06 |
| INDE | 14 | 0 | 4 | FOBS= | 112.2 | SIGMA= | 12.4 | PHAS= | 180.0 | FOM= | 0.09 |
| INDE | 14 | 0 | 5 | FOBS= | 94.4 | SIGMA= | 15.2 | PHAS= | 0.0 | FOM= | 0.22 |
| INDE | 14 | 0 | 6 | FOBS= | 78.3 | SIGMA= | 17.8 | PHAS= | 180.0 | FOM= | 0.00 |
| INDE | 14 | 0 | 7 | FOBS= | 92.6 | SIGMA= | 12.4 | PHAS= | 180.0 | FOM= | 0.03 |
| INDE | 14 | 1 | 0 | FOBS= | 224.1 | SIGMA= | 3.2 | PHAS= | 186.8 | FOM= | 0.30 |
| INDE | 14 | 1 | 1 | FOBS= | 109.0 | SIGMA= | 6.7 | PHAS= | 352.5 | FOM= | 0.34 |
| INDE | 14 | 1 | 2 | FOBS= | 182.2 | SIGMA= | 4.3 | PHAS= | 239.6 | FOM= | 0.33 |
| INDE | 14 | 1 | 3 | FOBS= | 92.4 | SIGMA= | 9.4 | PHAS= | 196.3 | FOM= | 0.16 |
| INDE | 14 | 1 | 4 | FOBS= | 111.3 | SIGMA= | 7.8 | PHAS= | 34.9 | FOM= | 0.07 |
| INDE | 14 | 1 | 5 | FOBS= | 149.4 | SIGMA= | 5.4 | PHAS= | 164.3 | FOM= | 0.05 |
| INDE | 14 | 1 | 6 | FOBS= | 80.0 | SIGMA= | 10.1 | PHAS= | 253.9 | FOM= | 0.02 |
| INDE | 14 | 1 | 7 | FOBS= | 69.3 | SIGMA= | 13.3 | PHAS= | 290.9 | FOM= | 0.02 |
| INDE | 14 | 2 | 0 | FOBS= | 101.6 | SIGMA= | 81.7 | PHAS= | 359.7 | FOM= | 0.08 |
| INDE | 14 | 2 | 1 | FOBS= | 74.2 | SIGMA= | 12.8 | PHAS= | 245.1 | FOM= | 0.03 |
| INDE | 14 | 2 | 2 | FOBS= | 57.9 | SIGMA= | 14.4 | PHAS= | 185.2 | FOM= | 0.12 |
| INDE | 14 | 2 | 3 | FOBS= | 96.3 | SIGMA= | 8.3 | PHAS= | 7.4 | FOM= | 0.24 |
| INDE | 14 | 2 | 4 | FOBS= | 114.0 | SIGMA= | 6.9 | PHAS= | 83.2 | FOM= | 0.04 |
| INDE | 14 | 2 | 5 | FOBS= | 90.9 | SIGMA= | 9.4 | PHAS= | 235.7 | FOM= | 0.06 |
| INDE | 14 | 2 | 6 | FOBS= | 117.9 | SIGMA= | 6.8 | PHAS= | 63.4 | FOM= | 0.03 |
| INDE | 14 | 2 | 7 | FOBS= | 53.3 | SIGMA= | 18.1 | PHAS= | 95.3 | FOM= | 0.05 |
| INDE | 14 | 3 | 0 | FOBS= | 68.0 | SIGMA= | 10.9 | PHAS= | 219.8 | FOM= | 0.22 |
| INDE | 14 | 3 | 2 | FOBS= | 102.4 | SIGMA= | 8.1 | PHAS= | 252.3 | FOM= | 0.07 |
| INDE | 14 | 3 | 3 | FOBS= | 62.2 | SIGMA= | 14.6 | PHAS= | 190.0 | FOM= | 0.05 |
| INDE | 14 | 3 | 4 | FOBS= | 55.9 | SIGMA= | 16.3 | PHAS= | 50.4 | FOM= | 0.14 |
| INDE | 14 | 3 | 5 | FOBS= | 58.7 | SIGMA= | 26.8 | PHAS= | 249.5 | FOM= | 0.14 |
| INDE | 14 | 3 | 6 | FOBS= | 67.7 | SIGMA= | 14.4 | PHAS= | 93.2 | FOM= | 0.04 |
| INDE | 14 | 3 | 7 | FOBS= | 41.7 | SIGMA= | 21.4 | PHAS= | 190.1 | FOM= | 0.03 |
| INDE | 14 | 4 | 0 | FOBS= | 86.4 | SIGMA= | 8.3 | PHAS= | 60.1 | FOM= | 0.27 |
| INDE | 14 | 4 | 1 | FOBS= | 73.2 | SIGMA= | 12.2 | PHAS= | 291.4 | FOM= | 0.05 |
| INDE | 14 | 4 | 2 | FOBS= | 139.6 | SIGMA= | 5.6 | PHAS= | 188.1 | FOM= | 0.42 |
| INDE | 14 | 4 | 3 | FOBS= | 135.8 | SIGMA= | 5.7 | PHAS= | 346.5 | FOM= | 0.26 |
| INDE | 14 | 4 | 4 | FOBS= | 120.0 | SIGMA= | 6.5 | PHAS= | 178.8 | FOM= | 0.05 |
| INDE | 14 | 4 | 5 | FOBS= | 49.8 | SIGMA= | 22.1 | PHAS= | 285.3 | FOM= | 0.06 |
| INDE | 14 | 4 | 6 | FOBS= | 64.9 | SIGMA= | 26.0 | PHAS= | 345.7 | FOM= | 0.01 |
| INDE | 14 | 4 | 7 | FOBS= | 55.8 | SIGMA= | 18.6 | PHAS= | 126.9 | FOM= | 0.04 |
| INDE | 14 | 5 | 0 | FOBS= | 130.0 | SIGMA= | 5.9 | PHAS= | 282.8 | FOM= | 0.41 |
| INDE | 14 | 5 | 2 | FOBS= | 135.9 | SIGMA= | 5.7 | PHAS= | 233.2 | FOM= | 0.05 |
| INDE | 14 | 5 | 3 | FOBS= | 111.5 | SIGMA= | 6.9 | PHAS= | 86.7 | FOM= | 0.07 |
| INDE | 14 | 5 | 4 | FOBS= | 63.6 | SIGMA= | 17.1 | PHAS= | 130.6 | FOM= | 0.06 |
| INDE | 14 | 5 | 5 | FOBS= | 77.3 | SIGMA= | 10.7 | PHAS= | 276.0 | FOM= | 0.21 |
| INDE | 14 | 5 | 6 | FOBS= | 64.7 | SIGMA= | 36.4 | PHAS= | 94.0 | FOM= | 0.10 |
| INDE | 14 | 5 | 7 | FOBS= | 46.3 | SIGMA= | 21.0 | PHAS= | 263.4 | FOM= | 0.01 |
| INDE | 14 | 6 | 0 | FOBS= | 193.2 | SIGMA= | 4.2 | PHAS= | 326.5 | FOM= | 0.44 |

Fig. 10A-147

```
INDE  14   6   1  FOBS=   86.2  SIGMA=   8.6  PHAS=  337.8  FOM=  0.01
INDE  14   6   2  FOBS=  102.0  SIGMA=   7.3  PHAS=  205.6  FOM=  0.31
INDE  14   6   3  FOBS=  122.6  SIGMA=   6.4  PHAS=  343.3  FOM=  0.36
INDE  14   6   4  FOBS=   40.2  SIGMA=  25.2  PHAS=  192.1  FOM=  0.13
INDE  14   6   5  FOBS=   70.8  SIGMA=  12.3  PHAS=  120.7  FOM=  0.17
INDE  14   6   6  FOBS=  112.6  SIGMA=   8.0  PHAS=   28.7  FOM=  0.02
INDE  14   6   7  FOBS=   78.9  SIGMA=  33.9  PHAS=  251.2  FOM=  0.09
INDE  14   7   0  FOBS=   90.6  SIGMA=   7.9  PHAS=   25.0  FOM=  0.17
INDE  14   7   2  FOBS=   82.1  SIGMA=   9.3  PHAS=   27.8  FOM=  0.34
INDE  14   7   3  FOBS=  141.8  SIGMA=   5.4  PHAS=  329.2  FOM=  0.27
INDE  14   7   4  FOBS=   96.1  SIGMA=   8.7  PHAS=  149.6  FOM=  0.12
INDE  14   7   5  FOBS=  156.7  SIGMA=   5.8  PHAS=  309.6  FOM=  0.45
INDE  14   7   6  FOBS=   87.1  SIGMA=   9.4  PHAS=  284.7  FOM=  0.01
INDE  14   7   7  FOBS=   84.9  SIGMA=  46.6  PHAS=  160.5  FOM=  0.01
INDE  14   8   0  FOBS=   72.4  SIGMA=  11.0  PHAS=  123.7  FOM=  0.11
INDE  14   8   1  FOBS=   34.9  SIGMA=  19.0  PHAS=  175.0  FOM=  0.11
INDE  14   8   2  FOBS=   59.5  SIGMA=  28.1  PHAS=  280.2  FOM=  0.02
INDE  14   8   3  FOBS=  145.6  SIGMA=   5.7  PHAS=  130.4  FOM=  0.27
INDE  14   8   4  FOBS=   61.5  SIGMA=  14.4  PHAS=  222.9  FOM=  0.11
INDE  14   8   5  FOBS=   22.1  SIGMA=  23.7  PHAS=  329.0  FOM=  0.41
INDE  14   8   6  FOBS=   71.0  SIGMA=  11.4  PHAS=  138.0  FOM=  0.05
INDE  14   8   7  FOBS=   71.7  SIGMA=  12.5  PHAS=  256.6  FOM=  0.04
INDE  14   9   0  FOBS=  163.1  SIGMA=   4.5  PHAS=  105.3  FOM=  0.61
INDE  14   9   1  FOBS=   90.1  SIGMA=   8.0  PHAS=  265.9  FOM=  0.06
INDE  14   9   2  FOBS=  174.2  SIGMA=   4.5  PHAS=  108.2  FOM=  0.17
INDE  14   9   3  FOBS=  118.6  SIGMA=   7.5  PHAS=  224.6  FOM=  0.02
INDE  14   9   4  FOBS=   82.1  SIGMA=  11.0  PHAS=  252.2  FOM=  0.09
INDE  14   9   5  FOBS=   71.7  SIGMA=  32.5  PHAS=   73.9  FOM=  0.07
INDE  14   9   6  FOBS=   43.8  SIGMA=  18.4  PHAS=  228.9  FOM=  0.05
INDE  14  10   2  FOBS=   52.0  SIGMA=  25.6  PHAS=  343.9  FOM=  0.10
INDE  14  10   3  FOBS=  143.1  SIGMA=   5.8  PHAS=  155.3  FOM=  0.01
INDE  14  10   4  FOBS=   38.7  SIGMA=  23.6  PHAS=   43.5  FOM=  0.02
INDE  14  10   6  FOBS=   41.2  SIGMA=  16.8  PHAS=  100.1  FOM=  0.02
INDE  14  11   0  FOBS=   70.9  SIGMA=  10.0  PHAS=  154.6  FOM=  0.11
INDE  14  11   1  FOBS=   49.3  SIGMA=  16.7  PHAS=  351.9  FOM=  0.07
INDE  14  11   2  FOBS=   60.7  SIGMA=  17.4  PHAS=   77.4  FOM=  0.03
INDE  14  11   3  FOBS=  102.2  SIGMA=   7.2  PHAS=  230.0  FOM=  0.09
INDE  14  11   4  FOBS=   86.4  SIGMA=   7.8  PHAS=  354.9  FOM=  0.75
INDE  14  11   6  FOBS=   63.4  SIGMA=  17.2  PHAS=  248.1  FOM=  0.04
INDE  14  12   0  FOBS=   53.7  SIGMA=  18.3  PHAS=   76.7  FOM=  0.17
INDE  14  12   1  FOBS=   61.1  SIGMA=  14.0  PHAS=  227.8  FOM=  0.10
INDE  14  12   2  FOBS=   84.5  SIGMA=   8.2  PHAS=  303.7  FOM=  0.04
INDE  14  12   3  FOBS=   52.4  SIGMA=  16.0  PHAS=  113.9  FOM=  0.05
INDE  14  12   4  FOBS=   87.5  SIGMA=   8.4  PHAS=  110.2  FOM=  0.10
INDE  14  12   5  FOBS=   63.9  SIGMA=  17.7  PHAS=  251.1  FOM=  0.04
INDE  14  13   0  FOBS=   86.4  SIGMA=   8.8  PHAS=  271.9  FOM=  0.08
INDE  14  13   1  FOBS=   91.6  SIGMA=   7.4  PHAS=  291.1  FOM=  0.15
INDE  14  13   2  FOBS=  109.7  SIGMA=   6.3  PHAS=  122.0  FOM=  0.19
INDE  14  13   3  FOBS=   35.3  SIGMA=  18.2  PHAS=   79.8  FOM=  0.14
INDE  14  13   4  FOBS=   72.5  SIGMA=  35.4  PHAS=  262.2  FOM=  0.05
INDE  14  14   0  FOBS=   69.6  SIGMA=  11.0  PHAS=  335.2  FOM=  0.12
INDE  14  14   1  FOBS=   76.9  SIGMA=   8.8  PHAS=  197.9  FOM=  0.04
INDE  14  14   2  FOBS=   54.1  SIGMA=  51.0  PHAS=  111.2  FOM=  0.19
INDE  14  14   3  FOBS=   46.4  SIGMA=  18.6  PHAS=  290.8  FOM=  0.05
INDE  14  14   4  FOBS=  120.5  SIGMA=   7.1  PHAS=   46.1  FOM=  0.02
INDE  14  14   5  FOBS=   46.8  SIGMA=  20.8  PHAS=  100.6  FOM=  0.05
INDE  14  15   0  FOBS=   87.3  SIGMA=   7.3  PHAS=  343.6  FOM=  0.15
INDE  14  15   1  FOBS=   64.6  SIGMA=  69.7  PHAS=  150.7  FOM=  0.28
INDE  14  15   2  FOBS=  115.2  SIGMA=   6.5  PHAS=  315.5  FOM=  0.18
INDE  14  15   4  FOBS=   47.1  SIGMA=  20.8  PHAS=  140.2  FOM=  0.04
INDE  14  16   0  FOBS=   60.1  SIGMA=  10.8  PHAS=  103.3  FOM=  0.23
INDE  14  16   1  FOBS=   52.9  SIGMA=  29.0  PHAS=    9.1  FOM=  0.07
INDE  14  16   3  FOBS=   94.6  SIGMA=   8.0  PHAS=  115.8  FOM=  0.12
INDE  14  16   4  FOBS=   76.8  SIGMA=  39.5  PHAS=  288.6  FOM=  0.08
INDE  14  17   0  FOBS=   86.7  SIGMA=  55.2  PHAS=   29.8  FOM=  0.10
INDE  14  17   1  FOBS=   69.6  SIGMA=  11.2  PHAS=  202.6  FOM=  0.09
INDE  14  17   2  FOBS=   67.3  SIGMA=  28.9  PHAS=   55.8  FOM=  0.11
INDE  14  17   3  FOBS=   74.2  SIGMA=  10.8  PHAS=  262.5  FOM=  0.03
INDE  14  18   0  FOBS=   80.4  SIGMA=   8.2  PHAS=  163.1  FOM=  0.07
INDE  14  18   1  FOBS=   42.0  SIGMA=  17.5  PHAS=  113.6  FOM=  0.04
INDE  14  18   2  FOBS=   81.7  SIGMA=   8.2  PHAS=   15.1  FOM=  0.08
```

Fig. 10A-148

```
INDE  14  18   3  FOBS=  100.6  SIGMA=  34.7  PHAS=  144.9  FOM=  0.08
INDE  14  19   0  FOBS=   91.0  SIGMA=   7.7  PHAS=   34.3  FOM=  0.31
INDE  14  19   1  FOBS=   93.7  SIGMA=   7.4  PHAS=  321.1  FOM=  0.10
INDE  14  19   2  FOBS=   83.0  SIGMA=  23.2  PHAS=   96.0  FOM=  0.04
INDE  14  20   0  FOBS=   85.6  SIGMA=   8.0  PHAS=  356.3  FOM=  0.11
INDE  14  20   1  FOBS=  126.2  SIGMA=  78.8  PHAS=  193.4  FOM=  0.06
INDE  15   0   0  FOBS=   55.5  SIGMA=  92.3  PHAS=  180.0  FOM=  0.06
INDE  15   0   2  FOBS=  201.0  SIGMA=   5.4  PHAS=    0.0  FOM=  0.45
INDE  15   0   3  FOBS=   50.3  SIGMA=  23.1  PHAS=  180.0  FOM=  0.02
INDE  15   0   6  FOBS=  100.1  SIGMA=  14.7  PHAS=    0.0  FOM=  0.11
INDE  15   1   0  FOBS=   61.8  SIGMA=  13.0  PHAS=  222.9  FOM=  0.01
INDE  15   1   2  FOBS=  205.0  SIGMA=   3.7  PHAS=  296.7  FOM=  0.05
INDE  15   1   3  FOBS=   63.7  SIGMA=  13.3  PHAS=  219.0  FOM=  0.05
INDE  15   1   5  FOBS=   89.4  SIGMA=   9.1  PHAS=  251.7  FOM=  0.13
INDE  15   1   6  FOBS=   77.5  SIGMA=  10.8  PHAS=  175.0  FOM=  0.01
INDE  15   2   0  FOBS=   63.2  SIGMA=  38.9  PHAS=  329.4  FOM=  0.08
INDE  15   2   1  FOBS=  203.3  SIGMA=   3.7  PHAS=  212.8  FOM=  0.13
INDE  15   2   2  FOBS=  127.7  SIGMA=   6.1  PHAS=  352.9  FOM=  0.29
INDE  15   2   3  FOBS=  108.3  SIGMA=   7.4  PHAS=   95.5  FOM=  0.07
INDE  15   2   4  FOBS=   60.6  SIGMA=  12.0  PHAS=   62.5  FOM=  0.34
INDE  15   2   5  FOBS=   85.4  SIGMA=  10.6  PHAS=  243.9  FOM=  0.06
INDE  15   2   6  FOBS=   90.0  SIGMA=   9.2  PHAS=  250.5  FOM=  0.02
INDE  15   3   0  FOBS=  144.6  SIGMA=   5.0  PHAS=  337.9  FOM=  0.53
INDE  15   3   1  FOBS=  137.1  SIGMA=   5.4  PHAS=  328.1  FOM=  0.12
INDE  15   3   2  FOBS=   62.5  SIGMA=  40.7  PHAS=  213.3  FOM=  0.07
INDE  15   3   3  FOBS=  104.2  SIGMA=   7.2  PHAS=   44.6  FOM=  0.19
INDE  15   3   4  FOBS=   72.8  SIGMA=  10.5  PHAS=  243.1  FOM=  0.78
INDE  15   3   5  FOBS=   84.7  SIGMA=  10.9  PHAS=  110.3  FOM=  0.05
INDE  15   3   6  FOBS=   74.6  SIGMA=  11.6  PHAS=   71.2  FOM=  0.02
INDE  15   4   0  FOBS=  131.3  SIGMA=   5.4  PHAS=   47.1  FOM=  0.39
INDE  15   4   1  FOBS=  146.1  SIGMA=   5.6  PHAS=  108.0  FOM=  0.34
INDE  15   4   2  FOBS=   45.9  SIGMA=  26.0  PHAS=  330.1  FOM=  0.12
INDE  15   4   3  FOBS=   95.1  SIGMA=   7.9  PHAS=  181.1  FOM=  0.00
INDE  15   4   4  FOBS=   83.7  SIGMA=  10.2  PHAS=  126.4  FOM=  0.03
INDE  15   4   5  FOBS=   86.4  SIGMA=   8.8  PHAS=  335.6  FOM=  0.04
INDE  15   4   6  FOBS=   62.7  SIGMA=  15.1  PHAS=  154.9  FOM=  0.04
INDE  15   5   0  FOBS=  106.5  SIGMA=   7.0  PHAS=   98.8  FOM=  0.31
INDE  15   5   1  FOBS=  128.6  SIGMA=   5.9  PHAS=  212.4  FOM=  0.20
INDE  15   5   2  FOBS=   78.6  SIGMA=  12.3  PHAS=  293.3  FOM=  0.19
INDE  15   5   3  FOBS=   72.6  SIGMA=  15.4  PHAS=   98.1  FOM=  0.39
INDE  15   5   4  FOBS=   63.8  SIGMA=  30.8  PHAS=  273.4  FOM=  0.12
INDE  15   5   5  FOBS=   54.1  SIGMA=  13.9  PHAS=  258.7  FOM=  0.01
INDE  15   5   6  FOBS=   50.1  SIGMA=  21.9  PHAS=  106.8  FOM=  0.02
INDE  15   6   0  FOBS=   95.8  SIGMA=   8.1  PHAS=   11.1  FOM=  0.17
INDE  15   6   1  FOBS=   93.8  SIGMA=   7.8  PHAS=  201.9  FOM=  0.10
INDE  15   6   2  FOBS=   61.5  SIGMA=  13.9  PHAS=   64.3  FOM=  0.12
INDE  15   6   3  FOBS=   74.4  SIGMA=  10.2  PHAS=  164.1  FOM=  0.09
INDE  15   6   4  FOBS=   52.6  SIGMA=  22.6  PHAS=  271.1  FOM=  0.13
INDE  15   6   5  FOBS=   47.5  SIGMA=  23.3  PHAS=   40.8  FOM=  0.08
INDE  15   7   0  FOBS=  140.4  SIGMA=   5.1  PHAS=  183.7  FOM=  0.06
INDE  15   7   1  FOBS=  142.7  SIGMA=   5.2  PHAS=  215.4  FOM=  0.17
INDE  15   7   2  FOBS=  134.2  SIGMA=   5.6  PHAS=  342.5  FOM=  0.11
INDE  15   7   3  FOBS=   43.0  SIGMA=  21.7  PHAS=   28.8  FOM=  0.12
INDE  15   7   5  FOBS=   65.8  SIGMA=  25.8  PHAS=  153.2  FOM=  0.06
INDE  15   8   0  FOBS=   70.6  SIGMA=  12.2  PHAS=  139.0  FOM=  0.13
INDE  15   8   1  FOBS=  112.7  SIGMA=   6.5  PHAS=  292.1  FOM=  0.22
INDE  15   8   2  FOBS=  116.0  SIGMA=   6.4  PHAS=    4.1  FOM=  0.13
INDE  15   8   4  FOBS=   88.8  SIGMA=   8.9  PHAS=  246.7  FOM=  0.08
INDE  15   8   5  FOBS=   63.5  SIGMA=  15.6  PHAS=   30.8  FOM=  0.09
INDE  15   9   0  FOBS=   79.4  SIGMA=   9.0  PHAS=  190.2  FOM=  0.07
INDE  15   9   1  FOBS=  109.6  SIGMA=   6.6  PHAS=  126.1  FOM=  0.09
INDE  15   9   2  FOBS=   37.0  SIGMA=  19.1  PHAS=  355.6  FOM=  0.07
INDE  15   9   3  FOBS=   60.9  SIGMA=  13.2  PHAS=  203.5  FOM=  0.04
INDE  15   9   4  FOBS=   81.4  SIGMA=  10.2  PHAS=  359.0  FOM=  0.03
INDE  15   9   5  FOBS=  120.3  SIGMA=   6.8  PHAS=  250.0  FOM=  0.07
INDE  15  10   0  FOBS=   58.1  SIGMA=  36.7  PHAS=  163.6  FOM=  0.09
INDE  15  10   1  FOBS=   47.7  SIGMA=  22.9  PHAS=  312.5  FOM=  0.17
INDE  15  10   2  FOBS=   38.8  SIGMA=  18.0  PHAS=  154.7  FOM=  0.16
INDE  15  10   3  FOBS=   57.7  SIGMA=  14.3  PHAS=   35.8  FOM=  0.01
INDE  15  10   4  FOBS=  107.2  SIGMA=   8.1  PHAS=  201.6  FOM=  0.03
INDE  15  10   5  FOBS=  108.5  SIGMA=  64.4  PHAS=  157.9  FOM=  0.02
```

Fig. 10A-149

```
INDE 15 11 0 FOBS=  92.3 SIGMA=  7.5 PHAS= 333.1 FOM= 0.20
INDE 15 11 1 FOBS=  56.3 SIGMA= 14.7 PHAS=  62.0 FOM= 0.03
INDE 15 11 2 FOBS=  67.5 SIGMA= 11.5 PHAS=  70.4 FOM= 0.03
INDE 15 11 3 FOBS=  85.9 SIGMA= 10.2 PHAS=  13.5 FOM= 0.06
INDE 15 11 4 FOBS=  43.4 SIGMA= 20.0 PHAS= 159.5 FOM= 0.03
INDE 15 12 0 FOBS=  53.8 SIGMA= 14.1 PHAS= 265.9 FOM= 0.07
INDE 15 12 1 FOBS=  63.5 SIGMA=  9.3 PHAS=  69.3 FOM= 0.96
INDE 15 12 2 FOBS=  46.6 SIGMA= 19.6 PHAS= 223.4 FOM= 0.10
INDE 15 12 3 FOBS=  58.5 SIGMA= 31.3 PHAS= 336.2 FOM= 0.04
INDE 15 13 0 FOBS=  55.5 SIGMA= 11.0 PHAS=  96.0 FOM= 0.78
INDE 15 13 1 FOBS=  60.5 SIGMA= 34.5 PHAS= 279.7 FOM= 0.09
INDE 15 13 2 FOBS=  86.8 SIGMA=  8.7 PHAS= 300.8 FOM= 0.02
INDE 15 13 3 FOBS= 111.8 SIGMA=  6.4 PHAS= 283.2 FOM= 0.19
INDE 15 14 0 FOBS=  81.1 SIGMA= 37.6 PHAS= 321.2 FOM= 0.07
INDE 15 14 1 FOBS=  61.7 SIGMA= 14.2 PHAS= 222.2 FOM= 0.01
INDE 15 14 2 FOBS=  48.2 SIGMA= 21.8 PHAS= 102.1 FOM= 0.04
INDE 15 14 3 FOBS=  59.8 SIGMA= 12.8 PHAS=  66.0 FOM= 0.01
INDE 15 15 0 FOBS=  68.8 SIGMA= 12.9 PHAS= 189.3 FOM= 0.06
INDE 15 15 1 FOBS=  42.6 SIGMA= 21.4 PHAS=  89.6 FOM= 0.03
INDE 15 15 2 FOBS=  49.9 SIGMA= 22.4 PHAS= 320.3 FOM= 0.04
INDE 15 16 0 FOBS=  93.5 SIGMA=  6.8 PHAS=  47.3 FOM= 0.14
INDE 15 17 0 FOBS=  41.2 SIGMA= 16.5 PHAS= 240.2 FOM= 0.04
INDE 15 17 1 FOBS=  59.5 SIGMA= 29.0 PHAS=  72.4 FOM= 0.04
INDE 16  0 0 FOBS=  64.2 SIGMA= 15.8 PHAS=   0.0 FOM= 0.04
INDE 16  0 1 FOBS=  36.1 SIGMA= 22.1 PHAS= 180.0 FOM= 0.11
INDE 16  0 2 FOBS=  73.8 SIGMA= 15.3 PHAS= 180.0 FOM= 0.01
INDE 16  0 3 FOBS= 102.4 SIGMA= 10.2 PHAS= 180.0 FOM= 0.12
INDE 16  0 4 FOBS=  99.8 SIGMA= 13.4 PHAS= 180.0 FOM= 0.03
INDE 16  1 0 FOBS= 261.3 SIGMA=  2.8 PHAS= 145.4 FOM= 0.27
INDE 16  1 1 FOBS=  86.0 SIGMA=  8.1 PHAS= 177.2 FOM= 0.06
INDE 16  1 2 FOBS= 114.8 SIGMA=  6.3 PHAS= 114.2 FOM= 0.17
INDE 16  1 3 FOBS=  64.1 SIGMA= 14.3 PHAS= 240.5 FOM= 0.01
INDE 16  1 4 FOBS=  71.3 SIGMA= 13.7 PHAS= 165.0 FOM= 0.01
INDE 16  2 0 FOBS=  66.2 SIGMA= 11.2 PHAS= 110.9 FOM= 0.15
INDE 16  2 1 FOBS= 132.5 SIGMA=  5.4 PHAS= 332.1 FOM= 0.17
INDE 16  2 2 FOBS= 133.1 SIGMA=  5.8 PHAS=  92.3 FOM= 0.08
INDE 16  2 3 FOBS=  57.5 SIGMA= 27.5 PHAS= 143.0 FOM= 0.05
INDE 16  2 4 FOBS=  98.9 SIGMA=  7.8 PHAS= 152.6 FOM= 0.03
INDE 16  3 0 FOBS=  77.1 SIGMA= 10.3 PHAS= 108.2 FOM= 0.08
INDE 16  3 1 FOBS=  55.6 SIGMA= 17.2 PHAS= 273.0 FOM= 0.26
INDE 16  3 2 FOBS=  66.9 SIGMA= 13.3 PHAS=  81.7 FOM= 0.06
INDE 16  3 3 FOBS=  64.1 SIGMA= 28.3 PHAS= 186.5 FOM= 0.06
INDE 16  3 4 FOBS=  72.5 SIGMA= 11.6 PHAS= 310.6 FOM= 0.02
INDE 16  4 1 FOBS=  82.9 SIGMA=  9.4 PHAS= 347.8 FOM= 0.29
INDE 16  4 2 FOBS=  57.4 SIGMA= 26.7 PHAS= 135.7 FOM= 0.03
INDE 16  4 3 FOBS=  60.7 SIGMA= 14.4 PHAS= 196.5 FOM= 0.06
INDE 16  4 4 FOBS=  75.6 SIGMA= 10.4 PHAS= 292.3 FOM= 0.09
INDE 16  5 1 FOBS=  37.6 SIGMA= 17.1 PHAS= 265.9 FOM= 0.53
INDE 16  5 2 FOBS= 102.3 SIGMA= 65.9 PHAS=  95.5 FOM= 0.03
INDE 16  5 3 FOBS=  54.4 SIGMA= 18.4 PHAS= 293.4 FOM= 0.02
INDE 16  5 4 FOBS=  83.1 SIGMA=  9.0 PHAS= 146.2 FOM= 0.01
INDE 16  6 0 FOBS=  62.1 SIGMA= 12.3 PHAS= 199.4 FOM= 0.47
INDE 16  6 1 FOBS=  59.1 SIGMA= 33.3 PHAS= 351.0 FOM= 0.05
INDE 16  6 2 FOBS=  94.5 SIGMA=  7.8 PHAS= 326.4 FOM= 0.06
INDE 16  6 3 FOBS=  91.5 SIGMA= 39.2 PHAS= 205.8 FOM= 0.07
INDE 16  6 4 FOBS=  54.2 SIGMA= 18.5 PHAS=  22.7 FOM= 0.07
INDE 16  7 0 FOBS=  46.8 SIGMA= 17.4 PHAS= 126.1 FOM= 0.08
INDE 16  7 1 FOBS=  58.9 SIGMA= 12.5 PHAS= 347.3 FOM= 0.12
INDE 16  7 2 FOBS= 178.9 SIGMA=  4.4 PHAS=  41.7 FOM= 0.78
INDE 16  7 3 FOBS= 104.5 SIGMA=  7.1 PHAS= 167.4 FOM= 0.09
INDE 16  8 1 FOBS=  81.8 SIGMA=  9.0 PHAS= 155.3 FOM= 0.04
INDE 16  8 2 FOBS=  50.2 SIGMA= 15.9 PHAS=  84.3 FOM= 0.04
INDE 16  8 3 FOBS=  93.6 SIGMA=  8.1 PHAS= 230.0 FOM= 0.14
INDE 16  9 0 FOBS=  35.3 SIGMA= 18.2 PHAS= 206.0 FOM= 0.05
INDE 16  9 1 FOBS= 179.0 SIGMA=  4.1 PHAS= 227.6 FOM= 0.56
INDE 16  9 2 FOBS=  42.6 SIGMA= 19.0 PHAS= 201.2 FOM= 0.05
INDE 16  9 3 FOBS=  91.7 SIGMA=  8.1 PHAS= 197.6 FOM= 0.04
INDE 16 10 0 FOBS=  38.6 SIGMA= 17.0 PHAS=  45.3 FOM= 0.12
INDE 16 10 1 FOBS=  64.8 SIGMA= 12.0 PHAS= 200.9 FOM= 0.03
INDE 16 10 2 FOBS=  51.2 SIGMA= 24.6 PHAS= 252.3 FOM= 0.01
INDE 16 11 0 FOBS= 111.7 SIGMA=  6.2 PHAS= 299.5 FOM= 0.05
```

Fig. 10A-150

```
INDE 16 11 1 FOBS= 120.4 SIGMA=  5.9 PHAS= 280.6 FOM= 0.07
INDE 16 11 2 FOBS=  76.0 SIGMA=  9.9 PHAS= 288.7 FOM= 0.00
INDE 16 12 0 FOBS=  70.4 SIGMA=  9.8 PHAS=  13.8 FOM= 0.02
INDE 16 12 1 FOBS=  52.6 SIGMA= 24.7 PHAS=  97.7 FOM= 0.01
INDE 16 13 0 FOBS=  53.6 SIGMA= 12.9 PHAS= 121.8 FOM= 0.05
INDE 16 13 1 FOBS= 109.8 SIGMA= 72.7 PHAS= 174.5 FOM= 0.01
INDE 16 14 0 FOBS=  50.1 SIGMA= 22.4 PHAS= 205.4 FOM= 0.05
INDE 17  0 0 FOBS=  42.5 SIGMA= 26.7 PHAS= 180.0 FOM= 0.01
INDE 17  0 2 FOBS=  94.1 SIGMA= 10.7 PHAS=   0.0 FOM= 0.01
INDE 17  1 0 FOBS=  83.2 SIGMA=  8.7 PHAS=  58.6 FOM= 0.04
INDE 17  1 1 FOBS=  69.2 SIGMA= 10.6 PHAS= 269.8 FOM= 0.01
INDE 17  1 2 FOBS= 100.3 SIGMA=  7.2 PHAS= 193.1 FOM= 0.04
INDE 17  2 0 FOBS=  69.4 SIGMA= 10.2 PHAS= 280.8 FOM= 0.02
INDE 17  2 1 FOBS=  69.3 SIGMA= 15.9 PHAS= 129.1 FOM= 0.03
INDE 17  2 2 FOBS=  64.3 SIGMA= 11.6 PHAS=  53.7 FOM= 0.03
INDE 17  3 0 FOBS=  42.4 SIGMA= 19.1 PHAS= 211.5 FOM= 0.10
INDE 17  3 2 FOBS=  60.4 SIGMA= 13.3 PHAS= 318.2 FOM= 0.02
INDE 17  4 0 FOBS=  89.2 SIGMA=  7.7 PHAS=   0.9 FOM= 0.05
INDE 17  4 1 FOBS=  74.5 SIGMA= 40.6 PHAS=   1.7 FOM= 0.07
INDE 17  5 0 FOBS=  42.2 SIGMA= 19.4 PHAS= 299.8 FOM= 0.13
INDE 17  5 1 FOBS=  62.8 SIGMA= 12.6 PHAS= 114.8 FOM= 0.06
INDE 17  6 0 FOBS=  45.2 SIGMA= 17.4 PHAS= 189.4 FOM= 0.02
INDE 17  6 1 FOBS=  89.3 SIGMA=  8.2 PHAS=  86.9 FOM= 0.05
INDE 17  7 0 FOBS=  71.2 SIGMA=  9.9 PHAS=  19.8 FOM= 0.11
INDE 17  7 1 FOBS= 103.6 SIGMA=  8.3 PHAS= 203.3 FOM= 0.08
INDE 17  8 0 FOBS=  87.4 SIGMA=  8.3 PHAS= 146.0 FOM= 0.04
INDE 17  9 0 FOBS=  59.2 SIGMA= 22.3 PHAS= 357.4 FOM= 0.09
```

Fig. 10A-151

CRYSTALLIZATION AND STRUCTURE DETERMINATION OF *STAPHYLOCOCCUS AUREUS* THYMIDYLATE KINASE

This application claims the benefit of U.S. Provisional Application Serial No. 60/147,117, filed Aug. 4, 1999, which is incorporated herein by reference in its entirety.

FIELD OF THE INVENTION

This invention relates to the crystallization and structure determination of thymidylate kinase (TMK) from Staphylococcus aureus.

BACKGROUND

Thymidylate kinase (TMK) catalyzes the synthesis of (deoxy)thymidine diphosphate (dTDP) from (deoxy)thymidine monophosphate (dTMP) and ATP along the pathway leading to the synthesis of (deoxy)thymidine triphosphate (dTTP) necessary for DNA synthesis (FIG. 1). Since the phosphorylation of dTDP to dTTP is conducted by a nonspecific diphosphate kinase, TMK is a key player in the regulation of DNA synthesis and is a potential antibacterial target. Interest in thymidylate kinase biochemistry increased when it was recently discovered that this enzyme serves as one of the activators for the AIDS drug, 3'-azido-3'-deoxythymidine (AZT) (L. W. Frick et al., *Biochem. Biophys. Res. Comm.* 154:124–9 (1988); A. Fridland et al., *Mol. Pharmacol.* 37:665–70 (1990)). Activation of AZT to azidothymidine triphosphate (AZT-TP) proceeds along cellular phosphorylation pathways to produce the species which is incorporated into growing DNA chains by HIV reverse transcriptase. Similar to its role in serving as a control point for the production of dTTP, thymidylate kinase catalyzes the rate limiting phosphorylation of AZT-monophosphate to AZT-diphosphate (AZT-DP). AZT-DP phosphorylation to AZT-TP is then catalyzed by a nonspecific diphosphate kinase.

SUMMARY OF THE INVENTION

In one aspect, the present invention provides a method for crystallizing an *S. aureus* thymidylate kinase molecule or molecular complex that includes preparing purified *S. aureus* thymidylate kinase at a concentration of about 1 mg/ml to about 50 mg/ml and crystallizing *S. aureus* thymidylate kinase from a solution including about 5 wt. % to about 50 wt. % PEG (preferably having a number average molecular weight between about 200 and about 20,000), about 0.05 M to about 0.5 M $MgCl_2$, and about 0 wt. % to about 20 wt. % DMSO, wherein the solution is buffered to a pH of about 6 to about 7. In another aspect, the present invention provides a method for crystallizing an *S. aureus* thymidylate kinase molecule or molecular complex that includes preparing purified *S. aureus* thymidylate kinase at a concentration of about 1 mg/ml to about 50 mg/ml and crystallizing *S. aureus* thymidylate kinase from a solution including about 2 mM to about 20 mM β,γ-difluoromethylene-bisphosphonate adenosine monophosphate and about 0 wt. % to about 20 wt. % DMSO, wherein the solution is buffered to a pH of about 6 to about 7

In another aspect, the present invention provides crystalline forms of an *S. aureus* thymidylate kinase molecule. In one embodiment, a crystal of *S. aureus* thymidylate kinase is provided having the trigonal space group symmetry $P2_1$.

In another aspect, the present invention provides a scalable three dimensional configuration of points derived from structure coordinates of at least a portion of an *S. aureus* thymidylate kinase molecule or molecular complex. In one embodiment, the scalable three dimensional set of points is derived from structure coordinates of at least the backbone atoms of the amino acids representing a TMP and/or TMP/ATP substrate binding pocket of an *S. aureus* thymidylate kinase molecule or molecular complex. In another embodiment, the scalable three dimensional configuration of points is derived from structure coordinates of at least a portion of a molecule or a molecular complex that is structurally homologous to an *S. aureus* thymidylate kinase molecule or molecular complex. On a molecular scale, the configuration of points derived from a homologous molecule or molecular complex have a root mean square deviation of less than about 2.1 Å from the structure coordinates of the molecule or complex In another aspect, the present invention provides a molecule or molecular complex that includes at least a portion of an *S. aureus* thymidylate kinase TMP and/or TMP/ATP substrate binding pocket. In one embodiment, the *S. aureus* thymidylate kinase TMP substrate binding pocket includes the amino acids listed in Table 1, preferably the amino acids listed in Table 2, and more preferably the amino acids listed in Table 3, the substrate binding pocket being defined by a set of points having a root mean square deviation of less than about 2.1 Å, preferably less than about 1.5 Å, more preferably less than about 1.0 Å, and most preferably less than about 0.5 Å from points representing the backbone atoms of the amino acids. In another embodiment, the *S. aureus* thymidylate kinase TMP/ATP substrate binding pocket includes the amino acids listed in Table 4, preferably the amino acids listed in Table 5, and more preferably the amino acids listed in Table 6, the substrate binding pocket being defined by a set of points having a root mean square deviation of less than about 2.1 Å, preferably less than about 1.5 Å, more preferably less than about 1.0 Å, and most preferably less than about 0.5 Å from points representing the backbone atoms of the amino acids.

TABLE 1

Residues within about 4 Å of the TMP binding pocket of *S. aureus* TMK

| GLU | 12 | LEU | 53 | ARG | 93 |
|---|---|---|---|---|---|
| ARG | 37 | LEU | 66 | SER | 97 |
| ILE | 48 | PHE | 67 | SER | 98 |
| ARG | 49 | SER | 70 | TYR | 101 |
| VAL | 52 | ARG | 71 | | |

TABLE 2

Residues within about 7 Å of the TMP binding pocket of *S. aureus* TMK

| GLY | 10 | VAL | 52 | TYR | 94 |
|---|---|---|---|---|---|
| GLU | 12 | LEU | 53 | ILE | 95 |
| ARG | 37 | GLU | 63 | ASP | 96 |
| GLU | 38 | MET | 65 | SER | 97 |
| PRO | 39 | LEU | 66 | SER | 98 |
| GLY | 45 | PHE | 67 | LEU | 99 |
| GLU | 38 | MET | 65 | SER | 97 |
| GLY | 45 | PHE | 67 | LEU | 99 |
| GLU | 46 | ALA | 68 | ALA | 100 |
| GLU | 47 | ALA | 69 | TYR | 101 |
| ILE | 48 | SER | 70 | GLN | 102 |
| ARG | 49 | ARG | 71 | ASN | 117 |
| LYS | 50 | ASP | 92 | PHE | 160 |
| ILE | 51 | ARG | 93 | TYR | 168 |

TABLE 3

Residues within about 10 Å of the TMP
binding pocket of S. aureus TMK

| | | | | | |
|---|---|---|---|---|---|
| PHE | 8 | ILE | 51 | TYR | 94 |
| GLU | 9 | VAL | 52 | ILE | 95 |
| GLY | 10 | LEU | 53 | ASP | 96 |
| PRO | 11 | GLU | 54 | SER | 97 |
| GLU | 12 | GLY | 55 | SER | 98 |
| GLY | 13 | MET | 58 | LEU | 99 |
| SER | 14 | ILE | 60 | ALA | 100 |
| LYS | 16 | THR | 62 | TYR | 101 |
| THR | 17 | GLU | 63 | GLN | 102 |
| ARG | 37 | ALA | 64 | GLY | 103 |
| GLU | 38 | MET | 65 | TYR | 104 |
| PRO | 39 | LEU | 66 | ALA | 105 |
| GLY | 40 | PHE | 67 | ARG | 106 |
| GLY | 41 | ALA | 68 | VAL | 113 |
| VAL | 42 | ALA | 69 | LEU | 116 |
| PRO | 43 | SER | 70 | ASN | 117 |
| THR | 44 | ARG | 71 | ILE | 143 |
| GLY | 45 | ARG | 72 | PHE | 160 |
| GLU | 46 | GLU | 73 | HIS | 161 |
| GLU | 47 | HIS | 74 | VAL | 164 |
| ILE | 48 | CYS | 91 | TYR | 168 |
| ARG | 49 | ASP | 92 | | |
| LYS | 50 | ARG | 93 | | |

TABLE 4

Residues within about 4 Å of the TMP/ATP
binding pocket of S. aureus TMK

| | | | | | |
|---|---|---|---|---|---|
| GLU | 12 | GLU | 38 | SER | 98 |
| GLY | 15 | PHE | 67 | TYR | 101 |
| LYS | 16 | ARG | 71 | GLN | 102 |
| THR | 17 | ASP | 92 | ARG | 142 |
| THR | 18 | ARG | 93 | LEU | 188 |
| ARG | 37 | SER | 97 | | |

TABLE 5

Residues within about 7 Å of the TMP/ATP
binding pocket of S. aureus TMK

| | | | | | |
|---|---|---|---|---|---|
| GLY | 10 | ARG | 49 | TYR | 101 |
| PRO | 11 | GLU | 63 | GLN | 102 |
| GLU | 12 | ALA | 64 | ARG | 106 |
| GLY | 13 | PHE | 67 | ASN | 117 |
| SER | 14 | ALA | 68 | LEU | 132 |
| GLY | 15 | ARG | 71 | GLU | 141 |
| LYS | 16 | ASP | 92 | ARG | 142 |
| THR | 17 | ARG | 93 | ILE | 143 |
| THR | 18 | TYR | 94 | PHE | 160 |
| VAL | 19 | ILE | 95 | ALA | 184 |
| ILE | 20 | ASP | 96 | GLN | 186 |
| ASN | 21 | SER | 97 | PRO | 187 |
| ARG | 37 | SER | 98 | LEU | 188 |
| GLU | 38 | LEU | 99 | GLU | 189 |
| | | ALA | 100 | VAL | 191 |

TABLE 6

Residues within about 10 Å of the TMP/ATP
binding pocket of S. aureus TMK

| | | | | | |
|---|---|---|---|---|---|
| PHE | 8 | ALA | 64 | VAL | 113 |
| GLU | 9 | MET | 65 | LEU | 116 |
| GLY | 10 | LEU | 66 | ASN | 117 |
| PRO | 11 | PHE | 67 | ALA | 120 |
| GLU | 12 | ALA | 68 | LEU | 132 |
| GLY | 13 | ALA | 69 | VAL | 134 |
| SER | 14 | SER | 70 | VAL | 138 |

TABLE 6-continued

Residues within about 10 Å of the TMP/ATP
binding pocket of S. aureus TMK

| | | | | | |
|---|---|---|---|---|---|
| GLY | 15 | ARG | 71 | GLY | 139 |
| LYS | 16 | ARG | 72 | ARG | 140 |
| THR | 17 | HIS | 74 | GLU | 141 |
| THR | 18 | CYS | 91 | ARG | 142 |
| VAL | 19 | ASP | 92 | ILE | 143 |
| ILE | 20 | ARG | 93 | ASP | 157 |
| ASN | 21 | TYR | 94 | PHE | 160 |
| GLU | 22 | ILE | 95 | HIS | 161 |
| MET | 35 | ASP | 96 | VAL | 164 |
| THR | 36 | SER | 97 | TYR | 168 |
| ARG | 37 | SER | 98 | ASN | 183 |
| GLU | 38 | LEU | 99 | ALA | 184 |
| PRO | 39 | ALA | 100 | ASP | 185 |
| GLY | 40 | TYR | 101 | GLN | 186 |
| GLU | 46 | GLN | 102 | PRO | 187 |
| ARG | 49 | GLY | 103 | LEU | 188 |
| VAL | 52 | TYR | 104 | GLU | 189 |
| LEU | 53 | ALA | 105 | ASN | 190 |
| ILE | 60 | ARG | 106 | VAL | 191 |
| GLU | 63 | ILE | 108 | VAL | 192 |

In another aspect, the present invention provides molecules or molecular complexes that are structurally homologous to an S. aureus thymidylate kinase molecule or molecular complex.

In another aspect, the present invention provides a machine readable storage medium including the structure coordinates of all or a portion of an S. aureus thymidylate kinase molecule, molecular complex, a structurally homologous molecule or complex, including structurally equivalent structures, as defined herein, particularly a substrate binding pocket thereof, or a similarly shaped homologous substrate binding pocket. A storage medium encoded with these data is capable of displaying on a computer screen, or similar viewing device, a three-dimensional graphical representation of a molecule or molecular complex which comprises a substrate binding pocket or a similarly shaped homologous substrate binding pocket.

In another aspect, the present invention provides a method for identifying inhibitors, ligands, and the like for an S. aureus thymidylate kinase molecule by providing the coordinates of a molecule of S. aureus thymidylate kinase to a computerized modeling system; identifying chemical entities that are likely to bind to or interfere with the molecule (e.g., screening a small molecule library); and, optionally, procuring or synthesizing and assaying the compounds or analogues derived therefrom for bioactivity. In another aspect, the present invention provides methods for designing inhibitors, ligands, and the like by providing the coordinates of a molecule of S. aureus thymidylate kinase to a computerized modeling system; designing a chemical entity that is likely to bind to or interfere with the molecule; and optionally synthesizing the chemical entity and assaying the chemical entity for bioactivity. In another aspect, the present invention provides inhibitors and ligands designed or identified by the above methods. In one embodiment, a composition is provided that includes an inhibitor or ligand designed or identified by the above method. In another embodiment, the composition is a pharmaceutical composition.

In another aspect, the present invention provides a method involving molecular replacement to obtain structural information about a molecule or molecular complex of unknown structure. The method includes crystallizing the molecule or molecular complex, generating an x-ray diffraction pattern from the crystallized molecule or molecular complex, and applying at least a portion of the structure coordinates set forth in FIG. 2 to the x-ray diffraction pattern to generate a three-dimensional electron density map of at least a portion of the molecule or molecular complex.

In another aspect, the present invention provides a method for homology modeling an *S. aureus* thymidylate kinase homolog.

Definitions

Two crystallographic data sets (with structure factors F) are considered isomorphous if, after scaling, $$\frac{\Delta F}{F} = \frac{\sum |F_1 - F_2|}{\sum F_1}$$

is less than about 35% for the reflections between 8 Å and 4 Å.

Abbreviations

The following abbreviations are used throughout this disclosure:
*Staphylococcus aureus* (*S. aureus*).
Thymidylate kinase (T. kinase or TMK).
Thymidine 5'-monophosphate (TMP).
Thymidine 5'-diphosphate (TDP).
Thymidine 5'-triphosphate (TTP).
Phospho(enol)pyruvate (PEP)
Reduced nicotinamide adenine dinucleotide (NADH)
Oxidized nicotinamide adenine dinucleotide (NAD$^+$)
Pyruvate kinase (PK)
Lactate dehydrogenase (LDH)
Nucleoside-5'-diphosphate kinase (NDP-Kinase)
(Deoxy)thymidine monophosphate (dTMP).
(Deoxy)thymidine diphosphate (dTDP).
(Deoxy)thymidine triphosphate (dTTP).
Adenosine 5'-diphosphate (ADP).
Adenosine 5'-triphosphate (ATP).
Isopropylthio-β-D-galactoside (IPTG).
Dithiothreitol (DTT).
Dimethyl sulfoxide (DMSO).
Polyethylene glycol (PEG).
Multiple anomalous dispersion (MAD).

The following amino acid abbreviations are used throughout this disclosure:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

BRIEF DESCRIPTION OF THE FIGURES

FIGS. 2 and 2A-1 through 2A-55 list the atomic structure coordinates for recombinant *S. aureus* thymidylate kinase (with a His$_6$ tag) as derived by x-ray diffraction from a crystal of that complex. The following abbreviations are used in FIG. 2:

"Atom" refers to the element whose coordinates are measured. The second column defines the number of the atom in the structure. The letters in the third column define the element. The fourth and fifth columns define the amino acid and the number of the amino acid in the structure, respectively.

"X, Y, Z" crystallographically define the atomic position of the element measured.

"Occ" is an occupancy factor that refers to the fraction of the molecules in which each atom occupies the position specified by the coordinates. A value of "1" indicates that each atom has the same conformation, i.e., the same position, in all molecules of the crystal.

"B" is a thermal factor that measures movement of the atom around its atomic center.

Figure 1:
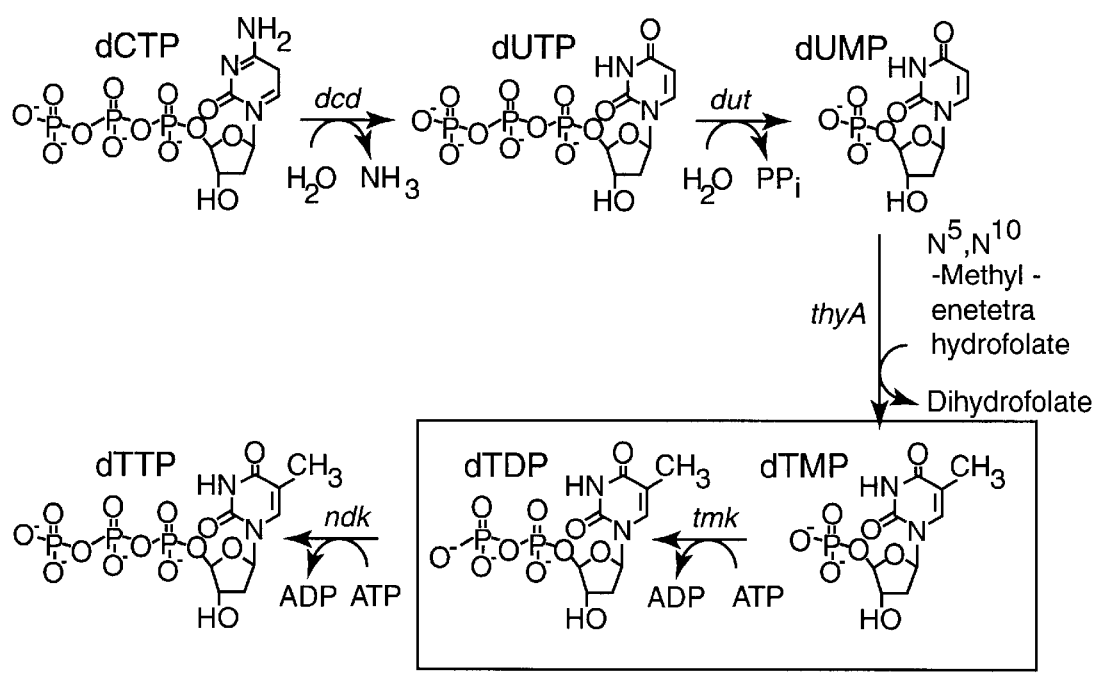
FIG. 1 shows the biosynthetic pathway for the synthesis of thymidylate. The reaction catalyzed by thymidylate kinase is boxed.
Figure 3A:
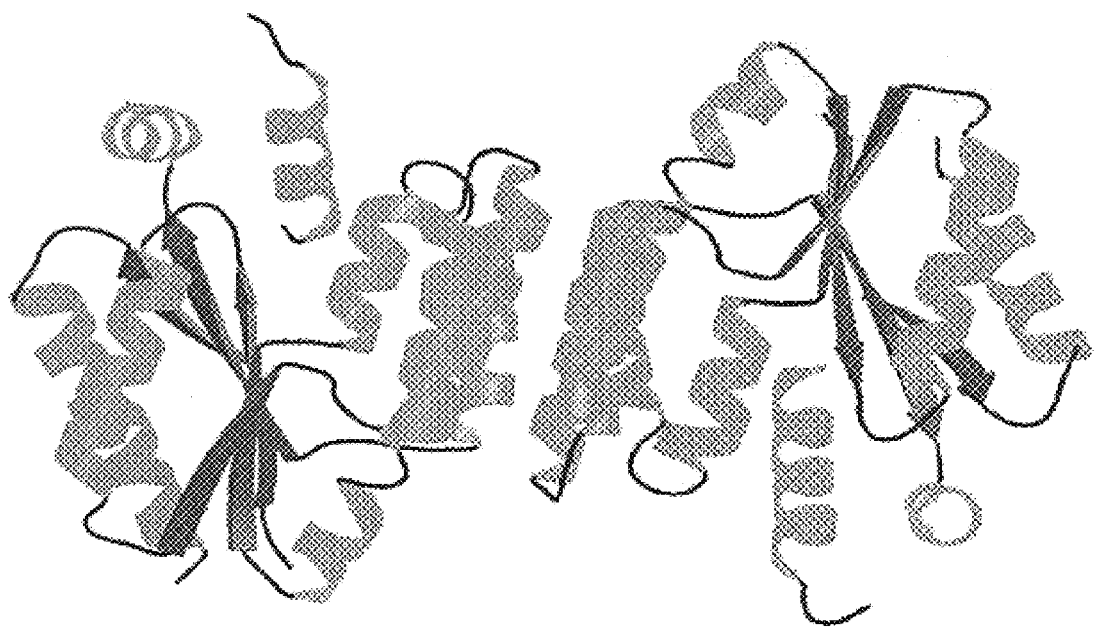
Figure 3B:
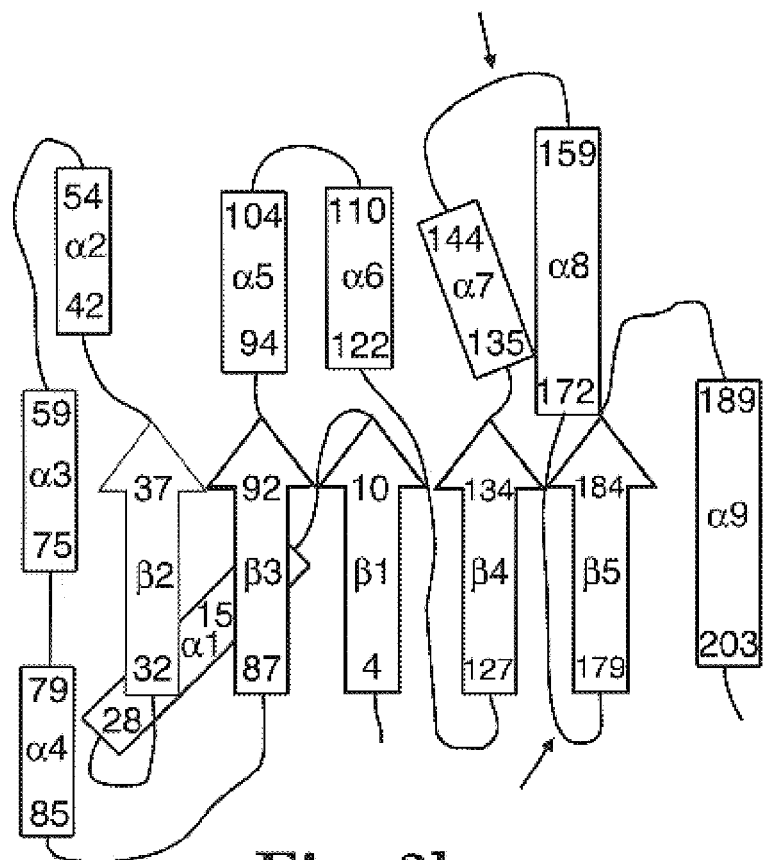

FIG. 3 depicts *S. aureus* thymidylate kinase using a ribbon diagram showing the backbone structure of the enzyme (3a) and a schematic diagram showing the secondary structure for a TMK monomer (3b). Disordered loops are indicated by arrows.

Figure 4:
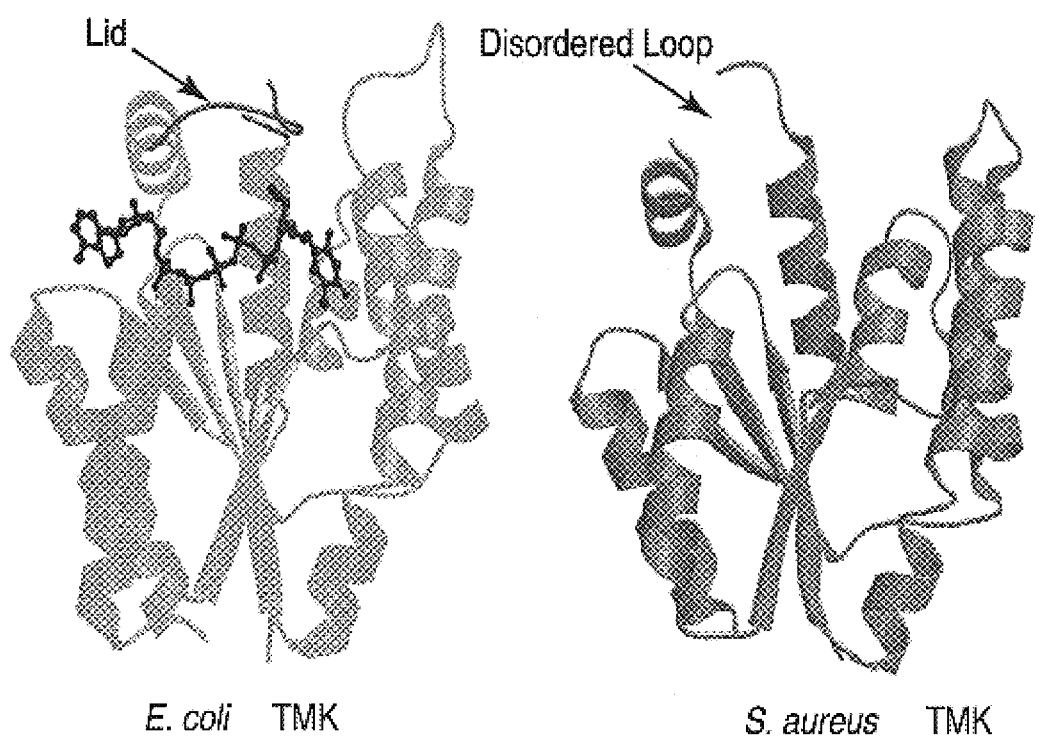

FIG. 4 depicts a structural comparison of *E. coli* TMK+ AP$_5$T and *S. aureus* TMK. The overall fold of the two proteins is well-conserved, but note that the lid in the *E. coli* TMK is not present in the *S. aureus* TMK due to the absence of a ligand.

Figure 5A:
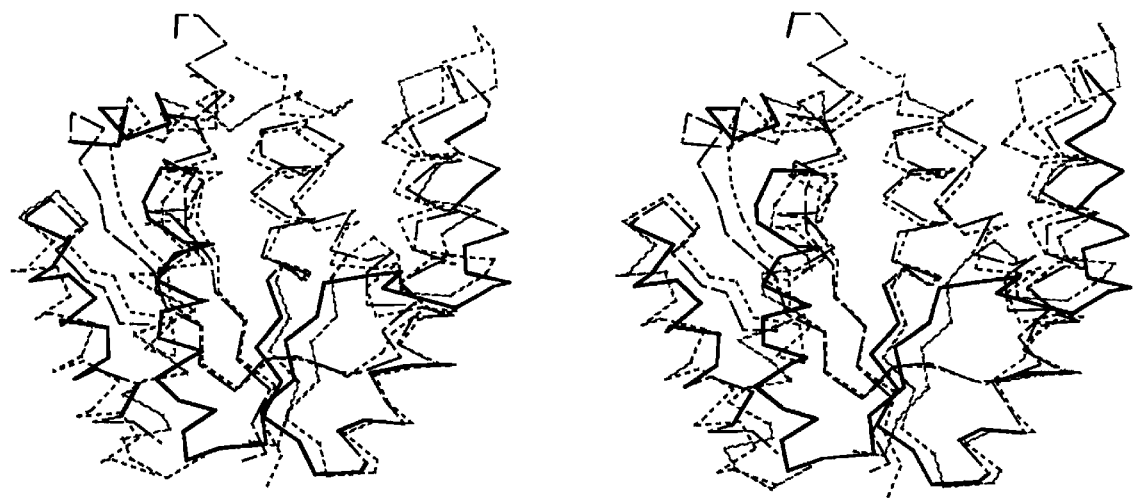

FIG. 5 depicts a stereo view of a superposition of *S. aureus* thymidylate kinase and *E. coli* thymidylate kinase (5a) and the amino acid sequence alignment of *S. aureus* thymidylate kinase (SEQ ID NO:1) (capital letters, upper sequence) and *E. coli* thymidylate kinase (SEQ ID NO:2) (lower sequence) (5b). Dots in the sequences indicate gaps inserted in order to optimize the alignment. Identical residues are indicated by | and similar residues are indicated by . and : symbols.

Figure 6A:
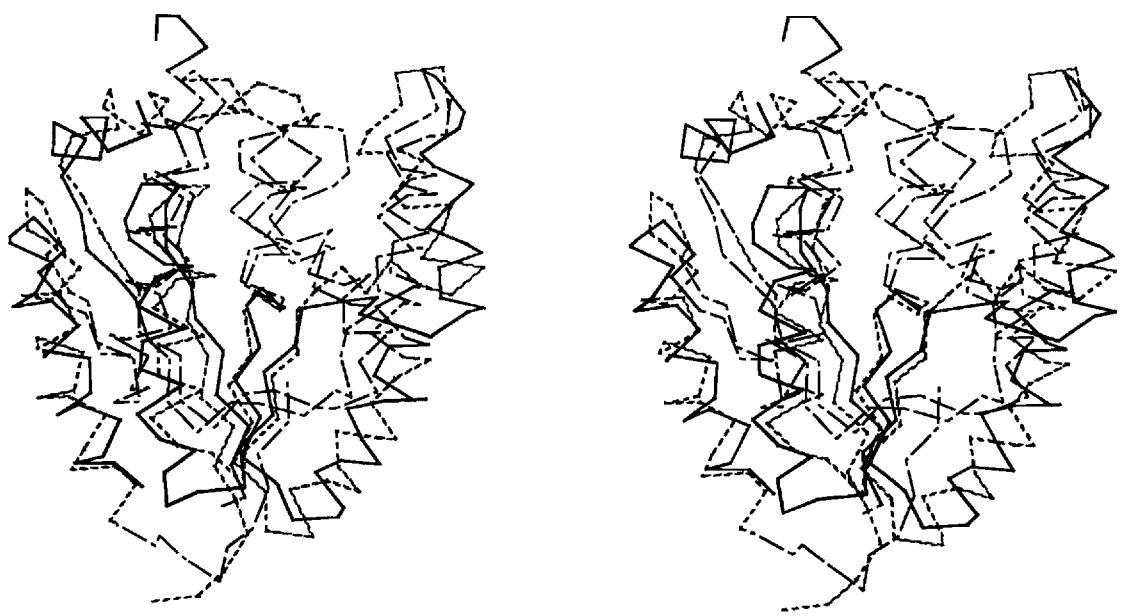

FIG. 6 depicts a stereo view of a superposition of *S. aureus* thymidylate kinase and *S. cerevisiae* thymidylate kinase (6a) and the sequence alignment of *S. aureus* thymidylate kinase (SEQ ID NO:1) (capital letters, upper sequence) and *S. cerevisiae* thymidylate kinase (SEQ ID NO:3) (lower sequence) (6b). Dots in the sequences indicate gaps inserted in order to optimize the alignment. Identical residues are indicated by | and similar residues are indicated by . and : symbols.

Figure 7A:
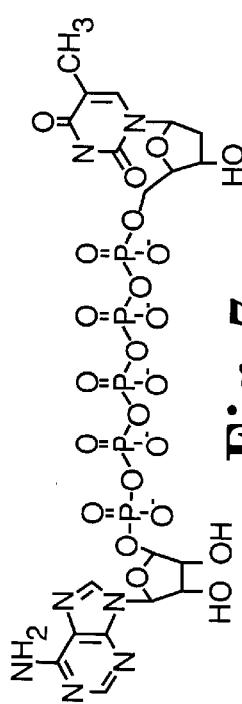
Figure 7B:
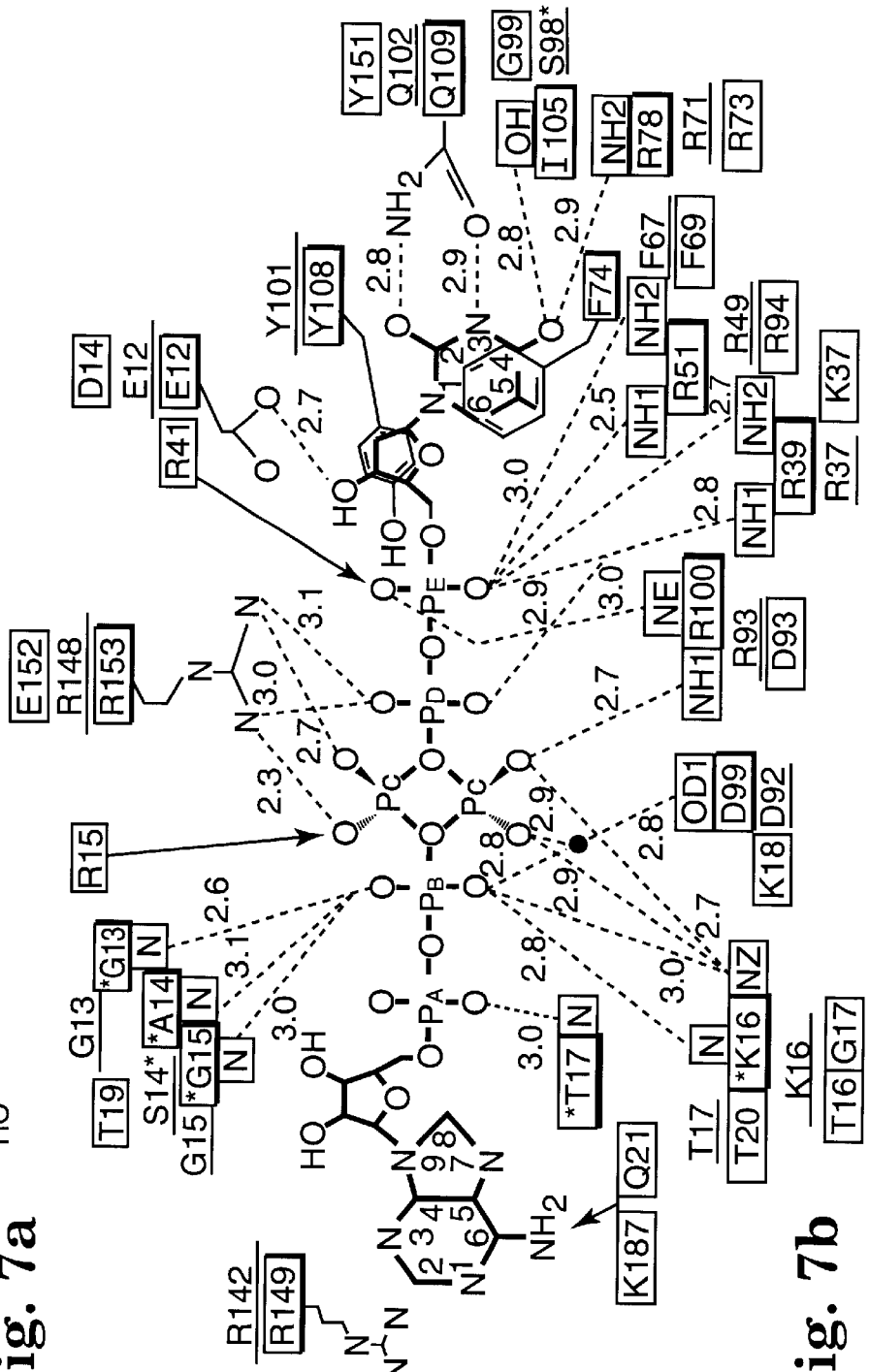

FIG. 7 depicts a substrate-based inhibitor (AP$_5$T) for thymidylate kinase with a K$_d$ of 20 nM for *E. coli* TMK (A. Lavie et al., *Biochemistry* 37:3677–86 (1998); A. Lavie et al., *Proc. Natl. Acad. Sci. USA*, 95:14045–50 (1998)) (7a) and protein ligand interactions for *E. coli* TMK (shaded boxes, from A. Lavie et al., *Proc. Natl. Acad. Sci. USA*, 95:14045–50 (1998)) with the corresponding residues from *S. aureus* TMK underlined (conservative mutations are marked with an asterisk) (7b). Active site residues from the *S. cerevisiae* are boxed (where no corresponding residue from *E. coli* TMK is present, an arrow indicates the point of contact with the substrate).

Figure 8A:
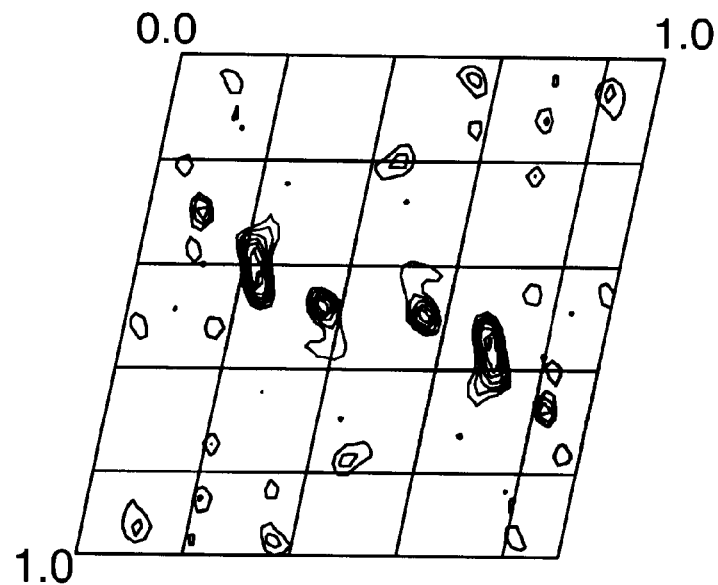
Figure 8B:
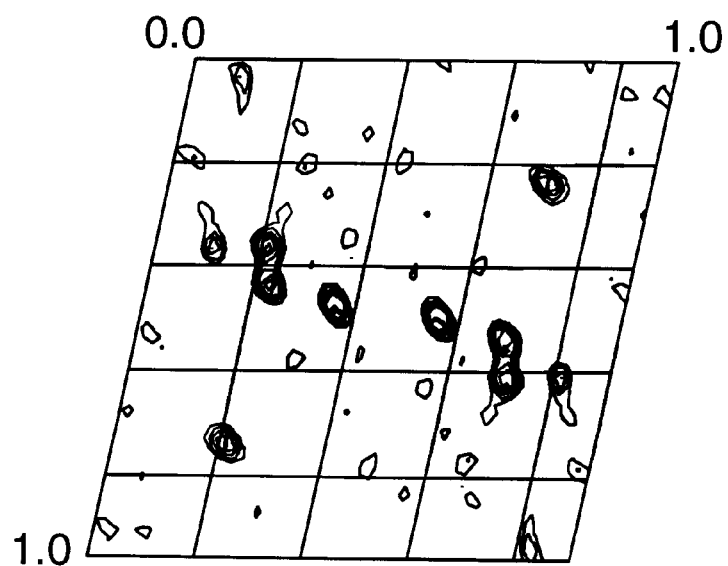

FIG. 8 depicts the anomalous difference Patterson maps at 2.7 Å (8a) and at 2.3 Å resolution (8b).

Figure 9A:
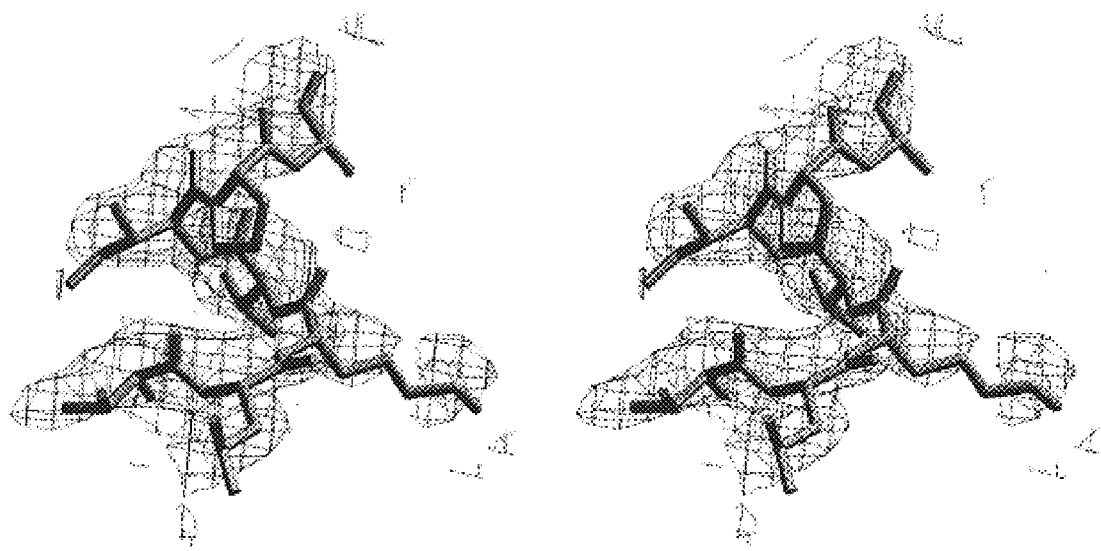
Figure 9B:
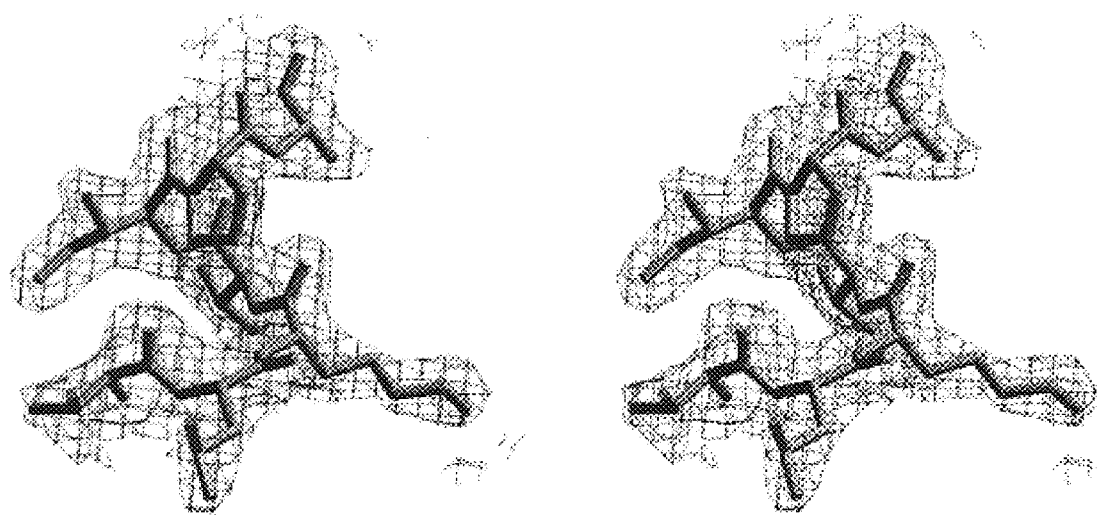

FIG. 9 depicts electron density maps of residues 76 to 82 from molecule 1 of *S. aureus* thymidylate kinase (SEQ ID NO:1) at 2.7Å (9a) and at 2.3Å resolution (9b).

FIGS. 10 and 10A-1 through 10A-151 list the structure factors and multiple anomalous dispersion phases for the crystal structure of S. aureus thymidylate kinase (SEQ ID NO:1). "INDE" refers to the indices h, k, and l (columns 2, 3, and 4 respectively) of the lattice planes. "FOBS" refers to the structure factor (F) of the observed reflections. "SIGMA" is the standard deviation for the observations. "PHAS" refers to the phase used for the observations. "FOM" refers to the figure of merit.

Figure 11A:
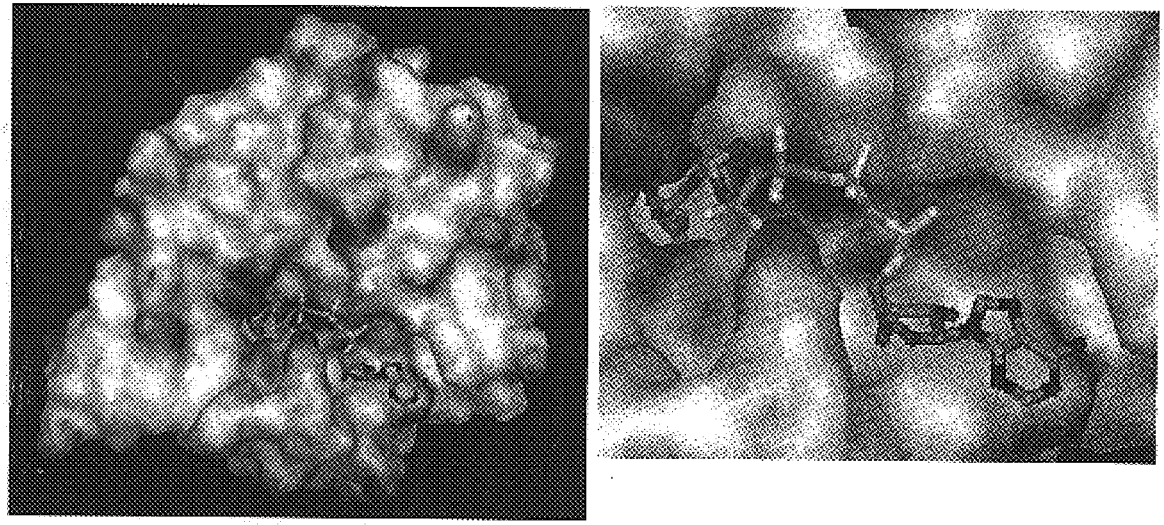
Figure 11B:
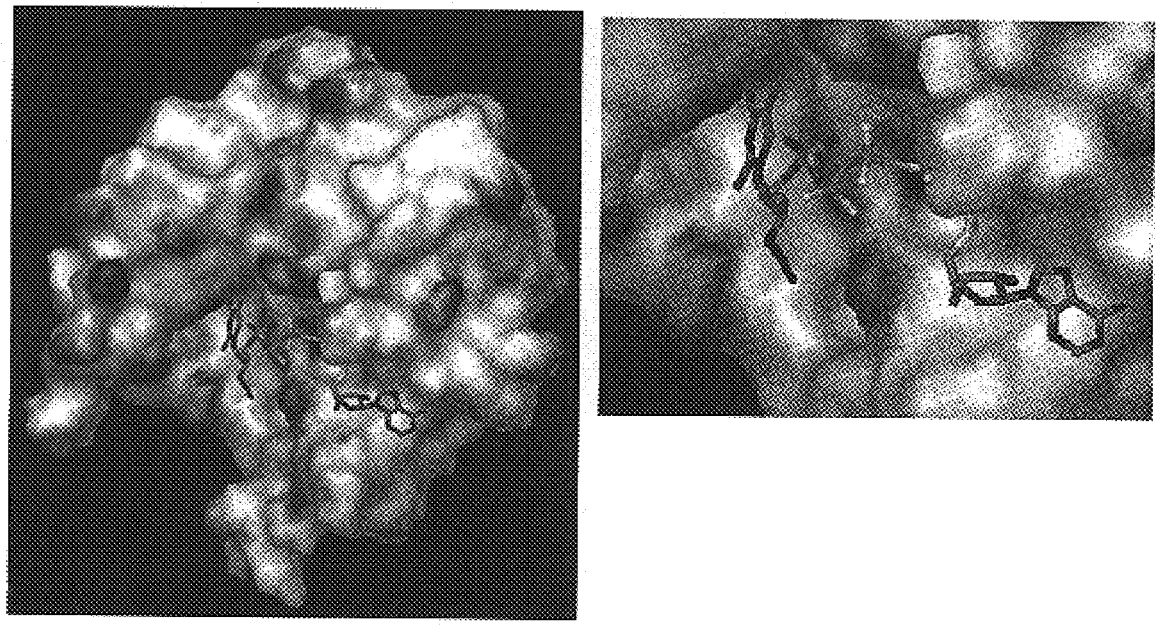

FIG. 11 depicts a surface representation of E. coli TMK with the inhibitor AP$_5$T (11a) and S. aureus TMK with a hypothetical positioning of AP$_5$T based on a structural alignment of C$_\alpha$ atoms from the E. coli TMK+AP$_5$T structure (11b).

DETAILED DESCRIPTION OF THE INVENTION

CrystaLline Form(s) and Method of Making

The three-dimensional structure of S. aureus thymidylate kinase was solved using high resolution x-ray crystallography to 2.3 Å resolution (see FIG. 2 and Example 1). Accordingly, the invention includes a TMK crystal and/or a crystal with TMK co-crystallized with a ligand, such as an inhibitor. Preferably, the crystal has trigonal space group symmetry P2$_1$. More preferably, the crystal comprises rectangular shaped unit cells, each unit cell having dimensions of a, b, and c; wherein a is about 40 Å to about 60 Å, b is about 80 Å to about 100 Å, and c is about 40 Å to about 60 Å; and wherein $\alpha=\gamma=90°$ and $\beta$ is about 80° to about 120°. The crystallized enzyme is a dimer with a single dimer in the asymmetric unit.

Purified S. aureus thymidylate kinase at a concentration of about 1 mg/ml to about 50 mg/ml may be crystallized, for example, by using a streak seeding procedure from a solution including about 5 wt. % to about 50 wt. % PEG (preferably having a number average molecular weight between about 200 and about 20,000), about 0.05 M to about 0.5 M MgCl$_2$, and about 0 wt. % to about 20 wt. % DMSO, wherein the solution is buffered to a pH of about 6 to about 7. Use of a buffer having a pK$_a$ of between about 5 and 8 is preferred. Molecular complexes of purified S. aureus thymidylate kinase at a concentration of about 1 mg/ml to about 50 mg/ml may also be crystallized, for example, from a solution including about 2 mM to about 20 mM β,γ-difluoromethylene-bisphosphonate adenosine monophosphate and about 0 wt. % to about 20 wt. % DMSO, wherein the solution is buffered to a pH of about 6 to about 7. A "molecular complex" means a protein in covalent or non-covalent association with a chemical entity. A buffer having a pK$_a$ of between about 5 and 8 is preferred for use in the crystallization method. A particularly preferred buffer is about 0.4M to about 2.0M sodium citrate. Variation in buffer and buffer pH as well as other additives such as PEG is apparent to those skilled in the art and may result in similar crystals.

The invention further includes an S. aureus thymidylate kinase crystal or S. aureus thymidylate kinase/ligand crystal that is isomorphous with an S. aureus thymidylate kinase crystal characterized by a unit cell having dimensions of a, b, and c; wherein a is about 40 Å to about 60 Å, b is about 80 Å to about 100 Å, and c is about 40 Å to about 60 Å; and wherein $\alpha=\gamma=90°$ and $\beta$ is about 80° to about 120°.

X-ray Crystallographic Analysis

Each of the constituent amino acids of S. aureus thymidylate kinase is defined by a set of structure coordinates as set forth in FIG. 2. The term "structure coordinates" refers to Cartesian coordinates derived from mathematical equations related to the patterns obtained on diffraction of a monochromatic beam of x-rays by the atoms (scattering centers) of an S. aureus thymidylate kinase complex in crystal form. The diffraction data are used to calculate an electron density map of the repeating unit of the crystal. The electron density maps are then used to establish the positions of the individual atoms of the S. aureus thymidylate kinase protein or protein/ligand complex.

Slight variations in structure coordinates can be generated by mathematically manipulating the S. aureus thymidylate kinase or S. aureus thymidylate kinase/ligand structure coordinates. For example, the structure coordinates set forth in FIG. 2 could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent. Structural equivalence is described in more detail below.

It should be noted that slight variations in individual structure coordinates of the S. aureus thymidylate kinase would not be expected to significantly alter the nature of chemical entities such as ligands that could associate with the substrate binding pockets. In this context, the phrase "associating with" refers to a condition of proximity between a chemical entity, or portions thereof, and an S. aureus thymidylate kinase molecule or portions thereof. The association may be non-covalent, wherein the juxtaposition is energetically favored by hydrogen bonding, van der Waals forces, or electrostatic interactions, or it may be covalent.

Thus, for example, a ligand that bound to a substrate binding pocket of S. aureus thymidylate kinase would also be expected to bind to or interfere with another substrate binding pocket whose structure coordinates define a shape that falls within the acceptable error.

It will be readily apparent to those of skill in the art that the numbering of amino acids in other isoforms of S. aureus thymidylate kinase may be different than that of S. aureus thymidylate kinase expressed in E. coli.

Active Site and Other Structural Features

Applicants' invention has provided, for the first time, information about the shape and structure of the substrate binding pockets of S. aureus thymidylate kinase. The structures of both the TMP and the TMP/ATP substrate binding pockets are elucidated. The secondary structure of the S. aureus thymidylate kinase monomer includes a five stranded parallel β sheet surrounded by nine α helices (FIG. 3). This solved crystal structure of S. aureus thymidylate kinase does not contain any ligand which has resulted in a disordered loop between helices α7 and α8 (FIG. 4). This loop has been called the "lid" in the structures of thymidylate kinase homologs from E. coli and S. cerevisiae. In E. coli the lid contains Arg 153 which is responsible for phosphate binding of the ATP substrate as shown in the X-ray crystal structure of the E. coli enzyme with the AP$_5$T inhibitor, a transition state analog of TMP/ATP (A. Lavie et al., Biochemistry 37:3677–86 (1998)). In contrast the analogous arginine in *S. cerevisiae* comes from the P loop (Arg 15) between β1 and α1 (A. Lavie et al., *Proc. Natl. Acad. Sci. USA*, 95:14045–50 (1998)). This distinction as further manifested in sequence differences between the P loop and lid regions has led to the classification of the *S. cerevisiae* enzyme as a class I thymidylate kinase (which also includes human thymidylate kinase) and the *E. coli* enzyme as a class II thymidylate kinase (A. Lavie, *Proc. Natl. Acad. Sci. USA*, 95:14045–50 (1998)). Fortunately, *S. aureus* (SEQ ID NO:1) has greater sequence similarity to the *E. coli* enzyme (SEQ ID NO:2, 38% identical, 59% similar) than the *S. cerevisiae* enzyme (SEQ ID NO:3, 28% identical, 46% similar) and contains R148 in the lid region suggesting it should be classified as a class II thymidylate kinase (FIGS. 5 and 6). This classification suggests that it might be possible to design inhibitors that are specific for the *S. aureus* enzyme and not eukaryotic thymidylate kinases.

Superposition of the *S. aureus* TMK with *E. coli* TMK gave a r.m.s. deviation of 2.19 Å for analogous residues (FIG. 5). Similarly, superposition of *S. aureus* TMK with *S. cerevisiae* TMK gave a r.m.s. deviation of 3.26 Å (FIG. 6). Analysis of the active site residues from *E. coli* TMK as observed in the $AP_5T$ inhibitor complex shows at least eleven residues that make direct hydrogen bonds to the inhibitor and another six residues make water mediated or hydrophobic interactions. Analysis of the active site residues from *S. aureus* TMK sequence reveals strong conservation of these active site residues with the *E. coli* active site (FIG. 7b); 15 of the 17 residues involved in the protein-inhibitor complex are identical while the two remaining residues are strongly conserved. An analogous comparison for the *S. cerevisiae* TMK (FIG. 7b) shows only four of 18 residues conserved within the active site suggesting that specificity between the *S. aureus* and eukaryotic thymidylate kinases might be attainable.

Comparing the liganded *E. coli* TMK structure with the unliganded *S. aureus* structure, it is apparent that a significant movement of the main chain around the active site (e.g. helix α2 and helix α7) including the ordering of the disordered residues must occur upon ligand binding. FIG. 11 shows where the $AP_5T$ inhibitor would be expected in the *S. aureus* TMK structure based on an alignment of the *E. coli* TMK-$AP_5T$ inhibitor complex. There does appear to be a surface in the *S. aureus* TMK structure which would complement the ATP and TMP substrates, although it is clear from this surface view that an important part of the structure, the lid, is missing from the *S. aureus* TMK structure. FIG. 8 clearly illustrates the role for this portion of the protein in completing the active site and closing off the thymidylate moiety from solvent.

Binding pockets are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or any parts of the binding pocket. An understanding of such associations helps lead to the design of drugs having more favorable associations with their target, and thus improved biological effects. Therefore, this information is valuable in designing potential inhibitors of *S. aureus* thymidylate kinase-like substrate binding pockets, as discussed in more detail below.

The term "binding pocket," as used herein, refers to a region of a molecule or molecular complex, that, as a result of its shape, favorably associates with another chemical entity. Thus, a binding pocket may include or consist of features such as cavities, surfaces, or interfaces between domains. Chemical entities that may associate with a binding pocket include, but are not limited to, cofactors, substrates, inhibitors, agonists, and antagonists.

The amino acid constituents of an *S. aureus* thymidylate kinase substrate binding pocket as defined herein are positioned in three dimensions in accordance with the structure coordinates listed in FIG. 2. In one aspect, the structure coordinates defining a substrate binding pocket of *S. aureus* thymidylate kinase include structure coordinates of all atoms in the constituent amino acids; in another aspect, the structure coordinates of a substrate binding pocket include structure coordinates of just the backbone atoms of the constituent atoms.

The TMP substrate binding pocket of *S. aureus* thymidylate kinase preferably includes the amino acids listed in Table 1, more preferably the amino acids listed in Table 2, and most preferably the amino acids listed in Table 3, as represented by the structure coordinates listed in FIG. 2. Alternatively, the TMP substrate binding pocket of *S. aureus* thymidylate kinase may be defined by those amino acids whose backbone atoms are situated within about 3.5 Å, more preferably within about 5Å, most preferably within about 7 Å, of one or more constituent atoms of a bound substrate or inhibitor. In yet another alternative, the TMP substrate binding pocket may be defined by those amino acids whose backbone atoms are situated within a sphere centered on the coordinates representing the alpha carbon atom of residue Ser98, the sphere having a radius of about 10 Å, preferably about 15 Å, and more preferably about 20 Å.

The TMP/ATP substrate binding pocket of *S. aureus* thymidylate kinase preferably includes the amino acids listed in Table 4, more preferably the amino acids listed in Table 5, and most preferably the amino acids listed in Table 6, as represented by the structure coordinates listed in FIG. 2. Alternatively, the TMP/ATP substrate binding pocket of *S. aureus* thymidylate kinase may be defined by those amino acids whose backbone atoms are situated within about 3.5 Å, more preferably within about 5 Å, most preferably within about 7 Å, of one or more constituent atoms of a bound substrate or inhibitor. In yet another alternative, the TMP/ATP substrate binding pocket may be defined by those amino acids whose backbone atoms are situated within a sphere centered on the coordinates representing the alpha carbon atom of residue Arg93, the sphere having a radius of about 10 Å, preferably about 15 Å, and more preferably about 20 Å.

The term "*S. aureus* thymidylate kinase-like substrate binding pocket" refers to a portion of a molecule or molecular complex whose shape is sufficiently similar to at least a portion of a substrate binding pocket of *S. aureus* thymidylate kinase as to be expected to bind related TMP and/or ATP structural analogues. A structurally equivalent substrate binding pocket is defined by a root mean square deviation from the structure coordinates of the backbone atoms of the amino acids that make up substrate binding pockets in *S. aureus* thymidylate kinase (as set forth in FIG. 2) of at most about 2.1 Å. How this calculation is obtained is described below.

Accordingly, the invention provides molecules or molecular complexes comprising an *S. aureus* thymidylate kinase substrate binding pocket or *S. aureus* thymidylate kinase-like substrate binding pocket, as defined by the sets of structure coordinates described above.

Three-dimensional Configurations

X-ray structure coordinates define a unique configuration of points in space. Those of skill in the art understand that a set of structure coordinates for protein or an protein/ligand complex, or a portion thereof, define a relative set of points that, in turn, define a configuration in three dimensions. A similar or identical configuration can be defined by an entirely different set of coordinates, provided the distances and angles between coordinates remain essentially the same. In addition, a scalable configuration of points can be defined by increasing or decreasing the distances between coordinates by a scalar factor while keeping the angles essentially the same.

The present invention thus includes the scalable three-dimensional configuration of points derived from the structure coordinates of at least a portion of an *S. aureus* thymidylate kinase molecule or molecular complex, as listed in FIG. 2, as well as structurally equivalent configurations, as described below. Preferably, the scalable three-dimensional configuration includes points derived from structure coordinates representing the locations of a plurality of the amino acids defining an *S. aureus* thymidylate kinase substrate binding pocket.

In one embodiment, the scalable three-dimensional configuration includes points derived from structure coordinates representing the locations the backbone atoms of a plurality of amino acids defining the *S. aureus* thymidylate kinase TMP substrate binding pocket, preferably the amino acids listed in Table 1, more preferably the amino acids listed in Table 2, and most preferably the amino acids listed in Table 3. Alternatively, the scalable three-dimensional configuration includes points derived from structure coordinates representing the locations of the side chain and the backbone atoms (other than hydrogens) of a plurality of the amino acids defining the *S. aureus* thymidylate kinase TMP substrate binding pocket, preferably the amino acids listed in Table 1, more preferably the amino acids listed in Table 2, and most preferably the amino acids listed in Table 3.

In another embodiment, the scalable three-dimensional configuration includes points derived from structure coordinates representing the locations the backbone atoms of a plurality of amino acids defining the *S. aureus* thymidylate kinase TMP/ATP substrate binding pocket, preferably the amino acids listed in Table 4, more preferably the amino acids listed in Table 5, and most preferably the amino acids listed in Table 6. Alternatively, the scalable three-dimensional configuration includes points derived from structure coordinates representing the locations of the side chain and the backbone atoms (other than hydrogens) of a plurality of the amino acids defining the *S. aureus* thymidylate kinase TMP/ATP substrate binding pocket, preferably the amino acids listed in Table 4, more preferably the amino acids listed in Table 5, and most preferably the amino acids listed in Table 6.

Likewise, the invention also includes the scalable three-dimensional configuration of points derived from structure coordinates of molecules or molecular complexes that are structurally homologous to *S. aureus* thymidylate kinase, as well as structurally equivalent configurations. Structurally homologous molecules or molecular complexes are defined below. Advantageously, structurally homologous molecules can be identified using the structure coordinates of *S. aureus* thymidylate kinase according to a method of the invention.

The configurations of points in space derived from structure coordinates according to the invention can be visualized as, for example, a holographic image, a stereodiagram, a model or a computer-displayed image, and the invention thus includes such images, diagrams or models.

Structurally Equivalent Crystal Structures

Various computational analyses can be used to determine whether a molecule or a substrate binding pocket portion thereof is "structurally equivalent," defined in terms of its three-dimensional structure, to all or part of *S. aureus* thymidylate kinase or its substrate binding pockets. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: (1) load the structures to be compared; (2) define the atom equivalences in these structures; (3) perform a fitting operation; and (4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention equivalent atoms are defined as protein backbone atoms (N, C$\alpha$, C, and O) for all conserved residues between the two structures being compared. A conserved residue is defined as a residue which is structurally or functionally equivalent. Only rigid fitting operations are considered.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any molecule or molecular complex or substrate binding pocket thereof, or any portion thereof, that has a root mean square deviation of conserved residue backbone atoms (N, C$\alpha$, C, O) of less than about 2.1 Å, when superimposed on the relevant backbone atoms described by the reference structure coordinates listed in FIG. 2, is considered "structurally equivalent" to the reference molecule. That is to say, the crystal structures of those portions of the two molecules are substantially identical, within acceptable error. Particularly preferred structurally equivalent molecules or molecular complexes are those that are defined by the entire set of structure coordinates listed in FIG. 2 ±a root mean square deviation from the conserved backbone atoms of those amino acids of not more than 2.1 Å. More preferably, the root mean square deviation is less than about 1.0 Å. Another embodiment of this invention is a molecular complex defined by the structure coordinates listed in FIG. 2 for those amino acids listed in Table 1, ±a root mean square deviation from the conserved backbone atoms of those amino acids of not more than 2.1 Å, preferably less than about 1.0 Å. Still another embodiment of this invention is a molecular complex defined by the structure coordinates listed in FIG. 2 for those amino acids listed in Table 4, ±a root mean square deviation from the conserved backbone atoms of those amino acids of not more than 2.1 Å, preferably less than about 1.0 Å.

The term "root mean square deviation" means the square root of the arithmetic mean of the squares of the deviations.

It is a way to express the deviation or variation from a trend or object. For purposes of this invention, the "root mean square deviation" defines the variation in the backbone of a protein from the backbone of S. aureus thymidylate kinase or a substrate binding pocket portion thereof, as defined by the structure coordinates of S. aureus thymidylate kinase described herein.

Machine Readable Storage Media

Transformation of the structure coordinates for all or a portion of S. aureus thymidylate kinase or the S. aureus thymidylate kinase/ligand complex or one of its substrate binding pockets, for structurally homologous molecules as defined below, or for the structural equivalents of any of these molecules or molecular complexes as defined above, into three-dimensional graphical representations of the molecule or complex can be conveniently achieved through the use of commercially-available software.

The invention thus further provides a machine-readable storage medium comprising a data storage material encoded with machine readable data which, when using a machine programmed with instructions for using said data, is capable of displaying a graphical three-dimensional representation of any of the molecule or molecular complexes of this invention that have been described above. In a preferred embodiment, the machine-readable data storage medium comprises a data storage material encoded with machine readable data which, when using a machine programmed with instructions for using said data, is capable of displaying a graphical three-dimensional representation of a molecule or molecular complex comprising all or any parts of an S. aureus thymidylate kinase substrate binding pocket or an S. aureus thymidylate kinase-like substrate binding pocket, as defined above. In another preferred embodiment, the machine-readable data storage medium comprises a data storage material encoded with machine readable data which, when using a machine programmed with instructions for using said data, is capable of displaying a graphical three-dimensional representation of a molecule or molecular complex defined by the structure coordinates of all of the amino acids listed in FIG. 2, ±a root mean square deviation from the backbone atoms of said amino acids of not more than 2.1 Å.

In an alternative embodiment, the machine-readable data storage medium comprises a data storage material encoded with a first set of machine readable data which comprises the Fourier transform of the structure coordinates set forth in FIG. 2, and which, when using a machine programmed with instructions for using said data, can be combined with a second set of machine readable data comprising the x-ray diffraction pattern of a molecule or molecular complex to determine at least a portion of the structure coordinates corresponding to the second set of machine readable data.

For example, a system for reading a data storage medium may include a computer comprising a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, track balls, touch pads, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may comprise CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of a binding pocket of this invention using a program such as QUANTA as described herein. Output hardware might also include a printer, so that hard copy output may be produced, or a disk drive, to store system output for later use.

In operation, a CPU coordinates the use of the various input and output devices, coordinates data accesses from mass storage devices, accesses to and from working memory, and determines the sequence of data processing steps. A number of programs may be used to process the machine-readable data of this invention. Such programs are discussed in reference to the computational methods of drug discovery as described herein. References to components of the hardware system are included as appropriate throughout the following description of the data storage medium.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

Stricturally Homologous Molecules, Molecular Complexes, and Crystal Structures The structure coordinates set forth in FIG. 2 can be used to aid in obtaining structural information about another crystallized molecule or molecular complex. The method of the invention allows determination of at least a portion of the three-dimensional structure of molecules or molecular complexes which contain one or more structural features that are similar to structural features of S. aureus thymidylate kinase, These molecules are referred to herein as "structurally homologous" to S. aureus thymidylate kinase, Similar structural features can include, for example, regions of amino acid identity, conserved active site or binding site motifs, and similarly arranged secondary structural elements (e.g., α helices and β sheets). Optionally, structural homology is determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the Blastp program, version 2.0.9, of the BLAST 2 search algorithm, as described by Tatusova et al., *FEMS Microbiol Lett* 174, 247–50 (1999), and available from the world wide web at ncbi.nlm.nih.gov/gorf/bl2.html. Preferably, the default values for all BLAST 2 search parameters are used, including matrix=BLOSUM62; open gap penalty=11, extension gap penalty=1, gap x_dropoff= 50, expect=10, wordsize=3, and filter on. In the comparison of two amino acid sequences using the BLAST search algorithm, structural similarity is referred to as "identity." Preferably, a structurally homologous molecule is a protein that has an amino acid sequence sharing at least 65% identity with a native or recombinant amino acid sequence of *S. aureus* thymidylate kinase (for example, SEQ ID NO:1). More preferably, a protein that is structurally homologous to *S. aureus* thymidylate kinase includes at least one contiguous stretch of at least 50 amino acids that shares at least 80% amino acid sequence identity with the analogous portion of the native or recombinant *S. aureus* thymidylate kinase (for example, SEQ ID NO:1). Methods for generating structural information about the structurally homologous molecule or molecular complex are well-known and include, for example, molecular replacement techniques.

Therefore, in another embodiment this invention provides a method of utilizing molecular replacement to obtain structural information about a molecule or molecular complex whose structure is unknown comprising the steps of:

(a) crystallizing the molecule or molecular complex of unknown structure;

(b) generating an x-ray diffraction pattern from said crystallized molecule or molecular complex; and (c) applying at least a portion of the structure coordinates set forth in FIG. 2 to the x-ray diffraction pattern to generate a three-dimensional electron density map of the molecule or molecular complex whose structure is unknown.

By using molecular replacement, all or part of the structure coordinates of *S. aureus* thymidylate kinase or the *S. aureus* thymidylate kinase/ligand complex as provided by this invention can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a structurally homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of *S. aureus* thymidylate kinase or the *S. aureus* thymidylate kinase/ligand complex according to FIG. 2 within the unit cell of the crystal of the unknown molecule or molecular complex so as best to account for the observed x-ray diffraction pattern of the crystal of the molecule or molecular complex whose structure is unknown. Phases can then be calculated from this model and combined with the observed x-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (E. Lattman, "Use of the Rotation and Translation Functions," in *Meth. Enzymol.*, 115, pp. 55–77 (1985); M. G. Rossman, ed., "The Molecular Replacement Method," *Int. Sci. Rev. Ser.*, No. 13, Gordon & Breach, New York (1972)).

Structural information about a portion of any crystallized molecule or molecular complex that is sufficiently structurally homologous to a portion of *S. aureus* thymidylate kinase can be resolved by this method. In addition to a molecule that shares one or more structural features with *S. aureus* thymidylate kinase as described above, a molecule that has similar bioactivity, such as the same catalytic activity, substrate specificity or ligand binding activity as *S. aureus* thymidylate kinase, may also be sufficiently structurally homologous to *S. aureus* thymidylate kinase to permit use of the structure coordinates of *S. aureus* thymidylate kinase to solve its crystal structure.

In a preferred embodiment, the method of molecular replacement is utilized to obtain structural information about a molecule or molecular complex, wherein the molecule or molecular complex comprises at least one *S. aureus* thymidylate kinase subunit or homolog. A "subunit" of *S. aureus* thymidylate kinase is an *S. aureus* thymidylate kinase molecule that has been truncated at the N-terminus or the C-terminus, or both. In the context of the present invention, a "homolog" of *S. aureus* thymidylate kinase is a protein that contains one or more amino acid substitutions, deletions, additions, or rearrangements with respect to the amino acid sequence of *S. aureus* thymidylate kinase (SEQ ID NO:1), but that, when folded into its native conformation, exhibits or is reasonably expected to exhibit at least a portion of the tertiary (three-dimensional) structure of *S. aureus* thymidylate kinase, For example, structurally homologous molecules can contain deletions or additions of one or more contiguous or noncontiguous amino acids, such as a loop or a domain. Structurally homologous molecules also include "modified" *S. aureus* thymidylate kinase molecules that have been chemically or enzymatically derivatized at one or more constituent amino acid, including side chain modifications, backbone modifications, and N- and C- terminal modifications including acetylation, hydroxylation, methylation, amidation, and the attachment of carbohydrate or lipid moieties, cofactors, and the like.

A heavy atom derivative of *S. aureus* thymidylate kinase is also included as an *S. aureus* thymidylate kinase homolog. The term "heavy atom derivative" refers to derivatives of *S. aureus* thymidylate kinase produced by chemically modifying a crystal of *S. aureus* thymidylate kinase, In practice, a crystal is soaked in a solution containing heavy metal atom salts, or organometallic compounds, e.g., lead chloride, gold thiomalate, thiomersal or uranyl acetate, which can diffuse through the crystal and bind to the surface of the protein. The location(s) of the bound heavy metal atom(s) can be determined by x-ray diffraction analysis of the soaked crystal. This information, in turn, is used to generate the phase information used to construct three-dimensional structure of the protein (T. L. Blundell and N. L. Johnson, *Protein Crystallography*, Academic Press (1976)).

Because *S. aureus* thymidylate kinase can crystallize in more than one crystal form, the structure coordinates of *S.* aureus thymidylate kinase as provided by this invention are particularly useful in solving the structure of other crystal forms of S. aureus thymidylate kinase or S. aureus thymidylate kinase complexes.

The structure coordinates of S. aureus thymidylate kinase as provided by this invention are particularly useful in solving the structure of S. aureus thymidylate kinase mutants. Mutants may be prepared, for example, by expression of S. aureus thymidylate kinase cDNA previously altered in its coding sequence by oligonucleotide-directed mutagenesis. Mutants may also be generated by site-specific incorporation of unnatural amino acids into thymidylate kinase proteins using the general biosynthetic method of C. J. Noren et al., Science, 244:182–188 (1989). In this method, the codon encoding the amino acid of interest in wild-type S. aureus thymidylate kinase is replaced by a "blank" nonsense codon, TAG, using oligonucleotide-directed mutagenesis. A suppressor tRNA directed against this codon is then chemically aminoacylated in vitro with the desired unnatural amino acid. The aminoacylated tRNA is then added to an in vitro translation system to yield a mutant S. aureus thymidylate kinase with the site-specific incorporated unnatural amino acid.

Selenocysteine or selenomethionine may be incorporated into wild-type or mutant S. aureus thymidylate kinase by expression of S. aureus thymidylate kinase-encoding cDNAs in auxotrophic E. coli strains (W. A. Hendrickson et al., EMBO J., 9(5):1665–1672 (1990)). In this method, the wild-type or mutagenized S. aureus thymidylate kinase cDNA may be expressed in a host organism on a growth medium depleted of either natural cysteine or methionine (or both) but enriched in selenocysteine or selenomethionine (or both). Alternatively, selenomethionine analogues may be prepared by down regulation methionine biosynthesis. (T. E. Benson et al., Nat. Struct. Biol., 2:644–53 (1995); G. D. Van Duyne et al., J. Mol. Biol. 229:105–24 (1993)).

The structure coordinates of S. aureus thymidylate kinase listed in FIG. 2 are also particularly useful to solve the structure of crystals of S. aureus thymidylate kinase, S. aureus thymidylate kinase mutants or S. aureus thymidylate kinase homologs co-complexed with a variety of chemical entities. This approach enables the determination of the optimal sites for interaction between chemical entities, including candidate S. aureus thymidylate kinase inhibitors and S. aureus thymidylate kinase. Potential sites for modification within the various binding site of the molecule can also be identified. This information provides an additional tool for determining the most efficient binding interactions, for example, increased hydrophobic interactions, between S. aureus thymidylate kinase and a chemical entity. For example, high resolution x-ray diffraction data collected from crystals exposed to different types of solvent allows the determination of where each type of solvent molecule resides. Small molecules that bind tightly to those sites can then be designed and synthesized and tested for their S. aureus thymidylate kinase inhibition activity.

All of the complexes referred to above may be studied using well-known x-ray diffraction techniques and may be refined versus 1.5–3 Å resolution x-ray data to an R value of about 0.20 or less using computer software, such as X-PLOR (Yale University, 81992, distributed by Molecular Simulations, Inc.; see, e.g., Blundell & Johnson, supra; Meth. Enzymol., Vol. 114 & 115, H. W. Wyckoff et al., eds., Academic Press (1985)). This information may thus be used to optimize known S. aureus thymidylate kinase inhibitors, and more importantly, to design new S. aureus thymidylate kinase inhibitors.

The invention also includes the unique three-dimensional configuration defined by a set of points defined by the structure coordinates for a molecule or molecular complex structurally homologous to S. aureus thymidylate kinase as determined using the method of the present invention, structurally equivalent configurations, and magnetic storage media comprising such set of structure coordinates.

Further, the invention includes structurally homologous molecules as identified using the method of the invention.

Homology Modeling

Using homology modeling, a computer model of an S. aureus thymidylate kinase homolog can be built or refined without crystallizing the homolog. First, a preliminary model of the S. aureus thymidylate kinase homolog is created by sequence alignment with S. aureus thymidylate kinase, secondary structure prediction, the screening of structural libraries, or any combination of those techniques. Computational software may be used to carry out the sequence alignments and the secondary structure predictions. Structural incoherences, e.g., structural fragments around insertions and deletions, can be modeled by screening a structural library for peptides of the desired length and with a suitable conformation. For prediction of the side chain conformation, a side chain rotamer library may be employed. If the S. aureus thymidylate kinase homolog has been crystallized, the final homology model can be used to solve the crystal structure of the homolog by molecular replacement, as described above. Next, the preliminary model is subjected to energy minimization to yield an energy minimized model. The energy minimized model may contain regions where stereochemistry restraints are violated, in which case such regions are remodeled to obtain a final homology model. The homology model is positioned according to the results of molecular replacement, and subjected to further refinement comprising molecular dynamics calculations.

Rational Drug Design

Computational techniques can be used to screen, identify, select and/or design chemical entities capable of associating with S. aureus thymidylate kinase or structurally homologous molecules. Knowledge of the structure coordinates for S. aureus thymidylate kinase permits the design and/or identification of synthetic compounds and/or other molecules which have a shape complementary to the conformation of the S. aureus thymidylate kinase binding site. In particular, computational techniques can be used to identify or design chemical entities, such as inhibitors, agonists and antagonists, that associate with an S. aureus thymidylate kinase substrate binding pocket or an S. aureus thymidylate kinase-like substrate binding pocket. Inhibitors may bind to or interfere with all or a portion of an active site of S. aureus thymidylate kinase, and can be competitive, non-competitive, or uncompetitive inhibitors; or interfere with dimerization by binding at the interface between the two monomers. Once identified and screened for biological activity, these inhibitors/agonists/antagonists may be used therapeutically or prophylactically to block S. aureus thymidylate kinase activity and, thus, inhibit the growth of the bacteria or cause its death. Structure-activity data for analogues of ligands that bind to or interfere with S. aureus thymidylate kinase or S. aureus thymidylate kinase-like substrate binding pockets can also be obtained computationally.

The term "chemical entity," as used herein, refers to chemical compounds, complexes of two or more chemical compounds, and fragments of such compounds or complexes. Chemical entities that are determined to associate with S. aureus thymidylate kinase are potential drug candidates.

Data stored in a machine-readable storage medium that is capable of displaying a graphical three-dimensional representation of the structure of S. aureus thymidylate kinase or a structurally homologous molecule, as identified herein, or portions thereof may thus be advantageously used for drug discovery. The structure coordinates of the chemical entity are used to generate a three-dimensional image that can be computationally fit to the three-dimensional image of S. aureus thymidylate kinase or a structurally homologous molecule. The three-dimensional molecular structure encoded by the data in the data storage medium can then be computationally evaluated for its ability to associate with chemical entities. When the molecular structures encoded by the data is displayed in a graphical three-dimensional representation on a computer screen, the protein structure can also be visually inspected for potential association with chemical entities.

One embodiment of the method of drug design involves evaluating the potential association of a known chemical entity with S. aureus thymidylate kinase or a structurally homologous molecule, particularly with an S. aureus thymidylate kinase substrate binding pocket or S. aureus thymidylate kinase-like substrate binding pocket. The method of drug design thus includes computationally evaluating the potential of a selected chemical entity to associate with any of the molecules or molecular complexes set forth above. This method comprises the steps of: (a) employing computational means to perform a fitting operation between the selected chemical entity and a substrate binding pocket or a pocket nearby the substrate binding pocket of the molecule or molecular complex; and (b) analyzing the results of said fitting operation to quantify the association between the chemical entity and the substrate binding pocket.

In another embodiment, the method of drug design involves computer-assisted design of chemical entities that associate with S. aureus thymidylate kinase, its homologs, or portions thereof. Chemical entities can be designed in a step-wise fashion, one fragment at a time, or may be designed as a whole or "de novo."

To be a viable drug candidate, the chemical entity identified or designed according to the method must be capable of structurally associating with at least part of an S. aureus thymidylate kinase or S. aureus thymidylate kinase-like substrate binding pockets, and must be able, sterically and energetically, to assume a conformation that allows it to associate with the S. aureus thymidylate kinase or S. aureus thymidylate kinase-like substrate binding pocket. Non-covalent molecular interactions important in this association include hydrogen bonding, van der Waals interactions, hydrophobic interactions, and electrostatic interactions. Conformational considerations include the overall three-dimensional structure and orientation of the chemical entity in relation to the substrate binding pocket, and the spacing between various functional groups of an entity that directly interact with the S. aureus thymidylate kinase-like substrate binding pocket or homologs thereof.

Optionally, the potential binding of a chemical entity to an S. aureus thymidylate kinase or S. aureus thymidylate kinase-like substrate binding pocket is analyzed using computer modeling techniques prior to the actual synthesis and testing of the chemical entity. If these computational experiments suggest insufficient interaction and association between it and the S. aureus thymidylate kinase or S. aureus thymidylate kinase-like substrate binding pocket, testing of the entity is obviated. However, if computer modeling indicates a strong interaction, the molecule may then be synthesized and tested for its ability to bind to or interfere with an S. aureus thymidylate kinase or S. aureus thymidylate kinase-like substrate binding pocket. Binding assays to determine if a compound actually interferes with S. aureus thymidylate kinase can also be performed and are well known in the art. Binding assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof.

One skilled in the art may use one of several methods to screen chemical entities or fragments for their ability to associate with an S. aureus thymidylate kinase or S. aureus thymidylate kinase-like substrate binding pocket. This process may begin by visual inspection of, for example, an S. aureus thymidylate kinase or S. aureus thymidylate kinase-like substrate binding pocket on the computer screen based on the S. aureus thymidylate kinase structure coordinates listed in FIG. 2 or other coordinates which define a similar shape generated from the machine-readable storage medium. Selected fragments or chemical entities may then be positioned in a variety of orientations, or docked, within the substrate binding pocket. Docking may be accomplished using software such as QUANTA and SYBYL, followed by energy minimization and molecular dynamics with standard molecular mechanics forcefields, such as CHARMM and AMBER.

Specialized computer programs may also assist in the process of selecting fragments or chemical entities. Examples include GRID (P. J. Goodford, *J. Med. Chem.* 28:849–857 (1985); available from Oxford University, Oxford, UK); MCSS (A. Miranker et al., *Proteins: Struct. Funct. Gen.*, 11:29–34 (1991); available from Molecular Simulations, San Diego, Calif.); AUTODOCK (D. S. Goodsell et al., *Proteins: Struct. Funct. Genet.* 8:195–202 (1990); available from Scripps Research Institute, La Jolla, Calif.); and DOCK (I. D. Kuntz et al., *J. Mol. Biol.* 161:269–288 (1982); available from University of California, San Francisco, Calif.).

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of S. aureus thymidylate kinase. This would be followed by manual model building using software such as QUANTA or SYBYL (Tripos Associates, St. Louis, Mo.).

Useful programs to aid one of skill in the art in connecting the individual chemical entities or fragments include, without limitation, CAVEAT (P. A. Bartlett et al., in *Molecular Recognition in Chemical and Biological problems,*" Special Publ., Royal Chem. Soc., 78:182–196 (1989); G. Lauri et al., *J. Comput. Aided Mol. Des.* 8:51–66 (1994); available from the University of California, Berkeley, Calif.); 3D database systems such as ISIS (available from MDL Information Systems, San Leandro, Calif.; reviewed in Y. C. Martin, *J. Med. Chem.* 35:2145–2154 (1992)); and HOOK (M. B. Eisen et al., *Proteins: Struc., Funct., Genet.* 19:199–221 (1994); available from Molecular Simulations, San Diego, Calif.).

S. aureus thymidylate kinase binding compounds may be designed "de novo" using either an empty binding site or optionally including some portion(s) of a known inhibitor (s). There are many de novo ligand design methods including, without limitation, LUDI (H.-J. Bohm, *J. Comp. Aid. Molec. Design.* 6:61–78 (1992); available from Molecular Simulations Inc., San Diego, Calif.); LEGEND (Y. Nishibata et al., *Tetrahedron,* 47:8985 (1991); available from Molecular Simulations Inc., San Diego, Calif.); Leap-Frog (available from Tripos Associates, St. Louis, Mo.); and SPROUT (V. Gillet et al., *J. Comput. Aided Mol. Design* 7:127–153 (1993); available from the University of Leeds, UK).

Once a compound has been designed or selected by the above methods, the efficiency with which that entity may bind to or interfere with an S. aureus thymidyl ate kinase or S. aureus thymidyl ate kinase-like substrate binding pocket may be tested and optimized by computational evaluation. For example, an effective S. aureus thymidylate kinase or S. aureus thymidylate kinase-like substrate binding pocket inhibitor must preferably demonstrate a relatively small difference in energy between its bound and free states (i.e., a small deformation energy of binding). Thus, the most efficient S. aureus thymidylate kinase or S. aureus thymidylate kinase-like substrate binding pocket inhibitors should preferably be designed with a deformation energy of binding of not greater than about 10 kcal/mole; more preferably, not greater than 7 kcal/mole. S. aureus thymidylate kinase or S. aureus thymidylate kinase-like substrate binding pocket inhibitors may interact with the substrate binding pocket in more than one conformation that is similar in overall binding energy. In those cases, the deformation energy of binding is taken to be the difference between the energy of the free entity and the average energy of the conformations observed when the inhibitor binds to the protein.

An entity designed or selected as binding to or interfering with an S. aureus thymidylate kinase or S. aureus thymidylate kinase-like substrate binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole, and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. 1995); AMBER, version 4.1 (P.A. Kollman, University of California at San Francisco, 1995); QUANTA/CHARMM (Molecular Simulations, Inc., San Diego, Calif. 1995); Insight II/Discover (Molecular Simulations, Inc., San Diego, Calif. 1995); DelPhi (Molecular Simulations, Inc., San Diego, Calif. 1995); and AMSOL (Quantum Chemistry Program Exchange, Indiana University). These programs may be implemented, for instance, using a Silicon Graphics workstation such as an Indigo$^2$ with "IMPACT" graphics. Other hardware systems and software packages will be known to those skilled in the art.

Another approach encompassed by this invention is the computational screening of small molecule databases for chemical entities or compounds that can bind in whole, or in part, to a S. aureus thymidylate kinase or S. aureus thymidylate kinase-like substrate binding pocket. In this screening, the quality of fit of such entities to the binding site may be judged either by shape complementarity or by estimated interaction energy (E. C. Meng et al., *J. Comp. Chem.,* 13, pp.505–524(1992)).

This invention also enables the development of chemical entities that can isomerize to short-lived reaction intermediates in the chemical reaction of a substrate or other compound that interferes with or with S. aureus thymidylate kinase. Time-dependent analysis of structural changes in S. aureus thymidylate kinase during its interaction with other molecules is carried out. The reaction intermediates of S. aureus thymidylate kinase can also be deduced from the reaction product in co-complex with S. aureus thymidylate kinase. Such information is useful to design improved analogues of known S. aureus thymidylate kinase inhibitors or to design novel classes of inhibitors based on the reaction intermediates of the S. aureus thymidylate kinase and inhibitor co-complex. This provides a novel route for designing S. aureus thymidylate kinase inhibitors with both high specificity and stability.

Yet another approach to rational drug design involves probing the S. aureus thymidylate kinase crystal of the invention with molecules comprising a variety of different functional groups to determine optimal sites for interaction between candidate S. aureus thymidylate kinase inhibitors and the protein. For example, high resolution x-ray diffraction data collected from crystals soaked in or co-crystallized with other molecules allows the determination of where each type of solvent molecule sticks. Molecules that bind tightly to those sites can then be further modified and synthesized and tested for their thymidylate kinase inhibitor activity (J. Travis, *Science,* 2:1374 (1993)).

In a related approach, iterative drug design is used to identify inhibitors of S. aureus thymidylate kinase. Iterative drug design is a method for optimizing associations between a protein and a compound by determining and evaluating the three-dimensional structures of successive sets of protein/compound complexes. In iterative drug design, crystals of a series of protein/compound complexes are obtained and then the three-dimensional structures of each complex is solved. Such an approach provides insight into the association between the proteins and compounds of each complex. This is accomplished by selecting compounds with inhibitory activity, obtaining crystals of this new protein/compound complex, solving the three dimensional structure of the complex, and comparing the associations between the new protein/compound complex and previously solved protein/compound complexes. By observing how changes in the compound affected the protein/compound associations, these associations may be optimized.

A compound that is identified or designed as a result of any of these methods can be obtained (or synthesized) and tested for its biological activity, e.g., inhibition of thymidylate kinase activity.

Pharmaceutical Compositions (Inhibitors)

Pharmaceutical compositions of this invention comprise an inhibitor of S. aureus TMK activity identified according to the invention, or a pharmaceutically acceptable salt thereof, and a pharmaceutically acceptable carrier, adjuvant, or vehicle. The term "pharmaceutically acceptable carrier" refers to a carrier(s) that is "acceptable" in the sense of being compatible with the other ingredients of a composition and not deleterious to the recipient thereof. Optionally, the pH of the formulation is adjusted with pharmaceutically acceptable acids, bases, or buffers to enhance the stability of the formulated compound or its delivery form.

Methods of making and using such pharmaceutical compositions are also included in the invention. The pharmaceutical compositions of the invention can be administered orally, parenterally, by inhalation spray, topically, rectally, nasally, buccally, vaginally, or via an implanted reservoir. Oral administration or administration by injection is preferred. The term parenteral as used herein includes subcutaneous, intracutaneous, intravenous, intramuscular, intra-articular, intrasynovial, intrastemal, intrathecal, intralesional, and intracranial injection or infusion techniques.

Dosage levels of between about 0.01 and about 100 mg/kg body weight per day, preferably between about 0.5 and about 75 mg/kg body weight per day of the S. aureus TMK inhibitory compounds described herein are useful for the prevention and treatment of S. aureus TMK mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

In order that this invention be more fully understood, the following examples are set forth. These examples are for the purpose of illustration only and are not to be construed as limiting the scope of the invention in any way.

EXAMPLES

Example 1

Analysis of the Structure of S. aureus Thymidylate Kinase

A. Expression, Purification and Crystallization

The M15-1C *Escherichia coli* construct expressing *S. aureus* thymidylate kinase was obtained as a strain in which the Qiagen pREP4 vector was replaced with pREP4UX. Genes and polypeptides derived from *S. aureus*, including *S. aureus* and thymidylate kinase, are published in EP 786519 A2 and WO 0012678, both assigned to Human Genome Sciences. This plasmid contains the argU gene which codes for the AGA tRNA and prevents the lysine for arginine substitution which occurred in the original construct from Human Genome Sciences. For preparation of the selenomethionine analogue of thymidylate kinase, the construct was grown in a minimal salts medium, M9, which contained glucose and $NH_4Cl$ as the sources of carbon and nitrogen. Endogenous methionine biosynthesis was then inhibited while adding an excess of selenomethionine to the growth medium just prior to IPTG induction of thymidylate kinase synthesis (T.E. Benson et al., *Nat. Struct. Biol.*, 2:644–53 (1995); G. D. Van Duyne et al., *J. Mol. Biol.* 229:105–24 (1993)). The formulation of basal M9 was $Na_2HPO_4$, 6 g; $KH_2PO_4$, 3 g; $NH_4Cl$, 1.0 g; and NaCl, 0.5 g per L of deionized water. The pH was adjusted to 7.4 with concentrated KOH and the medium was sterilized by autoclaving. Prior to inoculation, the following filter sterilized solutions were added per L of basal medium: 1M $MgSO_4$, 1.0 mL; 1M $CaCl_2$, 0.1 mL; trace metal salts solution, 0.1 mL, 10 mM thiamin, 1.0 mL; and 20% glucose, 20 mL. The trace metal salts solution contained per L of deionized water: $MgCl_2.6H_2O$, 39.44 g; $MnSO_4.H_2O$, 5.58 g; $FeSO_4.7H_2O$, 1.11 g; $Na_2MoO_4.2H_2O$, 0.48 g; $CaCl_2$, 0.33 g; NaCl, 0.12 g; and ascorbic acid, 1.0 g. Filter sterilized ampicillin and kanamycin were added to the medium at final concentrations of 100 mg/mL and 30 mg/mL, respectively.

Fermentations were prepared in 100 mL volumes of M9 medium contained in 500 mL wide mouth flasks. A 0.1 mL aliquot of the stock culture was inoculated into the medium and allowed to grow at 30° C. for 18–20 hours with a shaking rate of 200 rpm. The seed culture was harvested by centrifugation and then resuspended in an equal volume of M9 medium. The resuspended seed was used to inoculate expression fermentations at a rate of 3%. For expression, the culture was grown under the same conditions to an A600 of ~0.6. At this point, methionine biosynthesis was down regulated by the addition of L-lysine, L-threonine, and L-phenylalanine at a final concentration for each of 100 mg/mL and L-leucine, L-isoleucine, and L-valine at 50 mg/mL each. D,L-selenomethionine was added simultaneously to a final concentration of 100 mg/mL. After 15–20 minutes, expression of thymidylate kinase was induced by addition of IPTG (isopropyl thio-β-D-galactosidase, Gibco BRL) to 1 mM. Growth of the culture was continued for an additional 3.5 hours until an A600 of 1.5–1.6. Cells were then harvested by centrifugation and frozen at −80° C. Under these conditions, the average yield of cell paste was 3.0 to 3.5 g/L.

For protein purification, all buffers were chilled to 4° C. prior to use and all procedures were performed at 4° C. Cells (24.8 g wet weight) were resuspended in 125 mL of lysis buffer (25 mM Tris (pH 7.8), 500 mM NaCl, 10% glycerol, 25 mM imidazole, 5 mM 2-mercaptoethanol, 0.2 mg/mL DNAse I) and ruptured by using an American Instrument French Press at 16,000 PSI. The lysate was clarified by centrifugation at 39,200× g for 60 minutes in a JA20 rotor. The supematant was filtered by using a Nalgene 0.2 $\mu m$ filter unit. The filtered supernatant was applied at 74 cm/hr to a Qiagen NTA Superflow column (1.6 cm i.d. ×11 cm (CV=22 mL)) charged with nickel that was pre-equilibrated with EQ buffer (25 mM Tris (pH 7.8), 500 mM NaCl, 10% glycerol, 25 mM imidazole, 5 mM 2-mercaptoethanol). The column was washed with 7.7 CV of EQ buffer, 12.5 CV of wash buffer (25 mM Tris (pH 7.8), 500 mM NaCl, 10% glycerol, 50 mM imidazole, 5 mM 2-mercaptoethanol) and eluted with 1.4 CV of elution buffer (25 mM Tris (pH 7.8), 500 mM NaCl, 10% glycerol, 300 mM imidazole, 5 mM 2-mercaptoethanol). During the elution the linear velocity was decreased to 42 cm/hr. The eluted fraction was treated with DTT to achieve a final concentration of 10 mM and dialyzed extensively against nitrogen sparged dialysis buffer (25 mM Tris (pH 7.8), 500 mM NaCl, 10% glycerol, 10 mM DTT, pH 7.8).

The Mono Q analytical run was performed using 50 mL native TMK (14 mg/mL) diluted to 200 mL with 20 mM Tris (pH 8.0). The sample was loaded onto a Mono Q (Amersham Pharmacia Biotech) column equilibrated with 20 mM Tris (pH 8.0) and run through a 20–40% (20 mM Tris (pH 8.0)+1.0M NaCl) gradient in 40 mL with a flow rate of 1.0 mL/min. The Mono P column run was performed using 50 mL TMK (14 mg/mL) diluted to 200 mL with 25 mM bis-Tris (pH 6.71). The sample was injected onto a Mono P column (Amersham Pharmacia Biotech) equilibrated with 25 mM bis-Tris (pH 6.71) and run through a step gradient of 0-100-0% Polybuffer Mix 96/74 (20:1), pH 5.80. Gel filtration studies were carried out on a Superose 200 column with a 500 mL sample of thymidylate kinase at a concentration of 4.2 mg/mL using 50 mM Tris (pH 8.5), 500 mM NaCl, 5 mM 2-mercaptoethanol, and 0.5% glycerol at a flow rate of 1 mL/min. For dynamic light scattering experiments, samples were mixed in 1.5 ml eppendorf tubes, then sterile filtered through a 0.22 mm ceramic membrane (Whatman). 20 mL of solution is read in a quartz cuvette in a Dyna Pro Molecular Sizing Instrument (Protein Solutions, Inc., Charlottesville, Va.).

The native protein was exchanged into 50 mM Tris (pH 7.8), 5 mM 2-mercaptoethanol to a concentration of 15 mg/mL and screened for crystallization conditions using Crystal Screen I, Crystal Screen II, and MembFac Screen (Hampton Research, Laguna Niguel, Calif.). The most encouraging lead was from Hampton Crystal Screen I condition 23: 30% PEG 400, 0.1M Na HEPES pH 7.5, 0.2M $MgCl_2$. Follow up screens indicated that PIPES buffer was most conducive to crystal formation.

The initial crystals of the thymidylate kinase were stacks of small plates that were inseparable and unusable for diffraction studies. Biochemical analysis of the protein revealed that the sample was substantially pure by sodium dodecylsulfate polyacrylamide-gel electrophoresis (SDS-PAGE) analysis, but isoelectric focusing (IEF) gels revealed at least two distinct isoelectric species. It is likely, although yet unproven, that these isoelectric species were the cause of the morphology of the thymidylate kinase crystals. Further efforts at purification with a Mono Q column indicated that separation of these species would be difficult and it was not clear that large scale isoelectrofocusing using a Mono P column or preparative isoelectric focusing would improve the separation because of the small differences in pI. A series experiments exploring the feasibility of preparative isoelectric focusing experiments using PrIME (preparative isoelectric membrane electrophoresis) was hampered due to precipitation of the protein near its pI. Gel filtration did reveal that thymidylate kinase behaves as a dimer in solution, confirming earlier literature reports for the related *E. coli* and yeast TMK. The initial crystallization conditions contained 200 mM $MgCl_2$ and later experiments showed that at least 150 mM $MgCl_2$ was required for crystal formation. Dynamic light scattering experiments in the presence of $MgCl_2$ revealed an interesting phenomenon where protein aggregation was reduced in the presence of $MgCl_2$ over a number of hours leading to a monodisperse, dimeric sample suitable for crystallization.

The stacked plates were eventually transformed into single crystals through iterative streak seeding and crystallization on hanging or sitting drops with thymidylate kinase in 0.1 M PIPES (pH 6.6), 14–19% PEG 400, 0.2 M MgCl2. This technique involved taking the multinucleated crystals, crushing them into microcrystals, and using a dilution series of this suspension of microcrystals for seeding. It was observed that this second round of crystals were usually less multinucleated than when crystal formation was allowed to proceed via spontaneous nucleation. A second round of streak seeding was usually necessary in order to obtain multiple single crystals. Refinement of the streak seeding technique resulted in native and selenomethionine TMK crystals on the order of about 100 μm×about 100 μm×about 20 μm.

Subsequent crystallization experiments also indicated that a protein concentration of 7 mg/mL was able to yield suitable crystals. The crystallization solution was a cryoprotective agent making it straightforward to freeze the crystals in liquid nitrogen for data collection. Selenomethionine thymidylate kinase was exchanged into 10 mM Tris (pH 7.8), 10 mM DTT and concentrated to 7 or 14 mg/mL for crystallization experiments.

B. X-ray Diffraction Characterization

Thymidylate kinase crystals were generally too small for useful data collection using standard x-ray diffraction equipment. Therefore, all data collection was carried out at the Advanced Photon Source (Argonne, Ill.). The structure of *S. aureus* thymidylate kinase was determined by multiple anomalous dispersion (MAD) using synchrotron radiation. Crystals were of the space group $P2_1$ with cell constants a=49.8 Å, b=90.1 Å, c=46.5 Å, α=γ=90° and β=101.8°. The Matthews coefficient for these crystals assuming that there are two molecules in the asymmetric unit is 2.1 Å/Da with 40% solvent. Two MAD data sets were collected B one at 2.7 Å and one at 2.3 Å.

Two selenomethionine multiple anomalous dispersion (MAD) experiments were performed (2.7Å resolution and 2.3 Å resolution) using three different wavelengths (remote wavelength 1.0332 Å, 12000 eV, inflection point wavelength 0.979746 Å, 12654.8 eV, and the peak wavelength 0.979617 Å, 12656.5 eV).

C. Heavy Atom Derivative

Selenomethionine thymidylate kinase was expressed using downregulation of methionine biosynthesis (T.E. Benson et al., *Nat. Struct. Biol.*, 2:644–53 (1995); G. D. Van Duyne et al., *J. Mol. Biol.* 229:105–24 (1993)) and purified in order to obtain de novo phases by multiple anomalous dispersion (W. A. Hendrickson, Science 254:51–8 (1991)). Anomalous difference Patterson maps revealed six selenium sites (three for each of the two monomers in the asymmetric unit) (FIG. 9). Patterson maps at 2.7 Å showed that the atomic positions for the seleniums were not well resolved, but maps at 2.3 Å clearly defined the atomic positions of the heavy atoms. Unfortunately, the MAD phases for data collected at 2.3 Å were of lower quality than the phases at 2.7 Å, so initial model building was performed using the MAD phased map to 2.7 Å (FIG. 10). Subsequent refinement was conducted against the 2.3 Å data, and this higher resolution structure is the one reported here.

D. Phase Combination

Each of these individual data sets was indexed and integrated separately (see Tables 7 and 8 for integration statistics). The data sets were scaled to each other using the program SCALEIT in the CCP4 Program Suite (Collaborative Computational Project N4, *Acta Cryst.* D50:760–3 (1994)). Patterson maps revealed six selenium sites (three for each monomer in the asymmetric unit) whose locations were determined by direct methods using SHELX (G. M. Sheldrick & R. O. Gould, *Acta Cryst.* B51:423–31 (1995)). Heavy atom refinement and phase calculations were conducted using SHARP (E. La Fortelle et al., A Maximum-Likelihood Heavy-Atom Parameter Refinement and Phasing Program for the MIR and MAD Methods, P. Bourne & K. Watenpaugh, eds., Crystallographic Computing 7 (1997)). Phases calculated in SHARP were solvent flattened using the program SOLOMON (Collaborative Computational Project N4, *Acta Cryst.* D50:760–3 (1994)) and gave a significantly improved electron density map.

TABLE 7

Data collection and phasing statistics for structure of *S. aureus* TMK

| | λ 1.0332 Å (12000 eV) | λ 0.979746 Å (12654.8 eV) | λ 0.0979617 Å (12656.5 eV) |
|---|---|---|---|
| Resolution | 2.7 Å | 2.7 Å | 2.7 Å |
| No. observations | 76,132 | 62,273 | 76,145 |
| No. unique refl. | 10,901 | 10,941 | 10,928 |
| % completeness | 100% | 100% | 100% |
| $R_{sym}$ | 0.085 | 0.103 | 0.106 |
| $R_{cullis}$ acentrics | — | 0.61 | 0.67 |
| $R_{cullis}$ anamalous | 0.98 | 0.78 | 0.69 |
| Phasing power | | | |
| centrics | — | 1.28 | 1.21 |
| acentrics | — | 2.30 | 1.83 |

Mean figure of merit (to 2.7 Å resolution)

| | |
|---|---|
| before solvent flattening | 0.51 |
| after solvent flattening | 0.94 |

TABLE 8

Data collection and phasing statistics for structure of S. aureus TMK

| | λ 1.0332 Å (12000 eV) | λ 0.979746 Å (12654.8 eV) | λ 0.0979617 Å (12656.5 eV) |
|---|---|---|---|
| Resolution | 2.3 Å | 2.3 Å | 2.3 Å |
| No. observations | 76,712 | 123,553 | 123,372 |
| No. unique refl. | 17,661 | 17,887 | 17,991 |
| % completeness | 98.2% | 99.4% | 99.3% |
| $R_{sym}$ | 0.083 | 0.107 | 0.099 |
| $R_{cullis}$ acentrics | — | 0.56 | 0.61 |
| $R_{cullis}$ anamalous | 0.99 | 0.69 | 0.70 |
| Phasing power | | | |
| centrics | — | 1.34 | 1.38 |
| acentrics | — | 2.22 | 2.04 |

Mean figure of merit (to 2.3 Å resolution)

| before solvent flattening | 0.57 |
|---|---|
| after solvent flattening | 0.87 |

E. Model Building and Refinement

At this stage in the structure solution, the coordinates for *E. coli* thymidylate kinase greatly aided the process of model building for placement of the main chain backbone. Model building was done using the program CHAIN (J. S. Sack, *Journal of Molecular Graphics* 6:224–5 (1988)) and LORE (B. C. Finzel, *Meth Enzymol.* 277:230–42 (1997)). Refinement was carried out with XPLOR98 (A. T. Brunger, X-PLOR version 3.1: A system for X-ray Crystallography and NMR, New Haven: Yale Univ. Press, (1992)) incorporating bulk solvent correction during the refinement (J. S. Jiang & A. T. Brunger, *J. Mol. Biol.* 243:100–15 (1994)). Progress of the refinement was monitored by a decrease in both the R-factor and Free R-factor.

TABLE 9

Refinement Statistics for structure of S. aureus TMK

| | R-factor | Free R-factor | No. of reflections |
|---|---|---|---|
| 20 – 2.3 Å F ≥ 2σ | 0.2366 | 0.3084 | 15,908 |

| | Bonds (Å) | Angles (°) |
|---|---|---|
| r.m.s deviation from ideal geometry | 0.008 | 1.32 |

| | Number of atoms | Average B-factor |
|---|---|---|
| Protein | 2978 | 27.2 |
| Waters | 174 | 38.9 |
| Total | 3152 | 27.81 |

Stereochemistry of the model was checked using PROCHECK (R. A. Laskowski et al., *J. App. Cryst.* 26:283–91 (1993)) revealing no residues in disallowed regions of the Ramachandran plot. FIG. 9 was made using SETOR (S. V. Evans, *J. Mol. Graphics* 11:134–8 (1993)) and FIGS. 3a, 4 were produced in MOLSCRIPT (P. Kraulis, *J. Appl. Cryst.* 24:946–50 (1991)) and Raster 3D (E. A. Merritt & M. E. P. Murphy, *Acta Cryst.* D50:869–73 (1994)) while FIGS, 5a and 6a were produced in MOLSCRIPT (P. Kraulis, *J. Appl. Cryst.* 24:946–50 (1991)) alone.

F. Assays.

Binding assays to determine if a compound actually interferes with *S. aureus* thymidylate kinase can also be performed. For example, thymidylate kinase activity can be measured by coupling the formation of ADP and TDP to the reactions catalyzed by PD, LDH, and NDP-Kinase, as shown below. Oxidation of NADH is accompanied by a decrease in absorbance at 340 nm, which is measured spectrophotometrically.

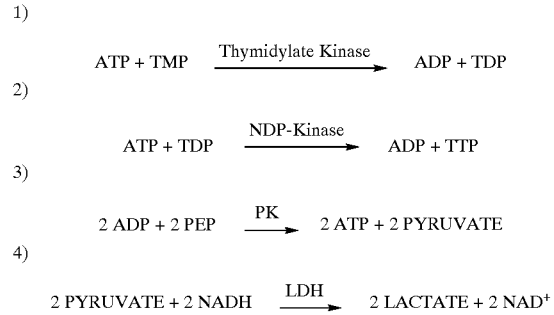

The standard reaction conditions employed during the kinetic characterization of the enzyme were: 50 mM HEPES, pH 8.0, 50 mM KCl, 2 mM $MgCl_2$, 4 U/ml PK, 5 U/ml LDH, 2 mM PEP, 1.5 mM ATP, 5 U/ml NDP-Kinase, 1.0 mM TMP, 0.22 mM NADH, and 0.8 μg/ml T. Kinase. All of the reagents except the T. Kinase were added to a cuvette and mixed, and the mixture was incubated at 24.5° C. for 2 minutes. To start the reaction, the T. Kinase was added, the contents of the cuvette were mixed, and the decrease in absorbance at 340 nm was monitored for 4–5 minutes.

Sequence Listing Free Text

| SEQ ID NO: 1 | recombinant *S. aureus* thymidylate kinase (with polyhistidine [$His_6$] sequence tag) |
|---|---|
| SEQ ID NO: 2 | *E. coli* thymidylate kinase |
| SEQ ID NO: 3 | *S. cerevisiae* thymidylate kinase |

---

What is claimed is:

1. A method for crystallizing *Staphylococcus aureus* (*S. aureus*) thymidylate kinase comprising:

preparing purified *S. aureus* thymidylate kinase at a concentration of about 1 mg/ml to about 50 mg/ml; and crystallizing *S. aureus* thymidylate kinase from a solution comprising the purified *S. aureus* thymidylate kinase, about 5 wt. % to about 50 wt. % poly(ethylene glycol) (PEG), about 0.05 M to about 0.5 M $MgCl_2$, and about 0 wt. % to about 20 wt. % dimethyl sulfoxide. (DMSO), wherein the solution is buffered to a pH of about 6 to about 7.

2. A crystal of *S. aureus* thymidylate kinase comprising atoms arranged in a spatial relationship represented by the structure coordinates listed in FIG. 2.

3. A crystal of *S. aureus* thymidylate kinase having amino acid sequence SEQ ID NO:1.

4. A crystal of *S. aureus* thymidylate kinase having amino acid sequence SEQ ID NO:1, with the proviso that at least one methionine is replaced with selenomethionine.

5. A crystal of *S. aureus* thymidylate kinase comprising a unit cell having dimensions of a, b, and c; wherein a is about 50 Å, b is about 90 Å, and c is about 47 Å; and wherein $\alpha=\gamma=90°$ and $\beta$ is about 102°.

6. A crystal of *Staphylococcus aureus* (*S. aureus*) thymidylate kinase prepared by a method comprising:

preparing purified *S. aureus* thymidylate kinase at a concentration of about 1 mg/ml to about 50 mg/ml; and crystallizing *S. aureus* thymidylate kinase from a solution comprising the purified *S. aureus* thymidylate kinase, about 5 wt. % to about 50 wt. % poly(ethylene glycol) (PEG), about 0.05 M to about 0.5 M $MgCl_2$, and about 0 wt. % to about 20 wt. % dimethyl sulfoxide (DMSO), wherein the solution is buffered to a pH of about 6 to about 7.

* * * * *

UNITED STATES PATENT AND TRADEMARK OFFICE
CERTIFICATE OF CORRECTION

PATENT NO.    : 6,689,595 B1
DATED         : February 10, 2004
INVENTOR(S)   : Timothy E. Benson It is certified that error appears in the above-identified patent and that said Letters Patent is hereby corrected as shown below:

<u>Drawings,</u>
Sheet 163 of 219, should read Sheet 160 of 219
Sheet 164 of 219, should read Sheet 161 of 219
Sheet 165 of 219, should read Sheet 162 of 219
Sheet 160 of 219, should read Sheet 163 of 219
Sheet 161 of 219, should read Sheet 164 of 219
Sheet 162 of 219, should read Sheet 165 of 219

<u>Column 2, Table 2,</u>
Line 7, delete "GLU 38 MET 65 SER 97"
Line 8, delete "GLY 45 PHE 67 LEU 99"

<u>Column 25,</u>
Line 49, delete "100 $\mu$mxabout 100 $\mu$mxabout" and insert -- 100 $\mu$m x about 100 $\mu$m x about --

Signed and Sealed this

Eighteenth Day of May, 2004

JON W. DUDAS
*Acting Director of the United States Patent and Trademark Office*

SEQUENCE LISTING

<160> NUMBER OF SEQ ID NOS: 3

<210> SEQ ID NO 1
<211> LENGTH: 214
<212> TYPE: PRT
<213> ORGANISM: Artificial Sequence

```
<220> FEATURE:
<223> OTHER INFORMATION: Description of Artificial Sequence: Recombinant
      Staphylococcus aureus thymidylate kinase with
      6-His tag

<400> SEQUENCE: 1

Met Gly Ser Ala Phe Ile Thr Phe Glu Gly Pro Glu Gly Ser Gly Lys
 1               5                  10                  15

Thr Thr Val Ile Asn Glu Val Tyr His Arg Leu Val Lys Asp Tyr Asp
            20                  25                  30

Val Ile Met Thr Arg Glu Pro Gly Gly Val Pro Thr Gly Glu Glu Ile
        35                  40                  45

Arg Lys Ile Val Leu Glu Gly Asn Asp Met Asp Ile Arg Thr Glu Ala
    50                  55                  60

Met Leu Phe Ala Ala Ser Arg Arg Glu His Leu Val Leu Lys Val Ile
65                  70                  75                  80

Pro Ala Leu Lys Glu Gly Lys Val Val Leu Cys Asp Arg Tyr Ile Asp
                85                  90                  95

Ser Ser Leu Ala Tyr Gln Gly Tyr Ala Arg Gly Ile Gly Val Glu Glu
            100                 105                 110

Val Arg Ala Leu Asn Glu Phe Ala Ile Asn Gly Leu Tyr Pro Asp Leu
        115                 120                 125

Thr Ile Tyr Leu Asn Val Ser Ala Glu Val Gly Arg Glu Arg Ile Ile
    130                 135                 140

Lys Asn Ser Arg Asp Gln Asn Arg Leu Asp Gln Glu Asp Leu Lys Phe
145                 150                 155                 160

His Glu Lys Val Ile Glu Gly Tyr Gln Glu Ile Ile His Asn Glu Ser
                165                 170                 175

Gln Arg Phe Lys Ser Val Asn Ala Asp Gln Pro Leu Glu Asn Val Val
            180                 185                 190

Glu Asp Thr Tyr Gln Thr Ile Ile Lys Tyr Leu Glu Lys Ile Arg Ser
        195                 200                 205

His His His His His His
    210

<210> SEQ ID NO 2
<211> LENGTH: 213
<212> TYPE: PRT
<213> ORGANISM: Escherichia coli

<400> SEQUENCE: 2

Met Arg Ser Lys Tyr Ile Val Ile Glu Gly Leu Glu Gly Ala Gly Lys
 1               5                  10                  15

Thr Thr Ala Arg Asn Val Val Val Glu Thr Leu Glu Gln Leu Gly Ile
            20                  25                  30

Arg Asp Met Val Phe Thr Arg Glu Pro Gly Gly Thr Gln Leu Ala Glu
        35                  40                  45

Lys Leu Arg Ser Leu Val Leu Asp Ile Lys Ser Val Gly Asp Glu Val
    50                  55                  60

Ile Thr Asp Lys Ala Glu Val Leu Met Phe Tyr Ala Ala Arg Val Gln
65                  70                  75                  80

Leu Val Glu Thr Val Ile Lys Pro Ala Leu Ala Asn Gly Thr Trp Val
                85                  90                  95

Ile Gly Asp Arg His Asp Leu Ser Thr Gln Ala Tyr Gln Gly Gly Gly
            100                 105                 110

Arg Gly Ile Asp Gln His Met Leu Ala Thr Leu Arg Asp Ala Val Leu
```

-continued

```
                115                 120                 125
Gly Asp Phe Arg Pro Asp Leu Thr Leu Tyr Leu Asp Val Thr Pro Glu
        130                 135                 140

Val Gly Leu Lys Arg Ala Arg Ala Arg Gly Glu Leu Asp Arg Ile Glu
145                 150                 155                 160

Gln Glu Ser Phe Asp Phe Phe Asn Arg Thr Arg Ala Arg Tyr Leu Glu
                165                 170                 175

Leu Ala Ala Gln Asp Lys Ser Ile His Thr Ile Asp Ala Thr Gln Pro
            180                 185                 190

Leu Glu Ala Val Met Asp Ala Ile Arg Thr Thr Val Thr His Trp Val
                195                 200                 205

Lys Glu Leu Asp Ala
        210

<210> SEQ ID NO 3
<211> LENGTH: 216
<212> TYPE: PRT
<213> ORGANISM: Saccharomyces cerevisiae

<400> SEQUENCE: 3

Met Met Gly Arg Gly Lys Leu Ile Leu Ile Glu Gly Leu Asp Arg Thr
1               5                   10                  15

Gly Lys Thr Thr Gln Cys Asn Ile Leu Tyr Lys Lys Leu Gln Pro Asn
                20                  25                  30

Cys Lys Leu Leu Lys Phe Pro Glu Arg Ser Thr Arg Ile Gly Gly Leu
            35                  40                  45

Ile Asn Glu Tyr Leu Thr Asp Asp Ser Phe Gln Leu Ser Asp Gln Ala
        50                  55                  60

Ile His Leu Leu Phe Ser Ala Asn Arg Trp Glu Ile Val Asp Lys Ile
65                  70                  75                  80

Lys Lys Asp Leu Leu Glu Gly Lys Asn Ile Val Met Asp Arg Tyr Val
                85                  90                  95

Tyr Ser Gly Val Ala Tyr Ser Ala Ala Lys Gly Thr Asn Gly Met Asp
            100                 105                 110

Leu Asp Trp Cys Leu Gln Pro Asp Val Gly Leu Leu Lys Pro Asp Leu
        115                 120                 125

Thr Leu Phe Leu Ser Thr Gln Asp Val Asp Asn Asn Ala Glu Lys Ser
    130                 135                 140

Gly Phe Gly Asp Glu Arg Tyr Glu Thr Val Lys Phe Gln Glu Lys Val
145                 150                 155                 160

Lys Gln Thr Phe Met Lys Leu Leu Asp Lys Glu Ile Arg Lys Gly Asp
                165                 170                 175

Glu Ser Ile Thr Ile Val Asp Val Thr Asn Lys Gly Ile Gln Glu Val
            180                 185                 190

Glu Ala Leu Ile Trp Gln Ile Val Glu Pro Val Leu Ser Thr His Ile
        195                 200                 205

Asp His Asp Lys Phe Ser Phe Phe
    210                 215
```